(12) United States Patent
Crew et al.

(10) Patent No.: US 11,458,123 B2
(45) Date of Patent: Oct. 4, 2022

(54) TAU-PROTEIN TARGETING PROTACS AND ASSOCIATED METHODS OF USE

(71) Applicant: Arvinas, Inc., New Haven, CT (US)

(72) Inventors: Andrew P. Crew, Guilford, CT (US); Michael Berlin, Flemington, NJ (US); Hanqing Dong, Madison, CT (US); Alexey Ishchenko, Walpole, MA (US)

(73) Assignee: ARVINAS OPERATIONS, INC., New Haven, CT (US)

( * ) Notice: Subject to any disclaimer, the term of this patent is extended or adjusted under 35 U.S.C. 154(b) by 0 days.

(21) Appl. No.: 15/801,243

(22) Filed: Nov. 1, 2017

(65) Prior Publication Data

US 2018/0125821 A1 May 10, 2018

Related U.S. Application Data

(60) Provisional application No. 62/415,830, filed on Nov. 1, 2016.

(51) Int. Cl.

| | | |
|---|---|---|
| *C07D 401/04* | (2006.01) | |
| *C07D 401/14* | (2006.01) | |
| *C07D 417/14* | (2006.01) | |
| *A61K 31/381* | (2006.01) | |
| *A61K 31/4166* | (2006.01) | |
| *A61K 31/495* | (2006.01) | |

(52) U.S. Cl.
CPC ........ *A61K 31/4166* (2013.01); *A61K 31/381* (2013.01); *A61K 31/495* (2013.01); *C07D 401/04* (2013.01); *C07D 401/14* (2013.01); *C07D 417/14* (2013.01); *C12Q 2600/106* (2013.01); *Y02A 50/30* (2018.01)

(58) Field of Classification Search
CPC .. A61K 31/4166; A61K 31/381; A61K 31/49; C07D 401/14; C07D 401/04; C07D 417/14
See application file for complete search history.

(56) References Cited

U.S. PATENT DOCUMENTS

| | | | |
|---|---|---|---|
| 6,306,663 | B1 | 10/2001 | Kenten et al. |
| 6,670,348 | B1 | 12/2003 | Rosen et al. |
| 7,030,141 | B2 | 4/2006 | Bigge et al. |
| 7,041,298 | B2 | 5/2006 | Deshaies et al. |
| 7,208,157 | B2 | 4/2007 | Sakamoto et al. |
| 7,244,851 | B2 | 7/2007 | Cohen et al. |
| 7,345,081 | B2 | 3/2008 | Cohen et al. |
| 7,419,975 | B2 | 9/2008 | Palermo et al. |
| 7,517,906 | B2 | 4/2009 | Condon et al. |
| 7,915,293 | B2 | 3/2011 | Ramesh |
| 9,500,653 | B2 | 11/2016 | Crews et al. |
| 9,632,089 | B2 | 4/2017 | Crews et al. |
| 2006/0128632 | A1 | 6/2006 | Sharma et al. |
| 2008/0051432 | A1 | 2/2008 | Zhang |
| 2008/0214501 | A1 | 9/2008 | Pan et al. |
| 2008/0219929 | A1 | 9/2008 | Wischik et al. |
| 2008/0269140 | A1 | 10/2008 | Wang et al. |
| 2010/0203012 | A1 | 8/2010 | Laurent et al. |
| 2011/0195043 | A1 | 8/2011 | Sun et al. |
| 2011/0269793 | A1 | 11/2011 | Macconi et al. |
| 2012/0270800 | A1 | 10/2012 | Verdine et al. |
| 2014/0235629 | A1 | 8/2014 | Bartberger et al. |
| 2014/0243372 | A1 | 8/2014 | Rew |
| 2014/0256706 | A1* | 9/2014 | Wang ..................... A61P 11/02 514/210.21 |
| 2014/0302523 | A1 | 10/2014 | Crews et al. |
| 2014/0356322 | A1 | 12/2014 | Crews et al. |
| 2015/0119435 | A1 | 4/2015 | Crews et al. |
| 2015/0291562 | A1* | 10/2015 | Crew ................... C07D 401/14 424/94.3 |
| 2015/0344473 | A1 | 10/2015 | Du et al. |
| 2016/0022642 | A1 | 1/2016 | Crews et al. |
| 2016/0045607 | A1 | 2/2016 | Crew et al. |

(Continued)

FOREIGN PATENT DOCUMENTS

| | | |
|---|---|---|
| CN | 1844118 A | 10/2006 |
| CN | 103688176 A | 3/2014 |

(Continued)

OTHER PUBLICATIONS

Mendelson et al. "Rapamycin as an Antiaging Therapeutic?: Targeting Mammalian Target of Rapamycin to Treat Hutchinson-Gilford Progeria and Neurodegenerative Diseases" Rejuv. Res. 2011, 14, 437-441. (Year: 2011).*

Lonskaya et al. "Nilotinib-induced autophagic changes increase endogenous parkin level and ubiquitination, leading to amyloid clearance" J. Mol. Med. 2014, 92, 373-386. (Year: 2014).*

Chamberlain et al. "Structure of the human Cereblon-DDB1-lenalidomide complex reveals basis for responsiveness to thalidomide analogs" Nat. Struct. Molec. Biol. 2014, 21, 803-810 (Year: 2014).*

Chemical Abstract Service STN Registry No. 1808162-87-9 [Entered STN: Sep. 25, 2015]. (Year: 2015).*

Chemical Abstract Service STN Registry No. 1036376-76-7 [Entered STN: Jul. 27, 2008]. (Year: 2008).*

(Continued)

*Primary Examiner* — Amanda L. Aguirre
(74) *Attorney, Agent, or Firm* — Bryan D. Zerhusen, Esq.; Nicholas R. Herrel, Esq.; Cantor Colburn LLP

(57) ABSTRACT

The present disclosure relates to bifunctional compounds, which find utility as modulators of tau protein. In particular, the present disclosure is directed to bifunctional compounds, which contain on one end a VHL or cereblon ligand which binds to the E3 ubiquitin ligase and on the other end a moiety which binds tau protein, such that tau protein is placed in proximity to the ubiquitin ligase to effect degradation (and inhibition) of tau. The present disclosure exhibits a broad range of pharmacological activities associated with degradation/inhibition of tau protein. Diseases or disorders that result from aggregation or accumulation of tau protein are treated or prevented with compounds and compositions of the present disclosure.

16 Claims, 1 Drawing Sheet

(56) References Cited

U.S. PATENT DOCUMENTS

| | | |
|---|---|---|
| 2016/0058872 A1 | 3/2016 | Crew et al. |
| 2016/0136230 A1 | 5/2016 | Campos et al. |
| 2016/0214972 A1 | 7/2016 | Jin et al. |
| 2016/0243247 A1 | 8/2016 | Bradner et al. |
| 2016/0272639 A1 | 9/2016 | Crew et al. |
| 2016/0368911 A1 | 12/2016 | Campos et al. |
| 2017/0008904 A1 | 1/2017 | Crew et al. |
| 2017/0037004 A1 | 2/2017 | Crew et al. |
| 2017/0065719 A1 | 3/2017 | Qian et al. |
| 2017/0121321 A1 | 5/2017 | Crews et al. |
| 2017/0281784 A1 | 10/2017 | Wang et al. |
| 2017/0307614 A1 | 10/2017 | Crews et al. |
| 2017/0327469 A1 | 11/2017 | Crew et al. |
| 2018/0015087 A1 | 1/2018 | Liu et al. |
| 2018/0072711 A1 | 3/2018 | Crew et al. |
| 2018/0099940 A1 | 4/2018 | Crew et al. |
| 2018/0125821 A1 | 5/2018 | Crew et al. |
| 2018/0147202 A1 | 5/2018 | Crew et al. |
| 2018/0155322 A1 | 6/2018 | Crew et al. |
| 2018/0177750 A1 | 6/2018 | Crew et al. |
| 2018/0179183 A1 | 6/2018 | Crew et al. |
| 2018/0193470 A1* | 7/2018 | Crew .................. A61K 47/545 |
| 2018/0215731 A1* | 8/2018 | Crew .................. C07D 401/14 |
| 2018/0228907 A1 | 8/2018 | Crew et al. |
| 2018/0237418 A1 | 8/2018 | Crew et al. |
| 2018/0256586 A1 | 9/2018 | Crew et al. |

FOREIGN PATENT DOCUMENTS

| | | |
|---|---|---|
| EA | 201390803 A1 | 9/2013 |
| EP | 2985285 | 2/2016 |
| JP | A 2004-525889 | 8/2004 |
| JP | A 2010-502627 | 1/2010 |
| RU | 2008112221 A | 10/2009 |
| RU | 2448101 C2 | 4/2012 |
| RU | 2011121567 A | 10/2012 |
| RU | 2012138709 A | 3/2014 |
| WO | WO 1998/003502 | 1/1998 |
| WO | WO 2000/066119 | 11/2000 |
| WO | WO 2002/066512 | 8/2002 |
| WO | WO 2002/100845 | 12/2002 |
| WO | WO 2005/097791 | 10/2005 |
| WO | WO 2006/069063 | 6/2006 |
| WO | WO 2006/113942 | 10/2006 |
| WO | WO 2007/101347 | 9/2007 |
| WO | WO 2007/106670 | 9/2007 |
| WO | WO 2007/130626 | 11/2007 |
| WO | WO 2008/011392 | 1/2008 |
| WO | WO 2008/014236 | 1/2008 |
| WO | WO 2008/109057 | 9/2008 |
| WO | WO 2008/128121 | 10/2008 |
| WO | WO 2008/128171 | 10/2008 |
| WO | WO 2008/134679 | 11/2008 |
| WO | WO 2009/015254 | 1/2009 |
| WO | WO 2009/060292 | 5/2009 |
| WO | WO 2010/107485 | 9/2010 |
| WO | WO 2010/141805 | 12/2010 |
| WO | WO 2011/008260 | 1/2011 |
| WO | WO 2011/119565 | 9/2011 |
| WO | WO 2012/003281 | 1/2012 |
| WO | WO 2012/040527 | 3/2012 |
| WO | WO 2012/078559 | 6/2012 |
| WO | WO 2012/090104 | 7/2012 |
| WO | WO 2013/071035 | 5/2013 |
| WO | WO 2013/071039 | 5/2013 |
| WO | WO 2013/106643 | 7/2013 |
| WO | WO 2013/106646 | 7/2013 |
| WO | WO 2013/170147 | 11/2013 |
| WO | WO 2013/175417 | 11/2013 |
| WO | WO 2013/176698 A1 | 11/2013 |
| WO | WO 2013/178570 | 12/2013 |
| WO | WO 2014/011712 | 1/2014 |
| WO | WO 2014/020502 | 2/2014 |
| WO | WO 2014/025759 | 2/2014 |
| WO | WO 2014/038606 | 3/2014 |
| WO | WO 2014/047024 | 3/2014 |
| WO | WO 2014/055461 | 4/2014 |
| WO | WO 2014/074658 | 5/2014 |
| WO | WO 2014/100065 | 6/2014 |
| WO | WO 2014/100071 | 6/2014 |
| WO | WO 2014/107713 | 7/2014 |
| WO | WO 2014/108452 | 7/2014 |
| WO | WO 2014/123418 | 8/2014 |
| WO | WO 2014/134201 | 9/2014 |
| WO | WO 2014/151863 | 9/2014 |
| WO | WO 2015/000868 | 1/2015 |
| WO | WO 2015/006524 | 1/2015 |
| WO | WO 2015/160845 | 10/2015 |
| WO | WO 2015/173225 A1 | 11/2015 |
| WO | WO 2016/118666 | 7/2016 |
| WO | WO 2016/146985 | 9/2016 |
| WO | WO 2016/169989 | 10/2016 |
| WO | WO 2016/172134 | 10/2016 |
| WO | WO 2016/197114 | 12/2016 |
| WO | WO 2017/011590 | 1/2017 |
| WO | WO 2017/020010 A1 | 2/2017 |
| WO | WO 2017/030814 | 2/2017 |
| WO | WO-2017024318 A1 * | 2/2017 | ......... A61K 31/4985 |
| WO | WO 2017/046036 A1 | 3/2017 |
| WO | WO 2017/079267 | 5/2017 |
| WO | WO 2017/117474 | 7/2017 |
| WO | WO 2017/161119 | 9/2017 |
| WO | WO 2017/184995 A1 | 10/2017 |
| WO | WO 2017/185036 | 10/2017 |
| WO | WO-2017176958 A1 * | 10/2017 | .............. A61P 35/00 |
| WO | WO-2017185034 A1 * | 10/2017 | ............. A61K 47/18 |
| WO | WO 2017/197051 | 11/2017 |
| WO | WO 2018/064589 A1 | 4/2018 |
| WO | WO 2018/089736 A1 | 5/2018 |
| WO | WO 2018/102067 A2 | 6/2018 |
| WO | WO 2018/144649 A1 | 8/2018 |
| WO | WO 2019/014429 | 1/2019 |
| WO | WO-2019014429 A1 * | 1/2019 |
| WO | WO 2019/042444 | 3/2019 |
| WO | WO 2019/199816 A1 | 10/2019 |
| WO | WO 2020/041331 A1 | 2/2020 |
| WO | WO 2020/176424 A1 | 9/2020 |

OTHER PUBLICATIONS

Fitilis et al. J. Phys. Chem. A 2008, 112, 4742-4748. (Year: 2008).*
Ahn, et al., "HIF-1alpha peptide derivatives with modifications at the hydroxyproline residue as activators of HIF-1alpha", Bioorg Med Chem Lett. 19(15), 2009, 4403-4405.
Ardecky, RJ, et al., "Design, synthesis and evaluation of inhibitor of apoptosis protein (IAP) antagonists that are highly selective for the BIR2 domain of XIAP", Bioorg. Med. Chem., 23(14): 4253-4257 (2013).
Ariza, M. et al, "Tau positron emission tomography (PET) imaging: past, present, and future", in Journal of Medicinal Chemistry 2015, 58, 4365-4382.
Asano M, et al., "Design, sterioselective synthesis, and biological evaluation of novel tri-cyclic compounds as inhibitor of apoptosis proteins (IAP) antagonists", Bioorg. Med. Chem., 21(18): 5725-5737 (2013).
Bargagna-Mohan, et al., "Use of PROTACS as molecular probes of angiogenesis", Bioorg Med Chem Lett. 15(11) 2005, 2724-2727.
Bondeson, et al., (2017) "Targeted Protein Degradation by Small Molecules." *Annu Rev Pharmacol Toxicol* 57:107-123.
Bondeson, et al., "Catalytic in vivo protein knockdown by small-molecule PROTACS", National Chem Biol. 11(8) Aug. 2015, 611-617.
Buckley, et al., "HaloPROTACS: use of small molecule PROTACS to induce degradation of HaloTag fusion proteins", ACS Chem Biol. 10(8), 2015, 1831-1837.
Buckley, et al., "Small-molecule inhibitors of the interaction between the E3 ligase VHL and HIF1a", Angew Chem Int Ed Engl.51(46), Oct. 12, 2012, 11463-11467.
Buckley, et al., "Targeting the von Hippel-Lindau E3 ubiquitin ligase using small molecules to disrupt the VHL/HIF-1α interaction", Journal of the American Chemical Society, Feb. 27, 2012, 134(10): 4465-4468.

(56) References Cited

OTHER PUBLICATIONS

Burslem, et al., (2017) "Small-Molecule Modulation of Protein Homeostasis." Chem Rev 117(17): 11269-11301.
Capitosti, S., et al., "Thalidomide analogues demonstrate dual inhibition of both angiogenesis and prostate cancer", Bioorganic & Medicinal Chemistry 12, (2004) 327-336.
Carmony, KC, et al., "PROTAC-Induced Proteolytic Targeting", Methods Mol. Biol., 2012, vol. 832, pp. 627-638.
CAS Registry No. 1004933-70-3, which entered STN on Feb. 21, 2008.
CAS Registry No. 871986-52-6 entered STN Jan. 16, 2006.
Chene, P., et al., "Inhibiting the p53-MDM2 interaction: an important target for cancer therapy" Nat. Rev. Cancer (2003), 3, 102-109.
Cohen, F, et al., "Orally bioavailable antagonists of inhibitor of apoptosis proteins based on an azabicyclooctane scaffold", J. Med. Chem., 52(6), 1723-1730 (2009).
Cohen, F. et al., "Antagonists of inhibitors of apoptosis proteins based on thiazole amide isosteres", Bioorg. Med. Chem. Lett., 20(7), 2229-2233 (2010).
Contino-Pepin, Christiane, et al., "Preliminary biological evaluations of new thalidomide analogues for multiple sclerosis application", Bioorganic & Medicinal Chemistry Letter 19 (2009), 878-881.
Corson, et al., "Design and applications of bifunctional small molecules: why two heads are better than one", ACS Chemical Biology vol. 3 No. 11, pp. 677-692; Nov. 21, 2008.
Crews, C. M., "Targeting the undruggable proteome: the small molecules of my dreams", Chem Biol 17, 551-555, doi:S1074-5521(10)00196-1 [pii] 10.1016/j.chembiol.2010.05.011 (2010).
Cromm, et al., (2017) "Targeted Protein Degradation: from Chemical Biology to Drug Discovery." Cell Chem Biol 24(9):1181-1190.
Cyrus, et al., "Jostling for position: optimizing linker location in the design of estrogen receptor-targeting PROTACs", Chem Med Chem. 5(7), Jul. 5, 2010, 979-985.
Cyrus, K. et al., "Impact of Linker Length on the Activity of PROTACs," Mol. Biosyst., 2011, vol. 7, No. 2, pp. 359-364.
Cyrus, K. et al., "Two-Headed PROTAC: An Effective New Tool for Targeted Protein Degradation," Chembiochem., 2010, vol. 11, pp. 1531-1534.
Di, J et al. "Reactivation of p53 by inhibiting Mdm2 E3 Ligase: a novel antitumor approach", Current Cancer Drug Targets (2011), 11(8), 987-994.
Ding, Q, et al., "Discovery of RG7388, a potent and selective p53-MDM2 inhibitor in clinical development", J Med Chem. Jul. 25, 2013; 56(14):5979-83. doi: 10.1021/jm400487c. Epub Jul. 16, 2013. PubMed PMID: 23808545 (J. Med. Chem. (2013)56, 5979-5983 Ding, et al).
Dixon, S. J. et al., "Identifying druggable disease-modifying gene products",. Curr Opin Chem Biol 13 , 549-555, doi:S1367-5931(09)00107-0 [pii] 10.1016/j.cbpa.2009.08.003 (2009).
Fischer, et al., "Structure of the DDB1-DRBN E3 Ubiquitin ligase in complex with thalidomide", Nature, vol. 000, pp. 1-5 (2014).
Flygare, J.A., et al. "Small-molecule pan-IAP antagonists: a patent review", Expert Opin. Ther. Pat., 20 (2), 251-267 (2010).
Gadd, M.S., et al., "Structural basis of PROTAC cooperative recognition for selective protein degradation", Nat Chem Biol 13, 514-521 (2017).
Galdeano, et al., "Structure-guided design and optimization of small molecules targeting the protein-protein interaction between the von hippel-lindau (VHL) E3 ubiquitin ligase and the Hypoxia inducible factor (HIF) alpha subunit with in vitro nanomolar affinities", Journal Med Chem, Aug. 2014, vol. 57, pp. 8657-8663.
Golub, et al., "Molecular classification of cancer: class discovery and class prediction by gene expression monitoring", Science 286, 531-537 (1991).
Gosink, M et al., "Redirecting the specificity of ubiquitination by modifying ubiquitin-conjugating enzymes", Pro. Natl. Acad Sci, vol. 92, pp. 9117-9121, 1995.
Haupt, Y. et al., "Mdm2 promotes the rapid degradation of p53", Nature 387, 296-299 (1997).
Hennessy, EJ, et al., "Discovery of aminopiperidine-based Smac mimetics as IAP antagonists", Bioorg. Med. Chem. Lett., 22(4), 1690-1694 (2012).
Hines, J., et al., "Posttranslational protein knockdown coupled to receptor tyrosine kinase activation with phosphoPROTACs", Proc Natl Acad Sci USA 110, 8942-8947 (2013).
Hird, AW, et al., "Structure-based design and synthesis of tricyclic IAP (Inhibitors of Apoptosis Proteins) inhibitors", Bioorg. Med. Chem. Lett., 24(7): 1820-1824 (2014).
Hon, et al., "Structural basis for the recognition of hydroxyproline in H1f-1 alpha by pVHL", Nature 417, Jun. 27, 2002, 975-978.
Huang, et al., (2016) "Drugging the undruggables: exploring the ubiquitin system for drug development." Cell Res 26(4):484-498.
Hughes, et al., (2017) "Molecular recognition of ternary complexes: a new dimension in the structure-guided design of chemical degraders." Essays Biochem 61 (5):505-516.
Ivan, M., et al., "HIFa Targeted for VHL-Mediated Destruction by Proline Hydroxylation: Implications for O2 Sensing", Science, vol. 292, No. 5516, pp. 464-468, 2001.
Jang, E.R. et al., "Targeted Degradation of Proteins by PROTACs," Curr. Protoc. Chem. Biol., 2010, vol. 2, No. 2, pp. 71-87.
Kim, K.S., "Discovery of tetrahydroisoquinoline-based bivalent heterodimeric IAP antagonists", Bioorg. Med. Chem. Lett. 24(21), 5022-5029 (2014).
Knott, Edward (1955). "Compounds containing sulphur chromophores. Part I. The action of bases on heterocyclic sulphide quarternary salts", Journal of The Chemical Society (resumed). 10.1039/jr9550000916. 949-954.
Kronke, et al, "Lenalidomide Causes Selective Degradation of IKZF1 and IKZF3 in Multiple Myeloma Cells", Science 343, 301-305 (2014).
Lai, A.C., et al., "Modular PROTAC Design for the Degradation of Oncogenic BCR-ABL", Angew Chem Int Ed Engl 55, 807-810 (2016).
Lai, et al., (2017) "Induced protein degradation: an emerging drug discovery paradigm." Nat Rev Drug Discov 16(2):101-114.
Lala, et al., "Role of nitric oxide in tumor progression: Lessons from experimental tumors", Cancer and Metastasis Reviews 17:91-106(1998).
Lebraud, H., et al., "Protein Degradation by In-Cell Self-Assembly of Proteolysis Targeting Chimeras", ACS Central Science, 2, 927-934 (2016).
Lee, et al., "Targeted Degradation of the Aryl Hydrocarbon Receptor by the PROTAC Approach: A Useful Chemical Genetic Tool", ChemBioChem vol. 8, Issue 17, pp. 2058-2062, Nov. 23, 2007.
Levine, et al., Targeting the androgen receptor with steroid conjugates, J. Med. Chem., vol. 57., No. 20. pp. 8224-8237, (2014).
Li, Yan, et al., "Single polymer-drug conjugate carrying two drugs for fixed-dose co-delivery", Medicinal Chemistry, 2014, vol. 4(10): 676-683.
Liu, K., et al., "Design and biological characterization of hybrid compounds of curcumin and thalidomide for multiple myeloma", Org. Biomol. Chem. 2013, 11, 4757-4763.
Lopez-Girona, A. et al., Cereblon is a direct protein target for immunomodulatory and antiproliferative activities of lenalidomide and pomalidomide, Leukemia 26: 2326-2335, 2012.
Lu, et al., "Hijacking the E3 ubiquitin ligase cereblon to efficiently target BRD4", Chem Biol 22(6), 2015, 755-763.
Lu, et al., "The myeloma drug lenalidomide promotes the cereblon-dependent destruction of ikaros proteins", Science 343, 305-309 (2014).
Maniaci C, et al. (2017) "Homo-PROTACs: bivalent small-molecule dimerizers of the VHL E3 ubiquitin ligase to induce self-degradation." Nat Commun 8(1):830 1-13.
Mannhold, R., et al., "IAP antagonists: promising candidates for cancer therapy", Drug Discov. Today, 15 (5-6), 210-219 (2010).
Medline Plus Trusted Health Information for You, www.nlm.nih.gov/medlineplus/cancer.html pp. 1-10, (2007).
Min, Jung-hyun, et al., "Structure of an HIV-1-alpha—pVHL complex: hydroxyproline recognition in signaling", Jun. 7, 2002, 296: 1886-1889.

(56) References Cited

OTHER PUBLICATIONS

Miyazaki, M., et al., "Discovery of DS-5272 as a promising candidate: a potent and orally active p53-MDM2 interaction inhibitor", Bioorg. Med. Chem. Lett. (2015) 23, 2360-2367.
Muller, G., et al., "Amino-Substituted Thalodomide Analogs: Potent Inhibitors of TNF-α Production", Bioorganic & Medicinal Chemistry Letters 9 (1999) 1625-1630.
Ndubaku, C, et al., "Antagonism of c-IAP and XIAP proteins is required for efficient induction of cell death by small-molecule IAP antagonists", ACS Chem Biol. Jul. 17, 2009;4(7):557-566.
Nekiesa, T.K., et al., "Chemical biology: Greasy tags for protein removal", Nature 487, 308-309 (2012).
Nekiesa, Targeted protein degradation by PROTACs. Pharmacology & Therapeutics 174, 138-144 (2017).
Nikolovska-Coleska, et al., "Interaction of a cyclic, Bivalent Smac Mimetic with the X-linked inhibitor of apoptosis protein", Biochemistry, 2008, 47(37), pp. 9811-9824.
Ohoka, N. et al. SNIPER(TACC3) induces cytoplasmic vacuolization and sensitizes cancer cells to Bortezomib. Cancer Sci. 108, 1032-1041 (2017).
Oost, T.K. et al., "Discovery of potent antagonists of the antiapoptotic protein XIAP for the treatment of cancer", Journal of Medicinal Chemistry 2004, 47, 4417-4426.
Ottis P, et al. (2017) "Assessing Different E3 Ligases for Small Molecule Induced Protein Ubiquitination and Degradation." *ACS Chem Biol* 12(10):2570-2578.
Ottis, et al., (2017) "Proteolysis-Targeting Chimeras: Induced Protein Degradation as a Therapeutic Strategy." *ACS Chem Biol* 12(4):892-898.
Perez, HL,"Discovery of potent heterodimeric antagonists of inhibitor of apoptosis proteins (IAPs) with sustained antitumor activity", J. Med. Chem. 58(3), 1556-1562 (2015).
Puppala, D. et al., "Development of an Aryl Hydrocarbon Receptor Antagonist Using the Proteolysis-Targeting chimeric Molecules Approach: A Potential Tool for Chemoprevention," Mol. Pharmacol., 2008, vol. 73, No. 4, pp. 1064-1071.
Raina, et al., (2017) "Targeted protein knockdown using small molecule degraders." *Curr Opin Chem Biol* 39:46-53.
Raina, K., et al., "PROTAC-induced BET protein degradation as a therapy for castration-resistant prostate cancer", Proc Natl Acad Sci USA 113, 7124-7129 (2016).
Remillard D, et al. (2017) "Degradation of the BAF Complex Factor BRD9 by Heterobifunctional Ligands." *Angew Chem Int Ed Engl* 56(21):5738-5743.
Rew, Y, et al., "Discovery of AM-7209, a potent and selective 4-amidobenzoic acid inhibitor of the MDM2-p53 interaction", J Med Chem. Dec. 26, 2014;57(24):10499-10511. doi: 10.1021/jm501550p. Epub Dec. 4, 2014. PubMed PMID: 25384157. (J. Med. Chem. (2014) 57, 10499-10511 Rew, et al.).
Rodriguez-Gonzalez, et al., "Targeting steroid hormone receptors for ubiquitination and degradation in breast and prostate cancer", Oncogene. 27(57), Dec. 4, 2008, 7201-7211.
Rotili D., et al., "Photoactivable peptides for identifying enzyme-substrate and protein-protein interactions", Chem Commun (Carob) 47(5), Feb. 2011, 1488-1490.
Ruchelman, A., et al., "Isosteric analogs of lenalidominde and pomalidomide: Synthesis and biological activity", Bioorganic & Medicinal Chemistry Letters 23 (2013) 360-365.
Sakamoto, et al., "Development of Protacs to target cancer-promoting proteins for ubiquitination and degradation", Mol Cell Proteomics. 2(12), Dec. 2003, 1350-1358.
Sakamoto, et al., "Protacs: chimeric molecules that target proteins to the Skp 1-Cullin-F box complex for ubiquitination and degradation", Proc Natl Acad Sci U S A.98(15), Jul. 17, 2001, 8554-8559.
Salami, J. & Crews, C. M. Waste disposal—An attractive strategy for cancer therapy. Science 355, 1163-1167 (2017).
Schiedel, M., et al., "Chemically Induced Degradation of Sirtuin 2 (Sirt2) by a Proteolysis Targeting Chimera (PROTAC) Based on Sirtuin Rearranging Ligands (SirReals)", J Med Chem. (2017), 61:482-491.

Schneektloth, et al., "Chemical Genetic Control of Protein Levels: Selective in Vivo Targeted Degradation", J Am Chem Soc. 126(12), Mar. 31, 2004, 3748-3754.
Schneekloth, et al., Targeted intracellular protein degradation induced by a small molecule: En route to chemical proteomics, Bioorg. Med. Chem. Lett. 18 (2008) 5904-5908.
Smith, et al., "Targeted Intracellular Protein Degradation Induced by a Small Molecule: En Route to Ghemical Proteomics", Bioorg Med Chem Lett. 18(22), Nov. 15, 2008, 5904-5908.
Stewart, Scott G., et al., "Efforts toward elucidating Thalidomide's molecular target: An Expedient Synthesis of the first Thalidomide Biotin Analogue" Org. Biomol., Chem., 2010, 8, 4059-4062.
STN transcript excerpt Nov. 24, 2017 "Compounds containing sulfur Chromophores v. Complex cyanines".
Stoppler, Melissa Conrad., Endometriosis [online], "Endometriosis Definition and Facts" URL http://www.medicinenet.com/endometriosis/article.htm, retrieved on Apr. 5, 2017.
Stoppler, Melissa Conrad., Endometriosis [online], "What about surgery for Endometriosis?" URL http://www.medicinenet.com/endometriosis/article.htm, retrieved on Apr. 5, 2017.
Sun, D, et al., "Discovery of AMG 232, a potent, selective, and orally bioavailable MDM2-p53 inhibitor in clinical development", J Med Chem. Feb. 27, 2014;57(4):1454-72. doi: 10.1021/jm401753e. Epub Feb. 5, 2014. PubMed PMID: 24456472.
Sun, et al., "Potent bivalent Smac mimetics: effect of the linker on binding to inhibitor apoptosis proteins (IAPs) and anticancer activity", J. Med. Chem. 53, 3306-3318 (2011).
Toure, et al., (2016) "Small-Molecule PROTACS: New Approaches to Protein Degradation." *Angew Chem Int Ed Engl* 55(6):1966-1973.
Turk, B. E., "Binding of thalidomide to alpha1-acid glycoprotein may be involved in its inhibition of tumor necrosis factor alpha production", Proc. Natl. Acad. Sci. U.S.A. 1996, 93, 7552-7556.
Vamos M., et al., "Expedient synthesis of highly potent antagonists of inhibitor of apoptosis proteins (IAPs) with unique selectivity for ML-IAP", ACS Chem. Biol., 8(4), 725-732 (2013).
Van Molle, et al., "Dissecting fragment-based lead discovery at the von Hippel-Lindau protein:hypoxia inducible factor 1a protein-protein interface", Chem Biol. 19(10), Oct. 26, 2012, 1300-1312.
Vassilev, et al., "In vivo activation of the p53 pathway by small-molecule antagonists of MDM2", Science 303, Feb. 6, 2004, 844-848.
Vazquez, A. et al., "The genetics of the p53 pathway, apoptosis and cancer therapy", Nat. Rev. Drug. Dis., 7, 979-982 (2008).
Vu, B. et al. "Discovery of RG7112: a small-molecule MDM2 inhibitor in clinical development", ACS Med. Chem. Lett. (2013)4, 466-469.
Wang J, et al., "Discovery of novel second mitochondrial-derived activator of caspase mimetics as selective inhibitor or apoptosis protein inhibitors", J. Pharmacol. Exp. Ther., 349(2): 319-29 (2014).
Wang, S., et al. "Small-molecule inhibitors of the MDM2-p53 protein-protein interaction (MDM2 inhibitors) in clinical trials for cancer treatment", J. Med. Chem. (2015) 58, 1038-1052.
Wang, S., et al. "Temporal activation of p53 by a specific MDM2 inhibitor is selectively toxic to tumors and leads to complete tumor growth inhabitation", PNAS USA (2008) 105, 3933-3938.
Winter, et al., "Phthalimide Conjugation as a strategy for in vivo target protein degradation", Science, 2015 vol. 348 (6241), pp. 1376-1381 [Pub online: May 21, 2015].
Zengerle, et al., "Selective Small Molecule Induced Degradation of the BET Bromodomain Protein BRD4" ACS Chemical Biology, Jun. 2, 2015, vol. 10, pp. 1770-1777.
ZHANG B.et al., "Small-molecule MDM2-p53 inhibitors: recent advances", Future Med. Chem. (2015) 7, 631-645.
Zhang, D. et al., "Targeted Degradation of Proteins by Small Molecules: A Novel Tool for Functional Proteomics," comb Chem. High Throughput Screen., 2004, vol. 7, No. 7, pp. 689-697.
International Search Report and Written Opinion for PCT/US2020/042645 dated Dec. 8, 2020.
Chu, Ting-Ting, et al., Specific Knockdown of Endogenous Tau Protein by Peptide-Directed Ubiquitin-Proteasome Degradation, Cell Chem Biol., Apr. 21, 2016, 23(4):453-461, doi: 10.1016/j.chembiol.2016.02.016.

(56) References Cited

OTHER PUBLICATIONS

Bohnert, et al., Plasma Protein Binding: From Discovery to Development, Journal of Pharmaceutical Sciences, vol. 102, No. 9, Sep. 2013, 2953-2994.

Gadhave, et al., The ubiquitin proteasomal system: a potential target for the management of Alzheimer's disease, J. Cell. Mol. Med. vol. 20, No. 7, 2016 pp. 1392-1407 (Jan. 17, 2016).

Harrington, et al., Cellular Models of Aggregation-dependent Template-directed Proteolysis to Characterize Tau Aggregation Inhibitors for Treatment of Alzheimer Disease, The Journal of Biological Chemistry vol. 290, No. 17, pp. 10862-10875, Apr. 24, 2015.

Li, et al., Thiadiazole—a Promising Structure in Medicinal Chemistry, ChemMedChem 2013, 8, 27-41 (Jan. 2013).

Pickhardt, et al., Identification of small molecule inhibitors of Tau aggregation by targeting monomeric Tau as a potential therapeutic approach for Tauopathies, Curr Alzheimer Res. 2015 ; 12(9):814-828, (Author manuscript; available in PMC Aug. 8, 2016).

Rapoport, et al. (2002) Tau is essential to β-amyloid-induced neurotoxicity, Apr. 30, 2002, PNAS, vol. 99, No. 9, 6364-6369.

Seo, et al., A Smart Near-Infrared Fluorescence Probe for Selective Detection of Tau Fibrils in Alzheimer's Disease, ACS Chem. Neurosci. 2016, 7, 1474-1481, Aug. 30, 2016.

Wood, et al., [11C]PBB3—a new PET ligand that identifies tau pathology in the brains of patients with AD, Nature Reviews Neurology 9, 599 (2013); published online Oct. 22, 2013; doi:10.1038/nrneurol.2013.216.

\* cited by examiner

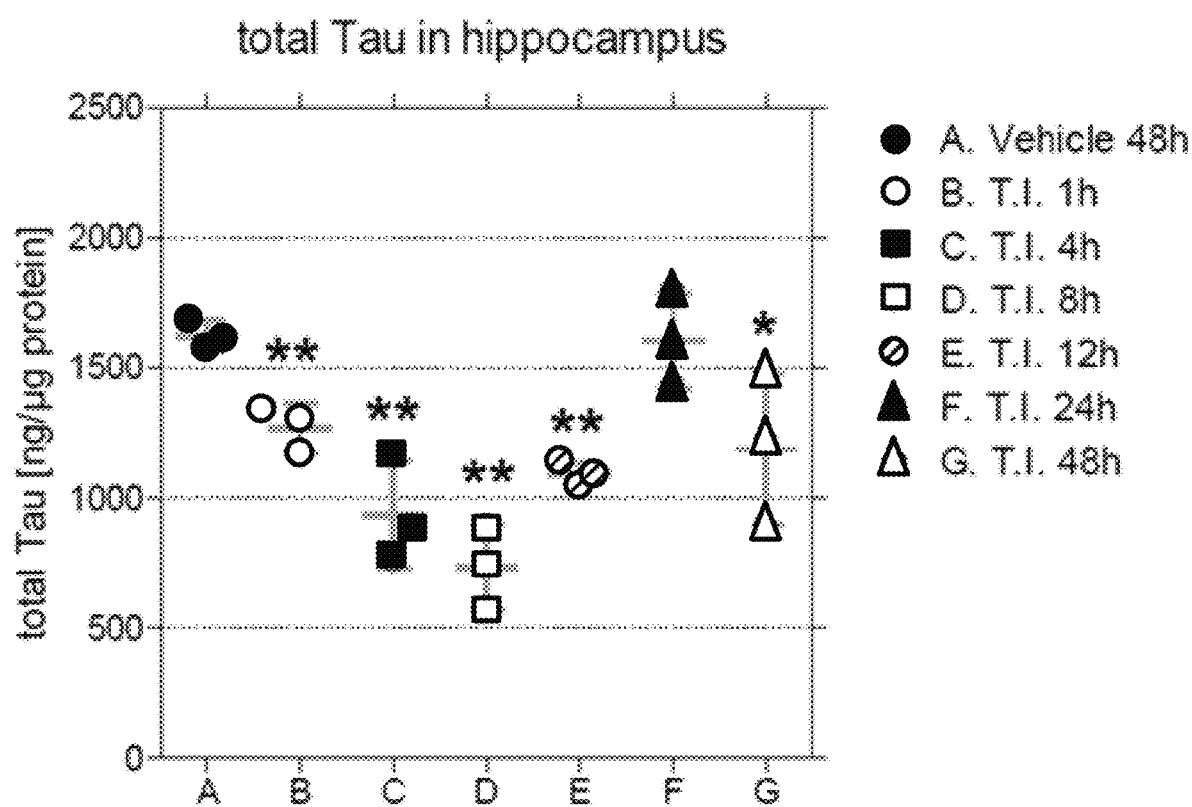

TAU-PROTEIN TARGETING PROTACS AND ASSOCIATED METHODS OF USE

CROSS-REFERENCE TO RELATED APPLICATIONS

The present disclosure claims priority to U.S. Provisional Application No. 62/415,830, filed on 1 Nov. 2016, which is incorporated herein by reference in its entirety.

INCORPORATION BY REFERENCE

U.S. patent application Ser. No. 15/230,354, filed on Aug. 5, 2016; and U.S. Patent Application Ser. No. 62/406,888, filed on Oct. 11, 2016; and U.S. patent application Ser. No. 14/686,640, filed on Apr. 14, 2015, published as U.S. Patent Application Publication No. 2015/0291562; and U.S. patent application Ser. No. 14/792,414, filed on Jul. 6, 2015, published as U.S. Patent Application Publication No. 2016/0058872; and U.S. patent application Ser. No. 14/371,956, filed on Jul. 11, 2014, published as U.S. Patent Application Publication No. 2014/0356322; and U.S. patent application Ser. No. 15/074,820, filed on Mar. 18, 2016, published as U.S. Patent Application Publication No. 2016/0272639, are incorporated herein by reference in their entirety. Furthermore, all references cited herein are incorporated by reference herein in their entirety.

BACKGROUND

1. Field of the Discovery

The present description relates to bifunctional compounds, which are useful for modifying intracellular ubiquitination and subsequent degradation of target polypeptides and proteins, in particular, Tau protein. Compounds of the present disclosure place target protein/polypeptide in proximity to a ubiquitin ligase to effect the ubiquitination and degradation (and inhibition) of Tau protein.

2. Background Information

Most small molecule drugs bind enzymes or receptors in tight and well-defined pockets. On the other hand, protein-protein interactions are notoriously difficult to target using small molecules due to their large contact surfaces and the shallow grooves or flat interfaces involved. E3 ubiquitin ligases (of which hundreds are known in humans) confer substrate specificity for ubiquitination, and therefore, are more attractive therapeutic targets than general proteasome inhibitors due to their specificity for certain protein substrates. The development of ligands of E3 ligases has proven challenging, in part due to the fact that they must disrupt protein-protein interactions. However, recent developments have provided specific ligands which bind to these ligases. For example, since the discovery of nutlins, the first small molecule E3 ligase inhibitors, additional compounds have been reported that target E3 ligases, but the field remains underdeveloped.

One E3 ligase with exciting therapeutic potential is the von Hippel-Lindau (VHL) tumor suppressor, the substrate recognition subunit of the E3 ligase complex VCB, which also consists of elongins B and C, Cul2 and Rbx1. The primary substrate of VHL is Hypoxia Inducible Factor 1α (HIF-1α), a transcription factor that upregulates genes such as the pro-angiogenic growth factor VEGF and the red blood cell inducing cytokine erythropoietin in response to low oxygen levels. The first small molecule ligands of Von Hippel Lindau (VHL) to the substrate recognition subunit of the E3 ligase were generated, and crystal structures were obtained confirming that the compound mimics the binding mode of the transcription factor HIF-1α, the major substrate of VHL.

Cereblon is a protein that in humans is encoded by the CRBN gene. CRBN orthologs are highly conserved from plants to humans, which underscores its physiological importance. Cereblon forms an E3 ubiquitin ligase complex with damaged DNA binding protein 1 (DDB1), Cullin-4A (CUL4A), and regulator of cullins 1 (ROC1). This complex ubiquitinates a number of other proteins. Through a mechanism which has not been completely elucidated, cereblon ubiquitination of target proteins results in increased levels of fibroblast growth factor 8 (FGF8) and fibroblast growth factor 10 (FGF10). FGF8 in turn regulates a number of developmental processes, such as limb and auditory vesicle formation. The net result is that this ubiquitin ligase complex is important for limb outgrowth in embryos. In the absence of cereblon, DDB1 forms a complex with DDB2 that functions as a DNA damage-binding protein.

The Tau protein is an abundant protein in the central nervous system primarily found in neuronal cells, although Tau is expressed at lower levels in other cells of the central nervous system. In a healthy neuron, Tau binds to microtubules and regulates microtubule stability, which is critical for axonal outgrowth and neuronal plasticity. When pathologically altered, Tau molecules are not able to stabilize microtubules and are prone to form insoluble aggregates. Once the Tau protein forms insoluble aggregates in cells, cellular dysfunction occurs, axonal transport is compromised, and neuronal loss ensues. Accumulation of abnormal Tau aggregates in neurons is an important pathological signature in multiple neurodegenerative disorders including Alzheimer's disease. In certain pathological conditions, Tau aggregation results in paired-helical filaments (PHFs), straight filaments (SFs) and/or neurofibrillary tangles (NFTs). The accumulation of PHFs and NFTs in neurons directly correlates with microtubule dysfunction and neuronal degeneration. Neurons containing tau PHFs, SFs, and or NFTs activate diverse cellular mechanisms to try and rid the cell of the abnormal protein aggregates.

More recent studies suggest that, instead of the large insoluble filaments, soluble Tau oligomers might play a more critical role in the onset and progression of disease prior to the development of PHF- or NFT-induced neurotoxicity. Oligomeric species of Tau may act as seeds for the aggregation of native Tau, thereby promoting neurotoxic Tau aggregation. Accumulating evidence has suggested that Tau aggregates can be transmitted from one cell to another by propagating in a prion-like manner.

Tau alteration and dysfunction and extensive neuron loss has long been associated with several neurodegenerative diseases now collectively called tauopathies.

The term "tauopathy" or "tauopathies" refers herein to a class of neurodegenerative diseases associated with the pathological aggregation of Tau protein in neurofibrillary or gliofibrillary tangles in the human brain. Examples of tauopathies include but are not limited to AD, Down's syndrome, frontotemporal lobular dementia (FTLD), cotricobasal degeneration (CBD) and progressive supranuclear palsy (PSP)

Due to its pathological significance in multiple neurodegenerative diseases, Tau is an important therapeutic target. Preventing Tau aggregation becomes a potential strategy to treat neurodegenerative disorders associated with Tau. So far, great effort has been made to identify molecular mechanisms of Tau aggregation and find therapeutics to halt the progression of neurodegeneration.

Tau aggregation inhibitors which demonstrated promising pre-clinical data have proven ineffective in recent clinical trials for the treatment of various tauopathies. Therefore, a need exists in the art for effective treatments of diseases and conditions that are related to the aggregation of Tau in neurodegenerative disorders such as tauopathies.

SUMMARY

The present disclosure describes bifunctional compounds, including compositions comprising the same, which function to recruit endogenous proteins to an E3 ubiquitin ligase for ubiquitination and subsequent degradation, and methods of using the same. In particular, the present disclosure provides bifunctional or proteolysis targeting chimeric (PROTAC) compounds, which find utility as modulators of targeted ubiquitination and degradation of Tau protein aggregates. In addition, the description provides methods of using an effective amount of the compounds as described herein for the treatment or amelioration of disease conditions due to accumulation or aggregation of Tau proteins such as tauopathies. These diseases or disorders include but are not limited to neurological or neurodegenerative disorders.

Thus, in one aspect, the disclosure provides compounds which function to recruit endogenous proteins, e.g., Tau, to E3 Ubiquitin Ligase for ubiquintination and degradation.

In any of the embodiments, the compounds have the following general structures

PTM-L-ULM

In certain embodiments, the compounds have the following general structures (A)

PTM-L-VLM (A)

In certain embodiments, the compounds have the following general structures (B)

PTM-L-CLM (B)

wherein, PTM represents protein targeting moiety, ULM represents E3 ubiquitin ligase targeting moiety including but not limited to VLM (VHL ligase-binding moiety) and CLM (cereblon ligase-binding moiety) and L represents a linker, e.g., a bond or a chemical linker moiety. As would be understood by the skilled artisan, the bifunctional compounds as described herein can be synthesized such that the number and position of the respective functional moieties can be varied as desired.

In certain embodiments, the PTMs in structure (A) are the ligands that bind to Tau as well as VHL E3 ubiquitin ligase.

In certain embodiments, the PTMs in structure (B) are the ligands that bind to Tau as well as CLM E3 ubiquitin ligase.

In certain embodiments, the compounds as described herein comprise multiple ULMs, multiple PTMs, multiple chemical linkers or a combination thereof. In an additional aspect, the description provides therapeutic compositions comprising an effective amount of a compound as described herein or salt form thereof, and a pharmaceutically acceptable carrier. The therapeutic compositions modulate protein degradation in a patient or subject, for example, an animal such as a human, and can be used for treating or ameliorating disease states or conditions which are modulated through the degraded protein. In certain embodiments, the therapeutic compositions as described herein may be used to effectuate the degradation of proteins of interest for the treatment or amelioration of a disease, e.g., neuronal disease. In yet another aspect, the present disclosure provides a method of ubiquitinating/degrading a target protein in a cell. In certain embodiments, the method comprises administering a bifunctional compound as described herein comprising an ULM and a PTM, which may be linked through a linker moiety, as otherwise described herein, wherein the ULM is coupled to the PTM and wherein the ULM recognizes a ubiquitin pathway protein e.g., an ubiquitin ligase, such as an E3 ubiquitin ligase more preferably VLM and CLM and the PTM recognizes the target protein (TBM) such that degradation of the target protein will occur when the target protein (e.g., Tau) is placed in proximity to the ubiquitin ligase, thus resulting in degradation of the target protein, inhibition of its effects and the control of protein levels. In another aspect, the target protein is Tau. The present disclosure provides treatment of a disease state or condition through control of protein levels, i.e. by lowering the level of that protein (e.g., Tau protein) in the cells of a patient via degradation.

In particular, PTM are molecules that bind to Tau protein (TBM), and ULM are molecules that bind to VHL E3 ubiquitin ligase and/or to CLM E3 ubiquitin ligase with the following general structures:

TBM-L-VLM/CLM

The PTM (protein-targeting moiety) of the PROTACs of current disclosure is represented by the general formulas I, II, III, IV, V, VI, VII, VIII, XI, X, and XI:

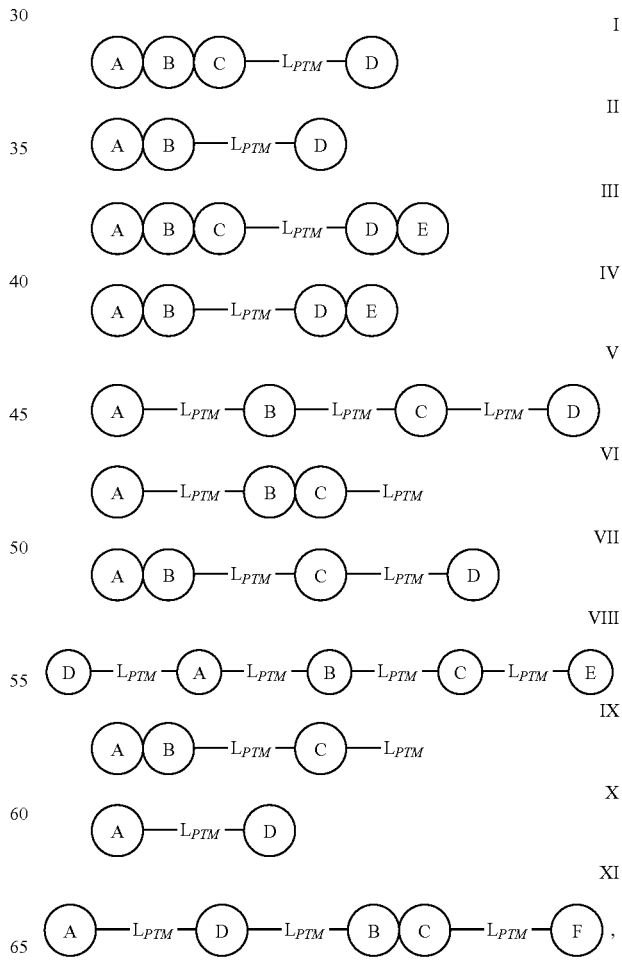

wherein:
A, B, C, D, E, and F are each independently selected from an optionally substituted 5- or 6-membered aryl or heteroaryl ring, an optionally substituted 4- to 7-membered cycloalkyl or a heterocycloalkyl, where contact between circles indicates ring fusion; and $L_{PTM}$ is selected from a bond, an alkyl, an alkenyl or an alkynyl, optionally interrupted by one or more rings (i.e., cycloalkyl, heterocycloalkyl, aryl or heteroaryl), or one or more functional groups which could include —O—, —S—, —NR$^1_{PTM}$— (where R$^1_{PTM}$ is selected from H or alkyl), —N=N—, —S(O)—, —SO$_2$—, —C(O)—, —NHC(O)—, —C(O)NH—, —NHSO$_2$—, —NHC(O)NH—, —NHC(O)O—, —OC(O)NH—, wherein the said functional group can be optionally located at either end of the linker (i.e., directly adjacent to the A, B, C, D, E, or F rings).

The above mentioned aryl and heteroaryl rings can be optionally substituted with 1-3 substituents each independently selected from alkyl, alkenyl, haloalkyl, halogen, hydroxyl, alkoxy, fluoroalkoxy, amino, alkylamino, dialkylamino, acylamino, trifluormethyl, and cyano, wherein the said alkyl and alkenyl groups can be further substituted.

In any aspect or embodiment described herein, at least one of A, B, C, F, or a combination thereof is selected from optionally substituted 5- or 6-membered aryl or heteroaryl rings.

In certain embodiments of the current disclosure, the PTM is represented by Formula I and/or II, where A, B and C are 5- or 6-membered fused aryl or heteroaryl rings, $L_{PTM}$ is selected from a bond or an alkyl, and D is selected from a 6-membered aryl, heteroaryl or heterocycloalkyl, wherein A, B, C and D are optionally substituted with alkyl, haloalkyl, halogen, hydroxyl, alkoxy, amino, alkylamino, dialkylamino, trifluoromethyl, or cyano.

In other embodiments, the PTM is represented by Formula III and/or IV, wherein A, B and C are 5- or 6-membered fused aryl or heteroaryl rings, $L_{PTM}$ is selected from a bond or an alkyl, and D and E are 5- or 6-membered fused aryl or heteroaryl rings, and wherein A, B, C, D and E are optionally substituted with alkyl, haloalkyl, halogen, hydroxyl, alkoxy, amino, alkylamino, dialkylamino, trifluoromethyl, or cyano.

In certain other embodiments of the current disclosure, the PTM is represented by Formula I, wherein A is a phenyl or a 6-membered heteroaryl ring, B is a 5-membered heteroaryl ring, C is a phenyl or a 6-membered heteroaryl ring, $L_{PTM}$ is a bond, and D is a 6-membered heteroaryl or a 6-membered heterocycloalkyl ring, wherein each A, B, C and D is optionally independently substituted with alkyl, haloalkyl, halogen, hydroxyl, alkoxy, amino, dialkylamino, trifluoromethyl, or cyano, with the proviso that a nitrogen atom of any of the A, B, C and D rings is not directly connected to a heteroatom or to a carbon atom of the $L_{PTM}$, to which another heteroatom is directly attached.

It will be understood that the general structures are exemplary and the respective moieties can be arranged spatially in any desired order, number or configuration.

In further embodiments, the description provides a bifunctional compound having a structure selected from the group consisting of Compounds 1-330 (e.g., a compound selected from Tables 1 and 2), a salt, a polymorph, and a prodrug thereof.

In further embodiments, the description provides a bifunctional compound having a structure selected from the Table 1 or Table 2 (e.g., a chemical structure selected from Compounds 1-330), a salt, a polymorph, and a prodrug thereof.

In another aspect, the description provides compositions comprising compounds as described herein, and a pharmaceutically acceptable carrier. In certain embodiments, the compositions are therapeutic or pharmaceutical compositions comprising an effective amount of a compound as described herein and a pharmaceutically acceptable carrier. In certain embodiments, the therapeutic or pharmaceutical compositions comprise an additional biologically active agent, e.g., an agent effective for the treatment of neuronal disease.

In any of the aspects or embodiments described herein, the therapeutic compositions comprising compounds described herein can be in any suitable dosage form, e.g., solid, or liquid, and configured to be delivered by any suitable route, e.g., oral, parenteral, intravenous, intraperitoneal, subcutaneous, intramuscular, etc.

In another aspect, the description provides methods of modulating Tau protein, their ubiquitination and the subsequent degradation in a subject, e.g., a cell, a tissue, mammal, or human patient, the method comprising administering an effective amount of a compound as described herein or a composition comprising an effective amount of the same to a subject, wherein the compound or composition comprising the same is effective in modulating Tau ubquitination and degradation in the subject.

In yet another aspect, the description provides methods of treating or ameliorating a symptom of a disease related to TAU activity in a subject, e.g., a cell, a tissue, mammal, or human patient, the method comprising administering an effective amount of a compound as described herein or a composition comprising an effective amount of the same to a subject in need thereof, wherein the compound or composition comprising the same is effective in treating or ameliorating a symptom of a disease related to TAU activity in the subject. In certain embodiments, the disease to be treated is neurological or neurodegenerative disease, e.g. Alzheimer, Parkinson, Dementia etc.

In a preferred embodiment, the subject is a human.

In an additional aspect, the description provides methods for identifying the effects of the degradation of proteins of interest in a biological system using compounds according to the present disclosure.

Where applicable or not specifically disclaimed, any one of the embodiments described herein are contemplated to be able to combine with any other one or more embodiments, even though the embodiments are described under different aspects of the disclosure. As such, the preceding general areas of utility are given by way of example only and are not intended to be limiting on the scope of the present disclosure and appended claims. Additional objects and advantages associated with the compositions, methods, and processes of the present disclosure will be appreciated by one of ordinary skill in the art in light of the instant claims, description, and examples. For example, the various aspects and embodiments of the disclosure may be utilized in numerous combinations, all of which are expressly contemplated by the present description. These additional advantages, objects, and embodiments are expressly included within the scope of the present disclosure. The publications and other materials used herein to illuminate the background of the disclosure, and in particular cases, to provide additional details respecting the practice, are incorporated by reference.

BRIEF DESCRIPTION OF THE DRAWINGS

The accompanying drawings, which are incorporated into and form a part of the specification, illustrate several embodiments of the present disclosure and, together with the description, serve to explain the principles of the disclosure. The drawings are only for the purpose of illustrating an embodiment of the disclosure and are not to be construed as limiting the disclosure. Further objects, features and advantages of the disclosure will become apparent from the following detailed description taken in conjunction with the accompanying FIGURES showing illustrative embodiments of the disclosure, in which:

The FIGURE shows total tau levels in hippocampal homogenates. Data are displayed as scattered dot blot. Statistically significant differences between the test item (TI) treated groups versus the vehicle control group according to One-way ANOVA followed by Dunneett's Multiple Comparison Test are indicated by asterisk ** $p<0.01$, * $p<0.05$.

DETAILED DESCRIPTION

The following is a detailed description provided to aid those skilled in the art in practicing the present disclosure. Those of ordinary skill in the art may make modifications and variations in the embodiments described herein without departing from the spirit or scope of the present disclosure. All publications, patent applications, patents, figures and other references mentioned herein are expressly incorporated by reference in their entirety.

The present description relates to the surprising and unexpected discovery that an E3 ubiquitin ligase protein can ubiquitinate a target protein once the E3 ubiquitin ligase protein and the target protein are brought into proximity by a chimeric construct (e.g., PROTAC) as described herein, which binds the E3 ubiquitin ligase protein (e.g., VHL and cereblon) and the target protein e.g., TAU. Accordingly, the present description provides compounds, compositions comprising the same and associated methods of use for ubiquitination and degradation of a chosen target protein.

The following terms are used to describe the present disclosure. In instances where a term is not specifically defined herein, that term is given an art-recognized meaning by those of ordinary skill applying that term in context to its use in describing the present disclosure.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the disclosure. The upper and lower limits of these smaller ranges may independently be included in the smaller ranges is also encompassed within the disclosure, subject to any specifically excluded limit in the stated range. Where the stated range includes one or both of the limits, ranges excluding either both of those included limits are also included in the disclosure.

The articles "a" and "an" as used herein and in the appended claims are used herein to refer to one or to more than one (i.e., to at least one) of the grammatical object of the article unless the context clearly indicates otherwise. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a nonlimiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, in certain methods described herein that include more than one step or act, the order of the steps or acts of the method is not necessarily limited to the order in which the steps or acts of the method are recited unless the context indicates otherwise.

The term "compound", as used herein, unless otherwise indicated, refers to any specific chemical compound disclosed herein and includes tautomers, regioisomers, geometric isomers, and where applicable, stereoisomers, including optical isomers (enantiomers) and other stereoisomers (diastereomers) thereof, as well as pharmaceutically acceptable salts and derivatives (including prodrug forms) thereof where applicable, in context. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds. The term also refers, in context to prodrug forms of compounds which have been modified to facilitate the administration and delivery of compounds to a site of activity. It is noted that in describing the present compounds, numerous substituents and variables associated with same, among others, are described. It is understood by those of ordinary skill that molecules which are described herein are stable compounds as generally described hereunder.

When the bond ⫽ is shown, both a double bond and single bond are represented within the context of the compound shown.

The term "patient" or "subject" is used throughout the specification to describe an animal, preferably a human or a domesticated animal, to whom treatment, including prophylactic treatment, with the compositions according to the present disclosure is provided. For treatment of those infections, conditions or disease states which are specific for a specific animal such as a human patient, the term patient refers to that specific animal, including a domesticated animal such as a dog or cat or a farm animal such as a horse, cow, sheep, etc. In general, in the present disclosure, the term patient refers to a human patient unless otherwise stated or implied from the context of the use of the term.

The term "effective" is used to describe an amount of a compound, composition or component which, when used within the context of its intended use, effects an intended result. The term effective subsumes all other effective amount or effective concentration terms, which are otherwise described or used in the present application.

The term "Ubiquitin Ligase" refers to a family of proteins that facilitate the transfer of ubiquitin to a specific substrate protein, targeting the substrate protein for degradation. For example, cereblon is an E3 Ubiquitin Ligase protein that alone or in combination with an E2 ubiquitin-conjugating enzyme causes the attachment of ubiquitin to a lysine on a target protein, and subsequently targets the specific protein substrates for degradation by the proteasome. Thus, E3 ubiquitin ligase alone or in complex with an E2 ubiquitin conjugating enzyme is responsible for the transfer of ubiquitin to targeted proteins. In general, the ubiquitin ligase is involved in polyubiquitination such that a second ubiquitin is attached to the first; a third is attached to the second, and so forth. Polyubiquitination marks proteins for degradation by the proteasome. However, there are some ubiquitination events that are limited to mono-ubiquitination, in which only a single ubiquitin is added by the ubiquitin ligase to a substrate molecule. Mono-ubiquitinated proteins are not targeted to the proteasome for degradation, but may instead be altered in their cellular location or function, for example, via binding other proteins that have domains capable of binding ubiquitin. Further complicating matters, different lysines on ubiquitin can be targeted by an E3 to make chains. The most common lysine is Lys48 on the ubiquitin chain. This is the lysine used to make polyubiquitin, which is recognized by the proteasome.

The term "protein target moiety" or PTM is used to describe a small molecule which binds to a target protein or other protein or polypeptide of interest and places/presents that protein or polypeptide in proximity to an ubiquitin ligase such that degradation of the protein or polypeptide by ubiquitin ligase may occur. Non-limiting examples of small molecule target protein binding moieties include compounds targeting Tau protein.

The term "target protein" is used to describe a protein or polypeptide, which is a target for binding to a compound according to the present disclosure and degradation by ubiquitin ligase hereunder. Such small molecule target protein binding moieties also include pharmaceutically acceptable salts, enantiomers, solvates and polymorphs of these compositions, as well as other small molecules that may target a protein of interest. These binding moieties are linked to ULM groups through linker groups L.

Tau protein target may be used in screens that identify compound moieties which bind to the protein and by incorporation of the moiety into compounds according to the present disclosure, the level of activity of the protein may be altered for therapeutic end result.

The term "disease state or condition" is used to describe any disease state or condition wherein protein dysregulation (i.e., the amount of protein expressed in a patient is elevated) occurs and where degradation of Tau protein in a patient may provide beneficial therapy or relief of symptoms to a patient in need thereof. In certain instances, the disease state or condition may be cured.

Disease states or conditions which may be treated using compounds according to the present disclosure include neuronal disease, for example, neurodegeneration, Huntington's disease and muscular dystrophy, Parkinson's disease, Alzheimer's disease, Batten disease, Injuries to the spinal cord and brain, Seizure disorders, epilepsy, brain tumors, meningitis, autoimmune diseases such as multiple sclerosis, Neurofibromatosis, Depression, Amyotrophic Lateral Sclerosis, Arteriovenous Malformation, Brain Aneurysm, Dural Arteriovenous Fistulae, Headache, Memory Disorders, Peripheral Neuropathy, Post-Herpetic Neuralgia, Spinal Cord Tumor, Stroke.

The term "neurological disorder" or "neurological disorders", as used herein, refers to any disorder, disease, and/or syndrome due to or resulting from neurologic, psychiatric, psychological, and/or cerebrovascular symptomology or origin. The term "neurological disorder" or "neurological disorders", as used herein, also refers to diseases, disorder or condition of the brain and nervous system or psychiatric disorders or conditions. Neurological disorders include, but are not limited to Absence of the Septum Pellucidum, Acquired Epileptiform Aphasia, Acute Disseminated Encephalomyelitis, ADHD, Adie's Pupil, Adie's Syndrome, Adrenoleukodystrophy, Agenesis of the Corpus Callosum, Agnosia, Aicardi Syndrome, AIDS-Neurological Complications, Alexander Disease, Alpers' Disease, Alternating Hemiplegia, Alzheimer's Disease, Amyotrophic Lateral Sclerosis, Anencephaly, Aneurysm, Angelman Syndrome, Angiomatosis, Anoxia, Aphasia, Apraxia, Arachnoid Cysts, Arachnoiditis, Arnold-Chiari Malformation, Arteriovenous Malformation, Asperger Syndrome, Ataxia, Ataxia, Telangiectasia, Ataxias and Cerebellar/Spinocerebellar Degeneration, Attention Deficit-Hyperactivity Disorder, Autism, Autonomic Dysfunction, Back Pain, Barth Syndrome Batten Disease, Becker's Myotonia, Behcet's Disease, Bell's Palsy, Benign Essential Blepharospasm, Benign Focal Amyotrophy, Benign Intracranial Hypertension, Bernhardt-Roth Syndrome, Binswanger's Disease, Blepharospasm, Bloch-Sulzberger Syndrome, Brachial Plexus Birth Injuries, Brachial Plexus Injuries, Bradbury-Eggleston Syndrome, Brain and Spinal Tumors, Brain Aneurysm, Brain Injury, Brown-Sequard Syndrome, Bulbospinal Muscular Atrophy, Canavan Disease, Carpal Tunnel Syndrome Causalgia, Cavernomas, Cavernous Angioma, Cavernous Malformation, Central Cervical Cord Syndrome, Central Cord Syndrome, Central Pain Syndrome, Cephalic Disorders, Cerebellar Degeneration, Cerebellar Hypoplasia, Cerebral Aneurysm, Cerebral Arteriosclerosis, Cerebral Atrophy, Cerebral Beriberi, Cerebral Gigantism, Cerebral Hypoxia, Cerebral Patsy, Cerebro-Oculo-Facio-Skeletal Syndrome, Charcot-Marie-Tooth Disease, Chiari Malformation, Chorea, Choreoacanthocytosis, Chronic Inflammatory Demyelinating Polyneuropathy (CIDP), Chronic Orthostatic Intolerance, Chronic Pain Cockayne Syndrome Type II, Coffin Lowry Syndrome, COFS, Colpocephaly, Coma and Persistent Vegetative State, Complex Regional Pain Syndrome, Congenital Facial Diplegia, Congenital Myasthenia, Congenital Myopathy, Congenital Vascular Cavernous, Malformations, Corticobasal Degeneration, Cranial Arteritis, Craniosynostosis, Creutzfeldt-Jakob Disease, Cumulative Trauma Disorders, Cushing's Syndrome, Cytomegalic Inclusion Body Disease, Cytomegalovirus Infection, Dancing Eyes-Dancing Feet Syndrome, Dandy-Walker Syndrome, Dawson Disease, De Morsier's Syndrome, Deep Brain Stimulation for Parkinson's Disease, Dejerine-Klumpke Palsy, Dementia, Dementia-Multi-Infarct, Dementia-Semantic, Dementia-Subcortical, Dementia With Lewy Bodies, Dentate Cerebellar Ataxia, Dentatorubral Atrophy, Dermatomyositis, Developmental Dyspraxia, Devic's Syndrome, Diabetic Neuropathy, Diffuse Sclerosis, Dysautonomia, Dysgraphia, Dyslexia, Dysphagia, Dyspraxia, Dyssynergia Cerebellaris, Myoclonica, Dyssynergia Cerebellaris Progressiva, Dystonias, Early Infantile Epileptic, Encephalopathy, Empty Sella Syndrome, Encephalitis Lethargica, Encephaloceles, Encephalopathy, Encephalotrigeminal Angiomatosis, Epilepsy, Erb-Duchenne and Dejerine-Klumpke Palsies, Erb's Palsy, Fabry's Disease, Fahr's Syndrome, Fainting, Familial Dysautonomia, Familial Hemangioma, Familial Idiopathic Basal Ganglia, Calcification, Familial Periodic Paralyses, Familial Spastic Paralysis, Febrile Seizures, Fisher Syndrome, Floppy Infant Syndrome, Friedreich's Ataxia, Frontotemporal, Dementia, Gaucher's Disease, Gerstmann's Syndrome, Gerstmann-Straussler-Scheinker, Disease, Giant Cell Arteritis, Giant Cell Inclusion Disease, Globoid Cell Leukodystrophy, Glossopharyngeal Neuralgia, Guillain-Barre Syndrome, Hallervorden-Spatz Disease, Head Injury, Headache, Hemicrania Continua, Hemifacial Spasm, Hemiplegia Alterans, Hereditary Neuropathies, Hereditary Spastic Paraplegia, Heredopathia Atactica Polyneuritiformis, Herpes Zoster, Herpes Zoster Oticus, Hirayama Syndrome, Holmes-Adie syndrome, Holoprosencephaly, HTLV-1 Associated, Myelopathy, Huntington's Disease, Hydranencephaly, Hydrocephalus, Hydrocephalus-Normal Pressure, Hydromyelia, Hyperactivity, Hypercortisolism, Hypersomnia, Hypertonia, Hypotonia, —Infantile, Hypoxia, Immune-Mediated Encephalomyelitis, Inclusion Body Myositis, Incontinentia Pigmenti, Infantile Hypotonia, Infantile Neuroaxonal Dystrophy, Infantile Phytanic Acid Storage Disease, Infantile Refsum Disease, Infantile Spasms, Inflammatory Myopathy, Iniencephaly, Intestinal Lipodystrophy, Intracranial Cysts, Intracranial Hypertension, Isaac's Syndrome, Joubert Syndrome, Kearns-Sayre Syndrome, Kennedy's Disease, Kinsbourne syndrome, Kleine-Levin Syndrome, Klippel-Feil Syndrome, Klippel-Trenaunay Syndrome (KTS), Kliver-Bucy Syndrome, Korsakoffs Amnesic Syndrome, Krabbe Disease, Kugelberg-Welander Disease, Kuru, Lambert-Eaton Myasthenic Syndrome, Landau-Kleffner Syndrome, Lateral Femoral, Cutaneous Nerve Entrapment, Lateral Medullary Syndrome, Learning Disabilities, Leigh's Disease, Lennox-Gastaut Syndrome, Lesch-Nyhan Syndrome, Leukodystrophy, Levine-Critchley Syndrome, Lewy Body Dementia, Lipid Storage Diseases, Lissencephaly, Locked-In Syndrome, Lou Gehrig's Disease, Lupus-Neurological, Sequelae, Lyme Disease-Neurological Complications, Machado-Joseph Disease, Macrencephaly, Mania, Megalencephaly, Melkersson-Rosenthal Syndrome, Meningitis, Meningitis and Encephalitis, Menkes Disease, Meralgia Paresthetica, Metachromatic, Leukodystrophy, Microcephaly, Migraine, Miller Fisher Syndrome, Mini-Strokes, Mitochondrial Myopathies, Mobius Syndrome, Monomelic Amyotrophy, Motor Neuron Diseases, Moyamoya Disease, Mucolipidoses, Mucopolysaccharidoses, Multifocal Motor Neuropathy, Multi-Infarct Dementia, Multiple Sclerosis, Multiple System Atrophy, Multiple System Atrophy with Orthostatic Hypotension, Muscular Dystrophy, Myasthenia-Congenital, Myasthenia Gravis, Myelinoclastic Diffuse Sclerosis, Myoclonic Encephalopathy of Infants, Myoclonus, Myopathy, Myopathy-Congenital, Myopathy-Thyrotoxic, Myotonia, Myotonia Congenita, Narcolepsy, Neuroacanthocytosis, Neurodegeneration with Brain Iron Accumulation, Neurofibromatosis, Neuroleptic Malignant Syndrome, Neurological Complications of AIDS, Neurological Complications Of Lyme Disease, Neurological Consequences of Cytomegalovirus Infection, Neurological Manifestations of Pompe Disease, Neurological Sequelae Of Lupus, Neuromyelitis Optica, Neuromyotonia, Neuronal Ceroid, Lipofuscinosis, Neuronal Migration Disorders, Neuropathy-Hereditary, Neurosarcoidosis, Neurotoxicity, Nevus Cavernosus, Niemann-Pick Disease, Normal Pressure Hydrocephalus, Occipital Neuralgia, Obesity, Occult Spinal Dysraphism Sequence, Ohtahara Syndrome, Olivopontocerebellar Atrophy, Opsoclonus Myoclonus, Orthostatic Hypotension, O'Sullivan-McLeod Syndrome, Overuse Syndrome, Pain-Chronic, Paine, Pantothenate Kinase-Associated Neurodegeneration, Paraneoplastic Syndromes, Paresthesia, Parkinson's Disease, Paroxysmal Choreoathetosis, Paroxysmal Hemicrania, Parry-Romberg, Pelizaeus-Merzbacher Disease, Pena Shokeir II Syndrome, Perineural Cysts, Periodic Paralyses, Peripheral Neuropathy, Periventricular Leukomalacia, Persistent Vegetative State, Pervasive Developmental Disorders, Phytanic Acid Storage Disease, Pick's Disease, Pinched Nerve, Piriformis Syndrome, Pituitary Tumors, Polymyositis, Pompe Disease, Porencephaly, Postherpetic Neuralgia, Postinfectious Encephalomyelitis, Post-Polio Syndrome, Postural Hypotension, Postural Orthostatic, Tachycardia Syndrome, Postural Tachycardia Syndrome, Primary Dentatum Atrophy, Primary Lateral Sclerosis, Primary Progressive Aphasia, Prion Diseases, Progressive Hemifacial Atrophy, Progressive Locomotor Ataxia, Progressive Multifocal, Leukoencephalopathy, Progressive Sclerosing Poliodystrophy, Progressive Supranuclear, Palsy, Prosopagnosia, Pseudotumor Cerebri, Ramsay Hunt Syndrome I (formerly known as), Ramsay Hunt Syndrome II (formerly known as), Rasmussen's Encephalitis, Reflex Sympathetic Dystrophy Syndrome, Refsum Disease, Refsum Disease-Infantile, Repetitive Motion Disorders, Repetitive Stress Injuries, Restless Legs Syndrome, Retrovirus-Associated Myelopathy, Rett Syndrome, Reye's Syndrome, Riley-Day Syndrome, Sacral Nerve Root Cysts, Saint Vitus Dance, Salivary Gland Disease, Sandhoff Disease, Schilder's Disease, Schizencephaly, Seitelberger Disease, Seizure Disorder, Semantic Dementia, Septo-Optic Dysplasia, Shaken Baby Syndrome, Shingles Shy-Drager Syndrome, Sjogren's Syndrome, Sleep Apnea, Sleeping Sickness, Sotos Syndrome, Spasticity, Spina Bifida, Spinal Cord Infarction, Spinal Cord Injury, Spinal Cord Tumors, Spinal Muscular Atrophy, Spinocerebellar Atrophy, Spinocerebellar, Degeneration, Steele-Richardson-Olszewski Syndrome, Stiff-Person Syndrome, Striatonigral Degeneration, Stroke, Sturge-Weber Syndrome, Subacute Sclerosing Panencephalitis, Subcortical Arteriosclerotic Encephalopathy, SUNCT Headache Swallowing Disorders, Sydenham Chorea, Syncope, Syphilitic Spinal Sclerosis, Syringohydromyelia, Syringomyelia, Systemic Lupus Erythematosus, Tabes Dorsalis Tardive Dyskinesia, Tarlov Cysts, Tay-Sachs Disease, Temporal Arteritis, Tethered Spinal Cord Syndrome, Thomsen's Myotonia, Thoracic Outlet Syndrome, Thyrotoxic Myopathy, Tic Douloureux, Todd's Paralysis, Tourette Syndrome, Transient Ischemic Attack, Transmissible Spongiform Encephalopathies, Transverse Myelitis, Traumatic Brain Injury, Tremor, Trigeminal Neuralgia, Tropical Spastic Paraparesis, Tuberous Sclerosis, Vascular Erectile Tumor, Vasculitis including Temporal Arteritis, Von Economo's Disease, Von Hippel-Lindau Disease (VHL), Von Recklinghausen's Disease, Wallenberg's Syndrome, Werdnig-Hoffman Disease, Wernicke-Korsakoff Syndrome, West Syndrome, Whiplash, Whipple's Disease, Williams Syndrome, Wilson's Disease, X-Linked Spinal and Bulbar Muscular Atrophy, or Zellweger Syndrome.

The term "bioactive agent" is used to describe an agent, other than a compound according to the present disclosure, which is used in combination with the compounds of the present disclosure as an agent with biological activity to assist in effecting an intended therapy, inhibition and/or prevention/prophylaxis for which the present compounds are used.

The term "pharmaceutically acceptable salt" is used throughout the specification to describe, where applicable, a salt form of one or more of the compounds described herein which are presented to increase the solubility of the compound in the gastic juices of the patient's gastrointestinal tract in order to promote dissolution and the bioavailability of the compounds. Pharmaceutically acceptable salts include those derived from pharmaceutically acceptable inorganic or organic bases and acids, where applicable. Suitable salts include those derived from alkali metals such as potassium and sodium, alkaline earth metals such as calcium, magnesium and ammonium salts, among numerous other acids and bases well known in the pharmaceutical art. Sodium and potassium salts are particularly preferred as neutralization salts of the phosphates according to the present disclosure.

The term "pharmaceutically acceptable derivative" is used throughout the specification to describe any pharmaceutically acceptable prodrug form (such as an ester, amide other prodrug group), which, upon administration to a patient, provides directly or indirectly the present compound or an active metabolite of the present compound.

The term "independently" is used herein to indicate that the variable, which is independently applied, varies independently from application to application.

The term "hydrocarbyl" shall mean a compound which contains carbon and hydrogen and which may be fully saturated, partially unsaturated or aromatic and includes aryl groups, alkyl groups, alkenyl groups and alkynyl groups.

The term "alkyl" shall mean within its context a linear, branch-chained or cyclic fully saturated hydrocarbon radical or alkyl group, preferably a $C_1$-$C_{10}$, more preferably a $C_1$-$C_6$, alternatively a $C_1$-$C_3$ alkyl group, which may be optionally substituted. Examples of alkyl groups are methyl, ethyl, n-butyl, sec-butyl, n-hexyl, n-heptyl, n-octyl, n-nonyl, n-decyl, isopropyl, 2-methylpropyl, cyclopropyl, cyclopropylmethyl, cyclobutyl, cyclopentyl, cyclopentylethyl, cyclohexylethyl and cyclohexyl, among others.

The term "lower alkyl" means the alkyl groups with no more than six carbon atoms.

The term "unsubstituted" shall mean substituted only with hydrogen atoms. A range of carbon atoms which includes $C_0$ means that carbon is absent and is replaced with H. Thus, a range of carbon atoms which is $C_0$-$C_6$ includes carbons atoms of 1, 2, 3, 4, 5 and 6 and for $C_0$, H stands in place of carbon. The term "substituted" or "optionally substituted" shall mean independently (i.e., where more than substituent occurs, each substituent is independent of another substituent) one or more substituents (independently up to five substitutents, preferably up to three substituents, often 1 or 2 substituents on a moiety in a compound according to the present disclosure and may include substituents which themselves may be further substituted) at a carbon (or nitrogen) position anywhere on a molecule within context, and includes as substituents hydroxyl, thiol, carboxyl, cyano (C≡N), nitro ($NO_2$), halogen (preferably, 1, 2 or 3 halogens, especially on an alkyl, especially a methyl group such as a trifluoromethyl), an alkyl group (preferably, $C_1$-$C_{10}$, more preferably, $C_1$-$C_6$), aryl (especially phenyl and substituted phenyl for example benzyl or benzoyl), alkoxy group (preferably, $C_1$-$C_6$ alkyl or aryl, including phenyl and substituted phenyl), thioether ($C_1$-$C_6$ alkyl or aryl), acyl (preferably, $C_1$-$C_6$ acyl), ester or thioester (preferably, $C_1$-$C_6$ alkyl or aryl) including alkylene ester (such that attachment is on the alkylene group, rather than at the ester function which is preferably substituted with a $C_1$-$C_6$ alkyl or aryl group), preferably, $C_1$-$C_6$ alkyl or aryl, halogen (preferably, F or Cl), amine (including a five- or six-membered cyclic alkylene amine, further including a $C_1$-$C_6$ alkyl amine or a $C_1$-$C_6$ dialkyl amine which alkyl groups may be substituted with one or two hydroxyl groups) or an optionally substituted —N($C_0$-$C_6$ alkyl)C(O)(O—$C_1$-$C_6$ alkyl) group (which may be optionally substituted with a polyethylene glycol chain to which is further bound an alkyl group containing a single halogen, preferably chlorine substituent), hydrazine, amido, which is preferably substituted with one or two $C_1$-$C_6$ alkyl groups (including a carboxamide which is optionally substituted with one or two $C_1$-$C_6$ alkyl groups), alkanol (preferably, $C_1$-$C_6$ alkyl or aryl), or alkanoic acid (preferably, $C_1$-$C_6$ alkyl or aryl). Substituents according to the present disclosure may include, for example —$SiR_1R_2R_3$ groups where each of $R_1$ and $R_2$ is as otherwise described herein and $R_3$ is H or a $C_1$-$C_6$ alkyl group, preferably $R_1$, $R_2$, $R_3$ in this context is a $C_1$-$C_3$ alkyl group (including an isopropyl or t-butyl group). Each of the above-described groups may be linked directly to the substituted moiety or alternatively, the substituent may be linked to the substituted moiety (preferably in the case of an aryl or heteroaryl moiety) through an optionally substituted —$(CH_2)_m$— or alternatively an optionally substituted —$(OCH_2)_m$—, —$(OCH_2CH_2)_m$— or —$(CH_2CH_2O)_m$— group, which may be substituted with any one or more of the above-described substituents. Alkylene groups —$(CH_2)_m$— or —$(CH_2)_n$— groups or other chains such as ethylene glycol chains, as identified above, may be substituted anywhere on the chain. Preferred substitutents on alkylene groups include halogen or $C_1$-$C_6$ (preferably $C_1$-$C_3$) alkyl groups, which may be optionally substituted with one or two hydroxyl groups, one or two ether groups (O—$C_1$-$C_6$ groups), up to three halo groups (preferably F), or a sidechain of an amino acid as otherwise described herein and optionally substituted amide (preferably carboxamide substituted as described above) or urethane groups (often with one or two $C_0$-$C_6$ alkyl substitutents, which group(s) may be further substituted). In certain embodiments, the alkylene group (often a single methylene group) is substituted with one or two optionally substituted $C_1$-$C_6$ alkyl groups, preferably $C_1$-$C_4$ alkyl group, most often methyl or O-methyl groups or a sidechain of an amino acid as otherwise described herein. In the present disclosure, a moiety in a molecule may be optionally substituted with up to five substituents, preferably up to three substituents. Most often, in the present disclosure moieties which are substituted are substituted with one or two substituents.

The term "substituted" (each substituent being independent of any other substituent) shall also mean within its context of use $C_1$-$C_6$ alkyl, $C_1$-$C_6$ alkoxy, halogen, amido, carboxamido, sulfone, including sulfonamide, keto, carboxy, $C_1$-$C_6$ ester (oxyester or carbonylester), $C_1$-$C_6$ keto, urethane —O—C(O)—$NR_1R_2$ or —N($R_1$)—C(O)—O—$R_1$, nitro, cyano and amine (especially including a $C_1$-$C_6$ alkylene-$NR_1R_2$, a mono- or di-$C_1$-$C_6$ alkyl substituted amines which may be optionally substituted with one or two hydroxyl groups). Each of these groups contain unless otherwise indicated, within context, between 1 and 6 carbon atoms. In certain embodiments, preferred substituents will include for example, —NH—, —NHC(O)—, —O—, =O, —(CH$_2$)$_m$— (here, m and n are in context, 1, 2, 3, 4, 5 or 6), —S—, —S(O)—, SO$_2$— or —NH—C(O)—NH—, —(CH$_2$)$_n$OH, —(CH$_2$)$_n$SH, —(CH$_2$)$_n$COOH, $C_1$-$C_6$ alkyl, —(CH$_2$)$_n$O—($C_1$-$C_6$ alkyl), —(CH$_2$)$_n$C(O)—($C_1$-$C_6$ alkyl), —(CH$_2$)$_n$OC(O)—($C_1$-$C_6$ alkyl), —(CH$_2$)$_n$C(O)O—($C_1$-$C_6$ alkyl), —(CH$_2$)$_n$NHC(O)—$R_1$, —(CH$_2$)$_n$C(O)—$NR_1R_2$, —(OCH$_2$)$_n$OH, —(CH$_2$O)$_n$COOH, $C_1$-$C_6$ alkyl, —(OCH$_2$)$_n$O—($C_1$-$C_6$ alkyl), —(CH$_2$O)$_n$C(O)—($C_1$-$C_6$ alkyl), —(OCH$_2$)$_n$NHC(O)—$R_1$, —(CH$_2$O)$_n$C(O)—$NR_1R_2$, —S(O)$_2$—$R_S$, —S(O)—$R_S$ ($R_S$ is $C_1$-$C_6$ alkyl or a —(CH$_2$)$_m$—$NR_1R_2$ group), NO$_2$, CN or halogen (F, Cl, Br, I, preferably F or Cl), depending on the context of the use of the substituent. $R_1$ and $R_2$ are each, within context, H or a $C_1$-$C_6$ alkyl group (which may be optionally substituted with one or two hydroxyl groups or up to three halogen groups, preferably fluorine). The term "substituted" shall also mean, within the chemical context of the compound defined and substituent used, an optionally substituted aryl or heteroaryl group or an optionally substituted heterocyclic group as otherwise described herein. Alkylene groups may also be substituted as otherwise disclosed herein, preferably with optionally substituted $C_1$-$C_6$ alkyl groups (methyl, ethyl or hydroxymethyl or hydroxyethyl is preferred, thus providing a chiral center), a sidechain of an amino acid group as otherwise described herein, an amido group as described hereinabove, or a urethane group O—C(O)—$NR_1R_2$ group where $R_1$ and $R_2$ are as otherwise described herein, although numerous other groups may also be used as substituents. Various optionally substituted moieties may be substituted with 3 or more substituents, preferably no more than 3 substituents and preferably with 1 or 2 substituents. It is noted that in instances where, in a compound at a particular position of the molecule substitution is required (principally, because of valency), but no substitution is indicated, then that substituent is construed or understood to be H, unless the context of the substitution suggests otherwise.

The term "aryl" or "aromatic", in context, refers to a substituted (as otherwise described herein) or unsubstituted monovalent aromatic radical having a single ring (e.g., benzene, phenyl, benzyl) or condensed rings (e.g., naphthyl, anthracenyl, phenanthrenyl, etc.) and can be bound to the compound according to the present disclosure at any available stable position on the ring(s) or as otherwise indicated in the chemical structure presented. Other examples of aryl groups, in context, may include heterocyclic aromatic ring systems "heteroaryl" groups having one or more nitrogen, oxygen, or sulfur atoms in the ring (moncyclic) such as imidazole, furyl, pyrrole, furanyl, thiene, thiazole, pyridine, pyrimidine, pyrazine, triazole, oxazole or fused ring systems such as indole, quinoline, indolizine, azaindolizine, benzofurazan, etc., among others, which may be optionally substituted as described above. Among the heteroaryl groups which may be mentioned include nitrogen-containing heteroaryl groups such as pyrrole, pyridine, pyridone, pyridazine, pyrimidine, pyrazine, pyrazole, imidazole, triazole, triazine, tetrazole, indole, isoindole, indolizine, azaindolizine, purine, indazole, quinoline, dihydroquinoline, tetrahydroquinoline, isoquinoline, dihydroisoquinoline, tetrahydroisoquinoline, quinolizine, phthalazine, naphthyridine, quinoxaline, quinazoline, cinnoline, pteridine, imidazopyridine, imidazotriazine, pyrazinopyridazine, acridine, phenanthridine, carbazole, carbazoline, perimidine, phenanthroline, phenacene, oxadiazole, benzimidazole, pyrrolopyridine, pyrrolopyrimidine and pyridopyrimidine; sulfur-containing aromatic heterocycles such as thiophene and benzothiophene; oxygen-containing aromatic heterocycles such as furan, pyran, cyclopentapyran, benzofuran and isobenzofuran; and aromatic heterocycles comprising 2 or more hetero atoms selected from among nitrogen, sulfur and oxygen, such as thiazole, thiadizole, isothiazole, benzoxazole, benzothiazole, benzothiadiazole, phenothiazine, isoxazole, furazan, phenoxazine, pyrazoloxazole, imidazothiazole, thienofuran, furopyrrole, pyridoxazine, furopyridine, furopyrimidine, thienopyrimidine and oxazole, among others, all of which may be optionally substituted.

The term "heterocycle" refers to a cyclic group which contains at least one heteroatom, i.e., O, N or S, and may be aromatic (heteroaryl) or non-aromatic. Thus, the heteroaryl moieties are subsumed under the definition of heterocycle, depending on the context of its use. Exemplary heteroaryl groups are described hereinabove. Exemplary non-aromatic heterocyclic groups for use in the present disclosure include, for example, pyrrolidinyl, pyrrolinyl, piperidinyl, piperazinyl, N-methylpiperazinyl, pyrazolidinyl, imidazolidinyl, morpholinyl, tetrahydropyranyl, azetidinyl, oxetanyl, oxathiolanyl, pyridone, 2-pyrrolidone, ethyleneurea, 1,3-dioxolane, 1,3-dioxane, 1,4-dioxane, phthalimide and succinimide, among others, as described herein.

The term "co-administration" or "combination therapy" shall mean that at least two compounds or compositions are administered to the patient at the same time, such that effective amounts or concentrations of each of the two or more compounds may be found in the patient at a given point in time. Although compounds according to the present disclosure may be co-administered to a patient at the same time, the term embraces both administration of two or more agents at the same time or at different times, provided that effective concentrations of all co-administered compounds or compositions are found in the subject at a given time. In certain preferred aspects of the present disclosure, one or more of the present compounds described above, are coadministered in combination with at least one additional bioactive agent, especially including an anticancer agent. In particularly aspects of the disclosure, the co-administration of compounds results in synergistic therapeutic, including anticancer therapy The present disclosure describes bifunctional compounds which function to recruit endogenous proteins to an E3 ubiquitin ligase for degradation, and methods of using the same. In particular, the present disclosure provides bifunctional or proteolysis targeting chimeric (PROTAC) compounds, which find utility as modulators of targeted ubiquitination of Tau proteins. An advantage of the compounds provided herein is that a broad range of pharmacological activities is possible, consistent with the degradation/inhibition of Tau protein.

As such, the present disclosure provides such compounds and compositions comprising an E3 ubiquitin ligase targeting moiety ("ULM") coupled to a Tau protein target binding moiety ("PTM"), which result in the ubiquitination of Tau protein, which leads to degradation (and/or inhibition) of the Tau protein. The present disclosure also provides a library of compositions and the use thereof.

The present description provides compounds which comprise a ligand, e.g., a small molecule ligand (i.e., having a molecular weight of below 2,000, 1,000, 500, or 200 Daltons), which is capable of binding to a ubiquitin ligase, such as VHL or cereblon. The compounds also comprise a moiety that is capable of binding to target protein, in such a way that the target protein is placed in proximity to the ubiquitin ligase to effect degradation (and/or inhibition) of that protein. Small molecule can mean, in addition to the above, that the molecule is non-peptidyl, that is, it is not generally considered a peptide, e.g., comprises fewer than 4, 3, or 2 amino acids. In accordance with the present description, the PTM, ULM or PROTAC molecule can be a small molecule.

In one embodiment, the description provides a composition useful for regulating protein activity. The composition comprises a ubiquitin pathway protein binding moiety (preferably for VHL or cereblon) according to a defined chemical structure and a Tau protein targeting moiety which are linked together, preferably through a linker, wherein the ubiquitin pathway protein binding moiety recognizes a ubiquitin pathway protein and the targeting moiety recognizes Tau target protein and wherein the ubiquitin pathway protein binding moiety is coupled to the Tau targeting moiety.

In another embodiment, the present disclosure provides a library of compounds. The library comprises more than one compound wherein each composition has a ubiquitin pathway protein binding moiety (preferably, VHL or cereblon) and a Tau protein binding moiety, wherein ULM is coupled (preferably, through a linker moiety) to Tau, and wherein the ubiquitin pathway protein binding moiety recognizes an ubiquitin pathway protein, in particular, an E3 ubiquitin ligase.

In another embodiment, the present disclosure provides a method of ubiquitinating/degrading a target protein (e.g. Tau) in a cell. The method comprises administering a bifunctional composition comprising an ubiquitin pathway protein binding moiety and a targeting moiety, preferably linked through a linker moiety, as otherwise described herein, wherein the ubiquitin pathway protein binding moiety is coupled to the targeting moiety and wherein the ubiquitin pathway protein binding moiety recognizes a ubiquitin pathway protein (e.g., VHL, cereblon) and the targeting moiety recognizes the target protein (e.g., Tau) such that degradation of the target protein will occur when the target protein is placed in proximity to the ubiquitin ligase, thus resulting in degradation/inhibition of the effects of the target protein and the control of protein levels. The control of protein levels afforded by the present disclosure provides treatment of a disease state or condition, which is modulated through the target protein by lowering the level of that protein in the cells of a patient.

In yet another embodiment, the present disclosure is directed to a method of treating a patient in need for a disease state or condition modulated through a protein (e.g., Tau) where the degradation of that protein will produce a therapeutic effect in that patient, the method comprising administering to a patient in need an effective amount of a compound according to the present disclosure, optionally in combination with another bioactive agent. The disease state or condition may be a disease caused by a microbial agent or other exogenous agent such as a virus, bacteria, fungus, protozoa or other microbe or may be a disease state, which is caused by overexpression of a protein i.e. accumulation or aggregation of Tau protein, which leads to a disease state and/or condition.

In one aspect, the present disclosure provides compounds useful for regulating protein activity. The composition comprises an E3 ubiquitin ligase, a ubiquitin pathway protein binding moiety, and a protein targeting moiety which are linked or coupled together, preferably through a linker, wherein the ubiquitin pathway protein binding moiety recognizes a ubiquitin pathway protein and the targeting moiety recognizes a target protein (e.g., Tau). Such compounds may be referred to herein as PROTAC compounds or PROTACs with the following general chemical structure:

ULM-L-PTM, or a pharmaceutically acceptable salt, enantiomer, stereoisomer, solvate, polymorph or prodrug thereof, wherein ULM is a small molecule E3 ubiquitin ligase binding moiety that binds an E3 ubiquitin ligase;

PTM is a small molecule comprising a Tau protein targeting moiety that degrades the Tau protein; and L is a bond or a chemical linking moiety connecting ULM and PTM.

In certain embodiments, the E3 ubiquitin ligase binding moiety targets a member of the group consisting of Von Hippel-Lindau (VLM), cereblon (CLM), mouse double-minute homolog2 (MLM), and IAP (ILM).

In one aspect, the description provides Tau protein binding moieties (PTM). In certain embodiments, PTM is represented by Formula I, Formula II, Formula III, Formula IV, Formula V, Formula VI, Formula, VII, Formula, VIII, Formula IX, Formula X, or Formula XI:

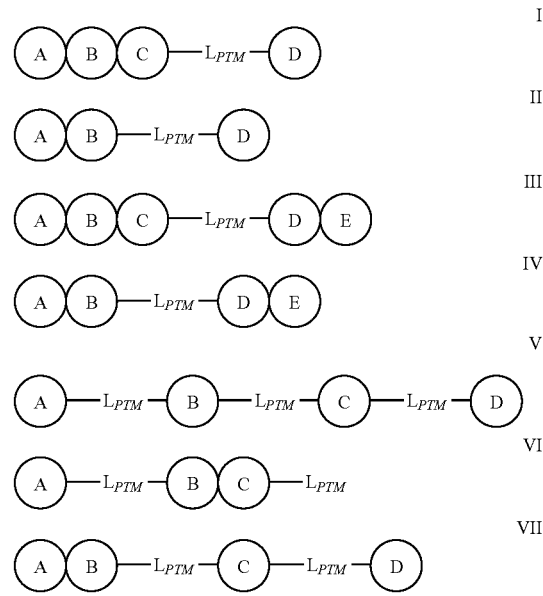

-continued

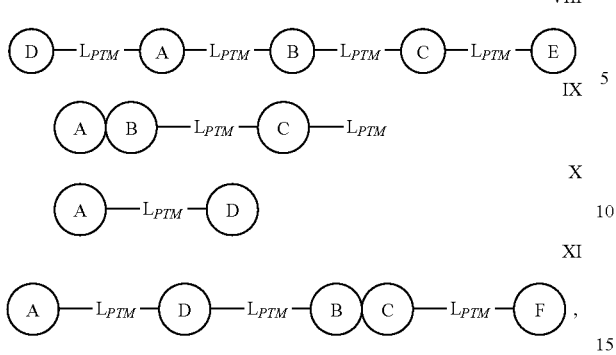

wherein:
A, B, C, D, E, and F are independently selected from an optionally substituted 5- or 6-membered aryl or heteroaryl ring, an optionally substituted 4- to 7-membered cycloalkyl or a heterocycloalkyl, where contact between circles indicates ring fusion; and
$L_{PTM}$ is selected from a bond, an alkyl, an alkenyl or an alkynyl, optionally interrupted by one or more rings (i.e., cycloalkyl, heterocycloalkyl, aryl or heteroaryl), or one or more functional groups selected from the groups —O—, —S—, —NR$^1_{PTM}$— (where R$^1_{PTM}$ is selected from H or alkyl), —N=N—, —S(O)—, —SO$_2$—, —C(O)—, —NHC(O)—, —C(O)NH—, —NHSO$_2$—, —NHC(O)NH—, —NHC(O)O—, or —OC(O)NH—, wherein the said functional group are optionally located at either end of the linker.

In certain embodiments, aryl and heteroaryl rings of A, B, C, D, E, and F of PTM are optionally substituted with 1-3 substituents each independently selected from alkyl, alkenyl, haloalkyl, halogen, hydroxyl, alkoxy, fluoroalkoxy, amino, alkylamino, dialkylamino, acylamino, trifluoromethyl, and cyano, wherein the said alkyl and alkenyl groups are further optionally substituted.

In certain embodiments, the rings of at least one of A, B, C, F, or a combination thereof is selected from optionally substituted 5- or 6-membered aryl or heteroaryl rings;

In certain embodiments, the PTM has the chemical structure of Formula I, wherein:
A, B and C rings are independently 5- or 6-membered fused aryl or heteroaryl rings;
$L_{PTM}$ is selected from a bond or an alkyl, and
D is selected from a 6-membered aryl, heteroaryl or heterocycloalkyl,
wherein A, B, C and D are optionally substituted with alkyl, haloalkyl, halogen, hydroxyl, alkoxy, amino, alkylamino, dialkylamino or cyano.

In certain additional embodiments, The PTM has the chemical structure of Formula I,
wherein:
A and C are a phenyl or a 6-membered heteroaryl ring;
B is a 5-membered heteroaryl ring;
$L_{PTM}$ is a bond; and
D is a 6-membered heteroaryl or a 6-membered heterocycloalkyl ring;
wherein each A, B, C and D is optionally independently substituted with alkyl, haloalkyl, halogen, hydroxyl, alkoxy, amino, dialkylamino or cyano, and wherein a nitrogen atom of any of the A, B, C and D rings is not directly connected to a heteroatom or to a carbon atom, to which another heteroatom is directly attached.

In other embodiments, the PTM has the chemical structure of Formula III or IV, wherein A, B and C are 5- or 6-membered fused aryl or heteroaryl rings, $L_{PTM}$ is selected from a bond or an alkyl, and D and E are 5- or 6-membered fused aryl or heteroaryl rings, wherein A, B, C, D and E are optionally substituted with alkyl, haloalkyl, halogen, hydroxyl, alkoxy, amino, alkylamino, dialkylamino or cyano.

In certain embodiments, the PTM is represented by following chemical structure:

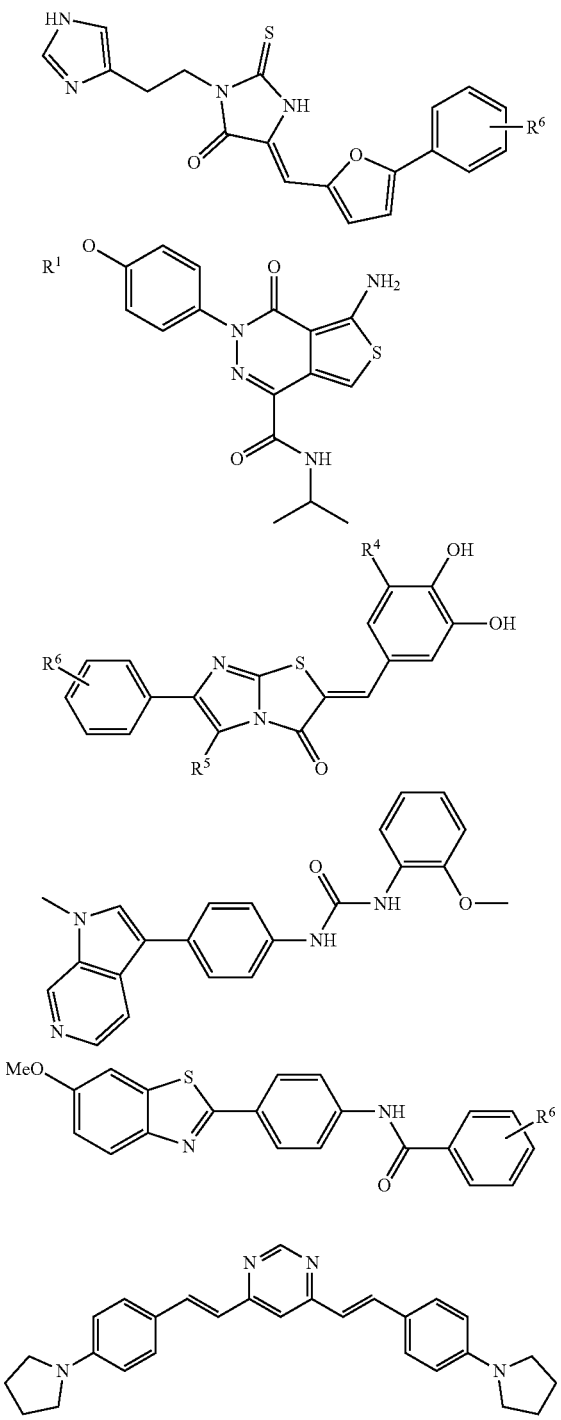

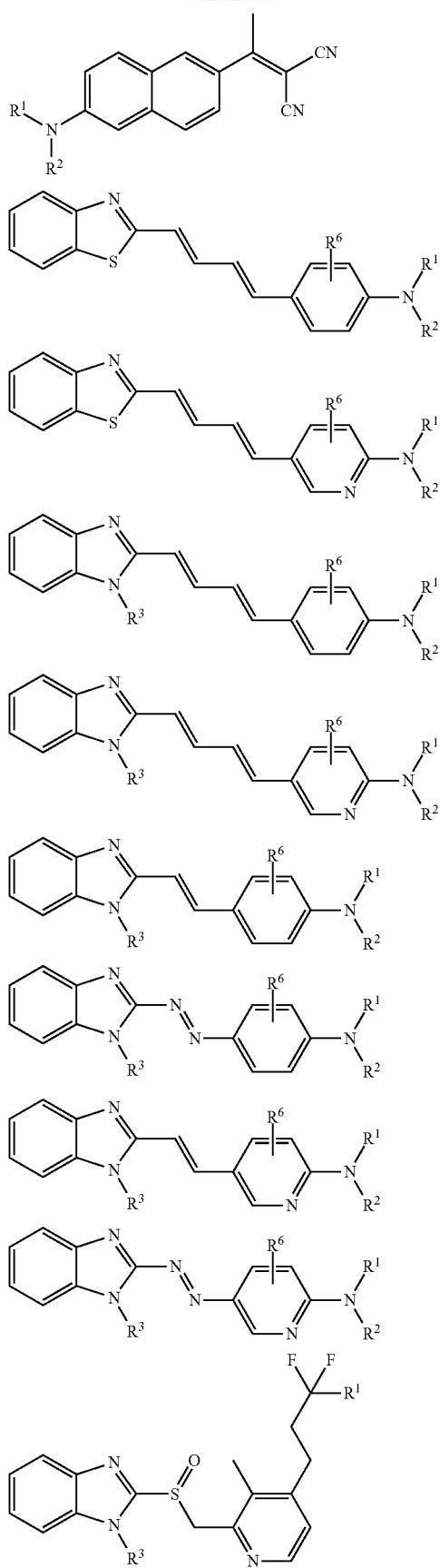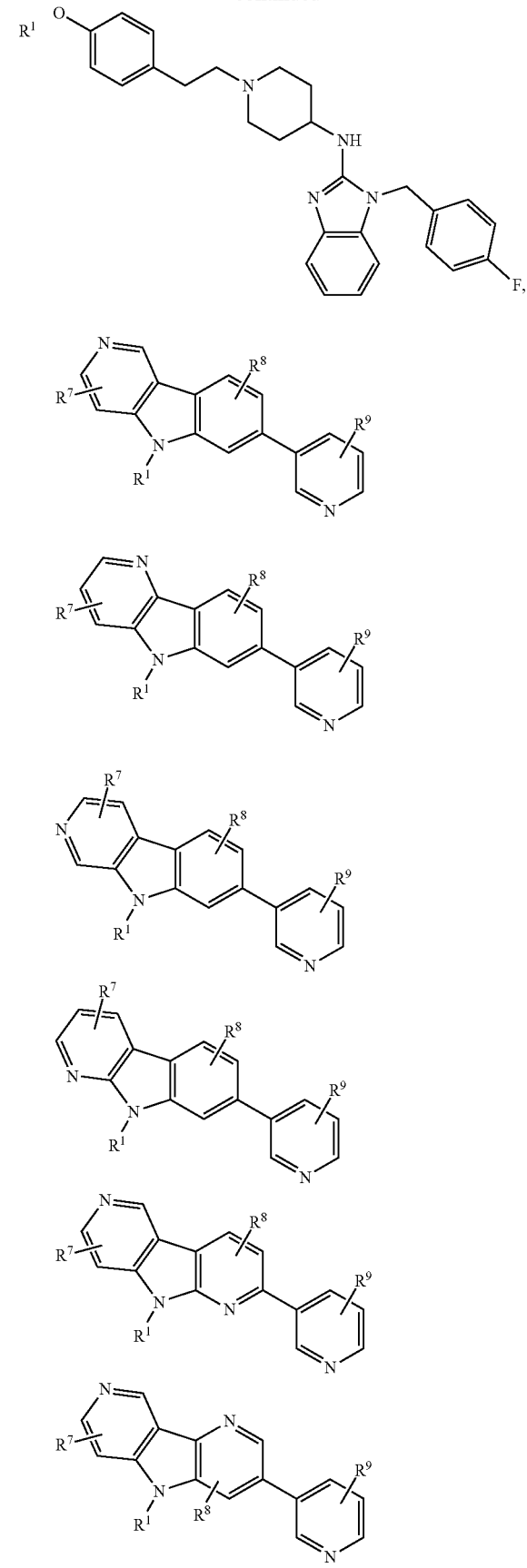

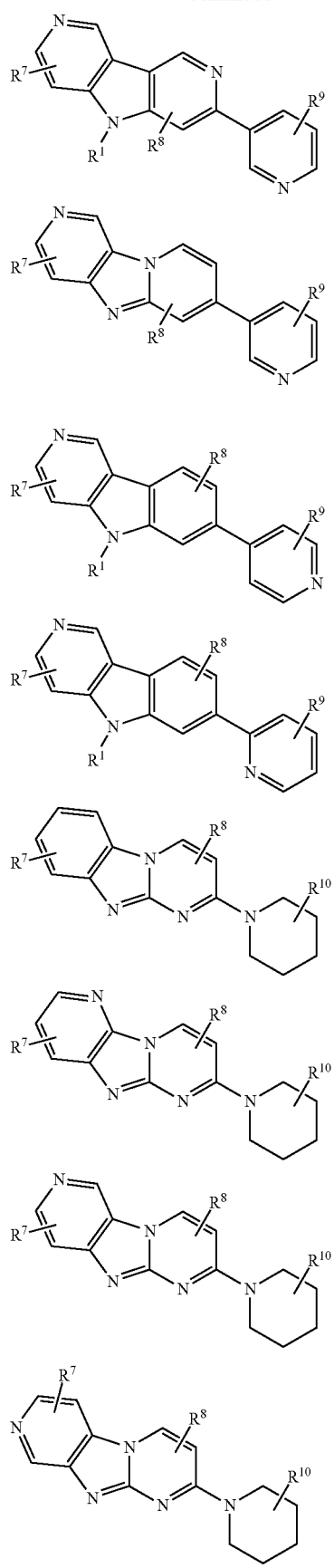
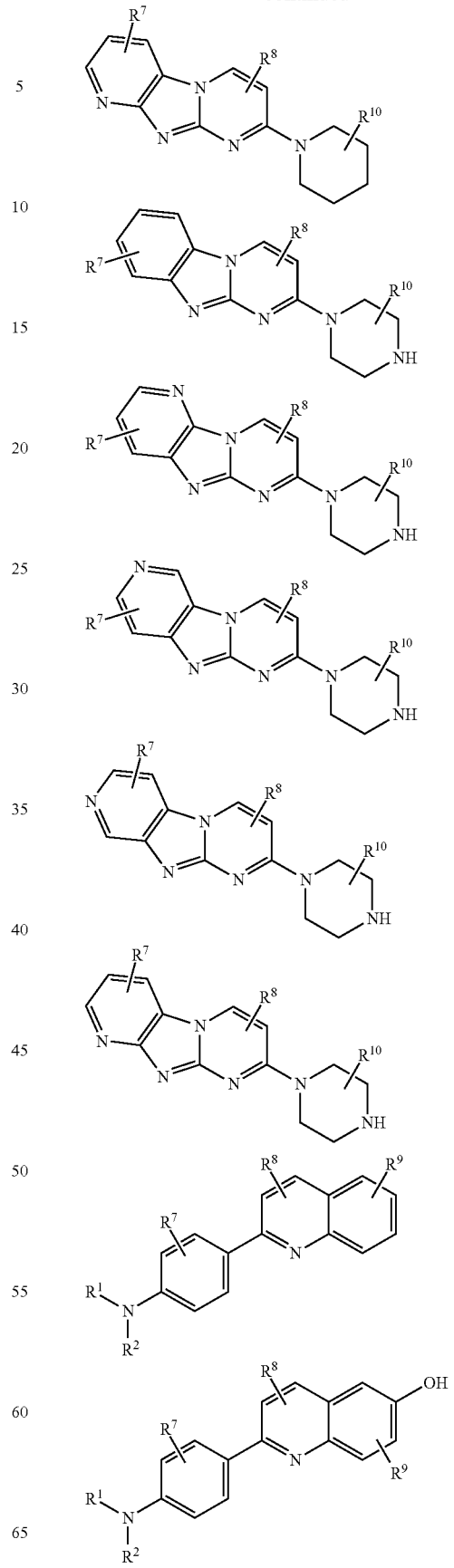

-continued

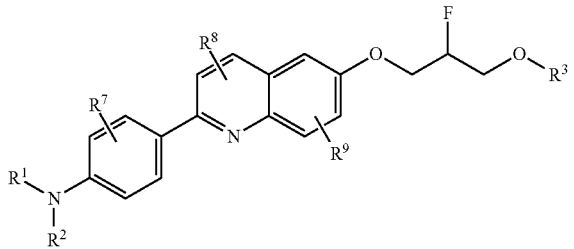

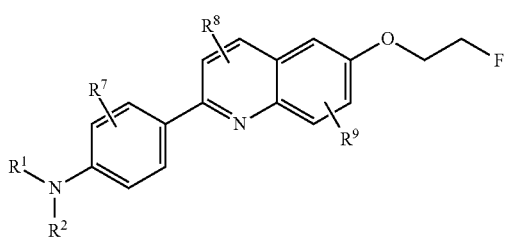

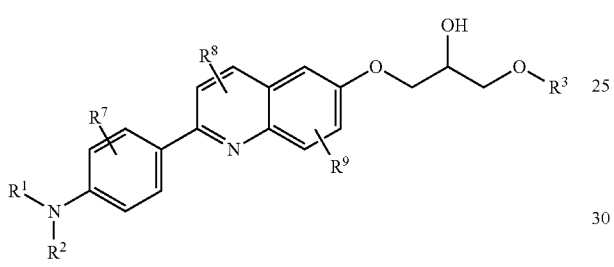

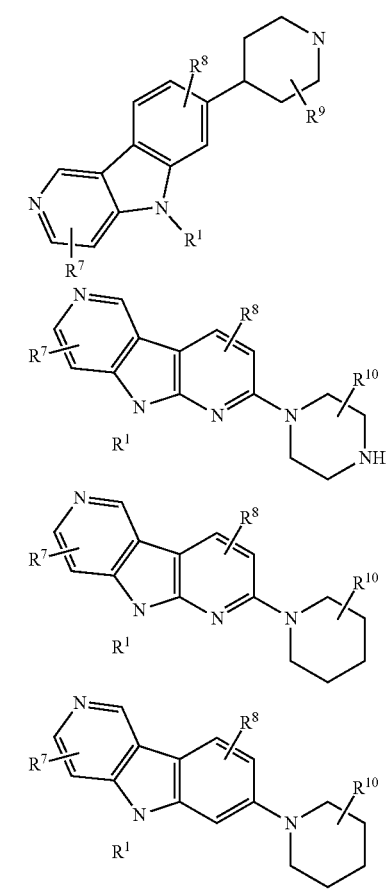

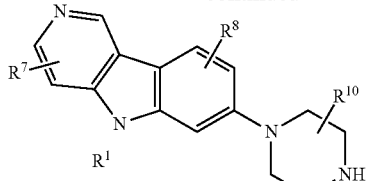

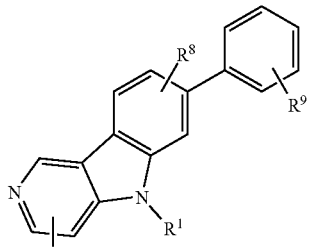

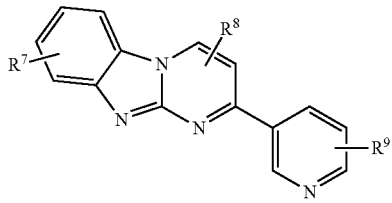

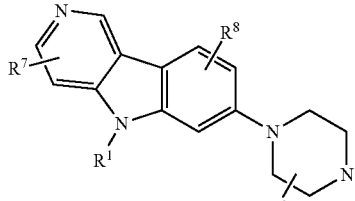

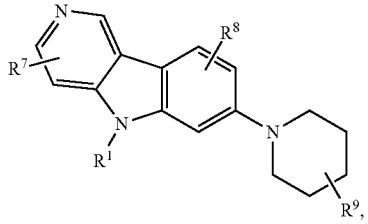

wherein:
$R^1$, $R^2$ and $R^3$ are independently selected from H, methyl, ethyl, 2-fluoroethyl and 2,2,2-trifluoroethyl;
$R^4$ and $R^5$ are independently selected from H, methyl, ethyl and halogen; and
$R^6$ is 1 to 2 substituents independently selected from H, methyl, ethyl and halogen, wherein the PTM is coupled to a ULM via L.

In any of the aspects or embodiments described herein, the PTM is covalently coupled to one or more ULM (VLM or CLM) groups, or a linker to which is attached one or more ULM (VLM or CLM) groups as described herein.

In certain embodiments, PTM is represented by chemical structure:
wherein:
$R^1$, $R^2$ and $R^3$ are independently selected from H, optionally substituted alkyl, methyl, ethyl, 2-fluoroethyl and 2,2,2-trifluoroethyl; and
$R^7$, $R^8$, $R^9$ and $R^{10}$ are 1 to 8 substituents independently selected from H, optionally substituted alkyl, haloalkyl, halogen, hydroxyl, alkoxy, amino, dialkylamino, acetylamino, trifluoromethyl or cyano, and wherein the PTM is coupled to a ULM (VLM or CLM) via L.

In certain additional embodiments, PTM is represented by chemical structure:
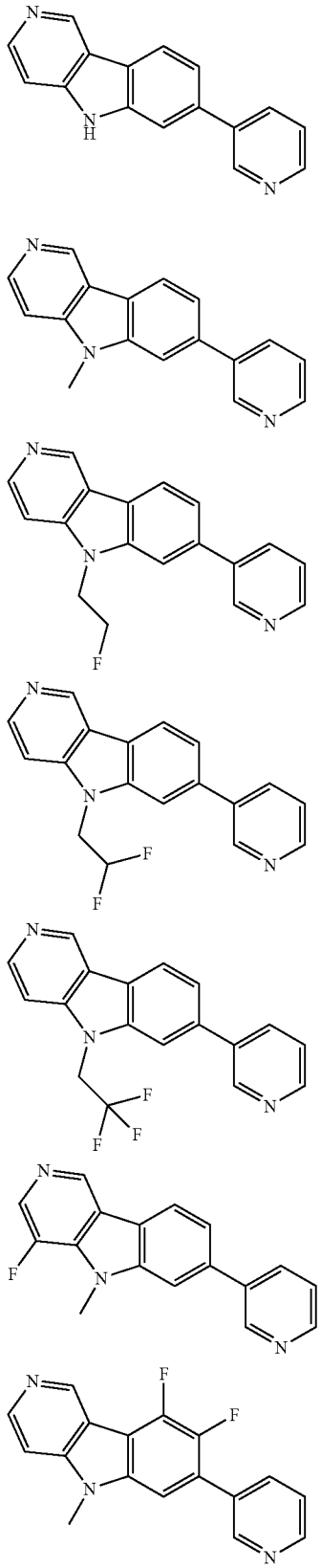
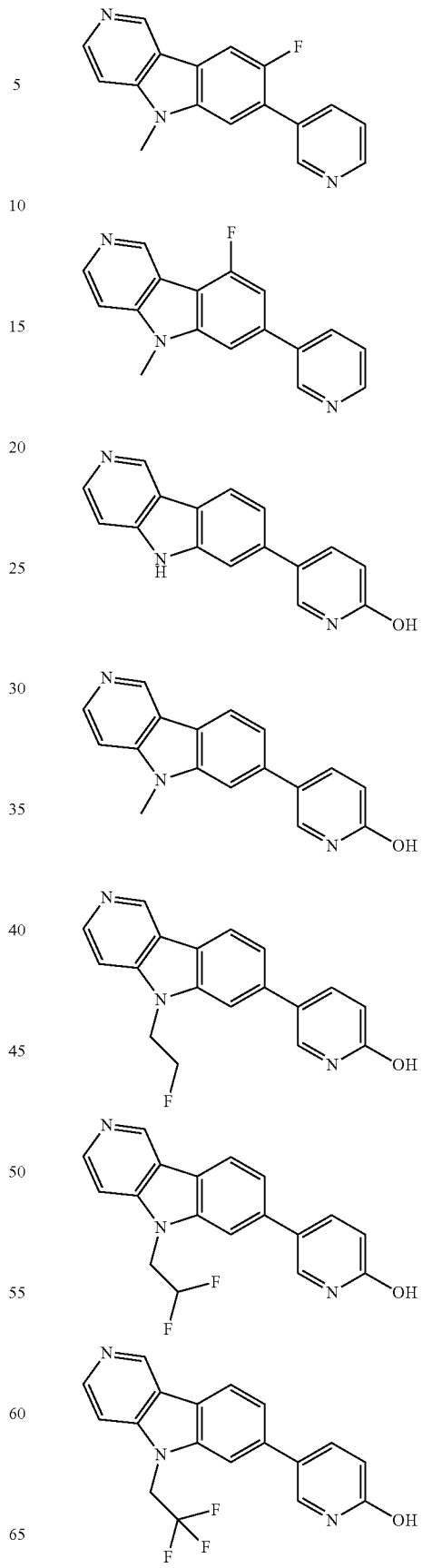

-continued
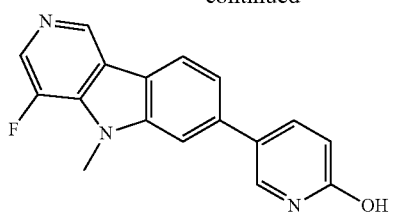
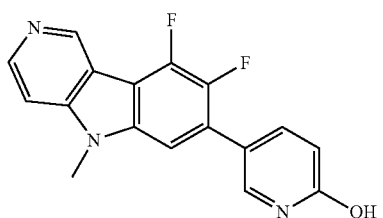
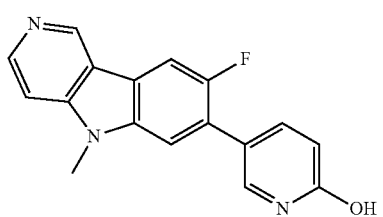

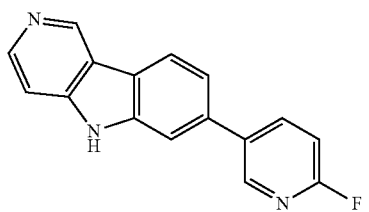
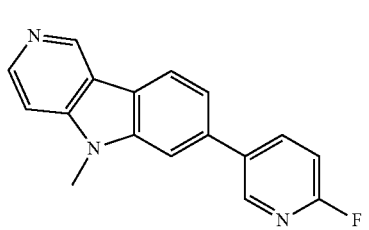
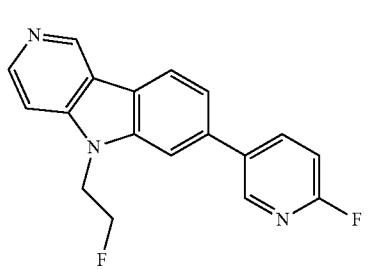
-continued
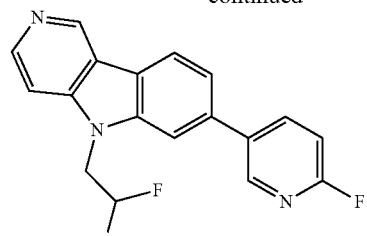
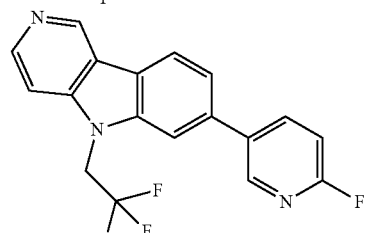
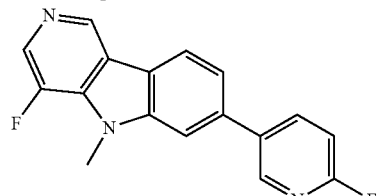
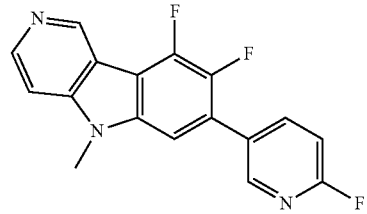
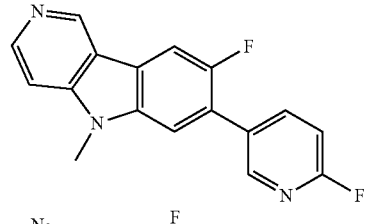
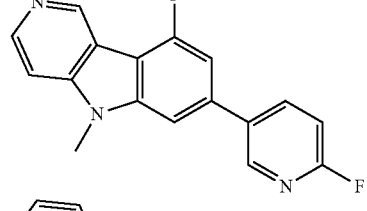
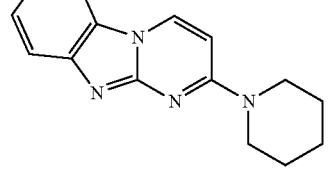
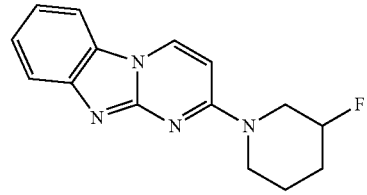

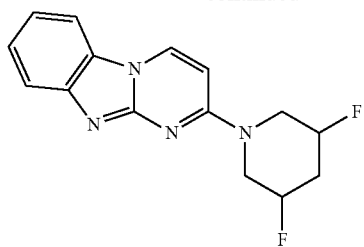
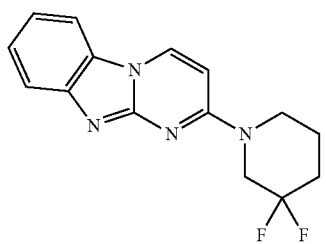
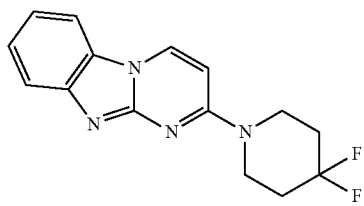
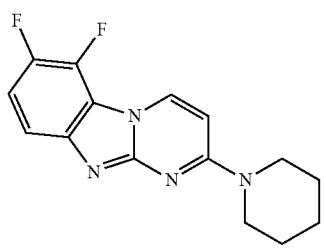
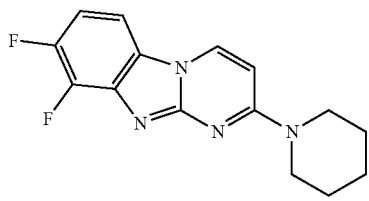
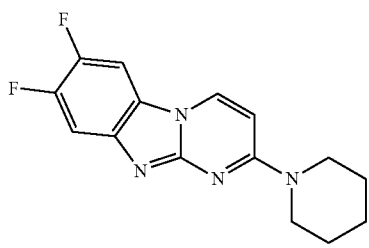
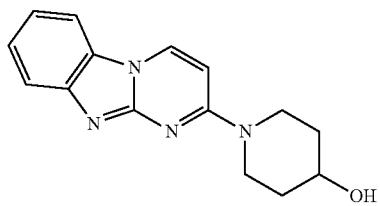
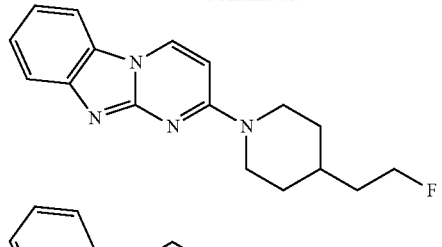
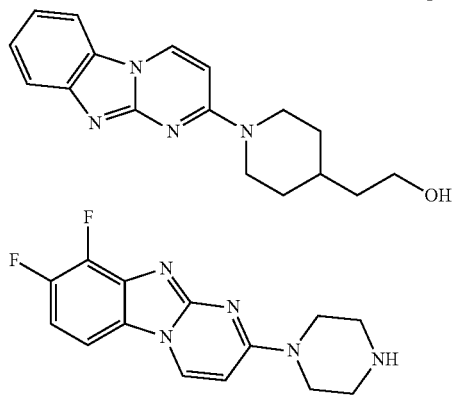
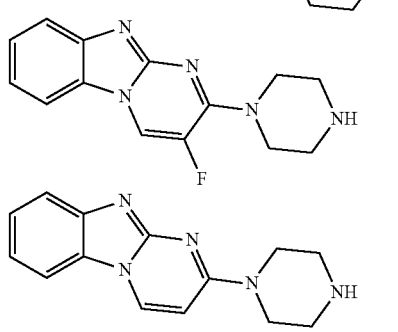
In certain embodiments linker attachment point to PTM is as indicated by the dotted line:
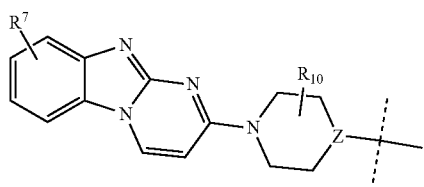
Z = N, CH
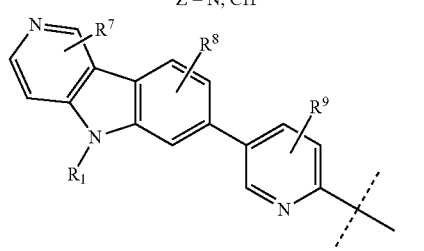
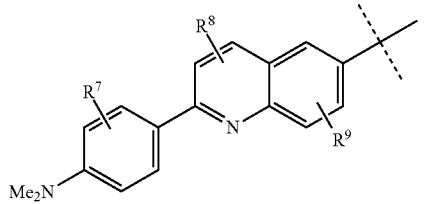

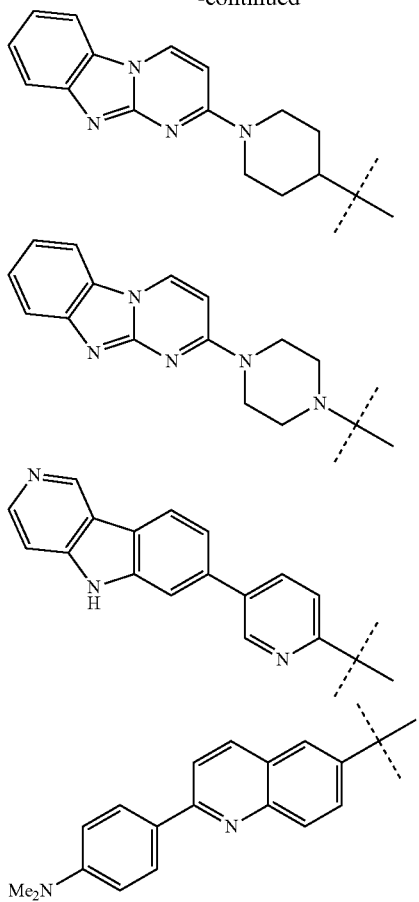

Exemplary VLMs:

In one aspect ULM is VHL.

In certain embodiments of the compounds as described herein, ULM is VLM and comprises a chemical structure selected from the group ULM-a:

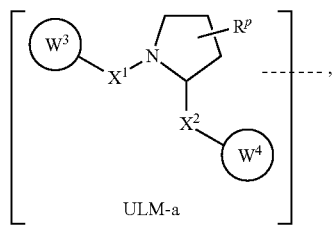

ULM-a wherein:
where a dashed line indicates the attachment of at least one PTM, another ULM or VLM or CLM (i.e., ULM' or VLM' or CLM'), or a chemical linker moiety coupling at least one PTM, a ULM' or VLM' or CLM' to the other end of the linker;

$X^1$, $X^2$ are each independently selected from the group of a bond, O, $NR^{Y3}$, $CR^{Y3}R^{Y4}$, C=O, C=S, SO, and $SO_2$;

$R^{Y3}$, $R^{Y4}$ are each independently selected from the group of H, linear or branched $C_{1-6}$ alkyl, optionally substituted by 1 or more halo, $C_{1-6}$ alkoxyl);

$R^P$ is 1, 2, or 3 groups, each independently selected from the group H, halo, —OH, $C_{1-3}$ alkyl;

$W^3$ is selected from the group of an optionally substituted -T-N($R^{1a}R^{1b}$), an optionally substituted -T-N($R^{1a}R^{1b}$) $X^3$, -T-Aryl, an optionally substituted -T-Heteroaryl, an optionally substituted -T-Heterocycle, an optionally substituted —$NR^1$-T-Aryl, an optionally substituted —$NR^1$-T-Heteroaryl or an optionally substituted —$NR^1$-T-Heterocycle;

$X^3$ is C=O, $R^1$, $R^{1a}$, $R^{1b}$;

$R^1$, $R^{1a}$, $R^{1b}$ are each independently selected from the group consisting of H, linear or branched $C_1$-$C_6$ alkyl group optionally substituted by 1 or more halo or —OH groups, $R^{Y3}$C=O, $R^{Y3}$C=S, $R^{Y3}$SO, $R^{Y3}SO_2$, N($R^{Y3}R^{Y4}$)C=O, N($R^{Y3}R^{Y4}$)C=S, N($R^{Y3}R^{Y4}$)SO, and N($R^{Y3}R^{Y4}$)$SO_2$;

where T is covalently bonded to X1;

$W^4$ is an optionally substituted —NR1-T-Aryl, an optionally substituted —NR1-T-Heteroaryl group or an optionally substituted —NR1-T-Heterocycle, where —NR1 is covalently bonded to X2 and R1 is H or $CH_3$, preferably H.

In any of the embodiments described herein, T is selected from the group of an optionally substituted alkyl, —$(CH_2)_n$— group, wherein each one of the methylene groups is optionally substituted with one or two substituents selected from the group of halogen, methyl, a linear or branched $C_1$-$C_6$ alkyl group optionally substituted by 1 or more halogen or —OH groups or an amino acid side chain optionally substituted; and n is 0 to 6, often 0, 1, 2, or 3, preferably 0 or 1.

In certain embodiments, $W^4$ is

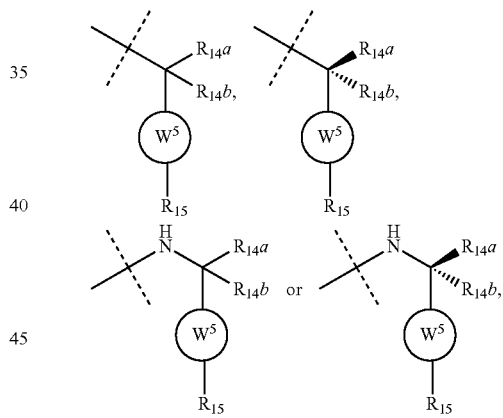

wherein $R_{14a}$, $R_{14b}$, are each independently selected from the group of H, haloalkyl, or optionally substituted alkyl;

In any of the aspects or embodiments described herein, $W^5$ is selected from the group of a phenyl or a 5-10 membered heteroaryl, $R_{15}$ is selected from the group of H, halogen, CN, OH, $NO_2$, $NR_{14a}R_{14b}$, $OR_{14a}$, $CONR_{14a}R_{14b}$, $NR_{14a}COR_{14b}$, $SO_2NR_{14a}R_{14b}$, $NR_{14a}SO_2R_{14b}$, optionally substituted alkyl, optionally substituted haloalkyl, optionally substituted haloalkoxy; aryl, heteroaryl, cycloalkyl, or cycloheteroalkyl;

In additional embodiments, $W^4$ substituents for use in the present disclosure also include specifically (and without limitation to the specific compound disclosed) the $W^4$ substituents which are found in the identified compounds disclosed herein. Each of these $W^4$ substituents may be used in conjunction with any number of $W^3$ substituents which are also disclosed herein.

In certain additional embodiments, ULM-a, is optionally substituted by 1-3 $R^P$ groups in the pyrrolidine moiety. Each $R^P$ is independently H, halo, —OH, C1-3alkyl.

In any of the embodiments described herein, the $W^3$, $W^4$ can independently be covalently coupled to a linker which is attached one or more PTM groups.

and wherein the dashed line indicates the site of attachment of at least one PTM, another ULM (ULM') or a chemical linker moiety coupling at least one PTM or a ULM' or both to ULM.

In certain embodiments, ULM is VHL and is represented by the structure:

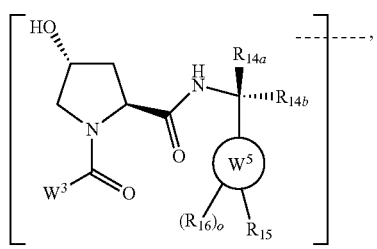

wherein:
$W^3$ is selected from the group of an optionally substituted aryl, optionally substituted heteroaryl, or

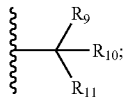

$R_9$ and $R_{10}$ are independently hydrogen, optionally substituted alkyl, optionally substituted cycloalkyl, optionally substituted hydroxyalkyl, optionally substituted heteroaryl, or haloalkyl, or $R_9$, $R_{10}$, and the carbon atom to which they are attached form an optionally substituted cycloalkyl;

$R_{11}$ is selected from the group of an optionally substituted heterocyclic, optionally substituted alkoxy, optionally substituted heteroaryl, optionally substituted aryl,

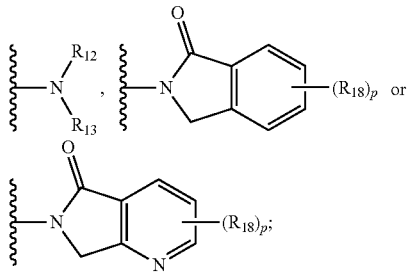

$R_{12}$ is selected from the group of H or optionally substituted alkyl;

$R_{13}$ is selected from the group of H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl;

$R_{14a}$, $R_{14b}$, are each independently selected from the group of H, haloalkyl, or optionally substituted alkyl;

$W^5$ is selected from the group of a phenyl or a 5-10 membered heteroaryl, $R_{15}$ is selected from the group of H, halogen, CN, OH, $NO_2$, $NR_{14a}R_{14b}$, $OR_{14a}$, $CONR_{14a}R_{14b}$, $NR_{14a}COR_{14b}$, $SO_2NR_{14a}R_{14b}$, $NR_{14a}SO_2R_{14b}$, optionally substituted alkyl, optionally substituted haloalkyl, optionally substituted haloalkoxy; aryl, heteroaryl, cycloalkyl, or cycloheteroalkyl (each independently optionally substituted);

$R_{16}$ is independently selected from the group of H, halo, optionally substituted alkyl, optionally substituted haloalkyl, hydroxy, or optionally substituted haloalkoxy;

o is 0, 1, 2, 3, or 4;

$R_{18}$ is independently selected from the group of halo, optionally substituted alkoxy, cyano, optionally substituted alkyl, haloalkyl, haloalkoxy or a linker; and p is 0, 1, 2, 3, or 4, and wherein the dashed line indicates the site of attachment of at least one PTM, another ULM (ULM') or a chemical linker moiety coupling at least one PTM or a ULM' or both to ULM.

In certain embodiments, $R_{15}$ is

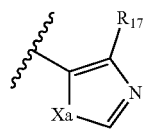

wherein $R_{17}$ is H, halo, optionally substituted $C_{3-6}$cycloalkyl, optionally substituted $C_{1-6}$alkyl, optionally substituted $C_{1-6}$alkenyl, and $C_{1-6}$haloalkyl; and Xa is S or O.

In certain embodiments, $R_{17}$ is selected from the group methyl, ethyl, isopropyl, and cyclopropyl.

In certain additional embodiments, $R_{15}$ is selected from the group consisting of:

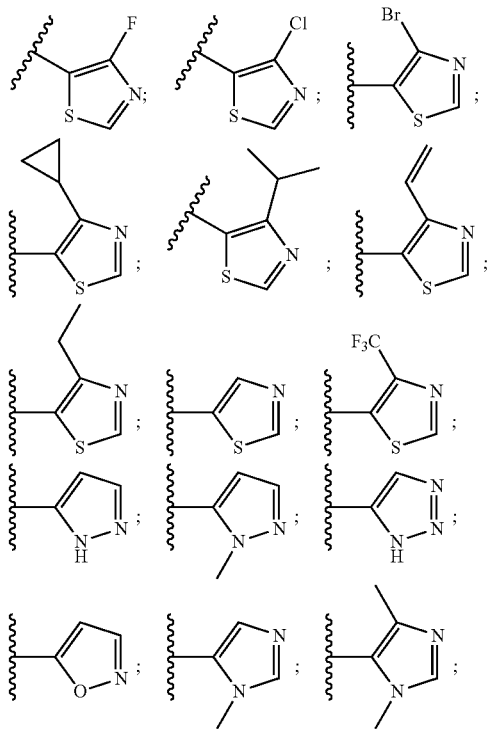

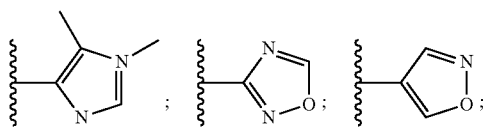
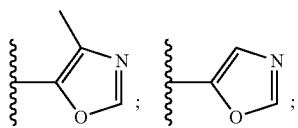
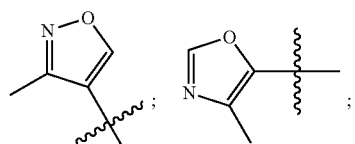
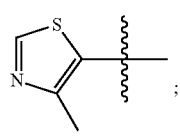
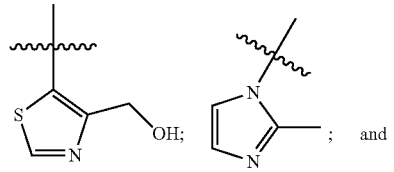
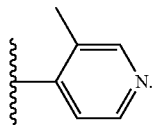
In certain embodiments, $R_{11}$ is selected from the group consisting of:
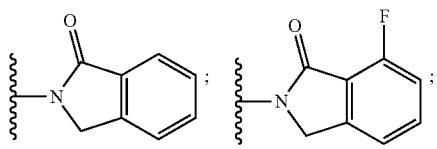
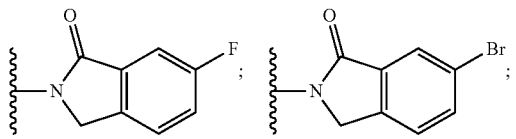
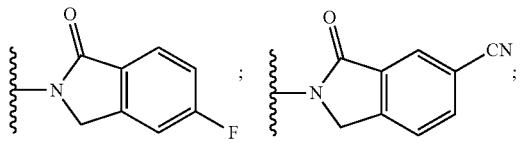
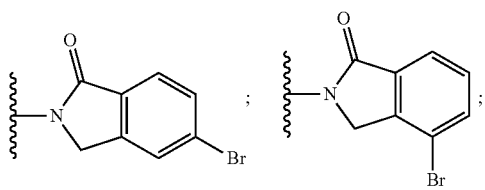
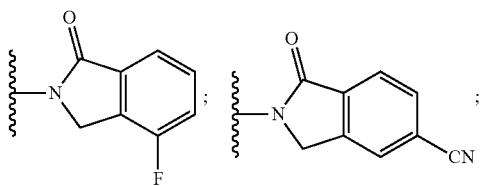
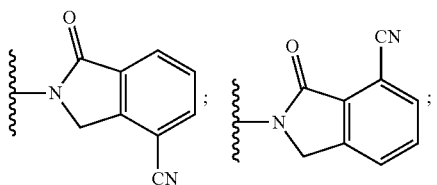
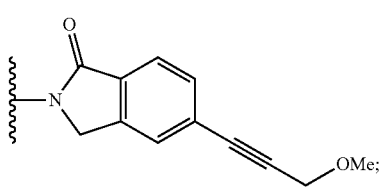
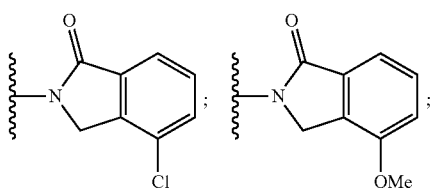
In certain embodiments, ULM has a chemical structure selected from the group of:
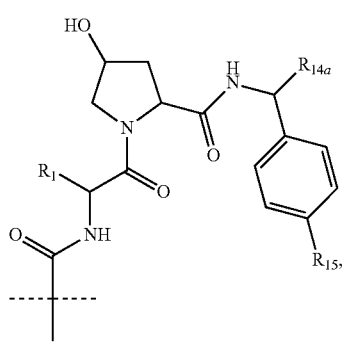

-continued

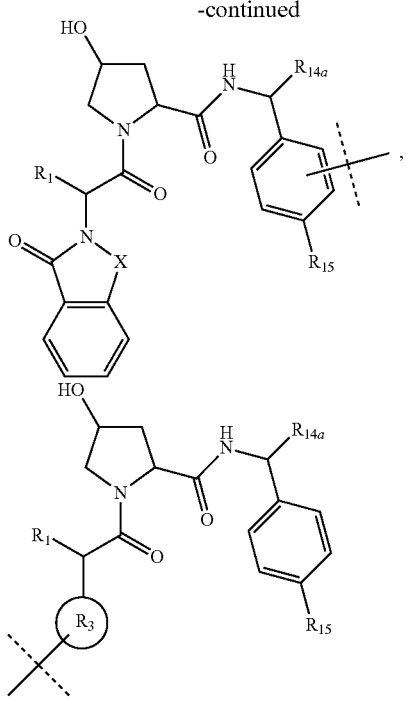

wherein:
R₁ is H, ethyl, isopropyl, tert-butyl, sec-butyl, cyclopropyl, cyclobutyl, cyclopentyl, or cyclohexyl; optionally substituted alkyl, optionally substituted hydroxyalkyl, optionally substituted heteroaryl, or haloalkyl;
R$_{14a}$ is H, haloalkyl, optionally substituted alkyl, methyl, fluoromethyl, hydroxymethyl, ethyl, isopropyl, or cyclopropyl;
R$_{15}$ is selected from the group consisting of H, halogen, CN, OH, NO₂, optionally substituted heteroaryl, optionally substituted aryl; optionally substituted alkyl, optionally substituted haloalkyl, optionally substituted haloalkoxy, cycloalkyl, or cycloheteroalkyl;
X is C, CH₂, or C=O
R₃ is a bond or an optionally substituted 5 or 6 membered heteroaryl; and wherein the dashed line indicates the site of attachment of at least one PTM, another ULM (ULM') or a chemical linker moiety coupling at least one PTM or a ULM' or both to ULM (ULM-a).

In certain embodiments, ULM comprises a group according to the chemical structure:

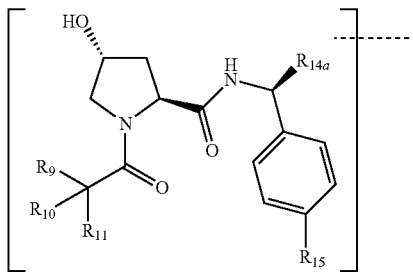

wherein:
R$_{14a}$ is H, haloalkyl, optionally substituted alkyl, methyl, fluoromethyl, hydroxymethyl, ethyl, isopropyl, or cyclopropyl;

R₉ is H;
R₁₀ is H, ethyl, isopropyl, tert-butyl, sec-butyl, cyclopropyl, cyclobutyl, cyclopentyl, or cyclohexyl;
R11 is

or optionally substituted heteroaryl;
p is 0, 1, 2, 3, or 4;
each R$_{18}$ is independently halo, optionally substituted alkoxy, cyano, optionally substituted alkyl, haloalkyl, haloalkoxy or a linker;
R12 is H, C=O;
R13 is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl,
R$_{15}$ is selected from the group consisting of H, halogen, Cl, CN, OH, NO₂, optionally substituted heteroaryl, optionally substituted aryl;

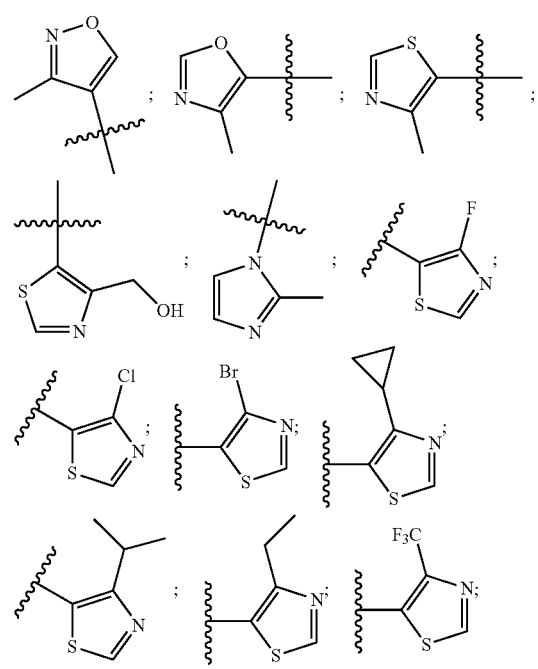

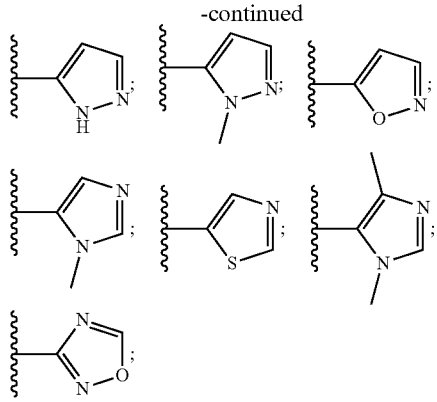
and
wherein the dashed line indicates the site of attachment of at least one PTM, another ULM (ULM') or a chemical linker moiety coupling at least one PTM or a ULM' or both to ULM.
In certain embodiments, the ULM is selected from the following structures:
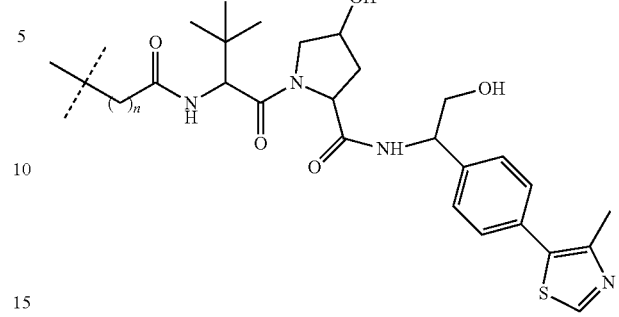
ULM-a2
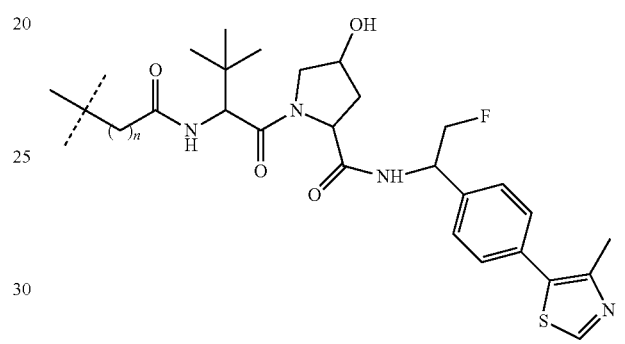
ULM-a3
ULM-a4
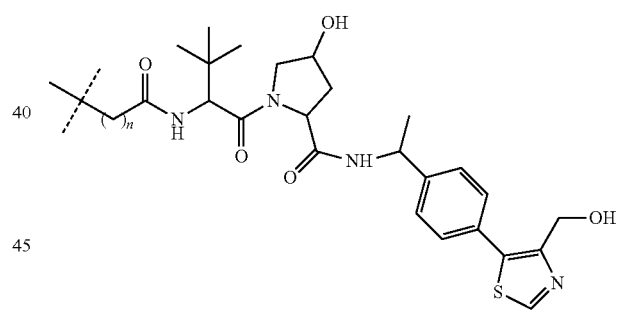
ULM-a5
ULM-a6
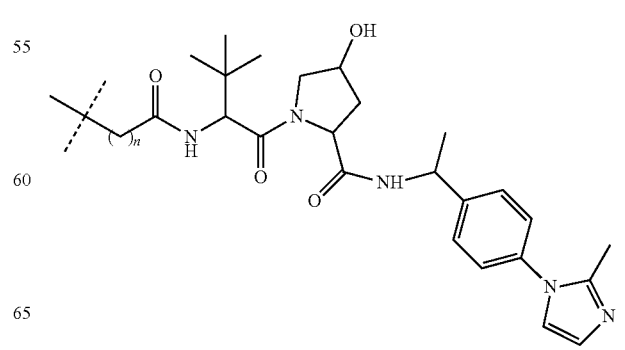
ULM-a7

ULM-a8
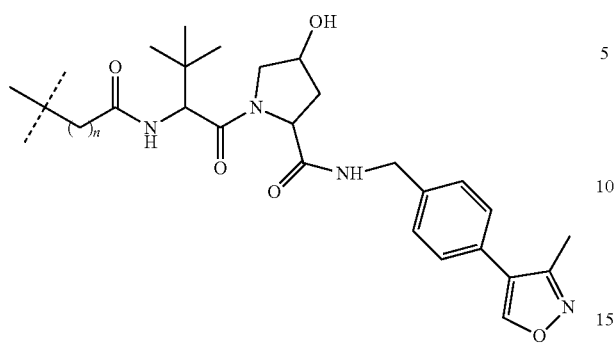
ULM-a12
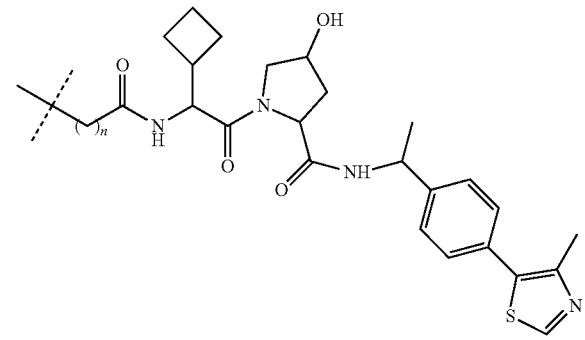
ULM-a9
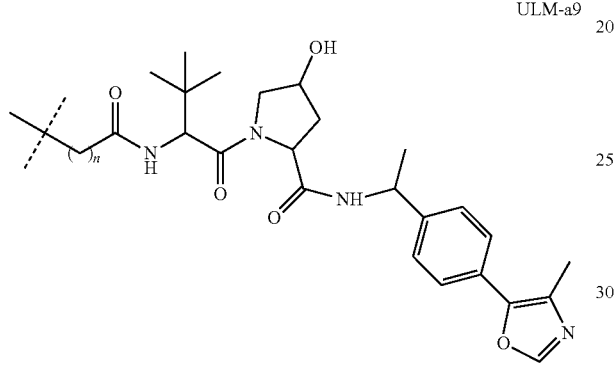
ULM-a13
ULM-a10
ULM-a14
ULM-a11
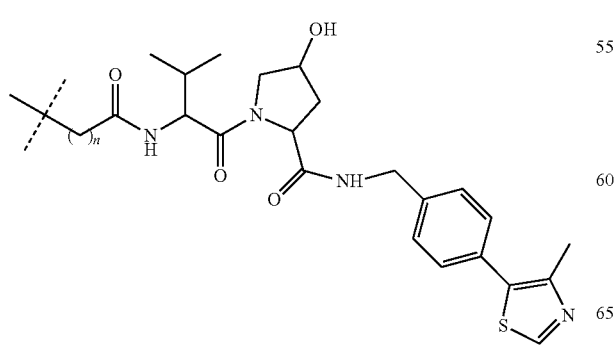
ULM-a15
where n is 0 or 1.

In certain embodiments, the ULM is selected from the following structures:
ULM-b1
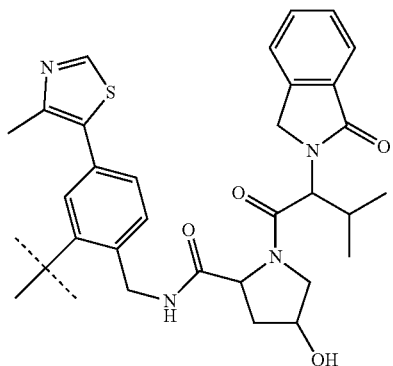
ULM-b2
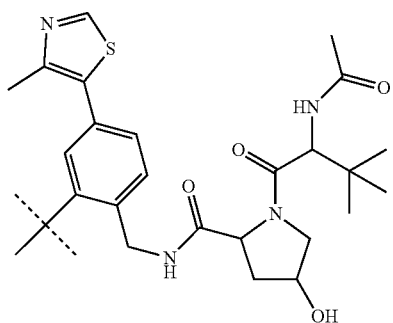
ULM-b3
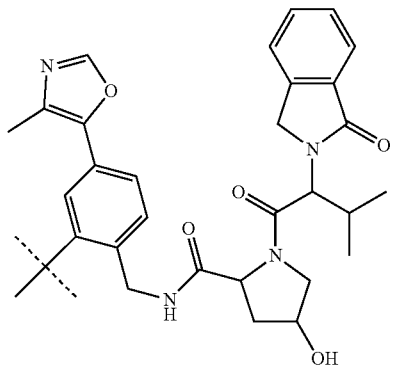
ULM-b4
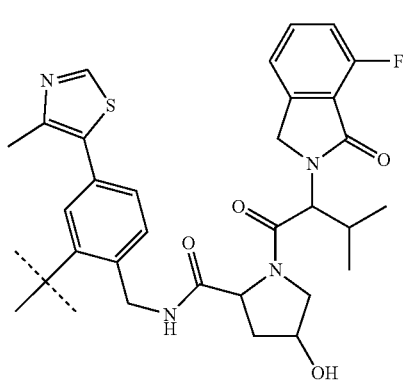
ULM-b5
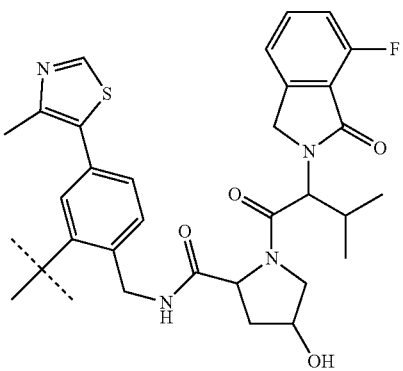
ULM-b6
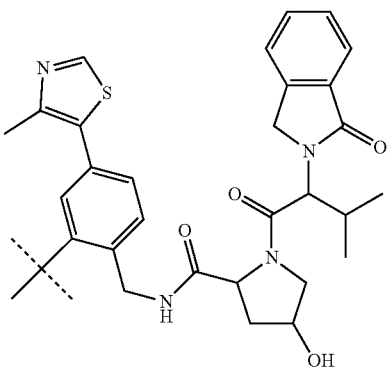
ULM-b7
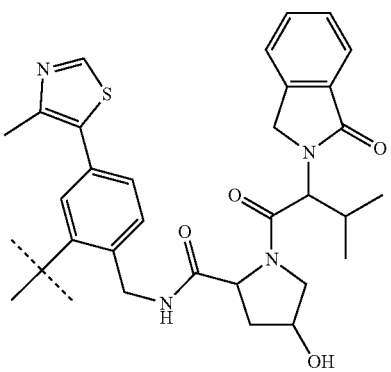
ULM-b8
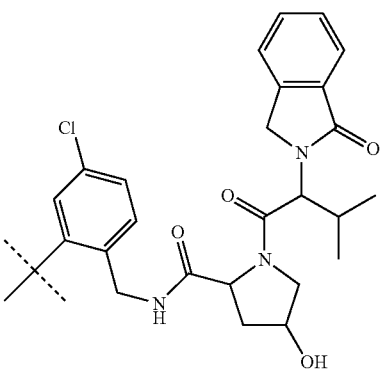

47 -continued
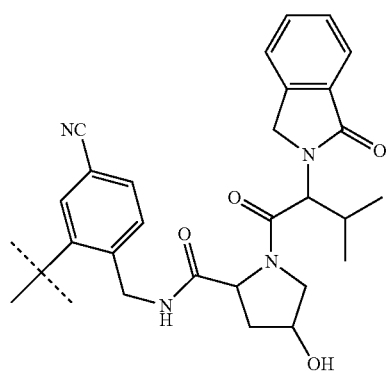
ULM-b9
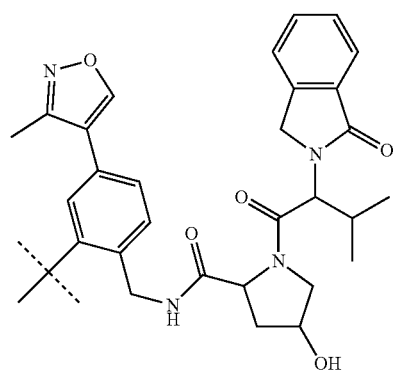
ULM-b7
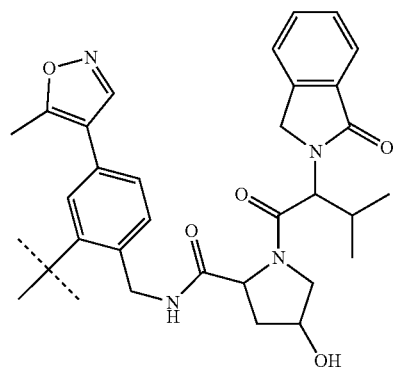
ULM-b8
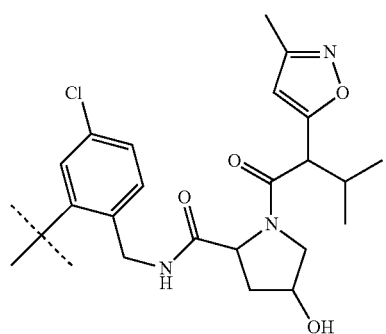
ULM-b9
48 -continued
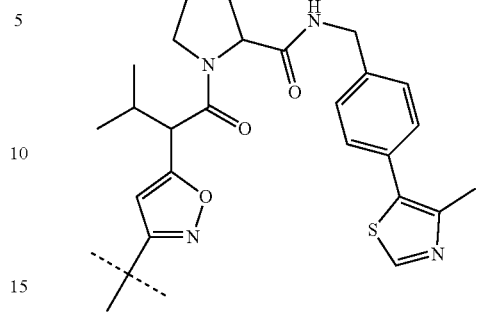
ULM-c1
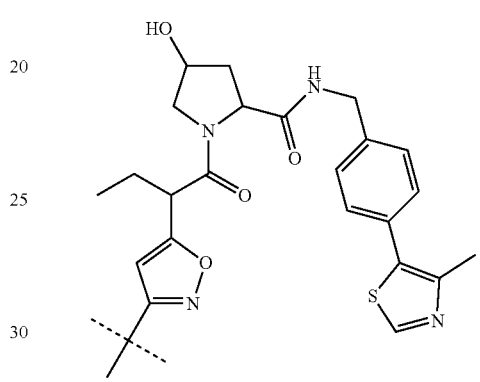
ULM-c2
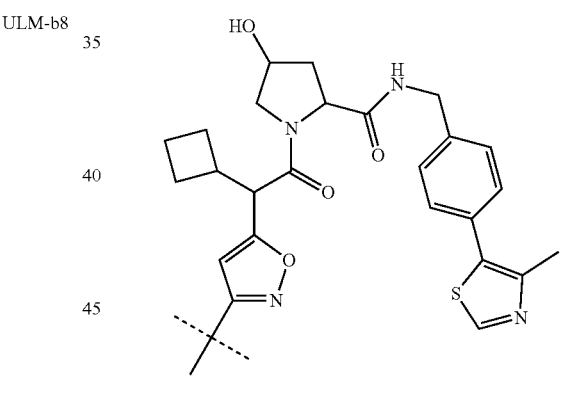
ULM-c3
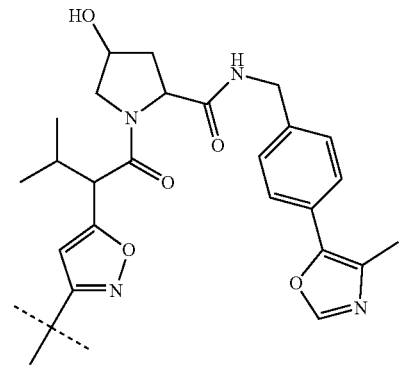
ULM-c4

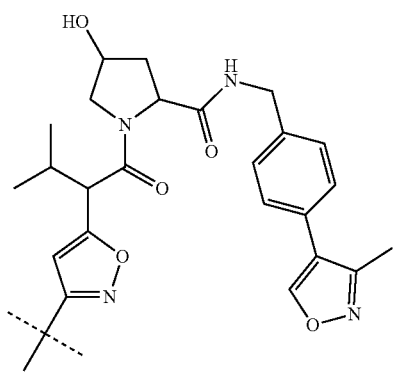
ULM-c5
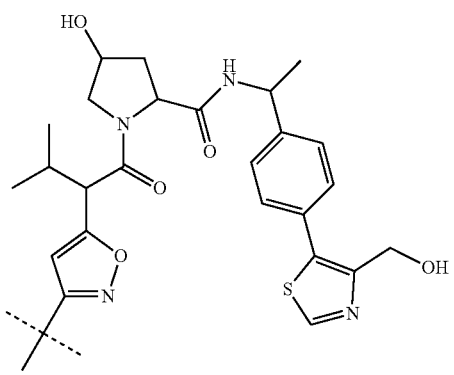
ULM-c9
ULM-c6
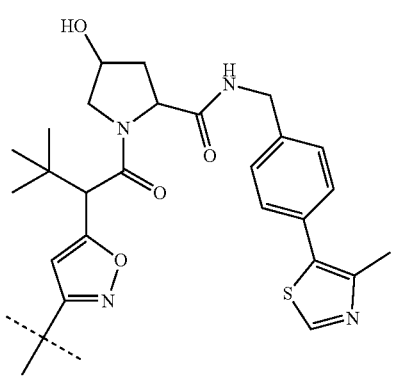
ULM-c10
ULM-c7
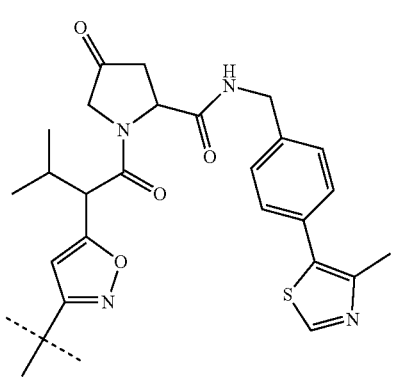
ULM-c11
ULM-c8
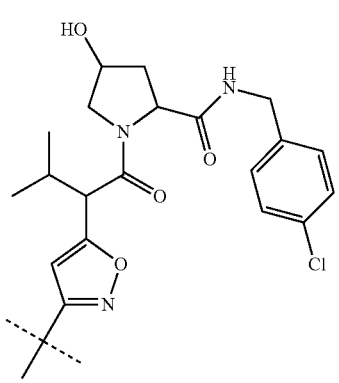
ULM-c12

ULM-c13
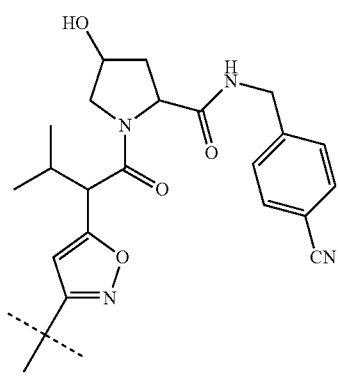
ULM-c14
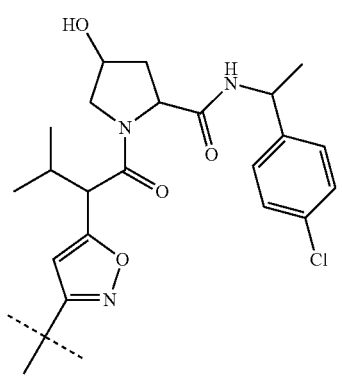
ULM-c15
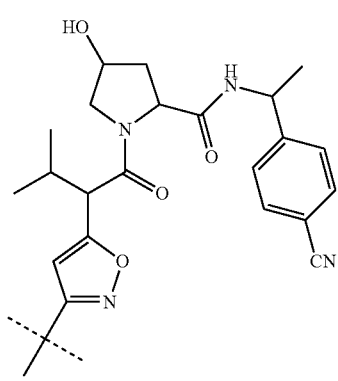
ULM-d1
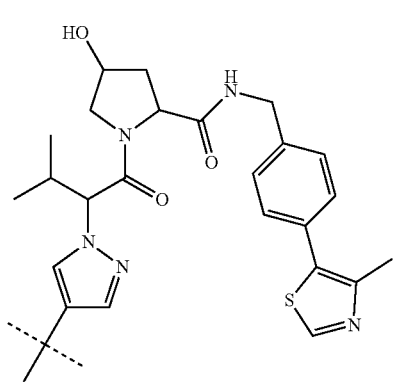
ULM-d2
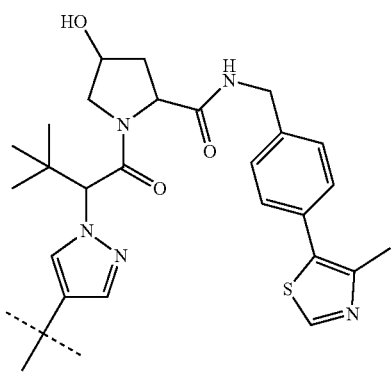
ULM-d3
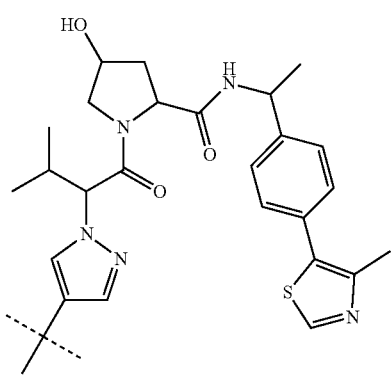
ULM-d4
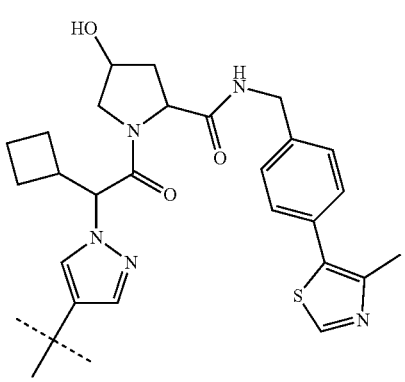
ULM-d5
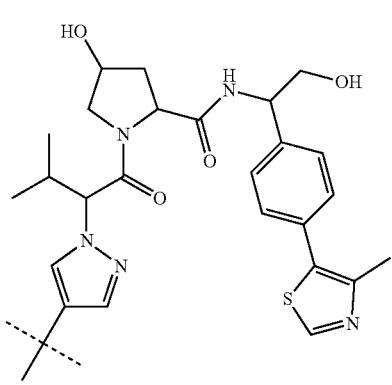

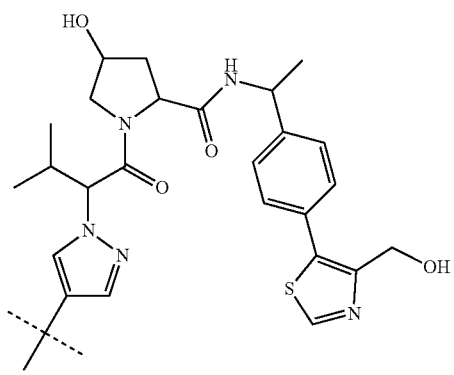
ULM-d6
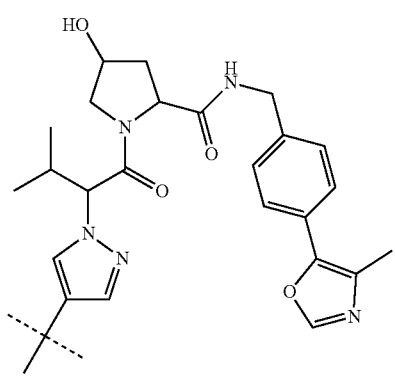
ULM-d7
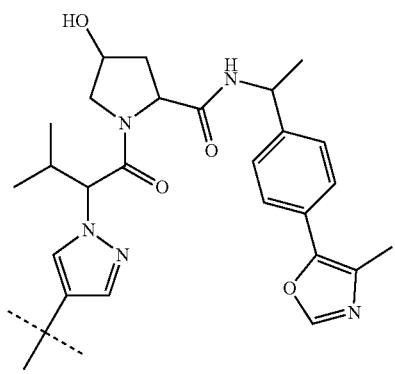
ULM-d8
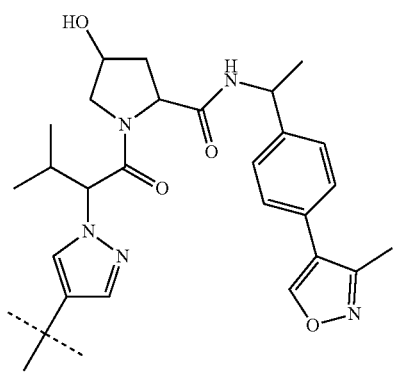
ULM-d9
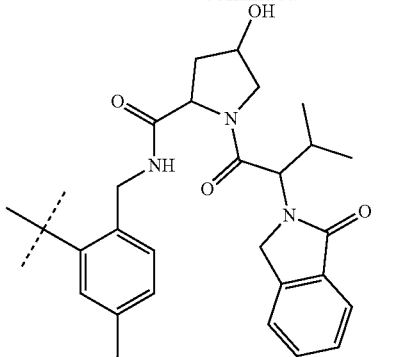
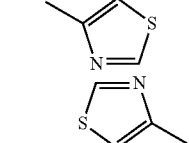
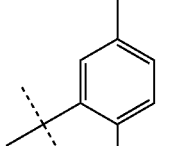
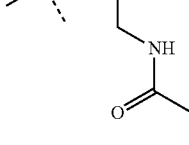
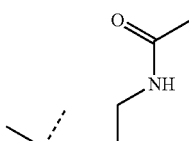
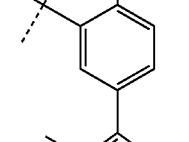
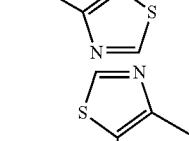
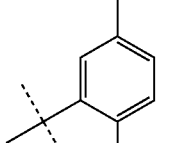
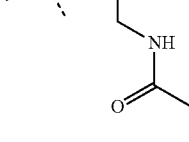

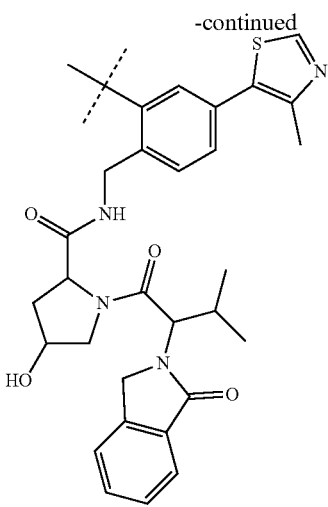

wherein the phenyl ring in ULM-a1 through ULM-a15, ULM-b1 through ULM-b12, ULM-c1 through ULM-c15 and ULM-d1 through ULM-d9 is optionally substituted with fluorine, lower alkyl and alkoxy groups, and wherein the dashed line indicates the site of attachment of at least one PTM, another ULM (ULM') or a chemical linker moiety coupling at least one PTM or a ULM' or both to ULM-a.

In one embodiment, the phenyl ring in ULM-a1 through ULM-a15, ULM-b1 through ULM-b12, ULM-c1 through ULM-c15 and ULM-d1 through ULM-d9 can be functionalized as the ester to make it a part of the prodrug.

In certain embodiments, the hydroxyl group on the pyrrolidine ring of ULM-a1 through ULM-a15, ULM-b1 through ULM-b12, ULM-c1 through ULM-c15 and ULM-d1 through ULM-d9, respectively, comprises an ester-linked prodrug moiety.

In any of the aspects or embodiments described herein, the ULM and where present, ULM', are each independently a group according to the chemical structure:

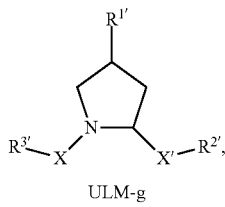

ULM-g wherein:
- $R^{1'}$ of ULM-g is an optionally substituted $C_1$-$C_6$ alkyl group, an optionally substituted —$(CH_2)_n$OH, an optionally substituted —$(CH_2)_n$SH, an optionally substituted $(CH_2)_n$—O—$(C_1$-$C_6)$alkyl group, an optionally substituted $(CH_2)_n$—WCOCW—$(C_0$-$C_6)$alkyl group containing an epoxide moiety WCOCW where each W is independently H or a $C_1$-$C_3$ alkyl group, an optionally substituted —$(CH_2)_n$COOH, an optionally substituted —$(CH_2)_n$C(O)—$(C_1$-$C_6$ alkyl), an optionally substituted —$(CH_2)_n$NHC(O)—$R_1$, an optionally substituted —$(CH_2)_n$C(O)—$NR_1R_2$, an optionally substituted —$(CH_2)_n$OC(O)—$NR_1R_2$, —$(CH_2O)_n$H, an optionally substituted —$(CH_2)_n$OC(O)—$(C_1$-$C_6$ alkyl), an optionally substituted —$(CH_2)_n$C(O)—O—$C_1$-$C_6$ alkyl), an optionally substituted —$(CH_2O)_n$COOH, an optionally substituted —$(OCH_2)_n$O—$(C_1$-$C_6$ alkyl), an optionally substituted —$(CH_2O)_n$C(O)—$(C_1$-$C_6$ alkyl), an optionally substituted —$(OCH_2)_n$NHC(O)—$R_1$, an optionally substituted —$(CH_2O)_n$C(O)—$NR_1R_2$, —$(CH_2CH_2O)_n$H, an optionally substituted —$(CH_2CH_2O)_n$COOH, an optionally substituted —$(OCH_2CH_2)_n$O—$(C_1$-$C_6$ alkyl), an optionally substituted —$(CH_2CH_2O)_n$C(O)—$(C_1$-$C_6$ alkyl), an optionally substituted —$(OCH_2CH_2)_n$NHC(O)—$R_1$, an optionally substituted —$(CH_2CH_2O)_n$C(O)—$NR_1R_2$, an optionally substituted —$SO_2R_S$, an optionally substituted $S(O)R_S$, $NO_2$, CN or halogen (F, Cl, Br, I, preferably F or Cl);

- $R_1$ and $R_2$ of ULM-g are each independently H or a $C_1$-$C_6$ alkyl group which may be optionally substituted with one or two hydroxyl groups or up to three halogen groups (preferably fluorine);

- $R_S$ of ULM-g is a $C_1$-$C_6$ alkyl group, an optionally substituted aryl, heteroaryl or heterocycle group or a —$(CH_2)_m NR_1R_2$ group;

- X and X' of ULM-g are each independently C=O, C=S, —S(O), S(O)$_2$, (preferably X and X' are both C=O);

- $R^{2'}$ of ULM-g is an optionally substituted —$(CH_2)_n$—(C=O)$_u$(NR$_1$)$_v$(SO$_2$)$_w$alkyl group, an optionally substituted —$(CH_2)_n$—(C=O)$_u$(NR$_1$)$_v$(SO$_2$)$_w$NR$_{1N}$R$_{2N}$ group, an optionally substituted —$(CH_2)_n$—(C=O)$_u$(NR$_1$)$_v$(SO$_2$)$_w$-Aryl, an optionally substituted —$(CH_2)_w$—(C=O)$_u$(NR$_1$)$_v$(SO$_2$)$_w$-Heteroaryl, an optionally substituted —$(CH_2)_n$—(C=O)$_v$NR(SO$_2$)$_w$-Heterocycle, an optionally substituted —NR$^1$—$(CH_2)_n$—C(O)$_u$(NR$_1$)$_v$(SO$_2$)$_w$-alkyl, an optionally substituted —NR$^1$—$(CH_2)_n$—C(O)$_u$(NR$_1$)$_v$(SO$_2$)$_w$—NR$_{1N}$R$_{2N}$, an optionally substituted —NR$^1$—$(CH_2)_n$—C(O)$_u$(NR$_1$)$_v$(SO$_2$)$_w$—NR$_1$C(O)R$_{1N}$, an optionally substituted —NR$^1$—$(CH_2)_n$—(C=O)$_u$(NR$_1$)$_v$(SO$_2$)$_w$-Aryl, an optionally substituted —NR$^1$—$(CH_2)_n$—(C=O)$_u$(NR$_1$)$_v$(SO$_2$)$_w$-Heteroaryl or an optionally substituted —NR$^1$—$(CH_2)_n$—(C=O)$_v$NR$_1$(SO$_2$)$_w$-Heterocycle, an optionally substituted —$X^{R2'}$-alkyl group; an optionally substituted —$X^{R2'}$-Aryl group; an optionally substituted —$X^{R2'}$-Heteroaryl group; an optionally substituted —$X^{R2'}$-Heterocycle group; an optionally substituted;

- $R^{3'}$ of ULM-g is an optionally substituted alkyl, an optionally substituted —$(CH_2)_n$—(O)$_u$(NR$_1$)$_v$(SO$_2$)$_w$-alkyl, an optionally substituted —$(CH_2)_n$—C(O)$_u$(NR$_1$)$_v$(SO$_2$)$_w$—NR$_{1N}$R$_{2N}$, an optionally substituted —$(CH_2)_n$—C(O)$_u$(NR$_1$)$_v$(SO$_2$)$_w$—NR$_1$C(O)R$_{1N}$, an optionally substituted —$(CH_2)_n$—C(O)$_u$(NR$_1$)$_v$(SO$_2$)$_w$—C(O)NR$_1$R$_2$, an optionally substituted —$(CH_2)_n$—C(O)$_u$(NR$_1$)$_v$(SO$_2$)$_w$-Aryl, an optionally substituted —$(CH_2)_n$—C(O)$_u$(NR$_1$)$_v$(SO$_2$)$_w$-Heteroaryl, an optionally substituted —$(CH_2)_n$—C(O)$_u$(NR$_1$)$_v$(SO$_2$)$_w$-Heterocycle, an optionally substituted —NR$^1$—$(CH_2)_n$—C(O)$_u$(NR$_1$)$_v$(SO$_2$)$_w$-alkyl, an optionally substituted —NR$^1$—$(CH_2)_n$—C(O)$_u$(NR$_1$)$_v$(SO$_2$)$_w$—NR$_{1N}$R$_{2N}$, an optionally substituted —NR$^1$—$(CH_2)_n$—C(O)$_u$(NR$_1$)$_v$(SO$_2$)$_w$—NR$_1$C(O)R$_{1N}$, an optionally substituted —NR$^1$—$(CH_2)_n$—C(O)$_u$(NR$_1$)$_v$(SO$_2$)$_w$-Aryl, an optionally substituted —NR$^1$—$(CH_2)_n$—C(O)$_u$(NR$_1$)$_v$(SO$_2$)$_w$-Heteroaryl, an optionally substituted —NR$^1$—$(CH_2)_n$—C(O)$_u$(NR$_1$)$_v$(SO$_2$)$_w$-Heterocycle, an optionally substituted —O—$(CH_2)$n-(C=O)$_u$(NR$_1$)$_v$(SO$_2$)$_w$-alkyl, an optionally substituted —O—$(CH_2)_n$—(C=O)$_u$(NR)$_v$(SO$_2$)$_w$—NR$_{1N}$R$_{2N}$, an optionally substituted —O—$(CH_2)$n-(C=O)$_u$(NR)$_v$(SO$_2$)$_w$—NR$_1$C(O)R$_{1N}$, an optionally substituted —O—(CH$_2$)n-(C=O)$_u$(NR$_1$)$_v$(SO$_2$)$_w$-Aryl, an optionally substituted —O—(CH$_2$)$_n$—(C=O)$_u$—(NR$_1$)$_v$(SO$_2$)$_w$-Heteroaryl or an optionally substituted —O—(CH$_2$)$_n$—(C=O)$_u$(NR$_1$)$_v$(SO$_2$)$_w$-Heterocycle; —(CH$_2$)$_n$—(V)$_{n'}$—(CH$_2$)$_n$—(V)$_{n'}$-alkyl group, an optionally substituted —(CH$_2$)$_n$—(V)$_{n'}$—(CH$_2$)$_n$—(V)$_{n'}$-Aryl group, an optionally substituted —(CH$_2$)$_n$—(V)$_{n'}$—(CH$_2$)$_n$—(V)$_{n'}$-Heteroaryl group, an optionally substituted —(CH$_2$)$_n$—(V)$_{n'}$—(CH$_2$)$_n$—(V)$_{n'}$-Heterocycle group, an optionally substituted —(CH$_2$)$_n$—N(R$_{1'}$)(C=O)$_{m'}$—(V)$_{n'}$-alkyl group, an optionally substituted —(CH$_2$)$_n$—N(R$_{1'}$)(C=O)$_{m'}$—(V)$_{n'}$-Aryl group, an optionally substituted —(CH$_2$)$_n$—N(R$_{1'}$)(C=O)$_{m'}$—(V)$_{n'}$-Heteroaryl group, an optionally substituted —(CH$_2$)$_n$—N(R')(C=O)$_{m'}$—(V)$_{n'}$-Heterocycle group, an optionally substituted —X$^{R3'}$-alkyl group; an optionally substituted —X$^{R3'}$-Aryl group; an optionally substituted —X$^{R3'}$-Heteroaryl group; an optionally substituted —X$^{R3'}$-Heterocycle group; an optionally substituted;

R$_{1N}$ and R$_{2N}$ of ULM-g are each independently H, C$_1$-C$_6$ alkyl which is optionally substituted with one or two hydroxyl groups and up to three halogen groups or an optionally substituted —(CH$_2$)$_n$-Aryl, —(CH$_2$)$_n$-Heteroaryl or —(CH$_2$)$_n$-Heterocycle group;

V of ULM-g is O, S or NR$_1$;

R$_1$ of ULM-g is the same as above;

R$^1$ and R$_1$ of ULM-g are each independently H or a C$_1$-C$_3$ alkyl group;

X$^{R2'}$ and X$^{R3'}$ of ULM-g are each independently an optionally substituted —CH$_2$)$_n$—, —CH$_2$)$_n$—CH(X$_v$)=CH(X$_v$)— (cis or trans), —CH$_2$)$_n$—CH≡CH—, —(CH$_2$CH$_2$O)$_n$— or a C$_3$-C$_6$ cycloalkyl group, where X$_v$ is H, a halo or a C$_1$-C$_3$ alkyl group which is optionally substituted;

each m of ULM-g is independently 0, 1, 2, 3, 4, 5, 6;
each m' of ULM-g is independently 0 or 1;
each n of ULM-g is independently 0, 1, 2, 3, 4, 5, 6;
each n' of ULM-g is independently 0 or 1;
each u of ULM-g is independently 0 or 1;
each v of ULM-g is independently 0 or 1;
each w of ULM-g is independently 0 or 1; and any one or more of R$^1$, R$^{2'}$, R$^{3'}$, X and X' of ULM-g is optionally modified to be covalently bonded to the PTM group through a linker group when PTM is not ULM', or when PTM is ULM', any one or more of R$^1$, R$^{2'}$, R$^{3'}$, X and X' of each of ULM and ULM' are optionally modified to be covalently bonded to each other directly or through a linker group, or a pharmaceutically acceptable salt, stereoisomer, solvate or polymorph thereof.

In any of the aspects or embodiments described herein, the ULM and when present, ULM', are each independently a group according to the chemical structure:

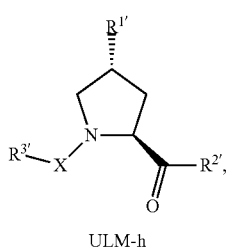

ULM-h wherein:
each of R$^1$, R$^{2'}$ and R$^{3'}$ of ULM-h are the same as above and X is C=O, C=S, —S(O) group or a S(O)$_2$ group, more preferably a C=O group, and any one or more of R$^{1'}$, R$^{2'}$ and R$^{3'}$ of ULM-h are optionally modified to bind a linker group to which is further covalently bonded to the PTM group when PTM is not ULM', or when PTM is ULM', any one or more of R$^1$, R$^{2'}$, R$^{3'}$ of each of ULM and ULM' are optionally modified to be covalently bonded to each other directly or through a linker group, or a pharmaceutically acceptable salt, enantiomer, diastereomer, solvate or polymorph thereof.

In any of the aspects or embodiments described herein, the ULM, and when present, ULM', are each independently according to the chemical structure:

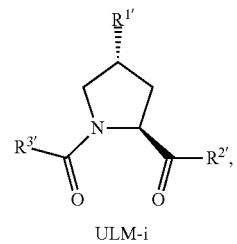

ULM-i wherein:
any one or more of R$^{1'}$, R$^{2'}$ and R$^{3'}$ of ULM-I are optionally modified to bind a linker group to which is further covalently bonded to the PTM group when PTM is not ULM', or when PTM is ULM', any one or more of R$^1$, R$^{2'}$, R$^{3'}$ of each of ULM and ULM' are optionally modified to be covalently bonded to each other directly or through a linker group, or a pharmaceutically acceptable salt, enantiomer, diastereomer, solvate or polymorph thereof.

In further preferred aspects of the invention, R$^{1'}$ of ULM-g through ULM-i is preferably a hydroxyl group or a group which may be metabolized to a hydroxyl or carboxylic group, such that the compound represents a prodrug form of an active compound. Exemplary preferred R$^{1'}$ groups include, for example, —(CH$_2$)$_n$OH, (CH$_2$)$_n$—O—(C$_1$-C$_6$)alkyl group, —(CH$_2$)$_n$COOH, —(CH$_2$O)$_n$H, an optionally substituted —(CH$_2$)$_n$OC(O)—(C$_1$-C$_6$ alkyl), or an optionally substituted —(CH$_2$)$_n$C(O)—O—(C$_1$-C$_6$ alkyl), wherein n is 0 or 1. Where R$^1$ is or contains a carboxylic acid group, a hydroxyl group or an amine group, the hydroxyl group, carboxylic acid group or amine (each of which may be optionally substituted), may be further chemically modified to provide a covalent link to a linker group to which the PTM group (including a ULM' group) is bonded;

X and X', where present, of ULM-g and ULM-h are preferably a C=O, C=S, —S(O) group or a S(O)$_2$ group, more preferably a C=O group;

R$^{2'}$ of ULM-g through ULM-i is preferably an optionally substituted —NR$^1$-T-Aryl, an optionally substituted —NR$^1$-T-Heteroaryl group or an optionally substituted —NR$^1$-T-Heterocycle, where R$^1$ is H or CH$_3$, preferably H and T is an optionally substituted —(CH$_2$)$_n$— group, wherein each one of the methylene groups may be optionally substituted with one or two substituents, preferably selected from halogen, an amino acid sidechain as otherwise described herein or a C$_1$-C$_3$ alkyl group, preferably one or two methyl groups, which may be optionally substituted; and n is 0 to 6, often 0, 1, 2 or 3, preferably 0 or 1. Alternatively, T may also be a —(CH$_2$O)$_n$— group, a —(OCH$_2$)$_n$— group, a —(CH$_2$CH$_2$O)$_n$— group, a —(OCH$_2$CH$_2$)$_n$— group, all of which groups are optionally substituted.

Preferred Aryl groups for R$^{2'}$ of ULM-g through ULM-i include optionally substituted phenyl or naphthyl groups, preferably phenyl groups, wherein the phenyl or naphthyl group is optionally connected to a PTM group (including a ULM' group) via a linker group, a halogen (preferably F or Cl), an amine, monoalkyl- or dialkyl amine (preferably, dimethylamine), F, Cl, OH, COOH, C$_1$-C$_6$ alkyl, preferably CH$_3$, CF$_3$, OMe, OCF$_3$, NO$_2$, or CN group (each of which may be substituted in ortho-, meta- and/or para-positions of the phenyl ring, preferably para-), an optionally substituted phenyl group (the phenyl group itself is optionally connected to a PTM group (including a ULM' group) via a linker group), and/or at least one of F, Cl, OH, COOH, CH$_3$, CF$_3$, OMe, OCF$_3$, NO$_2$, or CN group (in ortho-, meta- and/or para-positions of the phenyl ring, preferably para-), a naphthyl group, which may be optionally substituted, an optionally substituted heteroaryl, preferably an optionally substituted isoxazole including a methylsubstituted isoxazole, an optionally substituted oxazole including a methyl-substituted oxazole, an optionally substituted thiazole including a methyl substituted thiazole, an optionally substituted isothiazole including a methyl substituted isothiazole, an optionally substituted pyrrole including a methyl-substituted pyrrole, an optionally substituted imidazole including a methylimidazole, an optionally substituted benzimidazole or methoxybenzylimidazole, an optionally substituted oximidazole or methyloximidazole, an optionally substituted diazole group, including a methyldiazole group, an optionally substituted triazole group, including a methylsubstituted triazole group, an optionally substituted pyridine group, including a halo—(preferably, F) or methylsubstitutedpyridine group or an oxapyridine group (where the pyridine group is linked to the phenyl group by an oxygen), an optionally substituted furan, an optionally substituted benzofuran, an optionally substituted dihydrobenzofuran, an optionally substituted indole, indolizine or azaindolizine (2, 3, or 4-azaindolizine), an optionally substituted quinoline, an optionally substituted group according to the chemical structure:

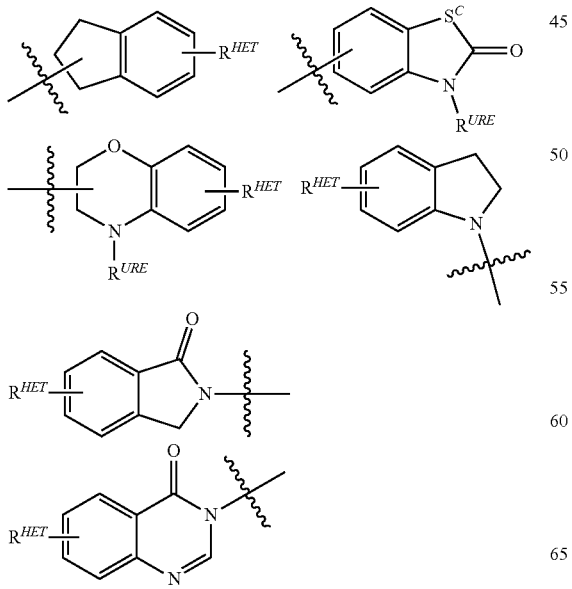

-continued

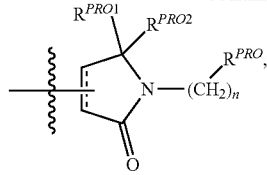

wherein:

S$^c$ of ULM-g through ULM-i is CHR$^{SS}$, NR$^{URE}$, or O;

R$^{HET}$ of ULM-g through ULM-i is H, CN, NO$_2$, halo (preferably Cl or F), optionally substituted C$_1$-C$_6$ alkyl (preferably substituted with one or two hydroxyl groups or up to three halo groups (e.g. CF$_3$), optionally substituted O(C$_1$-C$_6$ alkyl) (preferably substituted with one or two hydroxyl groups or up to three halo groups) or an optionally substituted acetylenic group —C≡C—R$_a$ where R$_a$ is H or a C$_1$-C$_6$ alkyl group (preferably C$_1$-C$_3$ alkyl);

R$^{SS}$ of ULM-g through ULM-i is H, CN, NO$_2$, halo (preferably F or Cl), optionally substituted C$_1$-C$_6$ alkyl (preferably substituted with one or two hydroxyl groups or up to three halo groups), optionally substituted O—(C$_1$-C$_6$ alkyl) (preferably substituted with one or two hydroxyl groups or up to three halo groups) or an optionally substituted —C(O)(C$_1$-C$_6$ alkyl) (preferably substituted with one or two hydroxyl groups or up to three halo groups);

R$^{URE}$ of ULM-g through ULM-i is H, a C$_1$-C$_6$ alkyl (preferably H or C$_1$-C$_3$ alkyl) or a —C(O)(C$_1$-C$_6$ alkyl) each of which groups is optionally substituted with one or two hydroxyl groups or up to three halogen, preferably fluorine groups, or an optionally substituted phenyl group, an optionally substituted heteroaryl, or an optionally substituted heterocycle, preferably for example piperidine, morpholine, pyrrolidine, tetrahydrofuran);

R$^{PRO}$ of ULM-g through ULM-i is H, optionally substituted C$_1$-C$_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a C$_1$-C$_3$ alkyl group, preferably methyl or a halo group, preferably F or Cl), benzofuran, indole, indolizine, azaindolizine;

R$^{PRO1}$ and R$^{PRO2}$ of ULM-g through ULM-i are each independently H, an optionally substituted C$_1$-C$_3$ alkyl group or together form a keto group; and each n of ULM-g through ULM-i is independently 0, 1, 2, 3, 4, 5, or 6 (preferably 0 or 1), or an optionally substituted heterocycle, preferably tetrahydrofuran, tetrahydrothiene, piperidine, piperazine or morpholine (each of which groups when substituted, are preferably substituted with a methyl or halo (F, Br, Cl), each of which groups may be optionally connected to a PTM group (including a ULM' group) via a linker group.

In certain preferred aspects,

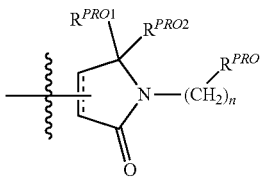

of ULM-g through ULM-i is a

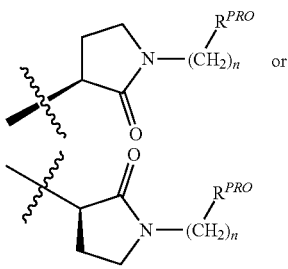

group,
where $R^{PRO}$ and n of ULM-g through ULM-i are the same as above.

Preferred heteroaryl groups for $R^{2'}$ of ULM-g through ULM-i include an optionally substituted quinoline (which may be attached to the pharmacophore or substituted on any carbon atom within the quinoline ring), an optionally substituted indole, an optionally substituted indolizine, an optionally substituted azaindolizine, an optionally substituted benzofuran, including an optionally substituted benzofuran, an optionally substituted isoxazole, an optionally substituted thiazole, an optionally substituted isothiazole, an optionally substituted thiophene, an optionally substituted pyridine (2-, 3, or 4-pyridine), an optionally substituted imidazole, an optionally substituted pyrrole, an optionally substituted diazole, an optionally substituted triazole, a tetrazole, an optionally substituted oximidazole, or a group according to the chemical structure:

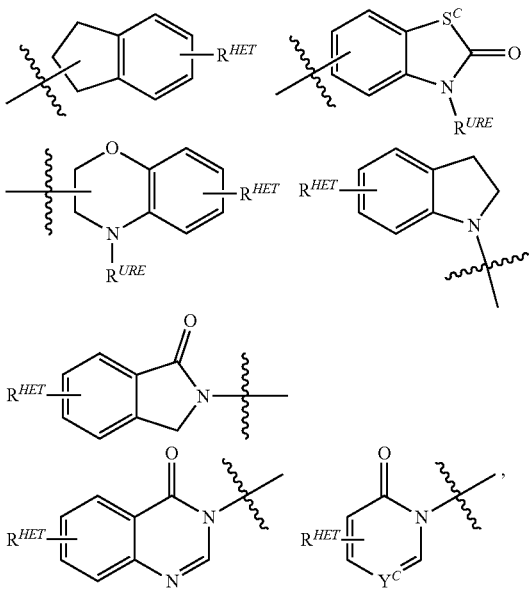

wherein:

$S^C$ of ULM-g through ULM-i is $CHR^{SS}$, $NR^{URE}$, or O;

$R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ of ULM-g through ULM-i is H or a $C_1$-$C_6$ alkyl group (preferably $C_1$-$C_3$ alkyl);

$R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);

$R^{URE}$ of ULM-g through ULM-i is H, a $C_1$-$C_6$ alkyl (preferably H or $C_1$-$C_3$ alkyl) or a —C(O)($C_1$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted, and $Y^C$ of ULM-g through ULM-i is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl), each of which groups may be optionally connected to a PTM group (including a ULM' group) via a linker group.

Preferred heterocycle groups for $R^2$ of ULM-g through ULM-i include tetrahydrofuran, tetrahydrothiene, tetrahydroquinoline, piperidine, piperazine, pyrrollidine, morpholine, oxane or thiane, each of which groups may be optionally substituted, or a group according to the chemical structure:

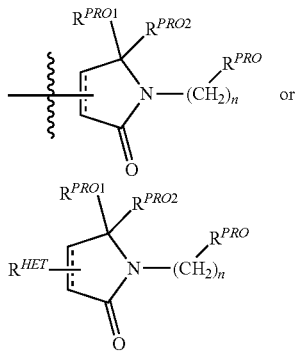

preferably, a

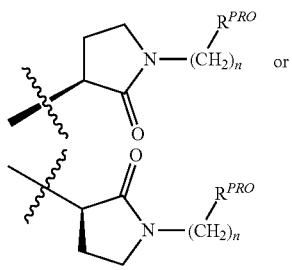

group,
wherein:
  $R^{PRO}$ of ULM-g through ULM-i is H, optionally substituted $C_1$-$C_6$ alkyl or an optionally substituted aryl, heteroaryl or heterocyclic group;
  $R^{PRO1}$ and $R^{PRO2}$ of ULM-g through ULM-i are each independently H, an optionally substituted $C_1$-$C_3$ alkyl group or together form a keto group and
  each n of ULM-g through ULM-i is independently 0, 1, 2, 3, 4, 5, or 6 (often 0 or 1), each of which groups may be optionally connected to a PTM group (including a ULM' group) via a linker group.

Preferred $R^{2'}$ substituents of ULM-g through ULM-i also include specifically (and without limitation to the specific compound disclosed) the $R^{2'}$ substituents which are found in the identified compounds disclosed herein (which includes the specific compounds which are disclosed in the present specification, and the figures which are attached hereto). Each of these $R^{2'}$ substituents may be used in conjunction with any number of $R^{3'}$ substituents which are also disclosed herein.

$R^{3'}$ of ULM-g through ULM-i is preferably an optionally substituted -T-Aryl, an optionally substituted -T-Heteroaryl, an optionally substituted -T-Heterocycle, an optionally substituted-$NR^1$-T-Aryl, an optionally substituted —$NR^1$-T-Heteroaryl or an optionally substituted-$NR^1$-T-Heterocycle, where $R^1$ is H or a $C_1$-$C_3$ alkyl group, preferably H or $CH_3$, T is an optionally substituted —$(CH_2)_n$— group, wherein each one of the methylene groups may be optionally substituted with one or two substituents, preferably selected from halogen, a $C_1$-$C_3$ alkyl group or the sidechain of an amino acid as otherwise described herein, preferably methyl, which may be optionally substituted; and n is 0 to 6, often 0, 1, 2, or 3 preferably 0 or 1. Alternatively, T may also be a —$(CH_2O)_n$— group, a —$(OCH_2)_n$— group, a —$(CH_2CH_2O)_n$— group, a —$(OCH_2CH_2)_n$— group, each of which groups is optionally substituted.

Preferred aryl groups for $R^{3'}$ of ULM-g through ULM-i include optionally substituted phenyl or naphthyl groups, preferably phenyl groups, wherein the phenyl or naphthyl group is optionally connected to a PTM group (including a ULM' group) via a linker group and/or a halogen (preferably F or Cl), an amine, monoalkyl- or dialkyl amine (preferably, dimethylamine), an amido group (preferably a —$(CH_2)_m$—$NR_1C(O)R_2$ group where m, $R_1$ and $R_2$ are the same as above), a halo (often F or Cl), OH, $CH_3$, $CF_3$, OMe, $OCF_3$, $NO_2$, CN or a $S(O)_2R_S$ group ($R_S$ is a a $C_1$-$C_6$ alkyl group, an optionally substituted aryl, heteroaryl or heterocycle group or a —$(CH_2)_m NR_1R_2$ group), each of which may be substituted in ortho-, meta- and/or para-positions of the phenyl ring, preferably para-), or an Aryl (preferably phenyl), Heteroaryl or Heterocycle. Preferably said substituent phenyl group is an optionally substituted phenyl group (i.e., the substituent phenyl group itself is preferably substituted with at least one of F, Cl, OH, SH, COOH, $CH_3$, $CF_3$, OMe, $OCF_3$, $NO_2$, CN or a linker group to which is attached a PTM group (including a ULM' group), wherein the substitution occurs in ortho-, meta- and/or para-positions of the phenyl ring, preferably para-), a naphthyl group, which may be optionally substituted including as described above, an optionally substituted heteroaryl (preferably an optionally substituted isoxazole including a methylsubstituted isoxazole, an optionally substituted oxazole including a methyl-substituted oxazole, an optionally substituted thiazole including a methyl substituted thiazole, an optionally substituted pyrrole including a methylsubstituted pyrrole, an optionally substituted imidazole including a methylimidazole, a benzylimidazole or methoxybenzylimidazole, an oximidazole or methyloximidazole, an optionally substituted diazole group, including a methyldiazole group, an optionally substituted triazole group, including a methylsubstituted triazole group, a pyridine group, including a halo— (preferably, F) or methylsubstitutedpyridine group or an oxapyridine group (where the pyridine group is linked to the phenyl group by an oxygen) or an optionally substituted heterocycle (tetrahydrofuran, tetrahydrothiophene, pyrrolidine, piperidine, morpholine, piperazine, tetrahydroquinoline, oxane or thiane. Each of the aryl, heteroaryl or heterocyclic groups may be optionally connected to a PTM group (including a ULM' group) via a linker group.

Preferred Heteroaryl groups for $R^{3'}$ of ULM-g through ULM-i include an optionally substituted quinoline (which may be attached to the pharmacophore or substituted on any carbon atom within the quinoline ring), an optionally substituted indole (including dihydroindole), an optionally substituted indolizine, an optionally substituted azaindolizine (2, 3 or 4-azaindolizine) an optionally substituted benzimidazole, benzodiazole, benzoxofuran, an optionally substituted imidazole, an optionally substituted isoxazole, an optionally substituted oxazole (preferably methyl substituted), an optionally substituted diazole, an optionally substituted triazole, a tetrazole, an optionally substituted benzofuran, an optionally substituted thiophene, an optionally substituted thiazole (preferably methyl and/or thiol substituted), an optionally substituted isothiazole, an optionally substituted triazole (preferably a 1,2,3-triazole substituted with a methyl group, a triisopropylsilyl group, an optionally substituted —$(CH_2)_m$—O—$C_1$-$C_6$ alkyl group or an optionally substituted —$(CH_2)_m$—C(O)—O—$C_1$-$C_6$ alkyl group), an optionally substituted pyridine (2-, 3, or 4-pyridine) or a group according to the chemical structure:

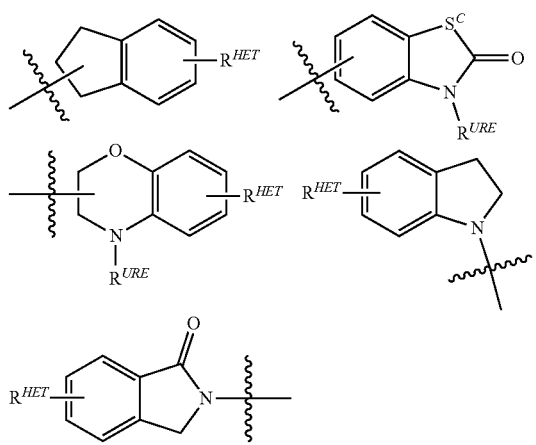

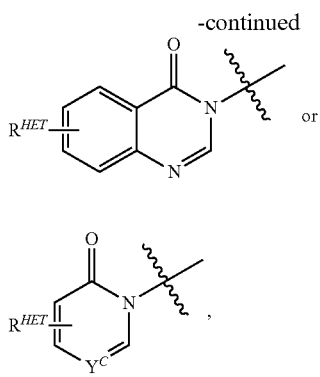 or

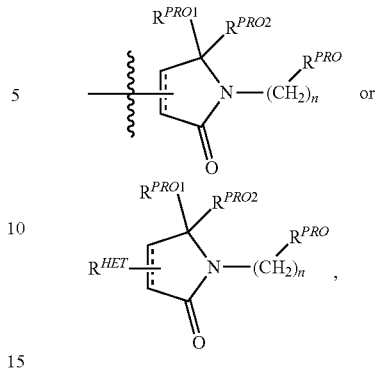 or

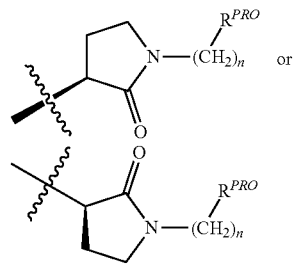

wherein:
- $S^c$ of ULM-g through ULM-i is $CHR^{SS}$, $NR^{URE}$, or O;
- $R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);
- $R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —$C(O)(C_1$-$C_6$ alkyl) (preferably substituted with one or two hydroxyl groups or up to three halo groups);
- $R^{URE}$ of ULM-g through ULM-i is H, a $C_1$-$C_6$ alkyl (preferably H or $C_1$-$C_3$ alkyl) or a —$C(O)(C_1$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted, and
- $Y^C$ of ULM-g through ULM-i is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl). Each of said heteroaryl groups may be optionally connected to a PTM group (including a ULM' group) via a linker group.

Preferred heterocycle groups for $R^{3'}$ of ULM-g through ULM-i include tetrahydroquinoline, piperidine, piperazine, pyrrollidine, morpholine, tetrahydrofuran, tetrahydrothiophene, oxane and thiane, each of which groups may be optionally substituted or a group according to the chemical structure:

preferably, a group,
wherein:
- $R^{PRO}$ of ULM-g through ULM-i is H, optionally substituted $C_1$-$C_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;
- $R^{PRO1}$ and $R^{PRO2}$ of ULM-g through ULM-i are each independently H, an optionally substituted $C_1$-$C_3$ alkyl group or together form a keto group, and
- each n of ULM-g through ULM-i is 0, 1, 2, 3, 4, 5, or 6 (preferably 0 or 1), wherein each of said Heterocycle groups may be optionally connected to a PTM group (including a ULM' group) via a linker group.

Preferred $R^{3'}$ substituents of ULM-g through ULM-i also include specifically (and without limitation to the specific compound disclosed) the $R^{3'}$ substituents which are found in the identified compounds disclosed herein (which includes the specific compounds which are disclosed in the present specification, and the figures which are attached hereto). Each of these $R^{3'}$ substituents may be used in conjunction with any number of $R^{2'}$ substituents, which are also disclosed herein.

In certain alternative preferred embodiments, $R^{2'}$ of ULM-g through ULM-i is an optionally substituted —$NR_1$—$X^{R2'}$-alkyl group, —$NR_1$—$X^{R2'}$-Aryl group; an optionally substituted —$NR_1$—$X^{R2'}$-HET, an optionally substituted —$NR_1$—$X^{R2'}$-Aryl-HET or an optionally substituted —$NR_1$—$X^{R2'}$-HET-Aryl, wherein:
R₁ of ULM-g through ULM-i is H or a $C_1$-$C_3$ alkyl group (preferably H);
$X^{R2'}$ of ULM-g through ULM-i is an optionally substituted —$(CH_2)_n$—, —$(CH_2)_n$—CH($X_v$)=CH($X_v$)-(cis or trans), —$(CH_2)_n$—CH≡CH—, —$(CH_2CH_2O)_n$— or a $C_3$-$C_6$ cycloalkyl group; and
$X_v$ of ULM-g through ULM-i is H, a halo or a $C_1$-$C_3$ alkyl group which is optionally substituted with one or two hydroxyl groups or up to three halogen groups;
Alkyl of ULM-g through ULM-i is an optionally substituted $C1$-$C_{10}$ alkyl (preferably a $C_1$-$C_6$ alkyl) group (in certain preferred embodiments, the alkyl group is end-capped with a halo group, often a Cl or Br);
Aryl of ULM-g through ULM-i is an optionally substituted phenyl or naphthyl group (preferably, a phenyl group); and
HET of ULM-g through ULM-i is an optionally substituted oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, benzofuran, indole, indolizine, azaindolizine, quinoline (when substituted, each preferably substituted with a $C_1$-$C_3$ alkyl group, preferably methyl or a halo group, preferably F or Cl) or a group according to the chemical structure:

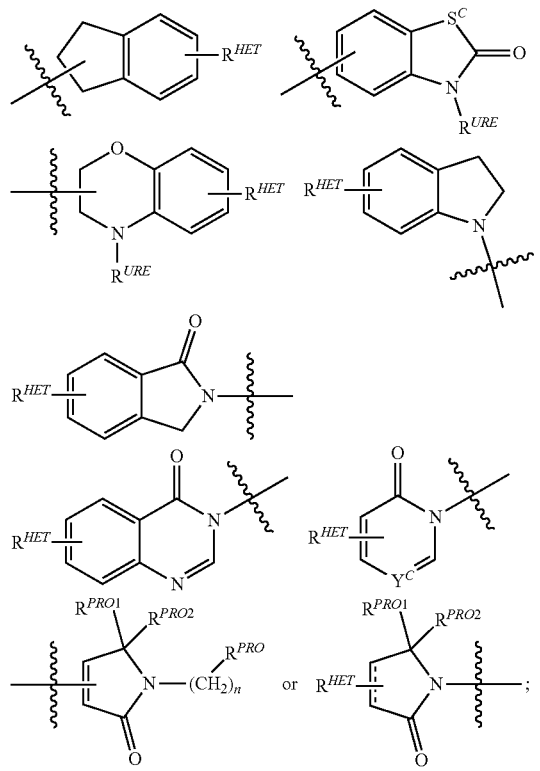

$S^c$ of ULM-g through ULM-i is $CHR^{SS}$, $NR^{URE}$, or O;
$R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);
$R^{URE}$ of ULM-g through ULM-i is H, a $C_1$-$C_6$ alkyl (preferably H or $C_1$-$C_3$ alkyl) or a —C(O)($C_1$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted;
$Y^C$ of ULM-g through ULM-i is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);
$R^{PRO}$ of ULM-g through ULM-i is H, optionally substituted $C_1$-$C_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;
$R^{PRO1}$ and $R^{PRO2}$ of ULM-g through ULM-i are each independently H, an optionally substituted $C_1$-$C_3$ alkyl group or together form a keto group, and
each n of ULM-g through ULM-i is independently 0, 1, 2, 3, 4, 5, or 6 (preferably 0 or 1).
Each of said groups may be optionally connected to a PTM group (including a ULM' group) via a linker group.
In certain alternative preferred embodiments of the present invention, $R^{3'}$ of ULM-g through ULM-i is an optionally substituted —$(CH_2)_n$—$(V)_{n'}$—$(CH_2)_n$—$(V)_{n'}$—$R^{S3'}$ group, an optionally substituted-$(CH_2)_n$—N($R_{1'}$)(C=O)$_{m'}$—$(V)_{n'}$—$R^{S3'}$ group, an optionally substituted —$X^{R3'}$-alkyl group, an optionally substituted —$X^{R3'}$-Aryl group; an optionally substituted —$X^{R3'}$-HET group, an optionally substituted —$X^{R3'}$-Aryl-HET group or an optionally substituted —$X^{R3'}$-HET-Aryl group,
wherein:
$R^{S3'}$ is an optionally substituted alkyl group ($C_1$-$C_{10}$, preferably $C_1$-$C_6$ alkyl), an optionally substituted Aryl group or a HET group;
$R_{1'}$ is H or a $C_1$-$C_3$ alkyl group (preferably H);
V is O, S or $NR_{1'}$;
$X^{R3}$ is —$(CH_2)_n$—, —$(CH_2CH_2O)_n$—, —$CH_2)_n$—CH($X_v$)=CH($X_v$)— (cis or trans), —$CH_2)_n$—CH≡CH—, or a $C_3$-$C_6$ cycloalkyl group, all optionally substituted;
$X_v$ is H, a halo or a $C_1$-$C_3$ alkyl group which is optionally substituted with one or two hydroxyl groups or up to three halogen groups;

Alkyl is an optionally substituted $C_1$-$C_{10}$ alkyl (preferably a $C_1$-$C_6$ alkyl) group (in certain preferred embodiments, the alkyl group is end-capped with a halo group, often a Cl or Br);

Aryl is an optionally substituted phenyl or napthyl group (preferably, a phenyl group); and HET is an optionally substituted oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, benzofuran, indole, indolizine, azaindolizine, quinoline (when substituted, each preferably substituted with a $C_1$-$C_3$ alkyl group, preferably methyl or a halo group, preferably F or Cl), or a group according to the chemical structure:

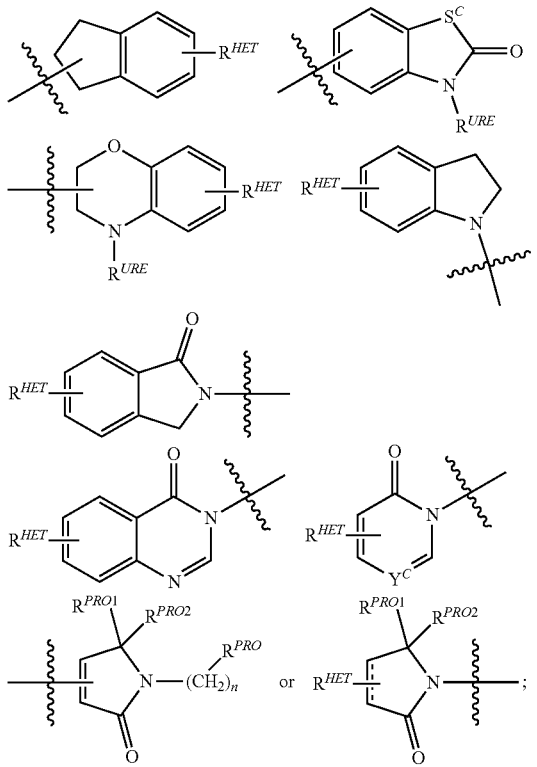

$S^c$ of ULM-g through ULM-i is $CHR^{SS}$, $NR^{URE}$, or O;

$R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);

$R^{URE}$ of ULM-g through ULM-i is H, a $C_1$-$C_6$ alkyl (preferably H or $C_1$-$C_3$ alkyl) or a —C(O)($C_0$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted;

$Y^C$ of ULM-g through ULM-i is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{PRO}$ of ULM-g through ULM-i is H, optionally substituted $C_1$-$C_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;

$R^{PRO1}$ and $R^{PRO2}$ of ULM-g through ULM-i are each independently H, an optionally substituted $C_1$-$C_3$ alkyl group or together form a keto group;

each n of ULM-g through ULM-i is independently 0, 1, 2, 3, 4, 5, or 6 (preferably 0 or 1);

each m' of ULM-g through ULM-i is 0 or 1; and each n' of ULM-g through ULM-i is 0 or 1;

wherein each of said compounds, preferably on the alkyl, Aryl or Het groups, is optionally connected to a PTM group (including a ULM' group) via a linker group.

In alternative embodiments, $R^{3'}$ of ULM-g through ULM-i is —$(CH_2)_n$-Aryl, —$(CH_2CH_2O)_n$-Aryl, —$(CH_2)_n$—HET or —$(CH_2CH_2O)_n$-HET, wherein:

said Aryl of ULM-g through ULM-i is phenyl which is optionally substituted with one or two substitutents, wherein said substituent(s) is preferably selected from —$(CH_2)_n$OH, $C_1$-$C_6$ alkyl which itself is further optionally substituted with CN, halo (up to three halo groups), OH, —$(CH_2)_nO(C_1$-$C_6$)alkyl, amine, mono- or di-($C_1$-$C_6$ alkyl) amine wherein the alkyl group on the amine is optionally substituted with 1 or 2 hydroxyl groups or up to three halo (preferably F, Cl) groups, or said Aryl group of ULM-g through ULM-i is substituted with —$(CH_2)_n$OH, —$(CH_2)_n$—O—($C_1$-$C_6$)alkyl, —$(CH_2)_n$—O—$(CH_2)_n$—($C_1$-$C_6$)alkyl, —$(CH_2)_n$—C(O)($C_0$-$C_6$) alkyl, —$(CH_2)_n$—C(O)O($C_0$-$C_6$)alkyl, —$(CH_2)_n$—OC(O)($C_0$-$C_6$)alkyl, amine, mono- or di-($C_1$-$C_6$ alkyl) amine wherein the alkyl group on the amine is optionally substituted with 1 or 2 hydroxyl groups or up to three halo (preferably F, Cl) groups, CN, $NO_2$, an optionally substituted —$(CH_2)_n$—$(V)_{m'}$—$CH_2)_n$—$(V)_{m'}$—($C_1$-$C_6$)alkyl group, a —$(V)_{m'}$—$(CH_2CH_2O)_n$—$R^{PEG}$ group where V is O, S or $NR_1$, $R_1$, is H or a $C_1$-$C_3$ alkyl group (preferably H) and $R^{PEG}$ is H or a $C_1$-$C_6$ alkyl group which is optionally substituted (including being optionally substituted with a carboxyl group), or said Aryl group of ULM-g through ULM-i is optionally substituted with a heterocycle, including a heteroaryl, selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, benzofuran, indole, indolizine, azaindolizine, (when substituted each preferably substituted with a $C_1$-$C_3$ alkyl group, preferably methyl or a halo group, preferably F or Cl), or a group according to the chemical structure:

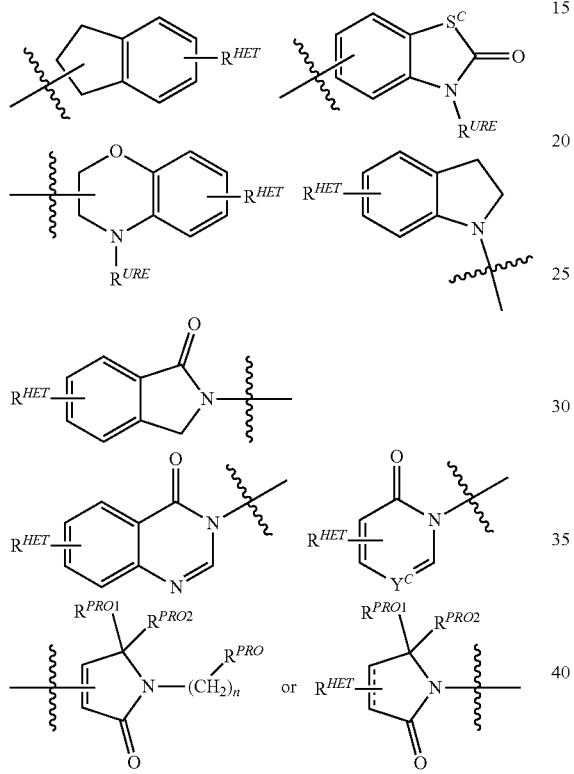

$S^C$ of ULM-g through ULM-i is $CHR^{SS}$, $NR^{URE}$, or O;

$R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);

$R^{URE}$ of ULM-g through ULM-i is H, a $C_1$-$C_6$ alkyl (preferably H or $C_1$-$C_3$ alkyl) or a —C(O)($C_0$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted;

$Y^C$ of ULM-g through ULM-i is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{PRO}$ of ULM-g through ULM-i is H, optionally substituted $C_1$-$C_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;

$R^{PRO1}$ and $R^{PRO2}$ of ULM-g through ULM-i are each independently H, an optionally substituted $C_1$-$C_3$ alkyl group or together form a keto group;

HET of ULM-g through ULM-i is preferably oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine, or a group according to the chemical structure:

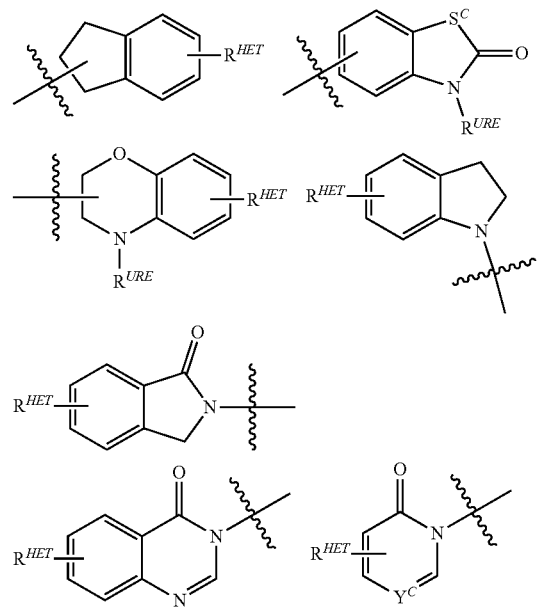

-continued

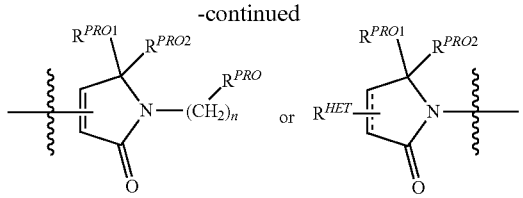

or

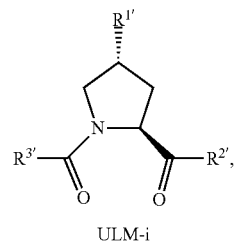

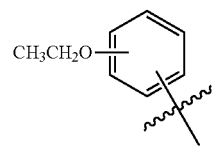

ULM-i $S^c$ of ULM-g through ULM-i is $CHR^{SS}$, $NR^{URE}$, or O;

$R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);

$R^{URE}$ of ULM-g through ULM-i is H, a $C_1$-$C_6$ alkyl (preferably H or $C_1$-$C_3$ alkyl) or a —C(O)($C_0$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted;

$Y^C$ of ULM-g through ULM-i is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{PRO}$ of ULM-g through ULM-i is H, optionally substituted $C_1$-$C_6$ alkyl or an optionally substituted aryl, heteroaryl or heterocyclic group;

$R^{PRO1}$ and $R^{PRO2}$ of ULM-g through ULM-i are each independently H, an optionally substituted $C_1$-$C_3$ alkyl group or together form a keto group;

each m' of ULM-g through ULM-i is independently 0 or 1; and each n of ULM-g through ULM-i is independently 0, 1, 2, 3, 4, 5, or 6 (preferably 0 or 1), wherein each of said compounds, preferably on said Aryl or HET groups, is optionally connected to a PTM group (including a ULM' group) via a linker group.

In still additional embodiments, preferred compounds include those according to the chemical structure:

wherein:

$R^{1'}$ of ULM-i is OH or a group which is metabolized in a patient or subject to OH;

$R^{2'}$ of ULM-i is a —NH—$CH_2$-Aryl-HET (preferably, a phenyl linked directly to a methyl substituted thiazole);

$R^3$ of ULM-i is a —$CHR^{CR3'}$—NH—C(O)—$R^{3P1}$ group or a —$CHR^{CR3'}$—$R^{3P2}$ group;

$R^{CR3'}$ of ULM-i is a $C_1$-$C_4$ alkyl group, preferably methyl, isopropyl or tert-butyl;

$R^{3P1}$ of ULM-i is $C_1$-$C_3$ alkyl (preferably methyl), an optionally substituted oxetane group (preferably methyl substituted, a —$(CH_2)_n OCH_3$ group where n is 1 or 2 (preferably 2), or a

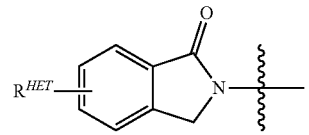

group (the ethyl ether group is preferably meta-substituted on the phenyl moiety), a morpholino group (linked to the carbonyl at the 2- or 3-position;

$R^{3P2}$ of ULM-i is a group;

Aryl of ULM-i is phenyl;

HET of ULM-i is an optionally substituted thiazole or isothiazole; and $R^{HET}$ of ULM-i is H or a halo group (preferably H);

or a pharmaceutically acceptable salt, stereoisomer, solvate or polymorph thereof, wherein each of said compounds is optionally connected to a PTM group (including a ULM' group) via a linker group.

In certain aspects, bifunctional compounds comprising a ubiquitin E3 ligase binding moiety (ULM), wherein ULM is a group according to the chemical structure:

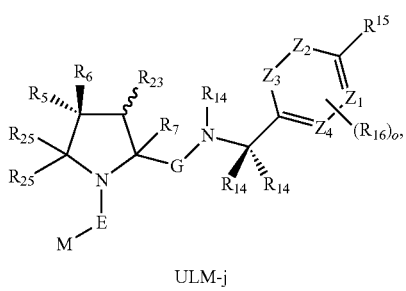

ULM-j wherein:
- each $R_5$ and $R_6$ of ULM-j is independently OH, SH, or optionally substituted alkyl or $R_5$, $R_6$, and the carbon atom to which they are attached form a carbonyl;
- $R_7$ of ULM-j is H or optionally substituted alkyl;
- E of ULM-j is a bond, C=O, or C=S;
- G of ULM-j is a bond, optionally substituted alkyl, —COOH or C=J;
- J of ULM-j is O or N—$R_8$;
- $R_8$ of ULM-j is H, CN, optionally substituted alkyl or optionally substituted alkoxy;
- M of ULM-j is optionally substituted aryl, optionally substituted heteroaryl, optionally substituted heterocyclic or

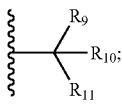

each $R_9$ and $R_{10}$ of ULM-j is independently H; optionally substituted alkyl, optionally substituted cycloalkyl, optionally substituted hydroxyalkyl, optionally substituted thioalkyl, a disulphide linked ULM, optionally substituted heteroaryl, or haloalkyl; or $R_9$, $R_{10}$, and the carbon atom to which they are attached form an optionally substituted cycloalkyl;

$R_{11}$ of ULM-j is optionally substituted heterocyclic, optionally substituted alkoxy, optionally substituted heteroaryl, optionally substituted aryl, or

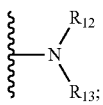

$R_{12}$ of ULM-j is H or optionally substituted alkyl;
$R_{13}$ of ULM-j is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl; optionally substituted (oxoalkyl) carbamate,
each $R_{14}$ of ULM-j is independently H, haloalkyl, optionally substituted cycloalkyl, optionally substituted alkyl or optionally substituted heterocycloalkyl;
$R_{15}$ of ULM-j is H, optionally substituted heteroaryl, haloalkyl, optionally substituted aryl, optionally substituted alkoxy, or optionally substituted heterocyclyl;

each $R_{16}$ of ULM-j is independently halo, optionally substituted alkyl, optionally substituted haloalkyl, CN, or optionally substituted haloalkoxy;
each $R_{25}$ of ULM-j is independently H or optionally substituted alkyl; or both $R_{25}$ groups can be taken together to form an oxo or optionally substituted cycloalkyl group;
$R_{23}$ of ULM-j is H or OH;
$Z_1$, $Z_2$, $Z_3$, and $Z_4$ of ULM-j are independently C or N; and
o of ULM-j is 0, 1, 2, 3, or 4, or a pharmaceutically acceptable salt, stereoisomer, solvate or polymorph thereof.

In certain embodiments, wherein G of ULM-j is C=J, J is O, $R_7$ is H, each $R_{14}$ is H, and o is 0.

In certain embodiments, wherein G of ULM-j is C=J, J is O, $R_7$ is H, each $R_{14}$ is H, $R_{15}$ is optionally substituted heteroaryl, and o is 0. In other instances, E is C=O and M is

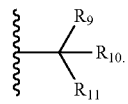

In certain embodiments, wherein E of ULM-j is C=O, $R_{11}$ is optionally substituted heterocyclic or

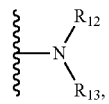

and M is

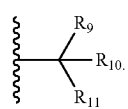

In certain embodiments, wherein E of ULM-j is C=O, M is

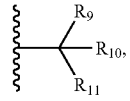

and $R_{11}$ is

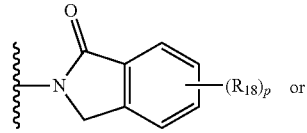 or

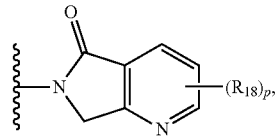

each $R_{18}$ is independently halo, optionally substituted alkoxy, cyano, optionally substituted alkyl, haloalkyl, or haloalkoxy; and p is 0, 1, 2, 3, or 4.

In certain embodiments, ULM and where present, ULM', are each independently a group according to the chemical structure:

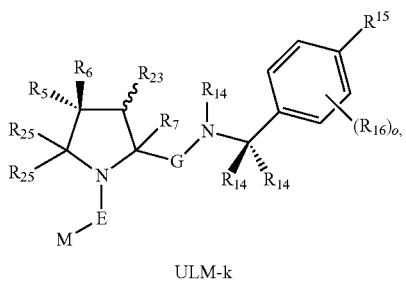

ULM-k wherein:
G of ULM-k is C=J, J is O;
$R_7$ of ULM-k is H;
each $R_{14}$ of ULM-k is H;
o of ULM-k is 0;
$R_{15}$ of ULM-k is

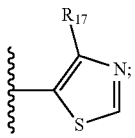

and
$R_{17}$ of ULM-k is H, halo, optionally substituted cycloalkyl, optionally substituted alkyl, optionally substituted alkenyl, and haloalkyl.

In other instances, $R_{17}$ of ULM-k is alkyl (e.g., methyl) or cycloalkyl (e.g., cyclopropyl).

In other embodiments, ULM and where present, ULM', are each independently a group according to the chemical structure:

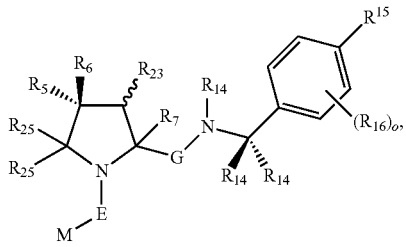

wherein:
G of ULM-k is C=J, J is O;
$R_7$ of ULM-k is H;
each $R_{14}$ of ULM-k is H;
o of ULM-k is 0; and
$R_{15}$ of ULM-k is selected from the group consisting of:

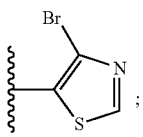

-continued

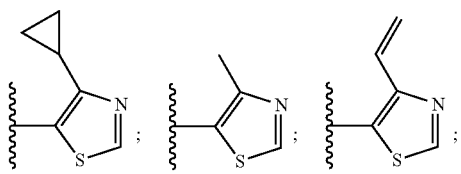
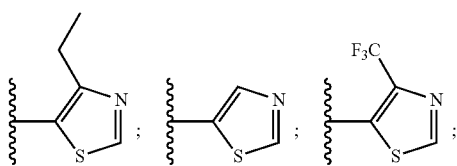
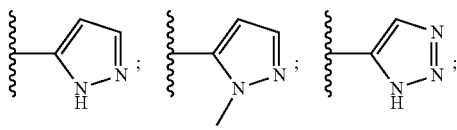
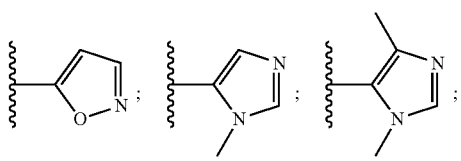
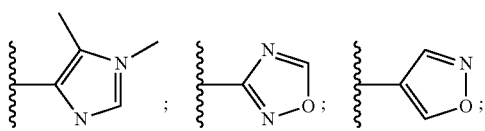
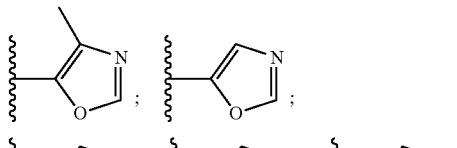
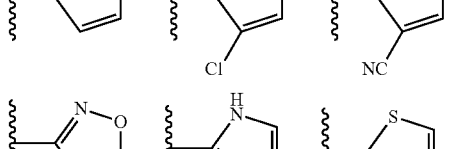
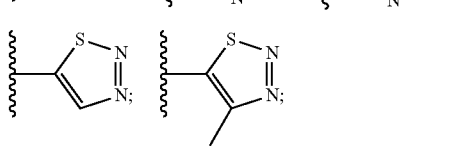
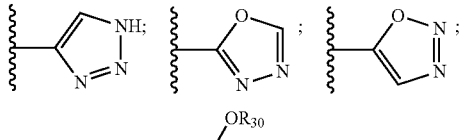
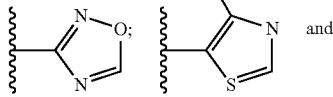 and

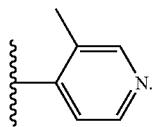
wherein $R_{30}$ of ULM-k is H or an optionally substituted alkyl.
In other embodiments, ULM and where present, ULM', are each independently a group according to the chemical structure:
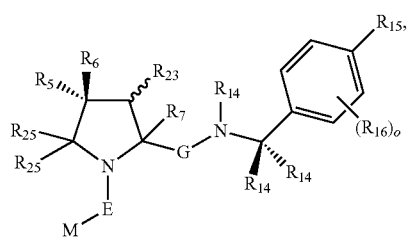
wherein:
E of ULM-k is C=O;
M of ULM-k is
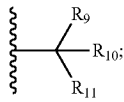
and
$R_{11}$ of ULM-k is selected from the group consisting of:
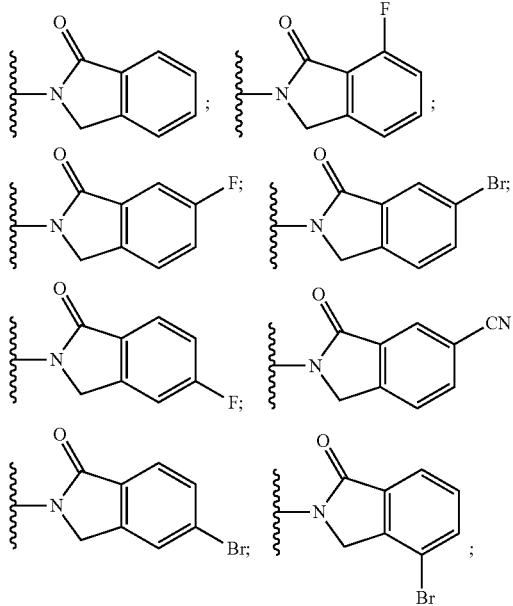
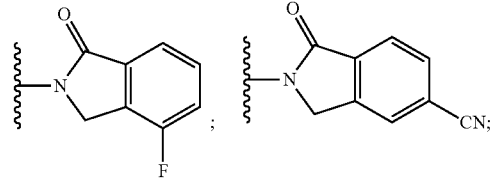
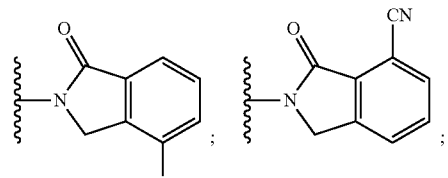
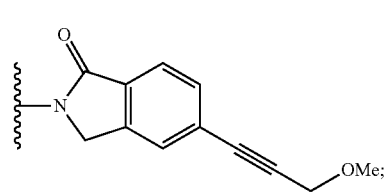
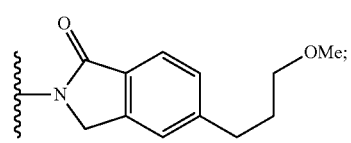
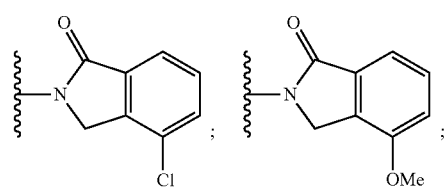
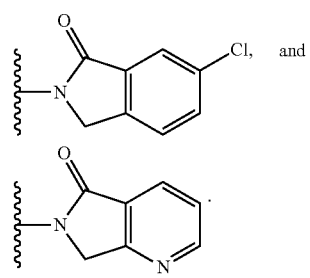
In still other embodiments, a compound of the chemical structure,
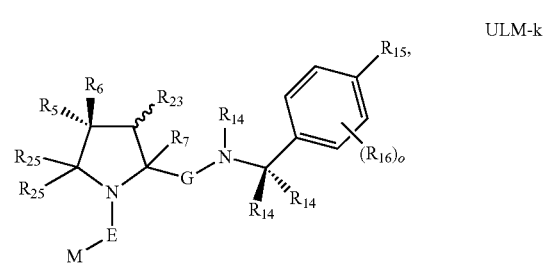

wherein:
E of ULM-k is C=O;
R$_{11}$ of ULM-k is

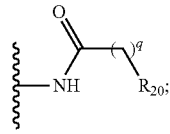

and
M of ULM-k is

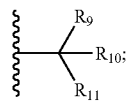

q of ULM-k is 1 or 2;
R$_{20}$ of ULM-k is H, optionally substituted alkyl, optionally substituted cycloalkyl, optionally substituted aryl, or

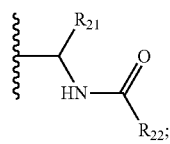

R$_{21}$ of ULM-k is H or optionally substituted alkyl; and
R$_{22}$ of ULM-k is H, optionally substituted alkyl, optionally substituted alkoxy, or haloalkyl.

In any embodiment described herein, R$_{11}$ of ULM-j or ULM-k is selected from the group consisting of:

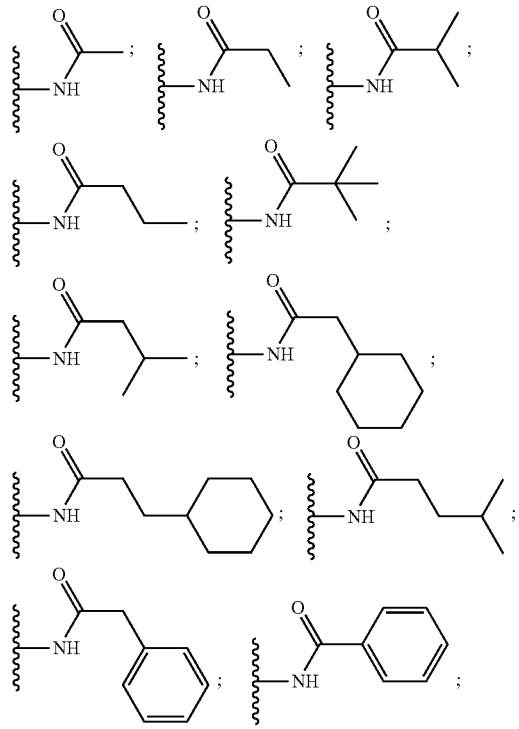

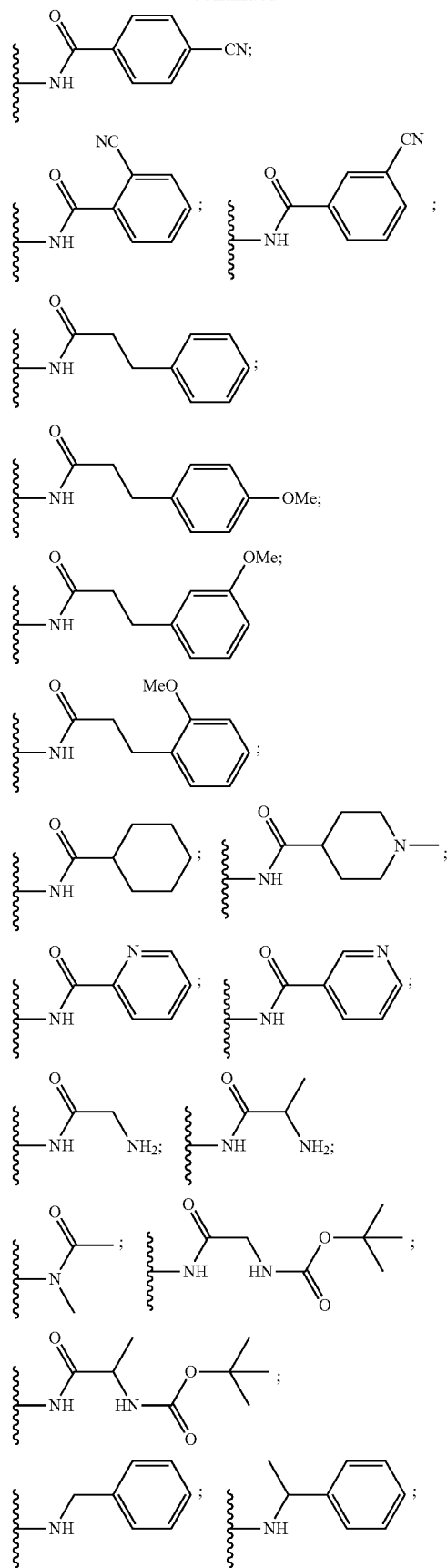

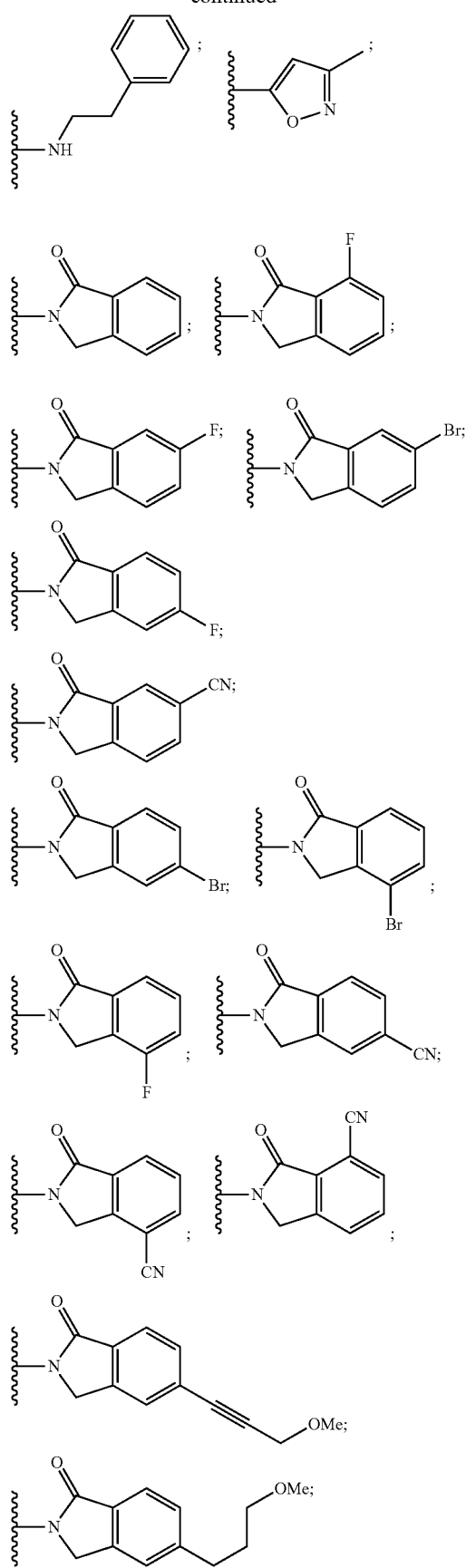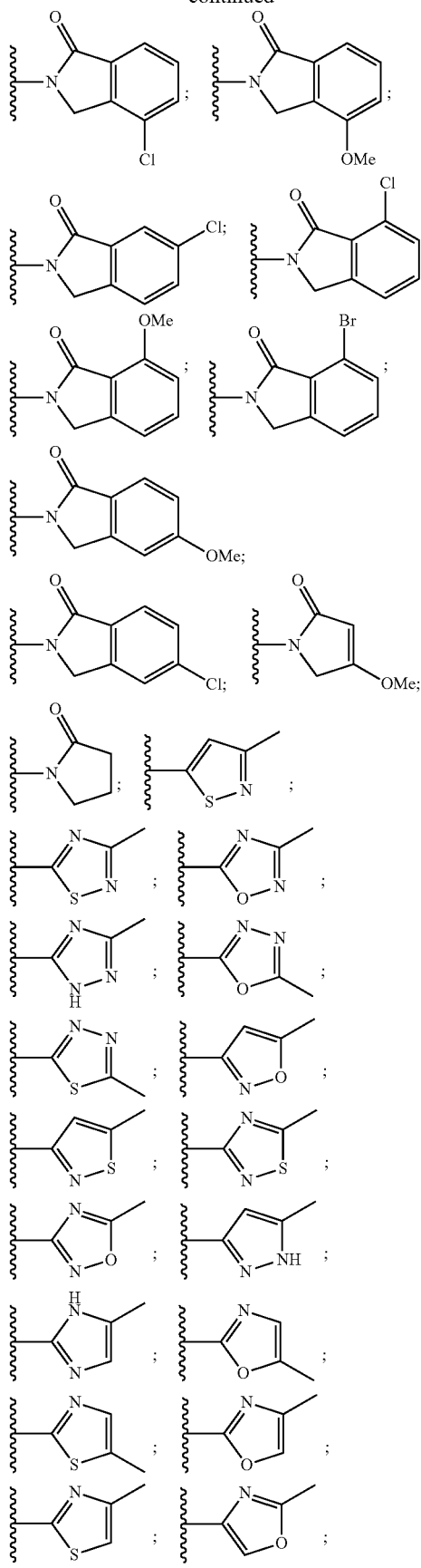

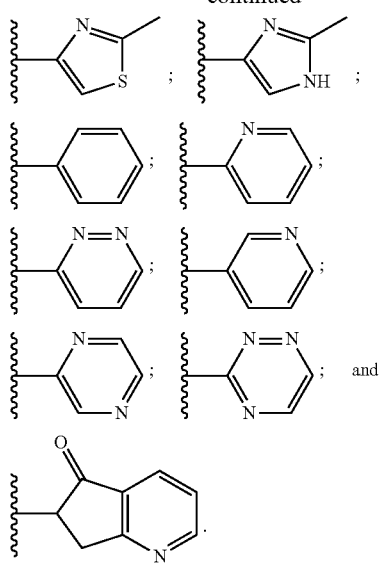
In certain embodiments, $R_{11}$ of ULM-j or ULM-k is selected from the group consisting of:
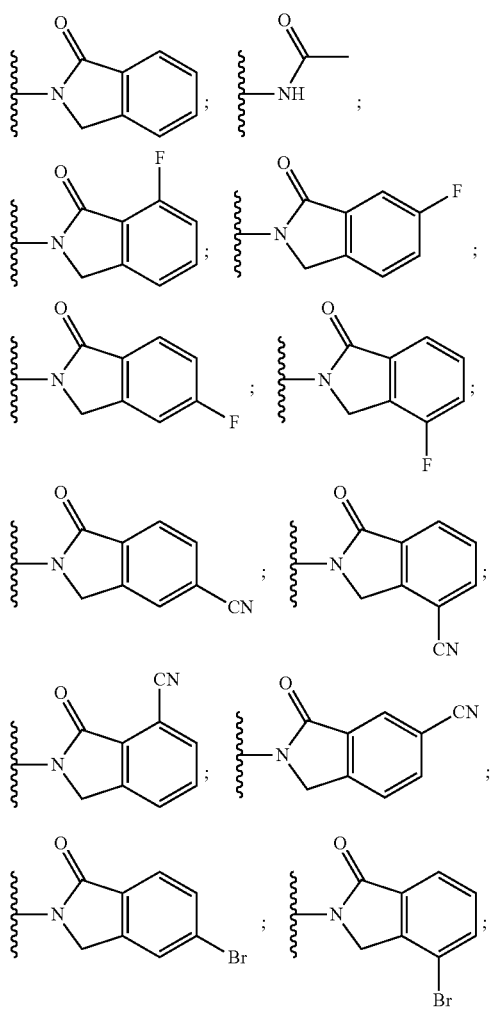
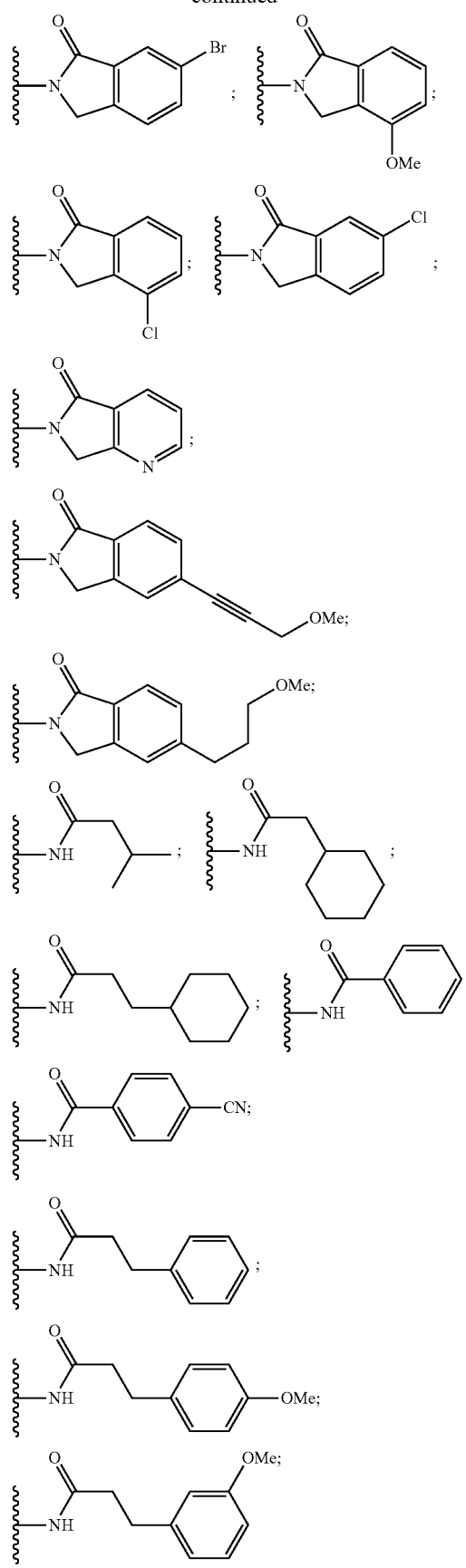

-continued

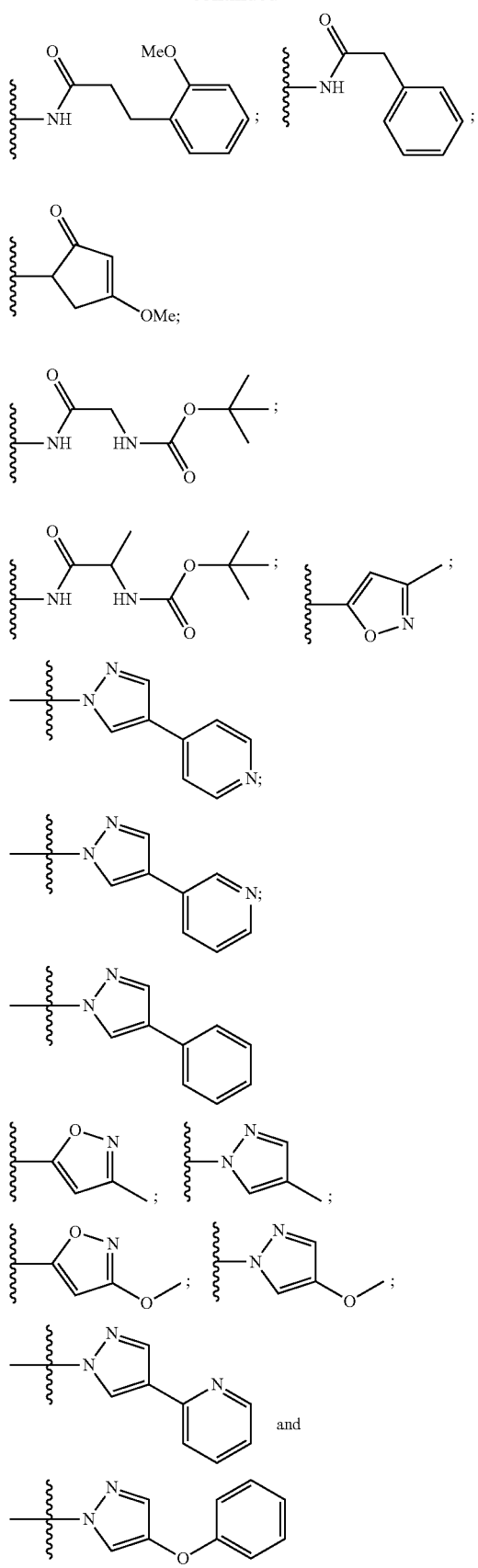

and

In certain embodiments, ULM (or when present ULM') is a group according to the chemical structure:

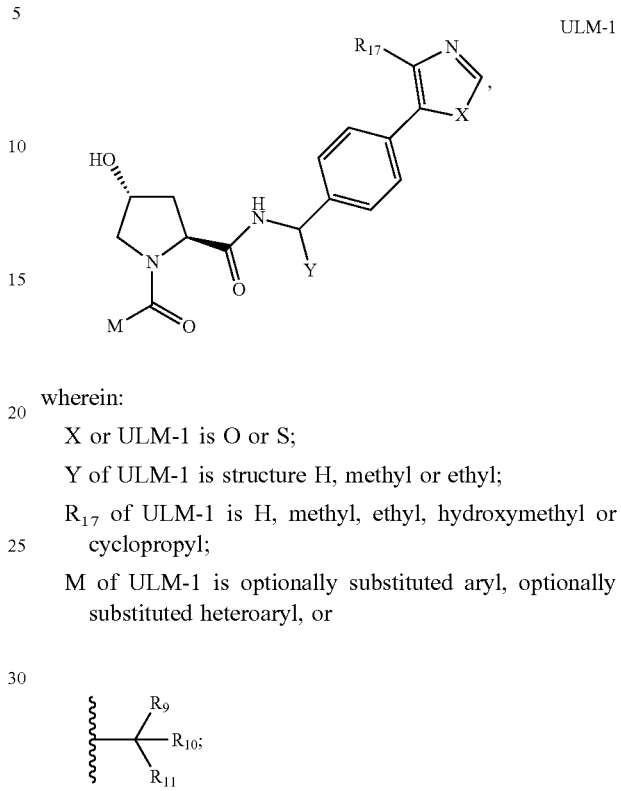

ULM-1 wherein:

X or ULM-1 is O or S;

Y of ULM-1 is structure H, methyl or ethyl;

$R_{17}$ of ULM-1 is H, methyl, ethyl, hydroxymethyl or cyclopropyl;

M of ULM-1 is optionally substituted aryl, optionally substituted heteroaryl, or

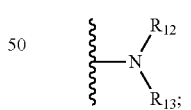

$R_9$ of ULM-1 is H;

$R_{10}$ of ULM-1 is H, optionally substituted alkyl, optionally substituted haloalkyl, optionally substituted heteroaryl, optionally substituted aryl, optionally substituted hydroxyalkyl, optionally substituted thioalkyl or cycloalkyl;

$R_{11}$ of ULM-1 is optionally substituted heteroaromatic, optionally substituted heterocyclic, optionally substituted aryl or $R_{12}$ of ULM-1 is H or optionally substituted alkyl; and $R_{13}$ of ULM-1 is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl; optionally substituted (oxoalkyl)carbamate.

In some embodiments, ULM and where present, ULM', are each independently a group according to the chemical structure:

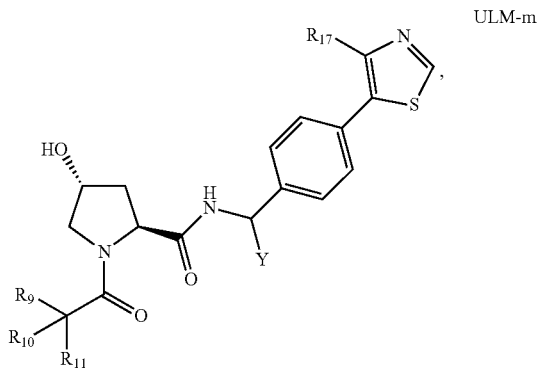

ULM-m wherein:
- Y of ULM-m is H, methyol or ethyl
- $R_9$ of ULM-m is H;
- $R_{10}$ is isopropyl, tert-butyl, sec-butyl, cyclopentyl, or cyclohexyl;
- $R_{11}$ of ULM-m is optionally substituted amide, optionally substituted isoindolinone, optionally substituted isooxazole, optionally substituted heterocycles.

In other preferred embodiments of the invention, ULM and where present, ULM', are each independently a group according to the chemical structure:

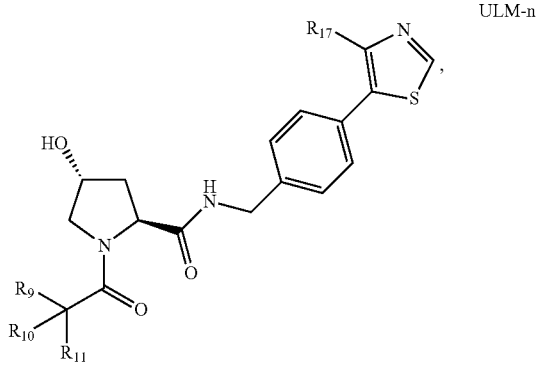

ULM-n wherein:
- $R_{17}$ of ULM-n is methyl, ethyl, or cyclopropyl; and
- $R_9$, $R_{10}$, and $R_{11}$ of ULM-n are as defined above. In other instances, $R_9$ is H; and
- $R_{10}$ of ULM-n is H, alkyl, or cycloalkyl (preferably, isopropyl, tert-butyl, sec-butyl, cyclopentyl, or cyclohexyl).

In any of the aspects or embodiments described herein, the ULM (or when present, ULM') as described herein may be a pharmaceutically acceptable salt, enantiomer, diastereomer, solvate or polymorph thereof. In addition, in any of the aspects or embodiments described herein, the ULM (or when present, ULM') as described herein may be coupled to a PTM directly via a bond or by a chemical linker.

In certain aspects of the invention, the ULM moiety is selected from the group consisting of:

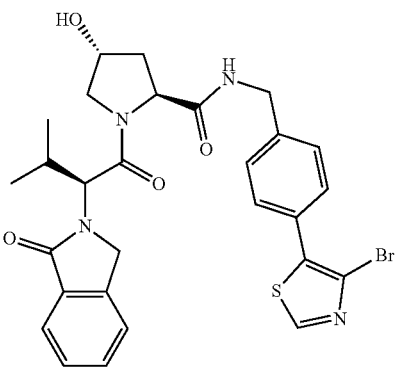

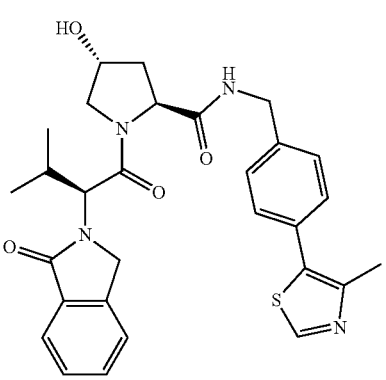

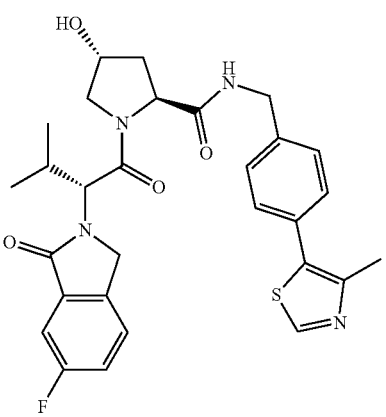

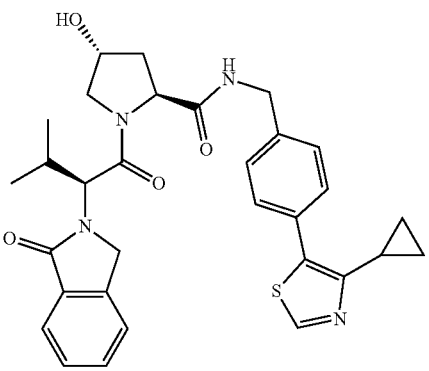

-continued
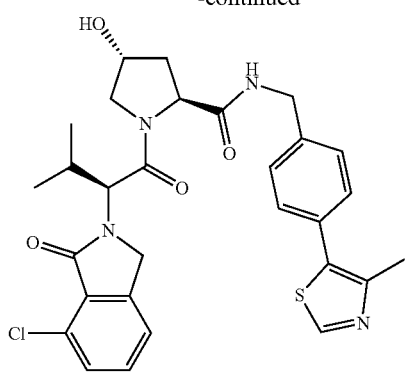
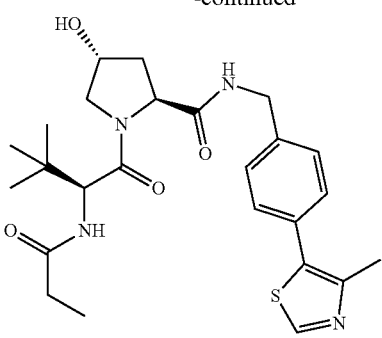
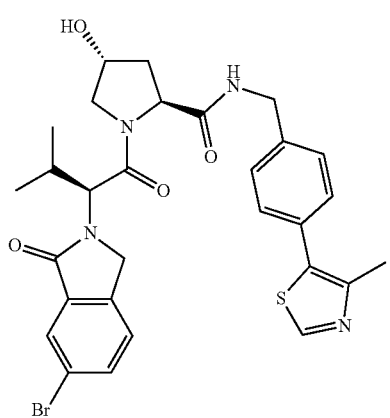
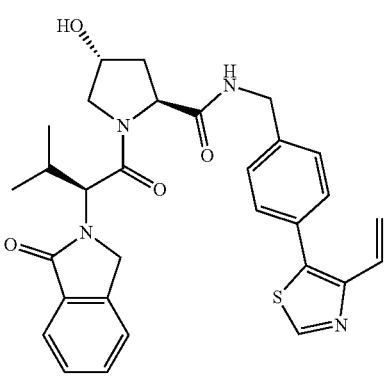
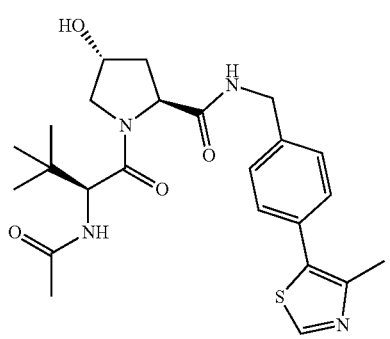
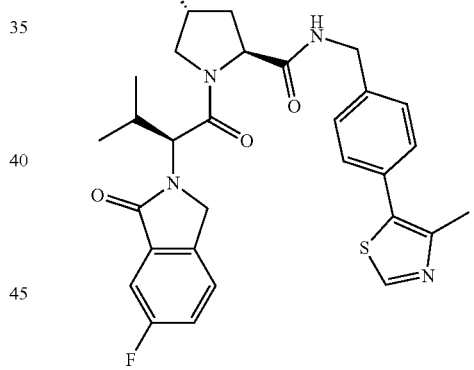
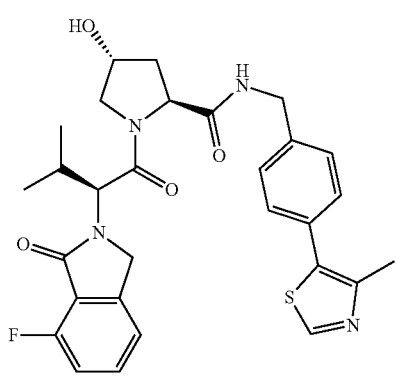
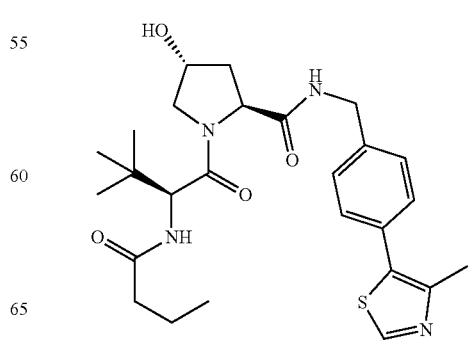

93
-continued
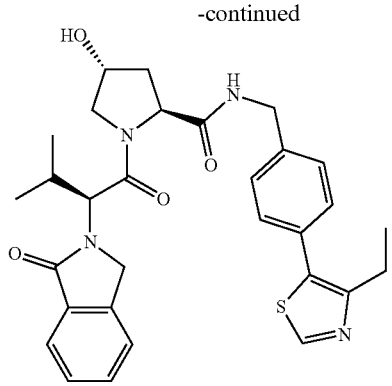
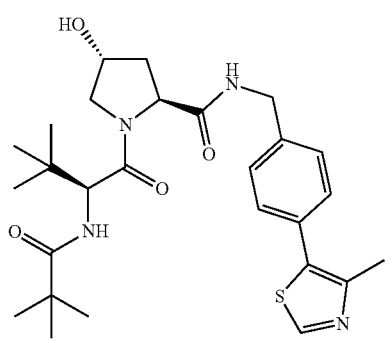
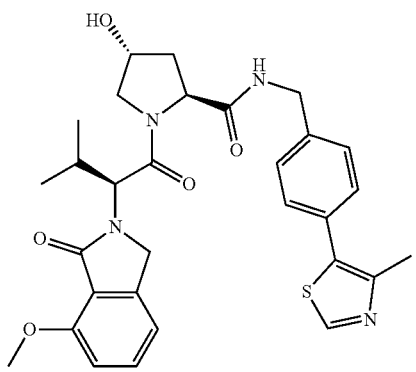
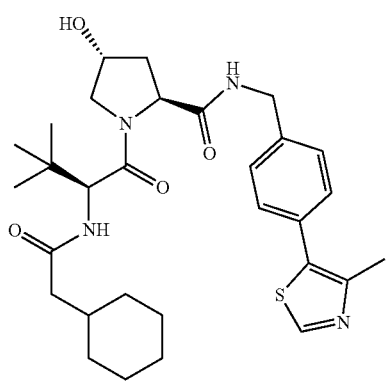
94
-continued
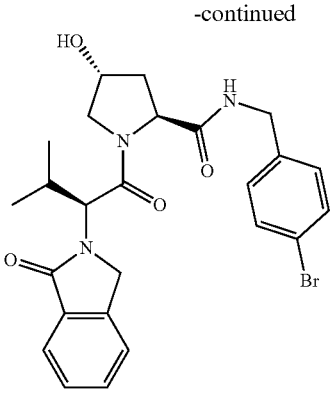
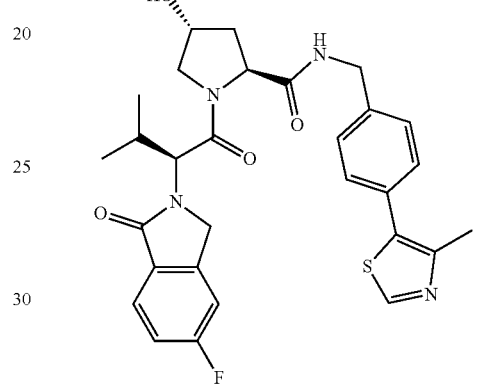
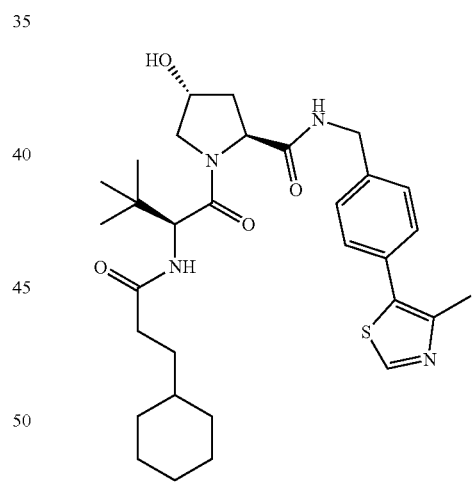
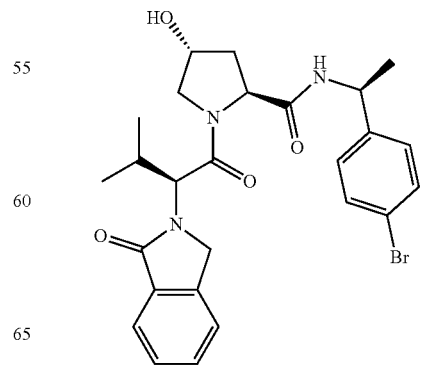

95
-continued
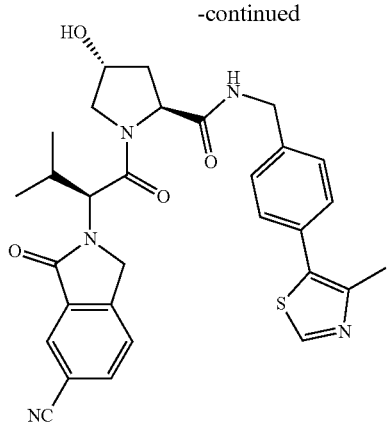
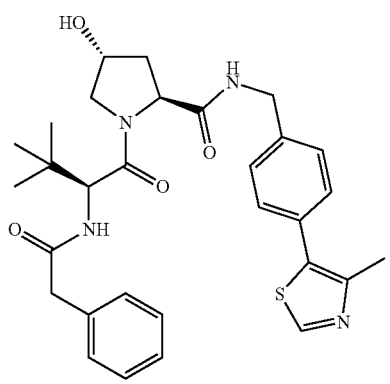
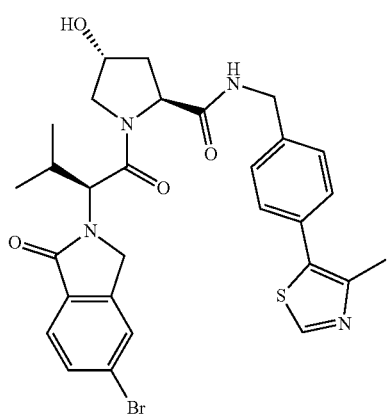
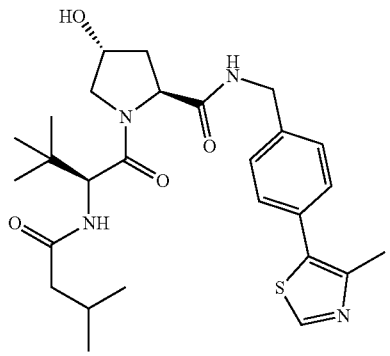
96
-continued
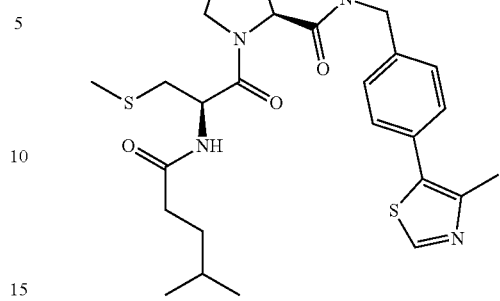
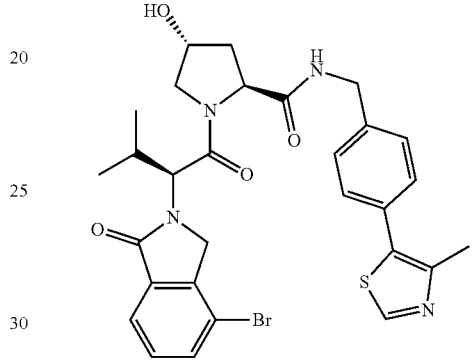
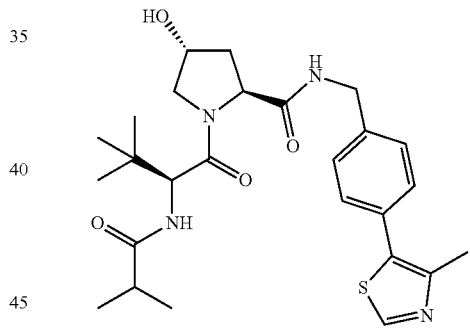
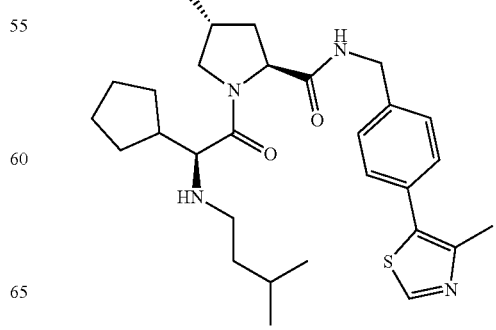

97
-continued
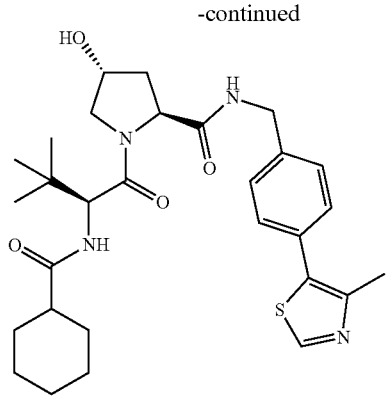
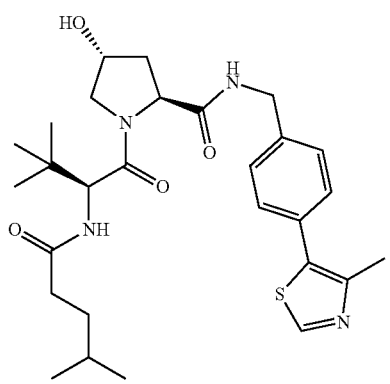
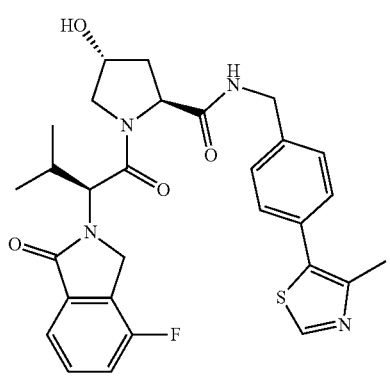
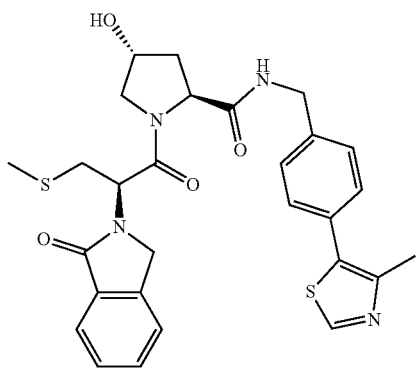
98
-continued
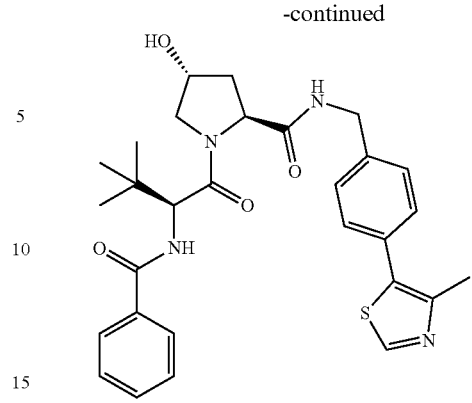
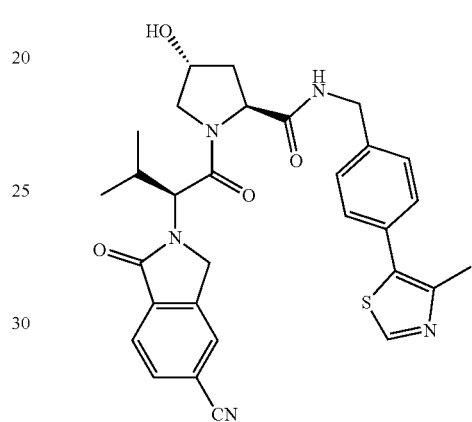
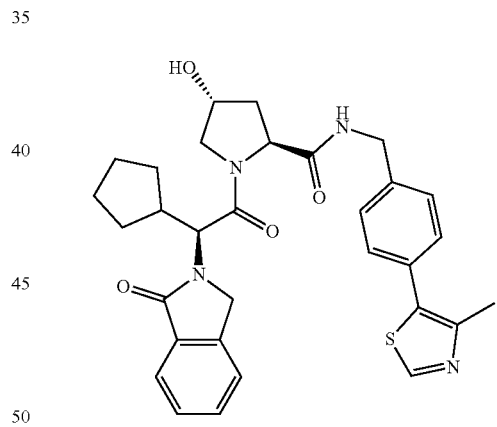
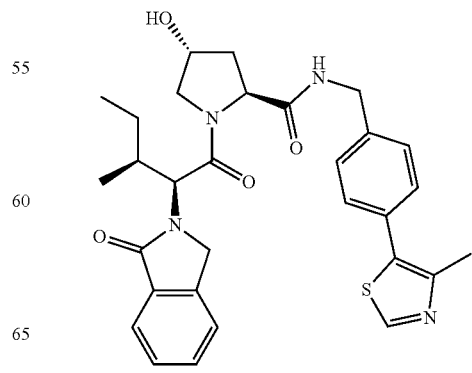

99
-continued
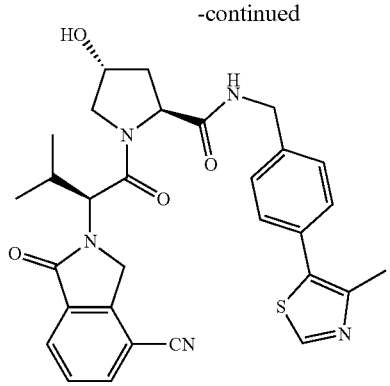
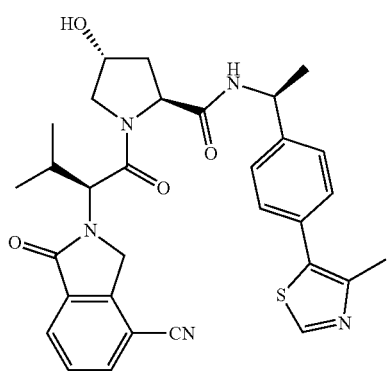
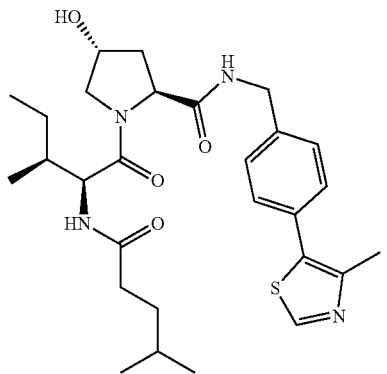
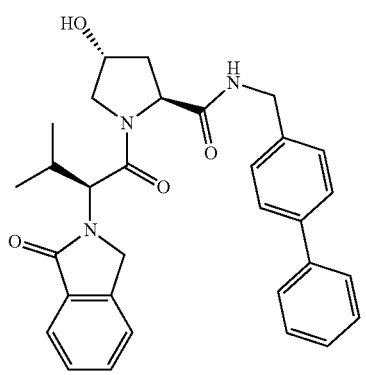
100
-continued
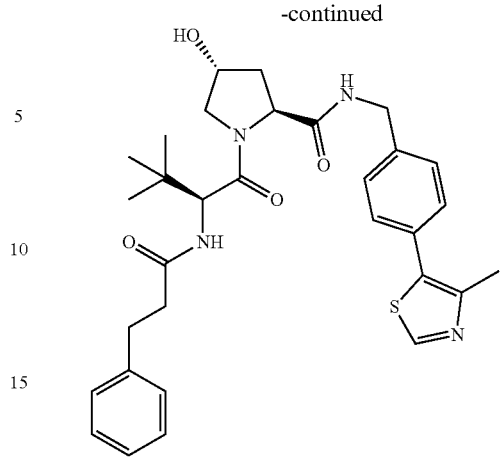
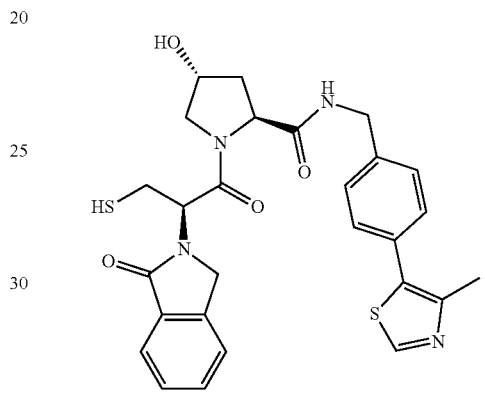
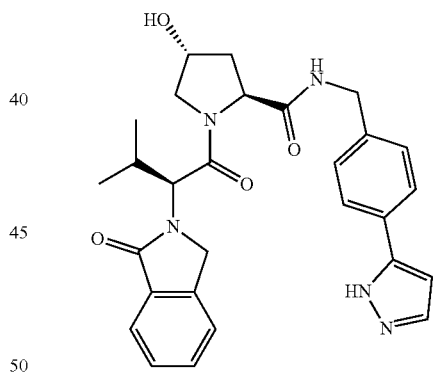
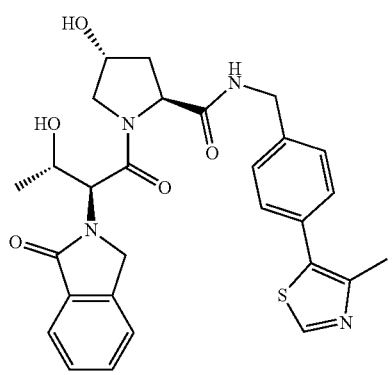

101
-continued
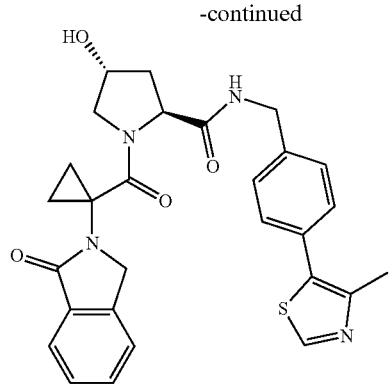
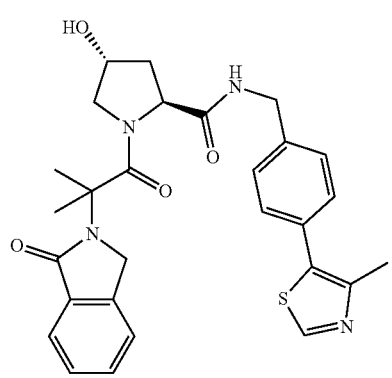
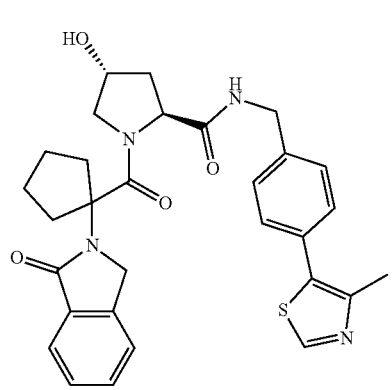
102
-continued
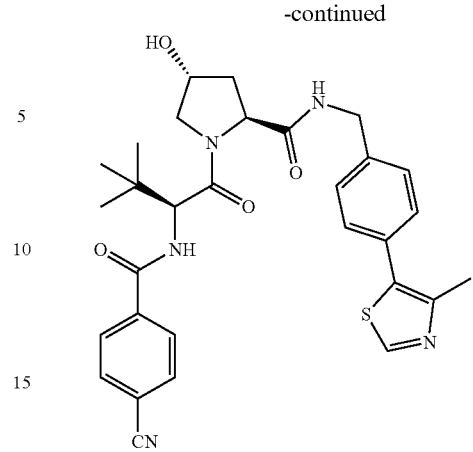
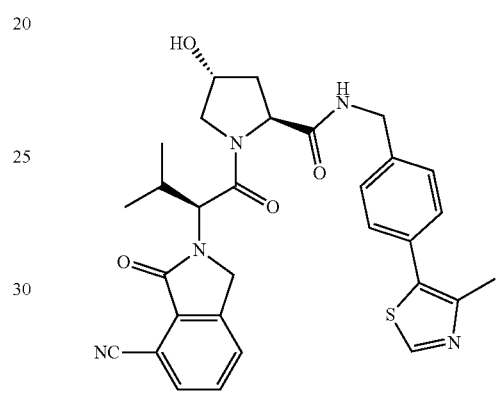
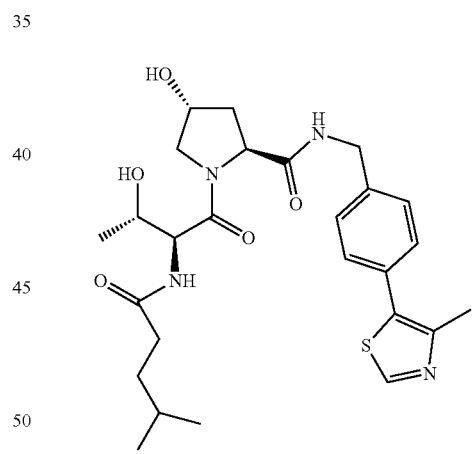
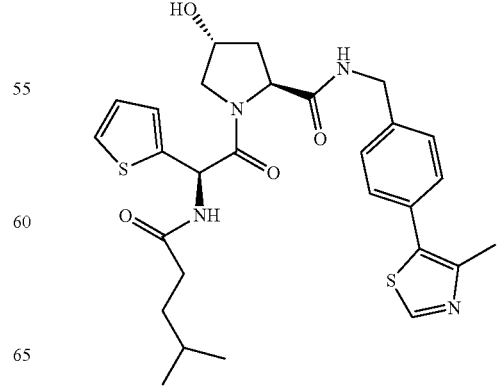

103
-continued
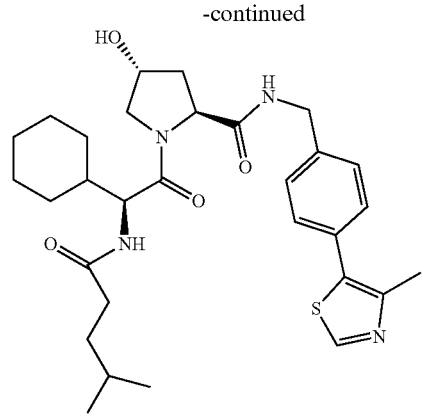
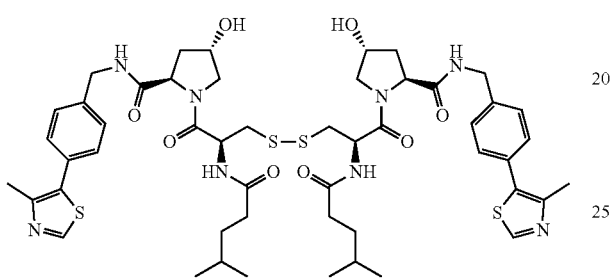
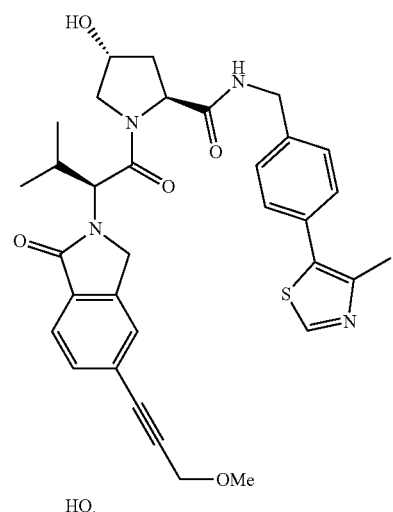
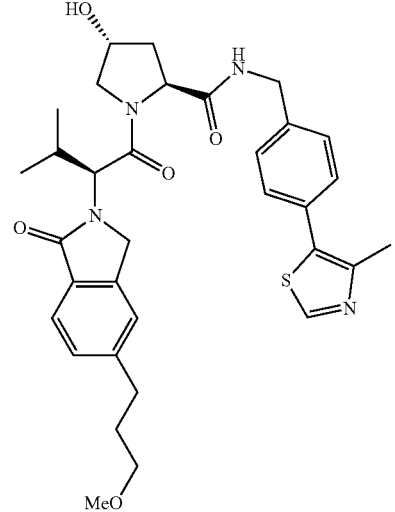
104
-continued
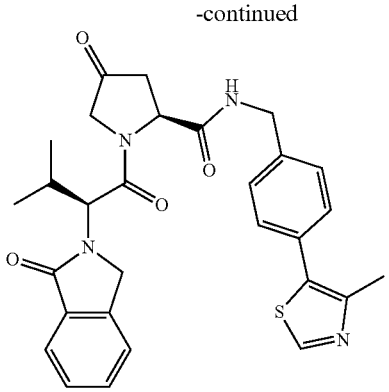
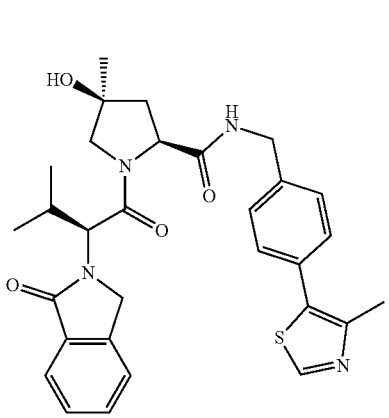
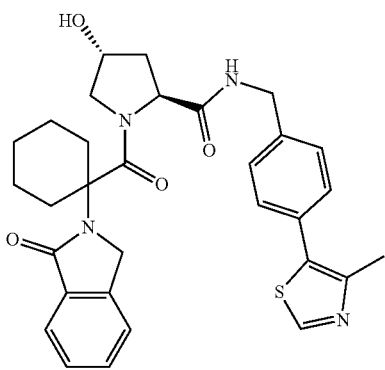
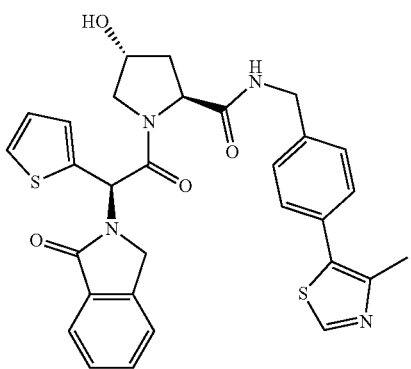

105
-continued
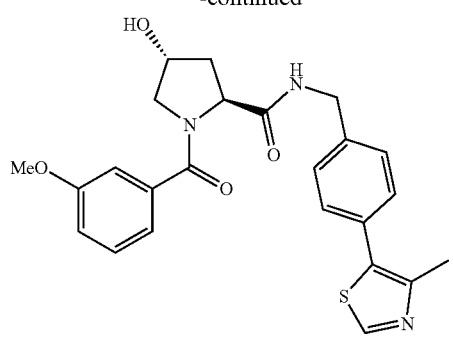
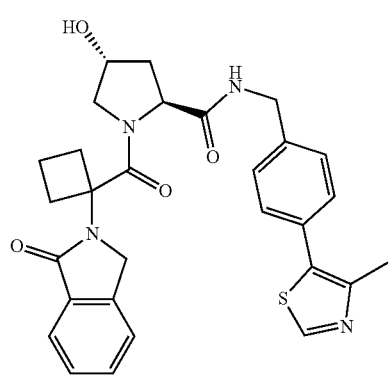
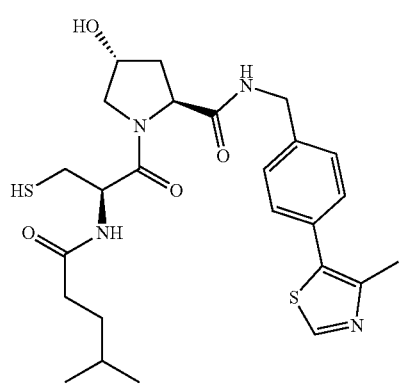
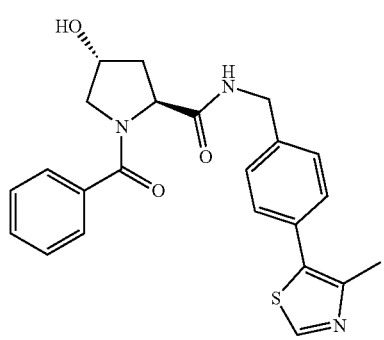
106
-continued
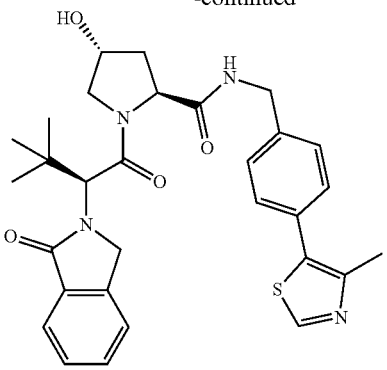
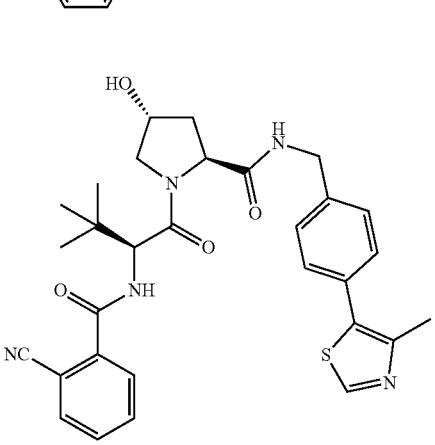
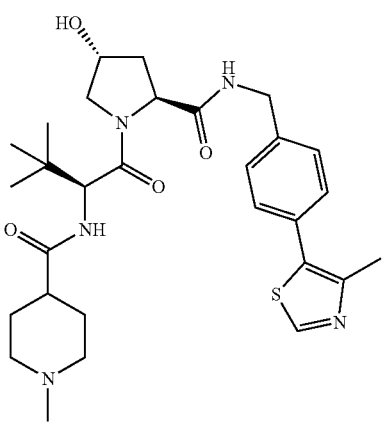
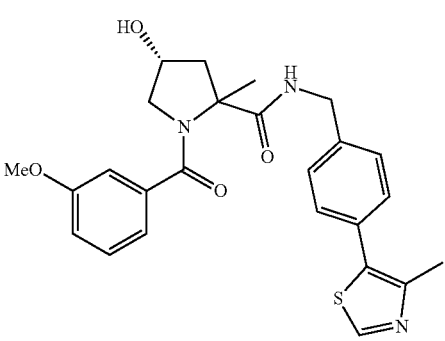

107
-continued
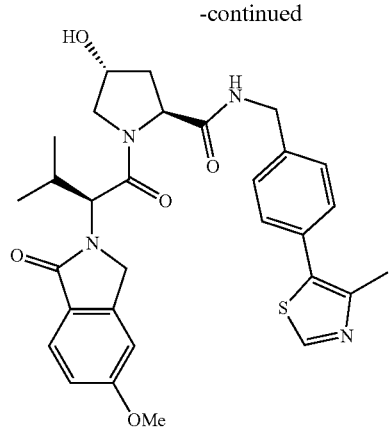
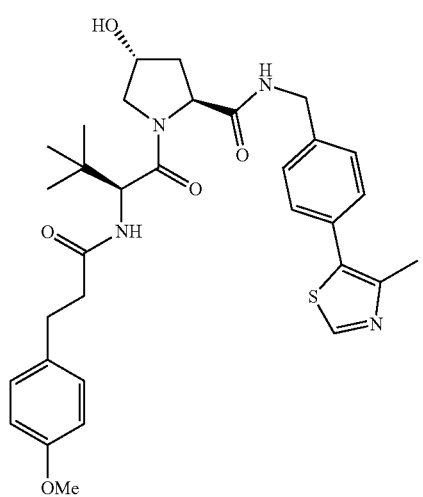
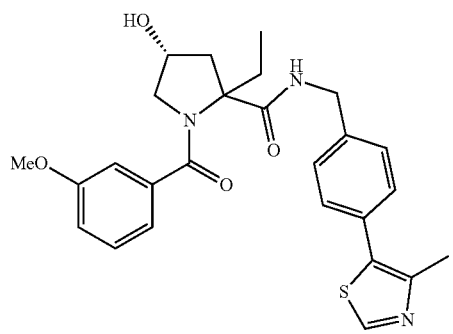
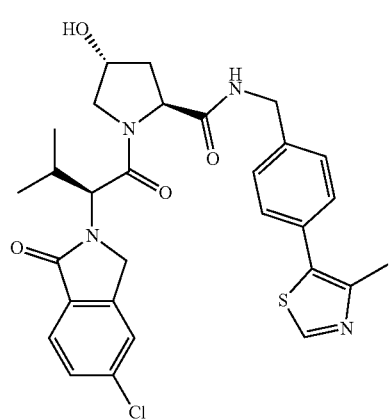
108
-continued
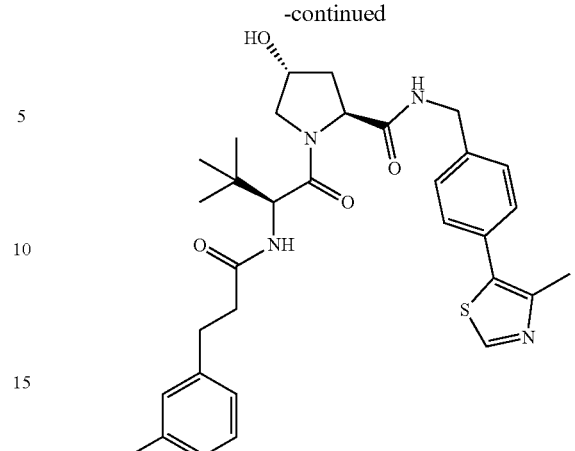
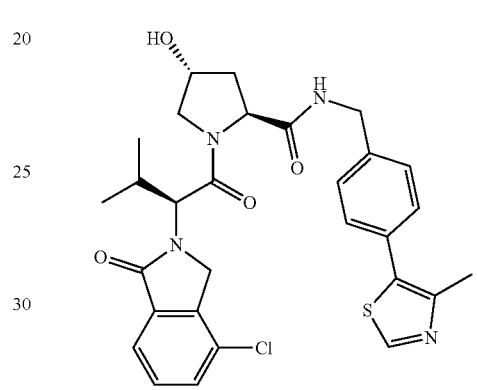
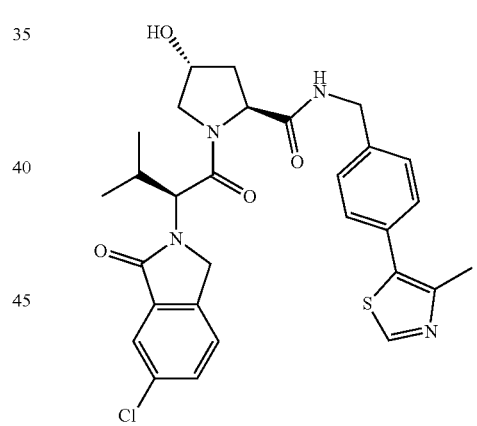
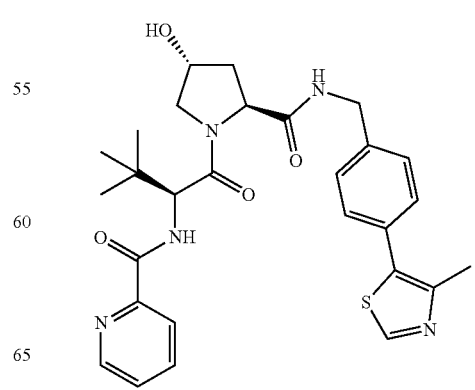

109
-continued
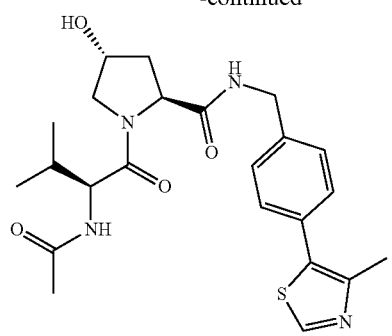
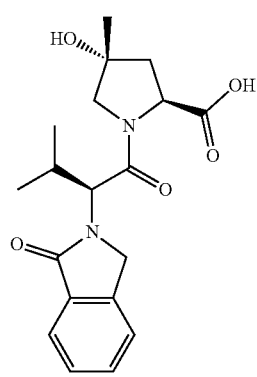
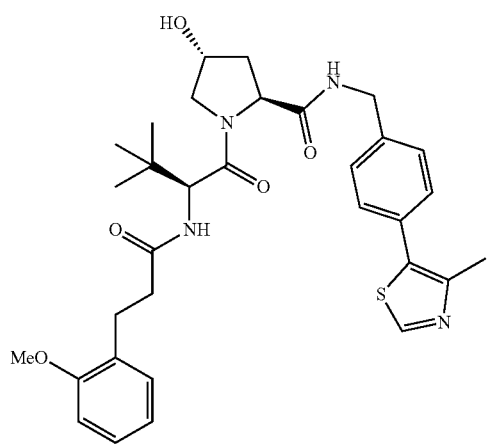
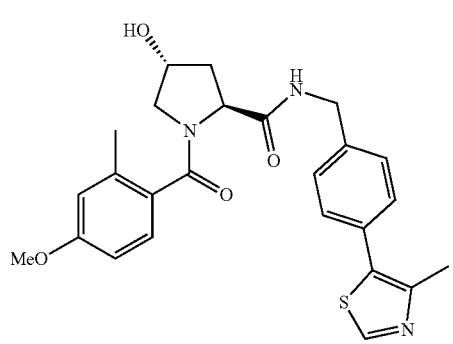
110
-continued
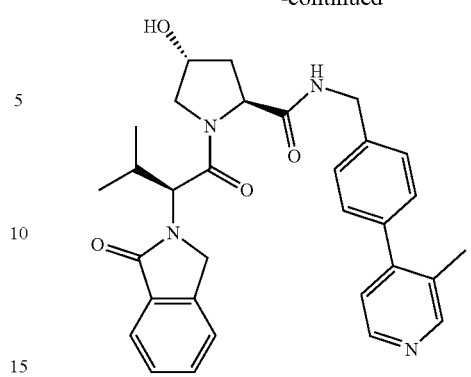
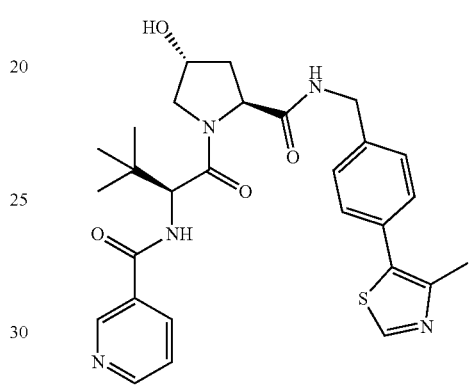
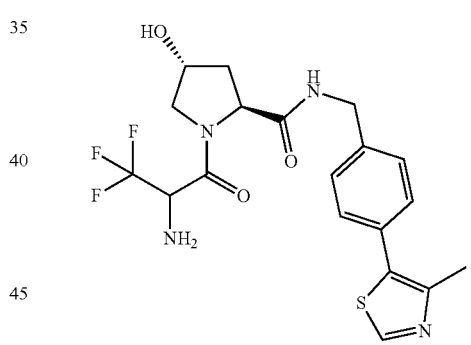
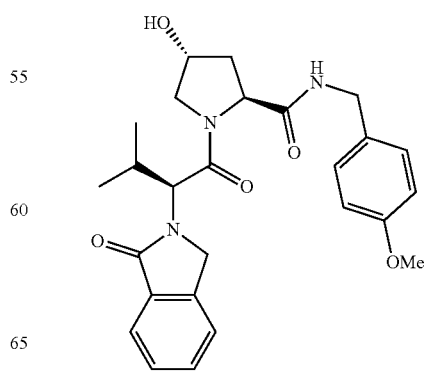

111
-continued
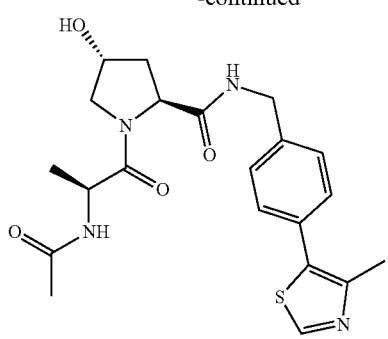
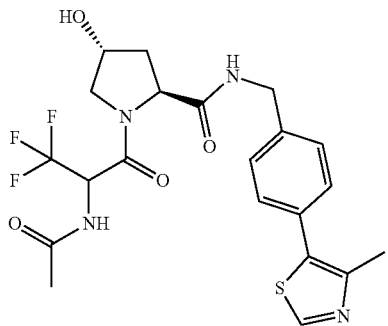
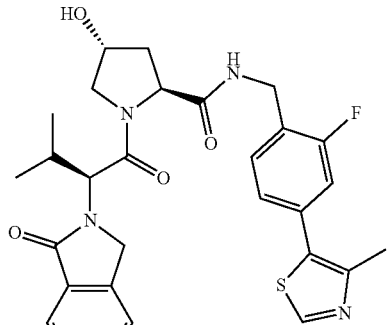
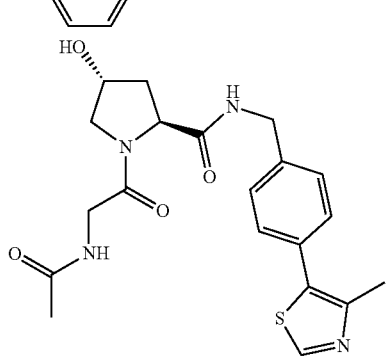
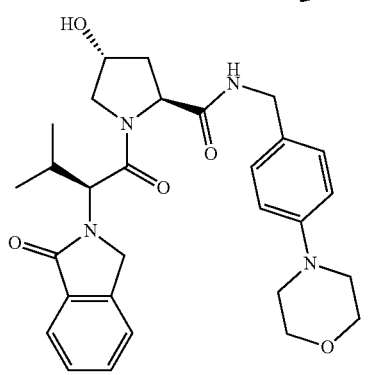
112
-continued
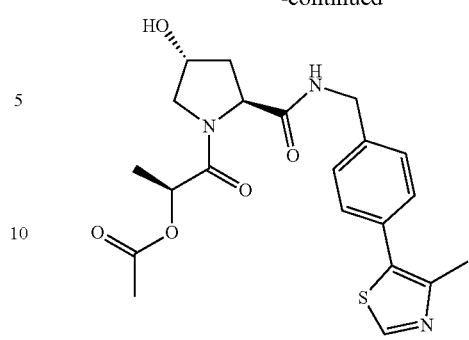
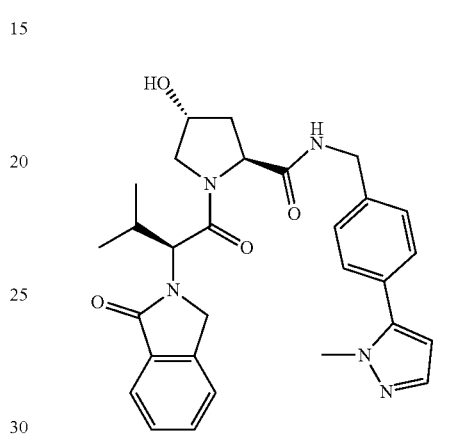

113
-continued
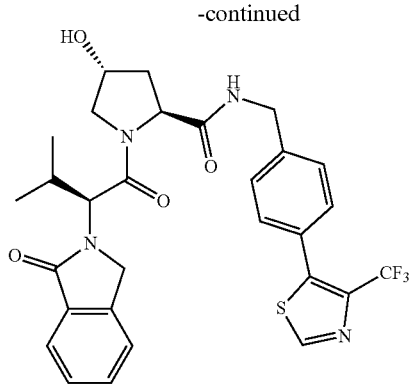
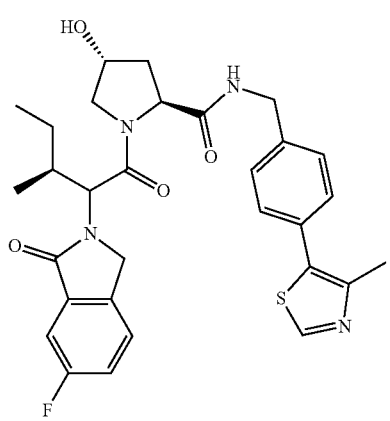
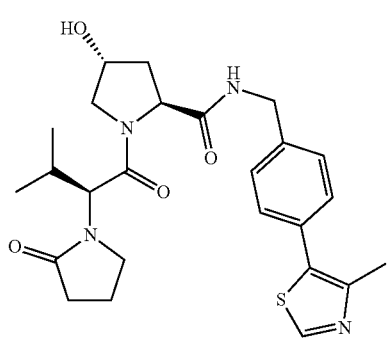
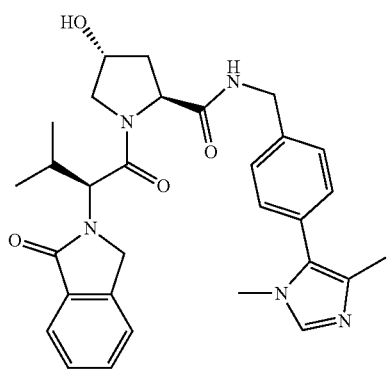
114
-continued
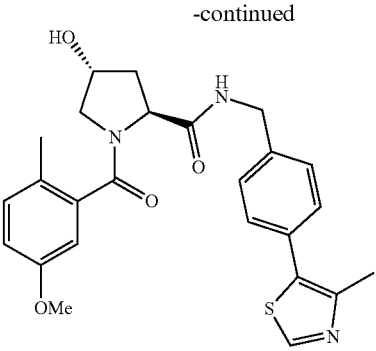
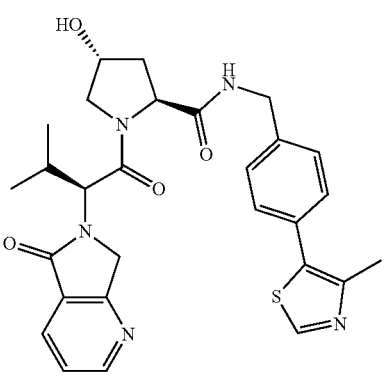
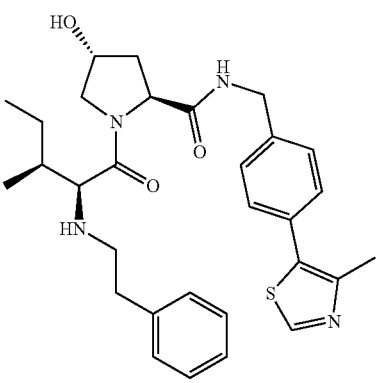
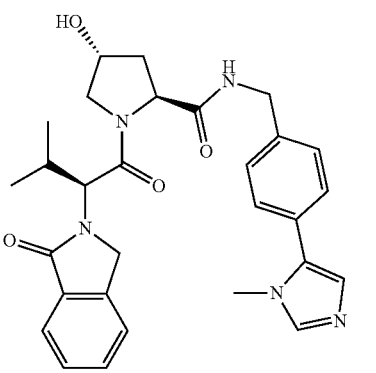

115
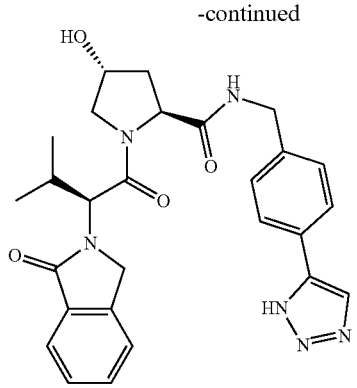
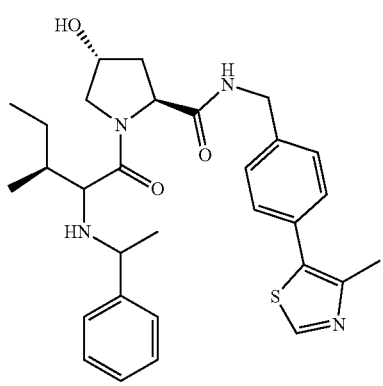
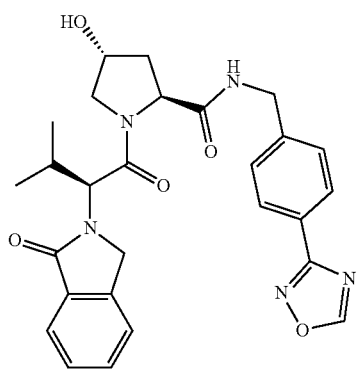
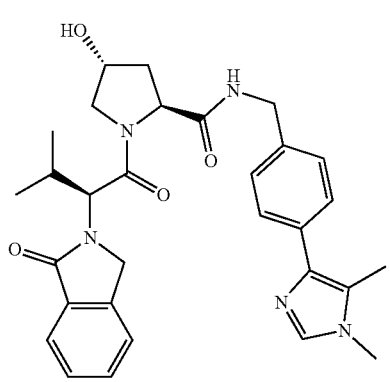
116
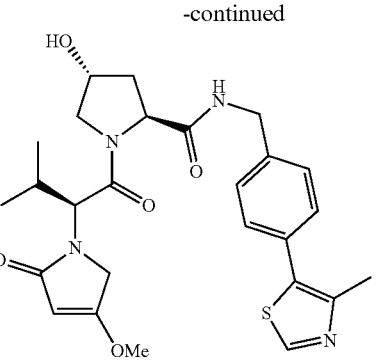
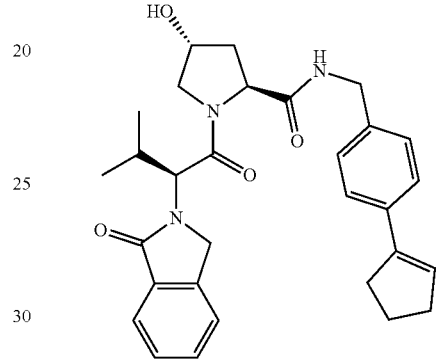
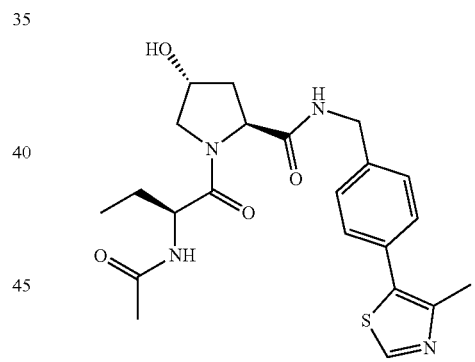
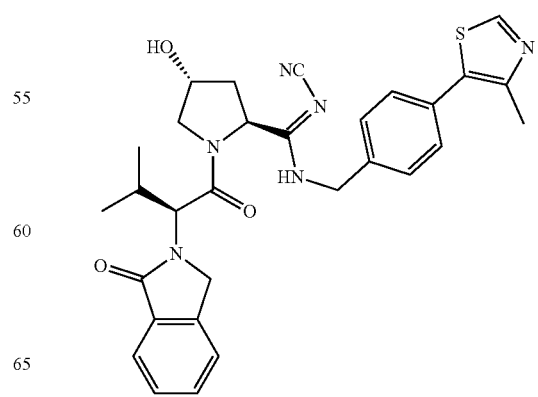

117
-continued
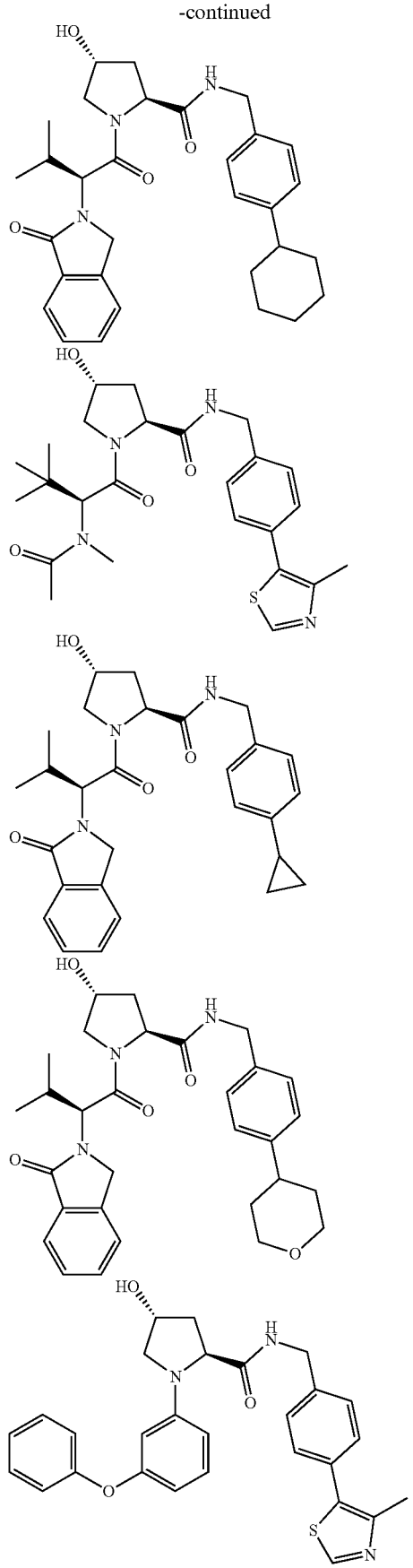
118
-continued
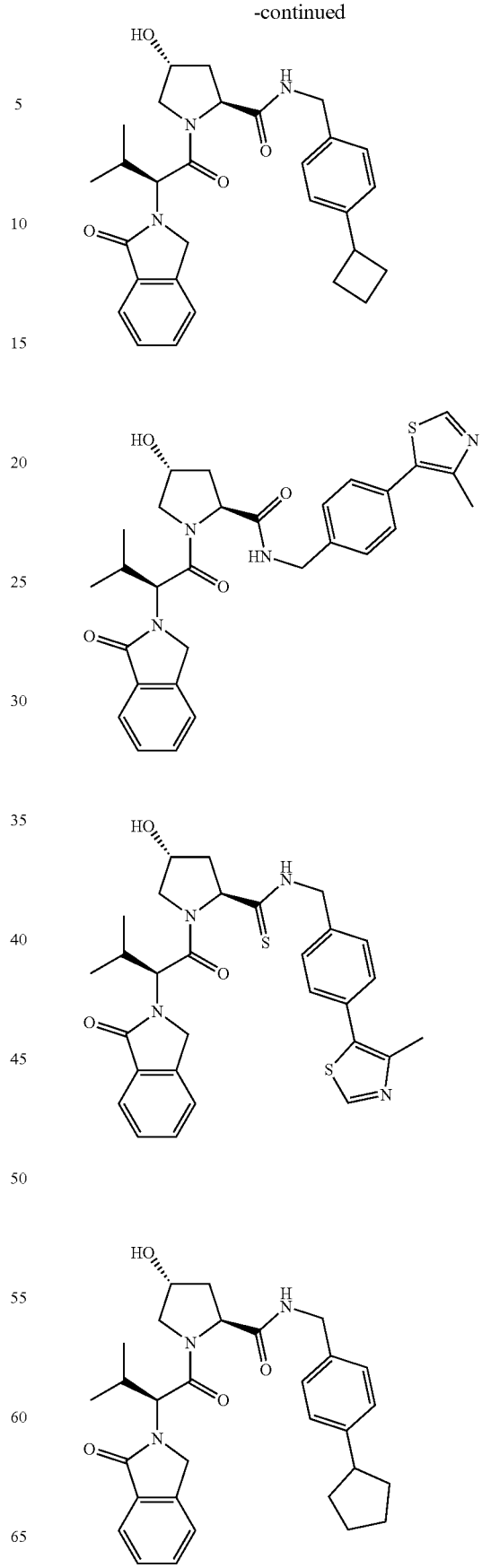

119
-continued
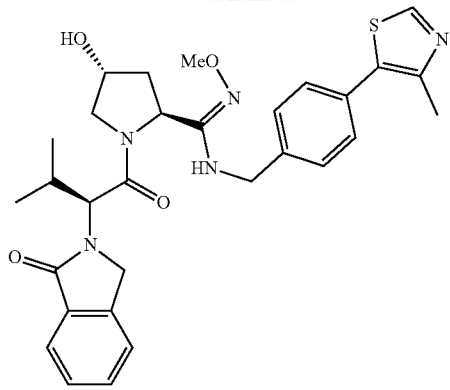
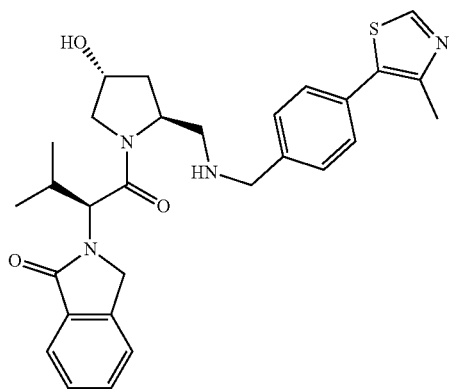
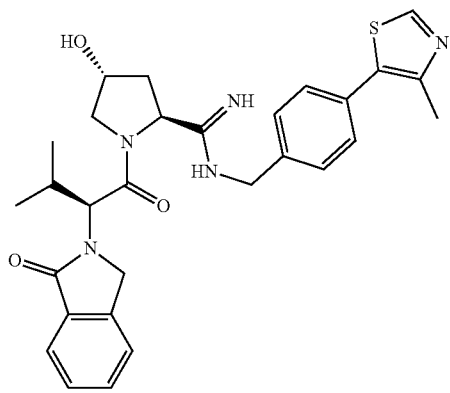
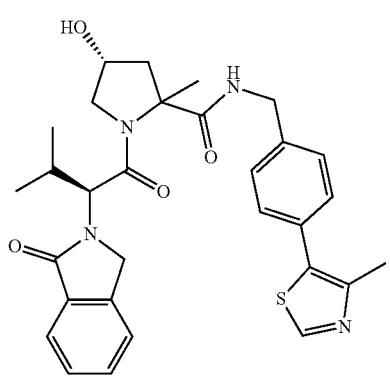
120
-continued
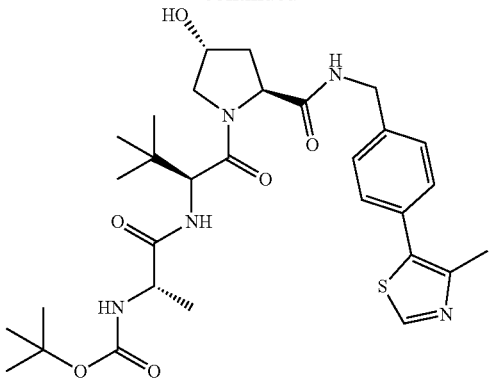
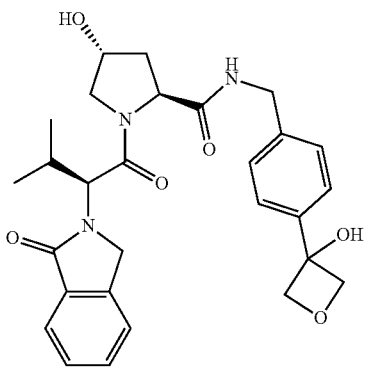
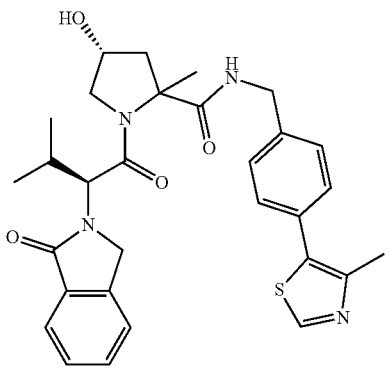
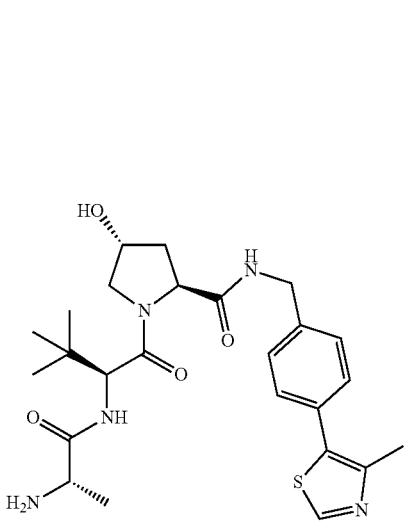

121
-continued
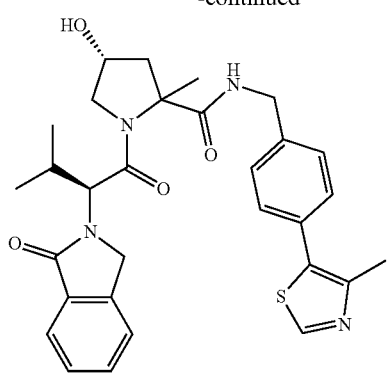
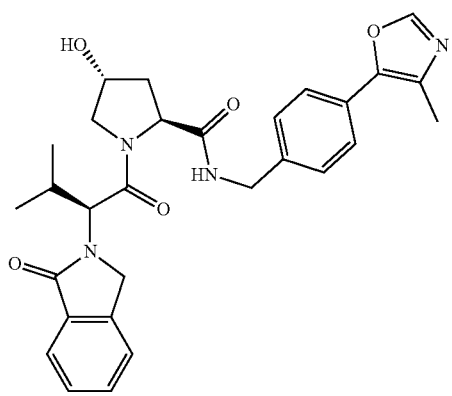
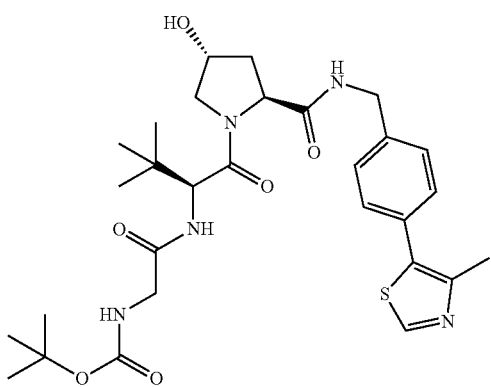
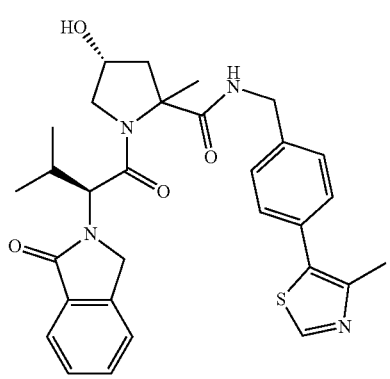
122
-continued
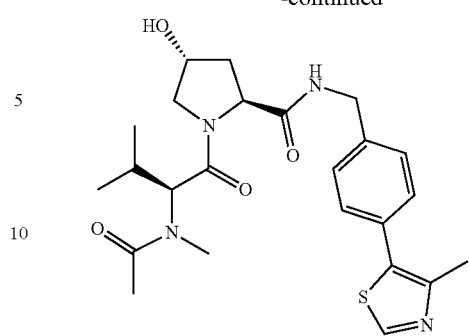
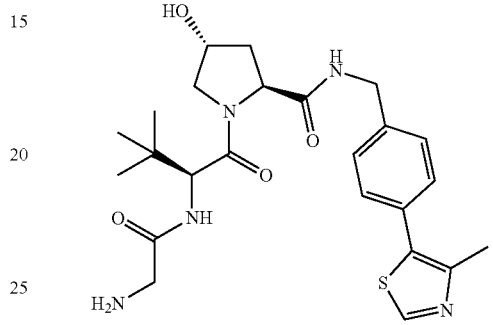
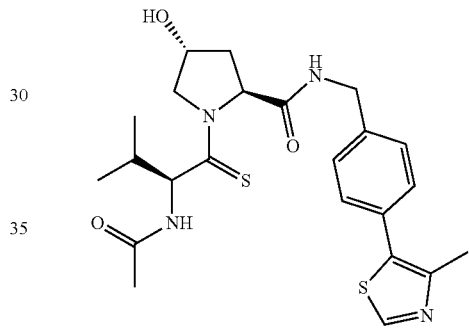
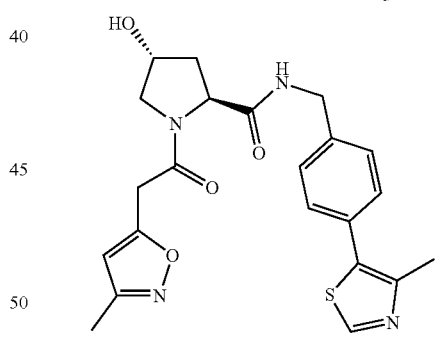
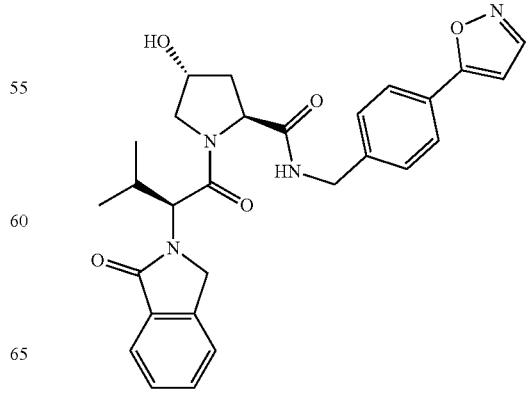

123
-continued
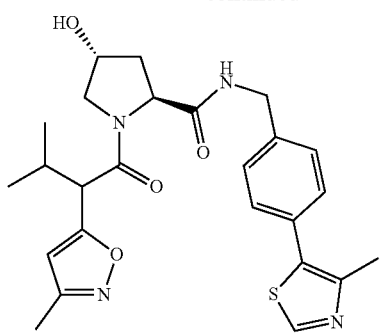
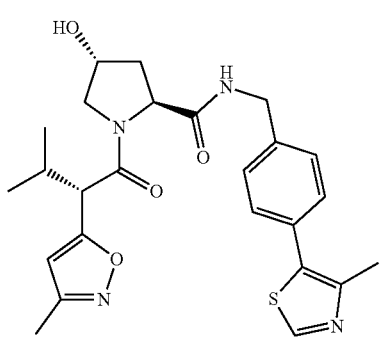
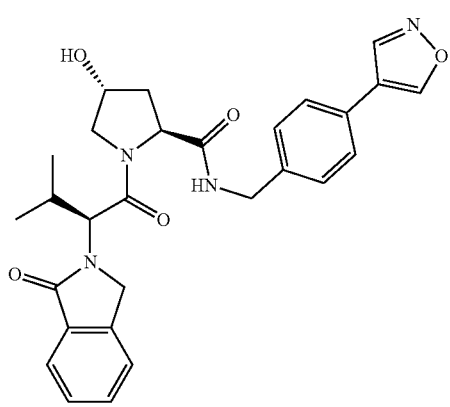
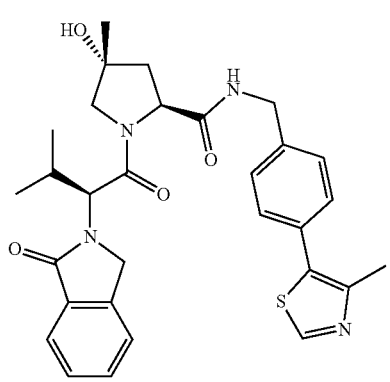
124
-continued
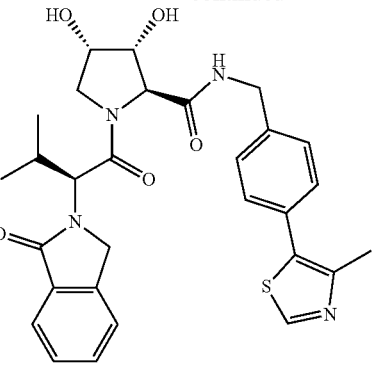
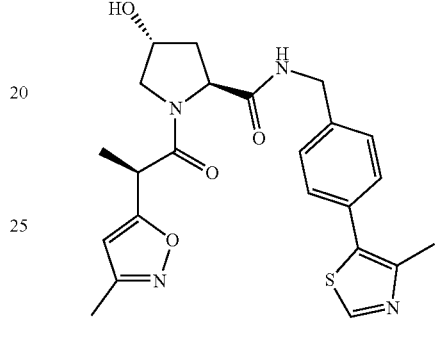
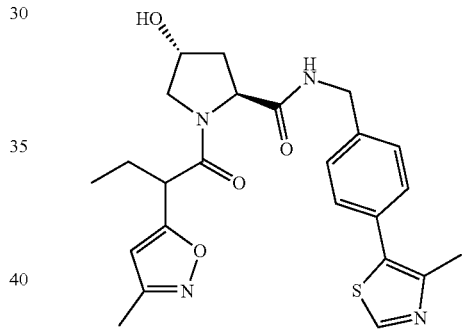
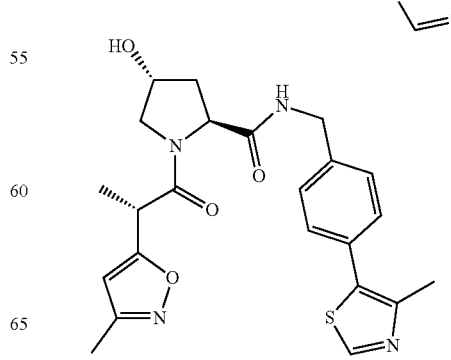

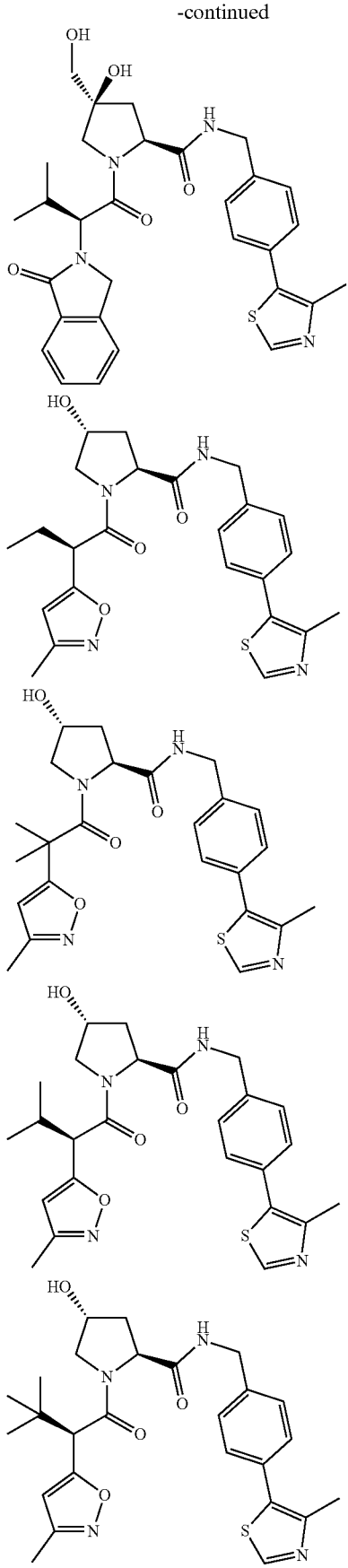
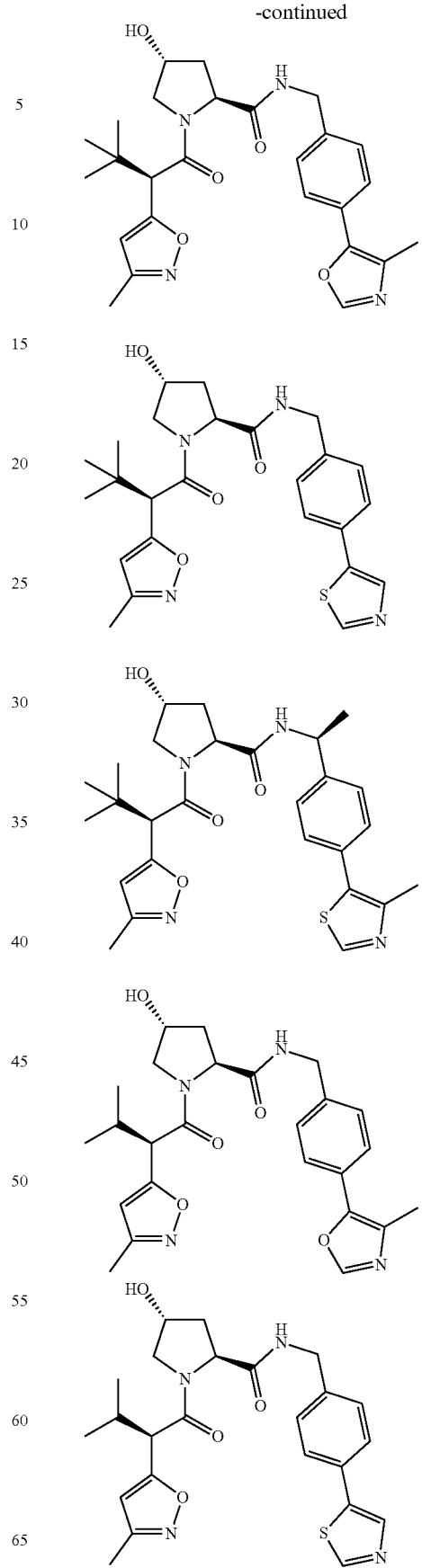

127
-continued
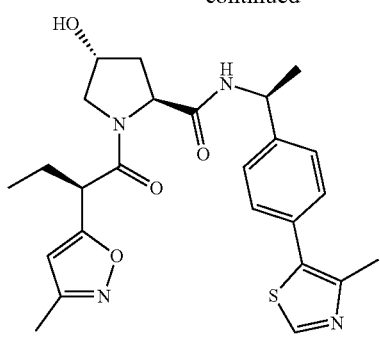
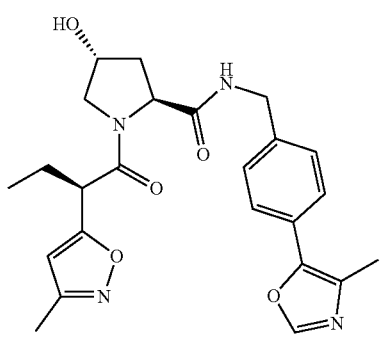
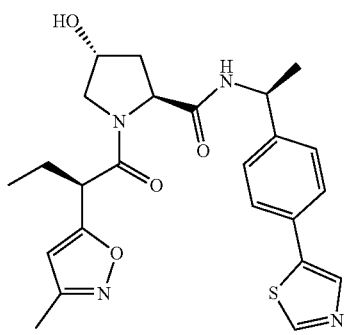
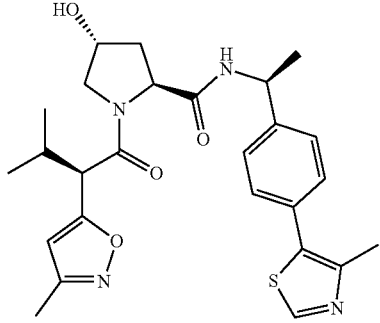
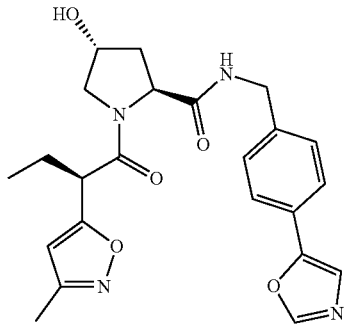
128
-continued
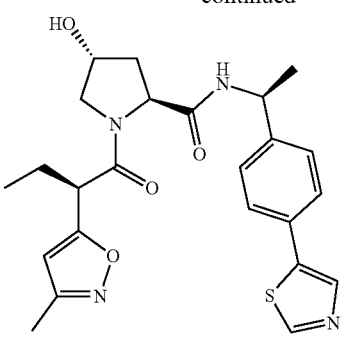
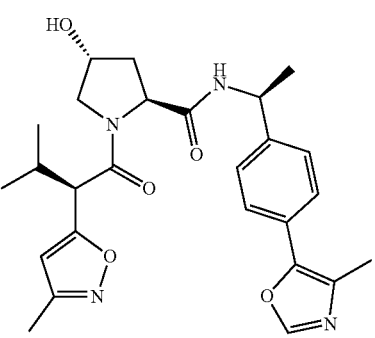
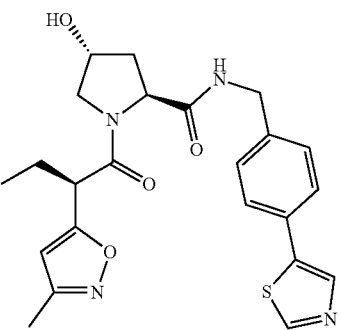
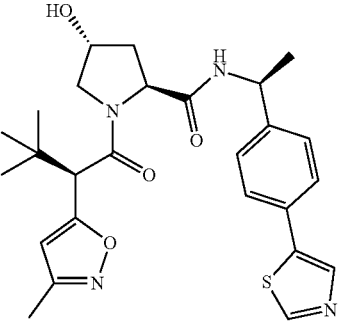
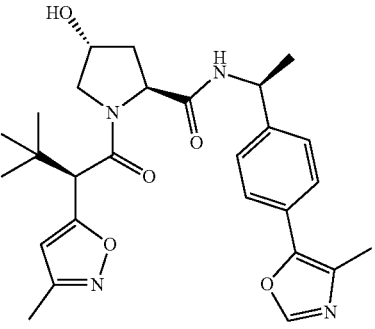

129
-continued
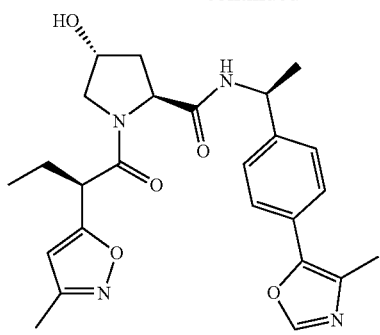
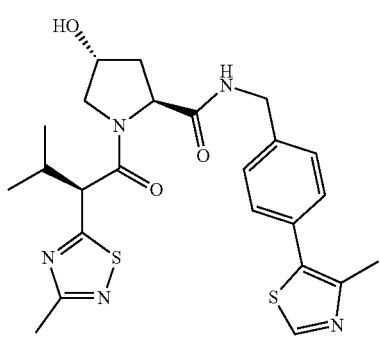
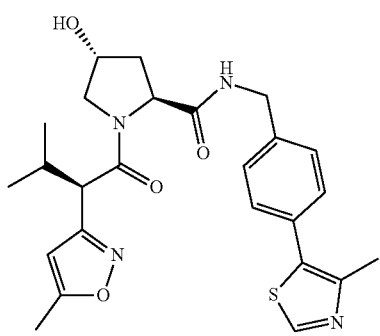
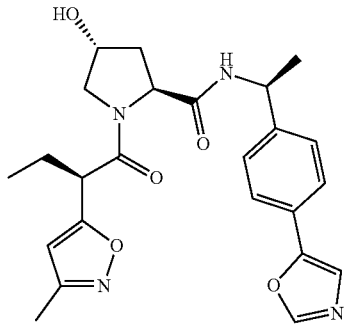
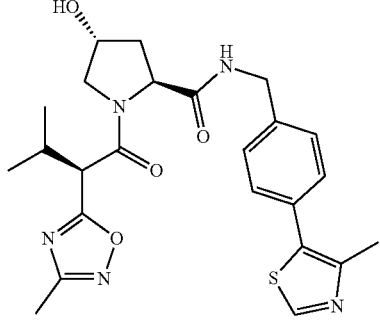
130
-continued
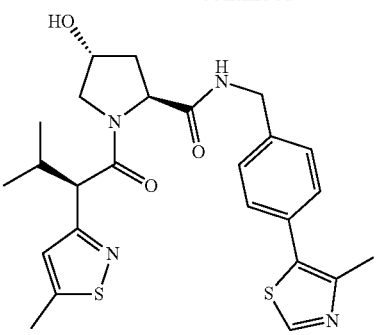
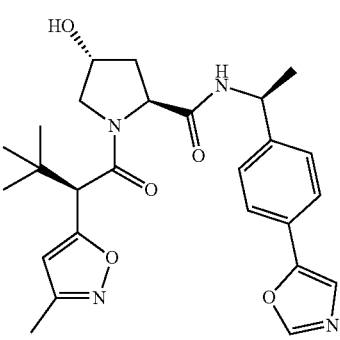
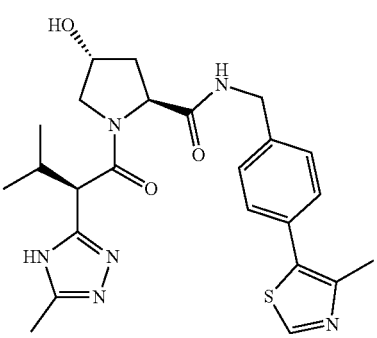
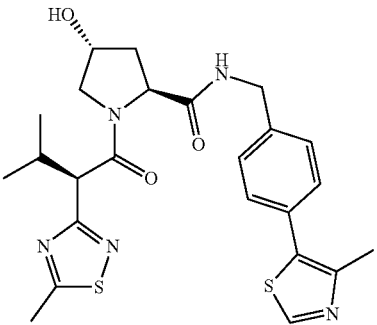
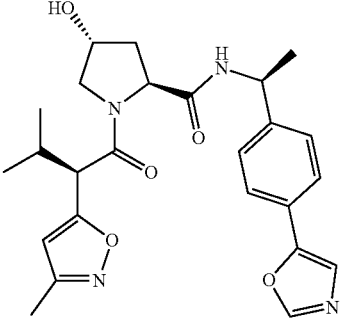

131
-continued
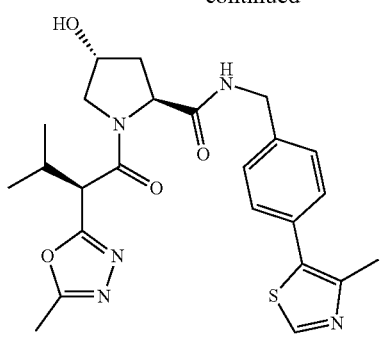
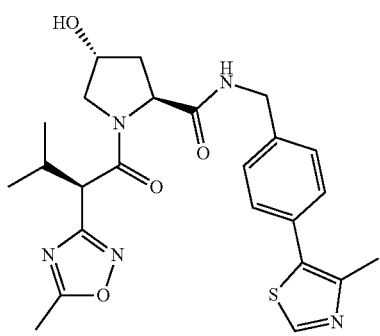
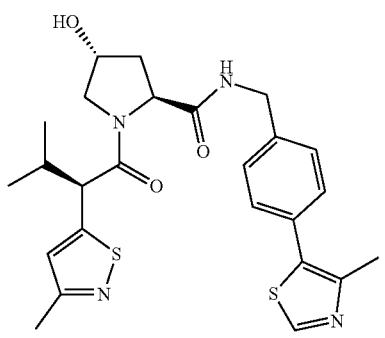
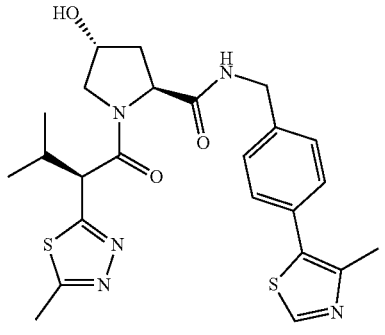
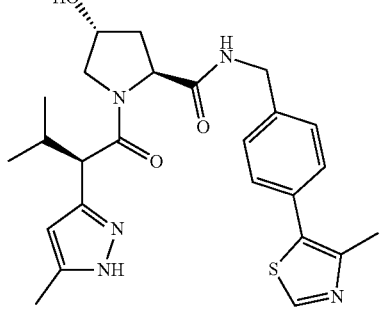
132
-continued
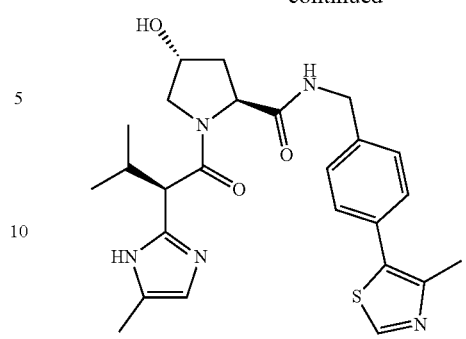
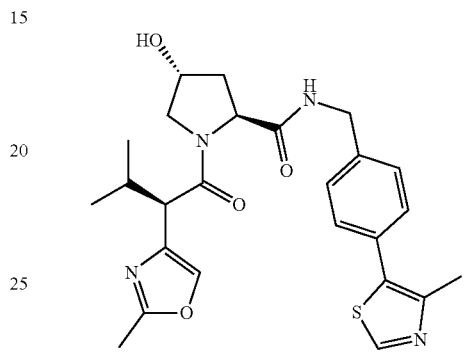

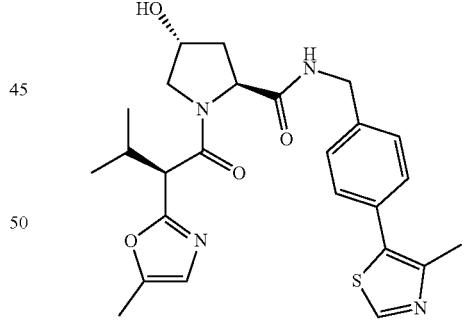
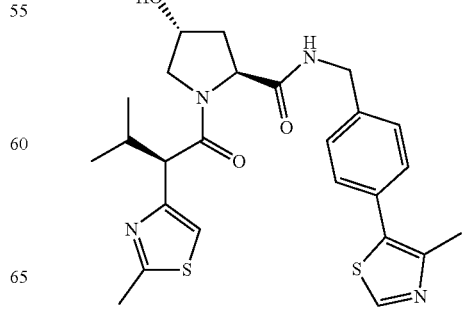

133
-continued
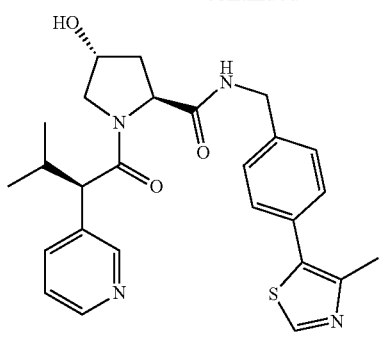
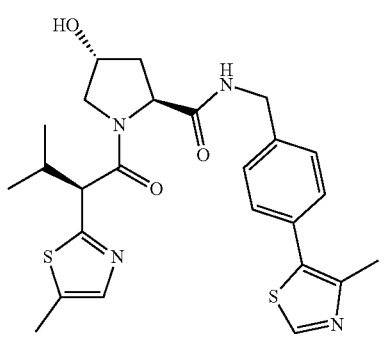
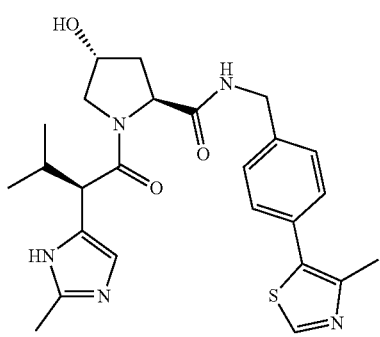
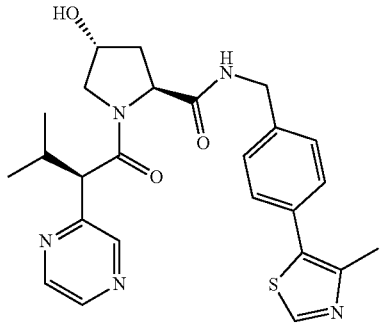
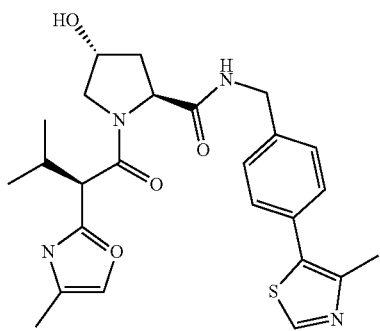
134
-continued
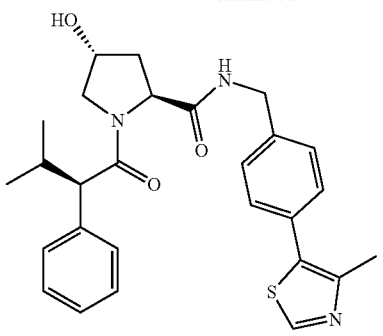
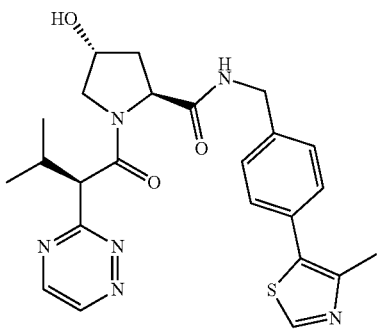
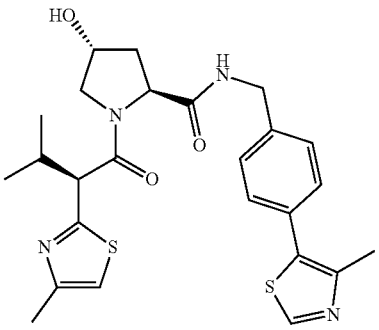
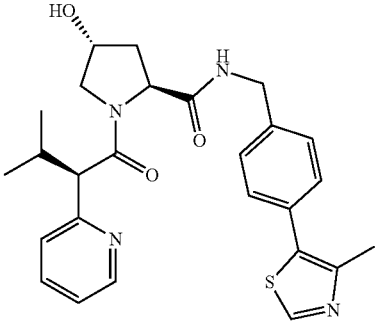
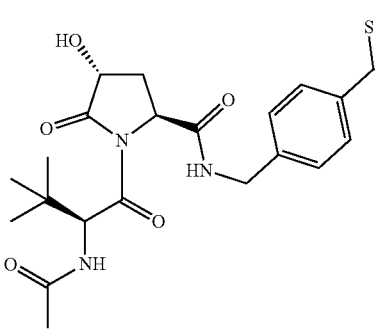

135
-continued
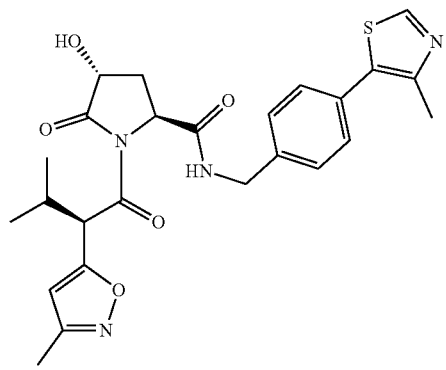
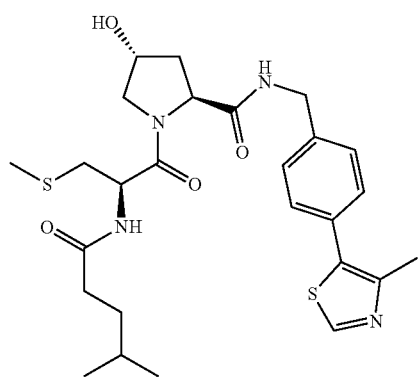
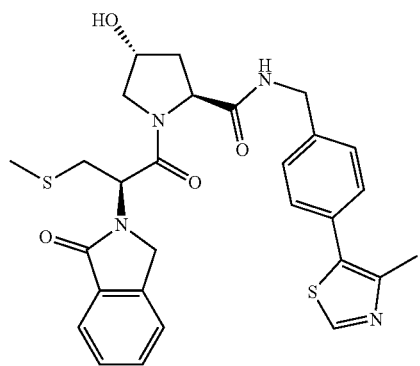
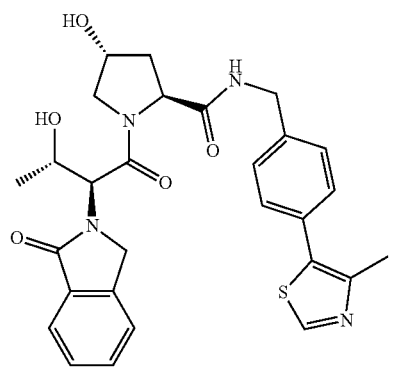
136
-continued
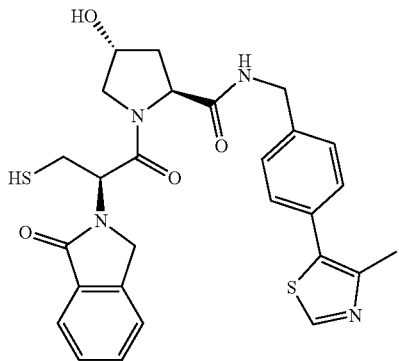
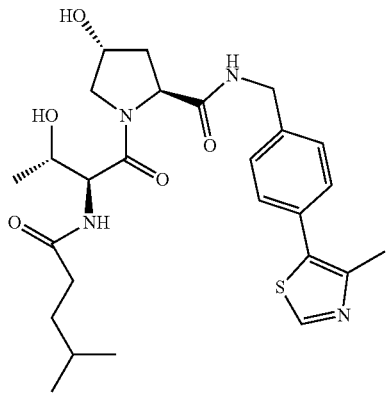
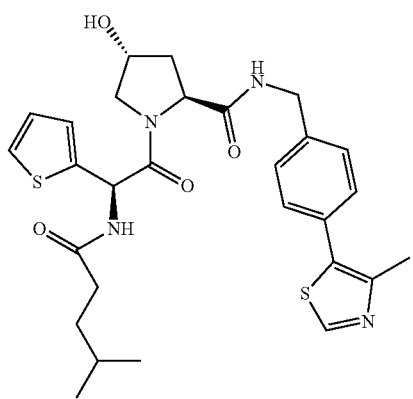
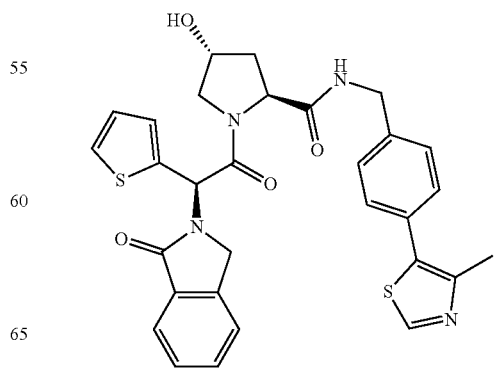

137
-continued
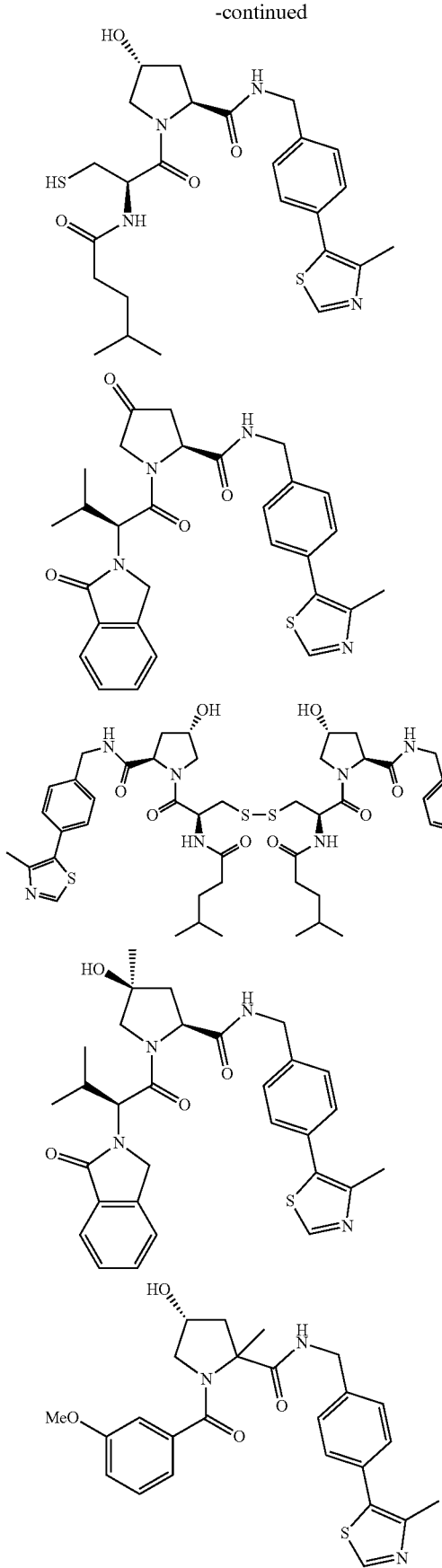
138
-continued
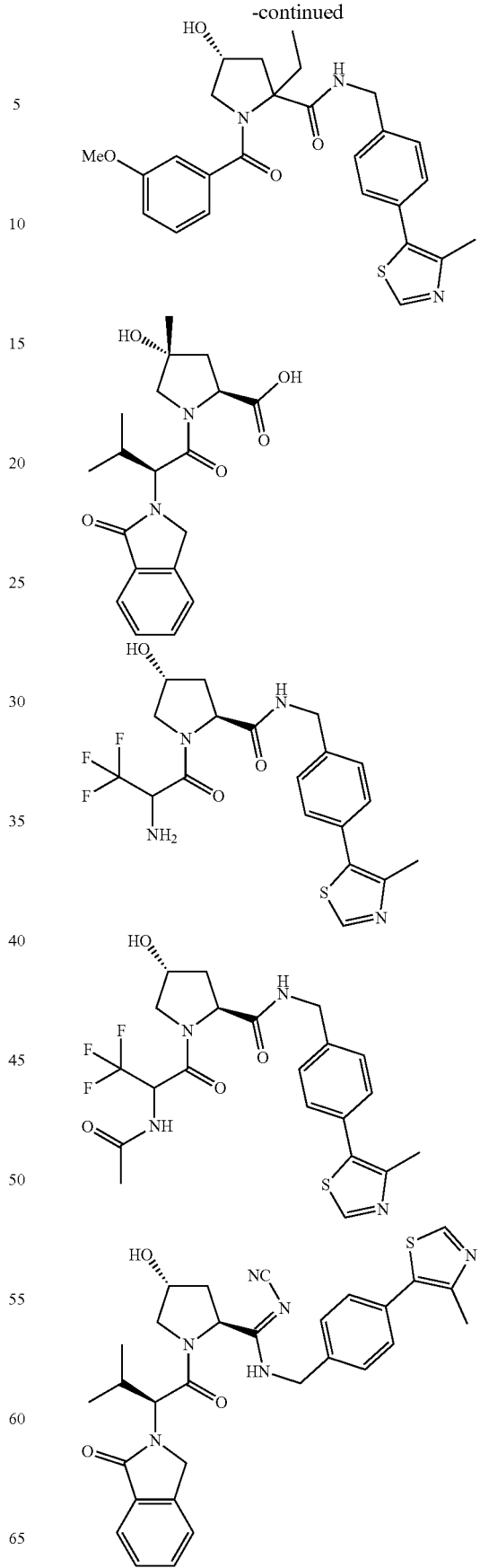

139
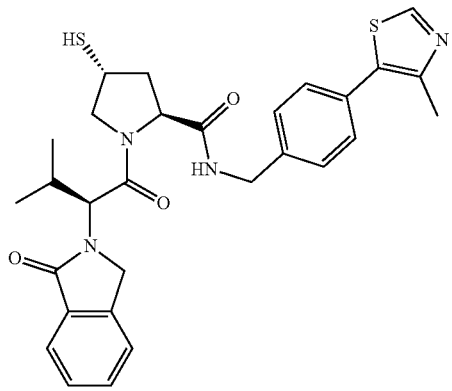
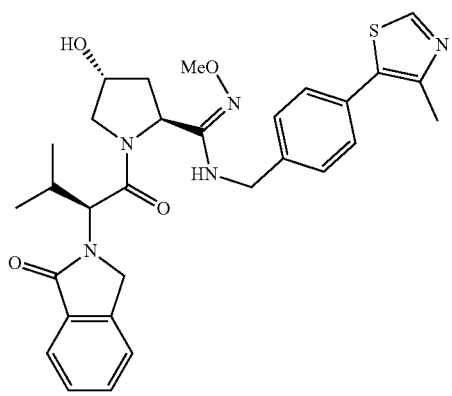
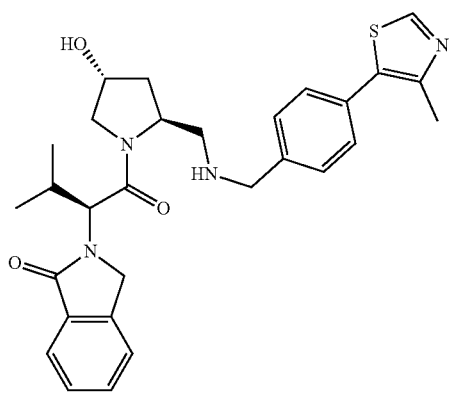
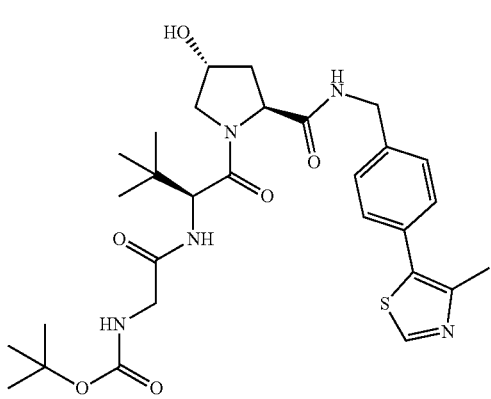
140
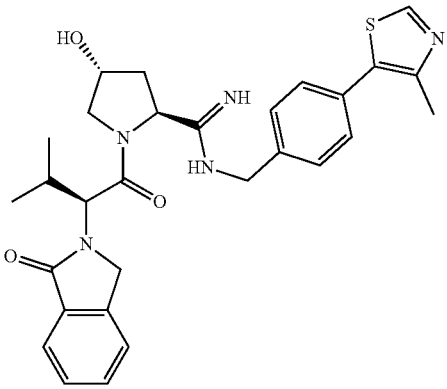
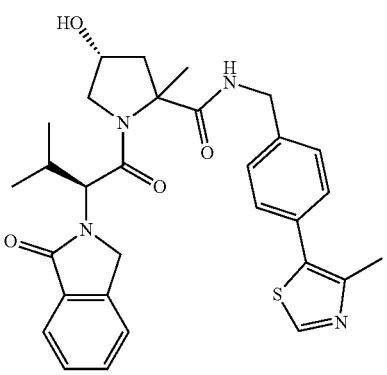
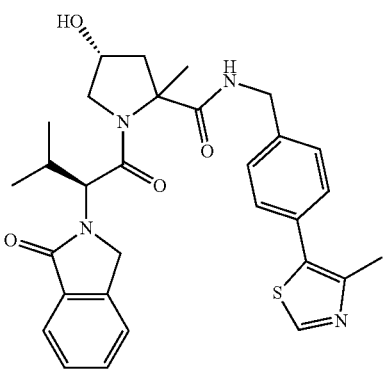
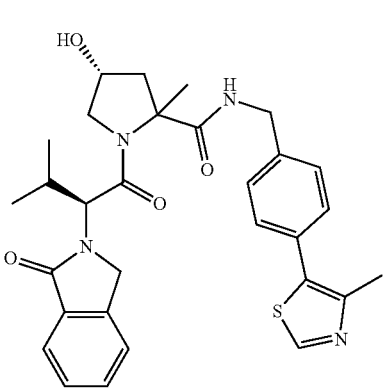

141
-continued
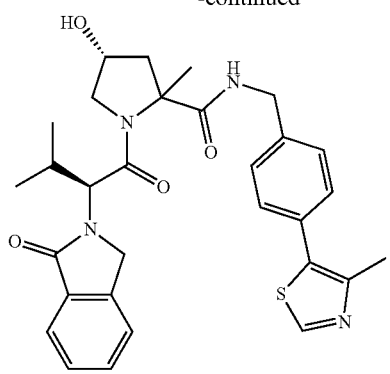
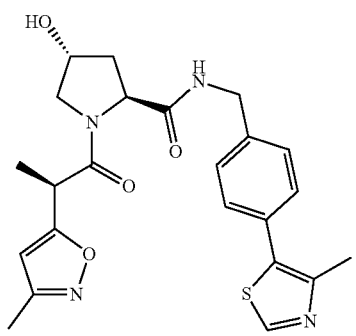
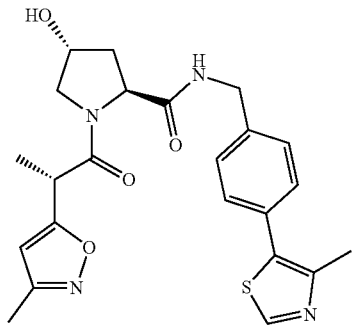
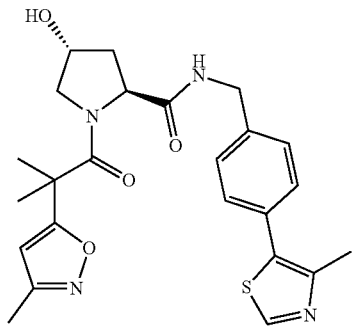
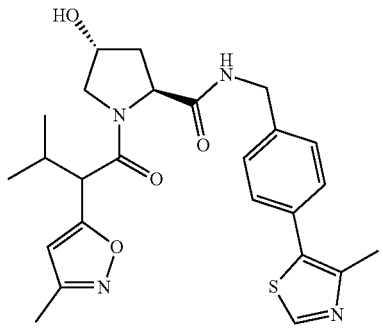
142
-continued
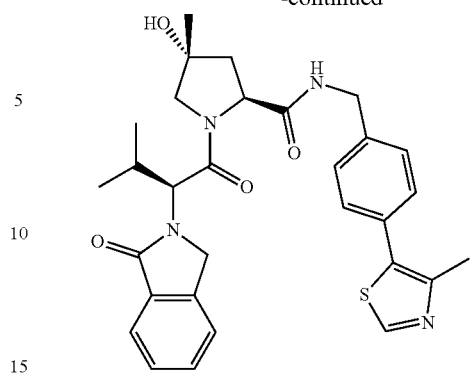
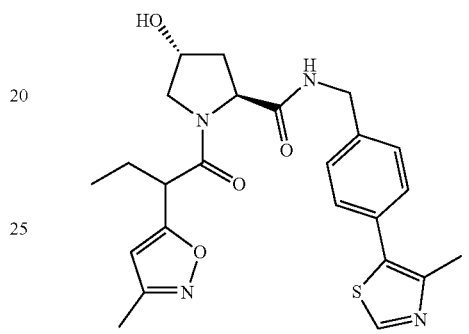
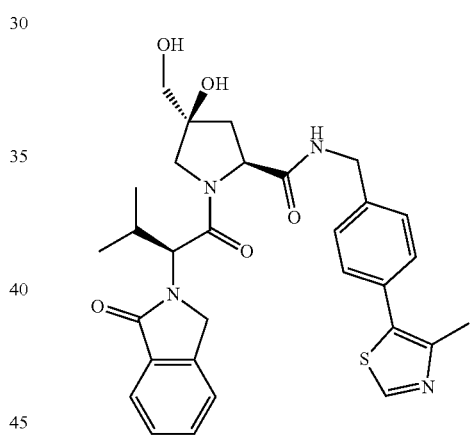
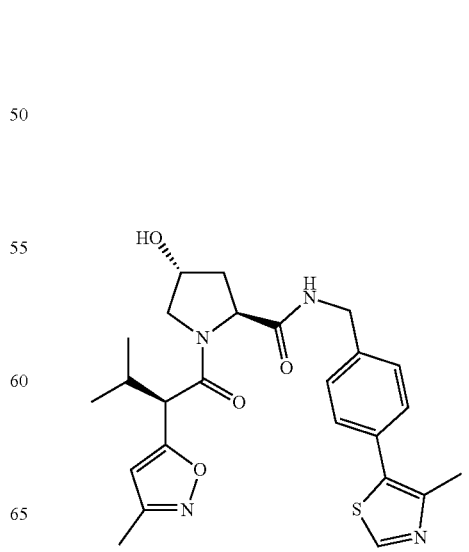

143
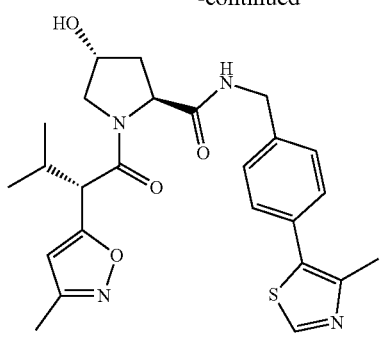
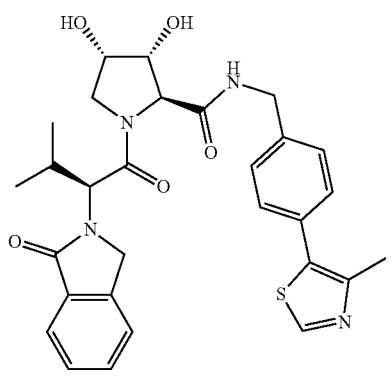
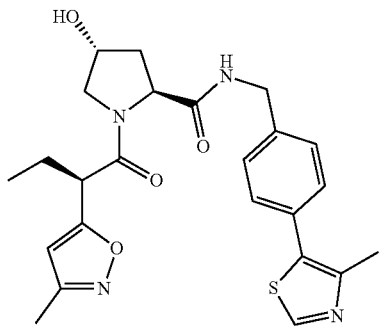
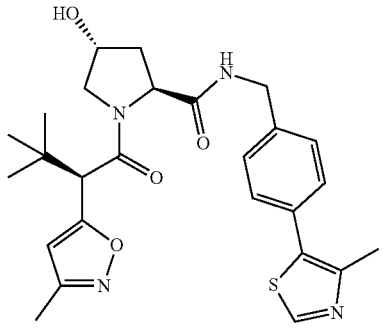
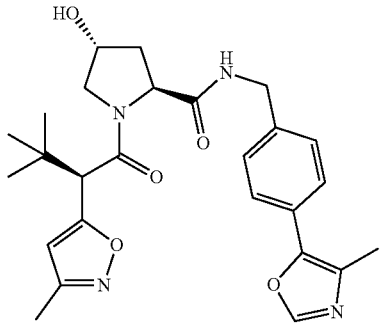
144
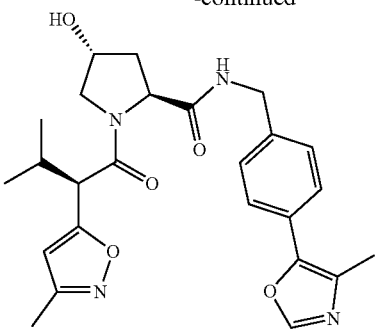
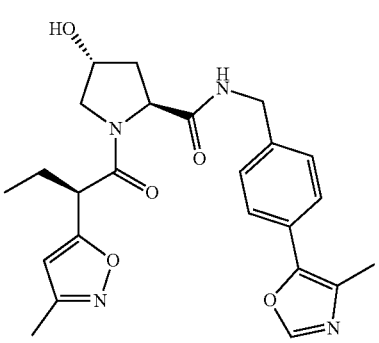 [SMILES: CC[C@@H](C(=O)N1C[C@H](O)C[C@H]1C(=O)NCc1ccc(-c2scnc2C)cc1)c1cc(C)no1]
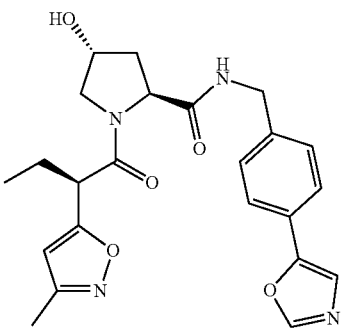
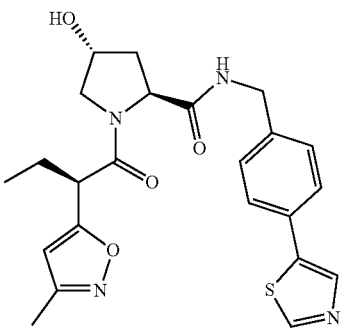
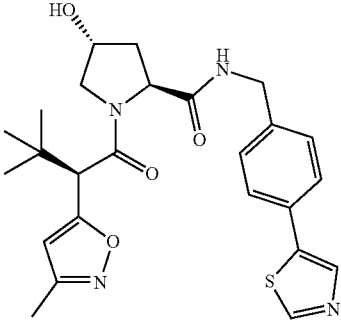

145
-continued
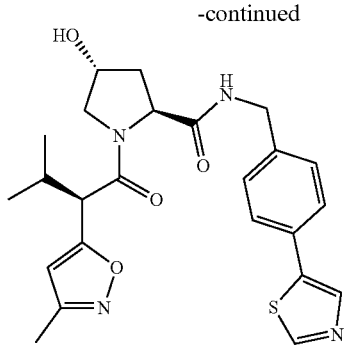
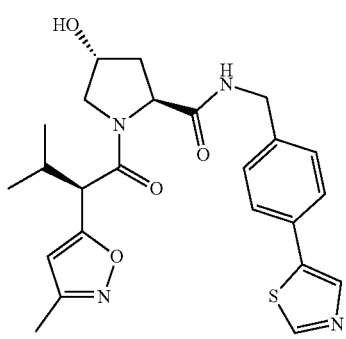
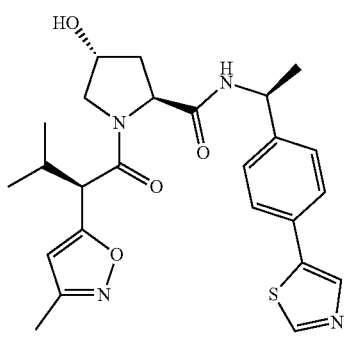
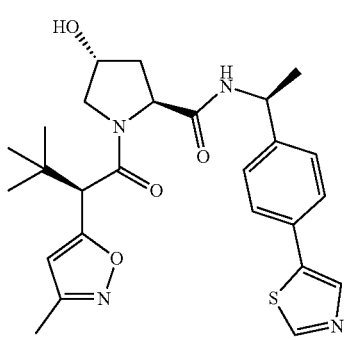
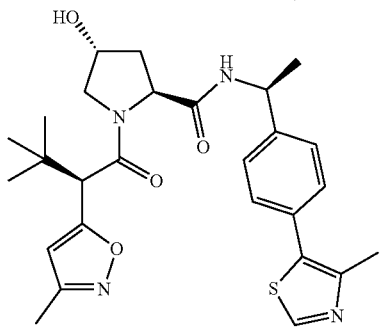
146
-continued
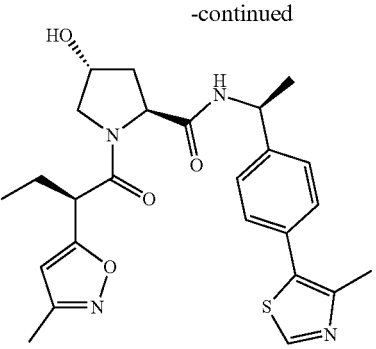
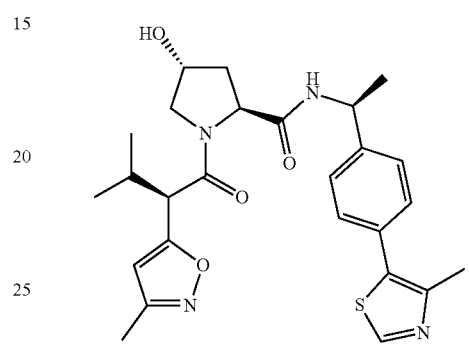
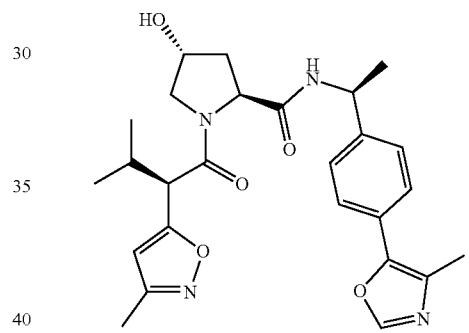
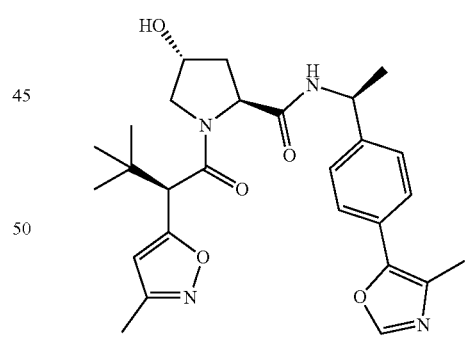
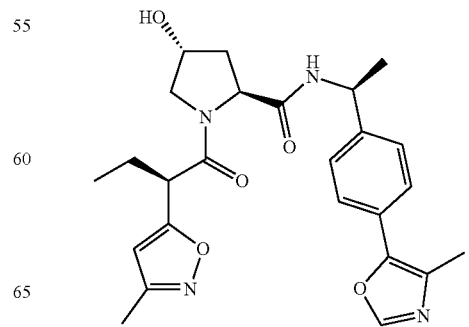

147
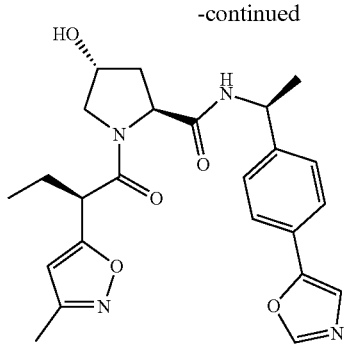
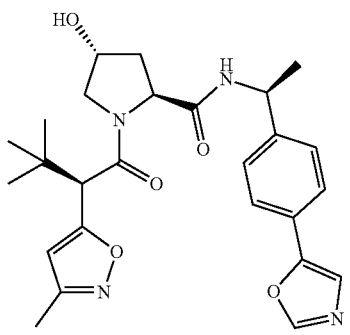
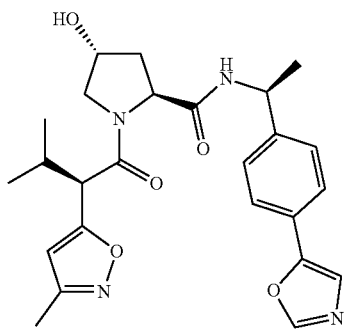
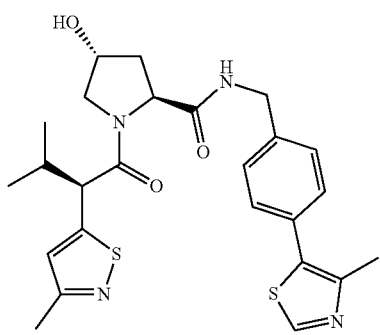
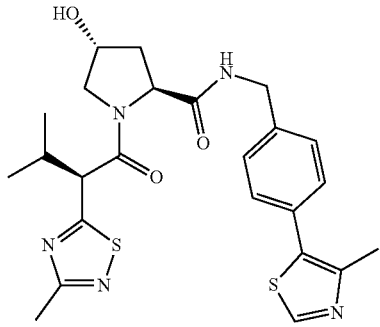
148
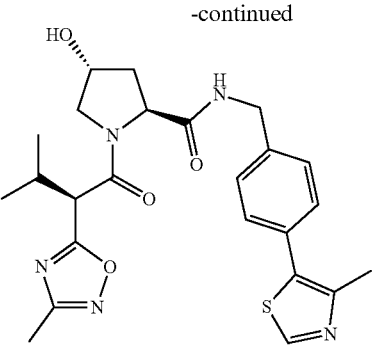
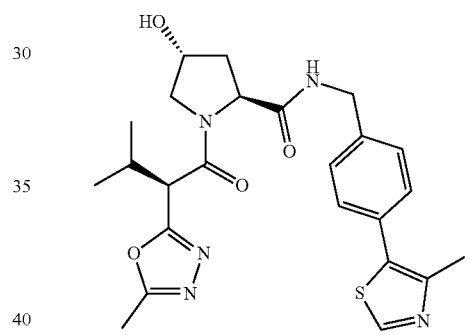
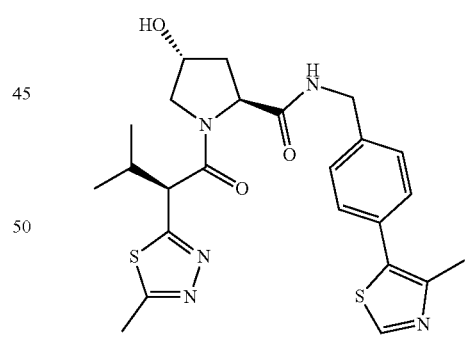
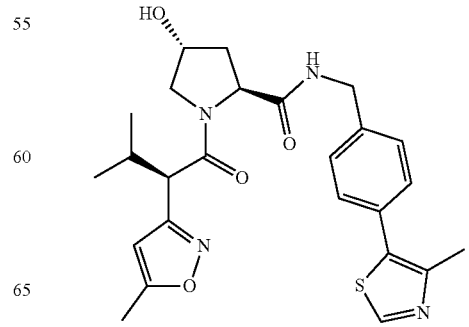

149
-continued
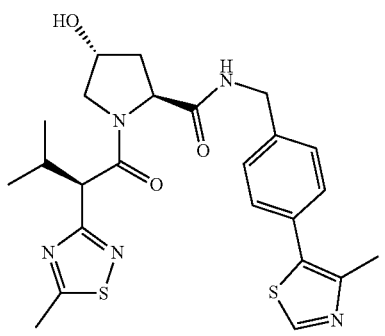
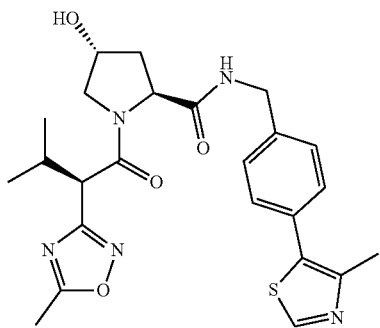
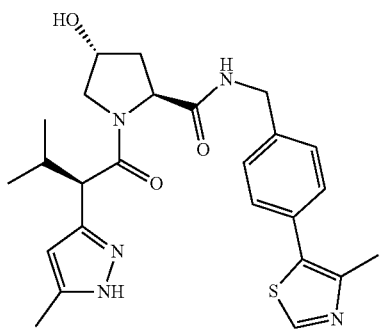
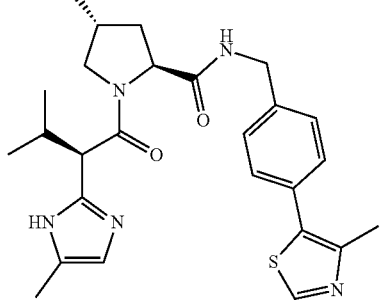
150
-continued
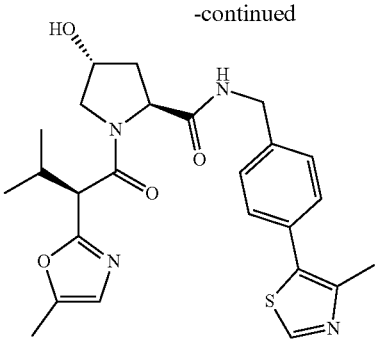
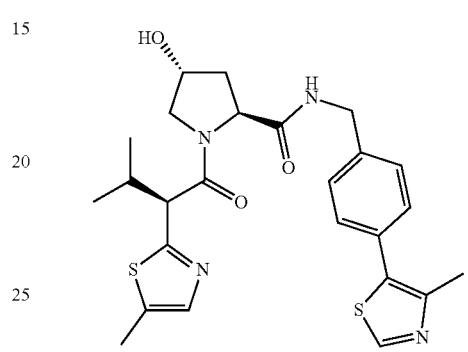
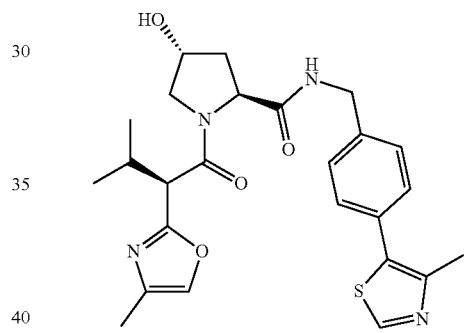

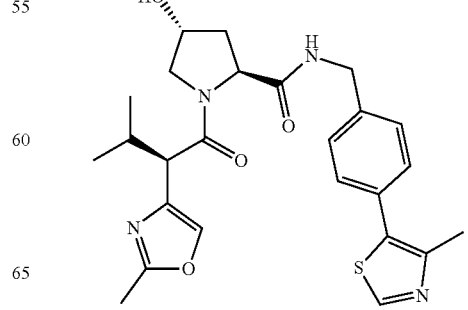

151
-continued
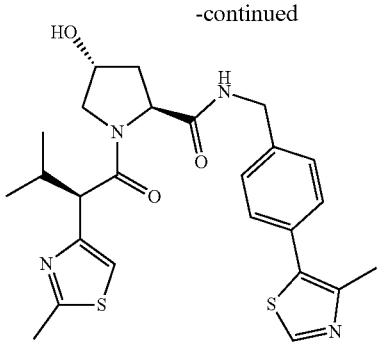
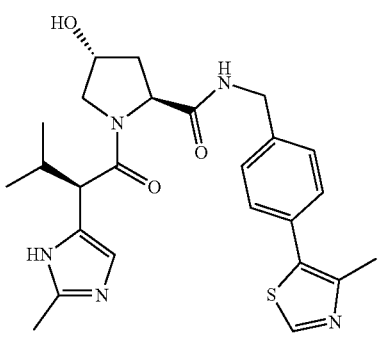
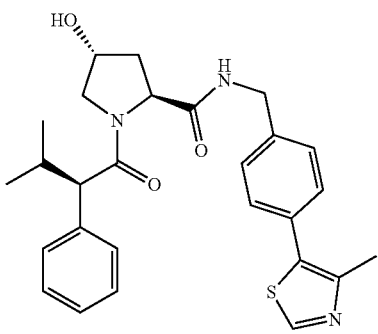
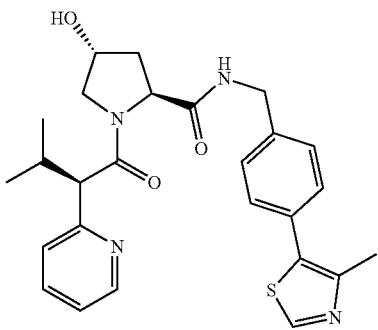
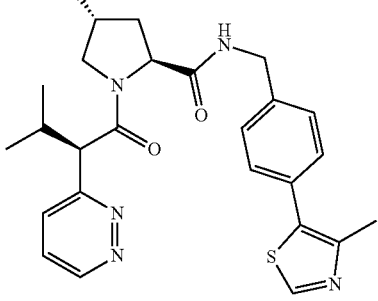
152
-continued
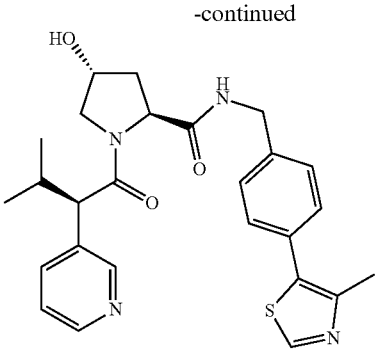
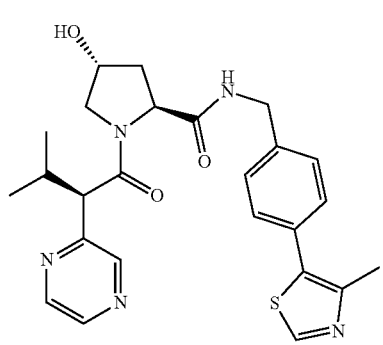
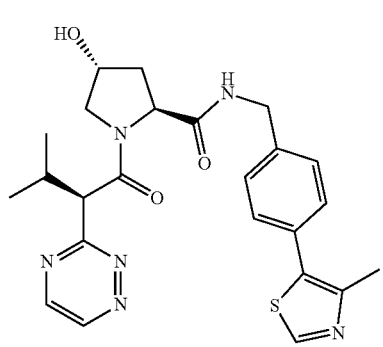
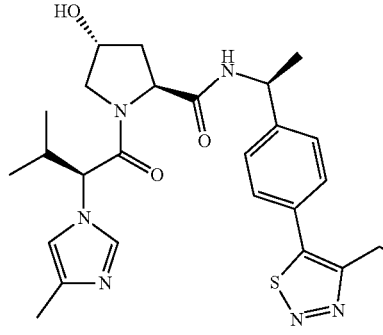
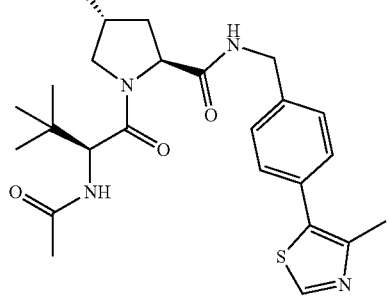

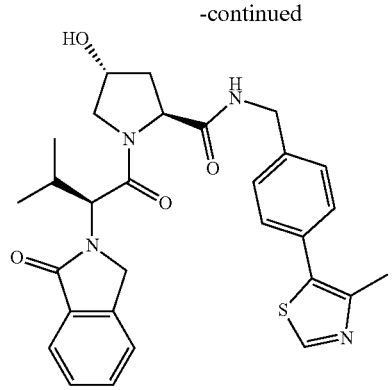
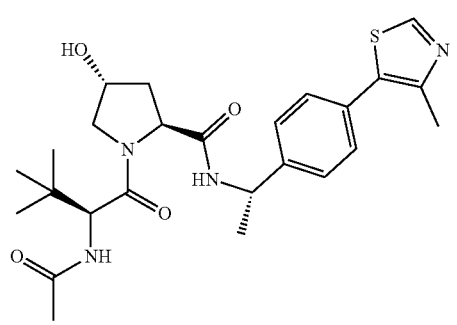
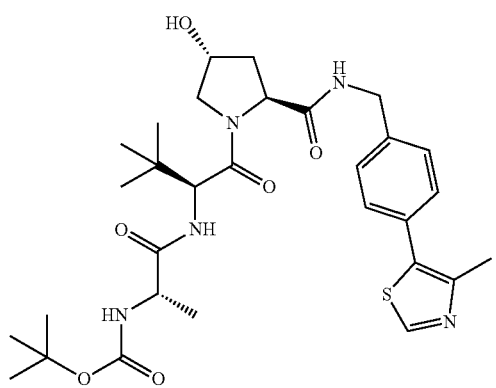
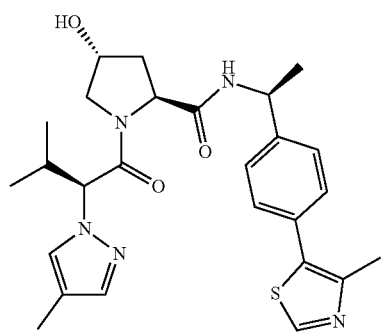
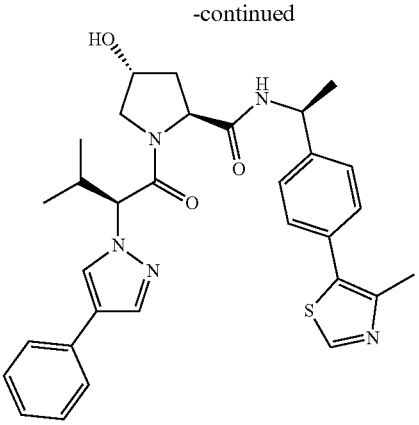
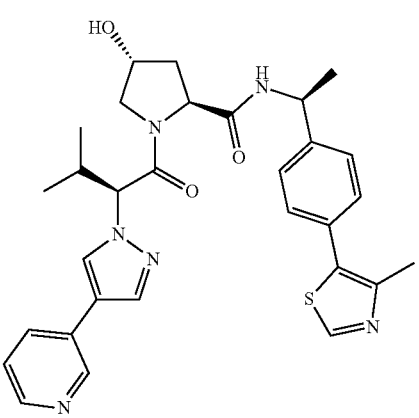
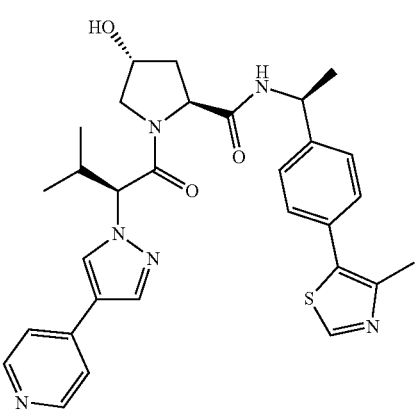
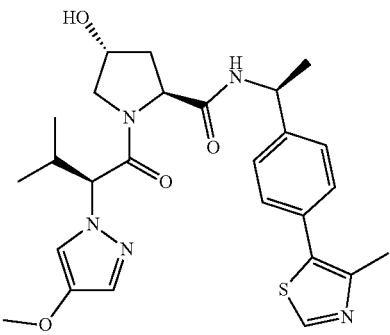

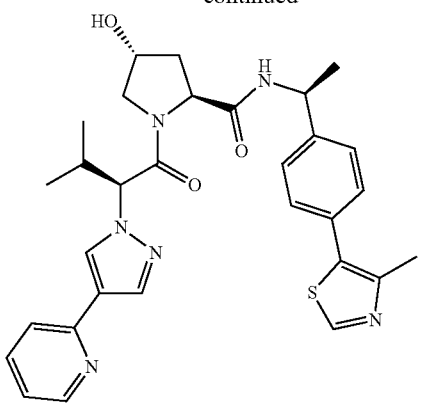

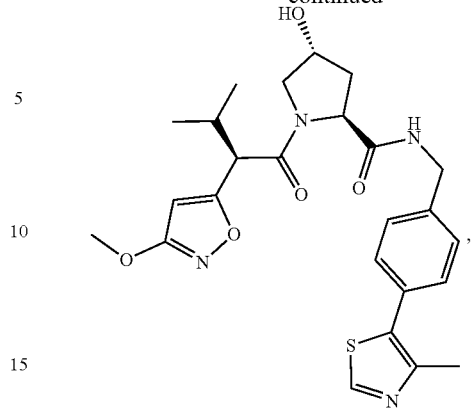

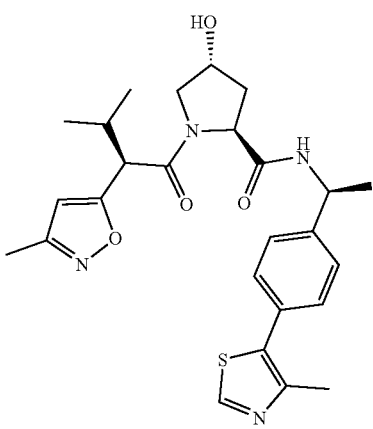

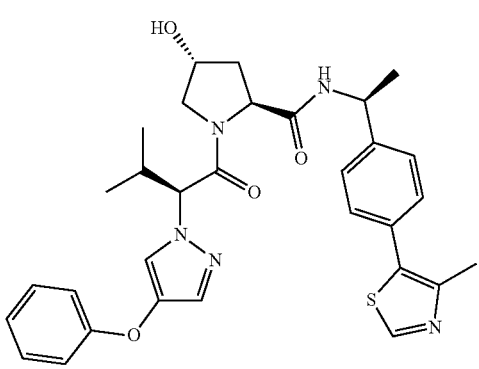

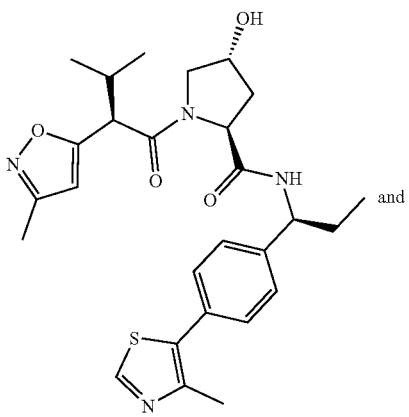

and wherein the VLM may be connected to a PTM via a linker, as described herein, at any appropriate location, including, e.g., an aryl, heteroaryl, phenyl, or phenyl of an indole group, optionally via any appropriate functional group, such as an amine, ester, ether, alkyl, or alkoxy.

Exemplary CLMs:

In any aspect or embodiment described herein, the description provides compounds useful for binding and/or inhibiting cereblon (e.g., the ULM is a CLM, the PTM is a CLM, or both the ULM and PTM are CLMs).

In some embodiments, the ULM is a CLM that is a thalidomide, lenalidomide, pomalidomide, analogs thereof, isosteres thereof, or derivatives thereof.

Neo-Imide Compounds

In certain embodiments, the CLM is selected from the group consisting of chemical structures:

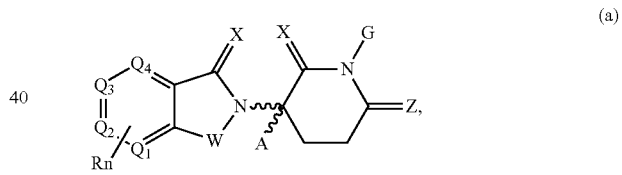

(a)


(b)


(c)

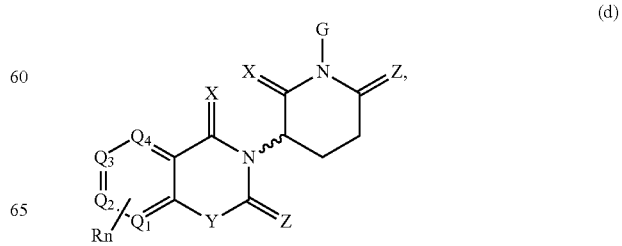

(d)

-continued

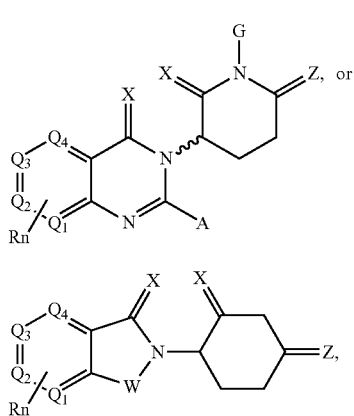

wherein:
- W is selected from the group consisting of CH$_2$, CHR, C=O, SO$_2$, NH, and N-alkyl;
- each X is independently selected from the group consisting of O, S, and H$_2$;
- Y is selected from the group consisting of CH$_2$, —C=CR', NH, N-alkyl, N-aryl, N-hetaryl, N-cycloalkyl, N-heterocyclyl, O, and S;
- Z is selected from the group consisting of O, S, and H$_2$;
- G and G' are independently selected from the group consisting of H, alkyl (linear, branched, optionally substituted with R'), OH, R'OCOOR, R'OCONRR", CH$_2$-heterocyclyl optionally substituted with R', and benzyl optionally substituted with R';
- Q$_1$, Q$_2$, Q$_3$, and Q$_4$ represent a carbon C substituted with a group independently selected from R', N or N-oxide;
- A is independently selected from the group H, alkyl, cycloalkyl, Cl and F;
- R comprises but is not limited to: —CONR'R", —OR', —NR'R", —SR', —SO$_2$R', —SO$_2$NR'R", —CR'R"—, —CR'NR'R"—, -aryl, -hetaryl, -alkyl (linear, branched, optionally substituted), -cycloalkyl, -heterocyclyl, —P(O)(OR')R", —P(O)R'R", —OP(O)(OR')R", —OP(O)R'R", —Cl, —F, —Br, —I, —CF$_3$, —CN, —NR'SO$_2$NR'R", —NR'CONR'R", —CONR'COR", —NR'C(=N—CN)NR'R", —C(=N—CN)NR'R", —NR'C(=N—CN)R", —NR'C(=C—NO$_2$)NR'R", —SO$_2$NR'COR", —NO$_2$, —CO$_2$R', —C(C=N—OR')R", —CR'=CR'R", —CCR', —S(C=O)(C=N—R')R", —SF$_5$ or —OCF$_3$;
- R' and R" are independently selected from the group consisting of a bond, H, N, N-oxide, alkyl (linear, branched), cycloalkyl, aryl, heteroaryl, heterocyclic, —C(=O)R, or heterocyclyl, each of which is optionally substituted;
- ⌇⌇⌇ represents a bond that may be stereospecific ((R) or (S)) or non-stereospecific; and
- R$_n$ comprises a functional group or an atom,
- wherein n is an integer from 1-4, and wherein:
  - when n is 1, R$_n$ is modified to be covalently joined to the linker group (L), and
  - when n is 2, 3, or 4, then one R$_n$ is modified to be covalently joined to the linker group (L), and any other R$_n$ is optionally modified to be covalently joined to a PTM, a CLM, a second CLM having the same chemical structure as the CLM, a CLM', a second linker, or any multiple or combination thereof.

Exemplary CLMs

In any of the compounds described herein, the CLM comprises a chemical structure selected from the group:

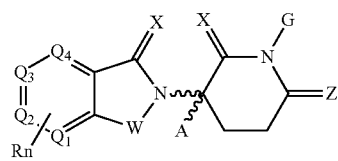

(a)

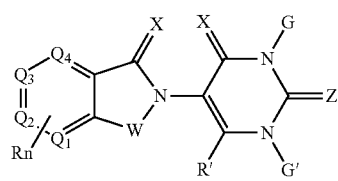

(b)

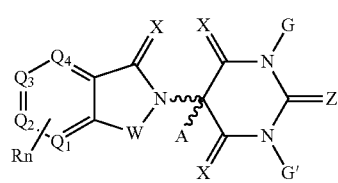

(c)

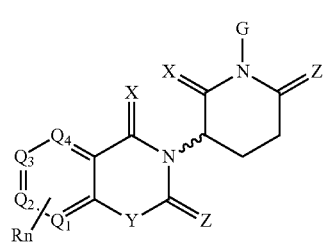

(d)

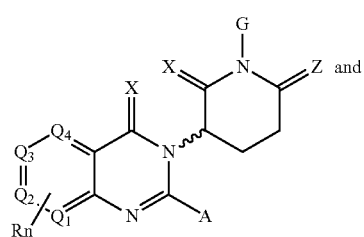

(e) and

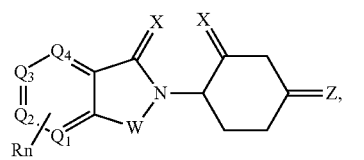

(f)

wherein:
- W is independently selected from the group CH$_2$, CHR, C=O, SO$_2$, NH, and N-alkyl;
- X is independently selected from the group O, S and H$_2$;
- Y is independently selected from the group CH$_2$, —C=CR', NH, N-alkyl, N-aryl, N-hetaryl, N-cycloalkyl, N-heterocyclyl, O, and S;
- Z is independently selected from the group O, and S or H$_2$ except that both X and Z cannot be H$_2$;
- G and G' are independently selected from the group H, alkyl (linear, branched, optionally substituted with R'), OH, R'OCOOR, R'OCONRR", CH$_2$-heterocyclyl optionally substituted with R', and benzyl optionally substituted with R';

Q1-Q4 represent a carbon C substituted with a group independently selected from R', N or N-oxide;

A is independently selected from the group H, alkyl, cycloalkyl, Cl and F;

R comprises, but is not limited to: —CONR'R", —OR', —NR'R", —SR', —SO₂R', —SO₂NR'R", —CR'R"—, —CR'NR'R"—, -aryl, -hetaryl, -alkyl (linear, branched, optionally substituted), -cycloalkyl, -heterocyclyl, —P(O)(OR')R", —P(O)R'R", —OP(O)(OR')R", —OP(O)R'R", —Cl, —F, —Br, —I, —CF₃, —CN, —NR'SO₂NR'R", —NR'CONR'R", —CONR'COR", —NR'C(=N—CN)NR'R", —C(=N—CN)NR'R", —NR'C(=N—CN)R", —NR'C(=C—NO₂)NR'R", —SO₂NR'COR", —NO₂, —CO₂R', —C(C=N—OR')R", —CR'=CR'R", —CCR', —S(C=O)(C=N—R')R", —SF₅ or —OCF₃

R' and R" are independently selected from the group consisting of a bond, H, N, N-oxide, alkyl (linear, branched), cycloalkyl, aryl, heteroaryl, heterocyclic, —C(=O)R, or heterocyclyl, each of which is optionally substituted;

n is an integer from 1-4;

∼∼∼ represents a bond that may be stereospecific ((R) or (S)) or non-stereospecific; and R$_n$ comprises 1-4 independent functional groups or atoms, and optionally, one of which is modified to be covalently joined to a ABM, a chemical linker group (L), a ULM, CLM (or CLM') or combination thereof.

In certain embodiments described herein, the CLM or ULM comprises a chemical structure selected from the group:

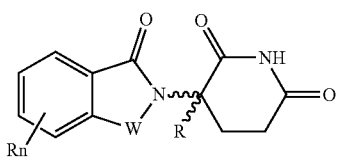

wherein:

W is independently selected from the group CH₂, C=O, NH, and N-alkyl;

R is independently selected from a H, methyl, alkyl;

∼∼∼ represents a bond that may be stereospecific ((R) or (S)) or non-stereospecific; and Rn comprises 1-4 independently selected functional groups or atoms, and optionally, one of which is modified to be covalently joined to a PTM, a chemical linker group (L), a CLM (or CLM') or combination thereof.

In some embodiments, the CLM is represented by the following structures with the dashed lines indicating linker attachment points:

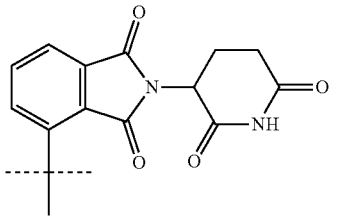

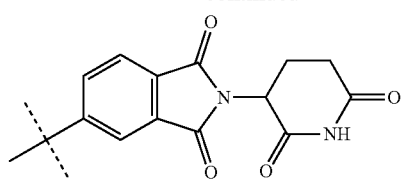

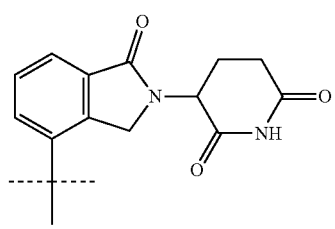

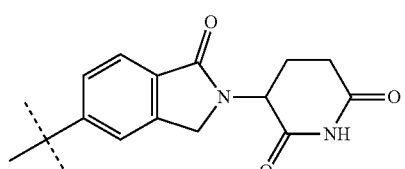

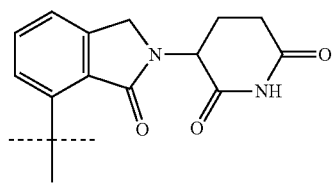

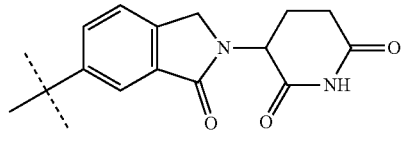

More specifically, non-limiting examples of CLMs include those shown below as well as those "hybrid" molecules that arise from the combination of 1 or more of the different features shown in the molecules below.

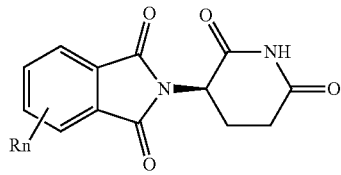

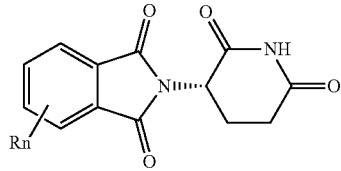

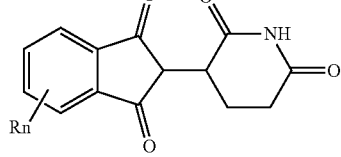

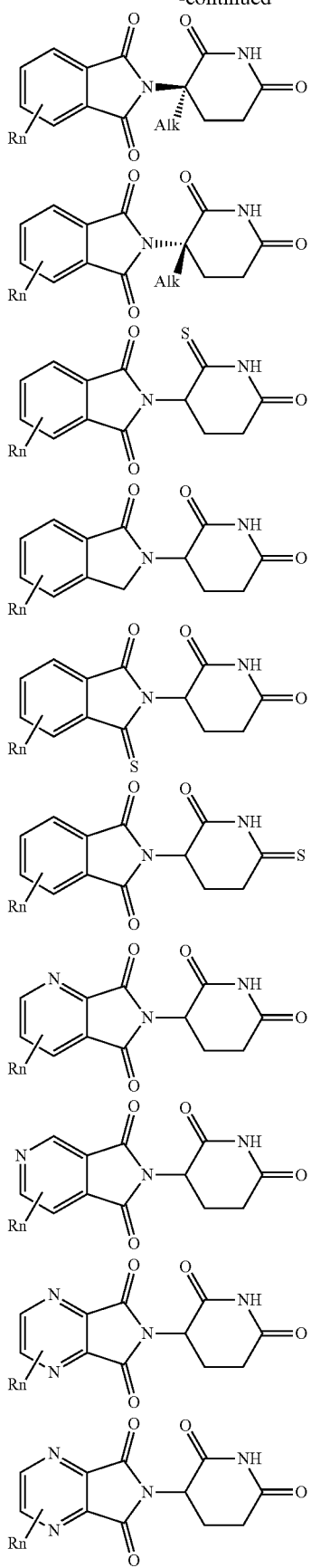
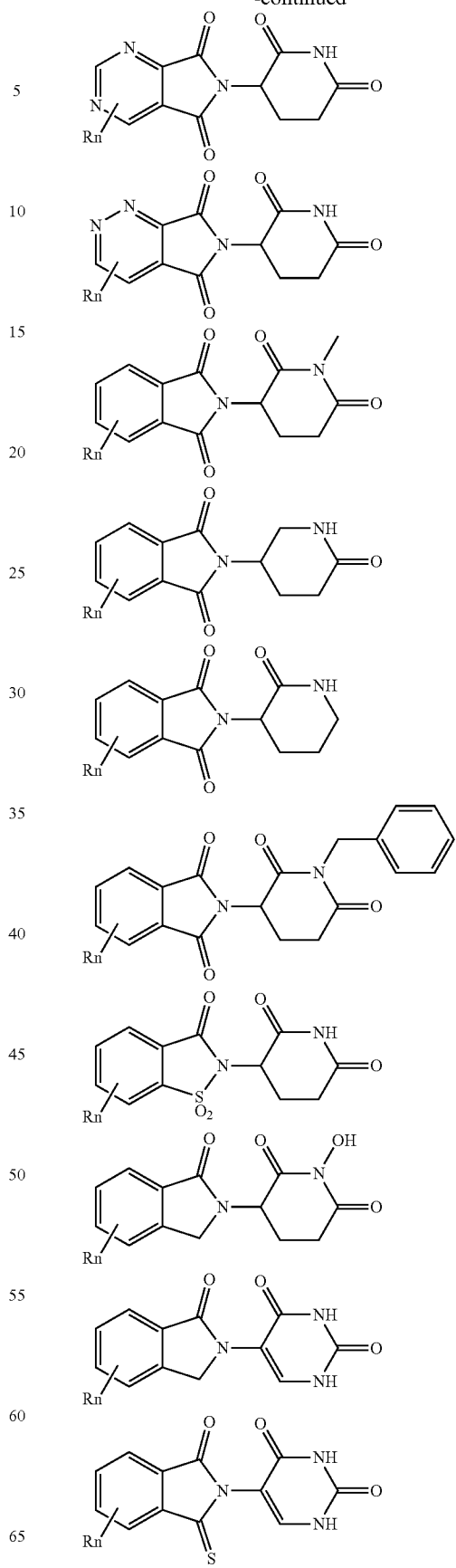

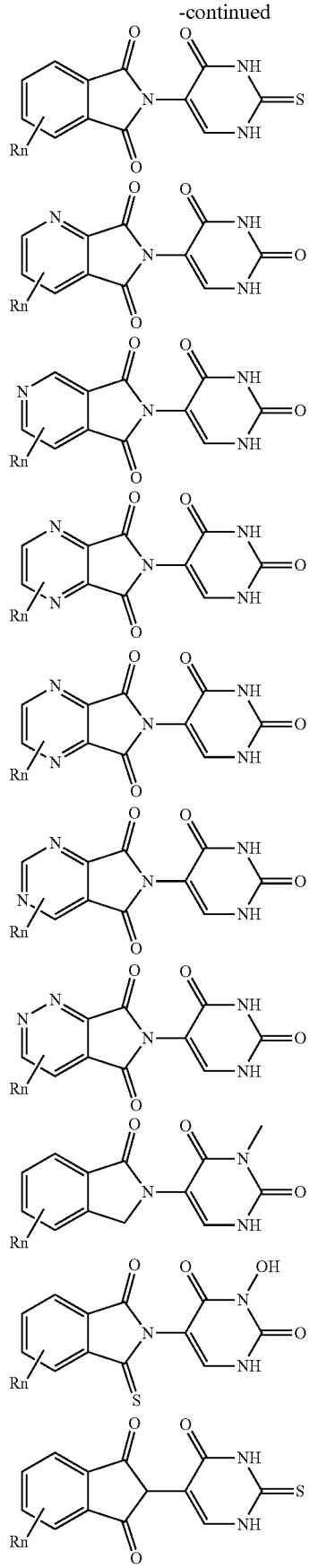
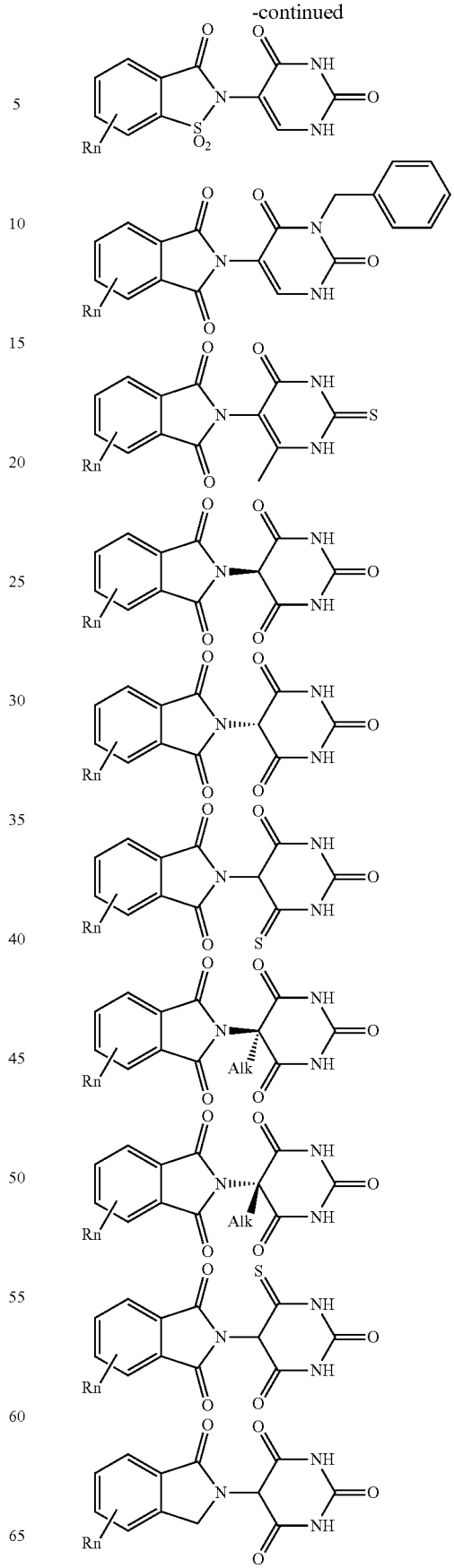

165
-continued
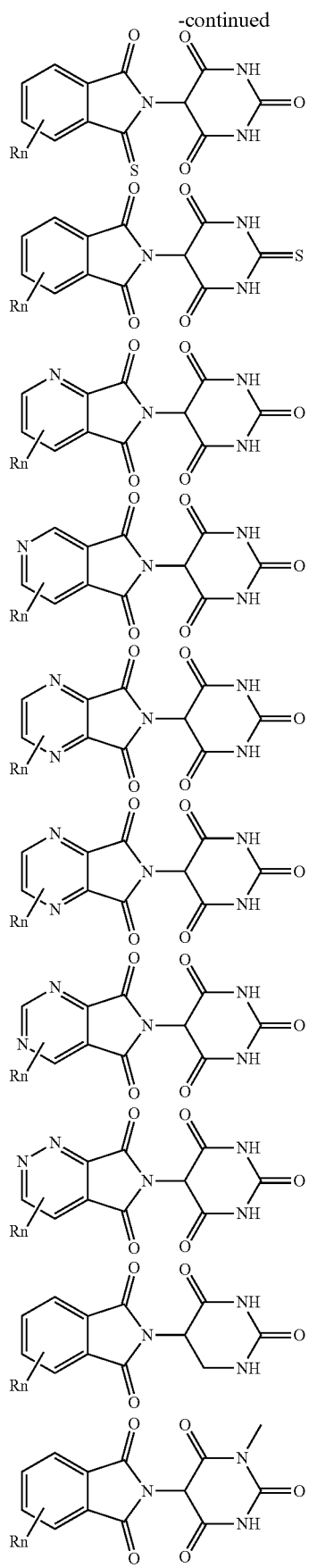
166
-continued
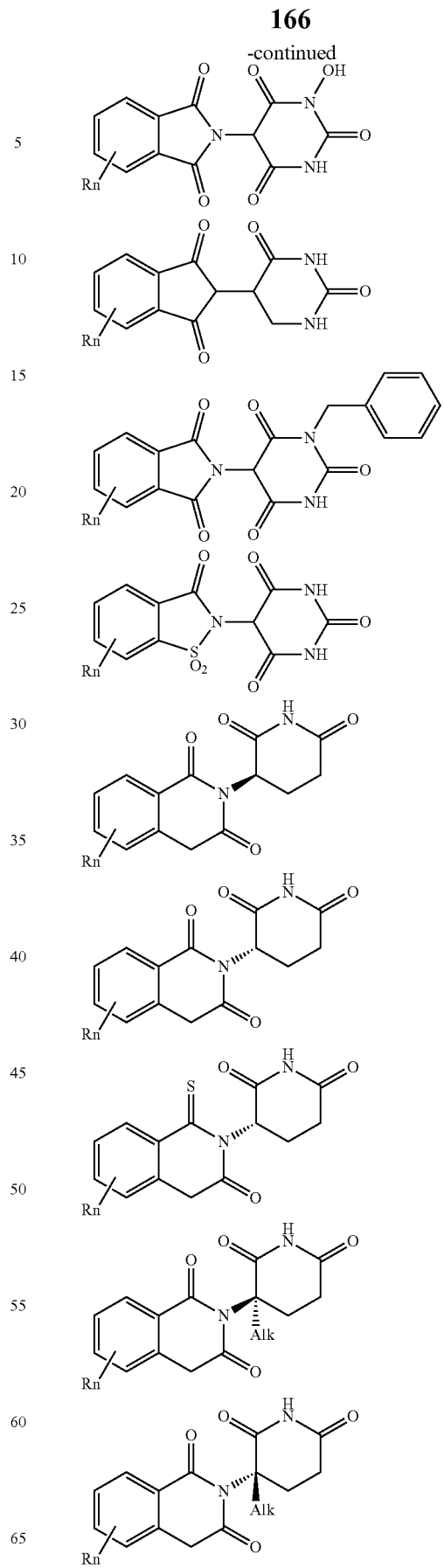

167
-continued
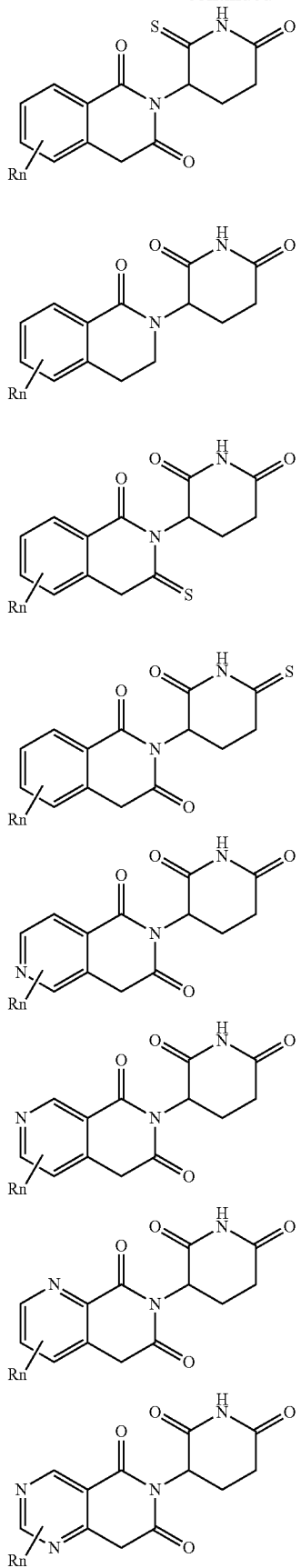
168
-continued
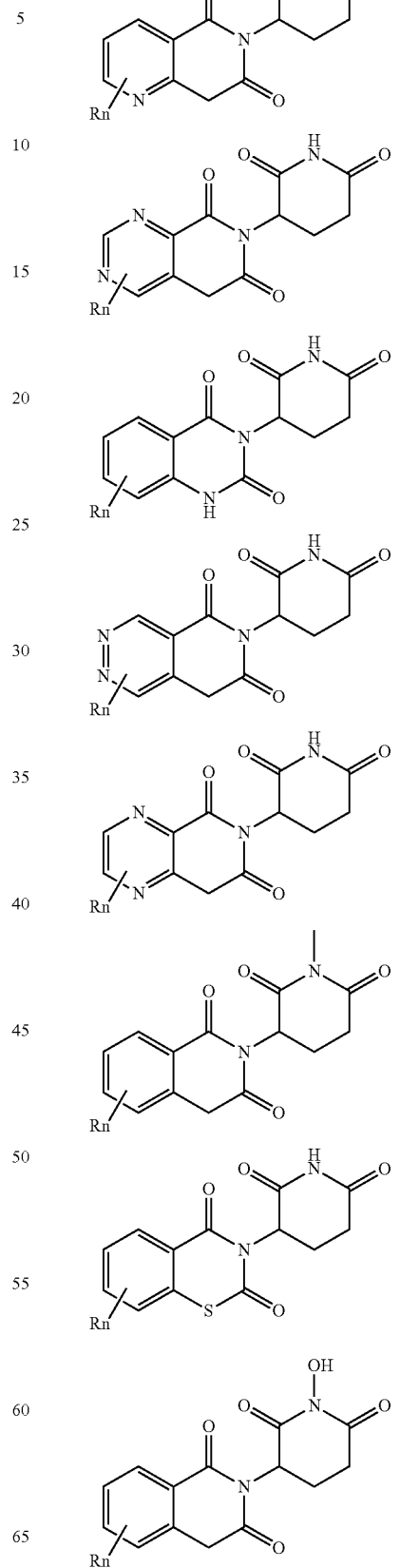

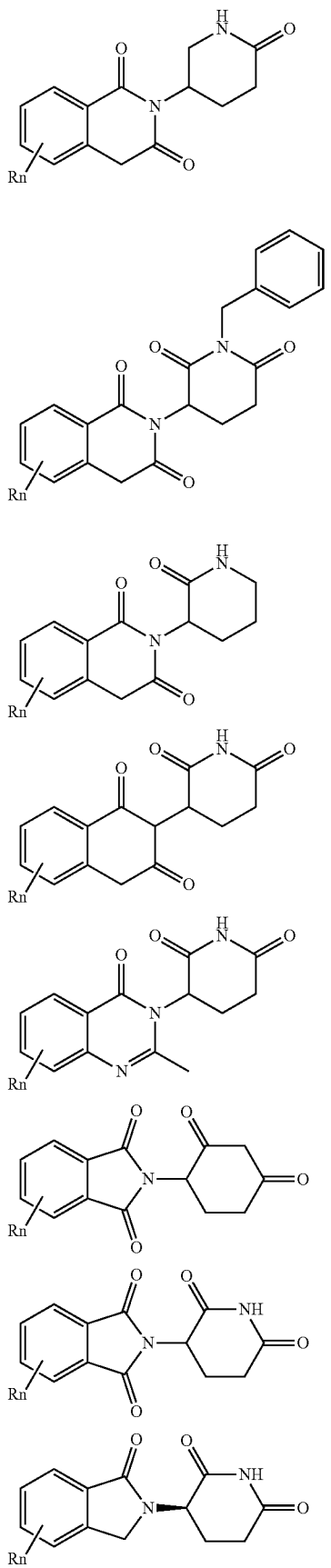
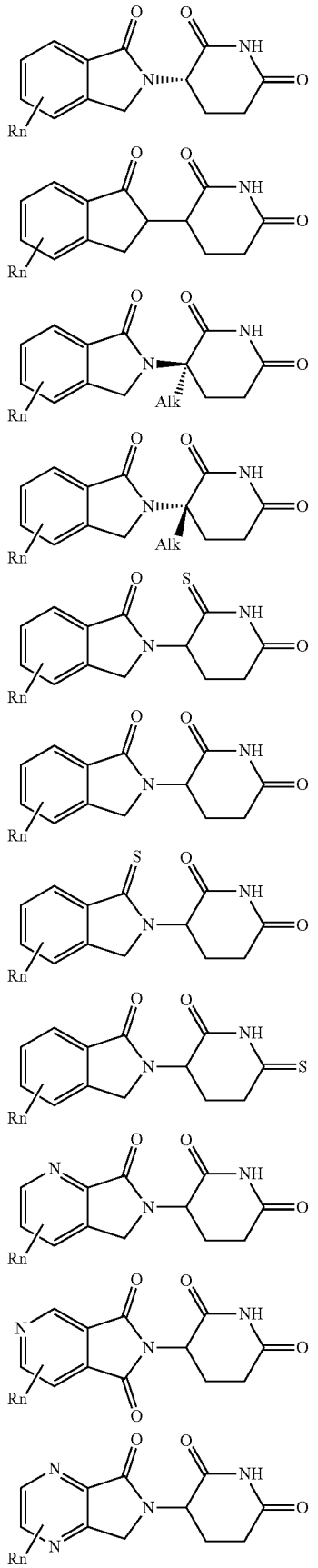

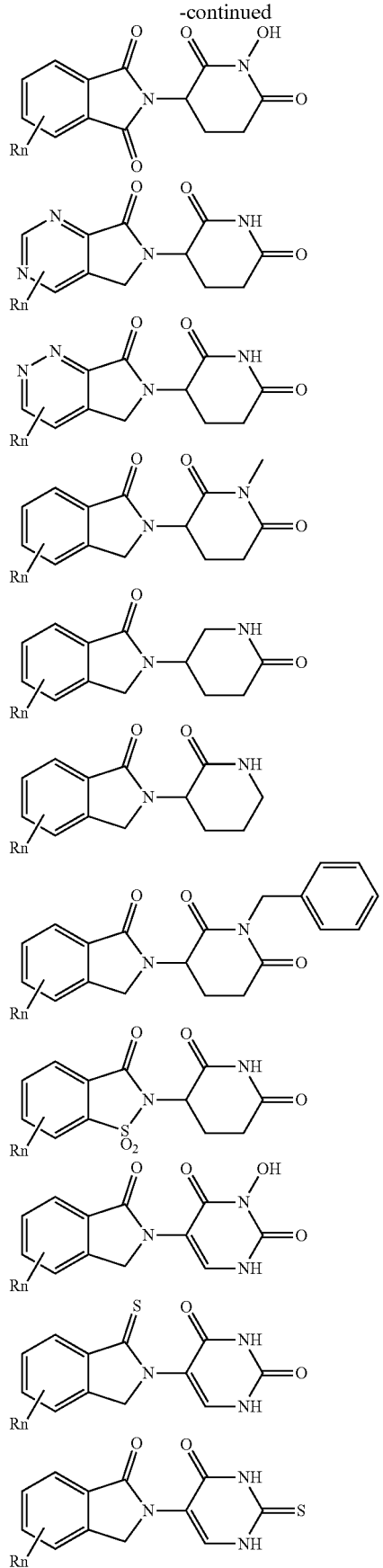
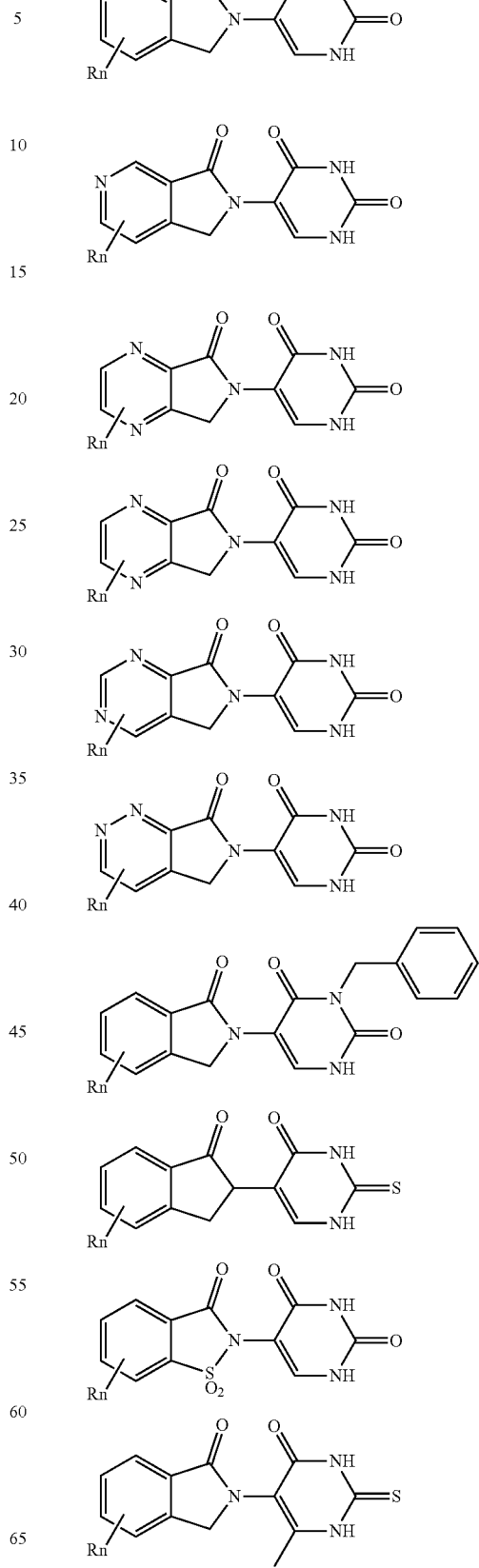

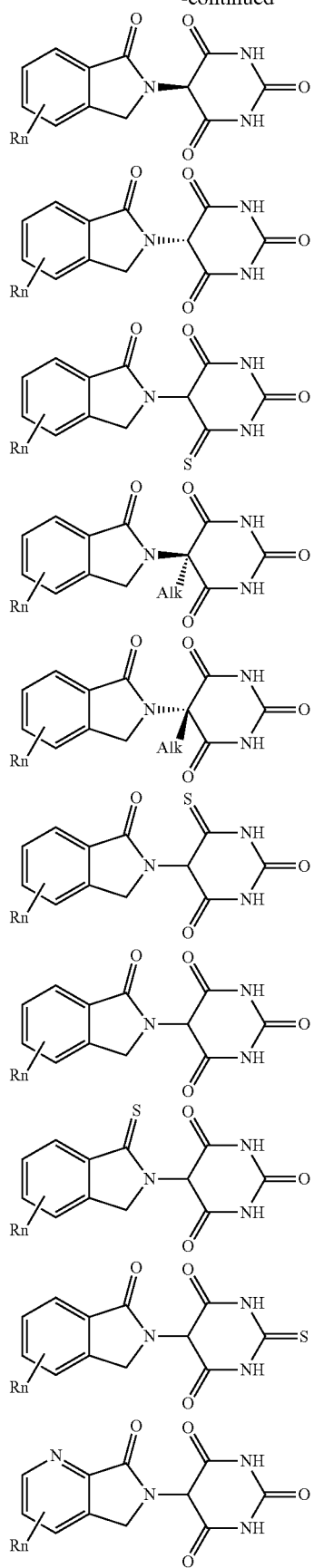
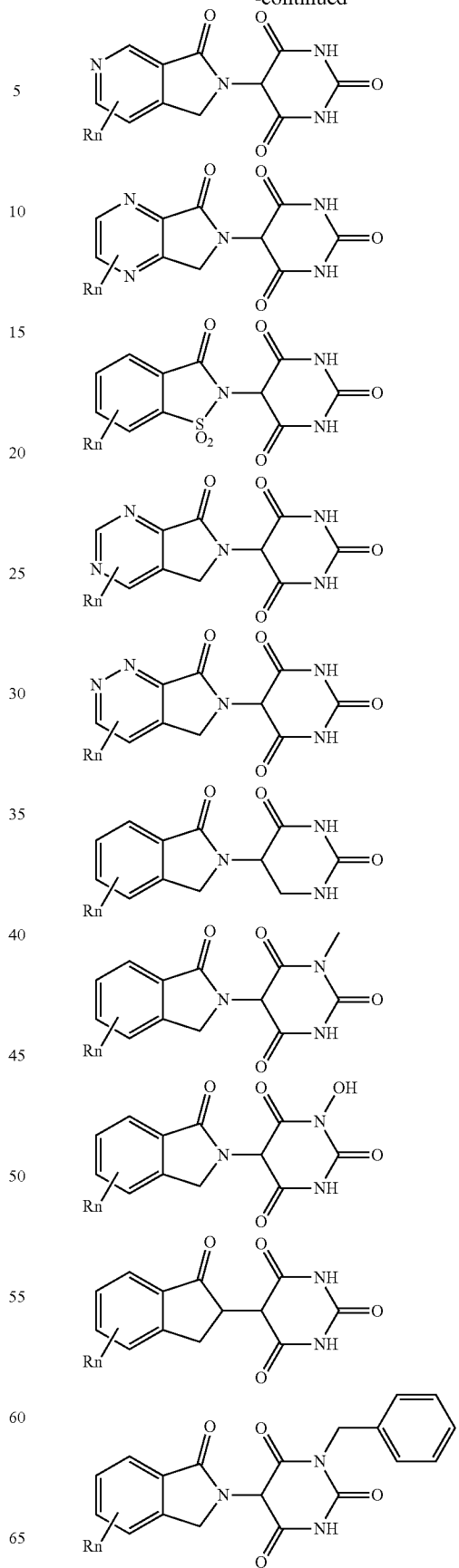

175
-continued
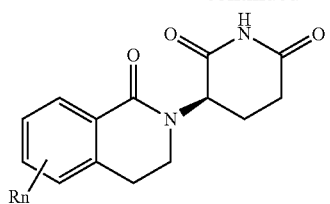
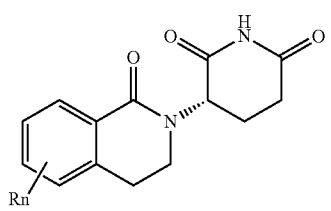
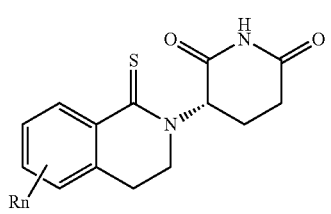
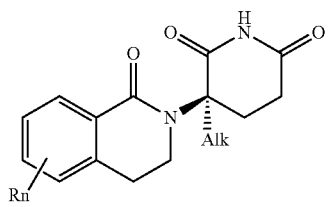
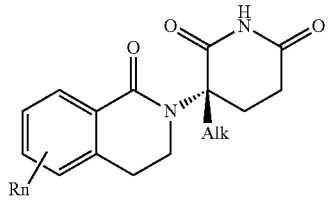
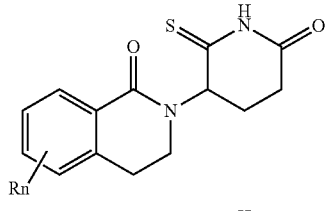
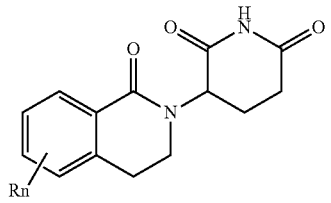
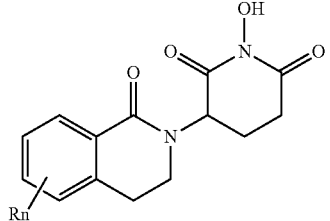
176
-continued
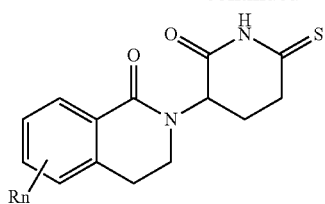
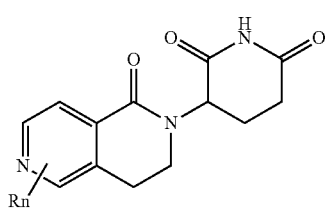
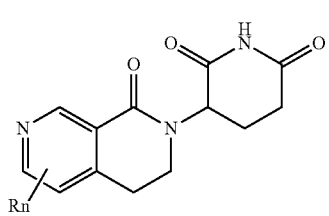
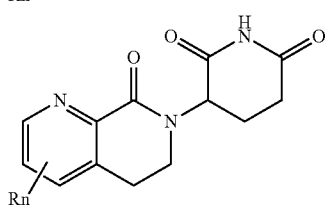
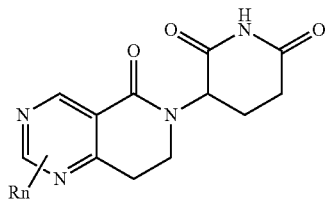
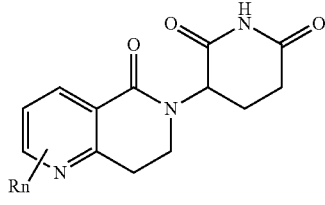
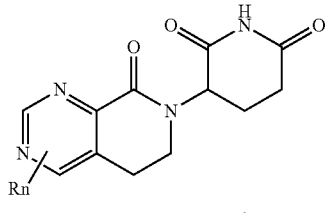
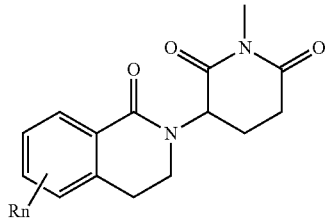

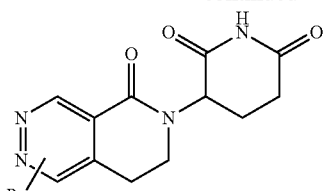
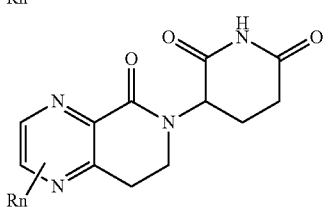
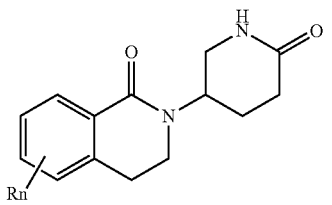
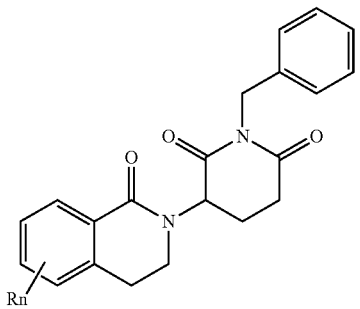
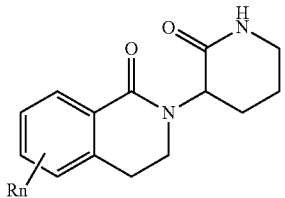
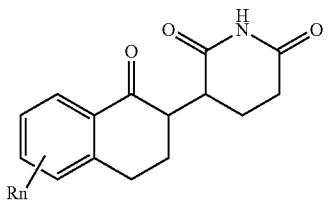
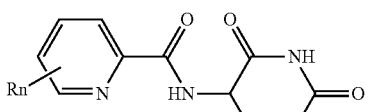
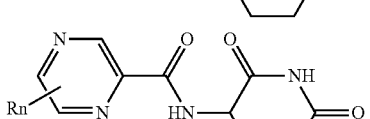
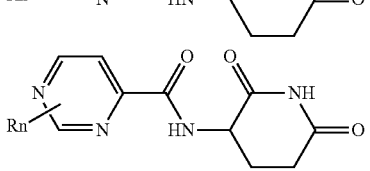
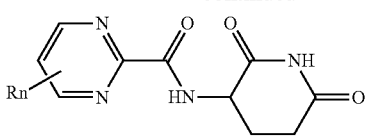
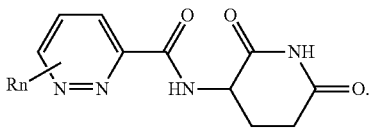
In any of the compounds described herein, the CLM comprises a chemical structure selected from the group:
(h)
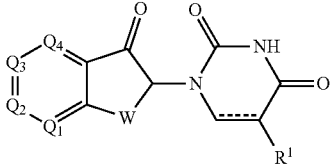
(i)
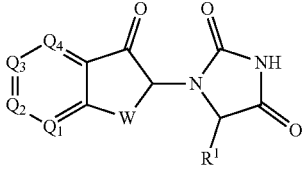
(j)
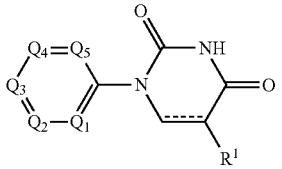
(k)
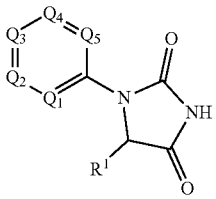
(l)
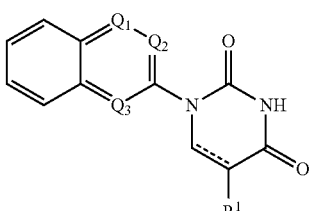
(m)
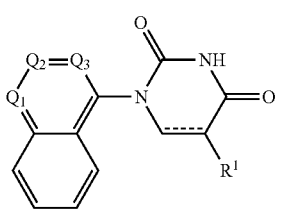

-continued

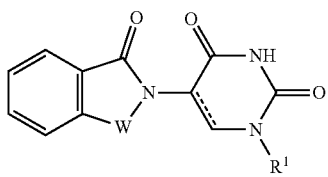
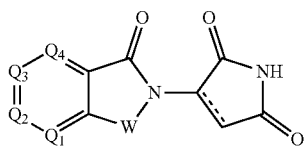
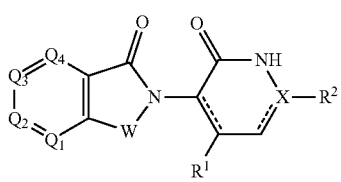
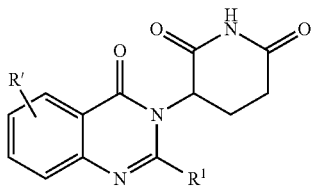
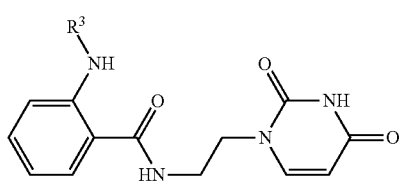
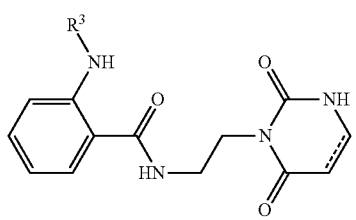
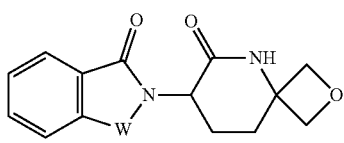
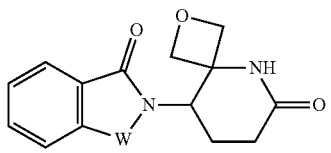
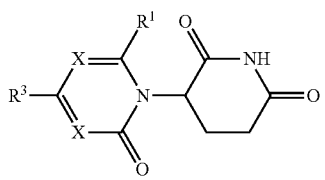

-continued (n)
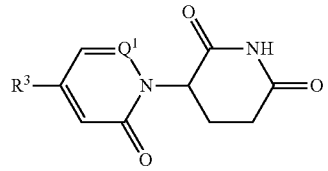

(o)
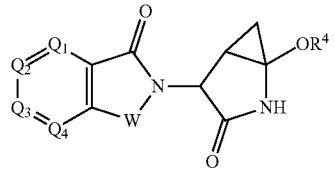

(p)
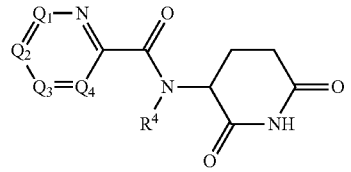

(q)
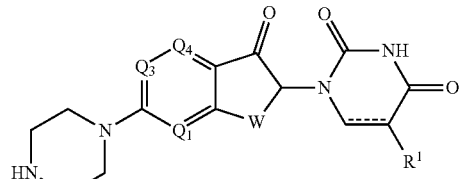

(r)
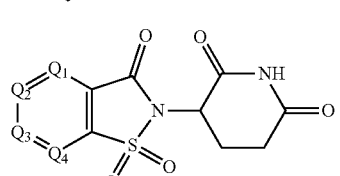

(s)
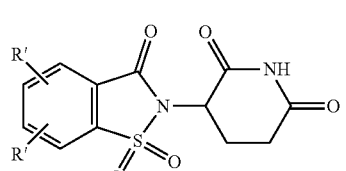

wherein:

W of Formulas (h) through (ab) is independently selected from $CH_2$, CHR, C=O, $SO_2$, NH, and N-alkyl;

$Q_1, Q_2, Q_3, Q_4, Q_5$ of Formulas (h) through (ab) are independently represent a carbon C substituted with a group independently selected from R', N or N-oxide;

$R^1$ of Formulas (h) through (ab) is selected from H, CN, C1-C3 alkyl;

$R^2$ of Formulas (h) through (ab) is selected from the group H, CN, C1-C3 alkyl, $CHF_2$, $CF_3$, CHO;

$R^3$ of Formulas (h) through (ab) is selected from H, alkyl, substituted alkyl, alkoxy, substituted alkoxy;

$R^4$ of Formulas (h) through (ab) is selected from H, alkyl, substituted alkyl;

$R^5$ of Formulas (h) through (ab) is H or lower alkyl;

X of Formulas (h) through (ab) is C, CH or N;

R' of Formulas (h) through (ab) is selected from H, halogen, alkyl, substituted alkyl, alkoxy, substituted alkoxy;

R of Formulas (h) through (ab) is H, OH, lower alkyl, lower alkoxy, cyano, halogenated lower alkoxy, or halogenated lower alkyl ⫶ of Formulas (h) through (ab) is a single or double bond; and the CLM is covalently joined to a PTM, a chemical linker group (L), a ULM, CLM (or CLM') or combination thereof.

In any aspect or embodiment described herein, the CLM or CLM' is covalently joined to a PTM, a chemical linker group (L), a ULM, a CLM, a CLM', or a combination thereof via an R group (such as, R, $R^1$, $R^2$, $R^3$, $R^4$ or R'), W, X, or a Q group (such as, $Q_1$, $Q_2$, $Q_3$, $Q_4$, or $Q_5$) of Formulas (h) through (ab).

In any of the embodiments described herein, the CLM or CLM' is covalently joined to a PTM, a chemical linker group (L), a ULM, a CLM, a CLM', or a combination thereof via W, X, R, $R^1$, $R^2$, $R^3$, $R^4$, $R^5$, R', $Q_1$, $Q_2$, $Q_3$, $Q_4$, and $Q_5$ of Formulas (h) through (ab).

In any of the embodiments described herein, the W, X, $R^1$, $R^2$, $R^3$, $R^4$, R', $Q_1$, $Q_2$, $Q_3$, $Q_4$, and $Q_5$ of Formulas (h) through (ab) can independently be covalently coupled to a linker and/or a linker to which is attached to one or more PTM, ULM, ULM', CLM or CLM' groups.

More specifically, non-limiting examples of CLMs include those shown below as well as "hybrid" molecules or compounds that arise from combining 1 or more features of the following compounds:

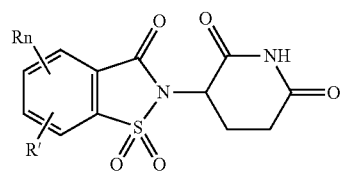 (ac)

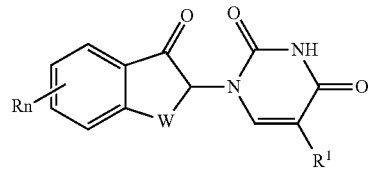 (ad)

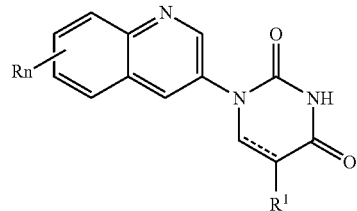 (ae)

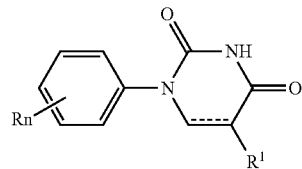 (af)

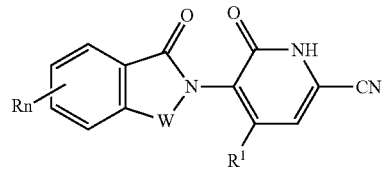 (ag)

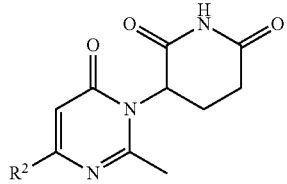 (ah)

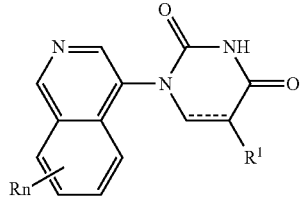 (ai)

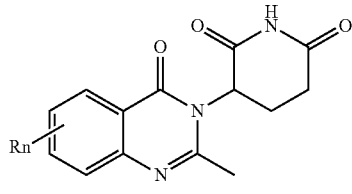 (aj)

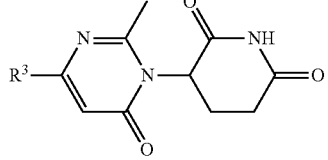 (ak)

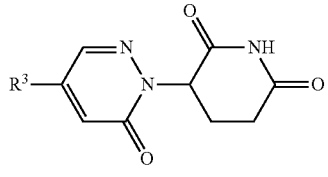 (al)

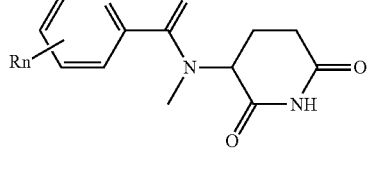 (am)

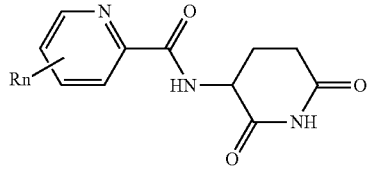 (an)

wherein:
W of Formulas (ac) through (an) is independently selected from the group $CH_2$, CHR, C=O, $SO_2$, NH, and N-alkyl;
$R^1$ of Formulas (ac) through (an) is selected from the group H, CN, C1-C3 alkyl;
$R^3$ of Formulas (ac) through (an) is selected from H, alkyl, substituted alkyl, alkoxy, substituted alkoxy;
R of Formulas (ac) through (an) is H;
⫶ is a single or double bond; and
Rn of Formulas (ac) through (an) comprises a functional group or an atom.

In any of the embodiments described herein, the W, $R^1$, $R^2$, $Q_1$, $Q_2$, $Q_3$, $Q_4$, and Rn of Formulas (ac) through (an) can independently be covalently coupled to a linker and/or a linker to which is attached one or more PTM, ULM, ULM', CLM or CLM' groups.

In any of the embodiments described herein, the $R^1$, $R^2$, $Q_1$, $Q_2$, $Q_3$, $Q_4$, and Rn of Formulas (ac) through (an) can independently be covalently coupled to a linker and/or a linker to which is attached one or more PTM, ULM, ULM', CLM or CLM' groups.

In any of the embodiments described herein, the $Q_1$, $Q_2$, $Q_3$, $Q_4$, and Rn of Formulas (ac) through (an) can independently be covalently coupled to a linker and/or a linker to which is attached one or more PTM, ULM, ULM', CLM or CLM' groups.

In any aspect or embodiment described herein, $R_n$ of Formulas (ac) through (an) is modified to be covalently joined to the linker group (L), a PTM, a ULM, a second CLM having the same chemical structure as the CLM, a CLM', a second linker, or any multiple or combination thereof.

In any aspect or embodiment described herein, the CLM is selected from:

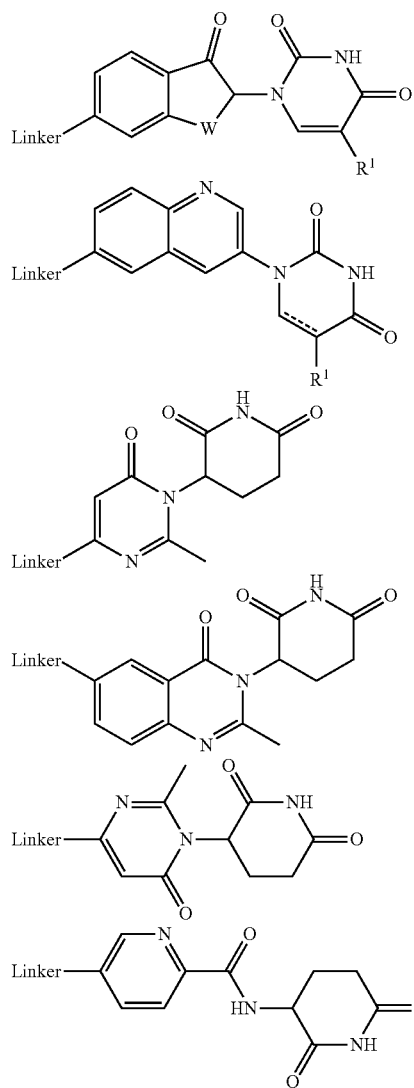

-continued

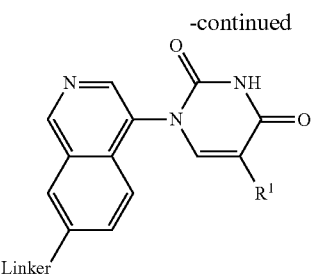

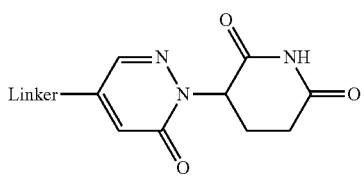

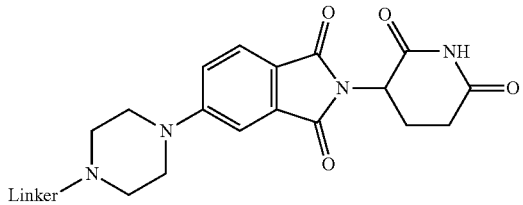

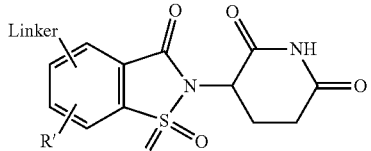

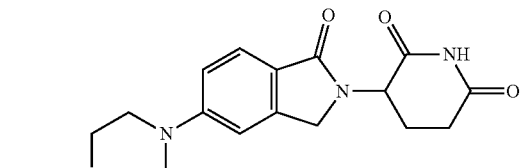

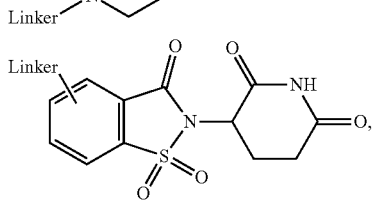

wherein R' is a halogen and $R^1$ is as described above with regard to Formulas (h) through (ab) or (ac) through (an).

In certain cases, the CLM can be imides that bind to cereblon E3 ligase. These imides and linker attachment point can be but not limited to the following structures:

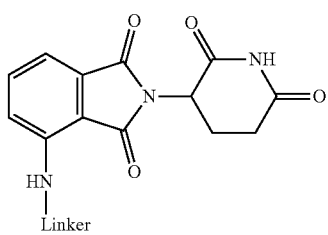

-continued

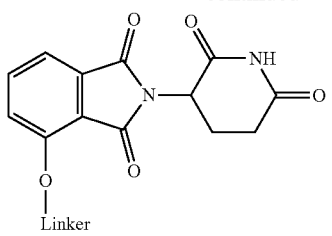

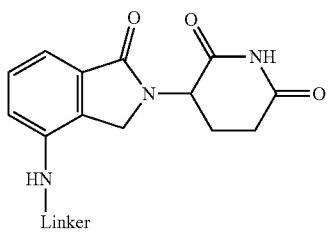

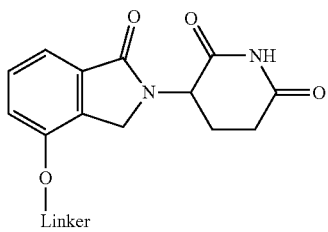

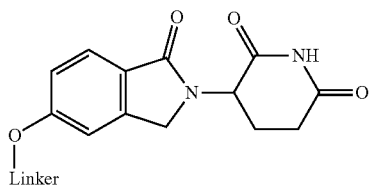

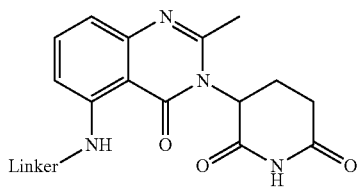

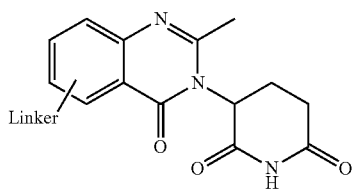

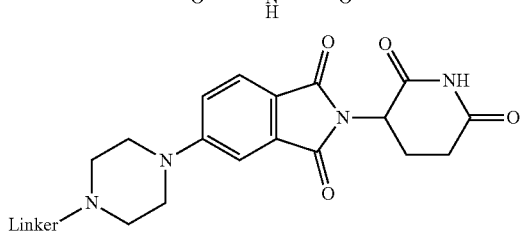

-continued

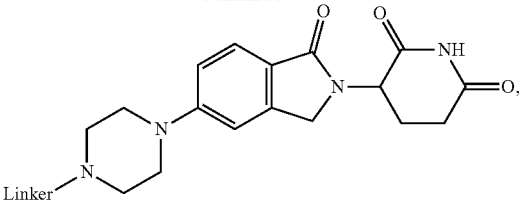

wherein R' is a halogen.

Exemplary Linkers:

In any of the aspects or embodiments comprising the structure ULM-L-PTM, the linker (L) comprises a chemical structural unit represented by the formula:

-(A)$_q$-, wherein:
A is a group which is connected to a ULM or PTM moiety; and
q is an integer greater than or equal to 1,
wherein A is selected from the group consisting of a bond, $CR^{L1}R^{L2}$, O, S, SO, $SO_2$, $NR^{L3}SO_2NR^{L3}$, $SONR^{L3}$, $CONR^{L3}$, $NR^{L3}CONR''$, $NR^{L3}SO_2NR''$, CO, $CR^{L1}=CR^{L2}$, C≡C, $SiR^{L1}R^{L2}$, P(O)$R^{L1}$, P(O)O$R^{L1}$, $NR^{L3}C(=NCN)NR^{L1}$, $NR^{L3}C(=NCN)$, $NR^{L3}C(=CNO_2)NR^{L4}$, $C_{3-11}$cycloalkyl optionally substituted with 0-6 $R^{L1}$ and/or $R^{L2}$ groups, $C_{3-11}$heterocyclyl optionally substituted with 0-6 $R^{L1}$ and/or $R^{L2}$ groups, aryl optionally substituted with 0-6 $R^{L1}$ and/or $R^{L2}$ groups, heteroaryl optionally substituted with 0-6 $R^{L1}$ and/or $R^{L2}$ groups, where $R^{L1}$ or $R^{L2}$, each independently are optionally linked to other groups to form cycloalkyl and/or heterocyclyl moiety, optionally substituted with 0-4 $R^{L5}$ groups;

$R^{L1}$, $R^{L2}$, $R^{L3}$, $R^{L4}$ and $R^{L5}$ are, each independently, H, halo, $C_{1-8}$alkyl, $OC_{1-8}$alkyl, $SC_{1-8}$alkyl, $NHC_{1-8}$alkyl, $N(C_{1-8}$alkyl$)_2$, $C_{3-11}$cycloalkyl, aryl, heteroaryl, $C_{3-11}$heterocyclyl, $OC_{1-8}$cycloalkyl, $SC_{1-8}$cycloalkyl, $NHC_{1-8}$cycloalkyl, $N(C_{1-8}$cycloalkyl$)_2$, $N(C_{1-8}$cycloalkyl)($C_{1-8}$alkyl), OH, $NH_2$, SH, $SO_2C_{1-8}$alkyl, P(O)($OC_{1-8}$alkyl)($C_{1-8}$alkyl), P(O)($OC_{1-8}$alkyl$)_2$, CC—$C_{1-8}$alkyl, CCH, CH=CH($C_{1-8}$alkyl), C($C_{1-8}$alkyl)=CH($C_{1-8}$alkyl), C($C_{1-8}$alkyl)=C($C_{1-8}$alkyl$)_2$, Si(OH)$_3$, Si($C_{1-8}$alkyl)$_3$, Si(OH)($C_{1-8}$alkyl$)_2$, $COC_{1-8}$alkyl, $CO_2H$, halogen, CN, $CF_3$, $CHF_2$, $CH_2F$, $NO_2$, SF$_5$, $SO_2NHC_{1-8}$alkyl, $SO_2N(C_{1-8}$alkyl$)_2$, $SONHC_{1-8}$alkyl, $SON(C_{1-8}$alkyl$)_2$, $CONHC_{1-8}$alkyl, $CON(C_{1-8}$alkyl$)_2$, $N(C_{1-8}$alkyl)$CONH(C_{1-8}$alkyl), $N(C_{1-8}$alkyl)$CON(C_{1-8}$alkyl$)_2$, $NHCONH(C_{1-8}$alkyl), $NHCON(C_{1-8}$alkyl$)_2$, $NHCONH_2$, $N(C_{1-8}$alkyl)$SO_2NH(C_{1-8}$alkyl), $N(C_{1-8}$alkyl) $SO_2N(C_{1-8}$alkyl$)_2$, NH $SO_2NH(C_{1-8}$alkyl), NH $SO_2N(C_{1-8}$alkyl$)_2$, NH $SO_2NH_2$.

In any aspect or embodiment described herein, the linker (L) comprises the following chemical structure:

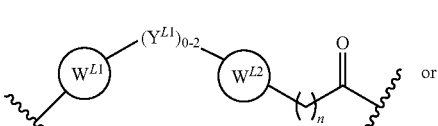 or

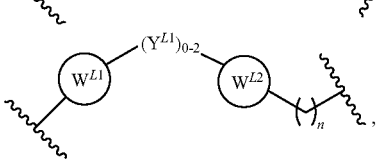

wherein:
W$^{L1}$ and W$^{L2}$ are each independently a 4-8 membered ring with 0-4 heteroatoms, optionally substituted with RQ, each RQ is independently a H, halo, OH, CN, CF$_3$, C1-C6 alkyl (linear, branched, optionally substituted), C1-C6 alkoxy (linear, branched, optionally substituted), or 2 RQ groups taken together with the atom they are attached to, form a 4-8 membered ring system containing 0-4 heteroatoms;
Y$^{L1}$ is each independently a bond, C1-C6 alkyl (linear, branched, optionally substituted) and optionally one or more C atoms are replaced with O; or C1-C6 alkoxy (linear, branched, optionally substituted); and
a dashed line indicates the attachment point to the PTM or ULM moieties.

In any aspect or embodiment described herein, the linker (L) comprises the following chemical structure:

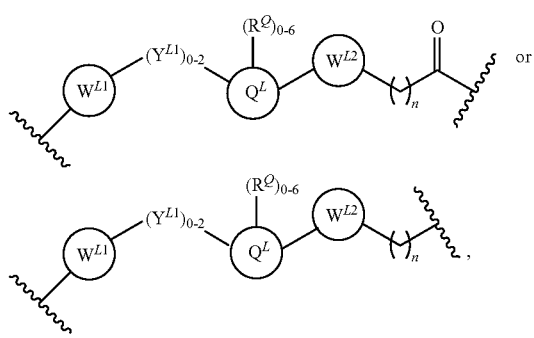

wherein:
W$^{L1}$ and W$^{L2}$ are each independently aryl, heteroaryl, cyclic, heterocyclic, C$_{1-6}$ alkyl, bicyclic, biaryl, biheteroaryl, or biheterocyclic, each optionally substituted with R$^Q$, each R$^Q$ is independently a H, halo, OH, CN, CF$_3$, hydroxyl, nitro, C≡CH, C$_{2-6}$ alkenyl, C$_{2-6}$ alkynyl, C$_1$-C$_6$ alkyl (linear, branched, optionally substituted), C$_1$-C$_6$ alkoxy (linear, branched, optionally substituted), OC$_{1-3}$alkyl (optionally substituted by 1 or more —F), OH, NH$_2$, NR$^{Y1}$R$^{Y2}$, CN, or 2 R$^Q$ groups taken together with the atom they are attached to, form a 4-8 membered ring system containing 0-4 heteroatoms;
Y$^{L1}$ is each independently a bond, NR$^{YL1}$, O, S, NR$^{YL2}$, CR$^{YL1}$R$^{YL2}$, C=O, C=S, SO, SO$_2$, C$_1$-C$_6$ alkyl (linear, branched, optionally substituted) and optionally one or more C atoms are replaced with O; C$_1$-C$_6$ alkoxy (linear, branched, optionally substituted);
Q$^L$ is a 3-6 membered alicyclic or aromatic ring with 0-4 heteroatoms, optionally bridged, optionally substituted with 0-6 R$^Q$, each R$^Q$ is independently H, C$_{1-6}$ alkyl (linear, branched, optionally substituted by 1 or more halo, C$_{1-6}$ alkoxyl), or 2 R$^Q$ groups taken together with the atom they are attached to, form a 3-8 membered ring system containing 0-2 heteroatoms);
R$^{YL1}$, R$^{YL2}$ are each independently H, OH, C$_{1-6}$ alkyl (linear, branched, optionally substituted by 1 or more halo, C$_{1-6}$ alkoxyl), or R$^1$, R$^2$ together with the atom they are attached to, form a 3-8 membered ring system containing 0-2 heteroatoms);
n is 0-10; and
a dashed line indicates the attachment point to the PTM or ULM moieties.

In some of the embodiments, linker (L) comprises a group represented by a general structure selected from the group consisting of:

—N(R)—(CH2)$_m$—O(CH2)$_n$—O(CH2)$_o$—O(CH2)$_p$—O(CH2)$_q$—O(CH2)$_r$-OCH2-,

—O—(CH2)$_m$—O(CH2)$_n$—O(CH2)$_o$—O(CH2)$_p$—O(CH2)$_q$—O(CH2)$_r$-OCH2-,

—O—(CH2)$_m$—O(CH2)$_n$—O(CH2)$_o$—O(CH2)$_p$—O(CH2)$_q$—O(CH2)$_r$—O—;

—N(R)—(CH2)$_m$—O(CH2)$_n$—O(CH2)$_o$—O(CH2)$_p$—O(CH2)$_q$—O(CH2)$_r$—O—;

(CH2)$_m$—O(CH2)$_n$—O(CH2)$_o$—O(CH2)$_p$—O(CH2)$_q$—O(CH2)$_r$—O—;

(CH2)$_m$—O(CH2)$_n$—O(CH2)$_o$—O(CH2)$_p$—O(CH2)$_q$—O(CH2)$_r$-OCH2-;

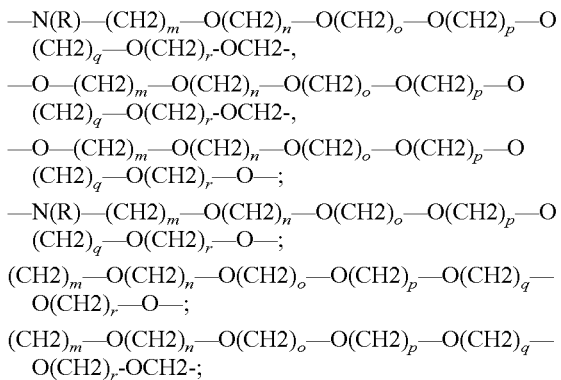

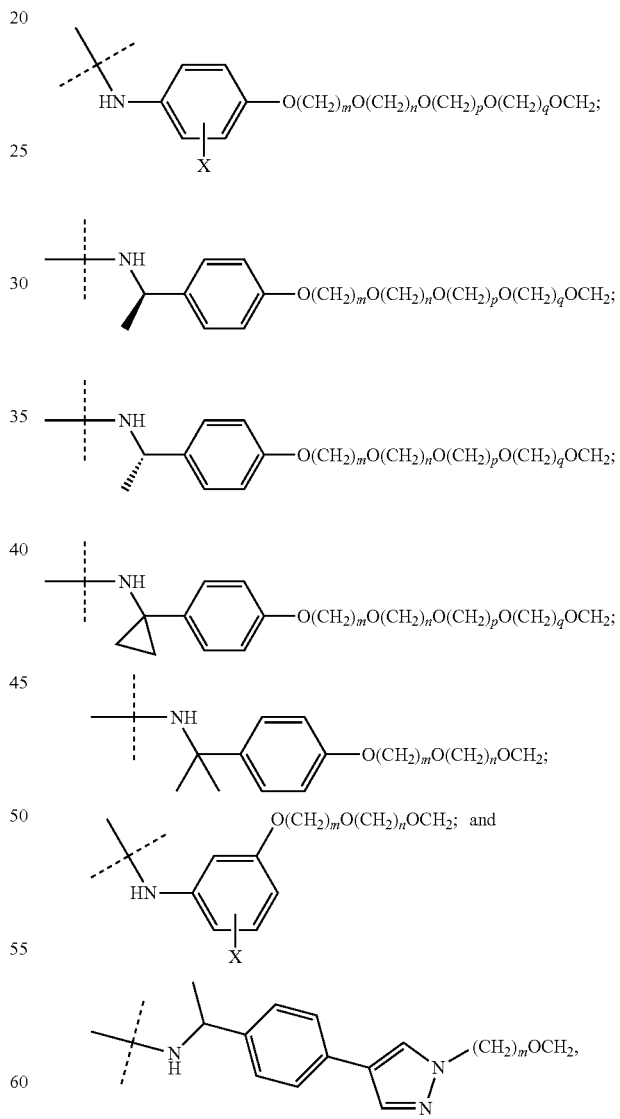

wherein each m, n, o, p, q, and r, is independently 0, 1, 2, 3, 4, 5, 6 with the proviso that when the number is zero, there is no N—O or O—O bond; R is selected from the group H, methyl or ethyl, and X is selected from the group H or F;

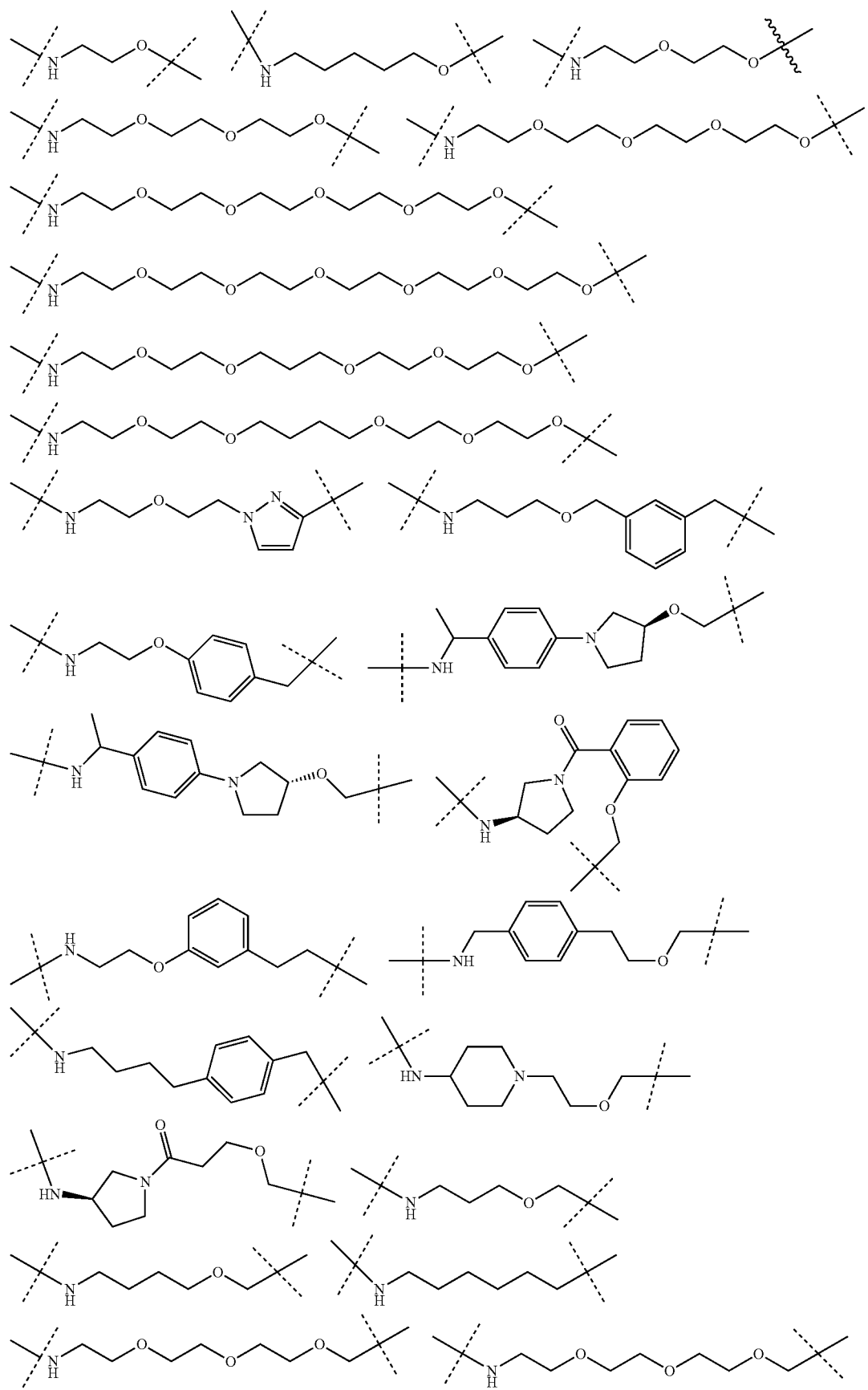

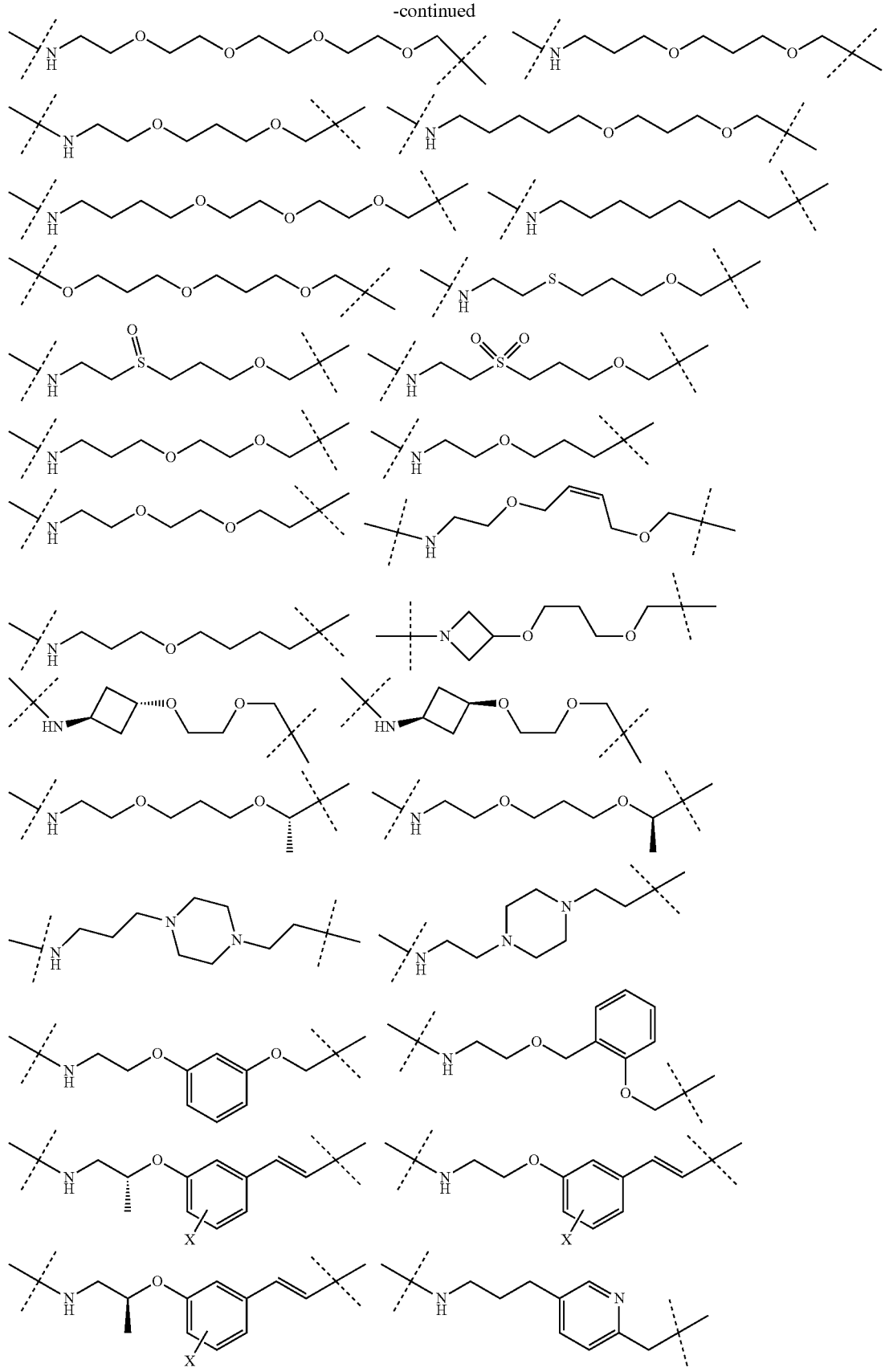

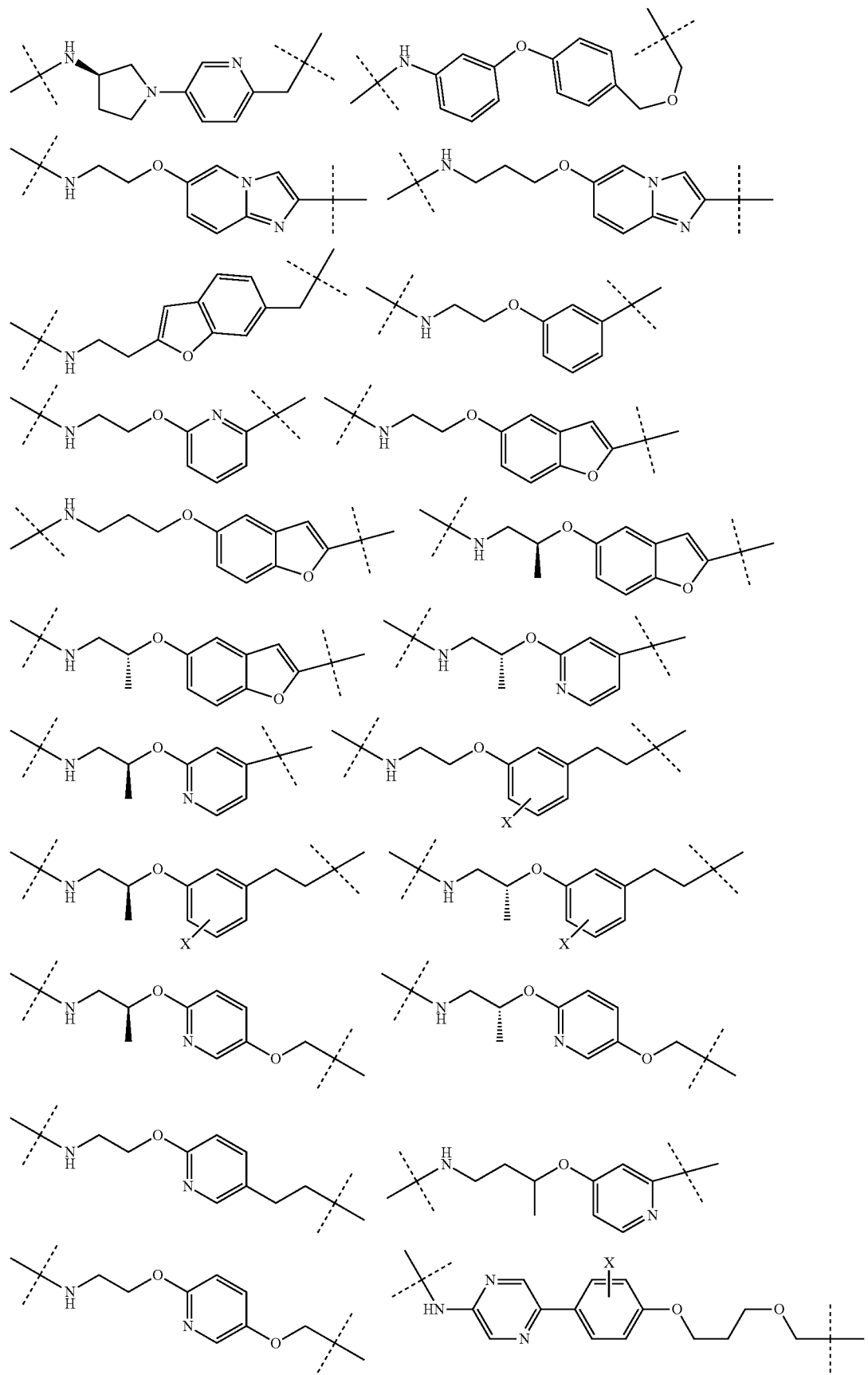

-continued
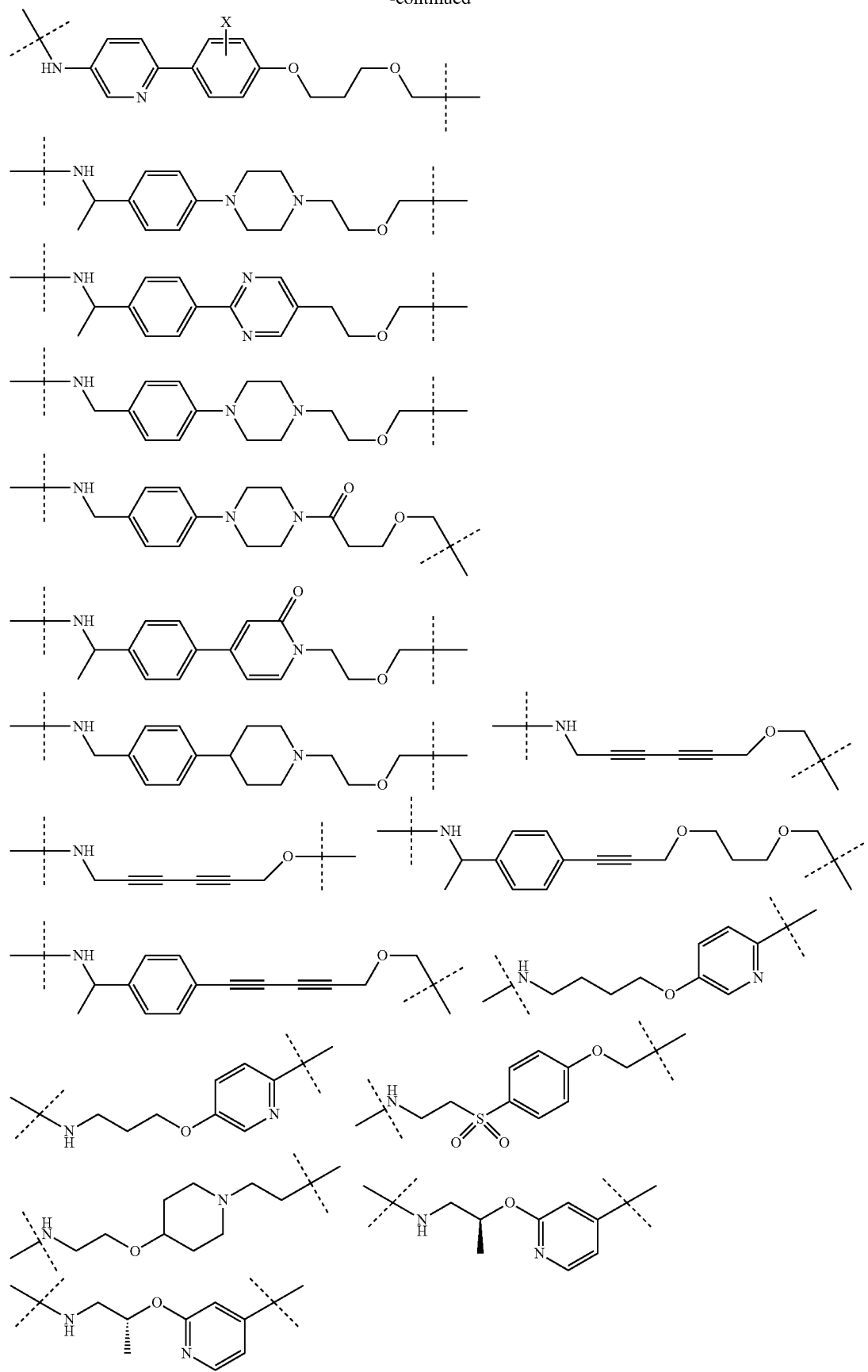

-continued
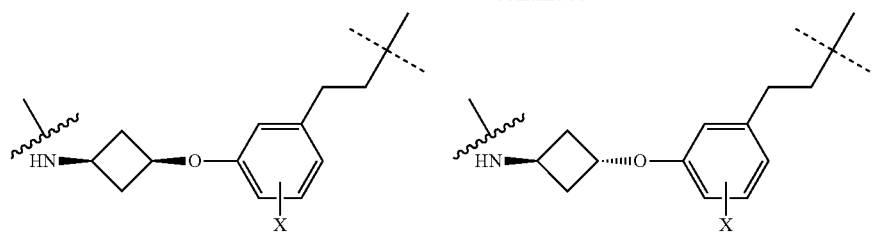
X = H, F
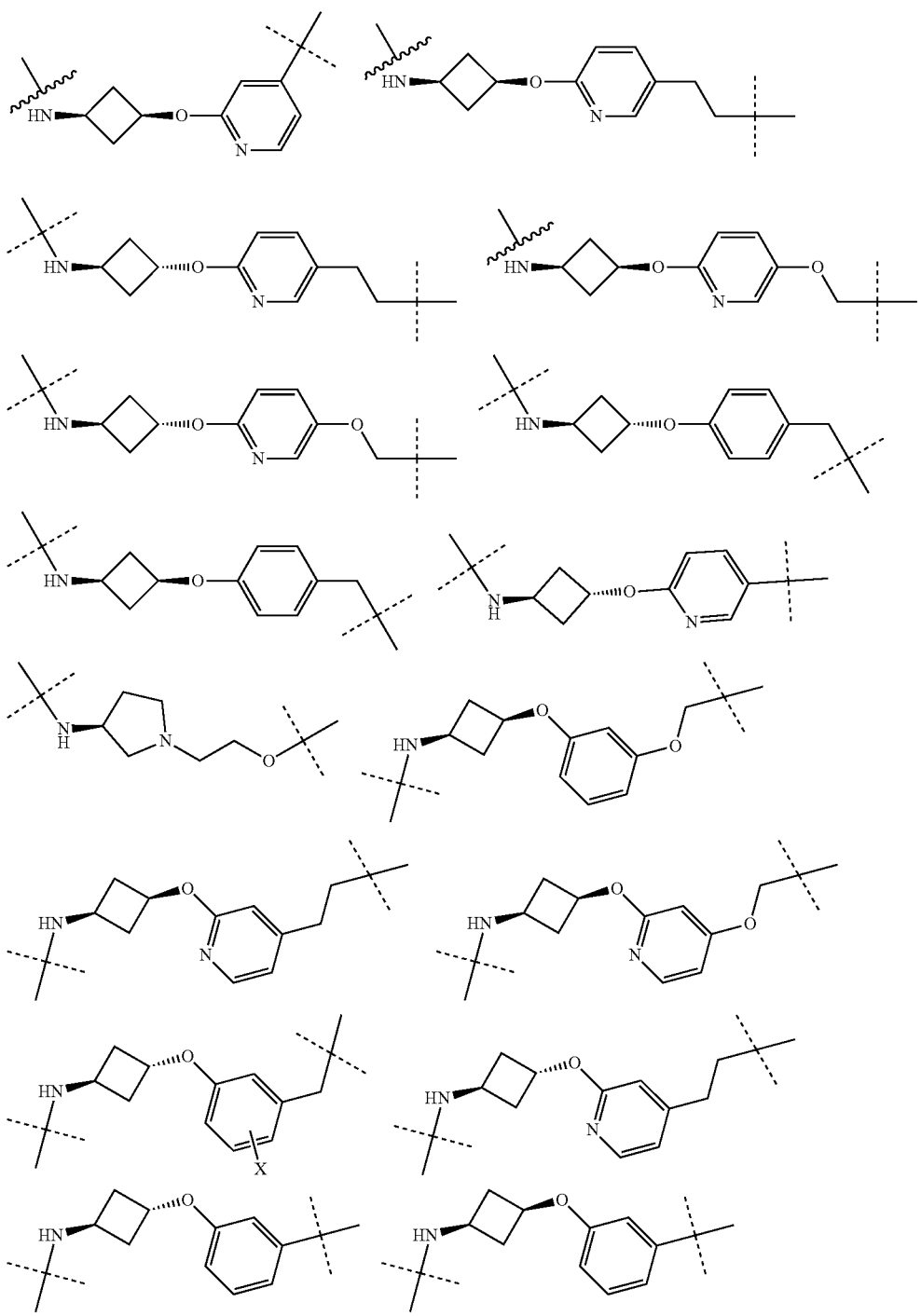

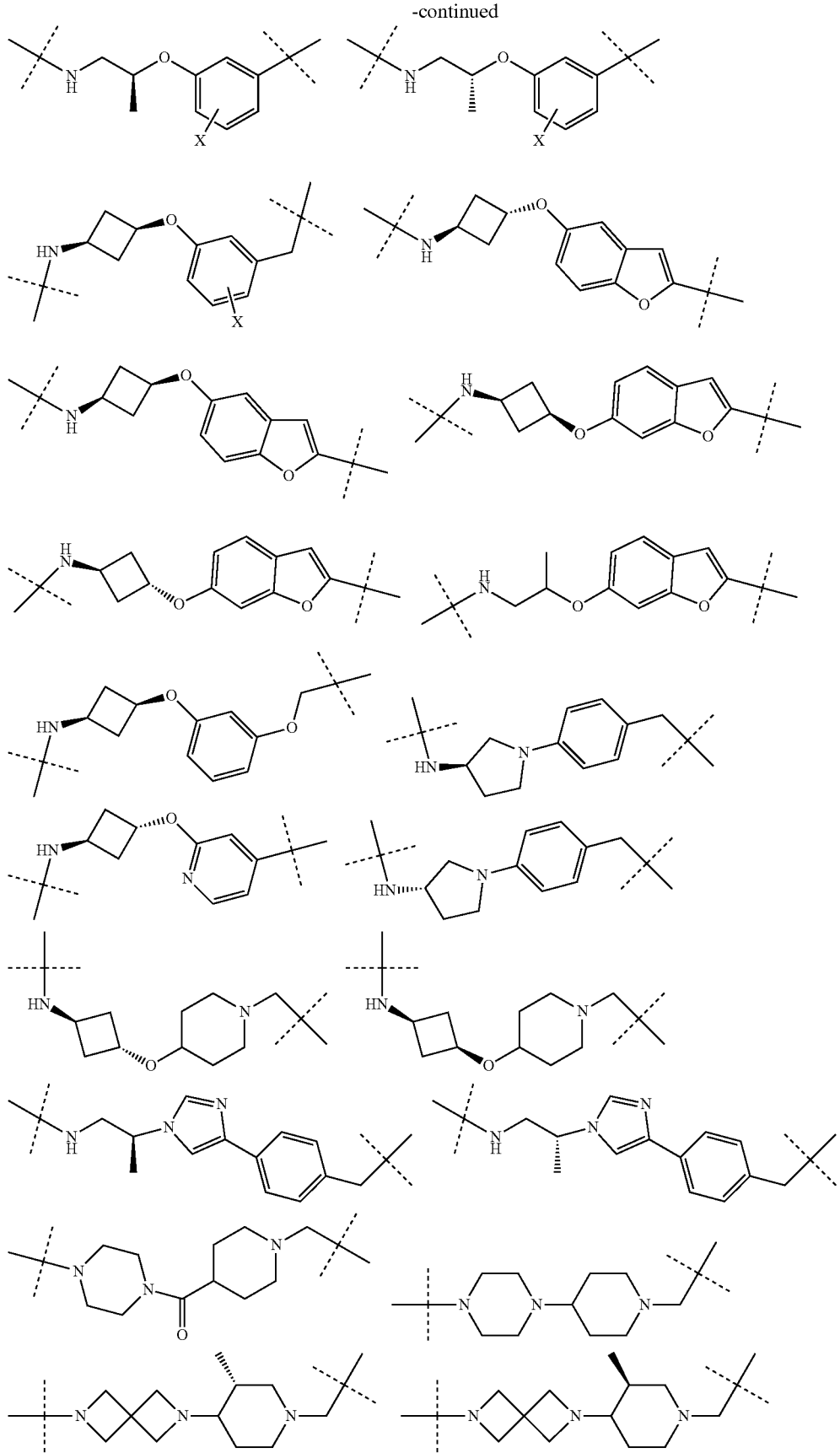

In some additional embodiments, linker (L) is selected from the group consisting of:
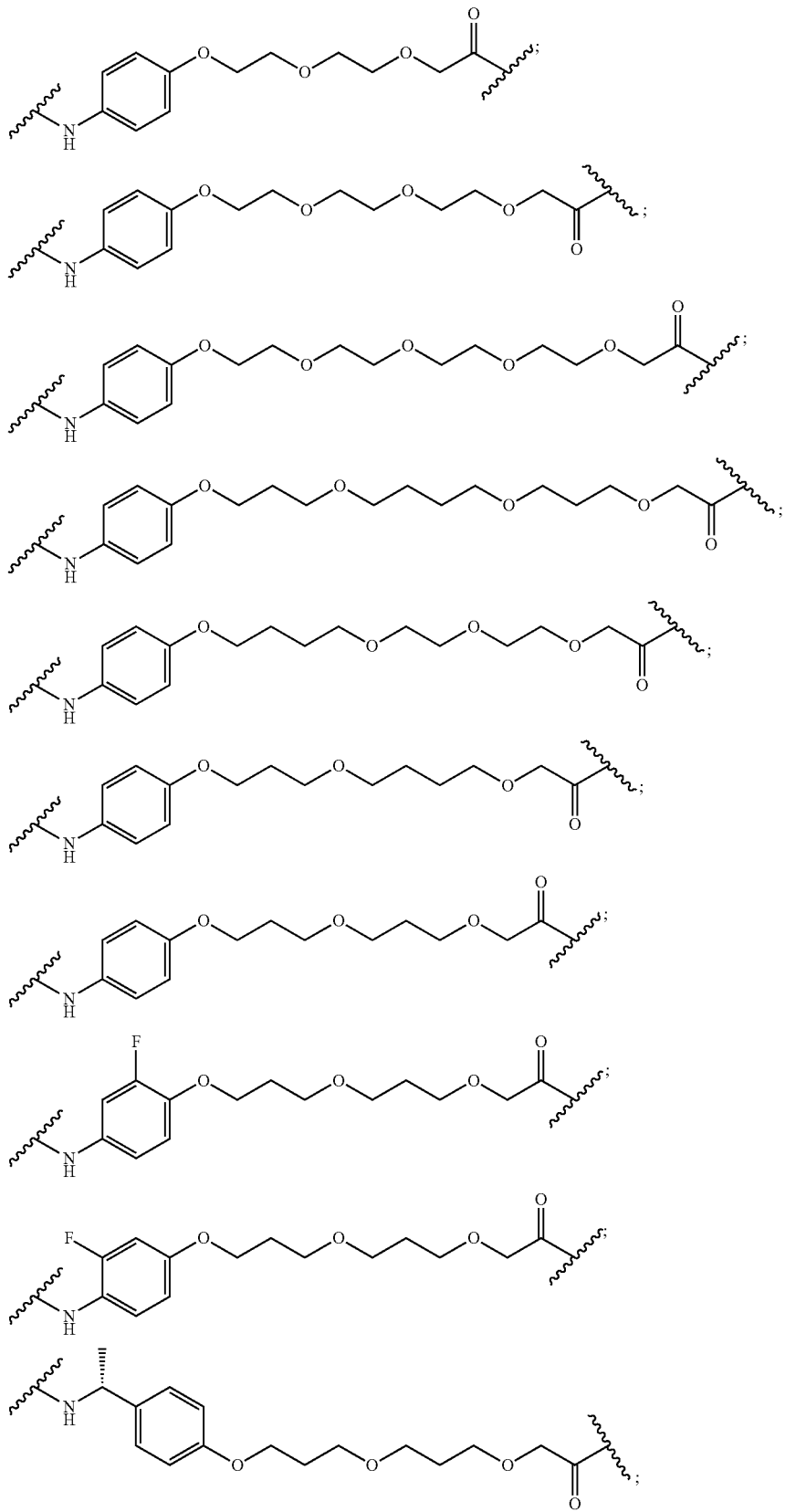

-continued
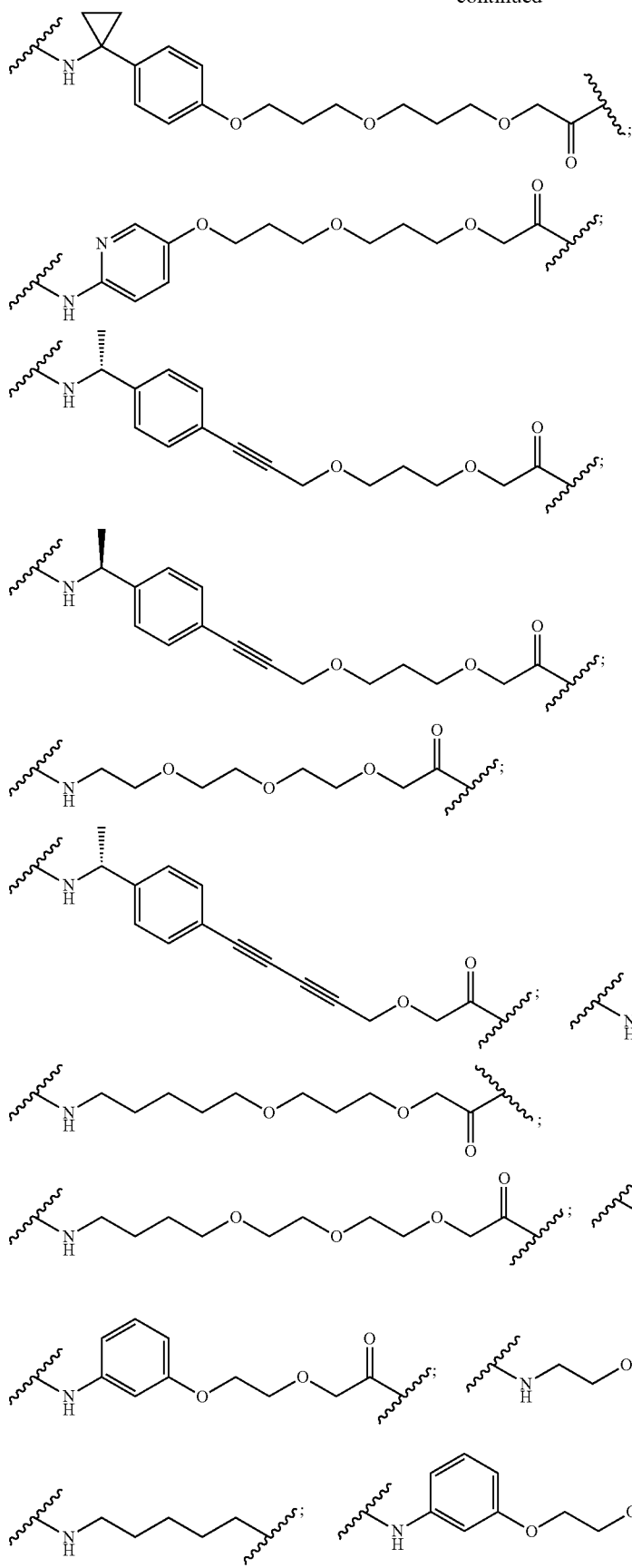

-continued
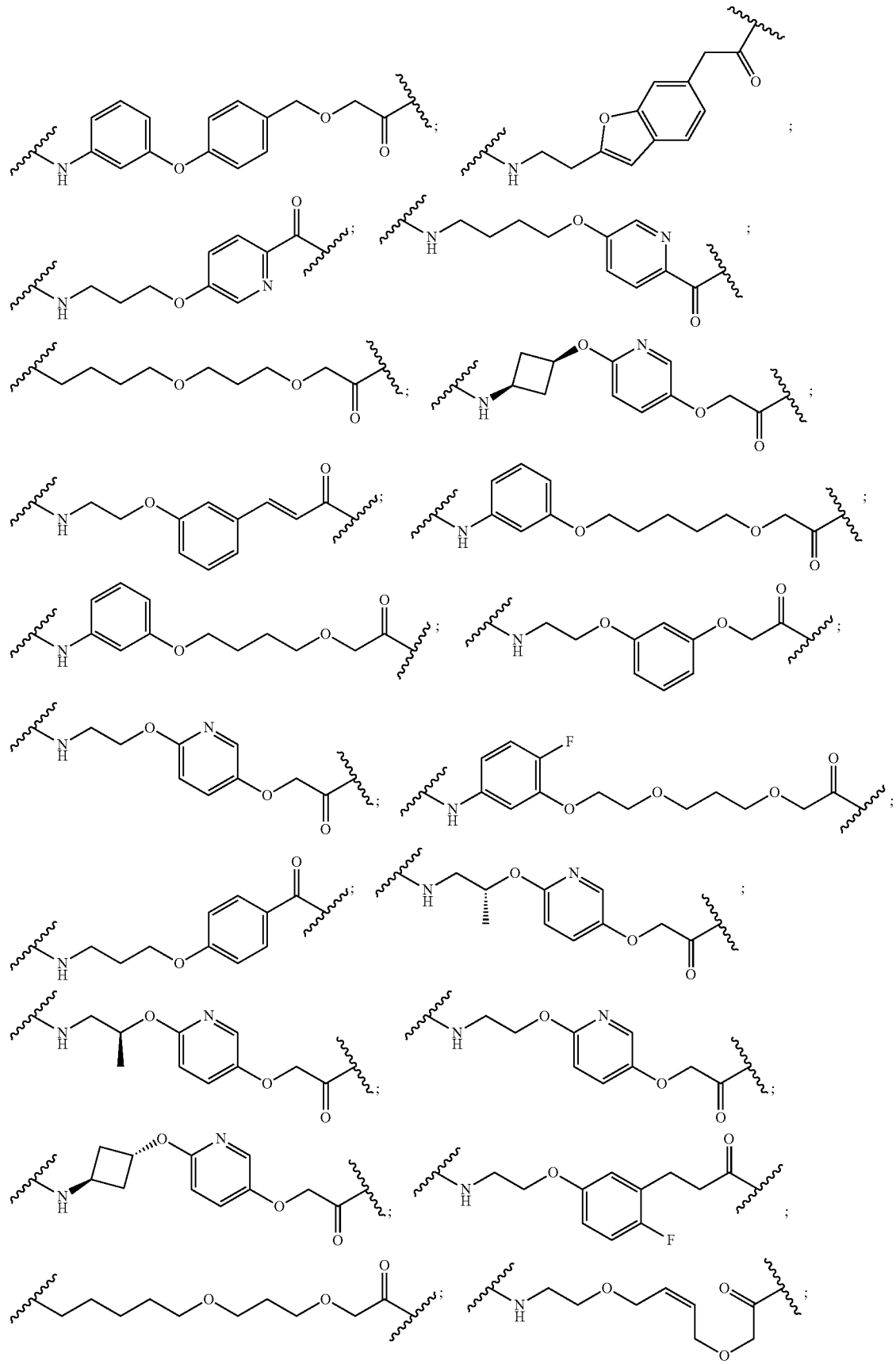

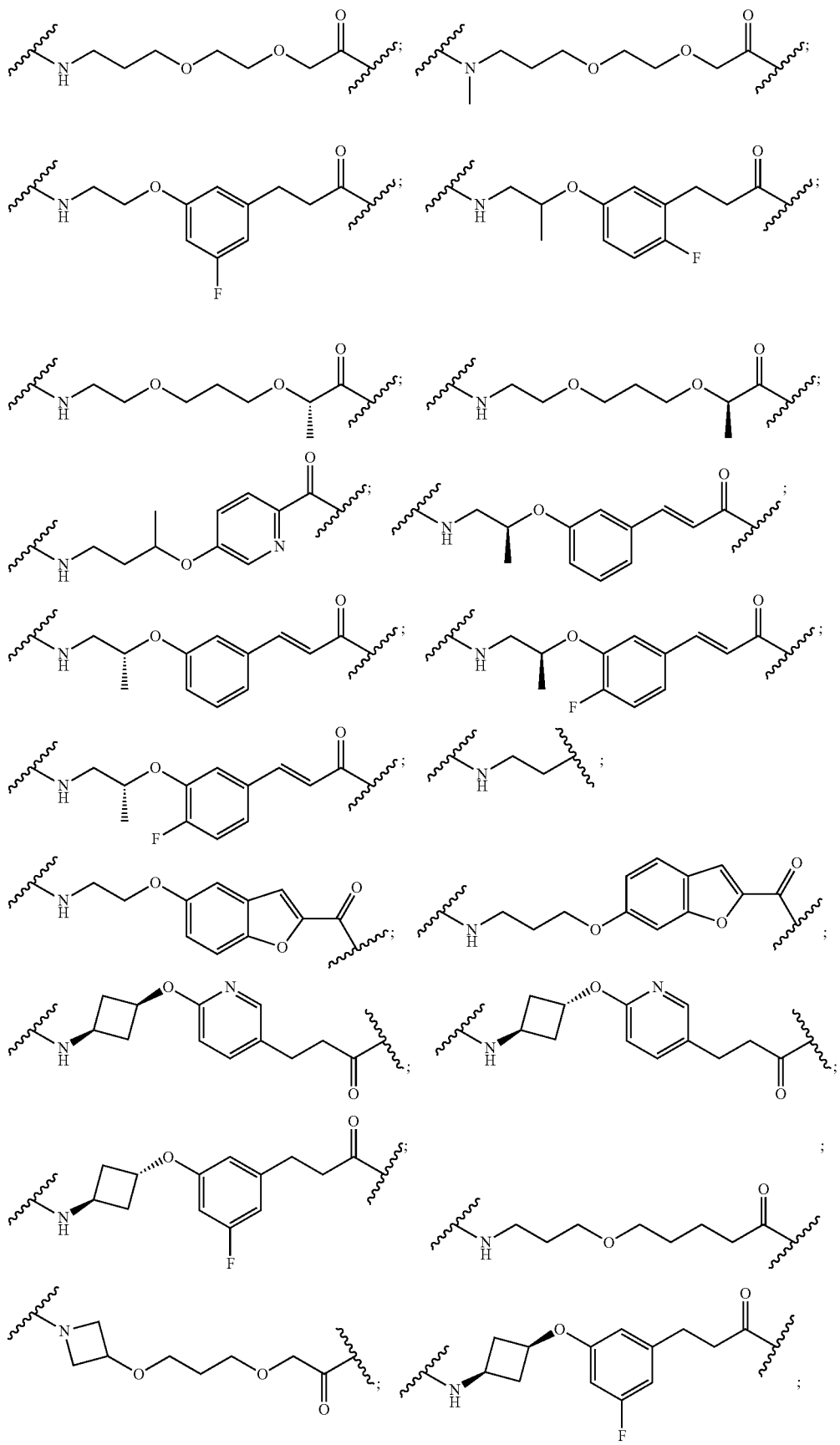

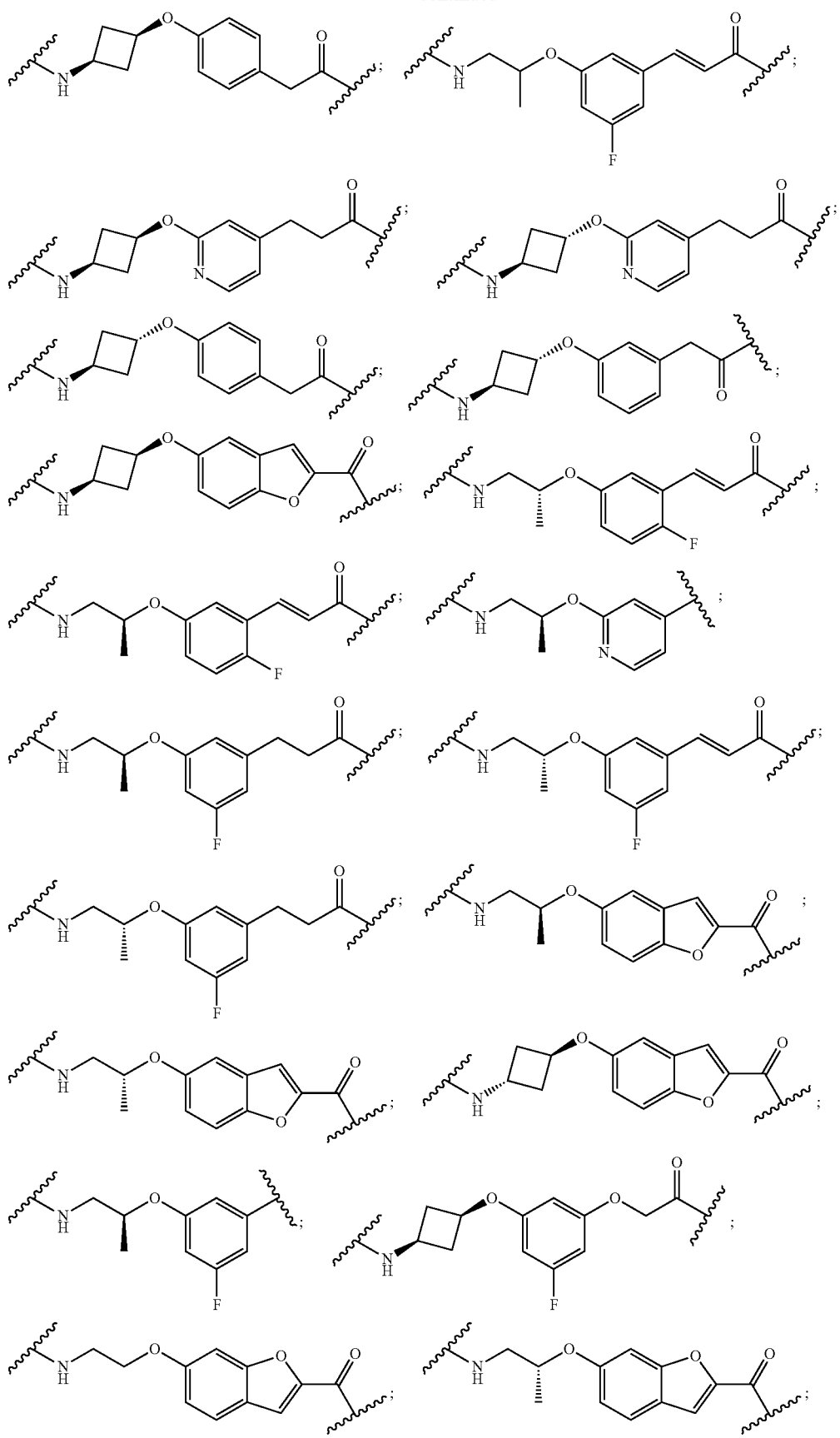

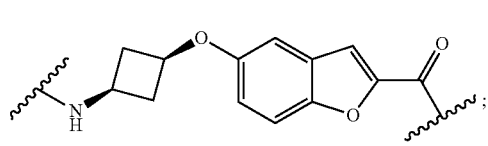
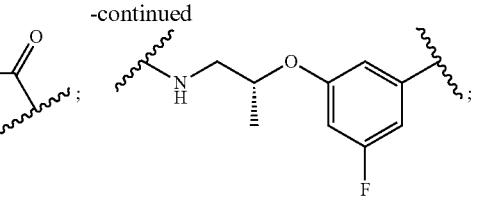
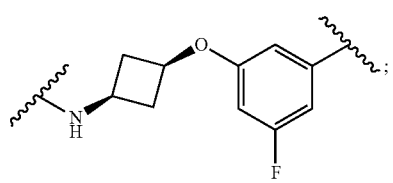
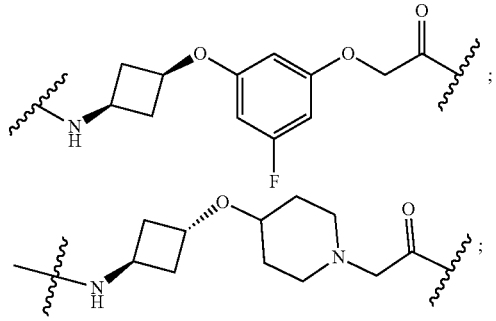
In some preferred embodiments, link (L) is selected from the group consisting of:
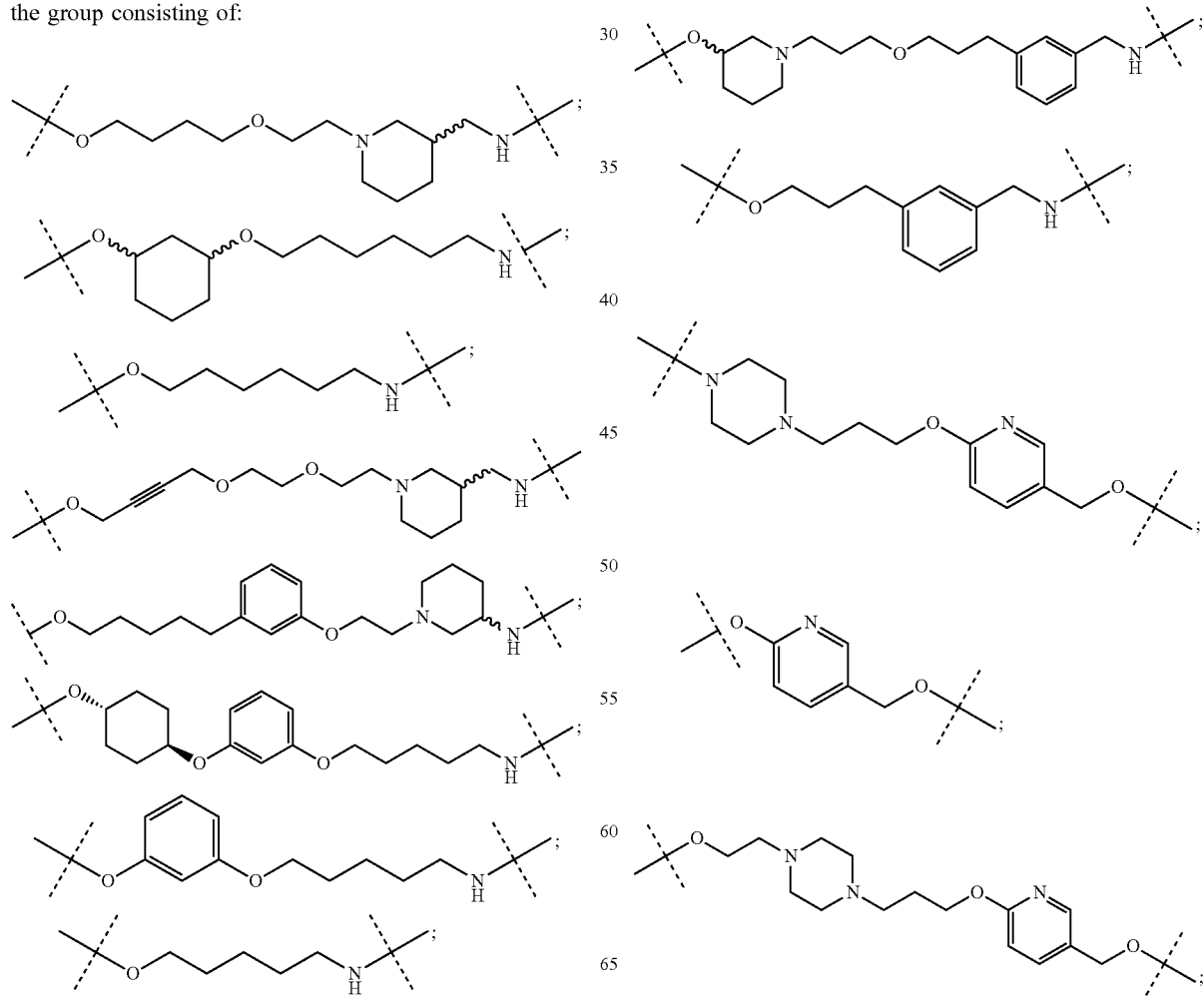

213
-continued
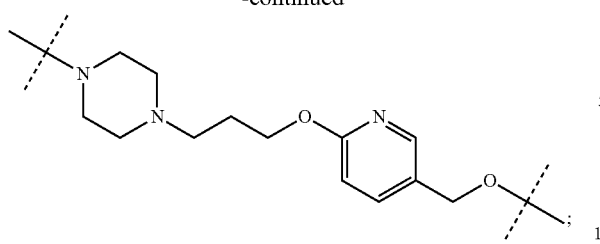
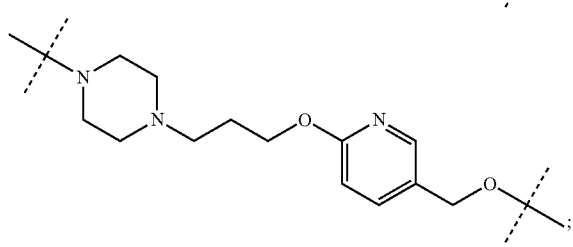
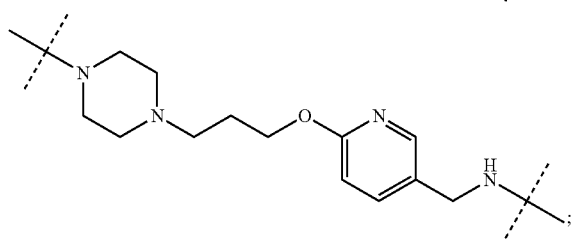
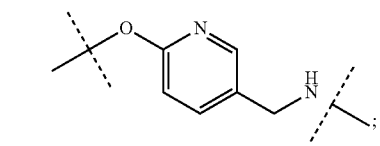
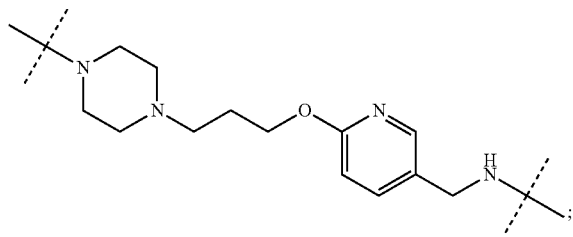
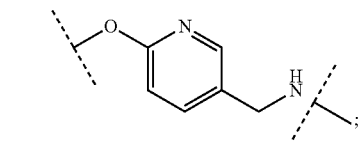
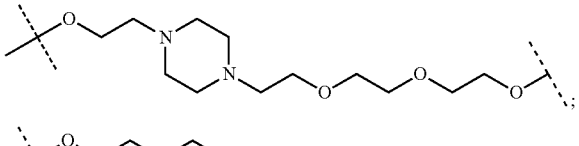
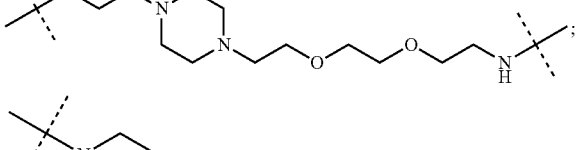
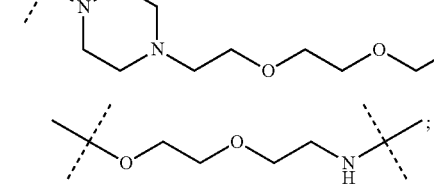
214
-continued
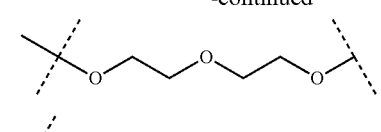
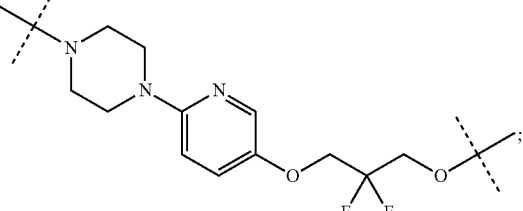
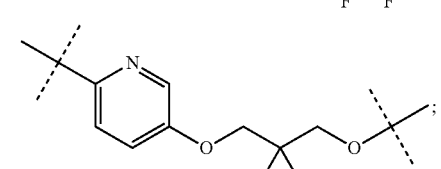
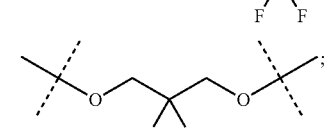
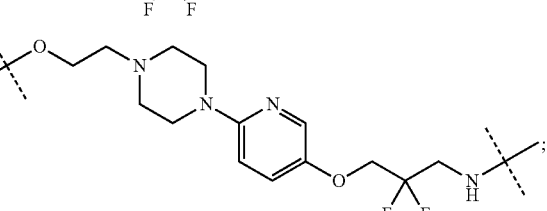
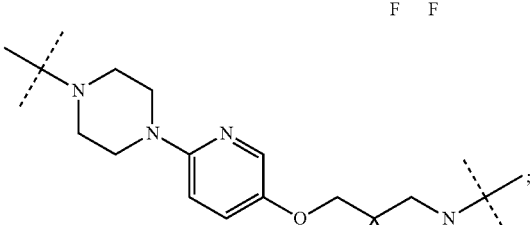
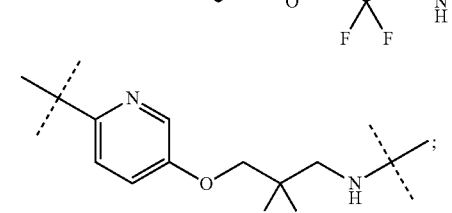
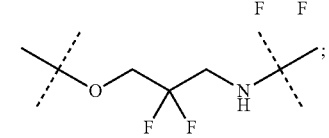
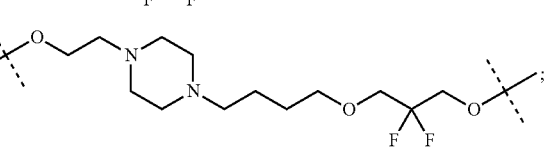
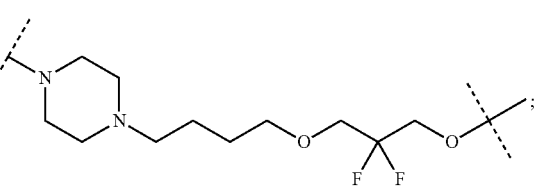

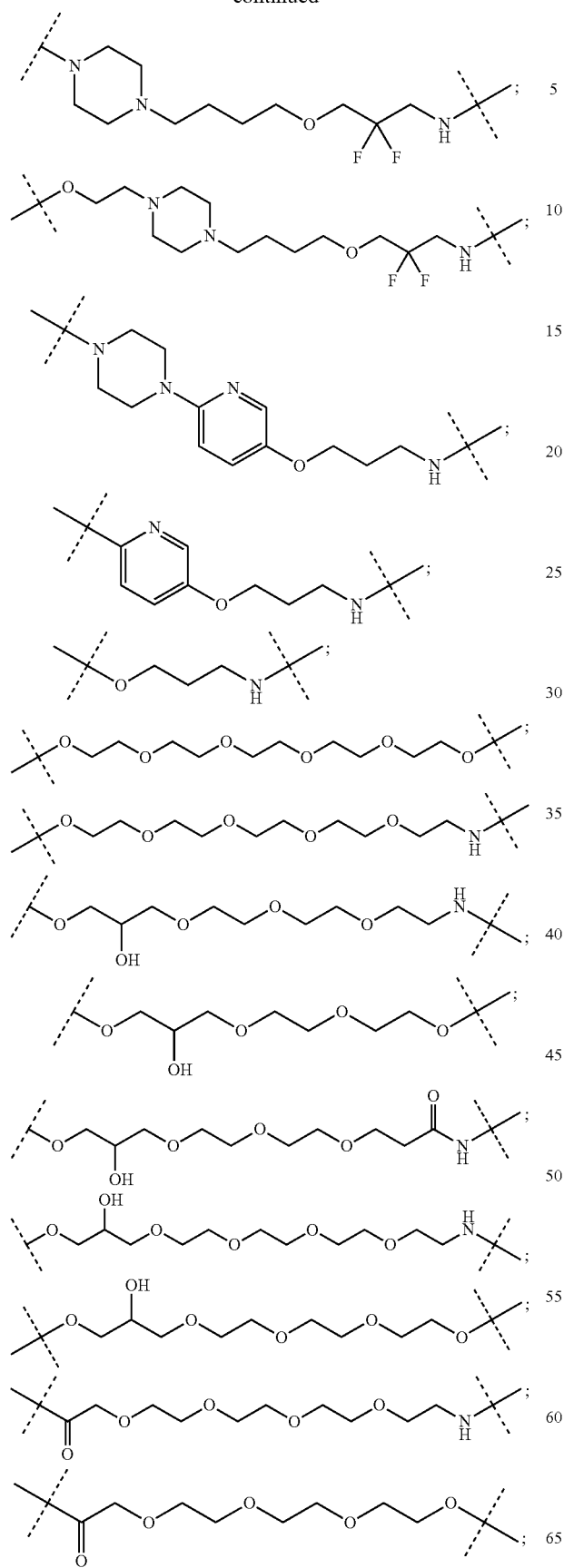
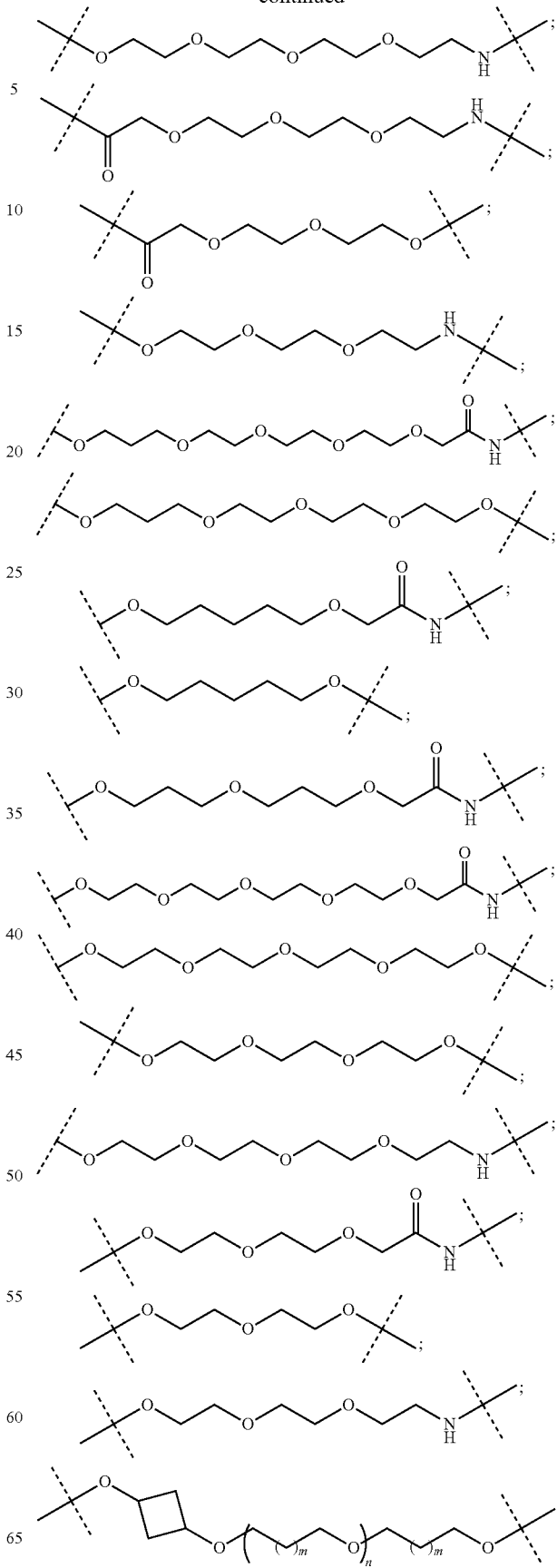

217
-continued
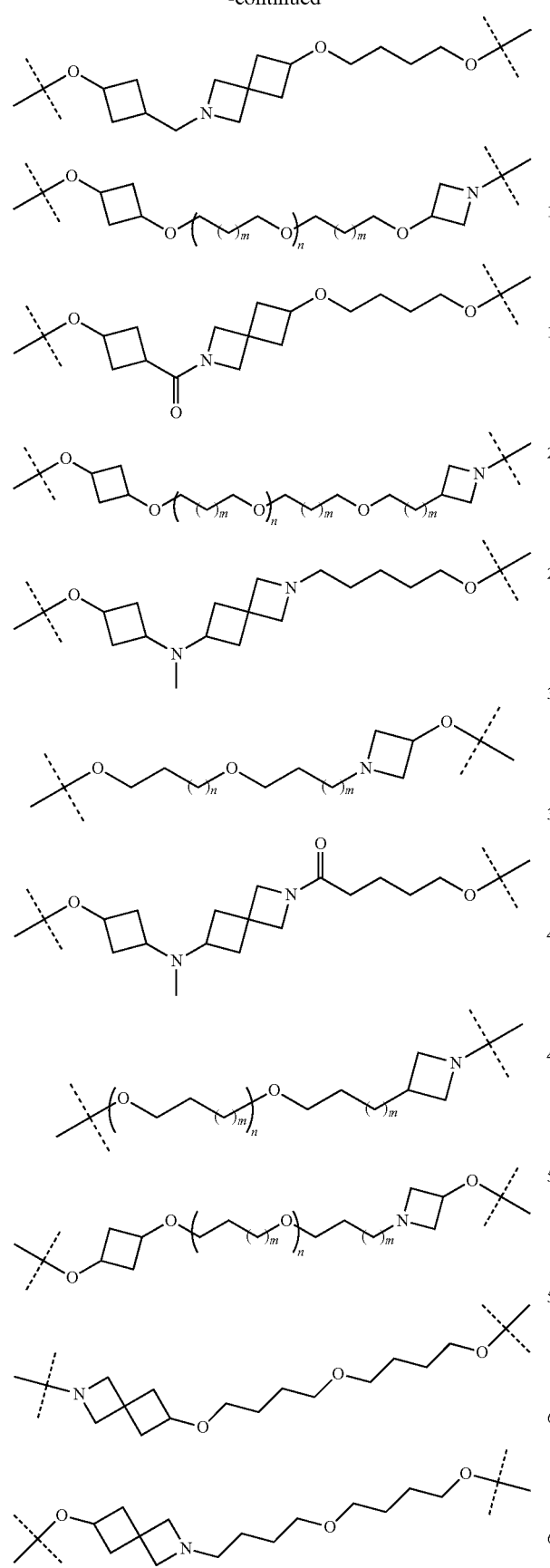
218
-continued
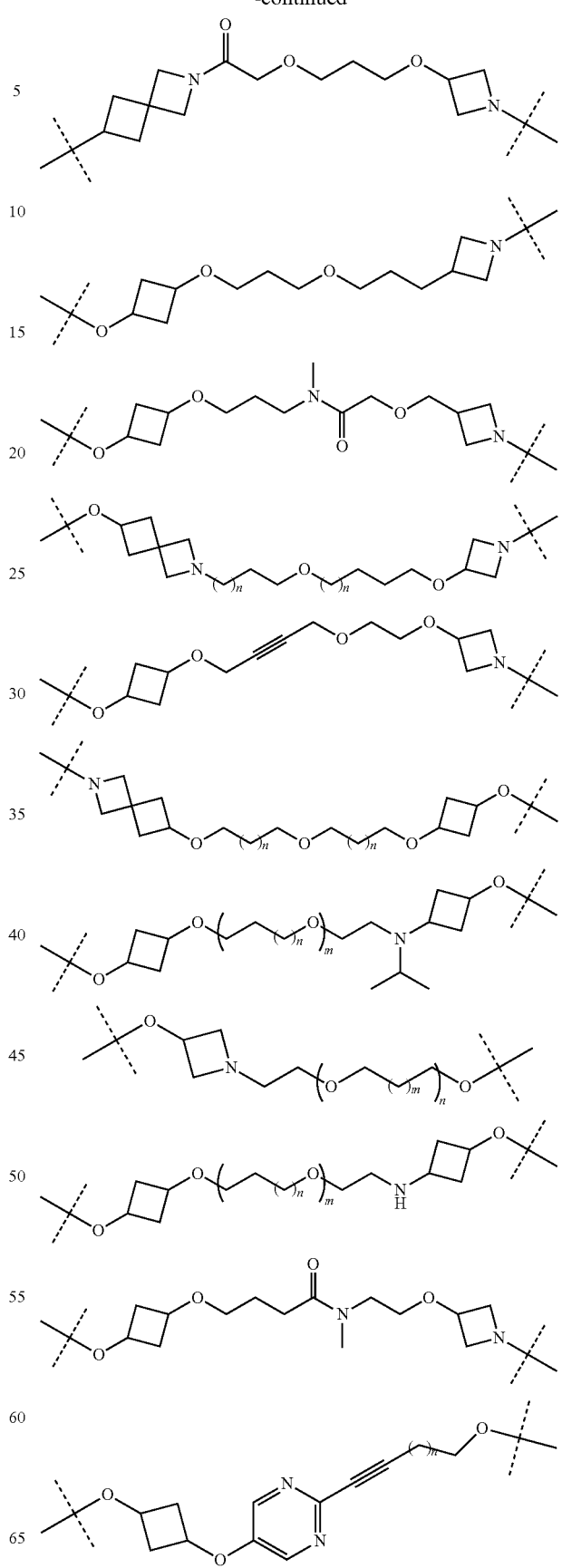

219
-continued
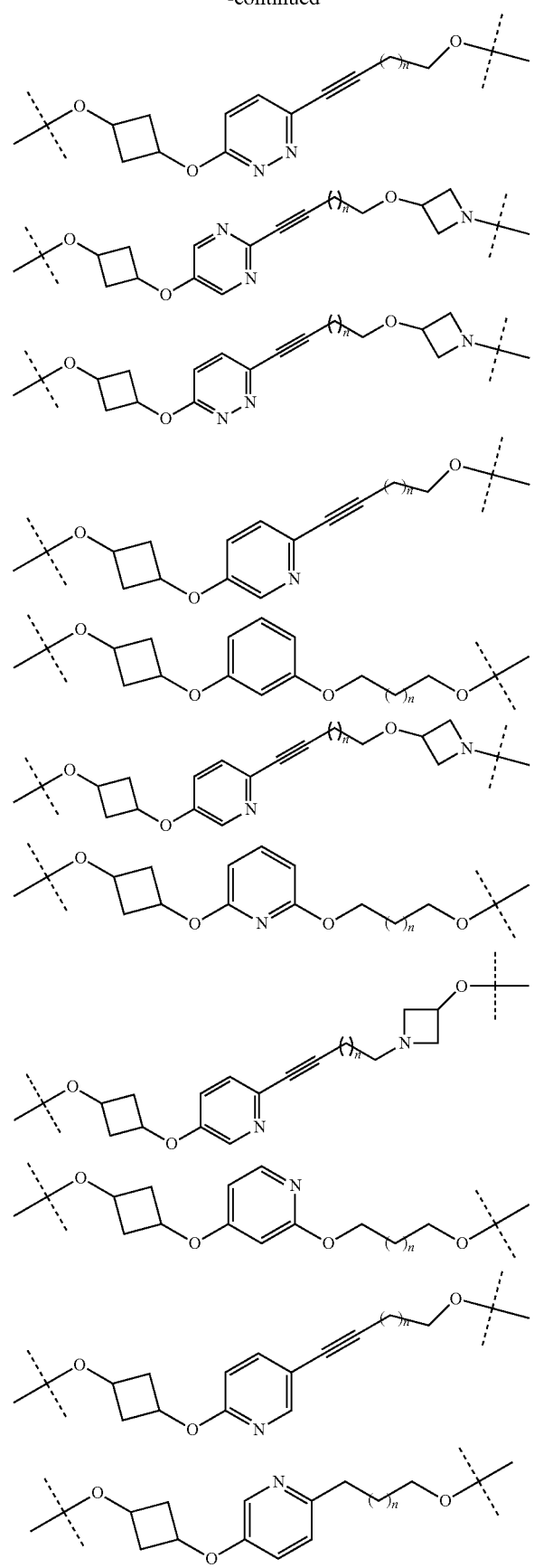
220
-continued
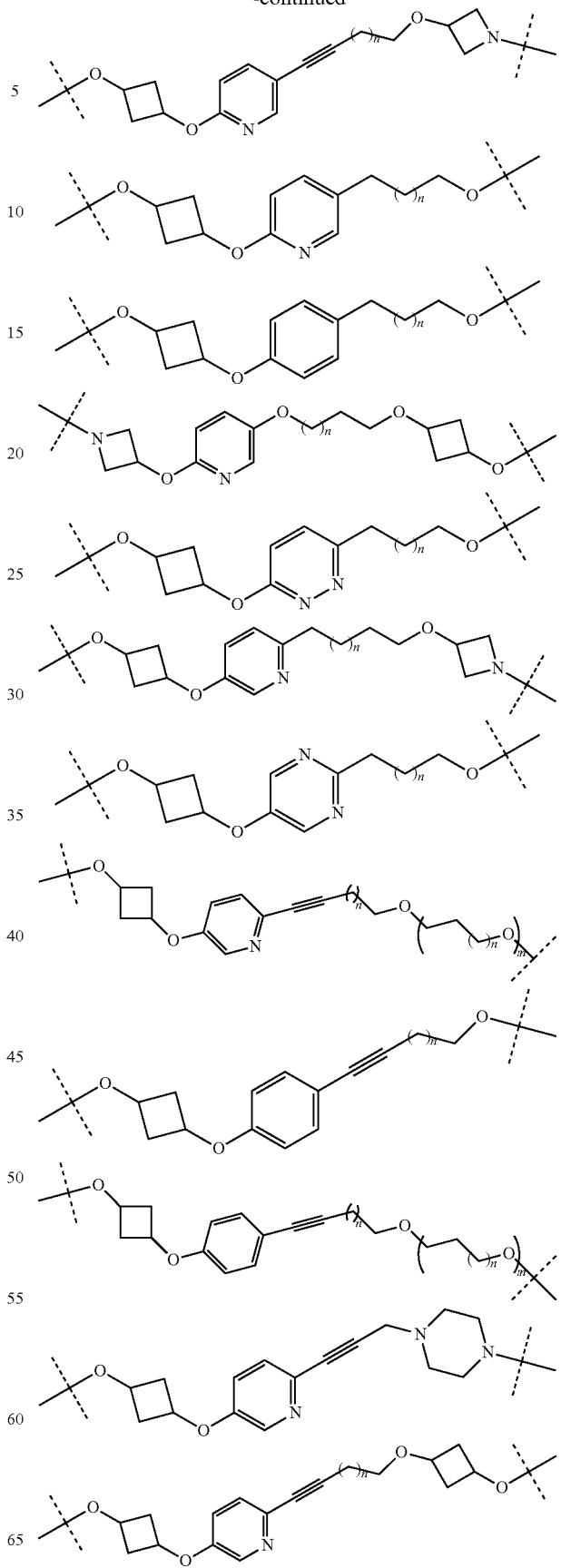

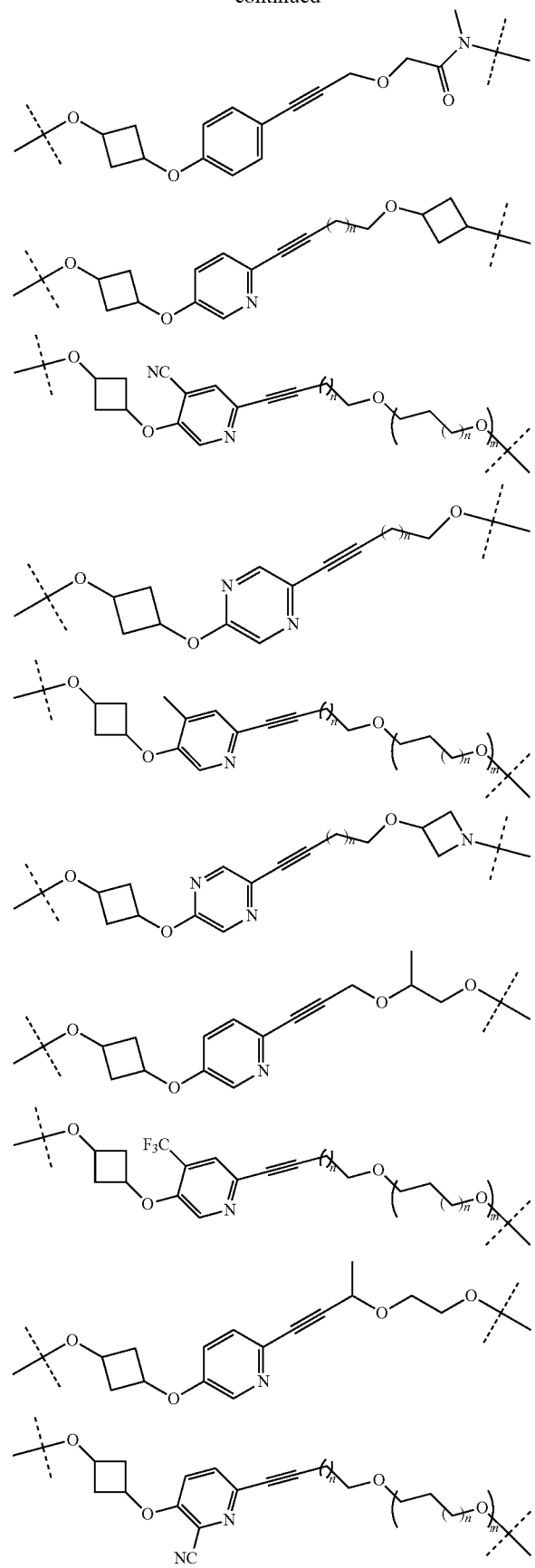
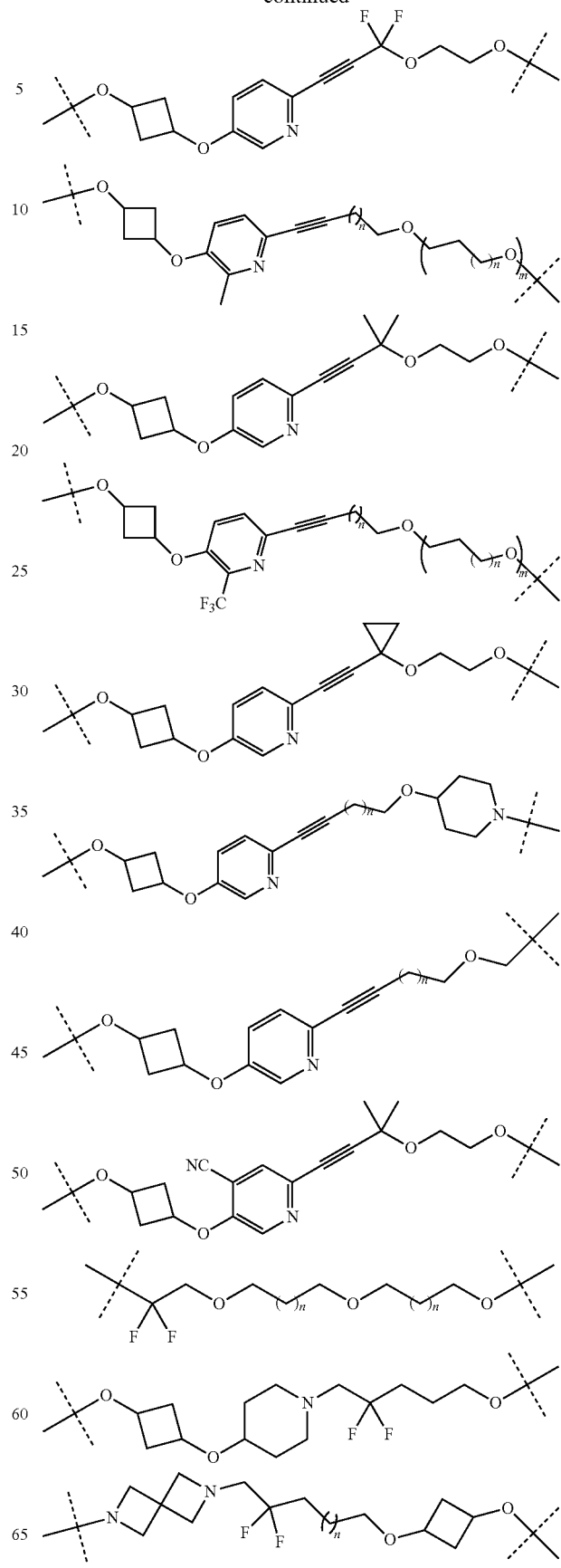

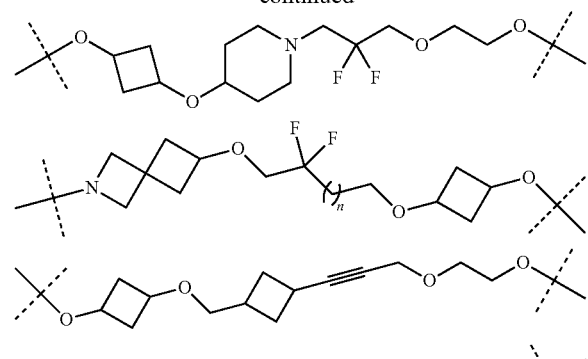
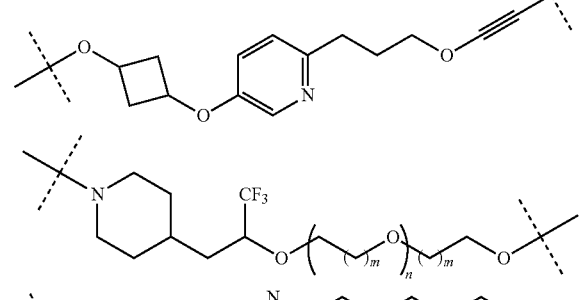
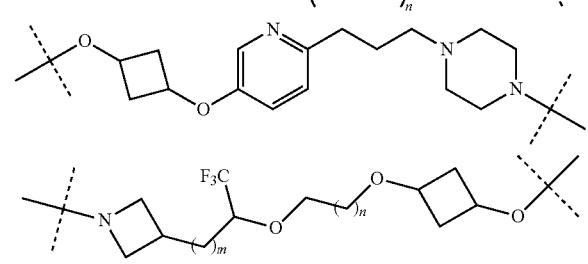
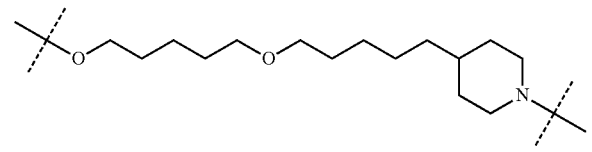
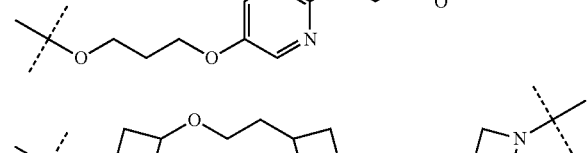
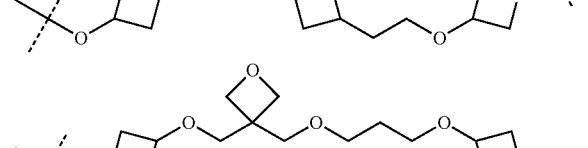
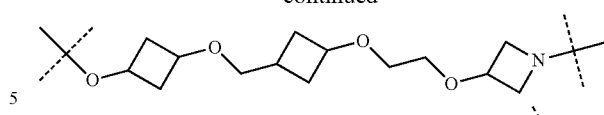
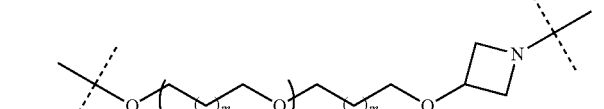
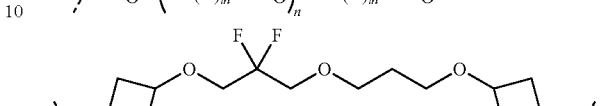
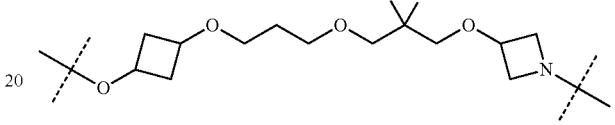
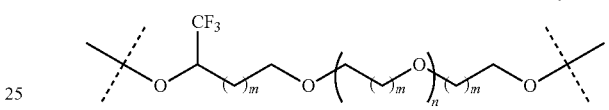
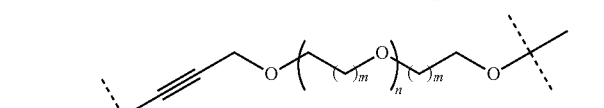
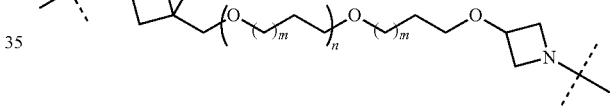
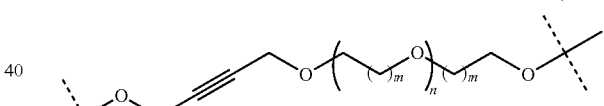
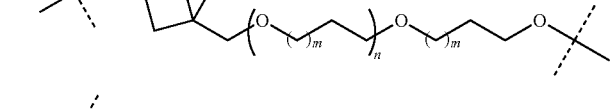
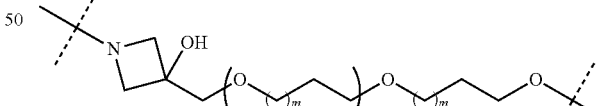
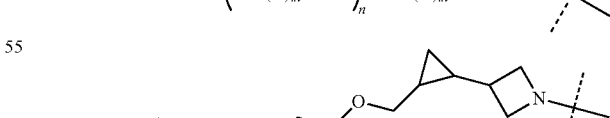

-continued
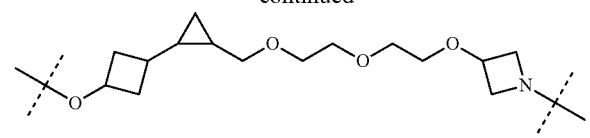
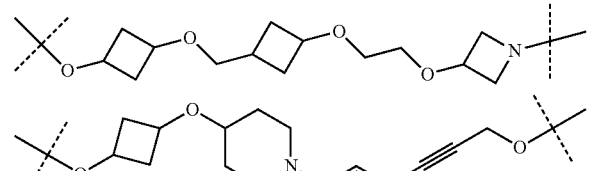
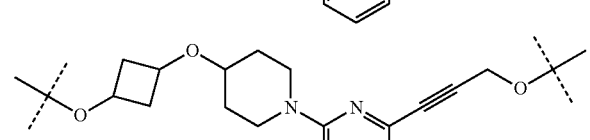
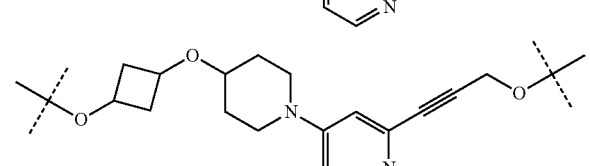
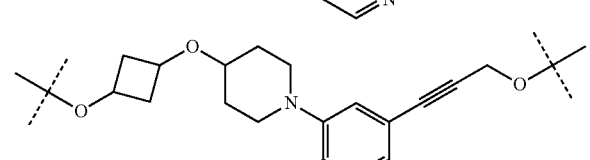
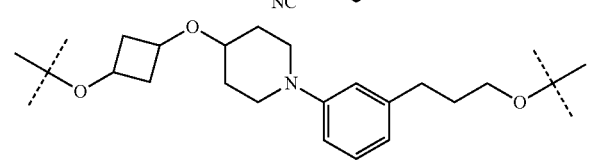
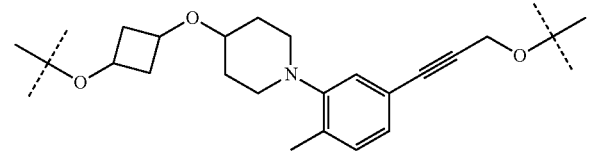
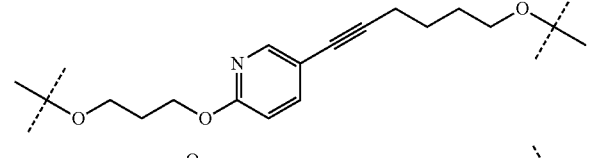
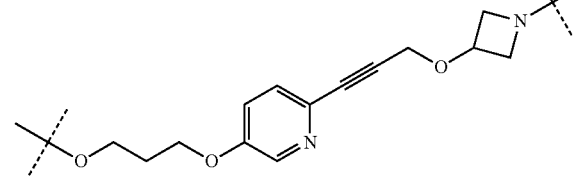
-continued
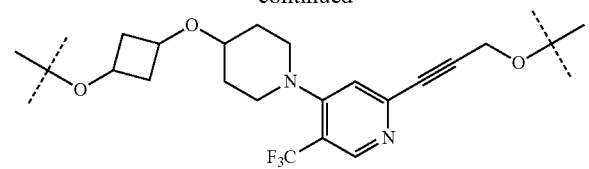
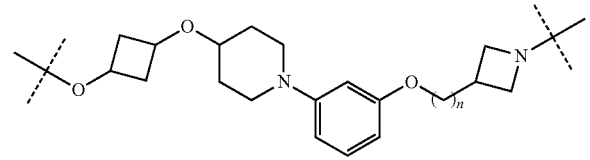
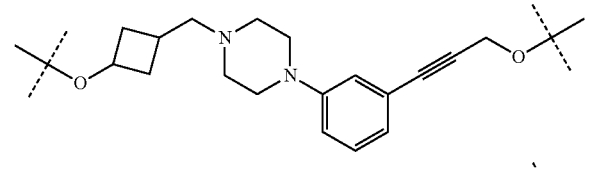
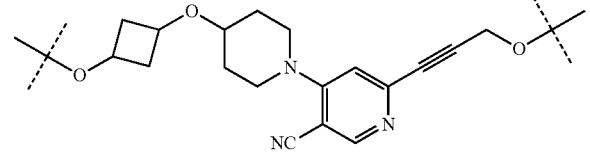
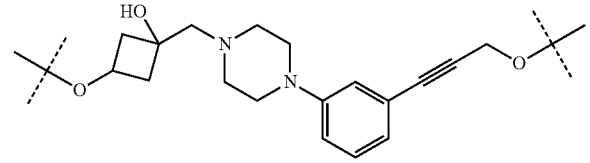
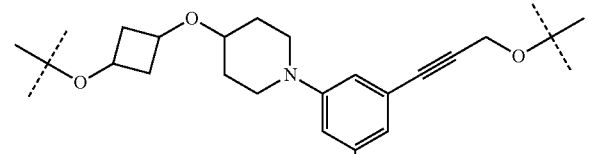
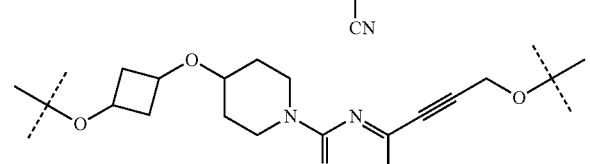
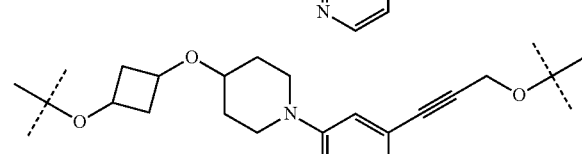
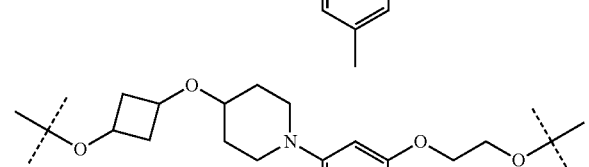
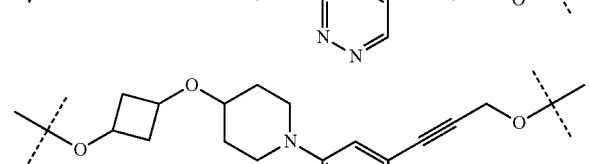
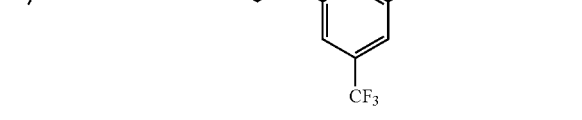

227
-continued
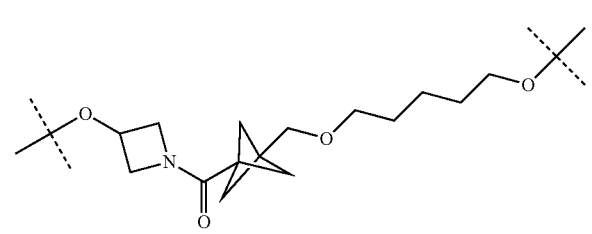
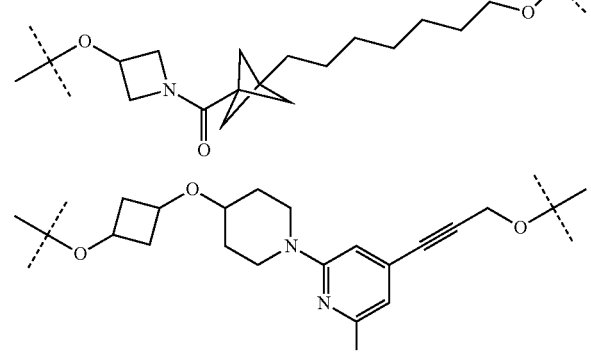
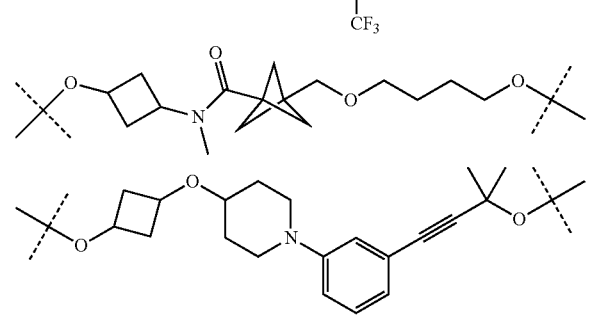
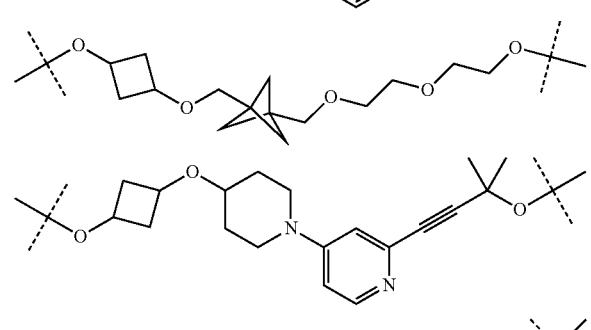
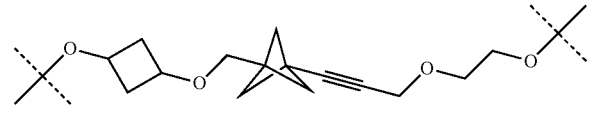
228
-continued
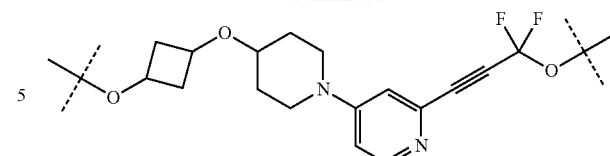
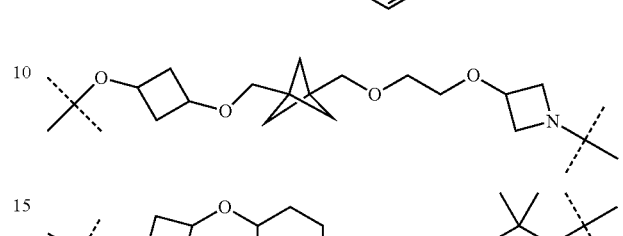
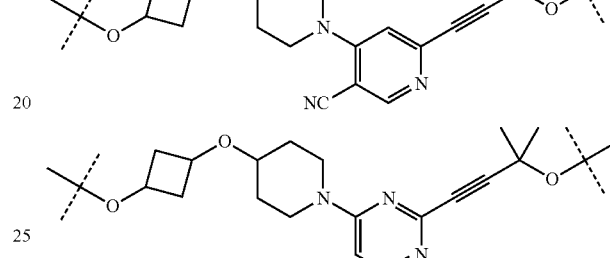
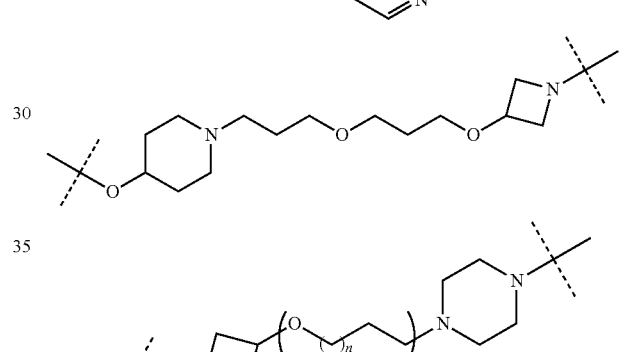
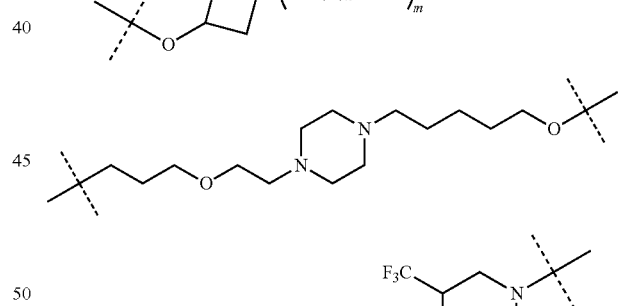
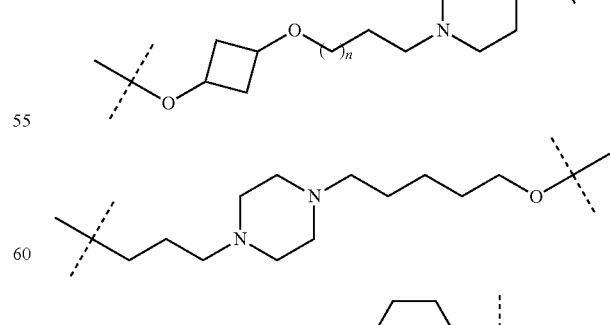
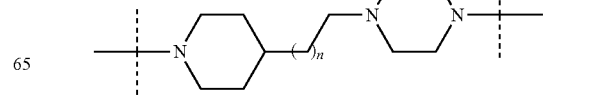

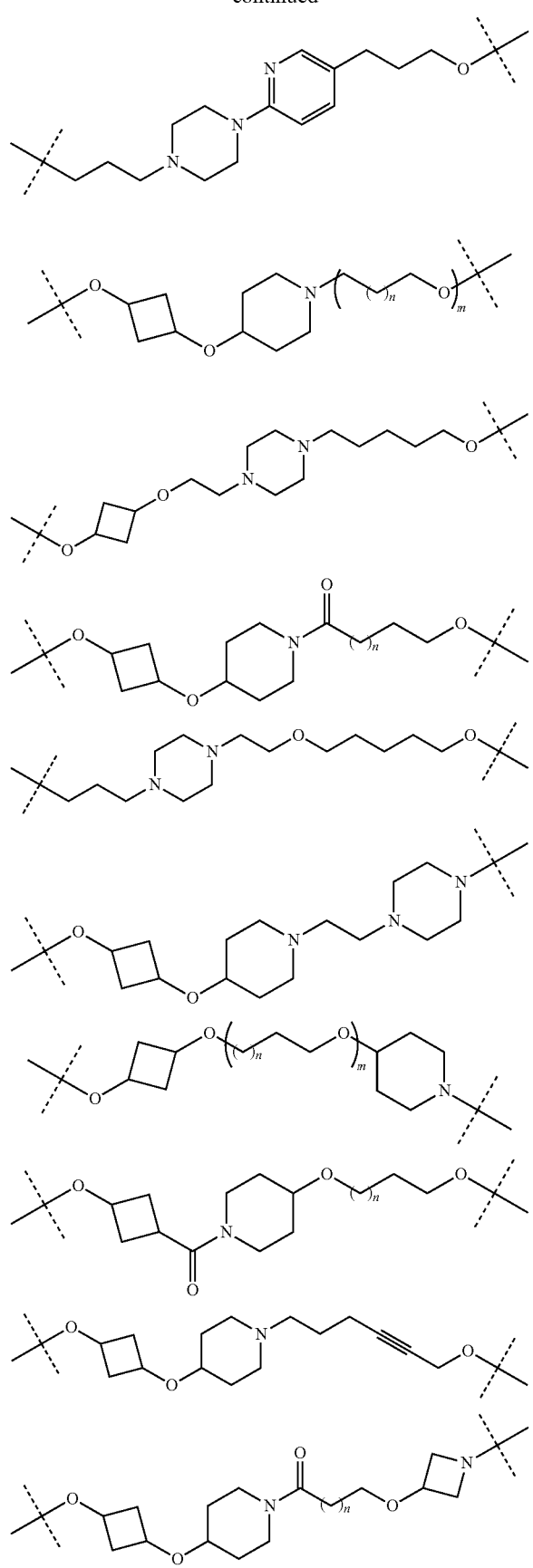
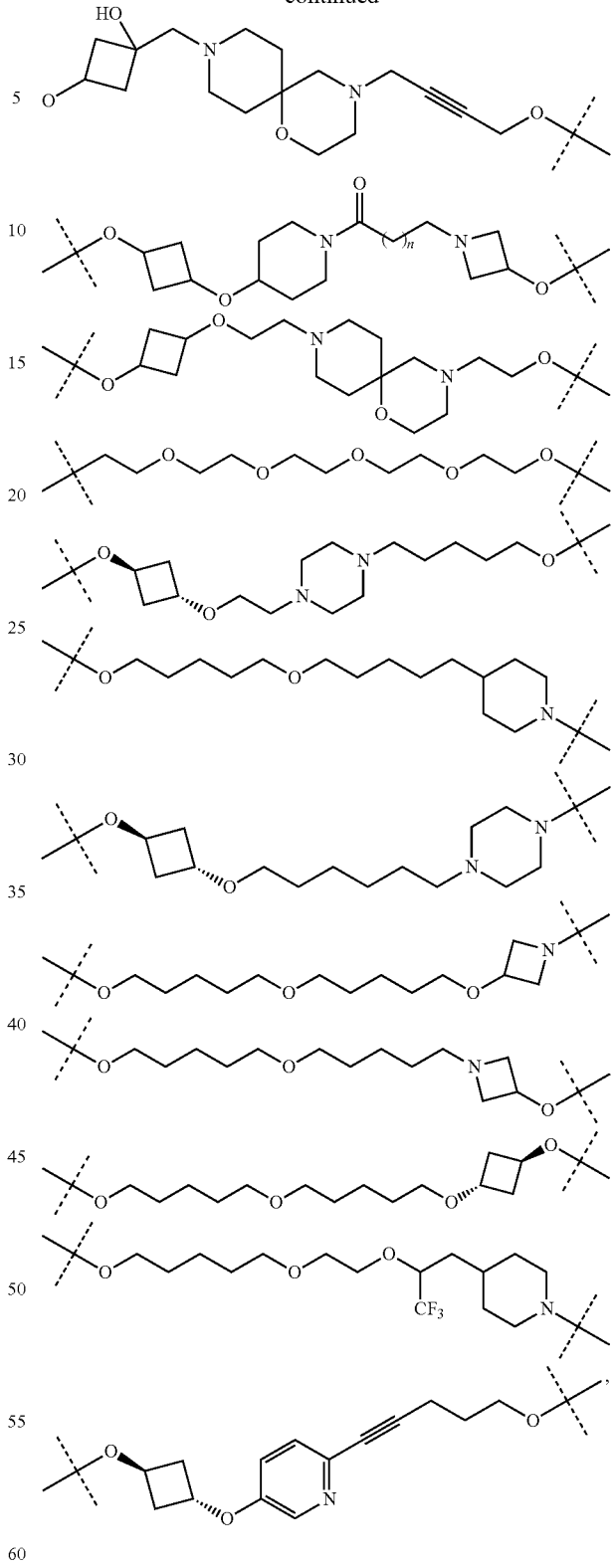
wherein each n and m is independently 0, 1, 2, 3, 4, 5, or 6.
In some embodiments, L is an optionally substituted polyethylenoxy group comprising from 1 to 10 units.
In some additional embodiments, L is a polyethylene group optionally substituted with aryl or phenyl comprising from 1 to 10 ethylene glycol units.

In any of the embodiments, the compound comprises multiple ULMs, multiple PTMs, multiple linkers or any combinations thereof.

Exemplary Tau-PROTAC Compounds

As described above, in certain aspects, the description provides bifunctional PROTAC compounds comprising at least one PTM group, a linker, and at least one ULM (VLM or CLM) group as described herein.

In certain embodiments, the compound is selected from the group consisting of compounds 1-330 (e.g., selected from Table 1 or 2), and salts and polymorphs thereof.

In certain embodiments, the compound is selected from Table 1 or 2 (i.e., the compound is selected from Compounds 1-330), and salts and polymorphs thereof.

In any aspect or embodiment described herein, the compound is selected from Formulas CI through CV:

Formula CI
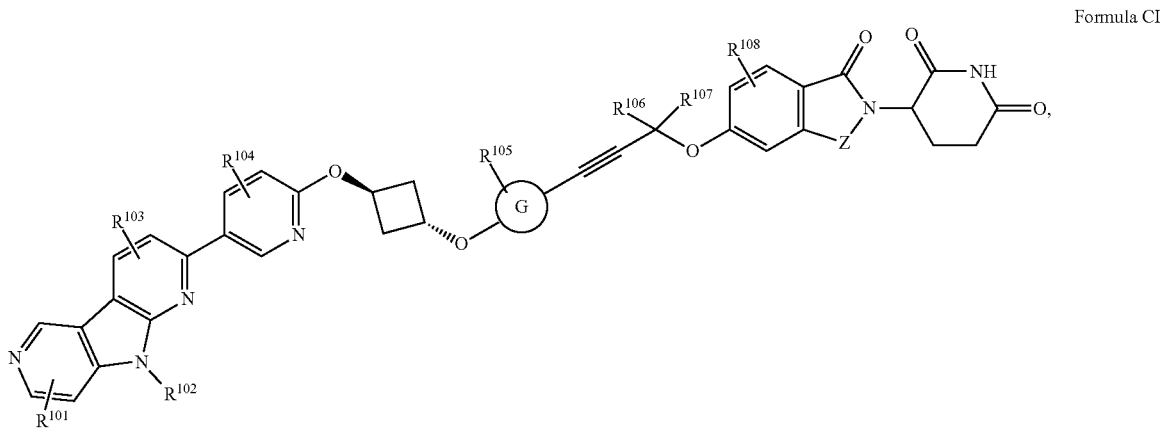

Formula CII
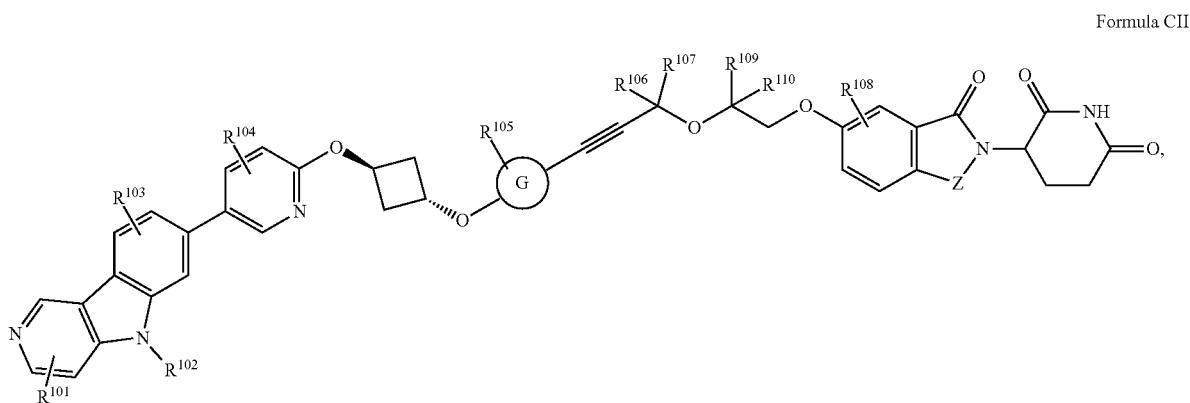

Formula CIII
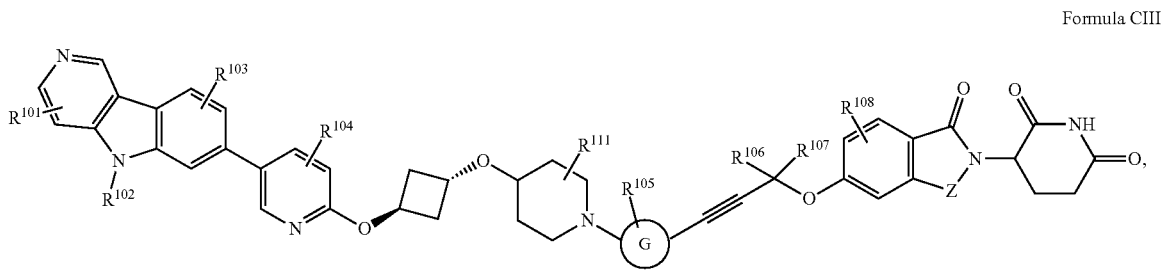

Formula CIV
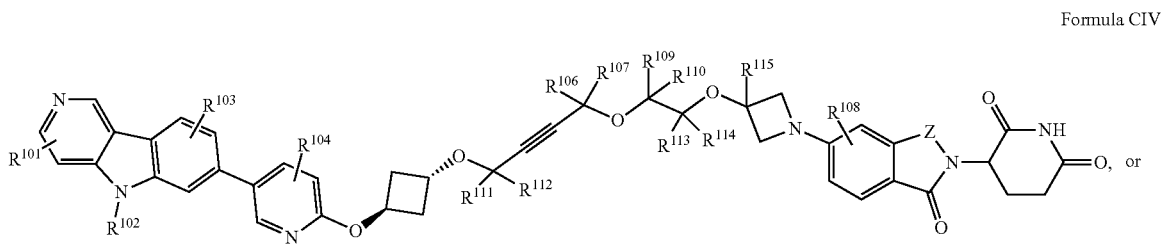

-continued

Formula CV

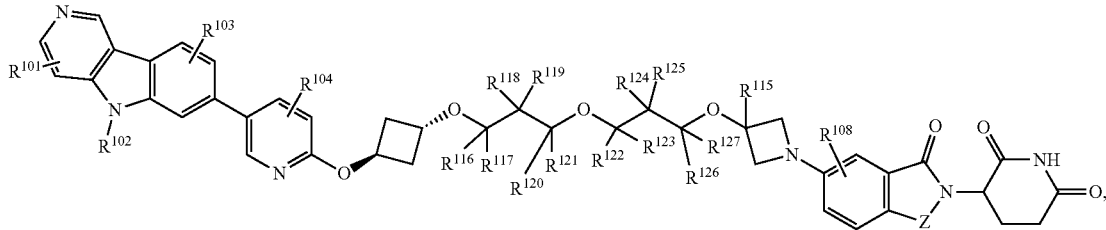

wherein:
- $R^{101}$ is 1-2 substituents independently selected from H, alkyl, halogen, haloalkyl or cyano;
- $R^{102}$ is selected from H, alkyl, haloalkyl, cycloalkyl or heterocycloalkyl;
- $R^{103}$ is 1-2 substituents independently selected from H, alkyl, halogen, haloalkyl or cyano;
- $R^{104}$ is 1-2 substituents independently selected from H, alkyl, halogen, haloalkyl or cyano;
- $R^{105}$ is 1-2 substituents independently selected from H, alkyl, halogen, haloalkyl or cyano;
- $R^{106}$, $R^{107}$, $R^{109}$, $R^{110}$, $R^{111}$, $R^{112}$, $R^{113}$, $R^{114}$, $R^{116}$, $R^{117}$, $R^{120}$, $R^{121}$, $R^{126}$, $R^{127}$, $R^{122}$ and $R^{123}$ are each independently selected from H, alkyl, halogen or haloalkyl;
- $R^{108}$ is 1-2 substituents independently selected from H, alkyl, halogen, haloalkyl, cyano or methoxy;
- $R^{115}$ is selected from H, alkyl and haloalkyl;
- $R^{118}$ and $R^{119}$ are independently selected from H, alkyl, halogen or haloalkyl, or $R^{118}$ and $R^{119}$ taken together with the carbon atom to which they are attached represent a 3-6-membered cycloalkyl or heterocycloalkyl ring, such as cyclopropane or an oxetane;
- $R^{124}$ and $R^{125}$ are independently selected from H, alkyl, halogen or haloalkyl, or $R^{124}$ and $R^{125}$ taken together with the carbon atom to which they are attached represent a 3-6-membered cycloalkyl or heterocycloalkyl ring, such as cyclopropane or an oxetane;
- G is a phenyl or a 5- or 6-membered heteroaryl ring; and
- Z is $CH_2$ or C=O.

In any aspect or embodiment described herein, at least one of:
- $R^{101}$ is H, F or Cl;
- $R^{102}$ is H, $CH_3$, or $CF_2H$;
- $R^{103}$ is H or F;
- $R^{104}$ is H, $CH_3$, F or CN;
- $R^{105}$ is H, CN, $CH_3$ or $CF_3$;
- $R^{106}$ and $R^{107}$ are each independently H, F or $CH_3$;
- $R^{108}$ is H, F or $CH_3O$;
- $R^{109}$ and $R^{110}$ are each independently H or $CH_3$;
- $R^{111}$ and $R^{112}$ are each independently H, F or $CH_3$;
- $R^{113}$ and $R^{114}$ are each independently H or $CH_3$;
- $R^{115}$ is H or $CH_3$;
- $R^{116}$ and $R^{117}$ are each independently H or $CH_3$;
- $R^{118}$ and $R^{119}$ are each independently H, $CH_3$, F, or $R^{118}$ and $R^{119}$ taken together with the carbon atom to which they are attached represent a cyclopropane or an oxetane ring;
- $R^{120}$ and $R^{121}$ are each independently H or $CH_3$;
- $R^{122}$ and $R^{123}$ are each independently H or $CH_3$;
- $R^{124}$ and $R^{125}$ are each independently H, $CH_3$, F, or $R^{124}$ and $R^{125}$ taken together with the carbon atom to which they are attached represent a cyclopropane or an oxetane ring;
- $R^{126}$ and $R^{127}$ are each independently H or $CH_3$;
- A is a pyridine or a pyrimidine;
- Z is $CH_2$ or C=O; or
- a combination thereof.

In any aspect or embodiment described herein, the compound is selected from the group consisting of: (2S,4R)-1-((S)-14-(5-(5H-pyrido[4,3-b]indol-7-yl)pyridin-2-yloxy)-2-tert-butyl-4-oxo-6,9,12-trioxa-3-azatetradecane)-4-hydroxy-N-(4-(4-methylthiazol-5-yl)benzyl)pyrrolidine-2-carboxamide (1); 4-(2-(2-(2-(2-(5-(5H-pyrido[4,3-b]indol-7-yl)pyridin-2-yloxy)ethoxy)ethoxy)ethoxy)ethylamino)-2-(2,6-dioxopiperidin-3-yl)isoindoline-1,3-dione (2); 4-(2-(2-(2-(5-(5H-pyrido[4,3-b]indol-7-yl)pyridin-2-yloxy)ethoxy)ethoxy)ethylamino)-2-(2,6-dioxopiperidin-3-yl)isoindoline-1,3-dione (3); 4-(14-(5-(5H-pyrido[4,3-b]indol-7-yl)pyridin-2-yloxy)-3,6,9,12-tetraoxatetradecylamino)-2-(2,6-dioxopiperidin-3-yl)isoindoline-1,3-dione (4); (2S,4R)-1-((S)-2-(2-(2-(2-(5-(5H-pyrido[4,3-b]indol-7-yl)pyridin-2-yloxy)ethoxy)ethoxy)acetamido)-3,3-dimethylbutanoyl)-4-hydroxy-N-(4-(4-methylthiazol-5-yl)benzyl)pyrrolidine-2-carboxamide (5); (2S,4R)-1-((S)-17-(5-(5H-pyrido[4,3-b]indol-7-yl)pyridin-2-yloxy)-2-tert-butyl-4-oxo-6,9,12,15-tetraoxa-3-azaheptadecane)-4-hydroxy-N-(4-(4-methylthiazol-5-yl)benzyl)pyrrolidine-2-carboxamide (6); (2S,4R)-1-((S)-14-(4-(benzo[4,5]imidazo[1,2-a]pyrimidin-2-yl)piperazin-1-yl)-2-(tert-butyl)-4-oxo-6,9,12-trioxa-3-azatetradecanoyl)-4-hydroxy-N-(4-(4-methylthiazol-5-yl)benzyl)pyrrolidine-2-carboxamide (7); (2S,4R)-1-((S)-2-tert-butyl-15-(2-(4-(dimethylamino)phenyl)quinolin-6-yloxy)-4-oxo-6,9,12-trioxa-3-azapentadecane)-4-hydroxy-N-(4-(4-methylthiazol-5-yl)benzyl)pyrrolidine-2-carboxamide (8); (2S,4R)-1-((S)-2-tert-butyl-18-(2-(4-(dimethylamino)phenyl)quinolin-6-yloxy)-4-oxo-6,9,12,15-tetraoxa-3-azaoctadecane)-4-hydroxy-N-(4-(4-methylthiazol-5-yl)benzyl)pyrrolidine-2-carboxamide (9); (2S,4R)-1-((S)-14-(4-(benzo[4,5]imidazo[1,2-a]pyrimidin-2-yl)piperazin-1-yl)-2-(tert-butyl)-4,14-dioxo-6,9,12-trioxa-3-azatetradecanoyl)-4-hydroxy-N-(4-(4-methylthiazol-5-yl)benzyl)pyrrolidine-2-carboxamide (10); (2S,4R)-1-((S)-14-(4-(benzo[4,5]imidazo[1,2-a]pyrimidin-2-yl)piperazin-1-yl)-2-(tert-butyl)-4-oxo-6,9,12-trioxa-3-azatetradecanoyl)-4-hydroxy-N-(4-(4-methyloxazol-5-yl)benzyl)pyrrolidine-2-carboxamide (11); (2S,4R)-1-((S)-17-(4-(benzo[4,5]imidazo[1,2-a]pyrimidin-2-yl)piperazin-1-yl)-2-(tert-butyl)-4-oxo-6,9,12,15-tetraoxa-3-azaheptadecanoyl)-4-hydroxy-N-(4-(4-methyloxazol-5-yl)benzyl)pyrrolidine-2-carboxamide (12); (2S,4R)-1-((S)-14-(4-(benzo[4,5]imidazo[1,2-a]pyrimidin-2-yl)piperazin-1-yl)-2-(tert-butyl)-4,14-dioxo-6,9,12-trioxa-3-azatetradecanoyl)-4-hydroxy-N-(4-(4-methyloxazol-5-yl)benzyl)pyrrolidine-2-carboxamide (13); (2S,4R)-1-((S)-17-(4-(benzo[4,5]imidazo[1,2-a]pyrimidin-2-yl)piperazin-1-yl)-2-(tert-butyl)-4,17-dioxo-6,9,12,15-tetraoxa-3- azaheptadecanoyl)-4-hydroxy-N-(4-(4-methyloxazol-5-yl) benzyl)pyrrolidine-2-carboxamide (14); (2S,4R)-1-((S)-14-(4-(benzo[4,5]imidazo[1,2-a]pyrimidin-2-yl)piperazin-1-yl)-2-(tert-butyl)-4-oxo-6,9,12-trioxa-3-azatetradecanoyl)-4-hydroxy-N—((S)-1-(4-(4-methylthiazol-5-yl)phenyl) ethyl)pyrrolidine-2-carboxamide (15); (2S,4R)-1-((S)-17-(4-(benzo[4,5]imidazo[1,2-a]pyrimidin-2-yl)piperazin-1-yl)-2-(tert-butyl)-4-oxo-6,9,12,15-tetraoxa-3-azaheptadecanoyl)-4-hydroxy-N—((S)-1-(4-(4-methylthiazol-5-yl) phenyl)ethyl)pyrrolidine-2-carboxamide (16); (2S,4R)-1-((S)-14-(4-(benzo[4,5]imidazo[1,2-a]pyrimidin-2-yl)piperazin-1-yl)-2-(tert-butyl)-4,14-dioxo-6,9,12-trioxa-3-azatetradecanoyl)-4-hydroxy-N—((S)-1-(4-(4-methylthiazol-5-yl)phenyl)ethyl)pyrrolidine-2-carboxamide (17); (2S,4R)-1-((S)-17-(4-(benzo[4,5]imidazo[1,2-a]pyrimidin-2-yl)piperazin-1-yl)-2-(tert-butyl)-4,17-dioxo-6,9,12,15-tetraoxa-3-azaheptadecanoyl)-4-hydroxy-N—((S)-1-(4-(4-methylthiazol-5-yl)phenyl)ethyl)pyrrolidine-2-carboxamide (18); (2S,4R)-1-((S)-14-(4-(benzo[4,5]imidazo[1,2-a]pyrimidin-2-yl)piperazin-1-yl)-2-(tert-butyl)-4-oxo-6,9,12-trioxa-3-azatetradecanoyl)-4-hydroxy-N—((S)-1-(4-(4-methyloxazol-5-yl)phenyl)ethyl)pyrrolidine-2-carboxamide (19); (2S,4R)-1-((S)-17-(4-(benzo[4,5]imidazo[1,2-a]pyrimidin-2-yl)piperazin-1-yl)-2-(tert-butyl)-4-oxo-6,9,12,15-tetraoxa-3-azaheptadecanoyl)-4-hydroxy-N—((S)-1-(4-(4-methyloxazol-5-yl)phenyl)ethyl)pyrrolidine-2-carboxamide (20); (2S,4R)-1-((S)-14-(4-(benzo[4,5]imidazo[1,2-a]pyrimidin-2-yl)piperazin-1-yl)-2-(tert-butyl)-4,14-dioxo-6,9,12-trioxa-3-azatetradecanoyl)-4-hydroxy-N—((S)-1-(4-(4-methyloxazol-5-yl)phenyl)ethyl)pyrrolidine-2-carboxamide (21); (2S,4R)-1-((S)-17-(4-(benzo[4,5]imidazo[1,2-a]pyrimidin-2-yl)piperazin-1-yl)-2-(tert-butyl)-4,17-dioxo-6,9,12,15-tetraoxa-3-azaheptadecanoyl)-4-hydroxy-N—((S)-1-(4-(4-methyloxazol-5-yl)phenyl)ethyl)pyrrolidine-2-carboxamide (22); (2S,4R)-1-((S)-17-(4-(benzo[4,5]imidazo[1,2-a]pyrimidin-2-yl)piperazin-1-yl)-2-(tert-butyl)-4-oxo-6,9,12,15-tetraoxa-3-azaheptadecanoyl)-4-hydroxy-N-(4-(4-methylthiazol-5-yl)benzyl)pyrrolidine-2-carboxamide (23); (2S,4R)-1-((S)-17-(4-(benzo[4,5]imidazo[1,2-a]pyrimidin-2-yl)piperazin-1-yl)-2-(tert-butyl)-4,17-dioxo-6,9,12,15-tetraoxa-3-azaheptadecanoyl)-4-hydroxy-N-(4-(4-methylthiazol-5-yl)benzyl)pyrrolidine-2-carboxamide (24); 4-((2-(2-(2-(2-(4-(benzo[4,5]imidazo[1,2-a]pyrimidin-2-yl)piperazin-1-yl)ethoxy)ethoxy)ethoxy)ethyl)amino)-2-(2,6-dioxopiperidin-3-yl)isoindoline-1,3-dione (25); 4-((14-(4-(benzo[4,5]imidazo[1,2-a]pyrimidin-2-yl)piperazin-1-yl)-3,6,9,12-tetraoxatetradecyl)amino)-2-(2,6-dioxopiperidin-3-yl)isoindoline-1,3-dione (26); (2S,4R)-1-((S)-2-(2-(2-(2-(2-(4-(dimethylamino)phenyl)quinolin-6-yloxy)ethoxy)ethoxy)acetamido)-3,3-dimethylbutanoyl)-4-hydroxy-N-(4-(4-methylthiazol-5-yl)benzyl)pyrrolidine-2-carboxamide (27); (2S,4R)-1-((S)-2-(2-(2-(2-(2-(4-(dimethylamino)phenyl)quinolin-6-yloxy)ethoxy)ethoxy)acetamido)-3,3-dimethylbutanoyl)-4-hydroxy-N—((S)-1-(4-(4-methylthiazol-5-yl)phenyl)ethyl)pyrrolidine-2-carboxamide (28); (2S,4R)-1-((S)-2-tert-butyl-14-(2-(4-(dimethylamino)phenyl) quinolin-6-yloxy)-4-oxo-6,9,12-trioxa-3-azatetradecane)-4-hydroxy-N-(4-(4-methylthiazol-5-yl)benzyl)pyrrolidine-2-carboxamide (29); (2S,4R)-1-((S)-2-tert-butyl-14-(2-(4-(dimethylamino)phenyl)quinolin-6-yloxy)-4-oxo-6,9,12-trioxa-3-azatetradecane)-4-hydroxy-N—((S)-1-(4-(4-methylthiazol-5-yl)phenyl)ethyl)pyrrolidine-2-carboxamide (30); (2S,4R)-1-((S)-2-tert-butyl-17-(2-(4-(dimethylamino)phenyl)quinolin-6-yloxy)-4-oxo-6,9,12,15-tetraoxa-3-azaheptadecane)-4-hydroxy-N—((S)-1-(4-(4-methylthiazol-5-yl)phenyl)ethyl)pyrrolidine-2-carboxamide (31); (2S,4R)-1-((S)-2-tert-butyl-17-(2-(4-(dimethylamino)phenyl)quinolin-6-yloxy)-4-oxo-6,9,12,15-tetraoxa-3-azaheptadecane)-4-hydroxy-N—((S)-1-(4-(4-methylthiazol-5-yl)phenyl)ethyl)pyrrolidine-2-carboxamide (32); (2S,4R)-1-((S)-2-(2-(4-(2-(4-(dimethylamino)phenyl)quinolin-6-yloxy)butoxy) acetamido)-3,3-dimethylbutanoyl)-4-hydroxy-N-(4-(4-methylthiazol-5-yl)benzyl)pyrrolidine-2-carboxamide (33); (2S,4R)-1-((S)-2-(2-(4-(2-(4-(dimethylamino)phenyl)quinolin-6-yloxy)butoxy)acetamido)-3,3-dimethylbutanoyl)-4-hydroxy-N—((S)-1-(4-(4-methylthiazol-5-yl)phenyl)ethyl)pyrrolidine-2-carboxamide (34); (2S,4R)-1-((S)-2-(2-(3-(3-(2-(4-(dimethylamino)phenyl)quinolin-6-yloxy)propoxy) propoxy)acetamido)-3,3-dimethylbutanoyl)-4-hydroxy-N-(4-(4-methylthiazol-5-yl)benzyl)pyrrolidine-2-carboxamide (35); (2S,4R)-1-((S)-2-(2-(3-(3-(2-(4-(dimethylamino)phenyl)quinolin-6-yloxy)propoxy)propoxy)acetamido)-3,3-dimethylbutanoyl)-4-hydroxy-N—((S)-1-(4-(4-methylthiazol-5-yl)phenyl)ethyl)pyrrolidine-2-carboxamide (36); (2S,4R)-1-((S)-2-(2-(5-(2-(4-(dimethylamino)phenyl)quinolin-6-yloxy)pentyloxy)acetamido)-3,3-dimethylbutanoyl)-4-hydroxy-N-(4-(4-methylthiazol-5-yl)benzyl)pyrrolidine-2-carboxamide (37); (2S,4R)-1-((S)-2-(2-(5-(2-(4-(dimethylamino)phenyl)quinolin-6-yloxy)pentyloxy) acetamido)-3,3-dimethylbutanoyl)-4-hydroxy-N—((S)-1-(4-(4-methylthiazol-5-yl)phenyl)ethyl)pyrrolidine-2-carboxamide (38); (2S,4R)-1-((S)-2-tert-butyl-18-(2-(4-(dimethylamino)phenyl)quinolin-6-yloxy)-4-oxo-6,9,12,15-tetraoxa-3-azaoctadecane)-4-hydroxy-N—((S)-1-(4-(4-methylthiazol-5-yl)phenyl)ethyl)pyrrolidine-2-carboxamide (39); 4-(15-(2-(4-(dimethylamino)phenyl)quinolin-6-yloxy)-3,6,9,12-tetraoxapentadecylamino)-2-(2,6-dioxopiperidin-3-yl)isoindoline-1,3-dione (40); 4-((2-(2-(2-(2-(4-(benzo[4,5]imidazo[1,2-a]pyrimidin-2-yl)piperazin-1-yl)-2-oxoethoxy)ethoxy)ethoxy)ethyl)amino)-2-(2,6-dioxopiperidin-3-yl)isoindoline-1,3-dione (41); 4-((14-(4-(benzo[4,5]imidazo[1,2-a]pyrimidin-2-yl)piperazin-1-yl)-14-oxo-3,6,9,12-tetraoxatetradecyl)amino)-2-(2,6-dioxopiperidin-3-yl) isoindoline-1,3-dione (42); (2S,4R)-1-((2S)-2-tert-butyl-15-(2-(4-(dimethylamino)phenyl)quinolin-6-yloxy)-14-hydroxy-4-oxo-6,9,12-trioxa-3-azapentadecane)-4-hydroxy-N-(4-(4-methylthiazol-5-yl)benzyl)pyrrolidine-2-carboxamide (43); 4-(2-(2-(2-(3-(2-(4-(dimethylamino)phenyl)quinolin-6-yloxy)propoxy)ethoxy)ethoxy)ethylamino)-2-(2,6-dioxopiperidin-3-yl)isoindoline-1,3-dione (44); 4-(15-(2-(4-(dimethylamino)phenyl)quinolin-6-yloxy)-14-hydroxy-3,6,9,12-tetraoxapentadecylamino)-2-(2,6-dioxopiperidin-3-yl) isoindoline-1,3-dione (45); (2S,4R)-1-((2S)-2-tert-butyl-18-(2-(4-(dimethylamino)phenyl)quinolin-6-yloxy)-17-hydroxy-4-oxo-6,9,12,15-tetraoxa-3-azaoctadecane)-4-hydroxy-N-(4-(4-methylthiazol-5-yl)benzyl)pyrrolidine-2-carboxamide (46); 4-(2-(2-(2-(3-(2-(4-(dimethylamino) phenyl)quinolin-6-yloxy)-2-hydroxypropoxy)ethoxy) ethoxy)ethylamino)-2-(2,6-dioxopiperidin-3-yl)isodoline-1,3-dione (47); 2-(2,6-dioxopiperidin-3-yl)-4-(14-(5-(5-methyl-5H-pyrido[4,3-b]indol-7-yl)pyridin-2-yloxy)-3,6,9,12-tetraoxatetradecylamino)isoindoline-1,3-dione (48); 3-(4-(14-(5-(5H-pyrido[4,3-b]indol-7-yl)pyridin-2-yloxy)-3,6,9,12-tetraoxatetradecylamino)-1-oxoisoindolin-2-yl)piperidine-2,6-dione (49); 3-(4-(14-(5-(5H-pyrido[4,3-b]indol-7-yl)pyridin-2-yloxy)-3,6,9,12-tetraoxatetradecyloxy)-1-oxoisoindolin-2-yl)piperidine-2,6-dione (50); 5-((14-((5-(5H-Pyrido[4,3-b]indol-7-yl)pyridin-2-yl)oxy)-3,6,9,12-tetraoxatetradecyl)oxy)-2-(2,6-dioxopiperidin-3-yl) isoindoline-1,3-dione (51); 5-((5-(4-(2-(3-(5-(5H-pyrido[4,3-b]indol-7-yl)pyridin-2-yl)propoxy)ethyl)piperazin-1-yl) pentyl)oxy)-2-(2,6-dioxopiperidin-3-yl)isoindoline-1,3- dione (52); 5-(4-(3-((1s,3 s)-3-((5-(5H-pyrido[4,3-b]indol-7-yl)pyridin-2-yl)oxy)cyclobutoxy)propyl)piperazin-1-yl)-2-(2,6-dioxopiperidin-3-yl)isoindoline-1,3-dione (53); 5-((5-(4-(3-(5-(5H-pyrido[4,3-b]indol-7-yl)pyridin-2-yl)propyl)piperazin-1-yl)pentyl)oxy)-2-(2,6-dioxopiperidin-3-yl)isoindoline-1,3-dione (54); 5-(3-(6-(4-(3-(5-(5H-pyrido[4,3-b]indol-7-yl)pyridin-2-yl)propyl)piperazin-1-yl)pyridin-3-yl)propoxy)-2-(2,6-dioxopiperidin-3-yl)isoindoline-1,3-dione (55); 5-((5-(4-(2-((1s,3 s)-3-((5-(5H-pyrido[4,3-b]indol-7-yl)pyridin-2-yl)oxy)cyclobutoxy)ethyl)piperazin-1-yl)pentyl)oxy)-2-(2,6-dioxopiperidin-3-yl)isoindoline-1,3-dione (56); 5-((14-(4-(5H-pyrido[4,3-b]indol-7-yl)piperidin-1-yl)-3,6,9,12-tetraoxatetradecyl)oxy)-2-(2,6-dioxopiperidin-3-yl)isoindoline-1,3-dione (57); 5-((5-(2-(4-(3-(5-(5H-pyrido[4,3-b]indol-7-yl)pyridin-2-yl)propyl)piperazin-1-yl)ethoxy)pentyl)oxy)-2-(2,6-dioxopiperidin-3-yl)isoindoline-1,3-dione (58); 5-((5-(4-(2-((1r,3r)-3-((5-(5H-pyrido[4,3-b]indol-7-yl)pyridin-2-yl)oxy)cyclobutoxy)ethyl)piperazin-1-yl)pentyl)oxy)-2-(2,6-dioxopiperidin-3-yl)isoindoline-1,3-dione (59); 5-(4-(3-((1r,3r)-3-((5-(5H-pyrido[4,3-b]indol-7-yl)pyridin-2-yl)oxy)cyclobutoxy)propyl)piperazin-1-yl)-2-(2,6-dioxopiperidin-3-yl)isoindoline-1,3-dione (60); 2-(2,6-dioxopiperidin-3-yl)-5-((5-(4-(3-(5-(5-(2,2,2-trifluoroethyl)-5H-pyrido[4,3-b]indol-7-yl)pyridin-2-yl)propyl)piperazin-1-yl)pentyl)oxy)isoindoline-1,3-dione (61); 3-(5-((5-(4-(3-(5-(5-methyl-5H-pyrido[4,3-b]indol-7-yl)pyridin-2-yl)propyl)piperazin-1-yl)pentyl)oxy)-1-oxoisoindolin-2-yl)piperidine-2,6-dione (62); 2-(2,6-dioxopiperidin-3-yl)-5-((5-(4-(3-(5-(5-methyl-5H-pyrido[4,3-b]indol-7-yl)-3-(trifluoromethyl)pyridin-2-yl)propyl)piperazin-1-yl)pentyl)oxy)isoindoline-1,3-dione (63); 5-(4-(3-(5-((1r,3r)-3-((5-(5H-pyrido[4,3-b]indol-7-yl)pyridin-2-yl)oxy)cyclobutoxy)pyridin-2-yl)propyl)piperazin-1-yl)-2-(2,6-dioxopiperidin-3-yl)isoindoline-1,3-dione (64); 5-((5-(4-((1r,3r)-3-((5-(5H-pyrido[4,3-b]indol-7-yl)pyridin-2-yl)oxy)cyclobutoxy)piperidin-1-yl)pentyl)oxy)-2-(2,6-dioxopiperidin-3-yl)isoindoline-1,3-dione (65); 5-(4-(2-(4-((1r,3r)-3-((5-(5H-pyrido[4,3-b]indol-7-yl)pyridin-2-yl)oxy)cyclobutoxy)piperidin-1-yl)ethyl)piperazin-1-yl)-2-(2,6-dioxopiperidin-3-yl)isoindoline-1,3-dione (66); 2-(2,6-dioxopiperidin-3-yl)-5-((14-((5-(5-methyl-5H-pyrido[4,3-b]indol-7-yl)-3-(trifluoromethyl)pyridin-2-yl)oxy)-3,6,9,12-tetraoxatetradecyl)oxy)isoindoline-1,3-dione (67); 2-(2,6-dioxopiperidin-3-yl)-5-(4-(5-((1r,3r)-3-((5-(5-methyl-5H-pyrido[4,3-b]indol-7-yl)pyridin-2-yl)oxy)cyclobutoxy)pentyl)piperazin-1-yl)isoindoline-1,3-dione (68); 2-(2,6-dioxopiperidin-3-yl)-5-((14-((5-(5-methyl-5H-pyrido[4,3-b]indol-7-yl)-4-(trifluoromethyl)pyridin-2-yl)oxy)-3,6,9,12-tetraoxatetradecyl)oxy)isoindoline-1,3-dione (69); 2-(2,6-dioxopiperidin-3-yl)-5-(2-(2-(2-(2-((1r,3r)-3-((5-(5-methyl-5H-pyrido[4,3-b]indol-7-yl)pyridin-2-yl)oxy)cyclobutoxy)ethoxy)ethoxy)ethoxy)isoindoline-1,3-dione (70); 2-(2,6-dioxopiperidin-3-yl)-5-((15-(5-(5-methyl-5H-pyrido[4,3-b]indol-7-yl)pyridin-2-yl)-3,6,9,12-tetraoxapentadec-14-yn-1-yl)oxy)isoindoline-1,3-dione (71); 5-((14-((5-(5H-pyrido[4,3-b]indol-7-yl)pyridin-2-yl)oxy)-3,6,9,12-tetraoxatetradecyl)oxy)-2-(2,6-dioxopiperidin-3-yl)-4,6,7-trifluoroisoindoline-1,3-dione (72); [5-((3-(5-((1r,3r)-3-((5-(5H-pyrido[4,3-b]indol-7-yl)pyridin-2-yl)oxy)cyclobutoxy)pyridin-2-yl)prop-2-yn-1-yl)oxy)-2-(2,6-dioxopiperidin-3-yl)isoindoline-1,3-dione] (73); 2-(2,6-dioxopiperidin-3-yl)-5-((15-(5-(5-methyl-5H-pyrido[4,3-b]indol-7-yl)pyridin-2-yl)-3,6,9,12-tetraoxapentadecyl)oxy)isoindoline-1,3-dione (74); 2-(2,6-dioxopiperidin-3-yl)-5-(4-(5-((5-((5-(5-methyl-5H-pyrido[4,3-b]indol-7-yl)pyridin-2-yl)oxy)pentyl)oxy)pentyl)piperidin-1-yl)isoindoline-1,3-dione (75); 2-(2,6-dioxopiperidin-3-yl)-5-(3-(3-(4-(3-(5-(5-methyl-5H-pyrido[4,3-b]indol-7-yl)pyridin-2-yl)prop-2-yn-1-yl)piperazin-1-yl)propoxy)azetidin-1-yl)isoindoline-1,3-dione (76); 5-(3-(5-((1r,3r)-3-((5-(5H-pyrido[4,3-b]indol-7-yl)pyridin-2-yl)oxy)cyclobutoxy)pyridin-2-yl)propoxy)-2-(2,6-dioxopiperidin-3-yl)isoindoline-1,3-dione (77); 2-(2,6-dioxopiperidin-3-yl)-5-(4-(6-((1r,3r)-3-((5-(5-methyl-5H-pyrido[4,3-b]indol-7-yl)pyridin-2-yl)oxy)cyclobutoxy)hexyl)piperazin-1-yl)isoindoline-1,3-dione (78); 2-(2,6-dioxopiperidin-3-yl)-5-(3-((5-((5-((5-(5-methyl-5H-pyrido[4,3-b]indol-7-yl)pyridin-2-yl)oxy)pentyl)oxy)pentyl)oxy)azetidin-1-yl)isoindoline-1,3-dione (79); 2-(2,6-dioxopiperidin-3-yl)-5-((1-(5-((5-((5-(5-methyl-5H-pyrido[4,3-b]indol-7-yl)pyridin-2-yl)oxy)pentyl)oxy)pentyl)azetidin-3-yl)oxy)isoindoline-1,3-dione (80); 5-((14-((5-(5H-pyrido[4,3-b]indol-7-yl)pyridin-2-yl)oxy)-3,6,9,12-tetraoxatetradecyl)oxy)-2-(2,6-dioxopiperidin-3-yl)-6-fluoroisoindoline-1,3-dione (81); 2-(2,6-dioxopiperidin-3-yl)-5-((5-(4-((1r,3r)-3-((5-(5-methyl-5H-pyrido[4,3-b]indol-7-yl)pyridin-2-yl)oxy)cyclobutoxy)piperidin-1-yl)pentyl)oxy)isoindoline-1,3-dione (82); 5-((5-(5-((1r,3r)-3-((5-(5H-pyrido[4,3-b]indol-7-yl)pyridin-2-yl)oxy)cyclobutoxy)pyridin-2-yl)pentyl)oxy)-2-(2,6-dioxopiperidin-3-yl)isoindoline-1,3-dione (83); 2-(2,6-dioxopiperidin-3-yl)-5-((6-(3-((1r,3r)-3-((5-(5-methyl-5H-pyrido[4,3-b]indol-7-yl)pyridin-2-yl)oxy)cyclobutoxy)phenoxy)hexyl)oxy)isoindoline-1,3-dione (84); 2-(2,6-dioxopiperidin-3-yl)-5-((1r,3r)-3-((5-((5-(5-methyl-5H-pyrido[4,3-b]indol-7-yl)pyridin-2-yl)oxy)pentyl)oxy)pentyl)oxy)cyclobutoxy)isoindoline-1,3-dione (85); 4-((14-(4-(5H-pyrido[4,3-b]indol-7-yl)phenoxy)-3,6,9,12-tetraoxatetradecyl)amino)-2-(2,6-dioxopiperidin-3-yl)isoindoline-1,3-dione (86); 6-((14-((5-(5H-pyrido[4,3-b]indol-7-yl)pyridin-2-yl)oxy)-3,6,9,12-tetraoxatetradecyl)oxy)-2-(2,6-dioxopiperidin-3-yl)-1H-pyrrolo[3,4-c]pyridine-1,3(2H)-dione (87); 2-(2,6-dioxopiperidin-3-yl)-5-((14-((5-(5-(2,2,2-trifluoroethyl)-5H-pyrido[4,3-b]indol-7-yl)oxy)-3,6,9,12-tetraoxatetradecyl)oxy)isoindoline-1,3-dione (88); 2-(2,6-dioxopiperidin-3-yl)-5-(4-(3,3,3-trifluoro-2-(2-((5-((5-(5-methyl-5H-pyrido[4,3-b]indol-7-yl)pyridin-2-yl)oxy)pentyl)oxy)ethoxy)propyl)piperidin-1-yl)isoindoline-1,3-dione (89); 2-(2,6-dioxopiperidin-3-yl)-5-(4-(4-((4-((5-(5-methyl-5H-pyrido[4,3-b]indol-7-yl)pyridin-2-yl)oxy)but-2-yn-1-yl)oxy)butoxy)butoxy)isoindoline-1,3-dione (90); 2-(2,6-dioxopiperidin-3-yl)-5-(4-(8-((1r,3r)-3-((5-(5-methyl-5H-pyrido[4,3-b]indol-7-yl)pyridin-2-yl)oxy)cyclobutoxy)octyl)piperazin-1-yl)isoindoline-1,3-dione (91); 5-((14-((3-chloro-5-(5-methyl-5H-pyrido[4,3-b]indol-7-yl)pyridin-2-yl)oxy)-3,6,9,12-tetraoxatetradecyl)oxy)-2-(2,6-dioxopiperidin-3-yl)isoindoline-1,3-dione (92); 5-((6-((5-(2,2-difluoro-2-(5-(5-methyl-5H-pyrido[4,3-b]indol-7-yl)pyridin-2-yl)ethoxy)pentyl)oxy)hexyl)oxy)-2-(2,6-dioxopiperidin-3-yl)isoindoline-1,3-dione (93); 2-(2,6-dioxopiperidin-3-yl)-5-((5-(5-((1r,3r)-3-((5-(5-methyl-5H-pyrido[4,3-b]indol-7-yl)pyridin-2-yl)oxy)cyclobutoxy)pyridin-2-yl)pent-4-yn-1-yl)oxy)isoindoline-1,3-dione (94); 2-(2,6-dioxopiperidin-3-yl)-5-((5-(5-((1r,3r)-3-((5-(5-methyl-5H-pyrido[4,3-b]indol-7-yl)pyridin-2-yl)oxy)cyclobutoxy)pyridin-2-yl)pentyl)oxy)isoindoline-1,3-dione (95); 2-(2,6-dioxopiperidin-3-yl)-5-(4-(6-((1r,3r)-3-((5-(5-methyl-5H-pyrido[4,3-b]indol-7-yl)pyridin-2-yl)oxy)cyclobutoxy)hexyl)-3-(trifluoromethyl)piperazin-1-yl)isoindoline-1,3-dione (96); 2-(2,6-dioxopiperidin-3-yl)-5-((6-(5-((1r,3r)-3-((5-(5-methyl-5H-pyrido[4,3-b]indol-7-yl)pyridin-2-yl)oxy)cyclobutoxy)pyridin-2-yl)hex-5-yn-1-yl)oxy)isoindoline-1,3-dione (97); 2-(2,6-dioxopiperidin-3-yl)-5-((6-(5-((1r,3r)-3-((5-(5-methyl-5H-pyrido[4,3-b]indol-7-yl)pyridin-2-yl)oxy)cyclobutoxy)pyridin-2-yl)hexyl)oxy)

isoindoline-1,3-dione (98); 2-(2,6-dioxopiperidin-3-yl)-5-((1-(3-(3-(((1r,3r)-3-((5-(5-methyl-5H-pyrido[4,3-b]indol-7-yl)pyridin-2-yl)oxy)cyclobutoxy)propoxy)propyl)azetidin-3-yl)oxy)isoindoline-1,3-dione (99); 2-(2,6-dioxopiperidin-3-yl)-5-(6-(4-(4-((5-(5-methyl-5H-pyrido[4,3-b]indol-7-yl)pyridin-2-yl)oxy)butoxy)butoxy)-2-azaspiro[3.3]heptan-2-yl)isoindoline-1,3-dione (100); 5-((1-(3-(3-(((1r,3r)-3-((5-(5H-pyrido[4,3-b]indol-7-yl)-3-(trifluoromethyl)pyridin-2-yl)oxy)cyclobutoxy)propoxy)propyl)azetidin-3-yl)oxy)-2-(2,6-dioxopiperidin-3-yl)isoindoline-1,3-dione (101); 2-(2,6-dioxopiperidin-3-yl)-5-((6-(6-(((1r,3r)-3-((5-(5-methyl-5H-pyrido[4,3-b]indol-7-yl)pyridin-2-yl)oxy)cyclobutoxy)pyridin-3-yl)hex-5-yn-1-yl)oxy)isoindoline-1,3-dione (102); 5-((14-((5-(8,9-difluoro-5H-pyrido[4,3-b]indol-7-yl)pyridin-2-yl)oxy)-3,6,9,12-tetraoxatetradecyl)oxy)-2-(2,6-dioxopiperidin-3-yl)isoindoline-1,3-dione (103); 2-(2,6-dioxopiperidin-3-yl)-5-(3-(3-(3-(((1r,3r)-3-((5-(5-methyl-5H-pyrido[4,3-b]indol-7-yl)pyridin-2-yl)oxy)cyclobutoxy)propoxy)propoxy)azetidin-1-yl)isoindoline-1,3-dione (104); 2-(2,6-dioxopiperidin-3-yl)-5-((1-(3-(3-(((1r,3r)-3-((5-(5-methyl-5H-pyrido[4,3-b]indol-7-yl)-3-(trifluoromethyl)pyridin-2-yl)oxy)cyclobutoxy)propoxy)propyl)azetidin-3-yl)oxy)isoindoline-1,3-dione (105); 2-(2,6-dioxopiperidin-3-yl)-5-((5-((5-(3-((5-(5-methyl-5H-pyrido[4,3-b]indol-7-yl)pyridin-2-yl)oxy)azetidin-1-yl)pentyl)oxy)pentyl)oxy)isoindoline-1,3-dione (106); 2-(2,6-dioxopiperidin-3-yl)-5-(4-(4-(6-((5-(5-methyl-5H-pyrido[4,3-b]indol-7-yl)pyridin-2-yl)oxy)-2-azaspiro[3.3]heptan-2-yl)butoxy)butoxy)isoindoline-1,3-dione (107); 2-(2,6-dioxopiperidin-3-yl)-5-((6-((6-(((1r,3r)-3-((5-(5-methyl-5H-pyrido[4,3-b]indol-7-yl)pyridin-2-yl)oxy)cyclobutoxy)pyridin-2-yl)oxy)hexyl)oxy)isoindoline-1,3-dione (108); 2-(2,6-dioxopiperidin-3-yl)-5-((6-((4-(((1r,3r)-3-((5-(5-methyl-5H-pyrido[4,3-b]indol-7-yl)pyridin-2-yl)oxy)cyclobutoxy)pyridin-2-yl)oxy)hexyl)oxy)isoindoline-1,3-dione (109); 2-(2,6-dioxopiperidin-3-yl)-5-((6-(6-(((1r,3r)-3-((5-(5-methyl-5H-pyrido[4,3-b]indol-7-yl)pyridin-2-yl)oxy)cyclobutoxy)pyridin-3-yl)hexyl)oxy)isoindoline-1,3-dione (110); 2-(2,6-dioxopiperidin-3-yl)-5-(3-((3-(5-(((1r,3r)-3-((5-(5-methyl-5H-pyrido[4,3-b]indol-7-yl)pyridin-2-yl)oxy)cyclobutoxy)pyridin-2-yl)prop-2-yn-1-yl)oxy)azetidin-1-yl)isoindoline-1,3-dione (111); 5-((14-((5-(8,9-difluoro-5-methyl-5H-pyrido[4,3-b]indol-7-yl)pyridin-2-yl)oxy)-3,6,9,12-tetraoxatetradecyl)oxy)-2-(2,6-dioxopiperidin-3-yl)isoindoline-1,3-dione (112); 5-((14-((4-chloro-5-(5-methyl-5H-pyrido[4,3-b]indol-7-yl)pyridin-2-yl)oxy)-3,6,9,12-tetraoxatetradecyl)oxy)-2-(2,6-dioxopiperidin-3-yl)isoindoline-1,3-dione (113); 2-(2,6-dioxopiperidin-3-yl)-5-((5-(4-(((1r,3r)-3-((5-(5-methyl-5H-pyrido[4,3-b]indol-7-yl)pyridin-2-yl)oxy)cyclobutoxy)butoxy)pentyl)oxy)isoindoline-1,3-dione (114); 2-(2,6-dioxopiperidin-3-yl)-5-((5-((5-((1-(5-(5-methyl-5H-pyrido[4,3-b]indol-7-yl)pyridin-2-yl)azetidin-3-yl)oxy)pentyl)oxy)pentyl)oxy)isoindoline-1,3-dione (115); 2-(2,6-dioxopiperidin-3-yl)-5-((2-(4-(4-((5-(5-methyl-5H-pyrido[4,3-b]indol-7-yl)pyridin-2-yl)oxy)butoxy)butyl)-2-azaspiro[3.3]heptan-6-yl)oxy)isoindoline-1,3-dione (116); 2-(2,6-dioxopiperidin-3-yl)-5-((3-(5-(((1r,3r)-3-((5-(5-methyl-5H-pyrido[4,3-b]indol-7-yl)pyridin-2-yl)oxy)cyclobutoxy)pyridin-2-yl)prop-2-yn-1-yl)oxy)isoindoline-1,3-dione (117); 2-(2,6-dioxopiperidin-3-yl)-5-(3-((3-(5-(((1r,3r)-3-((5-(5-methyl-5H-pyrido[4,3-b]indol-7-yl)-3-(trifluoromethyl)pyridin-2-yl)oxy)cyclobutoxy)pyridin-2-yl)prop-2-yn-1-yl)oxy)azetidin-1-yl)isoindoline-1,3-dione (118); (2S,4R)-1-((S)-17-((5-(5H-pyrido[4,3-b]indol-7-yl)-3-(trifluoromethyl)pyridin-2-yl)oxy)-2-(tert-butyl)-4-oxo-6,9,12,15-tetraoxa-3-azaheptadecanoyl)-4-hydroxy-N—((S)-1-(4-(4-methylthiazol-5-yl)phenyl)ethyl)pyrrolidine-2-carboxamide (119); (2S,4R)-1-((S)-2-(2-(2-((5-(5H-pyrido[4,3-b]indol-7-yl)pyridin-2-yl)oxy)ethoxy)acetamido)-3,3-dimethylbutanoyl)-4-hydroxy-N—((S)-1-(4-(4-methylthiazol-5-yl)phenyl)ethyl)pyrrolidine-2-carboxamide (120); (2S,4R)-1-((S)-20-((5-(5H-pyrido[4,3-b]indol-7-yl)pyridin-2-yl)oxy)-2-(tert-butyl)-4-oxo-6,9,12,15,18-pentaoxa-3-azaicosanoyl)-4-hydroxy-N—((S)-1-(4-(4-methylthiazol-5-yl)phenyl)ethyl)pyrrolidine-2-carboxamide (121); (2S,4R)-1-((S)-23-((5-(5H-pyrido[4,3-b]indol-7-yl)pyridin-2-yl)oxy)-2-(tert-butyl)-4-oxo-6,9,12,15,18,21-hexaoxa-3-azatricosanoyl)-4-hydroxy-N—((S)-1-(4-(4-methylthiazol-5-yl)phenyl)ethyl)pyrrolidine-2-carboxamide (122); 2-(2,6-dioxopiperidin-3-yl)-5-((5-(4-(((1r,3r)-3-((5-(5-methyl-5H-pyrido[4,3-b]indol-7-yl)-3-(trifluoromethyl)pyridin-2-yl)oxy)cyclobutoxy)piperidin-1-yl)pentyl)oxy)isoindoline-1,3-dione (123); 2-(2,6-dioxopiperidin-3-yl)-5-((6-(4-(((1r,3r)-3-((5-(5-methyl-5H-pyrido[4,3-b]indol-7-yl)pyridin-2-yl)oxy)cyclobutoxy)phenyl)hex-5-yn-1-yl)oxy)isoindoline-1,3-dione (124); 2-(2,6-dioxopiperidin-3-yl)-5-(3-(3-(3-(((1r,3r)-3-((5-(5-methyl-5H-pyrido[4,3-b]indol-7-yl)-3-(trifluoromethyl)pyridin-2-yl)oxy)cyclobutoxy)propoxy)propoxy)azetidin-1-yl)isoindoline-1,3-dione (125); 2-(2,6-dioxopiperidin-3-yl)-5-((5-(6-(methyl((1r,3r)-3-((5-(5-methyl-5H-pyrido[4,3-b]indol-7-yl)pyridin-2-yl)oxy)cyclobutyl)amino)-2-azaspiro[3.3]heptan-2-yl)pentyl)oxy)isoindoline-1,3-dione (126); 3-(5-(4-((1-(5-(5-methyl-5H-pyrido[4,3-b]indol-7-yl)pyridin-2-yl)piperidin-4-yl)methyl)piperazin-1-yl)-1-oxoisoindolin-2-yl)piperidine-2,6-dione (127); 3-(5-(4-(2-(1-(5-(5-methyl-5H-pyrido[4,3-b]indol-7-yl)pyridin-2-yl)piperidin-4-yl)ethyl)piperazin-1-yl)-1-oxoisoindolin-2-yl)piperidine-2,6-dione (128); 2-(2,6-dioxopiperidin-3-yl)-5-((1,1,1-trifluoro-6-(2-(2-(2-((5-(5-methyl-5H-pyrido[4,3-b]indol-7-yl)pyridin-2-yl)oxy)ethoxy)ethoxy)ethoxy)hexan-2-yl)oxy)isoindoline-1,3-dione (129); 2-(2,6-dioxopiperidin-3-yl)-5-(3-(3-(3-(4-((5-(5-methyl-5H-pyrido[4,3-b]indol-7-yl)-3-(trifluoromethyl)pyridin-2-yl)oxy)piperidin-1-yl)propoxy)propoxy)azetidin-1-yl)isoindoline-1,3-dione (130); 2-(2,6-dioxopiperidin-3-yl)-5-((17-((5-(5-methyl-5H-pyrido[4,3-b]indol-7-yl)pyridin-2-yl)oxy)-3,6,9,12,15-pentaoxaheptadecyl)oxy)isoindoline-1,3-dione (131); 2-(2,6-dioxopiperidin-3-yl)-5-((20-((5-(5-methyl-5H-pyrido[4,3-b]indol-7-yl)pyridin-2-yl)oxy)-3,6,9,12,15,18-hexaoxaicosyl)oxy)isoindoline-1,3-dione (132); 2-(2,6-dioxopiperidin-3-yl)-5-(3-(6-((5-(5-methyl-5H-pyrido[4,3-b]indol-7-yl)pyridin-2-yl)oxy)pentyl)oxy)hexyl)azetidin-1-yl)isoindoline-1,3-dione (133); 2-(2,6-dioxopiperidin-3-yl)-5-((6-(6-(((1r,3r)-3-((5-(5-methyl-5H-pyrido[4,3-b]indol-7-yl)pyridin-2-yl)oxy)cyclobutoxy)pyridazin-3-yl)hex-5-yn-1-yl)oxy)isoindoline-1,3-dione (134); 2-(2,6-dioxopiperidin-3-yl)-5-(4-((2-(((1r,3r)-3-((5-(5-methyl-5H-pyrido[4,3-b]indol-7-yl)pyridin-2-yl)oxy)cyclobutyl)methyl)-2-azaspiro[3.3]heptan-6-yl)oxy)butoxy)isoindoline-1,3-dione (135); 2-(2,6-dioxopiperidin-3-yl)-5-(4-((2-((1s,3s)-3-((5-(5-methyl-5H-pyrido[4,3-b]indol-7-yl)pyridin-2-yl)oxy)cyclobutane-1-carbonyl)-2-azaspiro[3.3]heptan-6-yl)oxy)butoxy)isoindoline-1,3-dione (136); 2-(2,6-dioxopiperidin-3-yl)-5-((5-(6-(methyl((1r,3r)-3-((5-(5-methyl-5H-pyrido[4,3-b]indol-7-yl)pyridin-2-yl)oxy)cyclobutyl)amino)-2-azaspiro[3.3]heptan-2-yl)-5-oxopentyl)oxy)isoindoline-1,3-dione (137); 5-((14-((5-(5-(difluoromethyl)-5H-pyrido[4,3-b]indol-7-yl)pyridin-2-yl)oxy)-3,6,9,12-tetraoxatetradecyl)oxy)-2-(2,6-dioxopiperidin-3-yl)isoindoline-1,3-dione (138); 2-(2,6-dioxopiperidin-3-yl)-5-((14-((3-fluoro-5-(5-methyl-5H-pyrido[4,3-b]indol-7-yl)pyridin-2-yl)oxy)-3,6,9,12-tetraoxatetradecyl)oxy)isoindoline-1,3-dione (139); 2-(2,6- dioxopiperidin-3-yl)-5-((14-((3-methyl-5-(5-methyl-5H-pyrido[4,3-b]indol-7-yl)pyridin-2-yl)oxy)-3,6,9,12-tetraoxatetradecyl)oxy)isoindoline-1,3-dione (140); 2-(2,6-dioxopiperidin-3-yl)-5-((6-(5-((1r,3r)-3-((5-(5-methyl-5H-pyrido[4,3-b]indol-7-yl)pyridin-2-yl)oxy)cyclobutoxy)pyrimidin-2-yl)hex-5-yn-1-yl)oxy)isoindoline-1,3-dione (141); 2-(2,6-dioxopiperidin-3-yl)-5-((1-(3-(5-((1r,3r)-3-((5-(5-methyl-5H-pyrido[4,3-b]indol-7-yl)-3-(trifluoromethyl)pyridin-2-yl)oxy)cyclobutoxy)pyridin-2-yl)prop-2-yn-1-yl)azetidin-3-yl)oxy)isoindoline-1,3-dione (142); 2-(2,6-dioxopiperidin-3-yl)-5-((14-((5-(5-methyl-5H-pyrido[4,3-b]indol-7-yl)-6-(trifluoromethyl)pyridin-2-yl)oxy)-3,6,9,12-tetraoxatetradecyl)oxy)isoindoline-1,3-dione (143); 2-(2,6-dioxopiperidin-3-yl)-5-(6-(6-((1s,3s)-3-(5-(5-methyl-5H-pyrido[4,3-b]indol-7-yl)pyridin-2-yloxy)cyclobutoxy)pyridin-3-yl)hex-5-ynyloxy)isoindoline-1,3-dione (144); 2-(2,6-dioxopiperidin-3-yl)-5-(6-(6-((1s,3s)-3-(5-(5-methyl-5H-pyrido[4,3-b]indol-7-yl) pyridin-2-yloxy)cyclobutoxy) pyridin-3-yl)hexyloxy)isoindoline-1,3-dione (145); 2-(2,6-dioxopiperidin-3-yl)-5-((6-(6-(3-((5-(5-methyl-5H-pyrido[4,3-b]indol-7-yl)pyridin-2-yl)oxy)propoxy)pyridin-3-yl)hex-5-yn-1-yl)oxy)isoindoline-1,3-dione (146); 2-(2,6-dioxopiperidin-3-yl)-5-((6-(4-((1r,3r)-3-((5-(5-methyl-5H-pyrido[4,3-b]indol-7-yl)pyridin-2-yl)oxy)cyclobutoxy)phenyl)hexyl)oxy)isoindoline-1,3-dione (147); 5-(3-(3-(3-((1r,3r)-3-((5-(5H-pyrido[4,3-b]indol-7-yl)-3-(trifluoromethyl)pyridin-2-yl)oxy)cyclobutoxy)propoxy)propoxy)azetidin-1-yl)-2-(2,6-dioxopiperidin-3-yl)isoindoline-1,3-dione (148); 2-(2,6-dioxopiperidin-3-yl)-5-((6-(6-((1r,3r)-3-((5-(5-methyl-5H-pyrido[4,3-b]indol-7-yl)pyridin-2-yl)oxy)cyclobutoxy)pyridazin-3-yl)hexyl)oxy)isoindoline-1,3-dione] (149); 5-(6-(2,2-difluoro-5-((1r,3r)-3-((5-(5-methyl-5H-pyrido[4,3-b]indol-7-yl)pyridin-2-yl)oxy)cyclobutoxy)pentyl)-2,6-diazaspiro[3.3]heptan-2-yl)-2-(2,6-dioxopiperidin-3-yl)isoindoline-1,3-dione (150); 2-(2,6-dioxopiperidin-3-yl)-5-((6-(5-((1r,3r)-3-((5-(5-methyl-5H-pyrido[4,3-b]indol-7-yl)pyridin-2-yl)oxy)cyclobutoxy)pyrimidin-2-yl)hexyl)oxy)isoindoline-1,3-dione (151); 2-(2,6-dioxopiperidin-3-yl)-5-((1-(3-(5-((1r,3r)-3-((5-(5-methyl-5H-pyrido[4,3-b]indol-7-yl)pyridin-2-yl)oxy)cyclobutoxy)pyridin-2-yl)prop-2-yn-1-yl)azetidin-3-yl)oxy)isoindoline-1,3-dione (152); 2-(2,6-dioxopiperidin-3-yl)-5-(3-(3,3,3-trifluoro-2-((5-((1r,3r)-3-((5-(5-methyl-5H-pyrido[4,3-b]indol-7-yl)pyridin-2-yl)oxy)cyclobutoxy)pentyl)oxy)propyl)azetidin-1-yl)isoindoline-1,3-dione (153); 2-(2,6-dioxopiperidin-3-yl)-5-(3-(2,2,2-trifluoro-1-((6-((1r,3r)-3-((5-(5-methyl-5H-pyrido[4,3-b]indol-7-yl)pyridin-2-yl)oxy)cyclobutoxy)hexyl)oxy)ethyl)azetidin-1-yl)isoindoline-1,3-dione (154); 2-(2,6-dioxopiperidin-3-yl)-5-(3-((5-(2-((1r,3r)-3-((5-(5-methyl-5H-pyrido[4,3-b]indol-7-yl)pyridin-2-yl)oxy)cyclobutoxy)ethoxy)pyridin-2-yl)oxy)azetidin-1-yl)isoindoline-1,3-dione (155); 2-(2,6-dioxopiperidin-3-yl)-5-(3-(3-(5-((1r,3r)-3-((5-(5-methyl-5H-pyrido[4,3-b]indol-7-yl)pyridin-2-yl)oxy)cyclobutoxy)pyridin-2-yl)propoxy)azetidin-1-yl)isoindoline-1,3-dione (156); 2-(2,6-dioxopiperidin-3-yl)-S-(4-((2-((1r,3r)-3-((5-(5-methyl-5H-pyrido[4,3-b]indol-7-yl)pyridin-2-yl)oxy)cyclobutane-1-carbonyl)-2-azaspiro[3.3]heptan-6-yl)oxy)butoxy)isoindoline-1,3-dione (157); 2-(2,6-dioxopiperidin-3-yl)-5-(2-((6-(4-((1r,3r)-3-((5-(5-methyl-5H-pyrido[4,3-b]indol-7-yl)pyridin-2-yl)oxy)cyclobutoxy)piperidin-1-yl)pyridazin-4-yl)oxy)ethoxy)isoindoline-1,3-dione (158); 2-(2,6-dioxopiperidin-3-yl)-5-(3-((3-(5-((1s,3 s)-3-((5-(5-methyl-5H-pyrido[4,3-b]indol-7-yl)pyridin-2-yl)oxy)cyclobutoxy)pyridin-2-yl)prop-2-yn-1-yl)oxy)azetidin-1-yl)isoindoline-1,3-dione (159); 2-(2,6-dioxopiperidin-3-yl)-5-(3-(3-(5-((1s,3 s)-3-((5-(5-methyl-5H-pyrido[4,3-b]indol-7-yl)pyridin-2-yl)oxy)cyclobutoxy)pyridin-2-yl)propoxy)azetidin-1-yl)isoindoline-1,3-dione (160); 2-(2,6-dioxopiperidin-3-yl)-5-(3-(2-(2-(2-((1r,3r)-3-((5-(5-methyl-5H-pyrido[4,3-b]indol-7-yl)pyridin-2-yl)oxy)cyclobutoxy)ethoxy)ethoxy)ethoxy)azetidin-1-yl)isoindoline-1,3-dione (161); 2-(2,6-dioxopiperidin-3-yl)-5-(3-(4-(4-((1r,3r)-3-((5-(5-methyl-5H-pyrido[4,3-b]indol-7-yl)pyridin-2-yl)oxy)cyclobutoxy)butoxy)butoxy)azetidin-1-yl)isoindoline-1,3-dione (162); 2-(2,6-dioxopiperidin-3-yl)-5-(3-(2-(2-((1r,3r)-3-((5-(5-methyl-5H-pyrido[4,3-b]indol-7-yl)pyridin-2-yl)oxy)cyclobutoxy)ethoxy)ethoxy)azetidin-1-yl)isoindoline-1,3-dione (163); 5-(6-(4-((1r,3r)-3-(5-(5H-pyrido[4,3-b]indol-7-yl)pyridin-2-yloxy)cyclobutoxy)piperidin-1-yl)-6-oxohexyloxy)-2-(2,6-dioxopiperidin-3-yl)isoindoline-1,3-dione (164); 5-((5-((1-((1r,3r)-3-((5-(5H-pyrido[4,3-b]indol-7-yl)pyridin-2-yl)oxy)cyclobutane-1-carbonyl)piperidin-4-yl)oxy)pentyl)oxy)-2-(2,6-dioxopiperidin-3-yl)isoindoline-1,3-dione (165); 5-((5-((1-((1 s,3 s)-3-((5-(5H-pyrido[4,3-b]indol-7-yl)pyridin-2-yl)oxy)cyclobutane-1-carbonyl)piperidin-4-yl)oxy)pentyl)oxy)-2-(2,6-dioxopiperidin-3-yl)isoindoline-1,3-dione (166); 2-(2,6-dioxopiperidin-3-yl)-5-(3-((3-(5-(3-((5-(5-methyl-5H-pyrido[4,3-b]indol-7-yl)pyridin-2-yl)oxy)propoxy)pyridin-2-yl)prop-2-yn-1-yl)oxy)azetidin-1-yl)isoindoline-1,3-dione (167); 2-(2,6-dioxopiperidin-3-yl)-5-(3-(3-(5-((5-(5-methyl-5H-pyrido[4,3-b]indol-7-yl)pyridin-2-yl)oxy)propoxy)pyridin-2-yl)propoxy)azetidin-1-yl)isoindoline-1,3-dione (168); 2-(2,6-dioxopiperidin-3-yl)-5-(3-(3-(((1r,3r)-3-((5-(5-methyl-5H-pyrido[4,3-b]indol-7-yl)pyridin-2-yl)oxy)cyclobutoxy)methyl)oxetan-3-yl)methoxy)propoxy)azetidin-1-yl)isoindoline-1,3-dione (169); 2-(2,6-dioxopiperidin-3-yl)-5-(3-(3-((1 s,3 s)-3-((5-(5-methyl-5H-pyrido[4,3-b]indol-7-yl)pyridin-2-yl)oxy)cyclobutoxy)propoxy)propoxy)azetidin-1-yl)isoindoline-1,3-dione (170); 5-((4,4-difluoro-5-(4-((1r,3r)-3-((5-(5-methyl-5H-pyrido[4,3-b]indol-7-yl)pyridin-2-yl)oxy)cyclobutoxy)piperidin-1-yl)pentyl)oxy)-2-(2,6-dioxopiperidin-3-yl)isoindoline-1,3-dione (171); 5-((6-(5-((1r,3r)-3-((5-(5H-pyrido[4,3-b]indol-7-yl)pyridin-2-yl)oxy)cyclobutoxy)pyridin-2-yl)hex-5-yn-1-yl)oxy)-2-(2,6-dioxopiperidin-3-yl)isoindoline-1,3-dione (172); 5-(2-((3-(5-((1r,3r)-3-((5-(5H-pyrido[4,3-b]indol-7-yl)pyridin-2-yl)oxy)cyclobutoxy)pyridin-2-yl)prop-2-yn-1-yl)oxy)ethoxy)-2-(2,6-dioxopiperidin-3-yl)isoindoline-1,3-dione (173); 2-(2,6-dioxopiperidin-3-yl)-5-(4-((3-(((1r,3r)-3-((5-(5-methyl-5H-pyrido[4,3-b]indol-7-yl)pyridin-2-yl)oxy)cyclobutoxy)methyl)bicyclo[1.1.1]pentan-1-yl)methoxy)butoxy)isoindoline-1,3-dione (174); 2-(2,6-dioxopiperidin-3-yl)-5-((5-((3-(3-((5-(5-methyl-5H-pyrido[4,3-b]indol-7-yl)pyridin-2-yl)oxy)azetidine-1-carbonyl)bicyclo[1.1.1]pentan-1-yl)methoxy)pentyl)oxy)isoindoline-1,3-dione (175); 5-(3-(3-(3-((1r,3r)-3-((5-(8,9-difluoro-5-methyl-5H-pyrido[4,3-b]indol-7-yl)pyridin-2-yl)oxy)cyclobutoxy)propoxy)propoxy)azetidin-1-yl)-2-(2,6-dioxopiperidin-3-yl)isoindoline-1,3-dione (176); 3-(5-(3-(3-(3-((1r,3r)-3-((5-(5-methyl-5H-pyrido[4,3-b]indol-7-yl)pyridin-2-yl)oxy)cyclobutoxy)propoxy)propoxy)azetidin-1-yl)-1-oxoisoindolin-2-yl)piperidine-2,6-dione (177); 2-(2,6-dioxopiperidin-3-yl)-5-(3-(((6-((1r,3r)-3-((5-(5-methyl-5H-pyrido[4,3-b]indol-7-yl)pyridin-2-yl)oxy)cyclobutoxy)hexyl)oxy)methyl)azetidin-1-yl)isoindoline-1,3-dione (178); 2-(2,6-dioxopiperidin-3-yl)-5-(2-((3-(5-((1r,3r)-3-((5-(5-methyl-5H-pyrido[4,3-b]indol-7-yl)pyridin-2-yl)oxy)cyclobutoxy)pyridin-2-yl)prop-2-yn-1-yl)oxy)ethoxy)isoindoline-1,3-dione (179); 3-(5-((3-(5-((1r,3r)-3-((5-(5H-pyrido[4,3-b]indol-7-yl)pyridin-2-yl)oxy)cyclobutoxy)pyridin-2-yl)prop-2-yn-1-yl)oxy)-1-oxoisoindolin-2-yl)piperidine-2,6-dione (180); 2-(2,6-dioxopiperidin-3-yl)-5-

(3-(2-((5-((1r,3r)-3-((5-(5-methyl-5H-pyrido[4,3-b]indol-7-yl)pyridin-2-yl)oxy)cyclobutoxy)pentyl)oxy)ethyl)azetidin-1-yl)isoindoline-1,3-dione (181); 5-(3-(3-(3-((1r,3r)-3-((5-(5H-pyrido[4,3-b]indol-7-yl)pyridin-2-yl)oxy)cyclobutoxy)propoxy)propoxy)azetidin-1-yl)-2-(2,6-dioxopiperidin-3-yl)isoindoline-1,3-dione (182); 5-((3-(5-((1s,3 s)-3-((5-(5H-pyrido[4,3-b]indol-7-yl)pyridin-2-yl)oxy)cyclobutoxy)pyridin-2-yl)prop-2-yn-1-yl)oxy)-2-(2,6-dioxopiperidin-3-yl)isoindoline-1,3-dione (183); 2-(2,6-dioxopiperidin-3-yl)-5-((7-(3-(3-((5-(5-methyl-5H-pyrido[4,3-b]indol-7-yl)pyridin-2-yl)oxy)azetidine-1-carbonyl)bicyclo[1.1.1]pentan-1-yl)heptyl)oxy)isoindoline-1,3-dione (184); (2S,4R)—N-(2-(2-((5-(5H-pyrido[4,3-b]indol-7-yl)pyridin-2-yl)oxy)ethoxy)-4-(4-methylthiazol-5-yl)benzyl)-4-hydroxy-1-((S)-3-methyl-2-(1-oxoisoindolin-2-yl)butanoyl)pyrrolidine-2-carboxamide (185); (2S,4R)—N-(2-(2-(2-((5-(5H-pyrido[4,3-b]indol-7-yl)pyridin-2-yl)oxy)ethoxy)ethoxy)-4-(4-methylthiazol-5-yl)benzyl)-4-hydroxy-1-((S)-3-methyl-2-(1-oxoisoindolin-2-yl)butanoyl)pyrrolidine-2-carboxamide (186); (2S,4R)—N-(2-(2-(2-(2-((5-(5H-pyrido[4,3-b]indol-7-yl)pyridin-2-yl)oxy)ethoxy)ethoxy)ethoxy)-4-(4-methylthiazol-5-yl)benzyl)-4-hydroxy-1-((S)-3-methyl-2-(1-oxoisoindolin-2-yl)butanoyl)pyrrolidine-2-carboxamide (187); 5-(2-((3-(4-((1r,3r)-3-((5-(5H-pyrido[4,3-b]indol-7-yl)pyridin-2-yl)oxy)cyclobutoxy)phenyl)prop-2-yn-1-yl)oxy)ethoxy)-2-(2,6-dioxopiperidin-3-yl)isoindoline-1,3-dione (188); 5-((3-(4-((1r,3r)-3-((5-(5H-pyrido[4,3-b]indol-7-yl)pyridin-2-yl)oxy)cyclobutoxy)phenyl)prop-2-yn-1-yl)oxy)-2-(2,6-dioxopiperidin-3-yl)isoindoline-1,3-dione (189); 2-(2,6-dioxopiperidin-3-yl)-5-(3-(2-(2-(2-((1r,3r)-3-((5-(5-methyl-5H-pyrido[4,3-b]indol-7-yl)pyridin-2-yl)oxy)cyclobutoxy)ethoxy)ethoxy)ethyl)azetidin-1-yl)isoindoline-1,3-dione (190); 2-(2,6-dioxopiperidin-3-yl)-5-(3-((3-(2-((1r,3r)-3-((5-(5-methyl-5H-pyrido[4,3-b]indol-7-yl)pyridin-2-yl)oxy)cyclobutoxy)ethoxy)propoxy)methyl)azetidin-1-yl)isoindoline-1,3-dione (191); 2-(2,6-dioxopiperidin-3-yl)-5-(3-((2-(2-((1r,3r)-3-((5-(5-methyl-5H-pyrido[4,3-b]indol-7-yl)pyridin-2-yl)oxy)cyclobutoxy)ethoxy)ethoxy)methyl)azetidin-1-yl)isoindoline-1,3-dione (192); 2-(2,6-dioxopiperidin-3-yl)-5-(3-(3-(2-(6-((5-(5-methyl-5H-pyrido[4,3-b]indol-7-yl)pyridin-2-yl)oxy)-2-azaspiro[3.3]heptan-2-yl)-2-oxoethoxy)propoxy)azetidin-1-yl)isoindoline-1,3-dione (193); 5-(3-((3-(5-((1r,3r)-3-((5-(5H-pyrido[4,3-b]indol-7-yl)pyridin-2-yl)oxy)cyclobutoxy)pyridin-2-yl)prop-2-yn-1-yl)oxy)azetidin-1-yl)-2-(2,6-dioxopiperidin-3-yl)isoindoline-1,3-dione (194); 5-((14-((5-(4-chloro-5-methyl-5H-pyrido[4,3-b]indol-7-yl)pyridin-2-yl)oxy)-3,6,9,12-tetraoxatetradecyl)oxy)-2-(2,6-dioxopiperidin-3-yl)isoindoline-1,3-dione (195); (2S,4R)—N-(2-(2-(2-(2-(2-((5-(5H-pyrido[4,3-b]indol-7-yl)pyridin-2-yl)oxy)ethoxy)ethoxy)ethoxy)ethoxy)-4-(4-methylthiazol-5-yl)benzyl)-4-hydroxy-1-((S)-3-methyl-2-(1-oxoisoindolin-2-yl)butanoyl)pyrrolidine-2-carboxamide (196); 5-(6-((2-(2,2-difluoro-5-((1r,3r)-3-((5-(5-methyl-5H-pyrido[4,3-b]indol-7-yl)pyridin-2-yl)oxy)cyclobutoxy)pentyl)oxy)-2-azaspiro[3.3]heptan-2-yl)-2-(2,6-dioxopiperidin-3-yl)isoindoline-1,3-dione (197); 2-(2,6-dioxopiperidin-3-yl)-5-((3-(3-(4-((1r,3r)-3-((5-(5-methyl-5H-pyrido[4,3-b]indol-7-yl)pyridin-2-yl)oxy)cyclobutoxy)piperidin-1-yl)phenyl)prop-2-yn-1-yl)oxy)isoindoline-1,3-dione (198); 3-((4-((2-(2,6-dioxopiperidin-3-yl)-1,3-dioxoisoindolin-5-yl)oxy)butoxy)methyl)-N-methyl-N-((1 r,3r)-3-((5-(5-methyl-5H-pyrido[4,3-b]indol-7-yl)pyridin-2-yl)oxy)cyclobutyl)bicyclo[1.1.1]pentane-1-carboxamide (199); 2-(2,6-dioxopiperidin-3-yl)-5-(3-((7-((1r,3r)-3-((5-(5-methyl-5H-pyrido[4,3-b]indol-7-yl)pyridin-2-yl)oxy)cyclobutoxy)heptyl)oxy)azetidin-1-yl)isoindoline-1,3-dione (200); (2S,4R)—N-(2-((14-((5-(5H-pyrido[4,3-b]indol-7-yl)pyridin-2-yl)oxy)-3,6,9,12-tetraoxatetradecyl)oxy)-4-(4-methylthiazol-5-yl)benzyl)-4-hydroxy-1-((S)-3-methyl-2-(1-oxoisoindolin-2-yl)butanoyl)pyrrolidine-2-carboxamide (201); 2-((1-(2-(2,6-dioxopiperidin-3-yl)-1,3-dioxoisoindolin-5-yl)azetidin-3-yl)methoxy)-N-methyl-N-(3-((1r,3r)-3-((5-(5-methyl-5H-pyrido[4,3-b]indol-7-yl)pyridin-2-yl)oxy)cyclobutoxy)propyl)acetamide (202); 2-((14-((2-(2,6-dioxopiperidin-3-yl)-1,3-dioxoisoindolin-5-yl)oxy)-3,6,9,12-tetraoxatetradecyl)oxy)-5-(5-methyl-5H-pyrido[4,3-b]indol-7-yl)nicotinonitrile (203); 5-((3-(5-((1r,3r)-3-((5-(8,9-difluoro-5H-pyrido[4,3-b]indol-7-yl)pyridin-2-yl)oxy)cyclobutoxy)pyridin-2-yl)prop-2-yn-1-yl)oxy)-2-(2,6-dioxopiperidin-3-yl)isoindoline-1,3-dione (204); 2-(2,6-dioxopiperidin-3-yl)-5-(3-(3-(4-((1r,3r)-3-((5-(5-methyl-5H-pyrido[4,3-b]indol-7-yl)pyridin-2-yl)oxy)cyclobutoxy)piperidin-1-yl)phenyl)propoxy)isoindoline-1,3-dione (205); 2-(2,6-dioxopiperidin-3-yl)-5-(3-((2-(2-(2-((1r,3r)-3-((5-(5-methyl-5H-pyrido[4,3-b]indol-7-yl)pyridin-2-yl)oxy)cyclobutoxy)ethoxy)ethoxy)ethoxy)methyl)azetidin-1-yl)isoindoline-1,3-dione (206); 5-((14-((5-(benzo[4,5]imidazo[1,2-a]pyrimidin-2-yl)pyridin-2-yl)oxy)-3,6,9,12-tetraoxatetradecyl)oxy)-2-(2,6-dioxopiperidin-3-yl)isoindoline-1,3-dione (207); 2-(2,6-dioxopiperidin-3-yl)-5-(2-(2-(2-(2-((1-(5-(5-methyl-5H-pyrido[4,3-b]indol-7-yl)pyridin-2-yl)azetidin-3-yl)oxy)ethoxy)ethoxy)ethoxy)ethoxy)isoindoline-1,3-dione (208); 2-(2,6-dioxopiperidin-3-yl)-5-(2-(2-((3-(((1r,3r)-3-((5-(5-methyl-5H-pyrido[4,3-b]indol-7-yl)pyridin-2-yl)oxy)cyclobutoxy)methyl)bicyclo[1.1.1]pentan-1-yl)methoxy)ethoxy)ethoxy)isoindoline-1,3-dione (209); 2-(2,6-dioxopiperidin-3-yl)-5-((15-(4-(5-methyl-5H-pyrido[4,3-b]indol-7-yl)piperazin-1-yl)-3,6,9,12-tetraoxapentadecyl)oxy)isoindoline-1,3-dione (210); 2-(2,6-dioxopiperidin-3-yl)-5-(3-(3-(2-(6-((5-(5-methyl-5H-pyrido[4,3-b]indol-7-yl)pyridin-2-yl)oxy)-2-azaspiro[3.3]heptan-2-yl)ethoxy)propoxy)azetidin-1-yl)isoindoline-1,3-dione (211); 2-(2,6-dioxopiperidin-3-yl)-5-(3-(2-((4-((1r,3r)-3-((5-(5-methyl-5H-pyrido[4,3-b]indol-7-yl)pyridin-2-yl)oxy)cyclobutoxy)but-2-yn-1-yl)oxy)ethoxy)azetidin-1-yl)isoindoline-1,3-dione (212); 2-(2,6-dioxopiperidin-3-yl)-5-(6-(2-(2-((1r,3r)-3-((5-(5-methyl-5H-pyrido[4,3-b]indol-7-yl)pyridin-2-yl)oxy)cyclobutoxy)ethoxy)ethoxy)-2-azaspiro[3.3]heptan-2-yl)isoindoline-1,3-dione (213); 2-(2,6-dioxopiperidin-3-yl)-5-(4-(3-(3-((1r,3r)-3-((5-(5-methyl-5H-pyrido[4,3-b]indol-7-yl)pyridin-2-yl)oxy)cyclobutoxy)propoxy)propyl)piperazin-1-yl)isoindoline-1,3-dione (214); 2-(2,6-dioxopiperidin-3-yl)-5-((1R,3r)-3-(isopropyl(2-(3-((1r,3R)-3-((5-(5-methyl-5H-pyrido[4,3-b]indol-7-yl)pyridin-2-yl)oxy)cyclobutoxy)propoxy)ethyl)amino)cyclobutoxy)isoindoline-1,3-dione (215); 2-(2,6-dioxopiperidin-3-yl)-5-(4-(2-(3-((1r,3r)-3-((5-(5-methyl-5H-pyrido[4,3-b]indol-7-yl)pyridin-2-yl)oxy)cyclobutoxy)propoxy)ethoxy)piperidin-1-yl)isoindoline-1,3-dione (216); 2-(2,6-dioxopiperidin-3-yl)-5-((1R,3r)-3-((2-(3-((1r,3R)-3-((5-(5-methyl-5H-pyrido[4,3-b]indol-7-yl)pyridin-2-yl)oxy)cyclobutoxy)propoxy)ethyl)amino)cyclobutoxy)isoindoline-1,3-dione (217); 2-(2,6-dioxopiperidin-3-yl)-5-((14-((5-(4-fluoro-5-methyl-5H-pyrido[4,3-b]indol-7-yl)pyridin-2-yl)oxy)-3,6,9,12-tetraoxatetradecyl)oxy)isoindoline-1,3-dione (218); 3-(5-((3-(5-((1r,3r)-3-((5-(8,9-difluoro-5H-pyrido[4,3-b]indol-7-yl)pyridin-2-yl)oxy)cyclobutoxy)pyridin-2-yl)prop-2-yn-1-yl)oxy)-1-oxoisoindolin-2-yl)piperidine-2,6-dione (219); 3-(5-(2-((3-(5-((1r,3r)-3-((5-(5H-pyrido[4,3-b]indol-7-yl)pyridin-2-yl)oxy)cyclobutoxy)pyridin-2-yl)prop-2-yn-1-yl)oxy)ethoxy)-1-oxoisoindolin-2-yl)piperidine-2,6-dione (220); 3-(5-(3-((3-(5-((1r,3r)-3-((5-(5H-pyrido[4,3-b]indol-7-yl)pyridin-2-yl)oxy)cyclobutoxy)pyridin-2-yl)prop-2-yn-1-yl)oxy)azetidin-1-yl)-1-oxoisoindolin-2-yl)piperidine-2,6-dione (221); 3-(5-((3-(5-((1r,3r)-3-((5-(5H-pyrido[4,3-b]indol-7-yl)pyridin-2-yl)oxy)cyclobutoxy)pyrimidin-2-yl)prop-2-yn-1-yl)oxy)-1-oxoisoindolin-2-yl)piperidine-2,6-dione (222); 3-(5-((3-(6-((1r,3r)-3-((5-(5H-pyrido[4,3-b]indol-7-yl)pyridin-2-yl)oxy)cyclobutoxy)pyridin-3-yl)prop-2-yn-1-yl)oxy)-1-oxoisoindolin-2-yl)piperidine-2,6-dione (223); 3-(5-(3-(3-(5-((1r,3r)-3-((5-(5H-pyrido[4,3-b]indol-7-yl)pyridin-2-yl)oxy)cyclobutoxy)pyridin-2-yl)propoxy)prop-1-yn-1-yl)-1-oxoisoindolin-2-yl)piperidine-2,6-dione (224); 3-(5-(3-((3-(5-((1r,3r)-3-((5-(5H-pyrido[4,3-b]indol-7-yl)pyridin-2-yl)oxy)cyclobutoxy)pyridin-2-yl)prop-2-yn-1-yl)oxy)propyl)-1-oxoisoindolin-2-yl)piperidine-2,6-dione (225); 3-(5-((3-(5-((1r,3r)-3-((5-(5H-pyrido[4,3-b]indol-7-yl)pyridin-2-yl)oxy)cyclobutoxy)pyridin-2-yl)prop-2-yn-1-yl)oxy)-4,6-difluoro-1-oxoisoindolin-2-yl)piperidine-2,6-dione (226); 3-(5-((1R,3r)-3-((3-(5-((1r,3R)-3-((5-(5H-pyrido[4,3-b]indol-7-yl)pyridin-2-yl)oxy)cyclobutoxy)pyridin-2-yl)prop-2-yn-1-yl)oxy)cyclobutoxy)-1-oxoisoindolin-2-yl)piperidine-2,6-dione (227); 3-(5-(4-(3-(5-((1r,3r)-3-((5-(5H-pyrido[4,3-b]indol-7-yl)pyridin-2-yl)oxy)cyclobutoxy)pyridin-2-yl)prop-2-yn-1-yl)piperazin-1-yl)-1-oxoisoindolin-2-yl)piperidine-2,6-dione (228); 2-((3-(5-((1r,3r)-3-((5-(5H-pyrido[4,3-b]indol-7-yl)pyridin-2-yl)oxy)cyclobutoxy)pyridin-2-yl)prop-2-yn-1-yl)oxy)-N-(2-(2,6-dioxopiperidin-3-yl)-1-oxoisoindolin-5-yl)-N-methylacetamide (229); 3-(5-((1R,3r)-3-((3-(5-((1r,3R)-3-((5-(5H-pyrido[4,3-b]indol-7-yl)pyridin-2-yl)oxy)cyclobutoxy)pyridin-2-yl)prop-2-yn-1-yl)oxy)cyclobutyl)-1-oxoisoindolin-2-yl)piperidine-2,6-dione (230); 3-(5-((3-(6-((1r,3r)-3-((5-(5H-pyrido[4,3-b]indol-7-yl)pyridin-2-yl)oxy)cyclobutoxy)pyridazin-3-yl)prop-2-yn-1-yl)oxy)-1-oxoisoindolin-2-yl)piperidine-2,6-dione (231); 3-(5-((3-(5-((1r,3r)-3-((5-(5H-pyrido[4,3-b]indol-7-yl)pyridin-2-yl)oxy)cyclobutoxy)pyrazin-2-yl)prop-2-yn-1-yl)oxy)-1-oxoisoindolin-2-yl)piperidine-2,6-dione (232); 3-(5-(2-((3-(5-((1r,3r)-3-((5-(5-methyl-5H-pyrido[4,3-b]indol-7-yl)pyridin-2-yl)oxy)cyclobutoxy)pyridin-2-yl)prop-2-yn-1-yl)oxy)ethoxy)-1-oxoisoindolin-2-yl)piperidine-2,6-dione (233); 3-(5-((3-(5-((1r,3r)-3-((5-(5-methyl-5H-pyrido[4,3-b]indol-7-yl)pyridin-2-yl)oxy)cyclobutoxy)pyridin-2-yl)prop-2-yn-1-yl)oxy)-1-oxoisoindolin-2-yl)piperidine-2,6-dione (234); 2-((1r,3r)-3-((6-(3-(2-((2-(2,6-dioxopiperidin-3-yl)-1,3-dioxoisoindolin-5-yl)oxy)ethoxy)prop-1-yn-1-yl)pyridin-3-yl)oxy)cyclobutoxy)-5-(5-methyl-5H-pyrido[4,3-b]indol-7-yl)nicotinonitrile (235); 5-(2-((3-(5-((1r,3r)-3-((5-(5-(difluoromethyl)-5H-pyrido[4,3-b]indol-7-yl)pyridin-2-yl)oxy)cyclobutoxy)pyridin-2-yl)prop-2-yn-1-yl)oxy)ethoxy)-2-(2,6-dioxopiperidin-3-yl)isoindoline-1,3-dione (236); 2-(2,6-dioxopiperidin-3-yl)-5-(2-((3-(5-((1r,3r)-3-((3-methyl-5-(5-methyl-5H-pyrido[4,3-b]indol-7-yl)pyridin-2-yl)oxy)cyclobutoxy)pyridin-2-yl)prop-2-yn-1-yl)oxy)ethoxy)isoindoline-1,3-dione (237); 2-((1r,3r)-3-((6-(3-(2-((2-(2,6-dioxopiperidin-3-yl)-1-oxoisoindolin-5-yl)oxy)ethoxy)prop-1-yn-1-yl)pyridin-3-yl)oxy)cyclobutoxy)-5-(5-methyl-5H-pyrido[4,3-b]indol-7-yl)nicotinonitrile (238); 3-(5-(2-((3-(5-((1r,3r)-3-((5-(5-(difluoromethyl)-5H-pyrido[4,3-b]indol-7-yl)pyridin-2-yl)oxy)cyclobutoxy)pyridin-2-yl)prop-2-yn-1-yl)oxy)ethoxy)-1-oxoisoindolin-2-yl)piperidine-2,6-dione (239); 3-(5-(2-((3-(5-((1r,3r)-3-((3-methyl-5-(5-methyl-5H-pyrido[4,3-b]indol-7-yl)pyridin-2-yl)oxy)cyclobutoxy)pyridin-2-yl)prop-2-yn-1-yl)oxy)ethoxy)-1-oxoisoindolin-2-yl)piperidine-2,6-dione (240); 3-(5-((3-(3-(4-((1r,3r)-3-((5-(5-methyl-5H-pyrido[4,3-b]indol-7-yl)pyridin-2-yl)oxy)cyclobutoxy)piperidin-1-yl)phenyl)prop-2-yn-1-yl)oxy)-1-oxoisoindolin-2-yl)piperidine-2,6-dione (241); 2-(2,6-dioxopiperidin-3-yl)-5-((3-(4-(4-((1r,3r)-3-((5-(5-methyl-5H-pyrido[4,3-b]indol-7-yl)pyridin-2-yl)oxy)cyclobutoxy)piperidin-1-yl)pyridin-2-yl)prop-2-yn-1-yl)oxy)isoindoline-1,3-dione (242); 3-(5-((3-(4-(4-((1r,3r)-3-((5-(5-methyl-5H-pyrido[4,3-b]indol-7-yl)pyridin-2-yl)oxy)cyclobutoxy)piperidin-1-yl)pyridin-2-yl)prop-2-yn-1-yl)oxy)-1-oxoisoindolin-2-yl)piperidine-2,6-dione (243); 2-(2,6-dioxopiperidin-3-yl)-5-((3-(4-(4-((1r,3r)-3-((5-(5-methyl-5H-pyrido[4,3-b]indol-7-yl)pyridin-2-yl)oxy)cyclobutoxy)piperidin-1-yl)pyrimidin-2-yl)prop-2-yn-1-yl)oxy)isoindoline-1,3-dione (244); 3-(5-((3-(4-(4-((1r,3r)-3-((5-(5-methyl-5H-pyrido[4,3-b]indol-7-yl)pyridin-2-yl)oxy)cyclobutoxy)piperidin-1-yl)pyrimidin-2-yl)prop-2-yn-1-yl)oxy)-1-oxoisoindolin-2-yl)piperidine-2,6-dione (245); 2-(2,6-dioxopiperidin-3-yl)-5-((3-(2-(4-((1r,3r)-3-((5-(5-methyl-5H-pyrido[4,3-b]indol-7-yl)pyridin-2-yl)oxy)cyclobutoxy)piperidin-1-yl)pyrimidin-4-yl)prop-2-yn-1-yl)oxy)isoindoline-1,3-dione (246); 3-(5-((3-(2-(4-((1r,3r)-3-((5-(5-methyl-5H-pyrido[4,3-b]indol-7-yl)pyridin-2-yl)oxy)cyclobutoxy)piperidin-1-yl)pyrimidin-4-yl)prop-2-yn-1-yl)oxy)-1-oxoisoindolin-2-yl)piperidine-2,6-dione (247); 2-(2,6-dioxopiperidin-3-yl)-5-(2-(3-(4-((1r,3r)-3-((5-(5-methyl-5H-pyrido[4,3-b]indol-7-yl)pyridin-2-yl)oxy)cyclobutoxy)piperidin-1-yl)propoxy)ethoxy)isoindoline-1,3-dione (248); 3-(5-(2-(3-(4-((1r,3r)-3-((5-(5-methyl-5H-pyrido[4,3-b]indol-7-yl)pyridin-2-yl)oxy)cyclobutoxy)piperidin-1-yl)propoxy)ethoxy)-1-oxoisoindolin-2-yl)piperidine-2,6-dione (249); 2-(2,6-dioxopiperidin-3-yl)-5-((6-(4-((1r,3r)-3-((5-(5-methyl-5H-pyrido[4,3-b]indol-7-yl)pyridin-2-yl)oxy)cyclobutoxy)piperidin-1-yl)hex-2-yn-1-yl)oxy)isoindoline-1,3-dione (250); 3-(5-((6-(4-((1r,3r)-3-((5-(5-methyl-5H-pyrido[4,3-b]indol-7-yl)pyridin-2-yl)oxy)cyclobutoxy)piperidin-1-yl)hex-2-yn-1-yl)oxy)-1-oxoisoindolin-2-yl)piperidine-2,6-dione (251); 2-(2,6-dioxopiperidin-3-yl)-5-(2-(2-(2-(2-(3-((5-(5-methyl-5H-pyrido[4,3-b]indol-7-yl)pyridin-2-yl)oxy)azetidin-1-yl)ethoxy)ethoxy)ethoxy)ethoxy)isoindoline-1,3-dione (252); N-(2-((1-(2-(2,6-dioxopiperidin-3-yl)-1,3-dioxoisoindolin-5-yl)azetidin-3-yl)oxy)ethyl)-N-methyl-4-((1r,3r)-3-((5-(5-methyl-5H-pyrido[4,3-b]indol-7-yl)pyridin-2-yl)oxy)cyclobutoxy)butanamide (253); 2-(2,6-dioxopiperidin-3-yl)-5-((1-(2-(4-((1r,3r)-3-((5-(5-methyl-5H-pyrido[4,3-b]indol-7-yl)pyridin-2-yl)oxy)cyclobutoxy)piperidin-1-yl)-2-oxoethyl)azetidin-3-yl)oxy)isoindoline-1,3-dione (254); 2-(2,6-dioxopiperidin-3-yl)-5-(3-(2-(4-((1r,3r)-3-((5-(5-methyl-5H-pyrido[4,3-b]indol-7-yl)pyridin-2-yl)oxy)cyclobutoxy)piperidin-1-yl)-2-oxoethoxy)azetidin-1-yl)isoindoline-1,3-dione (255); 2-(2,6-dioxopiperidin-3-yl)-5-(3-(3-(4-((1r,3r)-3-((5-(5-methyl-5H-pyrido[4,3-b]indol-7-yl)pyridin-2-yl)oxy)cyclobutoxy)piperidin-1-yl)phenoxy)azetidin-1-yl)isoindoline-1,3-dione (256); 2-(2,6-dioxopiperidin-3-yl)-5-(3-(3-(3-(((1s,3s)-1-hydroxy-3-((5-(5-methyl-5H-pyrido[4,3-b]indol-7-yl)pyridin-2-yl)oxy)cyclobutyl)methoxy)propoxy)propoxy)azetidin-1-yl)isoindoline-1,3-dione (257); 2-(2,6-dioxopiperidin-3-yl)-5-(2-(9-(2-((1r,3r)-3-((5-(5-methyl-5H-pyrido[4,3-b]indol-7-yl)pyridin-2-yl)oxy)cyclobutoxy)ethyl)-1-oxa-4,9-diazaspiro[5.5]undecan-4-yl)ethoxy)isoindoline-1,3-dione (258); 2-(2,6-dioxopiperidin-3-yl)-5-((4-(9-(((1s,3s)-1-hydroxy-3-((5-(5-methyl-5H-pyrido[4,3-b]indol-7-yl)pyridin-2-yl)oxy)cyclobutyl)methyl)-1-oxa-4,9-diazaspiro[5.5]undecan-4-yl)but-2-yn-1-yl)oxy)isoindoline-1,3-dione (259); 2-(2,6-dioxopiperidin-3-yl)-5-((3-(3-(4-(((1s,3s)-1-hydroxy-3-((5-(5-methyl-5H-pyrido[4,3-b]indol-7-yl)pyridin-2-yl)oxy)cyclobutyl)methyl)piperazin-1-yl)phenyl)prop-2-yn-1-yl)oxy)isoindoline-1,3-dione (260); 2-(2,6- dioxopiperidin-3-yl)-5-((3-(3-(4-(((1r,3r)-3-((5-(5-methyl-5H-pyrido[4,3-b]indol-7-yl)pyridin-2-yl)oxy)cyclobutyl)methyl)piperazin-1-yl)phenyl)prop-2-yn-1-yl)oxy)isoindoline-1,3-dione (261); 2-(2,6-dioxopiperidin-3-yl)-5-(2-(3-(3-(((1s,3s)-1-hydroxy-3-((5-(5-methyl-5H-pyrido[4,3-b]indol-7-yl)pyridin-2-yl)oxy)cyclobutyl)methoxy)propoxy)propoxy)ethoxy)isoindoline-1,3-dione (262); 2-(2,6-dioxopiperidin-3-yl)-5-(2-(3-(3-((3-hydroxy-1-(5-(5-methyl-5H-pyrido[4,3-b]indol-7-yl)pyridin-2-yl)azetidin-3-yl)methoxy)propoxy)propoxy)ethoxy)isoindoline-1,3-dione (263); 2-(2,6-dioxopiperidin-3-yl)-5-(3-(3-(3-((5'-(5-methyl-5H-pyrido[4,3-b]indol-7-yl)-3'H-spiro[cyclobutane-1,2'-furo[2,3-b]pyridin]-3-yl)oxy)propoxy)propoxy)azetidin-1-yl)isoindoline-1,3-dione (264); 5-((14-((5-(6,8-difluoro-5-methyl-5H-pyrido[4,3-b]indol-7-yl)pyridin-2-yl)oxy)-3,6,9,12-tetraoxatetradecyl)oxy)-2-(2,6-dioxopiperidin-3-yl)isoindoline-1,3-dione (265); 2-(2,6-dioxopiperidin-3-yl)-5-((14-((1-(5-methyl-5H-pyrido[4,3-b]indol-7-yl)piperidin-4-yl)oxy)-3,6,9,12-tetraoxatetradecyl)oxy)isoindoline-1,3-dione (266); 2-(2,6-dioxopiperidin-3-yl)-5-(3-(2-((1R,3r)-3-(2-((1r,3R)-3-((5-(5-methyl-5H-pyrido[4,3-b]indol-7-yl)pyridin-2-yl)oxy)cyclobutane)ethyl)cyclobutyl)ethoxy)azetidin-1-yl)isoindoline-1,3-dione (267); 2-(2,6-dioxopiperidin-3-yl)-5-(3-((S,2R)-2-((4-(((1r,3R)-3-((5-(5-methyl-5H-pyrido[4,3-b]indol-7-yl)pyridin-2-yl)oxy)cyclobutoxy)butoxy)methyl)cyclopropyl)azetidin-1-yl)isoindoline-1,3-dione (268); 2-(2,6-dioxopiperidin-3-yl)-5-(3-(4-(((1R,2R)-2-((1r,3R)-3-((5-(5-methyl-5H-pyrido[4,3-b]indol-7-yl)pyridin-2-yl)oxy)cyclobutyl)cyclopropyl)methoxy)butoxy)azetidin-1-yl)isoindoline-1,3-dione (269); 2-(2,6-dioxopiperidin-3-yl)-5-(3-(2-(2-(((1R,2R)-2-((1r,3R)-3-((5-(5-methyl-5H-pyrido[4,3-b]indol-7-yl)pyridin-2-yl)oxy)cyclobutyl)cyclopropyl)methoxy)ethoxy)ethoxy)azetidin-1-yl)isoindoline-1,3-dione (270); 2-(2,6-dioxopiperidin-3-yl)-5-(3-(2-((1R,3r)-3-(((1r,3R)-3-((5-(5-methyl-5H-pyrido[4,3-b]indol-7-yl)pyridin-2-yl)oxy)cyclobutoxy)methyl)cyclobutoxy)ethoxy)azetidin-1-yl)isoindoline-1,3-dione (271); 5-(3-(3-(2,2-difluoro-3-((1r,3r)-3-((5-(5-methyl-5H-pyrido[4,3-b]indol-7-yl)pyridin-2-yl)oxy)cyclobutoxy)propoxy)propoxy)azetidin-1-yl)-2-(2,6-dioxopiperidin-3-yl)isoindoline-1,3-dione (272); 5-(3-(2,2-difluoro-3-(3-((1r,3r)-3-((5-(5-methyl-5H-pyrido[4,3-b]indol-7-yl)pyridin-2-yl)oxy)cyclobutoxy)propoxy)propoxy)azetidin-1-yl)-2-(2,6-dioxopiperidin-3-yl)isoindoline-1,3-dione (273); 2-(2,6-dioxopiperidin-3-yl)-5-(2-((3-(5-((1r,3r)-3-((5-(5-methyl-5H-pyrido[4,3-b]indol-7-yl)pyridin-2-yl)oxy)cyclobutoxy)pyridin-2-yl)prop-2-yn-1-yl)oxy)propoxy)isoindoline-1,3-dione (274); 2-(2,6-dioxopiperidin-3-yl)-5-(2-((4-(5-((1r,3r)-3-((5-(5-methyl-5H-pyrido[4,3-b]indol-7-yl)pyridin-2-yl)oxy)cyclobutoxy)pyridin-2-yl)but-3-yn-2-yl)oxy)ethoxy)isoindoline-1,3-dione (275); 5-(2-((1,1-difluoro-3-(5-((1r,3r)-3-((5-(5-methyl-5H-pyrido[4,3-b]indol-7-yl)pyridin-2-yl)oxy)cyclobutoxy)pyridin-2-yl)prop-2-yn-1-yl)oxy)ethoxy)-2-(2,6-dioxopiperidin-3-yl)isoindoline-1,3-dione (276); 3-(5-((4-(5-((1r,3r)-3-((5-(5H-pyrido[4,3-b]indol-7-yl)pyridin-2-yl)oxy)cyclobutoxy)pyridin-2-yl)but-3-yn-1-yl)oxy)-1-oxoisoindolin-2-yl)piperidine-2,6-dione (277); 3-(5-(((3-(5-((1r,3r)-3-((5-(5H-pyrido[4,3-b]indol-7-yl)pyridin-2-yl)oxy)cyclobutoxy)pyridin-2-yl)prop-2-yn-1-yl)oxy)methyl)-1-oxoisoindolin-2-yl)piperidine-2,6-dione (278); 3-(5-(3-((4-(5-((1r,3r)-3-((5-(5H-pyrido[4,3-b]indol-7-yl)pyridin-2-yl)oxy)cyclobutoxy)pyridin-2-yl)but-3-yn-1-yl)oxy)azetidin-1-yl)-1-oxoisoindolin-2-yl)piperidine-2,6-dione (279); 5-(3-((4-(5-((1r,3r)-3-((5-(5H-pyrido[4,3-b]indol-7-yl)pyridin-2-yl)oxy)cyclobutoxy)pyridin-2-yl)but-3-yn-1-yl)oxy)azetidin-1-yl)-2-(2,6-dioxopiperidin-3-yl)isoindoline-1,3-dione (280); 5-(3-((5-(5-((1r,3r)-3-((5-(5H-pyrido[4,3-b]indol-7-yl)pyridin-2-yl)oxy)cyclobutoxy)pyridin-2-yl)pent-4-yn-1-yl)oxy)azetidin-1-yl)-2-(2,6-dioxopiperidin-3-yl)isoindoline-1,3-dione (281); 3-(5-(3-((5-(5-((1r,3r)-3-((5-(5H-pyrido[4,3-b]indol-7-yl)pyridin-2-yl)oxy)cyclobutoxy)pyridin-2-yl)pent-4-yn-1-yl)oxy)-1-oxoisoindolin-2-yl)piperidine-2,6-dione (282); 2-(2,6-dioxopiperidin-3-yl)-5-((1-(4-(5-((1r,3r)-3-((5-(5-methyl-5H-pyrido[4,3-b]indol-7-yl)pyridin-2-yl)oxy)cyclobutoxy)pyridin-2-yl)but-3-yn-1-yl)azetidin-3-yl)oxy)isoindoline-1,3-dione (283); 3-(5-((1-(4-(5-((1r,3r)-3-((5-(5-methyl-5H-pyrido[4,3-b]indol-7-yl)pyridin-2-yl)oxy)cyclobutoxy)pyridin-2-yl)but-3-yn-1-yl)azetidin-3-yl)oxy)-1-oxoisoindolin-2-yl)piperidine-2,6-dione (284); 5-(2-(2,2-difluoro-3-(4-((1r,3r)-3-((5-(5-methyl-5H-pyrido[4,3-b]indol-7-yl)pyridin-2-yl)oxy)cyclobutoxy)piperidin-1-yl)propoxy)ethoxy)-2-(2,6-dioxopiperidin-3-yl)isoindoline-1,3-dione (285); 2-(((1r,3r)-3-((6-(3-((2-(2,6-dioxopiperidin-3-yl)-1-oxoisoindolin-5-yl)oxy)prop-1-yn-1-yl)pyridin-3-yl)oxy)cyclobutoxy)-5-(5H-pyrido[4,3-b]indol-7-yl)nicotinonitrile (286); 3-(5-((3-(5-((1r,3r)-3-((3-methyl-5-(5H-pyrido[4,3-b]indol-7-yl)pyridin-2-yl)oxy)cyclobutoxy)pyridin-2-yl)prop-2-yn-1-yl)oxy)-1-oxoisoindolin-2-yl)piperidine-2,6-dione (287); 3-(5-((3-(5-((1r,3r)-3-((5-(4-chloro-5H-pyrido[4,3-b]indol-7-yl)pyridin-2-yl)oxy)cyclobutoxy)pyridin-2-yl)prop-2-yn-1-yl)oxy)-1-oxoisoindolin-2-yl)piperidine-2,6-dione (288); 3-(5-((3-(5-((1r,3r)-3-((5-(4-fluoro-5H-pyrido[4,3-b]indol-7-yl)pyridin-2-yl)oxy)cyclobutoxy)pyridin-2-yl)prop-2-yn-1-yl)oxy)-1-oxoisoindolin-2-yl)piperidine-2,6-dione (289); 3-(5-((3-(5-((1r,3r)-3-((5-(5-(difluoromethyl)-5H-pyrido[4,3-b]indol-7-yl)pyridin-2-yl)oxy)cyclobutoxy)pyridin-2-yl)prop-2-yn-1-yl)oxy)-1-oxoisoindolin-2-yl)piperidine-2,6-dione (290); 2-(2,6-dioxopiperidin-3-yl)-5-(2-((3-(3-(((1r,3r)-3-((5-(5-methyl-5H-pyrido[4,3-b]indol-7-yl)pyridin-2-yl)oxy)cyclobutoxy)methyl)bicyclo[1.1.1]pentan-1-yl)prop-2-yn-1-yl)oxy)ethoxy)isoindoline-1,3-dione (291); 2-(2,6-dioxopiperidin-3-yl)-5-(2-((3-((1R,3r)-3-(((1r,3R)-3-((5-(5-methyl-5H-pyrido[4,3-b]indol-7-yl)pyridin-2-yl)oxy)cyclobutoxy)methyl)cyclobutyl)prop-2-yn-1-yl)oxy)ethoxy)isoindoline-1,3-dione (292); 3-(5-(4-((3-(5-((1r,3r)-3-((5-(5H-pyrido[4,3-b]indol-7-yl)pyridin-2-yl)oxy)cyclobutoxy)pyridin-2-yl)prop-2-yn-1-yl)oxy)piperidin-1-yl)-1-oxoisoindolin-2-yl)piperidine-2,6-dione (293); 6-(2-((3-(5-((1r,3r)-3-((5-(5H-pyrido[4,3-b]indol-7-yl)pyridin-2-yl)oxy)cyclobutoxy)pyridin-2-yl)prop-2-yn-1-yl)oxy)ethoxy)-2-(2,6-dioxopiperidin-3-yl)-1H-pyrrolo[3,4-c]pyridine-1,3 (2H)-dione (294); 2-(2,6-dioxopiperidin-3-yl)-5-(3-(2-((3-(((1r,3r)-3-((5-(5-methyl-5H-pyrido[4,3-b]indol-7-yl)pyridin-2-yl)oxy)cyclobutoxy)methyl)bicyclo[1.1.1]pentan-1-yl)methoxy)ethoxy)azetidin-1-yl)isoindoline-1,3-dione (295); 2-(3-(2-((2-(2,6-dioxopiperidin-3-yl)-1,3-dioxoisoindolin-5-yl)oxy)ethoxy)prop-1-yn-11-yl)-5-((1r,3r)-3-((5-(5-methyl-5H-pyrido[4,3-b]indol-7-yl)pyridin-2-yl)oxy)cyclobutoxy)isonicotinonitrile (296); 2-(3-(2-((2-(2,6-dioxopiperidin-3-yl)-1-oxoisoindolin-5-yl)oxy)ethoxy)prop-1-yn-11-yl)-5-((1r,3r)-3-((5-(5-methyl-5H-pyrido[4,3-b]indol-7-yl)pyridin-2-yl)oxy)cyclobutoxy)isonicotinonitrile (297); 2-(2,6-dioxopiperidin-3-yl)-5-(2-((3-(4-methyl-5-((1r,3r)-3-((5-(5-methyl-5H-pyrido[4,3-b]indol-7-yl)pyridin-2-yl)oxy)cyclobutoxy)pyridin-2-yl)prop-2-yn-1-yl)oxy)ethoxy)isoindoline-1,3-dione (298); 3-(5-(2-((3-(4-methyl-5-((1r,3r)-3-((5-(5-methyl-5H-pyrido[4,3-b]indol-7-yl)pyridin-2-yl)oxy)cyclobutoxy)pyridin-2-yl)prop-2-yn-1-yl)oxy)ethoxy)-1-oxoisoindolin-2-yl)piperidine-2,6-dione (299); 3-(5-(2-((3-(5-((1r,3r)-3-((5-(5-methyl-5H-pyrido[4,3-b]indol-7-yl)pyridin-2-yl)oxy)cyclobutoxy)-4-

(trifluoromethyl)pyridin-2-yl)prop-2-yn-1-yl)oxy)ethoxy)-1-oxoisoindolin-2-yl)piperidine-2,6-dione (300); 2-(2,6-dioxopiperidin-3-yl)-5-(2-((3-(5-((1r,3r)-3-((5-(5-methyl-5H-pyrido[4,3-b]indol-7-yl)pyridin-2-yl)oxy)cyclobutoxy)-4-(trifluoromethyl)pyridin-2-yl)prop-2-yn-1-yl)oxy)ethoxy)isoindoline-1,3-dione (301); 6-(3-(2-((2-(2,6-dioxopiperidin-3-yl)-1,3-dioxoisoindolin-5-yl)oxy)ethoxy)prop-1-yn-1-yl)-13-((1r,3r)-3-((5-(5-methyl-5H-pyrido[4,3-b]indol-7-yl)pyridin-2-yl)oxy)cyclobutoxy)picolinonitrile (302); 6-(3-(2-((2-(2,6-dioxopiperidin-3-yl)-1-oxoisoindolin-5-yl)oxy)ethoxy)prop-1-yn-11-yl)-3-((1r,3r)-3-((5-(5-methyl-5H-pyrido[4,3-b]indol-7-yl)pyridin-2-yl)oxy)cyclobutoxy)picolinonitrile (303); 2-(2,6-dioxopiperidin-3-yl)-5-(2-((3-(6-methyl-5-((1r,3r)-3-((5-(5-methyl-5H-pyrido[4,3-b]indol-7-yl)pyridin-2-yl)oxy)cyclobutoxy)pyridin-2-yl)prop-2-yn-1-yl)oxy)ethoxy)isoindoline-1,3-dione (304); 3-(5-(2-((3-(6-methyl-5-((1r,3r)-3-((5-(5-methyl-5H-pyrido[4,3-b]indol-7-yl)pyridin-2-yl)oxy)cyclobutoxy)pyridin-2-yl)prop-2-yn-1-yl)oxy)ethoxy)-1-oxoisoindolin-2-yl)piperidine-2,6-dione (305); 2-(2,6-dioxopiperidin-3-yl)-5-(2-((3-(5-((1r,3r)-3-((5-(5-methyl-5H-pyrido[4,3-b]indol-7-yl)pyridin-2-yl)oxy)cyclobutoxy)-6-(trifluoromethyl)pyridin-2-yl)prop-2-yn-1-yl)oxy)ethoxy)isoindoline-1,3-dione (306); 3-(5-(2-((3-(5-((1r,3r)-3-((5-(5-methyl-5H-pyrido[4,3-b]indol-7-yl)pyridin-2-yl)oxy)cyclobutoxy)-6-(trifluoromethyl)pyridin-2-yl)prop-2-yn-1-yl)oxy)ethoxy)-1-oxoisoindolin-2-yl)piperidine-2,6-dione (307); 2-(2,6-dioxopiperidin-3-yl)-5-(2-((2-methyl-4-(5-((1r,3r)-3-((5-(5-methyl-5H-pyrido[4,3-b]indol-7-yl)pyridin-2-yl)oxy)cyclobutoxy)pyridin-2-yl)but-3-yn-2-yl)oxy)ethoxy)isoindoline-1,3-dione (308); 3-(5-(2-((2-methyl-4-(5-((1r,3r)-3-((5-(5-methyl-5H-pyrido[4,3-b]indol-7-yl)pyridin-2-yl)oxy)cyclobutoxy)pyridin-2-yl)but-3-yn-2-yl)oxy)ethoxy)-1-oxoisoindolin-2-yl)piperidine-2,6-dione (309); 3-(5-(2-(1-((5-((1r,3r)-3-((5-(5-methyl-5H-pyrido[4,3-b]indol-7-yl)pyridin-2-yl)oxy)cyclobutoxy)pyridin-2-yl)ethynyl)cyclopropoxy)ethoxy)-1-oxoisoindolin-2-yl)piperidine-2,6-dione (310); 2-(2,6-dioxopiperidin-3-yl)-5-(2-(1-((5-((1r,3r)-3-((5-(5-methyl-5H-pyrido[4,3-b]indol-7-yl)pyridin-2-yl)oxy)cyclobutoxy)pyridin-2-yl)ethynyl)cyclopropoxy)ethoxy)isoindoline-1,3-dione (311); 4-(3-((2-(2,6-dioxopiperidin-3-yl)-1,3-dioxoisoindolin-5-yl)oxy)prop-1-yn-1-yl)-2-(4-((1r,3r)-3-((5-(5-methyl-5H-pyrido[4,3-b]indol-7-yl)pyridin-2-yl)oxy)cyclobutoxy)piperidin-1-yl)benzonitrile (312); 4-(3-((2-(2,6-dioxopiperidin-3-yl)-1-oxoisoindolin-5-yl)oxy)prop-1-yn-1-yl)-2-(4-((1r,3r)-3-((5-(5-methyl-5H-pyrido[4,3-b]indol-7-yl)pyridin-2-yl)oxy)cyclobutoxy)piperidin-1-yl)benzonitrile (313); 3-(5-((3-(4-methyl-3-(4-((1r,3r)-3-((5-(5-methyl-5H-pyrido[4,3-b]indol-7-yl)pyridin-2-yl)oxy)cyclobutoxy)piperidin-1-yl)phenyl)prop-2-yn-1-yl)oxy)-1-oxoisoindolin-2-yl)piperidine-2,6-dione (314); 3-(5-((3-(3-(4-((1r,3r)-3-((5-(5-methyl-5H-pyrido[4,3-b]indol-7-yl)pyridin-2-yl)oxy)cyclobutoxy)piperidin-1-yl)-4-(trifluoromethyl)phenyl)prop-2-yn-1-yl)oxy)-1-oxoisoindolin-2-yl)piperidine-2,6-dione (315); 3-(5-((3-(4-(4-((1r,3r)-3-((5-(5-methyl-5H-pyrido[4,3-b]indol-7-yl)pyridin-2-yl)oxy)cyclobutoxy)piperidin-1-yl)-5-(trifluoromethyl)pyridin-2-yl)prop-2-yn-1-yl)oxy)-1-oxoisoindolin-2-yl)piperidine-2,6-dione (316); 6-(3-((2-(2,6-dioxopiperidin-3-yl)-1-oxoisoindolin-5-yl)oxy)prop-1-yn-1-yl)-4-(4-((1r,3r)-3-((5-(5-methyl-5H-pyrido[4,3-b]indol-7-yl)pyridin-2-yl)oxy)cyclobutoxy)piperidin-1-yl)nicotinonitrile (317); 3-(3-((2-(2,6-dioxopiperidin-3-yl)-1,3-dioxoisoindolin-5-yl)oxy)prop-1-yn-1-yl)-5-(4-((1r,3r)-3-((5-(5-methyl-5H-pyrido[4,3-b]indol-7-yl)pyridin-2-yl)oxy)cyclobutoxy)piperidin-1-yl)benzonitrile (318); 3-(3-((2-(2,6-dioxopiperidin-3-yl)-1-oxoisoindolin-5-yl)oxy)prop-1-yn-1-yl)-5-(4-((1r,3r)-3-((5-(5-methyl-5H-pyrido[4,3-b]indol-7-yl)pyridin-2-yl)oxy)cyclobutoxy)piperidin-1-yl)benzonitrile (319); 3-(5-((3-(3-methyl-5-(4-((1r,3r)-3-((5-(5-methyl-5H-pyrido[4,3-b]indol-7-yl)pyridin-2-yl)oxy)cyclobutoxy)piperidin-1-yl)phenyl)prop-2-yn-1-yl)oxy)-1-oxoisoindolin-2-yl)piperidine-2,6-dione (320); 3-(5-((3-(3-(4-((1r,3r)-3-((5-(5-methyl-5H-pyrido[4,3-b]indol-7-yl)pyridin-2-yl)oxy)cyclobutoxy)piperidin-1-yl)-5-(trifluoromethyl)phenyl)prop-2-yn-1-yl)oxy)-1-oxoisoindolin-2-yl)piperidine-2,6-dione (321); 3-(5-((3-(4-(4-((1r,3r)-3-((5-(5-methyl-5H-pyrido[4,3-b]indol-7-yl)pyridin-2-yl)oxy)cyclobutoxy)piperidin-1-yl)-6-(trifluoromethyl)pyridin-2-yl)prop-2-yn-1-yl)oxy)-1-oxoisoindolin-2-yl)piperidine-2,6-dione (322); 3-(5-((3-(2-(4-((1r,3r)-3-((5-(5-methyl-5H-pyrido[4,3-b]indol-7-yl)pyridin-2-yl)oxy)cyclobutoxy)piperidin-1-yl)-6-(trifluoromethyl)pyridin-4-yl)prop-2-yn-1-yl)oxy)-1-oxoisoindolin-2-yl)piperidine-2,6-dione (323); 2-(2,6-dioxopiperidin-3-yl)-5-((2-methyl-4-(3-(4-((1r,3r)-3-((5-(5-methyl-5H-pyrido[4,3-b]indol-7-yl)pyridin-2-yl)oxy)cyclobutoxy)piperidin-1-yl)phenyl)but-3-yn-2-yl)oxy)isoindoline-1,3-dione (324); 3-(5-((2-methyl-4-(3-(4-((1r,3r)-3-((5-(5-methyl-5H-pyrido[4,3-b]indol-7-yl)pyridin-2-yl)oxy)cyclobutoxy)piperidin-1-yl)phenyl)but-3-yn-2-yl)oxy)-1-oxoisoindolin-2-yl)piperidine-2,6-dione (325); 3-(5-((2-methyl-4-(4-((1r,3r)-3-((5-(5-methyl-5H-pyrido[4,3-b]indol-7-yl)pyridin-2-yl)oxy)cyclobutoxy)piperidin-1-yl)pyridin-2-yl)but-3-yn-2-yl)oxy)-1-oxoisoindolin-2-yl)piperidine-2,6-dione (326); 3-(5-((1,1-difluoro-3-(4-(4-((1r,3r)-3-((5-(5-methyl-5H-pyrido[4,3-b]indol-7-yl)pyridin-2-yl)oxy)cyclobutoxy)piperidin-1-yl)pyridin-2-yl)prop-2-yn-1-yl)oxy)-1-oxoisoindolin-2-yl)piperidine-2,6-dione (327); 3-(5-((2-methyl-4-(4-(4-((1r,3r)-3-((5-(5-methyl-5H-pyrido[4,3-b]indol-7-yl)pyridin-2-yl)oxy)cyclobutoxy)piperidin-1-yl)pyrimidin-2-yl)but-3-yn-2-yl)oxy)-1-oxoisoindolin-2-yl)piperidine-2,6-dione (328); 6-(3-((2-(2,6-dioxopiperidin-3-yl)-1-oxoisoindolin-5-yl)oxy)-3-methylbut-1-yn-1-yl)-4-(4-((1r,3r)-3-((5-(5-methyl-5H-pyrido[4,3-b]indol-7-yl)pyridin-2-yl)oxy)cyclobutoxy)piperidin-1-yl)nicotinonitrile (329); 2-(3-(2-((2-(2,6-dioxopiperidin-3-yl)-1-oxoisoindolin-5-yl)oxy)ethoxy)-3-methylbut-1-yn-1-yl)-5-((1r,3r)-3-((5-(5-methyl-5H-pyrido[4,3-b]indol-7-yl)pyridin-2-yl)oxy)cyclobutoxy)isonicotinonitrile (330).

The present description includes, where applicable, the compositions comprising the pharmaceutically acceptable salts, in particular, acid or base addition salts of compounds of the present disclosure.

The term "pharmaceutically acceptable salt" is used throughout the specification to describe, where applicable, a salt form of one or more of the compounds described herein which are presented to increase the solubility of the compound in the gastic juices of the patient's gastrointestinal tract in order to promote dissolution and the bioavailability of the compounds. Pharmaceutically acceptable salts include those derived from pharmaceutically acceptable inorganic or organic bases and acids, where applicable. Suitable salts include those derived from alkali metals such as potassium and sodium, alkaline earth metals such as calcium, magnesium and ammonium salts, among numerous other acids and bases well known in the pharmaceutical art. Sodium and potassium salts are particularly preferred as neutralization salts of the phosphates according to the present disclosure.

The acids which are used to prepare the pharmaceutically acceptable acid addition salts of the aforementioned base compounds useful in this disclosure are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3 naphthoate)] salts, among numerous others.

Pharmaceutically acceptable base addition salts may also be used to produce pharmaceutically acceptable salt forms of the compounds or derivatives according to the present disclosure. The chemical bases that may be used as reagents to prepare pharmaceutically acceptable base salts of the present compounds that are acidic in nature are those that form non-toxic base salts with such compounds. Such non-toxic base salts include, but are not limited to those derived from such pharmacologically acceptable cations such as alkali metal cations (eg., potassium and sodium) and alkaline earth metal cations (eg, calcium, zinc and magnesium), ammonium or water-soluble amine addition salts such as N-methylglucamine-(meglumine), and the lower alkanolammonium and other base salts of pharmaceutically acceptable organic amines, among others.

Compositions:

In another aspect, the description provides compositions comprising compounds as described herein, including salts thereof, and a pharmaceutically acceptable carrier. In certain embodiments, the compositions are therapeutic or pharmaceutical compositions comprising an effective amount of a compound as described herein and a pharmaceutically acceptable carrier.

The amount of compound in a pharmaceutical composition of the instant disclosure that may be combined with the carrier materials to produce a single dosage form will vary depending upon the host and disease treated, the particular mode of administration. Generally, an amount between 0.1 mg/kg and 1000 mg/kg body weight/day of active ingredients is administered dependent upon potency of the agent. Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects. The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the present disclosure, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The compositions of the present disclosure may be formulated in a conventional manner using one or more pharmaceutically acceptable carriers and may also be administered in controlled-release formulations. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

In any of the aspects or embodiments described herein, the PTM, ULM or both have an affinity ($IC_{50}$) for their respective target protein of less than about 500 µM, 450 µM, 400 µM, 350 µM, 300 µM, 250 µM, 200 µM, 150 µM, 100 µM, 50 µM, 10 µM, 0.10 µM, 0.01 µM, 0.001 µM, 0.1 nM, 0.01 nM, 0.001 nM or less. The determination of the $IC_{50}$ can be performed using methods well known to those of skill in the art in view of the present disclosure.

In any of the aspects or embodiments, the compounds as described herein effectuate the ubquitination of a target protein at sufficient levels or amounts to effectuate or induce degradation of the target protein.

The active compound is included in the pharmaceutically acceptable carrier or diluent in an amount sufficient to deliver to a patient a therapeutically effective amount for the desired indication, without causing serious toxic effects in the patient treated. A preferred dose of the active compound for all of the herein-mentioned conditions is in the range from about 10 ng/kg to 300 mg/kg, preferably 0.1 to 100 mg/kg per day, more generally 0.5 to about 25 mg per kilogram body weight of the recipient/patient per day. A typical topical dosage will range from 0.01-5% wt/wt in a suitable carrier.

The compound is conveniently administered in any suitable unit dosage form, including but not limited to one containing less than 1 mg, 1 mg to 3000 mg, preferably 5 to 500 mg of active ingredient per unit dosage form. An oral dosage of about 25-250 mg is often convenient.

The active ingredient is preferably administered to achieve peak plasma concentrations of the active compound of about 0.00001-30 mM, preferably about 0.1-30 µM. This may be achieved, for example, by the intravenous injection of a solution or formulation of the active ingredient, optionally in saline, or an aqueous medium or administered as a bolus of the active ingredient. Oral administration is also appropriate to generate effective plasma concentrations of active agent.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

If administered intravenously, preferred carriers are physiological saline or phosphate buffered saline (PBS).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound is then introduced into the container. The container is then swirled by hand to free lipid material from the sides of the container and to disperse lipid aggregates, thereby forming the liposomal suspension.

Modes of Administration

In any of the aspects or embodiments described herein, the therapeutic compositions comprising compounds described herein can be in any suitable dosage form configured to be delivered by any suitable route. For example, the compounds can be administered by any appropriate route, for example, orally, parenterally, intravenously, intradermally, subcutaneously, or topically, including transdermally, in liquid, cream, gel, or solid form, rectally, nasally, buccally, vaginally or via an implanted reservoir or by aerosol form.

The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

The compounds as described herein may be administered in single or divided doses by the oral, parenteral or topical routes. Administration of the active compound may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal, sublingual and suppository administration, among other routes of administration. Enteric coated oral tablets may also be used to enhance bioavailability of the compounds from an oral route of administration. The most effective dosage form will depend upon the pharmacokinetics of the particular agent chosen as well as the severity of disease in the patient.

Administration of compounds as sprays, mists, or aerosols for intra-nasal, intra-tracheal or pulmonary administration may also be used. Compounds as described herein may be administered in immediate release, intermediate release or sustained or controlled release forms. Sustained or controlled release forms are preferably administered orally, but also in suppository and transdermal or other topical forms. Intramuscular injections in liposomal form may also be used to control or sustain the release of compound at an injection site.

Sterile injectable forms of the compositions as described herein may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions as described herein may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added. Oral compositions will generally include an inert diluent or an edible carrier. They may be enclosed in gelatin capsules or compressed into tablets. For the purpose of oral therapeutic administration, the active compound or its prodrug derivative can be incorporated with excipients and used in the form of tablets, troches, or capsules. Pharmaceutically compatible binding agents, and/or adjuvant materials are included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

The active compound or pharmaceutically acceptable salt thereof can be administered as a component of an elixir, suspension, syrup, wafer, chewing gum or the like. A syrup may contain, in addition to the active compounds, sucrose as a sweetening agent and certain preservatives, dyes and colorings and flavors.

Alternatively, the pharmaceutical compositions as described herein may be administered in the form of suppositories for rectal administration. These can be prepared by mixing the agent with a suitable non-irritating excipient, which is solid at room temperature but liquid at rectal temperature and therefore will melt in the rectum to release the drug. Such materials include cocoa butter, beeswax and polyethylene glycols.

The pharmaceutical compositions of the disclosure may also be administered topically. Suitable topical formulations are readily prepared for each of these areas or organs. Topical application for the lower intestinal tract can be effected in a rectal suppository formulation (see above) or in a suitable enema formulation. Topically-acceptable transdermal patches may also be used. For topical applications, the pharmaceutical compositions may be formulated in a suitable ointment containing the active component suspended or dissolved in one or more carriers. Carriers for topical administration of the compounds of this disclosure include, but are not limited to, mineral oil, liquid petrolatum, white petrolatum, propylene glycol, polyoxyethylene, polyoxypropylene compound, emulsifying wax and water. In certain preferred aspects of the disclosure, the compounds may be coated onto a stent which is to be surgically implanted into a patient in order to inhibit or reduce the likelihood of occlusion occurring in the stent in the patient.

Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyl-dodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this disclosure may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

A patient or subject in need of therapy using compounds as described herein can be treated by administering to the patient (subject) an effective amount of the compound including pharmaceutically acceptable salts, solvates or polymorphs, thereof optionally in a pharmaceutically acceptable carrier or diluent, either alone, or in combination with other known agents.

Co-Administration

Disease states of conditions which may be treated using compounds or compositions according to the present description include, but not limited to, for example, cancer (e.g., prostate cancer), and Kennedy's disease. In certain embodiments, the therapeutic or pharmaceutical compositions comprise an effective amount of an additional biologically or bioactive active agent, e.g., an agent effective for the treatment of cancer, that is co-administered.

The term "co-administration" or "combination therapy" shall mean that at least two compounds or compositions are administered to the patient at the same time, such that effective amounts or concentrations of each of the two or more compounds may be found in the patient at a given point in time. Although compounds according to the present disclosure may be co-administered to a patient at the same time, the term embraces both administration of two or more agents at the same time or at different times, provided that effective concentrations of all co-administered compounds or compositions are found in the subject at a given time. In certain preferred aspects of the present disclosure, one or more of the present compounds described above, are co-administered in combination with at least one additional bioactive agent, especially including an anticancer agent. In particularly preferred aspects of the disclosure, the co-administration of compounds results in synergistic therapeutic, including anticancer therapy.

In another aspect, the description provides a composition comprising an effective amount of two or more of the PROTAC compounds as described herein, and a pharmaceutically acceptable carrier. In certain embodiments, the composition further comprises an effective or synergistic amount of another bioactive agent that is not a PROTAC compound.

Pharmaceutical compositions comprising combinations of an effective amount of at least one bifunctional compound according to the present disclosure, and one or more of the compounds otherwise described herein, all in effective amounts, in combination with a pharmaceutically effective amount of a carrier, additive or excipient, represents a further aspect of the present disclosure.

The term "bioactive agent" is used to describe an agent, other than the PROTAC compounds described herein, which is used in combination with the present compounds as an agent with biological activity to assist in effecting an intended therapy, inhibition and/or prevention/prophylaxis for which the present compounds are used. Preferred bioactive agents for use herein include those agents which assist in effecting an intended therapy, for example, P-gp inhibitors or agents that have pharmacological activity similar to that for which the present compounds are used or administered and include for example, anti-neurodegenerative agents.

The term "P-gp" is used to describe "permeability glycoprotein" or P-glycoprotein (ABCB1) which was discovered in 1976 in rodent cells. The presence of "endogenous or physiological" P-gp is a potential problem to achieving targeted exposure with therapeutic agents. P-gp is expressed at barrier tissue to sanctuary sites (e.g., blood-brain barrier) and at secretory/absorptive tissues (e.g., gastrointestinal tract) (Cordon-Cardo et al., 1989, 1990). The protein acts as a cellular defender and influences the overall pharmacokinetic profile of numerous drugs by actively pumping them out of the intracellular environment (effluxing) thereby reducing drug penetration of the barrier tissues. In particular, P-gp efflux reduces drug permeability across the gastrointestinal tract membranes and may lead to reduced systemic exposure of the drug. P-gp efflux also reduces drug access across the blood-brain barrier. P-gp inhibitors could indirectly contribute to efficacy by increasing PROTAC exposure, particularly CNS exposure.

The term "additional anti-neurodegenerative agent" is used to describe an anti-neurodegenerative agent, which may be combined with PROTAC compounds according to the present description to treat neurogenerative diseases.

In certain embodiments, the PROTAC(s) are used along with P-gp inhibitors.

In certain additional embodiments, the P-gp inhibitors are selected from the group consisting of, but not limited to, Amiodarone, Azithromycin, Captopril, Clarithromycin, Cyclosporine, Piperine, Quercetin, Quinidine, Quinine, Reserpine, Ritonavir, Tariquidar, Elacridar and Verapamil.

Methods of Treatment

In another aspect, the disclosure provides methods of modulating protein ubiquitination and degradation in a subject, e.g., a cell, a tissue, mammal, or human patient, the method comprising administering an effective amount of a PROTAC compound as described herein or a composition comprising an effective amount of the same to a subject, wherein the compound or composition comprising the same is effective in modulating protein ubquitination and degradation of the protein in the subject. In certain embodiments, the protein is Tau protein.

In certain embodiments, the description provides a method for regulating protein activity of Tau protein by degenerating Tau aggregates in a patient in need comprising administering to said patient an amount of a compound as described herein to a patient.

In still additional embodiments, the description provides a method of treating a disease state or condition in a patient wherein dysregulated protein activity (Tau aggregation and accumulation) is responsible for said disease state or condition, said method comprising administering to said patient an effective amount of a compound as described herein to said patient in order to regulate said protein activity in said patient. In certain embodiments, the protein is Tau.

The terms "treat", "treating", and "treatment", etc., as used herein, refer to any action providing a benefit to a patient for which the present compounds may be administered, including the treatment of any disease state or condition which is modulated through the protein to which the present compounds bind. Disease states or conditions, including neurological and neurodegenerative diseases, which may be treated using compounds according to the present disclosure are set forth hereinabove.

In another aspect, the disclosure provides methods of modulating Tau protein ubiquitination and degradation in a subject, e.g., a cell, a tissue, mammal, or human patient, the method comprising administering an effective amount of a compound as described herein or a composition comprising an effective amount of a compound as described herein to a subject, wherein the compound or composition comprising the same is effective in modulating Tau protein ubiquitination and degradation of the protein in the subject.

In another aspect, the disclosure provides methods of treating or ameliorating a symptom of a disease related to Tau accumulation or aggregation in a subject, e.g., a cell, a tissue, mammal, or human patient, the method comprising administering an effective amount of a compound as described herein or a composition comprising an effective amount of the same to a subject in need thereof, wherein the compound or composition comprising the same is effective in treating or ameliorating a symptom of a disease related to Tau aggregation in the subject.

In certain embodiments, the disease or disorder is a neurological disorder including but not limited to Absence of the Septum Pellucidum, Acquired Epileptiform Aphasia, Acute Disseminated Encephalomyelitis, ADHD, Adie's Pupil, Adie's Syndrome, Adreno-leukodystrophy, Agenesis of the Corpus Callosum, Agnosia, Aicardi Syndrome, AIDS-Neurological Complications, Alexander Disease, Alpers' Disease, Alternating Hemiplegia, Alzheimer's Disease, Amyotrophic Lateral Sclerosis, Anencephaly, Aneurysm, Angelman Syndrome, Angiomatosis, Anoxia, Aphasia, Apraxia, Arachnoid Cysts, Arachnoiditis, Arnold-Chiari Malformation, Arteriovenous Malformation, Asperger Syndrome, Ataxia, Ataxia, Telangiectasia, Ataxias and Cerebellar/Spinocerebellar Degeneration, Attention Deficit-Hyperactivity Disorder, Autism, Autonomic Dysfunction, Back Pain, Barth Syndrome Batten Disease, Becker's Myotonia, Behcet's Disease, Bell's Palsy, Benign Essential Blepharospasm, Benign Focal Amyotrophy, Benign Intracranial Hypertension, Bernhardt-Roth Syndrome, Binswanger's Disease, Blepharospasm, Bloch-Sulzberger Syndrome, Brachial Plexus Birth Injuries, Brachial Plexus Injuries, Bradbury-Eggleston Syndrome, Brain and Spinal Tumors, Brain Aneurysm, Brain Injury, Brown-Sequard Syndrome, Bulbospinal Muscular Atrophy, Canavan Disease, Carpal Tunnel Syndrome Causalgia, Cavernomas, Cavernous Angioma, Cavernous Malformation, Central Cervical Cord Syndrome, Central Cord Syndrome, Central Pain Syndrome, Cephalic Disorders, Cerebellar Degeneration, Cerebellar Hypoplasia, Cerebral Aneurysm, Cerebral Arteriosclerosis, Cerebral Atrophy, Cerebral Beriberi, Cerebral Gigantism, Cerebral Hypoxia, Cerebral Patsy, Cerebro-Oculo-Facio-Skeletal Syndrome, Charcot-Marie-Tooth Disease, Chiari Malformation, Chorea, Choreoacanthocytosis, Chronic Inflammatory Demyelinating Polyneuropathy (CIDP), Chronic Orthostatic Intolerance, Chronic Pain Cockayne Syndrome Type II, Coffin Lowry Syndrome, COFS, Colpocephaly, Coma and Persistent Vegetative State, Complex Regional Pain Syndrome, Congenital Facial Diplegia, Congenital Myasthenia, Congenital Myopathy, Congenital Vascular Cavernous, Malformations, Corticobasal Degeneration, Cranial Arteritis, Craniosynostosis, Creutzfeldt-Jakob Disease, Cumulative Trauma Disorders, Cushing's Syndrome, Cytomegalic Inclusion Body Disease, Cytomegalovirus Infection, Dancing Eyes-Dancing Feet Syndrome, Dandy-Walker Syndrome, Dawson Disease, De Morsier's Syndrome, Deep Brain Stimulation for Parkinson's Disease, Dejerine-Klumpke Palsy, Dementia, Dementia-Multi-Infarct, Dementia-Semantic, Dementia-Subcortical, Dementia With Lewy Bodies, Dentate Cerebellar Ataxia, Dentatorubral Atrophy, Dermatomyositis, Developmental Dyspraxia, Devic's Syndrome, Diabetic Neuropathy, Diffuse Sclerosis, Dysautonomia, Dysgraphia, Dyslexia, Dysphagia, Dyspraxia, Dyssynergia Cerebellaris, Myoclonica, Dyssynergia Cerebellaris Progressiva, Dystonias, Early Infantile Epileptic, Encephalopathy, Empty Sella Syndrome, Encephalitis Lethargica, Encephaloceles, Encephalopathy, Encephalotrigeminal Angiomatosis, Epilepsy, Erb-Duchenne and Dejerine-Klumpke Palsies, Erb's Palsy, Fabry's Disease, Fahr's Syndrome, Fainting, Familial Dysautonomia, Familial Hemangioma, Familial Idiopathic Basal Ganglia, Calcification, Familial Periodic Paralyses, Familial Spastic Paralysis, Febrile Seizures, Fisher Syndrome, Floppy Infant Syndrome, Friedreich's Ataxia, Frontotemporal, Dementia, Gaucher's Disease, Gerstmann's Syndrome, Gerstmann-Straussler-Scheinker, Disease, Giant Cell Arteritis, Giant Cell Inclusion Disease, Globoid Cell Leukodystrophy, Glossopharyngeal Neuralgia, Guillain-Barre Syndrome, Hallervorden-Spatz Disease, Head Injury, Headache, Hemicrania Continua, Hemifacial Spasm, Hemiplegia Alterans, Hereditary Neuropathies, Hereditary Spastic Paraplegia, Heredopathia Atactica Polyneuritiformis, Herpes Zoster, Herpes Zoster Oticus, Hirayama Syndrome, Holmes-Adie syndrome, Holoprosencephaly, HTLV-1 Associated, Myelopathy, Huntington's Disease, Hydranencephaly, Hydrocephalus, Hydrocephalus-Normal Pressure, Hydromyelia, Hyperactivity, Hypercortisolism, Hypersomnia, Hypertonia, Hypotonia,—Infantile, Hypoxia, Immune-Mediated Encephalomyelitis, Inclusion Body Myositis, Incontinentia Pigmenti, Infantile Hypotonia, Infantile Neuroaxonal Dystrophy, Infantile Phytanic Acid Storage Disease, Infantile Refsum Disease, Infantile Spasms, Inflammatory Myopathy, Iniencephaly, Intestinal Lipodystrophy, Intracranial Cysts, Intracranial Hypertension, Isaac's Syndrome, Joubert Syndrome, Kearns-Sayre Syndrome, Kennedy's Disease, Kinsbourne syndrome, Kleine-Levin Syndrome, Klippel-Feil Syndrome, Klippel-Trenaunay Syndrome (KTS), Kliver-Bucy Syndrome, Korsakoffs Amnesic Syndrome, Krabbe Disease, Kugelberg-Welander Disease, Kuru, Lambert-Eaton Myasthenic Syndrome, Landau-Kleffner Syndrome, Lateral Femoral, Cutaneous Nerve Entrapment, Lateral Medullary Syndrome, Learning Disabilities, Leigh's Disease, Lennox-Gastaut Syndrome, Lesch-Nyhan Syndrome, Leukodystrophy, Levine-Critchley Syndrome, Lewy Body Dementia, Lipid Storage Diseases, Lissencephaly, Locked-In Syndrome, Lou Gehrig's Disease, Lupus-Neurological, Sequelae, Lyme Disease-Neurological Complications, Machado-Joseph Disease, Macrencephaly, Mania, Megalencephaly, Melkersson-Rosenthal Syndrome, Meningitis, Meningitis and Encephalitis, Menkes Disease, Meralgia Paresthetica, Metachromatic, Leukodystrophy, Microcephaly, Migraine, Miller Fisher Syndrome, Mini-Strokes, Mitochondrial Myopathies, Mobius Syndrome, Monomelic Amyotrophy, Motor Neuron Diseases, Moyamoya Disease, Mucolipidoses, Mucopolysaccharidoses, Multifocal Motor Neuropathy, Multi-Infarct Dementia, Multiple Sclerosis, Multiple System Atrophy, Multiple System Atrophy with Orthostatic Hypotension, Muscular Dystrophy, Myasthenia-Congenital, Myasthenia Gravis, Myelinoclastic Diffuse Sclerosis, Myoclonic Encephalopathy of Infants, Myoclonus, Myopathy, Myopathy-Congenital, Myopathy-Thyrotoxic, Myotonia, Myotonia Congenita, Narcolepsy, Neuroacanthocytosis, Neurodegeneration with Brain Iron Accumulation, Neurofibromatosis, Neuroleptic Malignant Syndrome, Neurological Complications of AIDS, Neurological Complications Of Lyme Disease, Neurological Consequences of Cytomegalovirus Infection, Neurological Manifestations of Pompe Disease, Neurological Sequelae Of Lupus, Neuromyelitis Optica, Neuromyotonia, Neuronal Ceroid, Lipofuscinosis, Neuronal Migration Disorders, Neuropathy-Hereditary, Neurosarcoidosis, Neurotoxicity, Nevus Cavernosus, Niemann-Pick Disease, Normal Pressure Hydrocephalus, Occipital Neuralgia, Obesity, Occult Spinal Dysraphism Sequence, Ohtahara Syndrome, Olivopontocerebellar Atrophy, Opsoclonus Myoclonus, Orthostatic Hypotension, O'Sullivan-McLeod Syndrome, Overuse Syndrome, Pain-Chronic, Paine, Pantothenate Kinase-Associated Neurodegeneration, Paraneoplastic Syndromes, Paresthesia, Parkinson's Disease, Paroxysmal Choreoathetosis, Paroxysmal Hemicrania, Parry-Romberg, Pelizaeus-Merzbacher Disease, Pena Shokeir II Syndrome, Perineural Cysts, Periodic Paralyses, Peripheral Neuropathy, Periventricular Leukomalacia, Persistent Vegetative State, Pervasive Developmental Disorders, Phytanic Acid Storage Disease, Pick's Disease, Pinched Nerve, Piriformis Syndrome, Pituitary Tumors, Polymyositis, Pompe Disease, Porencephaly, Postherpetic Neuralgia, Postinfectious Encephalomyelitis, Post-Polio Syndrome, Postural Hypotension, Postural Orthostatic, Tachycardia Syndrome, Postural Tachycardia Syndrome, Primary Dentatum Atrophy, Primary Lateral Sclerosis, Primary Progressive Aphasia, Prion Diseases, Progressive Hemifacial Atrophy, Progressive Locomotor Ataxia, Progressive Multifocal, Leukoencephalopathy, Progressive Sclerosing Poliodystrophy, Progressive Supranuclear, Palsy, Prosopagnosia, Pseudotumor Cerebri, Ramsay Hunt Syndrome I (formerly known as), Ramsay Hunt Syndrome II (formerly known as), Rasmussen's Encephalitis, Reflex Sympathetic Dystrophy Syndrome, Refsum Disease, Refsum Disease-Infantile, Repetitive Motion Disorders, Repetitive Stress Injuries, Restless Legs Syndrome, Retrovirus-Associated Myelopathy, Rett Syndrome, Reye's Syndrome, Riley-Day Syndrome, Sacral Nerve Root Cysts, Saint Vitus Dance, Salivary Gland Disease, Sandhoff Disease, Schilder's Disease, Schizencephaly, Seitelberger Disease, Seizure Disorder, Semantic Dementia, Septo-Optic Dysplasia, Shaken Baby Syndrome, Shingles Shy-Drager Syndrome, Sjogren's Syndrome, Sleep Apnea, Sleeping Sickness, Sotos Syndrome, Spasticity, Spina Bifida, Spinal Cord Infarction, Spinal Cord Injury, Spinal Cord Tumors, Spinal Muscular Atrophy, Spinocerebellar Atrophy, Spinocerebellar, Degeneration, Steele-Richardson-Olszewski Syndrome, Stiff-Person Syndrome, Striatonigral Degeneration, Stroke, Sturge-Weber Syndrome, Subacute Sclerosing Panencephalitis, Subcortical Arteriosclerotic Encephalopathy, SUNCT Headache Swallowing Disorders, Sydenham Chorea, Syncope, Syphilitic Spinal Sclerosis, Syringohydromyelia, Syringomyelia, Systemic Lupus Erythematosus, Tabes Dorsalis Tardive Dyskinesia, Tarlov Cysts, Tay-Sachs Disease, Temporal Arteritis, Tethered Spinal Cord Syndrome, Thomsen's Myotonia, Thoracic Outlet Syndrome, Thyrotoxic Myopathy, Tic Douloureux, Todd's Paralysis, Tourette Syndrome, Transient Ischemic Attack, Transmissible Spongiform Encephalopathies, Transverse Myelitis, Traumatic Brain Injury, Tremor, Trigeminal Neuralgia, Tropical Spastic Paraparesis, Tuberous Sclerosis, Vascular Erectile Tumor, Vasculitis including Temporal Arteritis, Von Economo's Disease, Von Hippel-Lindau Disease (VHL), Von Recklinghausen's Disease, Wallenberg's Syndrome, Werdnig-Hoffman Disease, Wernicke-Korsakoff Syndrome, West Syndrome, Whiplash, Whipple's Disease, Williams Syndrome, Wilson's Disease, X-Linked Spinal and Bulbar Muscular Atrophy, or Zellweger Syndrome.

In certain embodiments, the disease or disorder is at least one of Huntington's disease, muscular dystrophy, Parkinson's disease, Alzheimer's disease, Batten disease, Injuries to the spinal cord and brain, Seizure disorders, epilepsy, brain tumors, meningitis, autoimmune diseases such as multiple sclerosis, Neurofibromatosis, Depression, Amyotrophic Lateral Sclerosis, Arteriovenous Malformation, Brain Aneurysm, Dural Arteriovenous Fistulae, Headache, Memory Disorders, Peripheral Neuropathy, Post-Herpetic Neuralgia, Spinal Cord Tumor and Stroke.

In certain embodiments, the disease or disorder is Alzheimer's disease.

In another aspect, the disclosure provides methods of treating or ameliorating a symptom of a disease related to Tau accumulation or aggregation in a subject, e.g., a cell, a tissue, mammal, or human patient, the method comprising administering an effective amount of a compound as described herein or a composition comprising an effective amount of the same and an effective or synergistic amount of another bioactive agent to a subject in need thereof, wherein the composition comprising the same is effective in treating or ameliorating a symptom of a disease related to Tau accumulation or aggregation in the subject by Tau degradation/inhibition.

In certain embodiments, the disease to be treated is Neurological disorder. In a preferred embodiment, the subject is a human.

In certain additional embodiments, the additional bioactive agent is an anti-neurodegenerative agent.

In alternative aspects, the present disclosure relates to a method for treating a disease state by degrading a protein or polypeptide through which a disease state or condition is modulated comprising administering to said patient or subject an effective amount of at least one compound as described hereinabove, optionally in combination with an additional bioactive agent. The method according to the present disclosure may be used to treat a large number of neurological disease states or conditions, by virtue of the administration of effective amounts of at least one compound described herein.

In another aspect, the disclosure provides methods for identifying the effects of the degradation of proteins of interest in a biological system using compounds according to the present disclosure.

Kits

In another aspect, the description provides kits comprising compounds or compositions as described herein. The kit may be promoted, distributed, or sold as a unit for performing the methods of the present disclosure. In addition, the kits of the present disclosure may preferably contain instructions, which describe a suitable use. Such kits can be conveniently used, e.g., in clinical settings, to treat patients with Neurological disorders.

Examples

The PROTAC compounds of the instant disclosure are effective in Tau degradation. Exemplary compounds are presented in Tables 1 and 2 with in vitro data of some selected compounds in Tables 2 and 3 showing degradation of tau protein. In vivo studies showing degradation of tau protein are illustrated in the FIGURE.

General Methods of Chemical Synthesis

The synthesis of the claimed chimeric compounds can be carried out according to the general synthetic procedures known in literature. Synthetic routes shown in the schemes in the present disclosure are described as one of the methods that can be used to obtain the desired compounds. Other methods can also be used for those skilled in the art of synthesis. The ULM and PTM described in schemes only represent one of many ULMs and PTMs in this application.

LC-MS Method for Purity Analysis (Quality Control)

LCMS Method:

Instrumentations: Agilent infinity 1260 LC; Agilent 6230 TOF mass spectrometer

The analysis is conducted on a Poroshell 120 EC C18 column (50 mm×3.0 mm internal diameter 2.7 μm packing diameter) at 45° C.

The solvents employed are:
A=0.1% v/v solution of formic acid in water.
B=0.1% v/v solution of formic acid in acetonitrile.

The gradient employed are as follows:

| Time (minutes) | Flow Rate (mL/min) | % A | % B |
|---|---|---|---|
| 0 | 1 | 95 | 5 |
| 0.5 | 1 | 95 | 5 |
| 3.0 | 1 | 1 | 99 |
| 4.0 | 1 | 1 | 99 |
| 4.1 | 1 | 95 | 5 |
| 4.5 | 1 | 95 | 5 |

The UV detection is an averaged signal from wavelength of 210 nm to 350 nm and mass spectra are recorded on a mass spectrometer using positive mode electrospray ionization.

Abbreviations

ACN: acetonitrile
$Boc_2O$: di-tert-butyl dicarbonate
DCM: dichloromethane.
DIPEA: N,N-diisopropylethylamine
DMA: N,N-dimethylacetamide
DMF: N,N-dimethylformamide
EA: ethyl acetate
HATU: 2-(7-aza-1H-benzotriazole-1-yl)-1,1,3,3-tetramethyluronium hexafluorophosphate
HPLC: high-performance liquid chromatography
LC-MS: liquid chromatography-mass spectrometry
Min: minutes
MTBE: methyl tert-butyl ether
PE: petroleum ether
RT: room temperature
SPB: sodium perborate
tBu: tert-butyl
TBACl: tetra-butyl ammonium chloride
TFA: trifluoroacetic acid
THF: tetrahydrofuran
TLC: thin layer chromatography
TMS: trimethylsilyl
$t_R$: retention rime
TsCl: p-toluene sulfonyl chloride
Intermediates of Ubiquitin E3 Ligase Targeting Moiety (ULM) and Protein Targeting Moiety (PTM)

Intermediate 1: (2S,4R)-1-[(2S)-2-amino-3,3-dimethylbutanoyl]-4-hydroxy-N-[[4-(4-methyl-1,3-thiazol-5-yl)phenyl]methyl]pyrrolidine-2-carboxamide hydrochloride (ULM-1)

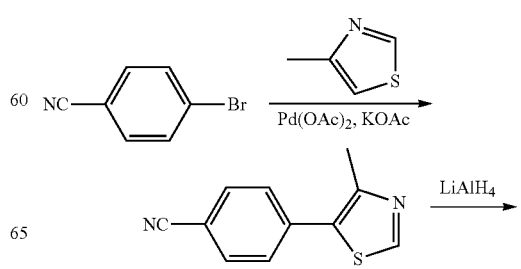

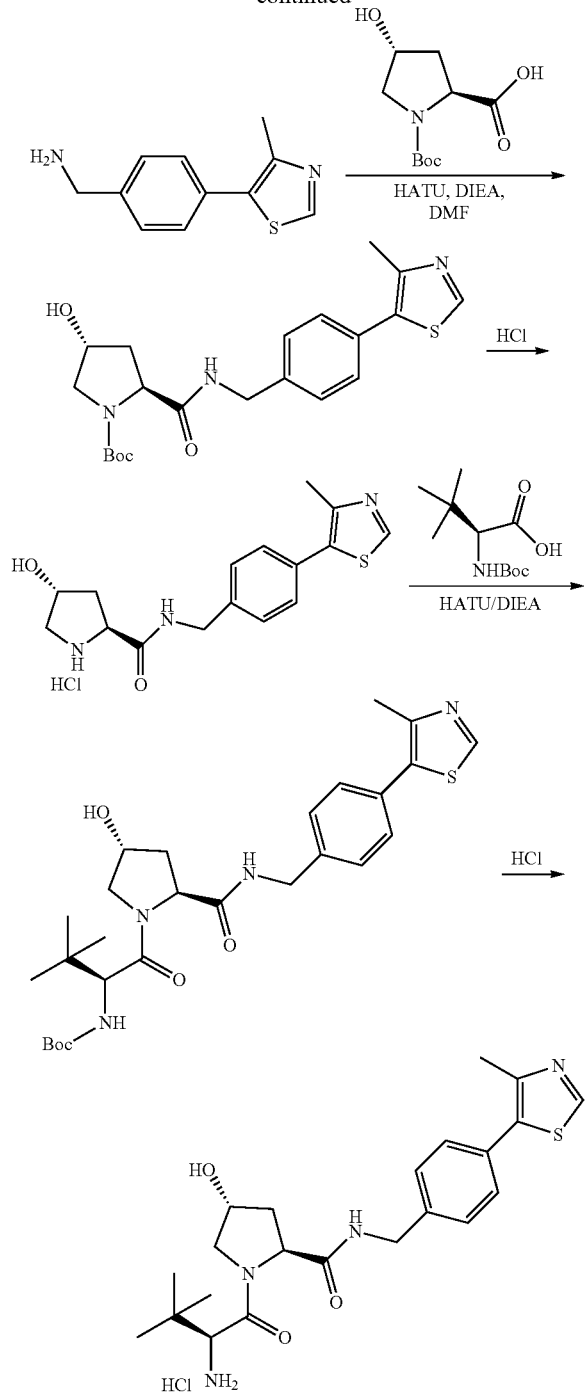

Step 1: Preparation of 4-(4-methyl-1,3-thiazol-5-yl)benzonitrile

To a stirred solution of 4-bromobenzonitrile (20 g, 109.88 mmol) in DMA (250 mL) under a nitrogen atmosphere was added 4-methyl-1,3-thiazole (21.88 g, 220.67 mmol), palladium (II) acetate (743 mg, 3.31 mmol) and potassium acetate (21.66 g, 220.71 mmol) at room temperature. The resulting mixture was heated to 150° C. and stirred at this temperature for 5 hours, at which time LC-MS indicated completion of the reaction. The mixture was cooled to room temperature, diluted with 1 L of water and extracted with ethyl acetate (300 mL×3). The organic layers were combined, washed with brine (200 mL), dried over anhydrous sodium sulfate and then concentrated under reduced pressure to give a crude residue, which was purified by flash silica gel column chromatography (eluent: ethyl acetate/ petroleum ether, v:v=1:5) to give the titled compound (yield: 91%) as a white solid.

Step 2: Preparation of [4-(4-methyl-1,3-thiazol-5-yl)phenyl]methanamine

To a stirred solution of 4-(4-methyl-1,3-thiazol-5-yl)benzonitrile (35 g, 174.77 mmol) in tetrahydrofuran (1000 mL) was added LiAlH$_4$ (20 g, 526.32 mmol) in portions at 0° C. in 10 minutes under a nitrogen atmosphere. The resulting mixture was then stirred at 60° C. for 3 hours, at which time LC-MS indicated completion of reaction. The mixture was cooled to 0° C., then quenched by the addition of water (20 mL, added slowly), aq. solution of NaOH (15%, 20 mL) and water (60 mL). The resulting mixture was then extracted with ethyl acetate (300 mL×2). The organic layers were combined, washed with brine (100 mL), dried over anhydrous sodium sulfate and then concentrated under reduced pressure to give a crude residue, which was purified by flash silica gel column chromatography (eluent: dichloromethane/ methanol (v:v=10:1)) to give the titled compound (yield: 56%) as a yellow oil.

Step 3: Preparation of tert-butyl (2S,4R)-4-hydroxy-2-([[4-(4-methyl-1,3-thiazol-5-yl)phenyl] methyl]carbamoyl)pyrrolidine-1-carboxylate To a stirred solution of (2S,4R)-1-[(tert-butoxy)carbonyl]-4-hydroxypyrrolidine-2-carboxylic acid (2.7 g, 11.68 mmol) in N,N-dimethylformamide (20 mL) was added DIPEA (2.52 g, 19.50 mmol), HATU (4.47 g, 11.76 mmol) and [4-(4-methyl-1,3-thiazol-5-yl)phenyl]methanamine (2 g, 9.79 mmol) at room temperature. The resulting mixture was stirred at room temperature overnight, at which time LC-MS indicated completion of reaction. The reaction mixture was diluted with 20 mL of water and extracted with ethyl acetate (50 mL×3). The organic layers were combined, washed with brine (50 mL), dried over anhydrous sodium sulfate and then concentrated under reduced pressure to give a crude residue, which was purified by flash silica gel column chromatography (eluent: dichloromethane/methanol (v:v=20:1)) to give the titled compound (yield: 56%) as a yellow solid.

Step 4: Preparation of (2S,4R)-4-hydroxy-N-[[4-(4-methyl-1,3-thiazol-5-yl)phenyl]methyl]pyrrolidine-2-carboxamide hydrochloride To 1 L round bottom flask containing tert-butyl (2S,4R)-4-hydroxy-2-([[4-(4-methyl-1,3-thiazol-5-yl)phenyl] methyl]carbamoyl)pyrrolidine-1-carboxylate (45 g, 107.78 mmol) in dioxane was added hydrogen chloride in dioxane (4N, 300 mL). The resulting solution was stirred for 2 hours at room temperature. The solids were collected by filtration to give the titled product (yield: 98%) as a yellow solid.

Step 5: Preparation of tert-butyl N-[(2S)-1-[(2S, 4R)-4-hydroxy-2-([[4-(4-methyl-1,3-thiazol-5-yl) phenyl]methyl]carbamoyl)pyrrolidin-1-yl]-3,3-dimethyl-1-oxobutan-2-yl]carbamate To a stirred solution of (2S)-2-{[(tert-butoxy)carbonyl] amino}-3,3-dimethylbutanoic acid (15.7 g, 68.0 mmol) in N,N-dimethylformamide (500 mL) was added DIPEA (29.2 g, 225.9 mmol), HATU (25.9 g, 68.1 mmol) and (2S,4R)-4-hydroxy-N-{[4-(4-methyl-1,3-thiazol-5-yl)-phenyl]methyl}pyrrolidine-2-carboxamide hydrochloride (20.0 g, 56.5 mmol) at room temperature.

The resulting solution was stirred at room temperature for 16 hours, LC-MS indicated formation of the desired product. The reaction mixture was diluted by water (200 mL) and extracted with ethyl acetate (200 mL×3). The organic layers were combined, washed with saturated aqueous solution of sodium chloride (50 mL×2), dried over anhydrous sodium sulfate and then concentrated under reduced pressure to give a crude residue, which was purified by flash silica gel chromatography (eluent: ethyl acetate/petroleum ether (v:v=2:1)) to give the title compound (yield: 51%) as a yellow solid.

Step 6: Synthesis of (2S,4R)-1-[(2S)-2-amino-3,3-dimethylbutanoyl]-4-hydroxy-N-[[4-(4-methyl-1,3-thiazol-5-yl)phenyl]methyl]pyrrolidine-2-carboxamide hydrochloride (ULM-1)

To a stirred solution of tert-butyl N-[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamate (12 g, 22.61 mmol) in dioxane (20 mL) was added a solution of hydrogen chloride in dioxane (4N, 80 mL) at room temperature. The resulting solution was stirred at room temperature for 2 hours, at which time LC-MS indicated completion of reaction. Precipitated solids were collected by filtration to give the titled product (yield: 48%) as a yellow solid.

d: 48%) as a yellow solid.
$^1$HNMR (400 MHz, CD$_3$OD): δ 9.84-9.82 (s, 1H), 7.58-7.54 (m, 4H), 4.71-4.41 (m, 4H), 4.13-4.08 (m, 1H), 3.86-3.71 (m, 2H), 3.36 (s, 1H), 2.60-2.58 (s, 3H), 2.35-2.07 (m, 2H), 1.19-1.12 (m, 9H). LC-MS (ES$^+$): m/z 431.11 [MH$^+$], $t_R$=0.73 min.

Intermediate 2: (2S,4R)-1-[(S)-2-amino-3,3-dimethylbutanoyl]-4-hydroxy-N—[(S)-1-(4-(4-methylthiazol-5-yl)phenyl)ethyl]-pyrrolidine-2-carboxamide hydrochloride (ULM-2)

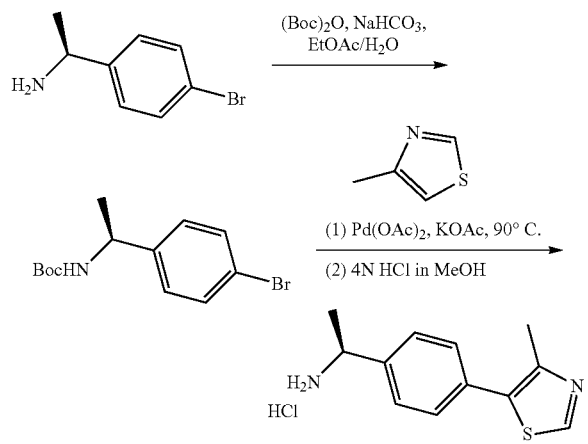

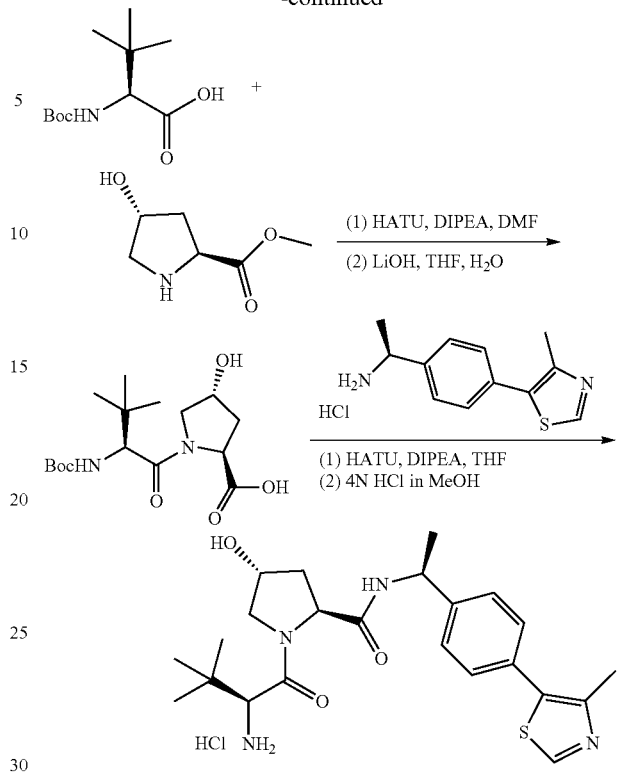

Step 1: Preparation of (S)-tert-butyl-1-(4-bromophenyl)-ethyl carbamate

To a mixture of (S)-1-(4-bromophenyl)ethanamine (3.98 g, 19.9 mmol) and NaHCO$_3$ (1.24 g, 14.8 mmol) in H$_2$O (10 mL) and ethyl acetate (10 mL) was added (Boc)$_2$O (5.20 g, 23.8 mmol) at 5° C. The reaction was continued to react for 2 hours. TLC showed reaction was complete. The reaction mixture was filtered. The solid was collected and suspended in a mixture of hexane (10 mL) and H$_2$O (10 mL) for 0.5 hours. The mixture was filtered and the solid was collected and dried in oven at 50° C. to afford the title compound as white solid (5.9 g, 98.7%).
$^1$HNMR (400 MHz, DMSO-d$_6$): δ 1.28 (d, J=7.2 Hz, 3H), 1.36 (s, 9H), 4.55-4.60 (m, 1H), 7.25 (d, J=8.4 Hz, 2H), 7.39 (br, 1H), 7.49 (d, J=8.4 Hz, 2H).

Step 2: Preparation of (S)-1-(4-(4-methylthiazol-5-yl)phenyl)ethanamine hydrochloride A mixture of (S)-tert-butyl-1-(4-bromophenyl)-ethyl carbamate (4.0 g, 13.3 mmol), 4-methylthiazole (2.64 g, 26.6 mmol), palladium (II) acetate (29.6 mg, 0.13 mmol) and potassium acetate (2.61 g, 26.6 mmol) in DMF (10 mL) was stirred at 90° C. under N$_2$ for 18 hours. After cooling to ambient temperature, the reaction mixture was filtered. To the filtrate was added H$_2$O (50 mL) and the resulting mixture was stirred at ambient temperature for 4 hours. The reaction mixture was filtered. The solid was collected by filtration and dried in oven at 50° C. to afford (S)-tert-butyl 1-(4-(4-methylthiazol-5-yl)phenyl)ethylcarbamate (3.48 g, 82.3%) as gray solid.
$^1$HNMR (400 MHz, DMSO-d$_6$): δ 1.33 (d, J=7.2 Hz, 3H), 1.38 (s, 9H), 2.46 (s, 3H), 4.64-4.68 (m, 1H), 7.23 (br d, 0.5H), 7.39 (d, J=8 Hz, 2H), 7.44 (d, J=8.4 Hz, 2H), 7.50 (br d, 0.5H), 8.99 (s, 1H); LC-MS [M+1]$^+$: 319.5

This solid material (1.9 g, 6.0 mmol) was dissolved in 4N hydrochloride in methanol (5 mL, 20 mmol, prepared from acetyl chloride and methanol) and the mixture was stirred at ambient temperature for 3 h then concentrated and triturated with ether. The mixture was filtered and the solid was collected and dried in oven at 60° C. to afford (S)-1-(4-(4-methylthiazol-5-yl)phenyl)ethanamine hydrochloride (1.3 g, 85%) as a light green solid.

$^1$HNMR (400 MHz, DMSO-d6): δ 1.56 (d, J=6.8 Hz, 3H), 2.48 (s, 3H), 4.41-4.47 (m, 1H), 7.57 (d, J=8.4 Hz, 2H), 7.67 (d, J=8.4 Hz), 8.75 (s, 3H), 9.17 (s, 1H); LC-MS [M+1]$^+$: 219.2.

Step 3: Preparation of (2S,4R)-1-{(S)-2-[(tert-butoxycarbonyl)amino]-3,3-dimethylbutanoyl}-4-hydroxypyrrolidine-2-carboxylic acid HATU (2.15 g, 5.7 mmol) was added to a solution of (S)-2-(tert-butoxycarbonyl)amino-3,3-dimethylbutanoic acid (1.25 g, 5.4 mol), (2S,4R)-methyl 4-hydroxypyrrolidine-2-carboxylate hydrochloride (0.98 g, 5.4 mmol) and DIPEA (2.43 g, 18.9 mmol) in DMF (10 mL) at 0° C. under nitrogen. The mixture was stirred at ambient temperature for 18 hours. TLC showed the reaction complete. The reaction mixture was quenched with water (30 mL) and extracted with ethyl acetate (15 mL×4). The combined organic layer was washed with the 5% citric acid (10 mL×2), saturated NaHCO$_3$ solution (10 mL×2), brine (10 mL×2) and dried over Na$_2$SO$_4$. The organic solution was filtered and concentrated to afford (2S,4R)-methyl 1-{(S)-2-[(tert-butoxycarbonyl)amino]-3,3-dimethylbutanoyl}-4-hydroxypyrrolidine-2-carboxylate as pale yellow oil (1.93 g, 100% yield). This crude product (1.93 g) and lithium hydroxide hydrate (2.2 g, 54 mmol) were taken into THF (20 mL) and H$_2$O (10 mL). The resulting mixture was stirred at ambient temperature for 18 hours. THF was removed by concentration. The residue was diluted with ice-water (10 mL) and slowly adjusted to pH 2-3 with 3N HCl. The resulting suspension was filtered, washed with H$_2$O (6 mL×2). The solid was collected by filtration and dried in oven at 50° C. to afford the title compound as a white solid (1.4 g, 75% for two steps).

$^1$HNMR (400 MHz, DMSO-d$_6$): δ 6.50 (d, J=9.6 Hz, 1H), 5.19 (br s, 1H), 4.32 (br s, 1H), 4.25 (t, J=8.4 Hz, 1H), 4.16 (d, J=9.2 Hz, 1H), 3.57-3.66 (m, 2H), 2.08-2.13 (m, 1H), 1.85-1.91 (m, 1H), 1.38 (s, 9H), 0.94 (s, 9H).

Step 4: Preparation of (2S,4R)-1-[(S)-2-amino-3,3-dimethylbutanoyl]-4-hydroxy-N—[(S)-1-(4-(4-methylthiazol-5-yl)phenyl)ethyl]-pyrrolidine-2-carboxamide hydrochloride (ULM-2)

HATU (1.6 g, 4.2 mmol) was added to a stirred solution containing (2S,4R)-1-{(S)-2-[(tert-butoxycarbonyl)amino]-3,3-dimethylbutanoyl}-4-hydroxypyrrolidine-2-carboxylic acid (1.21 g, 3.5 mmol), (S)-1-(4-(4-methylthiazol-5-yl)phenyl)ethanamine hydrochloride (0.9 g, 3.5 mmol), and DIPEA (1.36 g, 10.5 mmol) in anhydrous THF (15 mL) at 0° C. The resulting mixture was allowed to warm up to ambient temperature and continued to stir for 2 hours. TLC showed reaction completed. THF was removed by concentration. To the residue was added water (15 mL) and the resulting mixture was stirred for 4 hours. The resulting mixture was filtered. The solid was collected and dried in oven at 50° C. to give a white solid. This solid was taken into methanol (10 mL) and activated carbon (150 mg) was added. The resulting mixture was heated at 80° C. and stirred for 1 h. The mixture was filtered while it was hot. Water (5 mL) was added to the filtrate at 80° C. The resulting mixture was cooled to ambient temperature and continued to stir for 18 hours. The suspension was filtered. The solid was collected and dried in oven at 50° C. to afford tert-butyl-{(S)-1-[(2S, 4R)-4-hydroxy]-2-[(S)-1-(4-(4-methylthiazol-5-yl)phenyl)-ethylcarbamoyl]pyrrolidin-1-yl}-3,3-dimethyl-1-oxobutan-2-yl-carbamate (1.41 g, 74.2%) as a white solid.

$^1$H NMR (400 MHz, CDCl$_3$): δ 1.05 (s, 9H), 1.42 (s, 9H), 1.47 (d, J=7.2 Hz, 3H), 2.04-2.10 (m, 1H), 2.53 (s, 3H), 2.58-2.64 (m, 1H), 3.23 (s, 1H), 3.58 (dd, J=11.2 Hz, 3.2 Hz, 1H), 4.11 (d, J=11.6 Hz, 1H), 4.22 (d, J=9.2 Hz, 1H), 4.51 (br, 1H), 4.79 (t, J=8.0 Hz, 1H), 5.04-5.11 (m, 1H), 5.22 (d, J=8.8 Hz, 1H), 7.36-7.42 (m, 4H), 7.61 (d, J=7.6 Hz 1H), 8.68 (s, 1H).

This solid (1.04 g, 1.9 mmol) was dissolved in 4N hydrogen chloride in methanol (3.0 mL) and the mixture was stirred at ambient temperature for 3 hours. TLC showed reaction complete. The reaction mixture was concentrated to remove all volatiles under reduced pressure to give a light yellow solid. The solid was added to TBME (5 mL) and the resulting mixture was stirred at ambient temperature for 4 hours. The reaction mixture was filtered and the solid was collected and dried in oven at 50° C. to afford the title compound (0.92 g, 100%).

$^1$H NMR (400 MHz, DMSO-d6): δ 1.03 (s, 9H), 1.38 (d, J=7.2 Hz, 3H), 1.72-1.79 (m, 1H), 2.09-2.14 (m, 1H), 2.49 (s, 3H), 3.48-3.52 (m, 1H), 3.75-3.79 (m, 1H), 3.88-3.90 (m, 1H), 4.31 (br, 1H), 4.56 (t, J=8.4 Hz, 1H), 4.89-4.95 (m, 1H), 7.41 (d, J=8.4 Hz, 2H), 7.47 (d, J=8.4 Hz, 2H), 8.20 (br, 3H), 8.67 (d, J=7.6 Hz, 1H), 9.22 (s, 1H); 13C NMR (400 MHz, DMSO-d6): δ 170.7, 167.1, 153.0, 146.5, 145.7, 132.5, 129.4, 129.3, 126.9, 69.4, 59.3, 58.5, 56.9, 48.3, 38.4, 34.8, 26.6, 23.0, 15.7; LC-MS [M+1]$^+$: 445.6.

Intermediate 3: (2S,4R)-4-hydroxy-N-(2-hydroxy-4-(4-methylthiazol-5-yl)benzyl)-1-((S)-3-methyl-2-(1-oxoisoindolin-2-yl)butanoyl)pyrrolidine-2-carboxamide (ULM-3)

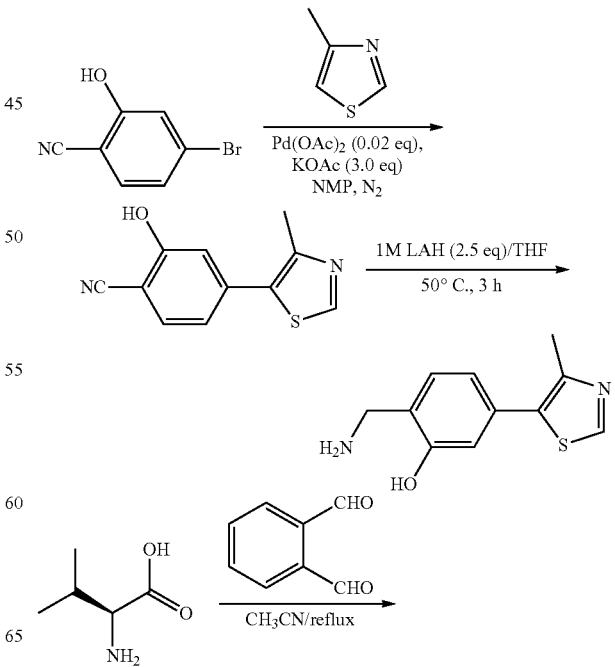

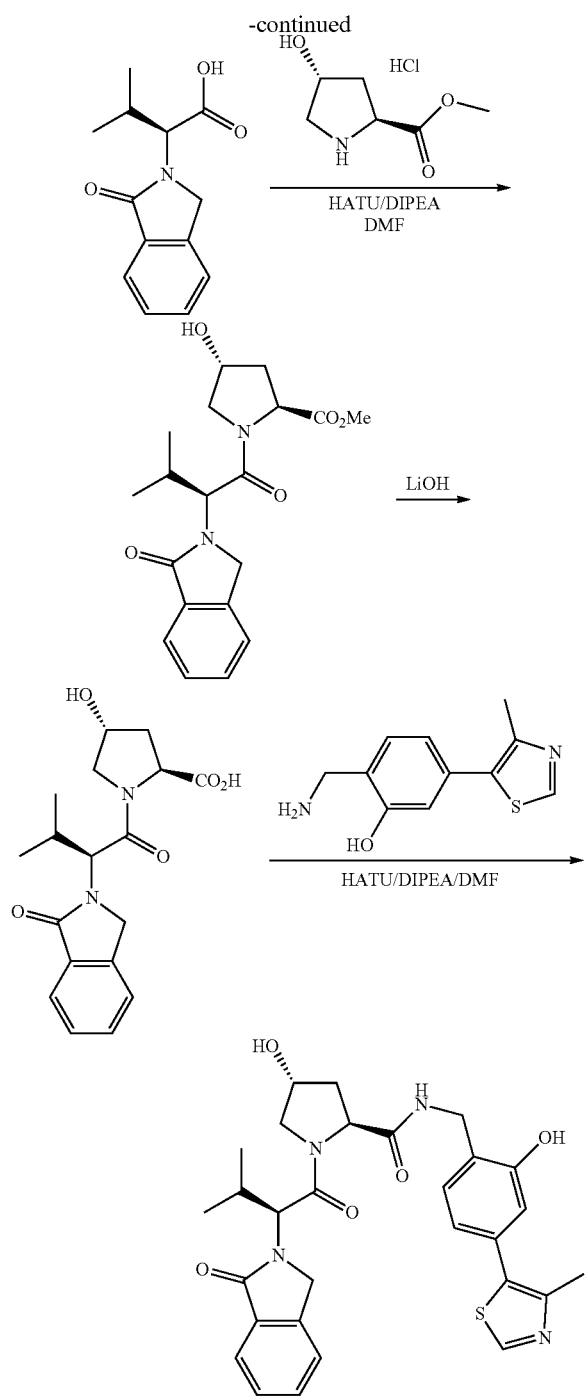

Step 1: Preparation of 2-hydroxy-4-(4-methylthiazol-5-yl) benzonitrile

A mixture of 4-bromo-2-hydroxybenzonitrile (15 g, 76 mmol), 4-methylthiazole (14 mL, 152 mmol), KOAc (14.9 g, 152 mmol) and Pd(OAc)$_2$ (0.34 g, 1.52 mmol) in dry NMP (125 mL) was stirred at 110° C. for 6 hours under nitrogen atmosphere. TLC showed the reaction was complete. The mixture was first cooled to room temperature, then partitioned between EtOAc and water. The combined organic fraction was filtered and the filtrate was washed with water, brine, dried over anhydrous Na$_2$SO$_4$, and concentrated. The residue was dissolved in toluene (100 mL) and re-evaporated to afford the crude product. The crude product was treated with cold MeOH (80 mL). The resulting precipitate was collected by filtration, washed with MeOH (20 mL), and dried under vacuum to afford the title compound as a light yellow solid (10.5 g, 64%).

LC/MS: 217.2 [M+1]$^+$.

$^1$HNMR (400 MHz, DMSO-d6): δ2.49 (s, 3H), 7.07 (dd, J=8.0, 1.6 Hz, 1H), 7.13 (d, J=1.6 Hz, 1H), 7.70 (d, J=8.0 Hz, 1H), 9.07 (s, 1H), 11.34 (s, 1H).

Step 2: Preparation of 2-(aminomethyl)-5-(4-methylthiazol-5-yl)phenol

To a solution of 2-hydroxy-4-(4-methylthiazol-5-yl)benzonitrile (2.9 g, 13.41 mmol) in dry THF (150 mL), was added LiAlH$_4$ (1.5 g, 40.23 mmol) in portions at 0° C. The resulting mixture was stirred at 50° C. for 3 h under nitrogen atmosphere. TLC showed the reaction was complete. The mixture was cooled in ice-water bath then Na$_2$SO$_4$·10H$_2$O (5 g) was added carefully and stirred at this temperature for 1 h. The mixture was filtered and the filter cake was washed with 10% MeOH in DCM for four times. The combined filtrates were concentrated to afford the crude 2-(aminomethyl)-5-(4-methylthiazol-5-yl)phenol as a light yellow solid (2.0 g, 68%). It was used in next step without further purification.

LCMS: 221.2[M+H]$^+$.

$^1$HNMR (400 MHz, DMSO-d6): δ2.43 (s, 3H), 3.54 (br, 2H), 6.11 (d, J=7.2 Hz, 1H), 6.40 (d, J=11.6 Hz, 1H), 6.83 (d, J=7.6 Hz, 1H), 8.81 (s, 1H).

Step 3: Preparation of (S)-3-methyl-2-(1-oxoisoindolin-2-yl) butanoic acid

L-Valine (4.37 g, 37.3 mmol) was added to a solution of phthalic dicarboxaldehyde (5.0 g, 37.3 mmol) in acetonitrile (350 mL). The resulting mixture was refluxed for 5 hours. The reaction mixture was filtered whilst hot and the filtrate was cooled to room temperature slowly. The resulting precipitate was filtered and dried to afford (S)-3-methyl-2-(1-oxoisoindolin-2-yl)butanoic acid as a white solid (6.45 g, 74%).

$^1$HNMR (400 MHz, DMSO-d6): δ 0.85 (d, J=6.8 Hz, 3H), 1.0 (d, J=6.8 Hz, 3H), 2.25-2.34 (m, 1H), 4.51 (d, J=4.4 Hz, 1H), 4.54 (d, J=3.6 Hz, 1H), 4.64 (d, J=18.0 Hz, 1H), 7.48-7.54 (m, 1H), 7.63 (d, J=3.6 Hz, 2H), 7.72 (d, J=7.6 Hz, 1H), 13.01 (br, 1H).

Step 4: Preparation of (2S,4R)-methyl 4-hydroxy-1-((S)-3-methyl-2-(1-oxoisoindolin-2-yl)butanoyl) pyrrolidine-2-carboxylate To a solution containing 4-hydroxy-L-proline methyl ester hydrochloride (1.0 g, 5.52 mmol), (S)-3-methyl-2-(1-oxoisoindolin-2-yl)butanoic acid (1.16 g, 4.97 mmol), and DIPEA (2.58 g, 20 mmol) in dry DMF (15 mL) was added HATU (3.8 g, 10 mmol) at 0° C. The resulting mixture was stirred at room temperature for 2 hours. The mixture was partitioned between EtOAc and water. The organic phase was washed with water, brine and dried over anhydrous Na$_2$SO$_4$. The residue was purified by silica gel chromatography using 30-50% EtOAc in hexane as eluent to afford the title compound as a light yellow solid (1.21 g, 67.6%).

LCMS: 361.3[M+1]$^+$.

Step 5: Preparation of (2S,4R)-4-hydroxy-1-((S)-3-methyl-2-(1-oxoisoindolin-2-yl)butanoyl)pyrrolidine-2-carboxylic acid A mixture containing (2S,4R)-methyl 4-hydroxy-1-((S)-3-methyl-2-(1-oxoisoindolin-2-yl)butanoyl)pyrrolidine-2-carboxylate (1.2 g, 3.33 mmol), LiOH.H$_2$O (559 mg, 13.32 mmol) in THF (20 mL) and H$_2$O (10 mL) was stirred at room temperature for 2 hours. TLC showed the reaction was complete. The reaction mixture was acidified with 1N HCl to pH 1-2, and extracted with EtOAc. The combined organic layer was washed with brine, dried over Na$_2$SO$_4$ and concentrated to afford the title compound as a light yellow solid (1.05 g, 91% yield).

$^1$HNMR (400 MHz, CDCl$_3$): δ0.91 (d, J=6.4 Hz, 3H), 1.05 (d, J=6.8 Hz, 3H), 2.30 (dd, J=8.4, 2.8 Hz, 2H), 2.44-2.50 (m, 1H), 3.75 (dd, J=11.2, 3.2 Hz, 1H), 4.42 (d, J=17.6 Hz, 1H), 4.50-4.55 (m, 2H), 4.66 (t, J=8.4 Hz, 1H), 4.75 (d, J=17.6 Hz, 1H), 4.83 (d, J=11.2 Hz, 1H), 7.42-7.45 (m, 2H), 7.51-7.56 (m, 1H), 7.78 (d, J=7.6 Hz, 1H).

Step 6: Preparation of (2S,4R)-4-hydroxy-N-(2-hydroxy-4-(4-methylthiazol-5-yl)benzyl)-1-((S)-3-methyl-2-(1-oxoisoindolin-2-yl)butanoyl)pyrrolidine-2-carboxamide To a solution containing (2S,4R)-4-hydroxy-1-((S)-3-methyl-2-(1-oxoisoindolin-2-yl)butanoyl)pyrrolidine-2-carboxylic acid (1.0 g, 2.89 mmol), 2-(aminomethyl)-5-(4-methylthiazol-5-yl)phenol (954 mg, 4.33 mmol), and DIPEA (1.5 g, 11.55 mmol) in DMF (20 mL) was added HATU (2.2 g, 5.77 mmol) at 0° C. The resulting mixture was stirred at room temperature for 1 h. TLC showed the reaction was complete. The mixture was partitioned between EtOAc and water. The organic phase was washed with water, brine and dried over anhydrous Na$_2$SO$_4$. The residue was purified by silica gel column chromatography using 2-5% MeOH in DCM to afford the title compound as a light yellow solid (650 mg, 43% yield).

LCMS: 549.2[M+H]$^+$ $^1$HNMR (400 MHz, CDCl$_3$): δ0.80 (d, J=6.8 Hz, 3H), 0.88 (d, J=6.8 Hz, 3H), 1.96-2.01 (m, 1H), 2.34-2.40 (m, 1H), 2.47-2.53 (m, 4H), 3.61 (dd, J=11.6, 3.6 Hz, 1H), 4.29-4.37 (m, 2H), 4.38-4.41 (m, 1H), 4.47-4.50 (m, 2H), 4.64-4.69 (m, 2H), 4.72 (s, 1H), 6.90 (dd, J=8.0, 2.0 Hz, 1H), 7.01 (d, J=2.0 Hz, 1H), 7.14 (d, J=8.0 Hz, 1H), 7.39-7.44 (m, 2H), 7.51-7.54 (m, 1H), 7.76 (d, J=7.6 Hz, 1H), 8.03 (t, J=6.4 Hz, 1H), 8.66 (s, 1H), 9.27 (br, 1H).

Intermediate 4: (2R,4S)-1-[(S)-2-amino-3,3-dimethylbutanoyl]-4-hydroxy-N—[(S)-1-(4-(4-methylthiazol-5-yl)phenyl)ethyl]-pyrrolidine-2-carboxamide hydrochloride (ULM-4)

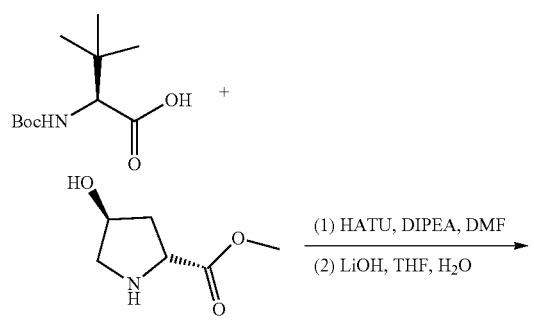

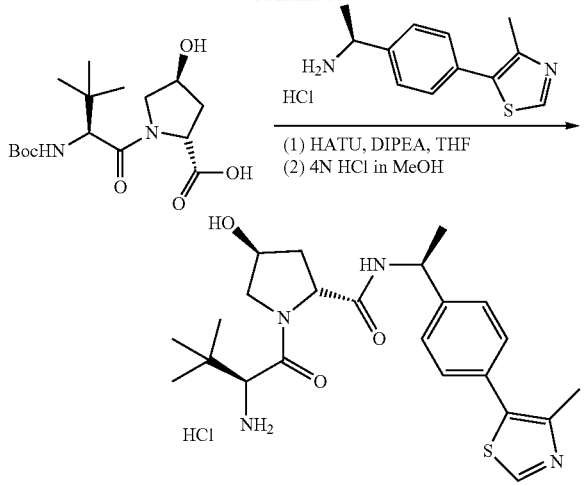

This compound was synthesized using the same method as descried in the preparation of ULM-2 using (2R,4S)-methyl 4-hydroxypyrrolidine-2-carboxylate hydrochloride.

$^1$HNMR (400 MHz, CD$_3$OD): δ 1.14 (s, 9H), 1.55 (d, J=6.8 Hz, 3H), 2.00-2.05 (m, 1H), 2.51-2.58 (m, 1H), 2.65 (s, 3H), 3.77-3.81 (m, 1H), 3.88-3.92 (m, 1H), 4.06 (br, 1H), 4.41-4.46 (m, 1H), 4.56-4.60 (m, 1H), 5.07-5.12 (m, 1H), 7.58 (d, J=8.0 Hz, 2H), 7.67 (d, J=8.0 Hz, 2H), 10.02 (s, 1H). LC-MS [M+H]$^+$: 445.3.

Intermediate 5 and Intermediate 6: tert-butyl-N-[(2S)-1-[(2S,4R)-4-hydroxy-2-{[(1R)-2-hydroxy-1-[4-(4-methyl-1,3-thiazol-5-yl)phenyl]ethyl]carbamoyl}pyrrolidin-1-yl]-3,3-dimethyl-1-oxobutan-2-yl]carbamate (ULM-5-A) and tert-butyl N-[(2S)-1-[(2S,4R)-4-hydroxy-2-{[(1S)-2-hydroxy-1-[4-(4-methyl-1,3-thiazol-5-yl)phenyl]ethyl]carbamoyl}pyrrolidin-1-yl]-3,3-dimethyl-1-oxobutan-2-yl]carbamate (ULM-5-B)

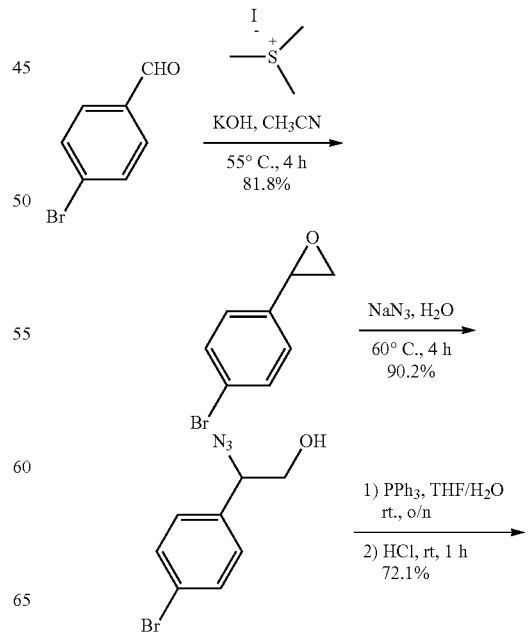

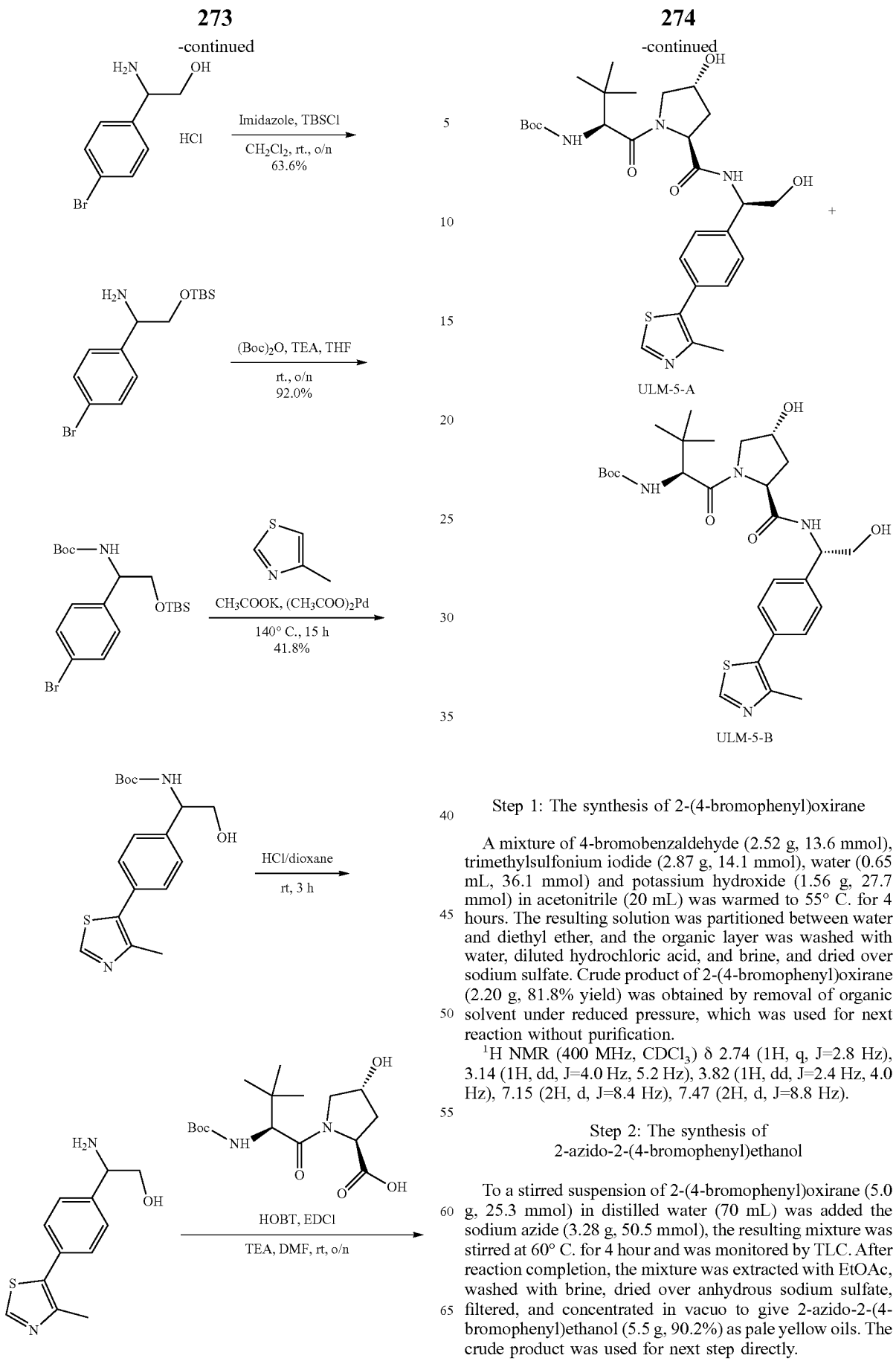

Step 1: The synthesis of 2-(4-bromophenyl)oxirane

A mixture of 4-bromobenzaldehyde (2.52 g, 13.6 mmol), trimethylsulfonium iodide (2.87 g, 14.1 mmol), water (0.65 mL, 36.1 mmol) and potassium hydroxide (1.56 g, 27.7 mmol) in acetonitrile (20 mL) was warmed to 55° C. for 4 hours. The resulting solution was partitioned between water and diethyl ether, and the organic layer was washed with water, diluted hydrochloric acid, and brine, and dried over sodium sulfate. Crude product of 2-(4-bromophenyl)oxirane (2.20 g, 81.8% yield) was obtained by removal of organic solvent under reduced pressure, which was used for next reaction without purification.

$^1$H NMR (400 MHz, CDCl$_3$) δ 2.74 (1H, q, J=2.8 Hz), 3.14 (1H, dd, J=4.0 Hz, 5.2 Hz), 3.82 (1H, dd, J=2.4 Hz, 4.0 Hz), 7.15 (2H, d, J=8.4 Hz), 7.47 (2H, d, J=8.8 Hz).

Step 2: The synthesis of 2-azido-2-(4-bromophenyl)ethanol

To a stirred suspension of 2-(4-bromophenyl)oxirane (5.0 g, 25.3 mmol) in distilled water (70 mL) was added the sodium azide (3.28 g, 50.5 mmol), the resulting mixture was stirred at 60° C. for 4 hour and was monitored by TLC. After reaction completion, the mixture was extracted with EtOAc, washed with brine, dried over anhydrous sodium sulfate, filtered, and concentrated in vacuo to give 2-azido-2-(4-bromophenyl)ethanol (5.5 g, 90.2%) as pale yellow oils. The crude product was used for next step directly.

¹H NMR (400 MHz, CDCl₃) δ 1.94 (1H, s), 3.63-3.66 (2H, m), 4.57 (1H, dd, J=5.2 Hz, 7.6 Hz), 7.15 (2H, d, J=8.4 Hz), 7.46 (2H, d, J=8.4 Hz).

Step 3: The synthesis of 2-amino-2-(4-bromophenyl)ethanol hydrochloride

To a solution of 2-azido-2-(4-bromophenyl)ethanol (2.0 g, 8.30 mmol) in tetrahydrofuran (20.0 mL) and water (5.00 mL) was added triphenylphosphine (4.35 g, 16.6 mmol). The reaction mixture was stirred at room temperature overnight and the solvent was removed in vacuo. The residue was dissolved in HCl/dioxane (4M, 10.0 mL) and stirred at room temperature for 1 hour. After being concentrated, the solid was washed with dichloromethane to give 2-amino-2-(4-bromophenyl)ethanol hydrochloride (1.5 g, 72.1% yield) as white solids.

¹H NMR (400 MHz, CDCl₃) δ 3.70 (2H, s), 4.28 (1H, s), 5.55 (1H, s), 7.47 (2H, d, J=8.4 Hz), 7.63 (2H, d, J=8.4 Hz), 8.61 (3H, s); LC/MS 216.2 [M+H]⁺.

Step 4: The synthesis of 1-(4-bromophenyl)-2-(tert-butyldimethylsilyloxy)ethanamine To a solution of 2-amino-2-(4-bromophenyl)ethanol hydrochloride (1.80 g, 7.17 mmol) in dichloromethane (50 mL) was added imidazole (1.95 g, 2.87 mmol) and tert-butyldimethylsilyl chloride (TBSCl) (1.63 g, 10.8 mmol) at room temperature. The reaction mixture was stirred at room temperature overnight and then quenched with water. The aqueous phase was extracted with dichloromethane (30 mL×3), the combined organic phases were dried over anhydrous sodium sulfate, filtered, and concentrated in vacuo to give crude compound. The crude product was purified by silica gel column chromatography (petroether/ethyl acetate=5:1) to give 1-(4-bromophenyl)-2-(tert-butyldimethylsilyloxy)ethanamine (1.50 g, 63.6%) as white solids.

LC/MS: 330.1 [M+H]⁺;

Step 5: The synthesis of tert-butyl 1-(4-bromophenyl)-2-(tert-butyldimethylsilyloxy)ethylcarbamate To a solution of 1-(4-bromophenyl)-2-(tert-butyldimethylsilyloxy)ethanamine (1.50 g, 4.56 mmol) in tetrahydrofuran (20 mL) was added triethylamine (0.69 g, 6.84 mmol) and di-tert-butyl dicarbonate (1.49 g, 6.84 mmol). The reaction mixture was stirred at room temperature overnight and then quenched with water. The aqueous phase was extracted with ethyl acetate (50 mL×3) and washed with brine. The combined organic phases were dried over anhydrous sodium sulfate, filtered and concentrated in vacuo to give crude compound. The crude product was purified by silica gel column chromatography (petroether/ethyl acetate=100:1) to give tert-butyl 1-(4-bromophenyl)-2-(tert-butyldimethylsilyloxy)ethylcarbamate (1.80 g, 92.0%) as pale yellow oils.

¹H NMR (400 MHz, CDCl₃) δ 0.01 (6H, d, J=9.6 Hz), 0.86 (9H, s), 1.42 (9H, s), 3.65-3.70 (2H, m), 4.60-4.63 (1H, m), 7.34 (2H, d, J=8.0 Hz), 7.39 (1H, d, J=8.8 Hz), 7.56 (2H, d, J=8.4 Hz).

Step 6: The synthesis of tert-butyl 2-hydroxy-1-(4-(4-methylthiazol-5-yl)phenyl)-ethylcarbamate A mixture of tert-butyl 1-(4-bromophenyl)-2-(tert-butyldimethylsilyloxy)ethylcarbamate (4.0 g, 9.32 mmol), 4-methylthiazole (1.85 g, 18.6 mmol), potassium acetate (1.82 g, 18.6 mmol), palladium (II) acetate (0.11 g, 0.47 mmol) were dissolved in dimethylacetamide and stirred under argon. The mixture was heated to 140° C. and stirred for 15 hours, then diluted with water. The aqueous phase was extracted with ethyl acetate (50 mL×3) and washed with brine. The combined organic layer was dried over sodium sulfate, filtered and concentrated under vacuum to give crude compound which was purified by silica gel column chromatography (petroether/ethyl acetate=100:1) to give tert-butyl 2-hydroxy-1-(4-(4-methylthiazol-5-yl)phenyl) ethylcarbamate (1.30 g, 41.8%) as pale yellow solids.

¹H NMR (400 MHz, CDCl₃) δ 1.38 (9H, s), 2.46 (3H, s), 3.52 (2H, t, J=6.0 Hz), 4.55-4.58 (1H, m), 4.84 (1H, t, J=6.0 Hz), 7.30 (1H, d, J=8.0 Hz), 7.38-7.45 (4H, m), 8.99 (1H, s); LC/MS 335.2 [M+H]⁺; Rt=1.859 min Step 7: The synthesis of 2-amino-2-(4-(4-methylthiazol-5-yl)phenyl)ethanol hydrochloride The tert-butyl 2-hydroxy-1-(4-(4-methylthiazol-5-yl)phenyl)ethylcarbamate (300 mg, 0.536 mmol) was dissolved in hydrochloric acid/dioxane (5 mL, 4M). The resulting reaction mixture was stirred at room temperature for 3 hours. The solvent was concentrated in vacuo to give 2-amino-2-(4-(4-methylthiazol-5-yl)phenyl)ethanol hydrochloride as white solids, which was used for the next step without further purification.

Step 8: The synthesis of tert-butyl N-[(2S)-1-[(2S,4R)-4-hydroxy-2-{[(1R)-2-hydroxy-1-[4-(4-methyl-1,3-thiazol-5-yl)phenyl]ethyl]carbamoyl}pyrrolidin-1-yl]-3,3-dimethyl-1-oxobutan-2-yl]carbamate (ULM-5-A) and tert-butyl N-[(2S)-1-[(2S,4R)-4-hydroxy-2-{[(1S)-2-hydroxy-1-[4-(4-methyl-1,3-thiazol-5-yl)phenyl]ethyl]carbamoyl}pyrrolidin-1-yl]-3,3-dimethyl-1-oxobutan-2-yl]carbamate (ULM-5-B)

A solution of 2-amino-2-(4-(4-methylthiazol-5-yl)phenyl) ethanol hydrochloride (1000 mg, 3.70 mmol), N-(3-dimethylaminopropyl)-N'-ethylcarbodiimide hydrochloride (EDCI) (995 mg, 5.19 mmol), 1-hydroxybenzotriazole (HOBT) (695 mg, 5.19 mmol), (2S,4R)-1-((S)-2-(tert-butoxycarbonylamino)-3,3-dimethylbutanoyl)-4-hydroxypyrrolidine-2-carboxylic acid (1273 mg, 3.70 mmol) and triethylamine (747 mg, 7.40 mmol) in N,N-dimethylformamide (50 mL) was stirred at room temperature overnight under agron, and then water (80 mL) was added to the mixture. The aqueous layer was extracted with ethyl acetate (50 mL×5). The combined organic layer was washed with brine (50 mL×3), dried over anhydrous sodium sulfate, and concentrated in vacuo. The crude product was purified by preparative TLC (dichloromethyl/methanol=15:1) to give tert-butyl (S)-1-((2S,4R)-4-hydroxy-2-((R)-2-hydroxy-1-(4-(4-methylthiazol-5-yl)phenyl)ethylcarbamoyl)pyrrolidin-1-yl)-3,3-dimethyl-1-oxobutan-2-ylcarbamate (700 mg) as pale yellow oils and tert-butyl (S)-1-((2S,4R)-4-hydroxy-2-((S)-2-hydroxy-1-(4-(4-methylthiazol-5-yl)phenyl) ethyl carbamoyl) pyrrolidin-1-yl)-3,3-dimethyl-1-oxobutan-2-ylcarbamate (500 mg) as pale yellow oils.

ULM-5-A: ¹H NMR (400 MHz, CDCl₃) δ 0.93 (9H, s), 1.39 (9H, s), 1.77-1.83 (1H, m), 2.01-2.06 (1H, m), 2.46 (3H, s), 3.54-3.60 (4H, m), 4.13-4.19 (1H, m), 4.29-4.36 (1H, m), 4.50 (1H, t, J=8.0 Hz), 4.78 (1H, t, J=5.6 Hz), 4.81-4.88 (1H, m), 5.12-5.16 (1H, m), 6.46 (1H, d, J=9.2

Hz), 7.36-7.46 (4H, m), 8.41 (1H, d, J=8.0 Hz), 8.99 (1H, s); LC/MS 561.2 [M+H]⁺; Rt=1.897 min ULM-5-B: ¹H NMR (400 MHz, CDCl₃) δ 0.87 (9H, s), 1.38 (9H, s), 1.92-2.06 (2H, m), 2.45 (3H, s), 3.56-3.69 (4H, m), 4.06-4.14 (1H, m), 4.36 (1H, s), 4.56 (1H, t, J=7.6 Hz), 4.76-4.81 (1H, m), 4.87 (1H, t, J=5.6 Hz), 5.146 (1H, d, J=2.8 Hz), 6.47 (1H, d, J=8.8 Hz), 7.37 (2H, d, J=8.0 Hz), 7.51 (2H, d, J=8.0 Hz), 8.37 (1H, d, J=7.6 Hz), 8.98 (1H, s); LC/MS 561.2 [M+H]⁺; Rt=1.887 min Intermediate 7: (2S,4R)—N-[(4-chloro-2-hydroxyphenyl)methyl]-4-hydroxy-1-[3-methyl-2-(3-methyl-1,2-oxazol-5-yl)butanoyl]pyrrolidine-2-carboxamide (ULM-6)

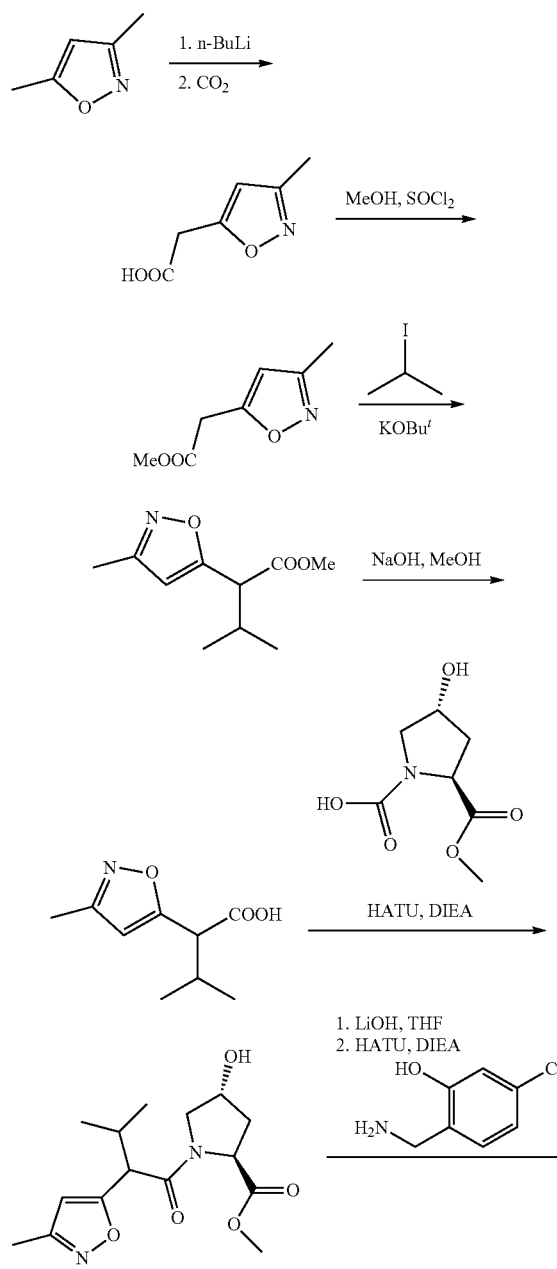

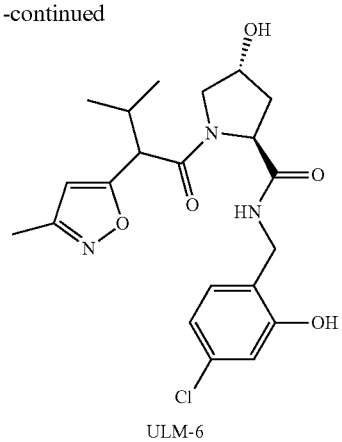

ULM-6

This key intermediate was prepared using the synthetic route above. The required 3-methylisoxazole-5-acetic acid was prepared according to the literature (J. Org. Chem. 66, 6595-6603, 2001). The alkylation with 2-iodopropane has been described in the literature. The desired ULM-6 was prepared using the same synthetic method as described in the preparation of intermediate ULM-3.

¹H NMR (400 MHz, CDCl₃): δ 9.33 (s, 0.5H), 9.20 (s, 0.5H), 8.07 (t, J=6.4 Hz, 0.5H), 7.83 (t, J=6.0 Hz, 0.5H), 6.99 (dd, J=2.4, 8.0 Hz, 1H), 6.89-6.90 (m, 1H), 6.76-6.78 (m, 1H), 6.02 (s, 0.5H), 5.99 (s, 0.5H), 5.80-5.83 (m, 0.5H), 4.35 (q, J=6.4 Hz, 1.5), 4.16-4.25 (m, 2H), 3.72-3.76 (m, 0.5H), 3.61 (d, J=9.2 Hz, 1.0H), 3.51-3.55 (m, 1.5H), 2.30-2.46 (m, 2.5H), 2.26 (s, 1.5H), 2.24 (s, 1.5H), 1.95-2.05 (m, 1H), 1.01 (d, J=6.8 Hz, 1.5H), 0.82-0.87 (m, 4.5H); LC-MS 436.1 [M+1]⁺; Rt=3.57 min.

PTM Synthesis:

Preferred PTM embodiments of the current disclosure can be prepared according to the synthetic routes in schemes 1-3 below. These routes can be modified and adapted to the synthesis of the particular PTM embodiment using general methods known to those skilled in the art.

Scheme 1

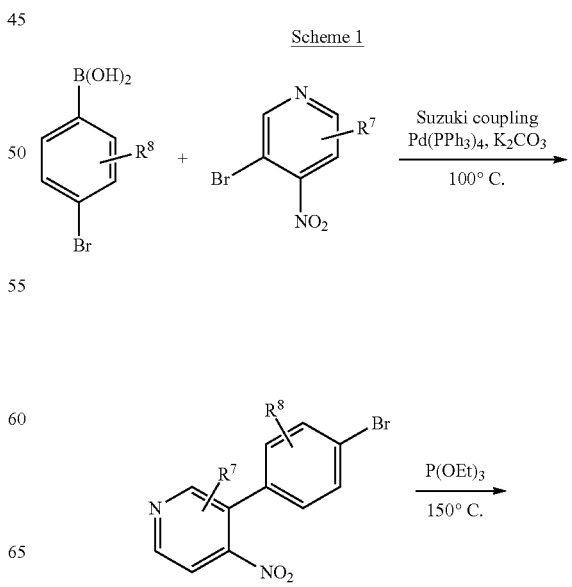

279
-continued
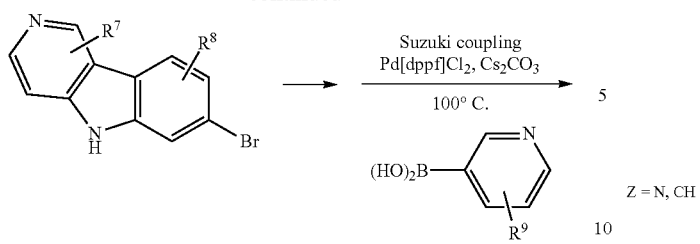
280
-continued
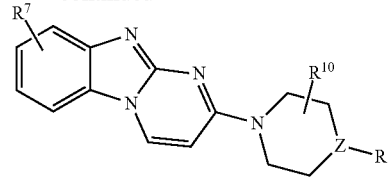
Z = N, CH
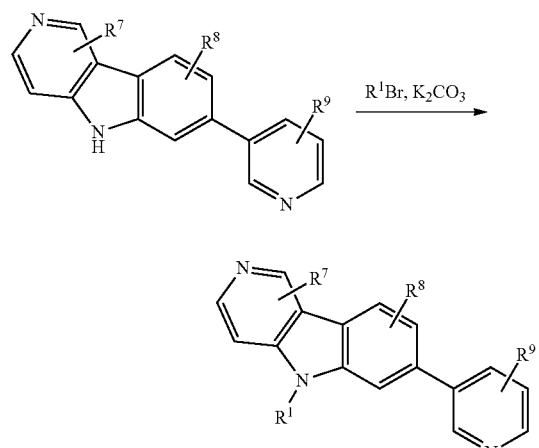
Scheme 3
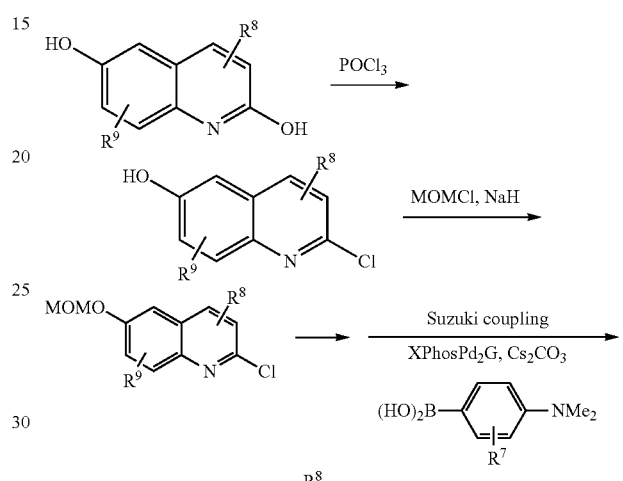
Scheme 2
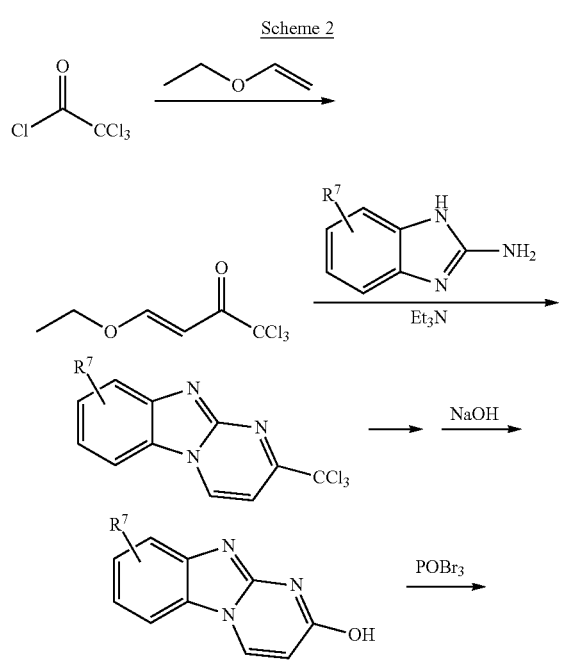
Exemplary PROTAC Synthesis:
Intermediate 1
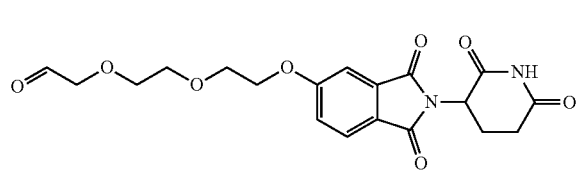 [SMILES: O=CCOCCOCCOc1ccc2c(c1)C(=O)N(C1CCC(=O)NC1=O)C2=O]

Step 1: 2-(2,6-dioxopiperidin-3-yl)-5-(2-(2-(2-hydroxyethoxy)ethoxy)ethoxy)isoindoline-1,3-dione

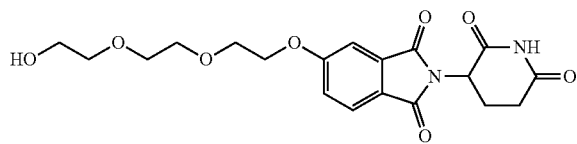 [SMILES: O=C1CCC(N2C(=O)c3ccc(OCCOCCOCCO)cc3C2=O)C(=O)N1]

To a solution of 2-(2,6-dioxopiperidin-3-yl)-5-hydroxyisoindoline-1,3-dione (500 mg, 1.82 mmol) in DMF (10 mL) were added K$_2$CO$_3$ (756 mg, 5.47 mmol) and 2-(2-(2-hydroxyethoxy)ethoxy)ethyl 4-methyl-benzenesulfonate (832 mg, 2.73 mmol) at 25° C. The resulting solution was stirred at 70° C. for 5 hours. After cooling to room temperature, the reaction was quenched with H$_2$O (10 mL), and the mixture was extracted with EtOAc (10 mL×2). The combined organic layers were dried over anhydrous sodium sulfate and concentrated. The residue was purified with silica gel column to afford the desired product (95 mg, 13% yield).

Step 2: 2-(2-(2-((2-(2,6-dioxopiperidin-3-yl)-1,3-dioxoisoindolin-5-yl)oxy)ethoxy)ethoxy)acetaldehyde

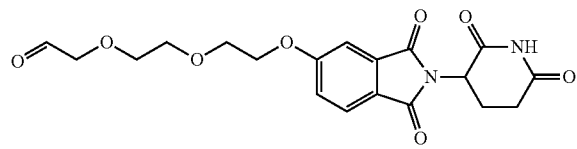 [SMILES: O=CCOCCOCCOc1ccc2c(c1)C(=O)N(C1CCC(=O)NC1=O)C2=O]

To a solution of 2-(2,6-dioxopiperidin-3-yl)-5-(2-(2-(2-hydroxyethoxy)ethoxy)ethoxy)isoindoline-1,3-dione (95 mg, 0.23 mmol) in CH$_3$CN (5 mL) was added IBX (130 mg, 0.46 mmol) at 25° C. The reaction was stirred at 80° C. for 2 hours. After cooling to room temperature, the mixture was filtered through Celite, and the filtrate was concentrated to afford crude intermediate 1, 2-(2-(2-((2-(2,6-dioxopiperidin-3-yl)-1,3-dioxoisoindolin-5-yl)oxy)ethoxy)ethoxy)acetaldehyde, (90 mg), which was used without further purification.

Intermediate 2

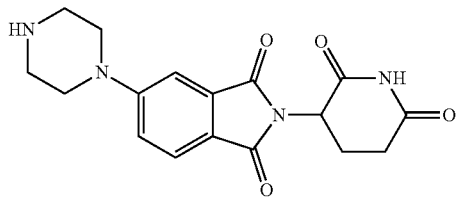 [SMILES: O=C1CCC(N2C(=O)c3ccc(N4CCNCC4)cc3C2=O)C(=O)N1]

To a solution of 2-(2,6-dioxopiperidin-3-yl)-5-fluoroisoindoline-1,3-dione (10 g, 36.2 mmol) in NMP (70 mL) was added tert-butyl piperazine-1-carboxylate (13.47 g, 72.5 mmol) and DIPEA (18.6 g, 14.5 mmol). The resulting mixture was stirred at 90° C. for 16 hours. After cooling to room temperature, the reaction was quenched with water (100 mL), and the mixture was extracted with ErOAc (300 mL×2). The combined organic layers were dried over Na$_2$SO$_4$, filtered and concentrated under reduced pressure. The residue was purified by silica gel column chromatography (PE/EA=100-2/1) to afford the desired product, 2-(2,6-dioxopiperidin-3-yl)-5-(piperazin-1-yl)isoindoline-1,3-dione (14 g, 31.67 mmol, 87.5% yield) as a light yellow solid.

Synthetic Scheme for Exemplary Compound 51

Step 1: 3-(4-bromophenyl)-4-nitropyridine

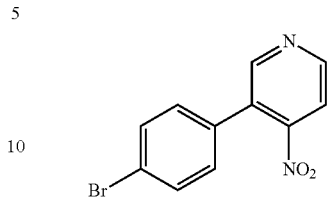

To a stirred solution of 3-bromo-4-nitropyridine (100 g, 492.6 mmol), (4-bromophenyl)boronic acid (98.6 g, 492.6 mmol), and potassium carbonate (203.9 g, 1.47 mol) in toluene (1000 ml)-water (100 ml) was added tetrakis(triphenylphosphine)palladium (14.8 g, 12.8 mmol) at room temperature under nitrogen atmosphere; the mixture was degassed with nitrogen three times. The resulting mixture was stirred at 50° C. overnight. TLC showed the reaction was complete. The solid was removed through filtration and washed with ethyl acetate (100 ml×3). The organic layer was collected and the aqueous layer was extracted with ethyl acetate (100 ml×2). The combined organic layers were washed with brine (400 ml), dried over anhydrous sodium sulfate, and concentrated under reduced pressure to give a crude residue which was purified by silica gel pad (eluted with 10-33% ethyl acetate in hexane) to afford 3-(4-bromophenyl)-4-nitropyridine (89 g, yield 65%) as yellow solid.

Step 2: 7-bromo-5H-pyrido[4,3-b]indole

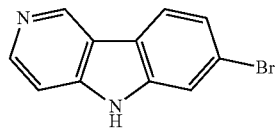 [SMILES: Brc1ccc2c(c1)[nH]c1ccncc12]

A mixture of 3-(4-bromophenyl)-4-nitropyridine (20.0 g, 71.7 mmol) in triethyl phosphate (400 ml) was stirred at 110° C. for 2 hours under nitrogen atmosphere. TLC showed the reaction was complete. The volatiles were evaporated under reduced pressure to give a residue which was purified by recrystallization (methanol) to afford 7-bromo-5H-pyrido[4,3-b]indole (11.0 g, yield 62%) as brown solid.

Step 3: 7-(6-Fluoropyridin-3-yl)-5H-pyrido[4,3-b]indole

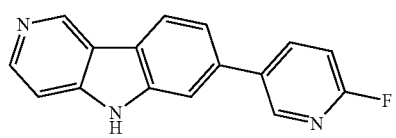 [SMILES: Fc1ccc(-c2ccc3c(c2)[nH]c2ccncc23)cn1]

A mixture of 7-bromo-5H-pyrido[4,3-b]indole (400 mg, 1.63 mmol), (6-fluoropyridin-3-yl)boronic acid (344 mg, 2.44 mmol), PdCl$_2$(dppf) (120 mg, 0.163 mmol), tBu$_3$PHBF$_4$ (95 mg, 0.326 mmol) and Cs$_2$CO$_3$ (1.1 g, 3.26 mmol) in dioxane/water (20 mL, 20:1) was heated to 90° C. for 4 hours under N$_2$. The solid was filtered and the filtrate was evaporated. The residue was purified by chromatography (silica gel, 200-300 mesh, CH$_2$Cl$_2$: MeOH=30:1) to afford 7-(6-Fluoropyridin-3-yl)-5H-pyrido[4,3-b]indole (250 mg, 59% yield).

Step 4: 14-((5-(5H-pyrido[4,3-b]indol-7-yl)pyridin-2-yl)oxy)-3,6,9,12-tetraoxatetradecan-1-ol

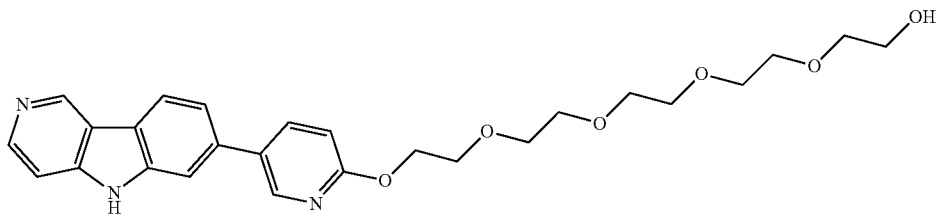 [SMILES: OCCOCCOCCOCCOCCOc1ccc(-c2ccc3c(c2)[nH]c2ccncc23)cn1]

To a solution of 3,6,9,12-tetraoxatetradecane-1,14-diol (270 mg, 1.13 mmol) in THF (10 mL) was added NaH (45 mg, 60%, 1.13 mmol) at 0° C. After stirring at 20° C. for 1 hour, a solution of 7-(6-Fluoropyridin-3-yl)-5H-pyrido[4,3-b]indole (150 mg, 0.57 mmol) in DMF (2.0 mL) was added. The resulting solution was stirred at 80° C. for 4 hours. After cooling to room temperature, the reaction was diluted with EA (30 mL), and the mixture was washed with brine. The organic phase was evaporated under reduced pressure. The residue was purified by silica gel column chromatography on silica gel (DCM/MeOH=4/1) to afford the desired product (200 mg, 72.89% yield) as a colorless oil.

Step 5: tert-butyl 7-(6-((14-hydroxy-3,6,9,12-tetraoxatetradecyl)oxy)pyridin-3-yl)-5H-pyrido[4,3-b]indole-5-carboxylate

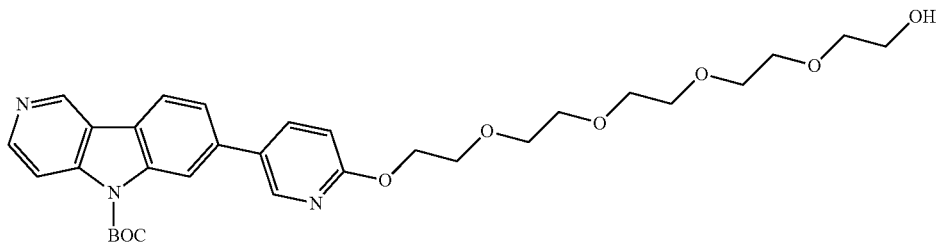 [SMILES: CC(C)(C)OC(=O)n1c2ccncc2c2ccc(-c3ccc(OCCOCCOCCOCCOCCO)nc3)cc21]

To a solution of 14-((5-(5H-pyrido[4,3-b]indol-7-yl)pyridin-2-yl)oxy)-3,6,9,12-tetraoxatetradecan-1-ol (150 mg, 0.31 mmol) in DCM (10 mL) were added NEt₃ (94.5 mg, 0.93 mmol) and Boc₂O (102.0 mg, 0.47 mmol). The resulting solution was stirred at ambient temperature for 12 hours. The solvent was removed under vacuum. The residue was diluted with EA (30 mL), and the mixture was washed with brine. The organic phase was dried over anhydrous sodium sulfate, and concentrated in vacuo to afford the desired product (120 mg, 66% yield), which was used in the next step without further purification.

Step 6: tert-butyl 7-(6-((14-((2-(2,6-dioxopiperidin-3-yl)-1,3-dioxoisoindolin-5-yl)oxy)-3,6,9,12-tetraoxatetradecyl)oxy)pyridin-3-yl)-5H-pyrido[4,3-b]indole-5-carboxylate

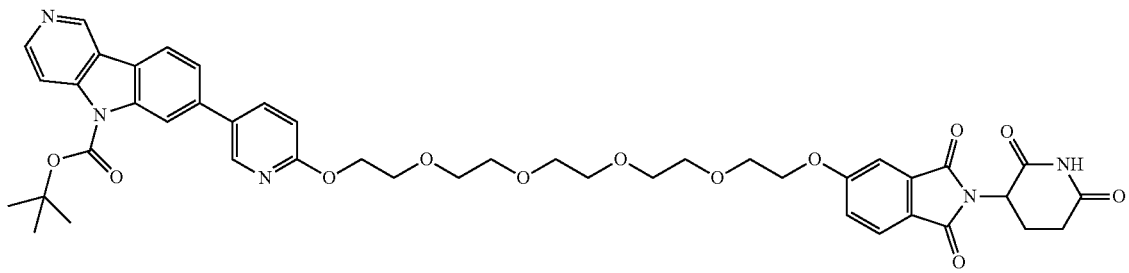 [SMILES: CC(C)(C)OC(=O)n1c2ccncc2c2ccc(-c3ccc(OCCOCCOCCOCCOCCOc4ccc5c(c4)C(=O)N(C4CCC(=O)NC4=O)C5=O)nc3)cc21]

To a solution of tert-butyl 7-(6-((14-hydroxy-3,6,9,12-tetraoxatetradecyl)oxy)pyridin-3-yl)-5H-pyrido[4,3-b]indole-5-carboxylate (120 mg, 0.31 mmol) and NEt₃ (93.9 mg, 0.93 mmol) in DCM (10 mL) was added MsCl (38.9 mg, 0.34 mmol) at 0° C. After stirring at 30° C. for 1 hour, the solvent was removed. The residue was diluted with EA (30 mL), and washed with brine. The organic phase was concentrated to give the intermediate mesylate.

To the stirred solution of mesylate (100 mg, 0.15 mmol) in dry DMF (10 mL) were added 2-(2,6-dioxopiperidin-3-yl)-5-hydroxyisoindoline-1,3-dione (45.6 mg, 0.17 mmol) and K₂CO₃ (31.4 mg, 0.23 mmol). The resulting mixture was stirred at 68° C. for 4 hours. The mixture was diluted by EtOAc (40 mL), washed with brine twice, and dried over anhydrous sodium sulfate. The organic phase was evaporated under reduced pressure. The residue was purified by prep-TLC (DCM/MeOH=20/1) to afford the desired product as a yellow solid (15 mg, 23.6% yield).

Step 7: 5-((14-((5-(5H-pyrido[4,3-b]indol-7-yl)pyridin-2-yl)oxy)-3,6,9,12-tetraoxatetradecyl)oxy)-2-(2,6-dioxopiperidin-3-yl)isoindoline-1,3-dione

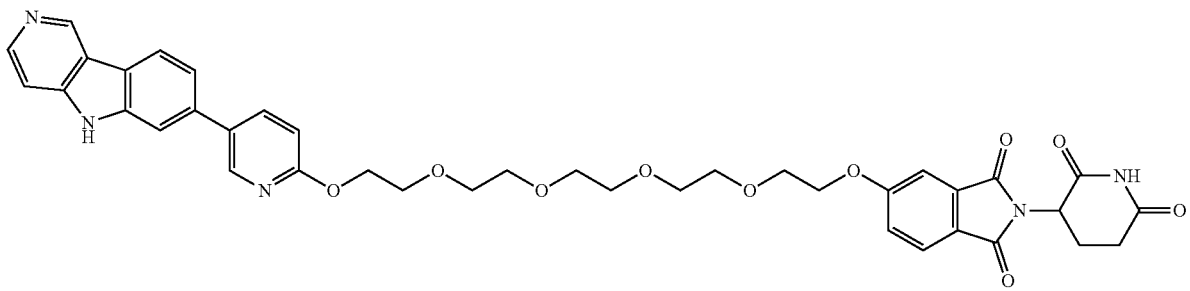 [SMILES: O=C1CCC(N2C(=O)c3ccc(OCCOCCOCCOCCOCCOc4ccc(-c5ccc6c(c5)[nH]c5ccncc56)cn4)cc3C2=O)C(=O)N1]

To a solution of tert-butyl 7-(6-((14-((2-(2,6-dioxopiperidin-3-yl)-1,3-dioxoisoindolin-5-yl)oxy)-3,6,9,12-tetraoxatetradecyl)oxy)pyridin-3-yl)-5H-pyrido[4,3-b]indole-5-carboxylate (30 mg, 0.036 mmol) in DCM (2 mL) was added TFA (5 mL). The mixture was stirred at ambient temperature for 4 hours. The mixture was evaporated under reduced pressure. The residue was purified by prep-HPLC to afford the title compound as a white solid (10 mg, 38% yield). ¹H NMR (400 MHz, CDCl₃): δ 12.34-12.48 (m, 1H), 9.19-9.29 (m, 1H), 8.80 (s, 1H), 8.29-8.42 (m, 1H), 8.02-8.14 (m, 1H), 7.95 (s, 1H), 7.69-7.81 (m, 1H), 7.60 (s, 2H), 7.17 (s, 1H), 7.09 (s, 1H), 6.62 (s, 1H), 4.97 (s, 1H), 4.43 (s, 2H), 4.14 (s, 2H), 3.88 (d, J=24.1 Hz, 3H), 3.78 (d, J=8.2 Hz, 3H), 3.69 (d, J=10.0 Hz, 6H), 2.80 (m, 4H), 1.99-2.29 (m, 4H). (M+H)⁺ 738.3.

Using procedures analogous to those for Compound 51, Compound 50 was also prepared.

Synthetic Scheme for Exemplary Compound 52

Step 1: tert-butyl 4-(2-hydroxyethyl)piperazine-1-carboxylate

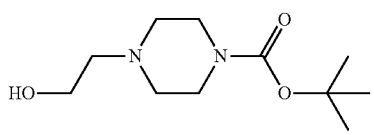 [SMILES: CC(C)(C)OC(=O)N1CCN(CCO)CC1]

The solution of 2-(piperazin-1-yl)ethanol (5 g, 38.5 mmol) and TEA (12 g, 115 mmol) was stirred in DCM at 0° C., Boc₂O was added, then the mixture was stirred at 10° C. overnight. Water was added. Then the mixture was extracted with DCM, dried and concentrated, and filtered through a silica gel pad to get 8.1 g product (92% yield).

Step 2: tert-butyl 4-(2-(prop-2-yn-1-yloxy)ethyl)piperazine-1-carboxylate

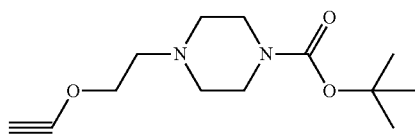 [SMILES: C#COCCN1CCN(C(=O)OC(C)(C)C)CC1]

The solution of tert-butyl 4-(2-hydroxyethyl)piperazine-1-carboxylate (3 g, 13 mmol) in THF was stirred at 0° C. NaH (624 mg, 15.6 mmol) was added, then, the mixture was stirred at room temperature for 1 hour. 3-bromoprop-1-yne (1.85 g, 15.6 mmol) was added, and stirring was continued at 70° C. overnight. Then the mixture was cooled to room temperature. Water was added, then the mixture was extracted with EA, dried with Na₂SO₄ and concentrated. Filtered through a silica gel pad (EA) to get 1.5 g product (43% yield).

Step 3: tert-butyl 4-(2-((3-(5-bromopyridin-2-yl)prop-2-yn-1-yl)oxy)ethyl)piperazine-1-carboxylate

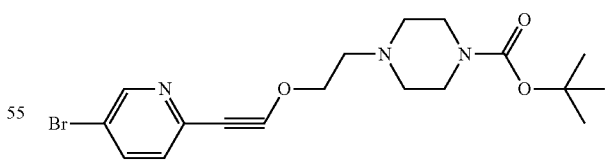

tert-butyl 4-(2-(prop-2-yn-1-yloxy)ethyl)piperazine-1-carboxylate (500 mg, 1.86 mmol), 2,5-dibromopyridine (442 mg, 1.86 mmol), Pd(PPh₃)₂Cl₂ (10%), CuI (11%), DIPEA and CH₃CN were stirred at 5° C. overnight, and EA was added. The mixture was washed by water, concentrated. Then filtered through a silica gel pad (EA) to get 450 mg product (57% yield).

Step 4: tert-butyl 4-(2-(3-(5-(5H-pyrido[4,3-b]indol-7-yl)pyridin-2-yl)propoxy)ethyl)piperazine-1-carboxylate

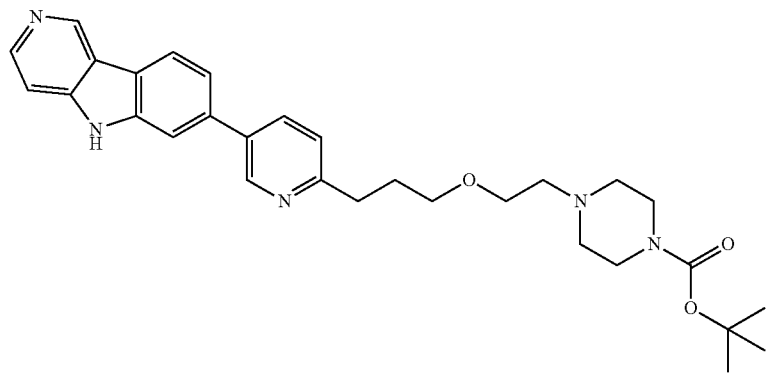 [SMILES: CC(C)(C)OC(=O)N1CCN(CCOCCCc2ccc(-c3ccc4c(c3)[nH]c3ccncc34)cn2)CC1]

7-(4,4,5,5-tetramethyl-1,3,2-dioxaborolan-2-yl)-5H-pyrido[4,3-b]indole-5-carboxylate [prepared by using procedure analogous to that of step 1 of Exemplary Compound 63] (300 mg, 0.76 mmol), Pd(aMphose)Cl$_2$ (50 mg, 10%), and CsF (450 mg, 2.96 mmol) was stirred in CH$_3$CN/H$_2$O (10:1) at 120° C. in the microwave for 40 minutes. The mixture was cooled to room temperature, and EA was added. The organic layer was washed by water, then filtered through a silica gel pad (DCM:MeOH=20:1) to get 100 mg tert-butyl 4-(2-(3-(5-(5H-pyrido[4,3-b]indol-7-yl)pyridin-2-yl)prop-2-ynyloxy)ethyl)piperazine-1-carboxylate. The crude product was dissolved in MeOH, Pd/C was added, and the mixture was stirred at 30° C. under 2 Mpa of H$_2$ for 2 hours, filtered and concentrated to produce 100 mg of product (26% yield).

Step 5: 7-(6-(3-(2-(piperazin-1-yl)ethoxy)propyl)pyridin-3-yl)-5H-pyrido[4,3-b]indole

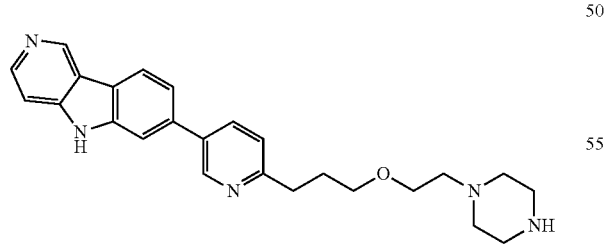

tert-butyl 4-(2-(3-(5-(5H-pyrido[4,3-b]indol-7-yl)pyridin-2-yl)propoxy)ethyl)piperazine-1-carboxylate (100 mg, 0.2 mmol) in HCl/dioxane solution (2 mL) was stirred at 5° C. for 1 hour. Concentrated to obtain 100 mg of crude product.

Step 6: 5-((5-(4-(2-(3-(5-(5H-pyrido[4,3-b]indol-7-yl)pyridin-2-yl)propoxy)ethyl)piperazin-1-yl)pentyl)oxy)-2-(2,6-dioxopiperidin-3-yl)isoindoline-1,3-dione

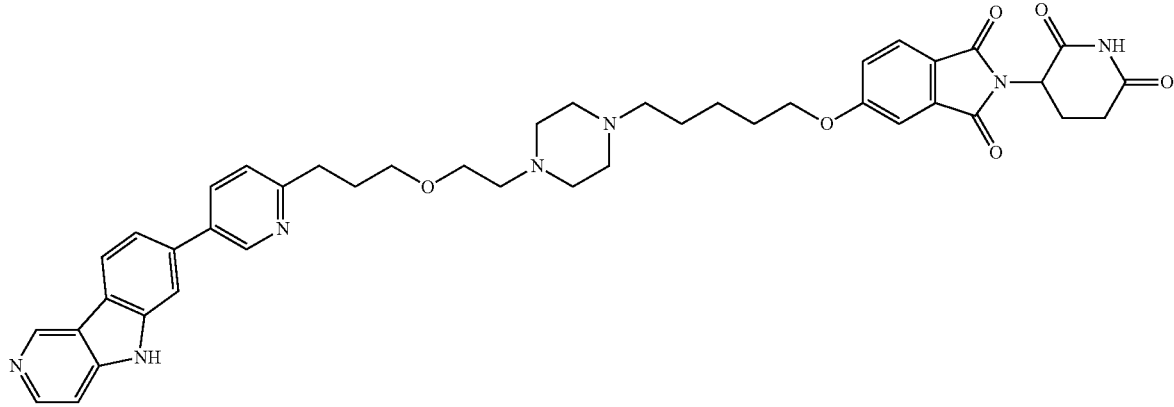 [SMILES: O=C1CCC(N2C(=O)c3ccc(OCCCCCN4CCN(CCOCCCc5ccc(-c6ccc7c(c6)[nH]c6ccncc67)cn5)CC4)cc3C2=O)C(=O)N1]

5-(2-(2,6-dioxopiperidin-3-yl)-1,3-dioxoisoindolin-5-yloxy)pentanal (86 mg, 0.24 mmol), NaBH$_4$CN (55 mg, 0.48 mmol) and CH$_3$COOH (cat.) was stirred in MeOH at 5° C. for 3 hours. Then DCM added. The organic layer was washed by water, concentrated, and filtered through silica gel pad (DCM:MeOH=8:1) to afford 11 mg of product.

$^1$HNMR (400 MHz, MeOD): δ 9.25 (s, 1H), 8.79 (s, 1H), 8.37-8.39 (d, J=8 Hz, 1H), 8.28-8.30 (d, J=8 Hz, 1H), 8.11-8.13 (d, J=8 Hz, 1H), 7.80 (s, 1H), 7.75-7.77 (d, J=8 Hz, 1H), 7.60 (s, 1H), 7.49-7.51 (d, J=8 Hz, 1H), 7.43-7.45 (d, J=8 Hz, 1H), 7.33 (s, 1H), 5.07-5.09 (m, 1H), 4.06-4.09 (m, 2H), 3.57-3.60 (m, 2H), 3.51-3.54 (m, 2H), 2.93-2.95 (m, 2H), 2.91-2.93 (m, 1H), 2.59-2.75 (m, 12H), 2.37-2.41 (m, 2H), 2.04-2.06 (m, 3H), 1.78-1.80 (m, 2H), 1.46-1.55 (m, 5H). (M+H)$^+$ 758.3.

Synthetic Scheme for Exemplary Compound 53

Step 1: (((1s,3s)-3-(allyloxy)cyclobutoxy)methyl)benzene

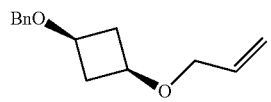 [SMILES: C=CCO[C@H]1C[C@@H](OCc2ccccc2)C1]

To a solution of (1s, 3s)-3-(benzyloxy)cyclobutanol (1.0 g, 5.61 mmol) in DMF (10 mL) was added NaH (60%, 0.336 g, 8.4 mmol) at 0° C. After stirring for 30 min, 3-bromoprop-1-ene was added dropwise at room temperature. The resulting solution was stirred at room temperature for 3 hours. After it was quenched with saturated solution NH$_4$Cl (20 mL), the mixture was extracted with EtOAc (20 mL×2). The combined organic layers were dried with Na$_2$SO$_4$ and concentrated under vacuum. The residue was purified by silica gel column with PE/EA=10-1: as eluent to afford the desired product (1.0 g, 82%) as a colorless oil.

Step 2: 3-((1s,3s)-3-(benzyloxy)cyclobutoxy)propan-1-ol

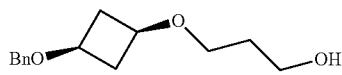 [SMILES: OCCCO[C@H]1C[C@@H](OCc2ccccc2)C1]

To a solution of (((1s,3s)-3-(allyloxy)cyclobutoxy)methyl)benzene (1.0 g, 4.58 mmol) in THF (20 mL) was added dicyclohexylborane in THF (1.0 M, 9.0 mL) at 0° C. After it was stirred at room temperature for 4 hours, NaOH (37%, 3.0 mL) and H$_2$O$_2$ (30%, 3.0 mL) were added to the mixture at 0° C. The resulting solution was stirred at room temperature overnight. The reaction was quenched with Na$_2$S$_2$O$_3$ (20 mL). The mixture was taken up in DCM. The organic phase was dried with Na$_2$SO$_4$ and concentrated under vacuum. The residue was purified on silica gel column with PE/EA=2:1 as eluent to afford the desired product (1.0 g, 100%) as a colorless oil.

Step 3: tert-butyl 4-(3-((1s,3s)-3-(benzyloxy)cyclobutoxy)propyl)piperazine-1-carboxylate

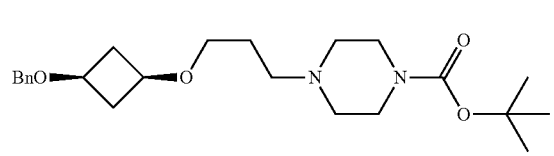 [SMILES: CC(C)(C)OC(=O)N1CCN(CCCO[C@H]2C[C@@H](OCc3ccccc3)C2)CC1]

To a solution of 3-((1s,3s)-3-(benzyloxy)cyclobutoxy)propan-1-ol (1.0 g, 4.58 mmol) and TEA (2.0 g, 19.8 mmol) in DCM (10 mL) was added MsCl (0.97 g, 9.2 mmol) at 0° C. After stirring at room temperature for 2 hours, the reaction was quenched with saturated solution of sodium bicarbonate (20 mL), and the mixture was extracted DCM (20 mL×2). The combined organic layers were dried with Na$_2$SO$_4$, and concentrated under vacuum to afford the desired product (1.1 g, crude), which was used in the next reaction without further purification.

To a solution of the above intermediate (1.1 g, crude) in DMF (10 mL) was added tert-butyl piperazine-1-carboxylate (1.60 g, 9.2 mmol). The resulting solution was heated to 90° C. for 4 hours. After cooling to room temperature, the reaction was quenched with water (20 mL) and the mixture was extracted with EtOAc (20 mL×3). The combined organic layers were dried over Na$_2$SO$_4$, and concentrated under vacuum. The residue was purified by silica gel column with PE/EA=2:1 as eluent to afford the desired product (980 mg, 58%) as a colorless oil.

Step 4: tert-butyl 4-(3-((1s,3s)-3-hydroxycyclobutoxy)propyl)piperazine-1-carboxylate

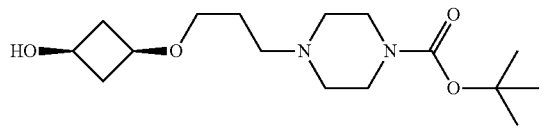 [SMILES: CC(C)(C)OC(=O)N1CCN(CCCO[C@H]2C[C@@H](O)C2)CC1]

A mixture of tert-butyl 4-(3-((1s,3s)-3-(benzyloxy)cyclobutoxy)propyl)piperazine-1-carboxylate (980 mg, 2.42 mmol) and Pd(OH)$_2$/C (300 mg, 20%) in CH$_3$OH (10 mL) was stirred at room temperature overnight under H$_2$ at 1 atm. The mixture was filtered through Celite, and the filtrate was concentrated to afford the desired product (700 mg, crude) which was used in the next reaction without further purification.

Step 5: tert-butyl 4-(3-((1s,3s)-3-((5-(5H-pyrido[4,3-b]indol-7-yl)pyridin-2-yl)oxy)cyclobutoxy)propyl)piperazine-1-carboxylate

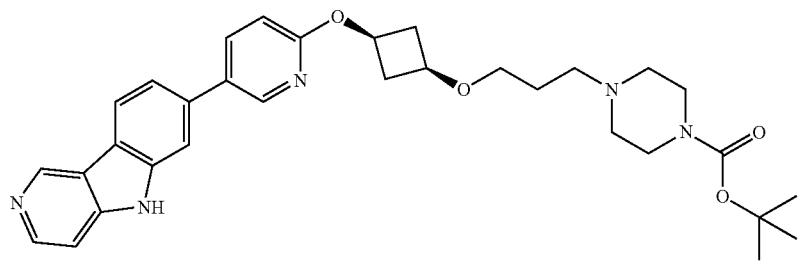 [SMILES: CC(C)(C)OC(=O)N1CCN(CCCO[C@H]2C[C@@H](Oc3ccc(-c4ccc5c(c4)[nH]c4ccncc45)cn3)C2)CC1]

To a solution of tert-butyl 4-(3-((1s,3s)-3-hydroxycyclobutoxy)propyl)piperazine-1-carboxylate (180 mg, 0.57 mmol) and 7-(6-Fluoropyridin-3-yl)-5H-pyrido[4,3-b]indole (100 mg, 0.379 mmol) in NMP (10 mL) was added NaH (60%, 100 mg, 2.5 mmol) at room temperature. The resulting solution was heated to 90° C. for 2 hours. After cooling to room temperature, the reaction was quenched with saturated solution of NH$_4$Cl (20 mL), and the mixture was extracted with EtOAc (20 mL×3). The combined organic layers were dried with Na$_2$SO$_4$ and concentrated under vacuum. The residue was purified by prep-TLC with DCM/CH$_3$OH (15:1) to afford the desired product (120 mg, 0.21 mmol) as a brown solid.

Step 6: 7-(6-((1s,3s)-3-(3-(piperazin-1-yl)propoxy)cyclobutoxy)pyridin-3-yl)-5H-pyrido[4,3-b]indole

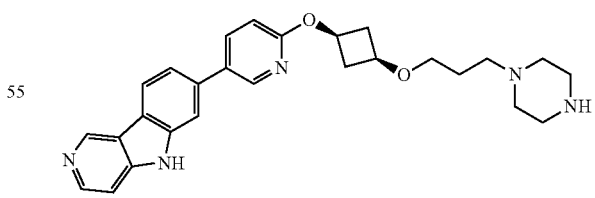

A mixture of tert-butyl 4-(3-((1s,3s)-3-((5-(5H-pyrido[4,3-b]indol-7-yl)pyridin-2-yl)oxy)cyclobutoxy)propyl)piperazine-1-carboxylate (120 mg, 0.21 mmol) in CH$_3$OH (2.0 mL) and HCl in 1,4-dioxane (4.0 mL) was stirred at room temperature for 2 hours. The solvent was removed under vacuum to afford the desired product (100 mg, crude), which was used in the next reaction without further purification.

Step 7: 5-(4-(3-(((1s,3s)-3-((5-(5H-pyrido[4,3-b]indol-7-yl)pyridin-2-yl)oxy)cyclobutoxy)propyl)piperazin-1-yl)-2-(2,6-dioxopiperidin-3-yl)isoindoline-1,3-dione

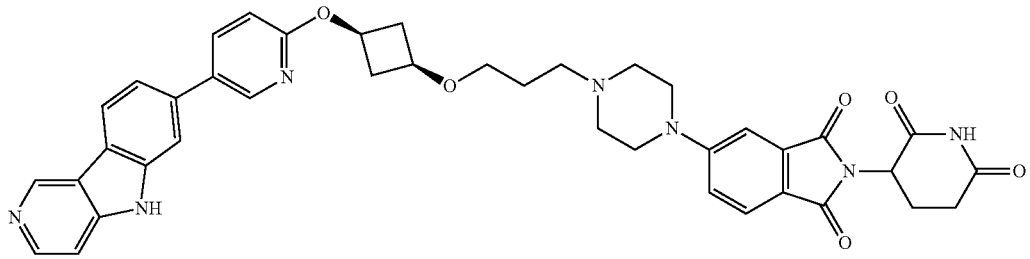 [SMILES: O=C1CCC(N2C(=O)c3ccc(N4CCN(CCCO[C@H]5C[C@@H](Oc6ccc(-c7ccc8c(c7)[nH]c7ccncc78)cn6)C5)CC4)cc3C2=O)C(=O)N1]

To a mixture of 7-(6-(((1 s,3s)-3-(3-(piperazin-1-yl)propoxy)cyclobutoxy)pyridin-3-yl)-5H-pyrido[4,3-b]indole (80 mg, crude) and DIEA (300 mg, 2.36 mmol) in NMP (2.0 mL) was added 2-(2,6-dioxopiperidin-3-yl)-5-fluoroisoindoline-1,3-dione (100 mg, 0.36 mmol). The mixture was microwave heated at 130° C. for 45 minutes. After cooling to room temperature, the reaction was taken up with EtOAc (100 mL). The mixture was washed with brine (20 mL×3). The organic phase was dried with Na$_2$SO$_4$, and concentrated under vacuum. The residue was purified by prep-TLC with DCM/CH$_3$OH/NH$_3$H$_2$O (15:1:0.1) to afford the title product (16.0 mg, 13%) as a yellow solid.

$^1$H NMR (400 MHz, CDCl$_3$): δ 9.34 (s, 1H), 8.55 (d, J=5.6 Hz, 1H), 8.44 (m, 2H), 8.20 (d, J=8.4 Hz, 1H), 7.87-7.92 (m, 3H), 7.68 (d, J=8.4 Hz, 1H), 7.60 (s, 1H), 7.48-7.50 (m, 1H), 7.38 (d, J=5.6 Hz, 1H), 7.06 (m, 1H), 6.84 (d, J=8.8 Hz, 2H), 4.93-4.94 (m, 2H), 3.75 (m, 2H), 3.42-3.49 (m, 6H), 2.72-2.98 (m, 5H), 2.61 (s, 4H), 2.53 (t, J=7.2 Hz, 2H), 2.15-2.18 (m, 2H), 1.81 (t, J=6.8 Hz, 2H). (M+H)$^+$ 714.3

Synthetic Scheme for Exemplary Compound 55

Step 1: tert-butyl I-4-(5-(3-methoxy-3-oxoprop-1-en-1-yl)pyridin-2-yl)piperazine-1-carboxylate

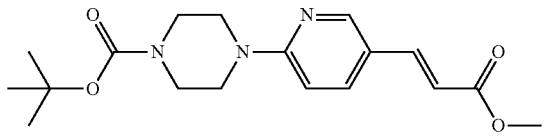

To a solution of tert-butyl 4-(5-formylpyridin-2-yl)piperazine-1-carboxylate (1.0 g, 3.44 mmol) and methyl 2-(dimethoxyphosphoryl)acetate (750 mg, 4.12 mmol) in THF (15 ml) was added DBU (1.57 g, 10.3 mmol). The reaction mixture was stirred at room temperature overnight. After it was quenched with water H$_2$O (10 mL), the mixture was extracted with ethyl acetate (50 mL). The organic phase was washed with brine, and dried over Na$_2$SO$_4$. It was filtered, and concentrated under vacuum. The residue was broken with petroleum ether to afford the desired product (800 mg, 2.3 mmol, yield: 66.9%) as a pale solid.

Step 2: tert-butyl 4-(5-(3-hydroxypropyl)pyridin-2-yl)piperazine-1-carboxylate

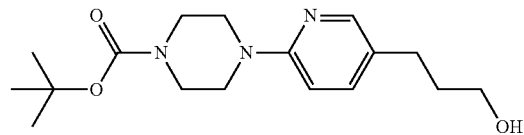 [SMILES: CC(C)(C)OC(=O)N1CCN(c2ccc(CCCO)cn2)CC1]

To a solution of tert-butyl I-4-(5-(3-methoxy-3-oxoprop-1-en-1-yl)pyridin-2-yl)piperazine-1-carboxylate.

(800 mg, 2.3 mmol) in CH$_3$OH (8 mL) and THF (35 mL) was added NaBH$_4$ (874 mg, 23.0 mmol). The mixture was heated to 80° C. for 3 hours. After cooling to room temperature, the reaction was quenched with 2N NH$_4$Cl, and the mixture was extracted with EtOAc (80 mL×3). The combined organic layers were washed with brine, and dried (Na$_2$SO$_4$), filtered and concentrated under reduced pressure. The residue was purified by silica gel column (EA:PE=1:1) to give the desired compound (420 mg, 1.31 mmol, yield: 57.0%) as a yellow oil.

Step 3: tert-butyl 4-(5-(3-((methylsulfonyl)oxy)propyl)pyridin-2-yl)piperazine-1-carboxylate

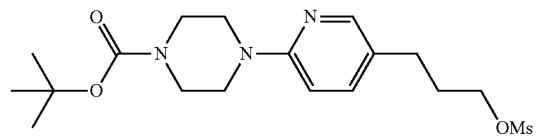 [SMILES: CC(C)(C)OC(=O)N1CCN(c2ccc(CCCOS(C)(=O)=O)cn2)CC1]

To a solution of tert-butyl 4-(5-(3-hydroxypropyl)pyridin-2-yl)piperazine-1-carboxylate (50 mg, 0.16 mmol) and Et$_3$N (48 mg, 0.48 mmol) in DCM (2 mL) was added MsCl (27 mg, 0.23 mmol). The reaction was stirred at room temperature for 1 hour. After it was quenched with water H$_2$O (30 mL), the mixture was extracted with DCM (20 mL). The organic phase was washed with brine, dried over Na$_2$SO$_4$, filtered, and concentrated under vacuum to give the crude desired compound (64 mg) as a yellow oil which was used in the next reaction without further purification.

Step 4: tert-butyl 4-(5-(3-((2-(2,6-dioxopiperidin-3-yl)-1,3-dioxoisoindolin-5-yl)oxy)propyl)pyridin-2-yl)piperazine-1-carboxylate

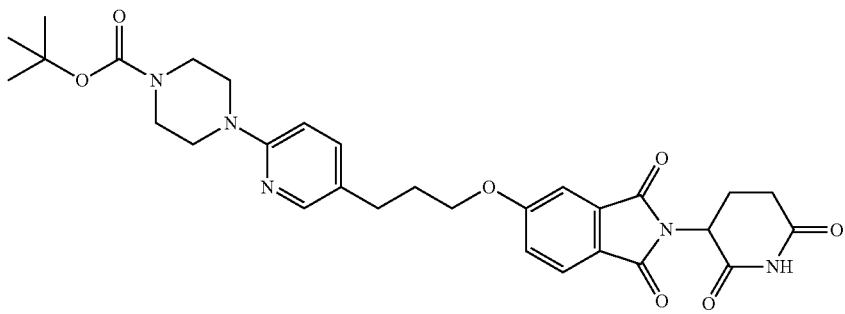 [SMILES: CC(C)(C)OC(=O)N1CCN(c2ccc(CCCOc3ccc4c(c3)C(=O)N(C3CCC(=O)NC3=O)C4=O)cn2)CC1]

To a solution of tert-butyl 4-(5-(3-((methylsulfonyl)oxy)propyl)pyridin-2-yl)piperazine-1-carboxylate (64 mg, 0.16 mmol) and 2-(2,6-dioxopiperidin-3-yl)-5-hydroxyisoindoline-1,3-dione (66 mg, 0.24 mmol) in DMF (5 ML) was added $K_2CO_3$ (55 mg, 0.40 mmol). The reaction mixture was stirred at 90° C. for 2 hours. After cooling to room temperature, the reaction was quenched water (5 mL), and the mixture was extracted with dichloromethane (30 mL). The organic phase was washed with water and brine, dried over $Na_2SO_4$, filtered, and concentrated under reduced pressure. The residue was purified by silica gel column (MeOH:DCM=1:100-1:20) to give the title product (30 mg, 0.052 mmol, yield: 32%).

Step 5: 2-(2,6-dioxopiperidin-3-yl)-5-(3-(6-(piperazin-1-yl)pyridin-3-yl)propoxy)isoindoline-1,3-dione

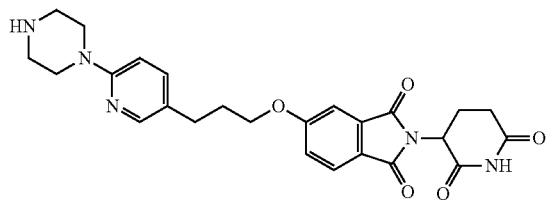 [SMILES: O=C1CCC(N2C(=O)c3ccc(OCCCc4ccc(N5CCNCC5)nc4)cc3C2=O)C(=O)N1]

To a solution of tert-butyl 4-(5-(3-((2-(2,6-dioxopiperidin-3-yl)-1,3-dioxoisoindolin-5-yl)oxy)propyl)pyridin-2-yl)piperazine-1-carboxylate (200 mg, 0.39 mmol) in dioxane (10 mL) was added 6N HCl in dioxane (2 mL, 12.0 mmol). The reaction mixture was stirred at room temperature for 2 hours. The solvent was removed under reduced pressure to give the crude title product (200 mg) as a yellow solid.

Step 6: (6-(3-Hydroxyprop-1-yn-1-yl)pyridin-3-yl)boronic Acid

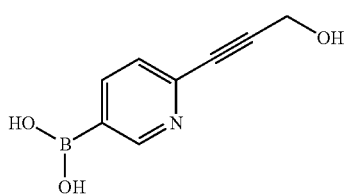 [SMILES: OCC#Cc1ccc(B(O)O)cn1]

To a solution of (6-bromopyridin-3-yl)boronic acid (1.0 g, 4.95 mmol) and prop-2-yn-1-ol (830 mg, 14.8 mmol) in THF (30 mL) were added $PdCl_2(PPh_3)_2$ (350 mg, 0.50 mmol), $^iPr_2NH$ (2 g, 19.8 mmol) and CuI (95 mg, 0.5 mmol). The reaction mixture was stirred at room temperature overnight. The mixture was filtered through Celite, and to the filtrate was added 1N NaOH (10 mL). The mixture was extracted with DCM. The pH was adjusted to around 6 with 2N HCl. The aqueous solution was extracted with ethyl acetate. The combined EtOAc layers were dried over $Na_2SO_4$, filtered, and evaporated to dryness under reduced pressure to give the desired compound (500 mg, 2.82 mmol, yield 57%) as a pale solid.

Step 7: 3-(5-(5H-pyrido[4,3-b]indol-7-yl)pyridin-2-yl)prop-2-yn-1-ol

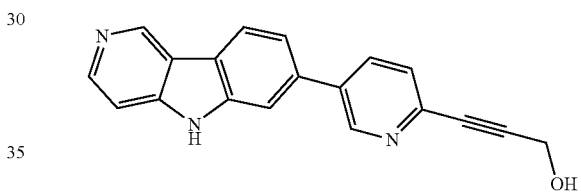

To the mixture of 7-bromo-5H-pyrido[4,3-b]indole (50 mg, 0.20 mmol) and (6-(3-Hydroxyprop-1-yn-1-yl)pyridin-3-yl)boronic acid (53 mg, 0.30 mmol) in dioxane (10 mL) and water (1.0 mL) were added $PdCl_2(dppf)$ (29 mg, 0.04 mmol), $Cs_2CO_3$ (130 mg, 0.40 mmol) and $^tBu_3PHBF_4$ (23 mg, 0.08 mmol). The mixture was stirred at 100° C. for 3 hours under $N_2$ atmosphere. After cooling to room temperature, the reaction was quenched with water (3 mL), and the mixture was extracted with EtOAc (20 mL×3). The combined organic layers were washed with brine, dried ($Na_2SO_4$), filtered and concentrated under reduced pressure. The residue was purified on silica gel column (MeOH:DCM=1:20-1:10) to give the desired compound (30 mg, 0.10 mmol, yield: 50.0%) as a yellow solid.

Step 8: 3-(5-(5H-pyrido[4,3-b]indol-7-yl)pyridin-2-yl)propan-1-ol

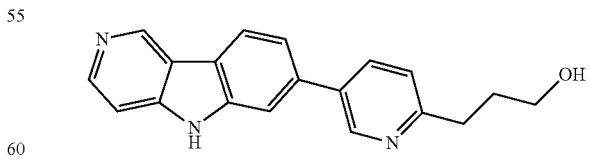

To a solution of 3-(5-(5H-pyrido[4,3-b]indol-7-yl)pyridin-2-yl)prop-2-yn-1-ol (30 mg, 0.10 mmol) in MeOH (2 mL) was added $Pd(OH)_2$/C (20%, 10 mg) and cat. Conc. HCl (0.1 mL). The reaction was stirred at room temperature for 2 hours under $H_2$ atmosphere. The mixture was filtered through Celite, and the filtrate was concentrated to give the crude desired compound (30 mg) as a yellow oil.

Step 9: 3-(5-(5H-pyrido[4,3-b]indol-7-yl)pyridin-2-yl)propanal

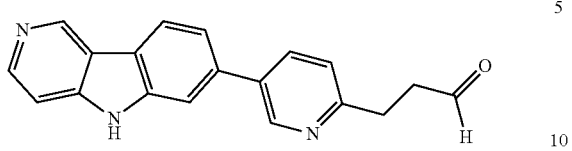

A solution of 3-(5-(5H-pyrido[4,3-b]indol-7-yl)pyridin-2-yl)propan-1-ol (100 mg, 0.33 mmol) in DMSO (4 mL) was mixed with IBX (231 mg, 0.82 mmol). The reaction mixture was stirred at 25° C. for 2 hours. The reaction was quenched with saturated $Na_2S_2O_3$ (2 mL) and saturated $NaHCO_3$ (2 mL). The mixture was extracted with dichloromethane (30 mL). The organic phase was washed with water and brine. It was dried over $Na_2SO_4$, filtered, and concentrated under reduced pressure to give the crude title product (60 mg) as a yellow oil.

Step 10: 5-(3-(6-(4-(3-(5-(5H-pyrido[4,3-b]indol-7-yl)pyridin-2-yl)propyl)piperazin-1-yl)pyridin-3-yl)propoxy)-2-(2,6-dioxopiperidin-3-yl)isoindoline-1,3-dione

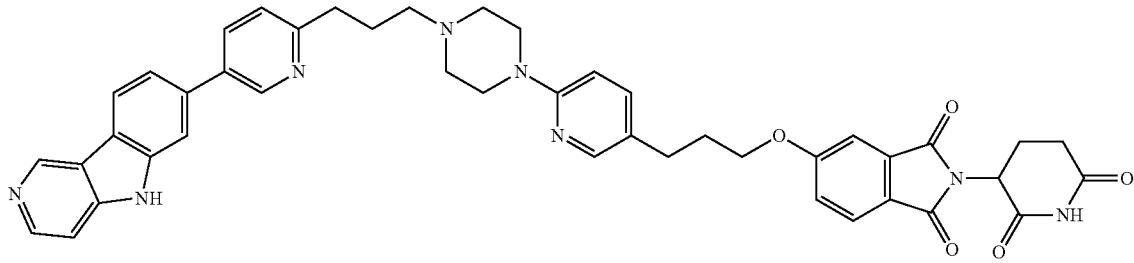 [SMILES: O=C1CCC(N2C(=O)c3ccc(OCCCc4ccc(N5CCN(CCCc6ccc(-c7ccc8c(c7)[nH]c7ccncc78)cn6)CC5)nc4)cc3C2=O)C(=O)N1]

To a solution of 3-(5-(5H-pyrido[4,3-b]indol-7-yl)pyridin-2-yl)propanal (100 mg, crude) in MeOH (10 mL) were added 2-(2,6-dioxopiperidin-3-yl)-5-(3-(6-(piperazin-1-yl)pyridin-3-yl)propoxy)isoindoline-1,3-dione (100 mg, 0.21 mmol) and $NaBH_3CN$ (41 mg, 0.66 mmol). The reaction mixture was stirred at room temperature for 1 hour. The mixture was diluted with water (6 ml) and extracted with DCM (20 mL×2). The combined organic layers were washed with water and brine, dried over $Na_2SO_4$, filtered, and concentrated under reduced pressure. The residue was purified by prep-HPLC to give the desired product (15 mg, 0.02 mmol) as a white solid.

$^1$H NMR (400 MHz, MeOD): δ 9.62 (s, 1H), 9.03 (s, 1H), 8.58 (d, J=6.8 Hz, 1H), 8.52 (d, J=8.0 Hz, 1H), 8.31-8.40 (m, 1H), 8.08 (s, 1H), 7.87-7.99 (m, 2H), 7.78-7.87 (m, 3H), 7.68-7.72 (m, 1H), 7.26-7.30 (m, 2H), 7.10-7.14 (m, 1H), 5.08-5.12 (m, 1H), 4.17 (t, J=6.0 Hz, 2H), 3.81-3.92 (m, 4H), 3.50-3.60 (m, 4H), 3.30-3.40 (m, 2H), 3.10-3.18 (m, 2H), 2.71-2.86 (m, 5H), 2.30-2.33 (m, 2H), 2.10-2.16 (m, 3H). (M+H)$^+$ 763.3

Synthetic Scheme for Exemplary Compound 56

5-((5-(4-(2-(((1 s,3 s)-3-((5-(5H-pyrido[4,3-b]indol-7-yl)pyridin-2-yl)oxy)cyclobutoxy)ethyl)piperazin-1-yl)pentyl)oxy)-2-(2,6-dioxopiperidin-3-yl)isoindoline-1,3-dione

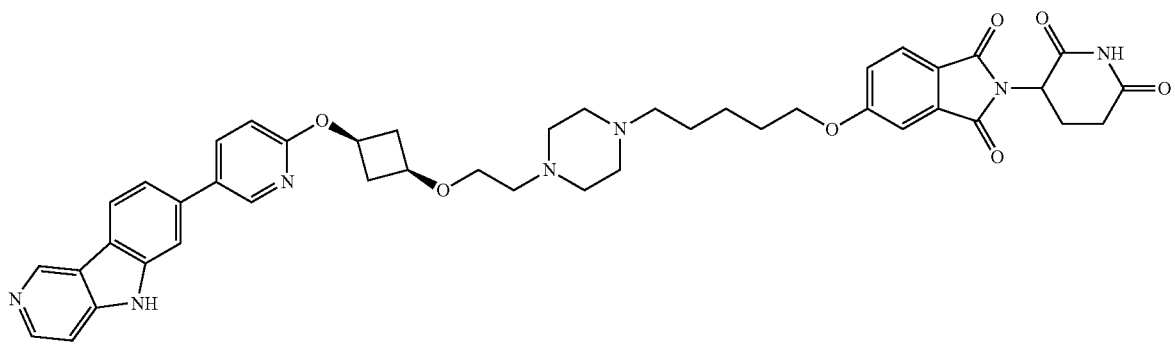 [SMILES: O=C1CCC(N2C(=O)c3ccc(OCCCCCN4CCN(CCO[C@H]5C[C@@H](Oc6ccc(-c7ccc8c(c7)[nH]c7ccncc78)cn6)C5)CC4)cc3C2=O)C(=O)N1]

Step 1: (1s,3s)-3-(benzyloxy)cyclobutan-1-ol

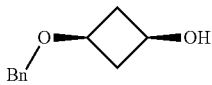 [SMILES: O[C@H]1C[C@@H](OCc2ccccc2)C1]

To a solution of 3-(benzyloxy)cyclobutanone (10.0 g, 56.75 mmol) in EtOH (100 mL) was added NaBH$_4$ (4.3 g, 68.1 mmol) at 0° C. The mixture was stirred at 10° C. for 2 hours. After the reaction was quenched with 10% NH$_4$Cl, the mixture was extracted with ethyl acetate (200 mL). The combined organic layers were washed with brine (150 mL), dried over anhydrous sodium sulfate and concentrated under vacuum to give crude the desired product (9.5 g) as a colorless oil, which was used in the next step without further purification.

Step 2: (((1s,3s)-3-(2,2-diethoxyethoxy)cyclobutoxy)methyl)benzene

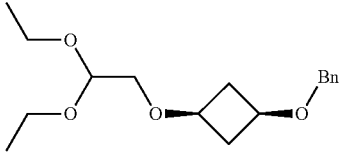 [SMILES: CCOC(CO[C@H]1C[C@@H](OCc2ccccc2)C1)OCC]

To a solution of (1 s,3s)-3-(benzyloxy)cyclobutan-1-ol (300 mg, crude, 1.69 mmol) in THF (10 mL) was added NaH (168 mg, 4.22 mmol, 60%). After stirring at 5° C. for 0.5 hours, 2-bromo-1,1-diethoxyethane (333 mg, 3.38 mmol) was added. The resulting mixture was stirred at 70° C. for 18 hours. After cooling to room temperature, the reaction was diluted with water (50 mL), and the mixture was extracted with EA. The organic phase was washed with brine, dried over MgSO$_4$, and concentrated. The residue was purified by chromatography (silica gel, PE:EA (50:1, v:v)) to afford the desired compound (220 mg) as a yellow solid.

Step 3: 2-((1s,3s)-3-(benzyloxy)cyclobutoxy)acetaldehyde

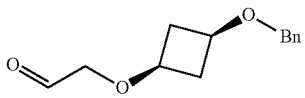 [SMILES: O=CCO[C@H]1C[C@@H](OCc2ccccc2)C1]

To a solution of (((1s,3s)-3-(2,2-diethoxyethoxy)cyclobutoxy)methyl)benzene (220 mg, 0.74 mmol) in CH$_3$CN (5 mL) was added HCl (2 mL, 2.5 mol/L in H$_2$O). The resulting mixture was stirred at 70° C. for 2 hours. TLC (PE:EA=3:1, Rf=0.5) showed that starting material was consumed. The mixture was diluted with water (50 mL) and extracted with EA. The organic phase was washed with NaHCO$_3$, brine. The solution was dried over MgSO$_4$ and concentrated to afford the desired compound (170 mg, crude) as a yellow oil, which was used in the next step without further purification.

Step 4: tert-butyl 4-(2-((1s,3s)-3-(benzyloxy)cyclobutoxy)ethyl)piperazine-1-carboxylate

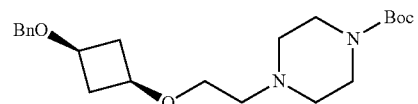

To a solution of 2-((1s,3s)-3-(benzyloxy)cyclobutoxy)acetaldehyde (170 mg, crude, 0.772 mmol) in MeOH (10 mL) were added tert-butyl piperazine-1-carboxylate (215 mg, 1.16 mmol), AcOH (1 drop) and NaBH$_3$CN (97 mg, 154 mmol). The resulting mixture was stirred at 10° C. for 18 hours. The reaction mixture was diluted with water (50 mL) and the mixture was extracted with EA. The organic phase was washed with brine, dried over MgSO$_4$, and concentrated. The residue was purified by chromatography (silica gel, PE:EA (1:1, v:v)) to afford the desired compound (280 mg) as a colorless oil.

Tert-Butyl 4-(2-((1s,3s)-3-(benzyloxy)cyclobutoxy)ethyl)piperazine-1-carboxylate was converted to the title compound, 5-((5-(4-(2-((1s,3s)-3-((5-(5H-pyrido[4,3-b]indol-7-yl)pyridin-2-yl)oxy)cyclobutoxy)ethyl)piperazin-1-yl)pentyl)oxy)-2-(2,6-dioxopiperidin-3-yl)isoindoline-1,3-dione, according to the scheme below using procedures described above for Exemplary Compound 42 and Exemplary Compound 53.

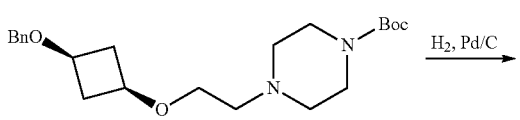

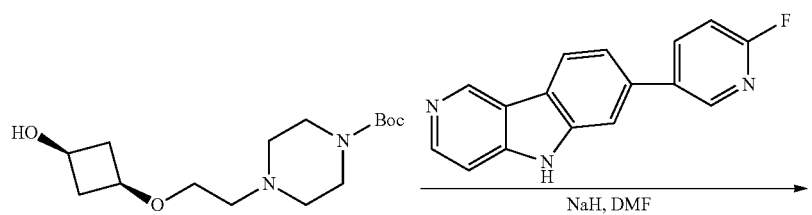

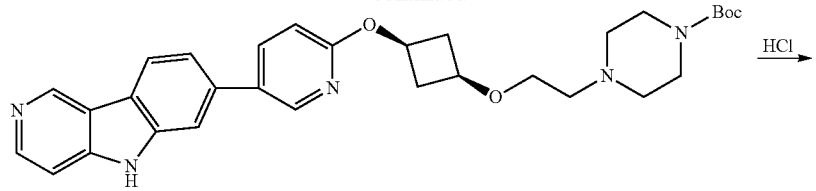
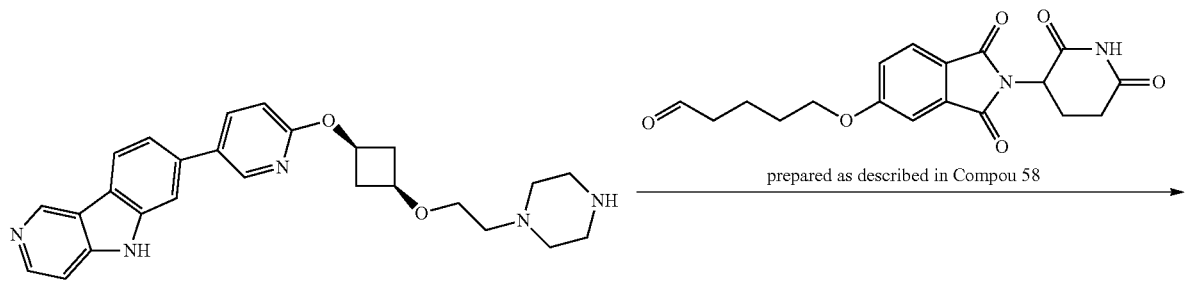
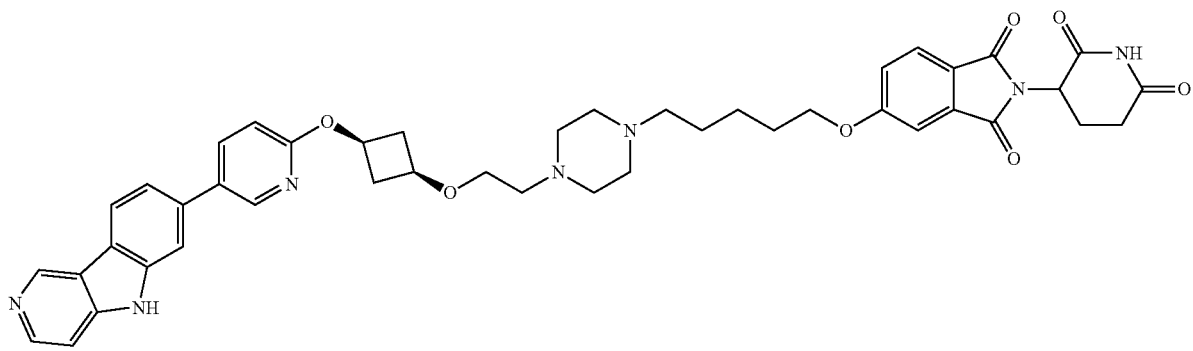
Compound 58
Exemplary Compound 56: $^{1}$H NMR (400 MHz, CDCl$_3$) δ 9.33 (s, 1H), 8.89 (s, 1H), 8.53 (s, 1H), 8.42 (s, 1H), 8.18 (d, J=8.2 Hz, 1H), 7.87 (d, J=6.2 Hz, 1H), 7.77 (d, J=8.2 Hz, 1H), 7.62 (s, 1H), 7.49 (d, J=7.7 Hz, 1H), 7.42 (s, 1H), 7.29 (d, J=11.5 Hz, 1H), 7.17 (d, J=6.5 Hz, 1H), 6.82 (d, J=8.2 Hz, 1H), 5.34 (s, 2H), 5.00-4.87 (m, 1H), 4.07 (s, 2H), 3.75 (s, 1H), 3.57 (s, 1H), 3.04-2.49 (m, 10H), 2.20 (m, 4H), 2.01 (s, 4H), 1.85 (s, 3H), 1.75-1.55 (m, 3H), 1.52 (s, 2H).
Exemplary Compound 54 and Exemplary Compound 58 were prepared according to the schemes below and using procedures analogous to those described above.
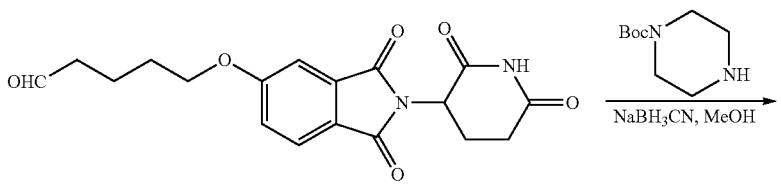
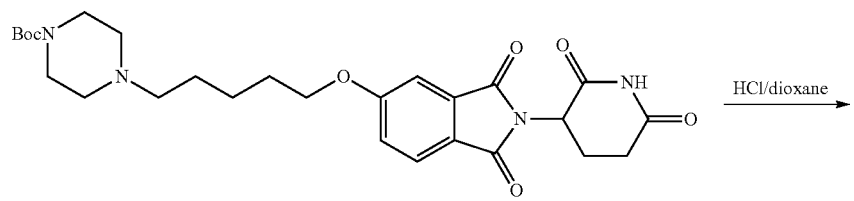

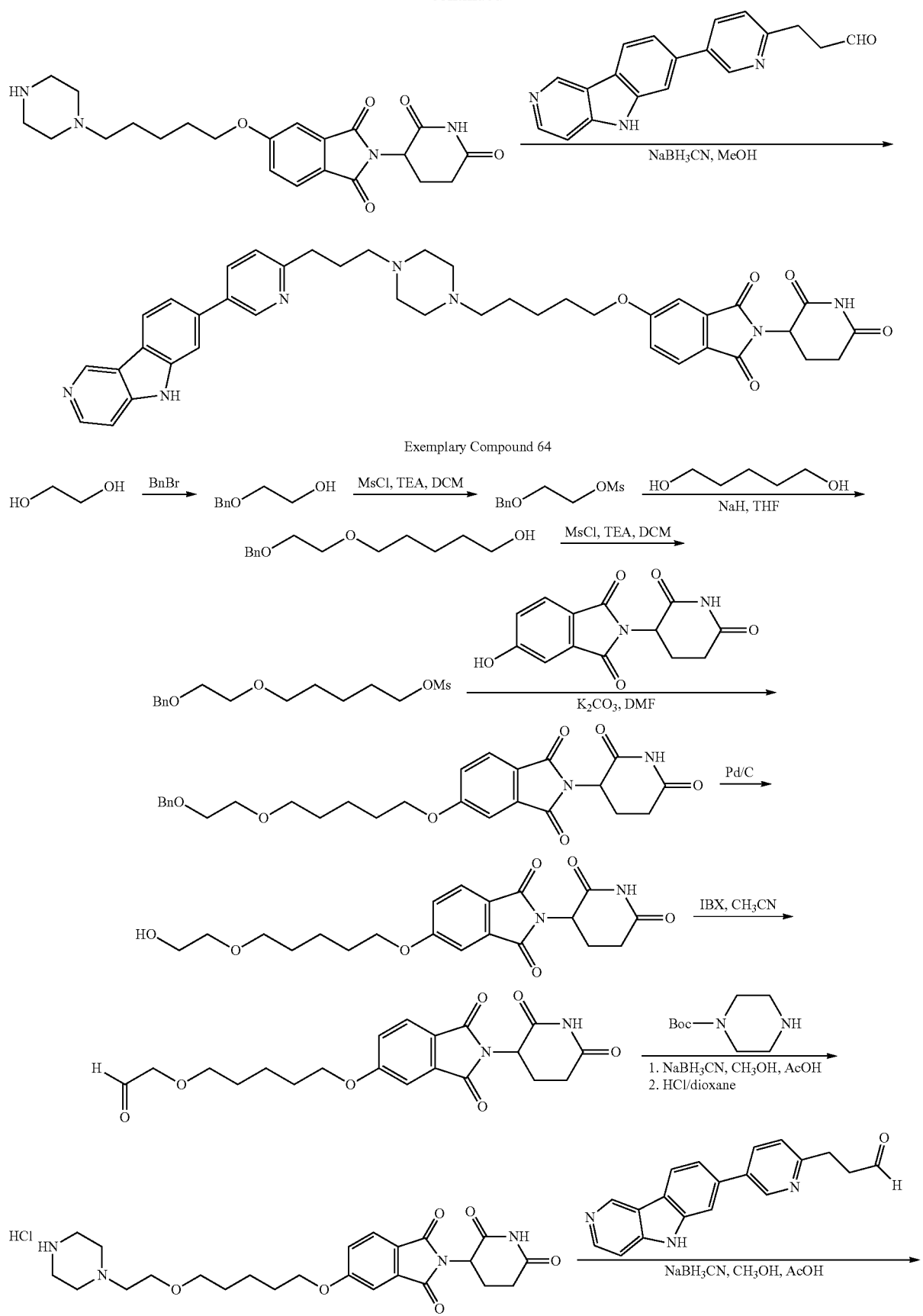
Exemplary Compound 64

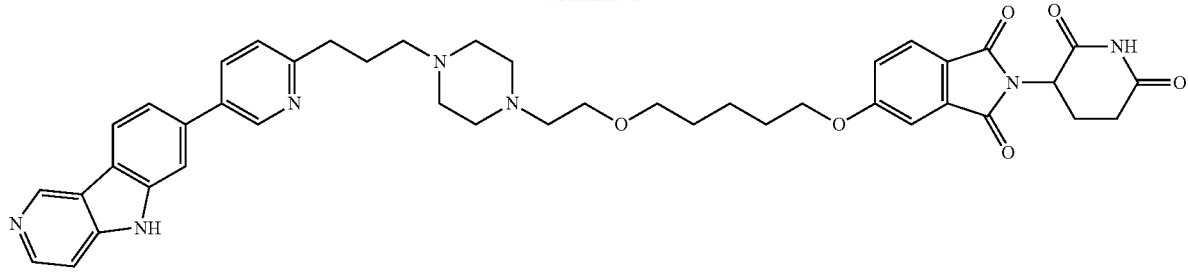

Exempry Compound 58

Synthetic Scheme for Exemplary Compound 57

Step 1: Benzyl 4-(5H-pyrido[4,3-b]indol-7-yl)-3,6-dihydropyridine-1(2H)-carboxylate

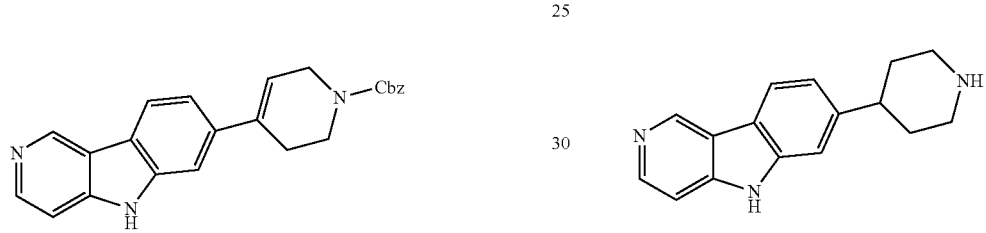

A mixture of 7-bromo-5H-pyrido[4,3-b]indole (492 mg, 2 mmol), benzyl 4-(4,4,5,5-tetramethyl-1,3,2-dioxaborolan-2-yl)-3,6-dihydropyridine-1(2H)-carboxylate (755 mg, 2.2 mmol), Pd(aMphose)Cl$_2$ (146 mg, 0.2 mmol) and CsF (1.2 g, 8 mmol) in dioxane/H$_2$O (20 mL/2 mL) was stirred at 90° C. for 16 hours. After cooling to room temperature, the reaction was quenched by the addition of water (30 mL). The mixture was extracted with ethyl acetate (20 mL×3). The combined organic layers were washed with brine (20 mL×2), dried over anhydrous sodium sulfate and concentrated under vacuum. The residue was applied onto a silica gel column eluting with dichloromethane/methanol to afford 260 mg (0.68 mmol, 34%) of the desired product.

Step 2: 7-(piperidin-4-yl)-5H-pyrido[4,3-b]indole

To a solution of benzyl 4-(5H-pyrido[4,3-b]indol-7-yl)-3,6-dihydropyridine-1(2H)-carboxylate (130 mg, 0.34 mmol) and one drop conc. HCl in CH$_3$OH (10 mL) was added Pd/C (13 mg, 10%) at room temperature. The resulting solution was stirred at room temperature overnight under 1 atm of H$_2$. Then the solid was filtered off and the filtrate was concentrated under vacuum to afford crude product (80 mg), which was used in the next reaction without further purification.

Step 3: 5-((14-(4-(5H-pyrido[4,3-b]indol-7-yl)piperidin-1-yl)-3,6,9,12-tetraoxatetradecyl)oxy)-2-(2,6-dioxopiperidin-3-yl)isoindoline-1,3-dione

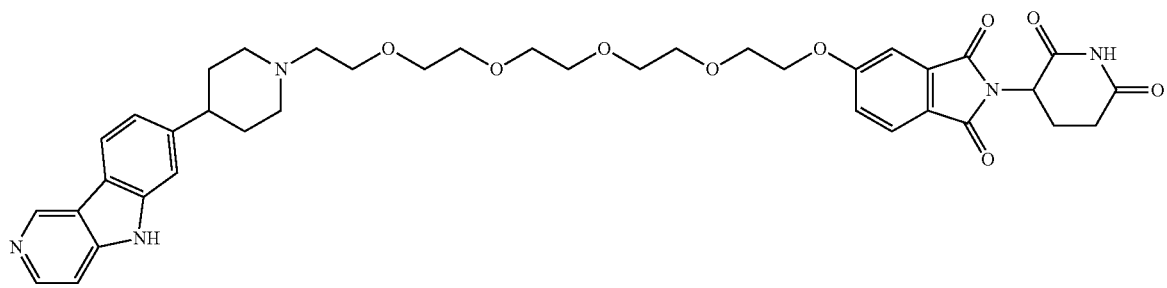 [SMILES: O=C1CCC(N2C(=O)c3ccc(OCCOCCOCCOCCOCCN4CCC(c5ccc6c(c5)[nH]c5ccncc56)CC4)cc3C2=O)C(=O)N1]

To a solution of 7-(piperidin-4-yl)-5H-pyrido[4,3-b]indole (80 mg, 0.32 mmol) and 14-((2-(2,6-dioxopiperidin-3-yl)-1,3-dioxoisoindolin-5-yl)oxy)-3,6,9,12-tetraoxatetradecanal (175 mg, 0.36 mmol) [prepared as described for intermediate 101 above] in CH₃OH (10 mL) were added NaBH₃CN (40 mg, 0.64 mmol) and one drop of CH₃COOH at room temperature. After stirring for 2 hours, the reaction was quenched by the addition of water (20 mL). The resulting solution was extracted with DCM (20 mL×3). The combined organic layers were washed with brine (20 mL×2), dried over anhydrous sodium sulfate and concentrated under vacuum. The residue was purified by prep-TLC with DCM/CH₃OH (10:1) to afford the desired product (18 mg, 0.025 mmol, 8%). $^1$H NMR (400 MHz, CD₃OD): δ 9.30 (s, 1H), 8.42-8.60 (m, 2H), 8.19 (d, J=8.0 Hz, 1H), 7.60-7.65 (m, 2H), 7.52 (s, 1H), 7.31 (d, J=8.0 Hz, 1H), 7.19 (s, 1H), 7.12-7.14 (m, 1H), 5.07-5.10 (m, 1H), 4.12 (t, J=4.0 Hz, 2H), 3.66-3.86 (m, 18H), 3.37 (s, 2H), 3.15-3.20 (m, 3H), 2.71-2.76 (m, 3H), 2.09-2.22 (m, 5H). (M+H)⁺ 728.3.

Synthetic Scheme for Exemplary Compound 60

5-(4-(3-((1r,3r)-3-((5-(5H-pyrido[4,3-b]indol-7-yl)pyridin-2-yl)oxy)cyclobutoxy)propyl)piperazin-1-yl)-2-(2,6-dioxopiperidin-3-yl)isoindoline-1,3-dione

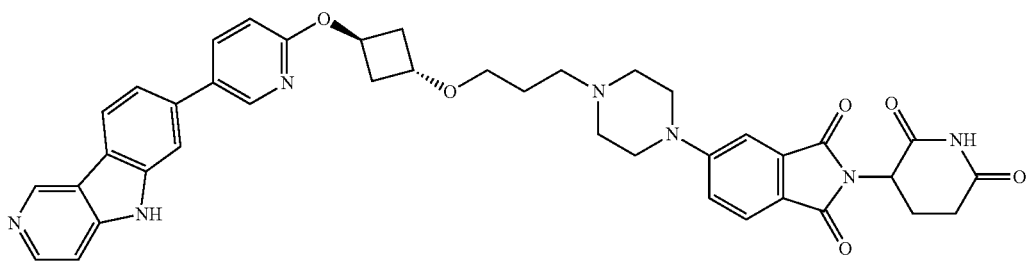 [SMILES: O=C1CCC(N2C(=O)c3ccc(N4CCN(CCCO[C@H]5C[C@H](Oc6ccc(-c7ccc8c(c7)[nH]c7ccncc78)cn6)C5)CC4)cc3C2=O)C(=O)N1]

Step 1: tert-butyl 4-(3-((1r,3r)-3-((4-nitrobenzoyl)oxy)cyclobutoxy)propyl)piperazine-1-carboxylate

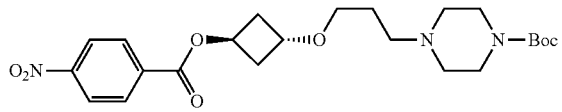 [SMILES: CC(C)(C)OC(=O)N1CCN(CCCO[C@H]2C[C@H](OC(=O)c3ccc([N+](=O)[O-])cc3)C2)CC1]

To a solution of tert-butyl-4-(3-((1s,3s)-3-hydroxycyclobutoxy)propyl)piperazine-1-carboxylate (530 mg, 1.68 mmol), triphenylphosphine (1.32 g, 5.06 mmol) and 4-nitrobenzoic acid (310 mg, 1.85 mmol) in THF (10 mL) was added DIAD (1.02 g, 5.06 mmol) dropwise at room temperature under N₂. After stirring at room temperature for 3 hours, it was quenched with water (20 mL), and the mixture was extracted with EtOAc (20 mL×2). The combined organic layers were concentrated under vacuum. The residue was purified by silica gel column with PE/EA from 2:1 to 1:1 as eluent to afford the desired product (350 mg, 45%) as a semi-solid.

Tert-butyl 4-(3-((1r,3r)-3-((4-nitrobenzoyl)oxy)cyclobutoxy)propyl)piperazine-1-carboxylate was converted to the title compound, 5-(4-(3-((1r,3r)-3-((5-(5H-pyrido[4,3-b]indol-7-yl)pyridin-2-yl)oxy)cyclobutoxy)propyl)piperazin-1-yl)-2-(2,6-dioxopiperidin-3-yl)isoindoline-1,3-dione, according to the following scheme and using procedures described above for Exemplary Compound 53.

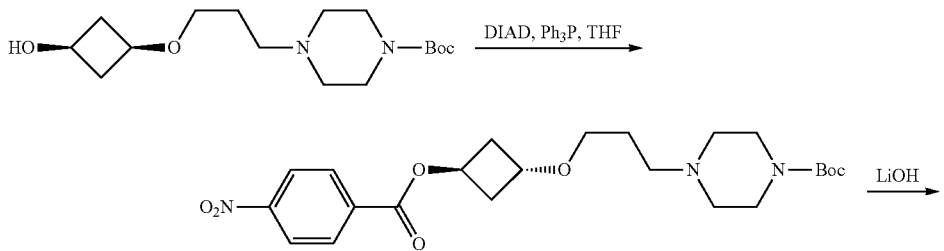

-continued
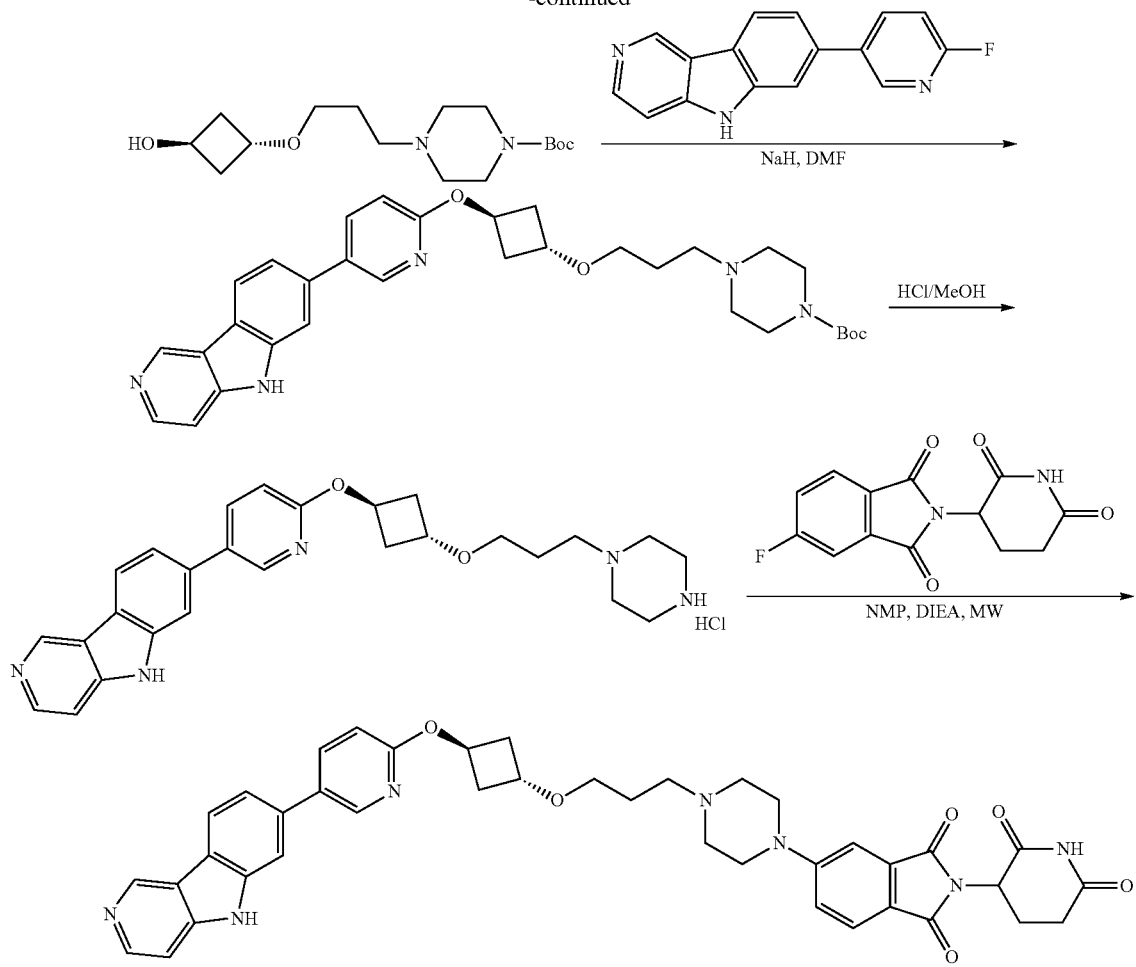
Compound 60
Compound 60: ¹H NMR (400 MHz, DMSO-d₆): δ 11.07 (s, 1H), 9.76 (s, 1H), 8.67 (d, J=6.0 Hz, 1H), 8.60 (s, 1H), 8.52 (d, J=8.4 Hz, 1H), 8.16 (d, J=8.4 Hz, 1H), 8.80-8.02 (m, 2H), 7.77 (t, J=8.4 Hz, 2H), 7.50 (s, 1H), 7.37 (d, J=8.0 Hz, 1H), 6.96 (d, J=8.8 Hz, 1H), 5.36 (m, 1H), 5.07-5.11 (m, 1H), 4.24 (br, 3H), 3.62 (br, 9H), 3.55 (s, 3H), 3.17-3.25 (m, 6H), 2.86-2.93 (m, 1H), 2.38-2.62 (m, 4H), 1.97-2.04 (m, 1H). (M+H)⁺ 714.3.
Synthetic Scheme for Exemplary Compound 61
2-(2,6-dioxopiperidin-3-yl)-5-((5-(4-(3-(5-(5-(2,2,2-trifluoroethyl)-5H-pyrido[4,3-b]indol-7-yl)pyridin-2-yl)propyl)piperazin-1-yl)pentyl)oxy)isoindoline-1,3-dione
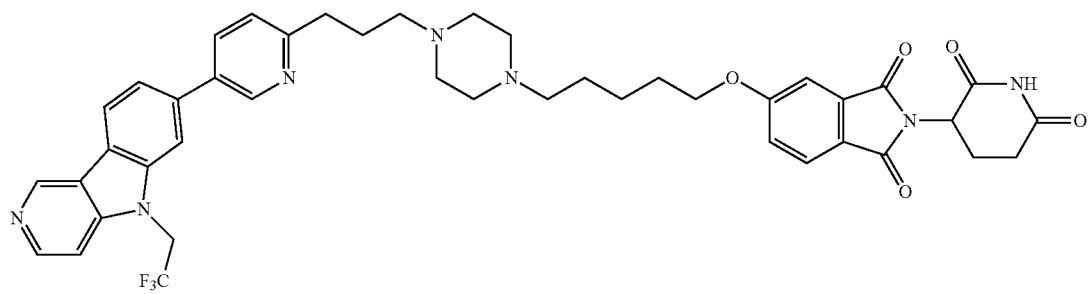 [SMILES: O=C1CCC(N2C(=O)c3ccc(OCCCCCN4CCN(CCCc5ccc(-c6ccc7c8cnccc8n(CC(F)(F)F)c7c6)cn5)CC4)cc3C2=O)C(=O)N1]

311

Step 1: 7-(6-(3-((tert-butyldimethylsilyl)oxy)propyl)pyridin-3-yl)-5H-pyrido[4,3-b]indole

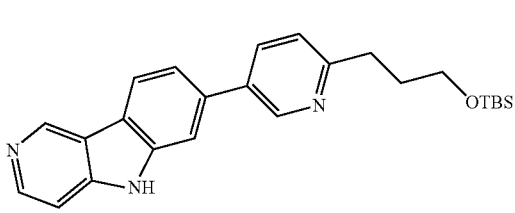 [SMILES: CC(C)(C)[Si](C)(C)OCCCc1ccc(-c2ccc3c(c2)[nH]c2ccncc23)cn1]

To a solution of 3-(5-(5H-pyrido[4,3-b]indol-7-yl)pyridin-2-yl)propan-1-ol (prepared as described for Compound 55; 100 mg, 0.33 mmol) in DCM (5 mL) were added imidazole (44.8 mg, 0.66 mmol) and TBSCl (59.6 mg, 0.40 mmol). The resulting solution was stirred at 40° C. for 3 hours. The solvent was removed under reduced pressure. The residue was diluted with EA (30 mL), the mixture was washed with brine. The organic layer was dried over anhydrous sodium sulfate, filtered and concentrated under vacuum. The residue was purified by silica gel column chromatography (DCM/MeOH=20/1, 0.2% Net$_3$) to afford the title product (100 mg. 73% yield).

Step 2: 7-(6-(3-((tert-butyldimethylsilyl)oxy)propyl)pyridin-3-yl)-5-(2,2,2-trifluoroethyl)-5H-pyrido[4,3-b]indole

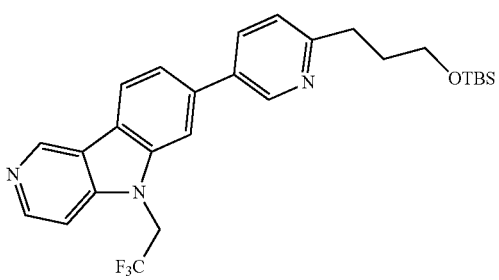 [SMILES: CC(C)(C)[Si](C)(C)OCCCc1ccc(-c2ccc3c4cnccc4n(CC(F)(F)F)c3c2)cn1]

To a solution of 7-(6-(3-((tert-butyldimethylsilyl)oxy)propyl)pyridin-3-yl)-5H-pyrido[4,3-b]indole (60 mg, 0.14 mmol) in DMF (5 mL) was added NaH (8.6 mg, 0.22 mmol) at 5° C. After stirring for 20 min, a solution of CF$_3$CH$_2$Otf (66.6 mg, 0.29 mmol) in DMF (1 mL) was added dropwise. The mixture was stirred for another 1 hour, and the reaction was diluted by EtOAc (40 mL), washed with brine, dried over anhydrous sodium sulfate. The filtrate was evaporated under reduced pressure. The residue was purified by column chromatography on silica gel (DCM/MeOH=40:1, 0.2% NH$_3$—H$_2$O) to afford the title product (55 mg, 92%).

312

Step 3: 3-(5-(5-(2,2,2-trifluoroethyl)-5H-pyrido[4,3-b]indol-7-yl)pyridin-2-yl)propan-1-ol

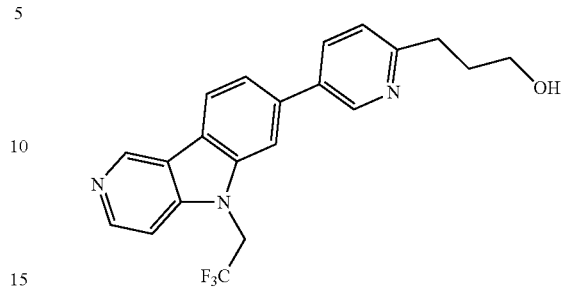

To a solution of 7-(6-(3-((tert-butyldimethylsilyl)oxy)propyl)pyridin-3-yl)-5-(2,2,2-trifluoroethyl)-5H-pyrido[4,3-b]indole (110 mg, 0.22 mmol) in CH$_3$OH (2 mL) was added HCl/Dioxane (6 N, 3 mL). The resulting solution was stirred at 5° C. for 1 hour. Then it was diluted with EtOAc (40 mL), and the mixture was washed with sat. NaHCO$_3$(a.q.) and brine, and dried over anhydrous sodium sulfate. The organic phase was evaporated under reduced pressure to afford crude title product (84.9 mg) which was used in the next reaction without further purification.

Step 4: 3-(5-(5-(2,2,2-trifluoroethyl)-5H-pyrido[4,3-b]indol-7-yl)pyridin-2-yl)propanal

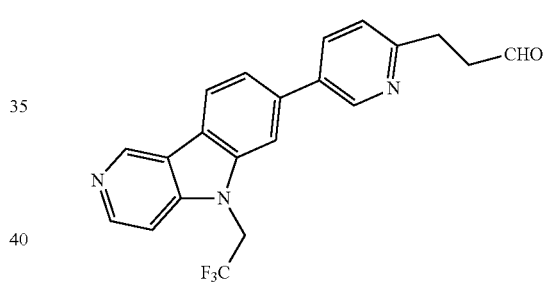

To a solution of 3-(5-(5-(2,2,2-trifluoroethyl)-5H-pyrido[4,3-b]indol-7-yl)pyridin-2-yl)propan-1-ol (90 mg, 0.23 mmol) in DMSO (2 mL) was added IBX (130.9 mg, 0.47 mL). The resulting mixture was stirred at 40° C. for 2 hours. The mixture was quenched by sat. Na$_2$S$_2$O$_3$ a.q. (5 mL) and sat. NaHCO$_3$ a.q. (5 mL). The mixture was extracted with EtOAc (20 mL×5). The combined organic layer was dried over anhydrous sodium sulfate, concentrated under vacuum to afford crude desired product (89.5 mg) which was used in the next reaction without further purification.

Step 5: tert-butyl 4-(5-((2-(2,6-dioxopiperidin-3-yl)-1,3-dioxoisoindolin-5-yl)oxy)pentyl)piperazine-1-carboxylate

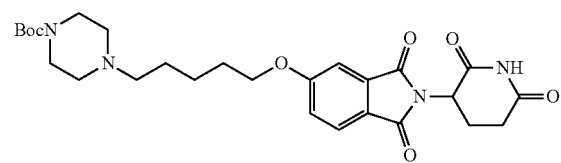 [SMILES: CC(C)(C)OC(=O)N1CCN(CCCCCOc2ccc3c(c2)C(=O)N(C2CCC(=O)NC2=O)C3=O)CC1]

To a solution of 5-((2-(2,6-dioxopiperidin-3-yl)-1,3-dioxoisoindolin-5-yl)oxy)pentanal (150 mg, 0.42 mmol) [prepared according to the procedures described above] in MeOH (5 mL) were added tert-butyl piperazine-1-carboxylate (77.9 mg, 0.42 mmol) and NaBH₃CN (52.6 mg, 0.84 mmol). The resulting solution was stirred at 40° C. for 2 hours. The solvent was evaporated under reduced pressure. The residue was diluted with EA (30 mL), and the mixture was washed with brine. The organic phase was dried over anhydrous sodium sulfate, filtered. The filtrate was concentrated in vacuo. The residue was purified by silica gel column chromatography (DCM/MeOH=60/1) to afford the desired product (200 mg, 90% yield).

Using BOC-deprotection and reductive amination procedures analogous to those described above, compounds of the steps 4 and 5 were converted into the final compound, 2-(2,6-dioxopiperidin-3-yl)-5-((5-(4-(3-(5-(5-(2,2,2-trifluoroethyl)-5H-pyrido[4,3-b]indol-7-yl)pyridin-2-yl)propyl)piperazin-1-yl)pentyl)oxy)isoindoline-1,3-dione.

$^1$H NMR (400 MHz, CD₃OD) δ 9.35 (s, 1H), 8.89 (s, 1H), 8.55 (d, J=5.8 Hz, 1H), 8.40 (d, J=8.0 Hz, 1H), 8.17-8.22 (m, 1H), 8.05 (s, 1H), 7.81 (d, J=8.3 Hz, 1H), 7.74 (d, J=5.6 Hz, 1H), 7.51 (d, J=8.2 Hz, 1H), 7.40 (s, 1H), 7.33 (s, 1H), 5.40 (d, J=9.1 Hz, 2H), 5.08-5.16 (m, 1H), 4.95 (s, 4H), 4.59 (s, 2H), 4.18 (t, J=6.2 Hz, 1H), 2.91-3.00 (m, 2H), 2.58-2.91 (m, 9H), 2.12-2.18 (m, 1H), 2.06 (s, 2H), 1.89 (s, 2H), 1.69 (s, 2H), 1.57 (s, 2H). (M+H)⁺ 796.3.

Synthetic Scheme for Exemplary Compound 62

3-(5-((5-(4-(3-(5-(5-methyl-5H-pyrido[4,3-b]indol-7-yl)pyridin-2-yl)propyl)piperazin-1-yl)pentyl)oxy)-1-oxoisoindolin-2-yl)piperidine-2,6-dione

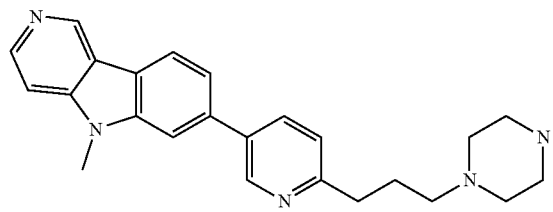

Step 1: tert-butyl 5-amino-4-(5-((5-hydroxypentyl)oxy)-1-oxoisoindolin-2-yl)-5-oxopentanoate

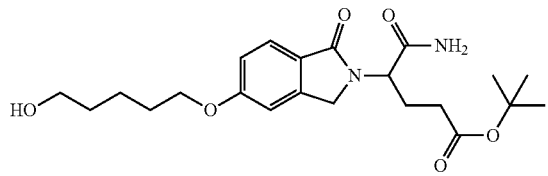 [SMILES: CC(C)(C)OC(=O)CCC(C(N)=O)N1Cc2cc(OCCCCCO)ccc2C1=O]

To a solution of tert-butyl 5-amino-4-(5-hydroxy-1-oxoisoindolin-2-yl)-5-oxopentanoate (500.0 mg, 1.0 eq), pentane-1,5-diol (187 mg, 1.2 eq) and PPh3 (590.0 mg, 1.5 eq) in anhydrous tetrahydrofuran (50 mL) was added DIAD (455 mg, 2.25 mmol, 1.5 eq). The resulting solution was stirred at room temperature for 16 hours. Then the reaction was quenched by the addition of water (100 mL). The resulting solution was extracted with ethyl acetate (50 mL×3). The combined organic layers were washed with brine (20 mL×2), dried over anhydrous sodium sulfate and concentrated under vacuum. The residue was applied onto a silica gel column with dichloromethane/methanol (10:1) to afford the desired product (560 mg, 1.33 mmol, 89%).

Step 2: 3-(5-((5-hydroxypentyl)oxy)-1-oxoisoindolin-2-yl)piperidine-2,6-dione

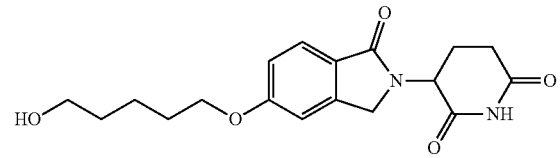 [SMILES: O=C1CCC(N2Cc3cc(OCCCCCO)ccc3C2=O)C(=O)N1]

To a solution of tert-butyl 5-amino-4-(5-((5-hydroxypentyl)oxy)-1-oxoisoindolin-2-yl)-5-oxopentanoate (560 mg, 1.0 eq) in MeCN (20 mL) was added p-TsA (253 mg, 3.0 eq) at room temperature. The resulting solution was stirred at 90° C. for 6 hours. Then the reaction was cooled to room temperature and quenched by the addition of water (10 mL). The resulting solution was extracted with ethyl acetate (15 mL×3). The combined organic layers were washed with brine (10 mL×2), dried over anhydrous sodium sulfate and concentrated under vacuum. The residue was applied onto a silica gel column with dichloromethane/methanol (10:1) to afford the desired product (190 mg, 0.55 mmol, 46%).

Step 3: 5-((2-(2,6-dioxopiperidin-3-yl)-1-oxoisoindolin-5-yl)oxy)pentanal

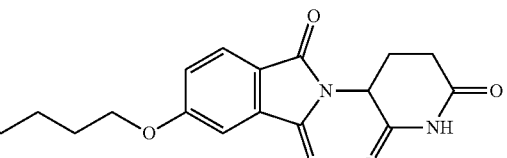

To a solution of 3-(5-((5-hydroxypentyl)oxy)-1-oxoisoindolin-2-yl)piperidine-2,6-dione (190 mg, 1.0 equiv) in DCM (20 mL) was added IBX (100 mg, 2 eq) at room temperature. The resulting solution was stirred at room temperature for 2 hours. Then the solid was filtered off and the filtrate was concentrated under vacuum to afford crude product (190 mg) which was used into next reaction without further purification.

315

Step 4: 7-bromo-5-methyl-5H-pyrido[4,3-b]indole

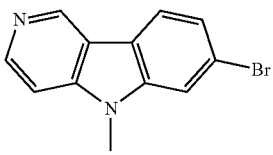

To a solution of 7-bromo-5H-pyrido[4,3-b]indole (8.0 g, 32.4 mmol) in N,N-dimethylformamide (50 ml) was added sodium hydride (1.4 g, 35.6 mmol, 60% in mineral oil) at 0° C., and the reaction mixture was stirred at 0° C. for 30 minutes. To the resulting mixture was added iodomethane (4.6 g, 32.4 mmol) at 0° C., and the reaction mixture was allowed to warm up to room temperature and stirred overnight. TLC showed the reaction was complete. The reaction mixture was quenched with water (30 ml) at 0° C., and extracted with ethyl acetate (50 ml×2). The combined organic layers were washed with water (80 ml) then brine (90 ml), dried over anhydrous sodium sulfate, and concentrated under reduced pressure to give a crude residue which was purified by silica gel flash chromatography (eluted with 20-40% ethyl acetate in hexane) to afford 7-bromo-5-methyl-5H-pyrido[4,3-b]indole (6.0 g, yield 71%) as brown solid.

Using procedures described above for the Exemplary Compound 61, 5-((2-(2,6-dioxopiperidin-3-yl)-1-oxoisoindolin-5-yl)oxy)pentanal was converted into the title compound, 3-(5-((5-(4-(3-(5-(5-methyl-5H-pyrido[4,3-b]indol-7-yl)pyridin-2-yl)propyl)piperazin-1-yl)pentyl)oxy)-1-oxoisoindolin-2-yl)piperidine-2,6-dione according to the scheme below.

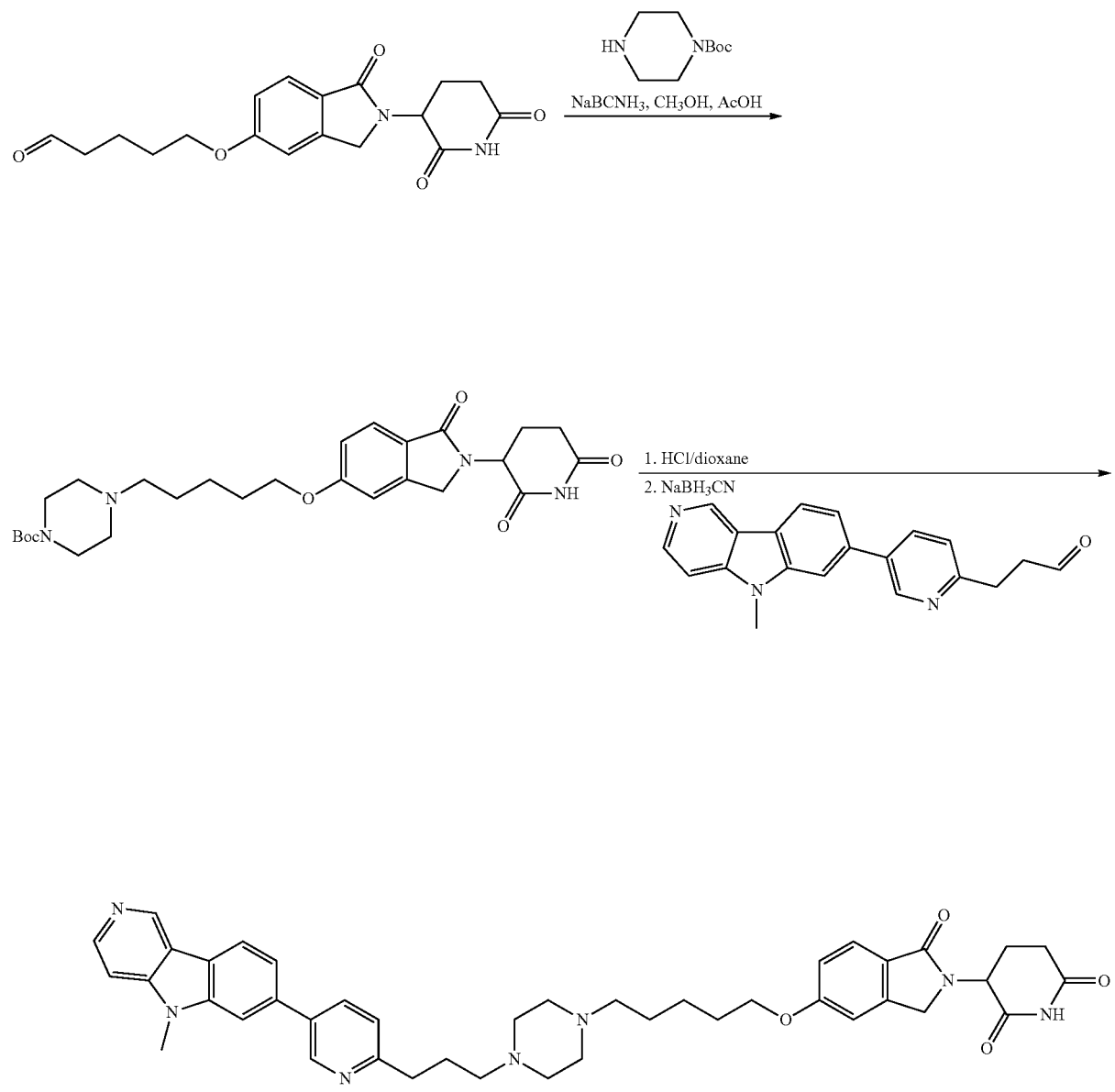

Compound 62

Exemplary Compound 62: ¹HNMR (400 MHz, MeOD): δ 9.27 (s, 1H), 8.86 (d, J=2.0 Hz, 1H), 8.46 (d, J=6.0 Hz, 1H), 8.33 (d, J=8.0 Hz, 1H), 8.16 (d, J=2.4 Hz, 1H), 7.90 (s, 1H), 7.59-7.70 (m, 3H), 7.47 (d, J=6.0 Hz, 1H), 7.03-7.09 (m, 2H), 5.06-5.12 (m, 1H), 4.42 (d, J=5.6 Hz, 2H), 4.07 (t, J=6.4 Hz, 2H), 3.99 (s, 3H), 2.89-2.96 (m, 3H), 2.51-2.75 (m, 13H), 2.12-2.24 (m, 1H), 2.01-2.03 (m, 3H), 1.82-1.84 (m, 2H), 1.52-1.63 (m, 6H). (M+H)⁺ 714.3.

Exemplary Compound 63

2-(2,6-dioxopiperidin-3-yl)-5-((5-(4-(3-(5-(5-methyl-5H-pyrido[4,3-b]indol-7-yl)-3-(trifluoromethyl)pyridin-2-yl)propyl)piperazin-1-yl)pentyl)oxy)isoindoline-1,3-dione

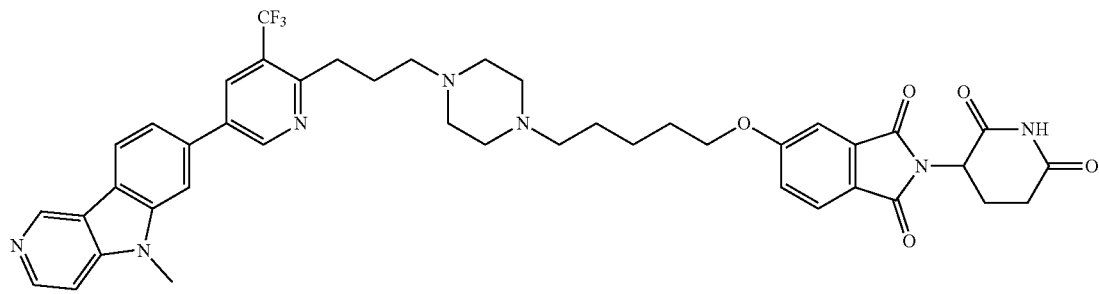 [SMILES: Cn1c2ccncc2c2ccc(-c3cnc(CCCN4CCN(CCCCCOc5ccc6c(c5)C(=O)N(C5CCC(=O)NC5=O)C6=O)CC4)c(C(F)(F)F)c3)cc21]

Step 1: 5-methyl-7-(4,4,5,5-tetramethyl-1,3,2-dioxaborolan-2-yl)-5H-pyrido[4,3-b]indole

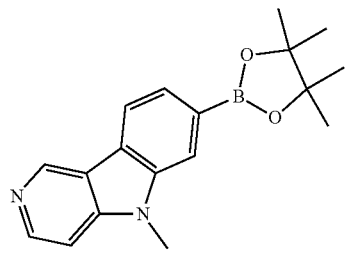 [SMILES: Cn1c2ccncc2c2ccc(B3OC(C)(C)C(C)(C)O3)cc21]

To a solution of 7-bromo-5-methyl-5H-pyrido[4,3-b]indole (150 mg, 0.577 mmol) in dioxane were added KOAc (114 mg, 1.15 mmol), Pd(dppf)Cl₂ (35 mg, 0.05 mmol), and 4,4,4',4',5,5,5',5'-octamethyl-2,2'-bi(1,3,2-dioxaborolane) (294 mg, 1.15 mmol) subsequently. The resulting solution was heated to 100° C. overnight under N₂. After cooling to room temperature, the reaction was quenched with water, the mixture was extracted with EtOAc (10 mL×2). The combined organic layers were washed with brine (10 mL). The organic phase was dried over Na₂SO₄, concentrated under vacuum to afford crude desired product (180 mg, crude), which was used into next reaction without further purification.

Step 2: 7-(6-chloro-5-(trifluoromethyl)pyridin-3-yl)-5-methyl-5H-pyrido[4,3-b]indole

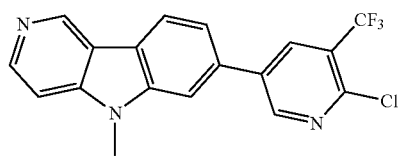 [SMILES: Cn1c2ccncc2c2ccc(-c3cnc(Cl)c(C(F)(F)F)c3)cc21]

To a mixture of 5-bromo-2-chloro-3-trifluoromethylpyridine (135 mg, 0.7 mmol) and 5-methyl-7-(4,4,5,5-tetramethyl-1,3,2-dioxaborolan-2-yl)-5H-pyrido[4,3-b]indole (180 mg, 0.58 mmol) in dioxane/H₂O (v/v=10/1, 10 mL) were added Pd(dppf)₂Cl₂ (20 mg, 10%) and CsF (180 mg, 1.16 mmol). The mixture was stirred at 80° C. overnight. The solution was quenched with water. The mixture was extracted with ethyl acetate (20 mL), and the combined organic layers were washed with brine (10 mL). The organic layer was dried over anhydrous sodium sulfate, filtered and concentrated under vacuum. The residue was purified by silica gel column chromatography to afford the desired product (170 mg, 95% yield).

Step 3: tert-butyl 4-(3-(5-(5-methyl-5H-pyrido[4,3-b]indol-7-yl)-3-(trifluoromethyl)pyridin-2-yl)prop-2-yn-1-yl)piperazine-1-carboxylate

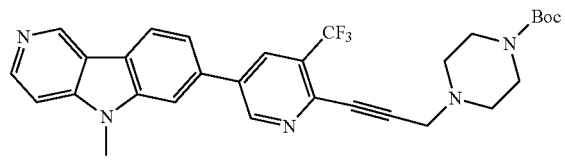 [SMILES: Cn1c2ccncc2c2ccc(-c3cnc(C#CCN4CCN(C(=O)OC(C)(C)C)CC4)c(C(F)(F)F)c3)cc21]

To a mixture of 7-(6-chloro-5-(trifluoromethyl)pyridin-3-yl)-5-methyl-5H-pyrido[4,3-b]indole (170 mg, 0.58 mmol) and tert-butyl 4-(prop-2-ynyl)piperazine-1-carboxylate (156 mg, 0.69 mmol) in DMF (10 mL) were added Pd(PPh₃)₂Cl₂ (17 mg, 10%), Cs₂CO₃ (378 mg, 1.16 mmol), DBU (30 mg, 0.116 mmol) and t-Bu₃P (25 mg, 0.116 mmol). The mixture was microwave-heated at 150° C. for 10 minutes. The reaction mixture was quenched with water. The mixture was extracted with ethyl acetate (20 mL). The combined organic layers were washed with brine (10 mL). The organic layer was dried over anhydrous sodium sulfate, filtered and concentrated under vacuum. The residue was purified by silica gel column chromatography to afford the desired product (200 mg).

Step 4: tert-butyl 4-(3-(5-(5-methyl-5H-pyrido[4,3-b]indol-7-yl)-3-(trifluoromethyl)pyridin-2-yl)propyl)piperazine-1-carboxylate To a solution of tert-butyl 4-(3-(5-(5-methyl-5H-pyrido[4,3-b]indol-7-yl)-3-(trifluoromethyl)pyridin-2-yl)prop-2-yn-1-yl)piperazine-1-carboxylate (200 mg) in ethanol was added Pd/C (20 mg). The mixture was stirred at 30° C. under $H_2$ atmosphere (3 Mpa) for 8 hours. The mixture was filtered through Celite, and the filtrate was concentrated under vacuum. The residue was purified by prep-HPLC to afford the desired product (25 mg).

Using BOC-deprotection and reductive amination procedures described above tert-butyl 4-(3-(5-(5-methyl-5H-pyrido[4,3-b]indol-7-yl)-3-(trifluoromethyl)pyridin-2-yl)propyl)piperazine-1-carboxylate was converted into the title compound, 2-(2,6-dioxopiperidin-3-yl)-5-((5-(4-(3-(5-(5-methyl-5H-pyrido[4,3-b]indol-7-yl)-3-(trifluoromethyl)pyridin-2-yl)propyl)piperazin-1-yl)pentyl)oxy)isoindoline-1,3-dione according to the scheme below.

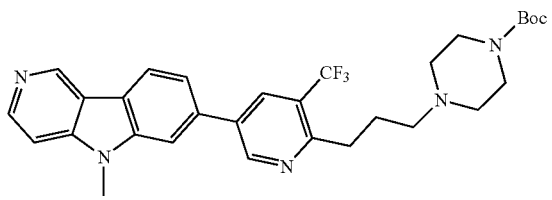 [SMILES: Cn1c2ccncc2c2ccc(-c3cnc(CCCN4CCN(C(=O)OC(C)(C)C)CC4)c(C(F)(F)F)c3)cc21]

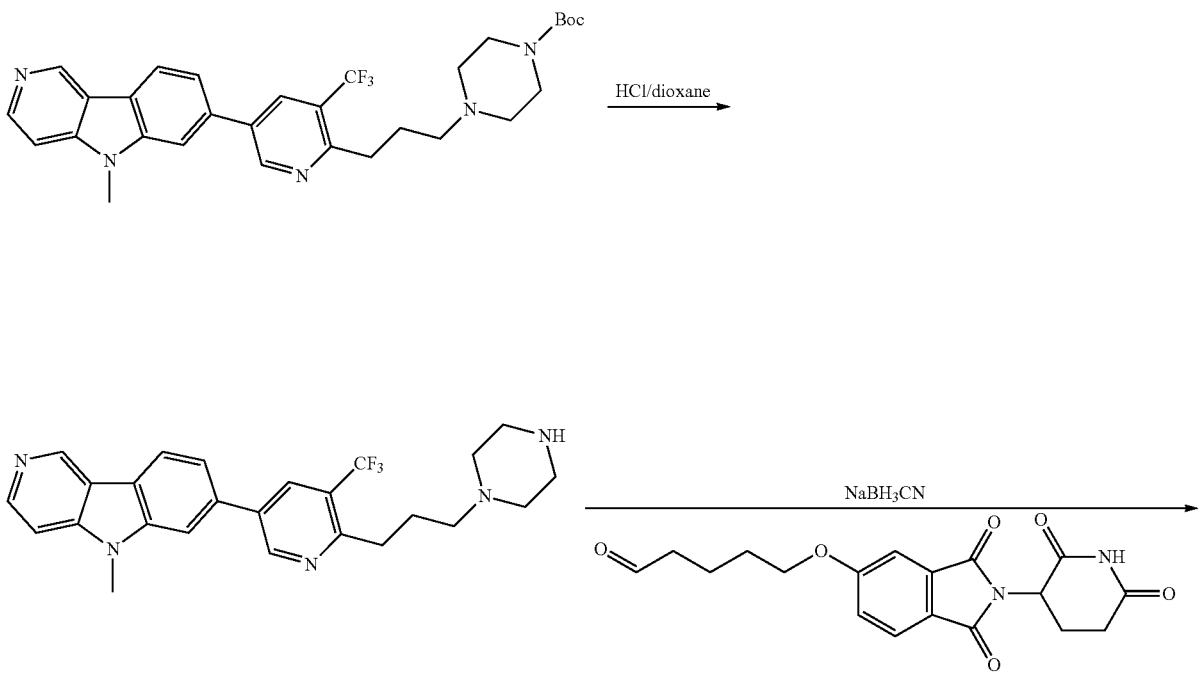

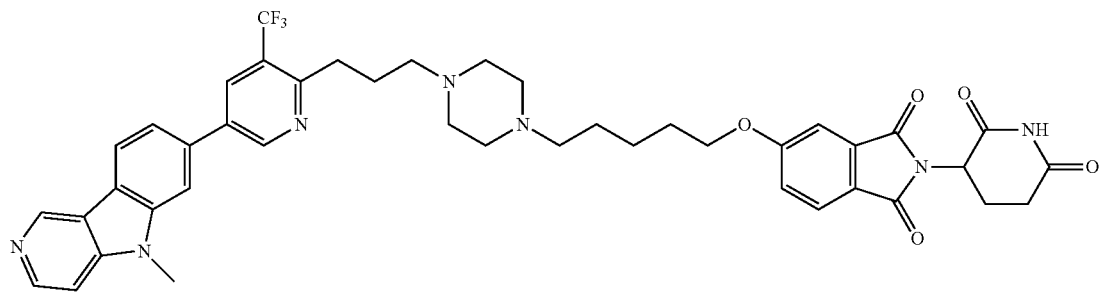

Compound 63

Exemplary Compound 63: $^1$H NMR (400 MHz, CD$_3$OD): δ 9.25 (s, 1H), 8.45 (s, 1H), 8.23 (d, J=7.6 Hz, 1H), 7.76 (d, J=8.4 Hz, 1H), 7.66 (s, 1H), 7.59 (d, J=8.0 Hz, 1H), 7.39 (d, J=8.4 Hz, 1H), 7.35 (s, 2H), 7.26-7.28 (m, 1H), 6.06 (s, 1H), 5.72 (s, 1H), 5.06-5.08 (m, 1H), 4.30 (d, J=6.4 Hz, 1H), 4.11-4.15 (m, 2H), 3.90-3.94 (m, 4H), 3.70-3.74 (m, 2H), 3.03-3.06 (m, 2H), 2.82-2.88 (m, 4H), 2.71-2.75 (m, 6H), 2.51-2.55 (m, 3H), 2.05-2.25 (m, 2H), 1.82-1.86 (m, 2H), 1.61-1.63 (m, 2H), 1.51-1.52 (m, 2H). (M+H)$^+$ 796.2.

Exemplary Compound 73

Step 1: 7-(6-((1s,3s)-3-(benzyloxy)cyclobutoxy)pyridin-3-yl)-5H-pyrido[4,3-b]indole

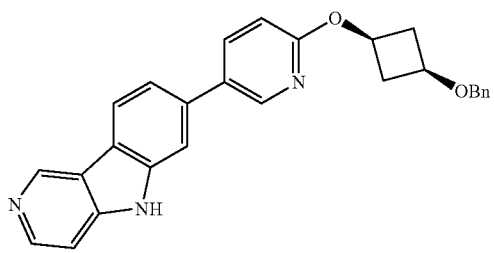 [SMILES: c1ccc(CO[C@H]2C[C@@H](Oc3ccc(-c4ccc5c(c4)[nH]c4ccncc45)cn3)C2)cc1]

To a solution of 7-(6-fluoropyridin-3-yl)-5H-pyrido[4,3-b]indole (1.1 g, 4.18 mmol) and (1s,3s)-3-(benzyloxy)cyclobutanol (745 mg, 4.18 mmol) in 1-methylpyrrolidin-2-one (2 ml) was added sodium hydride (60% in mineral oil) (334 mg, 8.35 mmol) at 0° C. The mixture was stirred at room temperature for 2 hours. TLC showed the reaction was complete. The mixture was partitioned between ethyl acetate (20 ml) and water (20 ml). The organic layer was collected, washed with brine (30 ml), dried over anhydrous sodium sulfate, and concentrated under reduced pressure to give a crude residue which was purified by silica gel flash chromatography (eluted with 2-5% methanol in dichloromethane) to afford 7-(6-((1s,3s)-3-(benzyloxy)cyclobutoxy)pyridin-3-yl)-5H-pyrido[4,3-b]indole (1.42 g, 82%) as white solid.

Step 2: (1s,3s)-3-((5-(5H-pyrido[4,3-b]indol-7-yl)pyridin-2-yl)oxy)cyclobutan-1-ol

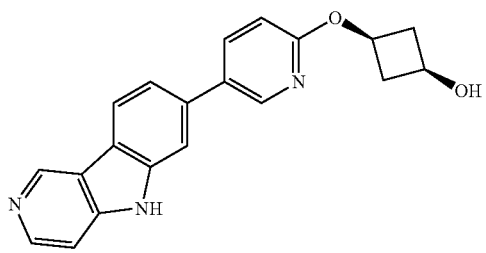 [SMILES: O[C@H]1C[C@@H](Oc2ccc(-c3ccc4c(c3)[nH]c3ccncc34)cn2)C1]

A mixture of 7-(6-((1s,3s)-3-(benzyloxy)cyclobutoxy)pyridin-3-yl)-5H-pyrido[4,3-b]indole (1.42 g, 3.37 mmol) and palladium on carbon (10%, 150 mg) in methanol (30 ml)-tetrahydrofuran (10 ml) was stirred at 50° C. for 2 hours under hydrogen atmosphere (hydrogen balloon). TLC showed the reaction was complete. Palladium on carbon was removed through filtration and washed with methanol (10 ml×2). The combined filtrate was concentrated under reduced pressure to afford (1s,3s)-3-((5-(5H-pyrido[4,3-b]indol-7-yl)pyridin-2-yl)oxy)cyclobutanol (1.57 g, crude) as white solid.

Step 3: tert-butyl 7-(6-((1s,3s)-3-hydroxycyclobutoxy)pyridin-3-yl)-5H-pyrido[4,3-b]indole-5-carboxylate

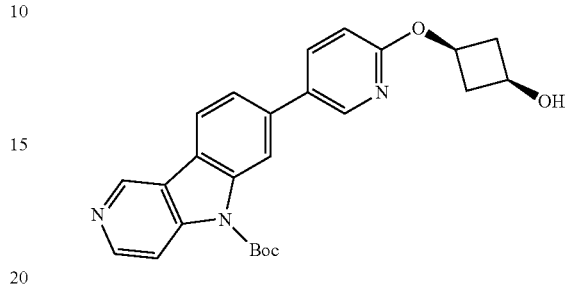

To a suspension of (1s,3s)-3-((5-(5H-pyrido[4,3-b]indol-7-yl)pyridin-2-yl)oxy)cyclobutanol (1.57 g, 4.27 mmol) and sodium carbonate (1.1 g, 10.69 mmol) in tetrahydrofuran (20 ml)-water (5 ml) was added di-tert-butyl carbonate (1.2 g, 5.55 mmol) at room temperature. The mixture was stirred at room temperature for 17 hours. TLC showed the reaction was complete. The mixture was concentrated and the residue was partitioned between ethyl acetate (20 ml) and water (30 ml). The organic layer was collected, washed with brine (20 ml), dried over anhydrous sodium sulfate, and concentrated under reduced pressure to give a crude residue which was purified by silica gel flash chromatography (eluted with 1-2% methanol in dichloromethane) to afford tert-butyl 7-(6-((1s,3s)-3-hydroxycyclobutoxy)pyridin-3-yl)-5H-pyrido[4,3-b]indole-5-carboxylate (1.1 g, two steps 73%) as white solid.

Step 4: tert-butyl 7-(6-((1s,3s)-3-((methylsulfonyl)oxy)cyclobutoxy)pyridin-3-yl)-5H-pyrido[4,3-b]indole-5-carboxylate

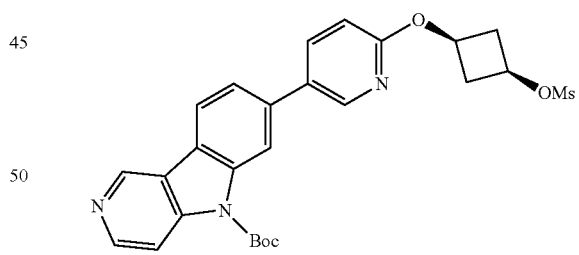

To a suspension of tert-butyl 7-(6-((1s,3s)-3-hydroxycyclobutoxy)pyridin-3-yl)-5H-pyrido[4,3-b]indole-5-carboxylate (500 mg, 1.16 mmol) and triethylamine (352 mg, 3.47 mmol) in dichloromethane (10 ml) was added methanesulfonyl chloride (530 mg, 4.63 mmol) at 0° C. The resulting mixture was allowed to warm up to room temperature and stirred at room temperature for 5 hours. TLC showed the reaction was completed. The mixture was diluted with dichloromethane (10 ml) and washed with water (10 ml). The organic layer was washed with brine (20 ml), dried over anhydrous sodium sulfate, and concentrated under reduced pressure to afford tert-butyl 7-(6-((1s,3s)-3-hydroxycyclobutoxy)pyridin-3-yl)-5H-pyrido[4,3-b]indole-5-carboxylate (700 mg, crude) which was used in next step without further purification.

Step 5: 7-(6-((1r,3r)-3-((6-iodopyridin-3-yl)oxy)cyclobutoxy)pyridin-3-yl)-5H-pyrido[4,3-b]indole

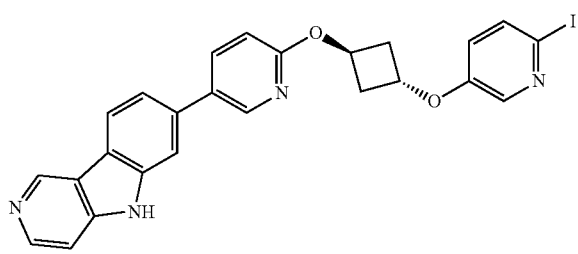 [SMILES: Ic1ccc(O[C@H]2C[C@H](Oc3ccc(-c4ccc5c(c4)[nH]c4ccncc45)cn3)C2)cn1]

A mixture of tert-butyl 7-(6-((1s,3s)-3-hydroxycyclobutoxy)pyridin-3-yl)-5H-pyrido[4,3-b]indole-5-carboxylate (350 mg, 0.69 mmol), 6-iodopyridin-3-ol (155 mg, 0.69 mmol) and cesium carbonate (452 mg, 1.39 mmol) in dry N,N-dimethylformamide (4 ml) was stirred at 90° C. for 12 hours. TLC showed the reaction was complete. The mixture was partitioned between ethyl acetate (30 ml) and water (40 ml). The organic layer was collected, washed with brine (30 ml), dried over anhydrous sodium sulfate, and concentrated under reduced pressure to give a crude residue which was purified by silica gel flash chromatography (eluted with 1-2% methanol in dichloromethane) to afford 7-(6-((1r,3r)-3-((6-iodopyridin-3-yl)oxy)cyclobutoxy)pyridin-3-yl)-5H-pyrido[4,3-b]indole (250 mg, 68%) as light yellow solid.

Step 6: [5-((3-(5-((1r,3r)-3-((5-(5H-pyrido[4,3-b]indol-7-yl)pyridin-2-yl)oxy)cyclobutoxy)pyridin-2-yl)prop-2-yn-1-yl)oxy)-2-(2,6-dioxopiperidin-3-yl)isoindoline-1,3-dione]

To a stirred solution of 7-(6-((1r,3r)-3-((6-iodopyridin-3-yl)oxy)cyclobutoxy)pyridin-3-yl)-5H-pyrido[4,3-b]indole (150 mg, 0.24 mmol), 2-(2,6-dioxopiperidin-3-yl)-5-(prop-2-yn-1-yloxy)isoindoline-1,3-dione (111 mg, 0.35 mmol) [prepared using procedure of step 1 from Exemplary Compound 180] and triethylamine (121 mg, 1.20 mmol) in N,N-dimethylformamide (2 ml) were added Bis(triphenylphosphine)palladium(II) chloride (8 mg, 0.01 mmol) and cuprous iodide (2 mg, 0.01 mmol) at room temperature under nitrogen atmosphere; the mixture was degassed with nitrogen three times. The resulting mixture was stirred at 65° C. under nitrogen overnight. TLC showed the reaction was complete. The mixture was partitioned between water (30 ml) and ethyl acetate (30 ml). The organic layer was collected and washed with brine (30 ml×2), dried over anhydrous sodium sulfate, and concentrated under reduced pressure to give a crude residue which was purified by silica gel flash column chromatography (eluted with 2% methanol in dichloromethane) to afford 5-((3-(5-((1r,3r)-3-((5-(5H-pyrido[4,3-b]indol-7-yl)pyridin-2-yl)oxy)cyclobutoxy)pyridin-2-yl)prop-2-yn-1-yl)oxy)-2-(2,6-dioxopiperidin-3-yl)isoindoline-1,3-dione (45 mg, yield 26%) as white solid.

$^{1}$H NMR (400 MHz, DMSOd-6): δ 2.04-2.07 (m, 1H), 2.57-2.77 (m, 6H), 2.86-2.93 (m, 1H), 5.10-5.14 (m, 2H), 5.32 (s, 2H), 5.39-5.48 (m, 1H), 6.97 (d, J=8.0 Hz, 1H), 7.32-7.33 (m, 1H), 7.46-7.58 (m, 5H), 7.77 (s, 1H), 7.90 (d, J=7.2 Hz, 1H), 8.14 (d, J=7.2 Hz, 1H), 8.25 (s, 1H), 8.30 (d, J=7.6 Hz, 1H), 8.43 (s, 1H), 8.56 (s, 1H), 9.36 (s, 1H), 11.12 (s, 1H), 11.82 (s, 1H). (M+H)$^{+}$ 719.4.

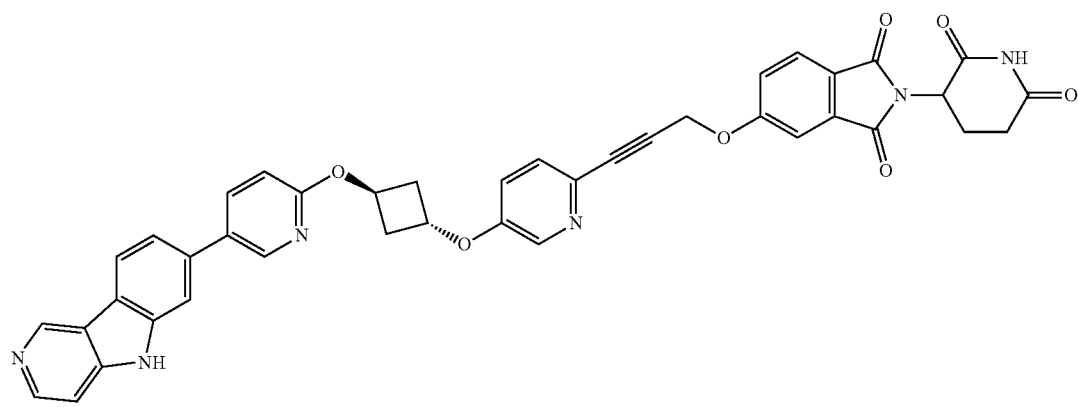 [SMILES: O=C1CCC(N2C(=O)c3ccc(OCC#Cc4ccc(O[C@H]5C[C@H](Oc6ccc(-c7ccc8c(c7)[nH]c7ccncc78)cn6)C5)cn4)cc3C2=O)C(=O)N1]

Synthetic Scheme for Exemplary Compound 77

Step 1: tert-butyl 7-(6-((1r,3r)-3-((6-(3-((2-(2,6-dioxopiperidin-3-yl)-1,3-dioxoisoindolin-5-yl)oxy)propyl)pyridin-3-yl)oxy)cyclobutoxy)pyridin-3-yl)-5H-pyrido[4,3-b]indole-5-carboxylate

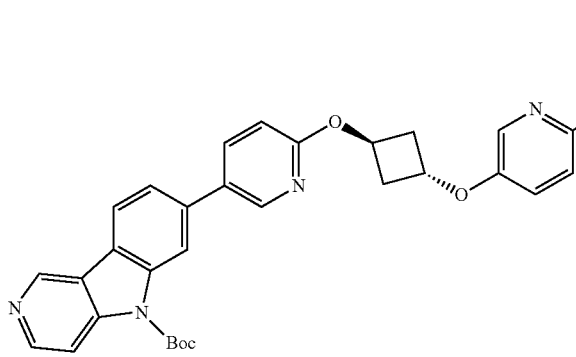

To a solution of tert-butyl 7-(6-((1r,3r)-3-((6-(3-((2-(2,6-dioxopiperidin-3-yl)-1,3-dioxoisoindolin-5-yl)oxy)prop-1-yn-1-yl)pyridin-3-yl)oxy)cyclobutoxy)pyridin-3-yl)-5H-pyrido[4,3-b]indole-5-carboxylate (15 mg) in MeOH was added Pd/C. The solution was stirred at 30° C. for 2 hours under H₂ (2 Mpa). The mixture was filtered through Celite, and the filtrate was concentrated under vacuum. The residue was purified by silica gel to afford the desired product (6 mg).

Step 2: 5-(3-(5-((1r,3r)-3-((5-(5H-pyrido[4,3-b]indol-7-yl)pyridin-2-yl)oxy)cyclobutoxy)pyridin-2-yl)propoxy)-2-(2,6-dioxopiperidin-3-yl)isoindoline-1,3-dione

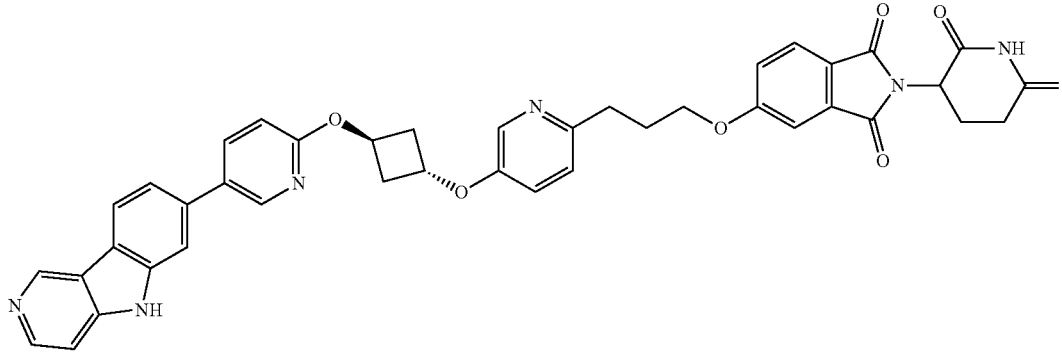

A solution of tert-butyl 7-(6-((1r,3r)-3-((6-(3-((2-(2,6-dioxopiperidin-3-yl)-1,3-dioxoisoindolin-5-yl)oxy)propyl)238pyridin-3-yl)oxy)cyclobutoxy)pyridin-3-yl)-5H-pyrido[4,3-b]indole-5-carboxylate (6 mg) in DCM/TFA (2 mL/1 mL) was stirred at room temperature for 4 hours. The solvent was removed under vacuum to afford 5-(3-(5-((1r,3r)-3-((5-(5H-pyrido[4,3-b]indol-7-yl)pyridin-2-yl)oxy)cyclobutoxy)pyridin-2-yl)propoxy)-2-(2,6-dioxopiperidin-3-yl)isoindoline-1,3-dione (5.5 mg).
¹H NMR (400 MHz, CD₃OD): δ 9.56 (s, 1H), 8.54-8.56 (m, 2H), 8.45 (d, J=8.4 Hz, 1H), 8.37 (d, J=2.4 Hz, 1H), 8.13 (d, J=8.0 Hz, 1H), 7.97 (d, J=8.0 Hz, 1H), 7.88 (d, J=8.8 Hz, 2H), 7.81 (d, J=8.4 Hz, 1H), 7.79 (s, 1H), 7.76-7.78 (d, J=8 Hz, 1H), 7.29 (s, 1H), 7.21 (d, J=8.0 Hz, 1H), 6.98 (d, J=8.0 Hz, 1H), 5.48-5.52 (m, 1H), 5.32-5.34 (m, 1H), 5.18-5.22 (m, 1H), 5.06-5.10 (m, 1H), 4.25-4.28 (m, 2H), 3.21-3.23 (m, 3H), 2.78-2.81 (m, 5H), 2.67-2.70 (m, 2H), 2.30-2.33 (m, 2H), 2.17-2.19 (m, 1H), 1.97-2.07 (m, 3H). (M+H)⁺ 723.5.

Synthetic Scheme for Exemplary Compound 94

Step 1: (1r,3r)-3-((6-(5-((triisopropylsilyl)oxy)pent-1-yn-1-yl)pyridin-3-yl)oxy)cyclobutan-1-ol

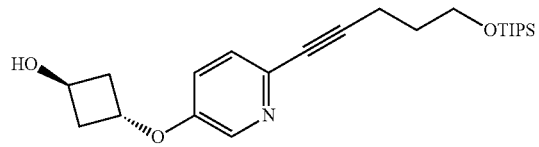

To a solution of (1r,3r)-3-((6-bromopyridin-3-yl)oxy)cyclobutan-1-ol (530 mg, 2.17 mmol) in dry THF (10 mL) was added triisopropyl(pent-4-yn-1-yloxy)silane (626 mg, 2.61 mmol), TEA (1.1 g, 10.86 mmol), CuI (45 mg, 0.24 mmol) and Pd(PPh₃)₂Cl₂ (110 mg, 4.34 mmol) at 25° C. under N₂. The resulting solution was stirred at 45° C. for 16 hours. The reaction was diluted with H₂O (10 mL). The resulting mixture was extracted with EtOAc (10 mL×2). The combined organic layers were dried over anhydrous sodium sulfate and concentrated. The residue was purified with silica gel column to afford the desired product (1r,3r)-3-((6-

(5-((triisopropylsilyl)oxy)pent-1-yn-1-yl)pyridin-3-yl)oxy) cyclobutan-1-ol (600 mg, 68% yield) as a colorless oil.

Step 2: 5-bromo-2-((1r,3r)-3-((6-(5-((triisopropylsilyl)oxy)pent-1-yn-1-yl)pyridin-3-yl)oxy)cyclobutoxy)pyridine

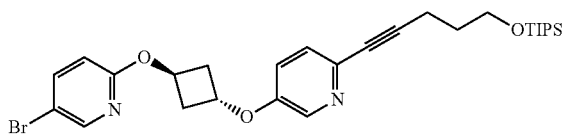

To a solution of (1r,3r)-3-((6-(5-((triisopropylsilyl)oxy)pent-1-yn-1-yl)pyridin-3-yl) oxy)cyclobutan-1-ol (300 mg, 0.74 mmol) in DMF (5 mL) was added NaH (45 mg, 1.11 mmol) at 0° C. The reaction was stirred at 0° C. for 0.5 hours, and 5-bromo-2-fluoropyridine (144 mg, 0.82 mmol) was added dropwise at 0° C. The reaction was stirred at 20° C. for 2 hours. The reaction was diluted with a solution of H₂O (10 mL). The resulting mixture was extracted with EtOAc (10 mL×2), the combined organic layers were dried over anhydrous sodium sulfate and concentration. The residue was purified with silica gel column to afford the desired product 5-bromo-2-((1r,3r)-3-((6-(5-((triisopropylsilyl)oxy)pent-1-yn-1-yl)pyridin-3-yl)oxy)cyclobutoxy)pyridine (240 mg, 58% yield) as a white solid.

Step 3: 5-methyl-7-(6-((1r,3r)-3-((6-(5-((triisopropylsilyl)oxy)pent-1-yn-1-yl)pyridin-3-yl)oxy)cyclobutoxy)pyridin-3-yl)-5H-pyrido[4,3-b]indole

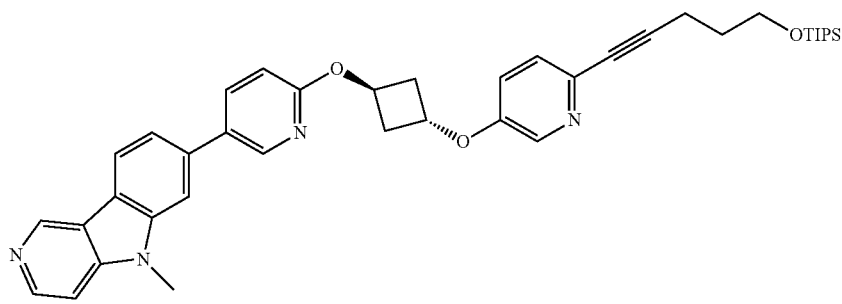

To a solution of 5-bromo-2-((1r,3r)-3-((6-(5-((triisopropylsilyl)oxy)pent-1-yn-1-yl) pyridin-3-yl)oxy)cyclobutoxy) pyridine (180 mg, 0.32 mmol) in 1,4-dioxane (5 ml) and H₂O (1 mL) was added 5-methyl-7-(6-(4,4,5,5-tetramethyl-1,3,2-dioxaborolan-2-yl)pyridin-3-yl)-5H-pyrido[4,3-b]indole (119 mg, 0.39 mmol), CsF (147 mg, 0.96 mmol) and Pd(aMphos)Cl₂ (34 mg, 0.06 mmol) at 15° C. under N₂. The resulting mixture was stirred at 80° C. for 5 hours. The mixture was quenched with H₂O (20 mL), extracted with EtOAc (10 mL×2). Then the combined organic layers were washed with brine (20 mL×2), dried over anhydrous sodium sulfate and concentrated. The residue was purified with silica gel column to afford the desired product 5-methyl-7-(6-((1r,3r)-3-((6-(5-((triisopropylsilyl)oxy)pent-1-yn-1-yl) pyridin-3-yl)oxy)cyclobutoxy)pyridin-3-yl)-5H-pyrido[4,3-b]indole (80 mg, 38% yield).

Step 4: 5-(5-((1r,3r)-3-((5-(5-methyl-5H-pyrido[4,3-b]indol-7-yl)pyridin-2-yl)oxy)cyclobutoxy)pyridin-2-yl)pent-4-yn-1-ol

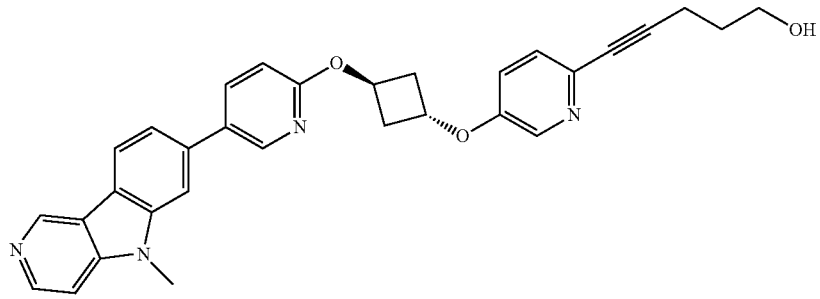 [SMILES: Cn1c2ccncc2c2ccc(-c3ccc(O[C@H]4C[C@H](Oc5ccc(C#CCCCO)nc5)C4)nc3)cc21]

To a solution of 5-methyl-7-(6-((1r,3r)-3-((6-(5-((triisopropylsilyl)oxy)pent-1-yn-1-yl)pyridin-3-yl)oxy)cyclobutoxy)pyridin-3-yl)-5H-pyrido[4,3-b]indole (90 mg, 0.14 mmol) in dry THF (10 mL) was added 1 M TBAF in THF (1 mL, 0.7 mmol) under N₂ at 15° C. The mixture was stirred at 40° C. for 1 hour under N₂ balloon. The mixture was concentrated. The residue was purified with prep-TLC to afford the desired product 5-(5-((1r,3r)-3-((5-(5-methyl-5H-pyrido[4,3-b]indol-7-yl)pyridin-2-yl)oxy)cyclobutoxy)pyridin-2-yl)pent-4-yn-1-ol (30 mg, 43% yield) as a white solid.

Step 5: 2-(2,6-dioxopiperidin-3-yl)-5-((5-(5-((1r,3r)-3-((5-(5-methyl-5H-pyrido[4,3-b]indol-7-yl)pyridin-2-yl)oxy)cyclobutoxy)pyridin-2-yl)pent-4-yn-1-yl)oxy)isoindoline-1,3-dione

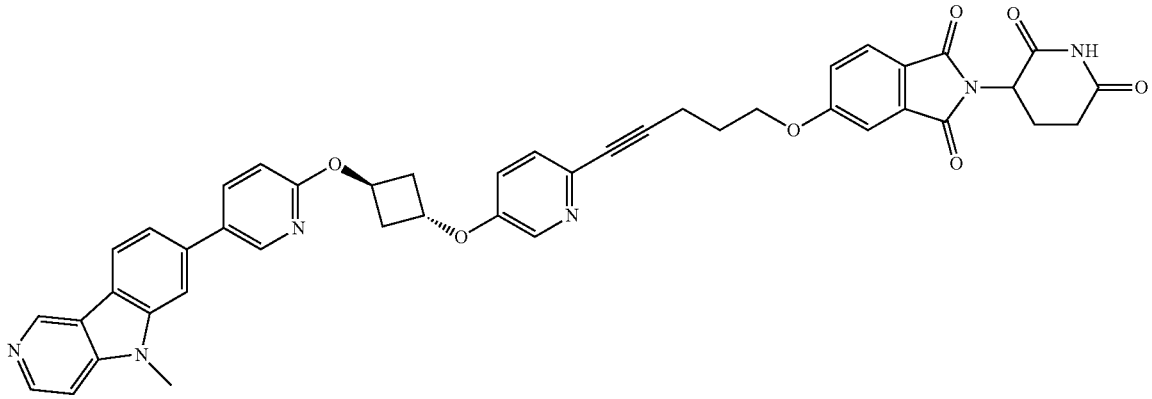 [SMILES: Cn1c2ccncc2c2ccc(-c3ccc(O[C@H]4C[C@H](Oc5ccc(C#CCCCOc6ccc7c(c6)C(=O)N(C6CCC(=O)NC6=O)C7=O)nc5)C4)nc3)cc21]

To a solution of 5-(5-((1r,3r)-3-((5-(5-methyl-5H-pyrido[4,3-b]indol-7-yl)pyridin-2-yl)oxy)cyclobutoxy)pyridin-2-yl)pent-4-yn-1-ol (25 mg, 0.05 mmol) in dry THF (2 mL) was added 2-(2,6-dioxopiperidin-3-yl)-5-hydroxyisoindoline-1,3-dione (20 mg, 0.07 mmol), PPh₃ (40 mg, 0.14 mmol) at 15° C. under N₂. DIAD (32 mg, 0.14 mmol) was added to the mixture at 40° C. under N₂. The resulting mixture was stirred at 40° C. for 0.5 hours. Cooled the mixture to 20° C. and quenched with H₂O (10 mL), extracted with EtOAc (10 mL×2). Then the combined organic layers were washed with brine (20 mL×5), dried over anhydrous sodium sulfate and concentrated. The residue was purified with prep-TLC to afford the desired product 2-(2,6-dioxopiperidin-3-yl)-5-((5-(5-((1r,3r)-3-((5-(5-methyl-5H-pyrido[4,3-b]indol-7-yl)pyridin-2-yl)oxy)cyclobutoxy)pyridin-2-yl)pent-4-yn-1-yl)oxy)isoindoline-1,3-dione (22 mg, 58% yield) as a white solid.

¹HNMR (400 MHz, DMSO-d₆): δ: 11.04 (s, 1H), 9.29 (s, 1H), 8.58 (d, J=2.0 Hz, 1H), 8.43 (d, J=5.6 Hz, 1H), 8.25 (d, J=8.0 Hz, 1H), 8.12-8.16 (m, 2H), 7.92 (s, 1H), 7.78 (d, J=7.6 Hz, 1H), 7.56 (d, J=6.0 Hz, 2H), 7.40 (s, 1H), 7.33 (d, J=8.4 Hz, 2H), 7.20-7.22 (m, 1H), 6.92 (d, J=4.4 Hz, 1H), 5.37 (s, 1H), 5.01-5.37 (m, 2H), 4.25 (t, J=6.0 Hz, 2H), 3.89 (s, 3H), 2.43-2.65 (m, 9H), 1.98 (t, J=6.4 Hz, 3H). (M+H)⁺ 761.5.

Synthetic Scheme for Exemplary Compound 117

Step 1: 5-methyl-7-(6-((1r,3r)-3-((6-(3-((tetrahydro-2H-pyran-2-yl)oxy)prop-1-yn-1-yl)pyridin-3-yl)oxy)cyclobutoxy)pyridin-3-yl)-5H-pyrido[4,3-b]indole

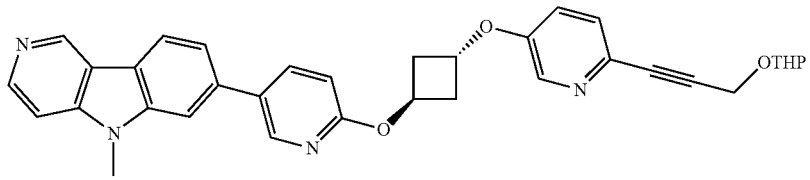

A mixture of (1s,3s)-3-((5-(5-methyl-5H-pyrido[4,3-b]indol-7-yl)pyridin-2-yl)oxy)cyclobutyl methanesulfonate (480 mg, 1.1 mmol) [prepared using procedure described in step 4 of Exemplary Compound 73], 6-(3-((tetrahydro-2H-pyran-2-yl)oxy)prop-1-yn-1-yl)pyridin-3-ol (256 mg, 1.1 mmol) and cesium carbonate (715 mg, 2.2 mmol) in N,N-dimethylformamide (15 ml) was stirred at 70° C. for 16 hours. TLC showed the reaction was complete. The reaction mixture was partitioned between water (20 ml) and ethyl acetate (40 ml). The organic layer was collected, washed with brine (50 ml), dried over sodium sulfate and evaporated under reduced pressure to give a crude residue which was purified by silica gel flash column chromatography (eluted with 0-30% ethyl acetate in hexane) to afford 5-methyl-7-(6-(((1r,3r)-3-((6-(3-((tetrahydro-2H-pyran-2-yl)oxy)prop-1-yn-1-yl)pyridin-3-yl)oxy)cyclobutoxy)pyridin-3-yl)-5H-pyrido[4,3-b]indole (350 mg, yield 57%) as white solid.

Step 2: 3-(5-(((1r,3r)-3-((5-(5-methyl-5H-pyrido[4,3-b]indol-7-yl)pyridin-2-yl)oxy)cyclobutoxy)pyridin-2-yl)prop-2-yn-1-ol

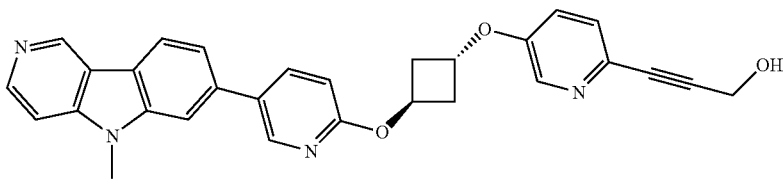 [SMILES: Cn1c2ccncc2c2ccc(-c3ccc(O[C@H]4C[C@H](Oc5ccc(C#CCO)nc5)C4)nc3)cc21]

To the solution of 5-methyl-7-(6-(((1r,3r)-3-((6-(3-((tetrahydro-2H-pyran-2-yl)oxy)prop-1-yn-1-yl)pyridin-3-yl)oxy)cyclobutoxy)pyridin-3-yl)-5H-pyrido[4,3-b]indole (350 mg, 0.62 mmol) in tetrahydrofuran (10 ml) was added aqueous hydrogen chloride (5 ml, 2M), and the reaction mixture was stirred at room temperature for 1 hours. TLC showed the reaction was complete. The reaction mixture was quenched with aqueous sodium bicarbonate solution (20 ml), and the reaction mixture was extracted with ethyl acetate (20 ml). The organic layer was collected, and the aqueous layer was extracted with ethyl acetate (10 ml×2). The combined organic layers were washed with brine (10 ml), dried over anhydrous sodium sulfate, and concentrated under reduced pressure to give 3-(5-(((1r,3r)-3-((5-(5-methyl-5H-pyrido[4,3-b]indol-7-yl)pyridin-2-yl)oxy)cyclobutoxy)pyridin-2-yl)prop-2-yn-1-ol (270 mg, crude) as white solid which was used in the next step without purification.

Step 3: 3-(5-(((1r,3r)-3-((5-(5-methyl-5H-pyrido[4,3-b]indol-7-yl)pyridin-2-yl)oxy)cyclobutoxy)pyridin-2-yl)prop-2-yn-1-yl 4-methylbenzenesulfonate

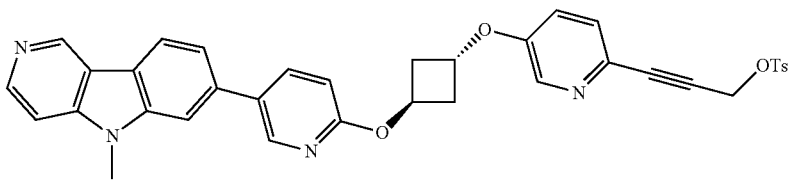 [SMILES: Cc1ccc(S(=O)(=O)OCC#Cc2ccc(O[C@H]3C[C@H](Oc4ccc(-c5ccc6c7cnccc7n(C)c6c5)cn4)C3)cn2)cc1]

A mixture of 3-(5-(((1r,3r)-3-((5-(5-methyl-5H-pyrido[4,3-b]indol-7-yl)pyridin-2-yl)oxy)cyclobutoxy)pyridin-2-yl)prop-2-yn-1-ol (200 mg, crude), triethylamine (127 mg, 1.26 mmol) and 4-methyl-benzenesulfonyl chloride (120 mg, 0.63 mmol) in dichloromethane (10 ml) was stirred at room temperature for 1 hour. The reaction mixture was quenched with water (20 ml), extracted with dichloromethane (30 ml). The organic layer was washed with brine (20 ml), dried over sodium sulfate and evaporated under reduced pressure to give a crude residue which was purified by silica gel flash column chromatography (eluted with 5% methanol in dichloromethane) to afford 3-(5-(((1r,3r)-3-((5-(5-methyl-5H-pyrido[4,3-b]indol-7-yl)pyridin-2-yl)oxy)cyclobutoxy)pyridin-2-yl)prop-2-yn-1-yl 4-methylbenzenesulfonate (130 mg, yield 49%) as white solid.

Step 4: 2-(2,6-dioxopiperidin-3-yl)-5-((3-(5-((1r,3r)-3-((5-(5-methyl-5H-pyrido[4,3-b]indol-7-yl)pyridin-2-yl)oxy)cyclobutoxy)pyridin-2-yl)prop-2-yn-1-yl)oxy)isoindoline-1,3-dione

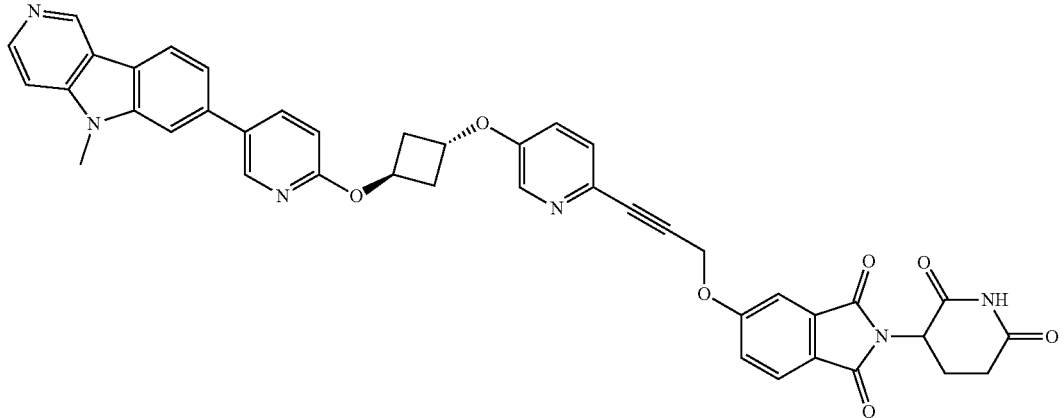 [SMILES: Cn1c2ccncc2c2ccc(-c3ccc(O[C@H]4C[C@H](Oc5ccc(C#CCOc6ccc7c(c6)C(=O)N(C6CCC(=O)NC6=O)C7=O)nc5)C4)nc3)cc21]

To a solution of 3-(5-((1r,3r)-3-((5-(5-methyl-5H-pyrido[4,3-b]indol-7-yl)pyridin-2-yl)oxy)cyclobutoxy)pyridin-2-yl)prop-2-yn-1-yl 4-methylbenzenesulfonate (130 mg, 0.21 mmol), potassium carbonate (85 mg, 0.62 mmol) and 2-(2,6-dioxopiperidin-3-yl)-5-hydroxyisoindoline-1,3-dione (57 mg, 0.21 mmol) in N,N-dimethylformamide (10 ml) was added potassium iodide (35 mg, 0.21 mmol) under nitrogen atmosphere. The resulting mixture was warmed to 50° C. and stirred for 16 hours. TLC showed the reaction was complete. The reaction mixture was partitioned between water (20 ml) and ethyl acetate (20 ml). The organic layer was collected, washed with brine (10 ml), dried over anhydrous sodium sulfate, and concentrated under reduced pressure to give the crude product which was purified by silica gel flash column chromatography (eluted with 8% methanol in dichloromethane) to afford 2-(2,6-dioxopiperidin-3-yl)-5-((3-(5-((1r,3r)-3-((5-(5-methyl-5H-pyrido[4,3-b]indol-7-yl)pyridin-2-yl)oxy)cyclobutoxy)pyridin-2-yl)prop-2-yn-1-yl)oxy)isoindoline-1,3-dione (21.3 mg, yield 14%) as yellow solid.

$^1$H NMR (400 MHz, CD$_3$OD): δ 1.92-1.94 (m, 1H), 2.02-2.10 (m, 2H), 2.62-2.65 (m, 5H), 3.90 (s, 3H), 4.97-5.02 (m, 2H), 5.10 (s, 2H), 5.37 (t, J=6 Hz, 1H), 6.85 (d, J=8.4 Hz, 1H), 7.20-7.22 (m, 1H), 7.34-7.41 (m, 2H), 7.45 (d, J=2.0 Hz, 1H), 7.50-7.56 (m, 2H), 7.75-7.77 (m, 2H), 8.02-8.06 (m, 2H), 8.21 (d, J=8.0 Hz, 1H), 8.37 (d, J=6.0 Hz, 1H), 8.42 (d, J=2.4 Hz, 1H), 9.18 (s, 1H). (M+H)$^+$ 733.4.

Using procedures analogous to those described above for Compound 83 (method of Compound 94), Compound 95, Compound 97 (method of Compound 94), Compound 98, Compound 183 (method of Compound 73), Compound 204 (combination of methods of Compound 73 and Compound 176) were prepared.

Synthetic Scheme for Exemplary Compound 102 and Exemplary Compound 110

2-(2,6-dioxopiperidin-3-yl)-5-((6-(6-((1r,3r)-3-((5-(5-methyl-5H-pyrido[4,3-b]indol-7-yl)pyridin-2-yl)oxy)cyclobutoxy)pyridin-3-yl)hex-5-yn-1-yl)oxy)isoindoline-1,3-dione (Exemplary Compound 102) and 2-(2,6-dioxopiperidin-3-yl)-5-((6-(6-((1r,3r)-3-((5-(5-methyl-5H-pyrido[4,3-b]indol-7-yl)pyridin-2-yl)oxy)cyclobutoxy)pyridin-3-yl)hexyl)oxy)isoindoline-1,3-dione (Exemplary Compound 110)

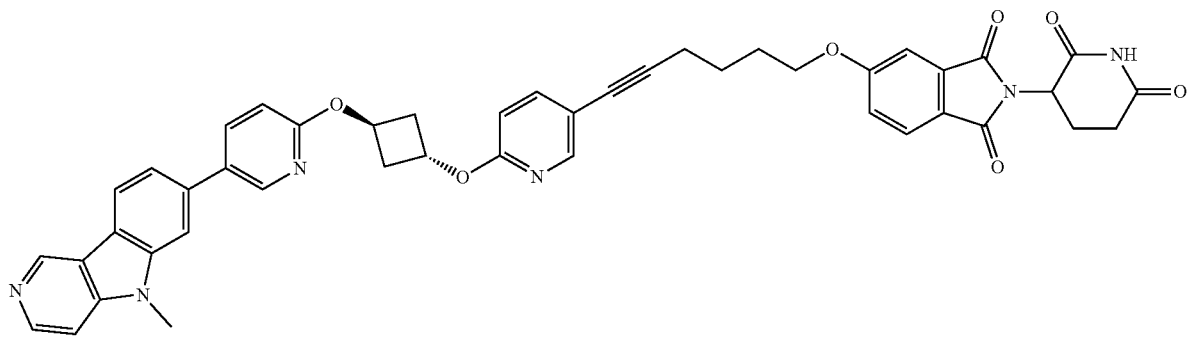

-continued

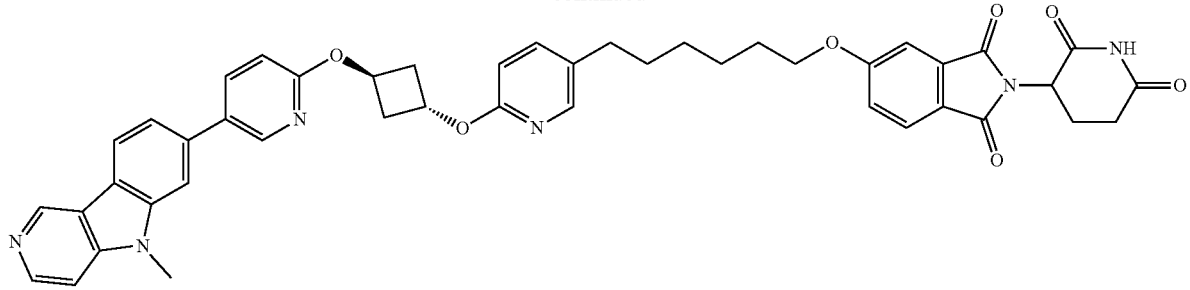

Step 1: 7-(6-((1r,3r)-3-((5-iodopyridin-2-yl)oxy) cyclobutoxy)pyridin-3-yl)-5-methyl-5H-pyrido[4,3-b]indole

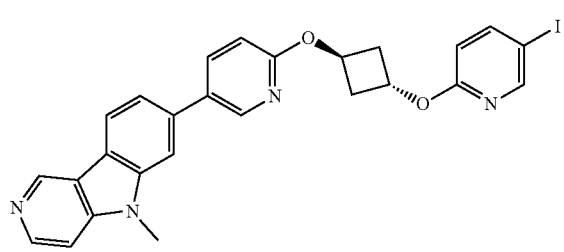 [SMILES: Cn1c2ccncc2c2ccc(-c3ccc(O[C@H]4C[C@H](Oc5ccc(I)cn5)C4)nc3)cc21]

To a solution of (1r,3r)-3-((5-(5-methyl-5H-pyrido[4,3-b]indol-7-yl)pyridin-2-yl)oxy)cyclobutanol (100 mg, 0.29 mmol) [prepared by using procedures analogous to the ones described for steps 1 and 2 for Compound 73] in 1-methylpyrrolidin-2-one (5 ml) was added sodium hydride (60% in mineral oil) (58 mg, 1.45 mmol) at 0° C., and the reaction mixture was stirred for 1 hour. Then to the reaction mixture 2-fluoro-5-iodopyridine (65 mg, 0.29 mmol) was added, and the mixture was stirred at room temperature for 2 hours. TLC showed the reaction complete. The reaction was quenched with water (10 ml) at 0° C., extracted with ethyl acetate (20 ml×2). The combined organic layers were washed with water (20 ml×2), dried over anhydrous sodium sulfate, and concentrated under reduced pressure to give a crude residue which was purified by silica gel flash chromatography (eluted with 5% methanol in dichloromethane) to afford 7-(6-((1r,3r)-3-((5-iodopyridin-2-yl)oxy)cyclobutoxy)pyridin-3-yl)-5-methyl-5H-pyrido[4,3-b]indole (100 mg, yield 63%) as a white solid.

Using procedures described for Compound 73, 7-(6-((1r,3r)-3-((5-iodopyridin-2-yl)oxy)cyclobutoxy)pyridin-3-yl)-5-methyl-5H-pyrido[4,3-b]indole was converted to the title compounds, 2-(2,6-dioxopiperidin-3-yl)-5-((6-(6-((1r,3r)-3-((5-(5-methyl-5H-pyrido[4,3-b]indol-7-yl)pyridin-2-yl)oxy)cyclobutoxy)pyridin-3-yl)hex-5-yn-1-yl)oxy)isoindoline-1,3-dione (Compound 102) and 2-(2,6-dioxopiperidin-3-yl)-5-((6-(6-((1r,3r)-3-((5-(5-methyl-5H-pyrido[4,3-b]indol-7-yl)pyridin-2-yl)oxy)cyclobutoxy)pyridin-3-yl)hexyl)oxy)isoindoline-1,3-dione (Compound 110) according to the scheme below.

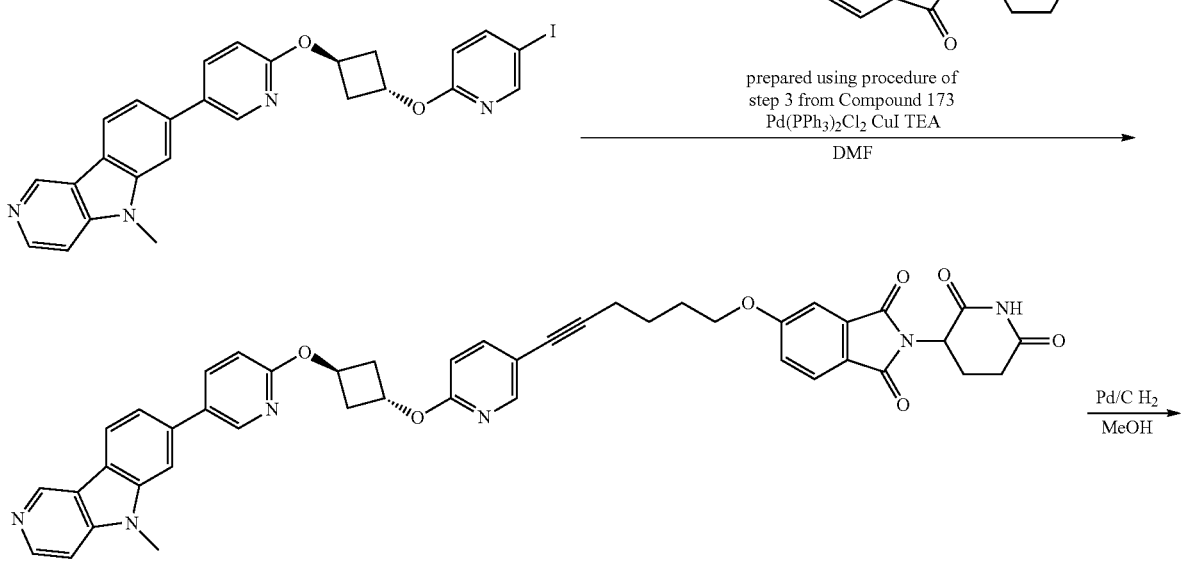

Compound 102

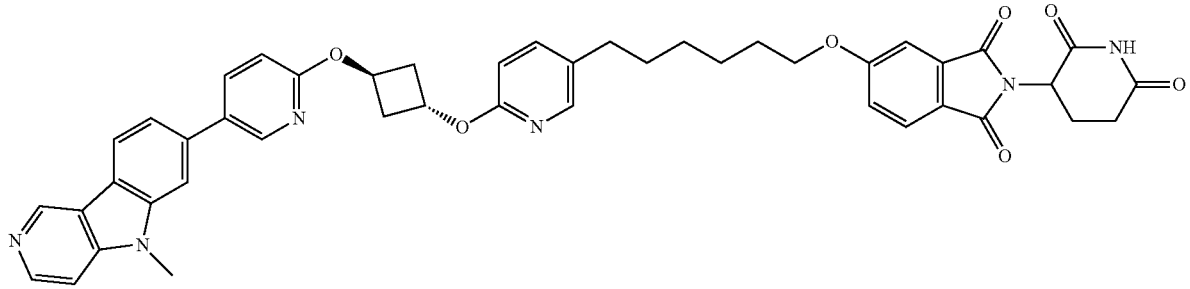

Compound 110

Compound 102: $^1$HNMR (400 MHz, DMSO-$d_6$): δ 1.73 (d, J=7.2 Hz, 2H), 1.91 (d, J=7.2 Hz, 2H), 2.01-2.08 (m, 1H), 2.51-2.67 (m, 8H), 2.83-2.94 (m, 1H), 3.96 (s, 3H), 4.24 (t, J=6.0 Hz, 2H), 5.12 (dd, J=12.8, 5.2 Hz, 1H), 5.31-5.52 (m, 2H), 6.99 (d, J=8.4 Hz, 1H), 6.83 (d, J=8.6 Hz, 1H), 7.36 (d, J=8.2 Hz, 1H), 7.44 (s, 1H), 7.75-7.58 (m, 3H), 7.82 (d, J=8.2 Hz, 1H), 7.99 (s, 1H), 8.10-8.28 (m, 2H), 8.33 (d, J=8.2 Hz, 1H), 8.52 (s, 1H), 8.64 (d, J=1.6 Hz, 1H), 9.40 (s, 1H), 11.11 (s, 1H). (M+H)$^+$ 775.5

Compound 110: $^1$H NMR (400 MHz, DMSO-$d_6$): δ 1.36 (d, J=7.6 Hz, 2H), 1.45 (d, J=6.8 Hz, 2H), 1.52-1.61 (m, 2H), 1.70-1.80 (m, 2H), 1.98-2.02 (m, 3H), 2.54-2.70 (m, 6H), 2.89 (t, J=16.6 Hz, 1H), 3.96 (s, 3H), 4.16 (d, J=5.0 Hz, 2H), 5.12 (dd, J=12.8, 4.4 Hz, 1H), 5.36-5.43 (m, 2H), 6.77 (d, J=8.4 Hz, 1H), 6.99 (d, J=8.0 Hz, 1H), 7.34 (d, J=8.8 Hz, 1H), 7.42 (s, 1H), 7.60-7.64 (m, 3H), 7.83 (d, J=8.0 Hz, 1H), 7.97 (dd, J=14.0, 6.4 Hz, 2H), 8.33 (d, J=8.4 Hz, 1H), 8.21 (d, J=8.0 Hz, 1H), 8.50 (d, J=4.8 Hz, 1H), 8.65 (s, 1H), 9.37 (s, 1H), 11.11 (s, 1H). (M+H)$^+$ 779.5

Synthetic Scheme for Exemplary Compound 173

5-(2-((3-(5-((1r,3r)-3-((5-(5H-pyrido[4,3-b]indol-7-yl)pyridin-2-yl)oxy)cyclobutoxy)pyridin-2-yl)prop-2-yn-1-yl)oxy)ethoxy)-2-(2,6-dioxopiperidin-3-yl)isoindoline-1,3-dione

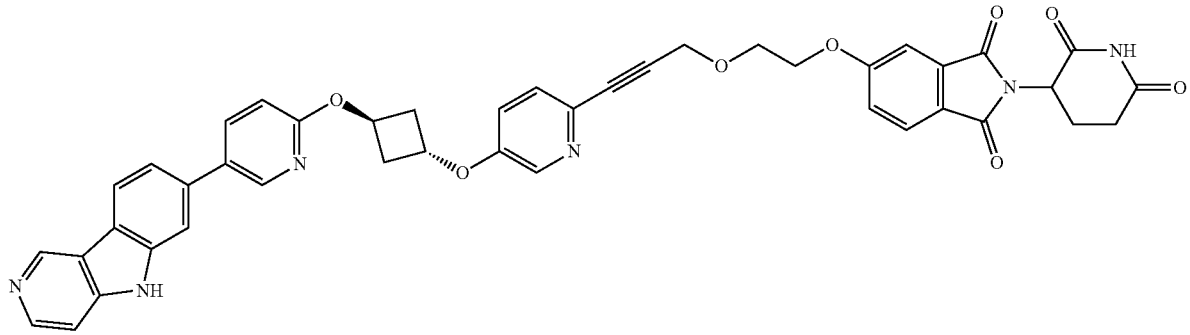 [SMILES: O=C1CCC(N2C(=O)c3ccc(OCCOCC#Cc4ccc(O[C@H]5C[C@H](Oc6ccc(-c7ccc8c(c7)[nH]c7ccncc78)cn6)C5)cn4)cc3C2=O)C(=O)N1]

Step 1: 2-(prop-2-yn-1-yloxy)ethan-1-ol

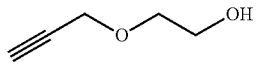

To a stirred mixture of sodium hydride (60% in mineral oil, 115 mg, 2.8 mmol) in anhydrous N,N-dimethylformamide (20 ml) at 0° C. was added ethane-1,2-diol (3.9 g, 63 mmol) and stirred at 0° C. for 0.5 hour. To the resulting mixture was added 3-bromoprop-1-yne (5.0 g, 42 mmol) at 0° C. and stirred at 50° C. overnight. TLC showed the reaction was complete. The reaction mixture was quenched with ice water (20 ml) and partitioned between ethyl acetate (80 ml) and water (100 ml). The organic layer was collected, and the aqueous layer was extracted with ethyl acetate (50 ml×2). The combined organic layers were washed with brine (80 ml), dried over anhydrous sodium sulfate, and concentrated under reduced pressure to give a crude residue which was purified by silica gel flash chromatography (eluted with 0-20% ethyl acetate in hexane) to afford 2-(prop-2-yn-1-yloxy)ethanol (3.4 g, yield 80%) as colorless oil.

Step 2: 2-(prop-2-yn-1-yloxy)ethyl 4-methylbenzenesulfonate

To a stirred solution of 2-(prop-2-yn-1-yloxy)ethanol (1 g, 10 mmol), triethylamine (3 g, 3 mmol) and N,N-dimethylpyridin-4-amine (20 mg, 1 mmol), in dichloromethane (20 ml) was added p-toluenesulfonic acid 2.9 g, 15 mmol) at 0° C. The reaction mixture was allowed to warm up to room temperature and stirred at room temperature overnight. The reaction mixture was diluted with dichloromethane (20 ml), washed with brine (50 ml), dried over anhydrous sodium sulfate and concentrated under reduced pressure to afford crude residue. It was purified by silica gel flash column chromatography (eluent 10-20% ethyl acetate in hexane) to afford 2-(prop-2-yn-1-yloxy)ethyl 4-methylbenzenesulfonate (700 mg, yield: 40%) as light yellow oil.

Step 3: 2-(2,6-dioxopiperidin-3-yl)-5-(2-(prop-2-yn-1-yloxy)ethoxy)isoindoline-1,3-dione

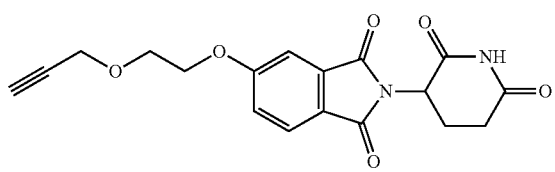 [SMILES: C#CCOCCOc1ccc2c(c1)C(=O)N(C1CCC(=O)NC1=O)C2=O]

To a stirred solution of 2-(prop-2-yn-1-yloxy)ethyl 4-methylbenzenesulfonate (700 mg, 2.8 mmol) and potassium carbonate (1.1 g, 8.3 mmol) in N,N-dimethylformamide (15 ml) was added 2-(2,6-dioxopiperidin-3-yl)-5-hydroxyisoindoline-1,3-dione (755 mg, 2.8 mmol) at room temperature. The resulting mixture was stirred at 50° C. overnight. TLC showed the reaction was complete. The mixture solution was cooled to room temperature. The reaction mixture was partitioned between ethyl acetate (20 ml) and water (30 ml); the organic layer was collected and the aqueous layer was extracted with ethyl acetate (20 ml×2). The combined organic layers were washed with brine (30 ml), dried over anhydrous sodium sulfate, and concentrated under reduced pressure to give a crude residue which was purified by silica gel flash chromatography (eluted with 0-50% ethyl acetate in hexane) to afford 2-(2,6-dioxopiperidin-3-yl)-5-(2-(prop-2-yn-1-yloxy)ethoxy)isoindoline-1,3-dione (290 mg, yield 30%) as light yellow solid.

2-(2,6-dioxopiperidin-3-yl)-5-(2-(prop-2-yn-1-yloxy)ethoxy)isoindoline-1,3-dione was reacted with 7-(6-((1r,3r)-3-((6-iodopyridin-3-yl)oxy)cyclobutoxy)pyridin-3-yl)-5H-pyrido[4,3-b]indole using procedure described for Compound 73 to produce the title compound, 5-(2-((3-(5-((1r,3r)-3-((5-(5H-pyrido[4,3-b]indol-7-yl)pyridin-2-yl)oxy)cyclobutoxy)pyridin-2-yl)prop-2-yn-1-yl)oxy)ethoxy)-2-(2,6-dioxopiperidin-3-yl)isoindoline-1,3-dione.

$^1$H NMR (400 MHz, DMSO-d6): δ 2.02-2.08 (m, 1H), 2.52-2.76 (m, 6H), 2.85-2.93 (m, 1H), 3.89-3.95 (m, 2H), 4.37-4.42 (m, 2H), 4.49 (s, 2H), 5.06-5.14 (m, 2H), 5.40-5.47 (m, 1H), 6.99 (d, J=8.4 Hz, 1H), 7.30-7.33 (m, 1H), 7.38-7.40 (m, 1H), 7.46-7.48 (m, 2H), 7.62-7.64 (m, 2H), 7.82-7.84 (m, 2H), 8.14-8.17 (m, 1H), 8.24 (d, J=2.8 Hz, 1H), 8.36-8.38 (m, 1H), 8.49 (d, J=6 Hz, 1H), 8.58 (d, J=2.0 Hz, 1H), 9.47 (s, 1H), 11.11 (s, 1H), 12.14-12.28 (m, 1H). (M+H)$^+$ 763.5.

Using procedures analogous to those described above Compounds 110 (method of Compound 102), 124, 144 (method of Compound 102), 145, 146, 147 (method of Compound 94), 172 (method of Compound 73), 179 (method of Compound 173), 188 (method of Compound 173), 189 (method of Compound 73) were prepared.

Synthetic Scheme for Exemplary Compound 180

Step 1: tert-butyl (S)-5-amino-5-oxo-4-(1-oxo-5-(prop-2-yn-1-yloxy)isoindolin-2-yl)pentanoate

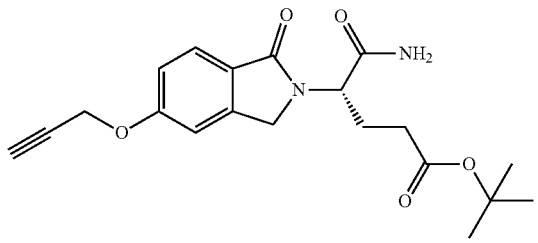 [SMILES: C#CCOc1ccc2c(c1)CN([C@@H](CCC(=O)OC(C)(C)C)C(N)=O)C2=O]

To a stirred solution of (S)-tert-butyl 5-amino-4-(5-hydroxy-1-oxoisoindolin-2-yl)-5-oxopentanoate (450 mg, 1.35 mmol), and 3-bromoprop-1-yne (192 mg, 1.62 mmol) in N,N-dimethylformamide (4 ml) was added potassium carbonate (372 mg, 2.69 mmol) and potassium iodide (22.4 mg, 0.135 mmol), and the mixture was stirred at 50° C. overnight under nitrogen. LCMS showed formation of desired product. The mixture was partitioned between ethyl acetate (50 ml) and water (30 ml). The organic layer was washed with brine (30 ml), dried over anhydrous sodium sulfate, and concentrated under reduced pressure to give a crude residue which was purified by silica gel flash chromatography (eluted with 50% ethyl acetate in hexane and added 5% methanol) to afford (S)-tert-butyl 5-amino-5-oxo-4-(1-oxo-5-(prop-2-yn-1-yloxy)isoindolin-2-yl)pentanoate (489 mg, yield 97%) as colorless oil.

Step 2: 3-(1-oxo-5-(prop-2-yn-1-yloxy)isoindolin-2-yl)piperidine-2,6-dione

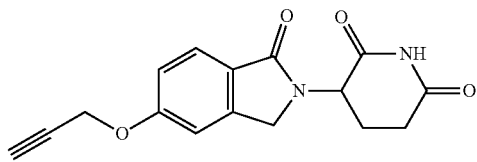 [SMILES: C#CCOc1ccc2c(c1)CN(C1CCC(=O)NC1=O)C2=O]

To a stirred solution of (S)-tert-butyl 5-amino-5-oxo-4-(1-oxo-5-(prop-2-yn-1-yloxy)isoindolin-2-yl)pentanoate (325 mg, 0.873 mmol) in anhydrous tetrahydrofuran (20 ml) was added dropwise potassium tert-butoxide (1N, in THF) (107.7 mg, 0.96 mmol) at 0° C. under nitrogen atmosphere. The reaction mixture was stirred at the same temperature for 20 minutes. LCMS showed formation of desired product. The reaction mixture was quenched with water (20 ml), and extracted with ethyl acetate (50 ml). The organic layer was collected, washed with water (20 ml), dried over anhydrous sodium sulfate, and concentrated under reduced pressure to give a crude residue which was purified by silica gel flash chromatography (eluted with 50% ethyl acetate in hexane and added 10% methanol) to afford 3-(1-oxo-5-(prop-2-yn-1-yloxy)isoindolin-2-yl)piperidine-2,6-dione (128 mg, yield 49%) as white solid.

Step 3: 3-(5-((3-(5-((1r,3r)-3-((5-(5H-pyrido[4,3-b]indol-7-yl)pyridin-2-yl)oxy)cyclobutoxy)pyridin-2-yl)prop-2-yn-1-yl)oxy)-1-oxoisoindolin-2-yl)piperidine-2,6-dione

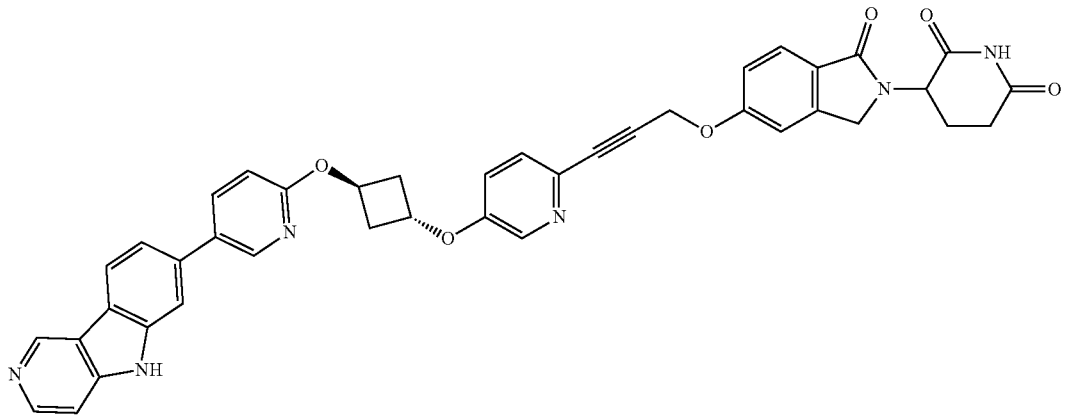 [SMILES: O=C1CCC(N2Cc3cc(OCC#Cc4ccc(O[C@H]5C[C@H](Oc6ccc(-c7ccc8c(c7)[nH]c7ccncc78)cn6)C5)cn4)ccc3C2=O)C(=O)N1]

To a stirred solution of 3-(1-oxo-5-(prop-2-yn-1-yloxy)isoindolin-2-yl)piperidine-2,6-dione (50 mg, 0.168 mmol), 7-(6-((1r,3r)-3-((6-iodopyridin-3-yl)oxy)cyclobutoxy)pyridin-3-yl)-5H-pyrido[4,3-b]indole (74 mg, 0.14 mmol) and triethylamine (70.7 mg, 0.70 mmol) in N,N-dimethylformamide (1 ml) were added trans-dichlorobis(triphenylphosphine) palladium(II) (4.91 mg, 0.007 mmol) and copper iodide (1.33 mg, 0.007 mmol) at room temperature under nitrogen atmosphere; the mixture was degassed with nitrogen three times. The resulting mixture was stirred at 65° C. for 12 hours. TLC showed the reaction was complete. TLC showed the reaction was complete. The mixture was partitioned between ethyl acetate (50 ml) and water (30 ml). The organic layer was washed with brine (30 ml), dried over anhydrous sodium sulfate, and concentrated under reduced pressure to give a crude residue which was purified by prep TLC (eluted with 10% methanol in dichloroethane) to afford 3-(5-((3-(5-((1r,3r)-3-((5-(5H-pyrido[4,3-b]indol-7-yl)pyridin-2-yl)oxy)cyclobutoxy)pyridin-2-yl)prop-2-yn-1-yl)oxy)-1-oxoisoindolin-2-yl)piperidine-2,6-dione (19 mg, 16%) as white solid.

$^1$HNMR (400 MHz, DMSO-d6): δ 1.97-2.00 (m, 1H), 2.33-2.44 (m, 2H), 2.55-2.67 (m, 4H), 2.86-2.96 (m, 1H), 4.29 (d, J=17.2 Hz, 1H), 4.42 (d, J=16.8 Hz, 1H), 5.06-5.10 (m, 2H), 5.18 (s, 2H), 5.42-5.45 (m, 1H), 6.99 (d, J=8.4 Hz, 1H), 7.17 (d, J=8.0 Hz, 1H), 7.29-7.33 (m, 2H), 7.50 (d, J=8.4 Hz, 1H), 7.68 (d, J=8.0 Hz, 2H), 7.74 (d, J=5.6 Hz, 1H), 7.89 (s, 1H), 8.16 (d, J=7.6 Hz, 1H), 8.24 (s, 1H), 8.41 (d, J=7.6 Hz, 1H), 8.53-8.59 (m, 2H), 9.56 (s, 1H), 10.97 (s, 1H), 12.54 (br, 1H). (M+H)$^+$ 705.4.

Synthetic Scheme for Exemplary Compound 64

5-(4-(3-(5-((1r,3r)-3-((5-(5H-pyrido[4,3-b]indol-7-yl)pyridin-2-yl)oxy)cyclobutoxy)pyridin-2-yl)propyl)piperazin-1-yl)-2-(2,6-dioxopiperidin-3-yl)isoindoline-1,3-dione

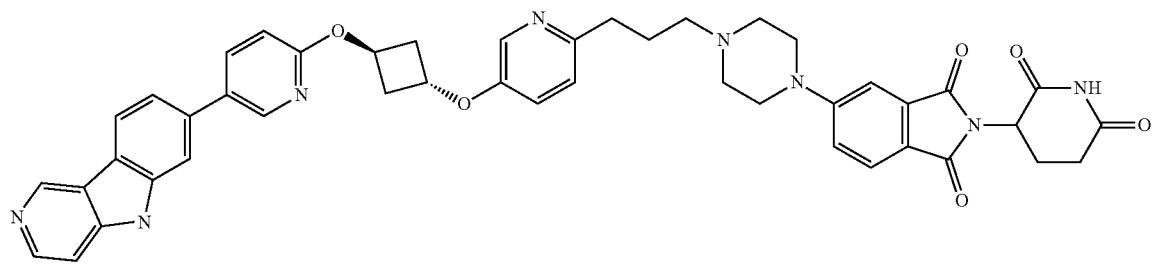 [SMILES: O=C1CCC(N2C(=O)c3ccc(N4CCN(CCCc5ccc(O[C@H]6C[C@H](Oc7ccc(-c8ccc9c(c8)[nH]c8ccncc89)cn7)C6)cn5)CC4)cc3C2=O)C(=O)N1]

The title compound was prepared according to the scheme below using procedures described above for other targets and common procedures known to those skilled in the art. The starting tert-butyl 7-(6-((1r,3r)-3-((6-(3-hydroxyprop-1-yn-1-yl)pyridin-3-yl)oxy)cyclobutoxy)pyridin-3-yl)-5H-pyrido[4,3-b]indole-5-carboxylate was prepared according to the procedures described for the Compound 117.
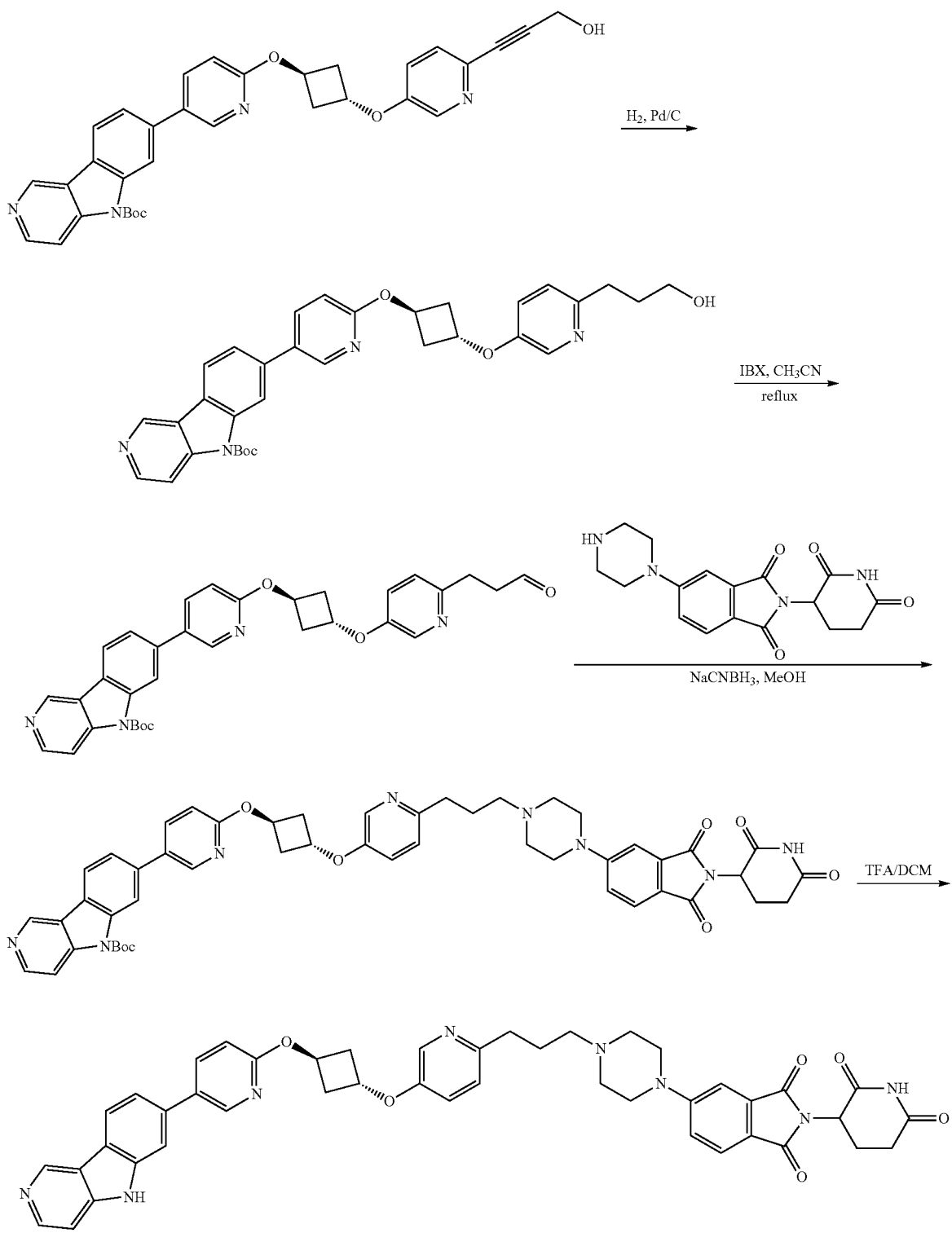

5-(4-(3-(5-((1r,3r)-3-((5-(5H-pyrido[4,3-b]indol-7-yl)pyridin-2-yl)oxy)cyclobutoxy)pyridin-2-yl)propyl)piperazin-1-yl)-2-(2,6-dioxopiperidin-3-yl)isoindoline-1,3-dione ¹H NMR (400 MHz, CD₃OD) δ 9.42 (s, 1H), 8.53 (d, J=2.3 Hz, 1H), 8.50 (d, J=6.1 Hz, 1H), 8.38 (d, J=8.1 Hz, 1H), 8.13 (d, J=8.0 Hz, 2H), 7.87 (s, 1H), 7.71-7.78 (m, 2H), 7.68 (d, J=8.3 Hz, 1H), 7.42 (s, 1H), 7.33 (s, 2H), 7.29 (d, J=8.6 Hz, 1H), 6.99 (d, J=8.6 Hz, 1H), 5.51 (s, 2H), 5.06-5.14 (m, 2H), 3.55 (s, 4H), 2.58-3.03 (m, 15H), 2.04 (m, 3H).

Synthetic Scheme for Exemplary Compound 67

Step 1: 14-((5-bromo-3-(trifluoromethyl)pyridin-2-yl)oxy)-3,6,9,12-tetraoxatetradecan-1-ol

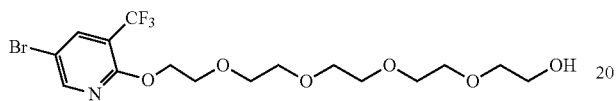

To a solution of pentaethylene glycol (330 mg, 1.38 mmol) in THF (5 mL) was added NaH (30 mg, 0.76 mmol) at 0° C. The solution was stirred at room temperature for 1 hour. Then 5-bromo-2-chloro-3-(trifluoromethyl)pyridine (180 mg, 0.69 mmol) was added. The resulting solution was stirred at 80° C. for 2 hours. The reaction solution was quenched with water. The mixture was extracted with ethyl acetate (20 mL). The combined organic layers were washed with brine (10 mL). The organic layer was dried over anhydrous sodium sulfate, filtered and concentrated to afford the desired compound (400 mg, crude), which was used into the next step without further purification.

Step 2: 14-((5-(5-methyl-5H-pyrido[4,3-b]indol-7-yl)-3-(trifluoromethyl)pyridin-2-yl)oxy)-3,6,9,12-tetraoxatetradecan-1-ol

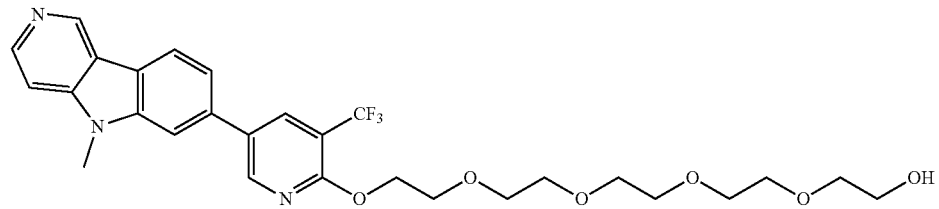 [SMILES: Cn1c2ccncc2c2ccc(-c3cnc(OCCOCCOCCOCCOCCO)c(C(F)(F)F)c3)cc21]

A mixture of 14-((5-bromo-3-(trifluoromethyl)pyridin-2-yl)oxy)-3,6,9,12-tetraoxatetradecan-1-ol (180 mg, 0.39 mmol), 5-methyl-7-(4,4,5,5-tetramethyl-1,3,2-dioxaborolan-2-yl)-5H-pyrido[4,3-b]indole (120 mg, 0.39 mmol) [prepared as described in step 1 of Compound 63], Pd(amphos)Cl₂ (20 mg, 10%) and CsF (118 mg, 0.78 mmol) in dioxane/H₂O (10/1, 5 mL) was stirred at 80° C. for 2 hours. The reaction mixture was quenched with water. The mixture was extracted with ethyl acetate (20 mL). The organic layer was dried over Na₂SO₄, filtered and concentrated under vacuum. The residue was purified by silica gel column chromatography to afford the desired compound (85 mg, 47% yield).

Step 3: 2-(2,6-dioxopiperidin-3-yl)-5-((14-((5-(5-methyl-5H-pyrido[4,3-b]indol-7-yl)-3-(trifluoromethyl)pyridin-2-yl)oxy)-3,6,9,12-tetraoxatetradecyl)oxy)isoindoline-1,3-dione

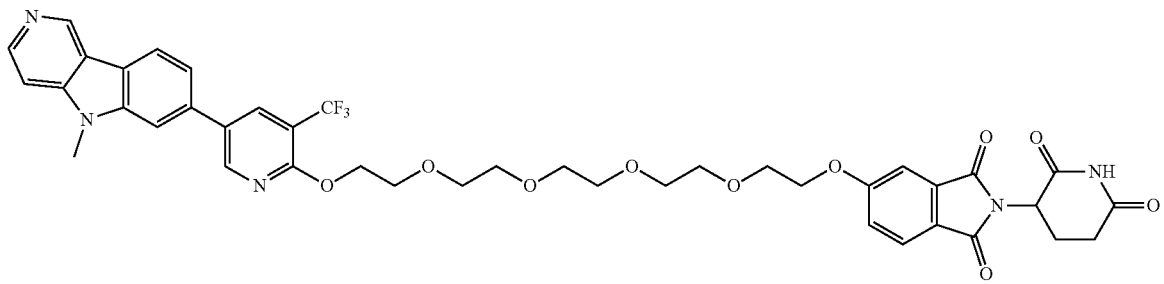 [SMILES: Cn1c2ccncc2c2ccc(-c3cnc(OCCOCCOCCOCCOCCOc4ccc5c(c4)C(=O)N(C4CCC(=O)NC4=O)C5=O)c(C(F)(F)F)c3)cc21]

To a solution of 14-((5-(5-methyl-5H-pyrido[4,3-b]indol-7-yl)-3-(trifluoromethyl)pyridin-2-yl)oxy)-3,6,9,12-tetraoxatetradecan-1-ol (85 mg, 0.15 mmol), 2-(2,6-dioxopiperidin-3-yl)-5-hydroxyisoindoline-1,3-dione (41 mg, 0.15 mmol) and PPh₃ (47 mg, 0.18 mmol) in THF was added DIAD (45 mg, 0.22 mmol) at 40° C. The mixture was stirred at 40° C. for 1 hour. The reaction solution was quenched with water. The mixture was extracted with ethyl acetate (20 mL). The combined organic layers were washed with brine (10 mL). The organic layer was dried over Na₂SO₄, filtered and concentrated under vacuum. The residue was purified by silica gel column chromatography to afford the title compound (34 mg, 28% yield).

¹H NMR (400 MHz, CD₃OD): δ 9.25 (s, 1H), 8.79 (s, 1H), 8.37-8.39 (d, J=8.0 Hz, 1H), 8.28-8.30 (d, J=8.0 Hz, 2H), 7.89 (s, 1H), 7.63-7.65 (d, J=8.0 Hz, 1H), 7.54-7.56 (m, 2H), 7.26 (s, 1H), 7.18-7.20 (m, 1H), 5.02-5.05 (m, 1H), 4.62-4.64 (m, 2H), 4.17-4.19 (m, 2H), 3.95 (s, 3H), 3.88-3.90 (m, 2H), 3.82-3.84 (m, 2H), 3.61-3.71 (m, 13H), 2.55-2.81 (m, 3H), 2.95-2.99 (m, 1H). (M+H)⁺ 820.5.

Using procedures of Compound 67 the following were prepared: Compound 69, Compound 113.

Synthetic Scheme for Exemplary Compound 65

Step 1:
4-((1r,3r)-3-(benzyloxy)cyclobutoxy)pyridine

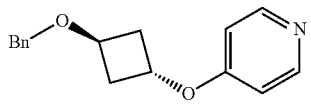

To a solution of pyridin-4-ol (3.20 g, 33.66 mmol, 1.5 eq) and 3-benzyloxycyclobutanol (4 g, 22.44 mmol, 1 eq) in tetrahydrofuran (200 mL) was added triphenylphosphine (7.06 g, 26.93 mmol, 1.2 eq) and diisopropyl azodicarboxylate (5.45 g, 26.93 mmol, 1.2 eq) in one portion at 10° C. under nitrogen. The mixture was stirred at 50° C. for 12 hours. The reaction mixture was concentrated under reduced pressure to remove tetrahydrofuran. Water (50 mL) was poured into the mixture and stirred for 1 minute. The aqueous phase was extracted with dichloromethane (50 mL×3). The combined organic phase was washed with brine (50 mL×2), dried with anhydrous sodium sulfate, filtered and concentrated in vacuum. The residue was purified by silica gel column chromatography (petroleum ether: tetrahydrofuran from 20:1 to 5:1). HPLC showed 41% of the product in 254 mm. The residue was purified by flash C18 column chromatography [acetonitrile: water (0.5% ammonium hydroxide)=5%-50%]. Compound 4-(3-benzyloxycyclobutoxy) pyridine (3.2 g, 12.53 mmol, 55% yield) was obtained as a white solid.

Step 2: 1-benzyl-4-((1r,3r)-3-(benzyloxy)cyclobutoxy)pyridin-1-ium bromide

To a solution of 4-(3-benzyloxycyclobutoxy)pyridine (4.2 g, 16.45 mmol, 1 eq) in toluene (65 mL) was added benzyl bromide (2.81 g, 16.45 mmol, 1 eq). The mixture was stirred at 80° C. for 12 hours. The reaction mixture was concentrated under reduced pressure to remove toluene. The crude product was triturated with petroleum ether (80 mL). Compound 1-benzyl-4-((1r,3r)-3-(benzyloxy)cyclobutoxy)pyridin-1-ium bromide (6.5 g, 15.25 mmol, 92% yield) was obtained as a white solid.

Step 3: 1-benzyl-4-((1r,3r)-3-(benzyloxy)cyclobutoxy)-1,2,3,6-tetrahydropyridine

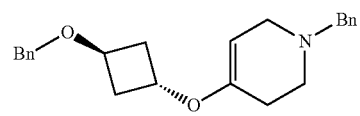 [SMILES: C1=C(O[C@H]2C[C@H](OCc3ccccc3)C2)CCN(Cc2ccccc2)C1]

To a solution of 1-benzyl-4-((1r,3r)-3-(benzyloxy)cyclobutoxy)pyridin-1-ium bromide (6.5 g, 15.25 mmol, 1 eq) in ethanol (120 mL) was added sodium borohydride (3.46 g, 91.47 mmol, 6 eq) at 0° C. The mixture was stirred at 15° C. for 4 hours. The reaction mixture was concentrated under reduced pressure to remove ethanol. The residue was diluted with water (25 mL) and extracted with ethyl acetate (50 mL×2). The combined organic phase was washed with saturated brine (40 mL×3), dried with anhydrous sodium sulfate, filtered and concentrated in vacuum. Compound 1-benzyl-4-(3-benzyloxycyclobutoxy)-3,6-dihydro-2H-pyridine (4.5 g, 12.88 mmol, 84% yield) was obtained as a colorless oil.

Step 4: (1r,3r)-3-((1-benzylpiperidin-4-yl)oxy)cyclobutan-1-ol

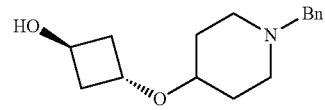 [SMILES: O[C@H]1C[C@H](OC2CCN(Cc3ccccc3)CC2)C1]

To a solution of 1-benzyl-4-(3-benzyloxycyclobutoxy)-3,6-dihydro-2H-pyridine (4.5 g, 12.88 mmol, 1 eq) in tetrahydrofuran (95 mL) and ethanol (70 mL) was added palladium on activated carbon catalyst (0.5 g, 10% purity) under nitrogen atmosphere. The suspension was degassed and purged with hydrogen for 3 times. The mixture was stirred under hydrogen (50 Psi) at 25° C. for 24 hours. LCMS showed the reaction was not completed. The mixture was then stirred at 35° C. for 12 hours. The reaction mixture was filtered and the filtrate was concentrated. The residue was purified by silica gel column chromatography (dichloromethane:methanol:ammonium hydroxide from 20:1:0 to 10:1:0.1). Compound 3-[(1-benzyl-4-piperidyl)oxy]cyclobutanol (2.8 g, 10.71 mmol, 83% yield) was obtained as a colorless oil.

Step 5: tert-butyl 4-((1r,3r)-3-hydroxycyclobutoxy)piperidine-1-carboxylate

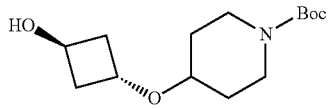 [SMILES: CC(C)(C)OC(=O)N1CCC(O[C@H]2C[C@H](O)C2)CC1]

To a solution of 3-[(1-benzyl-4-piperidyl)oxy]cyclobutanol (1.1 g, 4.21 mmol, 1 eq) in methanol (10 mL) was added palladium hydroxide (591 mg) and di-tert-butyl carbonate (1.84 g, 8.42 mmol, 2 eq) under nitrogen atmosphere. The suspension was degassed and purged with hydrogen for 3 times. The mixture was stirred under hydrogen (50 Psi) at 25° C. for 12 hours. The reaction mixture was filtered and the filter was concentrated. The residue was purified by silica gel chromatography (petroleum ether:ethyl acetate= 20:1 to 2:1). Compound tert-butyl 4-(3-hydroxycyclobutoxy)piperidine-1-carboxylate (820 mg, 3.02 mmol, 71% yield) was obtained as a colorless oil.

Step 6: tert-butyl 4-((1r,3r)-3-((5-bromopyridin-2-yl)oxy)cyclobutoxy)piperidine-1-carboxylate

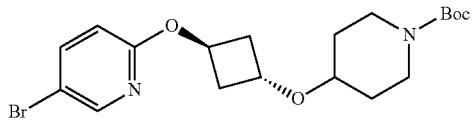 [SMILES: CC(C)(C)OC(=O)N1CCC(O[C@H]2C[C@H](Oc3ccc(Br)cn3)C2)CC1]

To a mixture of tert-butyl 4-(3-hydroxycyclobutoxy)piperidine-1-carboxylate (400 mg, 1.47 mmol, 1 eq) and 5-bromo-2-fluoro-pyridine (285 mg, 1.62 mmol, 1.1 eq) in dimethylformamide (8 mL) was added cesium carbonate (960 mg, 2.95 mmol, 2 eq) in one portion at 25° C. under nitrogen atmosphere. The mixture was stirred at 100° C. for 2 hours. The reaction mixture was poured into water (30 mL) and stirred for 5 minutes. The aqueous phase was extracted with ethyl acetate (20 mL×3). The combined organic phase was washed with brine (30 mL×3), dried with anhydrous sodium sulfate, filtered and concentrated in vacuum. The residue was purified by silica gel chromatography (1000 mesh silica gel, petroleum ether/ethyl acetate from 200:1 to 20:1). The product, tert-butyl 4-[3-[(5-bromo-2-pyridyl)oxy]cyclobutoxy]piperidine-1-carboxylate (560 mg, 1.30 mmol, 88% yield), was obtained as a colorless oil.

Step 7: tert-butyl 4-((1r,3r)-3-((5-(4,4,5,5-tetramethyl-1,3,2-dioxaborolan-2-yl)pyridin-2-yl)oxy)cyclobutoxy)piperidine-1-carboxylate

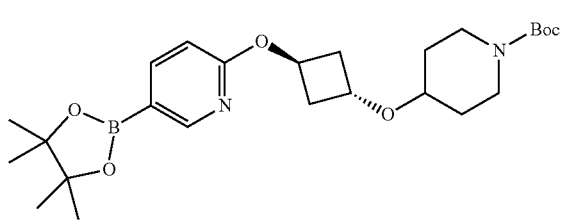 [SMILES: CC(C)(C)OC(=O)N1CCC(O[C@H]2C[C@H](Oc3ccc(B4OC(C)(C)C(C)(C)O4)cn3)C2)CC1]

To a suspension of tert-butyl 4-[3-[(5-bromo-2-pyridyl)oxy]cyclobutoxy]piperidine-1-carboxylate (560 mg, 1.31 mmol, 1 eq), 4,4,4',4',5,5,5',5'-octamethyl-2,2'-bi(1,3,2-dioxaborolane) (432 mg, 1.70 mmol, 1.3 eq) and potassium acetate (257 mg, 2.62 mmol, 2 eq) in dioxane (20 mL) was added [1,1'-bis(diphenylphosphino)ferrocene]dichloropalladium(II) (95 mg, 0.13 mmol, 0.1 eq). The mixture was degassed in vacuum and purged with nitrogen for 3 times. The mixture was heated to 80° C. and stirred at 80° C. for 15 hours. The mixture was filtered, and the filtrate was concentrated in vacuum. The residue was purified by silica gel column chromatography (petroleum ether/ethyl acetate from 20:1 to 10:1). Tert-butyl 4-[3-[[5-(4,4,5,5-tetramethyl-1,3,2-dioxaborolan-2-yl)-2-pyridyl]oxy]cyclobutoxy]piperidine-1-carboxylate (500 mg, 1.05 mmol, 80% yield) as a colorless oil was obtained.

Step 8: tert-butyl 4-((1r,3r)-3-((5-(5H-pyrido[4,3-b]indol-7-yl)pyridin-2-yl)oxy)cyclobutoxy)piperidine-1-carboxylate

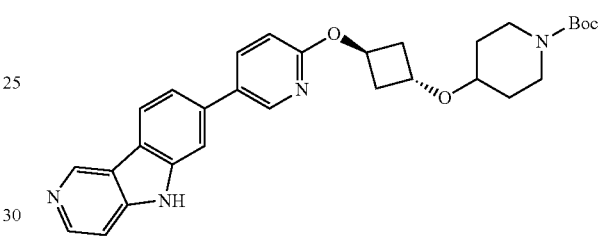

To a solution of tert-butyl 4-[3-[[5-(4,4,5,5-tetramethyl-1,3,2-dioxaborolan-2-yl)-2-pyridyl]oxy]cyclobutoxy]piperidine-1-carboxylate (240 mg, 0.50 mmol, 1 eq), 7-bromo-5H-pyrido[4,3-b]indole (125 mg, 0.50 mmol, 1 eq) and potassium carbonate (140 mg, 1.01 mmol, 2 eq) in a mixture of dimethylformamide (8 mL) and water (2 mL) was added [1,1'-bis(diphenylphosphino)ferrocene]dichloropalladium(II) (37 mg, 0.05 mmol, 0.1 eq). The mixture was degassed in vacuum and purged with nitrogen three times. The mixture was stirred at 100° C. for 3 hours. The mixture was poured into 50 mL saturated brine, and then extracted with ethyl acetate (50 mL×2). The combined organic layer was washed with brine (50 mL×3), dried over anhydrous sodium sulfate, filtered and concentrated in vacuum. The residue was purified by preparative thin layer chromatography (dichloromethane:methanol=20:1). Tert-butyl 4-[3-[[5-(5H-pyrido[4,3-b]indol-7-yl)-2-pyridyl]oxy]cyclobutoxy]piperidine-1-carboxylate (175 mg, 0.34 mmol, 67% yield) as an off-white solid was obtained.

Step 9: 7-(6-((1r,3r)-3-(piperidin-4-yloxy)cyclobutoxy)pyridin-3-yl)-5H-pyrido[4,3-b]indole

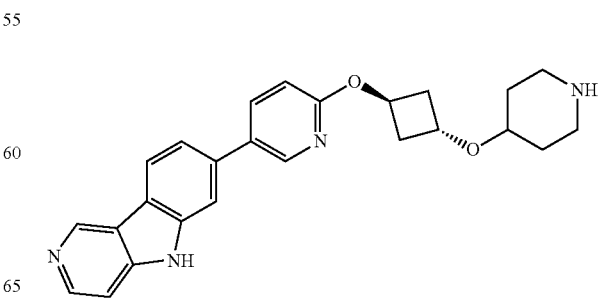

Tert-butyl 4-[3-[[5-(5H-pyrido[4,3-b]indol-7-yl)-2-pyridyl]oxy]cyclobutoxy]piperidine-1-carboxylate (170 mg, 0.33 mmol, 1 eq) in hydrochloric acid (4 M in dioxane, 8 mL, 100 eq) was stirred at 25° C. for 10 minutes. The mixture was concentrated in vacuum. The product 7-[6-[3-(4-piperidyloxy)cyclobutoxy]-3-pyridyl]-5H-pyrido[4,3-b]indole (190 mg, crude, hydrochloride) was obtained as a brown solid and was directly used in the next step without further purification.

Step 10: 5-((5,5-dimethoxypentyl)oxy)-2-(2,6-dioxopiperidin-3-yl)isoindoline-1,3-dione

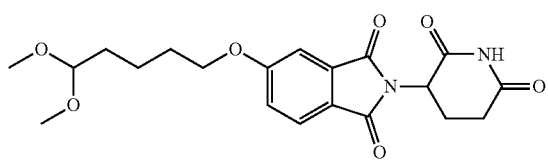 [SMILES: COC(CCCCOc1ccc2c(c1)C(=O)N(C1CCC(=O)NC1=O)C2=O)OC]

To a solution of 2-(2,6-dioxopiperidin-3-yl)-5-hydroxyisoindoline-1,3-dione (548 mg, 2.00 mmol, 1 eq) and 5-bromo-1,1-dimethoxypentane (506 mg, 2.40 mmol, 1.2 eq) in a mixture of acetone (3 mL) and dimethylformamide (3 mL) was added potassium carbonate (552 mg, 4.00 mmol, 2 eq). The mixture was heated to 50° C. and stirred at 50° C. for 2 hours. The mixture was poured into 50 mL 0.1 M aqueous hydrochloric acid, and then extracted with ethyl acetate (50 mL×2). The combined organic layer was washed with brine (50 mL×3), dried over anhydrous sodium sulfate, filtered and concentrated in vacuum. The residue was purified by preparative thin layer chromatography (dichloromethane:methanol=20:1). 5-((5,5-dimethoxypentyl)oxy)-2-(2,6-dioxopiperidin-3-yl)isoindoline-1,3-dione (120 mg, 0.30 mmol, 14% yield) as a colorless oil was obtained.

Step 11: 5-((2-(2,6-dioxopiperidin-3-yl)-1,3-dioxoisoindolin-5-yl)oxy)pentanal

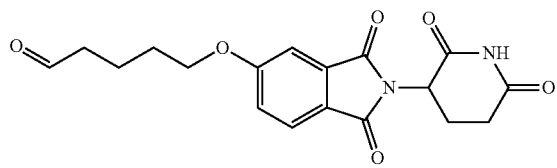 [SMILES: O=CCCCCOc1ccc2c(c1)C(=O)N(C1CCC(=O)NC1=O)C2=O]

To a mixture of 5-(5,5-dimethoxypentoxy)-2-(2,6-dioxo-3-piperidyl)isoindoline-1,3-dione (120 mg, 0.29 mmol, 1 eq) in tetrahydrofuran (10 mL) was added sulfuric acid (2 M in water, 7 mL, 50 eq) in one portion at 25° C. under nitrogen atmosphere. The mixture was stirred at 70° C. for 1 hour. The aqueous phase was extracted with ethyl acetate (20 mL×3). The combined organic phase was washed with saturated aqueous sodium bicarbonate (20 mL×2), and then brine (20 mL×3), dried with anhydrous sodium sulfate, filtered and concentrated in vacuum. The product 5-[2-(2,6-dioxo-3-piperidyl)-1,3-dioxo-isoindolin-5-yl]oxypentanal (93 mg, crude) was obtained as a light yellow solid.

Step 12: 5-((5-(4-((1r,3r)-3-((5-(5H-pyrido[4,3-b]indol-7-yl)pyridin-2-yl)oxy)cyclobutoxy)piperidin-1-yl)pentyl)oxy)-2-(2,6-dioxopiperidin-3-yl)isoindoline-1,3-dione

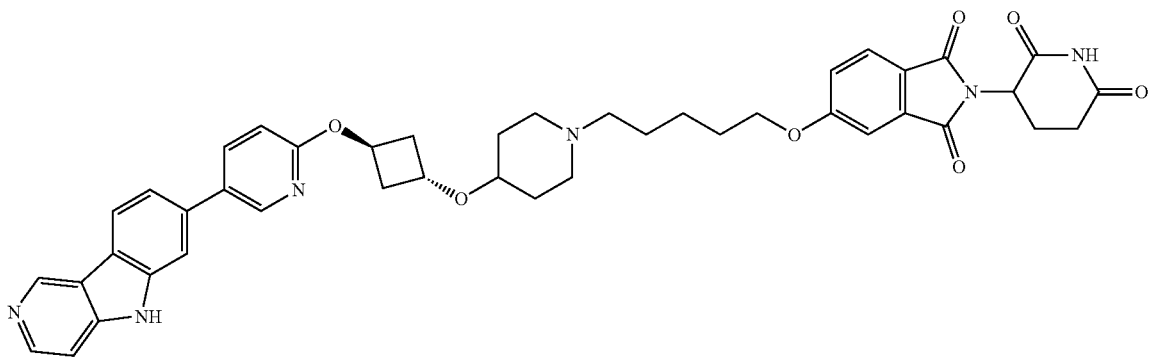 [SMILES: O=C1CCC(N2C(=O)c3ccc(OCCCCCN4CCC(O[C@H]5C[C@H](Oc6ccc(-c7ccc8c(c7)[nH]c7ccncc78)cn6)C5)CC4)cc3C2=O)C(=O)N1]

To a mixture of 7-[6-[3-(4-piperidyloxy)cyclobutoxy]-3-pyridyl]-5H-pyrido[4,3-b]indole (110 mg, 0.24 mmol, 1 eq, hydrochloride) in dichloroethane (2 mL) and methanol (5 mL) was added sodium acetate (40 mg, 0.49 mmol, 2 eq) in one portion at 20° C. The mixture was stirred at 20° C. for 10 minutes. 5-[2-(2,6-dioxo-3-piperidyl)-1,3-dioxo-isoindolin-5-yl]oxypentanal (88 mg, 0.24 mmol, 1 eq) was added. The mixture was stirred at 20° C. for 10 minutes. And then acetic acid (0.02 mL) and sodium cyanoborohydride (31 mg, 0.49 mmol, 2 eq) was added in one portion. The mixture was stirred at 35° C. for 40 minutes. The mixture was filtered and the filtrate was concentrated in vacuum. The residue was purified by Semi-preparative reverse phase HPLC (column: Phenomenex Synergi C18 150*25*10 um; mobile phase: [water (0.225% formic acid)—acetonitrile]; B %: 3%-33%, 10 min). The product 2-(2,6-dioxo-3-piperidyl)-5-[5-[4-[3-[[5-(5H-pyrido[4,3-b]indol-7-yl)-2-pyridyl]oxy]cyclobutoxy]-1-piperidyl]pentoxy]isoindoline-1,3-dione triformate (50.2 mg, 0.05 mmol, 21% yield) was obtained as an off-white solid.

$^1$H NMR: (400 MHz, DMSO-d6) δ: 11.80 (s, 1H), 11.11 (s, 1H), 9.35 (s, 1H), 8.55 (d, J=2.4 Hz, 1H), 8.42 (d, J=5.6 Hz, 1H), 8.29 (d, J=8.4 Hz, 1H), 8.18 (s, 3H), 8.11 (dd, J=2.4, 8.8 Hz, 1H), 7.83 (d, J=8.4 Hz, 1H), 7.76 (s, 1H), 7.55 (d, J=8.4 Hz, 1H), 7.48 (d, J=5.6 Hz, 1H), 7.42 (d, J=2.0 Hz, 1H), 7.35 (dd, J=2.0, 8.4 Hz, 1H), 6.92 (d, J=8.4 Hz, 1H), 5.30 (d, J=3.6 Hz, 1H), 5.11 (dd, J=5.6, 13.2 Hz, 1H), 4.35

(t, J=6.4 Hz, 1H), 4.17 (t, J=6.4 Hz, 2H), 2.93-2.84 (m, 2H), 2.77 (s, 2H), 2.63-2.54 (m, 3H), 2.37 (d, J=6.0 Hz, 4H), 2.22-1.98 (m, 4H), 1.87-1.74 (m, 4H), 1.53-1.38 (m, 6H). (M+H)+ 757.5
Using procedures, analogous to those described above, the following were prepared: Compounds 82, 123 (as described for Compounds 65 and 67 and detailed in the scheme below).
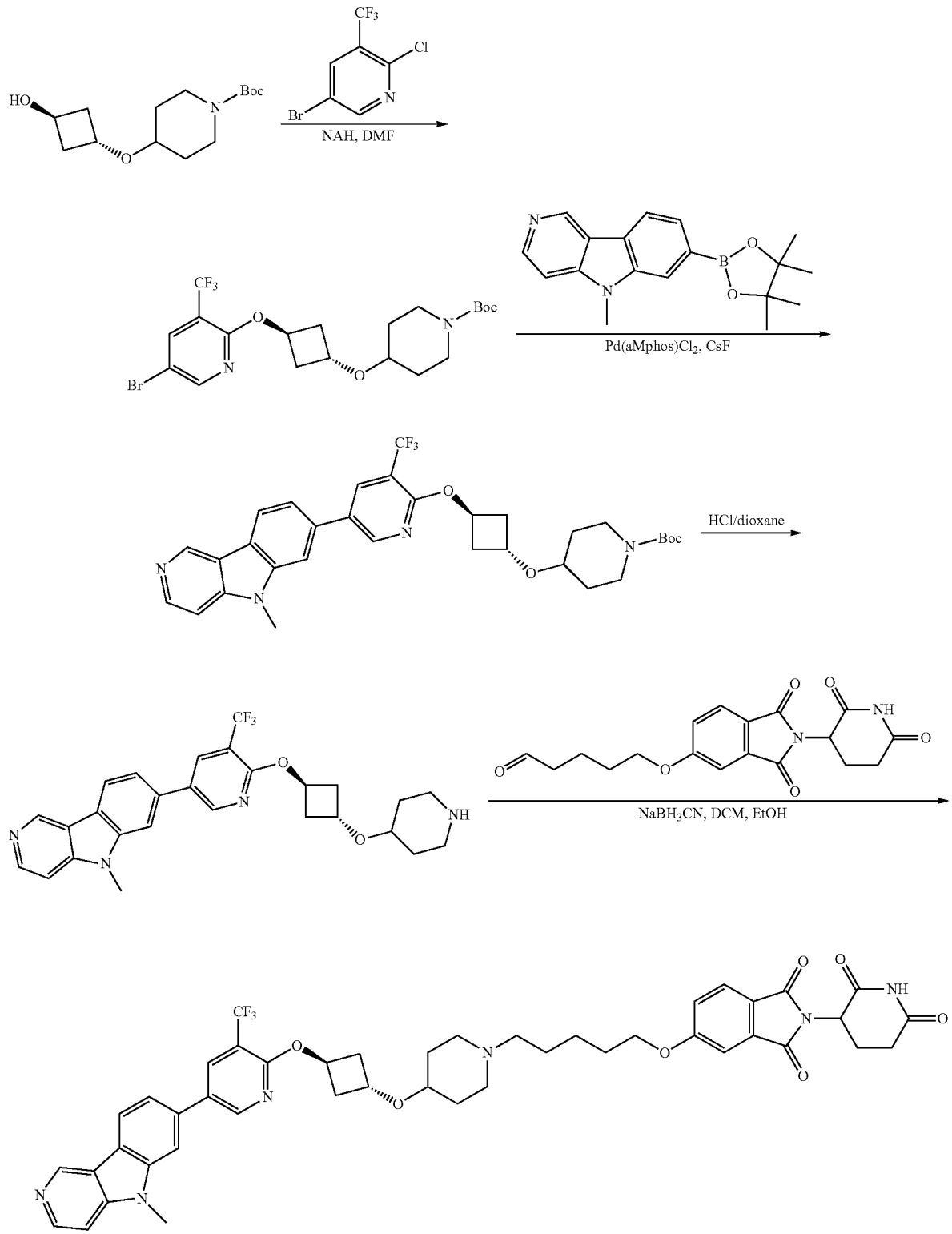
Compound 123

Synthetic Scheme for Exemplary Compound 66

5-(4-(2-(4-(((1r,3r)-3-((5-(5H-pyrido[4,3-b]indol-7-yl)pyridin-2-yl)oxy)cyclobutoxy)piperidin-1-yl)ethyl)piperazin-1-yl)-2-(2,6-dioxopiperidin-3-yl)isoindoline-1,3-dione

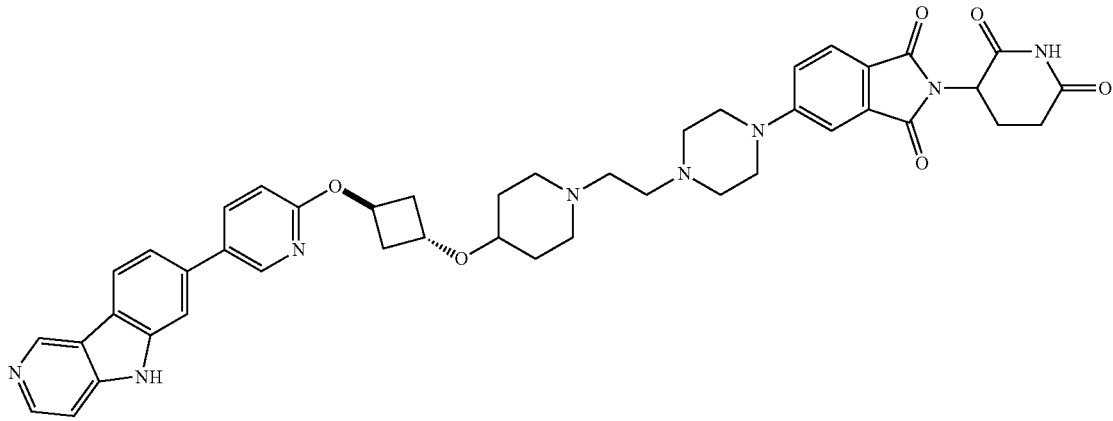 [SMILES: O=C1CCC(N2C(=O)c3ccc(N4CCN(CCN5CCC(O[C@H]6C[C@H](Oc7ccc(-c8ccc9c(c8)[nH]c8ccncc89)cn7)C6)CC5)CC4)cc3C2=O)C(=O)N1]

Step 1: benzyl 4-(2,2-diethoxyethyl)piperazine-1-carboxylate

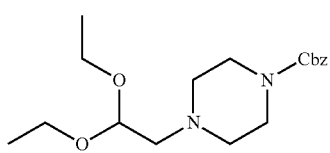 [SMILES: CCOC(CN1CCN(C(=O)OCc2ccccc2)CC1)OCC]

To a solution of benzyl piperazine-1-carboxylate (1.0, 4.54 mmol) in DMF (20 mL) was added $K_2CO_3$ (1.25 g, 9.0 mmol) and 2-bromo-1,1-diethoxyethane (1.0 g, 4.54 mmol). The resulting mixture was stirred at 80° C. for 20 hours. Then the reaction mixture was diluted with water (50 mL) and extracted with EA. The organic phase was washed with brine, dried over $MgSO_4$, and concentrated. The residue was purified by chromatography (silica gel, PE:EA=1:1) to afford the desired compound benzyl 4-(2,2-diethoxyethyl)piperazine-1-carboxylate (1.55 g) as a colorless oil.

Step 2: 1-(2,2-diethoxyethyl)piperazine

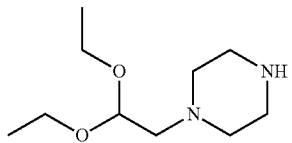

To a solution of benzyl 4-(2,2-diethoxyethyl)piperazine-1-carboxylate (1.55 g, 4.6 mmol) in MeOH (30 mL) was added $Pd(OH)_2$/C (0.3 g, 20%). The resulting mixture was stirred at 30° C. for 3 hours. Then the reaction mixture was filtered and concentrated to afford the desired compound 1-(2,2-diethoxyethyl)piperazine (0.9 g, crude) as a white solid, which was used to next step without further purification.

Step 3: 5-(4-(2,2-diethoxyethyl)piperazin-1-yl)-2-(2,6-dioxopiperidin-3-yl)isoindoline-1,3-dione

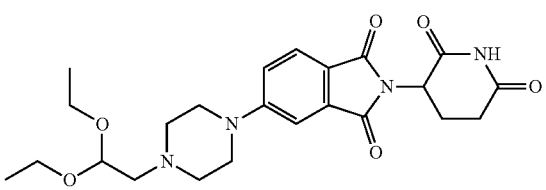 [SMILES: CCOC(CN1CCN(c2ccc3c(c2)C(=O)N(C2CCC(=O)NC2=O)C3=O)CC1)OCC]

To a solution of 1-(2,2-diethoxyethyl)piperazine (0.9 g, 4.45 mmol) in NMP (15 mL) was added DIEA (2.3 g, 17.8 mmol) and 2-(2,6-dioxopiperidin-3-yl)-5-fluoroisoindoline-1,3-dione (1.35 g, 4.9 mmol). The resulting mixture was stirred at 90° C. for 20 hours. Then the reaction mixture was diluted with water (50 mL) and extracted with DCM/MeOH (10/1). The organic phase was washed with brine, dried over $MgSO_4$, and concentrated. The residue was purified by chromatography (silica gel, DCM:MeOH (20:1) to afford the desired compound (1.4 g) as a yellow solid.

Step 4: 2-(4-(2-(2,6-dioxopiperidin-3-yl)-1,3-dioxoisoindolin-5-yl)piperazin-1-yl)acetaldehyde

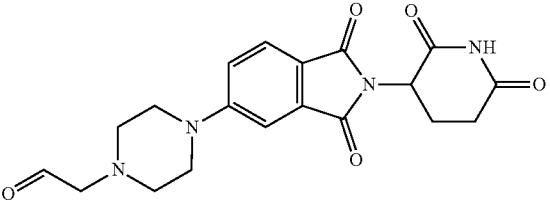 [SMILES: O=CCN1CCN(c2ccc3c(c2)C(=O)N(C2CCC(=O)NC2=O)C3=O)CC1]

A solution of 5-(4-(2,2-diethoxyethyl)piperazin-1-yl)-2-(2,6-dioxopiperidin-3-yl)isoindoline-1,3-dione (300 mg, 0.65 mmol) in HCl (5 mL in $H_2O$, 2.5 mol/L) was stirred at 50° C. for 20 hours. The mixture was basified with NaHCO₃ (20 mL) and extracted with EA. The organic phase was washed with brine, dried over MgSO₄, and concentrated to afford the desired compound (220 mg, crude) as yellow solid, which was used in the next step without further purification.

Step 5: 5-(4-(2-(4-((1r,3r)-3-((5-(5H-pyrido[4,3-b]indol-7-yl)pyridin-2-yl)oxy)cyclobutoxy)piperidin-1-yl)ethyl)piperazin-1-yl)-2-(2,6-dioxopiperidin-3-yl)isoindoline-1,3-dione To a solution of 2-(4-(2-(2,6-dioxopiperidin-3-yl)-1,3-dioxoisoindolin-5-yl)piperazin-1-yl)acetaldehyde (180 mg, 0.41 mmol) in MeOH/DMSO (8 mL, 1/1) was added 7-(6-((1r,3r)-3-(piperidin-4-yloxy)cyclobutoxy)pyridin-3-yl)-5H-pyrido[4,3-b]indole (97 mg, 0.24 mmol) [prepared as described in Compound 65], AcOH (1 drop) and NaBH₃CN (60 mg, 0.94 mmol). The resulting mixture was stirred at 10° C. for 2 hours. Then the reaction mixture was diluted with water (10 mL) and extracted with EA. The organic phase was washed with brine and filtered, and the crude material was purified by prep-HPLC to give the title compound (21.2 mg) as a yellow solid.

¹H NMR (400 MHz, DMSO-d₆): δ 13.21 (s, 1H), 11.08 (s, 2H), 9.76 (s, 1H), 8.67 (d, J=6.6 Hz, 1H), 8.61 (s, 1H), 8.52 (d, J=8.3 Hz, 1H), 8.17 (d, J=8.3 Hz, 1H), 8.02 (d, J=7.1 Hz, 2H), 7.82-7.72 (m, 3H), 7.46 (s, 2H), 7.35 (s, 2H), 6.96 (d, J=8.5 Hz, 1H), 5.34 (s, 1H), 5.08 (d, J=7.7 Hz, 2H), 4.40 (s, 2H), 3.23 (s, 4H), 3.15 (s, 4H), 3.02 (s, 4H), 2.95-2.83 (m, 4H), 2.59 (d, J=15.7 Hz, 4H), 2.44 (s, 2H), 2.01 (s, 5H), 1.77 (d, J=14.7 Hz, 2H). (M+H)⁺ 783.6.

Synthetic Scheme for Exemplary Compound 171

5-((4,4-difluoro-5-(4-((1r,3r)-3-((5-(5-methyl-5H-pyrido[4,3-b]indol-7-yl)pyridin-2-yl)oxy)cyclobutoxy)piperidin-1-yl)pentyl)oxy)-2-(2,6-dioxopiperidin-3-yl)isoindoline-1,3-dione

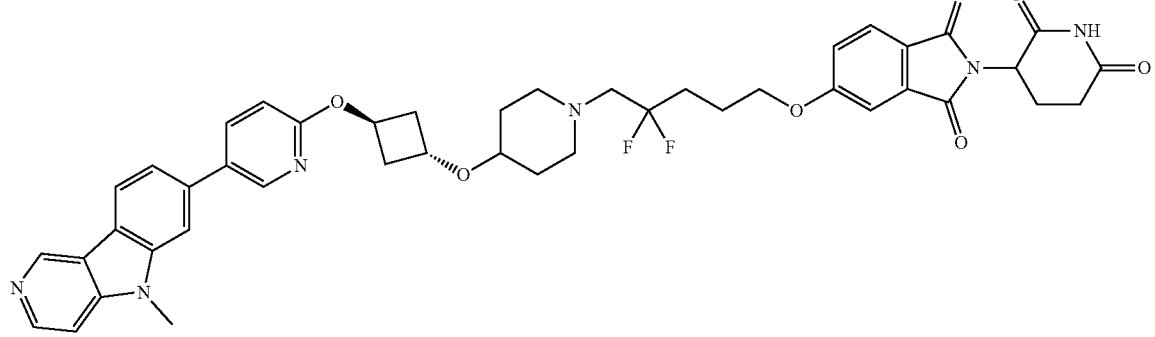

Step 1: 05-tert-butyl 01-ethyl 2,2-difluoropentanedioate

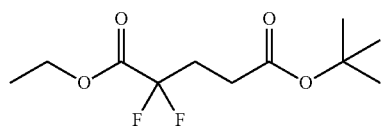 [SMILES: CCOC(=O)C(F)(F)CCC(=O)OC(C)(C)C]

A mixture of tert-butyl prop-2-enoate (10 g, 78.02 mmol, 1.00 eq), ethyl 2-bromo-2,2-difluoro-acetate (28.51 g, 140.44 mmol, 1.8 eq) and copper (10.41 g, 163.85 mmol, 2.10 eq) in tetrahydrofuran (100 mL) was heated to 55° C. under intense stirring; then N,N,N',N'-tetramethylethylenediamine (4.53 g, 39.01 mmol, 0.50 eq) followed by acetate acid (4.22 g, 70.22 mmol, 0.90 eq) were added. The dark blue-brown reaction mixture was stirred for 1 hour at 55° C. A 10% aqueous solution of ammonium chloride (100 mL) and ethyl acetate (500 mL) was added. The resulting mixture was stirred for 0.5 hours at room temperature and filtered through celite. The organic phase was washed with another portion of ammonium chloride solution (100 mL×5) to remove remaining copper complexes (blue color). The solution was dried with anhydrous sodium sulfate, filtered, and evaporated under vacuum. The residue was purified by silica gel chromatography (Petroleum ether/Ethyl acetate=500/1, 100/1) to afford 05-tert-butyl 01-ethyl 2,2-difluoropentanedioate (18.6 g, 73.74 mmol, 95% yield) as a yellow oil.

Step 2: tert-butyl 4,4-difluoro-5-hydroxy-pentanoate

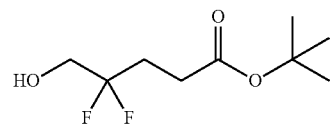

A suspension of sodium borohydride (3.24 g, 85.63 mmol, 1.20 eq) in ethanol (100 mL) was cooled to 0° C. in an ice bath, and a solution of 05-tert-butyl 01-ethyl 2,2-difluoropentanedioate (18 g, 71.36 mmol, 1.00 eq) in ethanol (100 mL) was added drop-wise from the addition funnel under vigorous stirring. The rate of dropping was carefully controlled to keep the reaction mixture temperature between 0-15° C. Then the mixture was stirred at 15° C. for 1 hour. The reaction mixture was quenched by dropwise addition of 5% aqueous citric acid (40 mL) with cooling. The aqueous phase was extracted with ethyl acetate (200 mL×3). The combined organic phase was washed with brine (200 mL×3), dried with anhydrous sodium sulfate, filtered and concentrated under vacuum. The residue was purified by silica gel chromatography (Petroleum ether/Ethyl acetate=20/1, 10/1) to afford tert-butyl 4,4-difluoro-5-hydroxy-pentanoate (14.2 g, 67.55 mmol, 95% yield) as a colorless oil.

Step 3: tert-butyl 4,4-difluoro-5-tetrahydropyran-2-yloxypentanoate

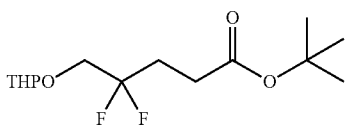

To a mixture of tert-butyl 4,4-difluoro-5-hydroxy-pentanoate (14.2 g, 67.55 mmol, 1.00 eq) and 4-methylbenzenesulfonic acid (642 mg, 3.38 mmol, 0.05 eq) in dichloromethane (50 mL) was added 3,4-dihydro-2H-pyran (17.05 g, 202.65 mmol, 3.00 eq) at −10° C. under nitrogen. Then the mixture was warmed to 25° C. and stirred for 16 hours. The reaction was quenched by saturated sodium bicarbonate solution (50 mL) and then extracted with dichloromethane (50 mL×3). The combined organic phase was washed with brine (50 mL×3), dried over anhydrous sodium sulfate, filtered and concentrated in vacuo. The residue was purified by silica gel chromatography (Petroleum ether/Ethyl acetate=500/1, 100/1) to afford tert-butyl 4,4-difluoro-5-tetrahydropyran-2-yloxypentanoate (17.2 g, crude) as a colorless oil.

Step 4: 4,4-Difluoro-5-tetrahydropyran-2-yloxy-pentan-1-ol

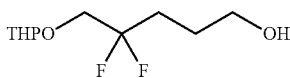

To a solution of lithium aluminum hydride (2.66 g, 70.12 mmol, 1.20 eq) in tetrahydrofuran (300 mL) was added a solution of tert-butyl 4,4-difluoro-5-tetrahydropyran-2-yloxy-pentanoate (17.2 g, 58.44 mmol, 1.00 eq) in tetrahydrofuran (60 mL) dropwise at 0° C. under nitrogen during which the temperature was maintained below 0° C. The reaction mixture was stirred at 0° C. for 1 hour. The reaction was quenched by water (2.6 mL), solution of sodium hydroxide in water (15%, 5.2 mL) and water (8 mL) at 0° C. The suspension was filtered through a pad of celite. The cake was washed with ethyl acetate (500 mL). The combined organic phase was washed with brine (200 mL×3), dried over anhydrous sodium sulfate, filtered and concentrated under vacuo. The residue was purified by silica gel chromatography (Petroleum ether/Ethyl acetate=20/1 to 10:1). 4,4-Difluoro-5-tetrahydropyran-2-yloxy-pentan-1-ol (10.9 g, 48.61 mmol, 83% yield) was obtained as a colorless oil.

Step 5: (4,4-difluoro-5-tetrahydropyran-2-yloxy-pentyl)4-methylbenzenesulfonate

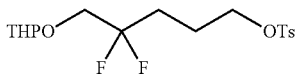

To a mixture of 4,4-difluoro-5-tetrahydropyran-2-yloxy-pentan-1-ol (10.9 g, 48.61 mmol, 1.00 eq) and p-toluenesulfonyl chloride (13.90 g, 72.91 mmol, 1.50 eq) in dichloromethane (100 mL) was added triethylamine (9.84 g, 97.22 mmol, 2.00 eq) in one portion at 0° C. under nitrogen. The mixture was warmed to 25° C. and stirred for 16 hours. The mixture was poured into ice-water (w/w=1/1) (30 mL) and stirred for 15 minutes. The aqueous phase was extracted with ethyl acetate (50 mL×3). The combined organic phase was washed with brine (50 mL×2), dried with anhydrous sodium sulfate, filtered and concentrated under vacuum. The residue was purified by silica gel chromatography (Petroleum ether/Ethyl acetate=20/1, 10/1) to afford (4,4-difluoro-5-tetrahydropyran-2-yloxy-pentyl)4-methylbenzenesulfonate (16.6 g, 43.87 mmol, 90% yield) as a colorless oil.

Step 6: Dimethyl 4-(4,4-difluoro-5-hydroxy-pentoxy)benzene-1,2-dicarboxylate

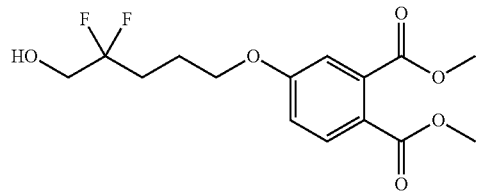 [SMILES: COC(=O)c1ccc(OCCCC(F)(F)CO)cc1C(=O)OC]

To a solution of (4,4-difluoro-5-tetrahydropyran-2-yloxy-pentyl) 4-methylbenzenesulfonate (1 g, 2.64 mmol, 1 eq) in N N-dimethylformamide (6 mL) was added cesium carbonate (1.72 g, 5.28 mmol, 2 eq) and dimethyl 4-hydroxybenzene-1,2-dicarboxylate (555 mg, 2.64 mmol, 1 eq). The mixture was stirred at 50° C. for 12 hours. LCMS showed starting material was consumed and desired compound was found. The mixture was filtered and poured into hydrochloric acid (1N, 30 mL), the aqueous phase was extracted with dichloromethane (20 mL×3). The combined organic phase was washed with brine (20 mL×2), dried with anhydrous sodium sulfate, filtered and concentrated in vacuum. The residue was purified by silica gel chromatography (Petroleum ether/Ethyl acetate=20/1, 5/1). Dimethyl 4-(4,4-difluoro-5-hydroxy-pentoxy)benzene-1,2-dicarboxylate (700 mg, 2.11 mmol, 79% yield) was obtained as a colorless oil.

Step 7: Dimethyl 4-[4,4-difluoro-5-(trifluoromethylsulfonyloxy)pentoxy]benzene-1,2-dicarboxylate

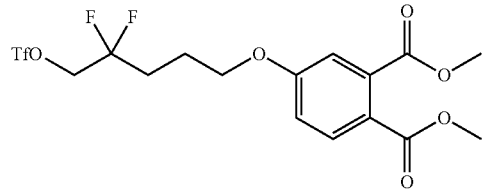 [SMILES: COC(=O)c1ccc(OCCCC(F)(F)COS(=O)(=O)C(F)(F)F)cc1C(=O)OC]

To a solution of dimethyl 4-(4,4-difluoro-5-hydroxy-pentoxy)benzene-1,2-dicarboxylate (600 mg, 1.81 mmol, 1 eq) in dichloromethane (10 mL) was added dropwise 2,6-dimethylpyridine (580 mg, 5.42 mmol, 3 eq) at 0° C. After addition, the mixture was stirred at this temperature for 10 minutes and then trifluoromethylsulfonyl trifluoromethanesulfonate (2.55 g, 9.03 mmol, 5 eq) was added dropwise at 0° C. The resulting mixture was stirred at 25° C. for 50 minutes. LCMS showed starting material was disappeared and desired compound was found. The mixture was concentrated in vacuum. The residue was further purified by Pre-thin-layer chromatography (petroleum ether:ethyl acetate=4:1). Dimethyl 4-[4,4-difluoro-5-(trifluoromethylsulfonyloxy)pentoxy]benzene-1,2-dicarboxylate (600 mg, 1.29 mmol, 71% yield) was obtained as a white solid.

Step 8: Dimethyl 4-[4,4-difluoro-5-[4-[3-[[5-(5-methylpyrido[4,3-b]indol-7-yl)-2-pyridyl]oxy]cyclobutoxy]-1-piperidyl]pentoxy]benzene-1,2-dicarboxylate

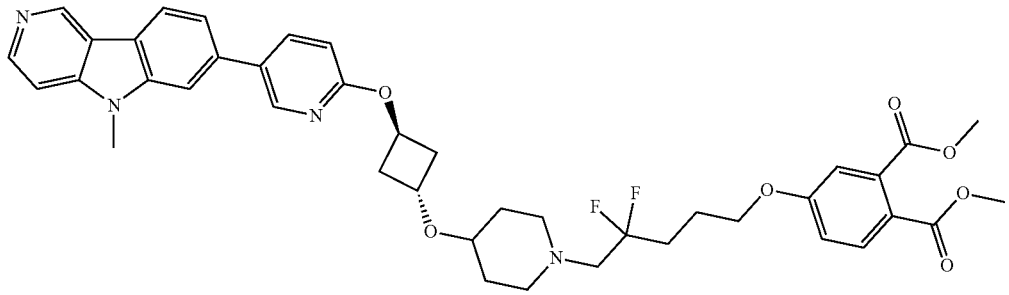 [SMILES: COC(=O)c1ccc(OCCCC(F)(F)CN2CCC(O[C@H]3C[C@H](Oc4ccc(-c5ccc6c7cnccc7n(C)c6c5)cn4)C3)CC2)cc1C(=O)OC]

To a solution of dimethyl 4-[4,4-difluoro-5-(trifluoromethylsulfonyloxy)pentoxy]benzene-1,2-dicarboxylate (150 mg, 0.3 mmol, 1 eq) in acetonitrile (1 mL) and dimethylsulfoxide (0.5 mL) was added potassium carbonate (133 mg, 1 mmol, 3 eq) and 5-methyl-7-[6-[3-(4-piperidyloxy)cyclobutoxy]-3-pyridyl]pyrido[4,3-b]indole (138 mg, 0.3 mmol, 1 eq) [prepared as described for Compound 82]. The mixture was stirred at 50° C. for 16 hr. LCMS showed starting material was almost disappeared and desired compound was found. The mixture was poured into water (20 mL) and the aqueous phase was extracted with ethyl acetate (20 mL×3). The combined organic phase was washed with brine (20 mL×2), dried with anhydrous sodium sulfate, filtered and concentrated in vacuum. The residue was further purified by Pre-thin-layer chromatography (petroleum ether: ethyl acetate=4:1). Dimethyl 4-[4,4-difluoro-5-[4-[3-[[5-(5-methylpyrido[4,3-b]indol-7-yl)-2-pyridyl]oxy]cyclobutoxy]-1-piperidyl]pentoxy]benzene-1,2-dicarboxylate (160 mg, 0.2 mmol, 66% yield) was obtained as a yellow oil.

Step 9: 4-[4,4-Difluoro-5-[4-[3-[[5-(5-methylpyrido[4,3-b]indol-7-yl)-2-pyridyl]oxy]cyclobutoxy]-1-piperidyl]pentoxy]phthalic Acid

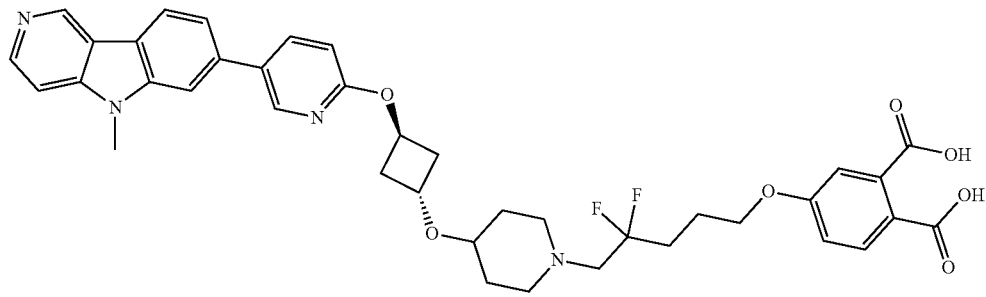 [SMILES: Cn1c2ccncc2c2ccc(-c3ccc(O[C@H]4C[C@H](OC5CCN(CC(F)(F)CCCOc6ccc(C(=O)O)c(C(=O)O)c6)CC5)C4)nc3)cc21]

To a solution of dimethyl 4-[4,4-difluoro-5-[4-[3-[[5-(5-methylpyrido[4,3-b]indol-7-yl)-2-pyridyl]oxy]cyclobutoxy]-1-piperidyl]pentoxy]benzene-1,2-dicarboxylate (120 mg, 0.16 mmol, 1 eq) in methanol (3 mL) and water (1.5 mL) was added potassium hydroxide (36 mg, 0.6 mmol, 4 eq). The mixture was stirred at 55° C. for 2 hr. LCMS showed starting material was consumed and desired compound was found. The reaction mixture was adjusted to pH=(7) by hydrochloric acid (1 M) and concentrated under reduced pressure to remove methanol and water. The residue was directly used for next step without further purification. 4-[4,4-Difluoro-5-[4-[3-[[5-(5-methylpyrido[4,3-b]indol-7-yl)-2-pyridyl]oxy]cyclobutoxy]-1-piperidyl]pentoxy]phthalic acid (110 mg, 0.1 mmol, 95% yield) was obtained as a yellow solid.

Step 10: 5-[4,4-Difluoro-5-[4-[3-[[5-(5-methylpyrido[4,3-b]indol-7-yl)-2-pyridyl]oxy]cyclobutoxy]-1-piperidyl]pentoxy]-2-(2,6-dioxo-3-piperidyl)isoindoline-1,3-dione

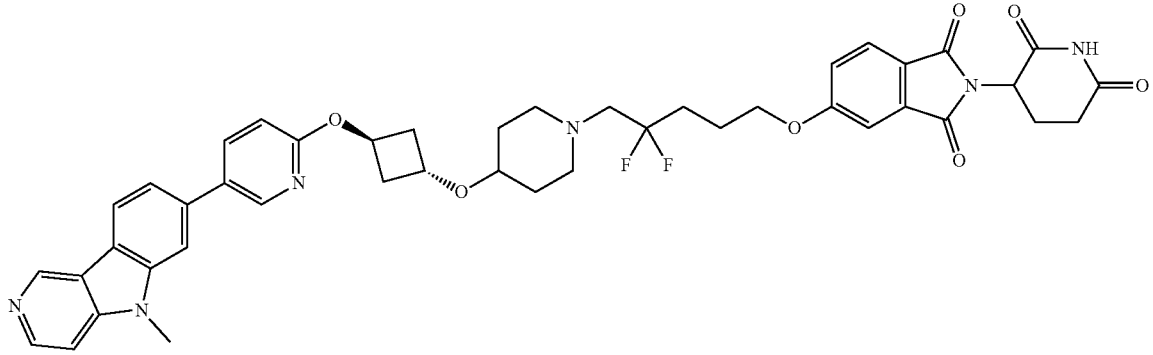 [SMILES: Cn1c2ccncc2c2ccc(-c3ccc(O[C@H]4C[C@H](OC5CCN(CC(F)(F)CCCOc6ccc7c(c6)C(=O)N(C6CCC(=O)NC6=O)C7=O)CC5)C4)nc3)cc21]

To a solution of 4-[4,4-difluoro-5-[4-[3-[[5-(5-methylpyrido[4,3-b]indol-7-yl)-2-pyridyl]oxy]cyclobutoxy]-1-piperidyl]pentoxy]phthalic acid (110 mg, 0.2 mmol, 1 eq) in acetic acid (2 mL) was added sodium acetate (37 mg, 0.5 mmol, 3 eq) the mixture was stirred at 25° C. for 1 hour. Then 3-aminopiperidine-2,6-dione (30 mg, 0.2 mmol, 1.2 eq, hydrochloric acid) was added into the mixture and heated to 120° C., stirred for additional 11 hours. LCMS showed starting material was consumed and desired compound was found. The mixture was concentrated in vacuum. The residue was purify by Pre-High Performance Liquid Chromatography column: Phenomenex Synergi C18 150*25*10 um; mobile phase: [water (0.225% formic acid)-acetonitrile]; B %: 14%-35%,7 minutes. 5-[4,4-Difluoro-5-[4-[3-[[5-(5-methylpyrido[4,3-b]indol-7-yl)-2-pyridyl]oxy]cyclobutoxy]-1-piperidyl]pentoxy]-2-(2,6-dioxo-3-piperidyl)isoindoline-1,3-dione (67 mg, 0.08 mmol, 50% yield, 98% purity, formic acid) was obtained as a gray solid.

$^1$H NMR: (400 MHz, DMSO-$d_6$) δ=11.11 (s, 1H), δ=9.35 (s, 1H) δ=8.64 (s, 1H), 8.49-8.48 (d, J=4 Hz 1H), 8.33-8.31 (d, J=8 Hz 1H), δ=8.17 (s, 1H), δ=7.97 (s, 1H) 7.85-7.83 (d, J=8 Hz 1H), 7.62-7.61 (d, J=4 Hz 2H), 7.43 (s, 1H), 6.94-6.92 (d, J=8 Hz 1H), 5.31-5.29 (m, 1H), 5.12-5.10 (m, 1H), 4.34 (s, 5H), 4.25-4.23 (d, J=8 Hz 1H), 3.95 (s, 3H), 2.77 (m, 2H), 2.73 (m, 4H), 2.53-2.52 (m, 1H), 2.39-2.38 (m, 4H), 1.91-1.90 (m, 4H), 1.75 (m, 2H), 1.43 (m, 2H), 1.41 (m, 2H). (M+H)$^+$ 807.5.

Synthetic Scheme for Exemplary Compound 164

Step 1: benzyl 6-(tosyloxy)hexanoate

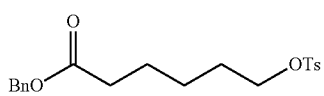 [SMILES: Cc1ccc(S(=O)(=O)OCCCCCC(=O)OCc2ccccc2)cc1]

To a mixture of benzyl 6-hydroxyhexanoate (1.1 g, 4.95 mmol) and triethylamine (1.0 g, 9.90 mmol) in dichloromethane (10 ml) was added 4-toluenesulfonyl chloride (1.88 g, 9.90 mmol) at 0° C. The mixture was stirred at room temperature for 1 hour. TLC showed the reaction was complete. The reaction mixture was diluted with dichloromethane (20 ml), washed with brine (20 ml), dried over anhydrous sodium sulfate, and concentrated under reduced pressure to give a crude residue which was purified by silica gel flash chromatography (eluted with 30-50% ethyl acetate in hexane) to afford benzyl 6-(tosyloxy)hexanoate (960 mg, yield 54%) as colorless oil.

Step 2: benzyl 6-(2-(2,6-dioxopiperidin-3-yl)-1,3-dioxoisoindolin-5-yloxy)hexanoate

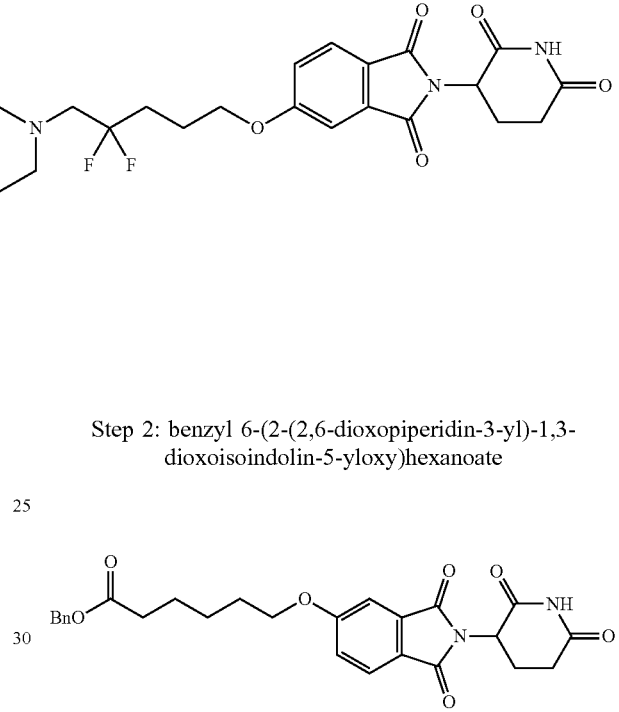

A mixture of benzyl 6-(tosyloxy)hexanoate (200 mg, 0.53 mmol) and 2-(2,6-dioxopiperidin-3-yl)-5-hydroxyisoindoline-1,3-dione (146 mg, 0.53 mmol), potassium carbonate (147 mg, 1.06 mmol) and potassium iodide (9 mg, 0.05 mmol) in N,N-dimethylformamide (3 ml) was stirred at 50° C. for 12 hours. TLC showed the reaction was complete. The reaction mixture was partitioned between water (15 ml) and with ethyl acetate (15 ml). The organic layer was collected, washed with brine (10 ml), dried over anhydrous sodium sulfate, and concentrated under reduced pressure to give a crude residue which was purified by silica gel flash chromatography (eluted with 2-5% methanol in dichloromethane) to afford benzyl 6-(2-(2,6-dioxopiperidin-3-yl)-1,3-dioxoisoindolin-5-yloxy)hexanoate (100 mg, yield 40%) as yellow solid.

Step 3: 6-(2-(2,6-dioxopiperidin-3-yl)-1,3-dioxoisoindolin-5-yloxy)hexanoic Acid

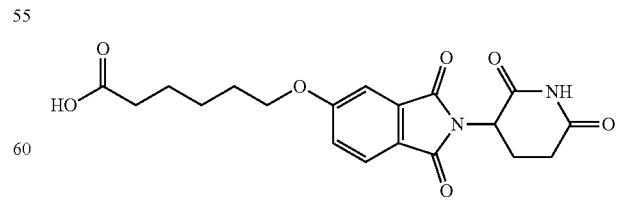

A mixture of benzyl 6-(2-(2,6-dioxopiperidin-3-yl)-1,3-dioxoisoindolin-5-yloxy)hexanoate (100 mg, 0.21 mmol) and palladium on activated carbon (20%, 50 mg) in methanol (2 ml) was stirred at room temperature for 1 hour under hydrogen atmosphere (hydrogen balloon). TLC showed the reaction was complete. The reaction mixture was filtered, and concentrated under reduced pressure to afford 6-(2-(2,6-dioxopiperidin-3-yl)-1,3-dioxoisoindolin-5-yloxy)hexanoic acid (70 mg, yield 86%) as yellow oil which was used in next step directly without further purification.

Step 4: 5-(6-(4-((1r,3r)-3-(5-(5H-pyrido[4,3-b]indol-7-yl)pyridin-2-yloxy)cyclobutoxy)piperidin-1-yl)-6-oxohexyloxy)-2-(2,6-dioxopiperidin-3-yl)isoindoline-1,3-dione

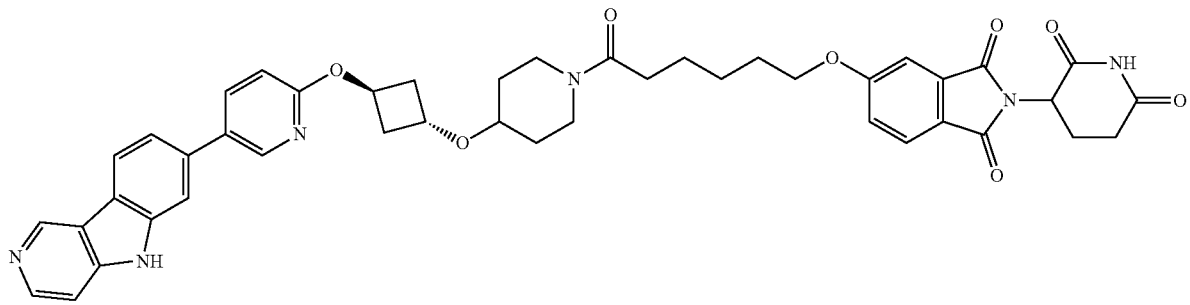 [SMILES: O=C1CCC(N2C(=O)c3ccc(OCCCCCC(=O)N4CCC(O[C@H]5C[C@H](Oc6ccc(-c7ccc8c(c7)[nH]c7ccncc78)cn6)C5)CC4)cc3C2=O)C(=O)N1]

To a mixture of 6-(2-(2,6-dioxopiperidin-3-yl)-1,3-dioxoisoindolin-5-yloxy)hexanoic acid (70 mg, 0.18 mmol) and 7-(6-((1r,3r)-3-(piperidin-4-yloxy)cyclobutoxy)pyridin-3-yl)-5H-pyrido[4,3-b]indole (75 mg, 0.18 mmol) [prepared as described in Compound 65] and triethylamine (56 mg, 0.56 mmol) in N,N-dimethylformamide (2 ml) was added (2-(7-aza-1H-benzotriazole-1-yl)-1,1,3,3-tetramethyluronium hexafluorophosphate) (212 mg, 0.56 mmol) at room temperature. The mixture was stirred at room temperature for 1 hour. TLC showed the reaction was complete. The reaction mixture was diluted with dichloromethane (50 ml), washed with brine (50 ml), dried over anhydrous sodium sulfate, and concentrated under reduced pressure to give a crude residue which was purified by silica gel flash chromatography (eluted with 2-5% methanol in dichloromethane) to afford the title compound (6.6 mg, yield 5%) as white solid.

$^1$H NMR (400 MHz, CDCl$_3$): δ 1.52-1.57 (m, 3H), 1.61-1.65 (m, 2H), 1.70-1.74 (m, 2H), 1.98-2.01 (m, 2H), 2.13-2.17 (m, 1H), 2.34-2.41 (m, 2H), 2.47-2.50 (m, 2H), 2.78-2.88 (m, 2H), 3.20-3.28 (m, 2H), 3.54-3.72 (m, 3H), 4.00-4.10 (m, 3H), 4.39-4.44 (m, 1H), 4.95 (dd, J=5.2, 12.0 Hz, 1H), 5.31-5.42 (m, 4H), 6.82 (d, J=8.4 Hz, 1H), 7.17 (d, J=8.8 Hz, 1H), 7.31-7.34 (m, 2H), 7.48-7.51 (m, 2H), 7.68 (s, 1H), 7.77 (d, J=8.8 Hz, 1H), 7.87 (d, J=7.2 Hz, 1H), 8.11 (d, J=8.0 Hz, 1H), 8.32 (s, 1H), 8.41-8.45 (m, 2H), 9.23 (s, 1H).

Synthetic Scheme for Exemplary Compounds 198 and 205

2-(2,6-dioxopiperidin-3-yl)-5-((3-(3-(4-((1r,3r)-3-((5-(5-methyl-5H-pyrido[4,3-b]indol-7-yl)pyridin-2-yl)oxy)cyclobutoxy)piperidin-1-yl)phenyl)prop-2-yn-1-yl)oxy)isoindoline-1,3-dione

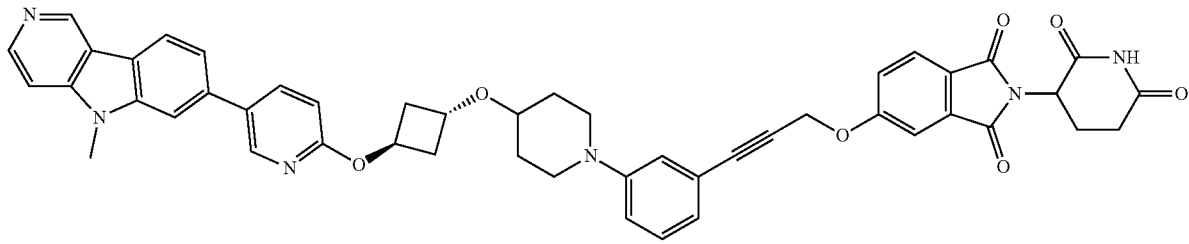 [SMILES: Cn1c2ccncc2c2ccc(-c3ccc(O[C@H]4C[C@H](OC5CCN(c6cccc(C#CCOc7ccc8c(c7)C(=O)N(C7CCC(=O)NC7=O)C8=O)c6)CC5)C4)nc3)cc21]

2-(2,6-dioxopiperidin-3-yl)-5-(3-(3-(4-((1r,3r)-3-((5-(5-methyl-5H-pyrido[4,3-b]indol-7-yl)pyridin-2-yl)oxy)cyclobutoxy)piperidin-1-yl)phenyl)propoxy)isoindoline-1,3-dione
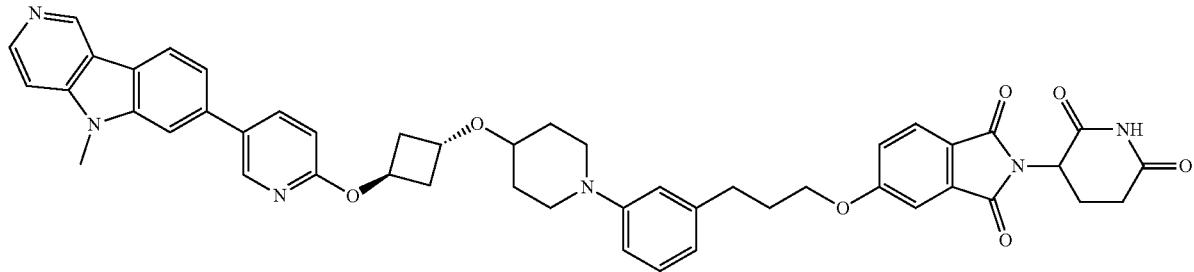 [SMILES: Cn1c2ccncc2c2ccc(-c3ccc(O[C@H]4C[C@H](OC5CCN(c6cccc(CCCOc7ccc8c(c7)C(=O)N(C7CCC(=O)NC7=O)C8=O)c6)CC5)C4)nc3)cc21]
Compounds 198 and 205 were prepared according to the synthetic scheme below using procedures described above and common procedures known to those skilled in the art:
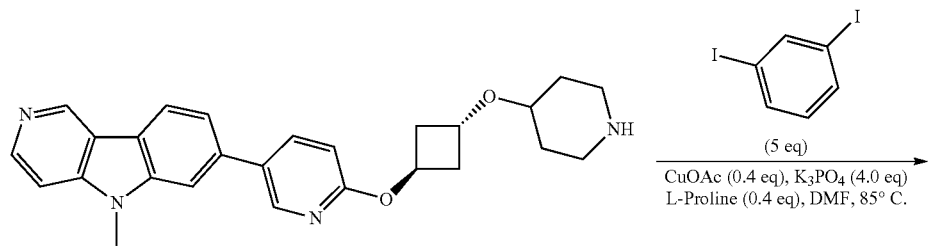
Prepared as described for Compound 82
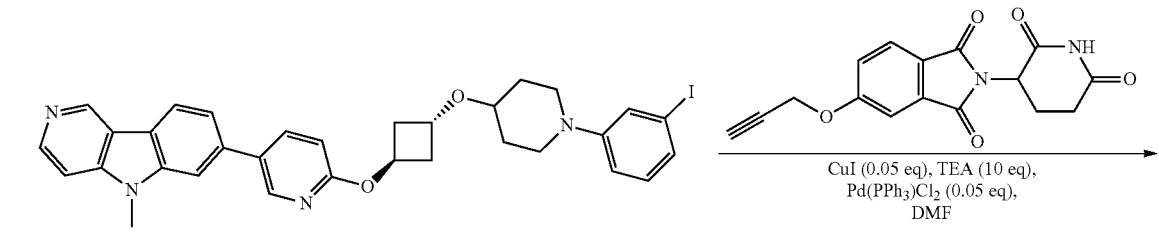
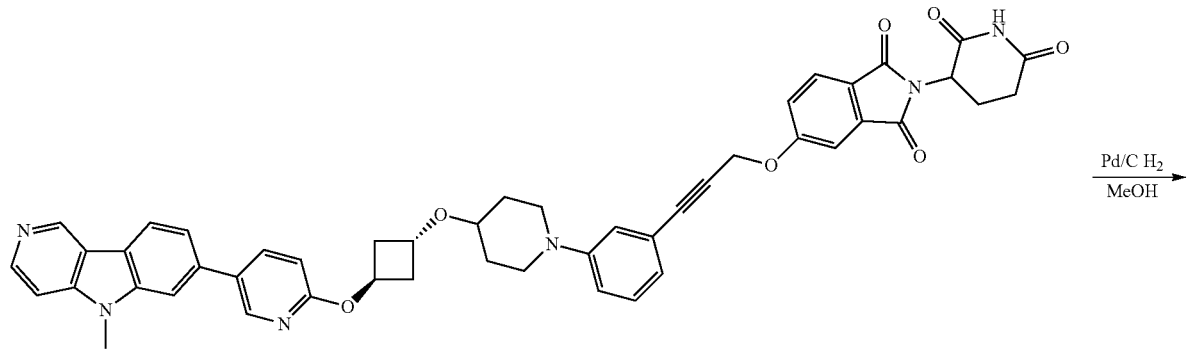
Compound 198

-continued
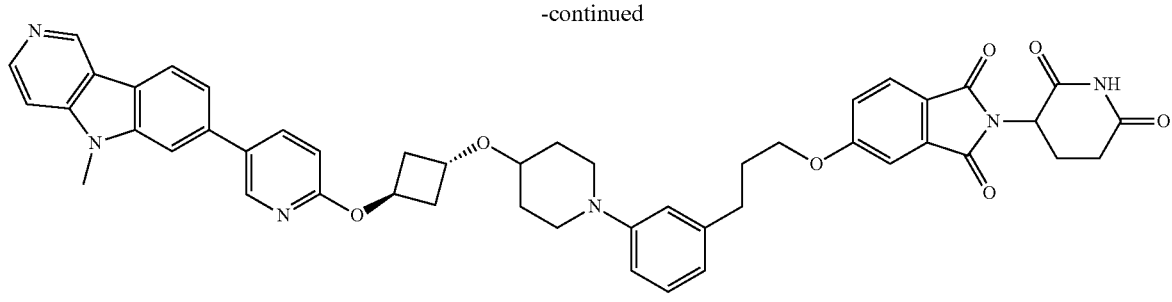
Compound 205
Synthetic Scheme for Exemplary Compound 68
2-(2,6-dioxopiperidin-3-yl)-5-(4-(5-((1r,3r)-3-((5-(5-methyl-5H-pyrido[4,3-b]indol-7-yl)pyridin-2-yl)oxy)cyclobutoxy)pentyl)piperazin-1-yl)isoindoline-1,3-dione
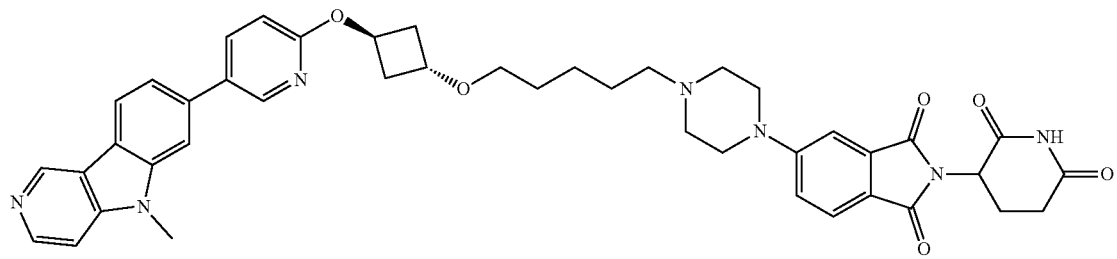 [SMILES: Cn1c2ccncc2c2ccc(-c3ccc(O[C@H]4C[C@H](OCCCCCN5CCN(c6ccc7c(c6)C(=O)N(C6CCC(=O)NC6=O)C7=O)CC5)C4)nc3)cc21]
Prepared according to the synthetic scheme below using procedures described above and common procedures known to those skilled in the art.
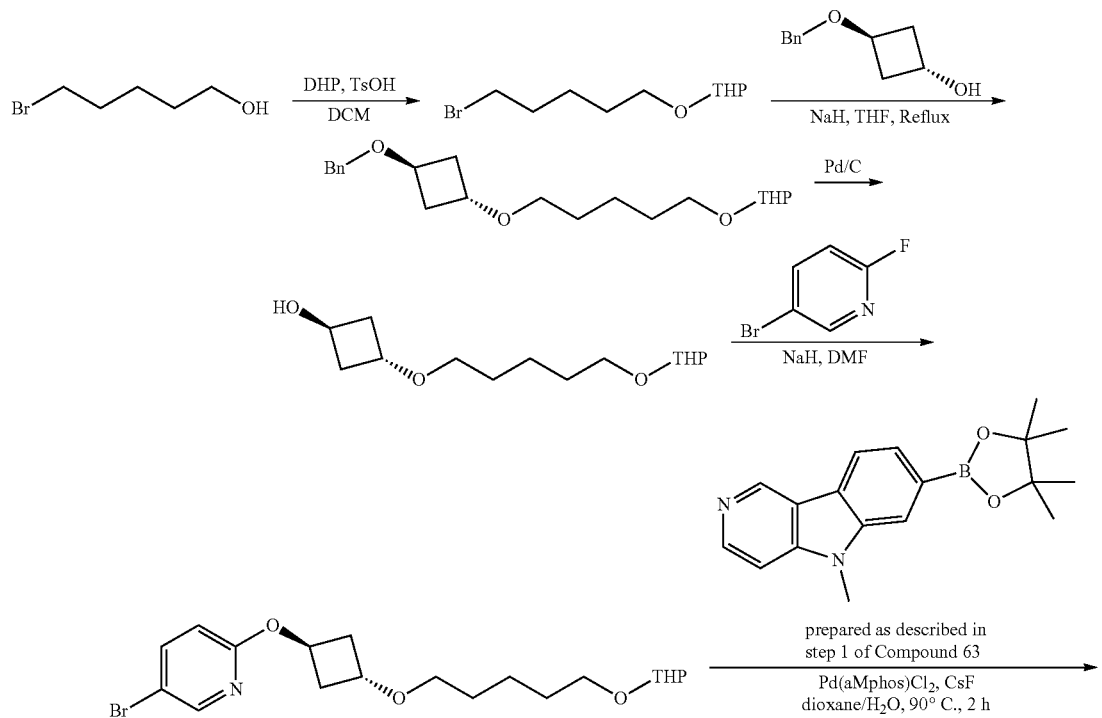

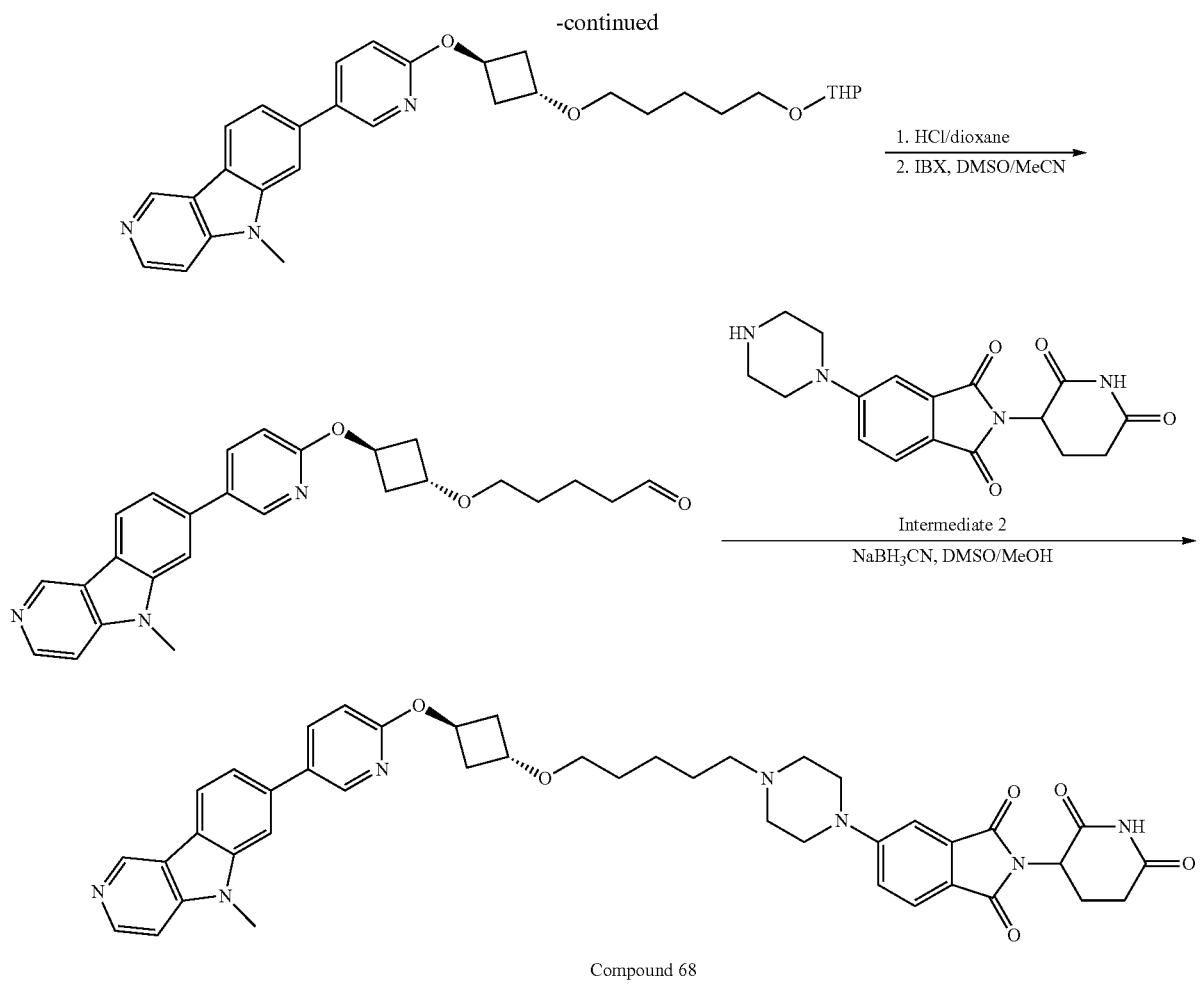

¹H NMR (400 MHz, DMSO-d6): δ 11.12 (s, 1H), 9.37 (s, 1H), 8.64 (s, 1H), 8.50 (d, J=4.0 Hz, 1H), 8.33 (d, J=12.0 Hz, 1H), 8.00 (s, 1H), 7.68-7.60 (m, 3H), 7.34 (d, J=4.0 Hz, 1H), 7.25 (dd, J=8.0 Hz, 4.0 Hz, 1H), 6.94 (d, J=8.0 Hz, 1H), 5.32 (t, J=4.0 Hz, 1H), 5.07 (dd, J=12.0 Hz, 8.0 Hz, 1H), 4.20-4.17 (m, 1H), 3.96 (s, 3H), 4.46 (s, 6H), 2.88-2.84 (m, 1H), 2.59-2.54 (m, 7H), 2.43-2.32 (m, 6H), 2.02-1.98 (m, 1H), 1.57-1.49 (m, 4H), 1.38-1.34 (m, 2H). (M+H)⁺ 756.6

Synthetic Scheme for Exemplary Compound 70

2-(2,6-dioxopiperidin-3-yl)-5-(2-(2-(2-(2-((1r,3r)-3-((5-(5-methyl-5H-pyrido[4,3-b]indol-7-yl)pyridin-2-yl)oxy)cyclobutoxy)ethoxy)ethoxy)ethoxy)ethoxy)isoindoline-1,3-dione Step 1: 2-((1r,3r)-3-(benzyloxy)cyclobutoxy)-5-bromopyridine

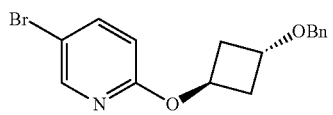

To a solution of (1r,3r)-3-(benzyloxy)cyclobutan-1-ol (500 mg, 2.8 mmol) in DMF (15 mL) was added NaH (336 mg, 8.4 mmol, 60%) at 0° C. The solution was stirred at 0°

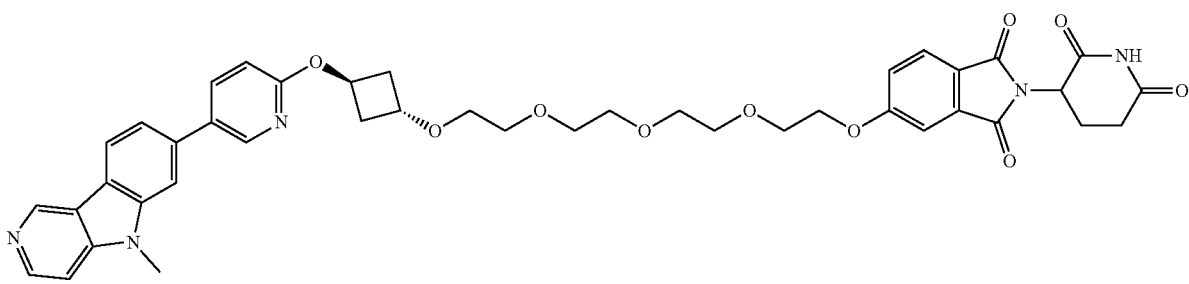 [SMILES: Cn1c2ccncc2c2ccc(-c3ccc(O[C@H]4C[C@H](OCCOCCOCCOCCOc5ccc6c(c5)C(=O)N(C5CCC(=O)NC5=O)C6=O)C4)nc3)cc21]

C. for 30 minutes. 5-bromo-2-fluoropyridine (1.0 g, 5.6 mmol) in DMF (3 mL) was added. The resulting solution was heated at 80° C. overnight. After cooling to room temperature, the mixture was quenched with water. The mixture was extracted with ethyl acetate, and the organic layer was washed with water and brine. The organic phase was dried over anhydrous sodium sulfate, filtered and concentrated under vacuum. The residue was purified by column chromatography on silica gel (PE:EA=100:1) to afford the desired compound (630 mg, 67% yield) as a colorless oil.

Step 2: (1r,3r)-3-((5-bromopyridin-2-yl)oxy)cyclobutan-1-ol

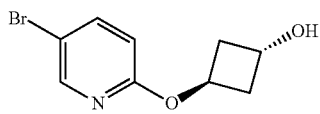

To a solution of 2-((1r,3r)-3-(benzyloxy)cyclobutoxy)-5-bromopyridine (630 mg, 1.88 mmol) in DCM (15 mL) was added BBr$_3$ (1.42 g, 5.65 mmol) at −78° C. The resulting solution was stirred at −78° C. for 0.5 hours. The solution was quenched with NaHCO$_3$. The layers were separated and the aqueous layer was extracted with DCM. The combined organic layers were concentrated to afford the desired compound (390 mg, crude) as a yellow solid, which was used directly in the next step without further purification.

Step 3: 5-bromo-2-((1r,3r)-3-((1-phenyl-2,5,8,11-tetraoxatridecan-13-yl)oxy)cyclobutoxy)pyridine

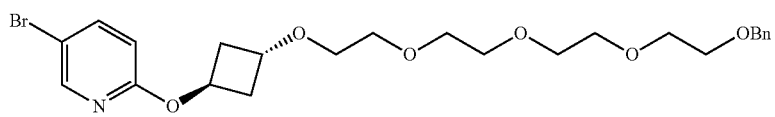 [SMILES: Brc1ccc(O[C@H]2C[C@H](OCCOCCOCCOCCOCc3ccccc3)C2)nc1]

To a solution of (1r,3r)-3-((5-bromopyridin-2-yl)oxy)cyclobutan-1-ol (390 mg, 1.64 mmol) in THF (15 mL) was added NaH (262 mg, 60%) at 0° C. The solution was stirred at 10° C. for 0.5 hours, and then 13-bromo-1-phenyl-2,5,8,11-tetraoxatridecane (570 mg, 1.64 mmol) was added. The resulting solution was stirred at 70° C. for 20 hours. The solution was quenched with water. The layers were separated and the aqueous layer was extracted with EA. The combined organic layers were washed with brine. The organic layer was dried over Na$_2$SO$_4$, filtered and concentrated. The residue was purified by column chromatography on silica gel with PE:EA (1:1) to afford the desired compound (350 mg) as a yellow solid.

5-bromo-2-((1r,3r)-3-((1-phenyl-2,5,8,11-tetraoxatridecan-13-yl)oxy)cyclobutoxy)pyridine was converted to the final compound, 2-(2,6-dioxopiperidin-3-yl)-5-(2-(2-(2-(2-((1r,3r)-3-((5-(5-methyl-5H-pyrido[4,3-b]indol-7-yl)pyridin-2-yl)oxy)cyclobutoxy)ethoxy)ethoxy)ethoxy)ethoxy)isoindoline-1,3-dione, according to the following scheme and using procedures described above and common procedures known to those skilled in the art.

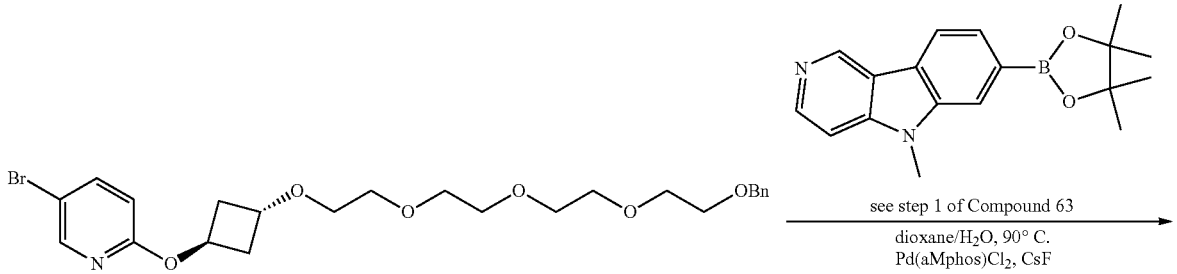

-continued

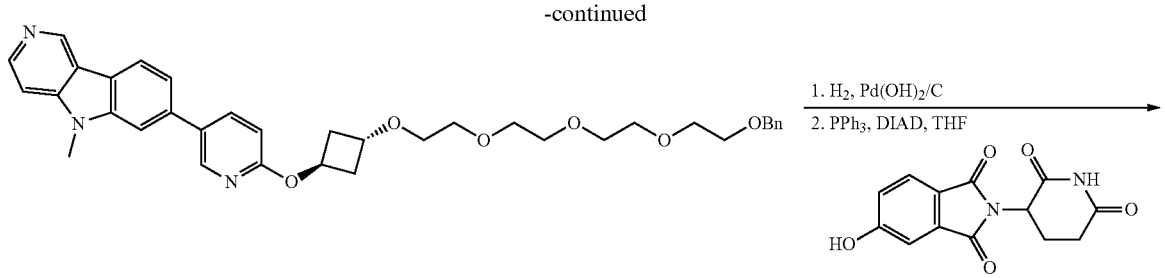

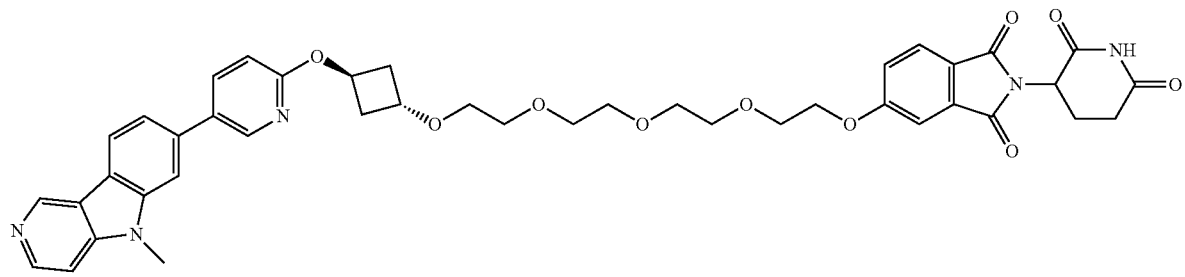

Compound 70

Compound 70: ¹H NMR (400 MHz, DMSO-d6): δ 11.10 (s, 1H), 9.36 (s, 1H), 8.62 (s, 1H), 8.50 (s, 1H), 8.31 (d, J=8.2 Hz, 1H), 8.18 (d, J=8.8 Hz, 1H), 7.97 (s, 1H), 7.81 (d, J=8.3 Hz, 1H), 7.60 (d, J=8.0 Hz, 2H), 7.43 (s, 1H), 7.35 (d, J=7.8 Hz, 1H), 6.93 (d, J=8.7 Hz, 1H), 5.31 (s, 1H), 5.11 (dd, J=12.8, 5.1 Hz, 1H), 4.31 (s, 2H), 4.22 (s, 1H), 3.95 (s, 3H), 3.79 (s, 2H), 3.64-3.48 (m, 10H), 3.45 (d, J=4.9 Hz, 3H), 2.86 (d, J=13.2 Hz, 1H), 2.45-2.40 (m, 2H), 2.37-2.30 (m, 2H), 2.02 (d, J=6.5 Hz, 1H). (M+H)⁺ 778.5.

Synthetic Scheme for Exemplary Compound 71

2-(2,6-dioxopiperidin-3-yl)-5-((15-(5-(5-methyl-5H-pyrido[4,3-b]indol-7-yl)pyridin-2-yl)-3,6,9,12-tetraoxapentadec-14-yn-1-yl)oxy)isoindoline-1,3-dione Step 1: 15-(5-bromopyridin-2-yl)-3,6,9,12-tetraoxapentadec-14-yn-1-ol

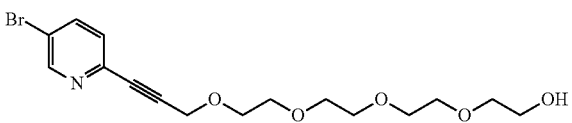

To a solution of 3,6,9,12-tetraoxapentadec-14-yn-1-ol (570 mg, 2.45 mmol) in dried THF (10 mL) were added 2,5-dibromopyridine (697.6 mg, 2.94 mmol), CuI (51.4 mg,

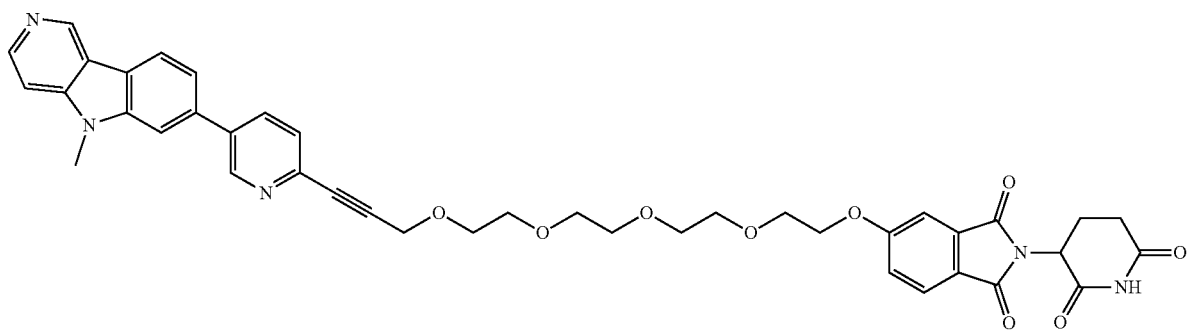 [SMILES: Cn1c2ccncc2c2ccc(-c3ccc(C#CCOCCOCCOCCOCCOc4ccc5c(c4)C(=O)N(C4CCC(=O)NC4=O)C5=O)nc3)cc21]

0.27 mmol) and Pd(PPh$_3$)$_2$Cl$_2$ (80 mg, 0.24 mmol) at 15° C. under N$_2$ atmosphere subsequently. The solution was stirred at 40° C. for 1.5 hours. The solution was quenched with H$_2$O (10 mL) and the mixture was extracted with EtOAc (10 mL×2). The combined organic layers were dried over anhydrous sodium sulfate, filtered and concentrated under vacuum. The residue was purified by silica gel column chromatography to afford the desired compound (530 mg, 56% yield) as a yellow oil.

15-(5-bromopyridin-2-yl)-3,6,9,12-tetraoxapentadec-14-yn-1-ol was converted to the final compound, 2-(2,6-dioxopiperidin-3-yl)-5-((15-(5-(5-methyl-5H-pyrido[4,3-b]indol-7-yl)pyridin-2-yl)-3,6,9,12-tetraoxapentadec-14-yn-1-yl)oxy)isoindoline-1,3-dione, according to the following scheme and using procedures described above and common procedures known to those skilled in the art.

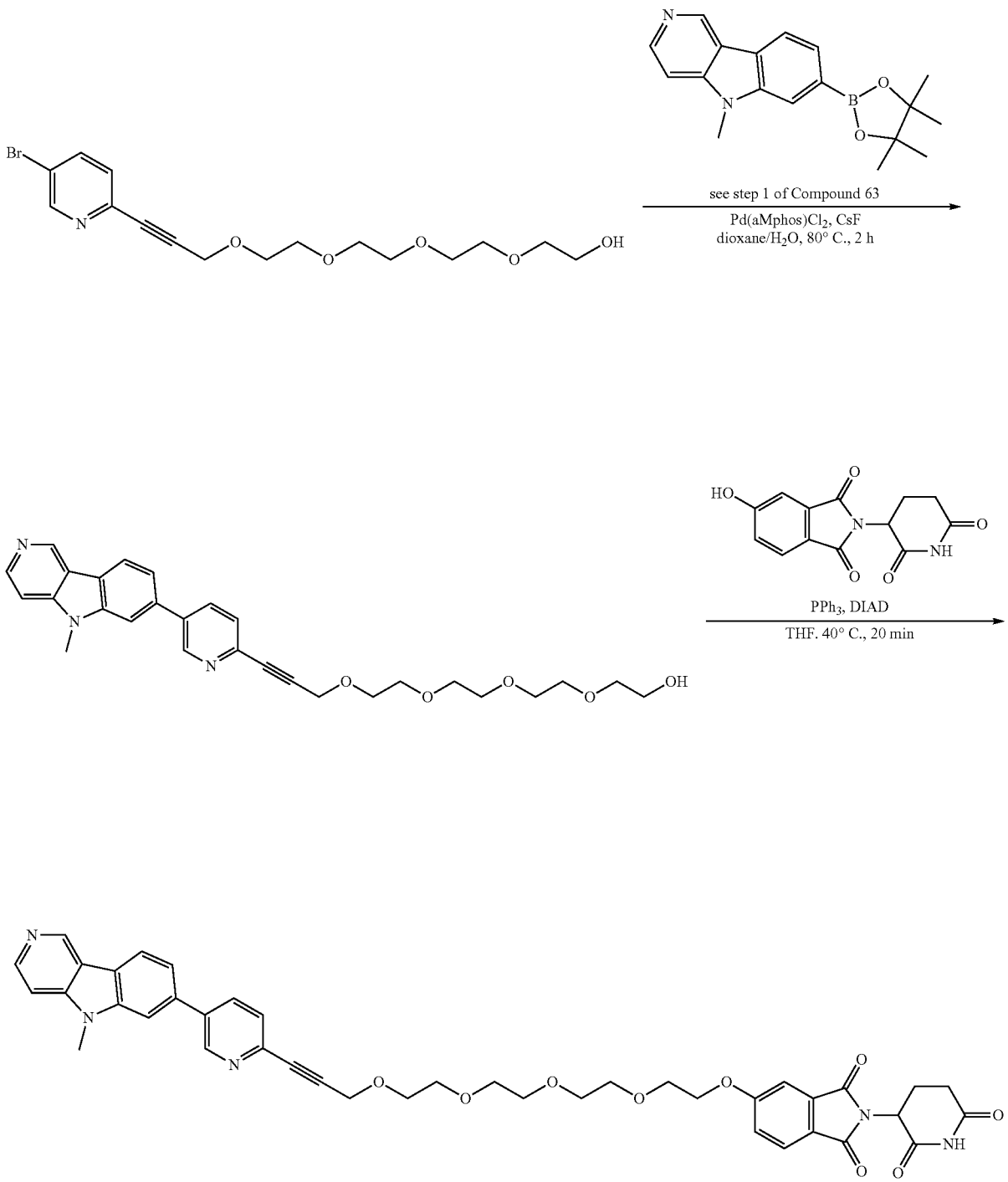

Compund 71

Compound 71: $^1$H NMR (400 MHz, DMSO-d$_6$): δ 9.39 (s, 1H), 8.38 (d, J=8.4 Hz, 1H), 8.30 (d, J=2.0 Hz, 1H), 8.28 (d, J=3.0 Hz, 1H), 8.11 (s, 1H), 7.80 (d, J=8.4 Hz, 1H), 7.72 (d, J=7.6 Hz, 1H), 7.63-7.68 (m, 2H), 7.44 (d, J=2.0 Hz, 1H), 7.34-7.36 (m, 1H), 5.08-5.12 (m, 1H), 4.48 (s, 2H), 4.31 (t, J=3.6 Hz, 2H), 3.98 (s, 3H), 3.80 (s, 3H), 3.53-3.79 (m, 12H), 1.95-2.08 (m, 2H). (M+H)$^+$ 746.5.

Synthetic Scheme for Exemplary Compound 74

2-(2,6-dioxopiperidin-3-yl)-5-((15-(5-(5-methyl-5H-pyrido[4,3-b]indol-7-yl)pyridin-2-yl)-3,6,9,12-tetraoxapentadecyl)oxy)isoindoline-1,3-dione

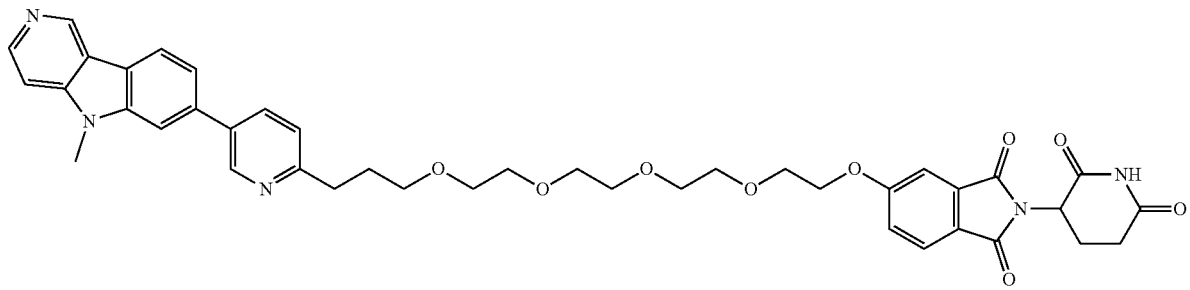 [SMILES: Cn1c2ccncc2c2ccc(-c3ccc(CCCOCCOCCOCCOCCOc4ccc5c(c4)C(=O)N(C4CCC(=O)NC4=O)C5=O)nc3)cc21]

Prepared according to the synthetic scheme below using procedures described above and common procedures known to those skilled in the art.

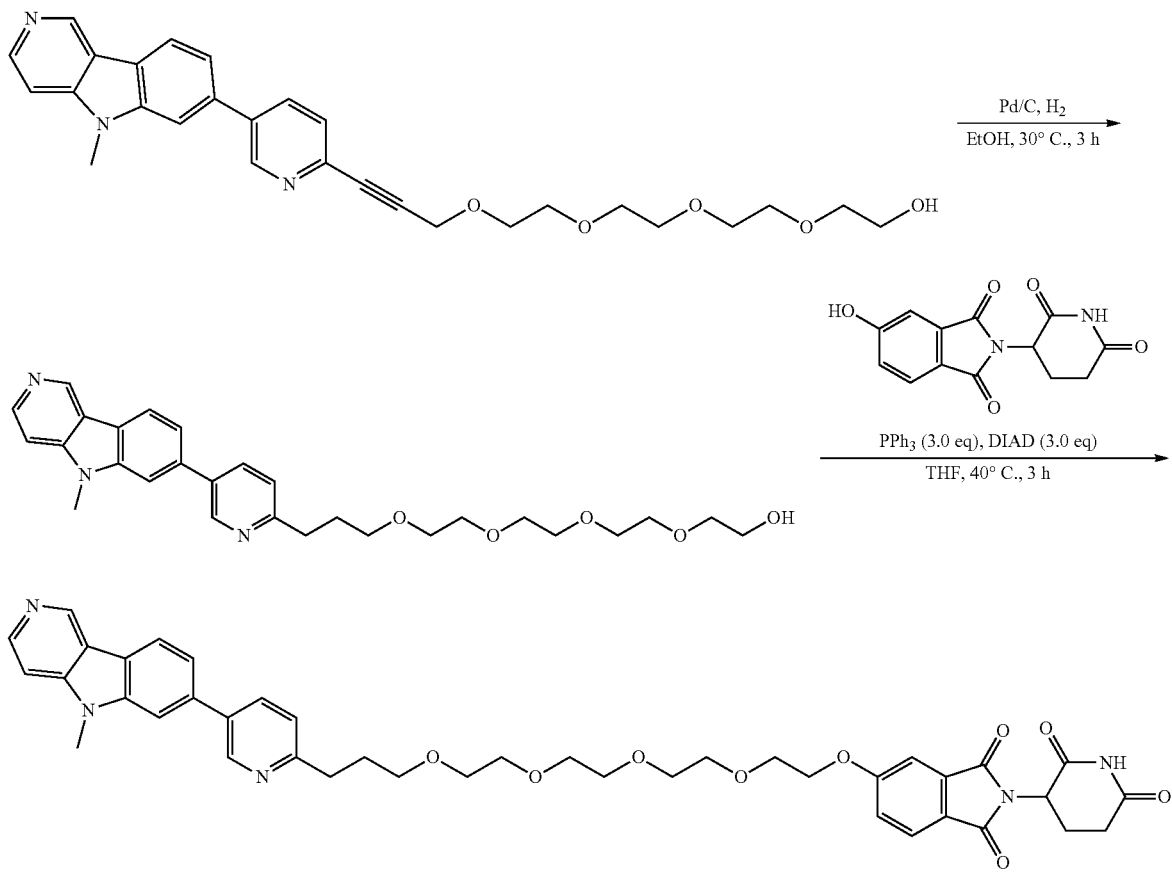

Compound 74

Compound 74: 1H NMR (400 MHz, CDCl₃): δ 9.65 (s, 1H), 9.22 (s, 1H), 8.67-8.73 (m, 2H), 8.47 (d, J=7.6 Hz, 1H), 8.36 (d, J=8.0 Hz, 1H), 7.97 (s, 1H), 7.83 (s, 1H), 7.81 (s, 1H), 7.59-7.71 (m, 2H), 7.04 (d, J=9.2 Hz, 2H), 4.93-4.96 (m, 1H), 4.10 (s, 5H), 3.87 (s, 1H), 3.55-3.76 (m, 18H), 3.26 (s, 2H), 2.12-2.16 (m, 2H). (M+H)⁺ 750.5.

Synthetic Scheme for Exemplary Compound 72

5-((14-((5-(5H-pyrido[4,3-b]indol-7-yl)pyridin-2-yl)oxy)-3,6,9,12-tetraoxatetradecyl)oxy)-2-(2,6-dioxopiperidin-3-yl)-4,6,7-trifluoroisoindoline-1,3-dione

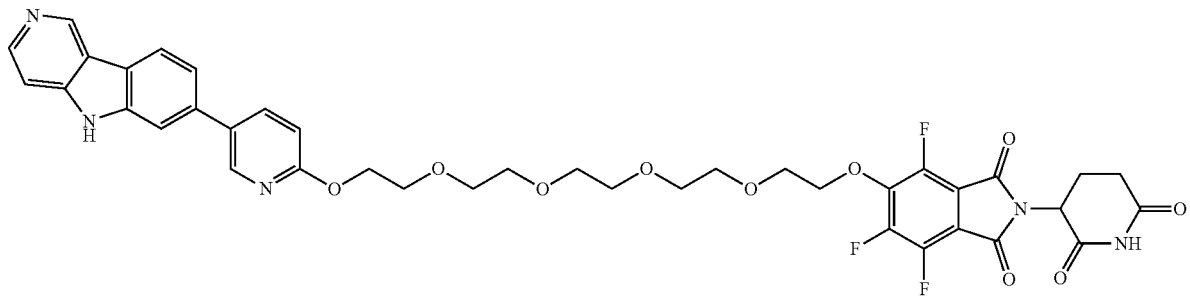 [SMILES: O=C1CCC(N2C(=O)c3c(F)c(F)c(OCCOCCOCCOCCOCCOc4ccc(-c5ccc6c(c5)[nH]c5ccncc56)cn4)c(F)c3C2=O)C(=O)N1]

Prepared according to the synthetic scheme below using procedures described above and common procedures known to those skilled in the art.

2-(2,6-dioxopiperidin-3-yl)-4,5,7-trifluoro-6-hydroxyisoindoline-1,3-dione was prepared as described below.

Step 1: 3,4,6-trifluoro-5-hydroxyphthalic Acid

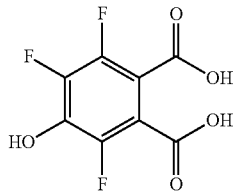 [SMILES: O=C(O)c1c(F)c(O)c(F)c(F)c1C(=O)O]

To a solution of 3,4,5,6-tetrafluorophthalic acid (1.18 g, 5 mmol) in water (20 mL) was added potassium hydroxide (2.24 g, 40 mmol, 8 eq). The resulting solution was heated to 90° C. for 9 hours. Then the reaction was cooled to room temperature and neutralized by HCl (1 N). The resulting solution was extracted with ethyl acetate (50 mL×3). The combined organic layers were washed with brine (20 mL×2), dried over anhydrous sodium sulfate and concentrated under vacuum to afford crude desired product (1.15 g) as white solid, which was used in the next step without purification.

Step 2: 2-(2,6-dioxopiperidin-3-yl)-4,5,7-trifluoro-6-hydroxyisoindoline-1,3-dione

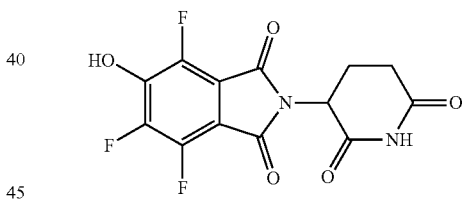

To a solution of 3,4,6-trifluoro-5-hydroxyphthalic acid (500 mg, 2.12 mmol), 3-aminopiperidine-2,6-dione (383 mg, 2.33 mmol) in AcOH was added AcONa (209 mg, 2.54 mmol). The resulting solution was stirred at 120° C. for 4 h. After cooling to room temperature, the solvent was removed under vacuum. Then it was quenched with water (30 mL). The resulting solution was extracted with EA (30 mL×3). The combined organic layers were washed with brine (10 mL×2), dried over anhydrous sodium sulfate and concentrated under vacuum to afford 2-(2,6-dioxopiperidin-3-yl)-4,5,7-trifluoro-6-hydroxyisoindoline-1,3-dione (400 mg, 1.22 mmol, 58%).

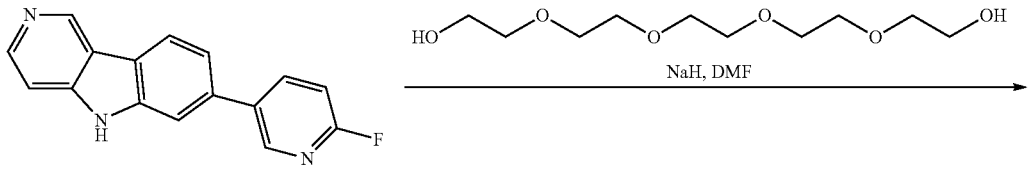

-continued
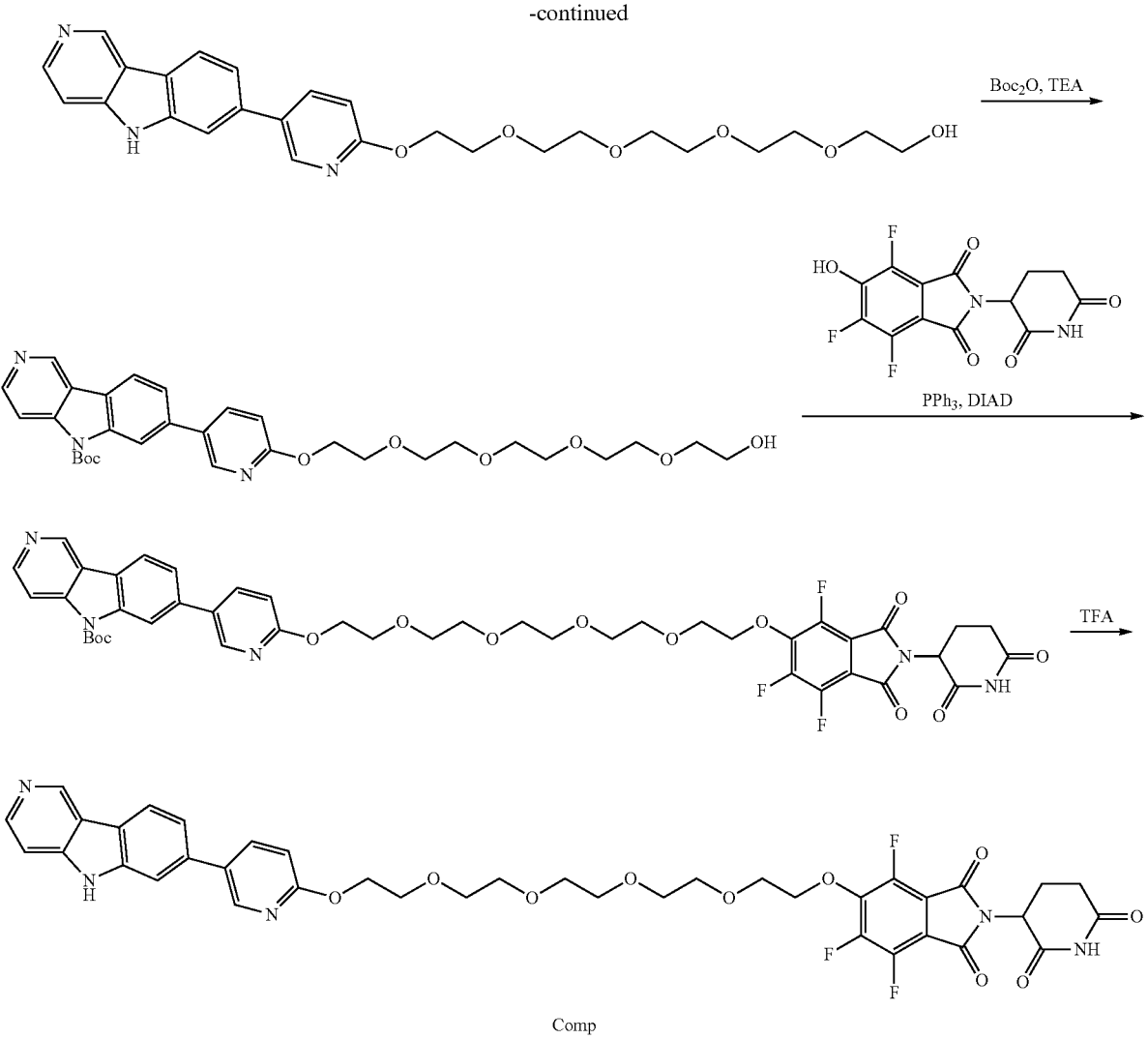
Compound 72: ¹H NMR (400 MHz, CD₃OD): δ 13.19 (s, 1H), 9.77 (s, 1H), 8.62-8.68 (m, 2H), 8.52 (d, J=8.0 Hz, 1H), 8.16 (s, 1H), 8.01-8.02 (m, 2H), 7.80-7.81 (m, 1H), 7.15-7.28 (m, 1H), 6.99 (d, J=8.0 Hz, 1H), 5.15-5.23 (m, 1H), 4.43-4.45 (m, 2H), 3.77-3.89 (m, 4H), 3.49-3.60 (m, 12H), 2.86-3.05 (m, 3H), 1.99-2.01 (m, 1H). (M+H)⁺ 792.5.
Synthetic Scheme for Exemplary Compound 81
5-((14-((5-(5H-pyrido[4,3-b]indol-7-yl)pyridin-2-yl)oxy)-3,6,9,12-tetraoxatetradecyl)oxy)-2-(2,6-dioxopiperidin-3-yl)-6-fluoroisoindoline-1,3-dione
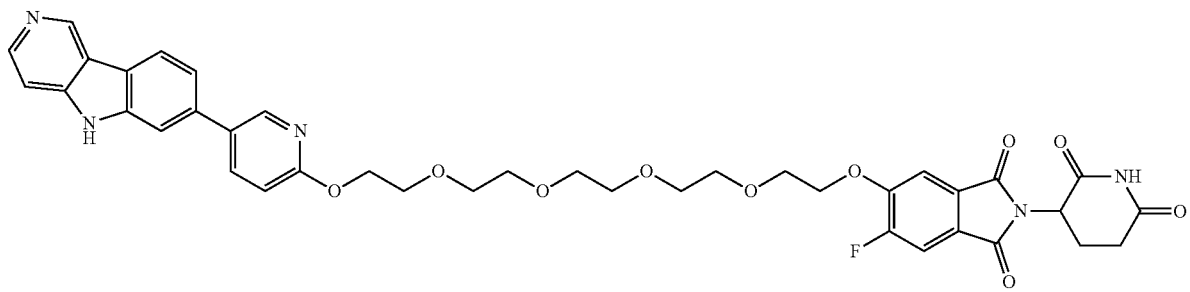 [SMILES: O=C1CCC(N2C(=O)c3cc(F)c(OCCOCCOCCOCCOCCOc4ccc(-c5ccc6c(c5)[nH]c5ccncc56)cn4)cc3C2=O)C(=O)N1]

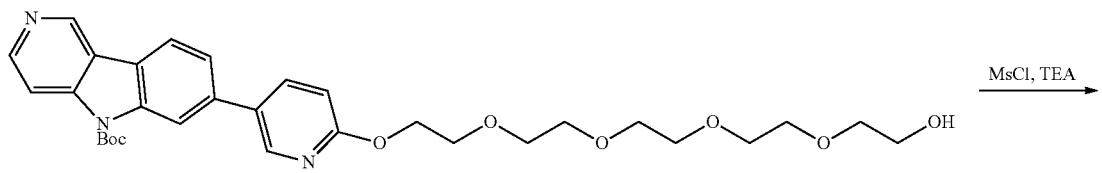
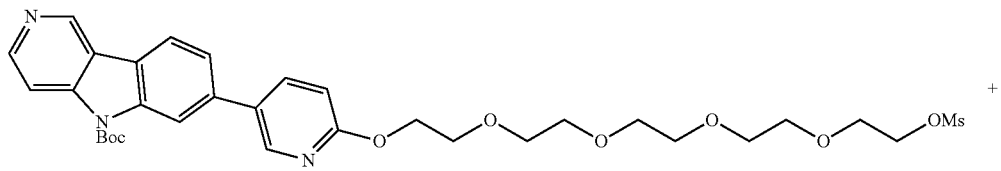
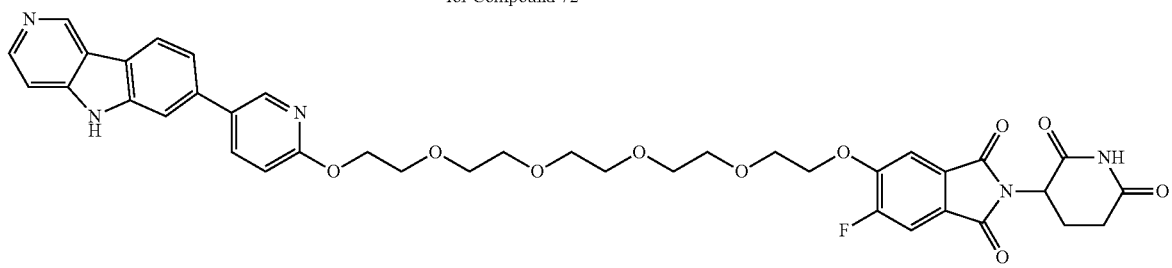
Compound 81: $^1$H NMR (400 MHz, CDCl$_3$): δ 9.31 (s, 1H), 8.51 (s, 1H), 8.40 (s, 1H), 8.11 (d, J=8.0 Hz, 1H), 7.82-7.83 (m, 1H), 7.60 (s, 1H), 7.37-7.45 (m, 3H), 6.84 (d, J=8.0 Hz, 1H), 4.92-4.95 (m, 1H), 4.53 (t, J=4.8 Hz, 2H), 4.24 (t, J=4.8 Hz, 2H), 3.89-3.91 (m, 4H), 3.67-3.75 (m, 12H), 2.74-2.92 (m, 3H), 2.12-2.16 (m, 1H). (M+H)$^+$ 756.5.
Synthetic Scheme of Exemplary Compound 75
2-(2,6-dioxopiperidin-3-yl)-5-(4-(5-((5-((5-(5-methyl-5H-pyrido[4,3-b]indol-7-yl)pyridin-2-yl)oxy)pentyl)oxy)pentyl)piperidin-1-yl)isoindoline-1,3-dione
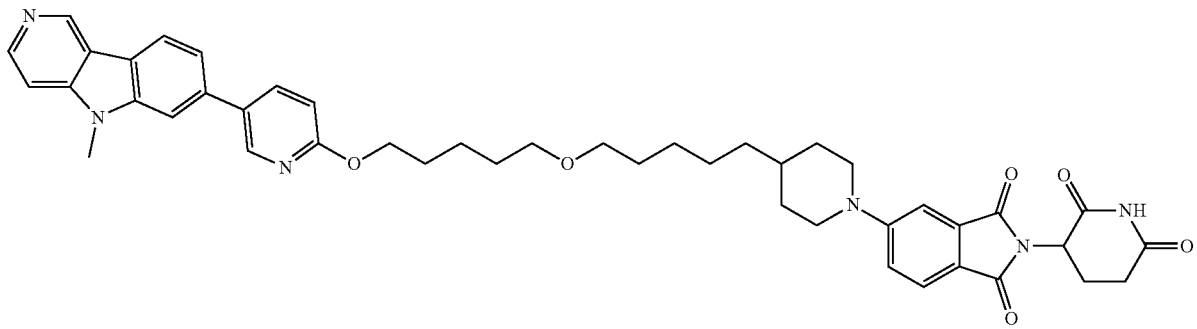 [SMILES: Cn1c2ccncc2c2ccc(-c3ccc(OCCCCCOCCCCCC4CCN(c5ccc6c(c5)C(=O)N(C5CCC(=O)NC5=O)C6=O)CC4)nc3)cc21]

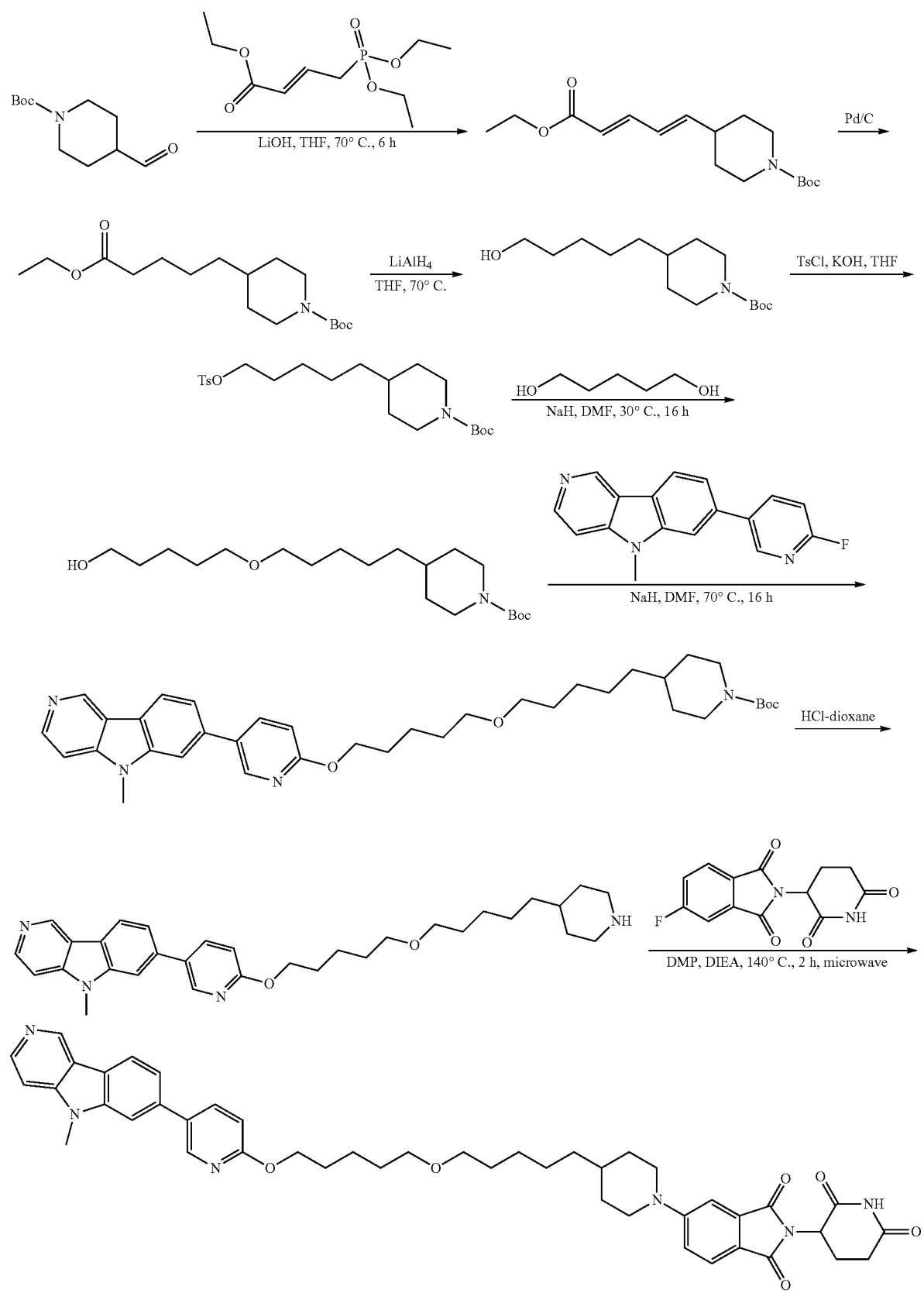
Compound 75

Compound 75: $^1$H NMR (400 MHz, DMSO-$d_6$): δ=11.07 (s, 1H), 9.38-9.32 (m, 1H), 8.66-8.63 (d, J=12 Hz 1H), 8.50-8.48 (m, J=8 Hz 1H), 8.36 (s, 2H), 8.34-8.29 (m, 1H), 8.21-8.14 (m, 1H), 7.99-7.94 (m, 1H), 7.61 (s, 3H), 7.28-7.22 (m, 1H), 7.19-7.12 (m, 1H), 6.96-6.89 (m, 1H), 5.09-5.00 (m, 1H), 4.36-4.29 (m, 2H), 3.95 (s, 5H), 3.34 (s, 4H), 2.87 (s, 2H), 2.99-2.78 (m, 1H), 2.82-2.73 (m, 1H), 2.04-1.93 (m, 1H), 1.82-1.65 (m, 4H), 1.61-1.52 (m, 2H), 1.52-1.41 (m, 5H), 1.28 (s, 4H), 1.22-1.05 (m, 4H). (M+H)$^+$ 771.6.

Synthetic Scheme for Exemplary Compound 76

2-(2,6-dioxopiperidin-3-yl)-5-(3-(3-(4-(3-(5-(5-methyl-5H-pyrido[4,3-b]indol-7-yl)pyridin-2-yl)prop-2-yn-1-yl)piperazin-1-yl)propoxy)azetidin-1-yl)isoindoline-1,3-dione

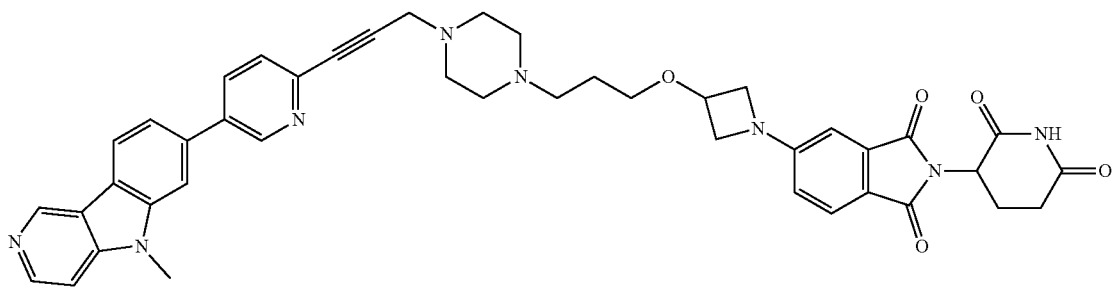 [SMILES: Cn1c2ccncc2c2ccc(-c3ccc(C#CCN4CCN(CCCOC5CN(c6ccc7c(c6)C(=O)N(C6CCC(=O)NC6=O)C7=O)C5)CC4)nc3)cc21]

Prepared according to the synthetic scheme below using procedures described above and common procedures to those skilled in the art.

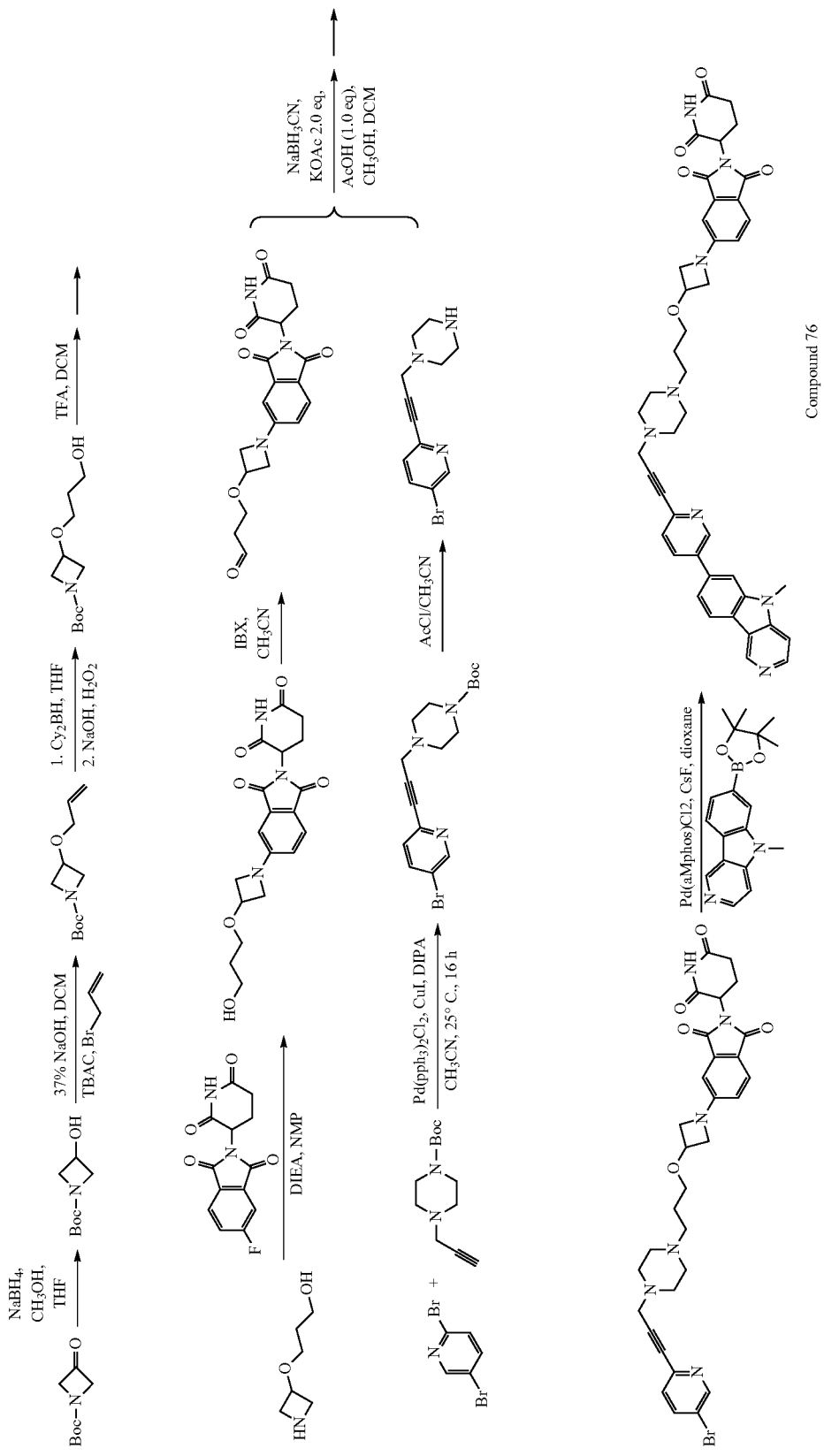

Compound 76: $^1$H NMR (400 MHz, CD$_3$OD): δ 9.32 (s, 1H), 8.96 (s, 1H), 8.45-8.52 (m, 2H), 8.37 (d, J=8.0 Hz, 1H), 8.27-8.31 (m, 1H), 7.98 (s, 1H), 7.61-7.98 (m, 4H), 6.82 (s, 1H), 6.65-6.67 (m, 1H), 5.01-5.05 (m, 1H), 4.59 (m, 1H), 4.27 (t, J=8.4 Hz, 1H), 4.02 (s, 3H), 3.88-3.91 (m, 2H), 3.70 (s, 2H), 3.57 (t, J=6.0 Hz, 2H), 3.41 (m, 1H), 3.13-3.17 (m, 2H), 2.66-2.86 (m, 11H), 2.02-2.03 (m, 3H). (M+H)$^+$ 751.5.

Synthetic Scheme for Exemplary Compound 78

2-(2,6-dioxopiperidin-3-yl)-5-(4-(6-((1r,3r)-3-((5-(5-methyl-5H-pyrido[4,3-b]indol-7-yl)pyridin-2-yl)oxy)cyclobutoxy)hexyl)piperazin-1-yl)isoindoline-1,3-dione

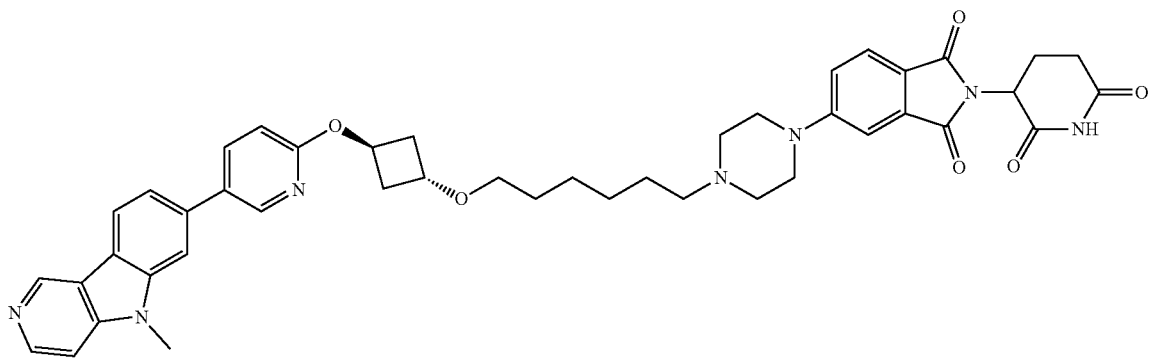

Prepared according to the synthetic scheme below using procedures described above and common procedures known to those skilled in the art.

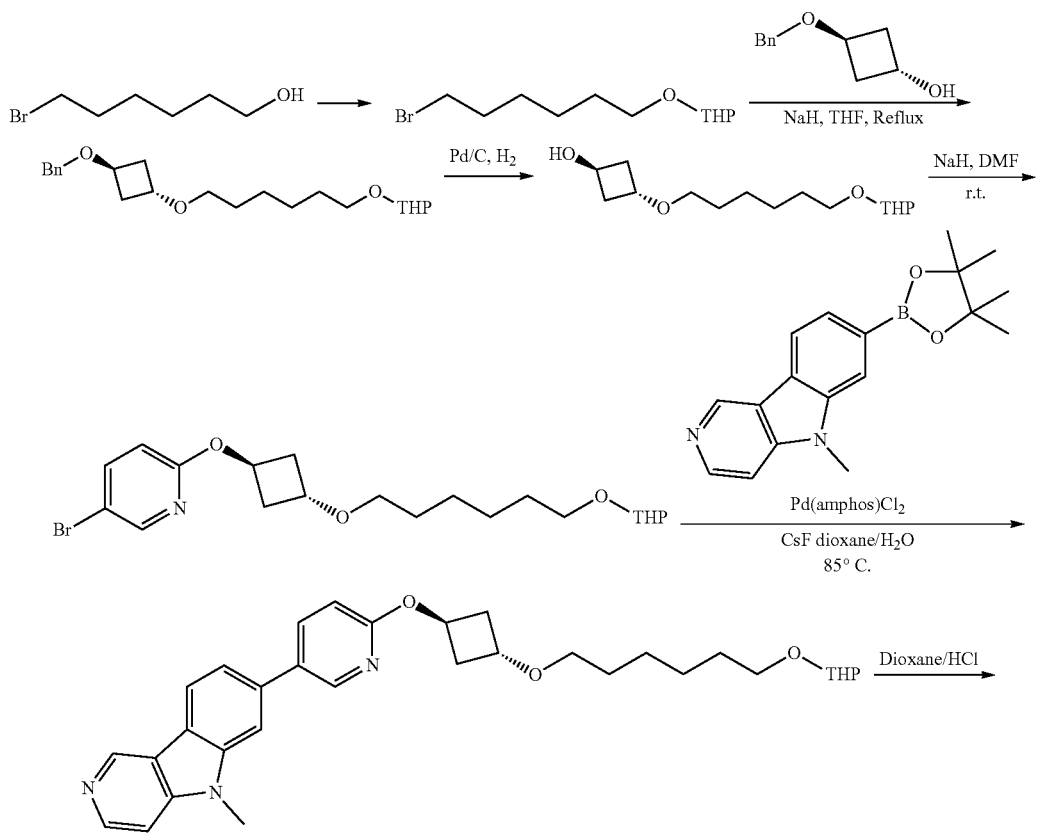

-continued
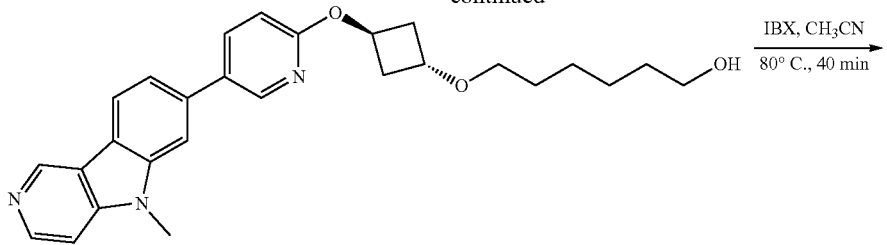
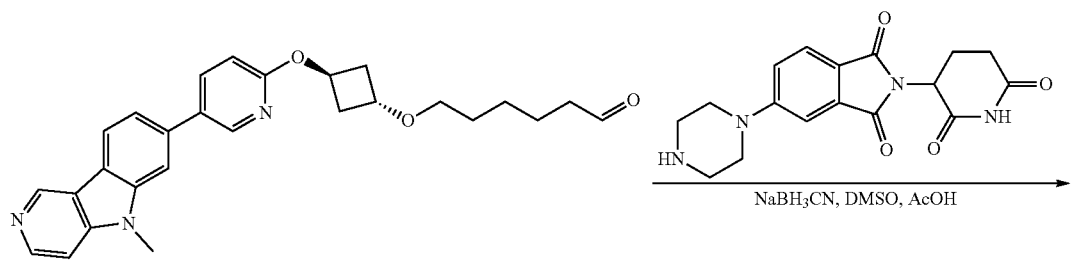
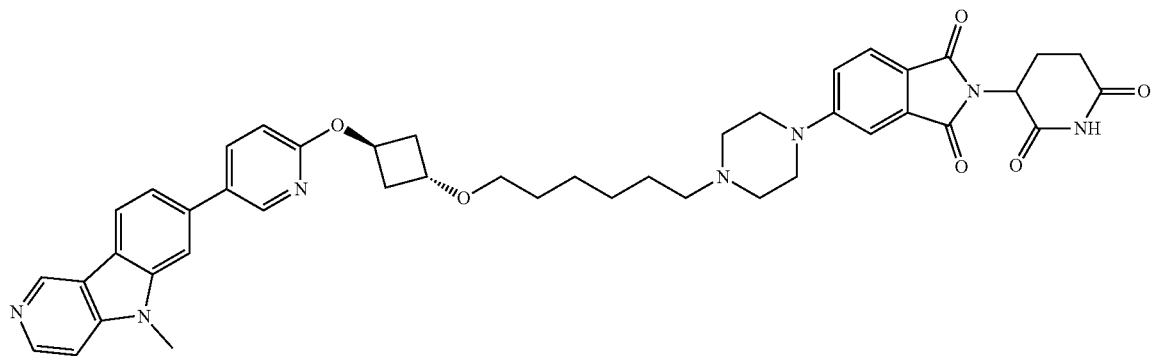 [SMILES: Cn1c2ccncc2c2ccc(-c3ccc(O[C@H]4C[C@H](OCCCCCCN5CCN(c6ccc7c(c6)C(=O)N(C6CCC(=O)NC6=O)C7=O)CC5)C4)nc3)cc21]
Compound 78
Compound 78: ¹H NMR (400 MHz, DMSO-d6): δ 11.08 (s, 1H), 9.35 (s, 1H), 8.64 (t, J=3.9 Hz, 1H), 8.49 (d, J=4.7 Hz, 1H), 8.32 (d, J=8.1 Hz, 1H), 8.19 (dd, J=8.6, 2.5 Hz, 1H), 7.98 (s, 1H), 7.68-7.48 (m, 3H), 7.31 (d, J=7.8 Hz, 1H), 7.20 (t, J=9.5 Hz, 1H), 6.94 (d, J=8.6 Hz, 1H), 5.07 (dd, J=12.9, 5.3 Hz, 1H), 4.33 (t, J=6.5 Hz, 2H), 3.95 (s, 3H), 3.65 (m, 1H), 3.51-3.41 (m, 3H), 3.36-3.23 (m, 5H), 2.95-2.83 (m, 1H), 2.43-2.28 (m, 6H), 2.05-1.96 (m, 1H), 1.79-1.73 (m, 1H), 1.67-1.61 (m, 1H), 1.42 (m, 7H). (M+H)⁺ 770.6.
Synthetic Scheme of Exemplary Compound 85
2-(2,6-dioxopiperidin-3-yl)-5-((1r,3r)-3-((5-((5-((5-(5-methyl-5H-pyrido[4,3-b]indol-7-yl)pyridin-2-yl)oxy)pentyl)oxy)pentyl)oxy)cyclobutoxy)isoindoline-1,3-dione
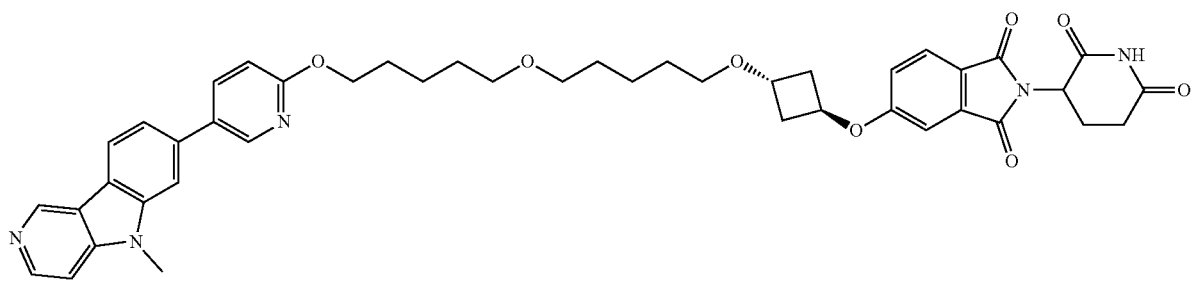 [SMILES: Cn1c2ccncc2c2ccc(-c3ccc(OCCCCCOCCCCCO[C@H]4C[C@H](Oc5ccc6c(c5)C(=O)N(C5CCC(=O)NC5=O)C6=O)C4)nc3)cc21]

Prepared according to the synthetic scheme below using procedures described above and common procedures known to those skilled in the art.
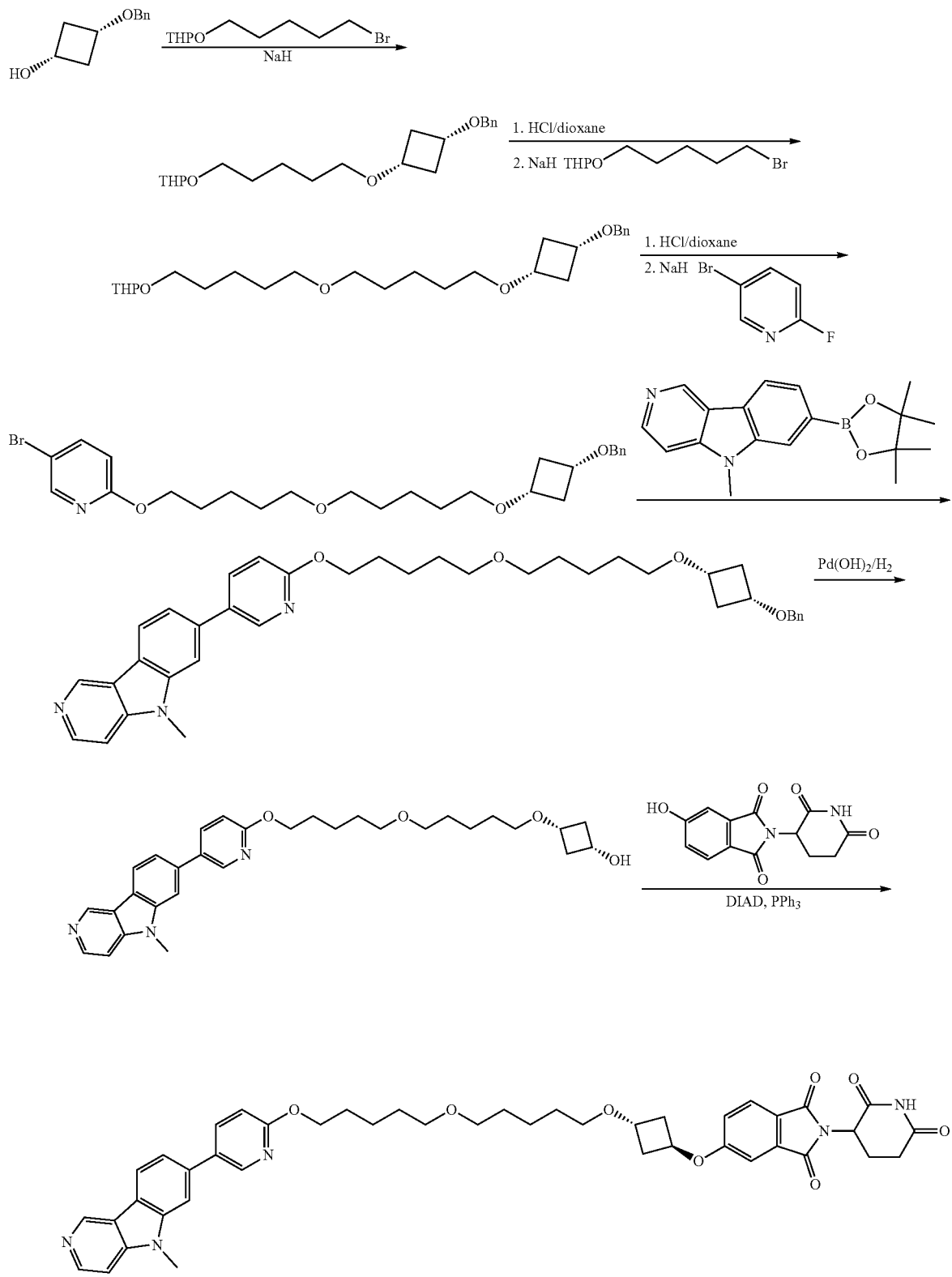
Compound 85

Compound 85: ¹H NMR (400 MHz, CDCl₃): δ 9.32 (s, 1H), 8.58-8.59 (d, J=4.0 Hz, 2H), 8.48 (s, 1H), 8.16-8.18 (d, J=8.0 Hz, 1H), 7.89-7.91 (d, J=8.0 Hz, 1H), 7.74-7.76 (d, J=8.0 Hz, 1H), 7.56 (s, 1H), 7.47-7.49 (d, J=8.0 Hz, 1H), 7.32-7.33 (d, J=4.0 Hz, 1H), 7.19 (s, 1H), 7.06-7.08 (d, J=8.0 Hz, 1H), 6.84-6.86 (d, J=8.0 Hz, 1H), 4.93 (m, 2H), 4.35-4.38 (m, 2H), 4.21 (s, 1H), 3.90 (s, 3H), 3.35-3.49 (m, 7H), 2.68-2.95 (m, 3H), 2.44-2.51 (m, 4H), 2.15 (m, 1H), 1.88 (m, 2H), 1.56-1.68 (m, 9H), 1.44 (d, J=8.0 Hz, 2H). (M+H)⁺ 774.6.

Synthetic Scheme of Exemplary Compound 79

2-(2,6-dioxopiperidin-3-yl)-5-(3-((5-((5-((5-(5-methyl-5H-pyrido[4,3-b]indol-7-yl)pyridin-2-yl)oxy)pentyl)oxy)pentyl)oxy)azetidin-1-yl)isoindoline-1,3-dione

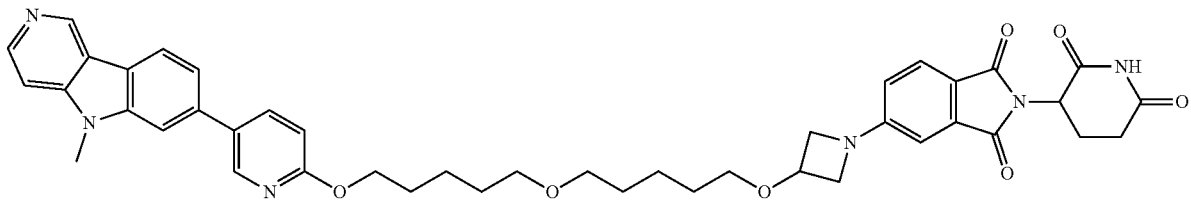 [SMILES: Cn1c2ccncc2c2ccc(-c3ccc(OCCCCCOCCCCCOC4CN(c5ccc6c(c5)C(=O)N(C5CCC(=O)NC5=O)C6=O)C4)nc3)cc21]

Prepared according to the synthetic scheme below using procedures described above and common procedures known to those skilled in the art.

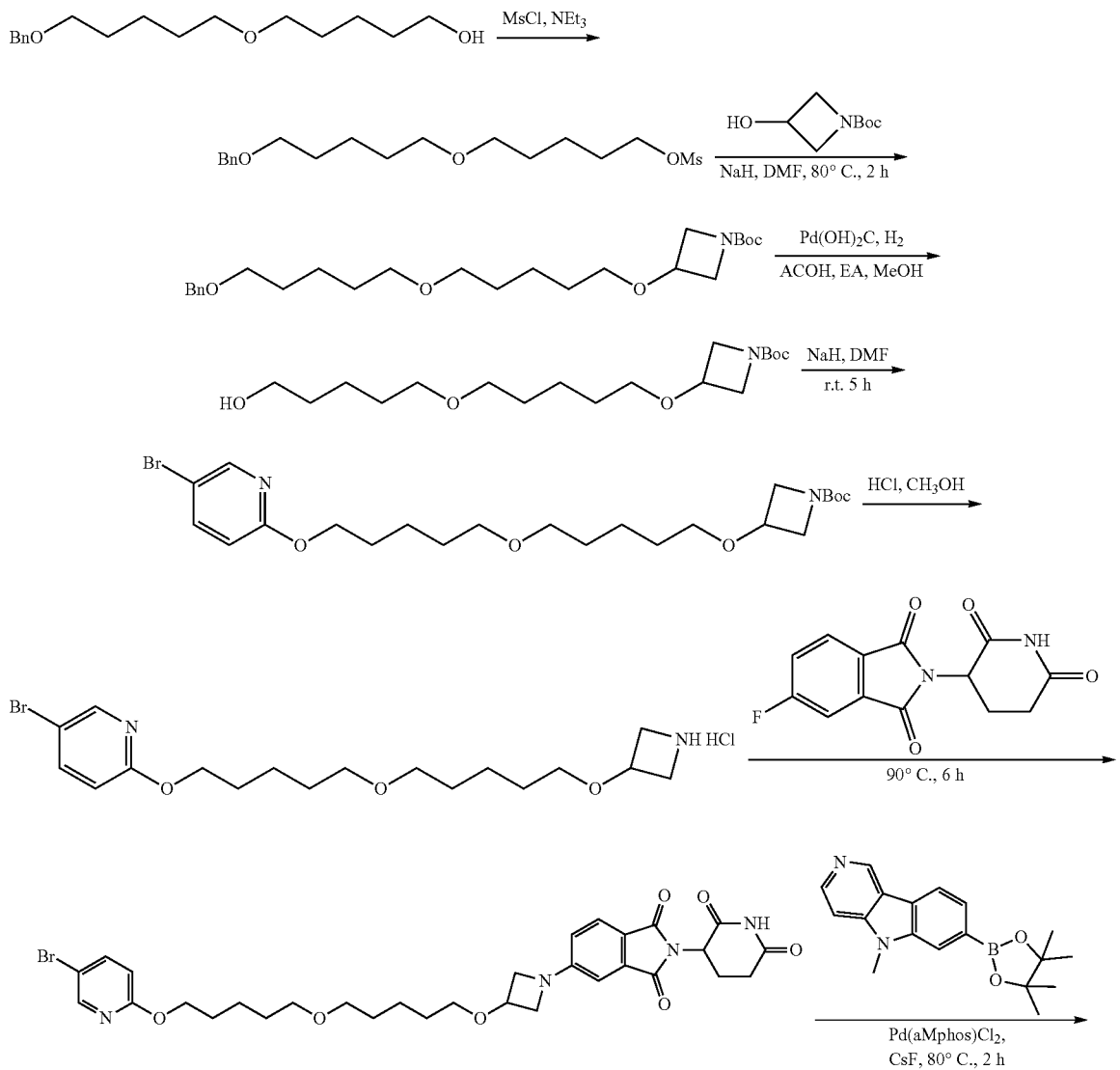

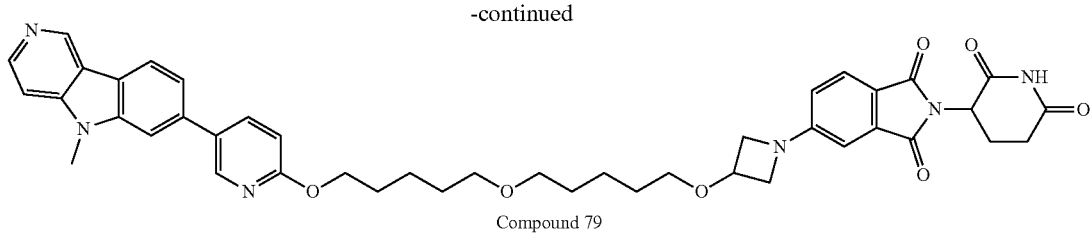

Compound 79

Compound 79: $^1$H NMR (400 MHz, CDCl$_3$): δ 9.35 (s, 1H), 8.59 (d, J=5.7 Hz, 1H), 8.49 (s, 1H), 8.28 (s, 1H), 8.21 (d, J=10.6 Hz, 1H), 8.00 (s, 1H), 7.91 (d, J=11.0 Hz, 1H), 7.63 (d, J=8.2 Hz, 1H), 7.57 (s, 1H), 7.51 (d, J=9.3 Hz, 1H), 7.37 (d, J=5.9 Hz, 1H), 6.85 (d, J=8.6 Hz, 1H), 6.77 (s, 1H), 4.92 (m, 1H), 4.45 (s, 1H), 4.36 (t, J=6.6 Hz, 2H), 4.16-4.26 (m, 2H), 3.83-3.98 (m, 4H), 3.44 (m, 4H), 2.63-2.92 (m, 3H), 2.11 (d, J=6.4 Hz, 2H), 1.79-1.89 (m, 3H), 1.44-1.70 (m, 10H). (M+H)$^+$ 759.6.

Synthetic Scheme for Exemplary Compound 80

2-(2,6-dioxopiperidin-3-yl)-5-((1-(5-((5-((5-(5-methyl-5H-pyrido[4,3-b]indol-7-yl)pyridin-2-yl)oxy)pentyl)oxy)pentyl)azetidin-3-yl)oxy)isoindoline-1,3-dione

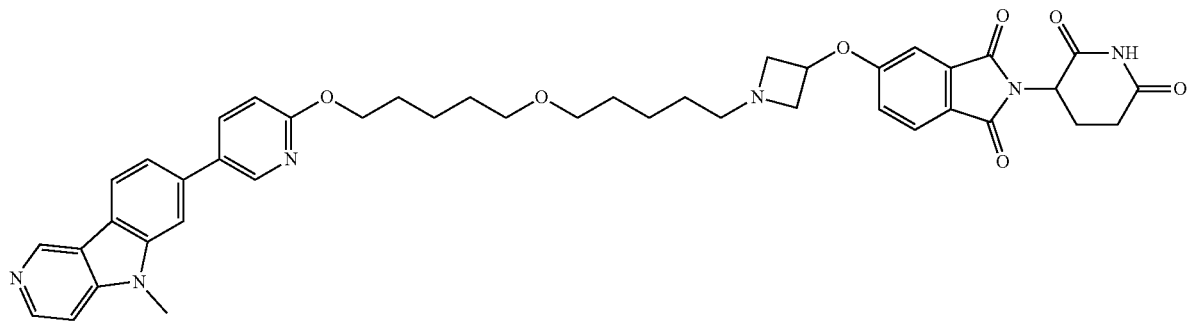 [SMILES: Cn1c2ccncc2c2ccc(-c3ccc(OCCCCCOCCCCCN4CC(Oc5ccc6c(c5)C(=O)N(C5CCC(=O)NC5=O)C6=O)C4)nc3)cc21]

Prepared according to the synthetic scheme below using procedures described above and common procedures known to those skilled in the art.

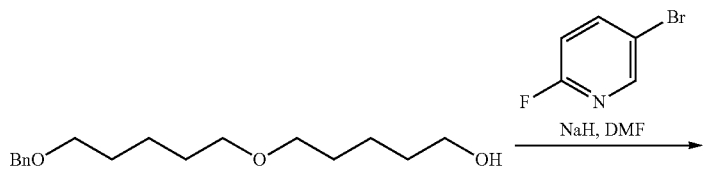

391 392
-continued
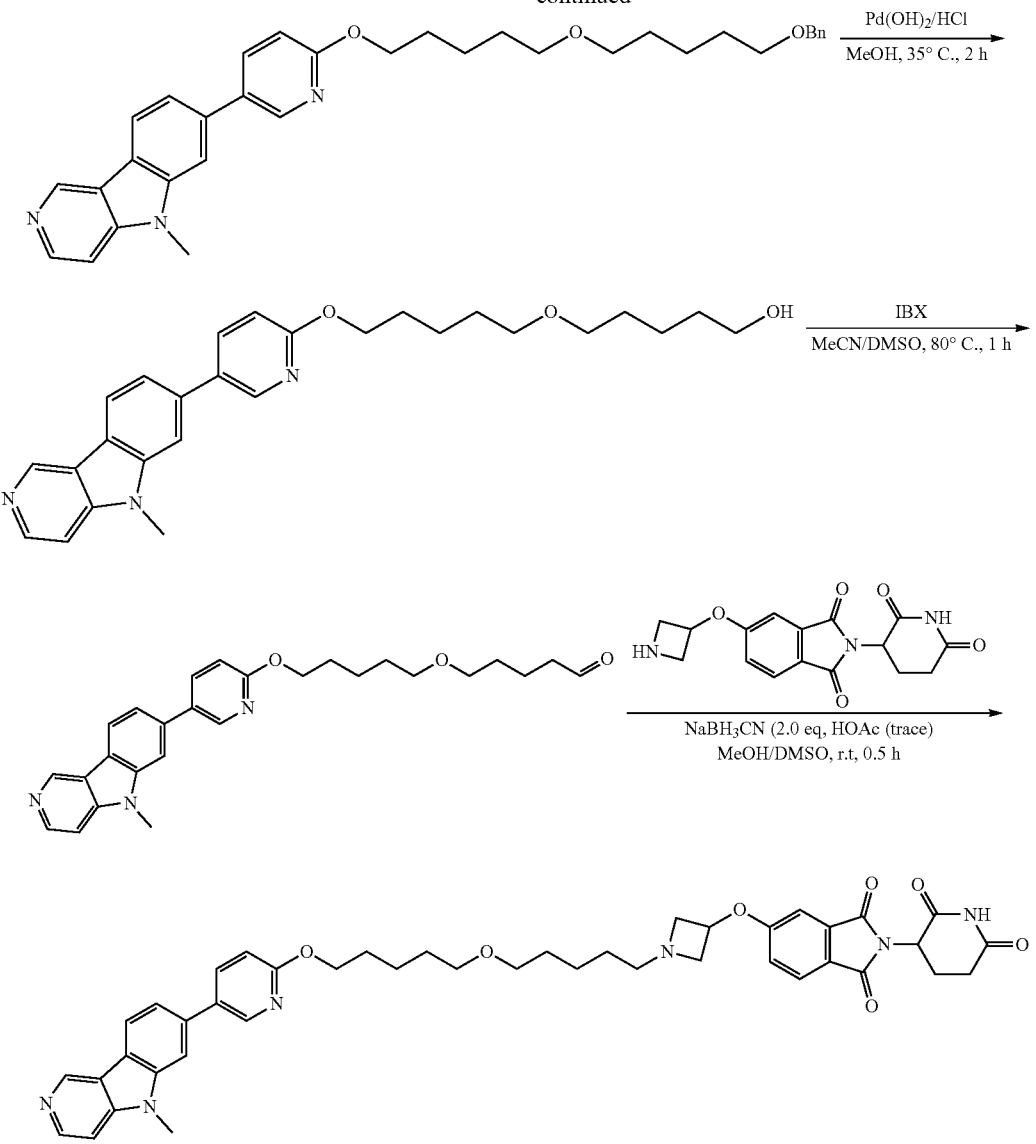
Compound 80
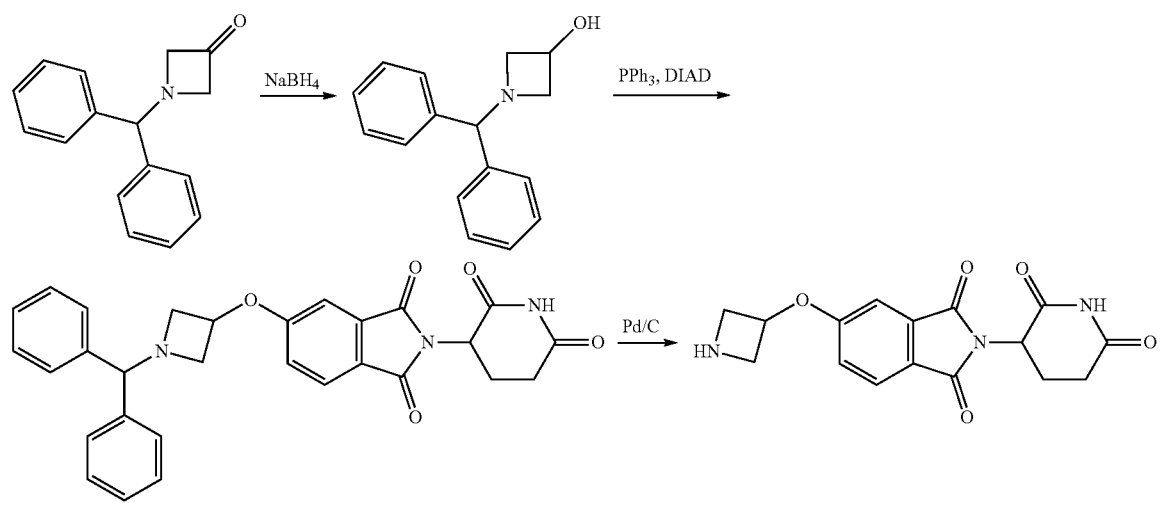

Compound 80: $^1$H NMR (400 MHz, DMSO-$d_6$): δ 11.12 (s, 1H), 9.35 (s, 1H), 8.63 (d, J=2.3 Hz, 1H), 8.50 (s, 1H), 8.31 (d, J=8.1 Hz, 1H), 8.18 (dd, J=8.6, 2.5 Hz, 1H), 7.96 (s, 1H), 7.80 (d, J=8.8 Hz, 1H), 7.60 (d, J=6.8 Hz, 2H), 7.23 (d, J=7.2 Hz, 2H), 6.93 (d, J=8.6 Hz, 1H), 5.10 (m, 1H), 5.02-4.95 (m, 1H), 4.32 (t, J=6.6 Hz, 2H), 3.95 (s, 3H), 3.70 (t, J=6.8 Hz, 2H), 2.99-2.95 (m, 2H), 2.86 (d, J=12.1 Hz, 2H), 2.64 (br, 1H), 2.55 (br, 2H), 2.33 (s, 2H), 2.06-1.96 (m, 3H), 1.81-1.70 (m, 3H), 1.60-1.40 (m, 8H). (M+H)$^+$ 759.6.

Synthetic Scheme for Exemplary Compound 84

2-(2,6-dioxopiperidin-3-yl)-5-((6-(3-((1r,3r)-3-((5-(5-methyl-5H-pyrido[4,3-b]indol-7-yl)pyridin-2-yl)oxy)cyclobutoxy)phenoxy)hexyl)oxy)isoindoline-1,3-dione

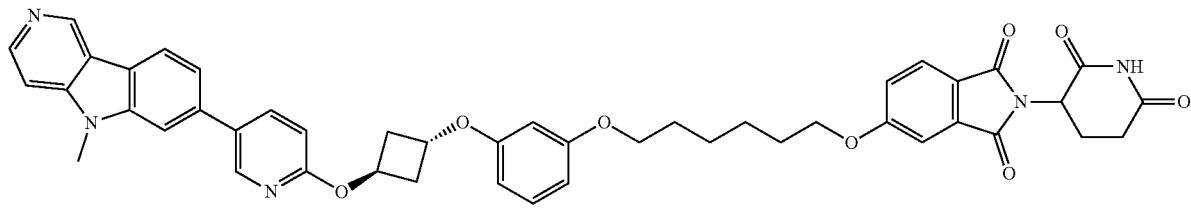 [SMILES: Cn1c2ccncc2c2ccc(-c3ccc(O[C@H]4C[C@H](Oc5cccc(OCCCCCCOc6ccc7c(c6)C(=O)N(C6CCC(=O)NC6=O)C7=O)c5)C4)nc3)cc21]

Step 1: 2-((6-(3-(benzyloxy)phenoxy)hexyl)oxy)tetrahydro-2H-pyran

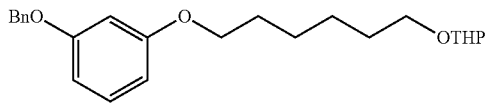

A solution of 3-(benzyloxy)phenol (1.13 g, 5.66 mmol), 2-((6-bromohexyl)oxy)tetrahydro-2H-pyran (1.0 g, 3.77 mmol) and Cs$_2$CO$_3$ (2.45 g, 7.55 mmol) in acetone (30 mL) was stirred at 70° C. overnight. The mixture was cooled to room temperature and quenched with water. The mixture was extracted with EA (200 mL), and the solution was washed with water (30 mL×3) and brine (30 mL). The organic phase was dried over anhydrous sodium sulfate and concentrated under vacuum. The residue was purified to afford the desired product (PE:EA=20:1) (1.2 g, yield=83%) as colorless oil.

Step 2: 3-((6-((tetrahydro-2H-pyran-2-yl)oxy)hexyl)oxy)phenol

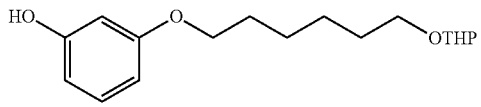

To a solution of 2-((6-(3-(benzyloxy)phenoxy)hexyl)oxy)tetrahydro-2H-pyran (1.2 g, 3.13 mmol) in MeOH (30 mL) was added Pd/C (200 mg) at room temperature. The resulting solution was stirred at room temperature overnight under H$_2$ 1 atm. The mixture was filtered, the filtrate was concentrated under vacuum to afford crude desired product (900 mg) as light yellow oil, which was used in the next step directly.

Step 3: 2-((6-(3-((1r,3r)-3-(benzyloxy)cyclobutoxy)phenoxy)hexyl)oxy)tetrahydro-2H-pyran

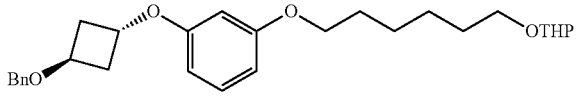

To a solution of 3-((6-((tetrahydro-2H-pyran-2-yl)oxy)hexyl)oxy)phenol (100 mg, 0.34 mmol), (1s,3s)-3-(benzyloxy)cyclobutanol (91 mg, 0.51 mmol), PPh$_3$ (267 mg, 1.02 mmol) in THF (5.0 mL) were added DIAD (206 mg, 1.02 mmol) at 40° C. under a nitrogen atmosphere. The resulting mixture was heated to 80° C. overnight. After cooling to room temperature, the reaction was quenched with water. The mixture was extracted with EA (50 mL), and the organic phase was washed with water (20 mL×3), brine (20 mL), dried over anhydrous sodium sulfate and concentrated under vacuum. The residue was purified to afford the desired product (PE:EA=5:1) (130 mg, yield=84%) as colorless oil.

2-((6-(3-((1r,3r)-3-(benzyloxy)cyclobutoxy)phenoxy)hexyl)oxy)tetrahydro-2H-pyran was converted into the final compound, 2-(2,6-dioxopiperidin-3-yl)-5-((6-(3-((1r,3r)-3-((5-(5-methyl-5H-pyrido[4,3-b]indol-7-yl)pyridin-2-yl)oxy)cyclobutoxy)phenoxy)hexyl)oxy)isoindoline-1,3-dione, according to the synthetic scheme below using procedures described above and common procedures known to those skilled in the art.

395 396
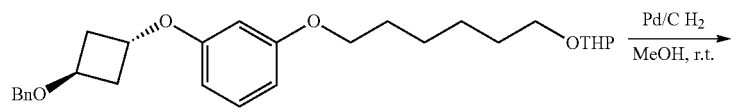
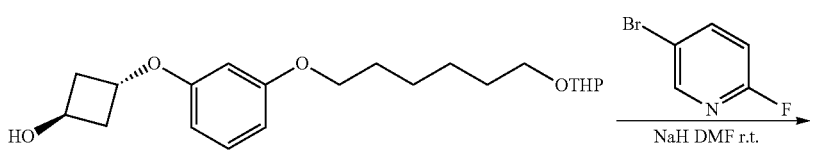
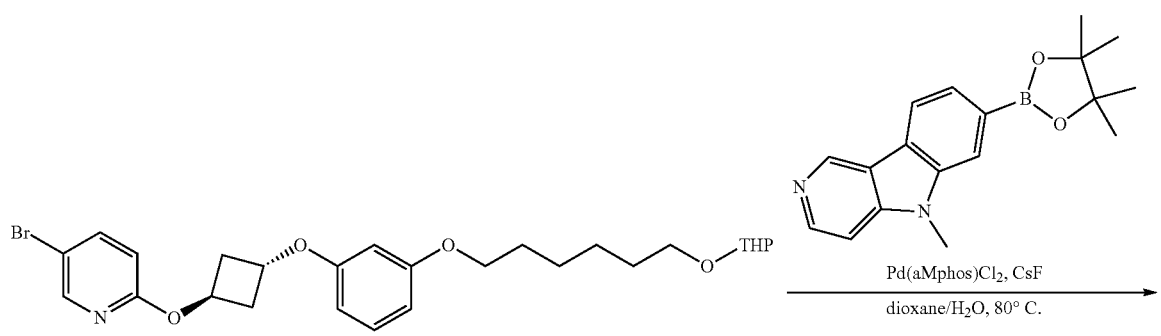
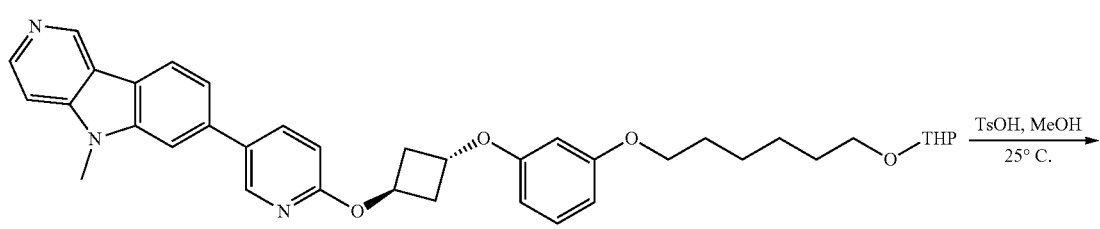
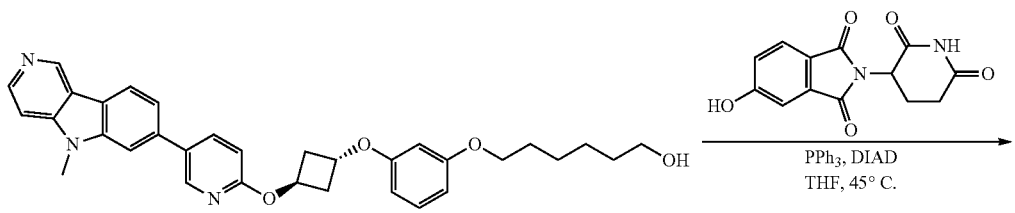
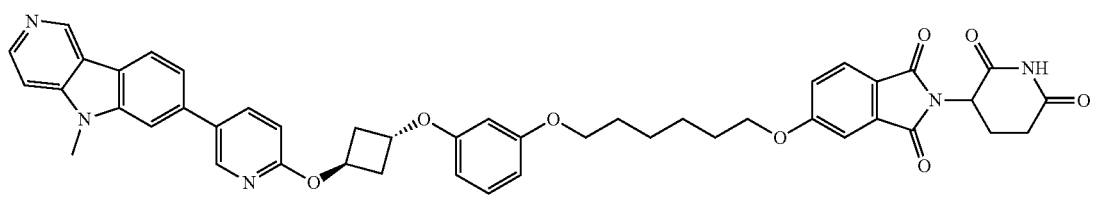
Compound 84

Compound 84: 1H NMR (400 MHz, CDCl₃): δ 93.4 (s, 1H), 8.58 (d, J=5.6 Hz, 1H), 8.21-8.48 (m, 2H), 8.20 (d, J=8.4 Hz, 1H), 7.88-7.91 (m, 1H), 7.76 (d, J=8.4 Hz, 1H), 7.56 (s, 1H), 7.51 (d, J=8.0 Hz, 1H), 7.33-7.36 (m, 2H), 7.16-7.18 (m, 2H), 6.86 (d, J=8.4 Hz, 1H), 6.39-6.51 (m, 3H), 5.52-5.54 (m, 1H), 4.94-4.96 (m, 2H), 4.07-4.10 (m, 2H), 3.91-3.97 (m, 5H), 3.22-3.24 (m, 1H), 2.69-2.76 (m, 7H), 2.14-2.16 (m, 1H), 1.82-1.86 (m, 4H), 1.54-1.57 (m, 4H). (M+H)⁺ 794.5.

Synthetic Scheme for Exemplary Compound 86

4-((14-(4-(5H-pyrido[4,3-b]indol-7-yl)phenoxy)-3,6,9,12-tetraoxatetradecyl)amino)-2-(2,6-dioxopiperidin-3-yl)isoindoline-1,3-dione

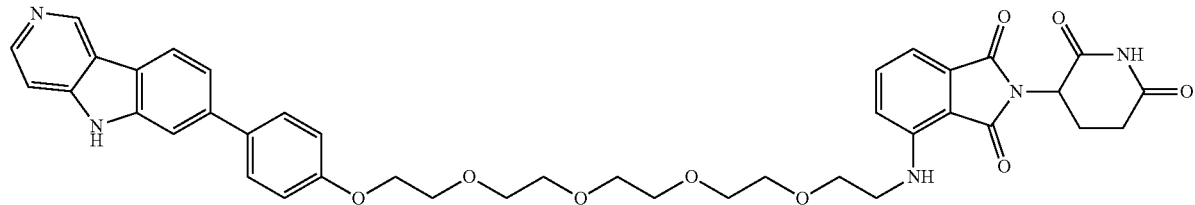 [SMILES: O=C1CCC(N2C(=O)c3cccc(NCCOCCOCCOCCOCCOc4ccc(-c5ccc6c(c5)[nH]c5ccncc56)cc4)c3C2=O)C(=O)N1]

Prepared according to the synthetic scheme below using procedures described above and common procedures known to those skilled in the art.

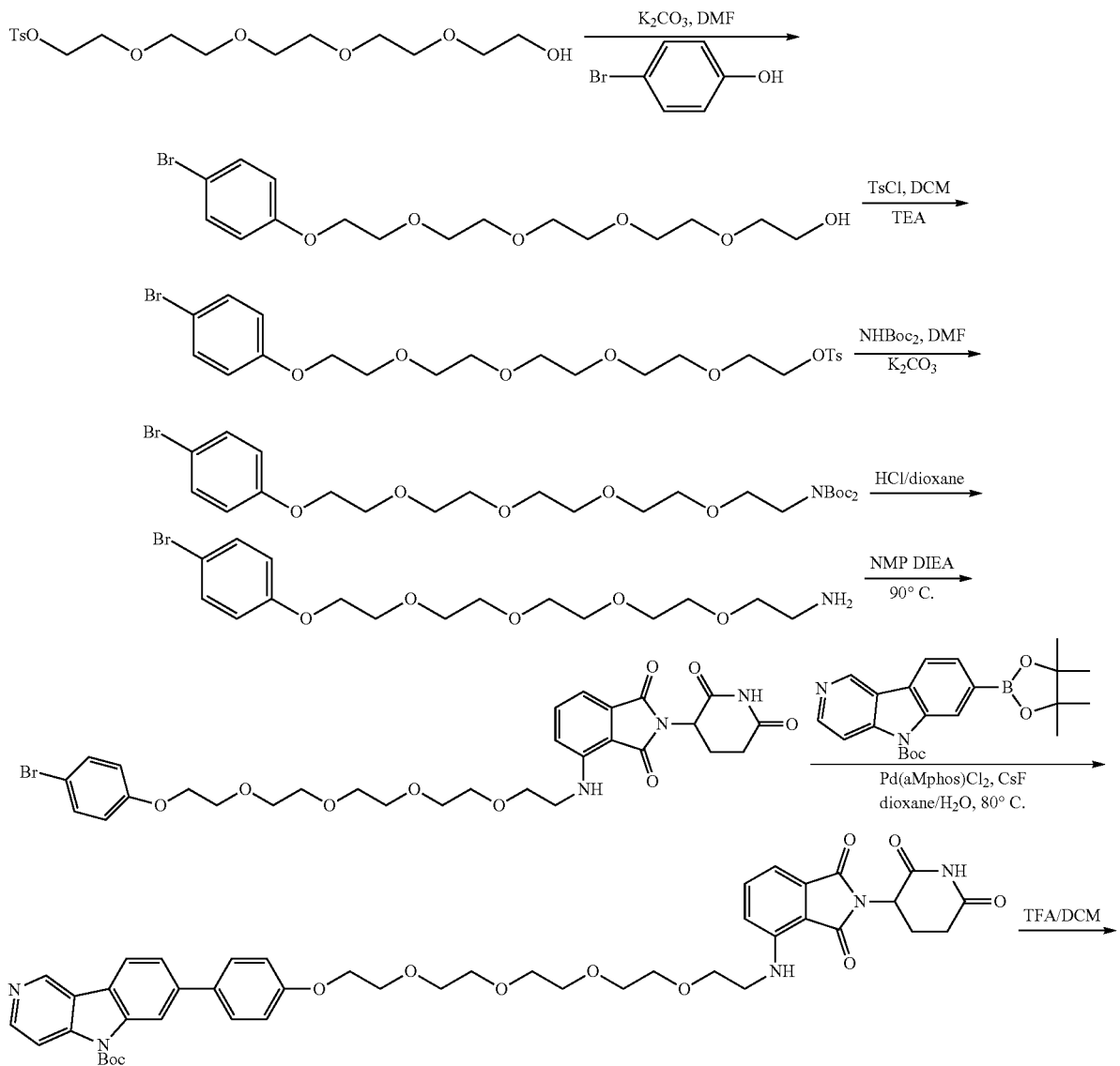

-continued

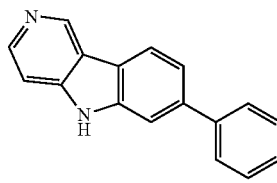 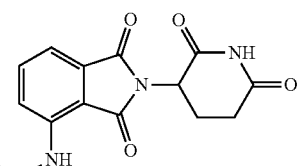

Compound 86

Compound 86: ¹H NMR (400 MHz, CDCl₃): δ 9.28 (s, 2H), 8.50 (s, 1H), 8.08 (s, 1H), 7.35-7.57 (m, 6H), 6.94-6.96 (m, 3H), 6.77 (s, 1H), 6.38 (s, 1H), 4.88-4.90 (m, 1H), 4.14 (s, 2H), 3.60-3.86 (m, 17H), 3.31-3.34 (m, 2H), 2.66-2.86 (m, 3H), 2.03-2.05 (m, 1H). (M+H)⁺ 736.5.

Synthetic Schedule for Exemplary Compound 87

6-((14-((5-(5H-pyrido[4,3-b]indol-7-yl)pyridin-2-yl)oxy)-3,6,9,12-tetraoxatetradecyl)oxy)-2-(2,6-dioxopiperidin-3-yl)-1H-pyrrolo[3,4-c]pyridine-1,3(2H)-dione

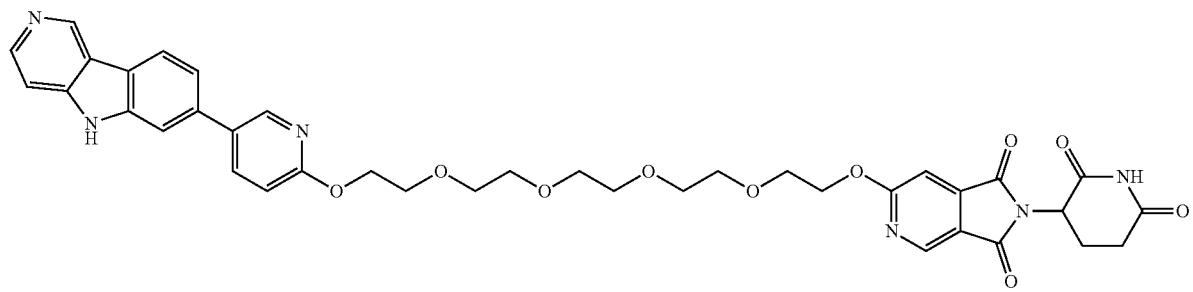 [SMILES: O=C1CCC(N2C(=O)c3cnc(OCCOCCOCCOCCOCCOc4ccc(-c5ccc6c(c5)[nH]c5ccncc56)cn4)cc3C2=O)C(=O)N1]

Step 1: 6-((14-((5-(5H-pyrido[4,3-b]indol-7-yl)pyridin-2-yl)oxy)-3,6,9,12-tetraoxatetradecyl)oxy)pyridine-3,4-dicarboxylic Acid

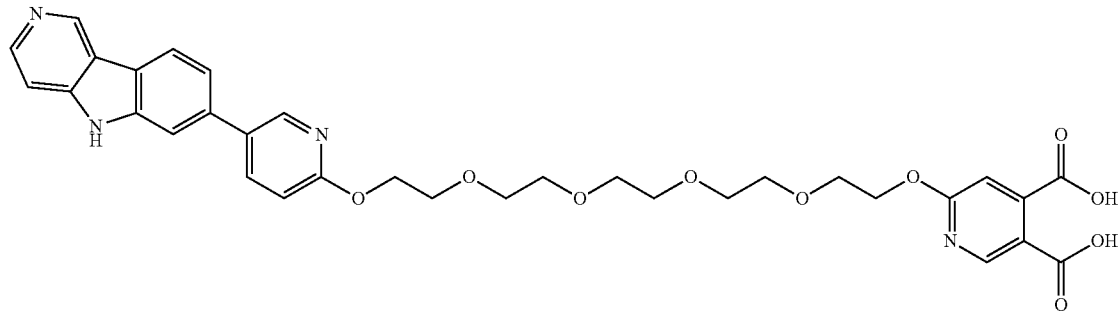 [SMILES: O=C(O)c1cnc(OCCOCCOCCOCCOCCOc2ccc(-c3ccc4c(c3)[nH]c3ccncc34)cn2)cc1C(=O)O]

To a solution of 14-((5-(5H-pyrido[4,3-b]indol-7-yl)pyridin-2-yl)oxy)-3,6,9,12-tetraoxatetradecan-1-ol (200.0 mg, 0.42 mmol) and 6-chloropyridine-3,4-dicarboxylic acid (166 mg, 0.83 mmol) in anhydrous tetrahydrofuran (4 mL) was added sodium hydride (162.0 mg, 4.2 mmol). The resulting solution was stirred at 100° C. with MW for 2 hour under N₂ atmosphere. The solution was cooled to room temperature and quenched with water (20 mL). The mixture was extracted with ethyl acetate (20 mL×3). The combined organic layers were washed with brine (20 mL×2). The organic layer was dried over anhydrous sodium sulfate, filtered and concentrated under vacuum. The residue was purified by silica gel column chromatography to afford the desired compound (50 mg, 0.077 mmol, 9% yield).

Step 2: 6-((14-((5-(5H-pyrido[4,3-b]indol-7-yl)pyridin-2-yl)oxy)-3,6,9,12-tetraoxatetradecyl)oxy)-2-(2,6-dioxopiperidin-3-yl)-1H-pyrrolo[3,4-c]pyridine-1,3(2H)-dione

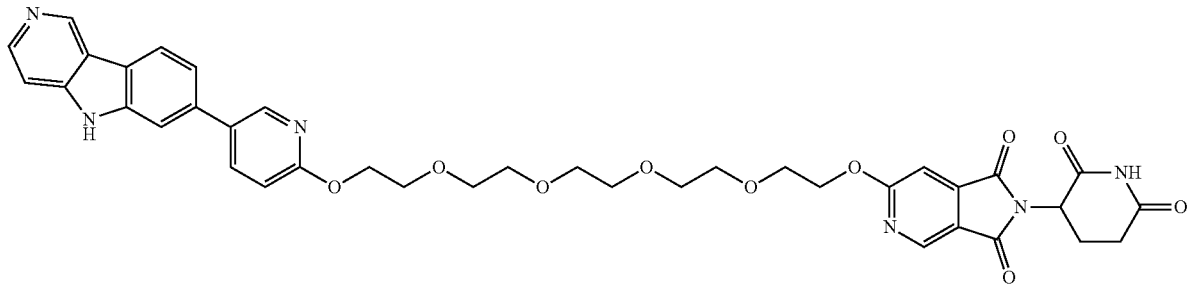 [SMILES: O=C1CCC(N2C(=O)c3cnc(OCCOCCOCCOCCOCCOc4ccc(-c5ccc6c(c5)[nH]c5ccncc56)cn4)cc3C2=O)C(=O)N1]

To a solution of 6-((14-((5-(5H-pyrido[4,3-b]indol-7-yl)pyridin-2-yl)oxy)-3,6,9,12-tetraoxatetradecyl)oxy)pyridine-3,4-dicarboxylic acid (50 mg, 0.077 mmol) and 3-aminopiperidine-2,6-dione (12 mg, 0.092 mmol) in AcOH (6 mL) was added NaOAc (6 mg, 0.092 mmol). The resulting solution was stirred at 120° C. for 16 hours. After cooling to room temperature, the reaction was quenched by the addition of water (20 mL). The mixture was extracted with EA (20 mL×3). The combined organic layers were washed with brine (20 mL×2), dried over anhydrous sodium sulfate and concentrated under vacuum. The residue was purified by prep-TLC with DCM/CH₃OH (10:1) to afford the title compound (4.0 mg, 0.005 mmol, 7% yield).

Compound 87: 1H NMR (400 MHz, CDCl₃): δ 9.28 (s, 1H), 8.42 (s, 1H), 8.37-8.39 (m, 2H), 8.06 (d, J=8.0 Hz, 1H), 7.80 (d, J=8.0 Hz, 1H), 7.62 (s, 1H), 7.40-7.45 (m, 3H), 6.09 (s, 1H), 6.82 (d, J=8.8 Hz, 1H), 4.94-4.99 (m, 1H), 4.54 (t, J=4.8 Hz, 4H), 3.86-3.91 (m, 4H), 3.66-3.75 (m, 12H), 2.73-2.92 (m, 3H), 2.20-2.22 (m, 1H). (M+H)⁺ 739.5.

Synthetic Scheme for Exemplary Compound 88

2-(2,6-dioxopiperidin-3-yl)-5-((14-((5-(5-(2,2,2-trifluoroethyl)-5H-pyrido[4,3-b]indol-7-yl)pyridin-2-yl)oxy)-3,6,9,12-tetraoxatetradecyl)oxy)isoindoline-1,3-dione

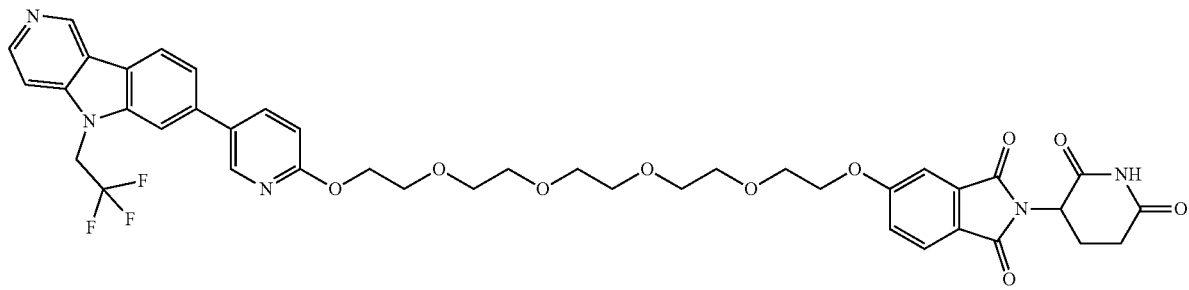 [SMILES: O=C1CCC(N2C(=O)c3ccc(OCCOCCOCCOCCOCCOc4ccc(-c5ccc6c7cnccc7n(CC(F)(F)F)c6c5)cn4)cc3C2=O)C(=O)N1]

Prepared according to the synthetic scheme below using procedures described above and common procedures known to those skilled in the art.

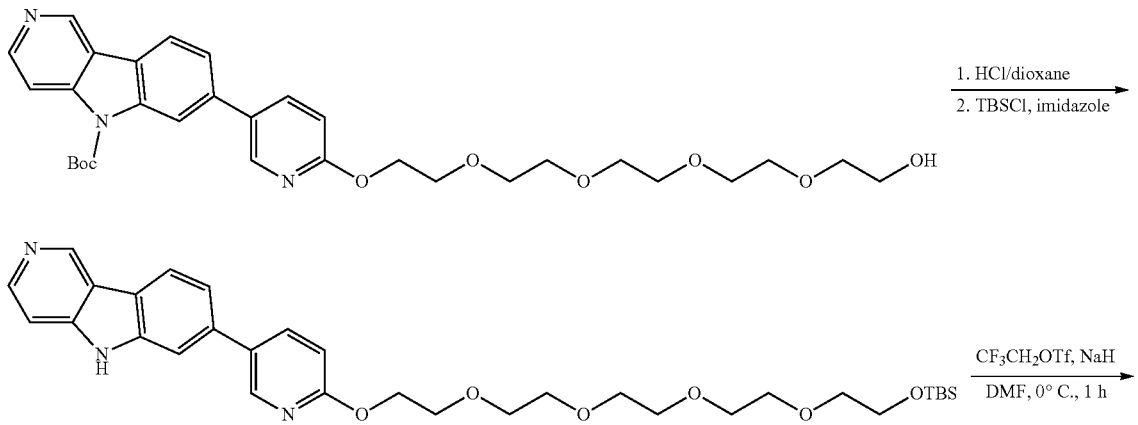

-continued
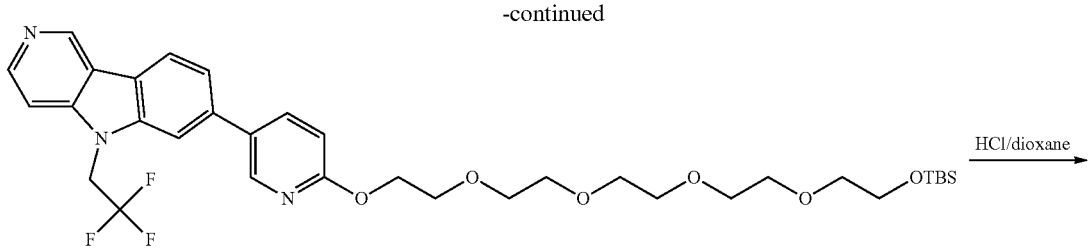
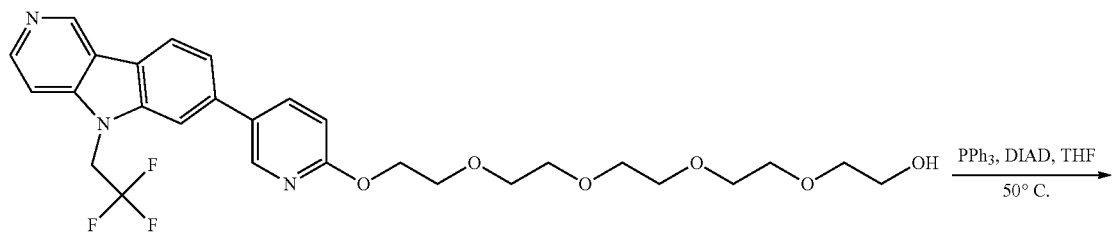
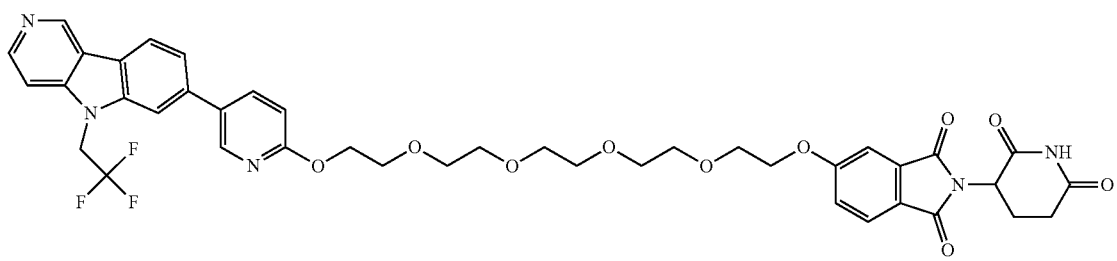
Compound 98
Compound 88: ¹H NMR (400 MHz, CDCl₃): δ 9.35 (s, 1H), 8.63 (d, J=7.6 Hz, 1H), 8.45 (s, 1H), 8.21 (d, J=8.0 Hz, 1H), 8.16 (s, 1H), 7.87-7.90 (m, 1H), 7.75 (d, J=8.4 Hz, 1H), 7.53-7.58 (m, 2H), 7.39 (s, 1H), 7.35 (s, 1H), 7.21 (d, J=8.4 Hz, 1H), 6.91 (d, J=8.8 Hz, 1H), 4.87-4.92 (m, 3H), 4.55 (t, J=4.8 Hz, 2H), 4.24 (t, J=4.8 Hz, 2H), 3.90 (t, J=4.4 Hz, 3H), 3.66-3.73 (m, 12H), 2.76-2.87 (m, 3H), 2.09-2.16 (m, 1H). (M+H)⁺ 820.5
Synthetic Scheme for Exemplary Compound 89
2-(2,6-dioxopiperidin-3-yl)-5-(4-(3,3,3-trifluoro-2-(2-((5-((5-(5-methyl-5H-pyrido[4,3-b]indol-7-yl)pyridin-2-yl)oxy)pentyl)oxy)ethoxy)propyl)piperidin-1-yl)isoindoline-1,3-dione
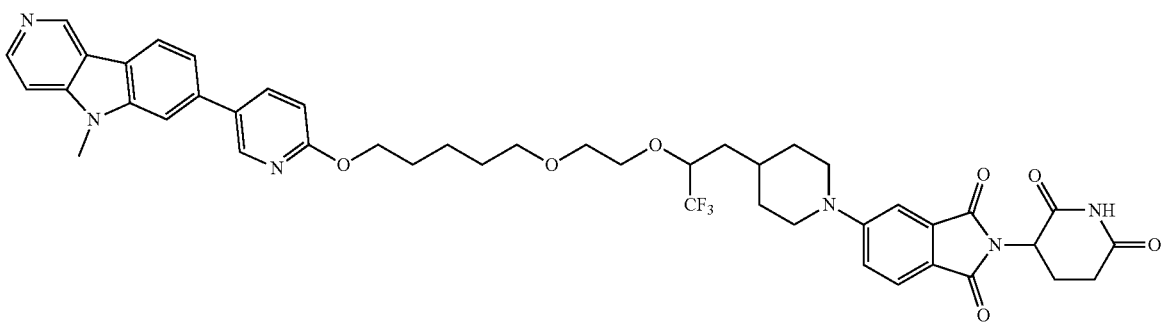 [SMILES: Cn1c2ccncc2c2ccc(-c3ccc(OCCCCCOCCOC(CC4CCN(c5ccc6c(c5)C(=O)N(C5CCC(=O)NC5=O)C6=O)CC4)C(F)(F)F)nc3)cc21]

Step 1: 2-(5-benzyloxypentoxy)acetate

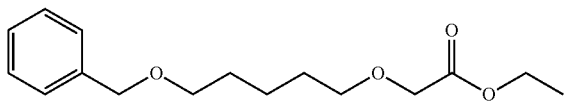 [SMILES: CCOC(=O)COCCCCCOCc1ccccc1]

To a solution of 5-benzyloxypentan-1-ol (1 g, 5.15 mmol, 1.0 eq) in dichloromethane (20 mL) was added ethyl 2-diazoacetate (704 mg, 6.18 mmol, 1.2 eq) and dirhodium tetraacetate (11 mg, 0.03 mmol). Then the mixture was stirred at 20° C. for 0.5 hour. The mixture was quenched with ethyl alcohol (10 mL) and then concentrated. The residue was purified by silica column chromatography (petroleum ether; ethyl acetate=50:1 to 4:1) to afford ethyl 2-(5-benzyloxypentoxy)acetate (700 mg, 2.50 mmol, 49% yield) as a yellow oil.

Step 2: 2-(5-benzyloxypentoxy)ethanol

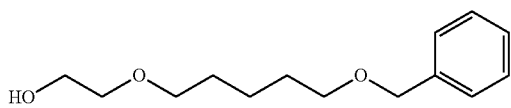 [SMILES: OCCOCCCCCOCc1ccccc1]

To a mixture of LiAlH$_4$ (189 mg, 4.99 mmol, 2.0 eq) in tetrahydrofuran (4 mL) was added a solution of ethyl 2-(5-benzyloxypentoxy)acetate (700 mg, 2.50 mmol, 1.0 eq) in tetrahydrofuran (10 mL) at 0° C. Then the mixture was stirred at 20° C. for 2 hours. The mixture was quenched with water (0.2 mL), aqueous sodium hydroxide (1 M, 0.2 mL), and more water (0.8 mL). Then filtered and concentrated. The residue was purified by silica column chromatography (petroleum ether:ethyl acetate=30:1 to 10:1) to afford 2-(5-benzyloxypentoxy)ethanol (400 mg, 1.68 mmol, 67% yield) was obtained as a white oil.

Step 3: 2-(5-benzyloxypentoxy)ethyl4-methylbenzenesulfonate

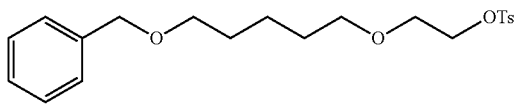 [SMILES: Cc1ccc(S(=O)(=O)OCCOCCCCCOCc2ccccc2)cc1]

To a mixture of 2-(5-benzyloxypentoxy)ethanol (400 mg, 1.68 mmol, 1.0 eq) and toluene sulfonyl chloride (640 mg, 3.36 mmol, 2.0 eq) in tetrahydrofuran (3 mL) was added potassium hydroxide (2.83 g, 50.35 mmol, 30.0 eq). Then the mixture was stirred at 20° C. for 0.5 hour. The mixture was diluted with water (10 mL), extracted with ethyl acetate (20 mL), washed with brine (20 mL), dried over anhydrous sodium sulfate and then concentrated. The mixture was purified by silica column chromatography (petroleum ether: ethyl acetate=30:1 to 10:1) to afford 2-(5-benzyloxypentoxy)ethyl4-methylbenzenesulfonate (570 mg, 1.45 mmol, 86% yield) as a white oil.

Step 4: tert-butyl 4-(3,3,3-trifluoro-2-hydroxy-propyl)piperidine-1-carboxylate

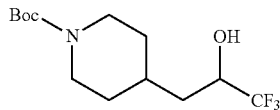

To a mixture of tert-butyl 4-(2-oxoethyl)piperidine-1-carboxylate (1.9 g, 8.36 mmol, 1.0 eq) and trimethyl(trifluoromethyl)silane (1.43 g, 10.03 mmol, 1.2 eq) in tetrahydrofuran (20 mL) was added tetrabutylammonium fluoride (1 M, 0.1 mL) at 0° C. Then the mixture was stirred at 20° C. for 1 hour. Then aqueous hydrochloric acid (1 M, 17 mL, 2.0 eq) was added into the mixture and stirred at 20° C. for additional 2 hours. The mixture was extracted with dichloromethane (100 mL), washed with brine (50 mL), dried over anhydrous sodium sulfate and then concentrated. The residue was purified by silica column chromatography (petroleum ether:ethyl acetate=100:1 to 10:1) to afford tert-butyl 4-(3,3,3-trifluoro-2-hydroxy-propyl) piperidine-1-carboxylate (2.0 g, 6.73 mmol, 80% yield) as a white solid.

Step 5: tert-butyl4-[2-[2-(5-benzyloxypentoxy)ethoxy]-3,3,3-trifluoro-propyl]piperidine-1-carboxylate

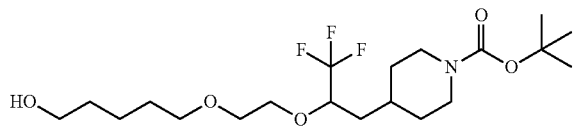 [SMILES: CC(C)(C)OC(=O)N1CCC(CC(OCCOCCCCCO)C(F)(F)F)CC1]

To a solution of tert-butyl 4-(3,3,3-trifluoro-2-hydroxy-propyl)piperidine-1-carboxylate (216 mg, 0.73 mmol, 1.0 eq) in dimethyl formamide (2 mL) was added sodium hydride (58 mg, 1.46 mmol, 60% in mineral oil, 2.0 eq) at 15° C. Then the mixture was stirred at 15° C. for 0.5 hour under nitrogen. 2-(5-benzyloxypentoxy)ethyl 4-methylbenzenesulfonate (200 mg, 0.51 mmol, 0.7 eq) was added into the mixture and stirred at 50° C. for additional 2.5 hours. The mixture was quenched with water (5 mL), extracted with ethyl acetate (20 mL×2), washed with brine (20 mL), dried over anhydrous sodium sulfate and then concentrated. The mixture was purified by silica column chromatography (petroleum ether:ethyl acetate=200:1 to 10:1) to afford tert-butyl4-[2-[2-(5-benzyloxypentoxy)ethoxy]-3,3,3-trifluoro-propyl]piperidine-1-carboxylate (300 mg, 0.58 mmol, 80% yield) as a white oil.

Tert-butyl4-[2-[2-(5-benzyloxypentoxy)ethoxy]-3,3,3-trifluoro-propyl]piperidine-1-carboxylate was converted to the title compound, 2-(2,6-dioxopiperidin-3-yl)-5-(4-(3,3,3-trifluoro-2-(2-((5-((5-(5-methyl-5H-pyrido[4,3-b]indol-7-yl)pyridin-2-yl)oxy)pentyl)oxy)ethoxy)propyl)piperidin-1-yl)isoindoline-1,3-dione, according to the synthetic scheme below using procedures described above and common procedures known to those skilled in the art.

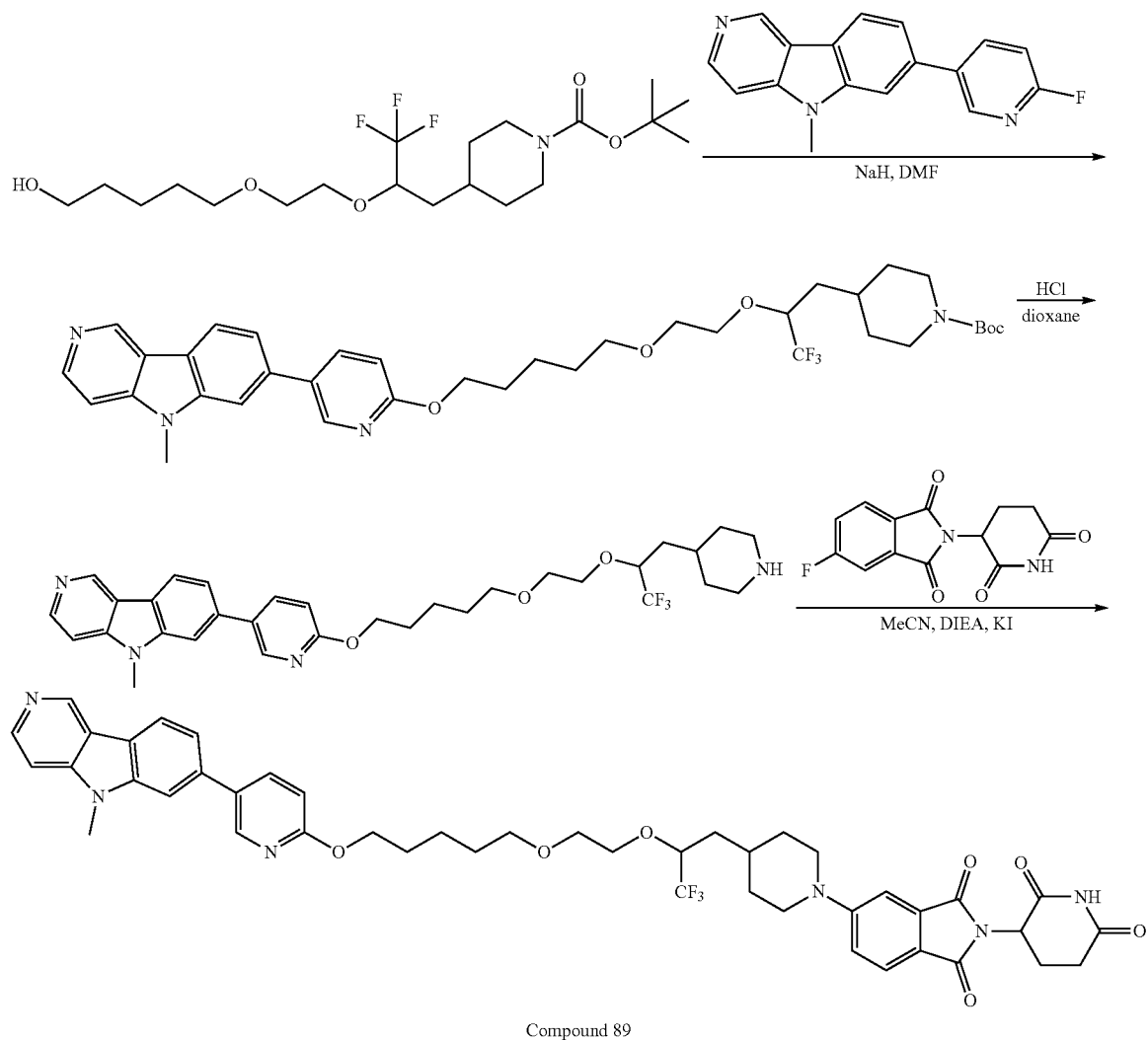
Compound 89: $^1$H NMR (400 MHz, DMSO-d$_6$) δ: 11.09 (s, 1H), 9.36 (s, 1H), 8.61 (d, J=2.4 Hz, 1H), 8.50 (d, J=5.6 Hz, 1H), 8.31 (d, J=8.0 Hz, 1H), 8.21 (s, 1H), 8.15 (dd, J=2.8, 8.8 Hz, 1H), 7.95 (s, 1H), 7.65-7.57 (m, 3H), 7.29 (s, 1H), 7.23-7.18 (m, 1H), 6.90 (d, J=8.8 Hz, 1H), 5.04 (dd, J=5.6, 12.8 Hz, 1H), 4.31 (t, J=6.4 Hz, 2H), 4.14 (br s, 1H), 4.10-3.99 (m, 3H), 3.96 (s, 3H), 3.87 (d, J=11.6 Hz, 2H), 3.74 (dd, J=5.6, 10.8 Hz, 2H), 3.02-2.81 (m, 4H), 1.98-1.86 (m, 2H), 1.85-1.72 (m, 4H), 1.63-1.15 (m, 9H). (M+H)$^+$ 841.6.
Synthetic Scheme for Exemplary Compound 90
2-(2,6-dioxopiperidin-3-yl)-5-(4-(4-((4-((5-(5-methyl-5H-pyrido[4,3-b]indol-7-yl)pyridin-2-yl)oxy)but-2-yn-1-yl)oxy)butoxy)butoxy)isoindoline-1,3-dione
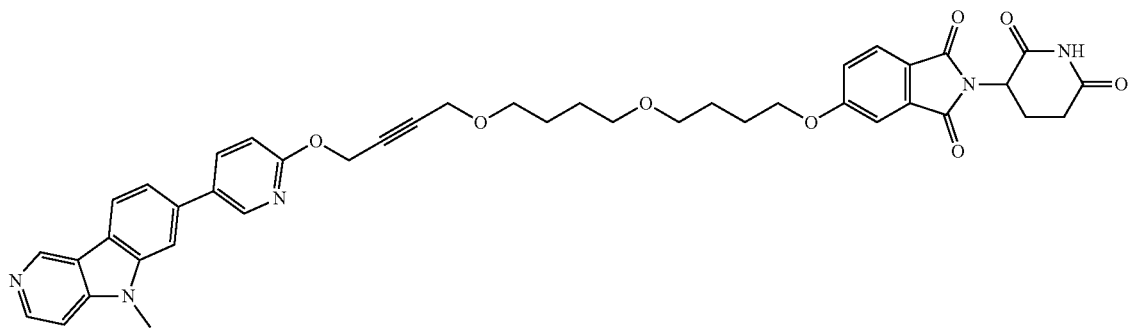 [SMILES: Cn1c2ccncc2c2ccc(-c3ccc(OCC#CCOCCCCOCCCCOc4ccc5c(c4)C(=O)N(C4CCC(=O)NC4=O)C5=O)nc3)cc21]

Prepared according to the synthetic scheme below using procedures described above and common procedures known to those skilled in the art.
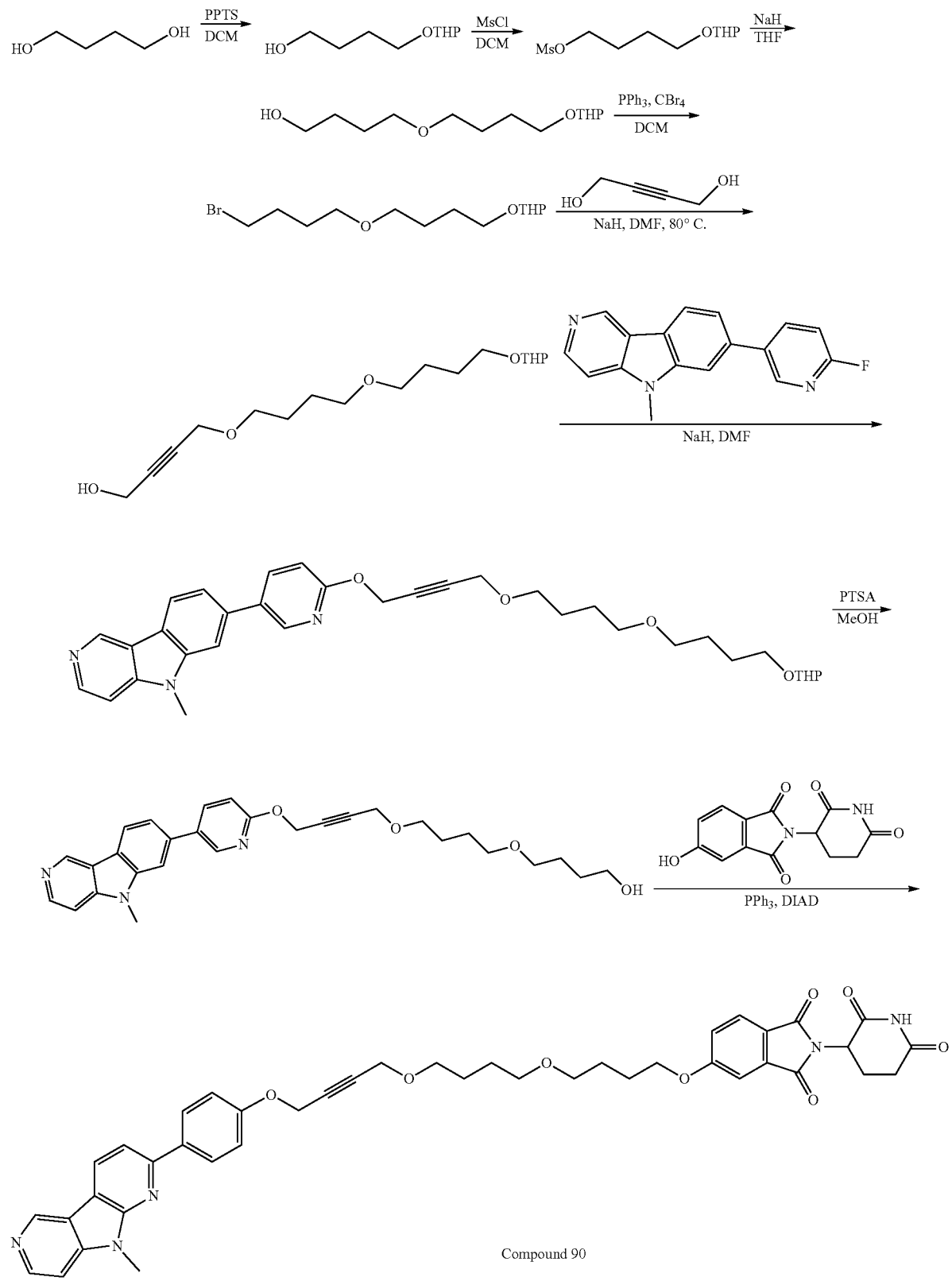
Compound 90

Compound 90: ¹HNMR (400 MHz, CDCl₃): δ 9.35 (s, 1H), 8.60 (s, 1H), 8.50 (s, 1H), 8.20 (d, J=8.0 Hz, 2H), 7.75 (d, J=8.0 Hz, 1H), 7.55 (s, 1H), 7.49 (d, J=8.0 Hz, 1H), 7.32 (d, J=10.0 Hz, 2H), 7.16 (d, J=8.0 Hz, 1H), 6.92 (d, J=8.4 Hz, 1H), 5.10 (s, 2H), 4.98-5.00 (m, 1H), 4.21 (s, 2H), 4.07-4.10 (m, 2H), 3.90 (s, 3H), 3.44-3.54 (m, 7H), 2.76-2.87 (m, 3H), 2.18-2.23 (m, 2H), 1.88-1.92 (m, 3H), 1.72-1.75 (m, 4H). M+H)⁺ 744.5.

Synthetic Scheme for Exemplary Compound 91

2-(2,6-dioxopiperidin-3-yl)-5-(4-(8-((1r,3r)-3-((5-(5-methyl-5H-pyrido[4,3-b]indol-7-yl)pyridin-2-yl)oxy)cyclobutoxy)octyl)piperazin-1-yl)isoindoline-1,3-dione

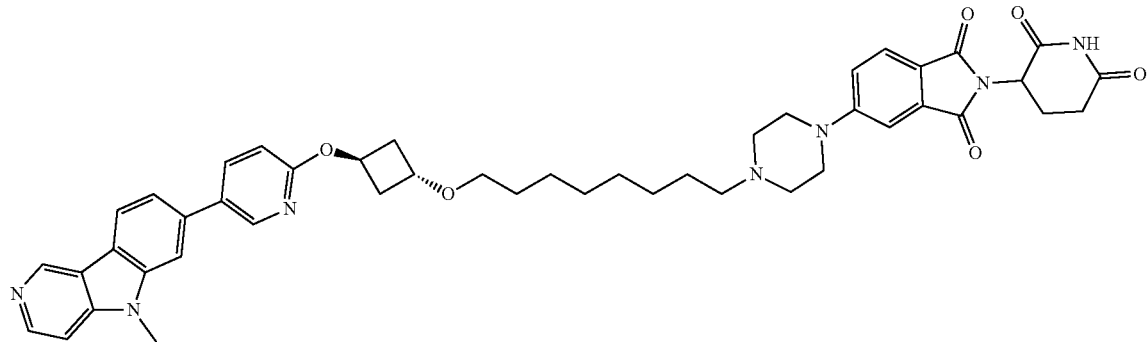 [SMILES: Cn1c2ccncc2c2ccc(-c3ccc(O[C@H]4C[C@H](OCCCCCCCCN5CCN(c6ccc7c(c6)C(=O)N(C6CCC(=O)NC6=O)C7=O)CC5)C4)nc3)cc21]

Prepared according to the synthetic scheme below using procedures described above and common procedures known to those skilled in the art.

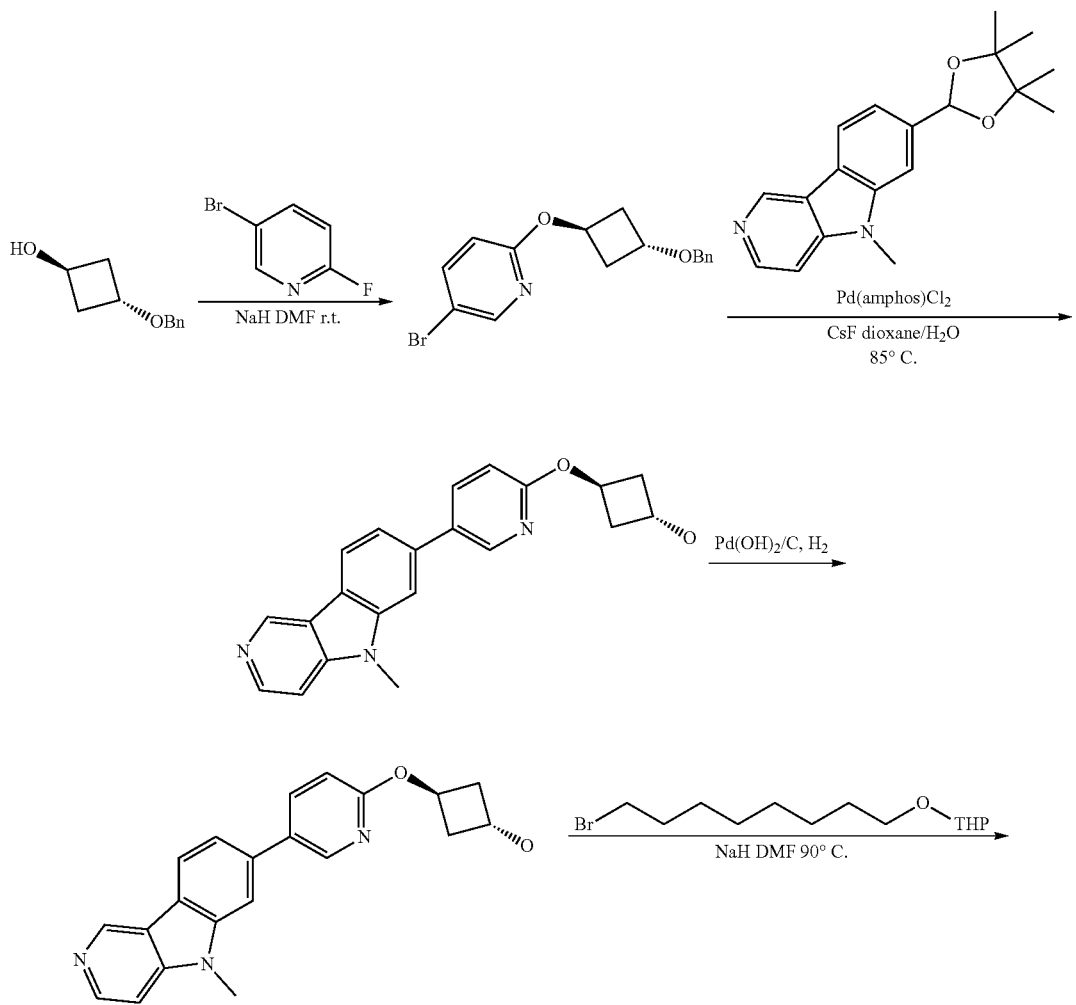

413    414
-continued
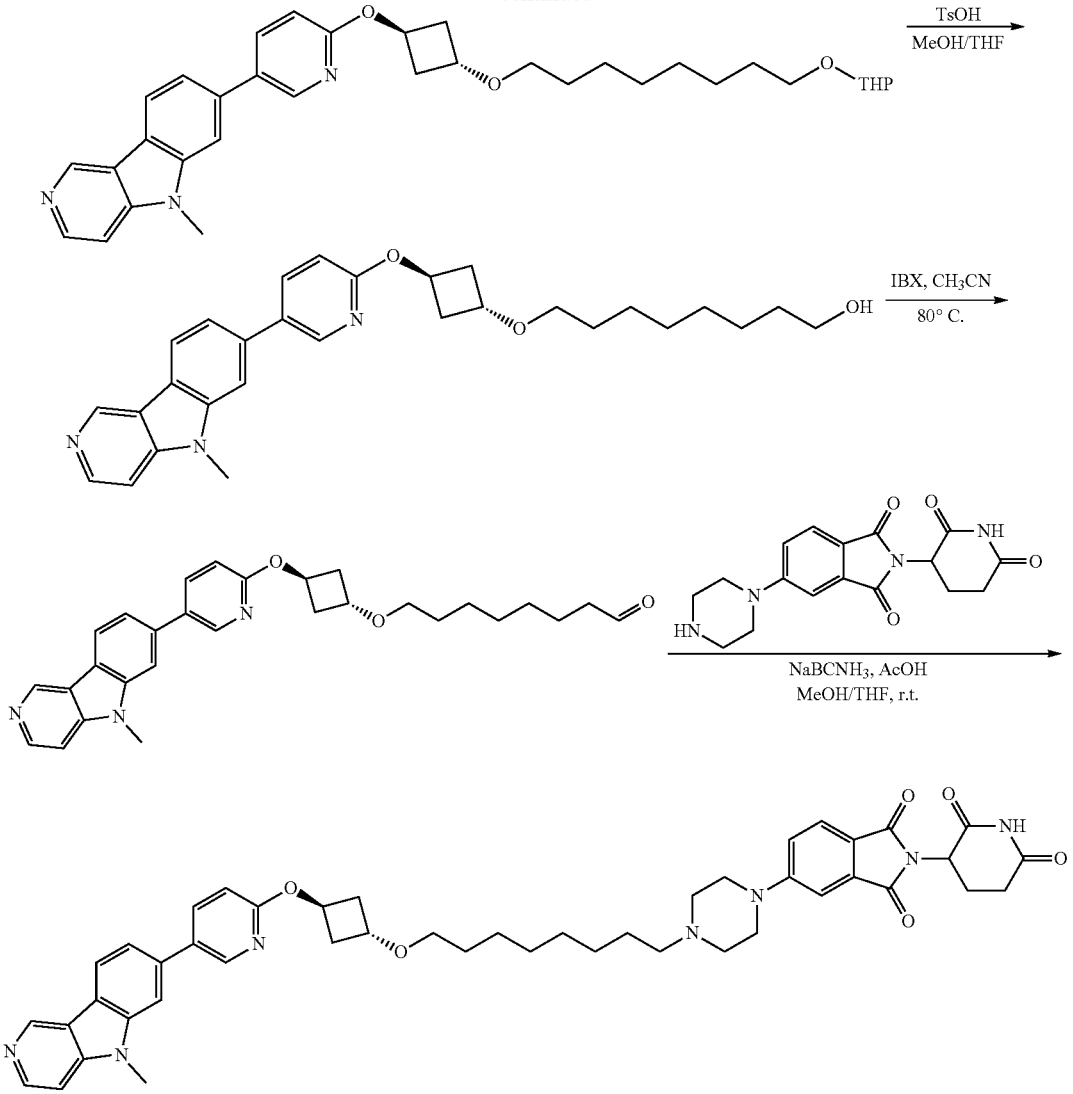
Compound 91
Compound 91: 1H NMR (400 MHz, CD$_3$OD): δ 9.33 (s, 1H), 8.51-8.53 (m, 2H), 8.33-8.34 (m, 1H), 8.09-8.11 (m, 1H), 7.84 (s, 1H), 7.59-7.62 (m, 3H), 7.30 (s, 1H), 7.17 (d, J=8.4 Hz, 1H), 6.90 (d, J=8.4 Hz, 1H), 5.32-5.35 (m, 1H), 3.99 (s, 3H), 3.40-3.47 (m, 13H), 2.69-2.71 (m, 6H), 2.502.52 (m, 4H), 2.03-2.18 (m, 5H), 1.59-1.60 (m, 6H). (M+H)$^+$ 798.6.
Synthetic Scheme for Exemplary Compound 92
5-((14-((3-chloro-5-(5-methyl-5H-pyrido[4,3-b]indol-7-yl)pyridin-2-yl)oxy)-3,6,9,12-tetraoxatetradecyl)oxy)-2-(2,6-dioxopiperidin-3-yl)isoindoline-1,3-dione
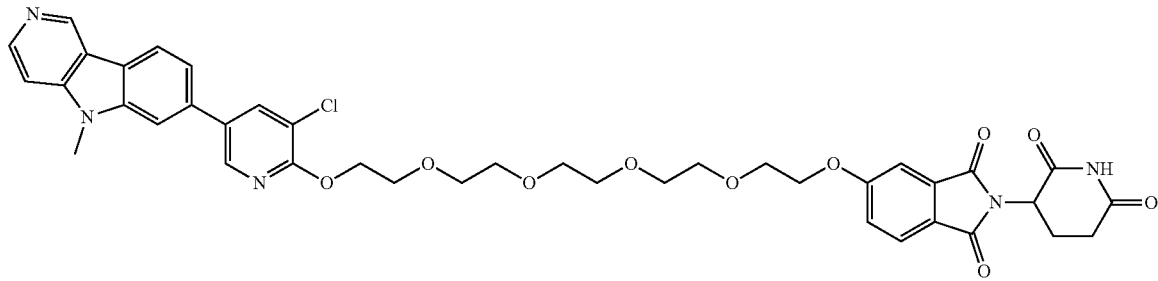 [SMILES: Cn1c2ccncc2c2ccc(-c3cnc(OCCOCCOCCOCCOCCOc4ccc5c(c4)C(=O)N(C4CCC(=O)NC4=O)C5=O)c(Cl)c3)cc21]

Prepared according to the synthetic scheme below using procedures described above and common procedures known to those skilled in the art.

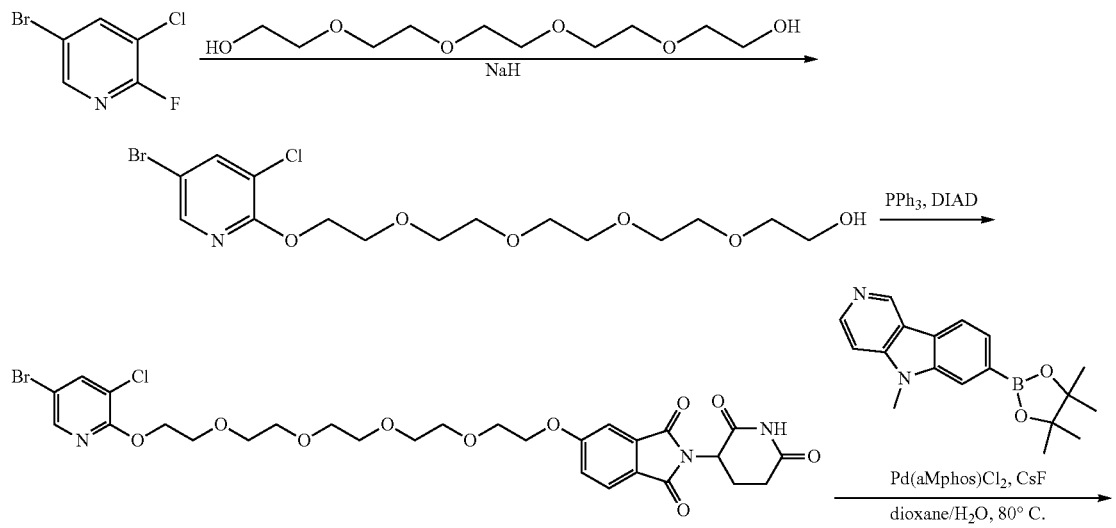

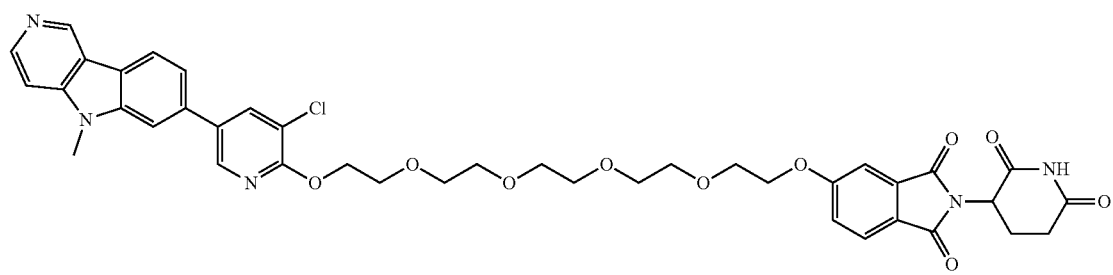

Compound 92

Compound 92: $^1$H NMR (400 MHz, CDCl$_3$): δ 9.32 (s, 1H), 8.68 (s, 1H), 8.58 (s, 1H), 8.35 (s, 1H), 8.18 (d, J=8.0 Hz, 1H), 7.97 (s, 1H), 7.74 (d, J=8.4 Hz, 1H), 7.52 (s, 1H), 7.45 (d, J=8.0 Hz, 1H), 7.27-7.34 (m, 2H), 7.20 (d, J=7.6 Hz, 1H), 4.92-4.96 (m, 1H), 4.61 (s, 2H), 4.23 (s, 2H), 3.89-3.94 (m, 8H), 3.68-3.78 (m, 11H), 2.72-2.90 (m, 3H), 2.01-2.12 (m, 1H). (M+H)$^+$ 786.5, 788.5.

Synthetic Scheme for Exemplary Compound 93

5-((6-((5-(2,2-difluoro-2-(5-(5-methyl-5H-pyrido[4,3-b]indol-7-yl)pyridin-2-yl)ethoxy)pentyl)oxy)hexyl)oxy)-2-(2,6-dioxopiperidin-3-yl)isoindoline-1,3-dione

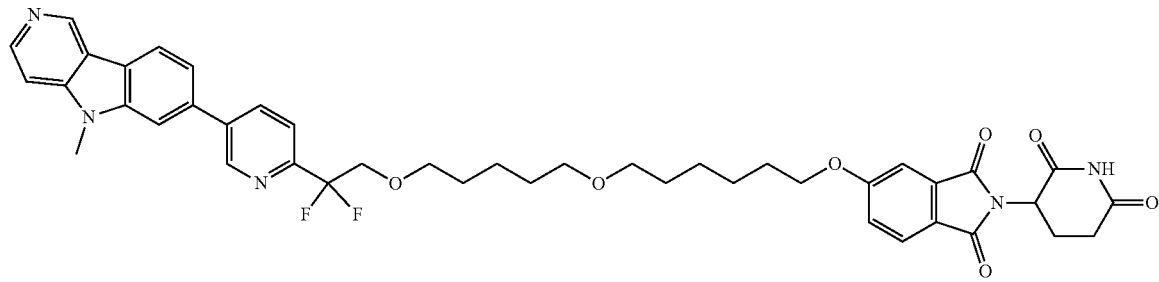 [SMILES: Cn1c2ccncc2c2ccc(-c3ccc(C(F)(F)COCCCCCOCCCCCCOc4ccc5c(c4)C(=O)N(C4CCC(=O)NC4=O)C5=O)nc3)cc21]

Prepared according to the synthetic scheme below using procedures described above and common procedures known to those skilled in the art.
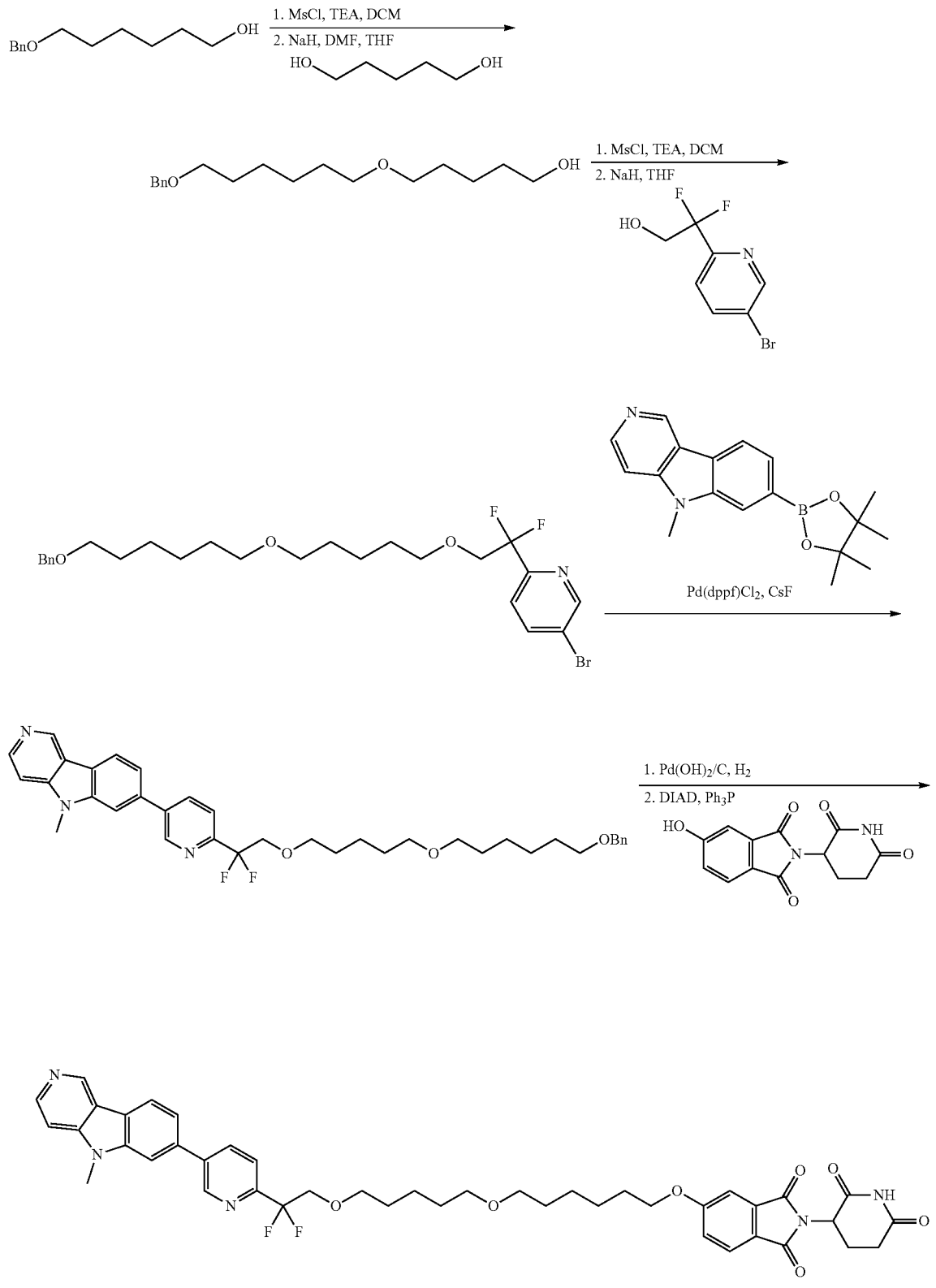
Compound 93

Compound 93: ¹H NMR (400 MHz, CDCl₃): δ 9.35 (br, 1H), 8.94 (s, 1H), 8.59 (s, 1H), 8.21 (d, J=8.0 Hz, 1H), 8.01-8.09 (m, 2H), 7.73 (d, J=8.4 Hz, 1H), 7.69 (d, J=8.0 Hz, 1H), 7.58 (s, 1H), 7.51 (d, J=8.4 Hz, 1H), 7.31 (d, J=5.2 Hz, 1H), 7.24 (s, 1H), 7.09 (dd, J=8.0, 2.0 Hz, 1H), 4.85-4.90 (m, 1H), 4.10 (t, J=8.0 Hz, 1H), 3.98 (t, J=6.4 Hz, 1H), 3.87 (s, 3H), 3.51 (t, J=6.4 Hz, 1H), 3.27-3.32 (m, 4H), 2.65-2.85 (m, 3H), 2.04-2.08 (m, 1H), 1.71-1.76 (m, 4H), 1.45-1.52 (m, 8H), 0.75-0.85 (m, 4H). (M+H)⁺ 782.5.

Synthetic Scheme for Exemplary Compound 96

2-(2,6-dioxopiperidin-3-yl)-5-(4-(6-(((1r,3r)-3-((5-(5-methyl-5H-pyrido[4,3-b]indol-7-yl)pyridin-2-yl)oxy)cyclobutoxy)hexyl)-3-(trifluoromethyl)piperazin-1-yl)isoindoline-1,3-dione

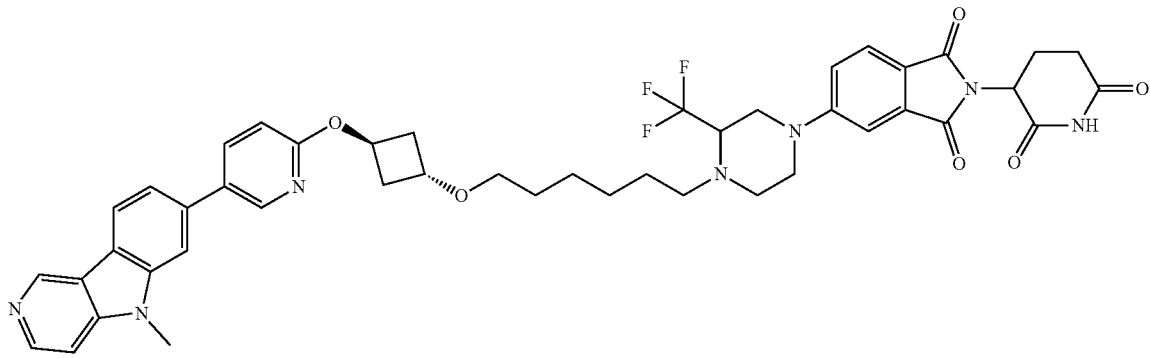 [SMILES: Cn1c2ccncc2c2ccc(-c3ccc(O[C@H]4C[C@H](OCCCCCCN5CCN(c6ccc7c(c6)C(=O)N(C6CCC(=O)NC6=O)C7=O)CC5C(F)(F)F)C4)nc3)cc21]

Prepared according to the synthetic schemes below using procedures described above and common procedures known to those skilled in the art.

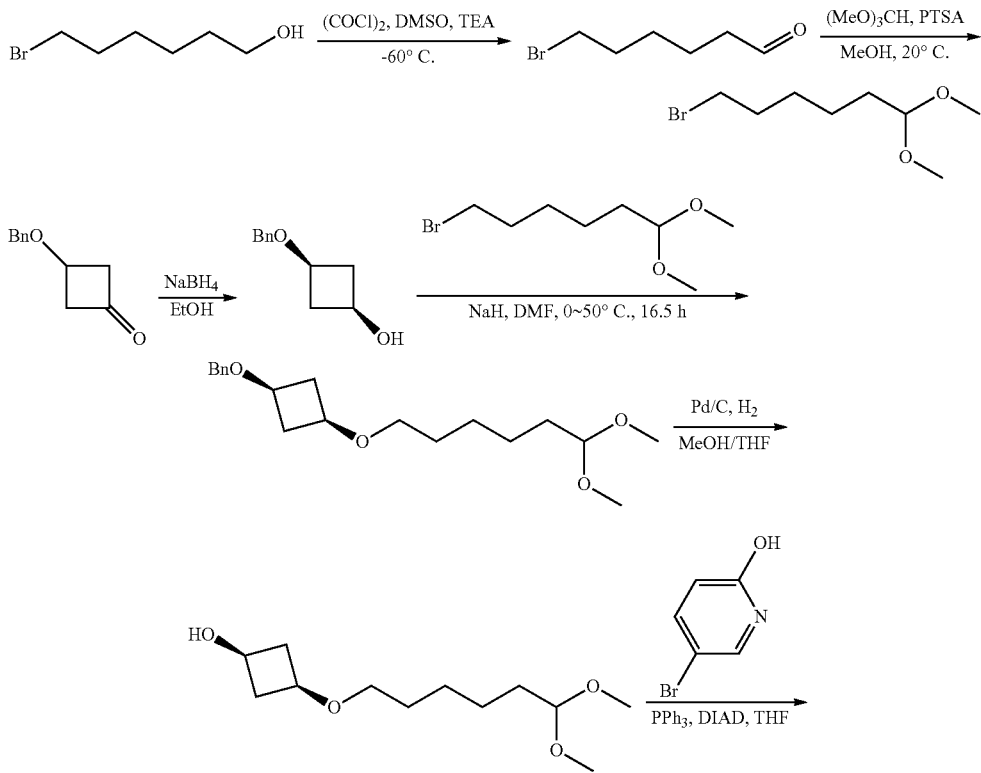

421 422
-continued
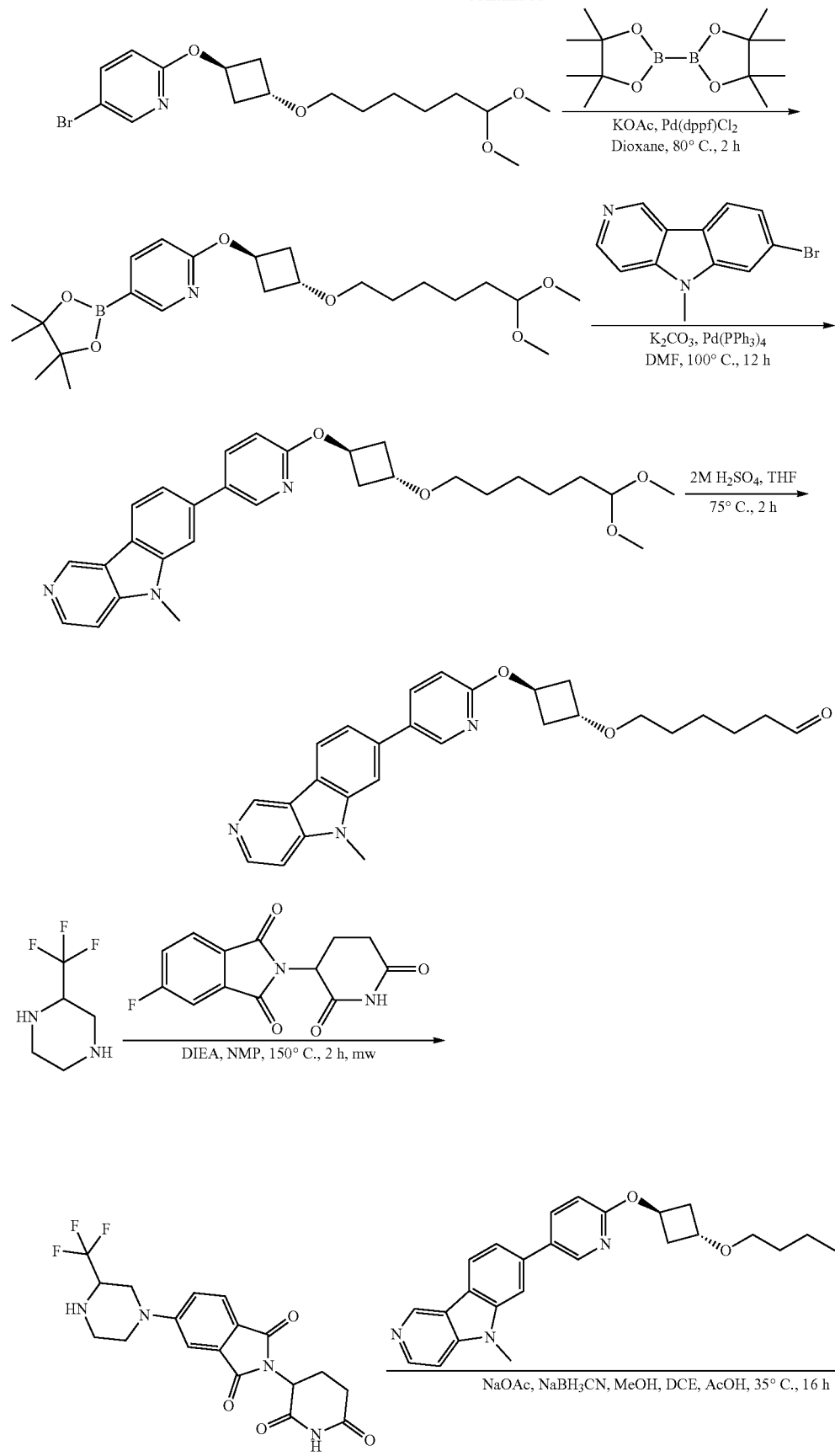

423

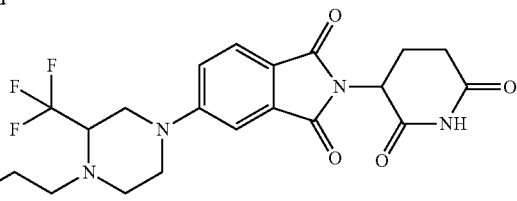

Compound 96

Compound 96: ¹H NMR: 400 MHz, DMSO-d6 δ: 11.09 (s, 1H), 9.38 (s, 1H), 8.64 (d, J=2.4 Hz, 1H), 8.51 (d, J=5.6 Hz, 1H), 8.33 (d, J=8.0 Hz, 1H), 8.19 (dd, J=2.4, 8.8 Hz, 1H), 8.14 (s, 1H), 7.99 (s, 1H), 7.72-7.59 (m, 3H), 7.21 (d, J=2.0 Hz, 1H), 7.12 (dd, J=2.0, 8.8 Hz, 1H), 6.94 (d, J=8.4 Hz, 1H), 5.38-5.26 (m, 1H), 5.06 (dd, J=5.3, 12.9 Hz, 1H), 4.24-4.13 (m, 1H), 3.96 (s, 3H), 3.95-3.88 (m, 1H), 3.72 (d, J=15.2 Hz, 1H), 3.68-3.63 (m, 1H), 3.53 (d, J=7.2 Hz, 1H), 3.31 (s, 2H), 3.07-2.75 (m, 4H), 2.74-2.54 (m, 4H), 2.44-2.29 (m, 4H), 2.06-1.94 (m, 1H), 1.50 (td, J=7.0, 13.8 Hz, 4H), 1.33 (s, 4H). (M+H)⁺ 838.6.

Synthetic Scheme for Exemplary Compound 99

2-(2,6-dioxopiperidin-3-yl)-5-((1-(3-(3-((1r,3r)-3-((5-(5-methyl-5H-pyrido[4,3-b]indol-7-yl)pyridin-2-yl)oxy)cyclobutoxy)propoxy)propyl)azetidin-3-yl)oxy)isoindoline-1,3-dione

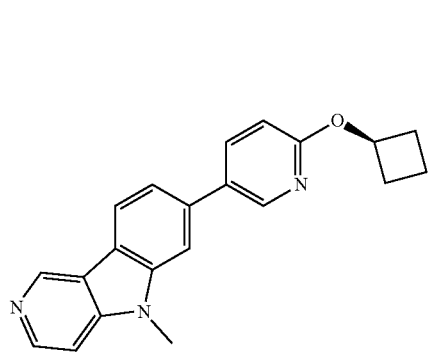

424

Step 2: 3-(3-((tetrahydro-2H-pyran-2-yl)oxy) propoxy)propan-1-ol

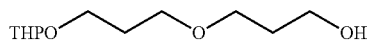

To a solution of propane-1,3-diol (4.6 g, 60 mmol) in N,N-dimethylformamide (50 ml) was added sodium hydride (60% in mineral oil) (0.88 g, 222 mmol) at 0° C., and the resulting mixture was stirred at 0° C. for 30 minutes. To the reaction mixture was added 2-(3-bromopropoxy)tetrahydro-2H-pyran (2.2 g, 20 mmol), and the resulting reaction mixture was stirred at 65° C. for 16 hours. The reaction mixture was quenched with water (150 ml) at 0° C. and extracted with ethyl acetate (200 ml×2). The combined organic layers were washed with brine (50 ml×2), dried over anhydrous sodium sulfate, and concentrated under reduced pressure to give a residue which was purified by silica gel flash chromatography (eluted with 30% ethyl acetate in hexane) to afford 3-(3-((tetrahydro-2H-pyran-2-yl)oxy) propoxy)propan-1-ol (0.9 g, yield 45%) as colorless oil.

Step 3: 3-(3-((tetrahydro-2H-pyran-2-yl)oxy) propoxy)propyl 4-methylbenzenesulfonate

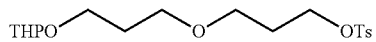

To a stirred solution of 3-(3-((tetrahydro-2H-pyran-2-yl)oxy)propoxy)propan-1-ol (900 mg, 4.1 mmol), triethylamine (1.1 ml, 8.25 mmol) in dichloromethane (30 ml) was added tosyl chloride (0.94 g, 4.95 mmol) and 4-dimethylaminopyridine (50 mg, 0.4 mmol) at 0° C. The resulting solution was allowed to warm up to room temperature and stirred at room temperature for 2 hours. The mixture was poured into water (20 ml) and extracted with dichlorometh-

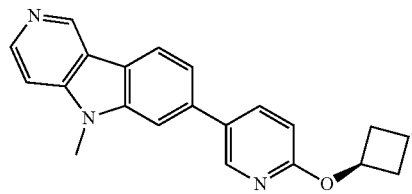

Step 1: 2-(3-bromopropoxy)tetrahydro-2H-pyran

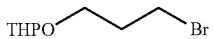

A mixture of 3-bromopropan-1-ol (5.56 g, 40 mmol), dihydropyran (4.0 g, 48 mmol) and p-toluenesulfonic acid (0.76 g, 4 mmol) in tetrahydrofuran (80 ml) was stirred at room temperature overnight. The reaction mixture was quenched with aqueous sodium bicarbonate solution (sat. 10 ml) and extracted with tert-butyl methyl ether (50 ml×3). The combined organic layers were washed with brine (50 ml), dried over anhydrous sodium sulfate, and concentrated under reduced pressure to give a crude residue which was purified by silica gel flash chromatography (eluted 10% ethyl acetate in hexane) to afford 2-(3-bromopropoxy)tetrahydro-2H-pyran (6.4 g, yield 72%) as colorless oil.

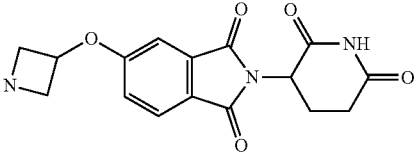

ane (20 ml×2). The combined organic layers were washed with brine (20 ml), dried over anhydrous sodium sulfate, and concentrated under reduced pressure to give a crude residue which was purified by silica gel flash column chromatography (eluted with 10-20% ethyl acetate in hexane) to afford 3-(3-(((tetrahydro-2H-pyran-2-yl)oxy)propoxy)propyl 4-methylbenzenesulfonate (1.2 g, yield 78%) as colorless oil.

Step 4: 2-(3-(3-((1r,3r)-3-(benzyloxy)cyclobutoxy) propoxy)propoxy)tetrahydro-2H-pyran

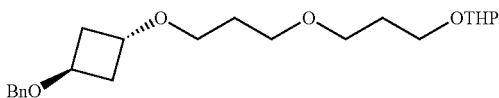

To a solution of (1r,3r)-3-(benzyloxy)cyclobutanol (200 mg, 1.12 mmol) in N,N-dimethylformamide (6 ml) was added sodium hydride (60% in mineral oil) (63 mg, 1.57 mmol) at 0° C., and the resulting mixture was stirred at room temperature for 30 minutes. 3-(3-((tetrahydro-2H-pyran-2-yl)oxy)propoxy)propyl 4-methylbenzenesulfonate (501 mg, 1.34 mmol) was added, and the resulting reaction mixture was stirred at room temperature for 2 hours. The reaction mixture was quenched with water (30 ml) at 0° C. and extracted with ethyl acetate (60 ml×2). The combined organic layers were washed with brine (30 ml), dried over anhydrous sodium sulfate, and concentrated under reduced pressure to give a residue which was purified by silica gel flash chromatography (eluted with 30% ethyl acetate in hexane) to afford 2-(3-(3-((1r,3r)-3-(benzyloxy)cyclobutoxy)propoxy)propoxy)tetrahydro-2H-pyran (234 g, yield 47%) as colorless oil.

Step 5: (1r,3r)-3-(3-(3-hydroxypropoxy)propoxy) cyclobutanol

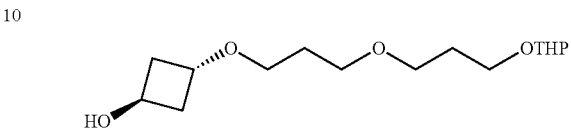

A mixture of 2-(3-(3-((1r,3r)-3-(benzyloxy)cyclobutoxy) propoxy)propoxy)tetrahydro-2H-pyran (468 g, 1.23 mmol), palladium on carbon (10%, 60 mg) in methanol (30 ml) was stirred at room temperature overnight under hydrogen atmosphere (hydrogen balloon). Palladium on carbon was removed through filtration and washed with methanol (5 ml×2). The combined filtrates were concentrated under reduced pressure to afford (1r,3r)-3-(3-(3-hydroxypropoxy) propoxy)cyclobutanol (240 mg, yield: 95%) as colorless oil.

Step 6: 3-(3-((1r,3r)-3-((5-(5-methyl-5H-pyrido[4,3-b]indol-7-yl)pyridin-2-yl)oxy)cyclobutoxy)propoxy) propan-1-ol

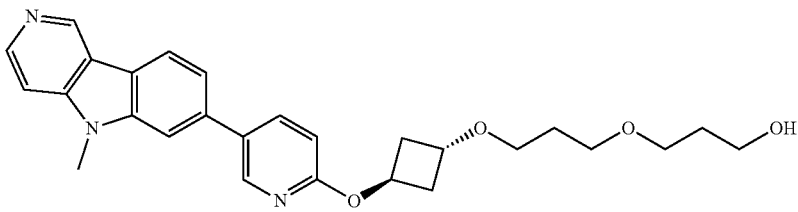 [SMILES: Cn1c2ccncc2c2ccc(-c3ccc(O[C@H]4C[C@H](OCCCOCCCO)C4)nc3)cc21]

To a solution of (1r,3r)-3-(3-(3-hydroxypropoxy) propoxy)cyclobutanol (100 mg, 0.49 mmol) in N,N-dimethylformamide (3 ml) was added sodium hydride (60% in mineral oil) (28 mg, 0.69 mmol) at 0° C., and the resulting mixture was stirred at room temperature for 30 minutes. 7-(6-fluoropyridin-3-yl)-5-methyl-5H-pyrido[4,3-b]indole (96 mg, 0.35 mmol) was added, and the resulting reaction mixture was stirred at room temperature for 3 hours. The reaction mixture was quenched with water (30 ml) at 0° C. and extracted with ethyl acetate (60 ml×2). The combined organic layers were washed with brine (30 ml), dried over anhydrous sodium sulfate, and concentrated under reduced pressure to give a residue which was purified by silica gel flash chromatography (eluted with 5% methanol in dichloromethane) to afford 3-(3-((1r,3r)-3-((5-(5-methyl-5H-pyrido[4,3-b]indol-7-yl)pyridin-2-yl)oxy)cyclobutoxy) propoxy)propan-1-ol (75 mg, yield 34%) as white solid.

Step 7: 3-(3-((1r,3r)-3-((5-(5-methyl-5H-pyrido[4,3-b]indol-7-yl)pyridin-2-yl)oxy)cyclobutoxy)propoxy) propanal

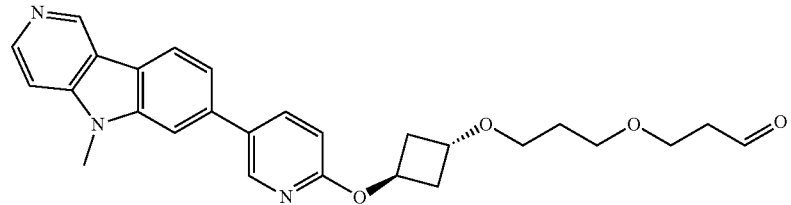 [SMILES: Cn1c2ccncc2c2ccc(-c3ccc(O[C@H]4C[C@H](OCCCOCCC=O)C4)nc3)cc21]

To a stirred solution of 3-(3-((1r,3r)-3-((5-(5-methyl-5H-pyrido[4,3-b]indol-7-yl)pyridin-2-yl)oxy)cyclobutoxy)propoxy)propan-1-ol (70 mg, 0.15 mmol) in dichloromethane (5 ml) was added Dess-Martin periodinane (129 mg, 0.3 mmol) at 0° C. The resulting reaction mixture was allowed to warm up to room temperature and stirred at this temperature for additional 30 minutes. The reaction mixture was quenched with aqueous solution of sodium bicarbonate (10 ml) and extracted with dichloromethane (20 ml×2), washed with brine (20 ml), dried over anhydrous sodium sulfate and concentrated under reduced pressure to afford crude 3-(3-((1r,3r)-3-((5-(5-methyl-5H-pyrido[4,3-b]indol-7-yl)pyridin-2-yl)oxy)cyclobutoxy)propoxy)propanal (80 mg, crude) as white solid which was used in next step without further purification.

Step 8: 2-(2,6-dioxopiperidin-3-yl)-5-((1-(3-(3-((1r,3r)-3-((5-(5-methyl-5H-pyrido[4,3-b]indol-7-yl)pyridin-2-yl)oxy)cyclobutoxy)propoxy)propyl)azetidin-3-yl)oxy)isoindoline-1,3-dione

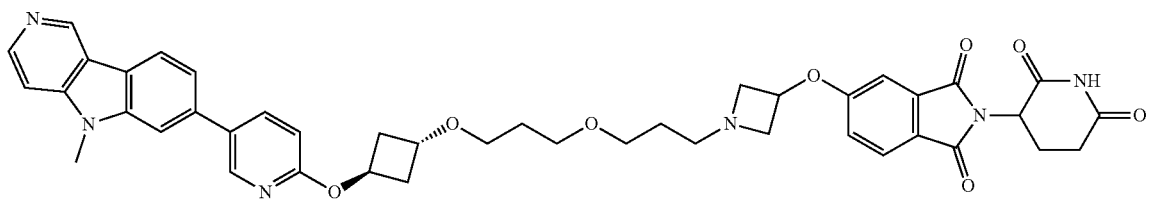 [SMILES: Cn1c2ccncc2c2ccc(-c3ccc(O[C@H]4C[C@H](OCCCOCCCN5CC(Oc6ccc7c(c6)C(=O)N(C6CCC(=O)NC6=O)C7=O)C5)C4)nc3)cc21]

A mixture of 5-(azetidin-3-yloxy)-2-(2,6-dioxopiperidin-3-yl)isoindoline-1,3-dione hydrochloride (70 mg, 0.17 mmol) [prepared as shown in scheme below using procedures described above and common procedures known to those skilled in the art], N-ethyl-N-isopropylpropan-2-amine (44 mg, 0.35 mmol), acetic acid (1 drop) and 3-(3-((1r,3r)-3-((5-(5-methyl-5H-pyrido[4,3-b]indol-7-yl)pyridin-2-yl)oxy)cyclobutoxy)propoxy)propanal (80 mg, 0.17 mmol) in methanol (5 ml) was stirred at room temperature for 30 min, followed by addition of sodium cyonobrohydriole (22 mg, 0.35 mmol) at room temperature. The resulting mixture was stirred at room temperature for 30 minutes. The reaction mixture was quenched with aqueous solution of sodium bicarbonate (sat. 10 ml) and extracted with ethyl acetate (20 ml), washed with brine (10 ml), dried over anhydrous sodium sulfate, and concentrated under reduced pressure to afford a crude residue which was purified by prep. TLC (eluted with 10% methanol in dichloromethane) to afford 2-(2,6-dioxopiperidin-3-yl)-5-((1-(3-(3-((1r,3r)-3-((5-(5-methyl-5H-pyrido[4,3-b]indol-7-yl)pyridin-2-yl)oxy)cyclobutoxy)propoxy)propyl)azetidin-3-yl)oxy)isoindoline-1,3-dione (20 mg, yield: 15%) as white solid.

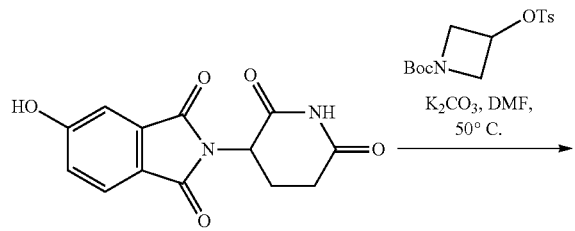

-continued

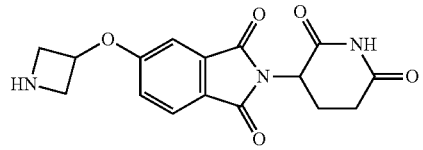

Compound 99: 1H NMR (400 Hz, DMSO-d6): δ 1.40-1.56 (m, 2H), 1.62-1.75 (m, 2H), 1.83-2.09 (m, 2H), 2.34-2.50 (m, 3H), 2.58-2.73 (m, 2H), 2.83-2.93 (m, 1H), 3.01-3.13 (m, 2H), 3.37-3.52 (m, 8H), 3.77 (s, 2H), 3.95 (s, 3H), 4.18 (s, 1H), 5.02-5.13 (m, 2H), 5.29-5.37 (m, 1H), 6.94 (d, J=8.0 Hz, 1H), 7.21-7.29 (m, 2H), 7.59-7.65 (m, 2H), 7.80 (d, J=7.2 Hz, 1H), 7.97 (s, 1H), 8.18 (d, J=7.6 Hz, 1H), 8.31 (d, J=7.6 Hz, 1H), 8.50 (d, J=5.2 Hz, 1H), 8.63 (s, 1H), 9.35 (s, 1H), 11.11 (s, 1H). (M+H)$^+$ 773.5.

Synthetic Scheme for Exemplary Compound 100
2-(2,6-dioxopiperidin-3-yl)-5-(6-(4-(4-((5-(5-methyl-5H-pyrido[4,3-b]indol-7-yl)pyridin-2-yl)oxy)butoxy)butoxy)-2-azaspiro[3.3]heptan-2-yl)isoindoline-1,3-dione
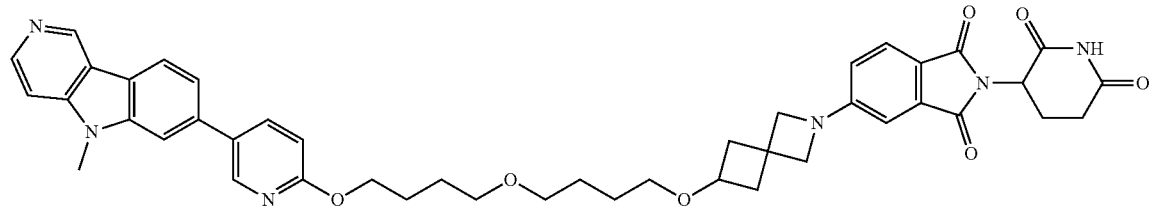 [SMILES: Cn1c2ccncc2c2ccc(-c3ccc(OCCCCOCCCCOC4CC5(C4)CN(c4ccc6c(c4)C(=O)N(C4CCC(=O)NC4=O)C6=O)C5)nc3)cc21]
Prepared according to the synthetic scheme below using procedures described above and common procedures known to those skilled in the art.
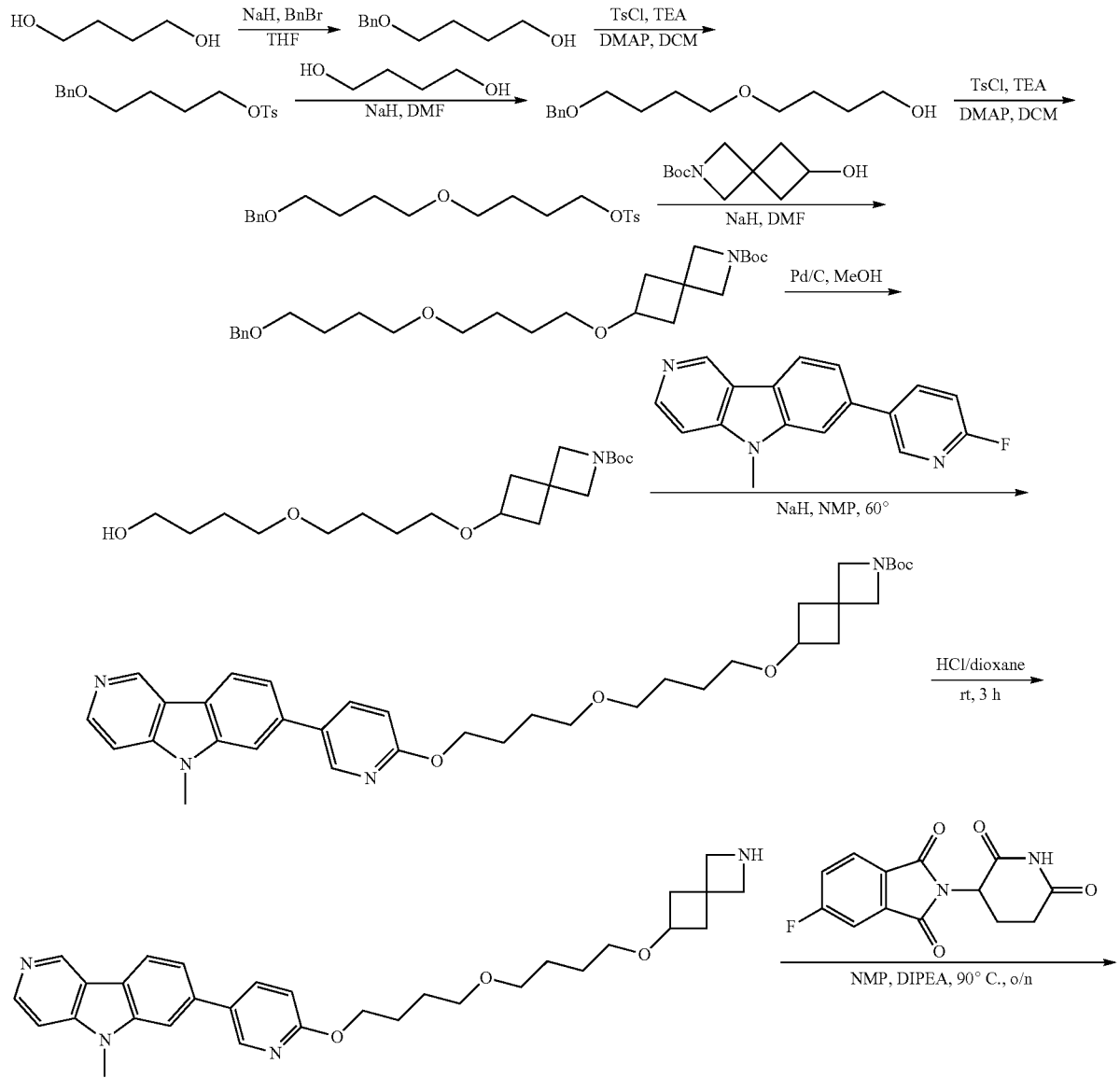

-continued

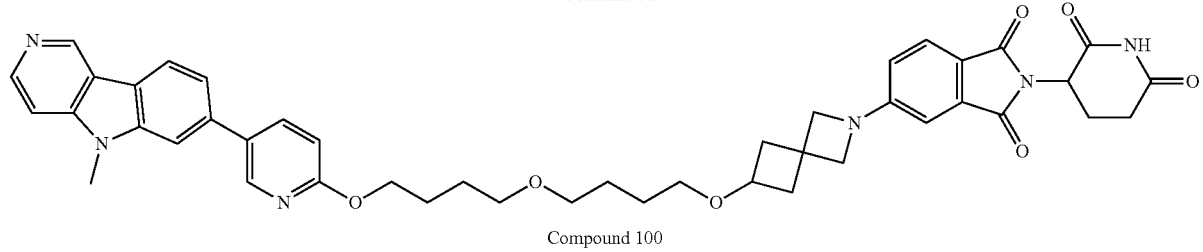

Compound 100

Compound 100: ¹H NMR (400 MHz, CDCl₃): δ 1.65-1.67 (m, 6H), 1.74-1.81 (m, 2H), 1.87-1.94 (m, 2H), 2.00-2.06 (m, 1H), 2.09-2.14 (m, 1H), 2.18-2.24 (m, 2H), 2.54-2.59 (m, 2H), 2.68-2.90 (m, 3H), 3.37-3.53 (m, 5H), 3.91 (t, J=7.6 Hz, 3H), 3.98 (d, J=8.0 Hz, 3H), 4.39 (t, J=6.4 Hz, 2H), 4.90-4.94 (m, 1H), 6.45 (d, J=1.6 Hz, 1H), 6.72 (d, J=1.6 Hz, 1H), 6.85 (d, J=8.4 Hz, 1H), 7.35 (d, J=6 Hz, 1H), 7.50 (d, J=8.0 Hz, 1H), 7.56 (s, 1H), 7.61 (d, J=8.0 Hz, 1H), 7.91 (d, J=2.4 Hz, 1H), 8.05 (s, 1H), 8.21 (d, J=8.0 Hz, 1H), 8.49 (d, J=2.4 Hz, 1H), 8.60 (d, J=5.6 Hz, 1H), 9.34 (s, 1H). (M+H)⁺ 771.6.

Synthetic Scheme of Exemplary Compound 101

5-((1-(3-(3-(((1r,3r)-3-((5-(5H-pyrido[4,3-b]indol-7-yl)-3-(trifluoromethyl)pyridin-2-yl)oxy)cyclobutoxy)propoxy)propyl)azetidin-3-yl)oxy)-2-(2,6-dioxopiperidin-3-yl)isoindoline-1,3-dione

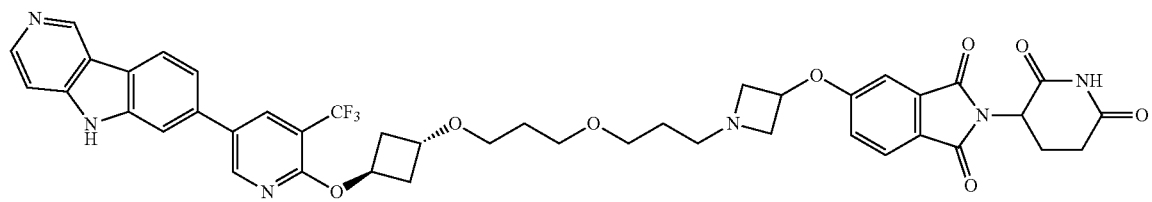 [SMILES: O=C1CCC(N2C(=O)c3ccc(OC4CN(CCCOCCCO[C@H]5C[C@H](Oc6ncc(-c7ccc8c(c7)[nH]c7ccncc78)cc6C(F)(F)F)C5)C4)cc3C2=O)C(=O)N1]

Prepared according to the synthetic scheme below using procedures described above and common procedures known to those skilled in the art.

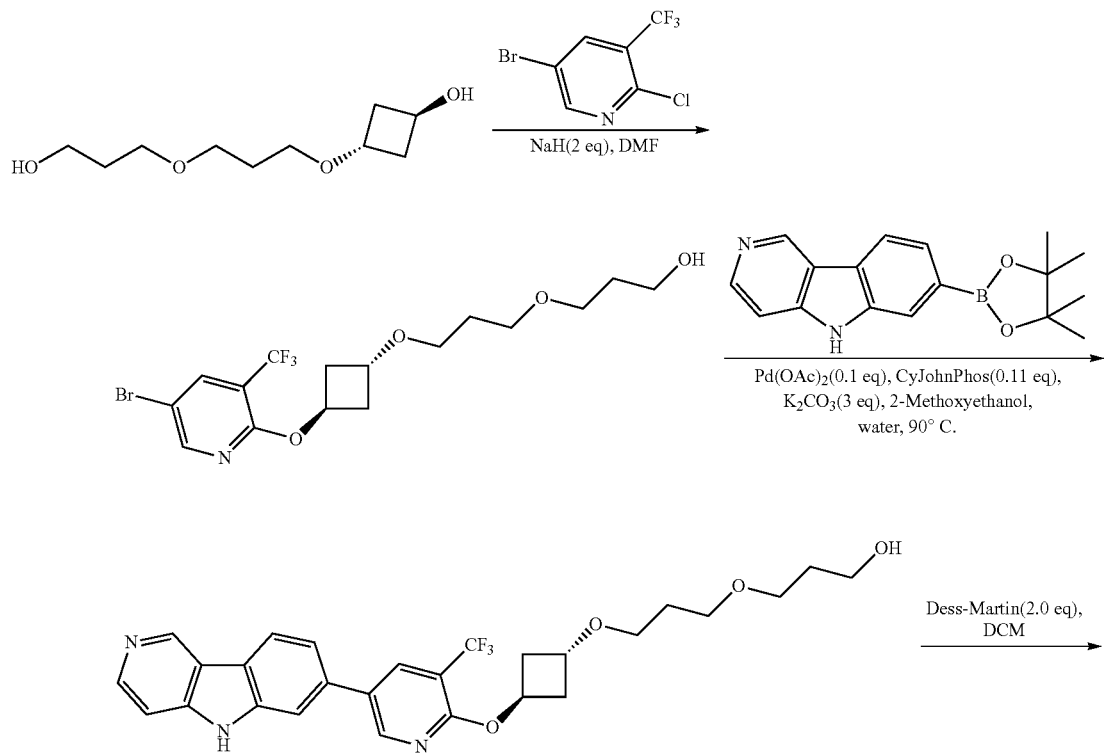

-continued
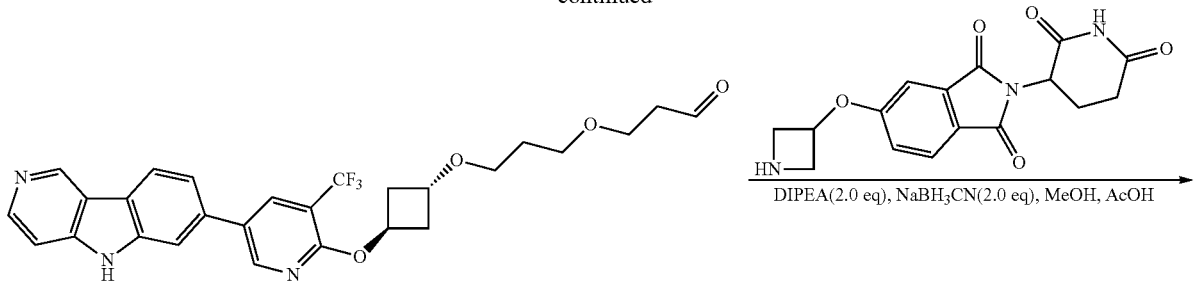
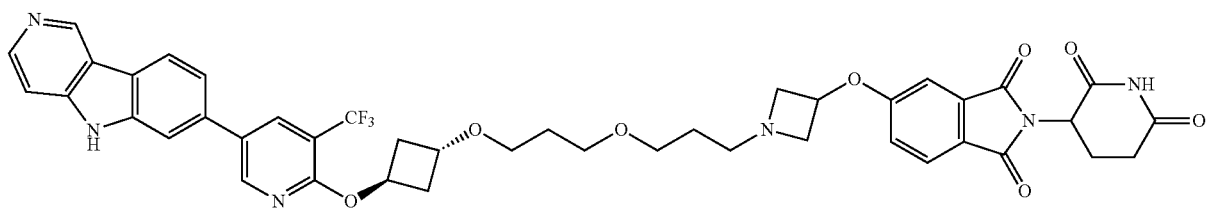
Compound 101
Compound 101: 1H NMR (400 Hz, D6-DMSO): δ 1.56-1.59 (m, 2H), 1.71-1.77 (m, 2H), 1.95-2.05 (m, 2H), 2.34-2.46 (m, 3H), 2.50-2.67 (m, 3H), 2.83-2.93 (m, 1H), 3.32-3.49 (m, 9H), 3.88-3.92 (m, 1H), 4.17-4.20 (m, 1H), 4.55 (t, J=5.6 Hz, 1H), 5.05-5.13 (m, 2H), 5.46-5.49 (m, 1H), 7.25-7.28 (m, 2H), 7.52 (d, J=5.6 Hz, 1H), 7.63 (d, J=8.0 Hz, 1H), 7.82 (d, J=8.0 Hz, 1H), 7.87 (s, 1H), 8.33 (d, J=8.0 Hz, 1H), 8.39 (s, 1H), 8.45 (d, J=6.0 Hz, 1H), 8.83 (s, 1H), 9.39 (s, 1H), 11.11 (s, 1H), 11.86 (s, 1H). (M+H)$^+$ 827.5.
Using analogous procedures the following were prepared: Compound 105.
Synthetic Scheme for Exemplary Compound 103
5-((14-((5-(8,9-difluoro-5H-pyrido[4,3-b]indol-7-yl)pyridin-2-yl)oxy)-3,6,9,12-tetraoxatetradecyl)oxy)-2-(2,6-dioxopiperidin-3-yl)isoindoline-1,3-dione
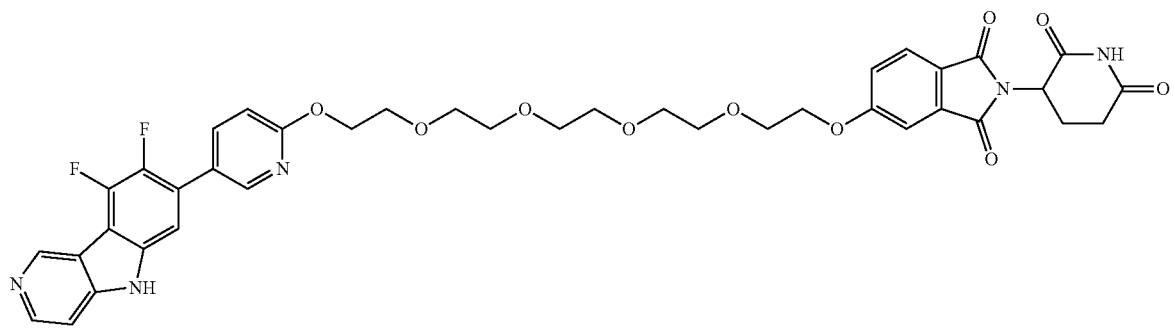 [SMILES: O=C1CCC(N2C(=O)c3ccc(OCCOCCOCCOCCOCCOc4ccc(-c5cc6[nH]c7ccncc7c6c(F)c5F)cn4)cc3C2=O)C(=O)N1]

Step 1: 5-bromo-2-((1-phenyl-2,5,8,11,14-pentaoxa-hexadecan-16-yl)oxy)pyridine

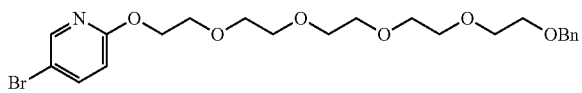 [SMILES: Brc1ccc(OCCOCCOCCOCCOCCOCc2ccccc2)nc1]

To a solution of compound 5-bromo-2-fluoropyridine (2.0 g, 9.5 mmol) in DMF (20 mL) was added 1-phenyl-2,5,8,11,14-pentaoxahexadecan-16-ol (2.6 g, 7.91 mmol) and NaH (950 mg, 24 mmol, 60%) at 0° C. The resulting mixture was stirred at 20° C. for 18 hours. TLC (PE:EA=1:1, Rf=0.5) showed 5-bromo-2-fluoropyridine was consumed. The mixture was diluted with EA (30 mL), washed with water (3*30 mL) and brine (30 mL). The organic layer was dried and concentrated to give crude product, which was purified by column chromatography on silica gel with PE:EA (1:1) to give the desired product (3.6 g) as a colorless oil.

Step 2: 2-((1-phenyl-2,5,8,11,14-pentaoxahexadecan-16-yl)oxy)-5-(4,4,5,5-tetramethyl-1,3,2-dioxaborolan-2-yl)pyridine

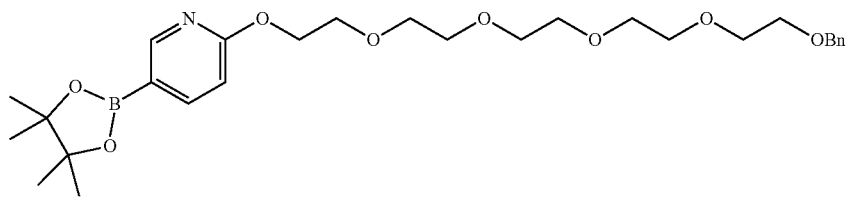 [SMILES: CC1(C)OB(c2ccc(OCCOCCOCCOCCOCCOCc3ccccc3)nc2)OC1(C)C]

To a solution of 5-bromo-2-((1-phenyl-2,5,8,11,14-pentaoxahexadecan-16-yl)oxy) pyridine (3.6 g, 7.22 mmol) in dioxane (50 mL) was added 4,4,4',4',5,5,5',5'-octamethyl-2,2'-bi (1,3,2-dioxaborolane) (3.7 g, 14.45 mmol), Pd(dppf)Cl$_2$ (530 mg) and AcOK (1.42 g, 14.45 mmol). The resulting solution was stirred at 90° C. for 18 hours. The mixture was filtered and concentrated. The crude was purified by column chromatography on silica gel with PE:EA (1:1) to afford the desired product (3.0 g, yield=78%) as a yellow oil.

Step 3: 5-(4-bromo-2,3-difluorophenyl)-2-((1-phenyl-2,5,8,11,14-pentaoxahexadecan-16-yl)oxy)pyridine

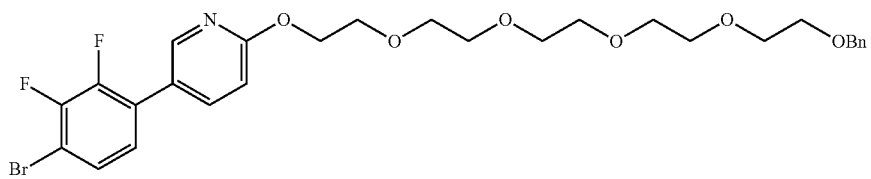 [SMILES: Fc1c(Br)ccc(-c2ccc(OCCOCCOCCOCCOCCOCc3ccccc3)nc2)c1F]

To a solution of 2-((1-phenyl-2,5,8,11,14-pentaoxahexadecan-16-yl) oxy)-5-(4,4,5,5-tetramethyl-1,3,2-dioxaborolan-2-yl)pyridine (2.8 g, 5.27 mmol) in dioxane/H$_2$O (55 mL, 10/1, v/v) was added 1,4-dibromo-2,3-difluorobenzene (1.72 g, 6.32 mmol, CsF (1.6 g, 10.54 mmol) and Pd(PPh$_3$) (300 mg). The resulting solution was stirred at 90° C. for 18 hours under N$_2$. After the reaction was over, the mixture was quenched with EA and extracted with EA. The organic layer was washed with brine, dried over Na$_2$SO$_4$, filtered and concentrated. The crude was purified by column chromatography on silica gel with PE:EA (1:1) to afford the desired product (1.5 g, yield=48%) as a brown oil.

Step 4: 5-(2,3-difluoro-4-(4,4,5,5-tetramethyl-1,3,2-dioxaborolan-2-yl)phenyl)-2-((1-phenyl-2,5,8,11,14-pentaoxahexadecan-16-yl)oxy)pyridine

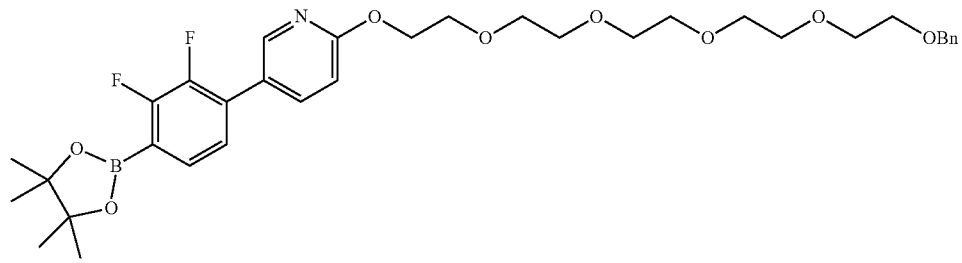 [SMILES: CC1(C)OB(c2ccc(-c3ccc(OCCOCCOCCOCCOCCOCc4ccccc4)nc3)c(F)c2F)OC1(C)C]

To a solution of 5-(4-bromo-2,3-difluorophenyl)-2-((1-phenyl-2,5,8,11,14-pentaoxahexadecan-16-yl)oxy) pyridine (1.0 g, 1.68 mmol) in dioxane (20 mL) was added 4,4,4',4',5,5,5',5'-octamethyl-2,2'-bi(1,3,2-dioxaborolane) (640 mg, 2.52 mmol), Pd(dppf)Cl$_2$ (120 mg) and AcOK (330 mg, 3.36 mmol). The resulting solution was stirred at 90° C. for 18 hours. LCMS showed 5-(4-bromo-2,3-difluorophenyl)-2-((1-phenyl-2,5,8,11,14-pentaoxahexadecan-16-yl) oxy)pyridine was consumed completely. The mixture was filtered and concentrated. The crude was purified by column chromatography on silica gel with PE:EA (3:2) to afford the desired product the desired product (660 mg, yield=95%) as a brown oil.

Step 5: 5-(2,3-difluoro-4-(4-nitropyridin-3-yl)phenyl)-2-((1-phenyl-2,5,8,11,14-pentaoxahexadecan-16-yl)oxy)pyridine

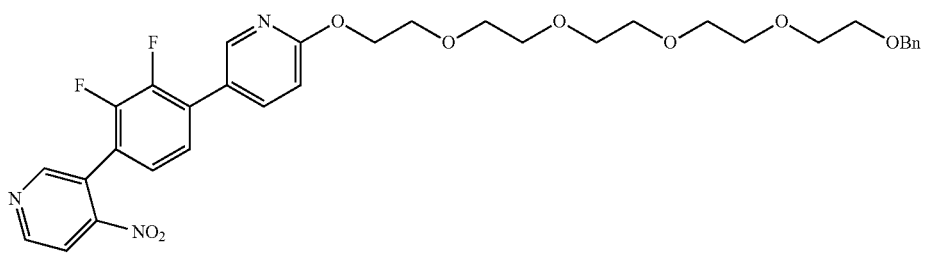 [SMILES: O=[N+]([O-])c1ccncc1-c1ccc(-c2ccc(OCCOCCOCCOCCOCCOCc3ccccc3)nc2)c(F)c1F]

To a solution of 5-(2,3-difluoro-4-(4,4,5,5-tetramethyl-1,3,2-dioxaborolan-2-yl) phenyl)-2-((1-phenyl-2,5,8,11,14-pentaoxahexadecan-16-yl) oxy) pyridine (350 mg, 0.544 mmol) in dioxane/H$_2$O (11 mL, 10/1, v/v) was added 3-bromo-4-nitropyridine (121 mg, 0.6 mmol), Na$_2$CO$_3$ (120 mg, 1.1 mmol) and Pd(PPh$_3$)$_4$ (63 mg). The mixture was stirred at 110° C. for 1 h under N$_2$. After the reaction, the mixture was extracted with ethyl acetate (20 mL) and washed with brine (30 mL). The organic solution was dried over anhydrous sodium sulfate and concentrated. The crude was purified by column chromatography on silica gel with PE/EA (1:3) to give the desired product (170 mg) as a yellow oil.

Step 6: 8,9-difluoro-7-(6-((1-phenyl-2,5,8,11,14-pentaoxahexadecan-16-yl)oxy)pyridin-3-yl)-5H-pyrido[4,3-b]indole

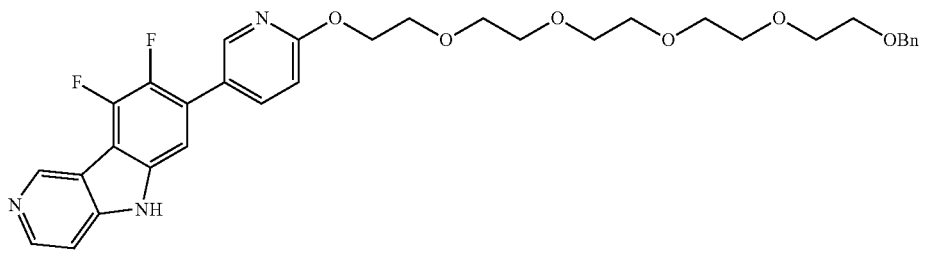 [SMILES: Fc1c(-c2ccc(OCCOCCOCCOCCOCCOCc3ccccc3)nc2)cc2[nH]c3ccncc3c2c1F]

A solution of 5-(2,3-difluoro-4-(4-nitropyridin-3-yl)phenyl)-2-((1-phenyl-2,5,8,11,14-pentaoxahexadecan-16-yl)oxy) pyridine (340 mg, 0.53 mmol) in P(Oet)$_3$ (3 mL) was stirred at 110° C. for 3 h. After the reaction, the mixture was purified by column chromatography on silica gel with DCM/MeOH (30:1) to give the desired product (205 mg) as a brown solid.

8,9-difluoro-7-(6-((1-phenyl-2,5,8,11,14-pentaoxahexadecan-16-yl)oxy)pyridin-3-yl)-5H-pyrido[4,3-b]indole was converted into the final compounds, 5-((14-((5-(8,9-difluoro-5H-pyrido[4,3-b]indol-7-yl)pyridin-2-yl)oxy)-3,6,9,12-tetraoxatetradecyl)oxy)-2-(2,6-dioxopiperidin-3-yl)isoindoline-1,3-dione (Compound 103) and 5-((14-((5-(8,9-difluoro-5-methyl-5H-pyrido[4,3-b]indol-7-yl)pyridin-2-yl)oxy)-3,6,9,12-tetraoxatetradecyl)oxy)-2-(2,6-dioxopiperidin-3-yl)isoindoline-1,3-dione (Compound 112), according to the synthetic scheme below using procedures described above and common procedures known to those skilled in the art.

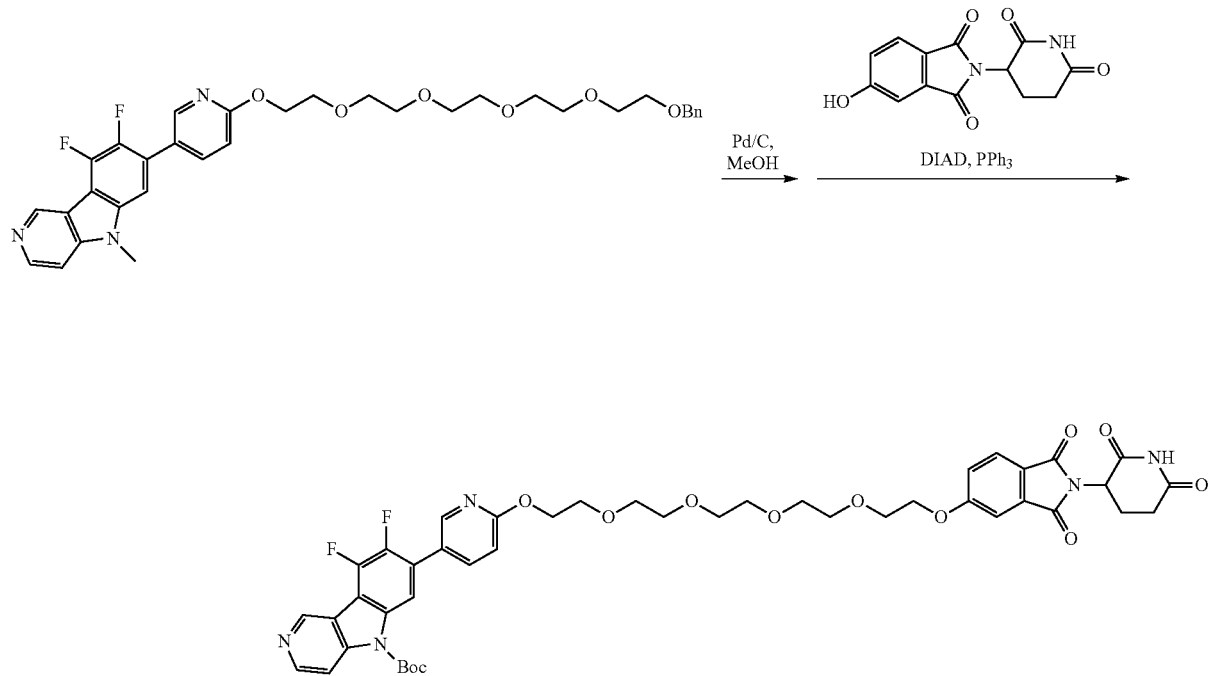

Compound 112

-continued
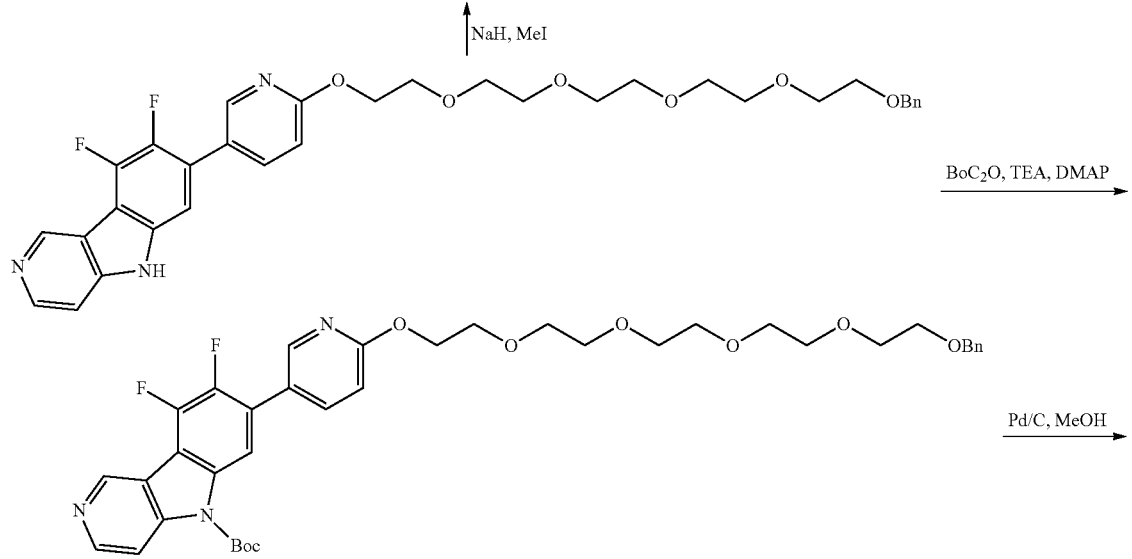
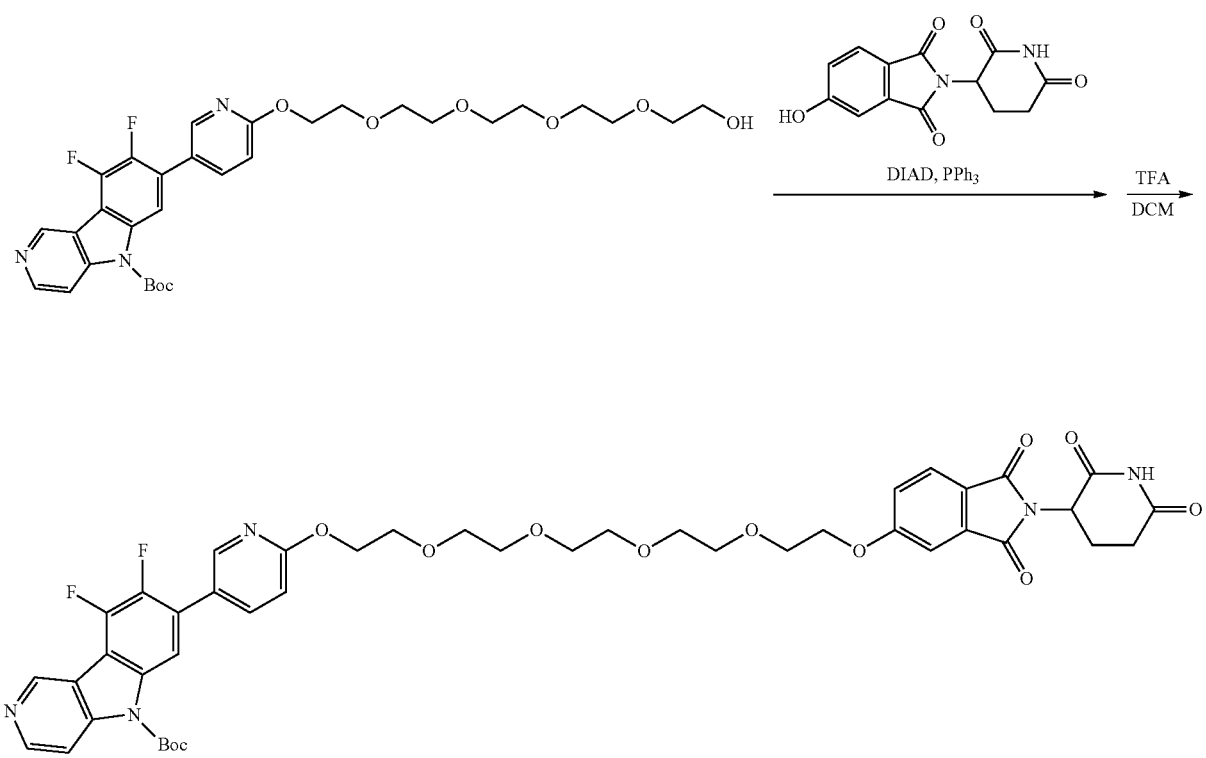
Compound 103
Compound 103: ¹H NMR (400 MHz, CD₃OD): δ 9.46 (s, 1H), 8.63 (d, J=6.8 Hz, 1H), 8.38 (s, 1H), 8.00 (d, J=6.8 Hz, 1H), 7.96 (d, J=8.8 Hz, 1H), 7.67 (d, J=8.4 Hz, 1H), 7.61 (d, J=4.8 Hz, 1H), 7.29 (s, 1H), 7.23 (d, J=8.4 Hz, 1H), 6.93 (d, J=8.8 Hz, 1H), 5.05 (m, 1H), 4.54-4.45 (m, 2H), 4.26-4.19 (m, 2H), 3.86 (m, 4H), 370-3.65 (m, 12H), 2.86-2.62 (m, 3H), 2.10-2.04 (m, 1H). (M+H)⁺ 774.5.
Compound 112: ¹HNMR (400 MHz, CDCl₃): δ: 11.09 (s, 1H), 9.25 (s, 1H), 8.50 (s, 1H), 8.59 (s, 1H), 8.07 (d, J=8.4 Hz, 1H), 7.79 (d, J=8.4 Hz, 1H), 7.69-7.73 (m, 2H), 7.75 (d, J=8.4 Hz, 1H), 7.42 (s, 1H), 7.34 (d, J=8.4 Hz, 1H), 7.02 (d, J=8.4 Hz, 1H), 5.08-5.13 (m, 1H), 4.46 (d, J=4.4 Hz, 2H), 4.30-4.34 (m, 2H), 3.95 (s, 3H), 3.79 (s, 4H), 3.60 (s, 4H), 3.56 (s, 4H), 3.53 (s, 4H), 2.85-2.88 (m, 1H), 2.61 (s, 2H). (M+H)⁺ 788.5.

Synthetic Scheme for Exemplary Compound 104
2-(2,6-dioxopiperidin-3-yl)-5-(3-(3-(3-(((1r,3r)-3-((5-(5-methyl-5H-pyrido[4,3-b]indol-7-yl)pyridin-2-yl)oxy)cyclobutoxy)propoxy)propoxy)azetidin-1-yl)isoindoline-1,3-dione
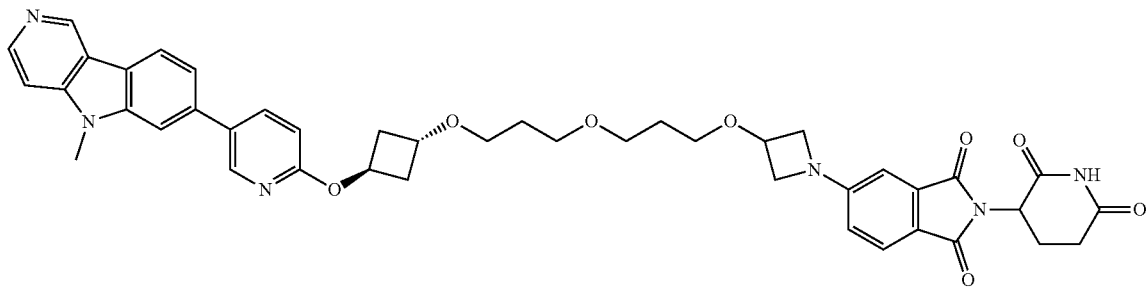 [SMILES: Cn1c2ccncc2c2ccc(-c3ccc(O[C@H]4C[C@H](OCCCOCCCOC5CN(c6ccc7c(c6)C(=O)N(C6CCC(=O)NC6=O)C7=O)C5)C4)nc3)cc21]
20
Prepared according to the synthetic scheme below using procedures described above and common procedures known to those skilled in the art.
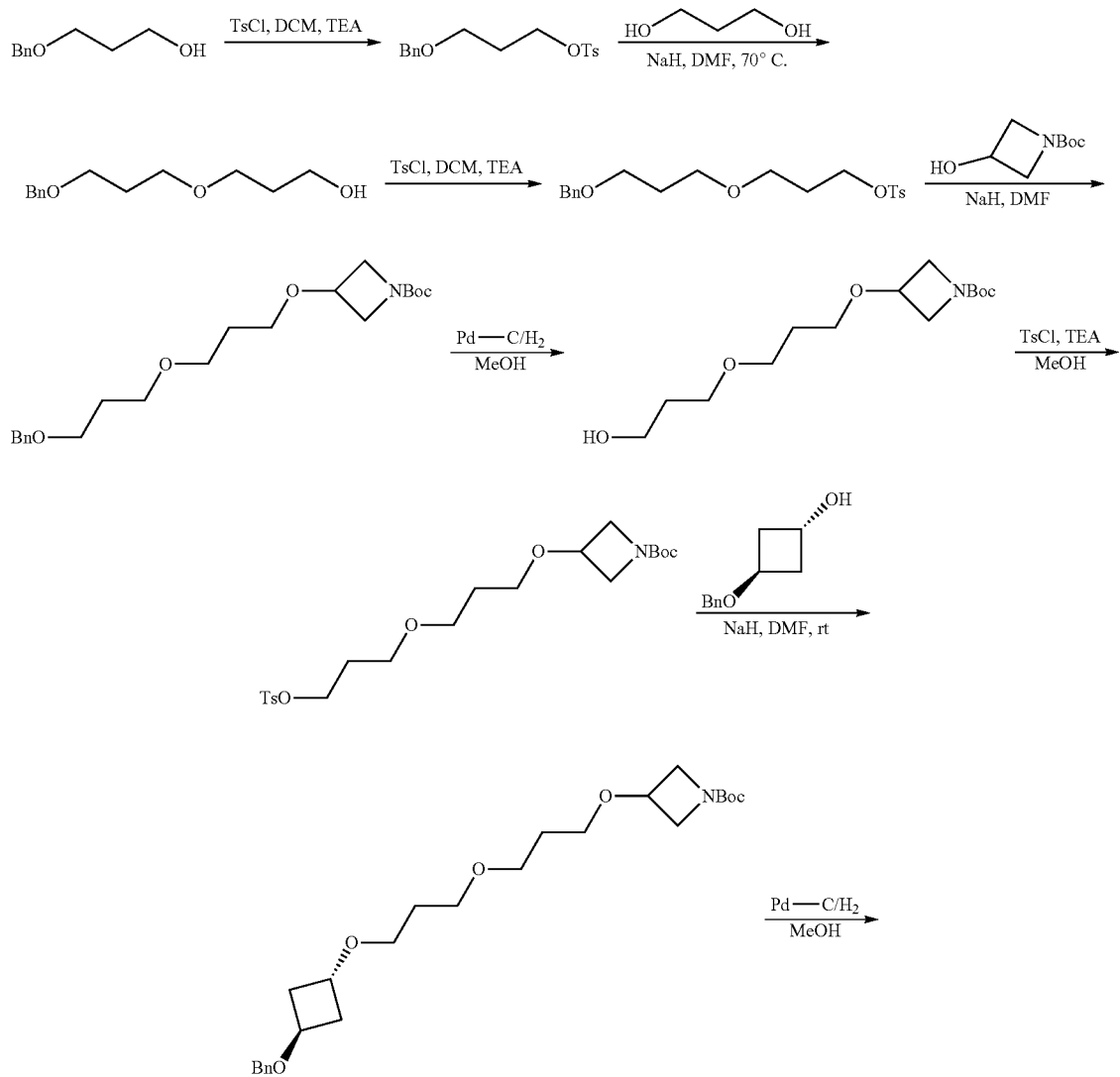

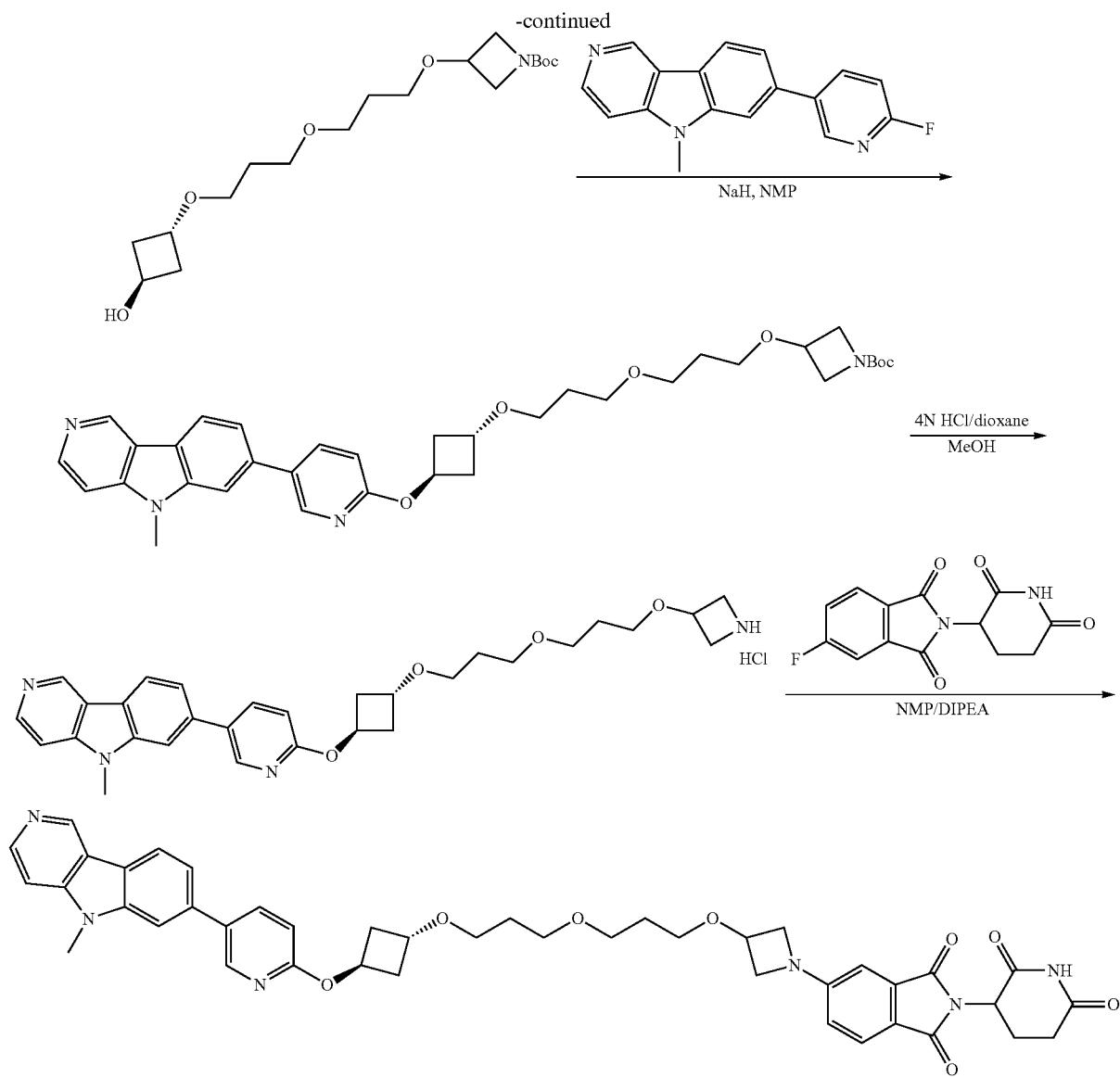

Compound 104

Compound 104: ¹H NMR (400 MHz, DMSO-d6): δ 1.73-1.79 (m, 4H), 1.97-1.99 (m, 2H), 2.31-2.37 (m, 2H), 2.40-2.49 (m, 2H), 2.54-2.59 (m, 1H), 2.83-2.88 (m, 1H), 3.38 (t, J=6.4 Hz, 2H), 3.43-3.49 (m, 6H), 3.82-3.85 (m, 2H), 3.75 (s, 3H), 4.16-4.18 (m, 1H), 4.20-4.26 (m, 2H), 4.43-4.47 (m, 1H), 5.02-5.07 (m, 1H), 5.31-5.34 (m, 1H), 6.62-6.64 (m, 1H), 6.78-6.79 (m, 1H), 6.93 (t, J=8.4 Hz, 1H), 7.59-6.72 (m, 3H), 7.96 (s, 1H), 8.17-8.19 (m, 1H), 8.30 (d, J=8.0 Hz, 1H), 8.49 (d, J=6.4 Hz, 1H), 8.62-8.63 (m, 1H), 9.35 (s, 1H), 11.06 (s, 1H). (M+H)⁺ 773.5.

Using procedures analogous to those described above the following compounds were prepared: 125 (while also using procedures described in Compound 67), 148 (while also using procedures described in Compound 67), Compound 170.

Synthetic Scheme for Exemplary Compound 106

Prepared according to the synthetic schemes below using procedures described above

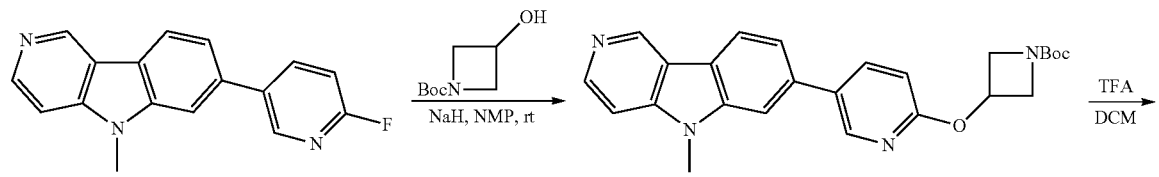

-continued
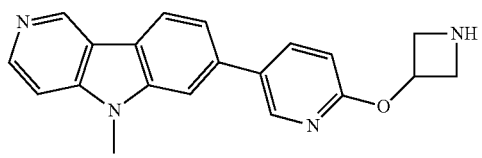
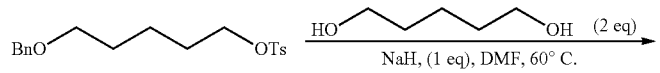
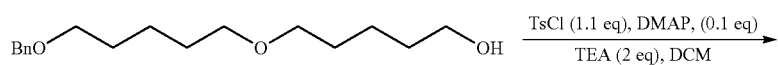
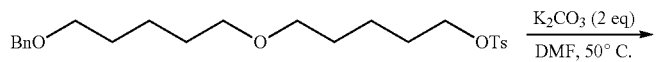
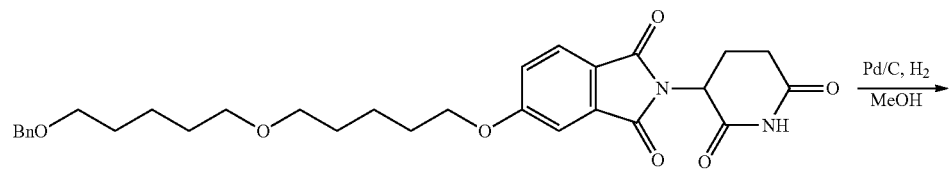
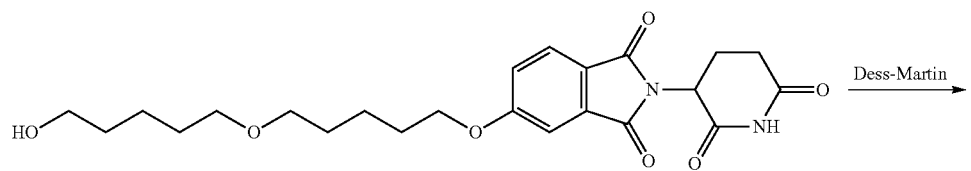
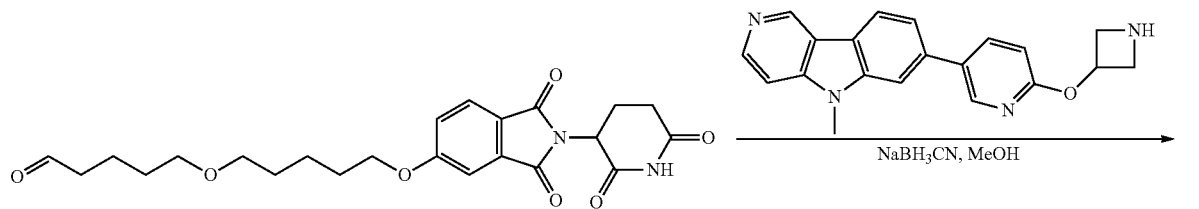
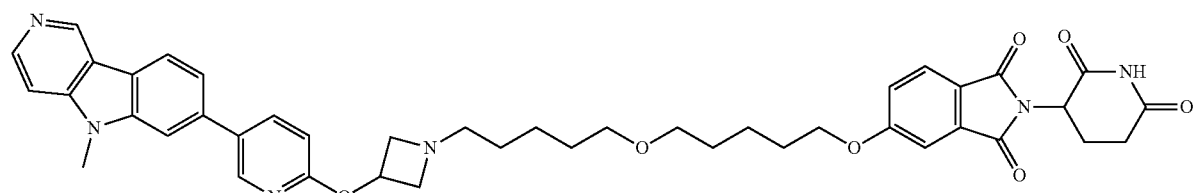
Compound 106

Compound 106: ¹H NMR (400 MHz, DMSO-d6): δ 1.54-1.68 (m, 10H), 1.84-1.88 (m, 2H), 2.12-2.14 (m, 1H), 2.77-2.93 (m, 5H), 3.40-3.45 (m, 4H), 3.64-3.75 (m, 4H), 3.91 (s, 3H), 4.09 (t, J=6.4 Hz, 2H), 4.39-4.46 (m, 1H), 4.89-4.99 (m, 1H), 5.41-5.50 (m, 1H), 6.90 (d, J=8.4 Hz, 1H), 7.14-7.2 (m, 1H), 7.32-7.35 (m, 2H), 7.48 (d, J=8.0 Hz, 1H), 7.55 (s, 1H), 7.76 (d, J=8.0 Hz, 1H), 7.92-8.00 (m, 1H), 8.21 (d, J=8.0 Hz, 1H), 8.43 (d, J=2.0 Hz, 1H), 8.59 (d, J=5.6 Hz, 1H), 9.33 (s, 1H). (M+H)⁺ 759.6.

Synthetic Scheme for Exemplary Compound 107

2-(2,6-dioxopiperidin-3-yl)-5-(4-(4-(6-((5-(5-methyl-5H-pyrido[4,3-b]indol-7-yl)pyridin-2-yl)oxy)-2-azaspiro[3.3]heptan-2-yl)butoxy)butoxy)isoindoline-1,3-dione

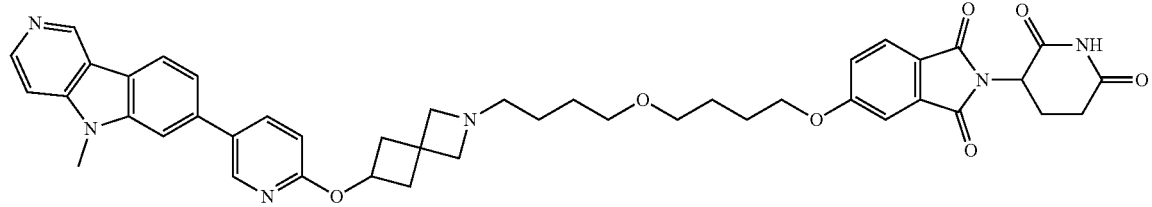 [SMILES: Cn1c2ccncc2c2ccc(-c3ccc(OC4CC5(C4)CN(CCCCOCCCCOc4ccc6c(c4)C(=O)N(C4CCC(=O)NC4=O)C6=O)C5)nc3)cc21]

Prepared according to the synthetic schemes below using procedures described above and common procedures known to those skilled in the art.

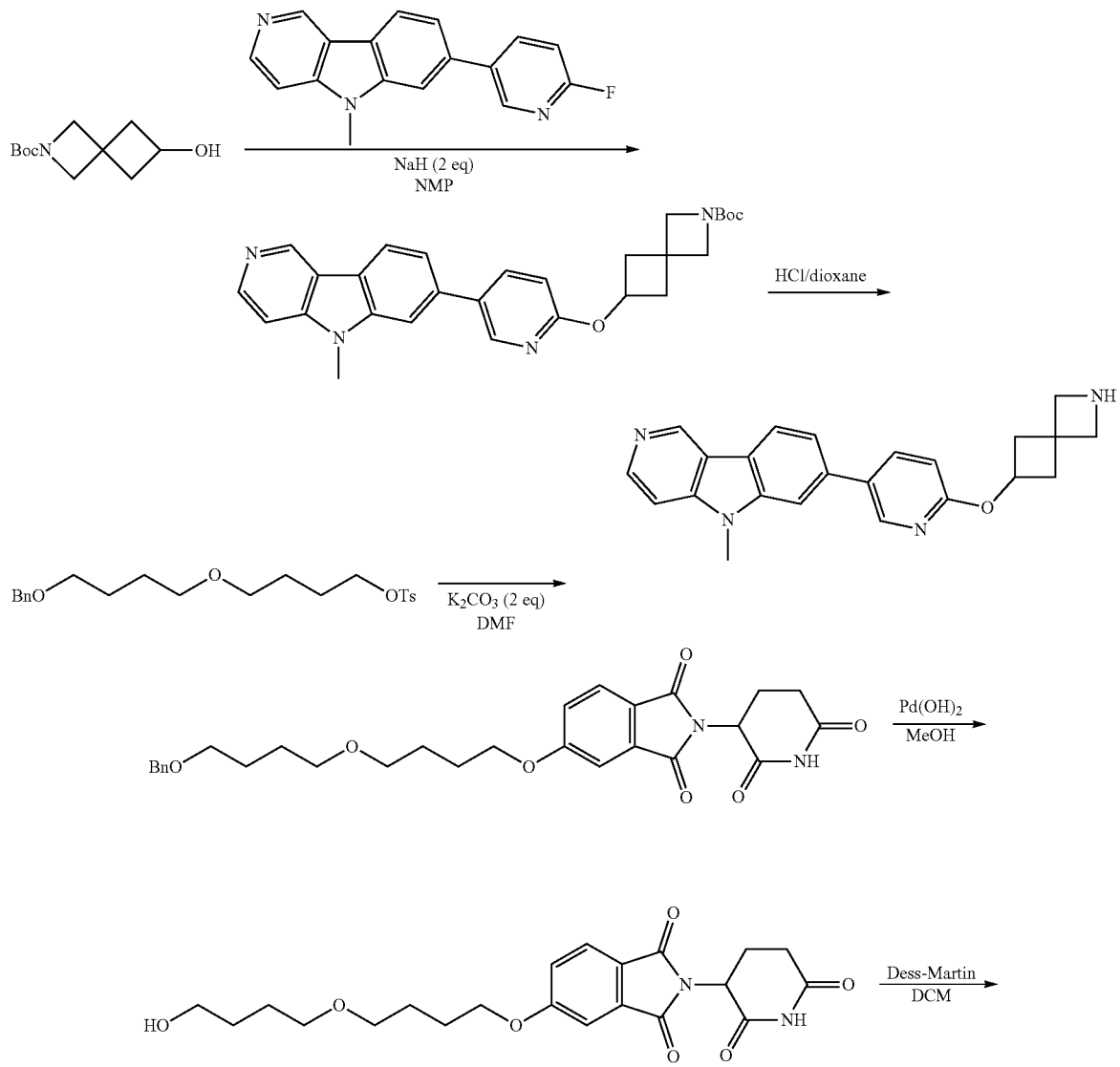

451

452

-continued

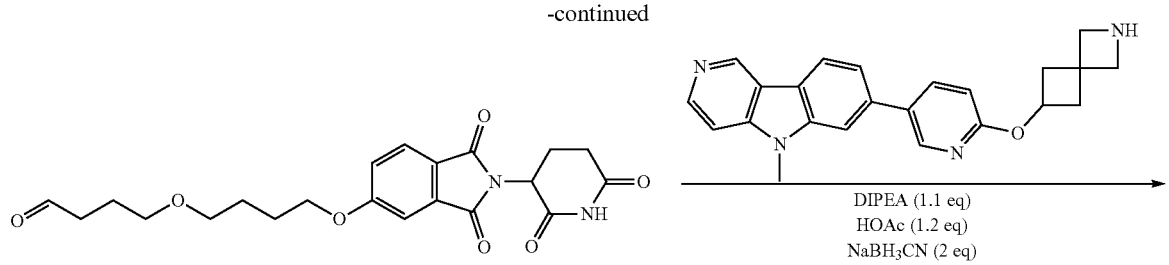

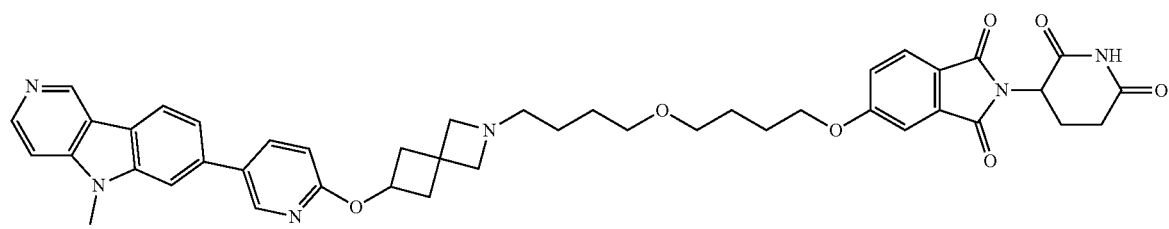

Compound 107

Compound 107: 1HNMR (400 MHz, CDCl$_3$): δ 1.61-1.65 (m, 2H), 1.72-1.77 (m, 4H), 1.90-1.93 (m, 2H), 1.99-2.04 (m, 1H), 2.14-2.22 (m, 3H), 2.44-2.49 (m, 2H), 2.78-3.01 (m, 6H), 3.44-3.49 (m, 4H), 3.92 (s, 3H), 3.99-4.05 (m, 2H), 4.14 (t, J=6.2 Hz, 2H), 4.94-4.98 (m, 1H), 5.17-5.20 (m, 1H), 6.81 (d, J=8.4 Hz, 1H), 7.19-7.21 (m, 1H), 7.33-7.37 (m, 2H), 7.49 (d, J=8.4 Hz, 1H), 7.56 (s, 1H), 7.78 (d, J=8.4 Hz, 1H), 7.90-7.93 (m, 1H), 8.21 (d, J=8.4 Hz, 1H), 8.35 (br, 1H), 8.45-8.46 (m, 1H), 8.59 (d, J=5.6 Hz, 1H), 9.34 (s, 1H). (M+H)$^+$ 771.6.

Synthetic Scheme for Exemplary Compound 108

2-(2,6-dioxopiperidin-3-yl)-5-((6-((6-((1r,3r)-3-((5-(5-methyl-5H-pyrido[4,3-b]indol-7-yl)pyridin-2-yl)oxy)cyclobutoxy)pyridin-2-yl)oxy)hexyl)oxy)isoindoline-1,3-dione

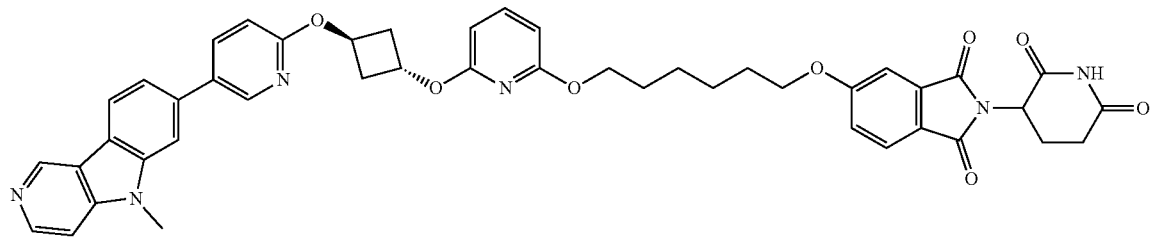 [SMILES: Cn1c2ccncc2c2ccc(-c3ccc(O[C@H]4C[C@H](Oc5cccc(OCCCCCCOc6ccc7c(c6)C(=O)N(C6CCC(=O)NC6=O)C7=O)n5)C4)nc3)cc21]

Prepared according to the synthetic scheme below using procedures described above and common procedures known to those skilled in the art.

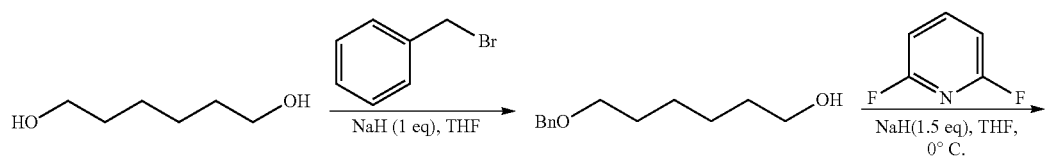

-continued
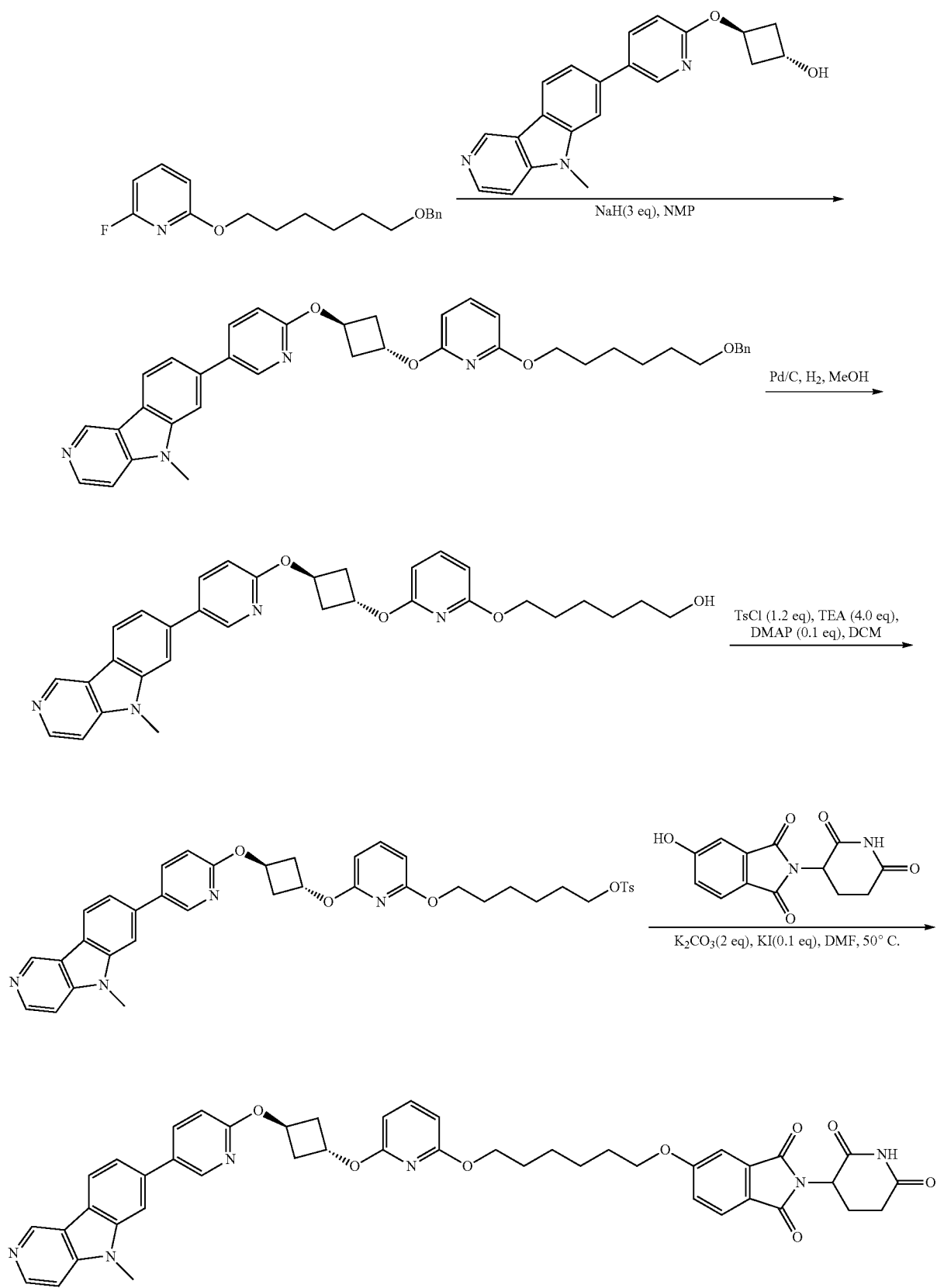
Compound 108

Compound 108: ¹H NMR (400 MHz, DMSOd-6): δ 1.43-1.44 (m, 4H), 1.70-1.74 (m, 4H), 1.98-2.04 (m, 1H), 2.44-2.47 (m, 1H), 2.56-2.60 (m, 1H), 2.65 (t, J=6.0 Hz, 4H), 2.83-2.92 (m, 1H), 3.95 (s, 3H), 4.10 (t, J=6.0 Hz, 2H), 4.22 (t, J=6.4 Hz, 2H), 5.07-5.11 (m, 1H), 5.30-5.35 (m, 1H), 5.39-5.45 (m, 1H), 6.34-6.37 (m, 2H), 6.98 (d, J=8.4 Hz, 1H), 7.24-7.26 (m, 1H), 7.33 (d, J=2.0 Hz, 1H), 7.59-7.65 (m, 3H), 7.72 (d, J=8.0 Hz, 1H), 7.97 (s, 1H), 8.17-8.21 (m, 1H), 8.31 (d, J=8.0 Hz, 1H), 8.50 (d, J=6.0 Hz, 1H), 8.65 (d, J=2.0 Hz, 1H), 9.36 (s, 1H), 11.10 (s, 1H). (M+H)⁺ 795.5.

Synthetic Scheme for Exemplary Compound 109

2-(2,6-dioxopiperidin-3-yl)-5-((6-((4-((1r,3r)-3-((5-(5-methyl-5H-pyrido[4,3-b]indol-7-yl)pyridin-2-yl)oxy)cyclobutoxy)pyridin-2-yl)oxy)hexyl)oxy)isoindoline-1,3-dione

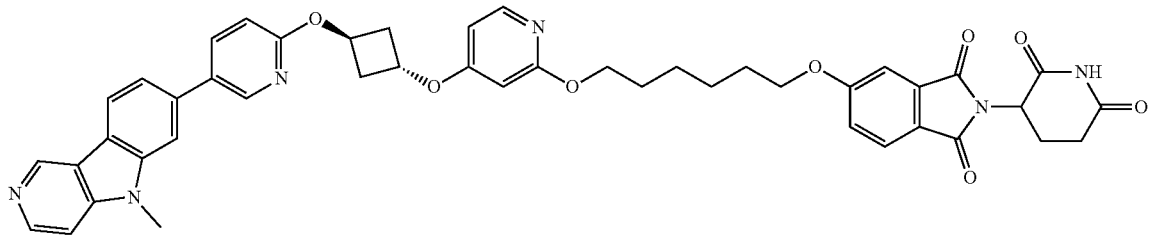 [SMILES: Cn1c2ccncc2c2ccc(-c3ccc(O[C@H]4C[C@H](Oc5ccnc(OCCCCCCOc6ccc7c(c6)C(=O)N(C6CCC(=O)NC6=O)C7=O)c5)C4)nc3)cc21]

Prepared according to the synthetic scheme below using procedures described above and common procedures known to those skilled in the art.

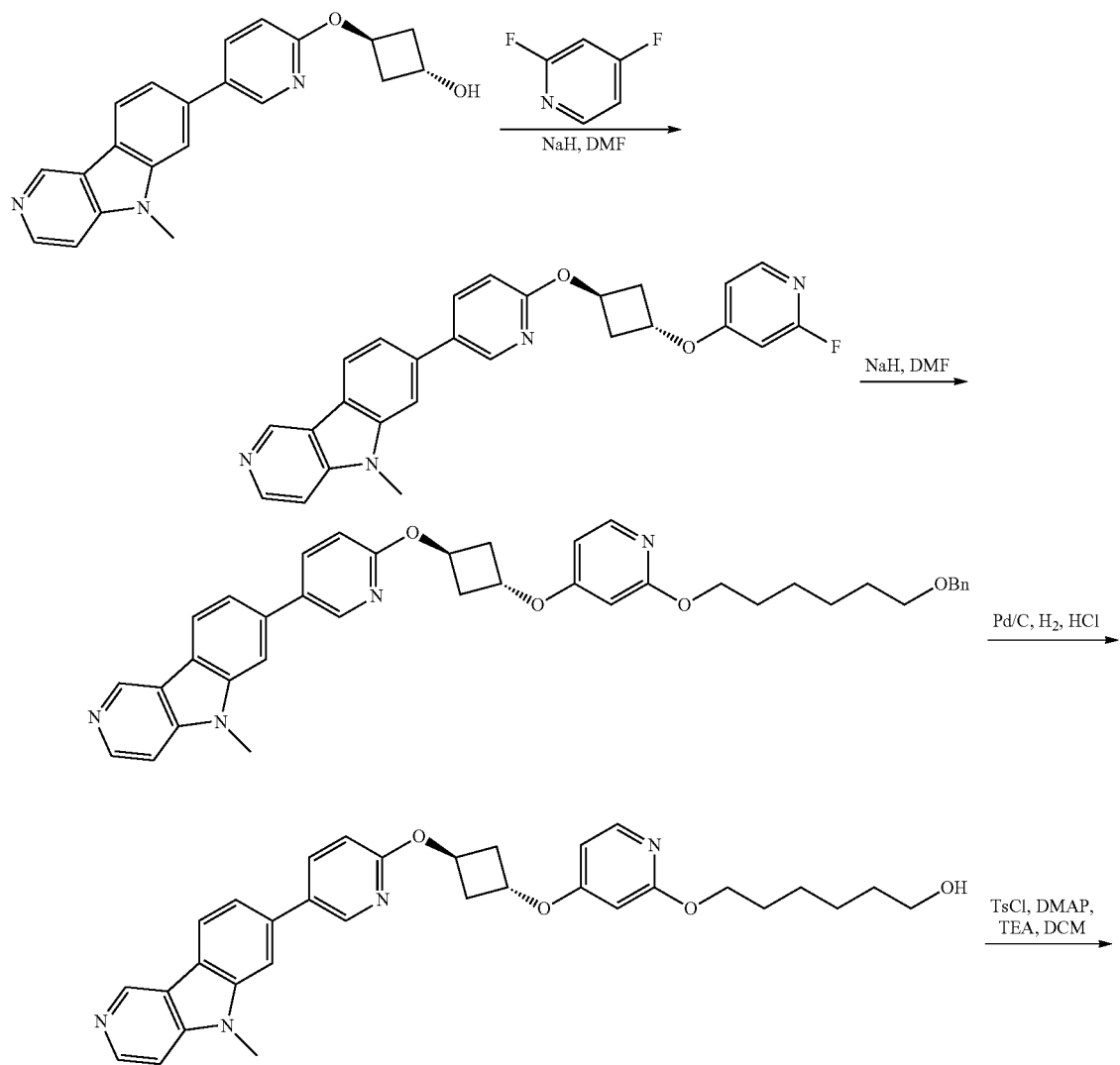

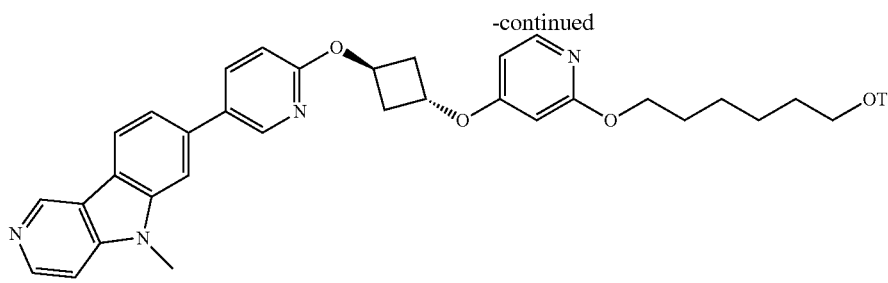
-continued
K₂CO₃, KI, DMF,
50° C., overnight
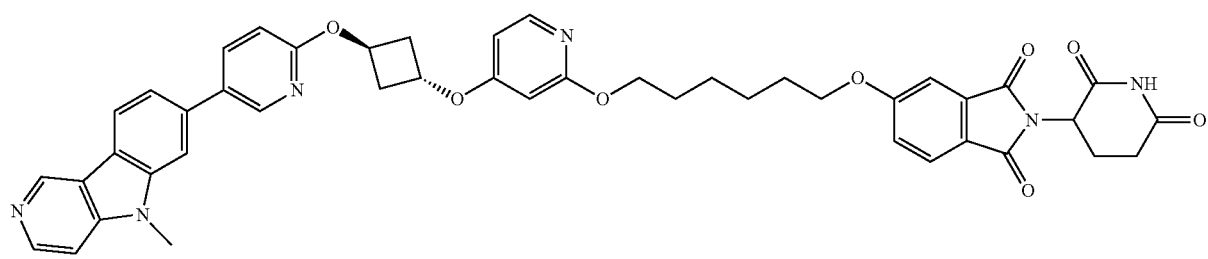
Compound 109
Compound 109: 1H NMR (400 MHz, DMSOd-6): δ 1.47 (s, 4H), 1.72-1.78 (m, 4H), 2.02-2.05 (m, 2H), 2.33 (s, 1H), 2.63-2.66 (m, 4H), 2.88-2.89 (m, 1H), 3.41-3.49 (m, 2H), 3.96 (s, 2H), 4.18-4.23 (m, 3H), 5.04-5.12 (m, 2H), 5.42 (br, 1H), 6.19 (s, 1H), 6.55-6.56 (m, 1H), 6.98 (d, J=8.4 Hz, 1H), 7.34 (d, J=7.2 Hz, 1H), 7.41 (s, 1H), 6.63 (s, 2H), 7.81-7.83 (m, 1H), 7.95-7.97 (m, 2H), 8.21 (d, J=8.4 Hz, 1H), 8.32 (d, J=7.2 Hz, 1H), 8.50 (d, J=4.0 Hz, 1H), 8.64 (s, 1H), 9.36 (s, 1H), 11.11 (s, 1H). (M+H)⁺ 795.5.
Synthetic Scheme for Exemplary Compound 111
2-(2,6-dioxopiperidin-3-yl)-5-(3-((3-(5-((1r,3r)-3-((5-(5-methyl-5H-pyrido[4,3-b]indol-7-yl)pyridin-2-yl)oxy)cyclobutoxy)pyridin-2-yl)prop-2-yn-1-yl)oxy)azetidin-1-yl)isoindoline-1,3-dione
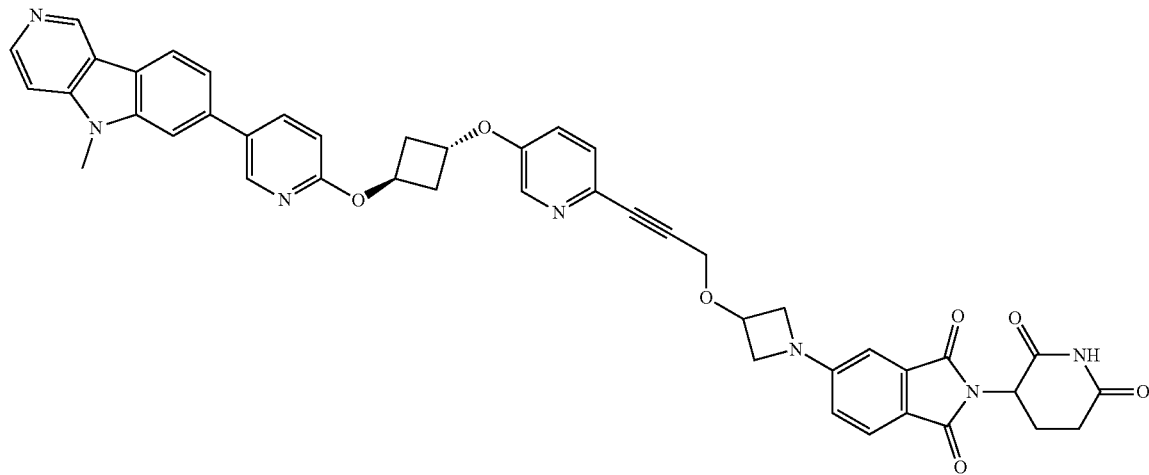 [SMILES: Cn1c2ccncc2c2ccc(-c3ccc(O[C@H]4C[C@H](Oc5ccc(C#CCOC6CN(c7ccc8c(c7)C(=O)N(C7CCC(=O)NC7=O)C8=O)C6)nc5)C4)nc3)cc21]

Step 1: tert-butyl 3-(prop-2-yn-1-yloxy)azetidine-1-carboxylate

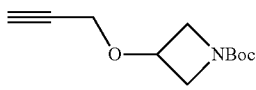

To a stirred solution of tert-butyl 3-hydroxyazetidine-6):-carboxylate 1.72-g, 12.2 mmol) in N,N-dimethylformamide (10 ml) was added sodium hydride (60% in mineral oil) (255 mg, 6.36 mmol) at 0° C., and the resulting mixture was stirred at 0° C. for 30 minutes. The reaction mixture was allowed to warm up to room temperature and stirred for additional 30 min, then 3-bromoprop-1-yne (818 mg, 6.94 mmol) was added, and the resulting reaction mixture was stirred at 50° C. overnight. LCMS showed the reaction was complete. The reaction mixture was quenched with water (10 ml) at 0° C. and extracted with ethyl acetate (30 ml×2). The combined organic layers were washed with brine (30 ml×2), dried over anhydrous sodium sulfate, and concentrated under reduced pressure to give a residue which was purified by silica gel flash chromatography (eluted with 10% ethyl acetate in hexane) to afford tert-butyl 3-(prop-2-yn-1-yloxy)azetidine-1-carboxylate (1.03 g, yield 84%) as colorless oil.

Step 2: tert-butyl 3-((3-(5-hydroxypyridin-2-yl)prop-2-yn-1-yl)oxy)azetidine-1-carboxylate

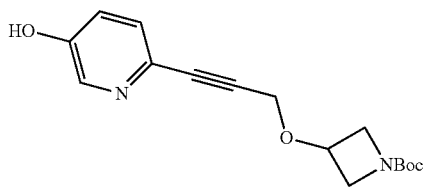 [SMILES: CC(C)(C)OC(=O)N1CC(OCC#Cc2ccc(O)cn2)C1]

To a stirred solution of tert-butyl 3-(prop-2-yn-1-yloxy)azetidine-1-carboxylate (900 mg, 4.27 mmol) and 6-bromopyridin-3-ol (734 mg, 4.27 mmol) in acetonitrile (10 ml) was added triethylamine (863 mg, 8.54 mmol) followed by bis(triphenylphosphine)palladium(II) chloride (150 mg, 0.214 mmol) and cuprous iodide (41 mg, 0.214 mmol) at room temperature under nitrogen atmosphere; the mixture was degassed with nitrogen three times. The reaction mixture was allowed to warm up to 65° C. and stirred overnight. TLC showed the reaction was complete. The mixture was partitioned between ethyl acetate (100 ml) and water (50 ml). The organic layer was washed with brine (50 ml), dried over anhydrous sodium sulfate, and concentrated under reduced pressure to give crude residue which was purified by silica gel flash column chromatography (eluted with 100% ethyl acetate in hexane) to afford tert-butyl 3-((3-(5-hydroxypyridin-2-yl)prop-2-yn-1-yl)oxy)azetidine-1-carboxylate (550 mg, yield 42%) as brown oil.

Step 3: tert-butyl 3-((3-(5-(((1r,3r)-3-((5-(5-methyl-5H-pyrido[4,3-b]indol-7-yl)pyridin-2-yl)oxy)cyclobutoxy)pyridin-2-yl)prop-2-yn-1-yl)oxy)azetidine-1-carboxylate

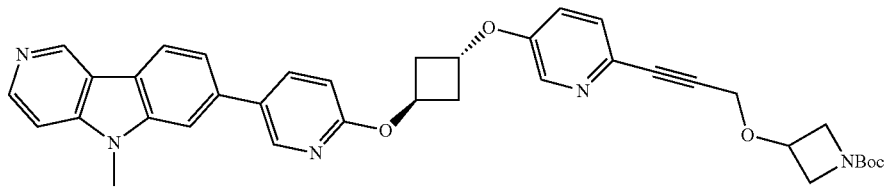 [SMILES: Cn1c2ccncc2c2ccc(-c3ccc(O[C@H]4C[C@H](Oc5ccc(C#CCOC6CN(C(=O)OC(C)(C)C)C6)nc5)C4)nc3)cc21]

A solution of tert-butyl 3-((3-(5-hydroxypyridin-2-yl)prop-2-yn-1-yl)oxy)azetidine-1-carboxylate (100 mg, 0.325 mmol), (1s,3 s)-3-((5-(5-methyl-5H-pyrido[4,3-b]indol-7-yl)pyridin-2-yl)oxy)cyclobutyl methanesulfonate (137 mg, 0.325 mmol) and cesium carbonate (211 mg, 0.65 mmol) in dry N,N-dimethylformamide (2 ml) was stirred at 70° C. for 36 hours. TLC showed the reaction was complete. The mixture was partitioned between ethyl acetate (50 ml) and water (25 ml). The organic layer was collected, washed with brine (25 ml), dried over anhydrous sodium sulfate, and concentrated under reduced pressure to give crude residue which was purified by silica gel flash column chromatography (eluted with 3% methanol in dichloromethane) to afford tert-butyl 3-((3-(5-((1r,3r)-3-((5-(5-methyl-5H-pyrido[4,3-b]indol-7-yl)pyridin-2-yl)oxy)cyclobutoxy)pyridin-2-yl)prop-2-yn-1-yl)oxy)azetidine-1-carboxylate (60 mg, yield 29%) as white solid.

Tert-butyl 3-((3-(5-((1r,3r)-3-((5-(5-methyl-5H-pyrido[4,3-b]indol-7-yl)pyridin-2-yl)oxy)cyclobutoxy)pyridin-2-yl)prop-2-yn-1-yl)oxy)azetidine-1-carboxylate was converted into the final compound, 2-(2,6-dioxopiperidin-3-yl)-5-(3-((3-(5-((1r,3r)-3-((5-(5-methyl-5H-pyrido[4,3-b]indol-7-yl)pyridin-2-yl)oxy)cyclobutoxy)pyridin-2-yl)prop-2-yn-1-yl)oxy)azetidin-1-yl)isoindoline-1,3-dione, according to the synthetic scheme below using procedures described above and common procedures known to those skilled in the art.

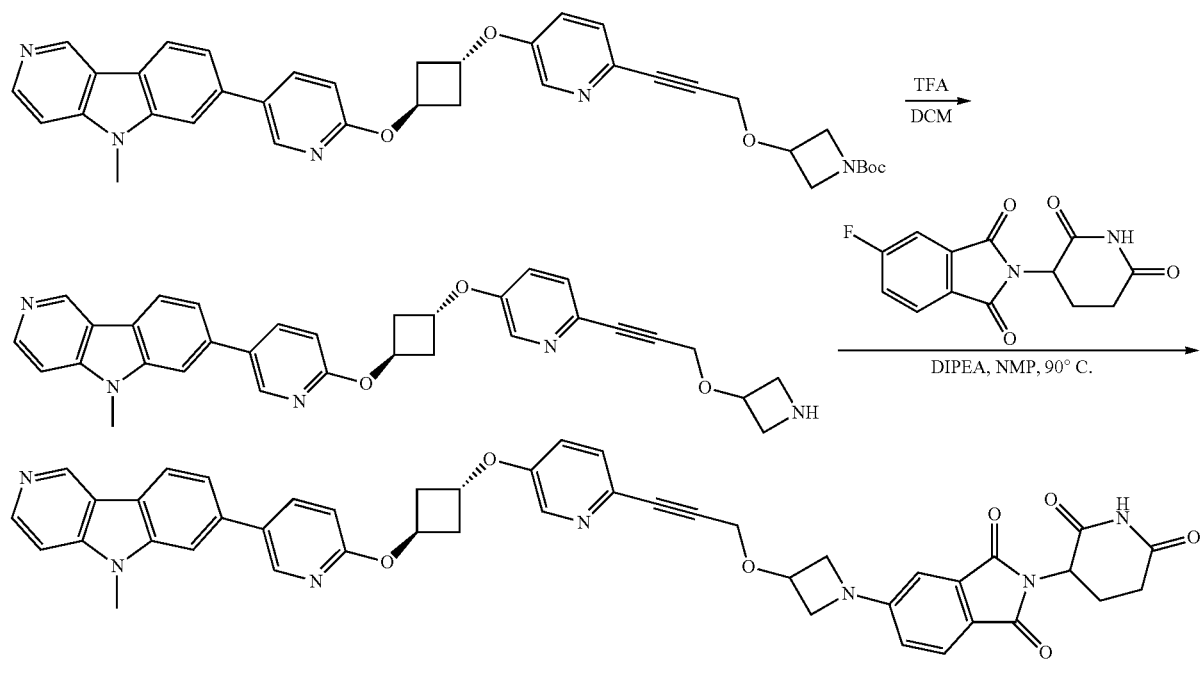

Compound 111

Compound 111: ¹HNMR (400 MHz, DMSO-d6): δ 1.98-2.02 (m, 1H), 2.54-2.73 (m, 6H), 2.83-2.92 (m, 1H), 3.95-3.97 (m, 5H), 4.31-4.34 (m, 2H), 4.50 (s, 2H), 4.67-4.72 (m, 1H), 5.04-5.13 (m, 2H), 5.42-5.48 (m, 1H), 6.67-6.69 (m, 1H), 6.82 (s, 1H), 6.69-7.01 (m, 1H), 7.33-7.36 (m, 1H), 7.53-7.55 (m, 1H), 7.63-7.67 (m, 3H), 8.01 (s, 1H), 8.21-8.26 (m, 2H), 8.33-8.37 (m, 1H), 8.51-8.55 (m, 1H), 8.65-8.66 (m, 1H), 9.39 (s, 1H), 11.07 (s, 1H). (M+H)⁺ 788.5.

Using analogous procedures the following exemplary compounds were prepared: 194.

Synthetic Scheme for Exemplary Compound 114

2-(2,6-dioxopiperidin-3-yl)-5-((5-(4-((1r,3r)-3-((5-(5-methyl-5H-pyrido[4,3-b]indol-7-yl)pyridin-2-yl)oxy)cyclobutoxy)butoxy)pentyl)oxy)isoindoline-1,3-dione

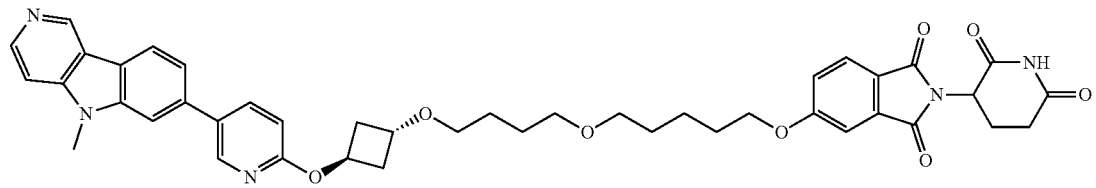 [SMILES: Cn1c2ccncc2c2ccc(-c3ccc(O[C@H]4C[C@H](OCCCCOCCCCCOc5ccc6c(c5)C(=O)N(C5CCC(=O)NC5=O)C6=O)C4)nc3)cc21]

Prepared according to the synthetic scheme below using procedures described above and common procedures known to those skilled in the art.

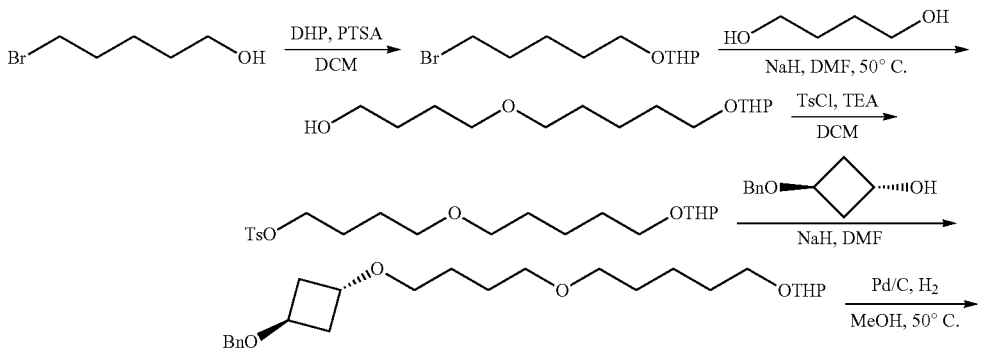

463 464
-continued
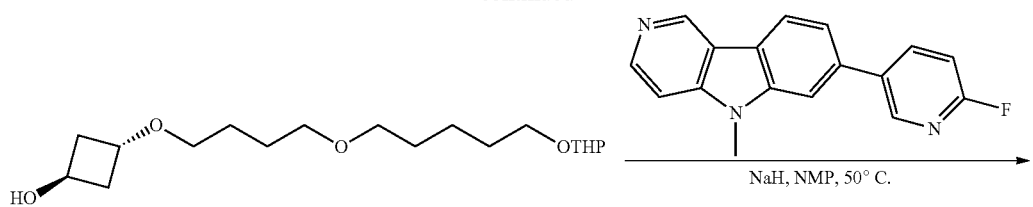
NaH, NMP, 50° C.
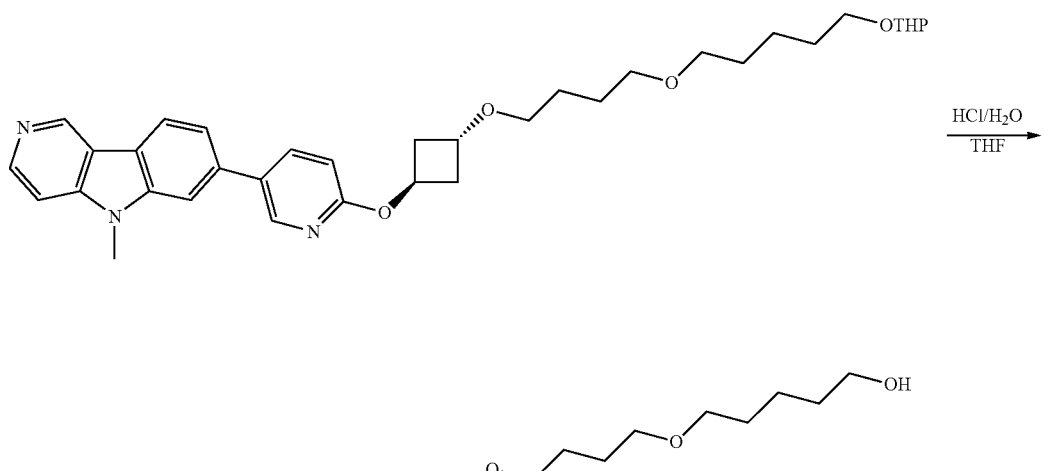
HCl/H₂O / THF
TsCl, TEA / DCM
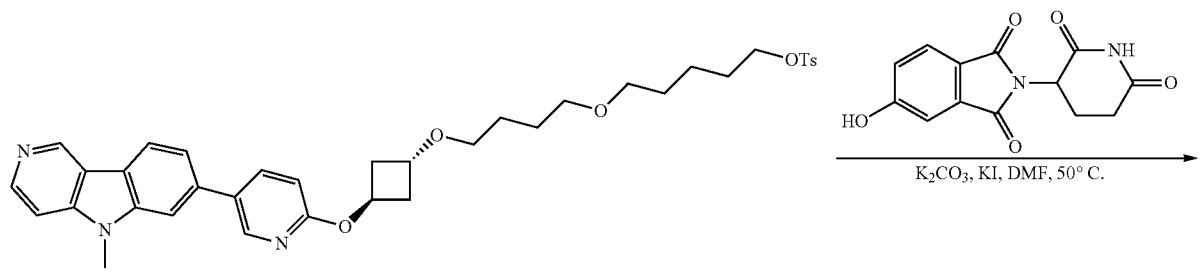
K₂CO₃, KI, DMF, 50° C.
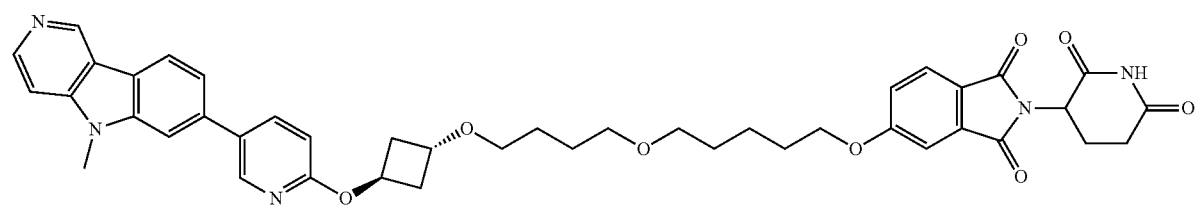
Compound 114

Compound 114: $^1$H NMR (400 MHz, CDCl$_3$): δ 1.52-1.59 (m, 2H), 1.63-1.67 (m, 5H), 1.83-1.90 (m, 1H), 2.11-2.16 (m, 2H), 2.43-2.54 (m, 4H), 2.71-2.92 (m, 4H), 3.39-3.49 (m, 6H), 3.95 (s, 3H), 4.08 (t, J=6.4 Hz, 2H), 4.23-4.29 (m, 1H), 4.94 (dd, J=5.2, 12.0 Hz, 1H), 6.83 (d, J=8.4 Hz, 1H), 7.17 (dd, J=2.0, 8.0 Hz, 1H), 7.32 (d, J=1.6 Hz, 1H), 7.44 (d, J=6.0 Hz, 1H), 7.54 (d, J=8.0 Hz, 1H), 7.60 (s, 1H), 7.75 (d, J=8.4 Hz, 1H), 7.91 (dd, J=2.4, 8.8 Hz, 1H), 8.14 (m, 1H), 8.21 (d, J=8.0 Hz, 1H), 8.48 (d, J=2.4 Hz, 1H), 8.58 (d, J=5.2 Hz, 1H), 9.34 (s, 1H). (M+H)$^+$ 760.5.

Using procedures analogous to those for Compound 140, the following were prepared: Compound 115.

Synthetic Scheme for Exemplary Compound 116

2-(2,6-dioxopiperidin-3-yl)-5-((2-(4-(4-((5-(5-methyl-5H-pyrido[4,3-b]indol-7-yl)pyridin-2-yl)oxy)butoxy)butyl)-2-azaspiro[3.3]heptan-6-yl)oxy)isoindoline-1,3-dione

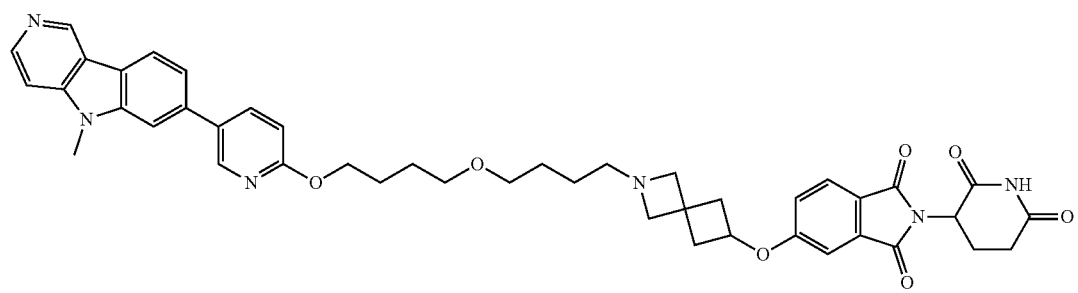 [SMILES: Cn1c2ccncc2c2ccc(-c3ccc(OCCCCOCCCCN4CC5(CC(Oc6ccc7c(c6)C(=O)N(C6CCC(=O)NC6=O)C7=O)C5)C4)nc3)cc21]

Prepared according to the synthetic schemes below using procedures described above and common procedures known to those skilled in the art.

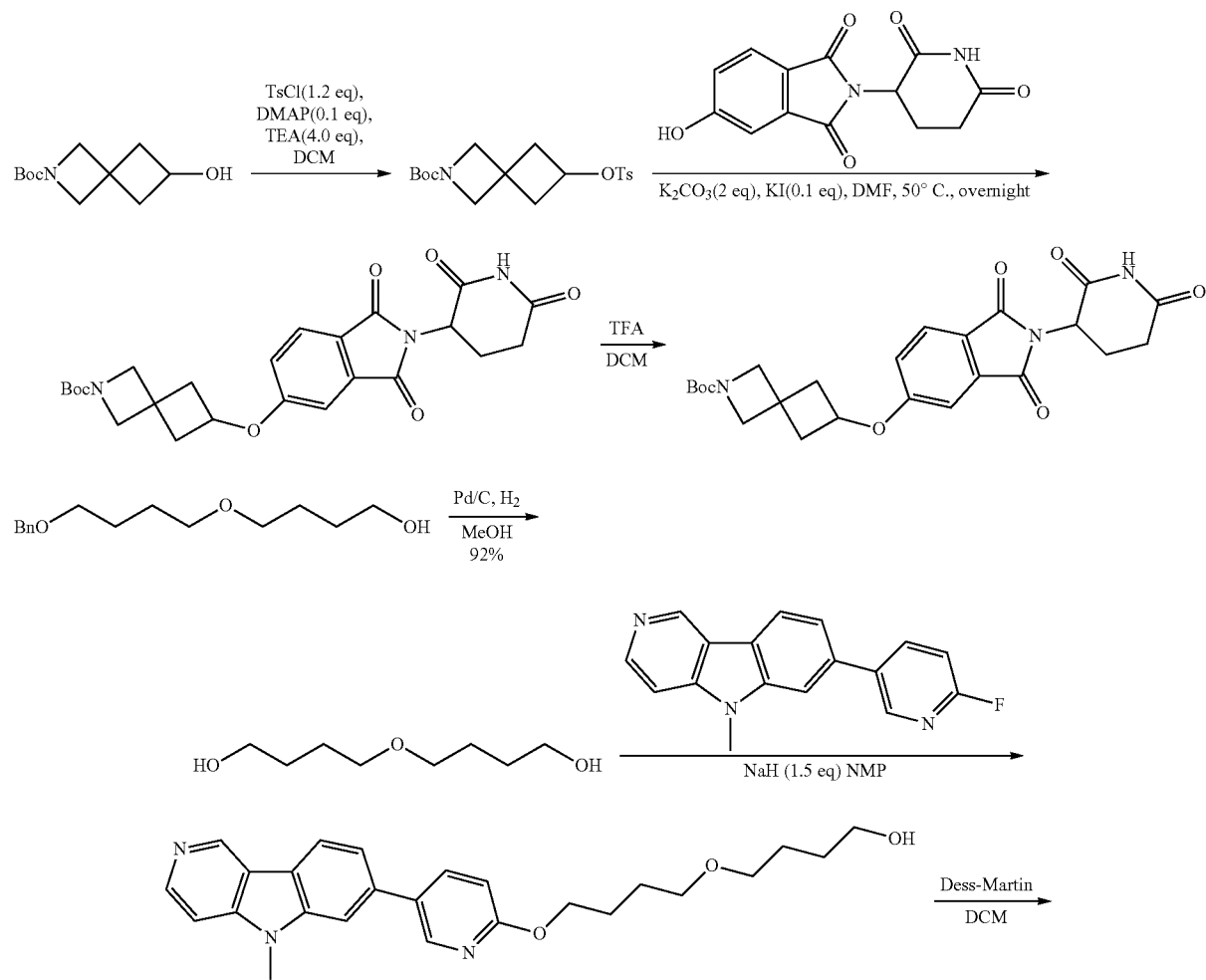

467 468
-continued
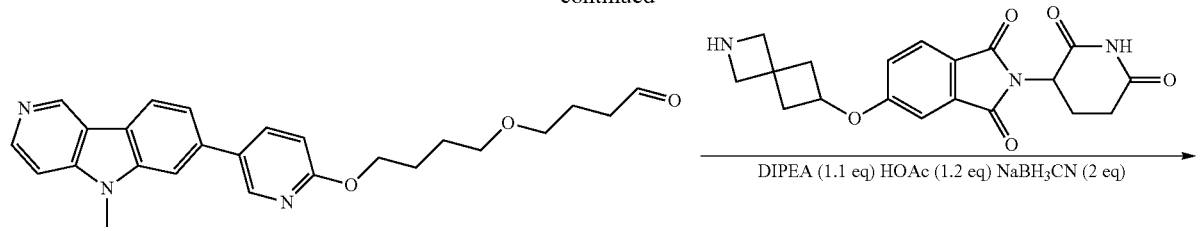
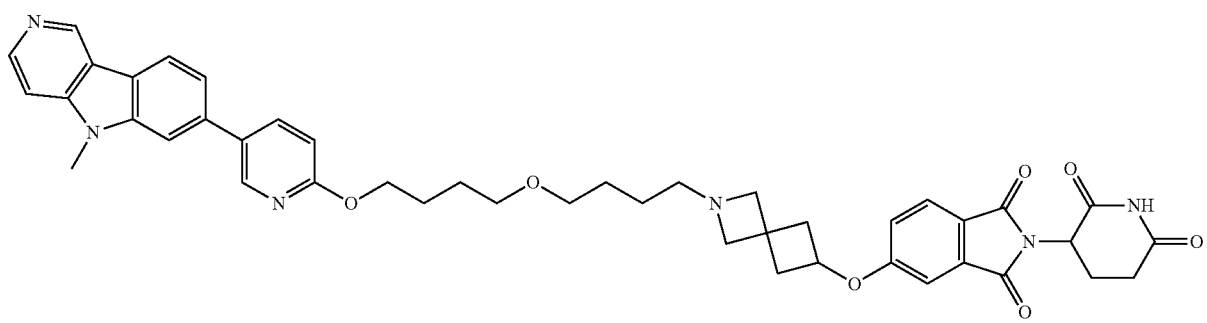
Compound 116
Compound 116: 1HNMR (400 MHz, CDCl$_3$): δ 1.39-1.42 (m, 2H), 1.47-1.52 (m, 2H), 1.64-1.70 (m, 2H), 1.77-1.82 (m, 2H), 2.01-2.07 (m, 1H), 2.21-2.26 (m, 2H), 2.54-2.64 (m, 3H), 2.75-2.90 (m, 5H), 3.42-3.45 (m, 3H), 3.61-3.71 (m, 4H), 3.95 (s, 3H), 4.35 (t, J=6.2 Hz, 2H), 4.78-4.82 (m, 1H), 5.09-5.13 (m, 1H), 6.94 (d, J=8.4 Hz, 1H), 7.20-7.25 (m, 2H), 7.60-7.63 (m, 2H), 7.79 (d, J=8.0 Hz, 1H), 7.97 (s, 1H), 8.18-8.20 (m, 1H), 8.31 (d, J=8.0 Hz, 1H), 8.48 (d, J=5.2 Hz, 1H), 8.65 (s, 1H), 9.34 (s, 1H), 11.11 (s, 1H). (M+H)$^+$ 771.6.
Synthetic Scheme for Compound 118
2-(2,6-dioxopiperidin-3-yl)-5-(3-((3-(5-((1r,3r)-3-((5-(5-methyl-5H-pyrido[4,3-b]indol-7-yl)-3-(trifluoromethyl)pyridin-2-yl)oxy)cyclobutoxy)pyridin-2-yl)prop-2-yn-1-yl)oxy)azetidin-1-yl)isoindoline-1,3-dione
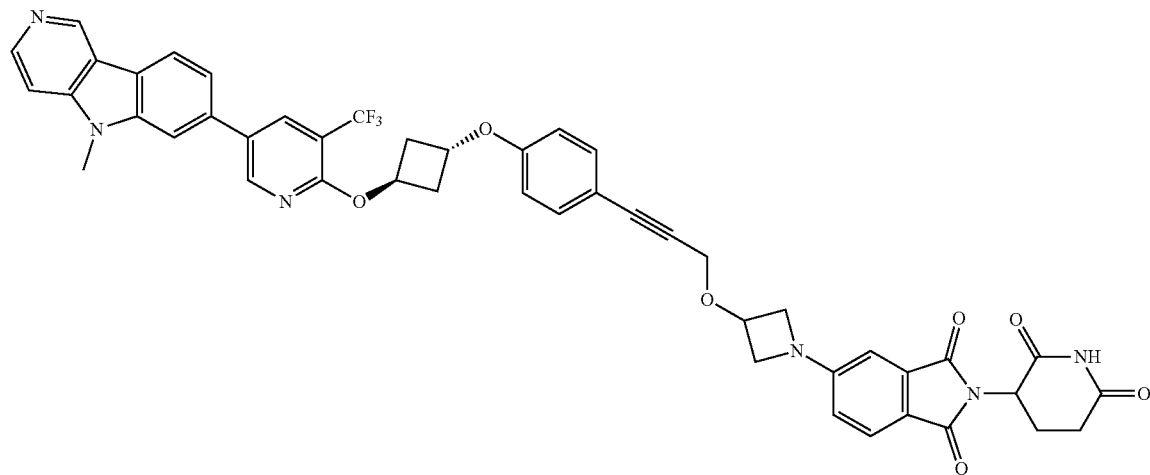 [SMILES: Cn1c2ccncc2c2ccc(-c3cnc(O[C@H]4C[C@H](Oc5ccc(C#CCOC6CN(c7ccc8c(c7)C(=O)N(C7CCC(=O)NC7=O)C8=O)C6)cc5)C4)c(C(F)(F)F)c3)cc21]

Prepared according to the synthetic schemes below using procedures described above and common procedures known to those skilled in the art.
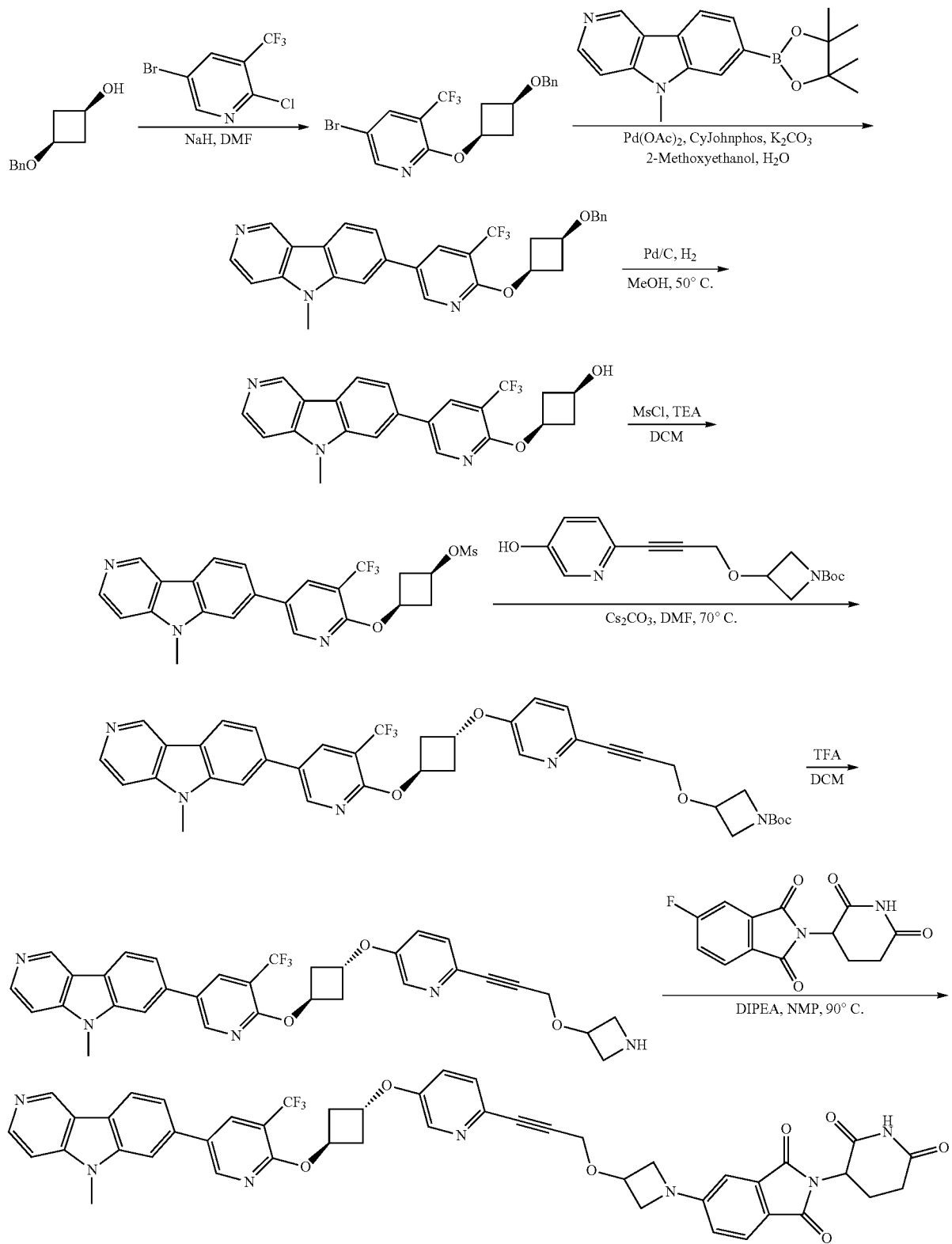
Compound 118

Compound 118: ¹H NMR (400 MHz, DMSO-d6): δ 1.98-2.03 (m, 1H), 2.09-2.15 (m, 1H), 2.20-2.24 (m, 1H), 2.70-2.87 (m, 5H), 4.01-4.04 (m, 4H), 4.29-4.34 (m, 1H), 4.46 (s, 2H), 4.75-4.79 (m, 1H), 4.89-4.95 (m, 1H), 5.00-5.06 (m, 1H), 5.33-5.40 (m, 2H), 5.65-5.70 (m, 1H), 6.53-6.55 (m, 1H), 6.79 (s, 1H), 7.08-7.11 (m, 1H), 7.40 (d, J=8.0 Hz, 1H), 7.56-7.65 (m, 4H), 7.95 (s, 1H), 8.19-8.30 (m, 3H), 8.60-8.64 (m, 2H), 9.38 (s, 1H). (M+H)⁺ 856.5.

Synthetic Scheme for Exemplary Compound 121

(2S,4R)-1-((S)-20-((5-(5H-pyrido[4,3-b]indol-7-yl)pyridin-2-yl)oxy)-2-(tert-butyl)-4-oxo-6,9,12,15,18-pentaoxa-3-azaicosanoyl)-4-hydroxy-N—((S)-1-(4-(4-methylthiazol-5-yl)phenyl)ethyl)pyrrolidine-2-carboxamide

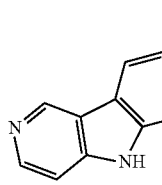
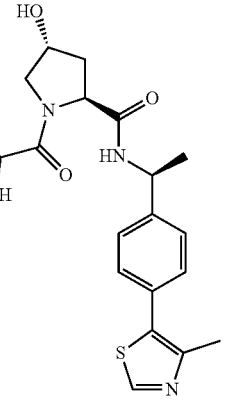

Step 1: 14-((5-bromopyridin-2-yl)oxy)-3,6,9,12-tetraoxatetradecan-1-ol

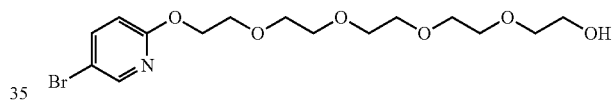

To a solution of 3,6,9,12-tetraoxatetradecane-1,14-diol (20 g, 83.93 mmol) in N,N-dimethylformamide (100 ml) was added sodium hydride (60% in mineral oil) (1.36 g, 34.09 mmol) at 0° C., and the resulting mixture was stirred at 0° C. for 30 minutes. Then 5-bromo-2-fluoropyridine (5 g, 28.41 mmol) was added, and the resulting reaction mixture was stirred at 50° C. for 2 hour. TLC showed the reaction was complete. The reaction mixture was quenched with water (150 ml) at 0° C. and extracted with ethyl acetate (150 ml×2). The combined organic layers was washed with brine (200 ml×2), dried over anhydrous sodium sulfate, and concentrated under reduced pressure to afford a crude residue which was purified by silica gel flash chromatography (eluted with 2% methanol in dichloromethane) to afford 14-((5-bromopyridin-2-yl)oxy)-3,6,9,12-tetraoxatetradecan-1-ol (8 g, yield 72%) as colorless oil.

Step 2: tert-butyl 17-((5-bromopyridin-2-yl)oxy)-3,6,9,12,15-pentaoxaheptadecan-1-oate

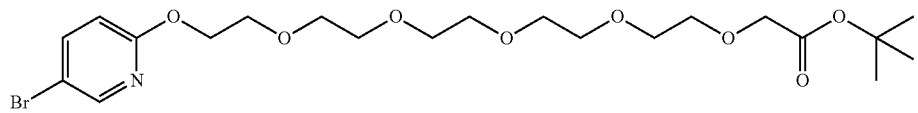 [SMILES: CC(C)(C)OC(=O)COCCOCCOCCOCCOCCOc1ccc(Br)cn1]

To a stirred solution of 14-((5-bromopyridin-2-yl)oxy)-3,6,9,12-tetraoxatetradecan-1-ol (2.00 g, 5.07 mmol) and tetrabutyl ammonium chloride (1.41 g, 5.07 mmol) in dichloromethane (20 ml) and sodium hydroxide (20 ml, 35% in water) was added tert-butyl 2-bromoacetate (2.97 g, 15.22 mmol) at 0° C. The reaction mixture was then allowed to warm up to room temperature and stirred at room temperature overnight. The organic layer was collected, the aqueous layer was extracted with dichloromethane (20 ml). The combined organic layers were washed with brine (20 ml), dried over anhydrous sodium sulfate, and concentrated under reduced pressure to give a crude residue which was purified by silica gel flash column chromatography (eluted with 50% ethyl acetate in hexane) to afford tert-butyl 17-((5-bromopyridin-2-yl)oxy)-3,6,9,12,15-pentaoxaheptadecan-1-oate (1.64 g, yield 64%) as colorless oil.

Step 3: tert-butyl 17-((5-(5H-pyrido[4,3-b]indol-7-yl)pyridin-2-yl)oxy)-3,6,9,12,15-pentaoxaheptadecan-1-oate

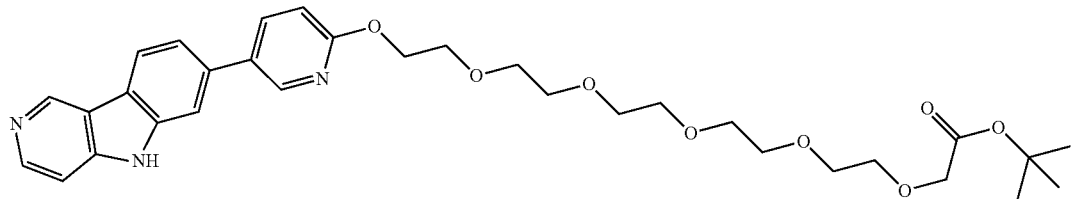 [SMILES: CC(C)(C)OC(=O)COCCOCCOCCOCCOCCOc1ccc(-c2ccc3c(c2)[nH]c2ccncc23)cn1]

To a stirred solution of 7-bromo-5H-pyrido[4,3-b]indole (300 mg, 1.22 mmol), 4,4,4',4',5,5,5',5'-octamethyl-2,2'-bi(1,3,2-dioxaborolane) (620 mg, 2.44 mmol), and potassium acetate (239 mg, 2.44 mmol) in dioxane (5 ml) was added 1,1'-Bis(diphenylphosphino)ferrocene palladium(II)dichloride (176 mg, 0.24 mmol) at room temperature under nitrogen atmosphere, the mixture was degassed with nitrogen three times. The result mixture was stirred at 90° C. overnight. LCMS showed the reaction was complete. To the reaction mixture were added 14-((5-bromopyridin-2-yl)oxy)-3,6,9,12-tetraoxatetradecan-1-ol (930 mg, 1.83 mmol), aqueous sodium carbonate solution (2N, 3.2 ml) and tetrakis(triphenylphosphine)palladium (70 mg, 0.06 mmol); the mixture was degassed with nitrogen three times. The resulting mixture was stirred at 80° C. for 3 hours under nitrogen atmosphere. The reaction mixture was partitioned between ethyl acetate (30 ml) and water (20 ml). The organic layer was collected and the aqueous layer was extracted with ethyl acetate (20 ml). The combined organic layers were washed with brine (30 ml), dried over anhydrous sodium sulfate, and concentrated under reduced pressure to give a crude residue which was purified by silica gel flash chromatography (eluted with 2% methanol in dichloromethane) to afford tert-butyl 17-((5-(5H-pyrido[4,3-b]indol-7-yl)pyridin-2-yl)oxy)-3,6,9,12,15-pentaoxaheptadecan-1-oate (260 mg, yield 36%) as grey oil.

Step 4: 17-((5-(5H-pyrido[4,3-b]indol-7-yl)pyridin-2-yl)oxy)-3,6,9,12,15-pentaoxaheptadecan-1-oic Acid

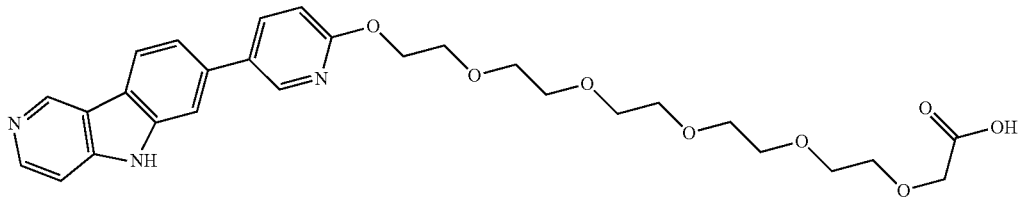 [SMILES: O=C(O)COCCOCCOCCOCCOCCOc1ccc(-c2ccc3c(c2)[nH]c2ccncc23)cn1]

A mixture of tert-butyl 17-((5-(5H-pyrido[4,3-b]indol-7-yl)pyridin-2-yl)oxy)-3,6,9,12,15-pentaoxaheptadecan-1-oate (130 mg, 0.22 mmol) and 2,2,2-trifluoroacetic acid (2 ml) in dichloromethane (1 ml) was stirred at room temperature for one hours. The volatiles were evaporated under reduced pressure to give 17-((5-(5H-pyrido[4,3-b]indol-7-yl)pyridin-2-yl)oxy)-3,6,9,12,15-pentaoxaheptadecan-1-oic acid (120 mg, crude) as brown solid which was used in next step directly without further purification.

Step 5: (2S,4R)-1-((S)-20-((5-(5H-pyrido[4,3-b]indol-7-yl)pyridin-2-yl)oxy)-2-(tert-butyl)-4-oxo-6,9,12,15,18-pentaoxa-3-azaicosan-1-oyl)-4-hydroxy-N—((S)-1-(4-(4-methylthiazol-5-yl)phenyl)ethyl)pyrrolidine-2-carboxamide

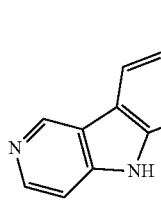
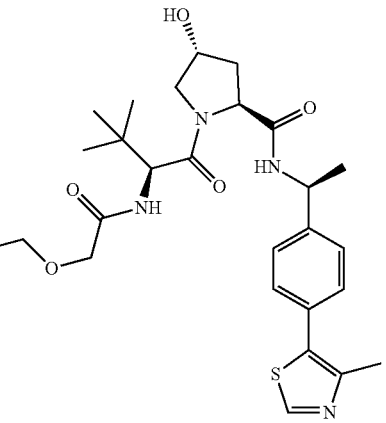

To a stirred solution of 17-((5-(5H-pyrido[4,3-b]indol-7-yl)pyridin-2-yl)oxy)-3,6,9,12,15-pentaoxaheptadecan-1-oic acid (120 mg, crude), (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide hydrochloride (105 mg, 0.22 mmol), and N-ethyl-N-isopropylpropan-2-amine (142 mg, 1.10 mmol) in anhydrous N,N-dimethylformamide (3 ml) was added HATU (2-(7-Aza-1H-benzotriazole-1-yl)-1,1,3,3-tetramethyluronium hexafluorophosphate) (167 mg, 0.44 mmol) at room temperature and stirred for 20 minutes. The mixture was partitioned between ethyl acetate (20 ml) and water (20 ml). The organic layer was collected, washed with brine (20 ml×2), dried over anhydrous sodium sulfate, and concentrated under reduced pressure to give a crude residue which was purified by preparative TLC (eluted with 10% methanol in dichloromethane) to afford (2S,4R)-1-((S)-20-((5-(5H-pyrido[4,3-b]indol-7-yl)pyridin-2-yl)oxy)-2-(tert-butyl)-4-oxo-6,9,12,15,18-pentaoxa-3-azaicosan-1-oyl)-4-hydroxy-N—((S)-1-(4-(4-methylthiazol-5-yl)phenyl)ethyl)pyrrolidine-2-carboxamide (28 mg, yield 13%) as white solid.

$^1$H NMR (400 MHz, DMSOd-6): δ 0.93 (s, 9H), 1.36-1.47 (m, 3H), 1.73-1.80 (m, 1H), 1.96-2.09 (m, 2H), 3.23-3.60 (m, 16H), 3.79 (t, J=3.6 Hz, 2H), 3.96 (s, 2H), 4.28 (s, 1H), 4.42-4.46 (m, 3H), 4.54 (d, J=9.6 Hz, 1H), 4.90 (t, J=7.6 Hz, 1H), 5.12 (s, 1H), 6.97 (d, J=8.4 Hz, 1H), 7.35-7.43 (m, 5H), 7.65-7.69 (m, 2H), 7.87 (s, 1H), 8.12-8.15 (m, 1H), 8.37-8.43 (m, 2H), 8.51 (d, J=5.6 Hz, 1H), 8.59 (d, J=1.6 Hz, 1H), 8.97 (s, 1H), 9.51 (s, 1H), 12.28 (s, 1H). (M+H)$^+$ 966.7.

Using analogous procedures the following were prepared: Compound 1, Compound 5, Compound 6, Compound 120, and Compound 122.

Synthetic Scheme for Exemplary Compound 119

(2S,4R)-1-((S)-17-((5-(5H-pyrido[4,3-b]indol-7-yl)-3-(trifluoromethyl)pyridin-2-yl)oxy)-2-(tert-butyl)-4-oxo-6,9,12,15-tetraoxa-3-azaheptadecanoyl)-4-hydroxy-N—((S)-1-(4-(4-methylthiazol-5-yl)phenyl)ethyl)pyrrolidine-2-carboxamide

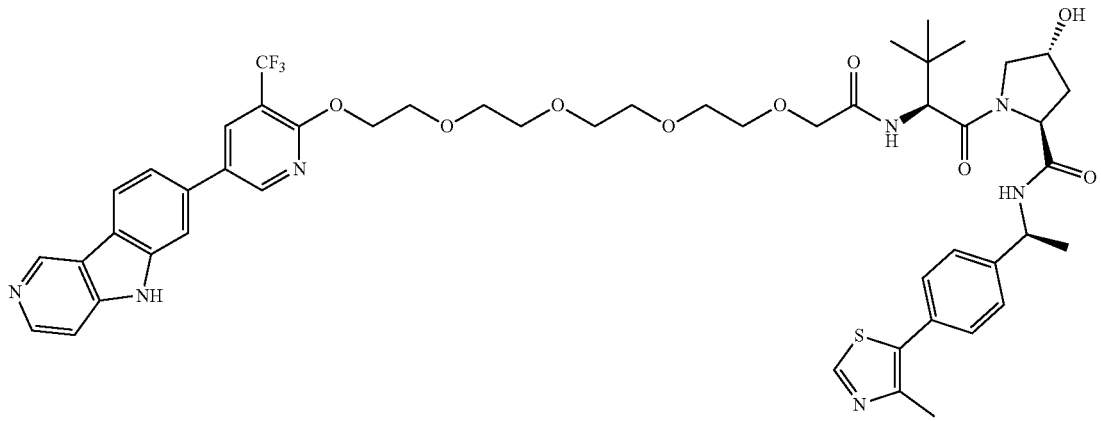 [SMILES: Cc1ncsc1-c1ccc([C@H](C)NC(=O)[C@@H]2C[C@@H](O)CN2C(=O)[C@@H](NC(=O)COCCOCCOCCOCCOc2ncc(-c3ccc4c(c3)[nH]c3ccncc34)cc2C(F)(F)F)C(C)(C)C)cc1]

Prepared according to the synthetic scheme below using procedures described above and common procedures known to those skilled in the art.
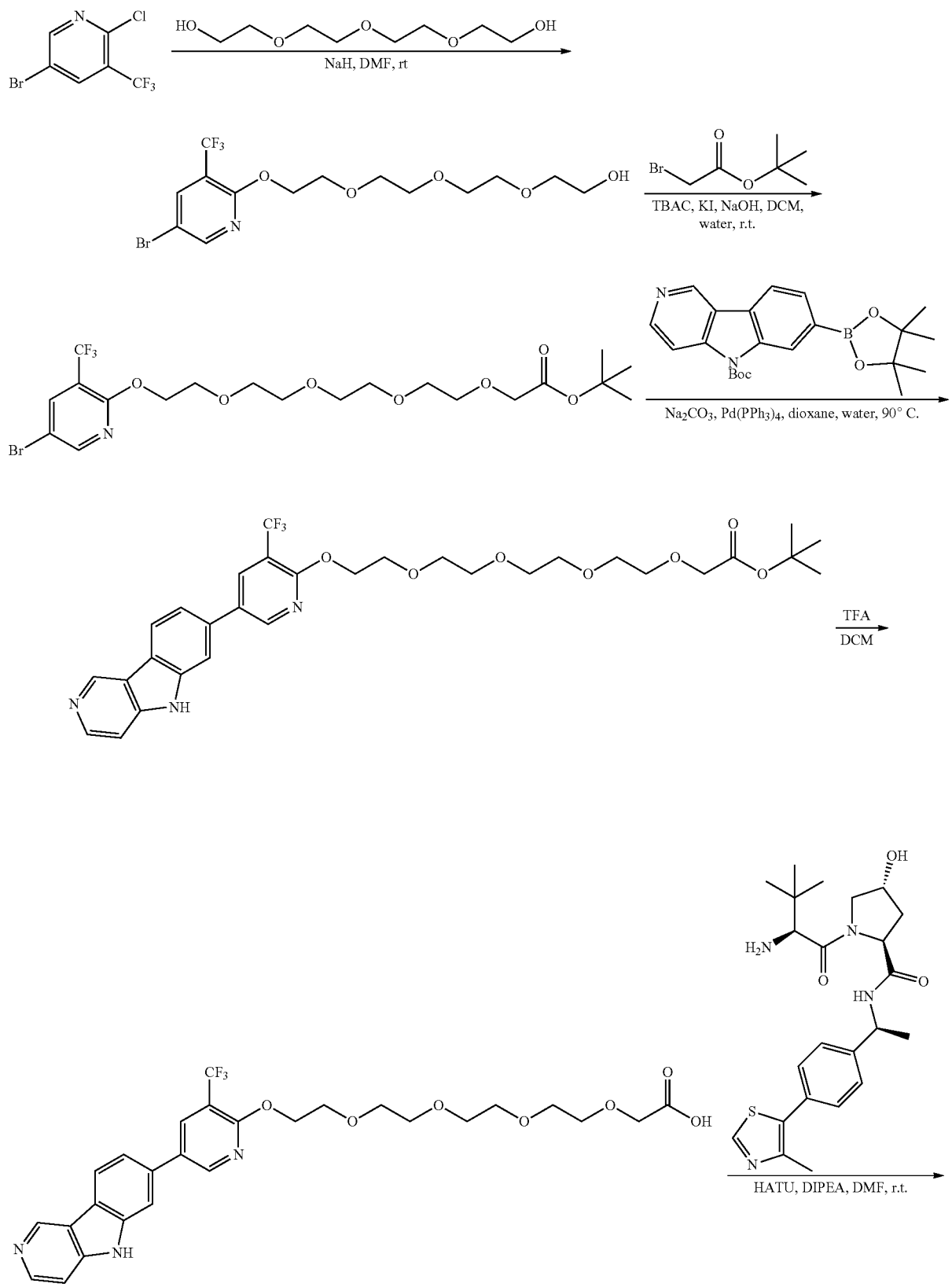

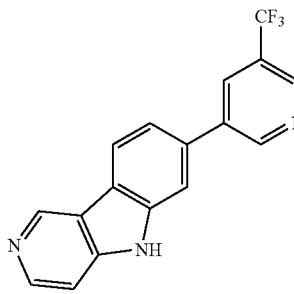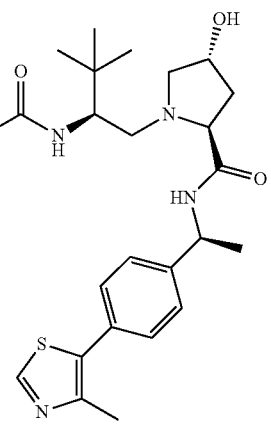

Compound 119

Compound 119: $^1$H NMR (400 MHz, DMSO-d$_6$): δ 0.93 (s, 9H), 1.35 (t, J=6.8 Hz, 3H), 1.77-1.78 (s, 1H), 2.02-2.04 (m, 1H), 2.44 (s, 3H), 3.53-3.64 (m, 14H), 3.80-3.85 (m, 2H), 3.95 (s, 2H), 4.28 (s, 1H), 4.44 (d, J=8.2 Hz, 1H), 4.54 (d, J=9.6 Hz, 1H), 4.58-4.63 (m, 2H), 4.90 (s, 1H), 5.12 (s, 1H), 7.26-7.50 (m, 5H), 7.54 (d, J=5.8 Hz, 1H), 7.66 (d, J=8.2 Hz, 1H), 7.90 (s, 1H), 8.35 (d, J=8.0 Hz, 1H), 8.42-8.45 (m, 3H), 8.85 (s, 1H), 8.97 (s, 1H), 9.41 (s, 1H), 11.92 (s, 1H). (M+H)$^+$ 990.7.

Synthetic Scheme for Exemplary Compound 126

2-(2,6-dioxopiperidin-3-yl)-5-((5-(6-(methyl((1r,3r)-3-((5-(5-methyl-5H-pyrido[4,3-b]indol-7-yl)pyridin-2-yl)oxy)cyclobutyl)amino)-2-azaspiro[3.3]heptan-2-yl)pentyl)oxy)isoindoline-1,3-dione

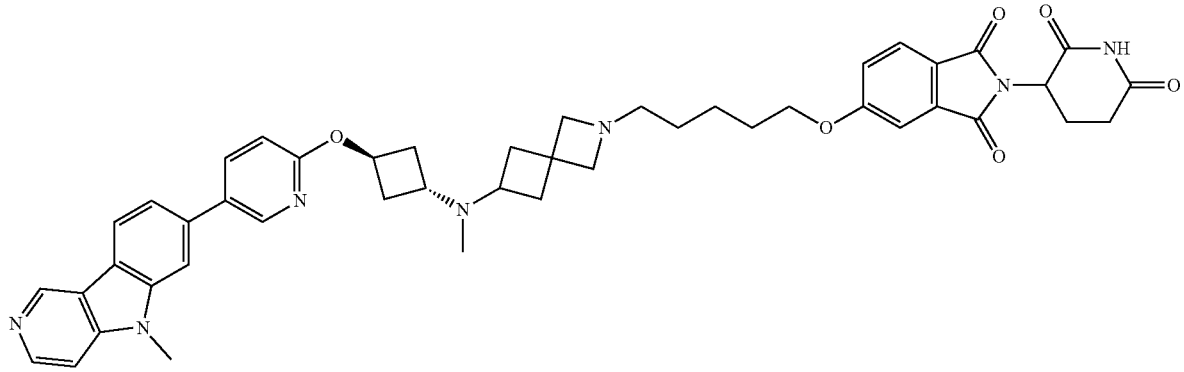 [SMILES: Cn1c2ccncc2c2ccc(-c3ccc(O[C@H]4C[C@H](N(C)C5CC6(C5)CN(CCCCCOc5ccc7c(c5)C(=O)N(C5CCC(=O)NC5=O)C7=O)C6)C4)nc3)cc21]

Step 1: (1r,3r)-3-(methylamino)cyclobutanol

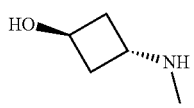

To a solution of tert-butyl ((1r,3r)-3-hydroxycyclobutyl) carbamate (2 g, 10.7 mmol) in tetrahydrofuran (30 ml) was added lithium aluminum hydride (1.6 g, 42.7 mmol) at 0° C. The mixture was stirred at 65° C. for 2 hours. TLC showed the reaction was complete. The mixture was quenched with water (1.6 ml), sodium hydroxide (1.6 ml, 15% in water) and water (4.8 ml) at 0° C. The mixture was stirred at room temperature for 15 minutes and filtered. The filtrate was dried over anhydrous sodium sulfate, and concentrated under reduced pressure to give a crude (1r,3r)-3-(methylamino)cyclobutanol (1.3 g) as colorless oil which was used in the next step without further purification.

Step 2: tert-butyl ((1r,3r)-3-hydroxycyclobutyl)(methyl)carbamate

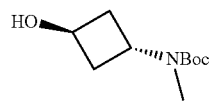

To a solution of (1r,3r)-3-(methylamino)cyclobutanol (1.3 g, 12.8 mmol) and triethylamine (2.6 g, 25.7 mmol) in dichloromethane (10 ml) was added di-tert-butyl carbonate (4.2 g, 19.28 mmol) at room temperature. The mixture was stirred at room temperature for 12 hours. TLC showed the reaction was complete. The mixture was diluted with dichloromethane (10 ml) and washed with aqueous hydrochloride acid (1N, 10 ml). The organic layer was collected, washed with brine (20 ml), dried over anhydrous sodium sulfate, and concentrated under reduced pressure to give a crude residue which was purified by silica gel flash chromatography (eluted with 33-50% ethyl acetate in hexane) to afford tert-butyl ((1r,3r)-3-hydroxycyclobutyl)(methyl)carbamate (1.2 g, two steps 56%) as colorless oil.

Step 3: tert-butyl methyl((1r,3r)-3-((5-(5-methyl-5H-pyrido[4,3-b]indol-7-yl)pyridin-2-yl)oxy)cyclobutyl)carbamate

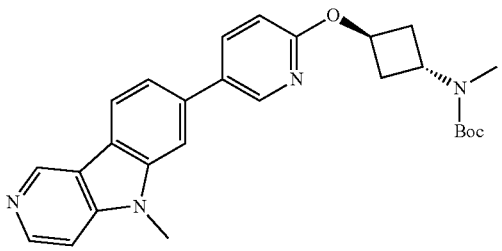 [SMILES: Cn1c2ccncc2c2ccc(-c3ccc(O[C@H]4C[C@H](N(C)C(=O)OC(C)(C)C)C4)nc3)cc21]

To a solution of 7-(6-fluoropyridin-3-yl)-5-methyl-5H-pyrido[4,3-b]indole (300 mg, 1.1 mmol) and tert-butyl ((1r,3r)-3-hydroxycyclobutyl)(methyl)carbamate (218 mg, 1.1 mmol) in 1-methylpyrrolidin-2-one (3 ml) was added sodium hydride (60% in mineral oil) at 0° C. The mixture was allowed to cool to room temperature and stirred at room temperature for 30 minutes. LC-MS showed the reaction was complete. The mixture was partitioned between ethyl acetate (30 ml) and water (30 ml). The organic layer was collected, washed with brine (20 ml), dried over anhydrous sodium sulfate, and concentrated under reduced pressure to give a crude residue which was purified by silica gel flash chromatography (eluted with 1-2% methanol in dichloromethane) to afford tert-butyl methyl((1r,3r)-3-((5-(5-methyl-5H-pyrido[4,3-b]indol-7-yl)pyridin-2-yl)oxy)cyclobutyl)carbamate (450 mg, 91%) as light yellow oil.

Step 4: afford tert-butyl 6-(methyl((1r,3r)-3-((5-(5-methyl-5H-pyrido[4,3-b]indol-7-yl)pyridin-2-yl)oxy)cyclobutyl)amino)-2-azaspiro[3.3]heptane-2-carboxylate

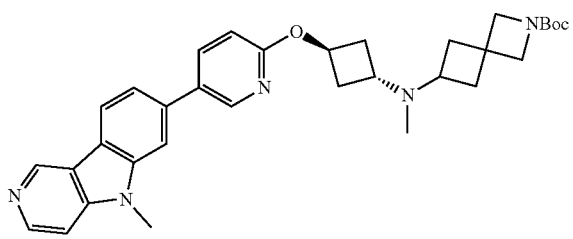 [SMILES: Cn1c2ccncc2c2ccc(-c3ccc(O[C@H]4C[C@H](N(C)C5CC6(C5)CN(C(=O)OC(C)(C)C)C6)C4)nc3)cc21]

A mixture of tert-butyl methyl((1r,3r)-3-((5-(5-methyl-5H-pyrido[4,3-b]indol-7-yl)pyridin-2-yl)oxy)cyclobutyl)carbamate (450 mg, 0.98 mmol) and 2,2,2-trifluoroacetic acid (2 ml) in dichloromethane (2 ml) was stirred at room temperature for 1 hour. TLC showed the reaction was complete. The volatiles were evaporated under reduced pressure. The residue was taken up in methanol (5 ml), followed by sequential addition of N-ethyl-N-isopropylpropan-2-amine (380 mg, 2.94 mmol), tert-butyl 6-oxo-2-azaspiro[3.3]heptane-2-carboxylate (207 mg, 0.98 mmol) and acetic acid (71 mg, 1.18 mmol) at 0° C. The resulting mixture was stirred at room temperature for 30 minutes and sodium cyanoborohydride (124 mg, 1.96 mmol) was added. The mixture was stirred at room temperature for 18 hours. TLC showed the reaction was complete. The mixture was concentrated and the residue was partitioned between ethyl acetate (20 ml) and water (20 ml). The organic layer was collected, washed with brine (20 ml), dried over anhydrous sodium sulfate, and concentrated under reduced pressure to give a crude residue which was purified by silica gel flash chromatography (eluted with 2-5% methanol in dichloromethane) to afford tert-butyl 6-(methyl((1r,3r)-3-((5-(5-methyl-5H-pyrido[4,3-b]indol-7-yl)pyridin-2-yl)oxy)cyclobutyl)amino)-2-azaspiro[3.3]heptane-2-carboxylate (240 mg, two steps 44%) as white solid.

Step 5: N-methyl-N-((1r,3r)-3-((5-(5-methyl-5H-pyrido[4,3-b]indol-7-yl)pyridin-2-yl)oxy)cyclobutyl)-2-azaspiro[3.3]heptan-6-amine

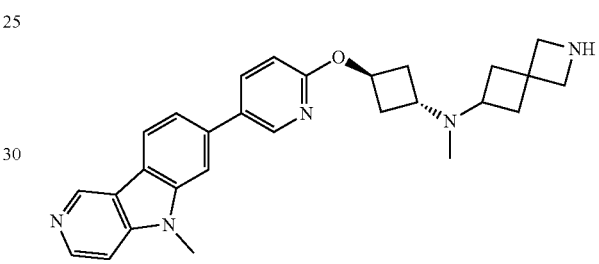

A mixture of tert-butyl 6-(methyl((1r,3r)-3-((5-(5-methyl-5H-pyrido[4,3-b]indol-7-yl)pyridin-2-yl)oxy)cyclobutyl)amino)-2-azaspiro[3.3]heptane-2-carboxylate (100 mg, 0.18 mmol) and 2,2,2-trifluoroacetic acid (0.5 ml) in anhydrous dichloromethane (0.5 ml) was stirred at room temperature for 1 hour. TLC showed the reaction was complete. The mixture was concentrated under reduced pressure to give crude N-methyl-N-((1r,3r)-3-((5-(5-methyl-5H-pyrido[4,3-b]indol-7-yl)pyridin-2-yl)oxy)cyclobutyl)-2-azaspiro[3.3]heptan-6-amine (100 mg) which was used in the next step without further purification.

Step 6: 2-(2,6-dioxopiperidin-3-yl)-5-((5-(6-(methyl((1r,3r)-3-((5-(5-methyl-5H-pyrido[4,3-b]indol-7-yl)pyridin-2-yl)oxy)cyclobutyl)amino)-2-azaspiro[3.3]heptan-2-yl)pentyl)oxy)isoindoline-1,3-dione

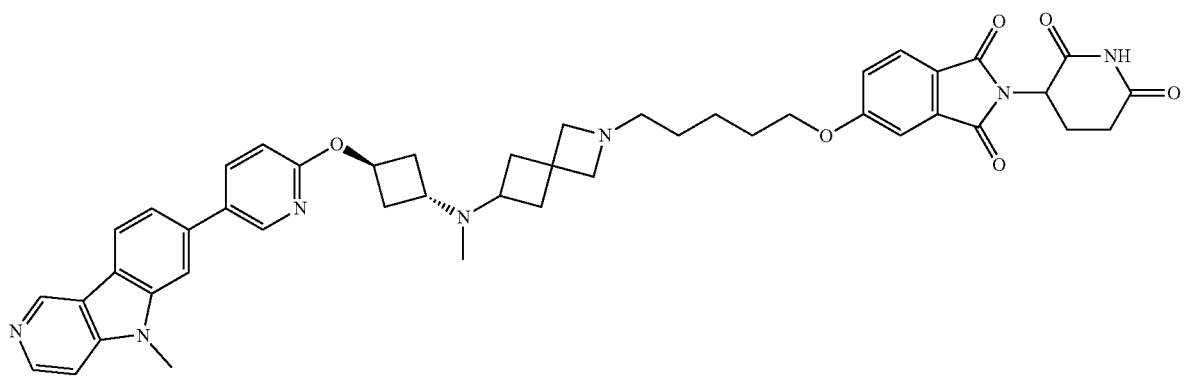 [SMILES: Cn1c2ccncc2c2ccc(-c3ccc(O[C@H]4C[C@H](N(C)C5CC6(C5)CN(CCCCCOc5ccc7c(c5)C(=O)N(C5CCC(=O)NC5=O)C7=O)C6)C4)nc3)cc21]

N-methyl-N-((1r,3r)-3-((5-(5-methyl-5H-pyrido[4,3-b]indol-7-yl)pyridin-2-yl)oxy)cyclobutyl)-2-azaspiro[3.3]heptan-6-amine (100 mg, crude) and N-ethyl-N-isopropyl-propan-2-amine (70 mg, 0.54 mmol) in methanol (10 ml) was added 5-((2-(2,6-dioxopiperidin-3-yl)-1,3-dioxoisoindolin-5-yl)oxy)pentanal (65 mg, 0.18 mmol) and acetic acid (13 mg, 0.21 mmol) at 0° C. The mixture was stirred at room temperature for 30 minutes and then sodium cyanoborohydride (23 mg, 0.36 mmol) was added. The mixture was stirred at room temperature for 16 hours. TLC showed the reaction was complete. The mixture was concentrated under reduced pressure to give a crude residue which was purified by HPLC to afford 2-(2,6-dioxopiperidin-3-yl)-5-((5-(6-(methyl((1r,3r)-3-((5-(5-methyl-5H-pyrido[4,3-b]indol-7-yl)pyridin-2-yl)oxy)cyclobutyl)amino)-2-azaspiro[3.3]heptan-2-yl)pentyl)oxy)isoindoline-1,3-dione (57.3 mg, two steps 40%) as white solid.

$^1$H NMR (400 MHz, DMSO-d6): δ 1.42-1.51 (m, 4H), 1.75-1.79 (m, 2H), 2.03-2.06 (m, 1H), 2.54 (s, 3H), 2.58-2.68 (m, 5H), 2.81-2.94 (m, 2H), 3.11-3.17 (m, 2H), 3.61-3.71 (m, 3H), 3.98-4.11 (m, 6H), 4.15 (s, 3H), 4.17-4.23 (m, 3H), 5.10-5.14 (m, 1H), 5.25-5.31 (m, 1H), 7.03 (d, J=8.4 Hz, 1H), 7.33-7.42 (m, 2H), 7.84-7.89 (m, 1H), 8.22-8.32 (m, 3H), 8.55 (d, J=8.0 Hz, 1H), 8.71 (s, 1H), 8.78 (d, J=6.4 Hz, 1H), 9.78 (s, 1H), 10.05 (brs, 1H), 10.51 (brs, 1H), 11.11 (s, 1H). (M+H)$^+$ 796.6.

Synthetic Scheme for Exemplary Compound 127

3-(5-(4-((1-(5-(5-methyl-5H-pyrido[4,3-b]indol-7-yl)pyridin-2-yl)piperidin-4-yl)methyl)piperazin-1-yl)-1-oxoisoindolin-2-yl)piperidine-2,6-dione

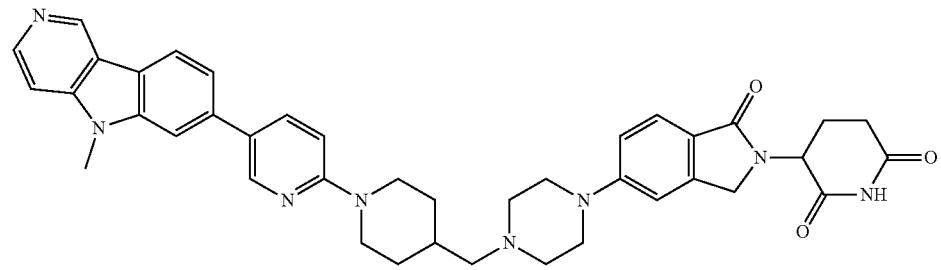 [SMILES: Cn1c2ccncc2c2ccc(-c3ccc(N4CCC(CN5CCN(c6ccc7c(c6)CN(C6CCC(=O)NC6=O)C7=O)CC5)CC4)nc3)cc21]

Step 1: (1-(5-(5-methyl-5H-pyrido[4,3-b]indol-7-yl)pyridin-2-yl)piperidin-4-yl)methanol

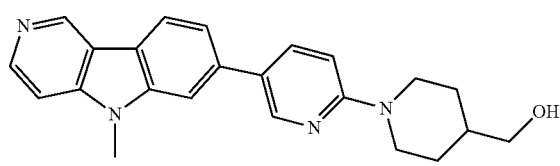 [SMILES: Cn1c2ccncc2c2ccc(-c3ccc(N4CCC(CO)CC4)nc3)cc21]

To the mixture of 7-(6-fluoropyridin-3-yl)-5-methyl-5H-pyrido[4,3-b]indole (200 mg, 0.72 mmol) and piperidin-4-ylmethanol (108 mg, 0.93 mmol) in 1-methylpyrrolidin-2-one (5 ml) was added potassium carbonate (298 mg, 2.16 mmol), and it was stirred at 100° C. overnight under nitrogen atmosphere. The cooled reaction mixture was partitioned between ethyl acetate (30 ml) and water (30 ml). The organic layer was collected, washed with brine (30 ml), dried over anhydrous sodium sulfate, and concentrated under reduced pressure to give a crude residue which was purified by silica gel flash chromatography (eluted with 2-5% methanol in dichloromethane) to afford (1-(5-(5-methyl-5H-pyrido[4,3-b]indol-7-yl)pyridin-2-yl)piperidin-4-yl)methanol (205 mg, yield 76%) as light yellow solid.

Step 2: 1-(5-(5-methyl-5H-pyrido[4,3-b]indol-7-yl)pyridin-2-yl)piperidine-4-carbaldehyde

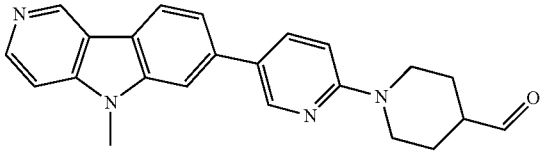 [SMILES: Cn1c2ccncc2c2ccc(-c3ccc(N4CCC(C=O)CC4)nc3)cc21]

To a solution of Dess-Martin periodinane (136 mg, 0.32 mmol) in dichloromethane (3 ml) (1-(5-(5-methyl-5H-pyrido[4,3-b]indol-7-yl)pyridin-2-yl)piperidin-4-yl)methanol (60 mg, 0.16 mmol) was added and stirred at room temperature for 1 hour under nitrogen atmosphere. The reaction mixture was partitioned between dichloromethane (20 ml) and water (20 ml). The organic layer was collected, washed with brine (20 ml), dried over anhydrous sodium sulfate, and concentrated under reduced pressure to give a crude residue which was purified by prep TLC (eluted with 3% methanol in dichloromethane) to afford 1-(5-(5-methyl-5H-pyrido[4,3-b]indol-7-yl)pyridin-2-yl)piperidine-4-carbaldehyde (58 mg, yield 97%) as white solid.

Step 3: tert-Butyl 4-(1-oxo-3H-isobenzofuran-5-yl)piperazine-1-carboxylate

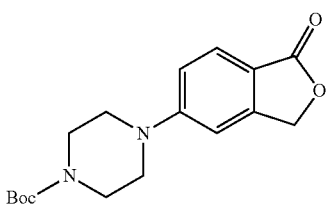 [SMILES: CC(C)(C)OC(=O)N1CCN(c2ccc3c(c2)COC3=O)CC1]

To a solution of 5-bromo-3H-isobenzofuran-1-one (45 g, 211.24 mmol, 1.00 eq) and tert-butyl piperazine-1-carboxylate (39.34 g, 211.24 mmol, 1.00 eq) in dioxane (500 mL) was added tris(dibenzylideneacetone)dipalladium(0) (19.34 g, 21.12 mmol, 0.10 eq), 4,5-bis (diphenylphosphino)-9,9-dimethylxanthene (12.22 g, 21.12 mmol, 0.10 eq) and potassium phosphate (89.68 g, 422.48 mmol, 2.00 eq). The mixture was heated to 100° C. for 16 hr under nitrogen protection. The mixture was filtered through a pad of celite and filtrate was concentrated in vacuum. The residue was triturated in ethyl acetate: petroleum ether (500 mL, v/v=1:2). Tert-butyl 4-(1-oxo-3H-isobenzofuran-5-yl)piperazine- 1-carboxylate (50 g, 122.5 mmol, 58% yield, 78% purity) was obtained as yellow solid.

Step 4: 4-(4-tert-butoxycarbonyl piperazin-1-yl)-2-(hydroxymethyl)benzoic Acid

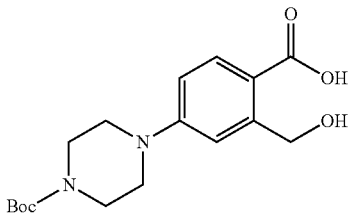 [SMILES: CC(C)(C)OC(=O)N1CCN(c2ccc(C(=O)O)c(CO)c2)CC1]

To a mixture of tert-butyl 4-(1-oxo-3H-isobenzofuran-5-yl)piperazine-1-carboxylate (47.8 g, 150.14 mmol, 1.00 eq) in tetrahydrofuran (150 mL), methanol (150 mL) and water (150 mL) was added sodium hydroxide (24 g, 600 mmol, 4.00 eq). The mixture was stirred at 25° C. for 1 hr. The solution was adjusted to pH=4-5 with aqueous hydrochloride solution (1M) and extracted with ethyl acetate (100 mL×5). The organic layers were concentrated in vacuum. The crude was triturated in ethyl acetate: petroleum ether (450 mL, v:v=1:2). 4-(4-tert-butoxycarbonyl piperazin-1-yl)-2-(hydroxymethyl)benzoic acid (40 g, 118.91 mmol, 79% yield) was obtained as yellow solid.

Step 5: tert-Butyl 4-[3-(hydroxymethyl)-4-methoxycarbonyl-phenyl]piperazine-1-carboxylate

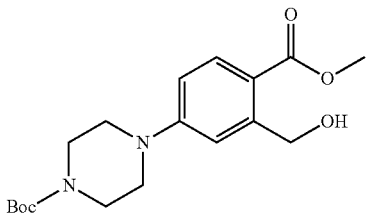 [SMILES: COC(=O)c1ccc(N2CCN(C(=O)OC(C)(C)C)CC2)cc1CO]

To a solution of 4-(4-tert-butoxycarbonylpiperazin-1-yl)-2-(hydroxymethyl)benzoic acid (20 g, 59.46 mmol, 1.00 eq) in methanol (100 mL) and ethyl acetate (100 mL) was added TMS-diazomethane (2 M, 89 mL, 3.00 eq) at −10° C. The solution was stirred at −10° C. for 0.25 hr. The solution was quenched with water (300 mL) and extracted with ethyl acetate (150 mL×3). The organic layer was dried over sodium sulfate and filtered. The filtrate was concentrated. Tert-Butyl 4-[3-(hydroxymethyl)-4-methoxycarbonyl-phenyl]piperazine-1-carboxylate (20.84 g, crude) was obtained as brown oil.

Step 6: tert-Butyl 4-[3-(bromomethyl)-4-methoxycarbonyl-phenyl]piperazine-1-carboxylate

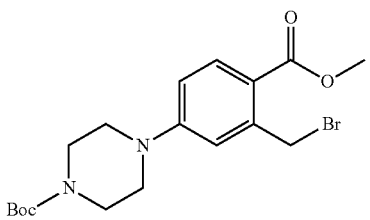 [SMILES: COC(=O)c1ccc(N2CCN(C(=O)OC(C)(C)C)CC2)cc1CBr]

To a solution of tert-butyl 4-[3-(hydroxymethyl)-4-methoxycarbonyl-phenyl]piperazine-1-carboxylate (20.84 g, 59.47 mmol, 1.00 eq) in tetrahydrofuran (200 mL) was added triphenylphosphine (23.4 g, 89.21 mmol, 1.50 eq) and tetrabromomethane (29.58 g, 89.21 mmol, 1.50 eq). The solution was stirred at 25° C. for 1 hr. The solution was quenched with water (200 mL) and extracted with ethyl acetate (100 mL×2). The organic layer was dried over sodium sulfate and filtered. The filtrate was concentrated in vacuum. The residue was purified by silica gel column chromatography (ethyl acetate: petroleum ether=1:50-1:8). Tert-Butyl 4-[3-(bromomethyl)-4-methoxycarbonyl-phenyl]piperazine-1-carboxylate (12 g, 29.03 mmol, 49% yield) was obtained as a pale-yellow oil.

Step 7: tert-Butyl 4-[2-(2,6-dioxo-3-piperidyl)-1-oxo-isoindolin-5-yl]piperazine-1-carboxylate

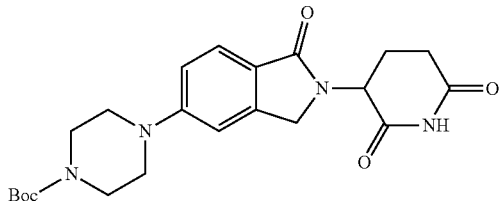 [SMILES: CC(C)(C)OC(=O)N1CCN(c2ccc3c(c2)CN(C2CCC(=O)NC2=O)C3=O)CC1]

To a solution of tert-butyl 4-[3-(bromomethyl)-4-methoxycarbonyl-phenyl]piperazine-1-carboxylate (12 g, 29.03 mmol, 1.00 eq) in acetonitrile (300 mL) was added 3-aminopiperidine-2,6-dione; hydrochloride (7.17 g, 43.55 mmol, 1.50 eq) and N-ethyl-N-isopropylpropan-2-amine (11.26 g, 87.09 mmol, 15 mL, 3.00 eq). The solution was stirred at 80° C. for 16 hr. LCMS showed reaction was almost complete. The reaction mixture was cooled to 20° C. and filtered. The solid was washed with acetonitrile (30 mL). tert-Butyl 4-[2-(2,6-dioxo-3-piperidyl)-1-oxo-isoindolin-5-yl]piperazine-1-carboxylate (6 g, 14 mmol, 48% yield) was obtained as a white solid.

Step 8: 3-(1-oxo-5-piperazin-1-yl-isoindolin-2-yl)piperidine-2,6-dione

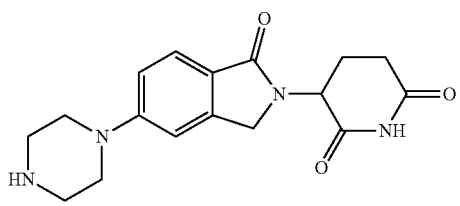 [SMILES: O=C1CCC(N2Cc3cc(N4CCNCC4)ccc3C2=O)C(=O)N1]

To a mixture of tert-butyl 4-[2-(2,6-dioxo-3-piperidyl)-1-oxo-isoindolin-5-yl]piperazine-1-carboxylate (6 g, 14 mmol, 1.00 eq) in dioxane (70 mL) was added hydrochloride/dioxane (4 M, 100 mL, 28.57 eq). The mixture was stirred at 25° C. for 2 hr. The mixture was poured into ethyl acetate (400 mL) and stirred for 30 minutes. The suspension was filtered and solid was collected. 3-(1-oxo-5-piperazin-1-yl-isoindolin-2-yl) piperidine-2,6-dione (5 g, 13.71 mmol, 98% yield, hydrochloric salt) was obtained as a white solid.

Step 9: 3-(5-(4-((1-(5-(5-methyl-5H-pyrido[4,3-b]indol-7-yl)pyridin-2-yl)piperidin-4-yl)methyl)piperazin-1-yl)-1-oxoisoindolin-2-yl)piperidine-2,6-dione

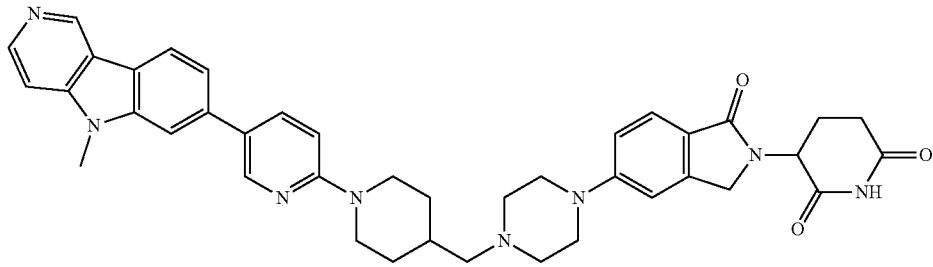 [SMILES: Cn1c2ccncc2c2ccc(-c3ccc(N4CCC(CN5CCN(c6ccc7c(c6)CN(C6CCC(=O)NC6=O)C7=O)CC5)CC4)nc3)cc21]

A mixture of 1-(5-(5-methyl-5H-pyrido[4,3-b]indol-7-yl)pyridin-2-yl)piperidine-4-carbaldehyde (58 mg, 0.15 mmol), N-ethyl-N-isopropylpropan-2-amine (32 mg, 0.23 mmol), 3-(1-oxo-5-(piperazin-1-yl)isoindolin-2-yl)piperidine-2,6-dione (51 mg, 0.15 mmol) and acetic acid (0.5 ml) in methanol (4 ml) was stirred at room temperature for 30 minutes. It was followed by the addition of sodium cyanoborohydride (21 mg, 2.10 mmol) and stirring for 1 hour at room temperature. The mixture was partitioned between ethyl acetate (30 ml) and brine (30 ml), dried over anhydrous sodium sulfate, and concentrated under reduced pressure to give a crude residue which was purified by prep TLC (eluted with 10% methanol in dichloromethane) to afford 3-(5-(4-((1-(5-(5-methyl-5H-pyrido[4,3-b]indol-7-yl)pyridin-2-yl)piperidin-4-yl)methyl)piperazin-1-yl)-1-oxoisoindolin-2-yl)piperidine-2,6-dione (57 mg, yield 53%) as light yellow solid.

$^1$H NMR (400 MHz, DMSO-d6): δ 1.11-1.23 (m, 4H), 1.82-1.99 (m, 4H), 2.30-2.39 (m, 3H), 2.60 (br, 4H), 2.86-2.94 (m, 3H), 3.17 (s, 2H), 3.98 (s, 3H), 4.10 (br, 1H), 4.21 (d, J=16.8 Hz, 1H), 4.32-4.41 (m, 3H), 5.05 (dd, J=13.2 Hz, 1H), 6.96 (d, J=9.2 Hz, 1H), 706-7.08 (m, 2H), 7.53 (d, J=8.4 Hz, 1H), 7.62 (d, J=8.0 Hz, 1H), 7.69 (d, J=6.0 Hz, 1H), 7.95 (s, 1H), 8.02 (dd, J=9.2 Hz, 1H), 8.30 (dd, J=8.4 Hz, 1H), 8.51 (d, J=5.6 Hz, 1H), 8.64 (s, 1H), 9.38 (s, 1H), 10.95 (s, 1H). (M+H)$^+$ 683.5.

Synthetic Scheme for Exemplary Compound 128

3-(5-(4-(2-(1-(5-(5-methyl-5H-pyrido[4,3-b]indol-7-yl)pyridin-2-yl)piperidin-4-yl)ethyl)piperazin-1-yl)-1-oxoisoindolin-2-yl)piperidine-2,6-dione

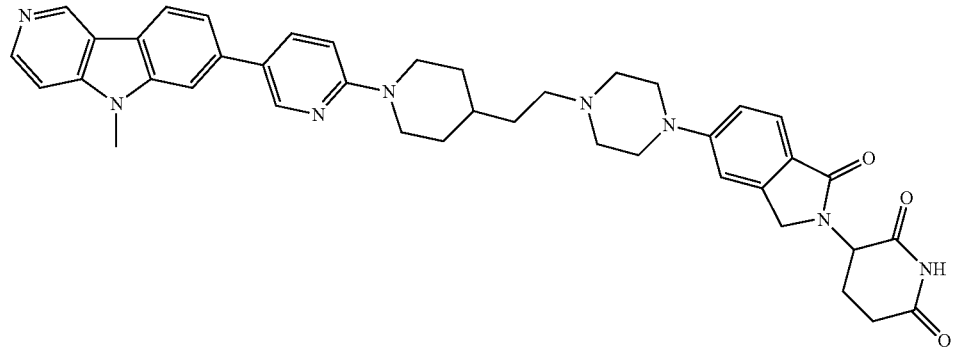 [SMILES: Cn1c2ccncc2c2ccc(-c3ccc(N4CCC(CCN5CCN(c6ccc7c(c6)CN(C6CCC(=O)NC6=O)C7=O)CC5)CC4)nc3)cc21]

Prepared according to the synthetic scheme below using procedures described for Compound 127.

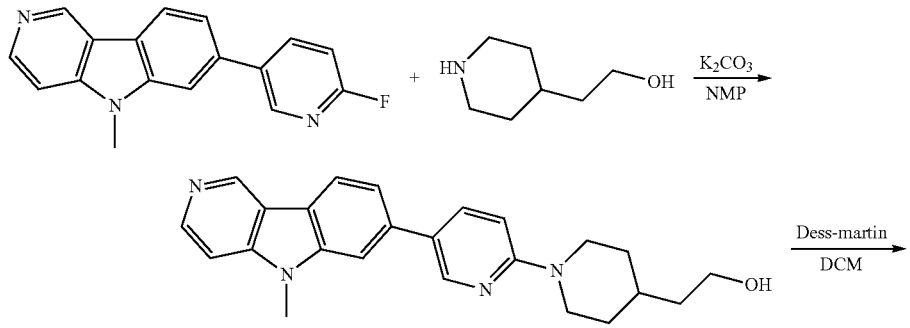

-continued

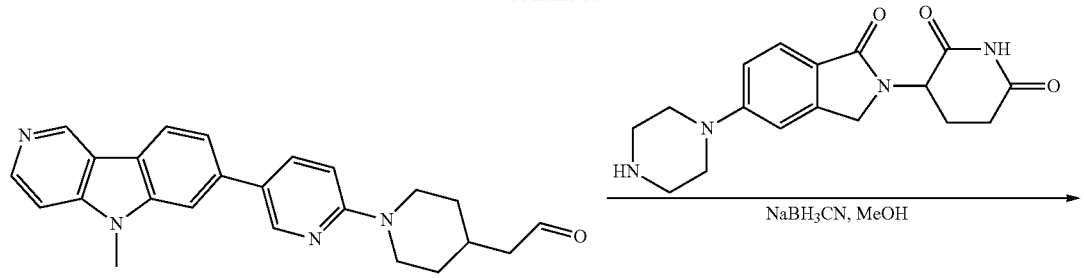

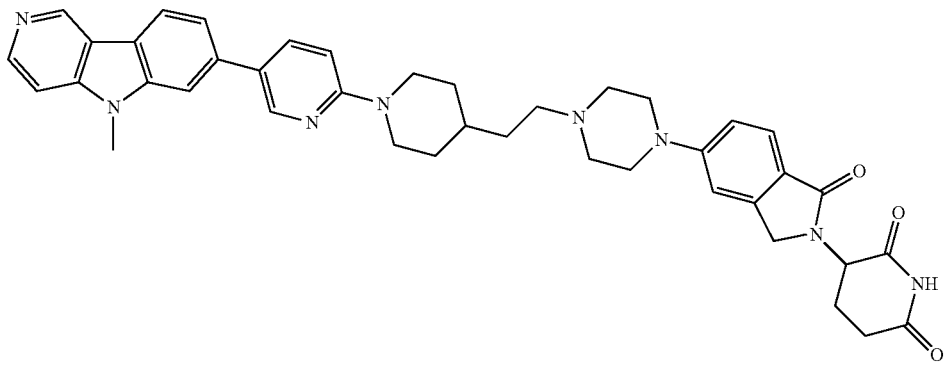

Compound 128

Compound 128: ¹H NMR (400 MHz, DMSO-d6) δ 1.16-1.23 (m, 3H), 1.40-1.50 (m, 2H), 1.61 (br, 1H), 1.76-1.78 (m, 2H), 1.94-1.96 (m, 1H), 2.38-2.41 (s, 3H), 2.51-2.56 (m, 4H), 2.82-2.90 (m, 3H), 3.29-3.33 (m, 4H), 3.95 (s, 3H), 4.18-4.22 (m, 1H), 4.30-4.39 (m, 3H), 5.02-5.08 (m, 1H), 6.95 (d, J=8.8 Hz, 1H), 7.05-7.06 (m, 2H), 7.50-7.69 (m, 3H), 7.91 (s, 1H), 8.00 (dd, J=8.8, 2.2 Hz, 1H), 8.28 (d, J=8.0 Hz, 1H), 8.48 (d, J=5.8 Hz, 1H), 8.62 (d, J=2.0 Hz, 1H), 9.33 (s, 1H), 10.95 (s, 1H). (M+H)⁺ 697.6.

Synthetic Scheme for Exemplary Compound 130

2-(2,6-dioxopiperidin-3-yl)-5-(3-(3-(3-(4-((5-(5-methyl-5H-pyrido[4,3-b]indol-7-yl)-3-(trifluoromethyl)pyridin-2-yl)oxy)piperidin-1-yl)propoxy)propoxy)azetidin-1-yl)isoindoline-1,3-dione

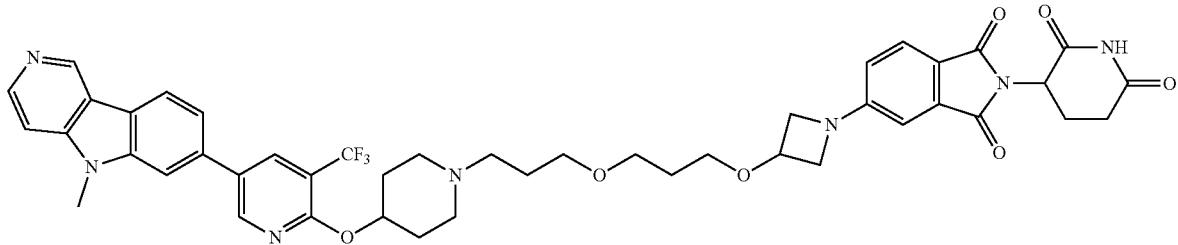 [SMILES: Cn1c2ccncc2c2ccc(-c3cnc(OC4CCN(CCCOCCCOC5CN(c6ccc7c(c6)C(=O)N(C6CCC(=O)NC6=O)C7=O)C5)CC4)c(C(F)(F)F)c3)cc21]

Prepared according to the synthetic scheme below using procedures described above and common procedures known to those skilled in the art.

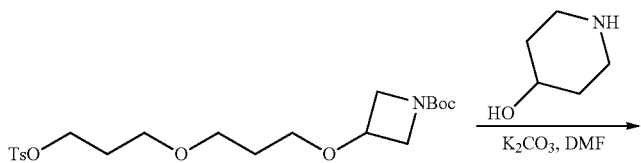

491
-continued
492
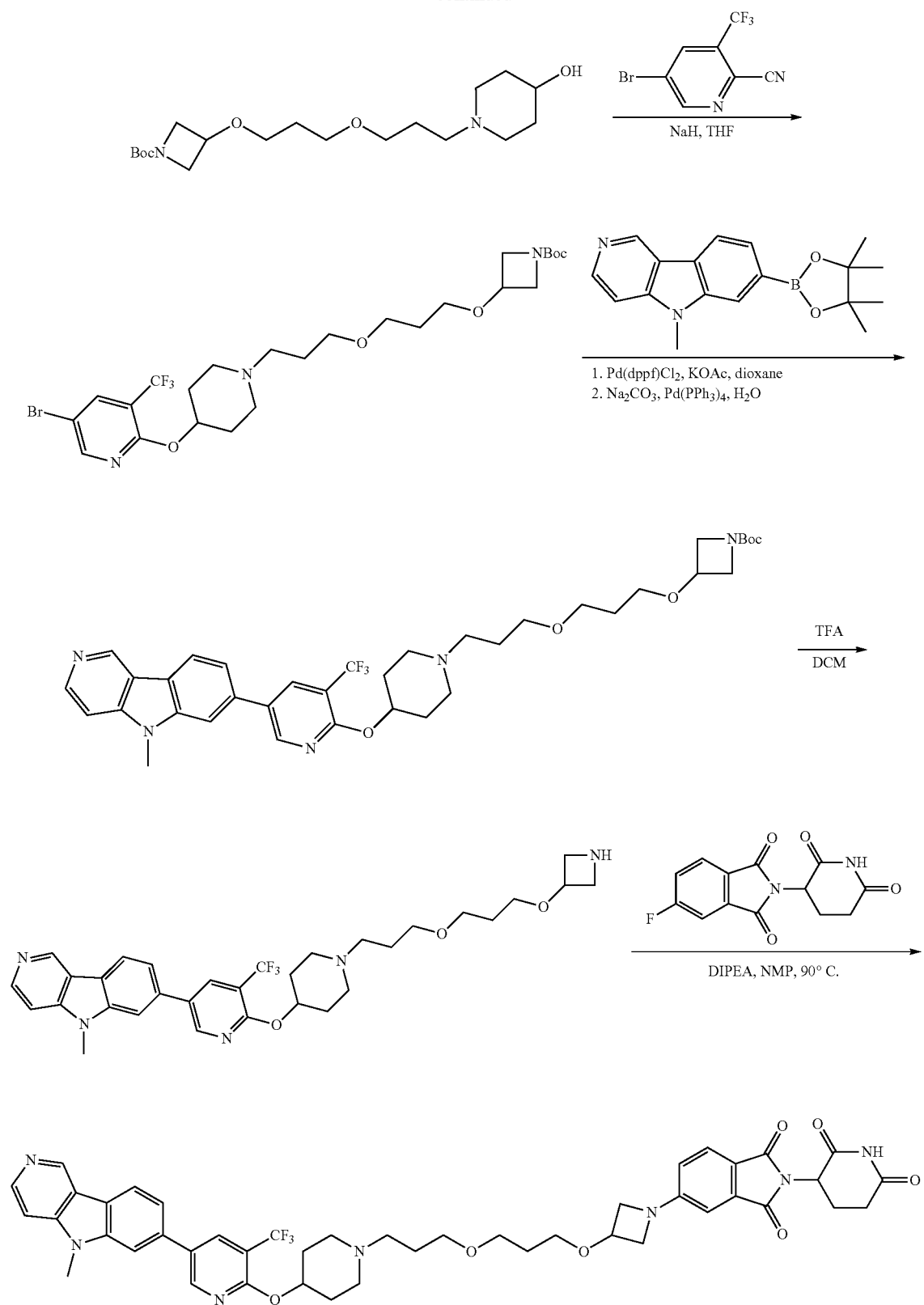
Compound 130

Compound 130: $^1$H NMR (400 MHz, DMSO-d6): δ 1.74-1.80 (m, 4H), 1.85-1.92 (m, 2H), 1.97-2.02 (m, 2H), 2.02-2.15 (m, 2H), 2.54-2.58 (m, 2H), 2.67-2.91 (m, 4H), 3.41-3.50 (m, 8H), 3.81-3.88 (m, 2H), 3.98 (s, 3H), 4.25 (t, J=7.8 Hz, 2H), 4.44-4.49 (m, 1H), 5.05 (dd, J=5.2, 12.8 Hz, 1H), 5.33-5.40 (m, 1H), 6.66 (dd, J=1.6, 8.4 Hz, 1H), 6.80 (d, J=1.2 Hz, 1H), 7.63-7.72 (m, 3H), 8.10 (s, 1H), 8.36 (d, J=8.4 Hz, 1H), 8.51 (d, J=4.8 Hz, 2H), 8.92 (s, 1H), 9.39 (s, 1H), 11.06 (s, 1H). (M+H)$^+$ 854.6.

Synthetic Scheme for Exemplary Compound 129

2-(2,6-dioxopiperidin-3-yl)-5-((1,1,1-trifluoro-6-(2-(2-(2-((5-(5-methyl-5H-pyrido[4,3-b]indol-7-yl)pyridin-2-yl)oxy)ethoxy)ethoxy)ethoxy)hexan-2-yl)oxy)isoindoline-1,3-dione

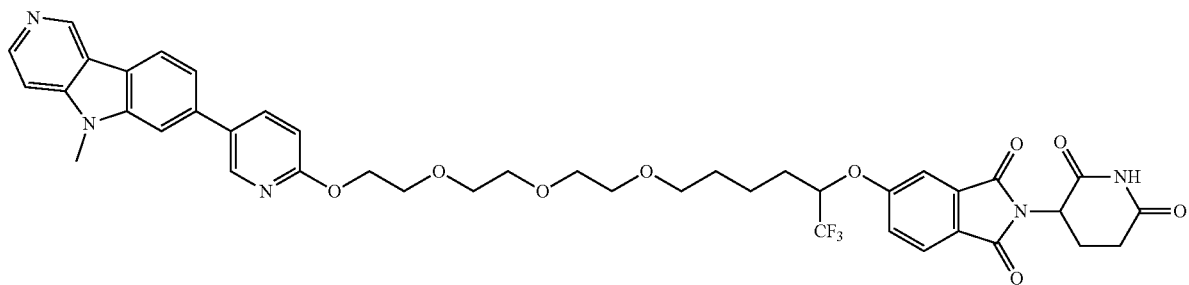 [SMILES: Cn1c2ccncc2c2ccc(-c3ccc(OCCOCCOCCOCCCCC(Oc4ccc5c(c4)C(=O)N(C4CCC(=O)NC4=O)C5=O)C(F)(F)F)nc3)cc21]

Step 1: 6-(2-(2-(2-(5-bromopyridin-2-yloxy)ethoxy)ethoxy)ethoxy)-1,1,1-trifluorohexan-2-ol

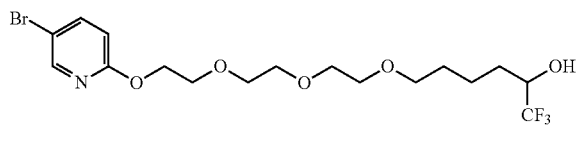 [SMILES: OC(CCCCOCCOCCOCCOc1ccc(Br)cn1)C(F)(F)F]

To a solution of 5-(2-(2-(2-(5-bromopyridin-2-yloxy)ethoxy)ethoxy)ethoxy) pentanal (575 mg, 1.47 mmol) [prepared according to the scheme below and using procedures described above and common procedures known to those skilled in the art] and CF$_3$Si(CH$_3$)$_3$ (320 mg, 2.21 mmol) in THF was added TBAF (1M, 2.2 mL, 2.20 mmol) at room temperature. The reaction was stirred at room temperature for 3 hours. After quenched with 1N HCl (3 mL), the mixture was extracted with EA (30 mL), washed with brine. The organic phase was dried, concentrated under vacuum. The residue was purified by a silica gel (PE:EA=2:1) to get 6-(2-(2-(2-(5-bromopyridin-2-yloxy)ethoxy)ethoxy)ethoxy)-1,1,1-trifluorohexan-2-ol (400 mg, 60% yield).

Step 2: 6-(2-(2-(2-(5-bromopyridin-2-yloxy)ethoxy)ethoxy)ethoxy)-1,1,1-trifluorohexan-2-yltrifluoromethanesulfonate

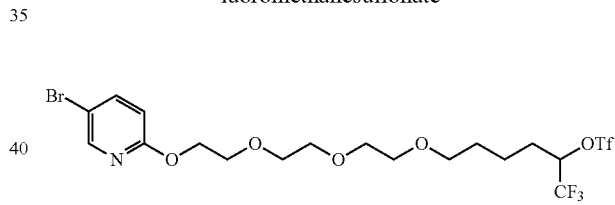

To a solution of 6-(2-(2-(2-(5-bromopyridin-2-yloxy)ethoxy)ethoxy)ethoxy)-1,1,1-trifluorohexan-2-ol (130 mg, 0.28 mmol) and pyridine (67 mg, 0.85 mmol) in DCM was added Tf$_2$O (120 mg, 0.42 mmol) at 0° C. The resulting solution warmed to room temperature for 1 hour. The reaction was diluted with DCM (10 mL), washed with water, brine and concentrated under vacuum to afford 6-(2-(2-(2-(5-bromopyridin-2-yloxy) ethoxy)ethoxy)ethoxy)-1,1,1-trifluorohexan-2-yltrifluoromethanesulfonate (160 mg, 96%).

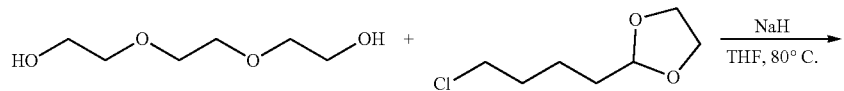

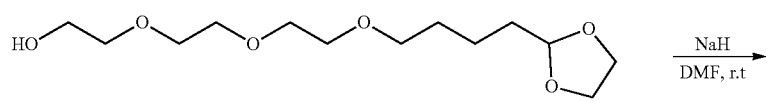

-continued
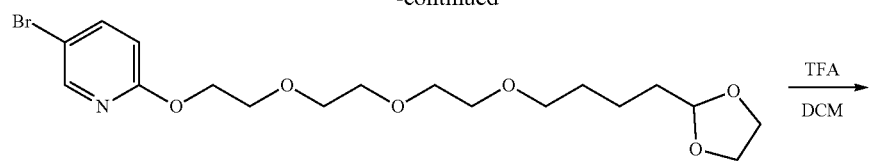
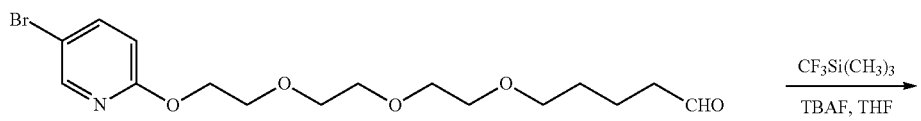
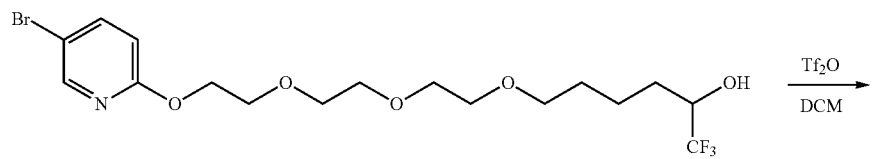
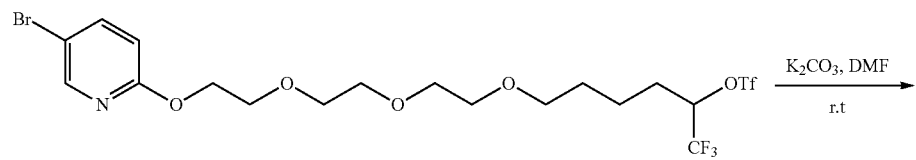
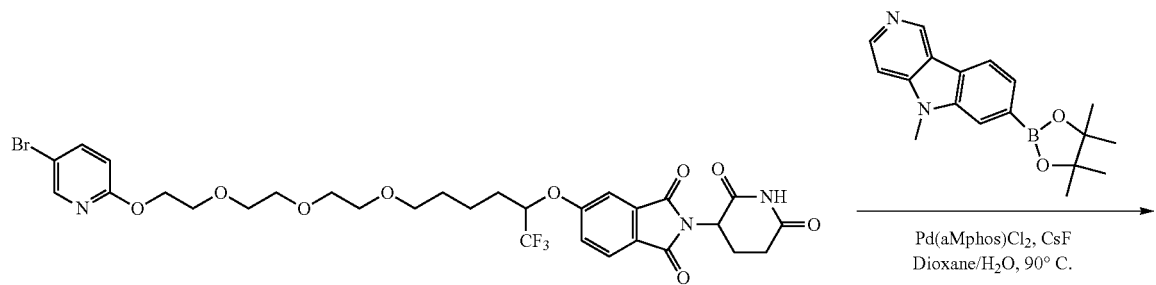
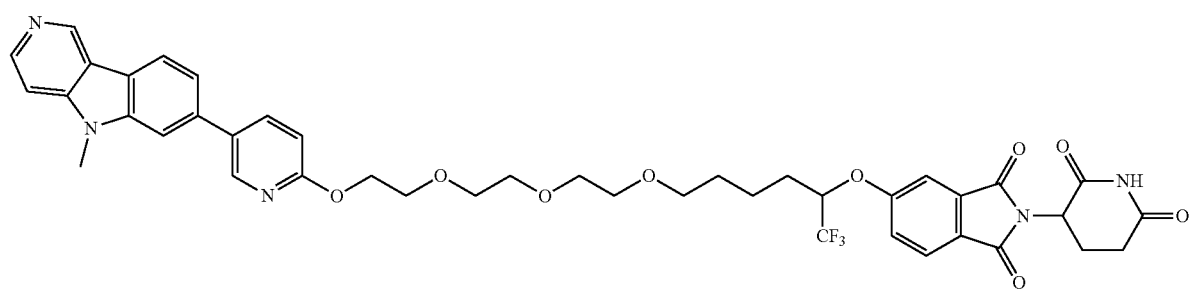
Compound 129

Compound 129: ¹HNMR (400 MHz, CDCl₃): δ 9.25 (s, 1H), 8.48 (s, 1H), 8.39 (s, 1H), 8.09 (d, J=8.0 Hz, 1H), 7.82 (d, J=8.0 Hz, 1H), 7.72 (d, J=8.4 Hz, 1H), 7.46 (s, 1H), 7.36-7.41 (m, 2H), 7.19-7.24 (m, 2H), 6.82 (d, J=8.8 Hz, 1H), 4.86-4.91 (m, 1H), 4.58-4.63 (m, 1H), 4.45-4.48 (m, 2H), 3.78-3.82 (m, 5H), 3.55-3.80 (m, 9H), 3.39-3.50 (m, 3H), 2.69-2.82 (m, 6H), 1.96-2.05 (m, 2H), 1.81-1.89 (m, 2H). (M+H)⁺ 818.5.

Synthetic Scheme for Exemplary Compound 131

2-(2,6-dioxopiperidin-3-yl)-5-((17-((5-(5-methyl-5H-pyrido[4,3-b]indol-7-yl)pyridin-2-yl)oxy)-3,6,9,12,15-pentaoxaheptadecyl)oxy)isoindoline-1,3-dione

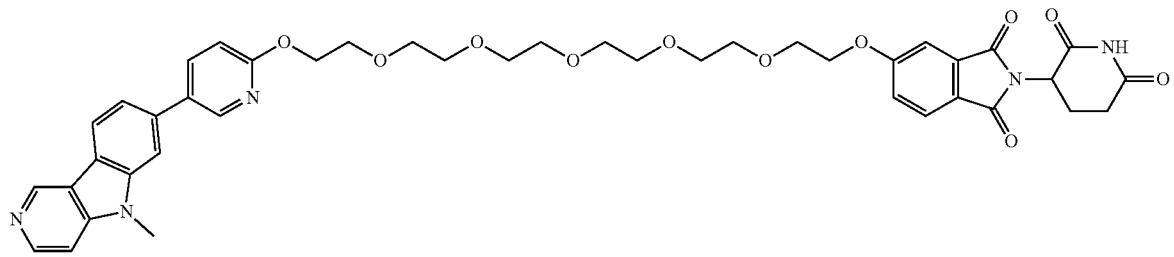 [SMILES: Cn1c2ccncc2c2ccc(-c3ccc(OCCOCCOCCOCCOCCOCCOc4ccc5c(c4)C(=O)N(C4CCC(=O)NC4=O)C5=O)nc3)cc21]

Prepared according to the scheme below using procedures described above and common procedures known to those skilled in the art.

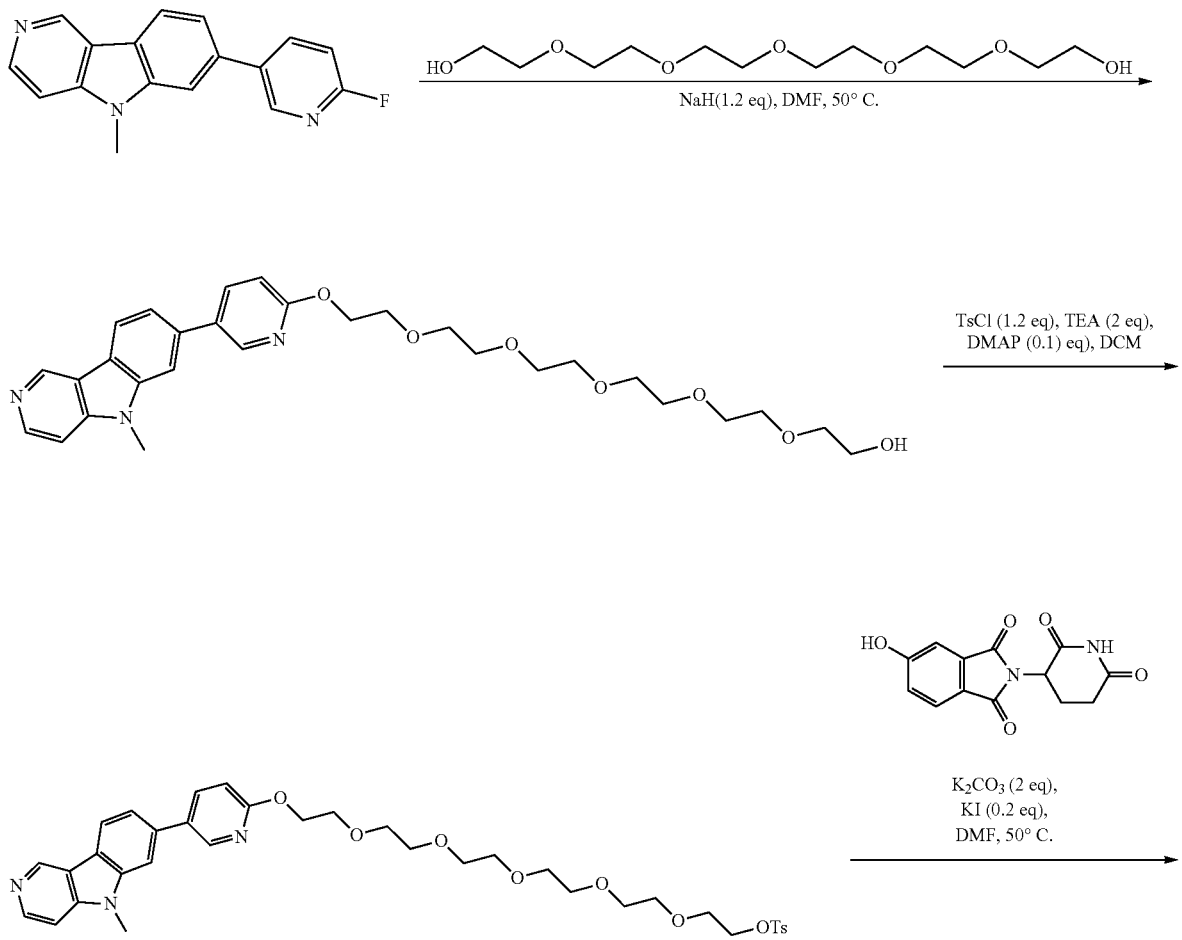

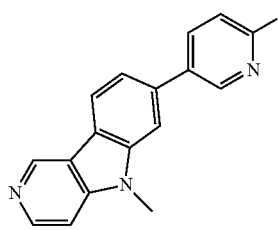 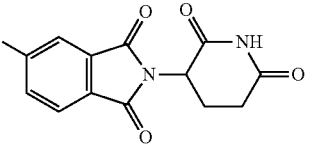

Compound 132

Using procedures analogous to those for Compound 131, the following were prepared: Compound 132.

Synthetic Scheme for Exemplary Compound 133

2-(2,6-dioxopiperidin-3-yl)-5-(3-(6-((5-((5-(5-methyl-5H-pyrido[4,3-b]indol-7-yl)pyridin-2-yl)oxy)pentyl)oxy)hexyl)azetidin-1-yl)isoindoline-1,3-dione

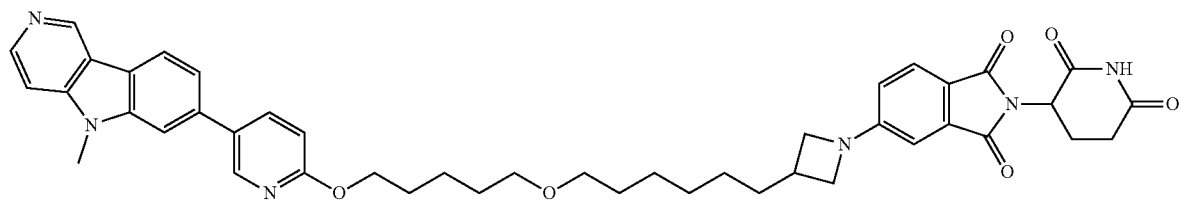 [SMILES: Cn1c2ccncc2c2ccc(-c3ccc(OCCCCCOCCCCCCC4CN(c5ccc6c(c5)C(=O)N(C5CCC(=O)NC5=O)C6=O)C4)nc3)cc21]

Step 1: (6-(benzyloxy)hexyl)magnesium bromide

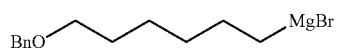

A suspension of (((6-bromohexyl)oxy)methyl)benzene (10 g, 0.037 mol), magnesium (1.33 g, 0.055 mol) and iodine (200 mg) in anhydrous tetrahydrofuran (100 ml) was stirred at 50° C. for 2 hours. Iodine disappeared and the mixture was stirred for another 1 hour to afford (6-(benzyloxy)hexyl)magnesium bromide (crude) which was used in the next step without further purification.

Step 2: tert-butyl 3-(6-(benzyloxy)hexyl)-3-hydroxyazetidine-1-carboxylate

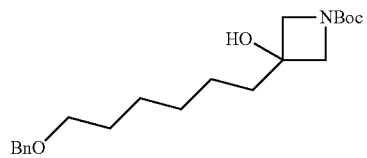 [SMILES: CC(C)(C)OC(=O)N1CC(O)(CCCCCCOCc2ccccc2)C1]

To the solution of tert-butyl 3-oxoazetidine-1-carboxylate (5.2 g, 0.031 mol) in anhydrous tetrahydrofuran (50 ml) was added (6-(benzyloxy)hexyl)magnesium bromide at 0° C. The resulting mixture was allowed to warm up to room temperature and stirred at room temperature for 16 hours. The mixture was filtered and the filtrate was concentrated. The residue was partitioned between ethyl acetate (50 ml) and water (100 ml). The organic layer was collected, washed with brine (30 ml), dried over anhydrous sodium sulfate, and concentrated under reduced pressure to give a crude residue which was purified by silica gel flash chromatography (eluted with 33-50% ethyl acetate in hexane) to afford tert-butyl 3-(6-(benzyloxy)hexyl)-3-hydroxyazetidine-1-carboxylate (1.7 g, two steps 12%) as colorless oil.

Step 3: tert-butyl 3-(6-(benzyloxy)hexylidene)azetidine-1-carboxylate

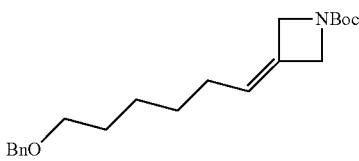 [SMILES: CC(C)(C)OC(=O)N1CC(=CCCCCCOCc2ccccc2)C1]

To a stirred solution of tert-butyl 3-(6-(benzyloxy)hexyl)-3-hydroxyazetidine-1-carboxylate (800 mg, 2.2 mmol) in toluene (10 ml) was added 1-methoxy-N-triethylammoniosulfonyl-methanimidate (Burgess reagent) (1.57 g, 6.6 mmol). The resulting solution was allowed to warm up to 90° C. and stirred at this temperature for 2 hours. The mixture was poured into water (20 ml) and extracted with ethyl acetate (20 ml×2). The combined organic layers were washed with brine (20 ml), dried over anhydrous sodium sulfate, and concentrated under reduced pressure to give a crude residue which was purified by silica gel flash column chromatography (eluted with 30% ethyl acetate in hexane)

to afford tert-butyl 3-(6-(benzyloxy)hexylidene)azetidine-1-carboxylate (125 mg, yield 16%) as colorless oil.

Step 4: tert-butyl 3-(6-hydroxyhexyl)azetidine-1-carboxylate

A mixture of tert-butyl 3-(6-(benzyloxy)hexylidene)azetidine-1-carboxylate (125 mg, 0.36 mmol), palladium on carbon (10%, 50 mg) in methanol (30 ml) was stirred at room temperature for 3 hours under hydrogen atmosphere (hydrogen balloon). TLC showed the reaction was complete. Palladium on carbon was removed through filtration and washed with methanol (5 ml×2). The combined filtrates were concentrated under reduced pressure to afford tert-butyl 3-(6-hydroxyhexyl)azetidine-1-carboxylate (88 mg, yield: 95%) as colorless oil.

Tert-butyl 3-(6-hydroxyhexyl)azetidine-1-carboxylate was converted to the final compound, 2-(2,6-dioxopiperidin-3-yl)-5-(3-(6-((5-((5-(5-methyl-5H-pyrido[4,3-b]indol-7-yl)pyridin-2-yl)oxy)pentyl)oxy)hexyl)azetidin-1-yl)isoindoline-1,3-dione, according to the scheme below and using procedures described above and common procedures known to those skilled in the art.

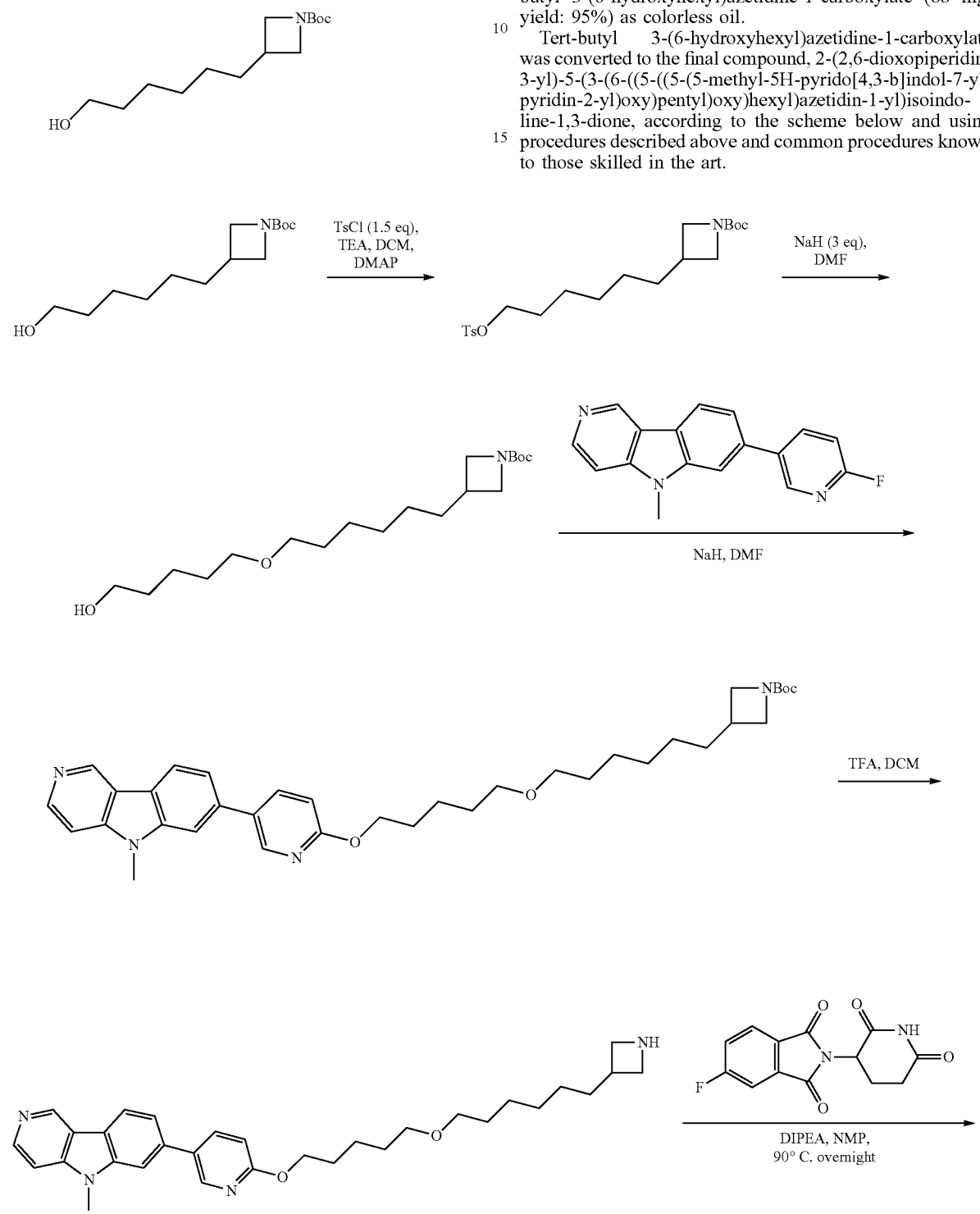

-continued

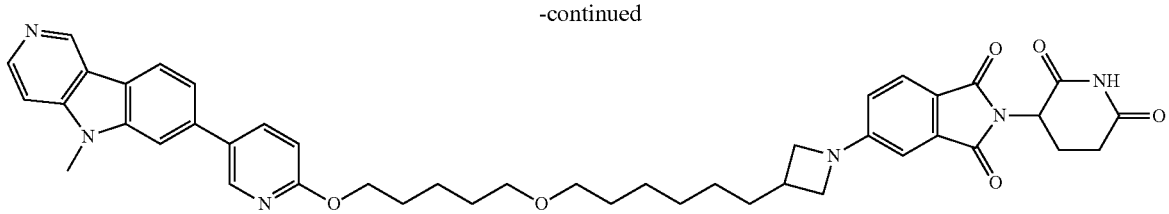

Compound 133

Compound 133: 1H NMR (400 Hz, D6-DMSO): δ 1.24-1.35 (m, 7H), 1.46-1.57 (m, 8H), 1.72-1.82 (m, 2H), 1.98-2.01 (m, 3H), 2.57-2.74 (m, 3H), 2.81-2.99 (m, 2H), 3.57-3.59 (m, 2H), 3.98 (s, 3H), 4.06-4.08 (m, 2H), 4.33 (s, 2H), 5.03-5.06 (m, 1H), 6.54-6.66 (m, 1H), 6.69 (s, 1H), 6.93-6.95 (m, 1H), 7.57-7.71 (m, 3H), 8.02 (s, 1H), 8.19-8.21 (m, 1H), 8.34-8.36 (m, 1H), 8.53-8.58 (m, 1H), 8.66 (s, 1H), 9.41 (s, 1H), 11.08 (s, 1H). (M+H)⁺ 757.6.

Synthetic Scheme for Exemplary Compound 134

2-(2,6-dioxopiperidin-3-yl)-5-((6-(6-(((1r,3r)-3-((5-(5-methyl-5H-pyrido[4,3-b]indol-7-yl)pyridin-2-yl)oxy)cyclobutoxy)pyridazin-3-yl)hex-5-yn-1-yl)oxy)isoindoline-1,3-dione

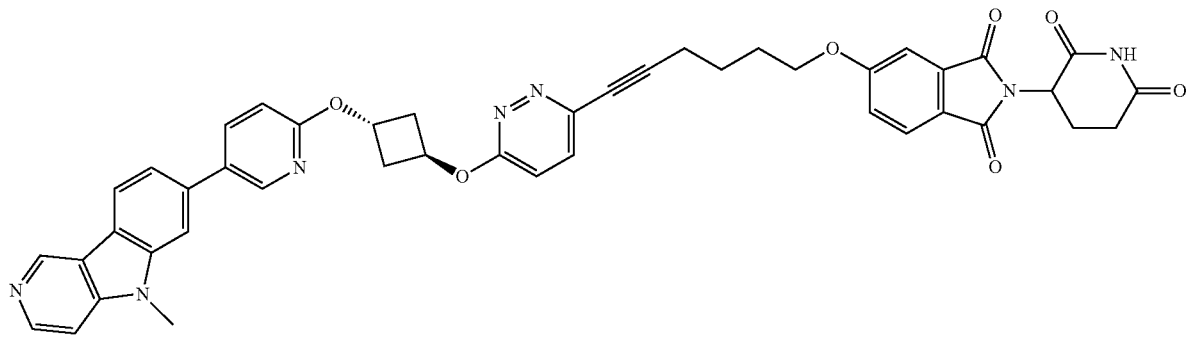 [SMILES: Cn1c2ccncc2c2ccc(-c3ccc(O[C@H]4C[C@H](Oc5ccc(C#CCCCCOc6ccc7c(c6)C(=O)N(C6CCC(=O)NC6=O)C7=O)nn5)C4)nc3)cc21]

Step 1: 3,6-diiodopyridazine

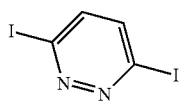

A mixture of 3,6-dichloropyridazine (5.0 g, 34.0 mmol) and sodium iodide (50 g, 0.68 mol) in acetone (50 ml) was stirred at 65° C. for 3 hours. The reaction mixture was quenched with water (100 ml) and extracted with ethyl acetate (200 ml×2). The combined organic layers were washed with brine (200 ml×2), dried over anhydrous sodium sulfate, and concentrated under reduced pressure to give a residue which was purified by silica gel flash column chromatography (eluted with 40% ethyl acetate in hexane) to afford 3,6-diiodopyridazine (5.4 g, 4.9 mol, 48% yield) as brown solid.

Step 2: 3-fluoro-6-iodopyridazine

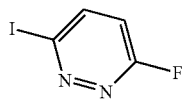

A mixture of 3,6-dichloropyridazine (1 g, 3.0 mmol), cesium fluoride (413 mg, 0.9 mol) in dimethyl sulphoxide (10 ml) was stirred at 140° C. overnight. The reaction mixture was partitioned between water (50 ml) and ethyl acetate (100 ml). The organic layer was collected, washed with brine (100 ml), dried over anhydrous sodium sulfate, and concentrated under reduced pressure to give a residue which was purified by silica gel flash column chromatography (eluted with 20% ethyl acetate in hexane) to afford 3-fluoro-6-iodopyridazine (840 mg).

Step 3: 7-(6-(((1r,3r)-3-((6-iodopyridazin-3-yl)oxy)cyclobutoxy)pyridin-3-yl)-5-methyl-5H-pyrido[4,3-b]indole

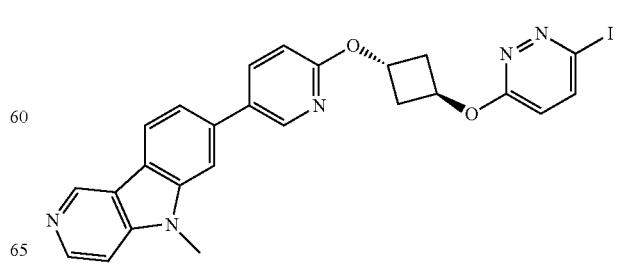

(1r,3r)-3-((5-(5-methyl-5H-pyrido[4,3-b]indol-7-yl)pyridin-2-yl)oxy)cyclobutanol (100 mg, 0.29 mmol), 3-fluoro-6-iodopyridazine (300 mg, 0.10 mmol) in 1-methylpyrrolidin-2-one (5 ml) was added sodium hydride (60% in mineral oil) (110 mg, 2.7 mmol) at 0° C. The resulting mixture was allowed to warm up to room temperature for 1 hour. The reaction mixture was quenched with water (10 ml) at 0° C. and extracted with ethyl acetate (20 ml×3). The combined organic layers were washed with brine (20 ml), dried over anhydrous sodium sulfate, and concentrated under reduced pressure to give a crude residue which was purified by silica gel flash chromatography (eluted with 20% methanol in dichloromethane) to afford 7-(6-((1r,3r)-3-((6-iodopyridazin-3-yl)oxy)cyclobutoxy)pyridin-3-yl)-5-methyl-5H-pyrido[4,3-b]indole (70 mg, 0.13 mmol, yield 44%) as brown solid.

7-(6-((1r,3r)-3-((6-iodopyridazin-3-yl)oxy)cyclobutoxy)pyridin-3-yl)-5-methyl-5H-pyrido[4,3-b]indole was converted to the final compound, 2-(2,6-dioxopiperidin-3-yl)-5-((6-(6-((1r,3r)-3-((5-(5-methyl-5H-pyrido[4,3-b]indol-7-yl)pyridin-2-yl)oxy)cyclobutoxy)pyridazin-3-yl)hex-5-yn-1-yl)oxy)isoindoline-1,3-dione, according to the scheme below and using procedures described above (step 6 of Compound 73 and step 1 of Compound 180).

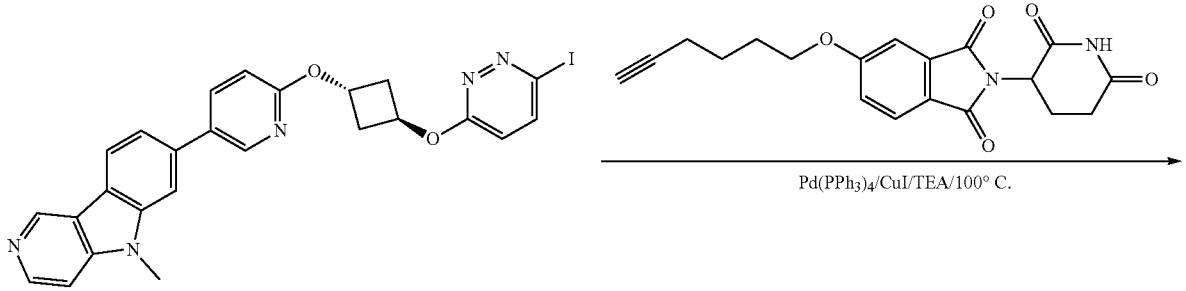

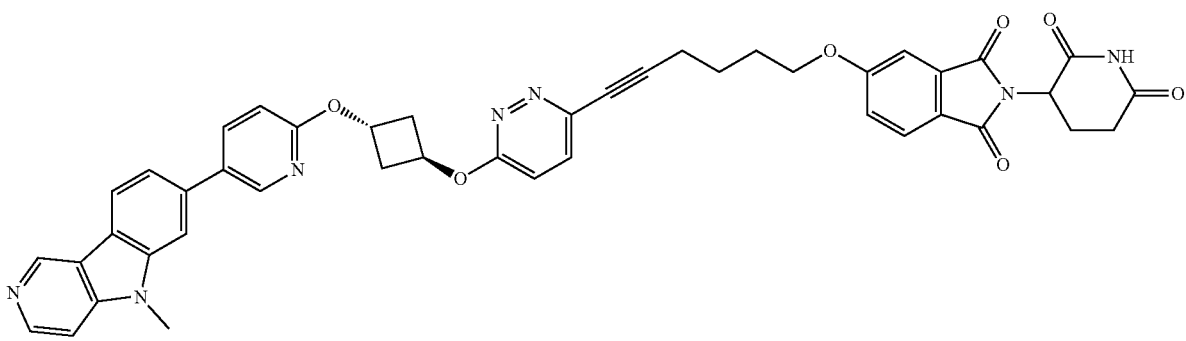

Compound 134

Compound 134: ¹HNMR (400 MHz, DMSO-d$_6$): δ 1.74-1.78 (m, 2H), 1.92-1.95 (m, 2H), 2.03-2.07 (m, 1H), 2.54-2.62 (m, 4H), 2.68-2.71 (m, 4H), 2.85-2.93 (m, 1H), 3.96 (s, 3H), 4.23-4.27 (m, 2H), 5.09-5.14 (m, 1H), 5.45-5.48 (m, 1H), 5.55-5.58 (m, 1H), 7.01 (d, J=8.8 Hz, 1H), 7.24-7.26 (m, 1H), 7.36-7.38 (m, 1H), 7.45 (m, 1H), 7.62-7.68 (m, 3H), 7.82 (d, J=8.0 Hz, 1H), 7.99 (s, 1H), 8.21-8.24 (m, 1H), 8.33 (d, J=8.0 Hz, 1H), 8.49-8.51 (m, 1H), 8.64-8.65 (m, 1H), 9.37 (s, 1H), 11.12 (s, 1H). (M+H)⁺ 776.5.

Additionally, Compound 149 was prepared from Compound 134 using hydrogenation procedure described previously for the conversion of Compound 102 to Compound 110.

Synthetic Scheme for Exemplary Compound 145

2-(2,6-dioxopiperidin-3-yl)-5-(4-((2-(((1r,3r)-3-((5-(5-methyl-5H-pyrido[4,3-b]indol-7-yl)pyridin-2-yl)oxy)cyclobutyl)methyl)-2-azaspiro[3.3]heptan-6-yl)oxy)butoxy)isoindoline-1,3-dione

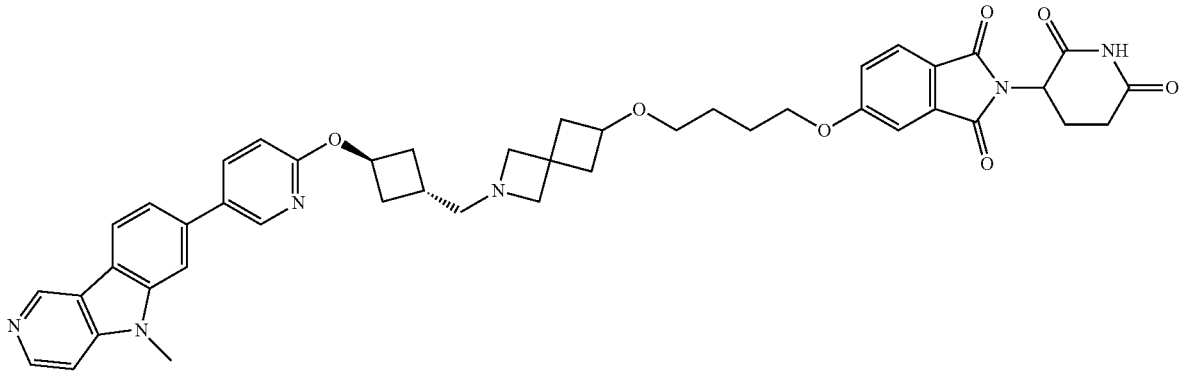 [SMILES: Cn1c2ccncc2c2ccc(-c3ccc(O[C@H]4C[C@H](CN5CC6(CC(OCCCCOc7ccc8c(c7)C(=O)N(C7CCC(=O)NC7=O)C8=O)C6)C5)C4)nc3)cc21]

Prepared according to the schemes below and using procedures described above and common procedures known to those skilled in the art.

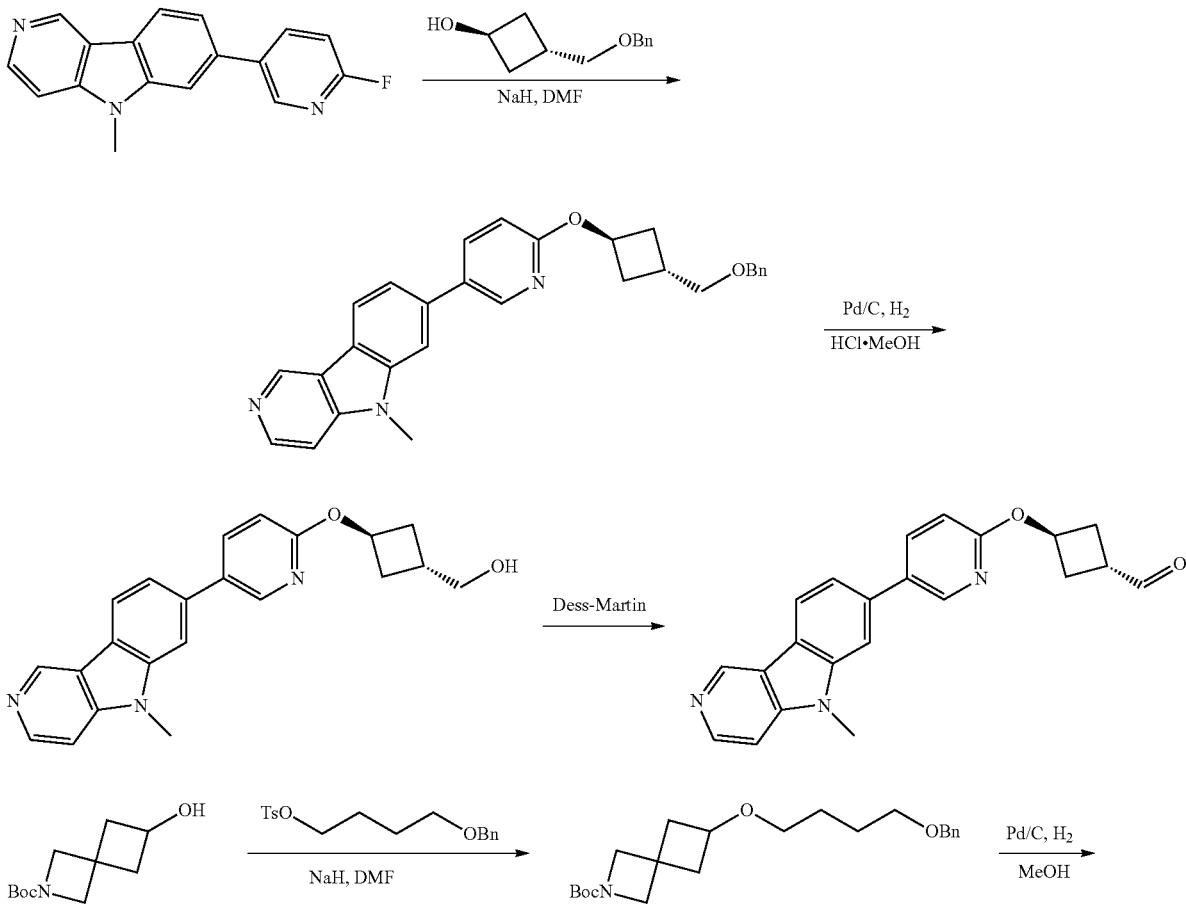

-continued
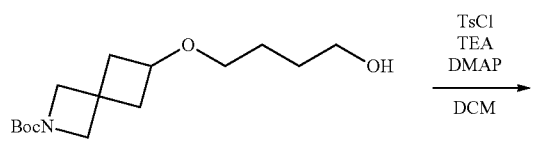
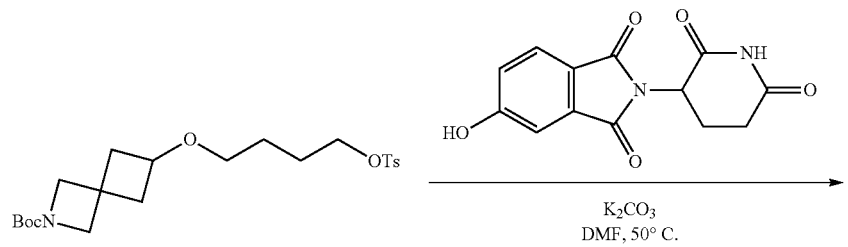
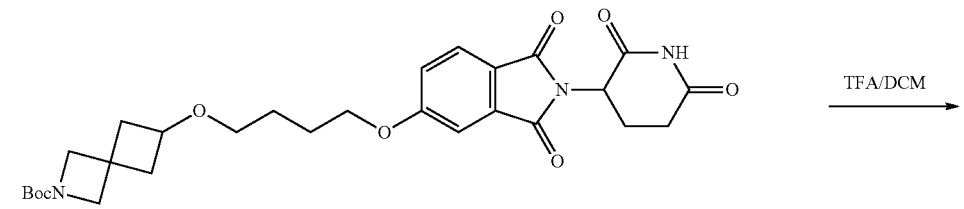
MB-019-C-7
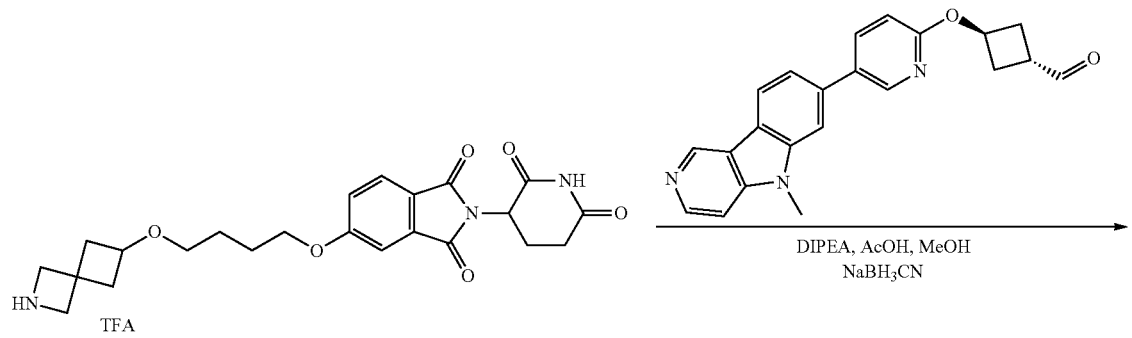
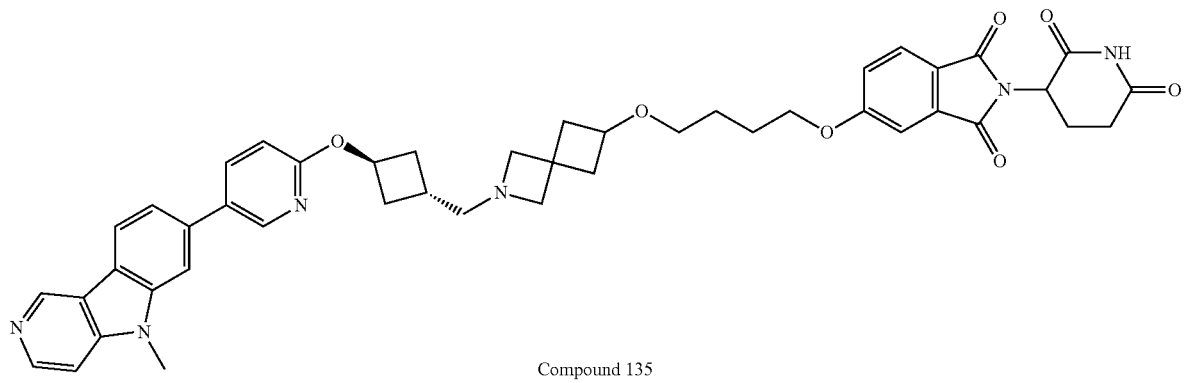
Compound 135

Compound 135: $^1$H NMR (400 MHz, DMSO-$d_6$): 1.60-1.80 (m, 6H), 1.92-2.07 (m, 5H), 2.16-2.26 (m, 3H), 2.34-2.40 (m, 2H), 2.55-2.67 (m, 4H), 2.84-2.93 (m, 1H), 3.26-3.31 (m, 4H), 3.78-3.82 (m, 1H), 3.96 (s, 3H), 4.18 (t, J=6.0 Hz, 2H), 5.05-5.27 (m, 2H), 6.90-6.94 (m, 1H), 7.33-7.35 (m, 1H), 7.42 (s, 1H), 7.60-7.63 (m, 2H), 7.83 (d, J=8.4 Hz, 1H), 7.98 (s, 1H), 8.17-8.20 (m, 1H), 8.32 (d, J=8.0 Hz, 1H), 8.51 (d, J=6.0 Hz, 1H), 8.62 (s, 1H), 9.36 (s, 1H), 11.12 (s, 1H). (M+H)$^+$ 783.6.

Synthetic Scheme for Exemplary Compound 136

2-(2,6-dioxopiperidin-3-yl)-5-(4-((2-((1 s,3 s)-3-((5-(5-methyl-5H-pyrido[4,3-b]indol-7-yl)pyridin-2-yl)oxy)cyclobutane-1-carbonyl)-2-azaspiro[3.3]heptan-6-yl)oxy)butoxy)isoindoline-1,3-dione

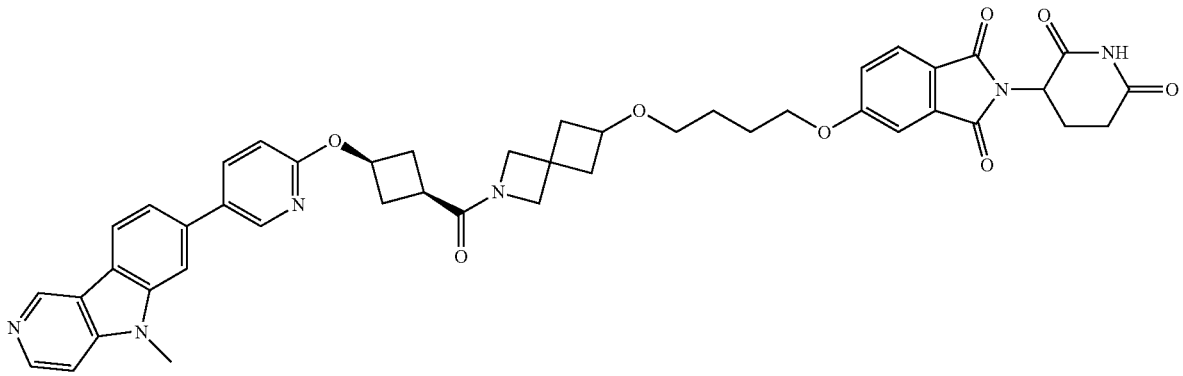 [SMILES: Cn1c2ccncc2c2ccc(-c3ccc(O[C@H]4C[C@@H](C(=O)N5CC6(CC(OCCCCOc7ccc8c(c7)C(=O)N(C7CCC(=O)NC7=O)C8=O)C6)C5)C4)nc3)cc21]

Prepared according to the schemes below and using procedures described above and common procedures known to those skilled in the art.

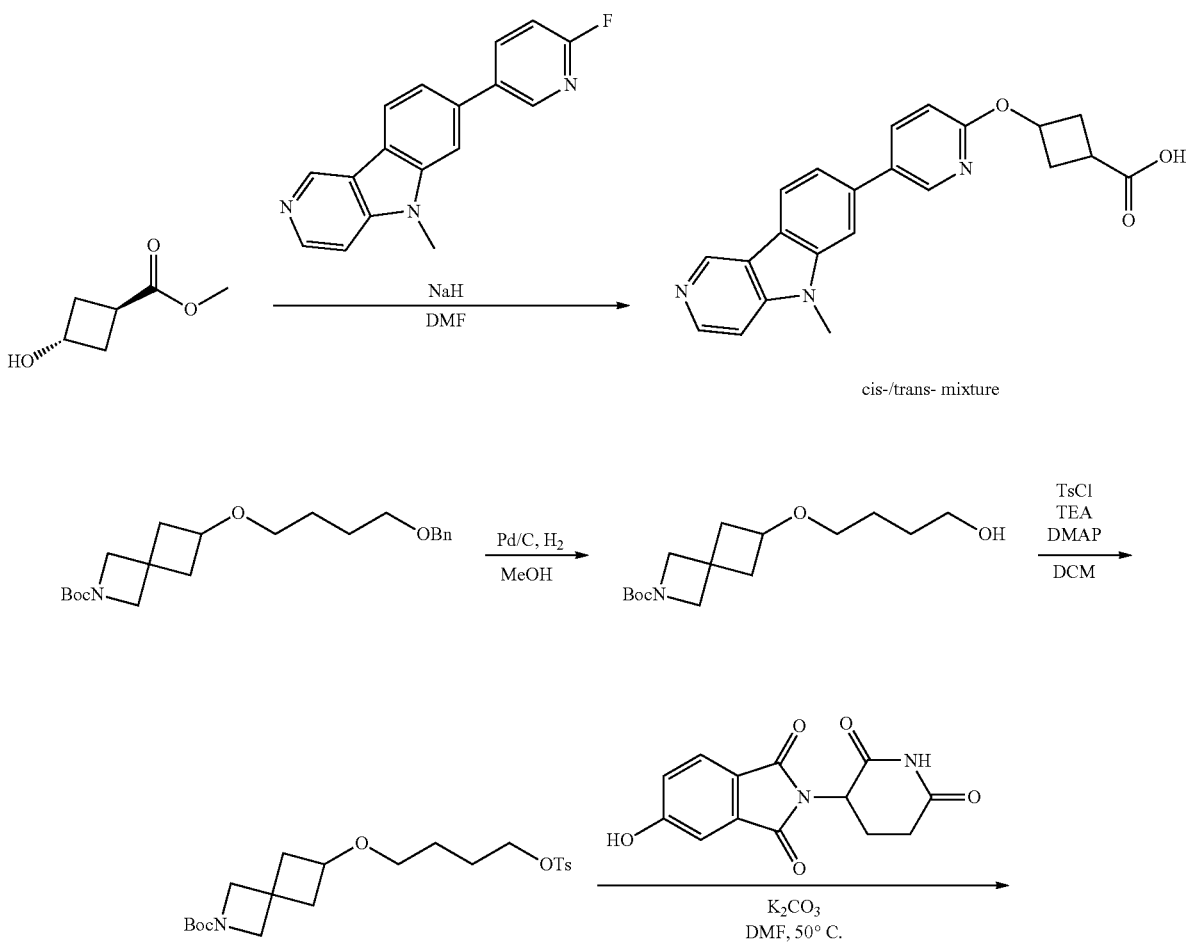

-continued

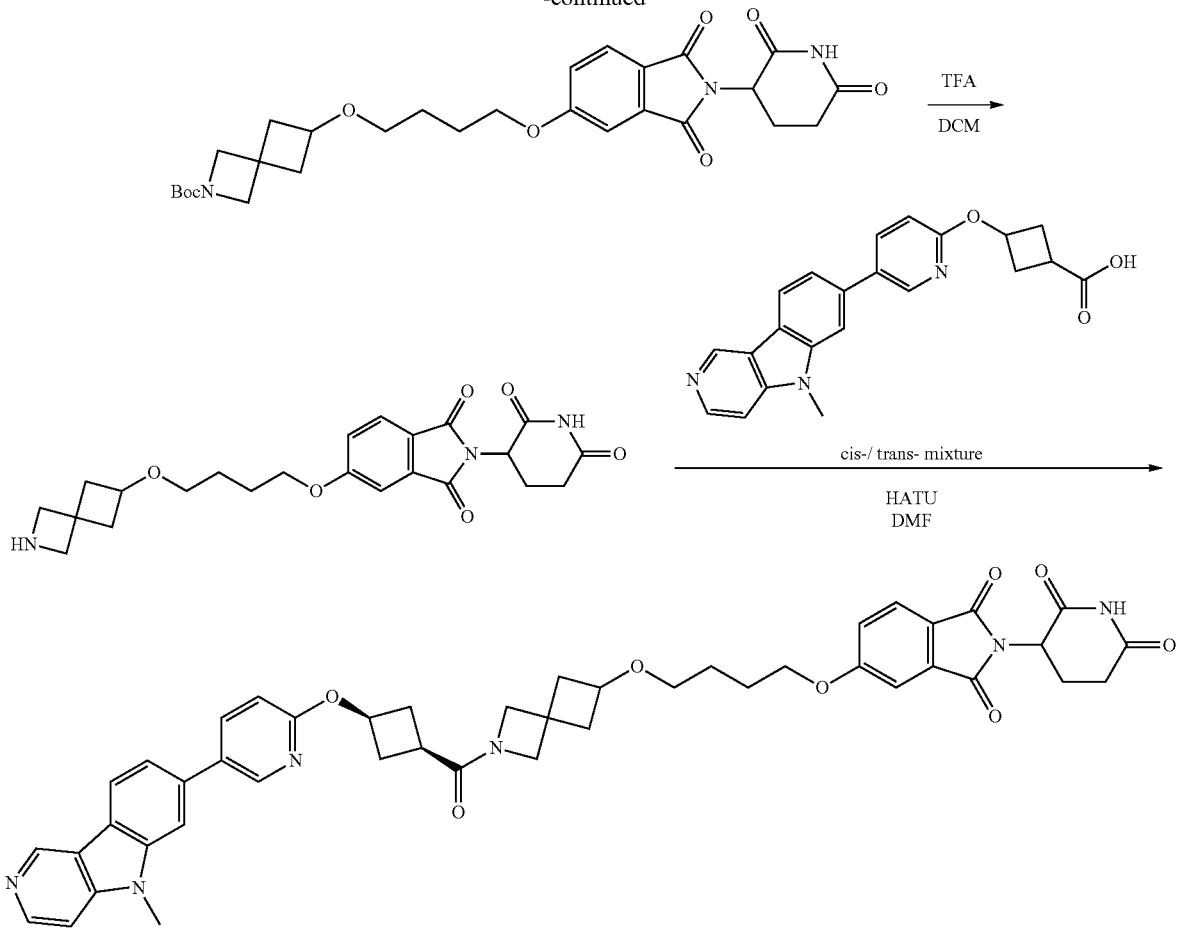

Compound 136
pure cis-isomer isolated from the cis-/trans- mixture

Compound 136: 1HNMR (400 MHz, DMSO-d₆): δ 1.61-1.65 (m, 2H), 1.77-1.80 (m, 2H), 1.99-2.08 (m, 4H), 2.14-2.20 (m, 2H), 2.44-2.46 (m, 3H), 2.55-2.61 (m, 4H), 2.72-2.76 (m, 1H), 2.85-2.93 (m, 1H), 3.79-3.84 (m, 3H), 3.96 (s, 3H), 4.04-4.09 (m, 2H), 4.17-4.20 (m, 2H), 5.10-5.14 (m, 2H), 6.93 (d, J=8.4 Hz, 1H), 7.34-7.42 (m, 2H), 7.61-7.65 (m, 2H), 7.83 (d, J=8.0 Hz, 1H), 7.99 (s, 1H), 8.18-8.20 (m, 1H), 8.32 (d, J=8.4 Hz, 1H), 8.50 (d, J=6.0 Hz, 1H), 8.62 (d, J=0.8 Hz, 1H), 9.37 (s, 1H), 11.12 (s, 1H). (M+H)⁺ 797.5.

Synthetic Scheme for Exemplary Compound 137

2-(2,6-dioxopiperidin-3-yl)-5-((5-(6-(methyl((1r,3r)-3-((5-(5-methyl-5H-pyrido[4,3-b]indol-7-yl)pyridin-2-yl)oxy)cyclobutyl)amino)-2-azaspiro[3.3]heptan-2-yl)-5-oxopentyl)oxy)isoindoline-1,3-dione

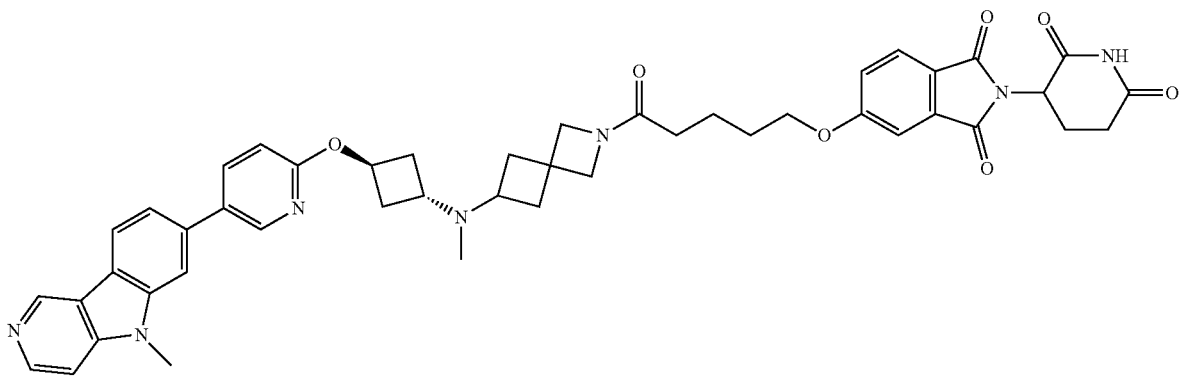 [SMILES: Cn1c2ccncc2c2ccc(-c3ccc(O[C@H]4C[C@H](N(C)C5CC6(C5)CN(C(=O)CCCCOc5ccc7c(c5)C(=O)N(C5CCC(=O)NC5=O)C7=O)C6)C4)nc3)cc21]

Step 1: Benzyl 5-hydroxypentanoate

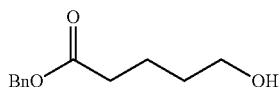 [SMILES: O=C(CCCCO)OCc1ccccc1]

A mixture of tetrahydro-2H-pyran-2-one (1 g, 10 mmol) and sodium hydroxide (400 mg, 10 mmol) in water (15 ml) was stirred at 70° C. for 16 hours. The mixture was concentrated under reduced pressure to give a crude residue which was dissolved in acetone (20 ml), followed by sequential addition of tetrabutylammonium bromide (161 mg, 0.5 mmol) and benzyl bromide (2 g, 12 mmol) at room temperature. The mixture was stirred at 60° C. for 4 hours. TLC showed the reaction was complete. The mixture was concentrated and the residue was partitioned between ethyl acetate (30 ml) and water (50 ml). The organic layer was collected, washed with brine (30 ml), dried over anhydrous sodium sulfate, and concentrated under reduced pressure to give a crude residue which was purified by silica gel flash chromatography (eluted with 33-50% ethyl acetate in hexane) to afford benzyl 5-hydroxypentanoate (500 mg, 24%) as light yellow solid.

Benzyl 5-hydroxypentanoate was converted to the final compound, 2-(2,6-dioxopiperidin-3-yl)-5-((5-(6-(methyl((1r,3r)-3-((5-(5-methyl-5H-pyrido[4,3-b]indol-7-yl)pyridin-2-yl)oxy)cyclobutyl)amino)-2-azaspiro[3.3]heptan-2-yl)-5-oxopentyl)oxy)isoindoline-1,3-dione, according to the schemes below and using procedures described above and common procedures known to those skilled in the art.

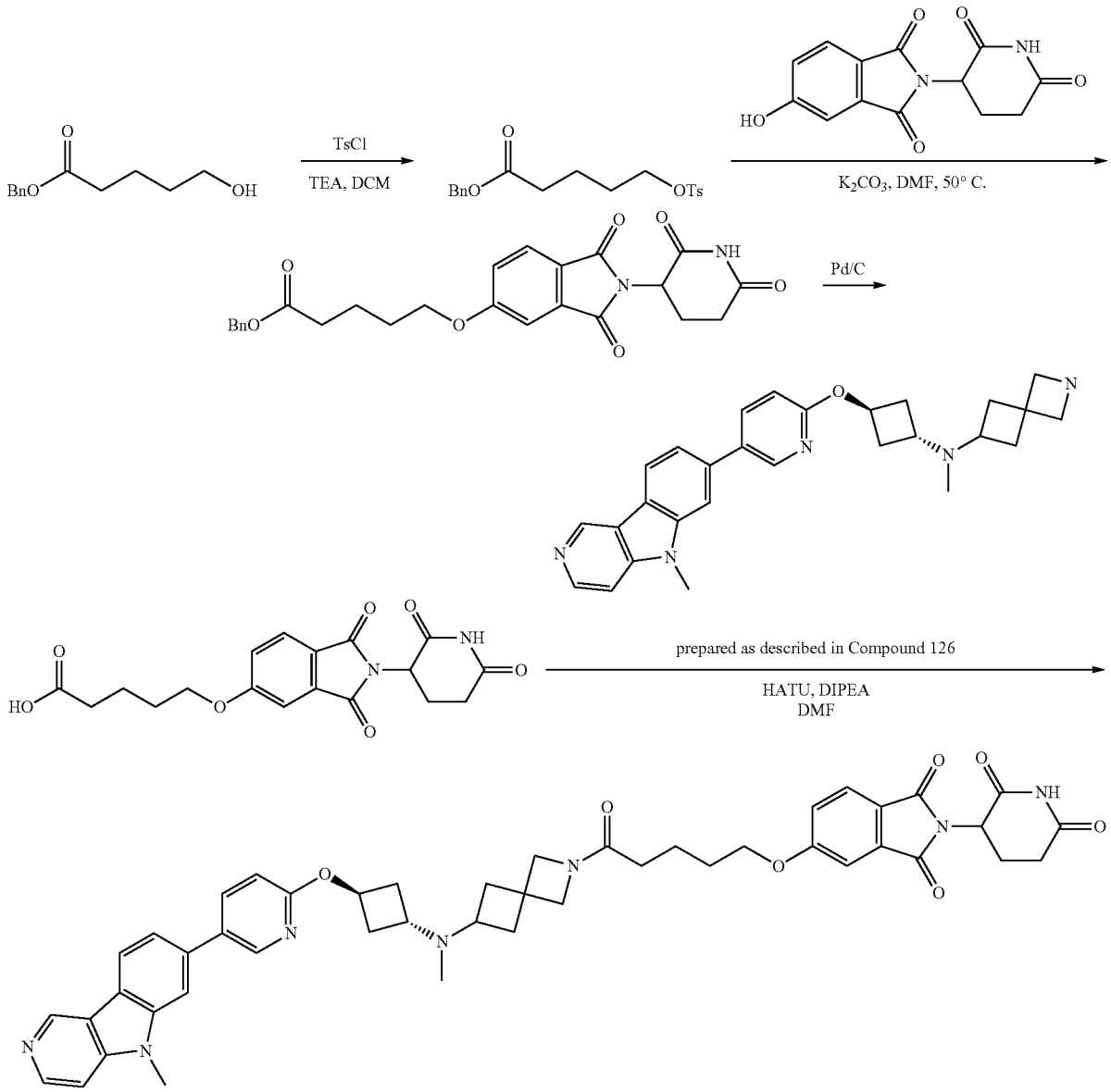

Compound 137

Compound 137: ¹H NMR (400 MHz, DMSO-d6): δ 1.58-1.63 (m, 2H), 1.72-1.77 (m, 2H), 2.03-2.11 (m, 3H), 2.33-2.47 (m, 8H), 2.54-2.62 (m, 2H), 2.78-2.90 (m, 3H), 3.41-3.48 (m, 3H), 3.75-3.79 (m, 1H), 3.80-3.87 (m, 1H), 4.02 (s, 3H), 4.06 (s, 1H), 4.13-4.18 (m, 3H), 5.10-5.14 (m, 1H), 5.25-5.28 (m, 1H), 6.96-7.00 (m, 1H), 7.33-7.42 (m, 2H), 7.70 (d, J=8.4 Hz, 1H), 7.80-7.84 (m, 2H), 8.06 (s, 1H), 8.23-8.26 (m, 1H), 8.39 (d, J=8.0 Hz, 1H), 8.57-8.67 (m, 2H), 9.49 (s, 1H), 11.12 (s, 1H). (M+H)⁺ 810.6.

Synthetic Scheme for Exemplary Compound 138

5-((14-((5-(5-(difluoromethyl)-5H-pyrido[4,3-b]indol-7-yl)pyridin-2-yl)oxy)-3,6,9,12-tetraoxatetradecyl)oxy)-2-(2,6-dioxopiperidin-3-yl)isoindoline-1,3-dione

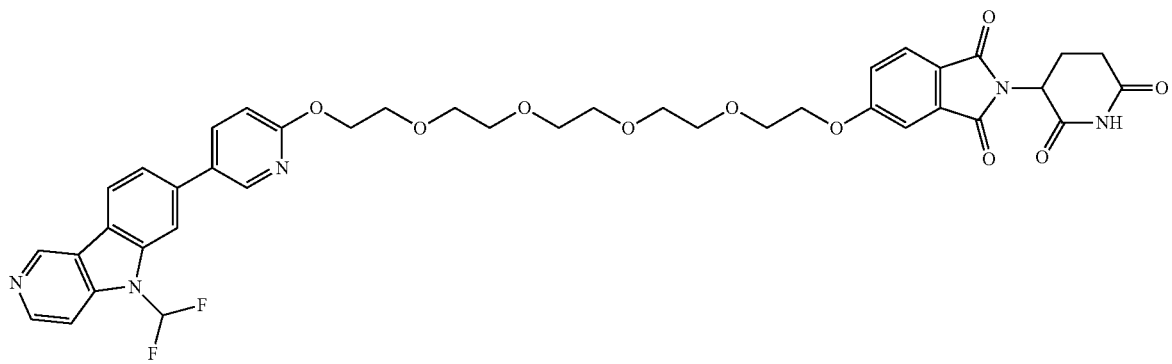 [SMILES: O=C1CCC(N2C(=O)c3ccc(OCCOCCOCCOCCOCCOc4ccc(-c5ccc6c7cnccc7n(C(F)F)c6c5)cn4)cc3C2=O)C(=O)N1]

Step 1: 5-(difluoromethyl)-7-(6-fluoropyridin-3-yl)-5H-pyrido[4,3-b]indole

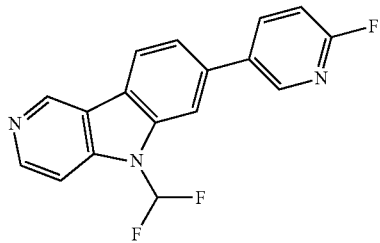 [SMILES: Fc1ccc(-c2ccc3c4cnccc4n(C(F)F)c3c2)cn1]

To a solution of 7-(6-fluoropyridin-3-yl)-5H-pyrido[4,3-b]indole (500 m g, 1.90 mmol) in dry N,N-dimethylformamide (6 ml) was added sodium hydride (60% in mineral oil) (380 mg, 9.50 mmol) at 0° C., and the resulting mixture was stirred at room temperature for 30 minutes. Then sodium 2-chloro-2,2-difluoroacetate (580 mg, 3.80 mmol) was added, and the resulting reaction mixture was stirred at 80° C. for 5 hours. The reaction mixture was quenched with water (30 ml) at 0° C. and extracted with ethyl acetate (30 ml). The combined organic layers were washed with brine (30 ml), dried over anhydrous sodium sulfate, and concentrated under reduced pressure to give a residue which was purified by silica gel flash chromatography (eluted with 50% ethyl acetate in hexane) to afford 5-(difluoromethyl)-7-(6-fluoropyridin-3-yl)-5H-pyrido[4,3-b]indole (35 mg, yield 6%) as yellow solid.

5-(Difluoromethyl)-7-(6-fluoropyridin-3-yl)-5H-pyrido[4,3-b]indole was converted to the final compound, 5-((14-((5-(5-(difluoromethyl)-5H-pyrido[4,3-b]indol-7-yl)pyridin-2-yl)oxy)-3,6,9,12-tetraoxatetradecyl)oxy)-2-(2,6-dioxopiperidin-3-yl)isoindoline-1,3-dione, according to the scheme below using procedures described above and common procedures known to those skilled in the art.

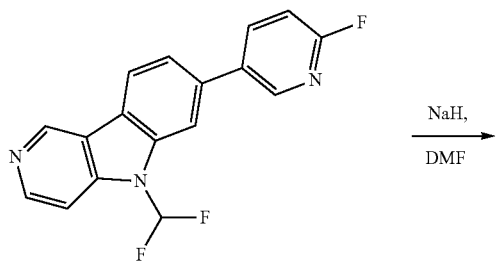

-continued
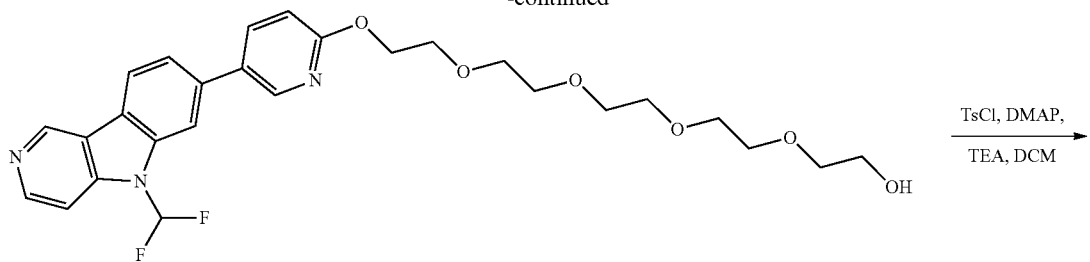
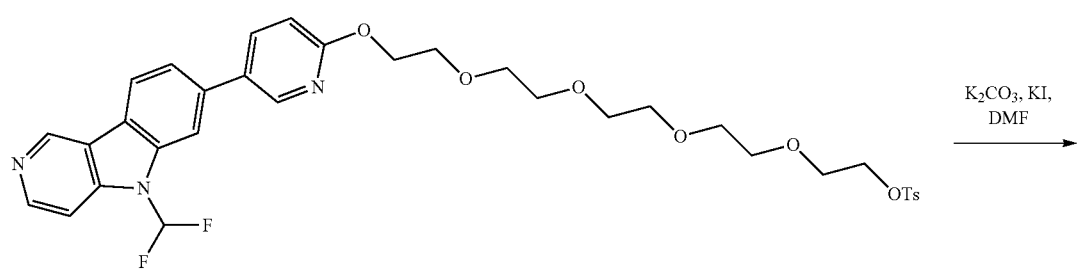
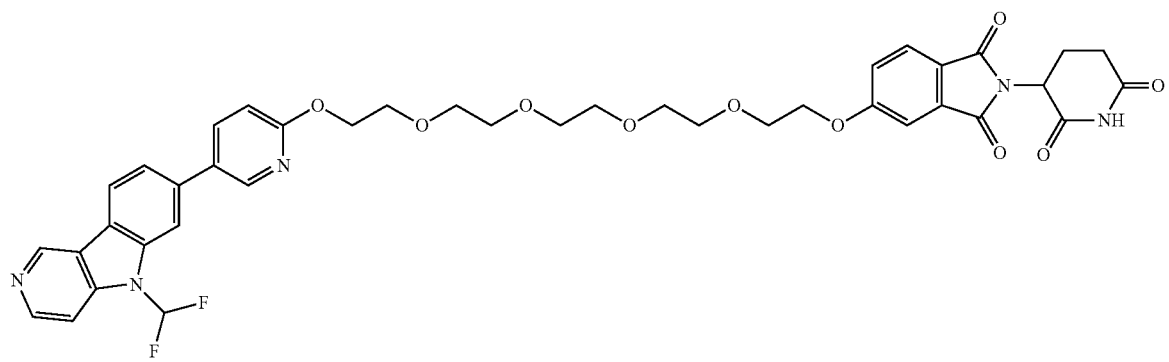
Compound 138
Compound 138: ¹H NMR (400 MHz, DMSO-d6): δ 2.01-2.04 (m, 1H), 2.56-2.67 (m, 2H), 2.83-2.93 (m, 1H), 3.52-3.59 (m, 12H), 3.78 (s, 4H), 4.29 (s, 2H), 4.45 (s, 2H), 5.11 (d, J=12.8 Hz, 1H), 6.98 (d, J=8.8 Hz, 1H), 7.34 (d, J=8.4 Hz, 1H), 7.43 (s, 1H), 7.76-7.83 (m, 3H), 8.14-8.18 (m, 2H), 8.36-8.50 (m, 2H), 8.61-8.65 (m, 2H), 9.49 (s, 1H), 11.11 (s, 1H). (M+H)⁺ 788.5.
Synthetic Scheme for Exemplary Compound 139
2-(2,6-dioxopiperidin-3-yl)-5-((14-((3-fluoro-5-(5-methyl-5H-pyrido[4,3-b]indol-7-yl)pyridin-2-yl)oxy)-3,6,9,12-tetraoxatetradecyl)oxy)isoindoline-1,3-dione
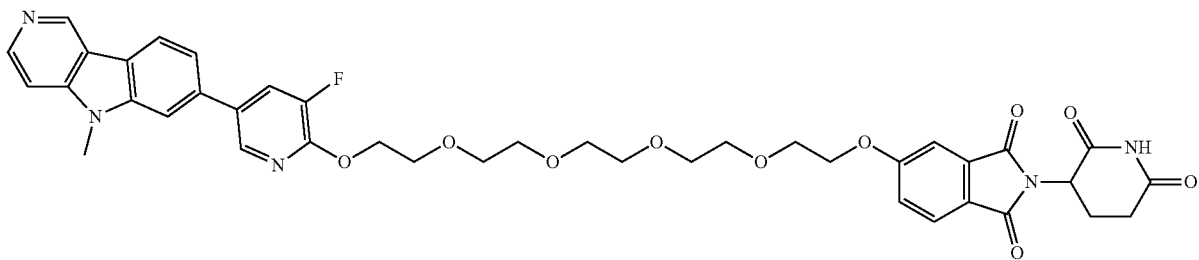 [SMILES: Cn1c2ccncc2c2ccc(-c3cnc(OCCOCCOCCOCCOCCOc4ccc5c(c4)C(=O)N(C4CCC(=O)NC4=O)C5=O)c(F)c3)cc21]

Prepared according to the scheme below using procedures described above and common procedures known to those skilled in the art.
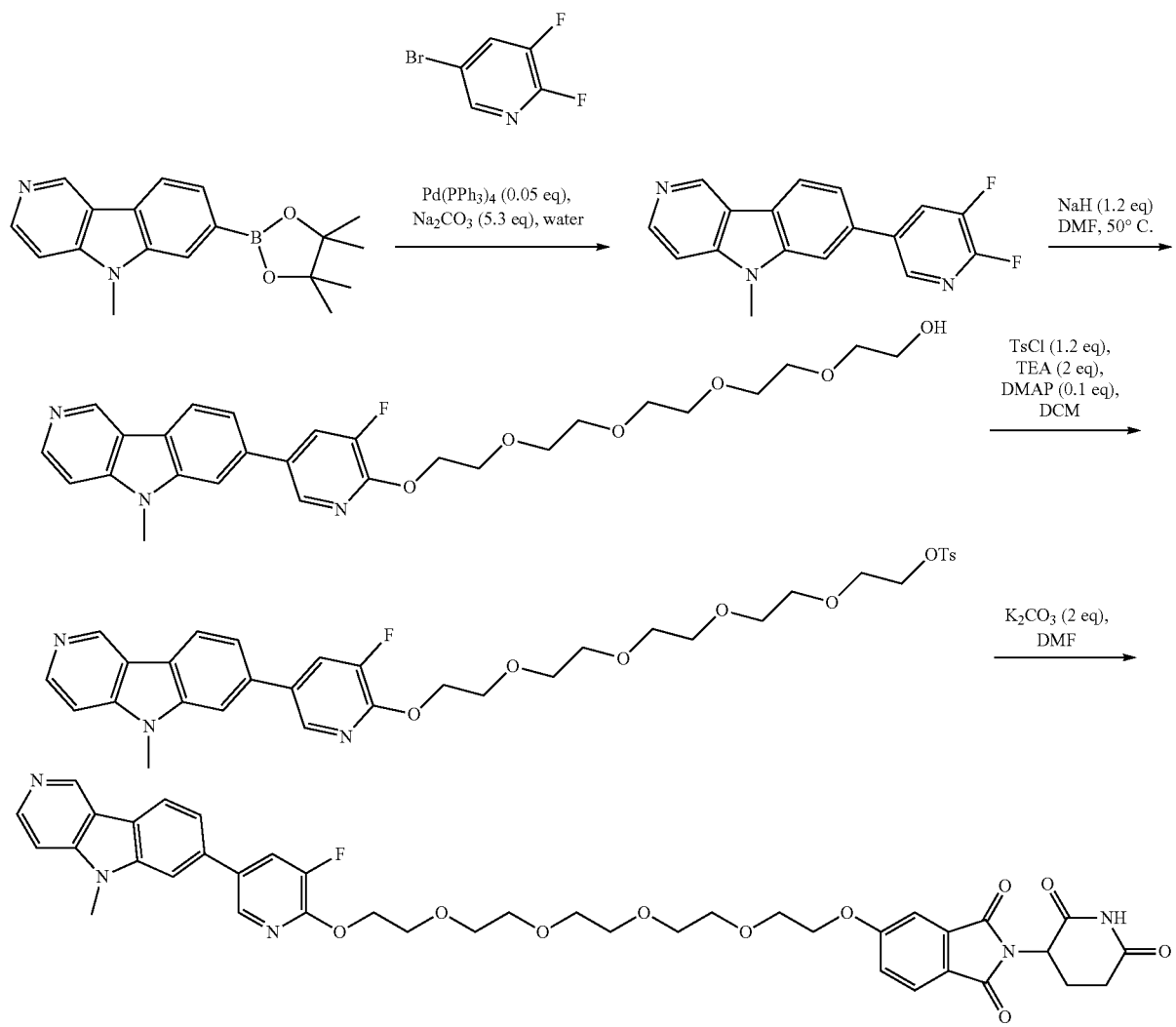
Compound 139
Synthetic Scheme for Exemplary Compound 140
2-(2,6-dioxopiperidin-3-yl)-5-((14-((3-methyl-5-(5-methyl-5H-pyrido[4,3-b]indol-7-yl)pyridin-2-yl)oxy)-3,6,9,12-tetraoxatetradecyl)oxy)isoindoline-1,3-dione
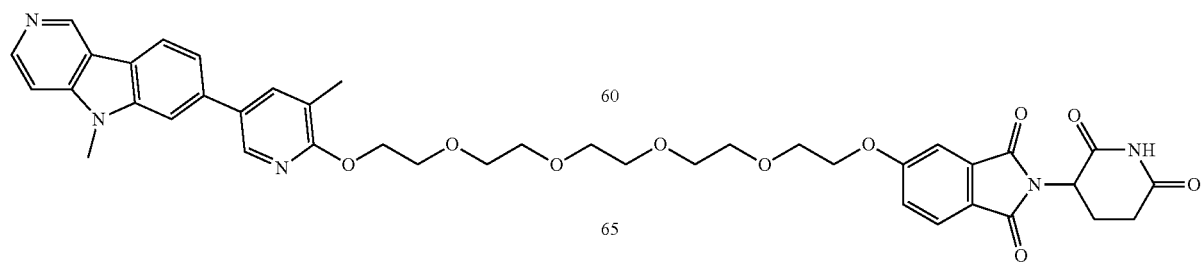

Step 1: 2-fluoro-5-iodo-3-methylpyridine

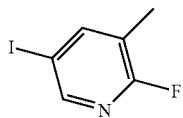

A mixture of 6-fluoro-5-methylpyridin-3-amine (300 mg, 2.4 mmol) in N,N-dimethylacetamide (10 ml) was added potassium iodide (395 mg, 2.4 mmol), iodine (306 g, 1.2 mmol), copper(I) iodide (137 mg, 0.72 mmol) and tert-butyl nitrite (1.7 g, 14.4 mmol) was stirred at 90° C. for 2 hours. The reaction mixture was quenched with water (30 ml) and extracted with ethyl acetate (20 ml). The combined organic layers were washed with brine (30 ml), dried over anhydrous sodium sulfate, and concentrated under reduced pressure to give a residue which was purified by silica gel flash chromatography (eluted with 10% ethyl acetate in hexane) to afford 2-fluoro-5-iodo-3-methylpyridine (350 mg, yield 62%) as white solid.

2-fluoro-5-iodo-3-methylpyridine was converted to the final compound, 2-(2,6-dioxopiperidin-3-yl)-5-((14-((3-methyl-5-(5-methyl-5H-pyrido[4,3-b]indol-7-yl)pyridin-2-yl)oxy)-3,6,9,12-tetraoxatetradecyl)oxy)isoindoline-1,3-dione, according to the scheme below using procedures described above and common procedures known to those skilled in the art.

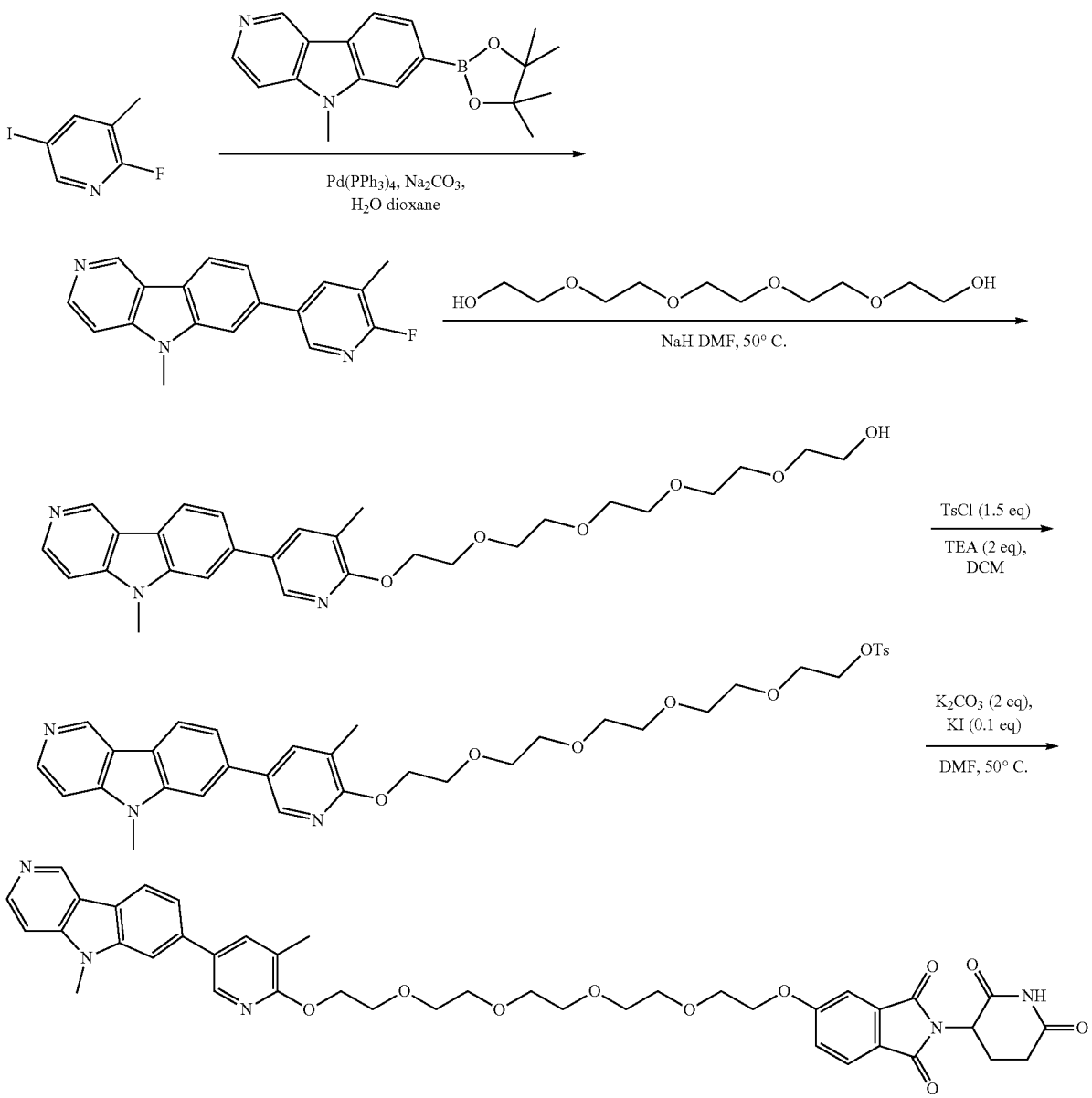

Compound 140

Synthetic Scheme for Exemplary Compound 141
2-(2,6-dioxopiperidin-3-yl)-5-((6-(5-(((1r,3r)-3-((5-(5-methyl-5H-pyrido[4,3-b]indol-7-yl)pyridin-2-yl)oxy)cyclobutoxy)pyrimidin-2-yl)hex-5-yn-1-yl)oxy)isoindoline-1,3-dione
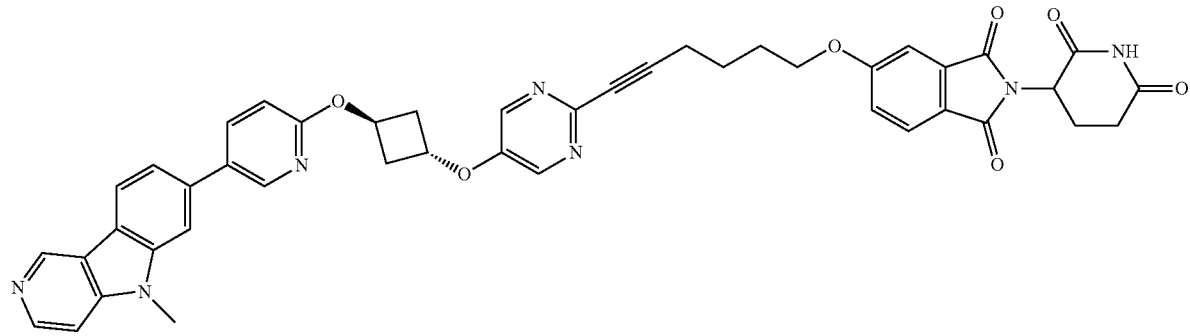 [SMILES: Cn1c2ccncc2c2ccc(-c3ccc(O[C@H]4C[C@H](Oc5cnc(C#CCCCCOc6ccc7c(c6)C(=O)N(C6CCC(=O)NC6=O)C7=O)nc5)C4)nc3)cc21]
Prepared according to the scheme below using procedures described above and common procedures known to those skilled in the art.
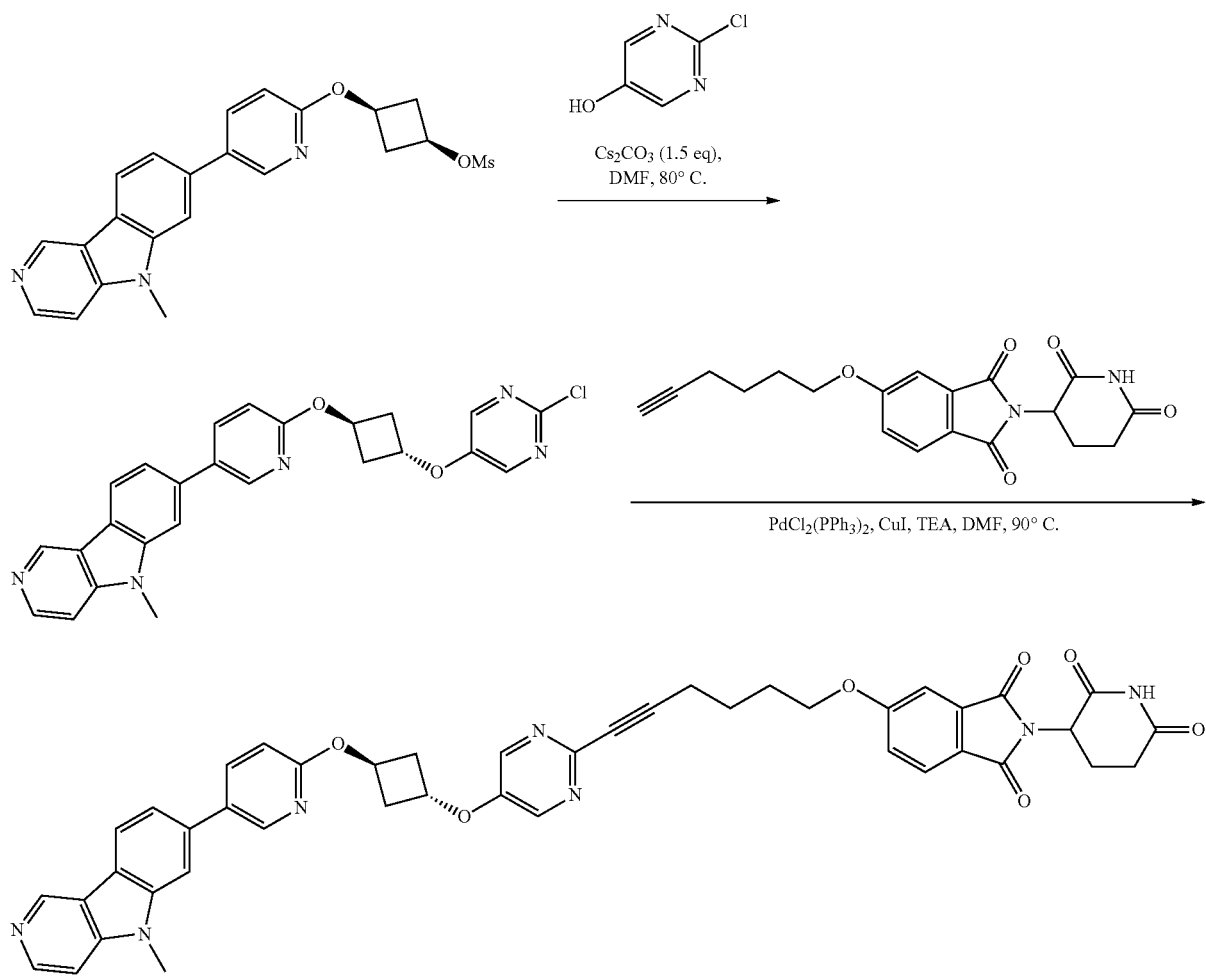
Compound 141

Additionally, Compound 151 was prepared from Compound 141 using hydrogenation procedure described previously for the conversion of Compound 102 to Compound. 110.

Synthetic Scheme for Exemplary Compound 142

2-(2,6-dioxopiperidin-3-yl)-5-((1-(3-(5-((1r,3r)-3-((5-(5-methyl-5H-pyrido[4,3-b]indol-7-yl)-3-(trifluoromethyl)pyridin-2-yl)oxy)cyclobutoxy)pyridin-2-yl)prop-2-yn-1-yl)azetidin-3-yl)oxy)isoindoline-1,3-dione

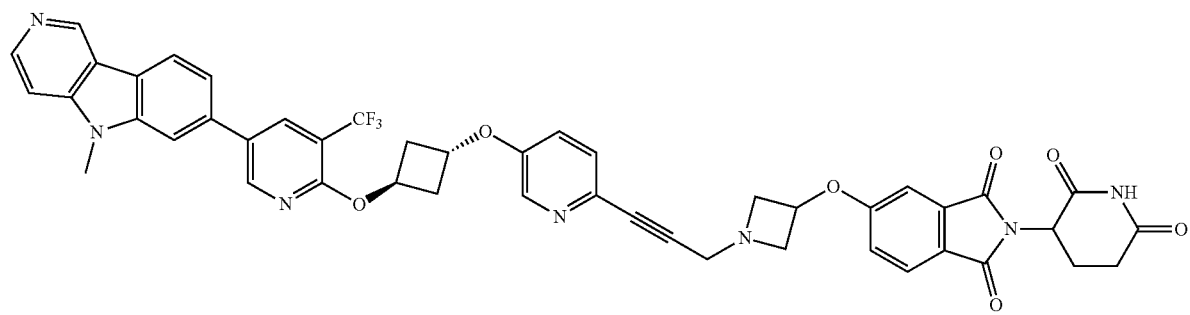 [SMILES: Cn1c2ccncc2c2ccc(-c3cnc(O[C@H]4C[C@H](Oc5ccc(C#CCN6CC(Oc7ccc8c(c7)C(=O)N(C7CCC(=O)NC7=O)C8=O)C6)nc5)C4)c(C(F)(F)F)c3)cc21]

Prepared according to the scheme below using procedures described above and common procedures known to those skilled in the art.

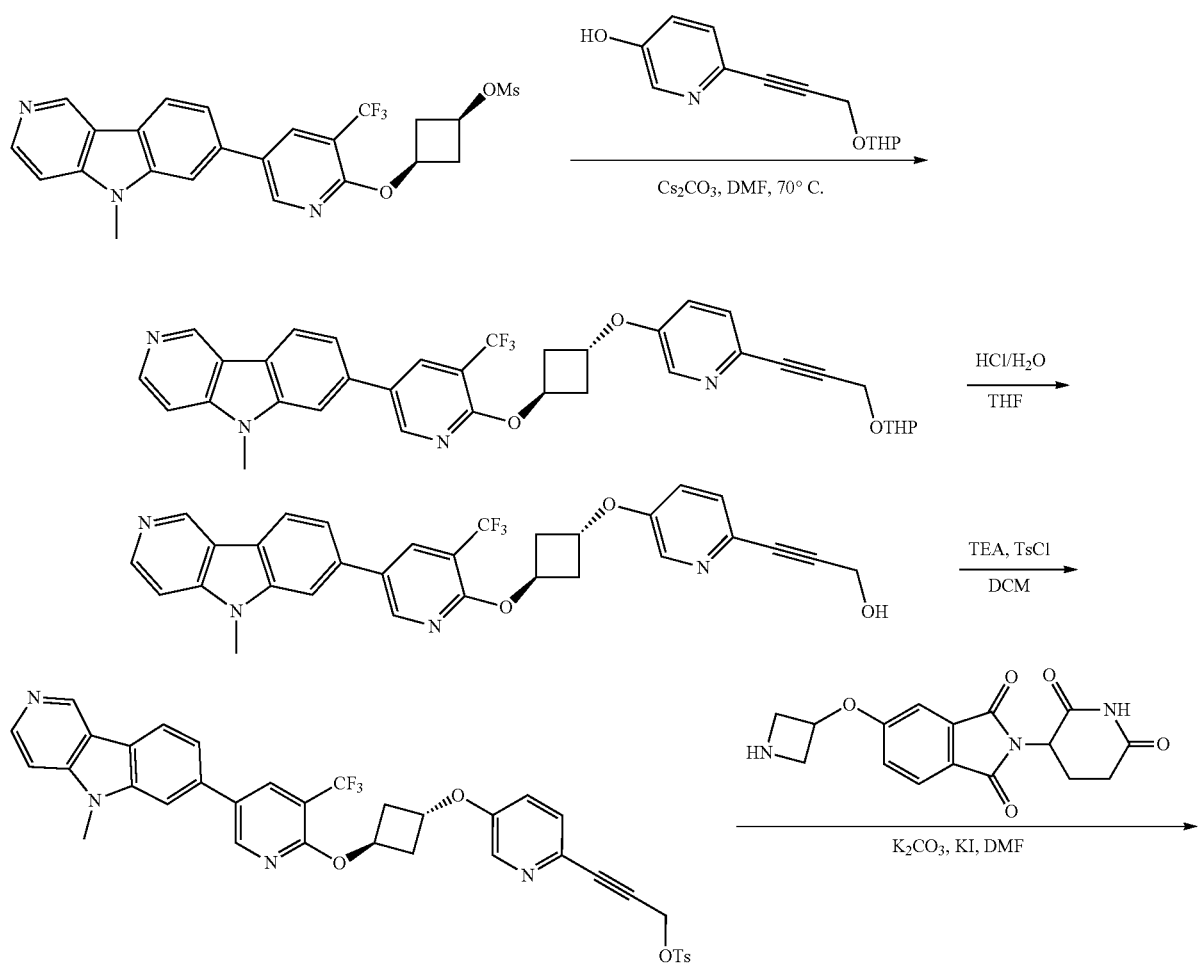

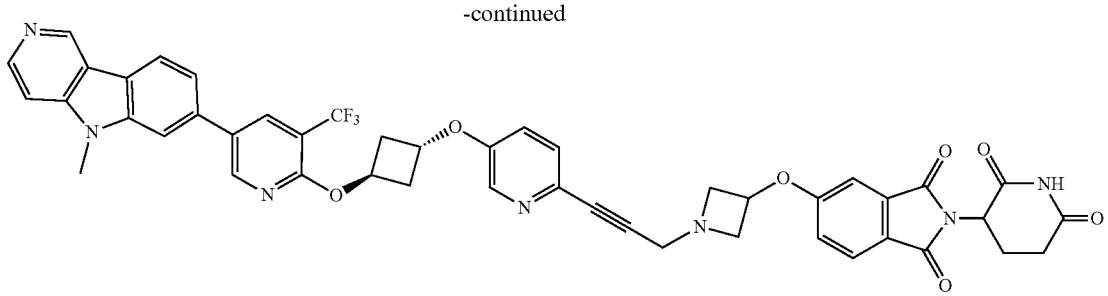

Compound 142

Synthetic Scheme for Exemplary Compound 143

2-(2,6-dioxopiperidin-3-yl)-5-((14-((5-(5-methyl-5H-pyrido[4,3-b]indol-7-yl)-6-(trifluoromethyl)pyridin-2-yl)oxy)-3,6,9,12-tetraoxatetradecyl)oxy)isoindoline-1,3-dione

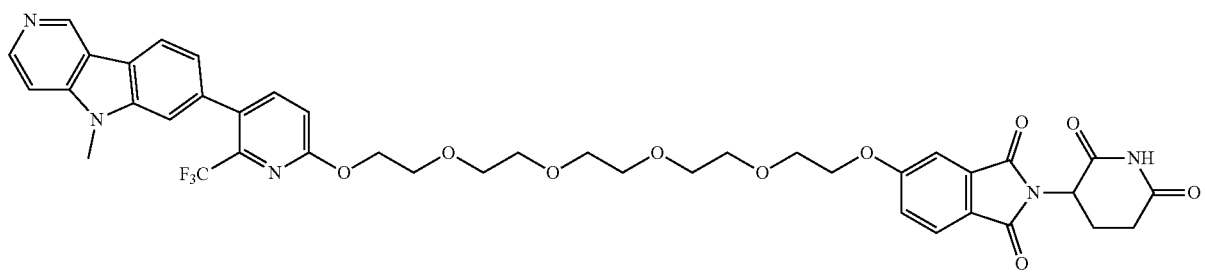 [SMILES: Cn1c2ccncc2c2ccc(-c3ccc(OCCOCCOCCOCCOCCOc4ccc5c(c4)C(=O)N(C4CCC(=O)NC4=O)C5=O)nc3C(F)(F)F)cc21]

Step 1: 6-chloro-3-iodo-2-(trifluoromethyl)pyridine

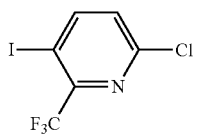

To a solution of lithium diisopropylamide (2 M in THF, 3.03 mmol) in tetrahydrofuran (15 ml) was added a solution of 2-chloro-6-(trifluoromethyl)pyridine (500 mg, 2.75 mmol) in tetrahydrofuran (5 ml) at −65° C. under nitrogen atmosphere. The dark brown solution was stirred at −65° C. for 30 minutes. To the reaction mixture was added a solution of iodine (0.7 g, 2.75 mmol) in tetrahydrofuran (5 ml) was added at −65° C. within 20 minutes. After additional 20 minutes stirring at the same temperature, the reaction mixture was quenched with hydrochloride acid (2M, 6 ml) at 0° C. and stirred for 20 minutes. The reaction mixture was extracted with ethyl acetate (30 ml). The combined organic layers were washed with brine (30 ml), dried over anhydrous sodium sulfate, and concentrated under reduced pressure to give a residue which was purified by silica gel flash chromatography (eluted with 1% ethyl acetate in hexane) to afford 6-chloro-3-iodo-2-(trifluoromethyl)pyridine (316 mg, yield 37%) as brown oil.

6-Chloro-3-iodo-2-(trifluoromethyl)pyridine was converted to the final compound, 2-(2,6-dioxopiperidin-3-yl)-5-((14-((5-(5-methyl-5H-pyrido[4,3-b]indol-7-yl)-6-(trifluoromethyl)pyridin-2-yl)oxy)-3,6,9,12-tetraoxatetradecyl)oxy)isoindoline-1,3-dione, according to the scheme below using procedures described above and common procedures known to those skilled in the art.

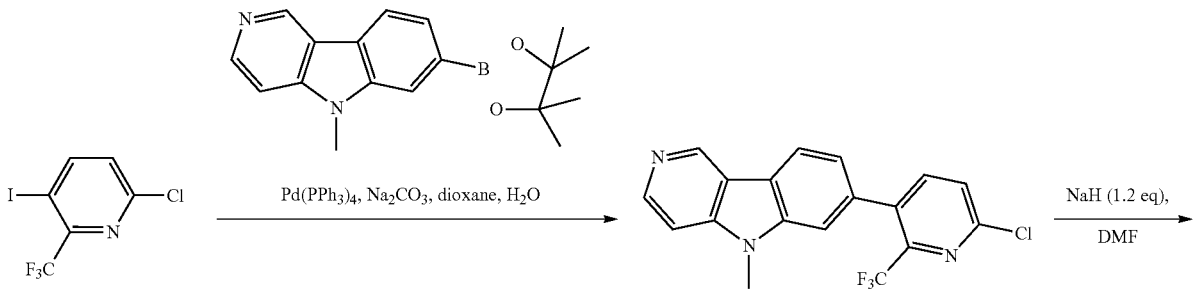

-continued
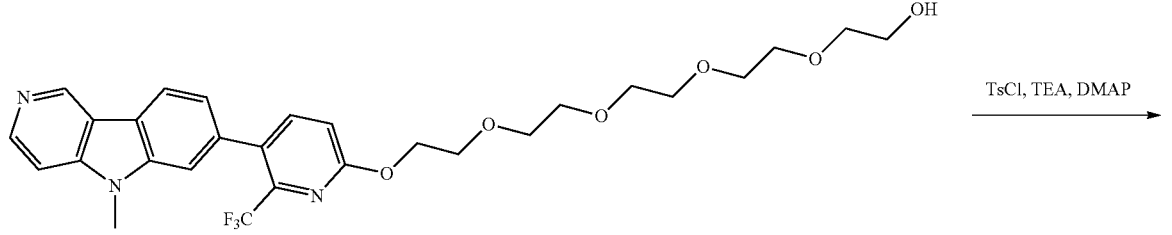
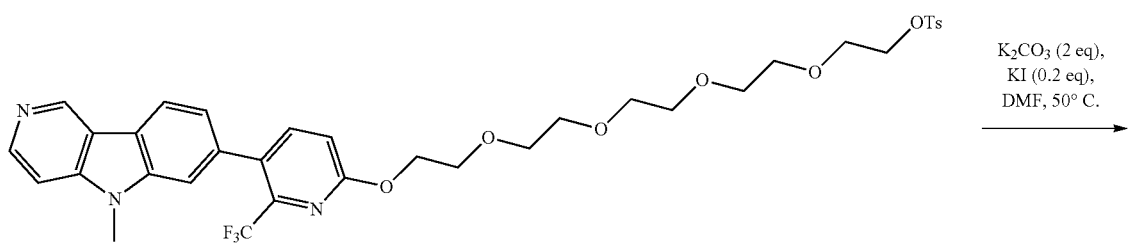
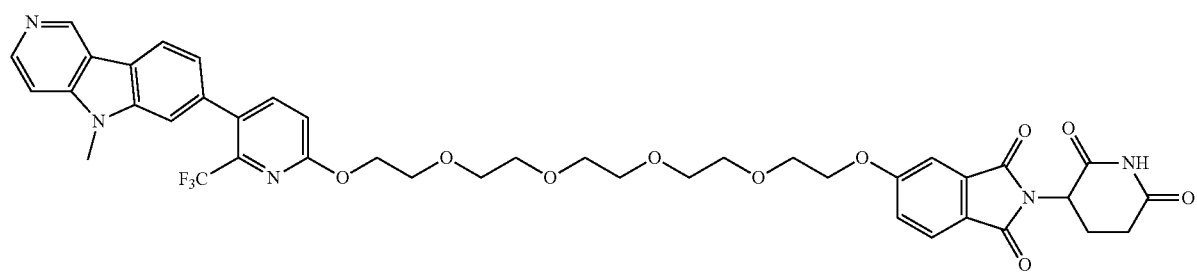
Compound 143
Synthetic Scheme for Exemplary Compound 146
2-(2,6-dioxopiperidin-3-yl)-5-((6-(6-(3-((5-(5-methyl-5H-pyrido[4,3-b]indol-7-yl)pyridin-2-yl)oxy)propoxy)pyridin-3-yl)hex-5-yn-1-yl)oxy)isoindoline-1,3-dione
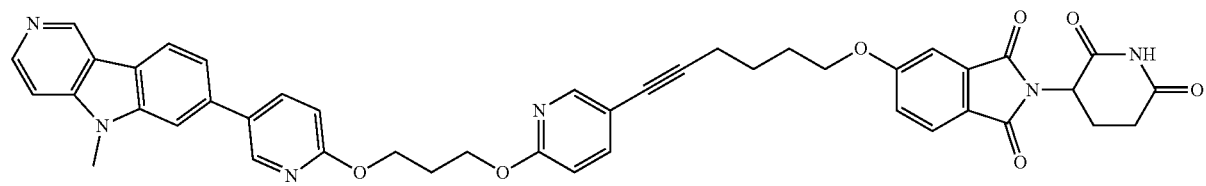 [SMILES: Cn1c2ccncc2c2ccc(-c3ccc(OCCCOc4ccc(C#CCCCCOc5ccc6c(c5)C(=O)N(C5CCC(=O)NC5=O)C6=O)cn4)nc3)cc21]
Prepared according to the scheme below using procedures described above and common procedures known to those skilled in the art.
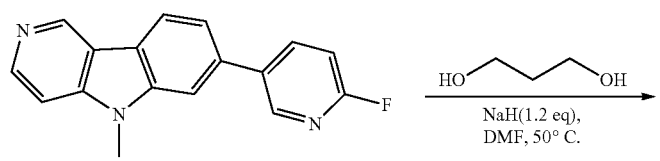

533                                                                    534
-continued
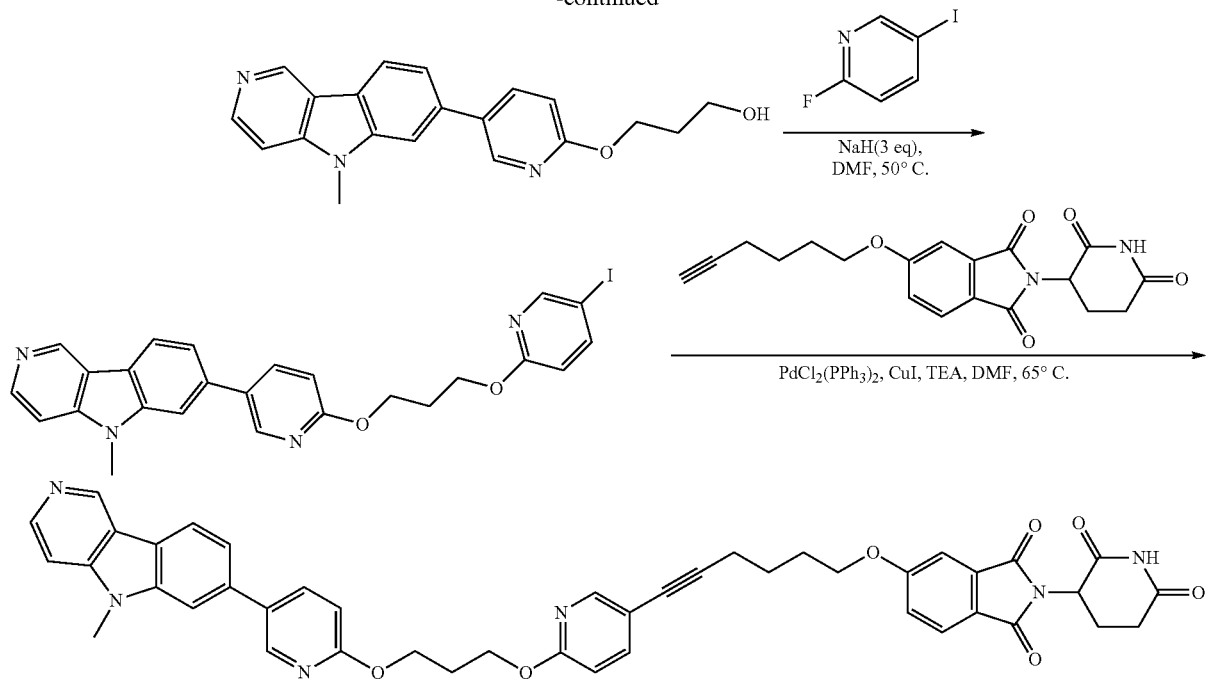
Compound 146
Synthetic Scheme for Exemplary Compound 152
2-(2,6-dioxopiperidin-3-yl)-5-((1-(3-(5-(((1r,3r)-3-((5-(5-methyl-5H-pyrido[4,3-b]indol-7-yl)pyridin-2-yl)oxy)cyclobutoxy)pyridin-2-yl)prop-2-yn-1-yl)azetidin-3-yl)oxy)isoindoline-1,3-dione
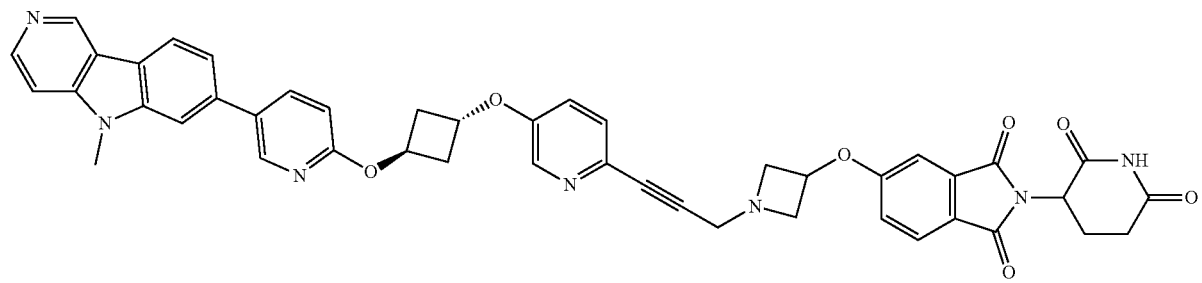 [SMILES: Cn1c2ccncc2c2ccc(-c3ccc(O[C@H]4C[C@H](Oc5ccc(C#CCN6CC(Oc7ccc8c(c7)C(=O)N(C7CCC(=O)NC7=O)C8=O)C6)nc5)C4)nc3)cc21]
Prepared according to the scheme below using procedures described above and common procedures known to those skilled in the art.
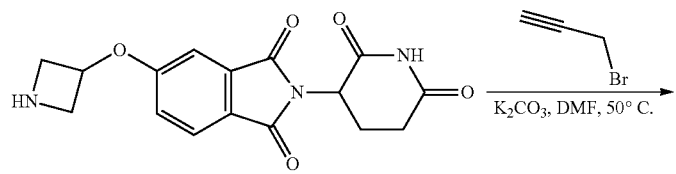

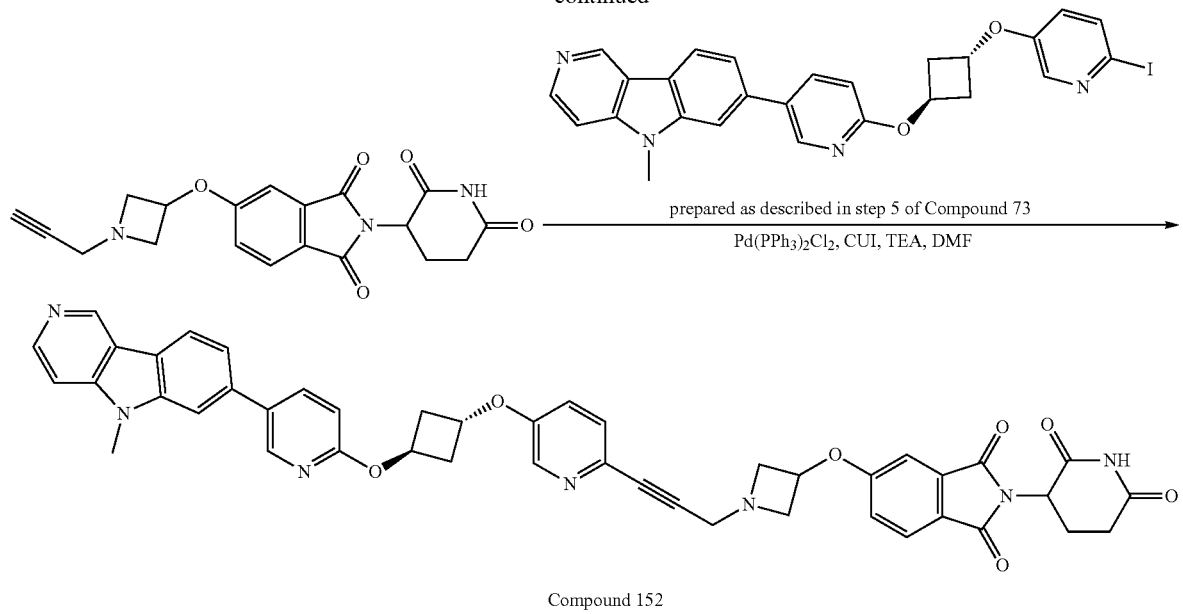

prepared as described in step 5 of Compound 73

Pd(PPh₃)₂Cl₂, CUI, TEA, DMF

Compound 152

Synthetic Scheme for Exemplary Compound 150

Step 1: 2-[5-(3-benzyloxycyclobutoxy)-2,2-difluoro-pentoxy]tetrahydropyran

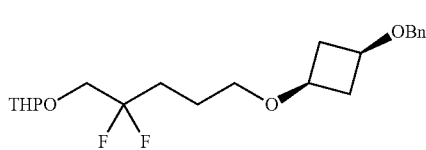

To a solution of 3-benzyloxycyclobutanol (2.59 g, 14.53 mmol, 1.10 eq) in N,N-dimethylformamide (100 mL) was added sodium hydride (581 mg, 14.53 mmol, 60% in mineral oil, 1.10 eq) at 0° C. under nitrogen. The mixture was stirred at 0° C. for 0.5 hours and added a solution of (4,4-difluoro-5-tetrahydropyran-2-yloxy-pentyl) 4-methyl-benzenesulfonate (5.0 g, 13.21 mmol, 1.00 eq) [prepared as described for Compound 171] in N,N-dimethylformamide (20 mL) dropwise at 0° C. The reaction mixture was stirred at 60° C. for 6 hours. The mixture was cooled to 25° C. and poured into ice-water (w/w=1/1) (30 mL) and stirred for 15 minutes. The aqueous phase was extracted with ethyl acetate (100 mL×3). The combined organic phase was washed with brine (100 mL×3), dried with anhydrous sodium sulfate, filtered and concentrated under vacuum. The residue was purified by silica gel chromatography (Petroleum ether/Ethyl acetate=1/0, 20/1) to afford 2-[5-(3-benzyloxycy-clobutoxy)-2,2-difluoro-pentoxy]tetrahydropyran (1.75 g, 4.21 mmol, 32% yield, 92% purity) as a colorless oil.

Step 2: 3-(4,4-difluoro-5-tetrahydropyran-2-yloxy-pentoxy)cyclobutanol

To a solution of 2-[5-(3-benzyloxycyclobutoxy)-2,2-difluoro-pentoxy]tetrahydropyran (1.75 g, 4.55 mmol, 1.00 eq) in methanol (30 mL) was added palladium on activated carbon catalyst (1.0 g, 10% purity) under nitrogen. The suspension was degassed under vacuum and purged with hydrogen several times. The mixture was stirred under hydrogen (15 psi) at 25° C. for 16 hours. The reaction mixture was filtered and the filter was concentrated. The crude product was purified by silica gel chromatography (Petroleum ether/Ethyl acetate=10:1 to 1:1) to give 3-(4,4-difluoro-5-tetrahydropyran-2-yloxy-pentoxy)cyclobutanol (1.2 g, 4.08 mmol, 90% yield) as a colorless oil.

Step 3: 5-Bromo-2-[3-(4,4-difluoro-5-tetrahydropyran-2-yloxy-pentoxy)cyclobutoxy]pyridine

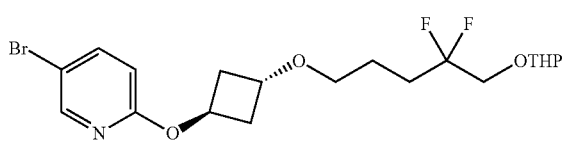

To a mixture of 3-(4,4-difluoro-5-tetrahydropyran-2-yloxy-pentoxy)cyclobutanol (1.2 g, 4.08 mmol, 1.00 eq) and 5-bromopyridin-2-ol (1.06 g, 6.12 mmol, 1.50 eq) in toluene (60 mL) was added 1,1'-(azodicarbonyl)dipiperidine (1.54 g, 6.12 mmol, 1.50 eq) and tributylphosphane (1.24 g, 6.12 mmol, 1.50 eq) in one portion at 0° C. under nitrogen. The mixture was stirred at 110° C. for 16 hours. The mixture was cooled to 25° C. and concentrated at reduced pressure at 45° C. The residue was poured into ice-water (w/w=1/1) (30 mL) and stirred for 15 minutes. The aqueous phase was extracted with ethyl acetate (50 mL×3). The combined organic phase was washed with brine (50 mL×2), dried with anhydrous sodium sulfate, filtered and concentrated in vacuum. The residue was purified by silica gel chromatography (Petroleum ether/Ethyl acetate=100/1, 50/1). 5-Bromo-2-[3-(4,4-difluoro-5-tetrahydropyran-2-yloxy-pentoxy)cyclobutoxy]pyridine (1.36 g, 3.02 mmol, 74.0% yield) was obtained as a yellow oil.

Step 4: 5-[3-[(5-bromo-2-pyridyl)oxy]cyclobutoxy]-2,2-difluoro-pentan-1-ol

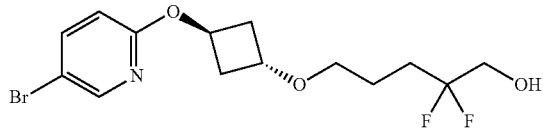 [SMILES: OCC(F)(F)CCCO[C@H]1C[C@H](Oc2ccc(Br)cn2)C1]

To a mixture of 5-bromo-2-[3-(4,4-difluoro-5-tetrahydropyran-2-yloxy-pentoxy) cyclobutoxy]pyridine (1.1 g, 2.44 mmol, 1.00 eq) in tetrahydrofuran (25 mL) was added hydrogen chloride (4 M, 10 mL, 16.38 eq) in one portion under nitrogen. Then the mixture was stirred at 25° C. for 1 hour. The mixture was poured into saturated sodium hydrogencarbonate (20 mL) and stirred for 15 minutes. The aqueous was extracted with ethyl acetate (50 mL×3). The combined organic phase was washed with brine (50 mL×3), dried with anhydrous sodium sulfate, filtered and concentrated under vacuum. The residue was purified by silica gel chromatography (Petroleum ether/Ethyl acetate=10/1, 5/1) to afford 5-[3-[(5-bromo-2-pyridyl)oxy]cyclobutoxy]-2,2-difluoro-pentan-1-ol (700 mg, 1.91 mmol, 78% yield) as a colorless oil.

Step 5: [5-[3-[(5-bromo-2-pyridyl)oxy]cyclobutoxy]-2,2-difluoro-pentyl]trifluoromethanesulfonate

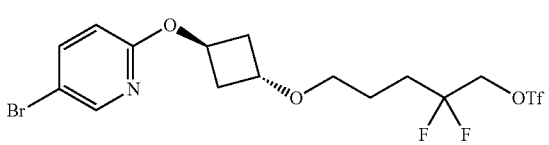 [SMILES: O=S(=O)(OCC(F)(F)CCCO[C@H]1C[C@H](Oc2ccc(Br)cn2)C1)C(F)(F)F]

To a mixture of 5-[3-[(5-bromo-2-pyridyl)oxy]cyclobutoxy]-2,2-difluoro-pentan-1-ol (400 mg, 1.09 mmol, 1.00 eq) and triethylamine (552 mg, 5.46 mmol, 5.00 eq) in dichloromethane (10 mL) was trifluoromethanesulfonyl chloride (368 mg, 2.18 mmol, 2.00 eq) at 0° C. under nitrogen. After the addition had finished, the reaction mixture was stirred at 25° C. for 1 hour. The mixture was concentrated in vacuum at 40° C. The residue was purified by silica gel chromatography (Petroleum ether/Ethyl acetate=5/1) to afford [5-[3-[(5-bromo-2-pyridyl)oxy]cyclobutoxy]-2,2-difluoro-pentyl]trifluoromethanesulfonate (465 mg, 0.93 mmol, 85% yield) as a colorless oil.

Step 6: tert-butyl 6-[2-(2,6-dioxo-3-piperidyl)-1,3-dioxo-isoindolin-5-yl]-2,6-diazaspiro[3.3]heptane-2-carboxylate

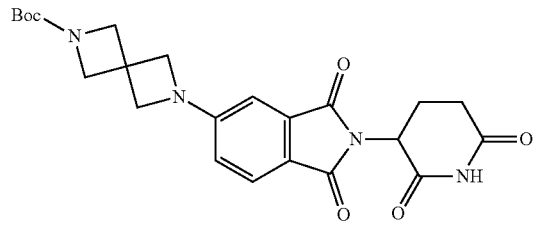 [SMILES: CC(C)(C)OC(=O)N1CC2(C1)CN(c1ccc3c(c1)C(=O)N(C1CCC(=O)NC1=O)C3=O)C2]

To a mixture of 2-(2,6-dioxo-3-piperidyl)-5-fluoro-isoindoline-1,3-dione (300 mg, 1.09 mmol, 1.00 eq) and tert-butyl 2,6-diazaspiro[3.3]heptane-2-carboxylate; oxalic acid (317 mg, 0.65 mmol, 0.60 eq) in (methylsulfinyl)methane (5 mL) was added N,N-diisopropylethylamine (561 mg, 4.34 mmol, 4.00 eq) in one portion under nitrogen. The mixture was heated to 120° C. and stirred for 16 hours. The mixture was poured into ice-water (w/w=1/1) (30 mL) and stirred for 10 minutes. The aqueous phase was extracted with ethyl acetate (50 mL×3). The combined organic phase was washed with brine (50 mL×3), dried with anhydrous sodium sulfate, filtered and concentrated in vacuum. The residue was triturated by Petroleum ether: Ethyl acetate (1:1, 50 mL) to afford tert-butyl 6-[2-(2,6-dioxo-3-piperidyl)-1,3-dioxo-isoindolin-5-yl]-2,6-diazaspiro[3.3]heptane-2-carboxylate (420 mg, 0.92 mmol, 85% yield) as a yellow solid.

Step 7: 5-(2,6-diazaspiro[3.3]heptan-2-yl)-2-(2,6-dioxo-3-piperidyl)isoindoline-1,3-dione

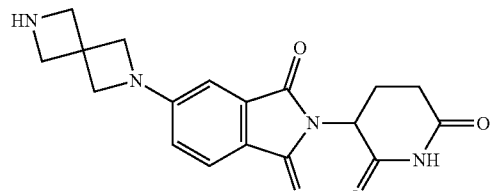

A mixture of tert-butyl 6-[2-(2,6-dioxo-3-piperidyl)-1,3-dioxo-isoindolin-5-yl]-2,6-diazaspiro[3.3]heptane-2-carboxylate (420 mg, 0.92 mmol, 1.00 eq) in trifluoroacetic acid (1 mL) and dichloromethane (10 mL) was stirred at 25° C. for 1 hour under nitrogen. TLC showed the reaction was completed. The mixture was concentrated in reduced pressure at 45° C. The mixture was purified by semi-preparative reverse phase HPLC (column: Phenomenex Synergi Max-RP 250*50 mm*10 um; mobile phase: [water (0.225% FA)-ACN]; B %: 5ACN %-30ACN %,15 min; 50% min) to afford 5-(2,6-diazaspiro[3.3]heptan-2-yl)-2-(2,6-dioxo-3-piperidyl)isoindoline-1,3-dione formate (260 mg, 0.64 mmol, 70% yield) as a yellow solid.

Step 8: 5-[6-[5-[3-[(5-bromo-2-pyridyl)oxy]cyclobutoxy]-2,2-difluoro-pentyl]-2,6-diazaspiro[3.3]heptan-2-yl]-2-(2,6-dioxo-3-piperidyl)isoindoline-1,3-dione

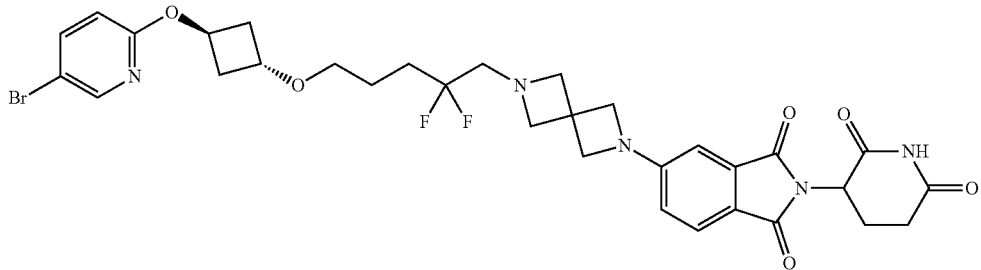 [SMILES: O=C1CCC(N2C(=O)c3ccc(N4CC5(CN(CC(F)(F)CCCO[C@H]6C[C@H](Oc7ccc(Br)cn7)C6)C5)C4)cc3C2=O)C(=O)N1]

To a mixture of [5-[3-[(5-bromo-2-pyridyl)oxy]cyclobutoxy]-2,2-difluoro-pentyl]trifluoromethanesulfonate (460 mg, 0.92 mmol, 1.00 eq) and 5-(2,6-diazaspiro[3.3]heptan-2-yl)-2-(2,6-dioxo-3-piperidyl)isoindoline-1,3-dione formate (443 mg, 1.11 mmol, 1.20 eq) in acetonitrile (25 mL) and (methylsulfinyl)methane (5 mL) was added potassium carbonate (255 mg, 1.85 mmol, 2.00 eq) in one portion at 25° C. under nitrogen. The mixture was stirred at 25° C. for 10 hours. LC-MS showed [5-[3-[(5-bromo-2-pyridyl)oxy]cyclobutoxy]-2,2-difluoro-pentyl]trifluoromethanesulfonate was consumed completely and one main peak with desired MS was detected. The suspension was filtered and concentrated in vacuum. The residue was diluted with ethyl acetate (100 mL), washed with brine (30 mL×3), dried with anhydrous sodium sulfate, filtered and concentrated in vacuum. The residue was purified by silica gel chromatography (Petroleum ether/Ethyl acetate=1/1, 1/3) to afford 5-[6-[5-[3-[(5-bromo-2-pyridyl)oxy]cyclobutoxy]-2,2-difluoro-pentyl]-2,6-diazaspiro[3.3]heptan-2-yl]-2-(2,6-dioxo-3-piperidyl)isoindoline-1,3-dione (320 mg, 0.45 mmol, 49% yield) as a yellow solid.

Step 9: 5-[6-[2,2-difluoro-5-[3-[[5-(4,4,5,5-tetramethyl-1,3,2-dioxaborolan-2-yl)-2-pyridyl]oxy]cyclobutoxy]pentyl]-2,6-diazaspiro[3.3]heptan-2-yl]-2-(2,6-dioxo-3-piperidyl)isoindoline-1,3-dione

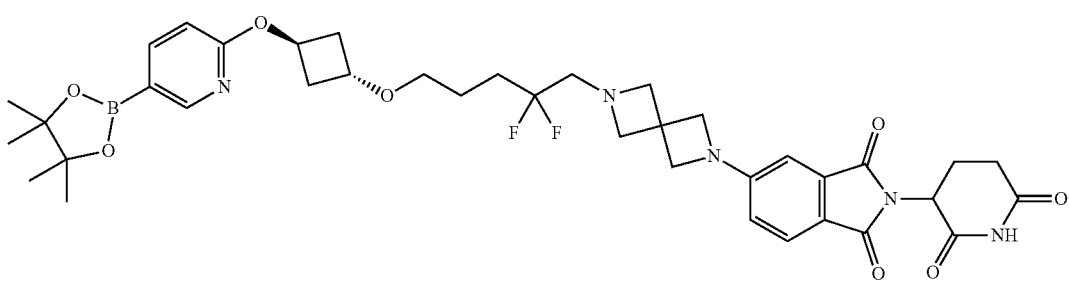 [SMILES: CC1(C)OB(c2ccc(O[C@H]3C[C@H](OCCCC(F)(F)CN4CC5(C4)CN(c4ccc6c(c4)C(=O)N(C4CCC(=O)NC4=O)C6=O)C5)C3)nc2)OC1(C)C]

5-[6-[5-[3-[(5-bromo-2-pyridyl)oxy]cyclobutoxy]-2,2-difluoro-pentyl]-2,6-diazaspiro[3.3]heptan-2-yl]-2-(2,6-dioxo-3-piperidyl)isoindoline-1,3-dione (200 mg, 0.28 mmol, 1.00 eq), 4,4,5,5-tetramethyl-2-(4,4,5,5-tetramethyl-1,3,2-dioxaborolan-2-yl)-1,3,2-dioxaborolane (86 mg, 0.34 mmol, 1.20 eq), potassium acetate (55 mg, 0.56 mmol, 2.00 eq) and 1,1'-bis(diphenylphosphino)ferrocene-palladium(ii)dichloride dichloromethane complex (23 mg, 0.02 mmol, 0.10 eq) in dioxane (10 mL) was de-gassed and then heated to 90° C. for 2 hours under nitrogen. The reaction mixture was filtered and the filter was concentrated. The crude product was purified by prep-TLC (dichloromethane:methanol=20:1) to give 5-[6-[2,2-difluoro-5-[3-[[5-(4,4,5,5-tetramethyl-1,3,2-dioxaborolan-2-yl)-2-pyridyl]oxy]cyclobutoxy]pentyl]-2,6-diazaspiro[3.3]heptan-2-yl]-2-(2,6-dioxo-3-piperidyl)isoindoline-1,3-dione (200 mg, 0.26 mmol, 94% yield) as a yellow oil.

Step 10: 5-[6-[2,2-difluoro-5-[3-[[5-(5-methylpyrido[4,3-b]indol-7-yl)-2-pyridyl]oxy]cyclobutoxy]pentyl]-2,6-diazaspiro[3.3]heptan-2-yl]-2-(2,6-dioxo-3-piperidyl)isoindoline-1,3-dione

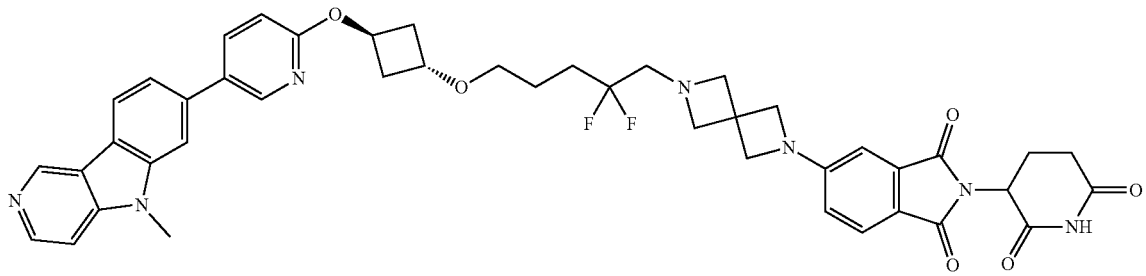 [SMILES: Cn1c2ccncc2c2ccc(-c3ccc(O[C@H]4C[C@H](OCCCC(F)(F)CN5CC6(C5)CN(c5ccc7c(c5)C(=O)N(C5CCC(=O)NC5=O)C7=O)C6)C4)nc3)cc21]

5-[6-[2,2-difluoro-5-[3-[[5-(4,4,5,5-tetramethyl-1,3,2-dioxaborolan-2-yl)-2-pyridyl]oxy]cyclobutoxy]pentyl]-2,6-diazaspiro[3.3]heptan-2-yl]-2-(2,6-dioxo-3-piperidyl)isoindoline-1,3-dione (200 mg, 0.26 mmol, 1.00 eq), 7-bromo-5-methyl-pyrido[4,3-b]indole (69 mg, 0.26 mmol, 1.00 eq), sodium carbonate (56 mg, 0.53 mmol, 2.00 eq) and 1,1'-bis(diphenylphosphino)ferrocene-palladium(ii)dichloride dichloromethane complex (21 mg, 0.02 mmol, 0.10 eq) in N,N-dimethylformamide (5 mL) and water (0.5 mL) was de-gassed and then heated to 90° C. for 2 hours under nitrogen. LCMS showed the reaction was completed. The mixture was cooled to 25° C. and filtered. The residue was diluted with ethyl acetate (50 mL), washed with brine (30 mL×3), dried over anhydrous sodium sulfate, concentrated in vacuum. The mixture was purified by semi-preparative reverse phase HPLC (18-48% acetonitrile+0.225% formic acid in water, over 10 min). Then the collected fraction was concentrated to remove most of the acetonitrile. The solution was lyophilized. 5-[6-[2,2-difluoro-5-[3-[[5-(5-methylpyrido[4,3-b]indol-7-yl)-2-pyridyl]oxy]cyclobutoxy]pentyl]-2,6-diazaspiro[3.3]heptan-2-yl]-2-(2,6-dioxo-3-piperidyl)isoindoline-1,3-dione formate (21.6 mg, 0.02 mmol, 9% yield, 95% purity) was obtained as a yellow solid.

$^1$H NMR: (400 MHz, DMSO-$d_6$) δ: 10.95 (s, 1H), 9.14 (br s, 1H), 8.15 (s, 1H), 7.52 (d, J=9.0 Hz, 1H), 7.18-7.04 (m, 5H), 6.83 (d, J=6.7 Hz, 2H), 6.65 (d, J=8.5 Hz, 1H), 6.61 (s, 1H), 6.54-6.47 (m, 3H), 6.26 (d, J=8.5 Hz, 2H), 5.05 (dd, J=5.0, 13.3 Hz, 1H), 4.38-4.26 (m, 1H), 4.24-4.11 (m, 1H), 3.78 (br t, J=6.5 Hz, 4H), 3.54-3.31 (m, 3H), 3.03-2.83 (m, 8H), 2.62-2.52 (m, 3H), 2.47-2.31 (m, 1H), 2.21-2.04 (m, 3H), 2.01-1.87 (m, 3H), 1.71 (br d, J=10.7 Hz, 2H). (M+H)$^+$ 804.5.

Synthetic Scheme for Exemplary Compound 153

2-(2,6-dioxopiperidin-3-yl)-5-(3-(3,3,3-trifluoro-2-((5-((1r,3r)-3-((5-(5-methyl-5H-pyrido[4,3-b]indol-7-yl)pyridin-2-yl)oxy)cyclobutoxy)pentyl)oxy)propyl)azetidin-1-yl)isoindoline-1,3-dione

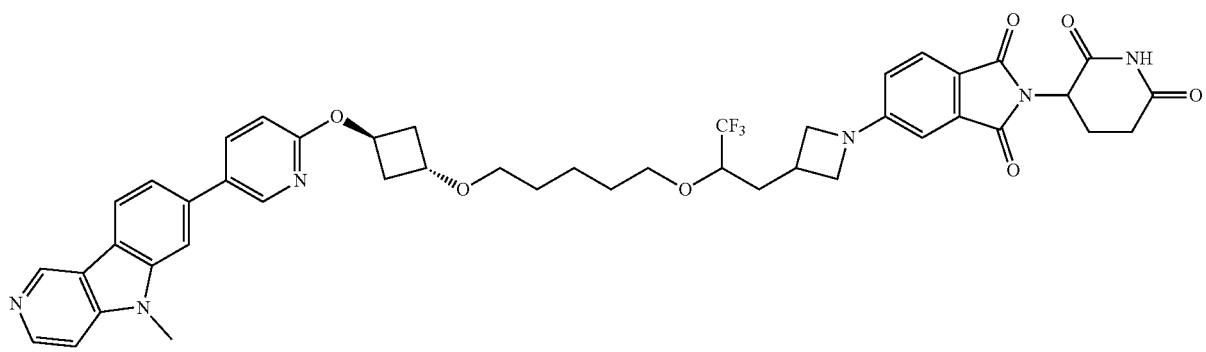 [SMILES: Cn1c2ccncc2c2ccc(-c3ccc(O[C@H]4C[C@H](OCCCCCOC(CC5CN(c6ccc7c(c6)C(=O)N(C6CCC(=O)NC6=O)C7=O)C5)C(F)(F)F)C4)nc3)cc21]

Prepared according to the schemes below using procedures described above and common procedures known to those skilled in the art.

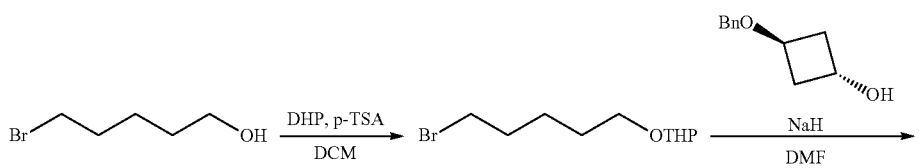

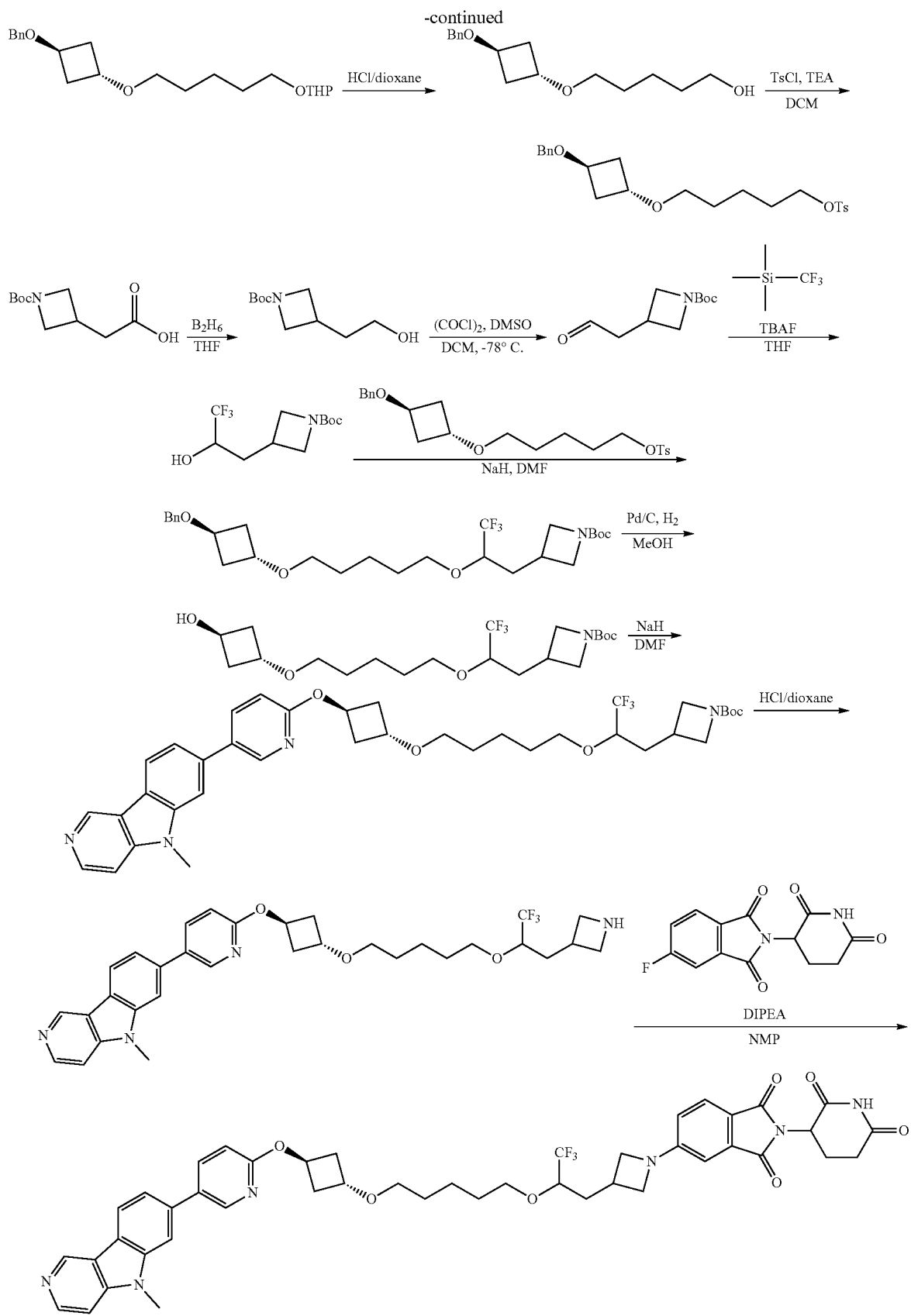
Compound 153

Using procedures of Compound 153 the following were prepared: Compound 154.

Synthetic Scheme for Exemplar Compound 155

2-(2,6-dioxopiperidin-3-yl)-5-(3-((5-(2-((1r,3r)-3-((5-(5-methyl-5H-pyrido[4,3-b]indol-7-yl)pyridin-2-yl)oxy)cyclobutoxy)ethoxy)pyridin-2-yl)oxy)azetidin-1-yl)isoindoline-1,3-dione

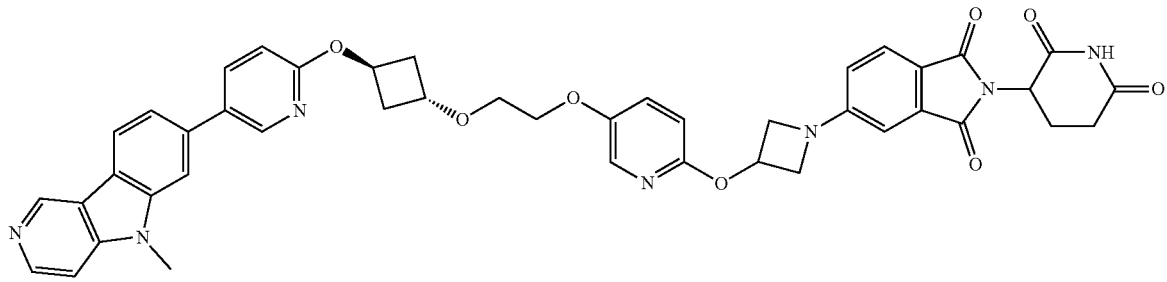 [SMILES: Cn1c2ccncc2c2ccc(-c3ccc(O[C@H]4C[C@H](OCCOc5ccc(OC6CN(c7ccc8c(c7)C(=O)N(C7CCC(=O)NC7=O)C8=O)C6)nc5)C4)nc3)cc21]

Prepared according to the schemes below using procedures described above and common procedures known to those skilled in the art.

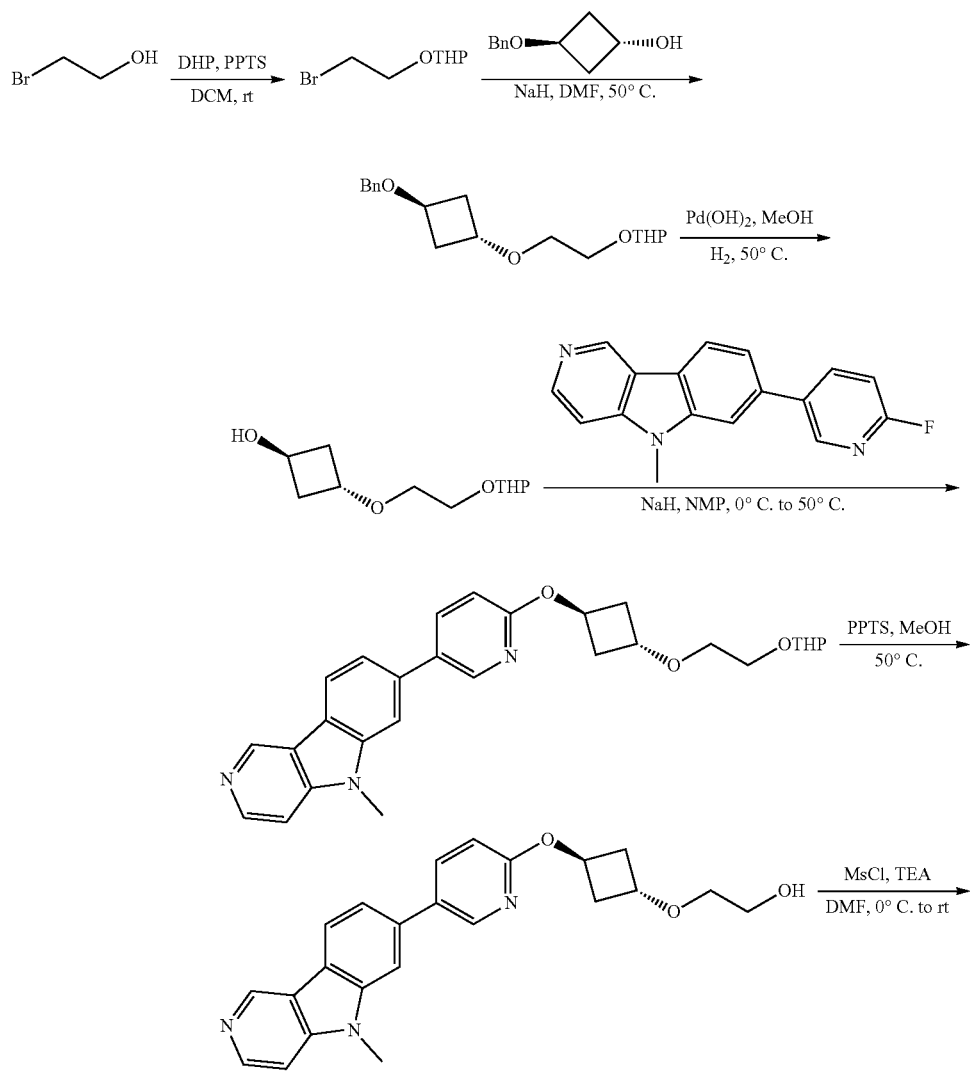

547 548
-continued
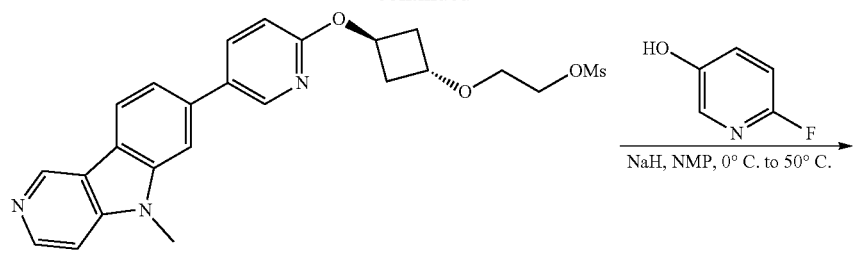
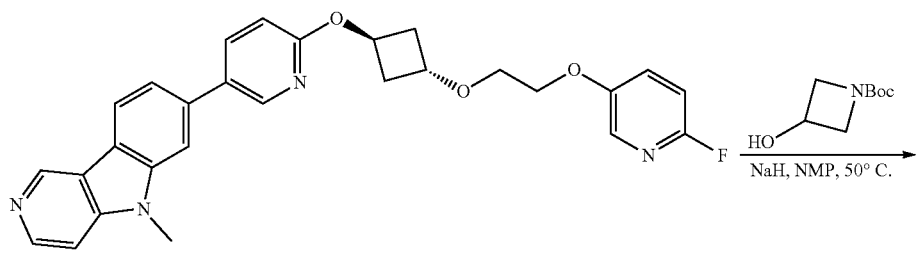
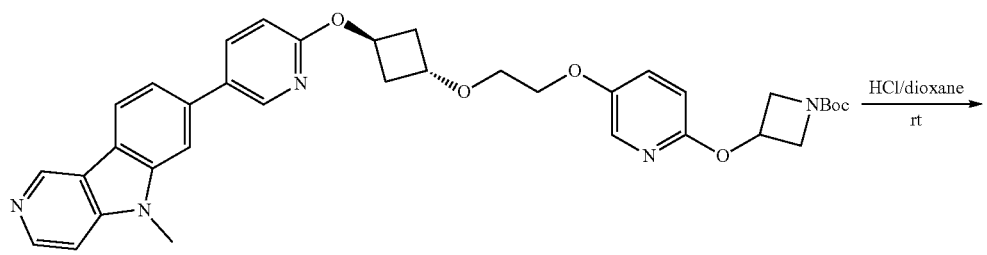
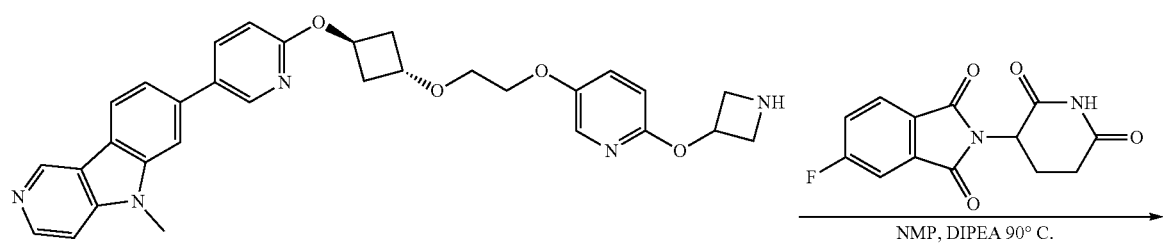
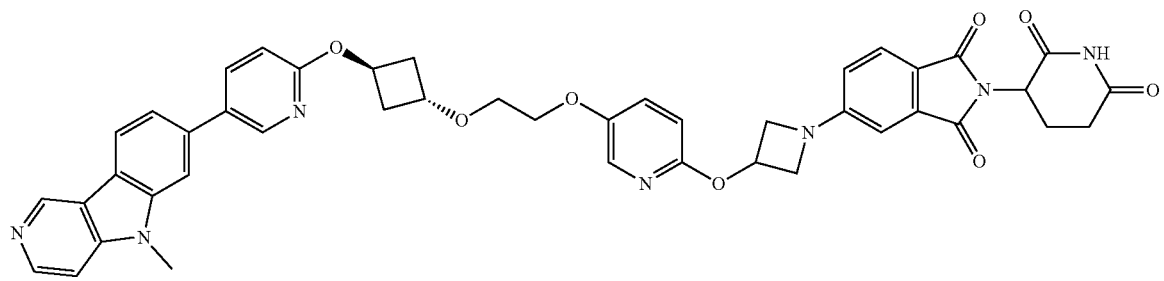
Compound 155

Synthetic Scheme for Exemplary Compound 156
2-(2,6-dioxopiperidin-3-yl)-5-(3-(3-(5-((1r,3r)-3-((5-(5-methyl-5H-pyrido[4,3-b]indol-7-yl)pyridin-2-yl)oxy)cyclobutoxy)pyridin-2-yl)propoxy)azetidin-1-yl)isoindoline-1,3-dione
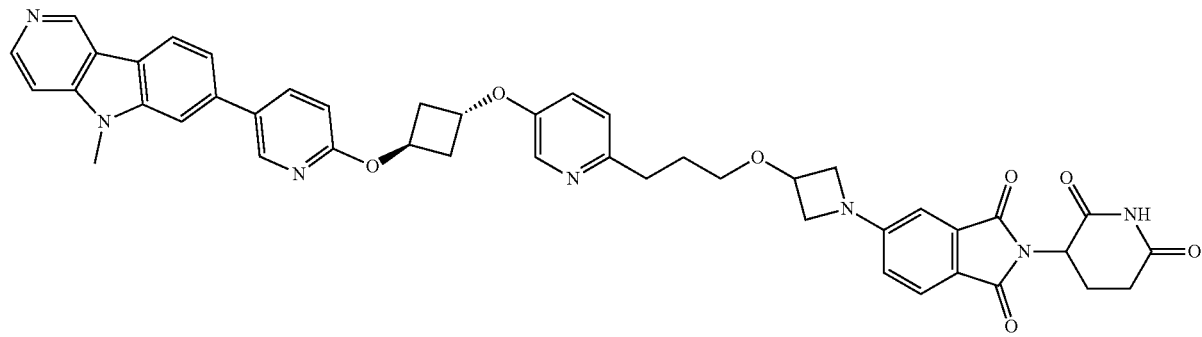 [SMILES: Cn1c2ccncc2c2ccc(-c3ccc(O[C@H]4C[C@H](Oc5ccc(CCCOC6CN(c7ccc8c(c7)C(=O)N(C7CCC(=O)NC7=O)C8=O)C6)nc5)C4)nc3)cc21]
Prepared according to the schemes below and using procedures described above and common procedures known to those skilled in the art.
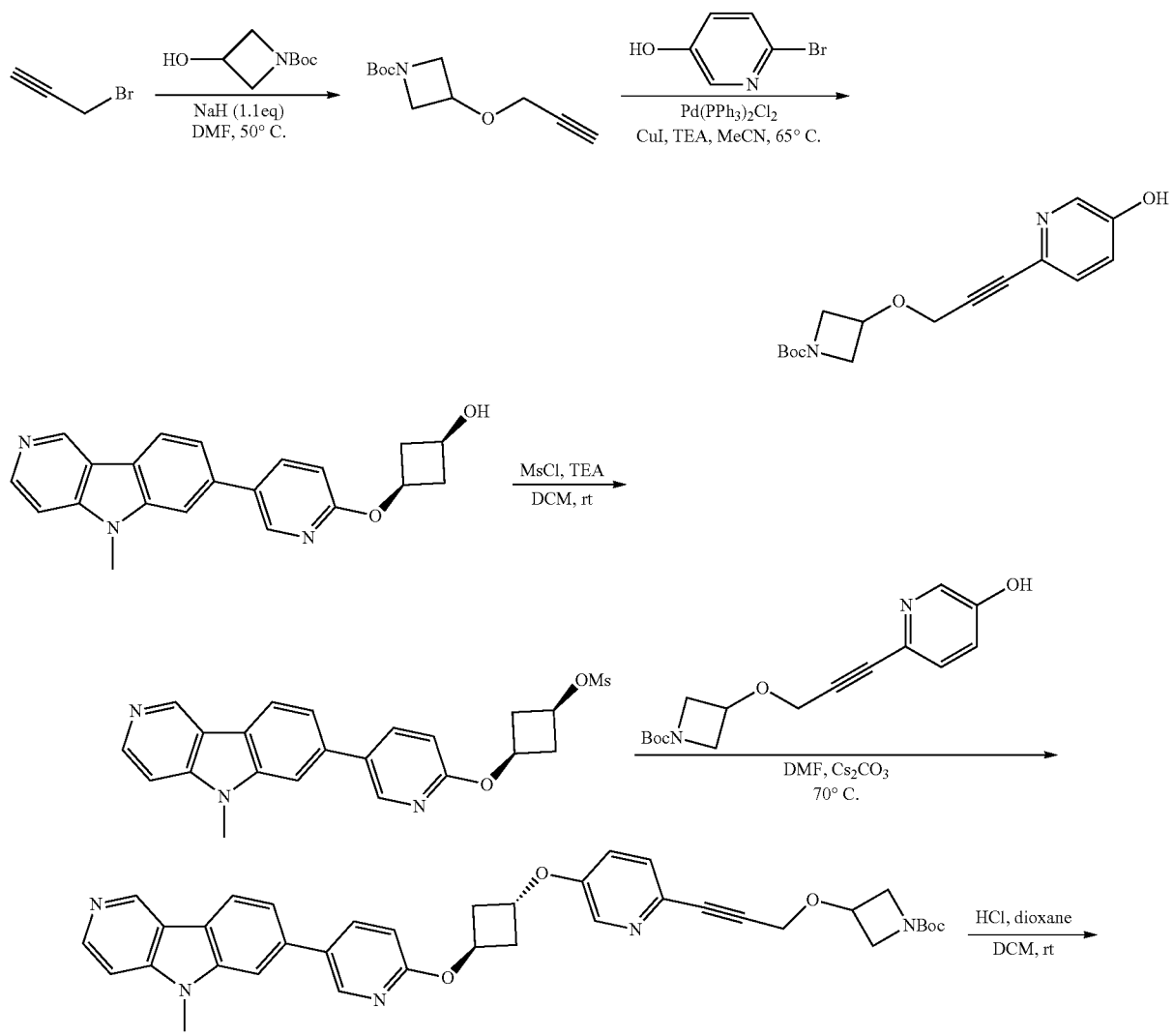

551 552
-continued
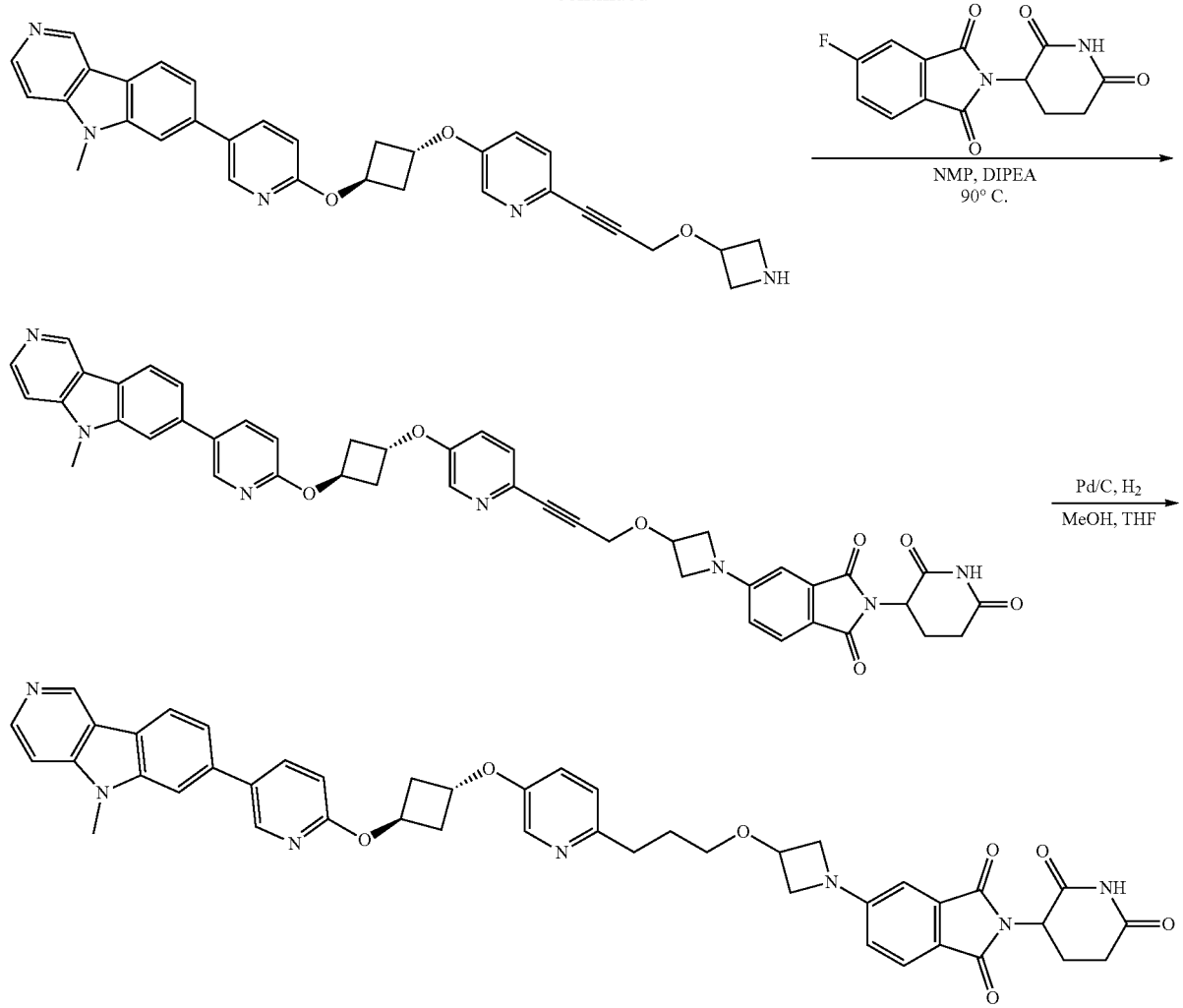
Compound 156
Synthetic Scheme for Exemplary Compound 157
2-(2,6-dioxopiperidin-3-yl)-5-(4-((2-((1r,3r)-3-((5-(5-methyl-5H-pyrido[4,3-b]indol-7-yl)pyridin-2-yl)oxy)cyclobutane-1-carbonyl)-2-azaspiro[3.3]heptan-6-yl)oxy)butoxy)isoindoline-1,3-dione
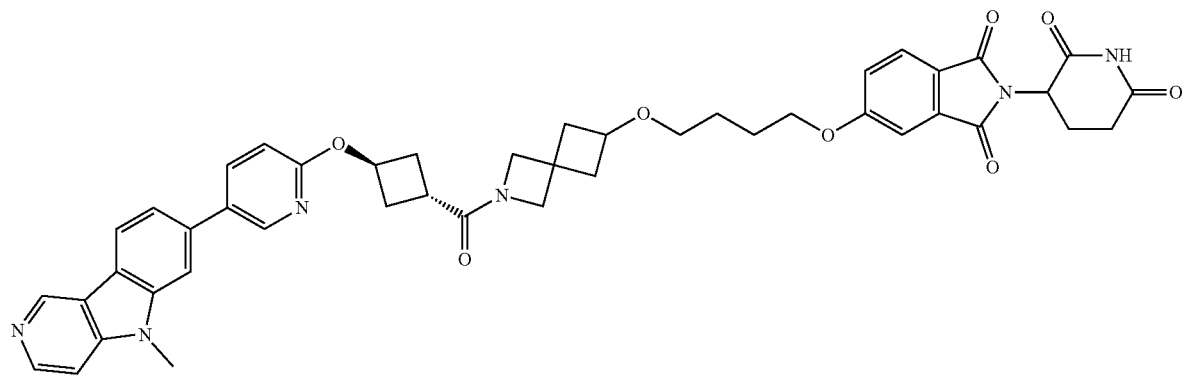 [SMILES: Cn1c2ccncc2c2ccc(-c3ccc(O[C@H]4C[C@H](C(=O)N5CC6(CC(OCCCCOc7ccc8c(c7)C(=O)N(C7CCC(=O)NC7=O)C8=O)C6)C5)C4)nc3)cc21]

Step 1: (1r,3r)-3-((5-(5-methyl-5H-pyrido[4,3-b]indol-7-yl)pyridin-2-yl)oxy)cyclobutanecarboxylic

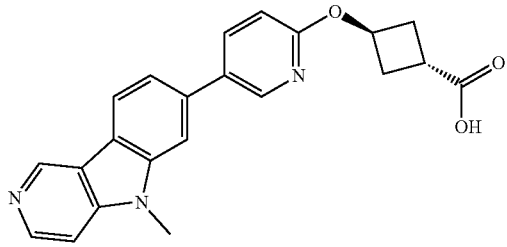 [SMILES: Cn1c2ccncc2c2ccc(-c3ccc(O[C@H]4C[C@H](C(=O)O)C4)nc3)cc21]

To a solution of (1r,3r)-3-((5-(5-methyl-5H-pyrido[4,3-b]indol-7-yl)pyridin-2-yl)oxy)cyclobutanecarbaldehyde (70 mg, 0.20 mmol) in tetrahydrofuran (1 ml) and water (1 ml) was added sodium chlorite (62 mg, 0.63 mmol), sodium dihydrogen phosphate dehydrate (168 mg, 1.08 mmol) and 2-methylbut-2-ene (233 mg, 3.33 mmol), then the mixture was stirred at room temperature overnight. TLC showed the reaction was complete. The reaction mixture was diluted with dichloromethane (20 ml), washed with water (10 ml×3), brine (10 ml), dried over anhydrous sodium sulfate, and concentrated under reduced pressure to give crude (1r,3r)-3-((5-(5-methyl-5H-pyrido[4,3-b]indol-7-yl)pyridin-2-yl)oxy)cyclobutanecarboxylic acid as yellow solid.

(1r,3r)-3-((5-(5-methyl-5H-pyrido[4,3-b]pyridin-2-yl)oxy)cyclobutanecarboxylic acid was converted to the final compound, 2-(2,6-dioxopiperidin-3-yl)-5-(4-((2-((1r,3r)-3-((5-(5-methyl-5H-pyrido[4,3-b]indol-7-yl)pyridin-2-yl)oxy)cyclobutane-1-carbonyl)-2-azaspiro[3.3]heptan-6-yl)oxy)butoxy)isoindoline-1,3-dione, according to the scheme below and using procedure described above for Compound 153.

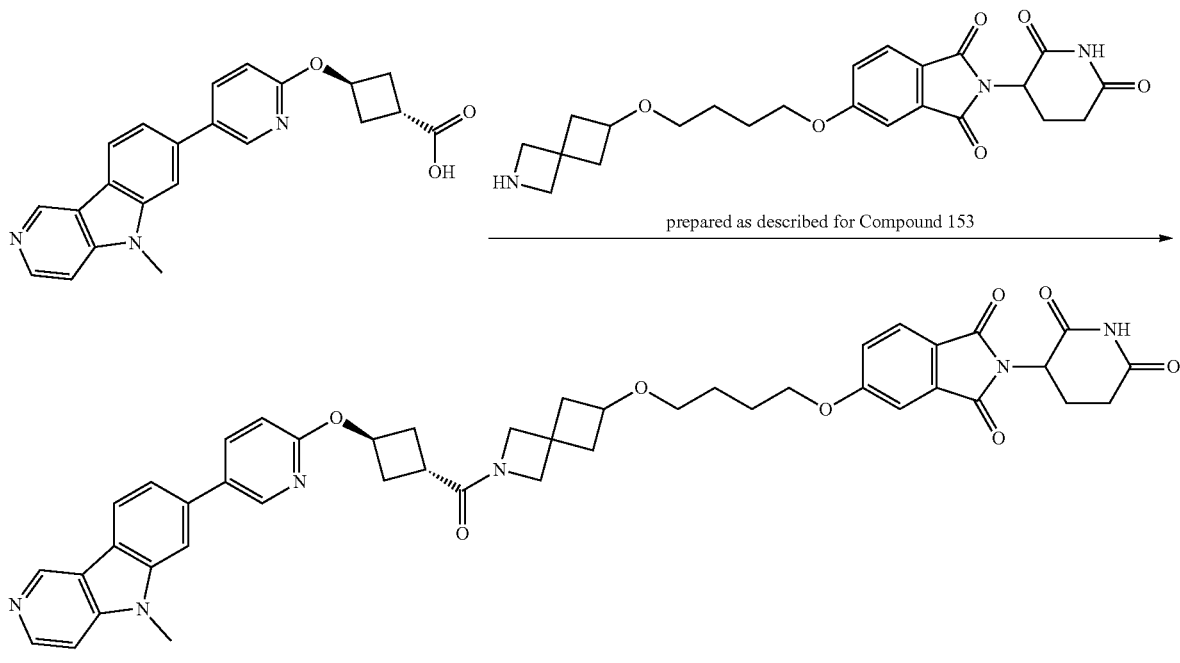

Compound 157

Synthetic Scheme for Exemplary Compound 158

2-(2,6-dioxopiperidin-3-yl)-5-(2-((6-(4-((1r,3r)-3-((5-(5-methyl-5H-pyrido[4,3-b]indol-7-yl)pyridin-2-yl)oxy)cyclobutoxy)piperidin-1-yl)pyridazin-4-yl)oxy)ethoxy)isoindoline-1,3-dione

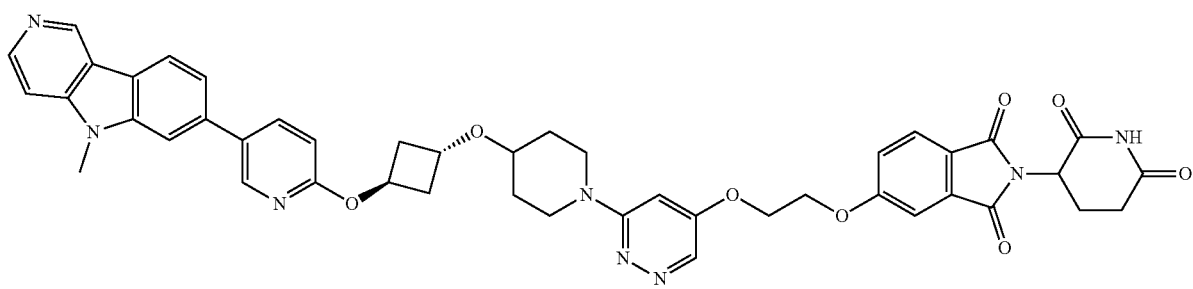 [SMILES: Cn1c2ccncc2c2ccc(-c3ccc(O[C@H]4C[C@H](OC5CCN(c6cc(OCCOc7ccc8c(c7)C(=O)N(C7CCC(=O)NC7=O)C8=O)cnn6)CC5)C4)nc3)cc21]

Step 1: 5-(2-(benzyloxy)ethoxy)-3-chloropyridazine

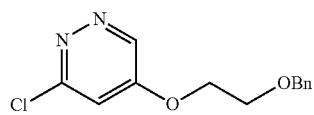 [SMILES: Clc1cc(OCCOCc2ccccc2)cnn1]

To a stirred solution of 2-(benzyloxy)ethanol (440 mg, 2.895 mmol) and 3,5-dichloropyridazine (428 mg, 2.895 mmol) in 1-methyl-2-pyrrolidinone (5 ml) was added sodium hydride (60% in oil) (347 mg, 8.68 mmol) at 0° C. Then the mixture was stirred at room temperature for 1 hour. The reaction mixture was quenched with aqueous ammonium chloride solution (15 ml) at 0° C., and extracted with ethyl acetate (20 ml×3). The organic layer was with brine (20 ml×2), dried over anhydrous sodium sulfate and concentrated under reduced pressure to give a crude residue which was purified by silica gel flash column chromatography (eluted with 15% ethyl acetate in hexane) to give 5-(2-(benzyloxy)ethoxy)-3-chloropyridazine (680 mg, 89% yield) as light brown oil.

Step 2: (1r,3r)-3-((1-(5-(2-(benzyloxy)ethoxy)pyridazin-3-yl)piperidin-4-yl)oxy)cyclobutanol

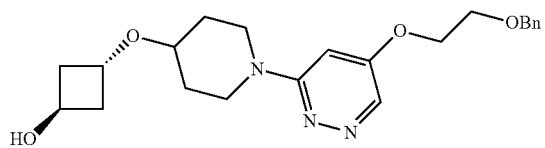 [SMILES: O[C@H]1C[C@H](OC2CCN(c3cc(OCCOCc4ccccc4)cnn3)CC2)C1]

To the mixture of 5-(2-(benzyloxy)ethoxy)-3-chloropyridazine (240 mg, 0.910 mmol) and (1r,3r)-3-(piperidin-4-yloxy)cyclobutanol (155 mg, 0.910 mmol) [prepared via hydrogenation of (1r,3r)-3-((1-benzylpiperidin-4-yl)oxy)cyclobutan-1-ol as described in step 5 of Compound 65 but without di-tert-butyl carbonate present] in toluene (5 ml) were added Pd$_2$(dba)$_3$ (83 mg, 0.091 mmol), (+/−)-2,2'-Bis(diphenylphosphino)-1,1'-binaphthyl (56 mg, 0.091 mmol) and cesium carbonate (739 mg, 2.27 mmol) under nitrogen. Then the mixture was heated to 90° C. overnight. TLC showed the reaction was complete. The reaction mixture was extracted with ethyl acetate (30 ml×3). The organic layer was with brine (10 ml×2), dried over anhydrous sodium sulfate and concentrated under reduced pressure to give a crude residue which was purified by silica gel flash column chromatography (eluted with 8% ethyl acetate in hexane) to give (1r,3r)-3-((1-(5-(2-(benzyloxy)ethoxy)pyridazin-3-yl)piperidin-4-yl)oxy)cyclobutanol (135 mg, 38% yield) as light yellow oil.

(1r,3r)-3-((1-(5-(2-(benzyloxy)ethoxy)pyridazin-3-yl)piperidin-4-yl)oxy)cyclobutanol was converted to the final compound, 2-(2,6-dioxopiperidin-3-yl)-5-(2-((6-(4-((1r,3r)-3-((5-(5-methyl-5H-pyrido[4,3-b]indol-7-yl)pyridin-2-yl)oxy)cyclobutoxy)piperidin-1-yl)pyridazin-4-yl)oxy)ethoxy)isoindoline-1,3-dione, according to the scheme below and using procedures described above and common procedures known to those skilled in the art.

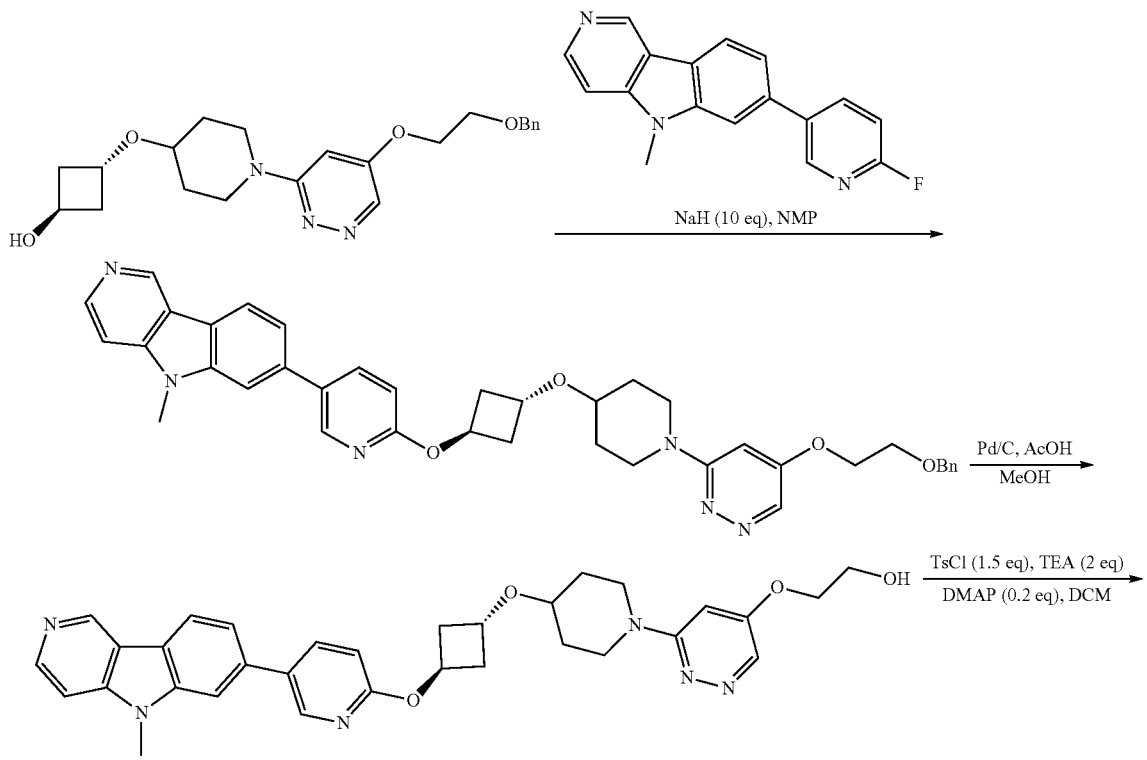

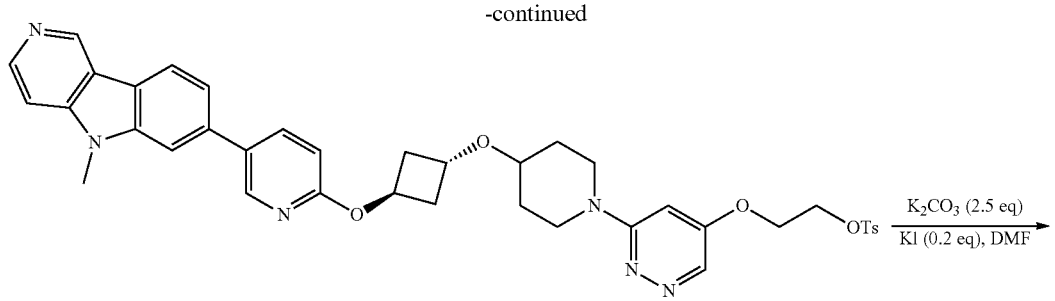
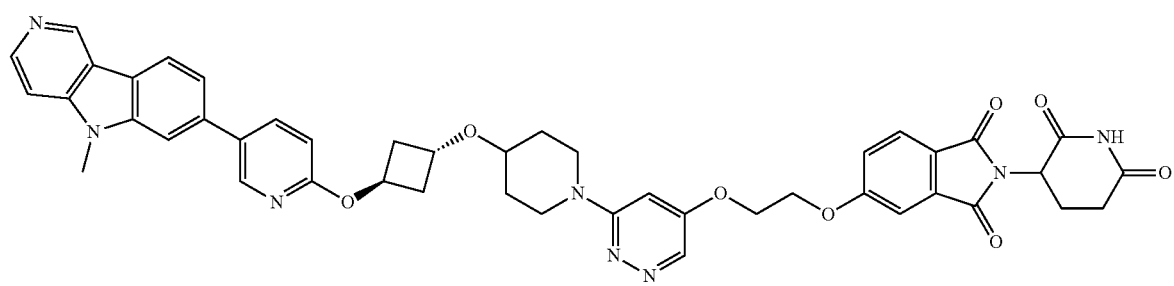
Compound 158
Synthetic Scheme for Exemplary Compound 159 and Compound 160
2-(2,6-dioxopiperidin-3-yl)-5-(3-((3-(5-(((1 s,3 s)-3-((5-(5-methyl-5H-pyrido[4,3-b]indol-7-yl)pyridin-2-yl)oxy)cyclobutoxy)pyridin-2-yl)prop-2-yn-1-yl)oxy)azetidin-1-yl)isoindoline-1,3-dione
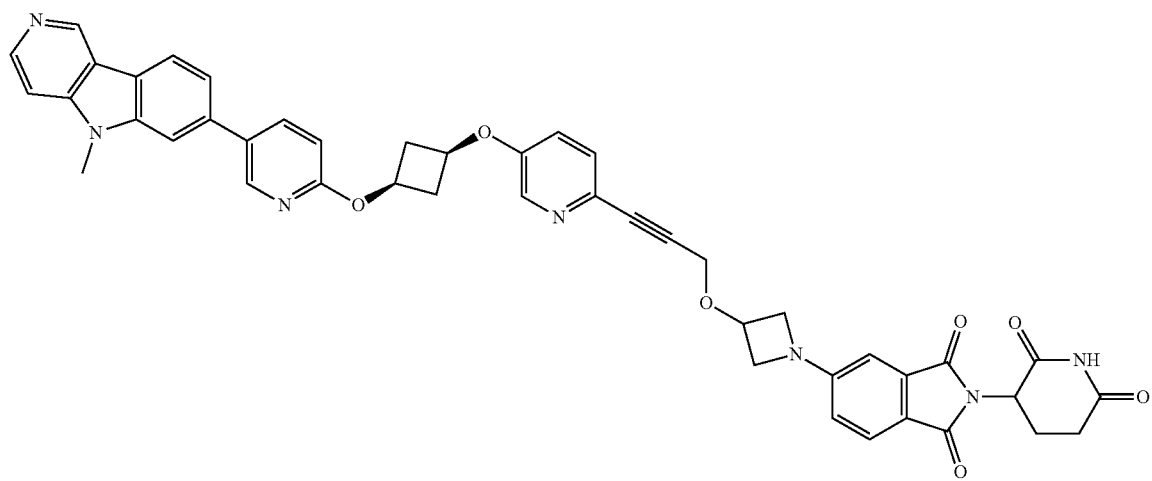 [SMILES: Cn1c2ccncc2c2ccc(-c3ccc(O[C@H]4C[C@@H](Oc5ccc(C#CCOC6CN(c7ccc8c(c7)C(=O)N(C7CCC(=O)NC7=O)C8=O)C6)nc5)C4)nc3)cc21]

2-(2,6-dioxopiperidin-3-yl)-5-(3-(3-(5-(((1 s,3s)-3-((5-(5-methyl-5H-pyrido[4,3-b]indol-7-yl)pyridin-2-yl)oxy)cyclobutoxy)pyridin-2-yl)propoxy)azetidin-1-yl)isoindoline-1,3-dione
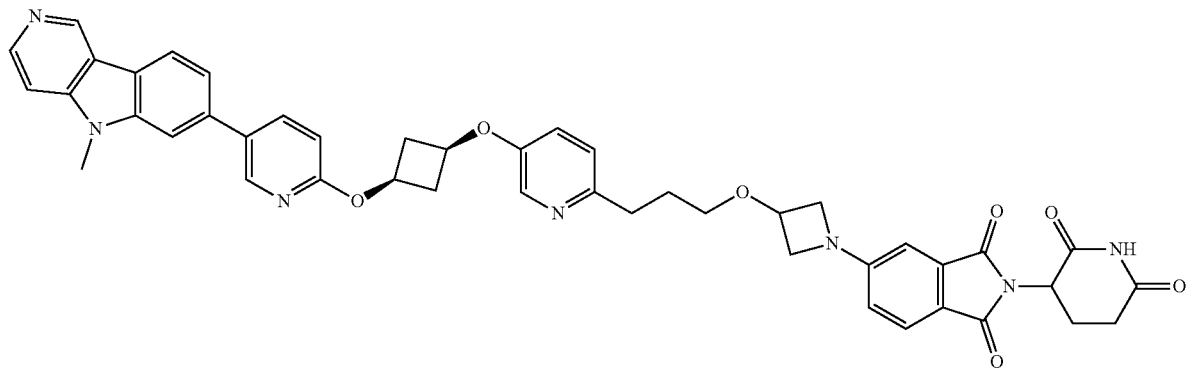 [SMILES: Cn1c2ccncc2c2ccc(-c3ccc(O[C@H]4C[C@@H](Oc5ccc(CCCOC6CN(c7ccc8c(c7)C(=O)N(C7CCC(=O)NC7=O)C8=O)C6)nc5)C4)nc3)cc21]
Prepared according to the scheme below and using procedures described above and common procedures known to those skilled in the art.
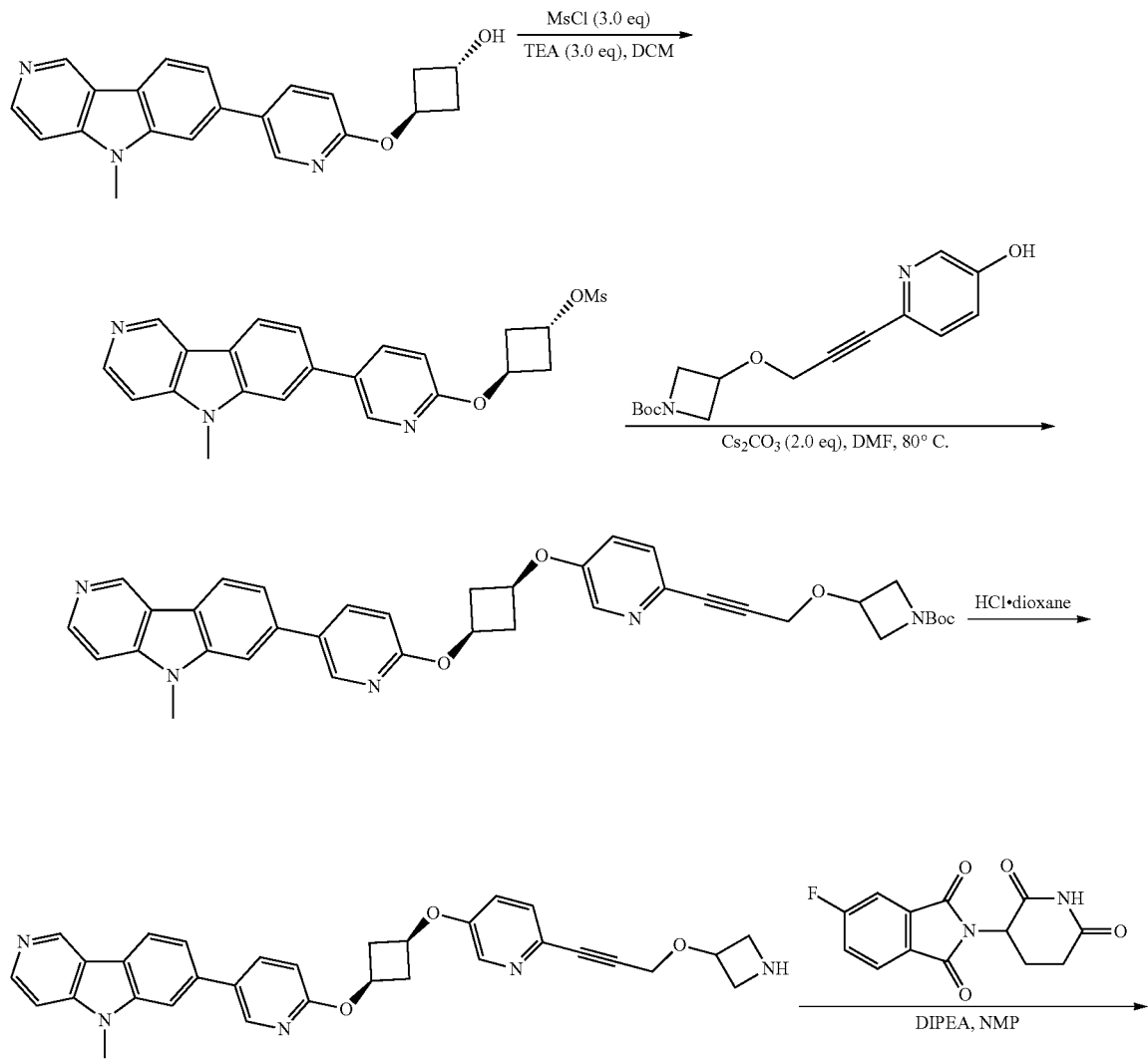

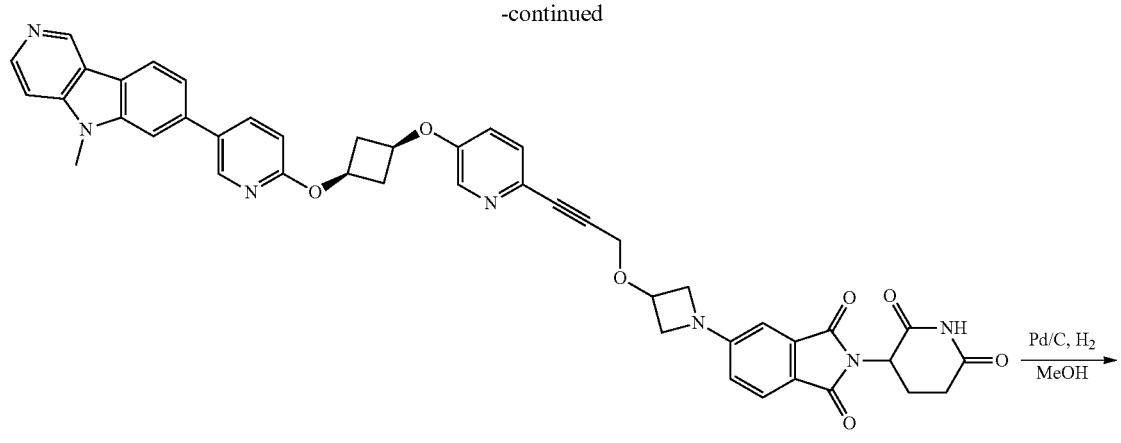
Compound 159
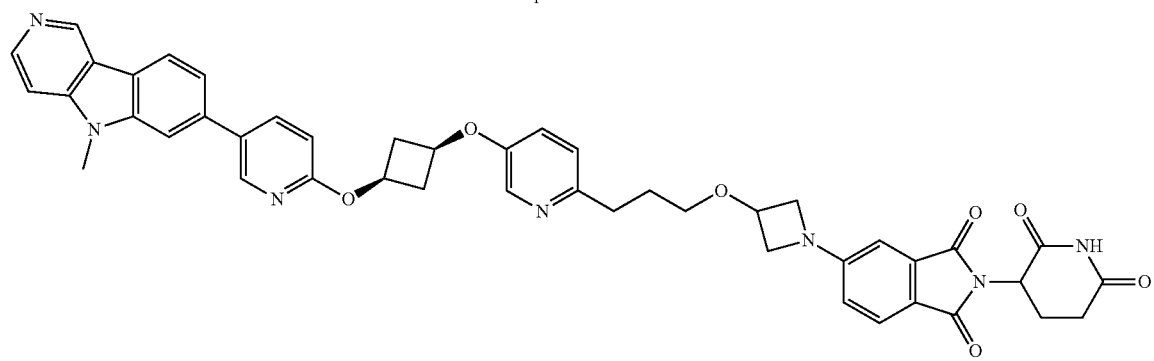
Compound 160
Synthetic Scheme for Exemplary Compound 161
2-(2,6-dioxopiperidin-3-yl)-5-(3-(2-(2-(2-((1r,3r)-3-((5-(5-methyl-5H-pyrido[4,3-b]indol-7-yl)pyridin-2-yl)oxy)cyclobutoxy)ethoxy)ethoxy)ethoxy)azetidin-1-yl)isoindoline-1,3-dione
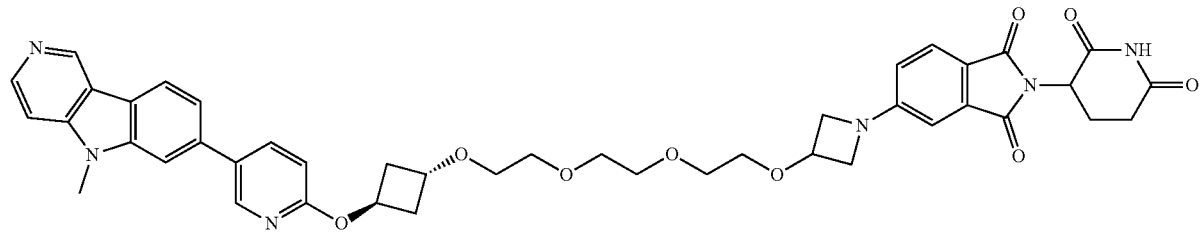 [SMILES: Cn1c2ccncc2c2ccc(-c3ccc(O[C@H]4C[C@H](OCCOCCOCCOC5CN(c6ccc7c(c6)C(=O)N(C6CCC(=O)NC6=O)C7=O)C5)C4)nc3)cc21]
Prepared according to the scheme below and using procedures described above and common procedures known to those skilled in the art.

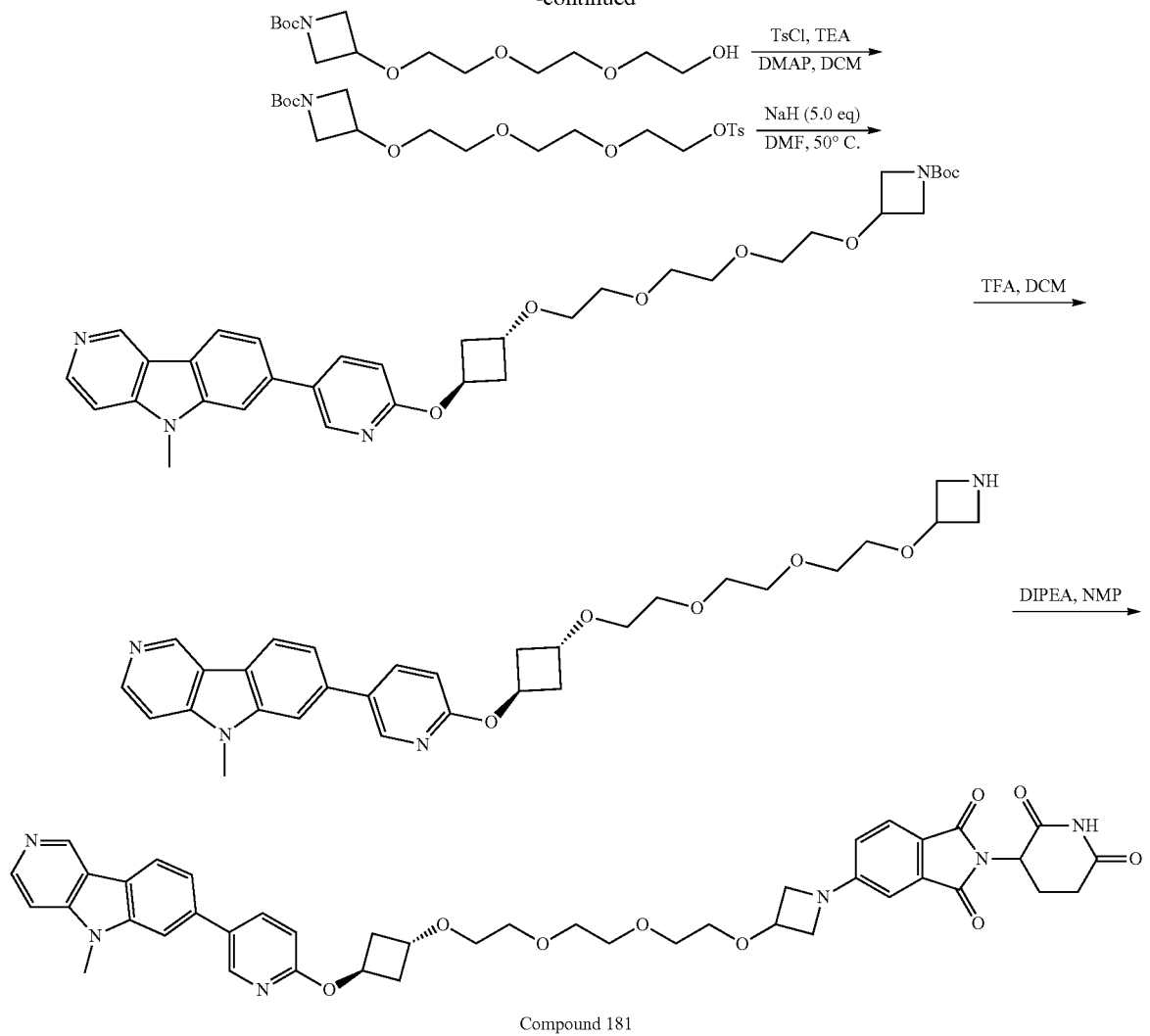
Compound 181
Based on the general approach of the Compound 163 and using common procedures known to those skilled in the art additional compounds were prepared: 162, 165, 178, 181, and 182.
Synthetic Scheme for Exemplary Compounds 165 and 166
5-((5-((1-(((1r,3r)-3-((5-(5H-pyrido[4,3-b]indol-7-yl)pyridin-2-yl)oxy)cyclobutane-1-carbonyl)piperidin-4-yl)oxy)pentyl)oxy)-2-(2,6-dioxopiperidin-3-yl)isoindoline-1,3-dione
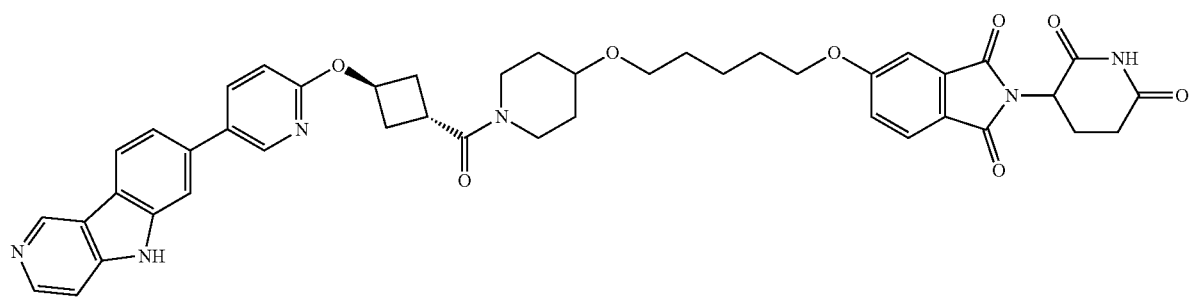 [SMILES: O=C1CCC(N2C(=O)c3ccc(OCCCCCOC4CCN(C(=O)[C@H]5C[C@H](Oc6ccc(-c7ccc8c(c7)[nH]c7ccncc78)cn6)C5)CC4)cc3C2=O)C(=O)N1]

5-((5-((1-((1r,3r)-3-((5-(5H-pyrido[4,3-b]indol-7-yl)pyridin-2-yl)oxy)cyclobutane-1-carbonyl)piperidin-4-yl)oxy)pentyl)oxy)-2-(2,6-dioxopiperidin-3-yl)isoindoline-1,3-dione
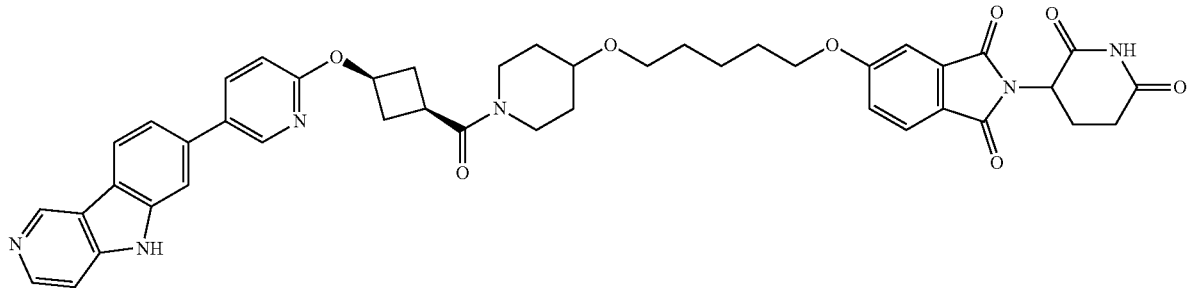 [SMILES: O=C1CCC(N2C(=O)c3ccc(OCCCCCOC4CCN(C(=O)[C@H]5C[C@@H](Oc6ccc(-c7ccc8c(c7)[nH]c7ccncc78)cn6)C5)CC4)cc3C2=O)C(=O)N1]
Prepared according to the scheme below and using procedures described above and common procedures known to those skilled in the art.
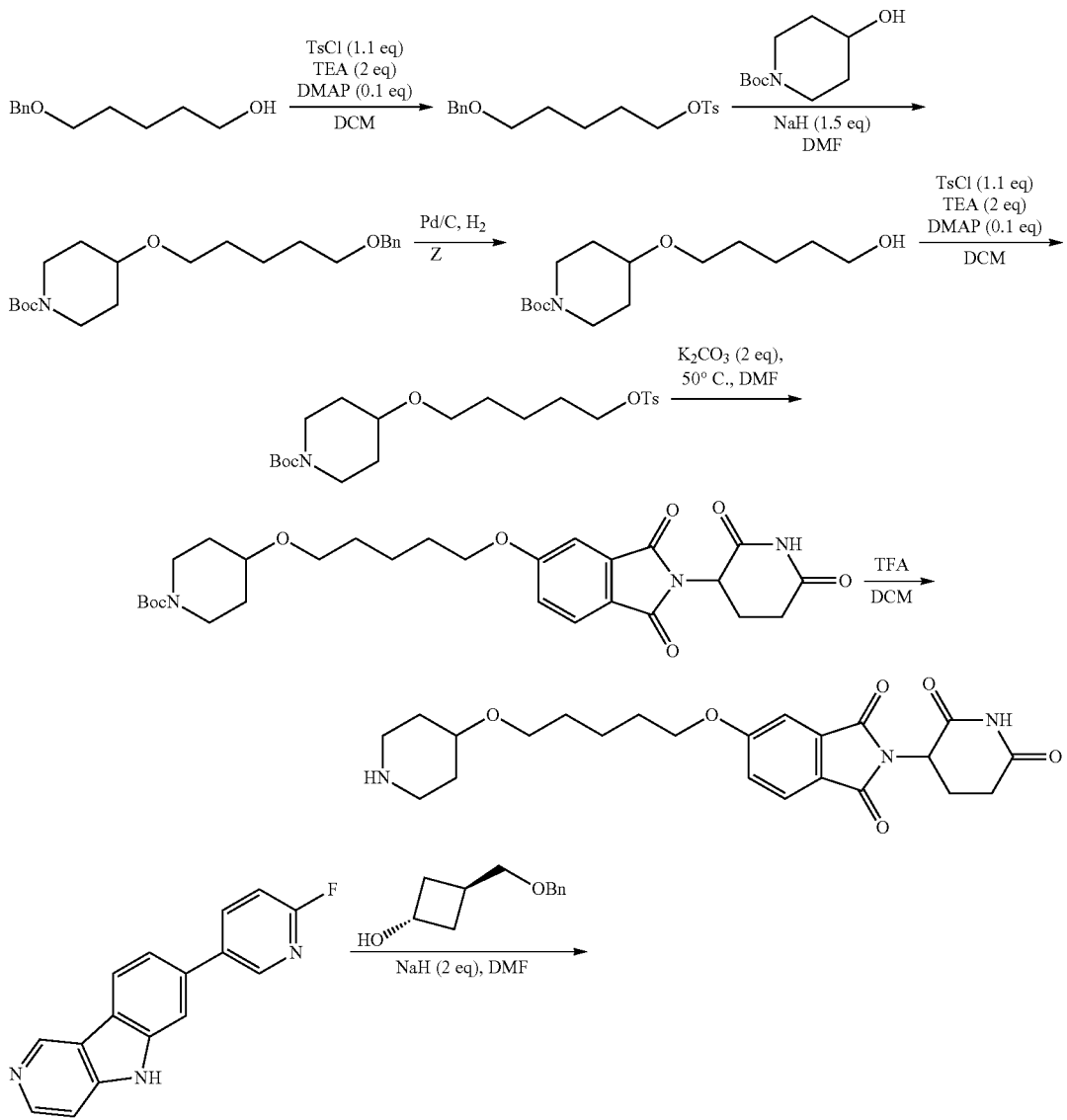

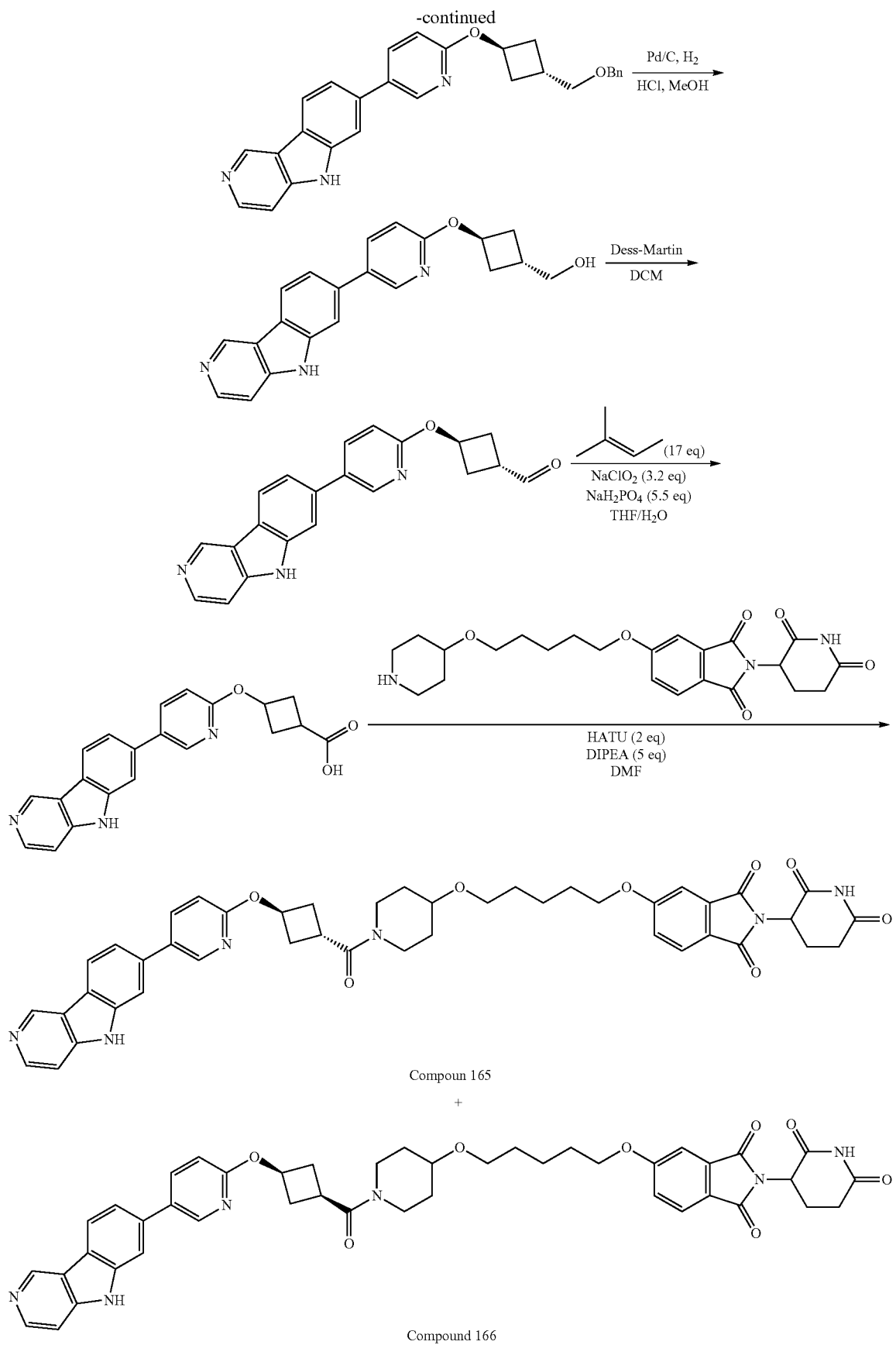

Synthetic Scheme for Exemplary Compounds 167 and 168

2-(2,6-dioxopiperidin-3-yl)-5-(3-((3-(5-(3-((5-(5-methyl-5H-pyrido[4,3-b]indol-7-yl)pyridin-2-yl)oxy)propoxy)pyridin-2-yl)prop-2-yn-1-yl)oxy)azetidin-1-yl)isoindoline-1,3-dione

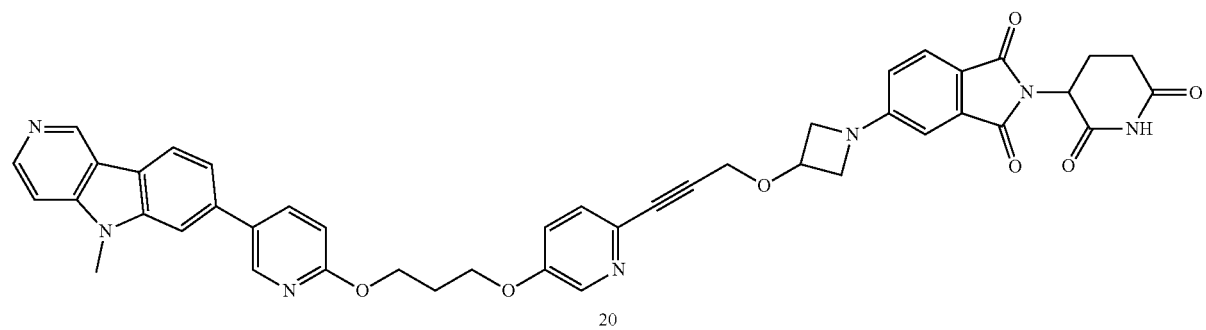

2-(2,6-dioxopiperidin-3-yl)-5-(3-(3-(5-(3-((5-(5-methyl-5H-pyrido[4,3-b]indol-7-yl)pyridin-2-yl)oxy)propoxy)pyridin-2-yl)propoxy)azetidin-1-yl)isoindoline-1,3-dione

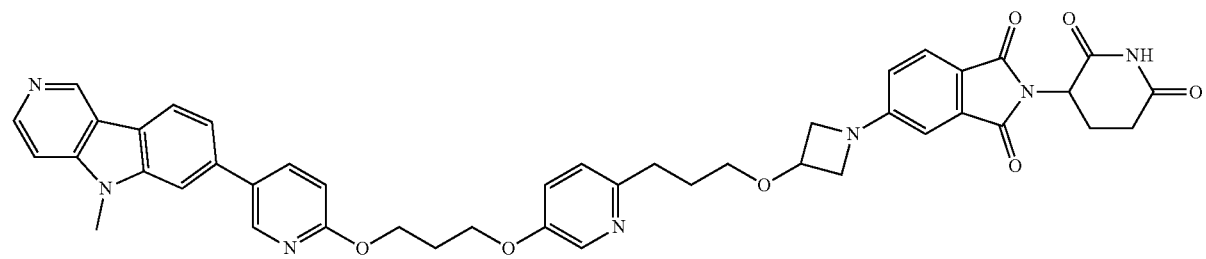 [SMILES: Cn1c2ccncc2c2ccc(-c3ccc(OCCCOc4ccc(CCCOC5CN(c6ccc7c(c6)C(=O)N(C6CCC(=O)NC6=O)C7=O)C5)nc4)nc3)cc21]

Prepared according to the scheme below and using procedures described above and common procedures known to those skilled in the art.

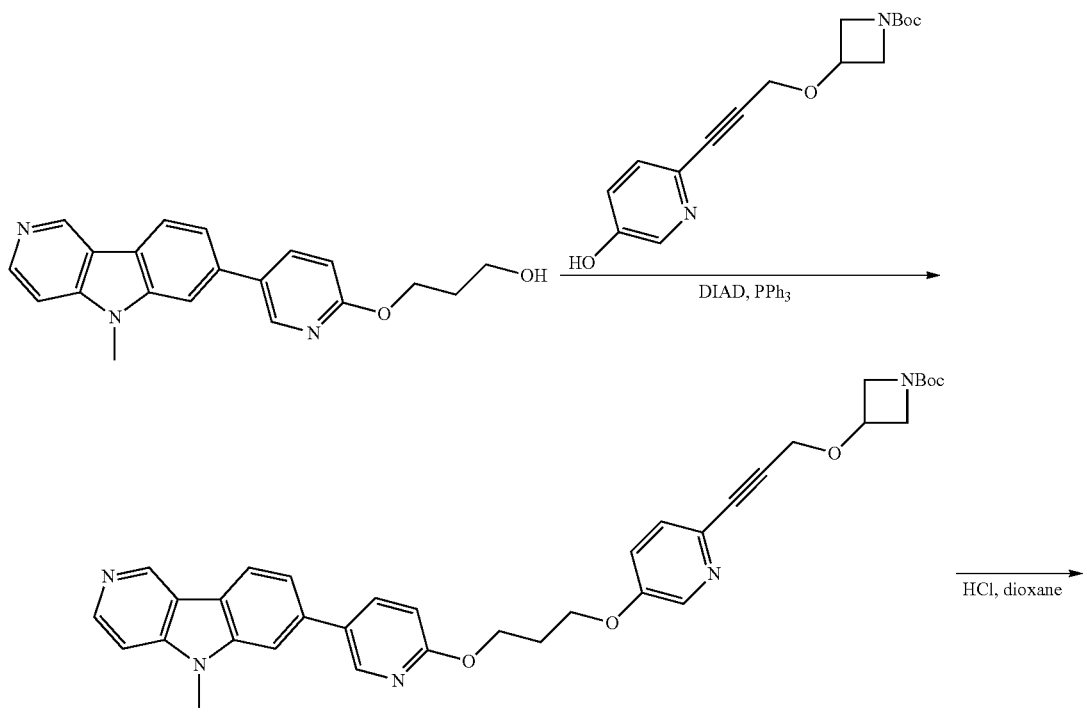

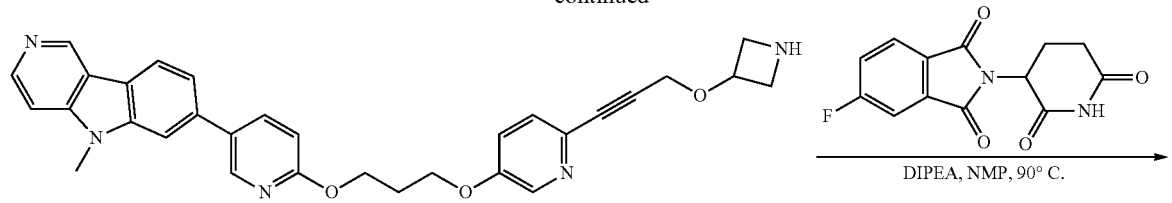
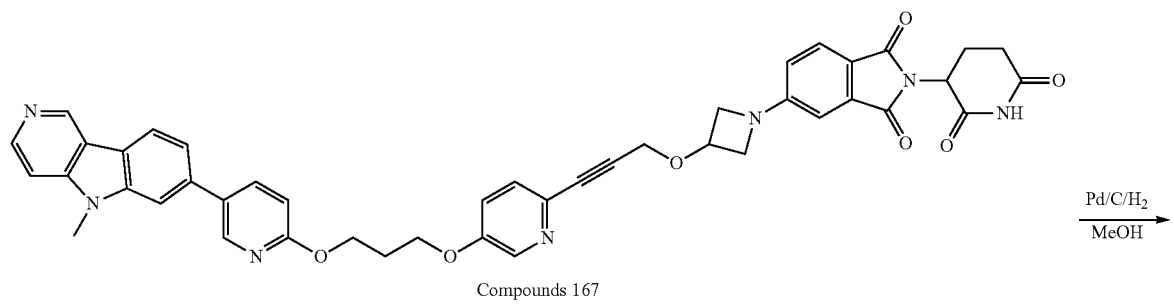
Compounds 167
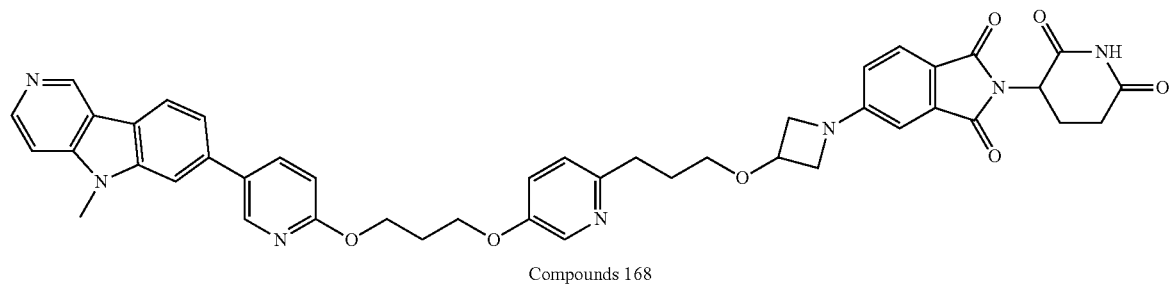 [SMILES: Cn1c2ccncc2c2ccc(-c3ccc(OCCCOc4ccc(CCCOC5CN(c6ccc7c(c6)C(=O)N(C6CCC(=O)NC6=O)C7=O)C5)nc4)nc3)cc21]
Compounds 168
Synthetic Scheme for Exemplary Compound 169
2-(2,6-dioxopiperidin-3-yl)-5-(3-(3-((3-(((1r,3r)-3-((5-(5-methyl-5H-pyrido[4,3-b]indol-7-yl)pyridin-2-yl)oxy)cyclobutoxy)methyl)oxetan-3-yl)methoxy)propoxy)azetidin-1-yl)isoindoline-1,3-dione
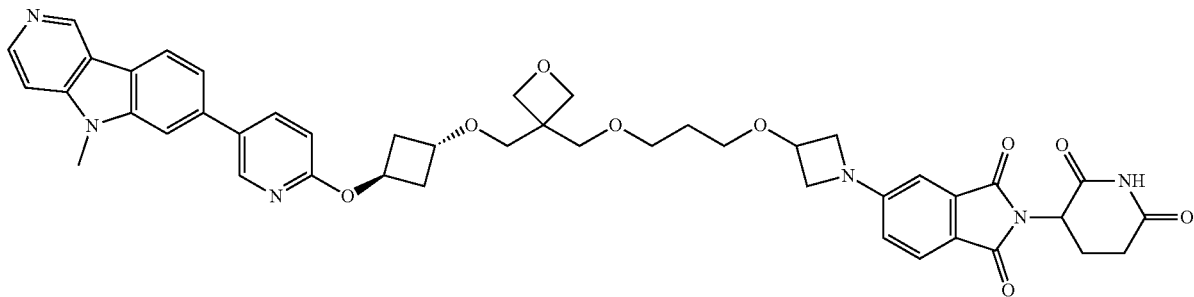 [SMILES: Cn1c2ccncc2c2ccc(-c3ccc(O[C@H]4C[C@H](OCC5(COCCCOC6CN(c7ccc8c(c7)C(=O)N(C7CCC(=O)NC7=O)C8=O)C6)COC5)C4)nc3)cc21]
Prepared according to the scheme below and using procedures described above and common procedures known to those skilled in the art.
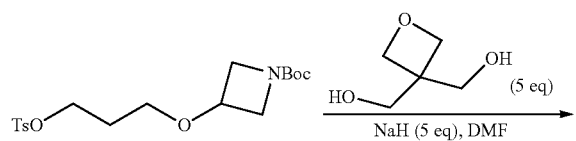

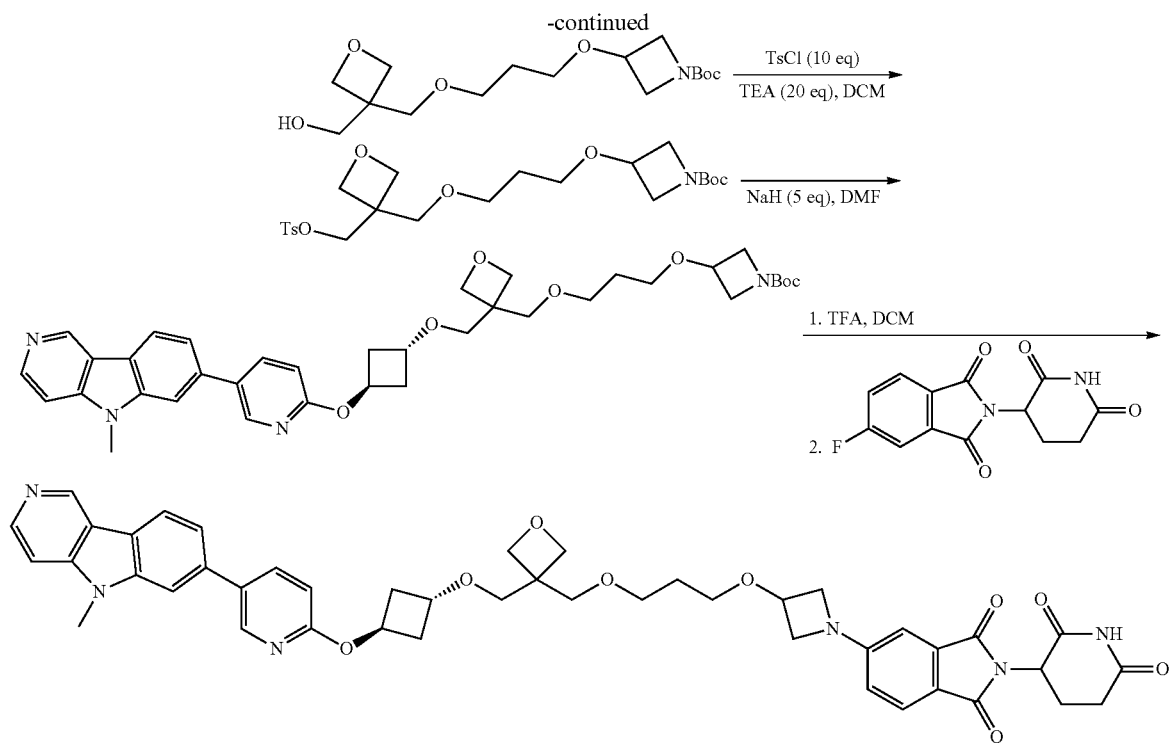

Compounds 169

Synthetic Scheme for Exemplary Compound 174

2-(2,6-dioxopiperidin-3-yl)-5-(4-((3-(((1r,3r)-3-((5-(5-methyl-5H-pyrido[4,3-b]indol-7-yl)pyridin-2-yl)oxy)cyclobutoxy)methyl)bicyclo[1.1.1]pentan-1-yl)methoxy)butoxy)isoindoline-1,3-dione

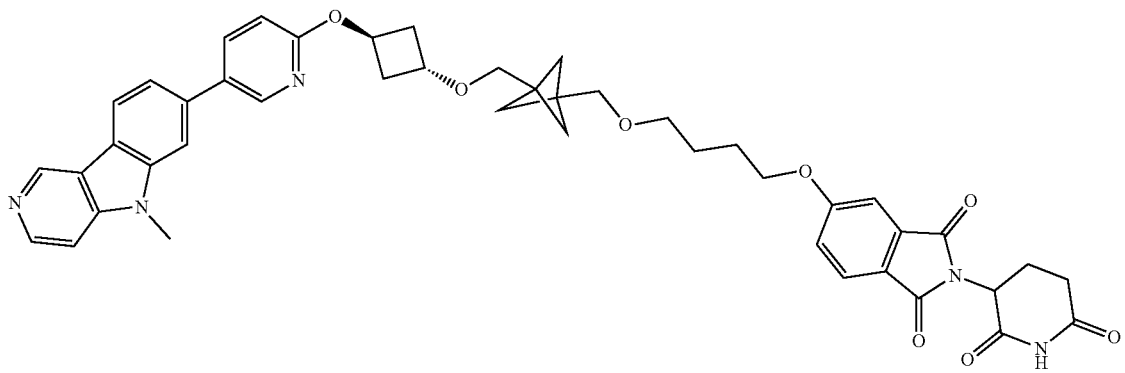 [SMILES: Cn1c2ccncc2c2ccc(-c3ccc(O[C@H]4C[C@H](OCC56CC(COCCCCOc7ccc8c(c7)C(=O)N(C7CCC(=O)NC7=O)C8=O)(C5)C6)C4)nc3)cc21]

Step 1: bicyclo[1.1.1]pentane-1,3-diyldimethanol

To a solution of dimethyl bicyclo[0.1.1.1]pentane-1,3-dicarboxylate (500 mg, 2.72 mmol) in tetrahydrofuran (5 ml) was added lithium aluminum hydride (419 mg, 10.87 mmol) at 0° C., and the resulting mixture was stirred at room temperature for 2 hours. TLC showed the reaction was complete. The reaction mixture was quenched with water (1 ml), sodium hydroxide (2 ml, 10% in water) and water (1 ml). The solid was removed through filtration, and the filtrate was dried over anhydrous sodium sulfate, concentrated under reduced pressure to afford to afford bicyclo[1.1.1]pentane-1,3-diyldimethanol (256 mg crude, yield 70%) as light yellow oil.

Bicyclo[1.1.1]pentane-1,3-diyldimethanol was converted to the final compound, 2-(2,6-dioxopiperidin-3-yl)-5-(4-((3-(((1r,3r)-3-((5-(5-methyl-5H-pyrido[4,3-b]indol-7-yl)pyridin-2-yl)oxy)cyclobutoxy)methyl)bicyclo[1.1.1]pentan-1-yl)methoxy)butoxy)isoindoline-1,3-dione, according to the scheme below and using procedures described above and common procedures known to those skilled in the art.

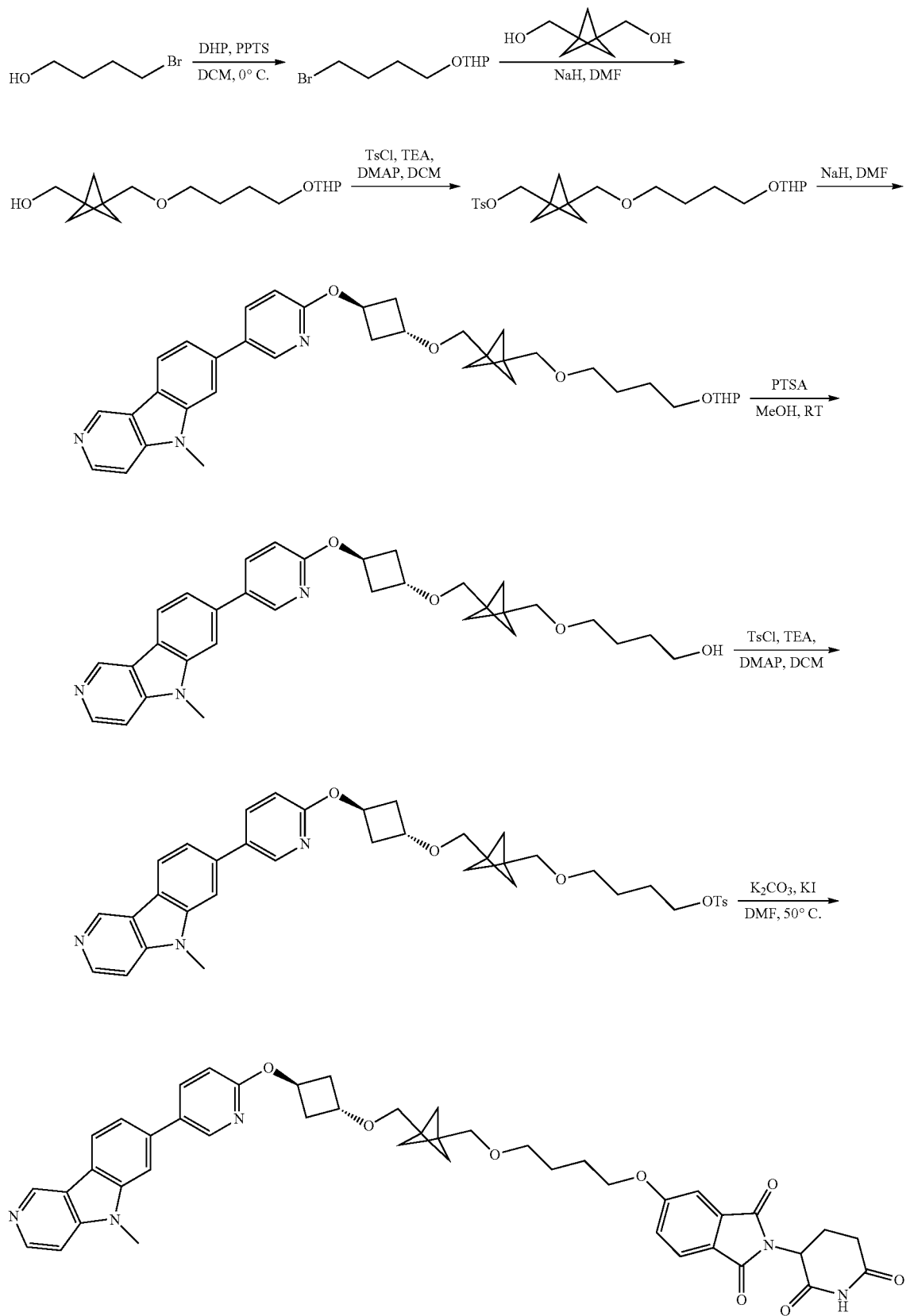
Compound 174

Synthetic Scheme for Exemplary Compound 175

2-(2,6-dioxopiperidin-3-yl)-5-((5-((3-(3-((5-(5-methyl-5H-pyrido[4,3-b]indol-7-yl)pyridin-2-yl)oxy)azetidine-1-carbonyl)bicyclo[1.1.1]pentan-1-yl)methoxy)pentyl)oxy)isoindoline-1,3-dione

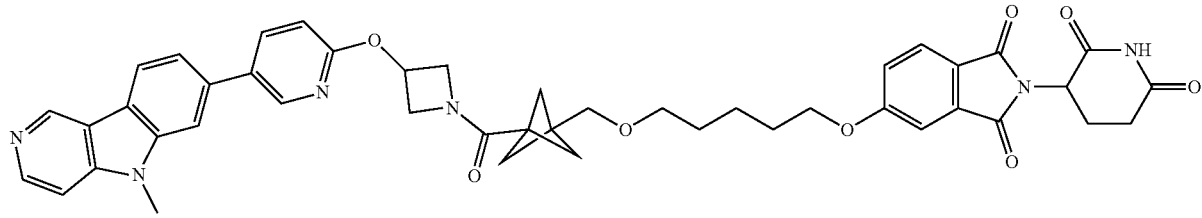 [SMILES: Cn1c2ccncc2c2ccc(-c3ccc(OC4CN(C(=O)C56CC(COCCCCCOc7ccc8c(c7)C(=O)N(C7CCC(=O)NC7=O)C8=O)(C5)C6)C4)nc3)cc21]

Step 1: 3-(Hydroxymethyl)bicyclo[1.1.1]pentane-1-carboxylate

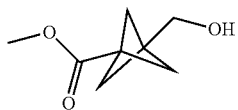

To a solution of dimethyl bicyclo[1.1.1]pentane-1,3-dicarboxylate (1 g, 5.43 mmol) in tetrahydrofuran (10 ml) was added lithium borohydride (120 mg, 5.43 mmol) at 0° C. under nitrogen. The mixture was allowed to warm up to room temperature and stirred at room temperature for 5 hours. The mixture was quenched with aqueous hydrochloride acid (1N) till pH 3-4, and extracted with dichloromethane (10 ml×2). The organic layers were combined, washed with brine (10 ml), dried over sodium sulfate and concentrated under reduced pressure to give a crude residue which was purified by silica gel flash chromatography (eluted with 20-33% ethyl acetate in hexane) to afford methyl 3-(hydroxymethyl)bicyclo[1.1.1]pentane-1-carboxylate (400 mg, 47%) as colorless oil.

3-(Hydroxymethyl)bicyclo[1.1.1]pentane-1-carboxylate was converted to the final compound, 2-(2,6-dioxopiperidin-3-yl)-5-((5-((3-(3-((5-(5-methyl-5H-pyrido[4,3-b]indol-7-yl)pyridin-2-yl)oxy)azetidine-1-carbonyl)bicyclo[1.1.1]pentan-1-yl)methoxy)pentyl)oxy)isoindoline-1,3-dione, according to the schemes below and using procedures described above and common procedures known to those skilled in the art.

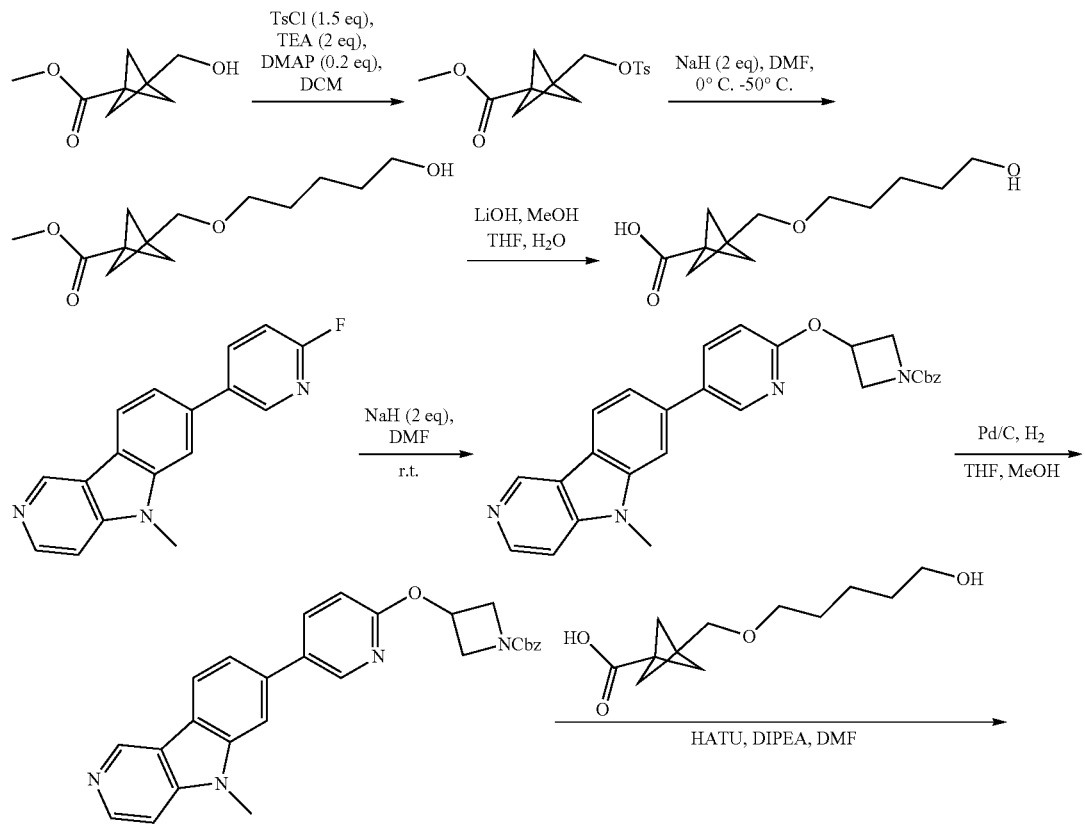

-continued
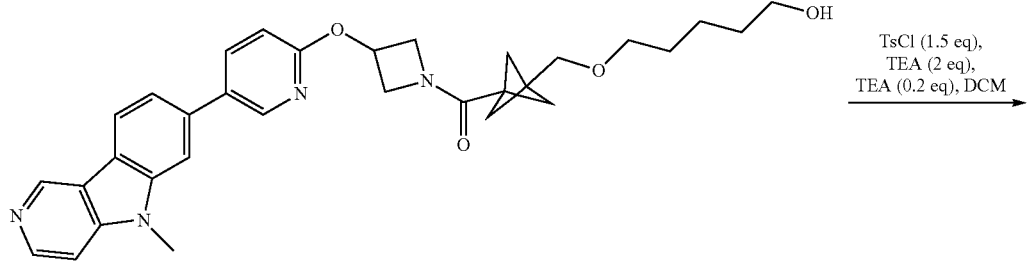
TsCl (1.5 eq),
TEA (2 eq),
TEA (0.2 eq), DCM
→
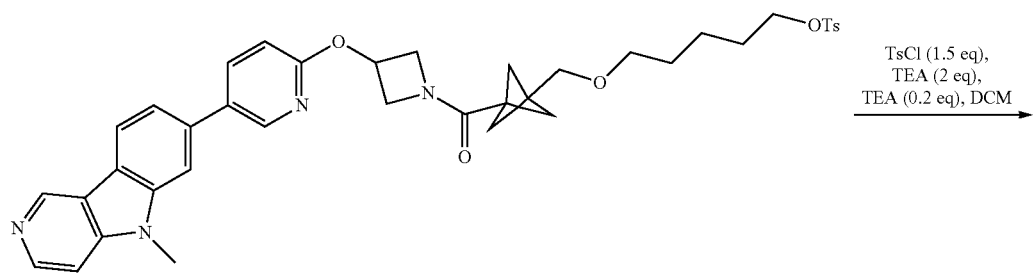
TsCl (1.5 eq),
TEA (2 eq),
TEA (0.2 eq), DCM
→
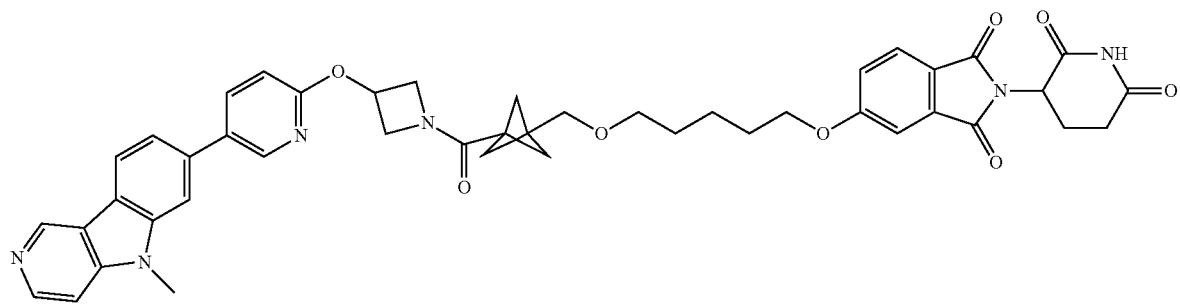
Compound 175
Synthetic Scheme for Exemplary Compound 176
5-(3-(3-(3-((1r,3r)-3-((5-(8,9-difluoro-5-methyl-5H-pyrido[4,3-b]indol-7-yl)pyridin-2-yl)oxy)cyclobutoxy)propoxy)propoxy)azetidin-1-yl)-2-(2,6-dioxopiperidin-3-yl)isoindoline-1,3-dione
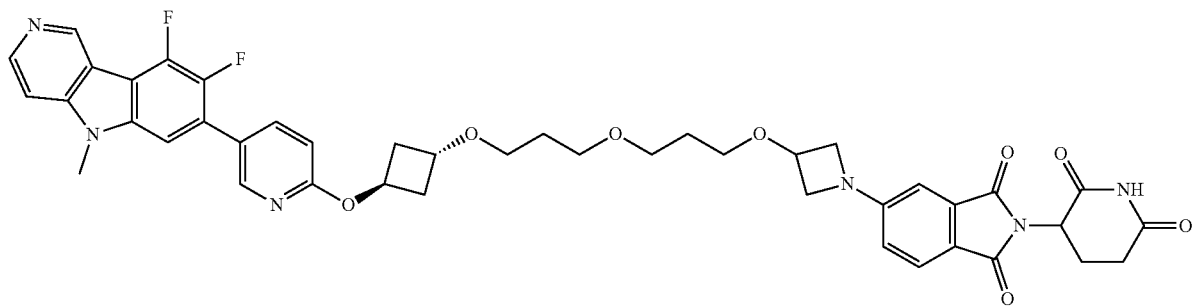 [SMILES: Cn1c2ccncc2c2c(F)c(F)c(-c3ccc(O[C@H]4C[C@H](OCCCOCCCOC5CN(c6ccc7c(c6)C(=O)N(C6CCC(=O)NC6=O)C7=O)C5)C4)nc3)cc21]

Prepared according to the schemes below and using procedures described above for Compound 104 (in modified sequence) and common procedures known to those skilled in the art.
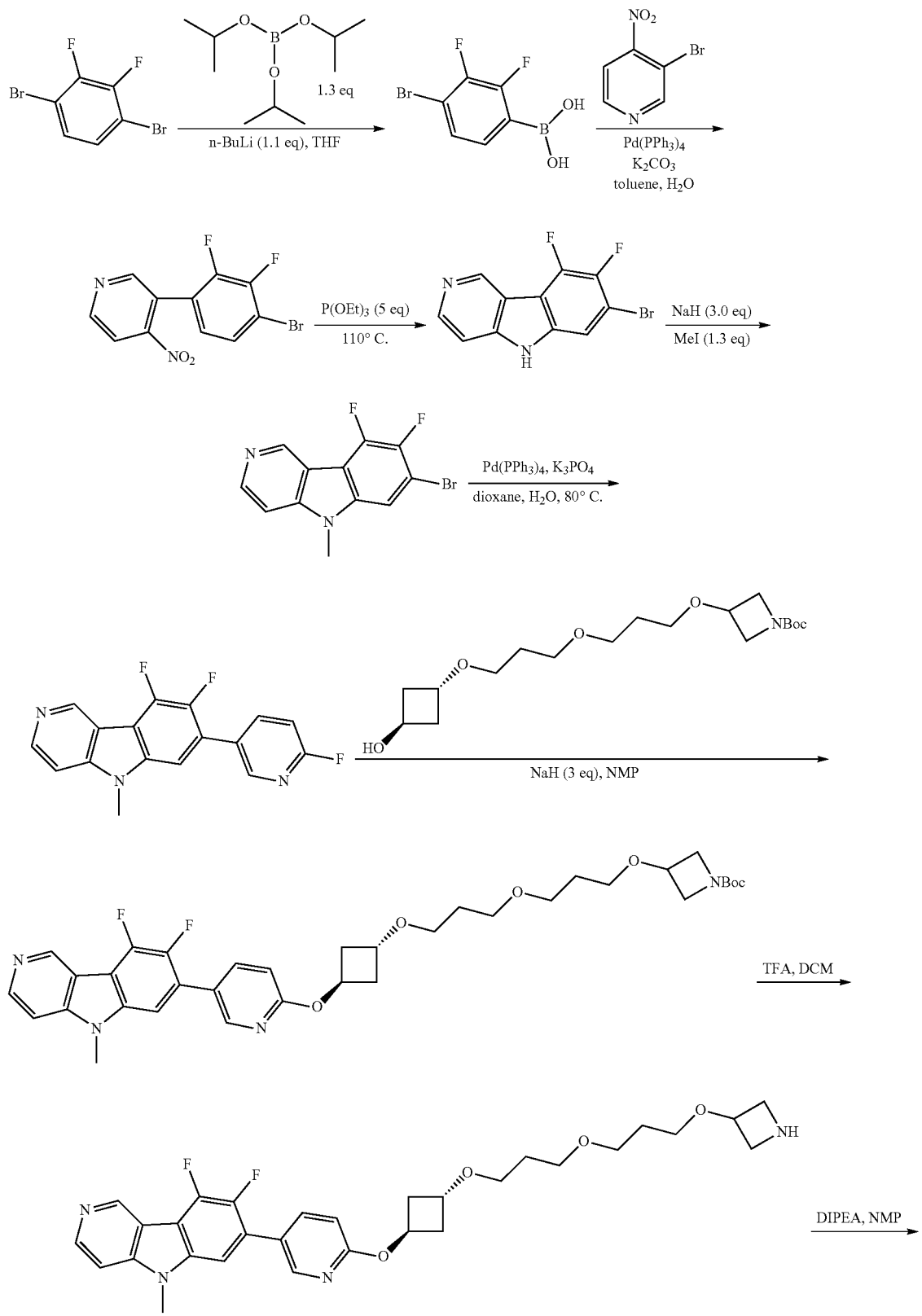

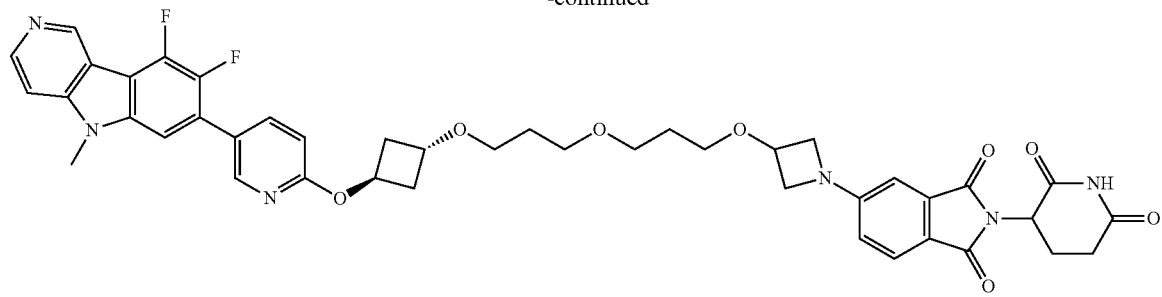

Compound 176

Synthetic Scheme for Exemplary Compound 177

3-(5-(3-(3-(3-((1r,3r)-3-((5-(5-methyl-5H-pyrido[4,3-b]indol-7-yl)pyridin-2-yl)oxy)cyclobutoxy)propoxy)propoxy)azetidin-1-yl)-1-oxoisoindolin-2-yl)piperidine-2,6-dione

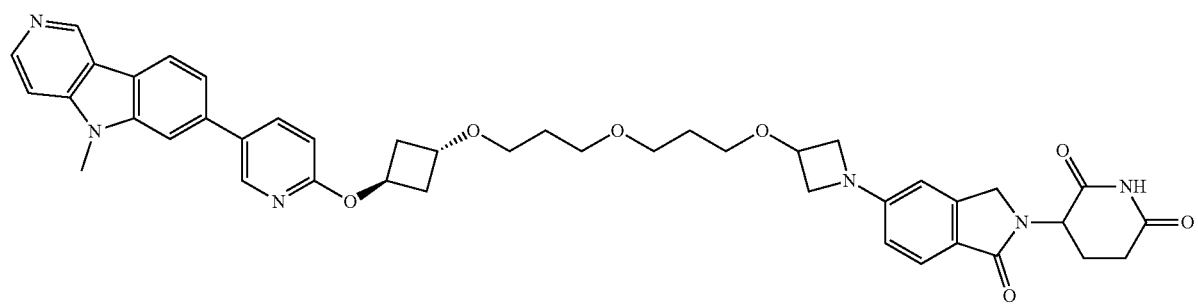 [SMILES: Cn1c2ccncc2c2ccc(-c3ccc(O[C@H]4C[C@H](OCCCOCCCOC5CN(c6ccc7c(c6)CN(C6CCC(=O)NC6=O)C7=O)C5)C4)nc3)cc21]

Step 1: 5-(3-(3-(3-((1r,3r)-3-((5-(5H-pyrido[4,3-b]indol-7-yl)-3-(trifluoromethyl)pyridin-2-yl)oxy)cyclobutoxy)propoxy)propoxy)azetidin-1-yl)-2-(2,6-dioxopiperidin-3-yl)isoindoline-1,3-dione

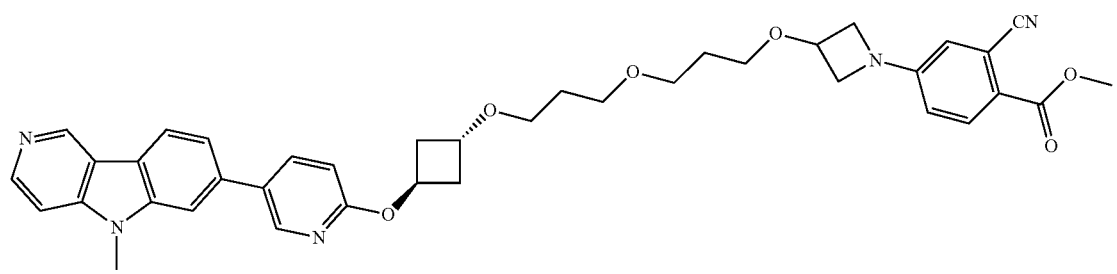 [SMILES: COC(=O)c1ccc(N2CC(OCCCOCCCO[C@H]3C[C@H](Oc4ccc(-c5ccc6c7cnccc7n(C)c6c5)cn4)C3)C2)cc1C#N]

A mixture of 7-(6-((1r,3r)-3-(3-(3-(azetidin-3-yloxy)propoxy)propoxy)cyclobutoxy)pyridin-3-yl)-5-methyl-5H-pyrido[4,3-b]indole (crude, 0.390 mmol) [prepared as described for Compound 104], N-ethyl-N-isopropylpropan-2-amine (86 mg, 1.17 mmol) and methyl 2-cyano-4-fluorobenzoate (90 mg, 0.468 mmol) in 1-methyl-2-pyrrolidinone (3 ml) was stirred at 90° C. for 16 hour. TLC showed the reaction was complete. The reaction mixture was partitioned between ethyl acetate (20 ml) and water (30 ml). The organic layer was collected, washed with brine (20 ml), dried over anhydrous sodium sulfate and concentrated under reduced pressure to give a crude residue which was purified by silica gel flash column chromatography (eluted with 2-4% methanol in dichloromethane) to afford 5-(3-(3-(3-((1r,3r)-3-((5-(5H-pyrido[4,3-b]indol-7-yl)-3-(trifluoromethyl)pyridin-2-yl)oxy)cyclobutoxy)propoxy)propoxy)azetidin-1-yl)-2-(2,6-dioxopiperidin-3-yl)isoindoline-1,3-dione (160 mg, yield 61%) as light yellow oil.

Step 2: Methyl 2-formyl-4-(3-(3-(3-((1r,3r)-3-((5-(5-methyl-5H-pyrido[4,3-b]indol-7-yl)pyridin-2-yl)oxy)cyclobutoxy)propoxy)propoxy)azetidin-1-yl)benzoate

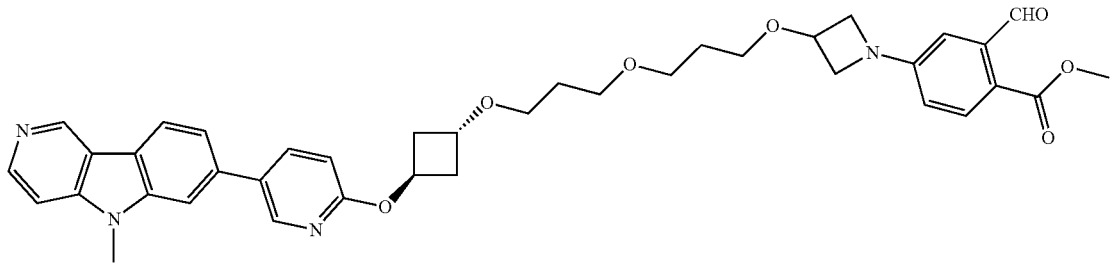 [SMILES: COC(=O)c1ccc(N2CC(OCCCOCCCO[C@H]3C[C@H](Oc4ccc(-c5ccc6c7cnccc7n(C)c6c5)cn4)C3)C2)cc1C=O]

To the mixture of methyl 2-cyano-4-(3-(3-(3-((1r,3r)-3-((5-(5-methyl-5H-pyrido[4,3-b]indol-7-yl)pyridin-2-yl)oxy)cyclobutoxy)propoxy)propoxy)azetidin-1-yl)benzoate (160 mg, 0.237 mmol) in pyridine (3 ml)-water (1.5 ml)-acetic acid (1.5 ml) was added sodium hypophosphite (125 mg, 1.179 mmol) and Raney nickel (85% in water) (300 mg) at room temperature. The resulting mixture was stirred at 50° C. for 2 hours. The mixture was diluted with ethyl acetate (30 ml), washed with water (30 ml×2), diluted hydrochloride acid solution (1 N, 30 ml), brine (50 ml), dried over anhydrous sodium sulfate, and concentrated under reduced pressure to give a crude residue which was purified by silica gel flash chromatography (eluted with 2-5% methanol in dichloromethane:) to afford methyl 2-formyl-4-(3-(3-(3-((1r,3r)-3-((5-(5-methyl-5H-pyrido[4,3-b]indol-7-yl)pyridin-2-yl)oxy)cyclobutoxy)propoxy)propoxy)azetidin-1-yl)benzoate (90 mg, yield 56%) as brown oil.

Step 3: 3-(5-(3-(3-(3-((1r,3r)-3-((5-(5-methyl-5H-pyrido[4,3-b]indol-7-yl)pyridin-2-yl)oxy)cyclobutoxy)propoxy)propoxy)azetidin-1-yl)-1-oxoisoindolin-2-yl)piperidine-2,6-dione

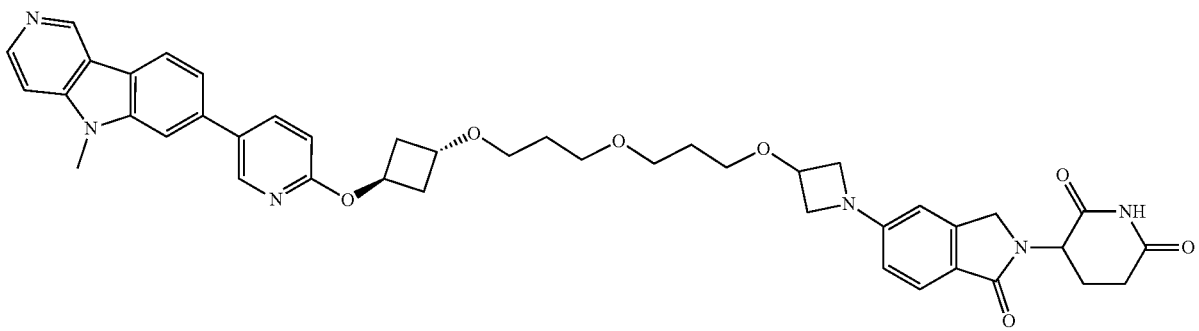 [SMILES: Cn1c2ccncc2c2ccc(-c3ccc(O[C@H]4C[C@H](OCCCOCCCOC5CN(c6ccc7c(c6)CN(C6CCC(=O)NC6=O)C7=O)C5)C4)nc3)cc21]

A mixture of 3-aminopiperidine-2,6-dione (32 mg, 0.199 mmol)N-ethyl-N-isopropylpropan-2-amine (34 mg, 0.199 mmol), acetic acid (0.5 ml) and methyl 2-formyl-4-(3-(3-(3-((1r,3r)-3-((5-(5-methyl-5H-pyrido[4,3-b]indol-7-yl)pyridin-2-yl)oxy)cyclobutoxy)propoxy)propoxy)azetidin-1-yl)benzoate (90 mg, 0.133 mmol) in methanol (5 ml) was stirred at room temperature for 15 min. Then sodium cyanoborohydride (16 mg, 0.400 mmol) was added and stirred at room temperature overnight. TLC showed the reaction was complete. The reaction mixture was partitioned between dichloromethane (30 ml) and water (10 ml), the organic layer was collected, washed with brine (10 ml×2), dried over anhydrous sodium sulfate and concentrated under reduced pressure to give a crude residue which was purified by Prep-TLC (8% methanol in ethyl acetate) to afford the title compound (50 mg, yield 50%) as white solid.

$^1$H NMR (400 MHz, DMSO-d6): δ 1.71-1.80 (m, 4H), 1.90-1.93 (m, 1H), 2.28-2.37 (m, 3H), 2.40-2.44 (m, 2H), 2.56-2.57 (m, 1H), 2.83-2.92 (m, 1H), 3.37 (t, J=6.0 Hz, 2H), 3.43-3.48 (m, 6H), 3.67-3.70 (m, 2H), 3.95 (s, 3H), 4.11-4.19 (m, 4H), 4.23-4.27 (m, 1H), 4.42-4.44 (m, 1H), 4.99-5.03 (m, 1H), 5.31-5.34 (m, 1H), 6.46-6.49 (m, 2H), 6.94 (d, J=8.8 Hz, 1H), 7.47 (d, J=8.4 Hz, 1H), 7.60-7.63 (m, 2H), 7.97 (s, 1H), 8.17-8.20 (m, 1H), 8.32 (d, J=8.0 Hz, 1H), 8.50 (d, J=6.0 Hz, 1H), 8.64 (d, J=2.0 Hz, 1H), 9.37 (s, 1H), 10.92 (s, 1H). (M+H)$^+$ 759.6.

Synthetic Scheme for Exemplary Compound 184

2-(2,6-dioxopiperidin-3-yl)-5-((7-(3-(3-((5-(5-methyl-5H-pyrido[4,3-b]indol-7-yl)pyridin-2-yl)oxy)azetidine-1-carbonyl)bicyclo[1.1.1]pentan-1-yl)heptyl)oxy)isoindoline-1,3-dione

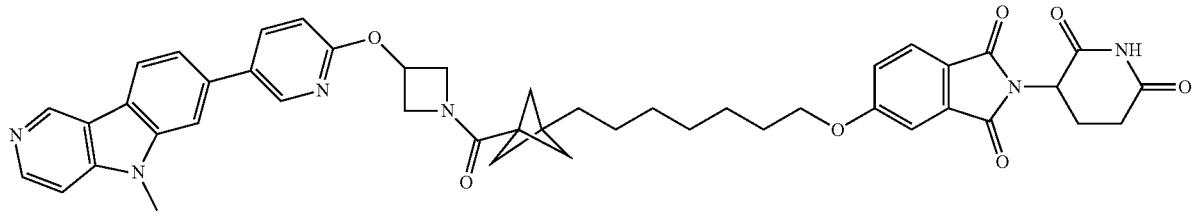 [SMILES: Cn1c2ccncc2c2ccc(-c3ccc(OC4CN(C(=O)C56CC(CCCCCCCOc7ccc8c(c7)C(=O)N(C7CCC(=O)NC7=O)C8=O)(C5)C6)C4)nc3)cc21]

Step 1: (6-(benzyloxy)hexyl)triphenylphosphonium bromide

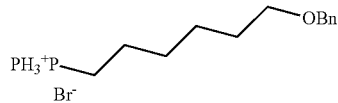

A mixture of (((6-bromohexyl)oxy)methyl)benzene (2.7 g, 10 mmol) and triphenylphosphine (2.6 g, 10 mmol) in acetonitrile (10 ml) was stirred at reflux for 40 hours. The reaction mixture was allowed to cool to room temperature and concentrated under reduced pressure to afford (6-(benzyloxy)hexyl)triphenylphosphonium bromide (5 g, yield: 94%) as colorless oil.

Step 2: Methyl 3-formylbicyclo[1.1.1]pentane-1-carboxylate

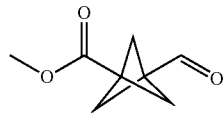

To a stirred solution of methyl 3-(hydroxymethyl)bicyclo[1.1.1]pentane-1-carboxylate (156 mg, 1 mmol) in dichloromethane (10 ml) was added Dess-Martin periodinane (840 mg, 2.0 mmol) at 0° C. The resulting reaction mixture was allowed to warm up to room temperature and stirred at this temperature for additional 1 h. The reaction mixture was quenched with aqueous solution of sodium sulfite (10 ml) and extracted with dichloromethane (20 ml×2), washed with brine (20 ml×2), dried over anhydrous sodium sulfate, and concentrated under reduced pressure to afford a crude residue which was purified by silica gel flash chromatography (eluted with 20% ethyl acetate in hexane) to afford methyl 3-formylbicyclo[1.1.1]pentane-1-carboxylate (110 mg, yield 70%) as colorless oil.

Step 3: Methyl 3-(7-(benzyloxy)hept-1-en-1-yl)bicyclo[1.1.1]pentane-1-carboxylate

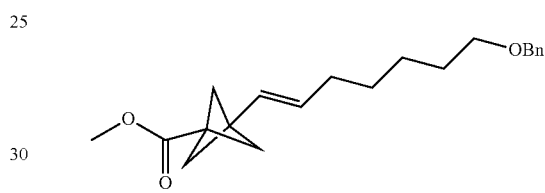

To a solution of (6-(benzyloxy)hexyl)triphenylphosphonium bromide (373 mg, 0.70 mmol) in anhydrous tetrahydrofuran (6 ml) was added n-butyllithium (2.5 M in hexane) (0.28 mL, 0.7 mmol) dropwise at −20° C. and the resulting mixture was stirred at the same temperature for 30 min. Methyl 3-formylbicyclo[1.1.1]pentane-1-carboxylate (90 mg, 0.58 mmol) in anhydrous tetrahydrofuran (1 ml) was added dropwise. The resulting reaction mixture was warmed to room temperature slowly and stirred at the same temperature for 30 min. The reaction mixture was quenched with water (10 ml) at 0° C. and extracted with ethyl acetate (20 ml×2). The combined organic layers were washed with brine (20 ml), dried over anhydrous sodium sulfate, and concentrated under reduced pressure to give a residue which was purified by silica gel flash chromatography (eluted with 10% ethyl acetate in hexane) to afford methyl 3-(7-(benzyloxy)hept-1-en-1-yl)bicyclo[1.1.1]pentane-1-carboxylate (56 mg, yield 29%) as colorless oil.

Methyl 3-(7-(benzyloxy)hept-1-en-1-yl)bicyclo[1.1.1]pentane-1-carboxylate was converted to the final compound, 2-(2,6-dioxopiperidin-3-yl)-5-((7-(3-(3-((5-(5-methyl-5H-pyrido[4,3-b]indol-7-yl)pyridin-2-yl)oxy)azetidine-1-carbonyl)bicyclo[1.1.1]pentan-1-yl)heptyl)oxy)isoindoline-1,3-dione, according to the schemes below and using procedures described above and common procedures known to those skilled in the art.

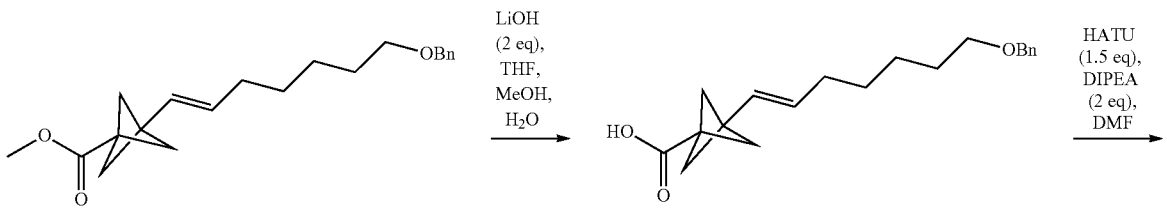

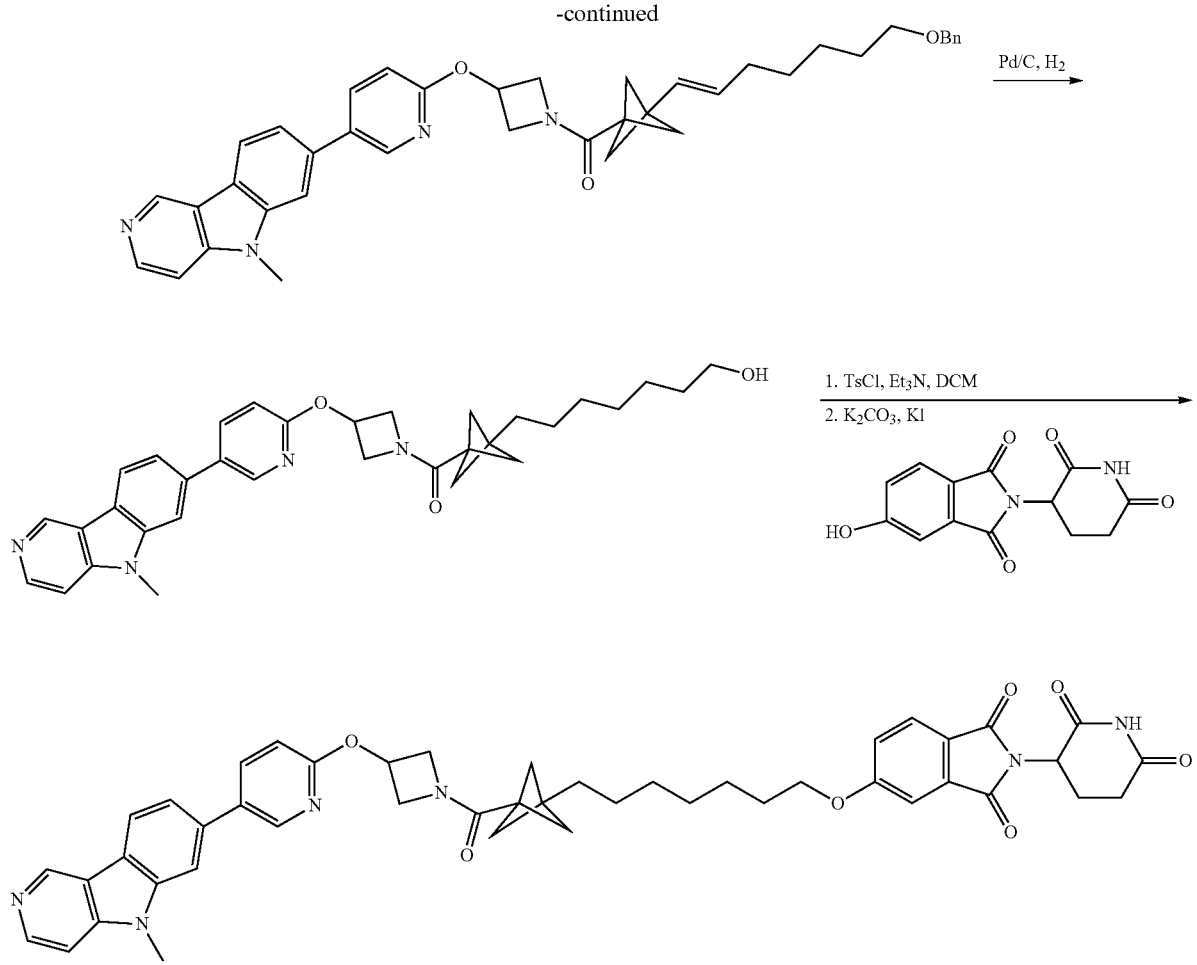
Compound 184
Synthetic Scheme for Exemplary Compound 185
(2S,4R)—N-(2-(2-((5-(5H-pyrido[4,3-b]indol-7-yl)pyridin-2-yl)oxy)ethoxy)-4-(4-methylthiazol-5-yl)benzyl)-4-hydroxy-1-((S)-3-methyl-2-(1-oxoisoindolin-2-yl)butanoyl)pyrrolidine-2-carboxamide
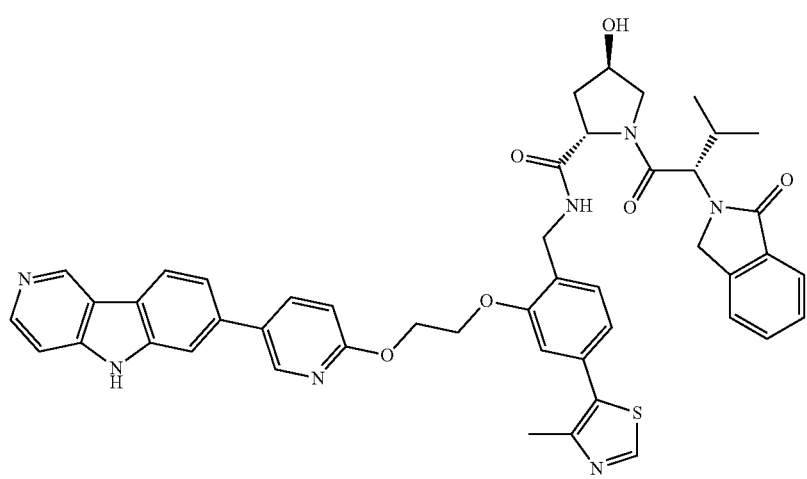 [SMILES: Cc1ncsc1-c1ccc(CNC(=O)[C@@H]2C[C@@H](O)CN2C(=O)[C@H](C(C)C)N2Cc3ccccc3C2=O)c(OCCOc2ccc(-c3ccc4c(c3)[nH]c3ccncc34)cn2)c1]

Prepared according to the scheme below and using procedures described above and common procedures known to those skilled in the art.
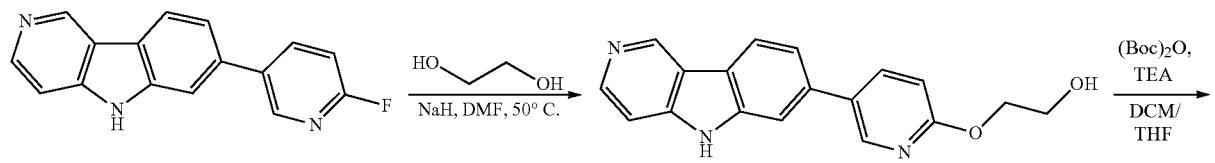
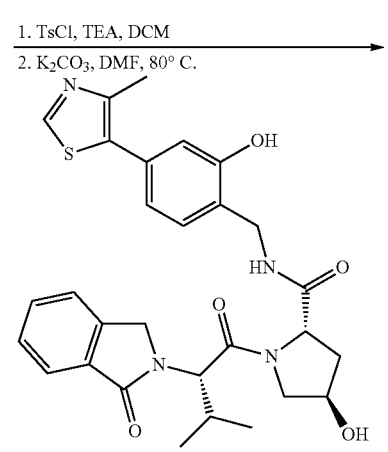
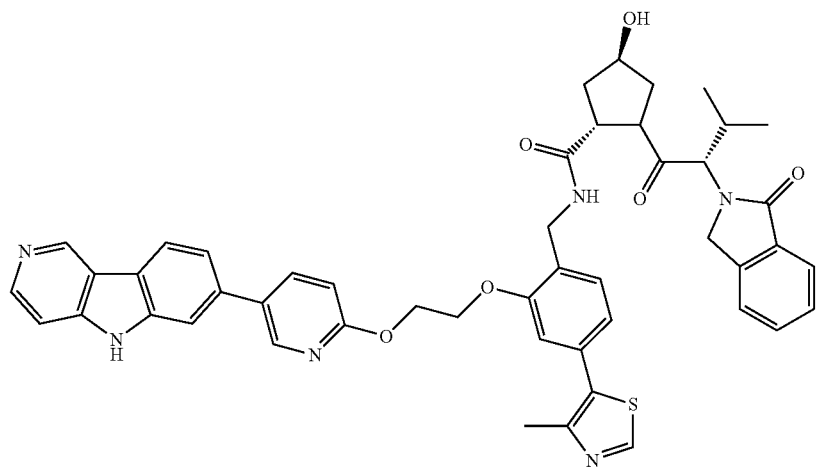
Compound 185

Using procedures analogous to those for Compound 185 the following were prepared: Compounds 186, 187, 196, 201.

Synthetic Scheme for Exemplary Compound 193

2-(2,6-dioxopiperidin-3-yl)-5-(3-(3-(2-(6-((5-(5-methyl-5H-pyrido[4,3-b]indol-7-yl)pyridin-2-yl)oxy)-2-azaspiro[3.3]heptan-2-yl)-2-oxoethoxy)propoxy)azetidin-1-yl)isoindoline-1,3-dione

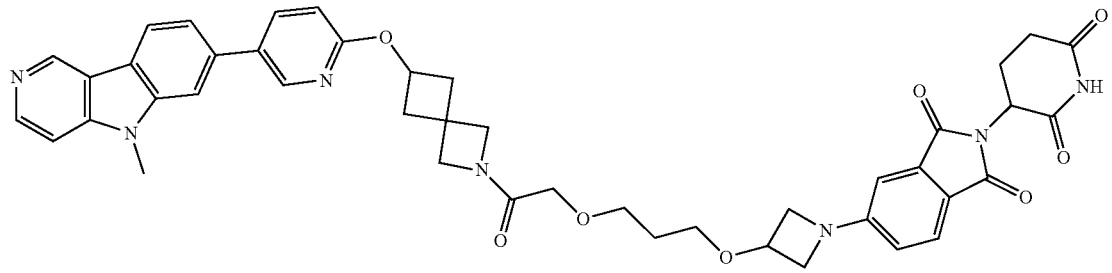 [SMILES: Cn1c2ccncc2c2ccc(-c3ccc(OC4CC5(C4)CN(C(=O)COCCCOC4CN(c6ccc7c(c6)C(=O)N(C6CCC(=O)NC6=O)C7=O)C4)C5)nc3)cc21]

Prepared according to the schemes below and using procedures described above and common procedures known to those skilled in the art.

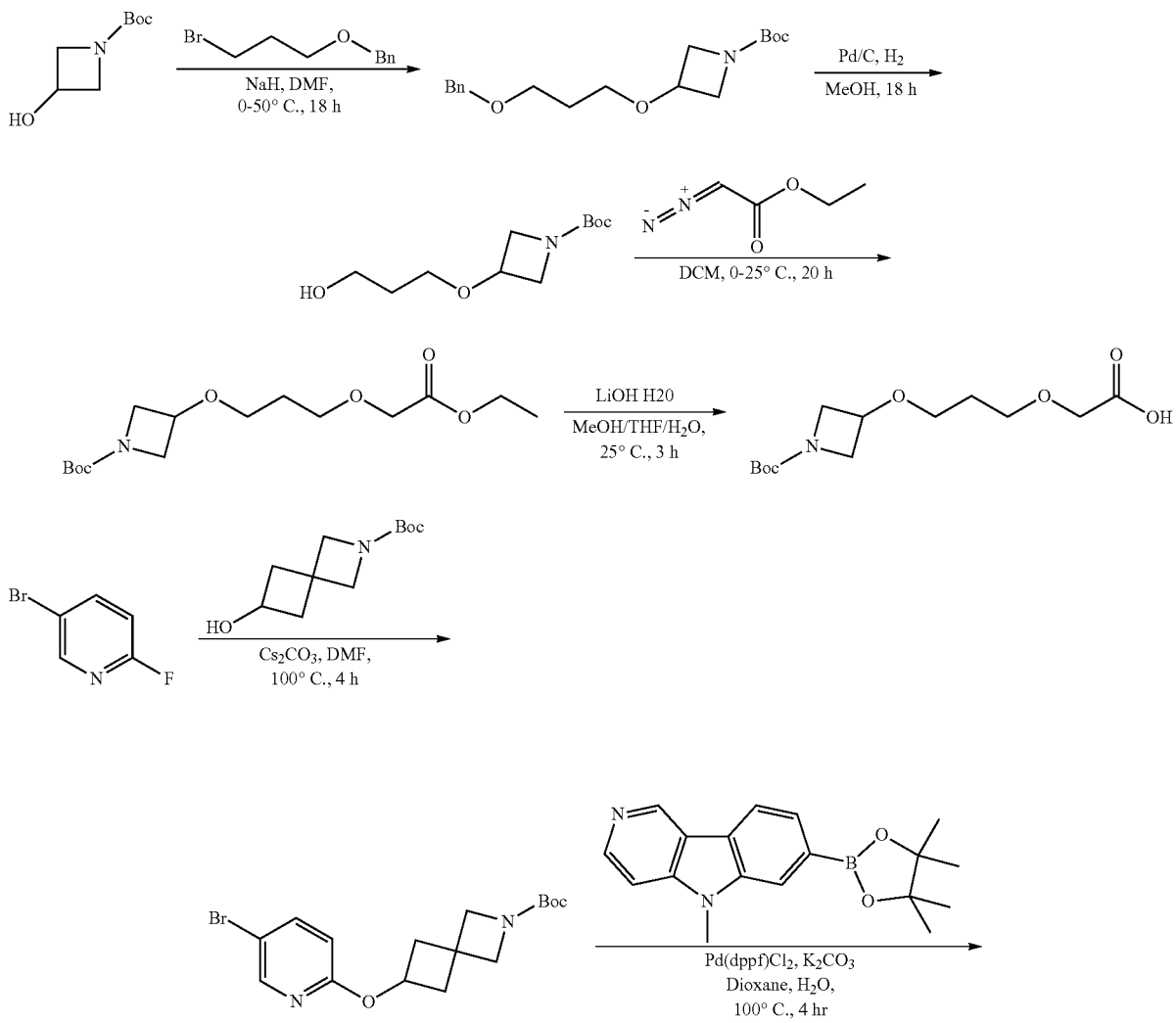

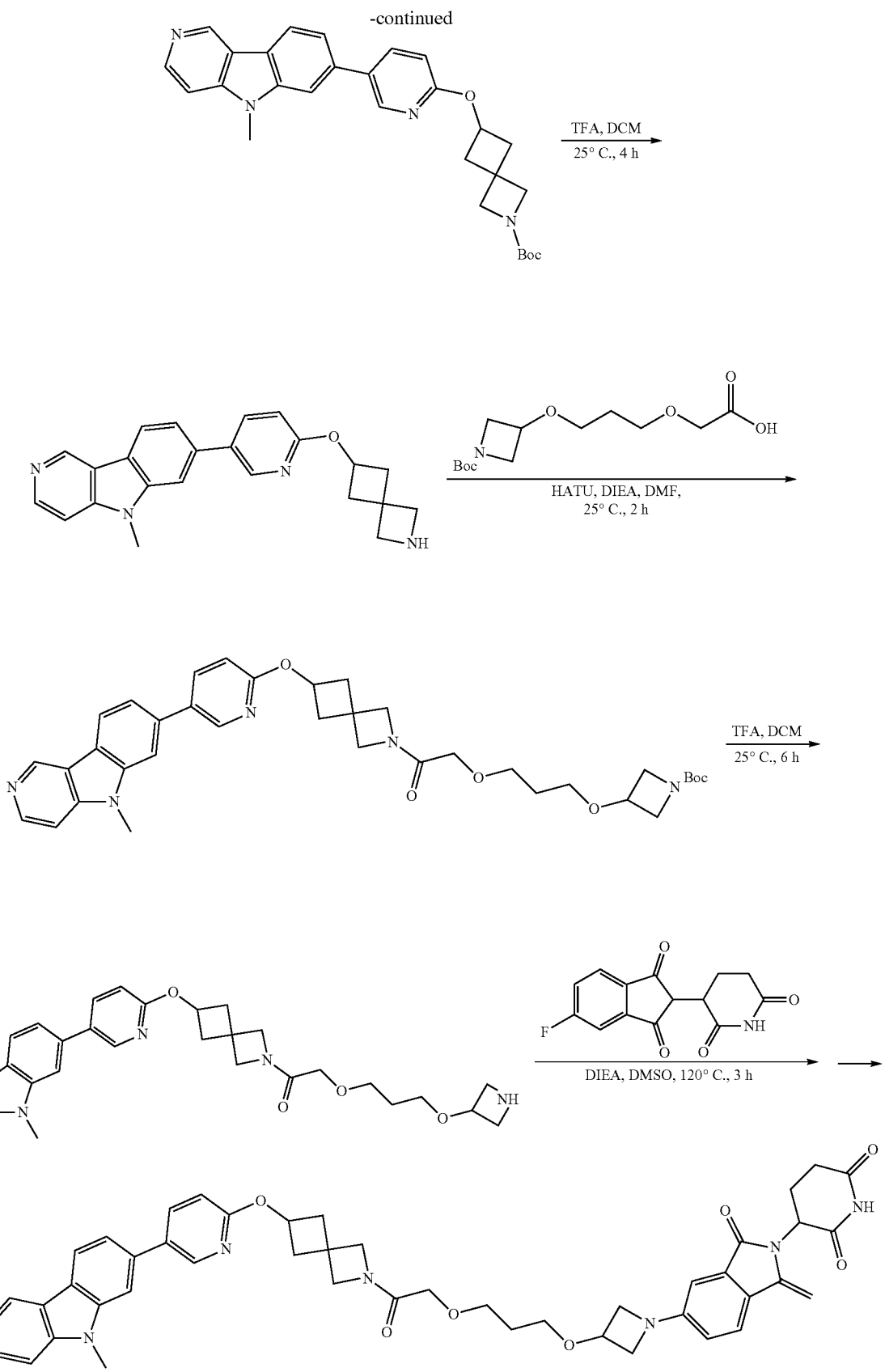
Compound 193

Synthetic Scheme for Exemplary Compound 195

5-((14-((5-(4-chloro-5-methyl-5H-pyrido[4,3-b]indol-7-yl)pyridin-2-yl)oxy)-3,6,9,12-tetraoxatetradecyl)oxy)-2-(2,6-dioxopiperidin-3-yl)isoindoline-1,3-dione

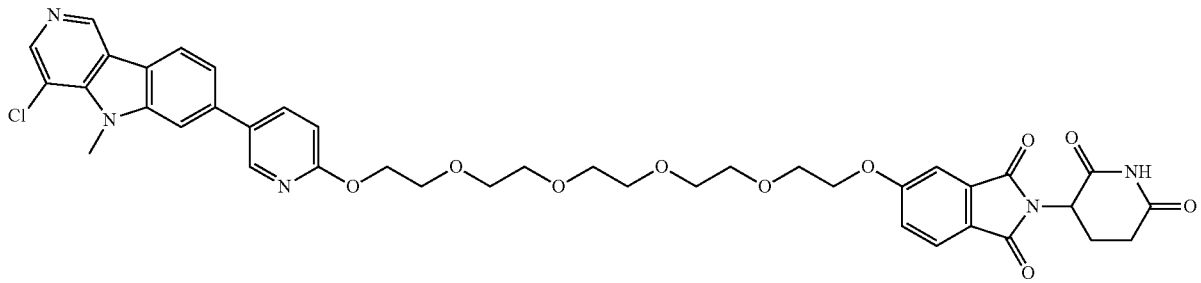 [SMILES: Cn1c2cc(-c3ccc(OCCOCCOCCOCCOCCOc4ccc5c(c4)C(=O)N(C4CCC(=O)NC4=O)C5=O)nc3)ccc2c2cncc(Cl)c21]

Step 1: 3-bromo-5-chloropyridin-4-amine

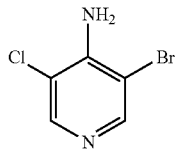

To a solution of 3-chloropyridin-4-amine (10 g, 77.78 mmol) in acetonitrile (100 ml) was added N-bromosuccinimide (14.5 g, 81.67 mmol) at room temperature, and the resulting mixture was stirred at 60° C. for overnight under nitrogen. The reaction mixture was quenched with water (50 ml) and extracted with ethyl acetate (50 ml×2). The combined organic layers were washed with brine (50 ml×2), dried over anhydrous sodium sulfate, and concentrated to give a residue which was purified by silica gel flash chromatography (eluted with 20-50% ethyl acetate in hexane) to afford 3-bromo-5-chloropyridin-4-amine (8.8 g, yield 54%) as white solid.

Step 2: 3-(4-bromophenyl)-5-chloropyridin-4-amine

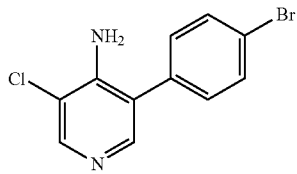 [SMILES: Nc1c(Cl)cncc1-c1ccc(Br)cc1]

A mixture of 3-bromo-5-chloropyridin-4-amine (5 g, 24.10 mmol), bis(pinacolato)diboron (12 g, 48320 mmol), potassium acetate (4.7 g, 48.20 mmol) and 1,1'-bis(diphenylphosphino)ferrocene palladium(II)dichloride (3.5 g, 4.82 mmol) in dioxane (100 ml) was stirred at 90° C. overnight under nitrogen. TLC showed the reaction was complete. To this mixture solution was added 1,4-dibromobenzene (11.4 g, 48.20 mmol), potassium carbonate (6.7 g, 48.20 mmol) and water (30 ml). tetrakis(triphenylphosphine)palladium (1.4 g, 1.21 mmol) was added and the mixture was stirred at 90° C. overnight under nitrogen. The reaction mixture was filtered and the filtrate was partitioned between ethyl acetate (100 ml) and water (100 ml), the organic layer was washed with brine (20 ml×2), dried over anhydrous sodium sulfate and concentrated under reduced pressure to give a crude residue which was purified by silica gel flash chromatography (eluted with 20-50% ethyl acetate in hexane) to afford 3-(4-bromophenyl)-5-chloropyridin-4-amine (2.3 g, yield 34%) as yellow solid.

Step 3: 4-azido-3-(4-bromophenyl)-5-chloropyridine

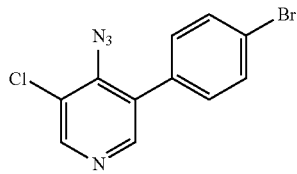 [SMILES: [N-]=[N+]=Nc1c(Cl)cncc1-c1ccc(Br)cc1]

To a solution of 3-(4-bromophenyl)-5-chloropyridin-4-amine (2.5 g, 8.8 mmol) in 2,2,2-trifluoroacetic acid (10 ml) was added sodium nitrite (1.5 g, 22.0 mmol) at 0° C. during 20 min, and the reaction mixture was stirred at 0° C. for 1 hour. To the reaction mixture was added sodium azide (1.43 g, 22.0 mmol) at 0° C.; the resulting mixture was allowed to warm up to room temperature and stirred overnight. The reaction mixture was basified with sodium carbonate till pH 8, and partitioned between ethyl acetate (30 ml) and water (50 ml). The organic layer was collected, and the aqueous layer was extracted with ethyl acetate (30 ml×2). The combined organic layers were washed with brine (20 ml), dried over anhydrous sodium sulfate, and concentrated under reduced pressure to give a crude residue which was purified by silica gel flash chromatography (eluted with 30% ethyl acetate in hexane) as 4-azido-3-(4-bromophenyl)-5-chloropyridine (850 mg, yield 31%) as yellow solid.

Step 4

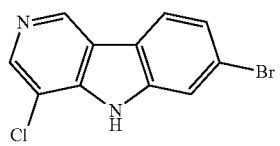 [SMILES: Clc1cncc2c1[nH]c1cc(Br)ccc12]

599

A mixture of 4-azido-3-(4-bromophenyl)-5-chloropyridine (850 mg, 2.75 mmol) in decalin (10 ml) was stirred in a sealed tube at 150° C. for 10 hours. After cooling to room temperature, the reaction mixture was triturated with hexane (20 ml). The resulting solid was collected by filtration and dried under vacuum to afford 7-bromo-4-chloro-5H-pyrido[4,3-b]indole (600 mg, yield 77%) as yellow solid which was used in next step directly without further purification.

600

7-bromo-4-chloro-5H-pyrido[4,3-b]indole was converted to the final compound, 5-((14-((5-(4-chloro-5-methyl-5H-pyrido[4,3-b]indol-7-yl)pyridin-2-yl)oxy)-3,6,9,12-tetraoxatetradecyl)oxy)-2-(2,6-dioxopiperidin-3-yl)isoindoline-1,3-dione, according to the scheme below and using procedures described above and common procedures known to those skilled in the art.

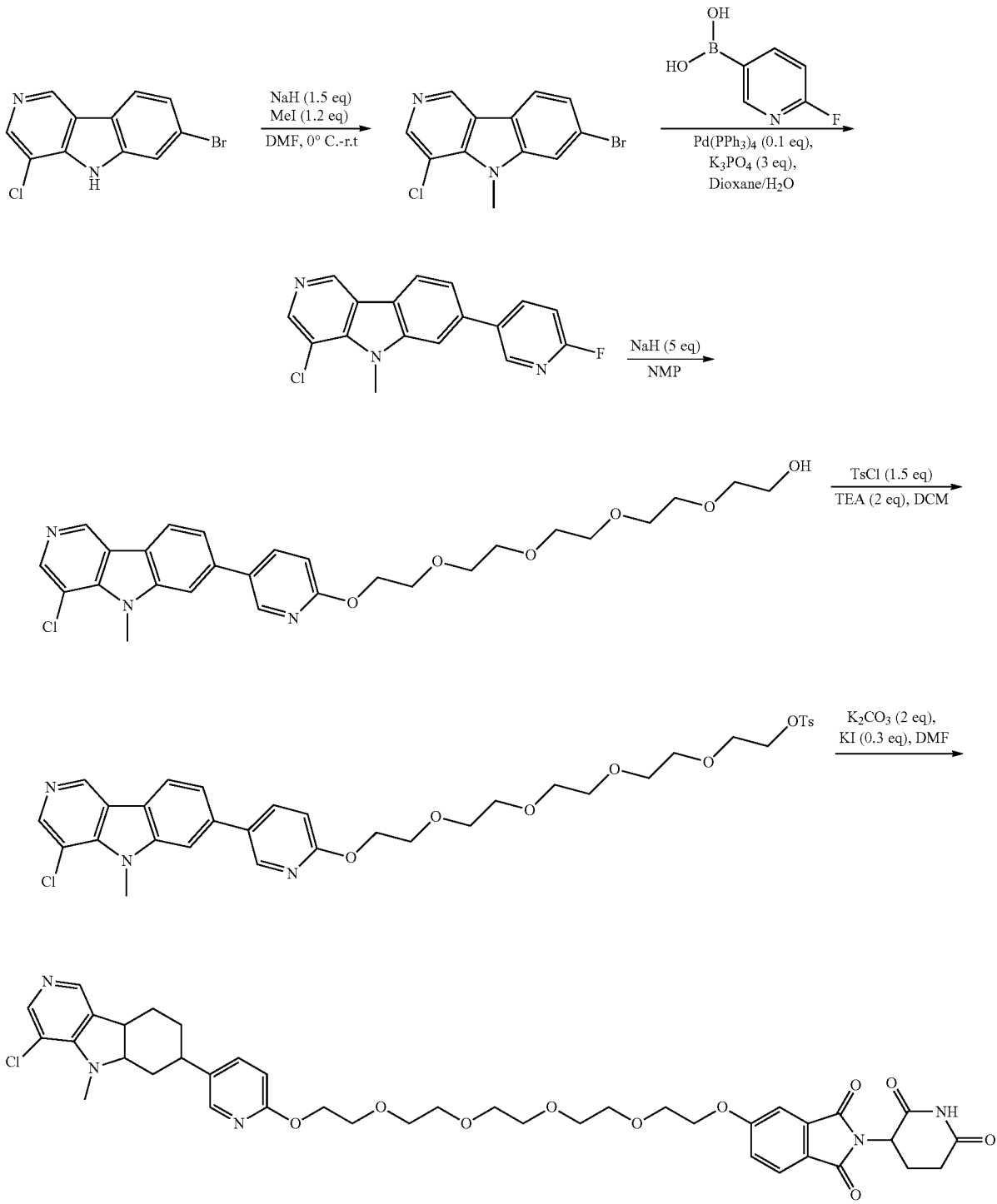

Compound 195

Synthetic Scheme for Exemplary Compound 197
5-(6-((2,2-difluoro-5-((1r,3r)-3-((5-(5-methyl-5H-pyrido[4,3-b]indol-7-yl)pyridin-2-yl)oxy)cyclobutoxy)pentyl)oxy)-2-azaspiro[3.3]heptan-2-yl)-2-(2,6-dioxopiperidin-3-yl)isoindoline-1,3-dione
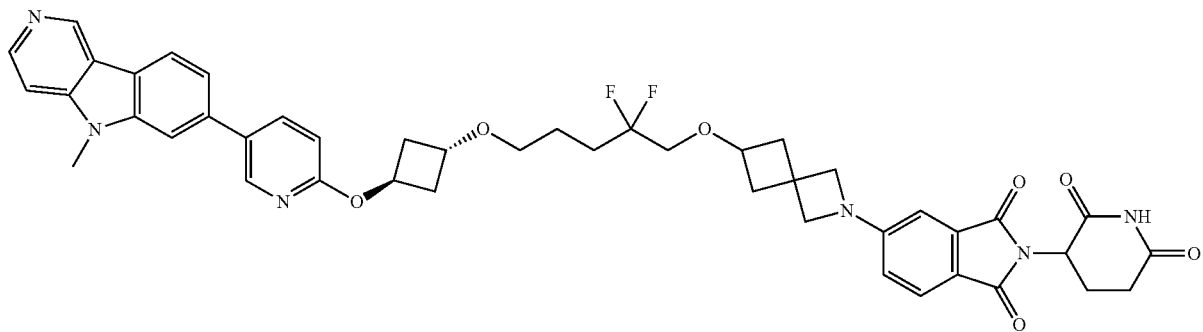 [SMILES: Cn1c2ccncc2c2ccc(-c3ccc(O[C@H]4C[C@H](OCCCC(F)(F)COC5CC6(C5)CN(c5ccc7c(c5)C(=O)N(C5CCC(=O)NC5=O)C7=O)C6)C4)nc3)cc21]
Prepared according to the scheme below and using procedures described above and common procedures known to those skilled in the art.
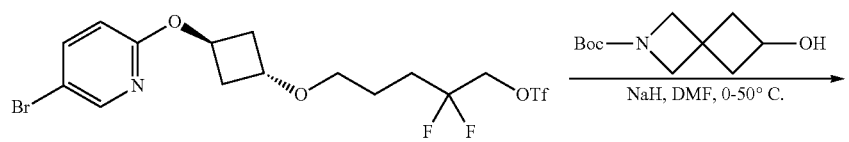
prepared as described in step 5 for Compound 150
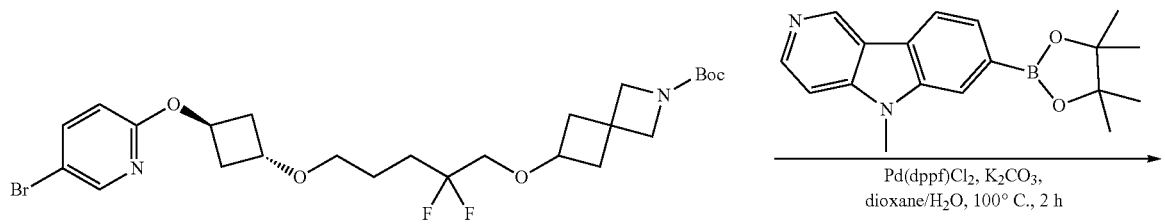
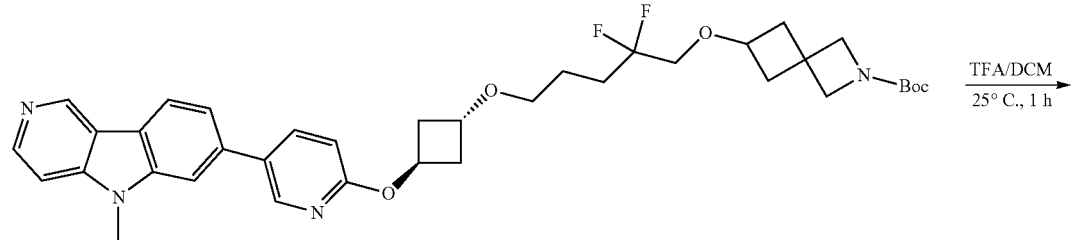
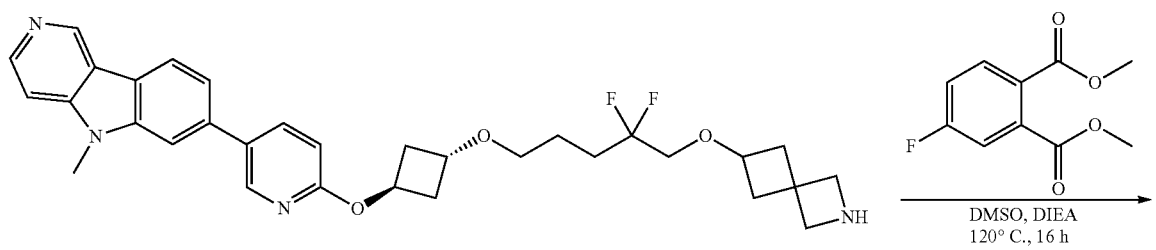

-continued
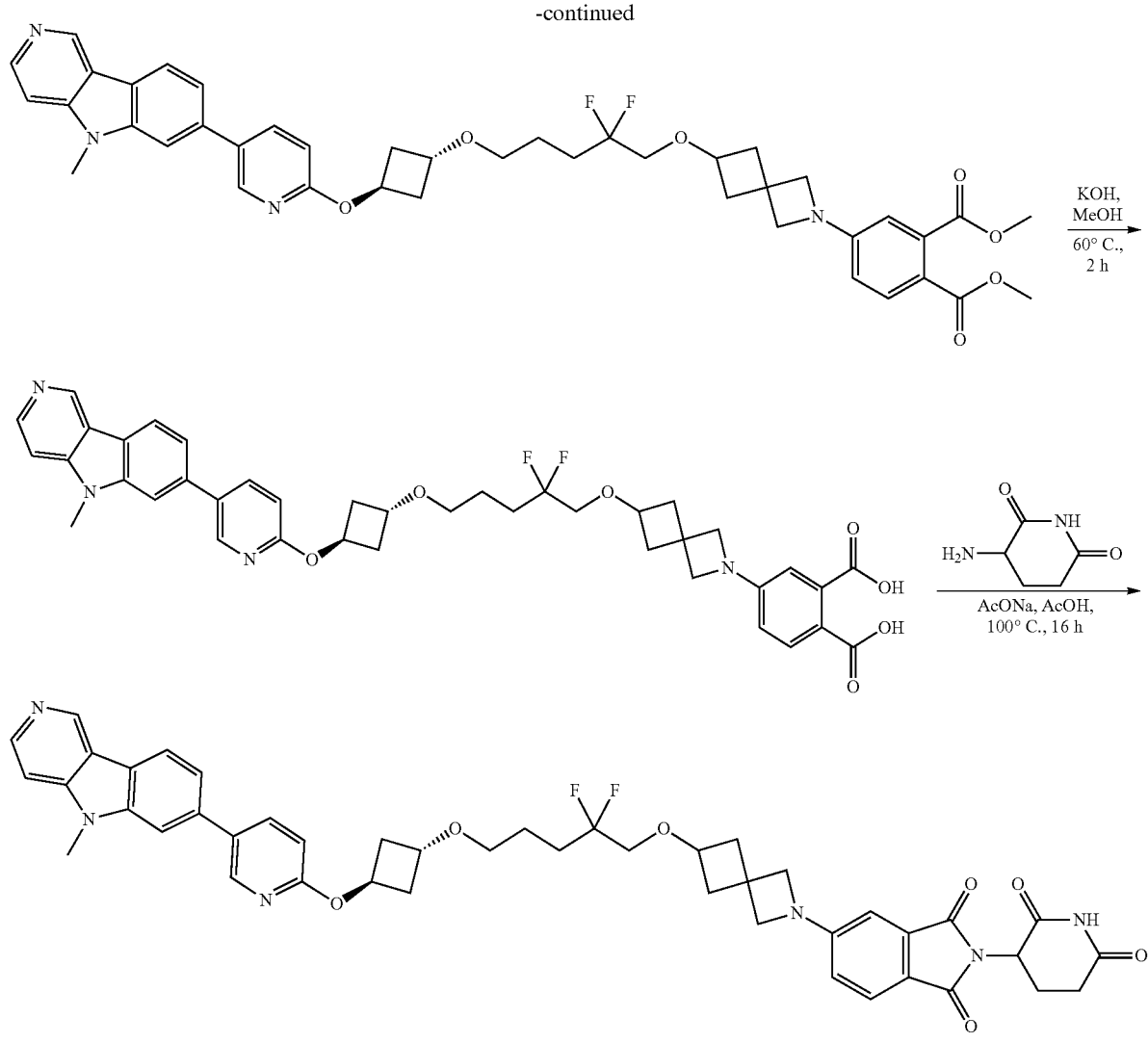
Compound 197
Synthetic Scheme for Exemplary Compound 199
3-((4-((2-(2,6-dioxopiperidin-3-yl)-1,3-dioxoisoindolin-5-yl)oxy)butoxy)methyl)-N-methyl-N-((1r,3r)-3-((5-(5-methyl-5H-pyrido[4,3-b]indol-7-yl)pyridin-2-yl)oxy)cyclobutyl)bicyclo[1.1.1]pentane-1-carboxamide
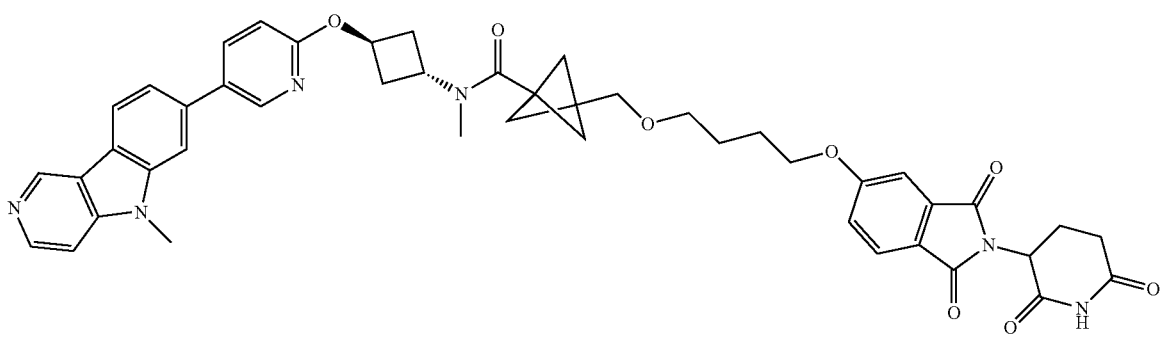 [SMILES: Cn1c2ccncc2c2ccc(-c3ccc(O[C@H]4C[C@H](N(C)C(=O)C56CC(COCCCCOc7ccc8c(c7)C(=O)N(C7CCC(=O)NC7=O)C8=O)(C5)C6)C4)nc3)cc21]

Prepared according to the scheme below and using procedures described above and common procedures known to those skilled in the art.
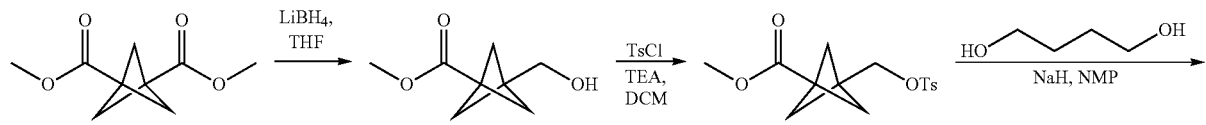
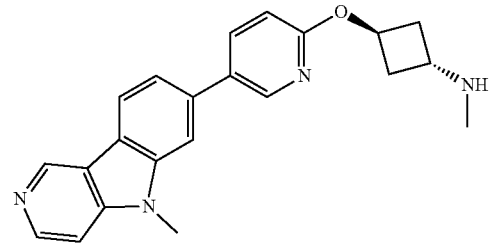
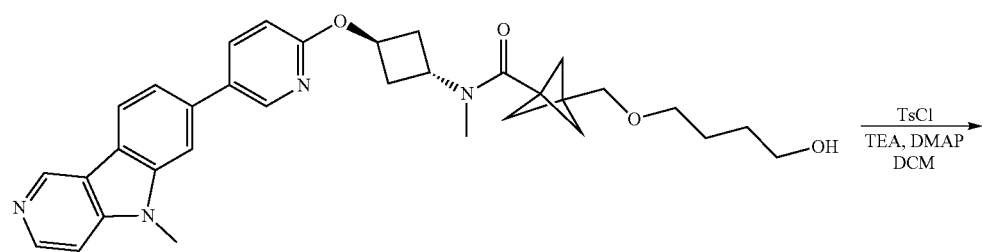
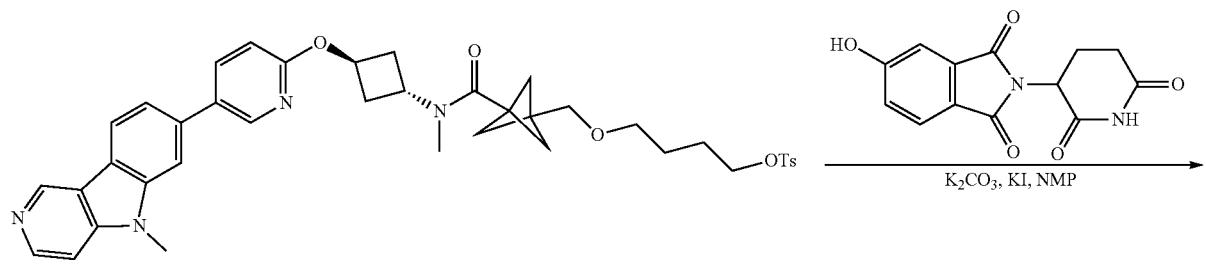
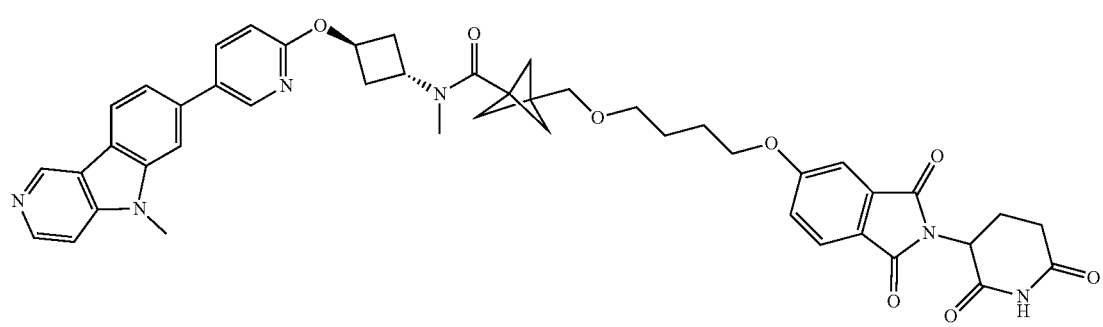
Compound 199

Synthetic Scheme for Exemplary Compound 202
2-((1-(2-(2,6-dioxopiperidin-3-yl)-1,3-dioxoisoindolin-5-yl)azetidin-3-yl)methoxy)-N-methyl-N-(3-((1r,3r)-3-((5-(5-methyl-5H-pyrido[4,3-b]indol-7-yl)pyridin-2-yl)oxy)cyclobutoxy)propyl)acetamide
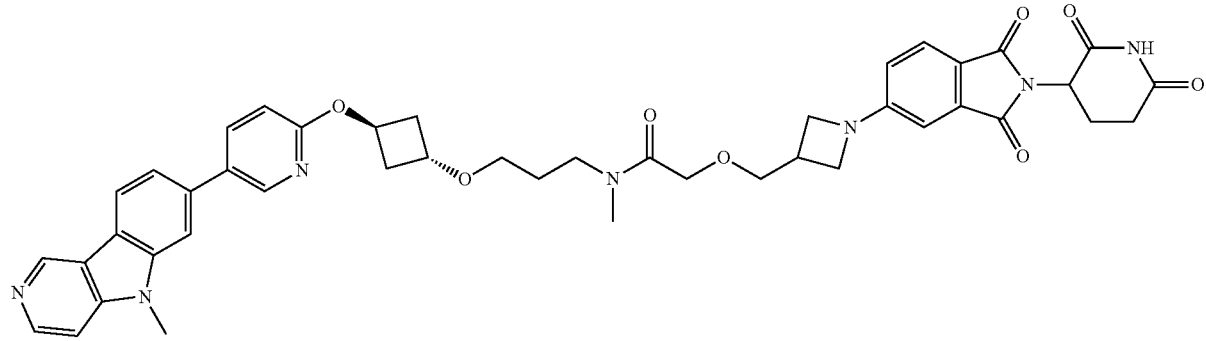 [SMILES: CN(CCCO[C@H]1C[C@H](Oc2ccc(-c3ccc4c5cnccc5n(C)c4c3)cn2)C1)C(=O)COCC1CN(c2ccc3c(c2)C(=O)N(C2CCC(=O)NC2=O)C3=O)C1]
Prepared according to the schemes below and using procedures described above and common procedures known to those skilled in the art.
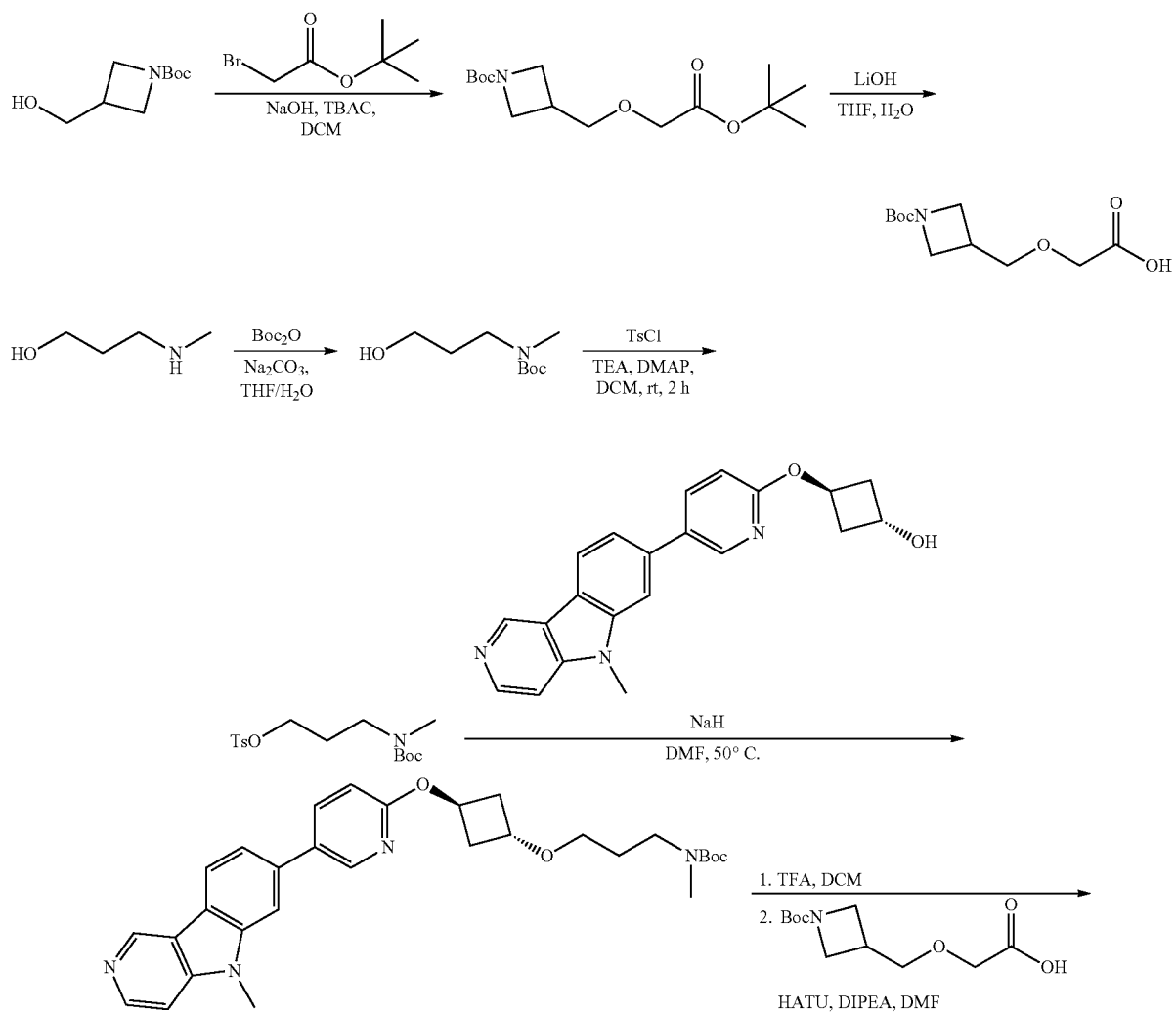

-continued
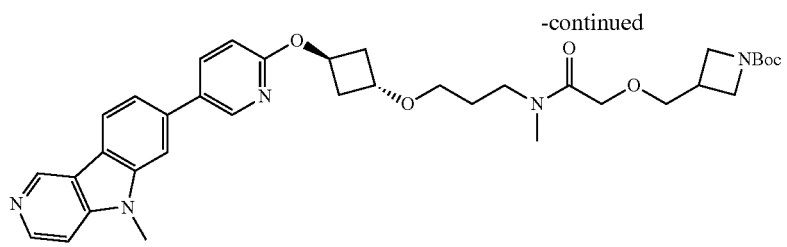
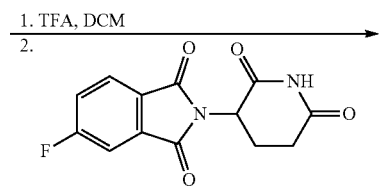
1. TFA, DCM
2.
DIPEA, NMP
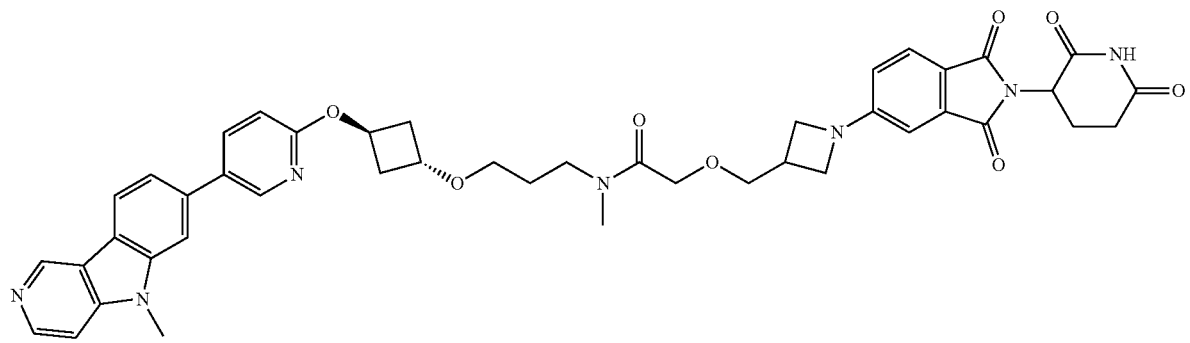
Compound 202
Synthetic Scheme for Exemplar Compound 203
2-((14-((2-(2,6-dioxopiperidin-3-yl)-1,3-dioxoisoin-dolin-5-yl)oxy)-3,6,9,12-tetraoxatetradecyl)oxy)-5-(5-methyl-5H-pyrido[4,3-b]indol-7-yl)nicotinonitrile
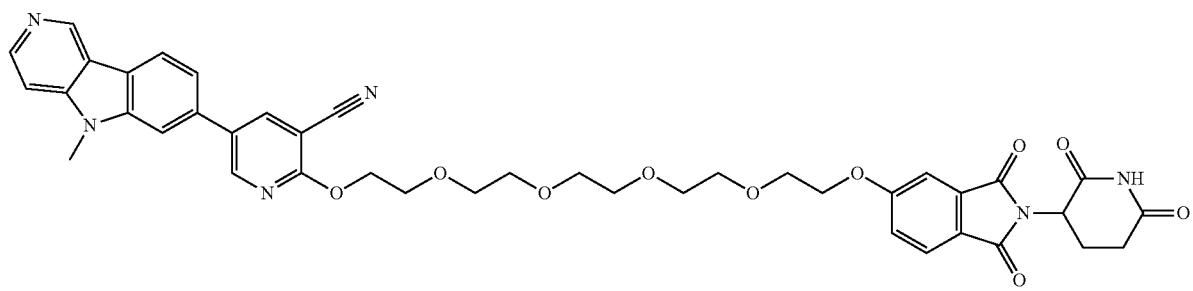 [SMILES: Cn1c2ccncc2c2ccc(-c3cnc(OCCOCCOCCOCCOCCOc4ccc5c(c4)C(=O)N(C4CCC(=O)NC4=O)C5=O)c(C#N)c3)cc21]
Prepared according to the scheme below and using procedures described above and common procedures known to those skilled in the art.
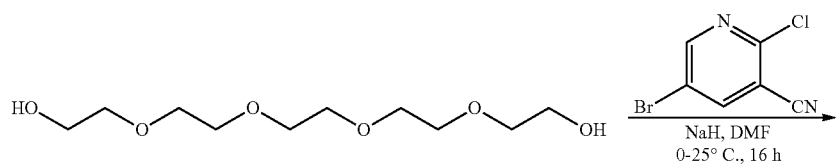
NaH, DMF
0-25° C., 16 h
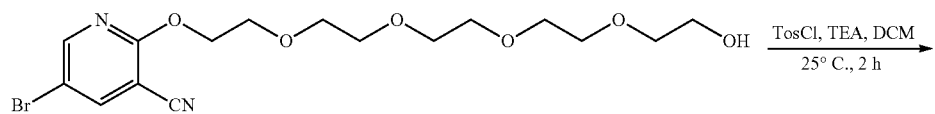
TosCl, TEA, DCM
25° C., 2 h

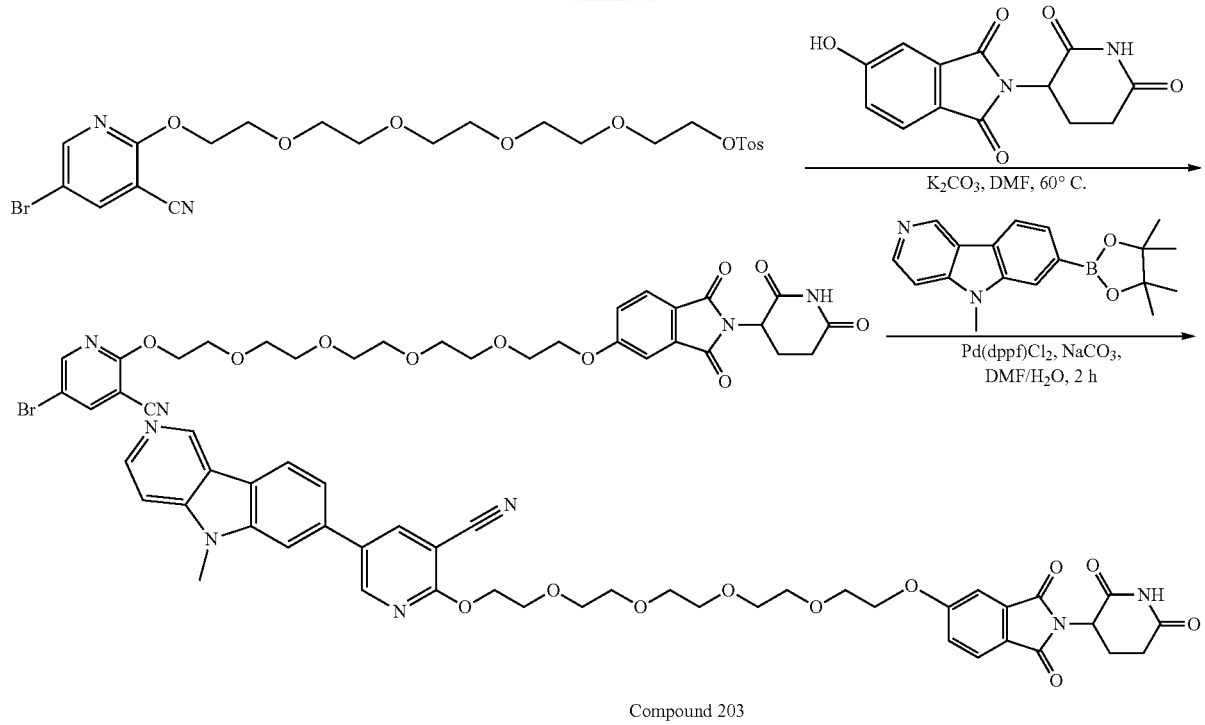

Compound 203

Synthetic Scheme for Exemplar Compound 207

5-((14-((5-(benzo[4,5]imidazo[1,2-a]pyrimidin-2-yl)pyridin-2-yl)oxy)-3,6,9,12-tetraoxatetradecyl)oxy)-2-(2,6-dioxopiperidin-3-yl)isoindoline-1,3-dione

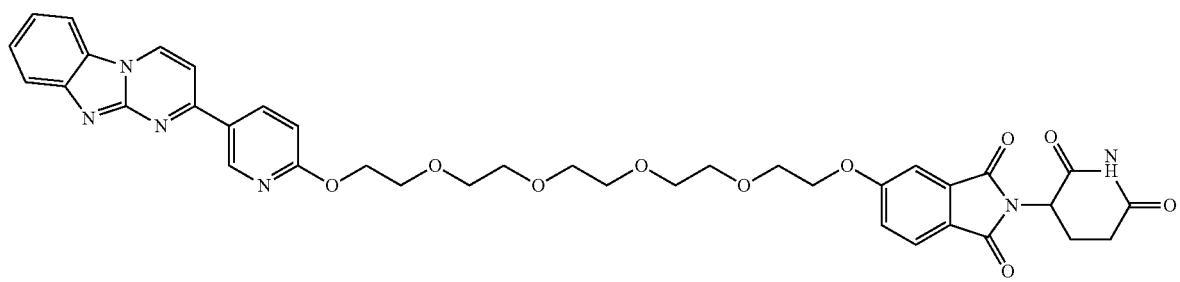 [SMILES: O=C1CCC(N2C(=O)c3ccc(OCCOCCOCCOCCOCCOc4ccc(-c5ccn6c(n5)nc5ccccc56)cn4)cc3C2=O)C(=O)N1]

Step 1: (E)-1,1,1-trichloro-4-ethoxy-but-3-en-2-one

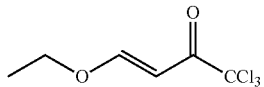

To a solution of 2,2,2-trichloroacetyl chloride (31.52 g, 173.36 mmol, 19 mL, 1 eq) was added dropwise ethyl vinyl ether (25 g, 346.71 mmol, 33 mL, 2 eq) at 0° C. After addition, the mixture was stirred at this temperature for 5 h, and then the mixture was warmed to 25° C. for 16 h. The mixture was stirred at 130° C. under reduced pressure to let gas (hydrogen chloride) evaporate to form a deep black color solution. The process required for 1 h or waited until no gas came out. The residue was concentrated under reduced pressure. The crude product (E)-1,1,1-trichloro-4-ethoxy-but-3-en-2-one (39.3 g, crude) was obtained as a black oil.

Step 2: 2-(trichloromethyl)pyrimido[1,2-a]benzimidazole

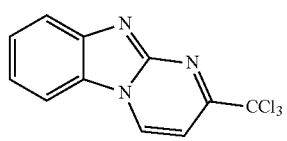

To a mixture of (E)-1,1,1-trichloro-4-ethoxy-but-3-en-2-one (39.2 g, 180.25 mmol, 1.09 eq) and 1H-benzimidazol-2-amine (22 g, 165.23 mmol, 1 eq) in toluene (500 mL) was added triethylamine (20.06 g, 198.27 mmol, 27 mL, 1.2 eq) in one portion at 25° C. under nitrogen. The mixture was stirred at 120° C. for 4 h. The mixture was cooled to 25° C.

and concentrated under reduced pressure at 55° C. The crude product 2-(trichloromethyl)pyrimido[1,2-a]benzimidazole (56.3 g, crude) was obtained as brown solid.

Step 3: Pyrimido[1,2-a]benzimidazol-2-ol

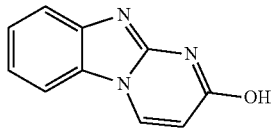 [SMILES: Oc1ccn2c(n1)nc1ccccc12]

To a mixture of 2-(trichloromethyl)pyrimido[1,2-a]benzimidazole (55.2 g, 192.64 mmol, 1 eq) in acetonitrile (950 mL) was added sodium hydroxide (10.2 g, 255.02 mmol, 1.32 eq) in Water (246 mL) in one portion at 20° C. under nitrogen. The mixture was stirred at 100° C. for 2 h. The mixture was cooled to 25° C. and concentrated in reduced pressure at 55° C. Ice was added to the resulting residue, and the pH of the solution was adjusted to 8 with hydrochloric acid (1 N, 130 mL). The solid was filtered, and dried under high vacuum. The filter was cooled to 10° C., some precipitate was formed, the cake was collected by filtered and concentrated under reduced pressure to give a residue. Compound pyrimido[1,2-a]benzimidazol-2-ol (9.3 g, 50.22 mmol, 26% yield) was obtained as a yellow solid, and crude product (about 7.3 g) was obtained.

Step 4: 2-Bromopyrimido[1,2-a]benzimidazole

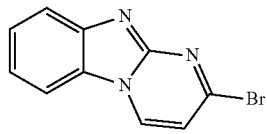 [SMILES: Brc1ccn2c(n1)nc1ccccc12]

To a solution of pyrimido[1,2-a]benzimidazol-2-ol (0.5 g, 2.70 mmol, 1 eq) in 1,1-dichloroethane (18 mL) and N,N-dimethylformamide (0.18 mL) was added phosphoryl tribromide (1.55 g, 5.40 mmol, 2 eq) in one portion at 20° C. under nitrogen. The mixture was stirred at 100° C. for 6 h. The mixture was cooled to 25° C. and concentrated under reduced pressure at 45° C. The residue was poured into ice-water (w/w=1/1, 30 mL) and stirred for 10 min. The aqueous phase was adjusted to pH=8 with a saturated aqueous solution of sodium bicarbonate. During this period, some precipitate was formed. The cake was collected by filtration and dried under high vacuum. The crude product 2-bromopyrimido[1,2-a]benzimidazole (0.65 g, crude) was obtained as a yellow solid.

2-Bromopyrimido[1,2-a]benzimidazole was converted to the final compound, 5-((14-((5-(benzo[4,5]imidazo[1,2-a]pyrimidin-2-yl)pyridin-2-yl)oxy)-3,6,9,12-tetraoxatetradecyl)oxy)-2-(2,6-dioxopiperidin-3-yl)isoindoline-1,3-dione, according to the scheme below and using procedures described above and common procedures known to those skilled in the art.

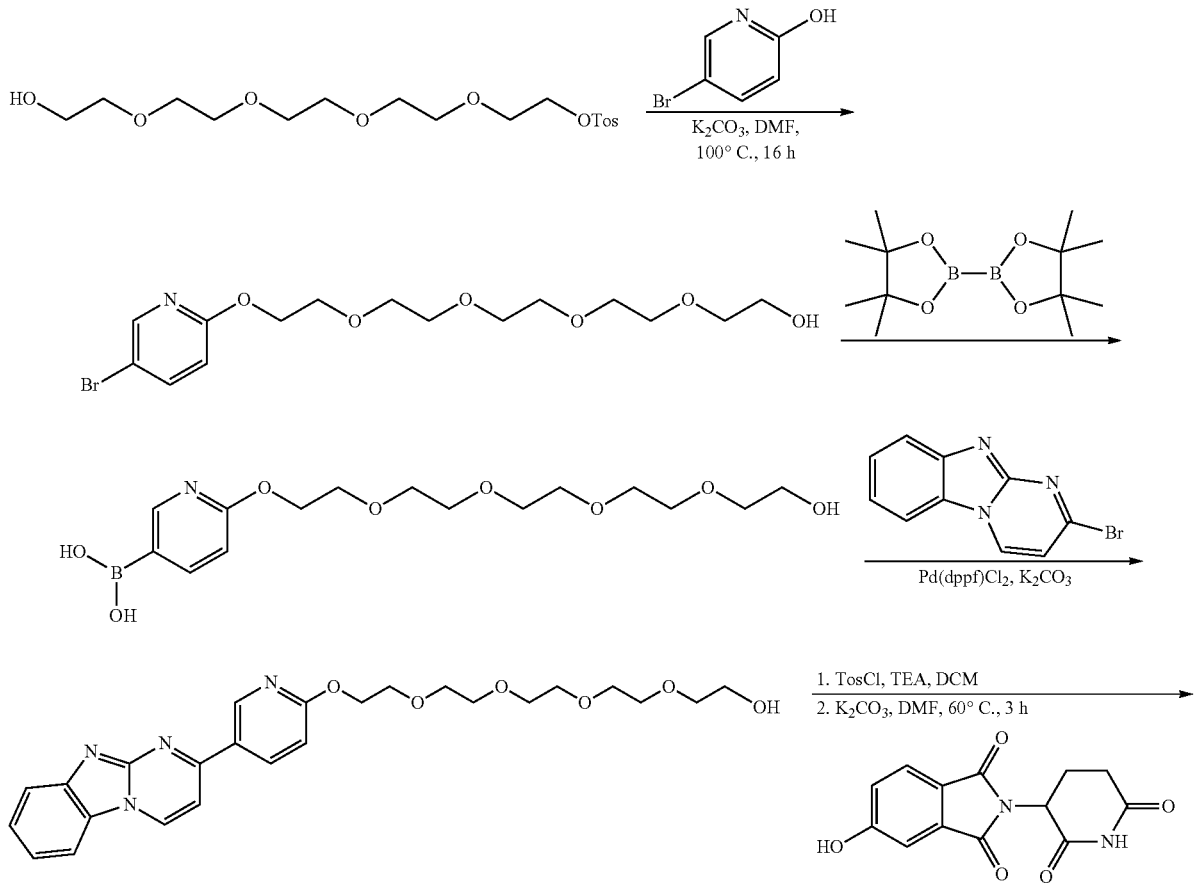

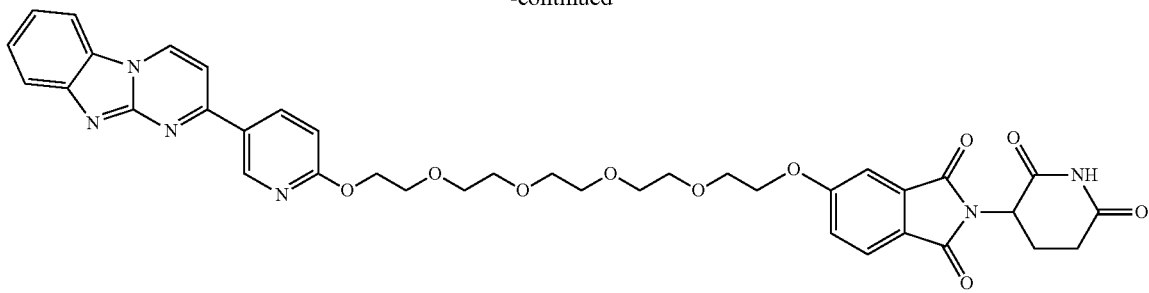
Compound 207
Synthetic Scheme for Exemplary Compound 208
2-(2,6-dioxopiperidin-3-yl)-5-(2-(2-(2-(2-((1-(5-(5-methyl-5H-pyrido[4,3-b]indol-7-yl)pyridin-2-yl)azetidin-3-yl)oxy)ethoxy)ethoxy)ethoxy)ethoxy)isoindoline-1,3-dione
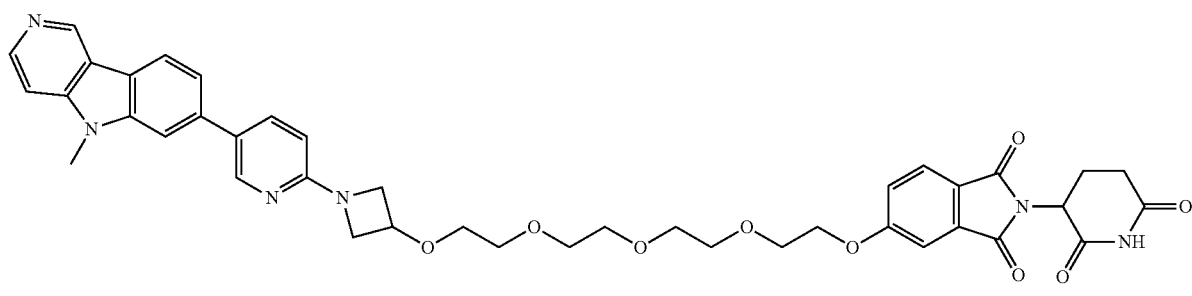 [SMILES: Cn1c2ccncc2c2ccc(-c3ccc(N4CC(OCCOCCOCCOCCOc5ccc6c(c5)C(=O)N(C5CCC(=O)NC5=O)C6=O)C4)nc3)cc21]
Prepared according to the scheme below and using procedures described above and common procedures known to those skilled in the art.
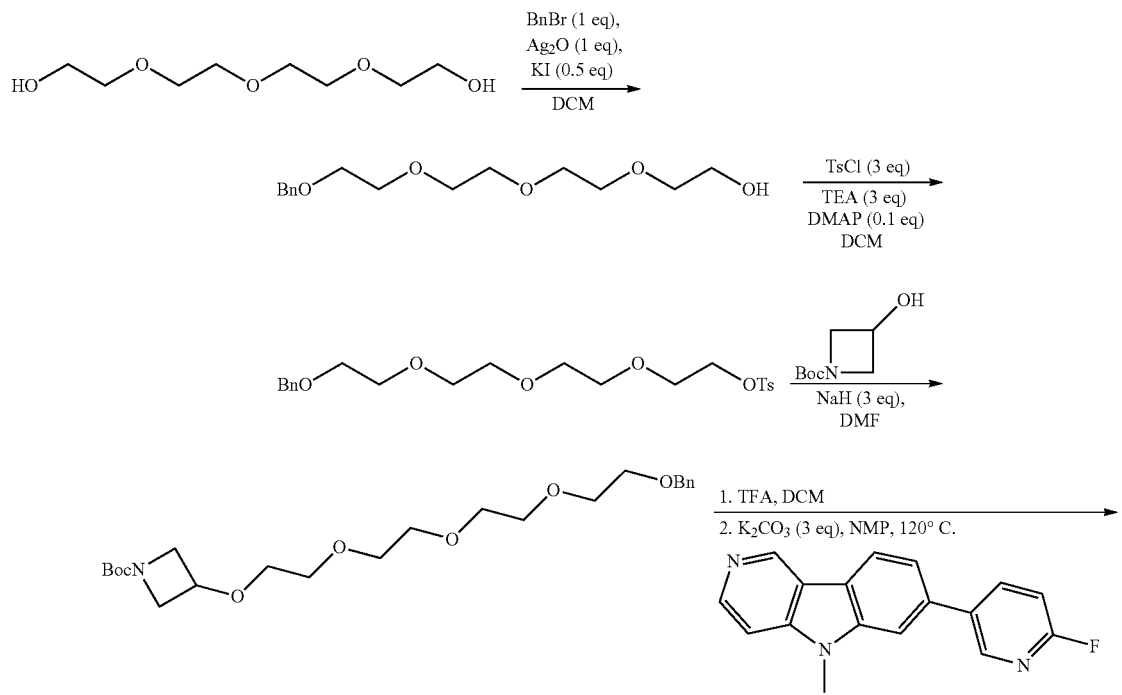

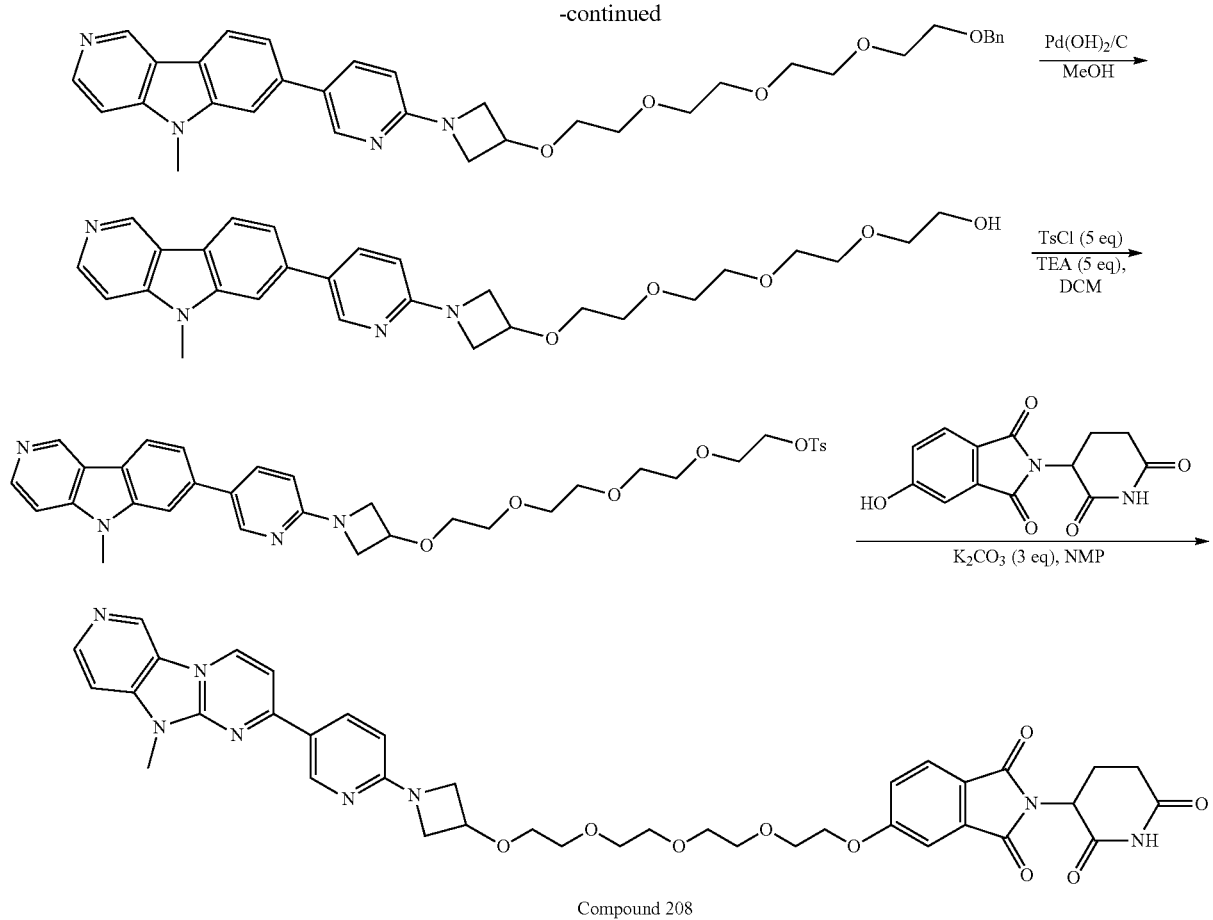
Compound 208
Synthetic Scheme for Exemplary Compound 209
2-(2,6-dioxopiperidin-3-yl)-5-(2-(2-((3-(((1r,3r)-3-((5-(5-methyl-5H-pyrido[4,3-b]indol-7-yl)pyridin-2-yl)oxy)cyclobutoxy)methyl)bicyclo[1.1.1]pentan-1-yl)methoxy)ethoxy)ethoxy)isoindoline-1,3-dione
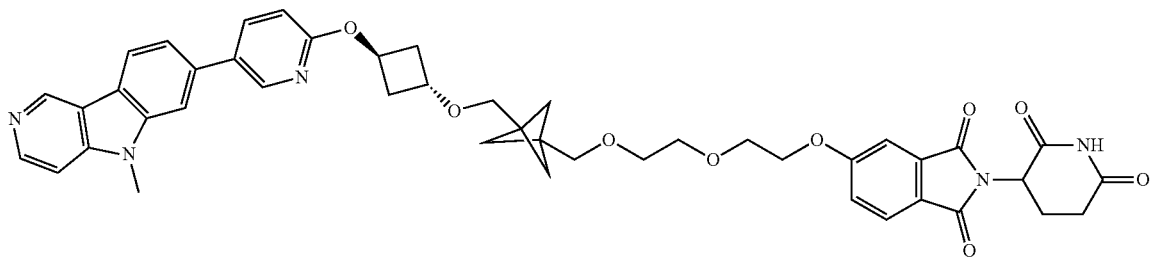 [SMILES: Cn1c2ccncc2c2ccc(-c3ccc(O[C@H]4C[C@H](OCC56CC(COCCOCCOc7ccc8c(c7)C(=O)N(C7CCC(=O)NC7=O)C8=O)(C5)C6)C4)nc3)cc21]
Prepared according to the scheme below and using procedures described above and common procedures known to those skilled in the art.

619                                    620
-continued
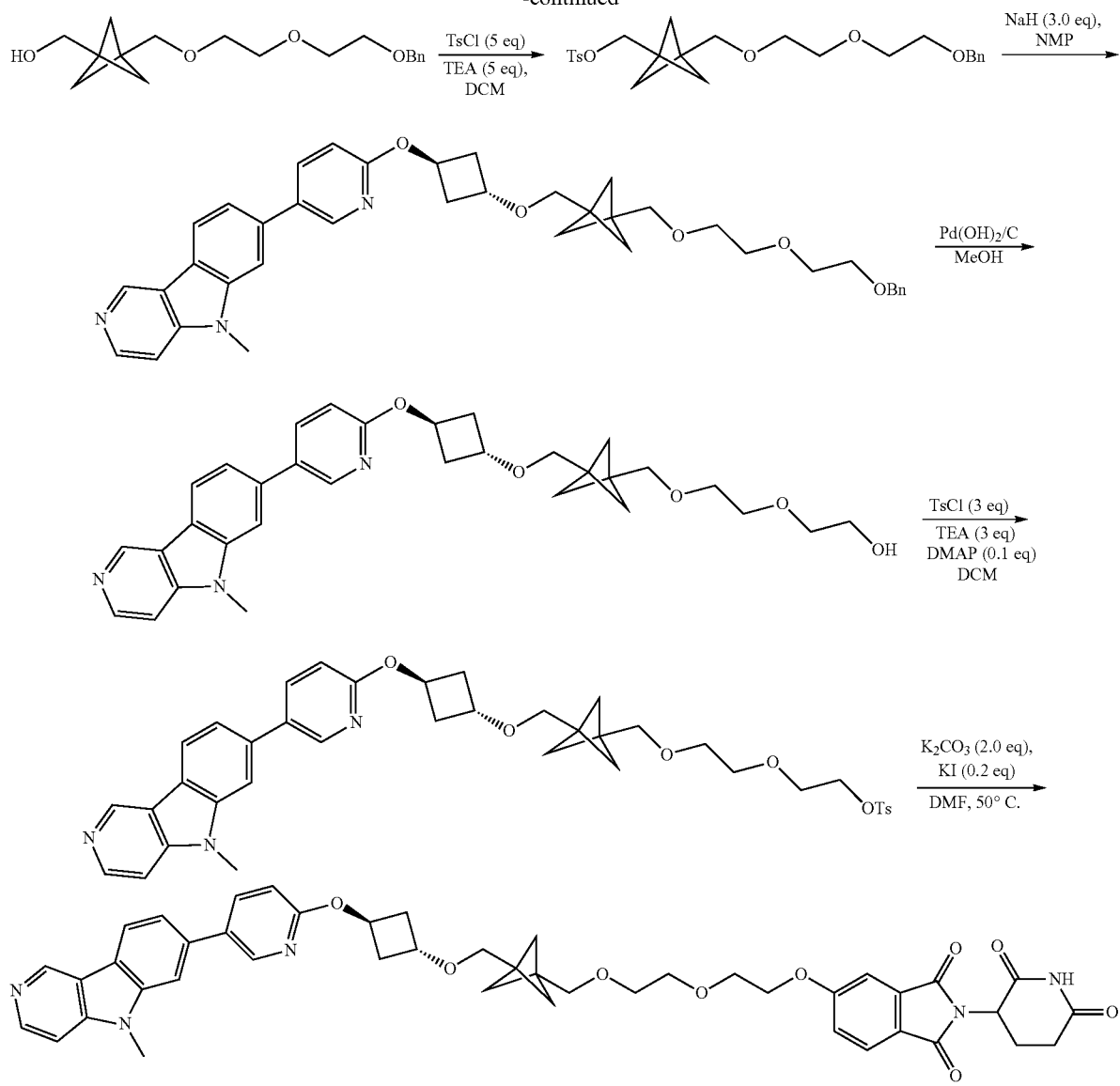
Compound 209
Synthetic Scheme for Exemplary Compound 210
2-(2,6-dioxopiperidin-3-yl)-5-((15-(4-(5-methyl-5H-pyrido[4,3-b]indol-7-yl)piperazin-1-yl)-3,6,9,12-tetraoxapentadecyl)oxy)isoindoline-1,3-dione
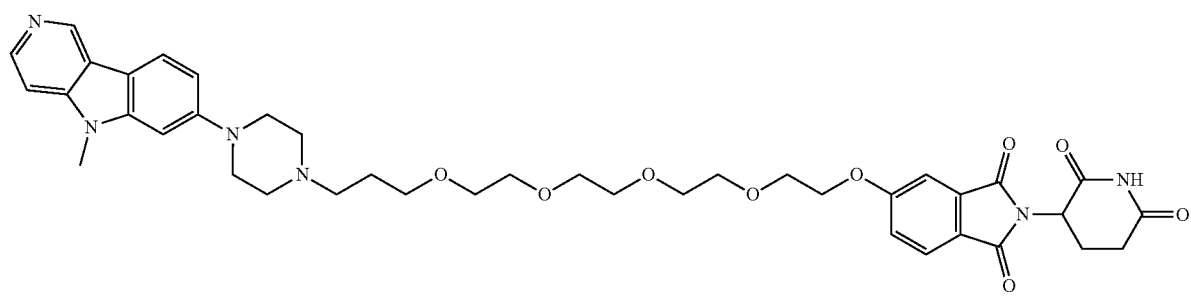 [SMILES: Cn1c2ccncc2c2ccc(N3CCN(CCCOCCOCCOCCOCCOc4ccc5c(c4)C(=O)N(C4CCC(=O)NC4=O)C5=O)CC3)cc21]

621

Step 1: tert-Butyl 4-(5-methylpyrido[4,3-b]indol-7-yl)piperazine-1-carboxylate

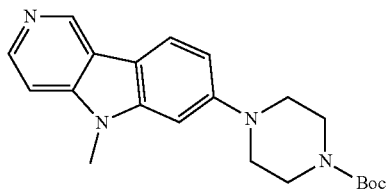 [SMILES: Cn1c2ccncc2c2ccc(N3CCN(C(=O)OC(C)(C)C)CC3)cc21]

To a solution of 7-bromo-5-methyl-pyrido[4,3-b]indole (1 g, 3.83 mmol, 1 eq) and tert-butyl piperazine-1-carboxylate (2.14 g, 11.49 mmol, 3 eq) in dioxane (20 mL) was added (±)-2,2'-bis(diphenylphosphino)-1,1'-binaphthalene (71 mg, 0.11 mmol, 0.03 eq), cesium carbonate (3.74 g, 11.49 mmol, 3 eq) and palladium(II) acetate (86 mg, 0.38 mmol, 0.1 eq) under nitrogen, then degassed under vacuum and purged with nitrogen three times. The mixture was stirred at 100° C. for 16 hours. The reaction mixture was concentrated to remove solvent and then extracted with ethyl acetate (80 mL×3). The combined organic layers were washed with brine 30 mL, dried over anhydrous sodium sulfate, filtered and concentrated under reduced pressure to give a residue. The residue was purified by silica gel column chromatography (petroleum ether/ethyl acetate=2/1 to dichloromethane/methanol=10/1) to give crude product, the crude product was purified by semi-preparative reverse phase HPLC (column: Phenomenex luna C18 250*50 mm*10 um; mobile phase: [water (0.225% FA)-ACN]; B %: 27%-52%,30; 79% min). tert-Butyl 4-(5-methylpyrido[4,3-b]indol-7-yl)piperazine-1-carboxylate (700 mg, 1.91 mmol, 49% yield) was obtained as a white solid.

622

Step 2: 5-Methyl-7-piperazin-1-yl-pyrido[4,3-b]indole

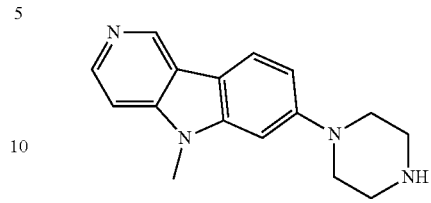

To a solution of tert-butyl 4-(5-methylpyrido[4,3-b]indol-7-yl)piperazine-1-carboxylate (700 mg, 1.91 mmol, 1 eq) in dichloromethane (4 mL) was added hydrochloric acid/dioxane (4 M, 8 mL, 16.75 eq), then was stirred 25° C. for 1 h. TLC (dichloromethane/methanol=10/1) showed the starting material was consumed completely. The reaction mixture was concentrated to give a residue. 5-Methyl-7-piperazin-1-yl-pyrido[4,3-b]indole (580 mg, crude, HCl) was obtained as a white solid without any purification.

Step 3

To a solution of 5-methyl-7-piperazin-1-yl-pyrido[4,3-b]indole (366 mg, 1.21 mmol, 1 eq, HCl) and dimethyl 4-[2-[2-[2-[2-[3-(p-tolylsulfonyloxy)propoxy]ethoxy]ethoxy]ethoxy]ethoxy]benzene-1,2-dicarboxylate (725 mg, 1.21 mmol, 1 eq) [prepared according to the scheme below and using procedures described above and common procedures known to those skilled in the art]. in N,N-dimethylformamide (10 mL) was added N,N-diisopropylethylamine (626 mg, 4.84 mmol, 0.8 mL, 4 eq), then stirred at 80° C. for 16 h. The reaction mixture was concentrated to give a residue. The residue was purified by semi-preparative reverse phase HPLC (column: Phenomenex luna C18 250*50 mm*10 um; mobile phase: [water (0.225% FA)-ACN]; B %: 10%-40%,30 min, 40% min). Dimethyl 4-[2-[2-[2-[2-[3-[4-(5-methylpyrido[4,3-b]indol-7-yl) piperazin-1-yl]propoxy]ethoxy]ethoxy]ethoxy]benzene-1,2-dicarboxylate (131 mg, 0.19 mmol, 15% yield, 100% purity) was obtained as a brown oil.

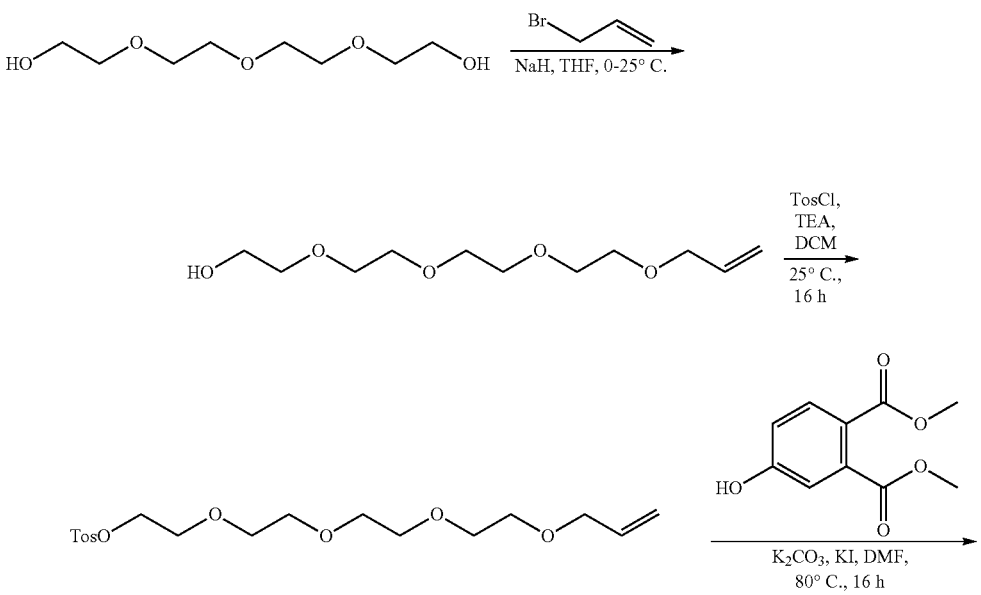

-continued

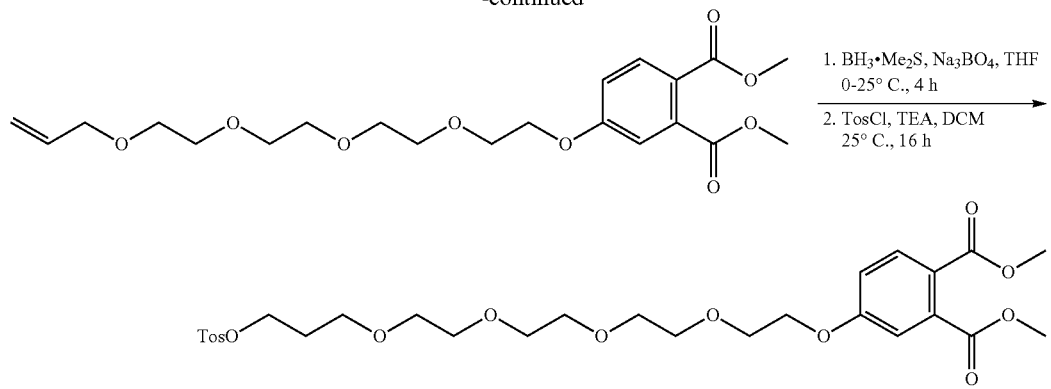

Step 4: 2-(2,6-dioxopiperidin-3-yl)-5-((15-(4-(5-methyl-5H-pyrido[4,3-b]indol-7-yl)piperazin-1-yl)-3,6,9,12-tetraoxapentadecyl)oxy)isoindoline-1,3-dione

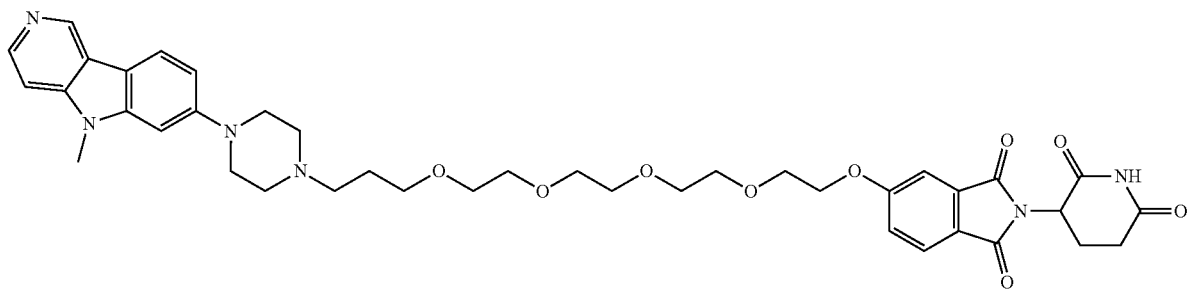 [SMILES: Cn1c2ccncc2c2ccc(N3CCN(CCCOCCOCCOCCOCCOc4ccc5c(c4)C(=O)N(C4CCC(=O)NC4=O)C5=O)CC3)cc21]

Dimethyl 4-[2-[2-[2-[2-[3-[4-(5-methylpyrido[4,3-b]indol-7-yl)piperazin-1-yl]propoxy]ethoxy]ethoxy]ethoxy]ethoxy]benzene-1,2-dicarboxylate (120 mg, 0.17 mmol, 1 eq), 3-aminopiperidine-2,6-dione (142 mg, 0.86 mmol, 5 eq, HCl) and lithium iodide (347 mg, 2.60 mmol, 15 eq) were taken up into a microwave tube in pyridine (4 mL). The sealed tube was heated at 120° C. for 2 h under microwave. The reaction mixture was concentrated to give a residue. The residue was purified by semi-preparative reverse phase HPLC (8-38% acetonitrile+0.225% formic acid in water, over 10 min), then the collected fraction was concentrated to remove most of the acetonitrile and then lyophilized to give crude product. Then the crude product was purified by prep-TLC (dichloromethane/methanol=10/1), 10 mL water and 0.2 mL 1M hydrochloric acid was added and then lyophilized to give the product. 2-(2,6-dioxopiperidin-3-yl)-5-((15-(4-(5-methyl-5H-pyrido[4,3-b]indol-7-yl)piperazin-1-yl)-3,6,9,12-tetraoxapentadecyl)oxy)isoindoline-1,3-dione dihydrochloride (20 mg, 0.02 mmol, 14% yield) was obtained as an off-white solid.

$^1$H NMR: (400 MHz, DMSO-d6) δ: 15.03 (br s, 1H), 11.18-10.95 (m, 2H), 9.55 (s, 1H), 8.64 (br d, J=6.5 Hz, 1H), 8.30 (br d, J=8.3 Hz, 1H), 8.09 (br d, J=6.9 Hz, 1H), 7.81 (br d, J=8.5 Hz, 1H), 7.48-7.23 (m, 4H), 5.11 (br dd, J=5.0, 12.7 Hz, 1H), 4.30 (br s, 2H), 4.11 (br d, J=13.1 Hz, 2H), 4.02 (s, 3H), 3.78 (br s, 2H), 3.70-3.48 (m, 18H), 3.19 (br s, 3H), 2.96-2.82 (m, 1H), 2.62-2.55 (m, 3H), 2.04 (br s, 3H). (M+H)$^+$ 757.6.

Synthetic Scheme for Exemplary Compound 211

2-(2,6-dioxopiperidin-3-yl)-5-(3-(3-(2-(6-((5-(5-methyl-5H-pyrido[4,3-b]indol-7-yl)pyridin-2-yl)oxy)-2-azaspiro[3.3]heptan-2-yl)ethoxy)propoxy)azetidin-1-yl)isoindoline-1,3-dione Prepared according to the schemes below and using procedures described above and common procedures known to those skilled in the art.
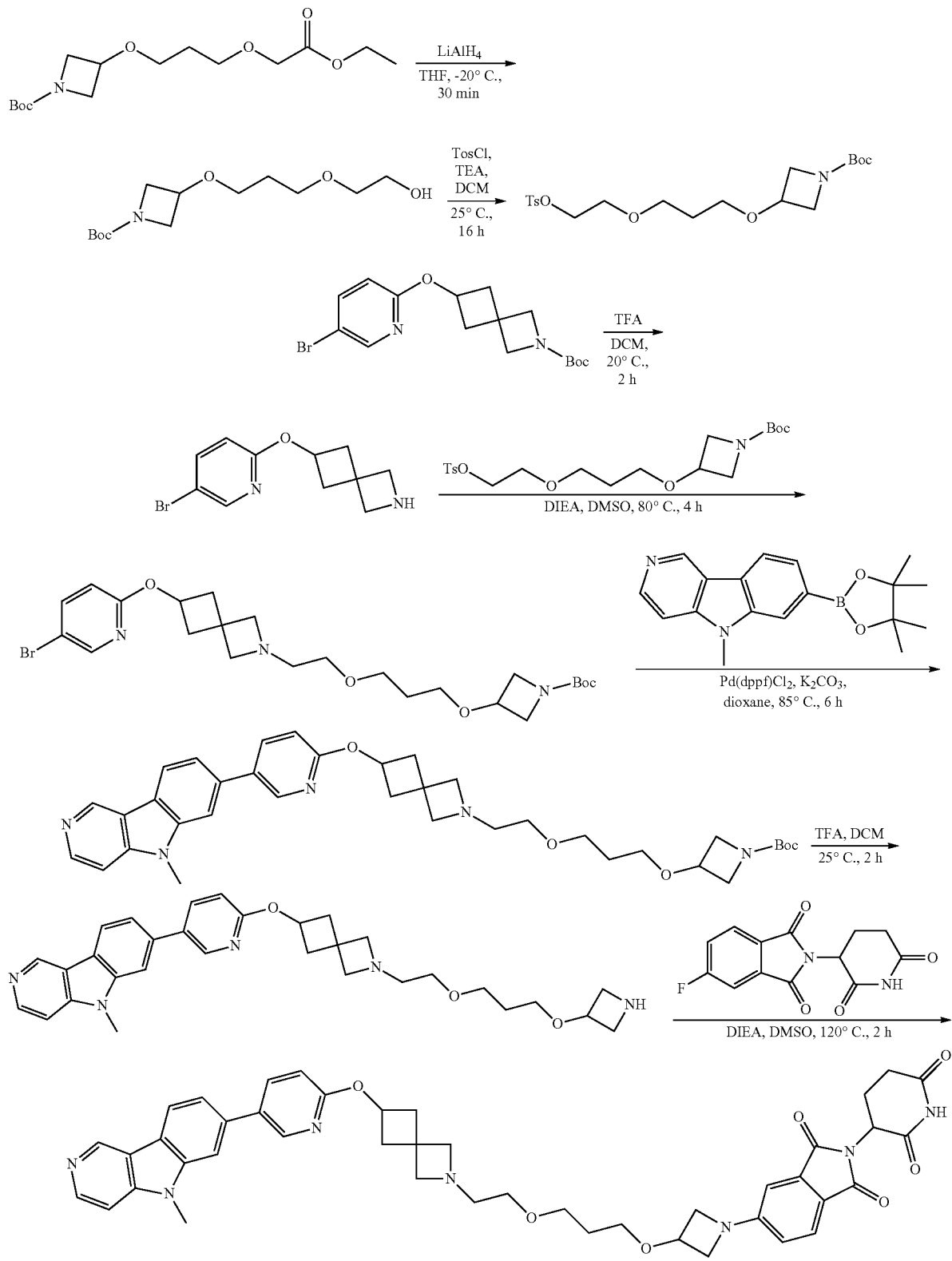
Compound 211

Synthetic Scheme for Exemplary Compound 212

2-(2,6-dioxopiperidin-3-yl)-5-(3-(2-((4-((1r,3r)-3-((5-(5-methyl-5H-pyrido[4,3-b]indol-7-yl)pyridin-2-yl)oxy)cyclobutoxy)but-2-yn-1-yl)oxy)ethoxy)azetidin-1-yl)isoindoline-1,3-dione

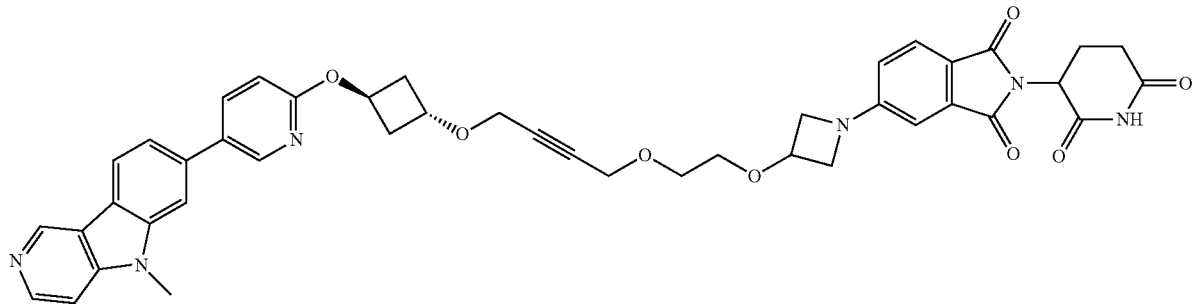 [SMILES: Cn1c2ccncc2c2ccc(-c3ccc(O[C@H]4C[C@H](OCC#CCOCCOC5CN(c6ccc7c(c6)C(=O)N(C6CCC(=O)NC6=O)C7=O)C5)C4)nc3)cc21]

Step 1: tert-Butyl 3-(2-ethoxy-2-oxo-ethoxy)azetidine-1-carboxylate

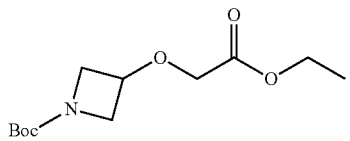 [SMILES: CCOC(=O)COC1CN(C(=O)OC(C)(C)C)C1]

To a mixture of tert-butyl 3-hydroxyazetidine-1-carboxylate (3 g, 17.32 mmol, 1 eq) and diacetoxyrhodium (766 mg, 1.73 mmol, 0.1 eq) in dichloromethane (50 mL) was added ethyl 2-diazoacetate (11.86 g, 103.92 mmol, 6 eq) dropwise at 0° C. The reaction mixture was stirred at 25° C. for 4 hours. TLC showed the starting material was not consumed. Then the reaction was stirred at 25° C. for another 16 hours. To the reaction solution was added acetic acid. Then the reaction was extracted with dichloromethane (30 mL×3), and concentrated under vacuum to get the residue. The residue was purified by silica gel column chromatography (Petroleum ether/Ethyl acetate=30/1 to 8:1) to get the product. tert-Butyl 3-(2-ethoxy-2-oxo-ethoxy)azetidine-1-carboxylate (2.24 g, 8.64 mmol, 50% yield) was obtained as a light yellow oil.

Step 2: tert-Butyl 3-(2-hydroxyethoxy)azetidine-1-carboxylate

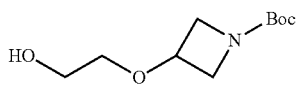

To a suspension of lithium aluminum hydride (229.51 mg, 6.05 mmol, 0.7 eq) in tetrahydrofuran (30 mL) was added a solution of tert-butyl 3-(2-ethoxy-2-oxo-ethoxy) azetidine-1-carboxylate (2.24 g, 8.64 mmol, 1 eq) in tetrahydrofuran (10 mL) at −20° C. The reaction mixture was stirred at 0° C. for 0.5 hour. The reaction solution was added water (20 mL), the organic layer was extracted with ethyl acetate (40 mL×3). Then the combined organic phase was dried over anhydrous sodium sulfate, filtered and concentrated under reduced pressure to give a residue. The residue was purified silica gel column chromatography (Petroleum ether/Ethyl acetate=200/1 to 1:1) to get the product. tert-Butyl 3-(2-hydroxyethoxy)azetidine-1-carboxylate (828 mg, 3.81 mmol, 44% yield) was obtained as a light yellow oil.

Step 3: 4-[(4-methoxyphenyl)methoxy]but-2-yn-1-ol

To a solution of but-2-yne-1,4-diol (5 g, 58.08 mmol, 1 eq) N,N-in dimethyl formamide (50 mL) was added sodium hydride (2.32 g, 58.08 mmol, 60% in mineral oil, 1 eq) at 0° C. The mixture was stirred at 0° C. for 0.5 hour. Then methoxybenzylchloride (9.55 g, 60.98 mmol, 8.3 mL, 1.05 eq) was added into the mixture at 0° C. slowly, the mixture was stirred at 25° C. for 4 hours. The reaction was added water (40 mL). The solution was extracted with ethyl acetate (40 mL×3). Then the combined organic phase was washed with brine (20 mL×2), dried with anhydrous sodium sulfate, filtered and concentrated under vacuum to get the residue. The residue was purified by silica gel column chromatography (Petroleum ether/Ethyl acetate=30/1 to 3:1) to get the product. 4-[(4-methoxyphenyl)methoxy]but-2-yn-1-ol (2.64 g, 12.80 mmol, 22% yield) was obtained as a light yellow oil.

Step 4: 1-(4-bromobut-2-ynoxymethyl)-4-methoxybenzene

To a solution of 4-[(4-methoxyphenyl)methoxy]but-2-yn-1-ol (1 g, 4.85 mmol, 1 eq) and perbromomethane (1.61 g, 4.85 mmol, 1 eq) in dichloromethane (10 mL) was added triphenylphosphine (1.40 g, 5.33 mmol, 1.1 eq) at 0° C. The solution was stirred at 25° C. for 16 hours. TLC showed the starting material was consumed completely. The reaction solution was concentrated under vacuum to get the residue. The residue was purified by silica gel column chromatography (Petroleum ether/Ethyl acetate=1/0 to 80:1) to get the product. 1-(4-bromobut-2-ynoxymethyl)-4-methoxy-benzene (1 g, 3.72 mmol, 77% yield) was obtained as a light yellow oil.

The final compound, 2-(2,6-dioxopiperidin-3-yl)-5-(3-(2-((4-((1r,3r)-3-((5-(5-methyl-5H-pyrido[4,3-b]indol-7-yl)pyridin-2-yl)oxy)cyclobutoxy)but-2-yn-1-yl)oxy)ethoxy)azetidin-1-yl)isoindoline-1,3-dione, was prepared according to the schemes below and using procedures described above and common procedures known to those skilled in the art.
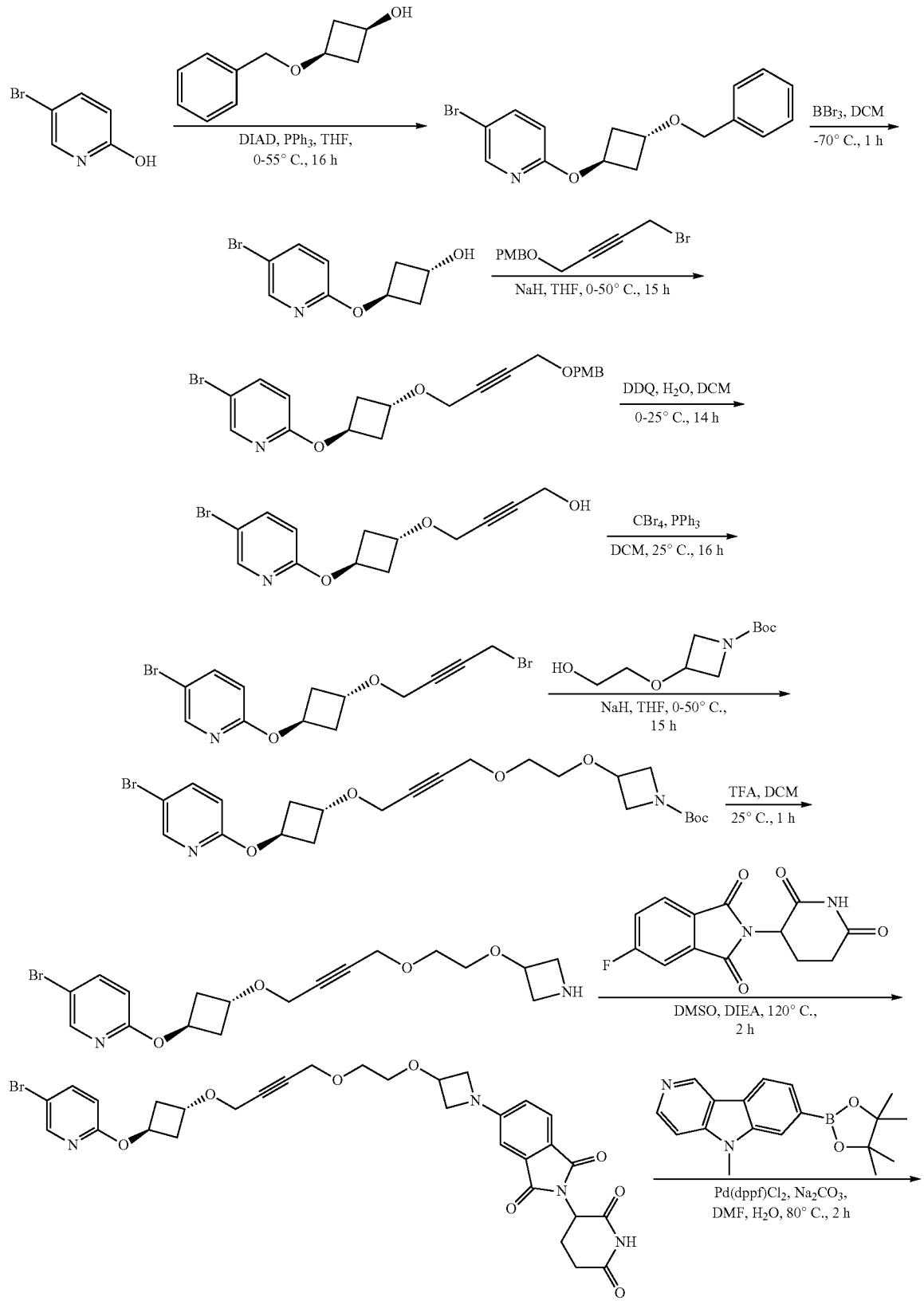

-continued
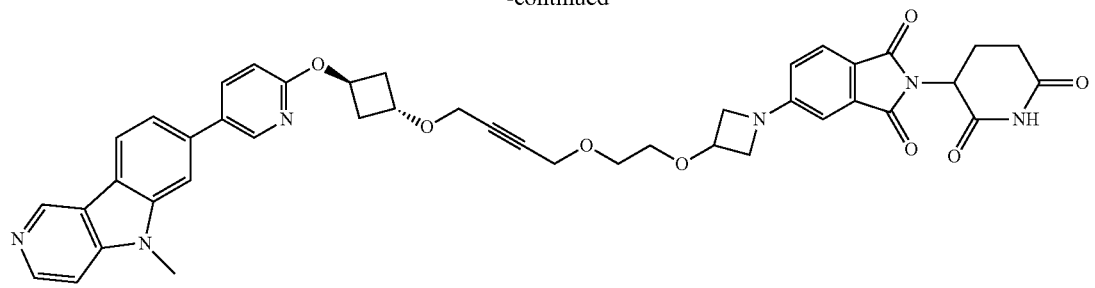
Compound 212
Synthetic Scheme for Exemplary Compound 213
2-(2,6-dioxopiperidin-3-yl)-5-(6-(2-(2-((1r,3r)-3-((5-(5-methyl-5H-pyrido[4,3-b]indol-7-yl)pyridin-2-yl)oxy)cyclobutoxy)ethoxy)ethoxy)-2-azaspiro[3.3]heptan-2-yl)isoindoline-1,3-dione
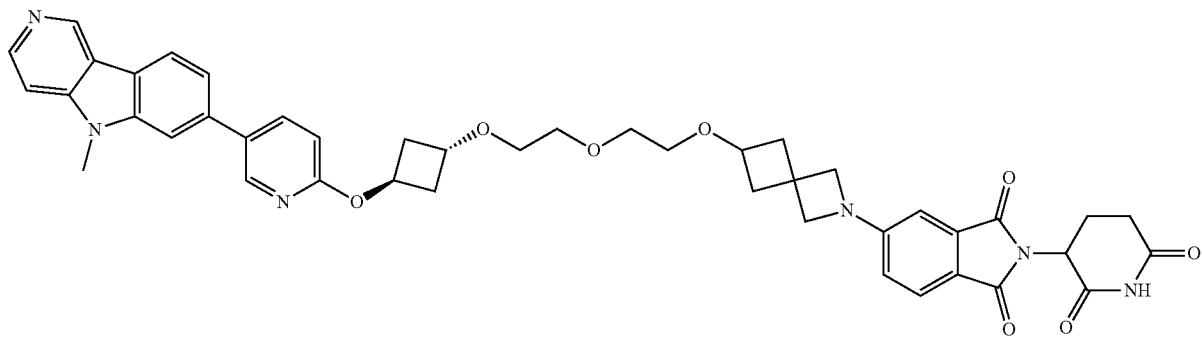 [SMILES: Cn1c2ccncc2c2ccc(-c3ccc(O[C@H]4C[C@H](OCCOCCOC5CC6(C5)CN(c5ccc7c(c5)C(=O)N(C5CCC(=O)NC5=O)C7=O)C6)C4)nc3)cc21]
Prepared according to the schemes below and using procedures described above and common procedures known to those skilled in the art.
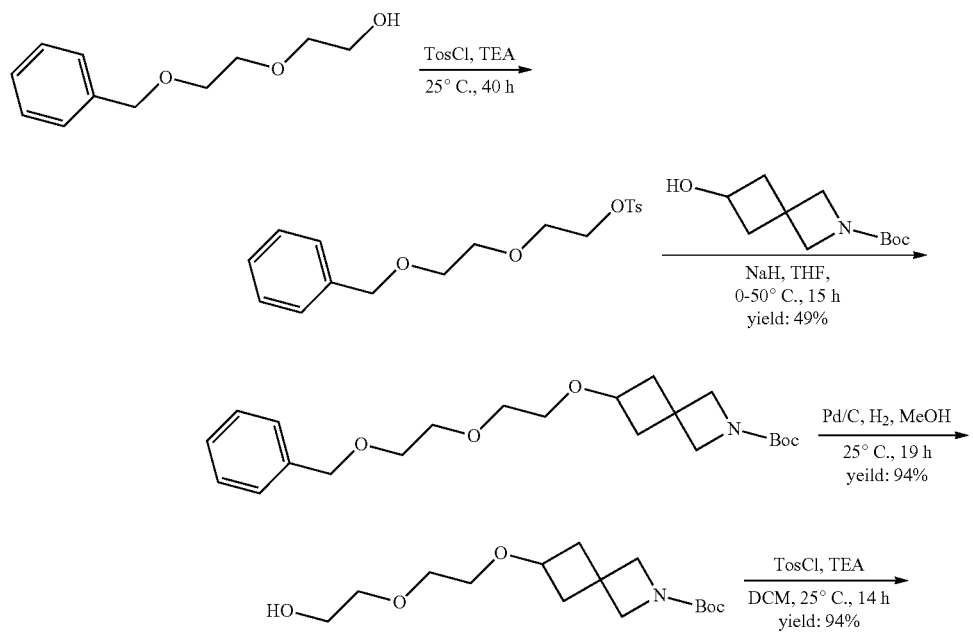

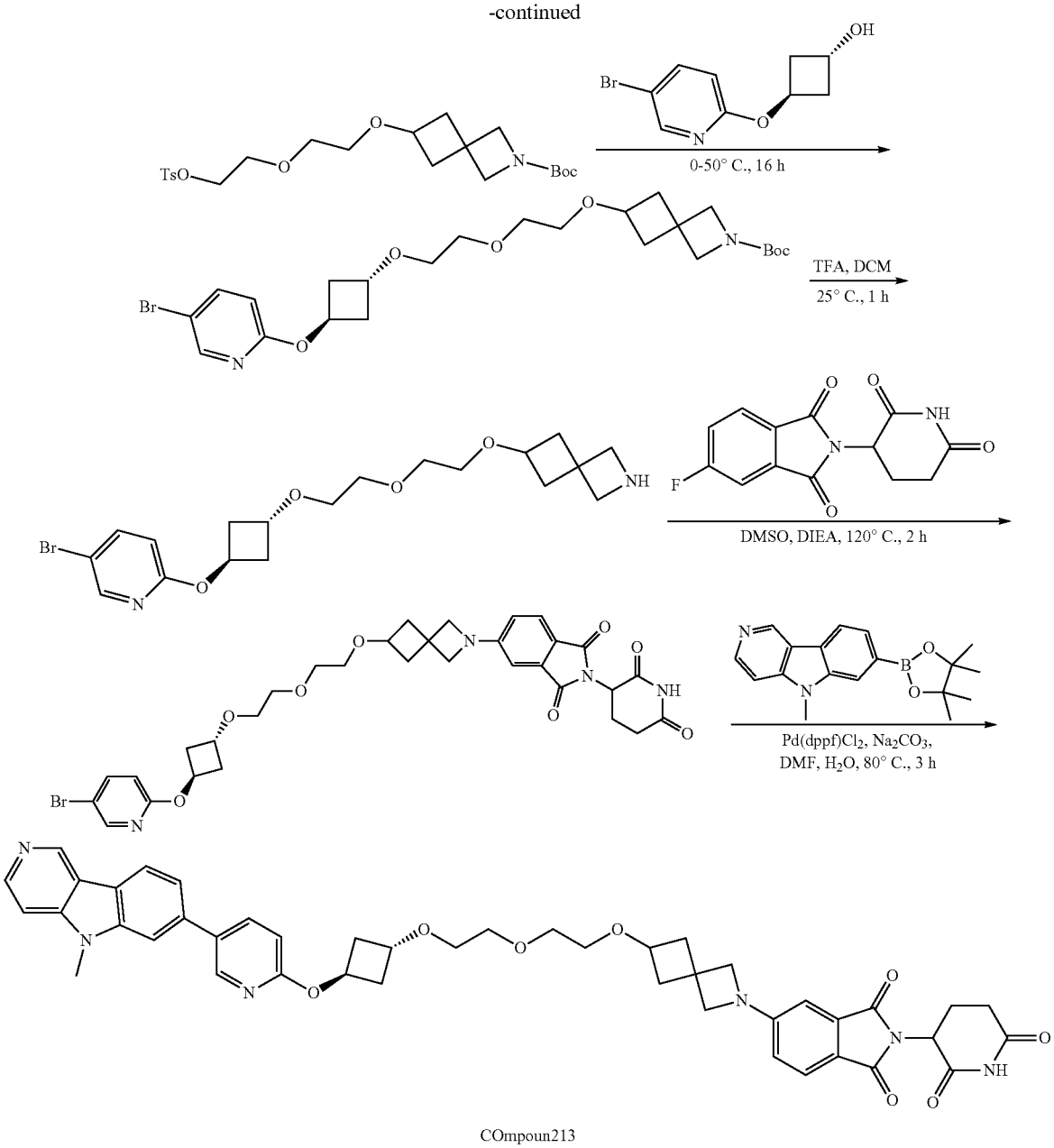

Compound 213

Additional examples are being contemplated in the context of the current invention and are detailed below. They can be prepared as described in the accompanying schemes, or by using procedures analogous to those described above (as indicated).

Synthetic Scheme for Compounds 215 and 217

Can be prepared according to the schemes below and using procedures described above and common procedures known to those skilled in the art.

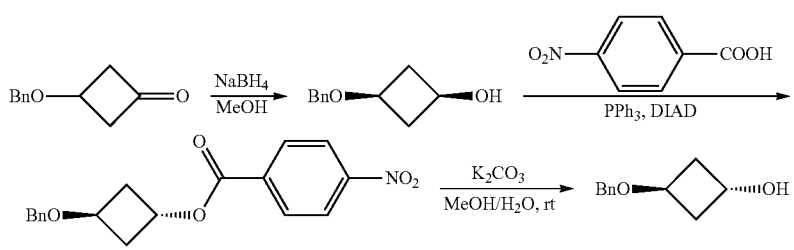

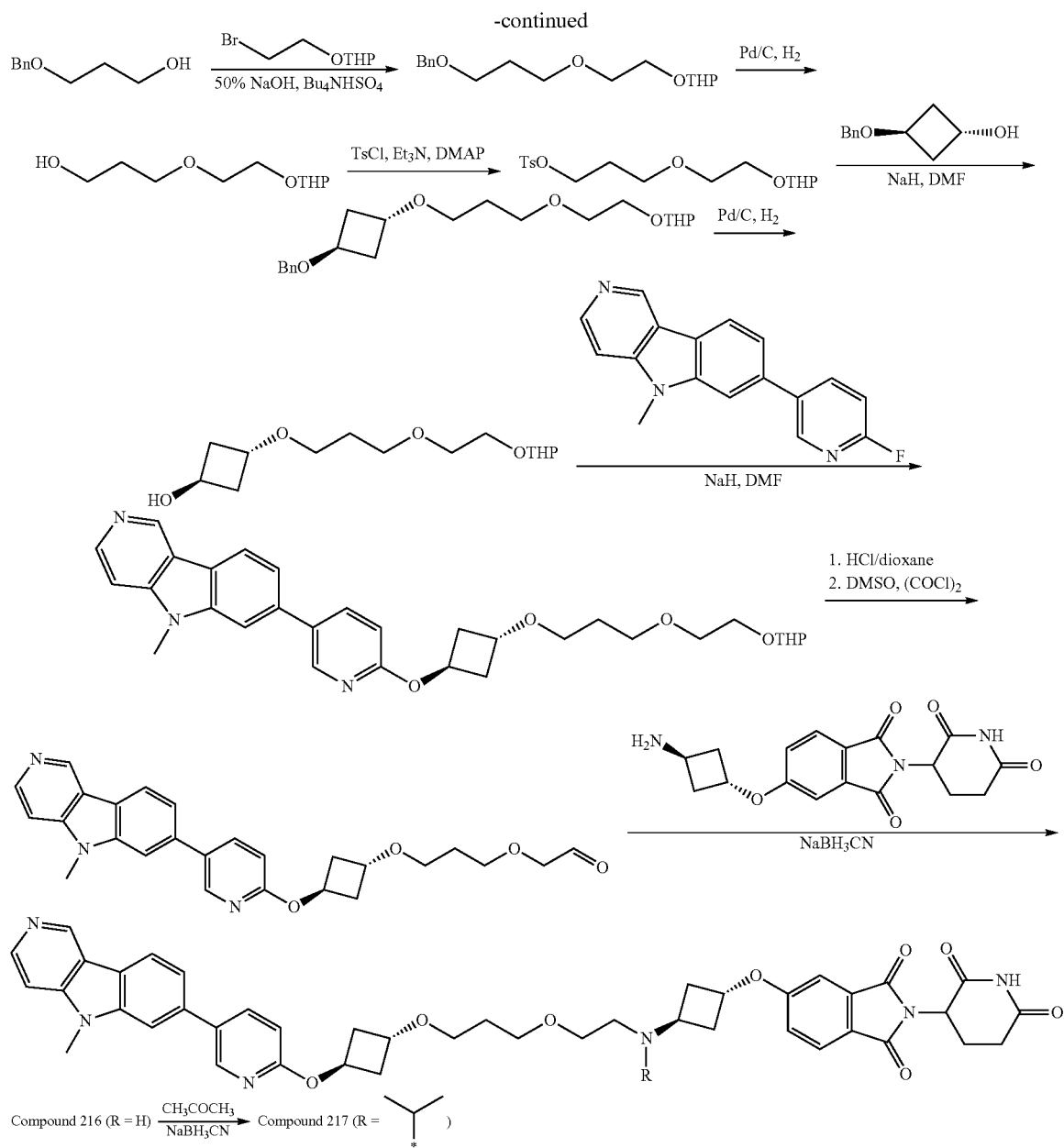

Alternatively, one skilled in the art will recognize that different sequence of steps and/or different protecting groups can be used in the assembly of the linkers of the examples described below. In addition, different sequence of attaching the linker to the PTM and ULM can be used for different examples, and sometimes different sequence of linker assembly and PTM/ULM attachment can be used interchangeably for a given example (i.e., attach PTM first, then ULM, or attach ULM first, then PTM). For example, linker for Compound 216 can be assembled as shown in the scheme below.

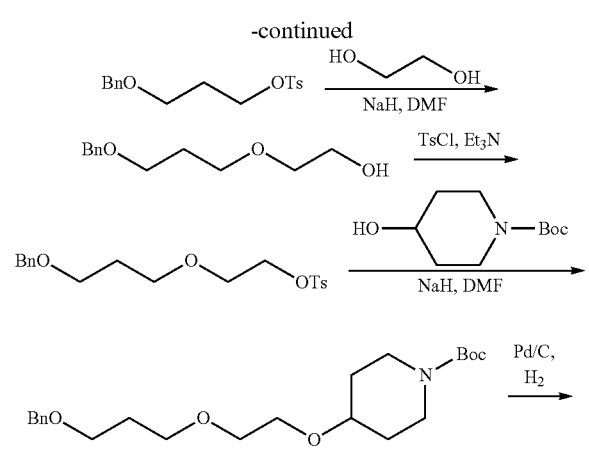

637
-continued
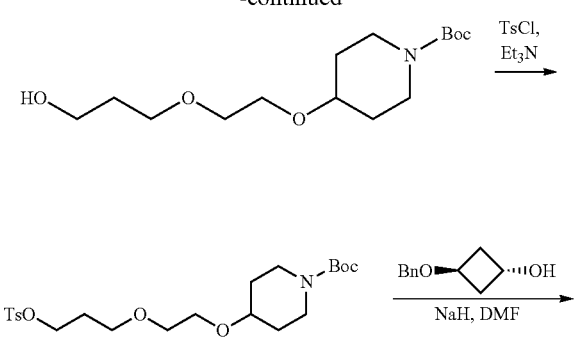
638
-continued
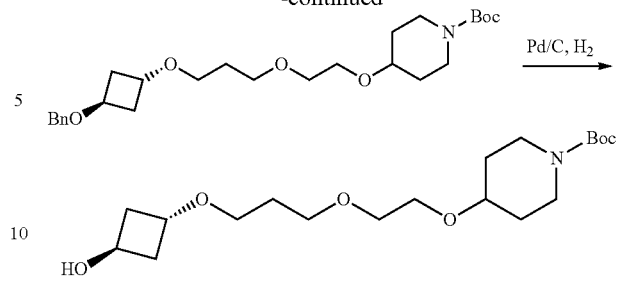
Compound 216 can then be synthesized according to the scheme below.
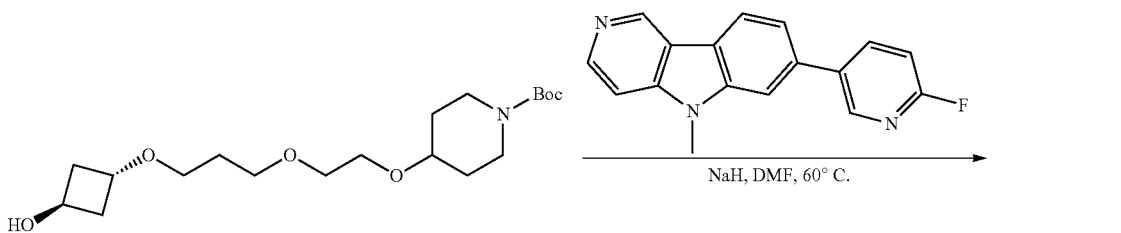
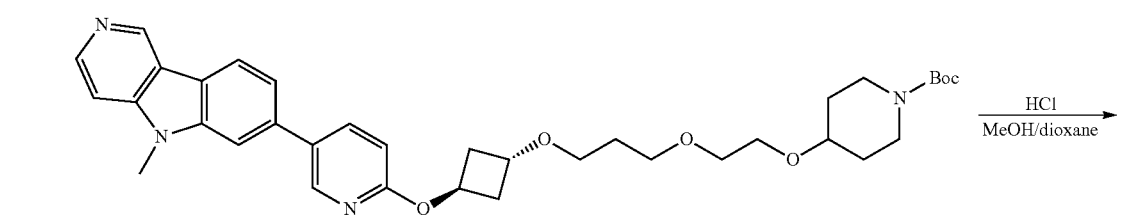
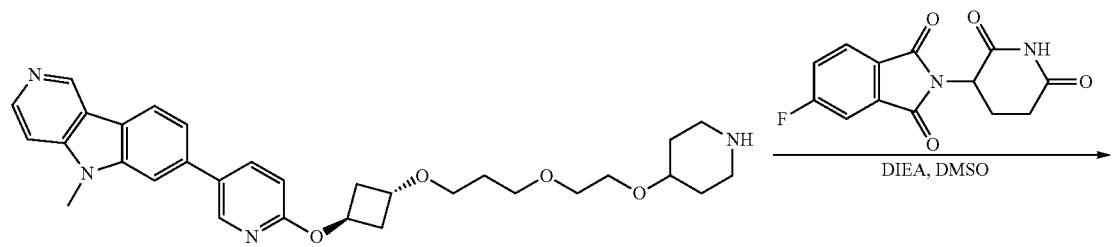
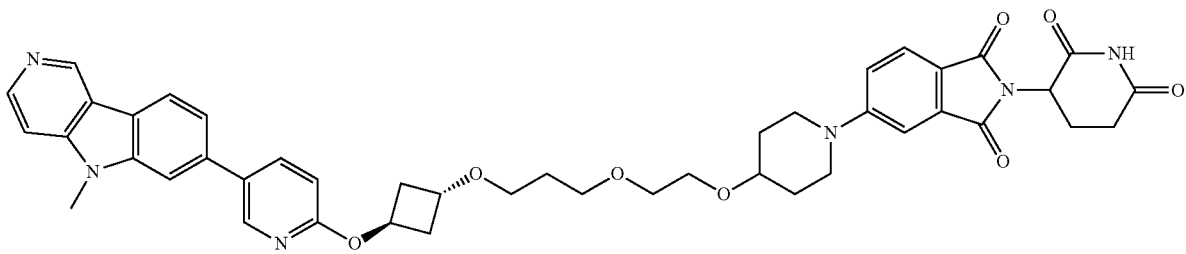
Compound 216

Alternatively, Compound 216 can be synthesized using a different sequence of PTM and ULM attachment according to the scheme below.
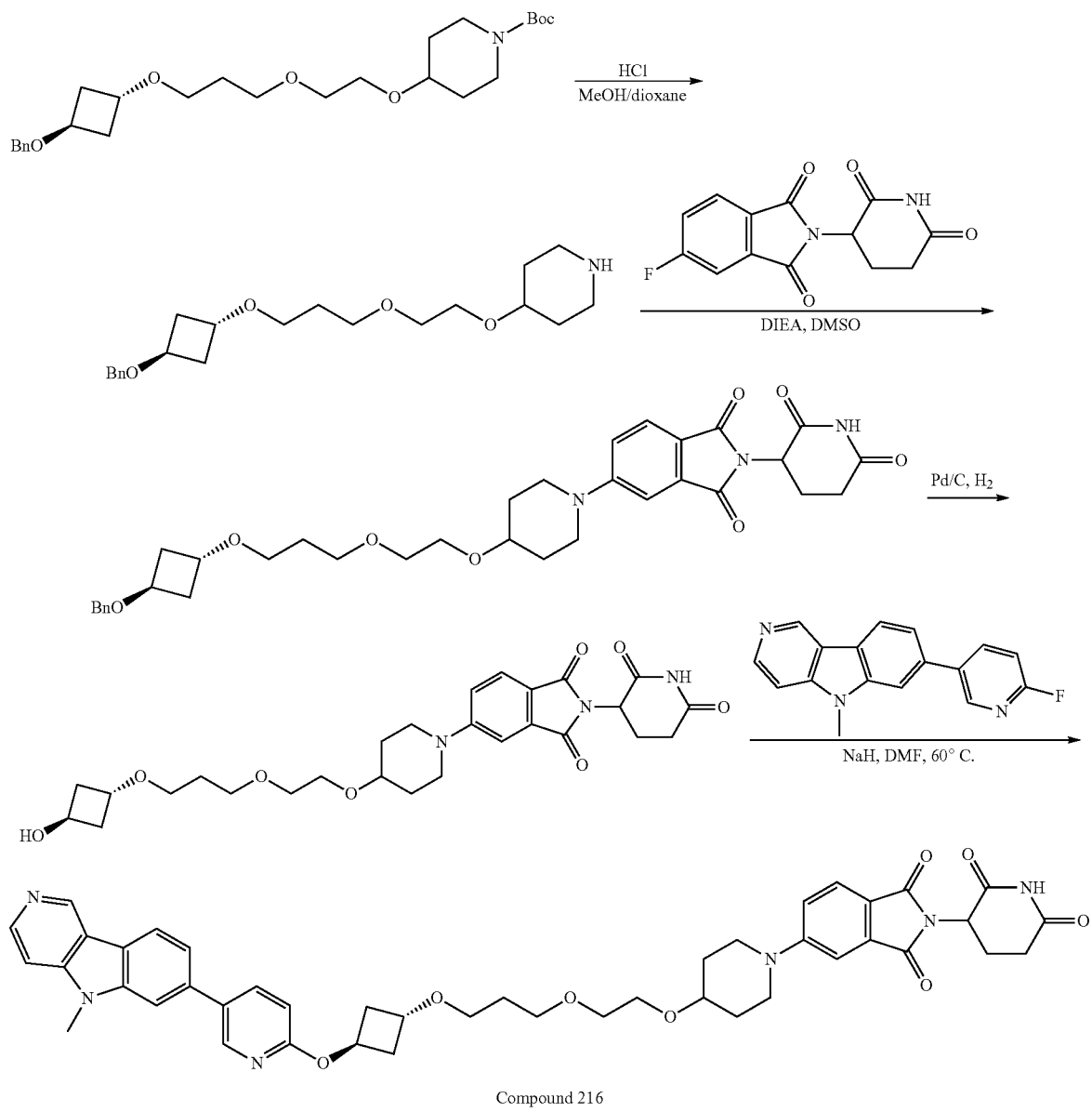
Synthetic Scheme for Exemplary Compound 4
4-((14-((5-(5H-pyrido[4,3-b]indol-7-yl)pyridin-2-yl)oxy)-3,6,9,12-tetraoxatetradecyl)amino)-2-(2,6-dioxopiperidin-3-yl)isoindoline-1,3-dione
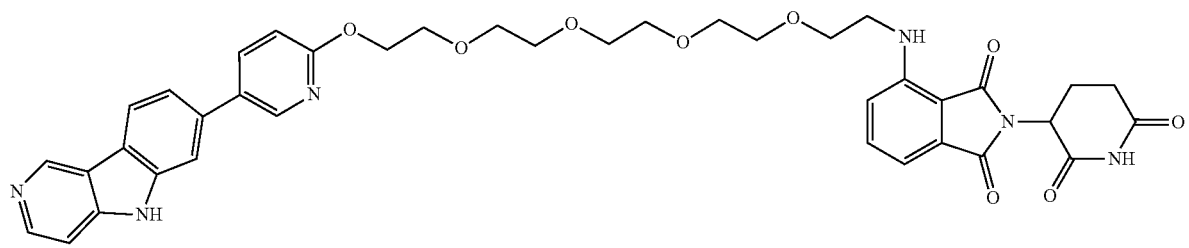 [SMILES: O=C1CCC(N2C(=O)c3cccc(NCCOCCOCCOCCOCCOc4ccc(-c5ccc6c(c5)[nH]c5ccncc56)cn4)c3C2=O)C(=O)N1]

Prepared according to the scheme below and using procedures described above and common procedures known to those skilled in the art.

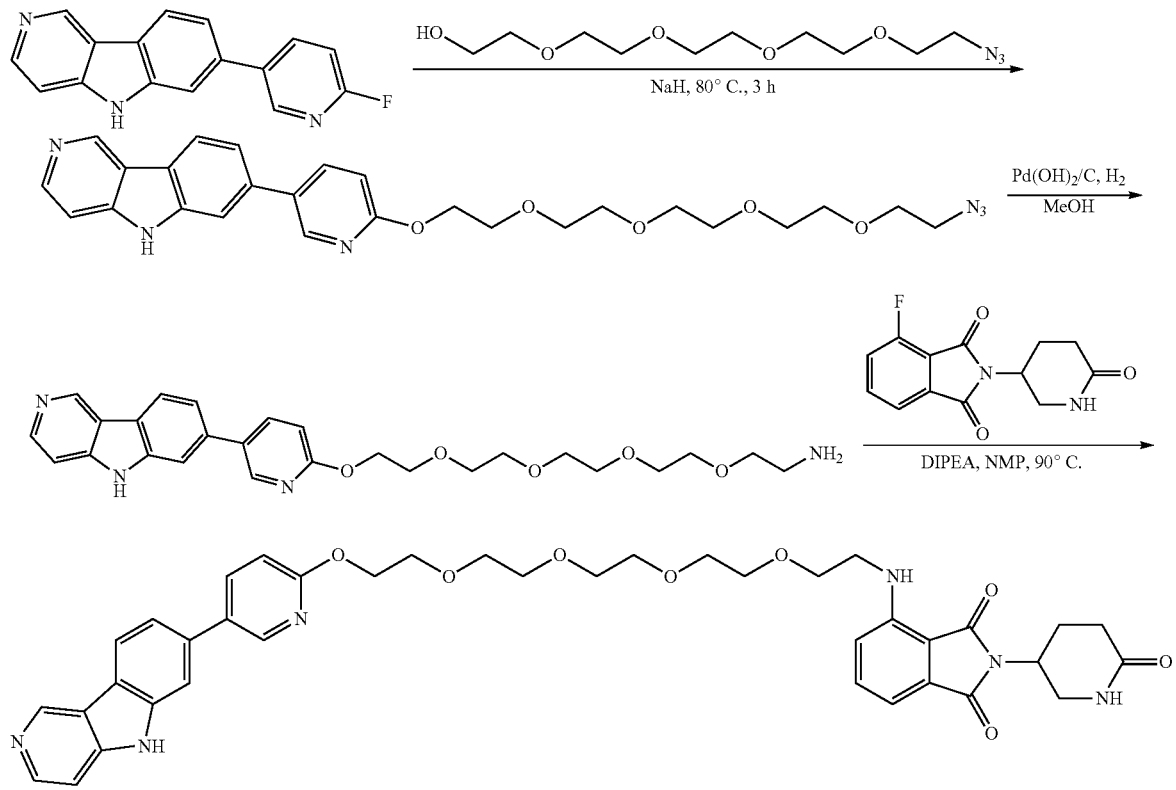

Compound 4

¹H NMR (400 MHz, CDCl₃): δ 9.30 (s, 1H), 8.90 (br, 1H), 8.52 (d, J=5.6 Hz, 1H), 8.42 (d, J=2.8 Hz, 1H), 8.14 (d, J=8.0 Hz, 1H), 7.49 (dd, J=2.4, 8.8 Hz, 1H), 7.57 (s, 1H), 7.26-7.46 (m, 3H), 6.97 (d, J 7.2 Hz, 1H), 6.81-6.87 (m, 2H), 6.35-6.46 (m, 1H), 4.89-4.98 (m, 1H), 4.54 (t, J=4.8 Hz, 2H), 3.90 (t, J=4.8 Hz, 2H), 3.61-3-74 (m, 15H), 3.37-3.81 (m, 2H), 2.65-2.92 (m, 3H), 2.07-2.15 (m, 1H).

Using procedures described for Compound 4 the following were prepared: Compound 2, Compound 3, and Compound 48.

Synthetic Scheme for Exemplary Compound 7

(2S,4R)-1-((S)-14-(4-(benzo[4,5]imidazo[1,2-a]pyrimidin-2-yl)piperazin-1-yl)-2-(tert-butyl)-4-oxo-6,9,12-trioxa-3-azatetradecanoyl)-4-hydroxy-N-(4-(4-methylthiazol-5-yl)benzyl)pyrrolidine-2-carboxamide

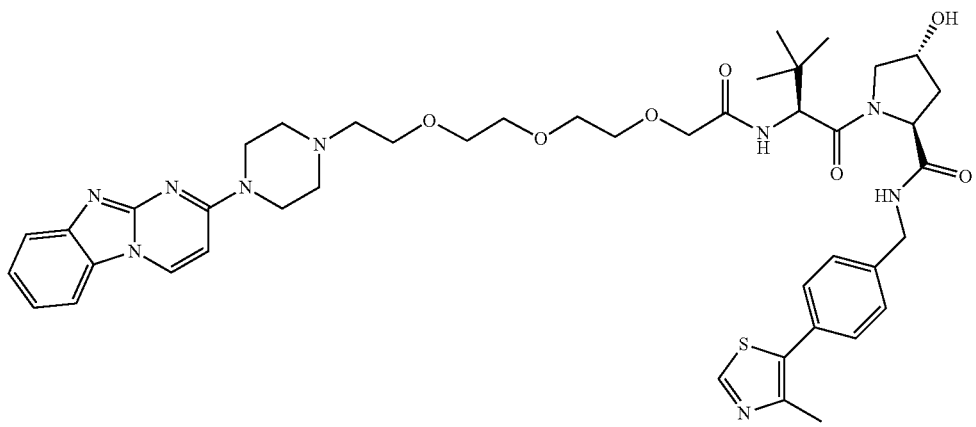 [SMILES: Cc1ncsc1-c1ccc(CNC(=O)[C@@H]2C[C@@H](O)CN2C(=O)[C@@H](NC(=O)COCCOCCOCCN2CCN(c3ccn4c(n3)nc3ccccc34)CC2)C(C)(C)C)cc1]

Prepared according to the scheme below using procedures described above and common procedures known to those skilled in the art.
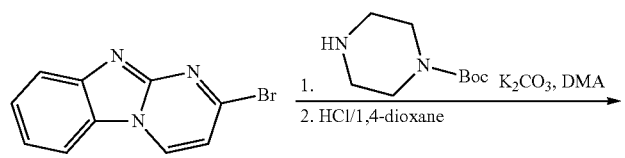
prepared as described for compound 207
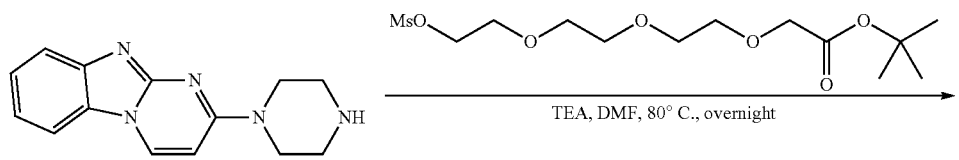
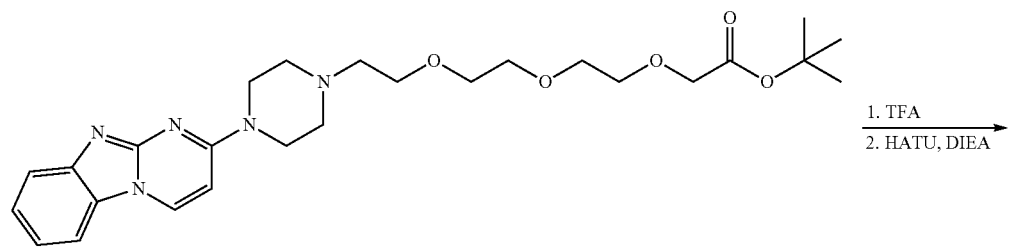
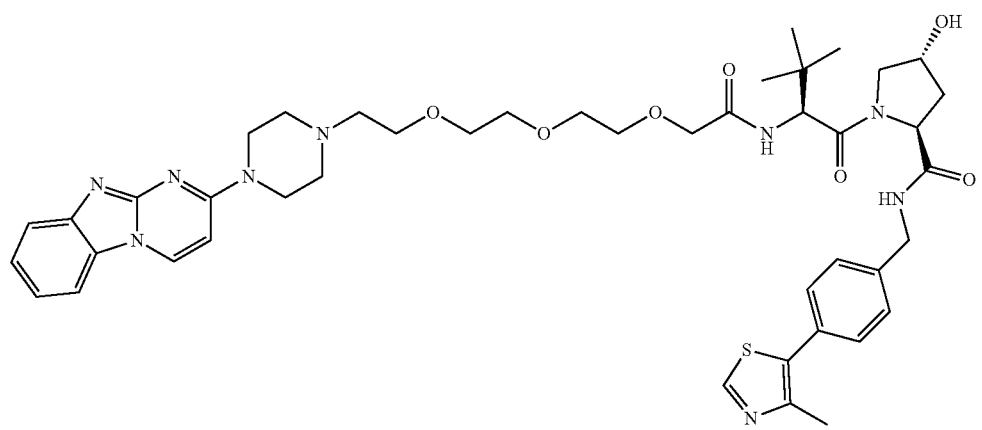
Compound 7

¹H NMR (400 MHz, MeOD): δ 8.85 (s, 1H), 8.71 (d, J=7.6 Hz, 1H), 7.70 (d, J=8.0 Hz, 1H), 7.55 (d, J=8.0 Hz, 1H), 7.34-7.42 (m, 5H), 7.22-7.23 (m, 1H), 6.76 (d, J=7.6 Hz, 1H), 4.68 (s, 1H), 4.47-4.57 (m, 4H), 4.30-4.39 (m, 1H), 4.05 (s, 3H), 3.56-4.87 (m, 23H), 2.64 (s, 4H), 2.45 (s, 3H), 2.19 (br, 1H), 2.04 (br, 1H), 1.03 (s, 9H).

Using procedures described for Compound 7 the following were prepared: Compound 11, Compound 12, Compound 15, Compound 16, Compound 19, Compound 20, Compound 23, Compound 25, Compound 26.

Synthetic Scheme for Exemplary Compound 10

(2S,4R)-1-((S)-14-(4-(benzo[4,5]imidazo[1,2-a]pyrimidin-2-yl)piperazin-1-yl)-2-(tert-butyl)-4,14-dioxo-6,9,12-trioxa-3-azatetradecanoyl)-4-hydroxy-N—((S)-1-(4-(4-methylthiazol-5-yl)phenyl)ethyl) pyrrolidine-2-carboxamide

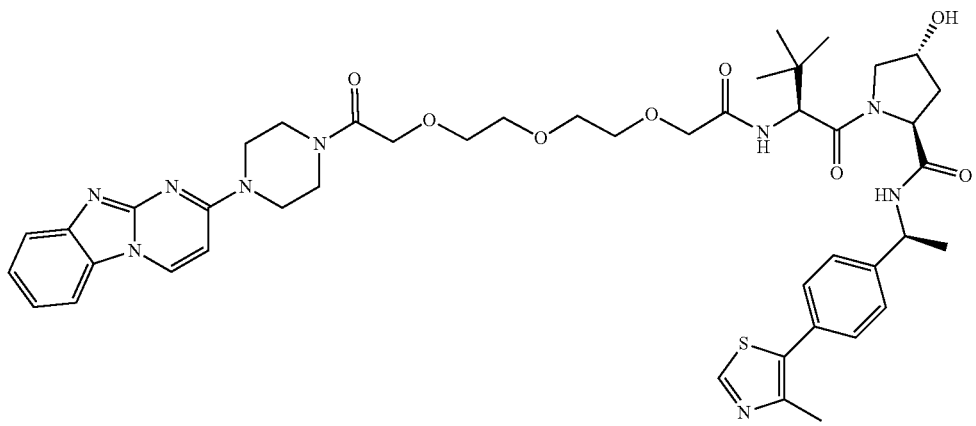 [SMILES: Cc1ncsc1-c1ccc([C@H](C)NC(=O)[C@@H]2C[C@@H](O)CN2C(=O)[C@@H](NC(=O)COCCOCCOCC(=O)N2CCN(c3ccn4c(n3)nc3ccccc34)CC2)C(C)(C)C)cc1]

Prepared according to the scheme below and using procedures described above and common procedures known to those skilled in the art.

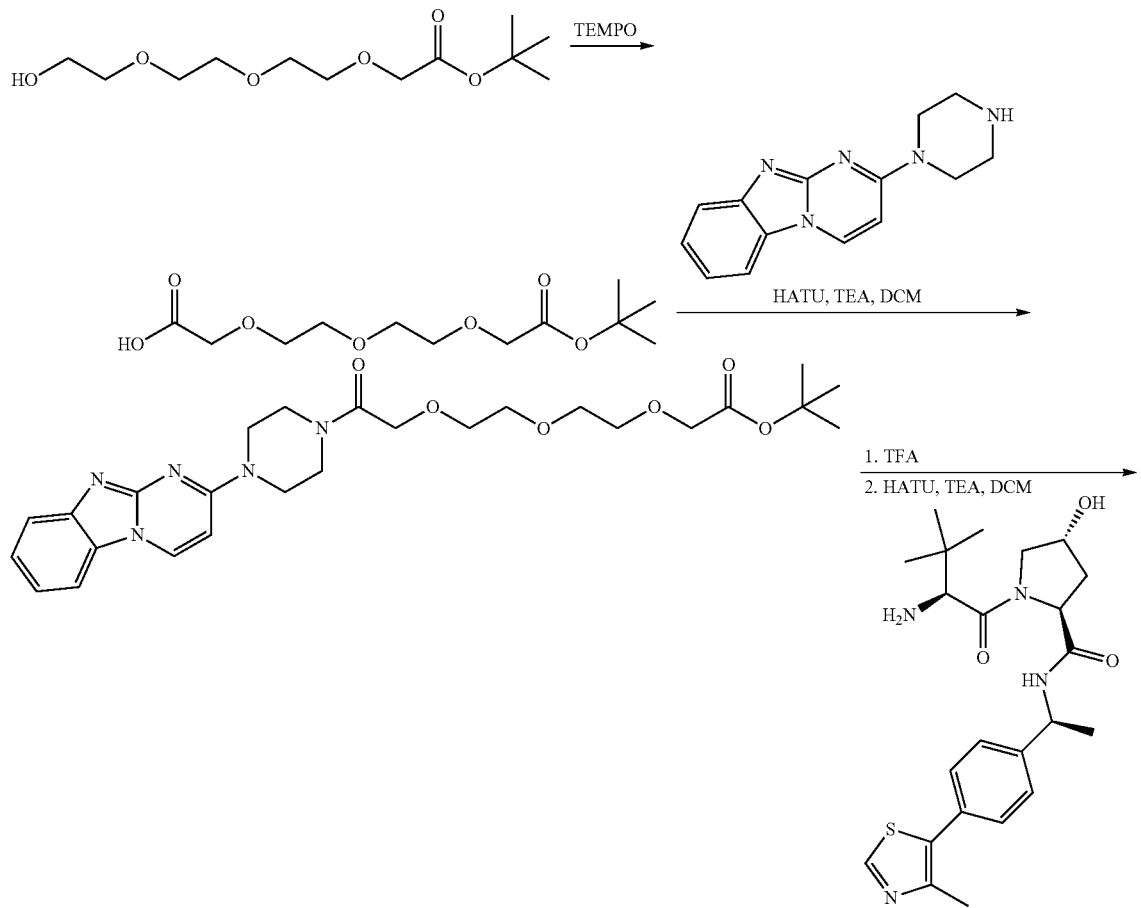

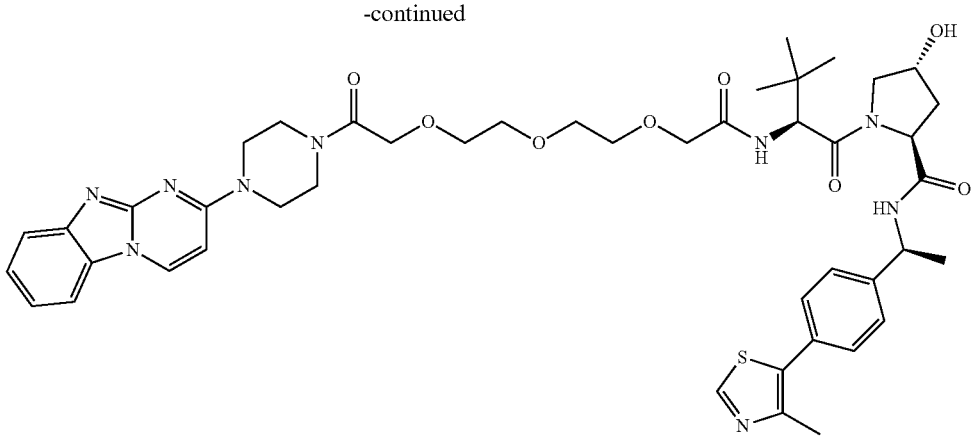

Compound 10

$^1$H NMR (400 MHz, MeOD): δ 8.85 (s, 1H), 8.78 (d, J=7.6 Hz, 1H), 7.83 (d, J=7.6 Hz, 1H), 7.57 (d, J=7.6 Hz, 1H), 7.35-7.40 (m, 6H), 7.23 (t, J=8.0 Hz, 1H), 4.98-5.00 (m, 1H), 4.67 (s, 1H), 4.55-4.57 (m, 1H), 4.34-4.43 (m, 3H), 3.83-4.03 (m, 7H), 3.72-3.74 (m, 16H), 2.46 (s, 3H), 2.17-2.21 (m, 1H), 1.95-2.10 (m, 1H), 1.31 (d, J=8.8 Hz, 3H), 1.03 (s, 9H).

Using procedures described for compound 10 additional compounds were prepared: 13, 14, 17, 18, 21, 22, 24, 41, 42.

Synthetic Scheme for Exemplary Compound 43

(2S,4R)-1-((2S)-2-(tert-butyl)-15-((2-(4-(dimethyl-amino)phenyl)quinolin-6-yl)oxy)-14-hydroxy-4-oxo-6,9,12-trioxa-3-azapentadecanoyl)-4-hydroxy-N-(4-(4-methylthiazol-5-yl)benzyl)pyrrolidine-2-carboxamide

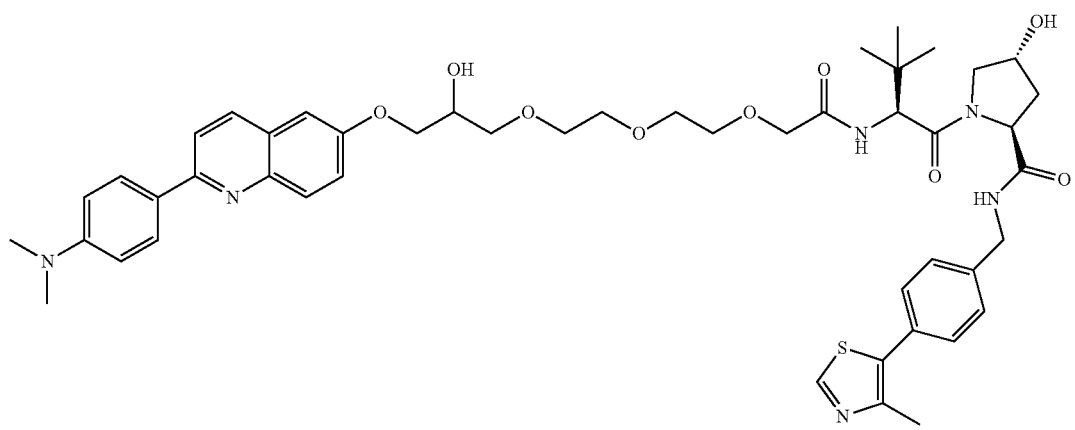 [SMILES: Cc1ncsc1-c1ccc(CNC(=O)[C@@H]2C[C@@H](O)CN2C(=O)[C@@H](NC(=O)COCCOCCOCC(O)COc2ccc3nc(-c4ccc(N(C)C)cc4)ccc3c2)C(C)(C)C)cc1]

Prepared according to the schemes below using procedures described above and common procedures known to those skilled in the art.

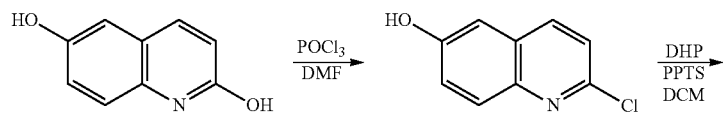

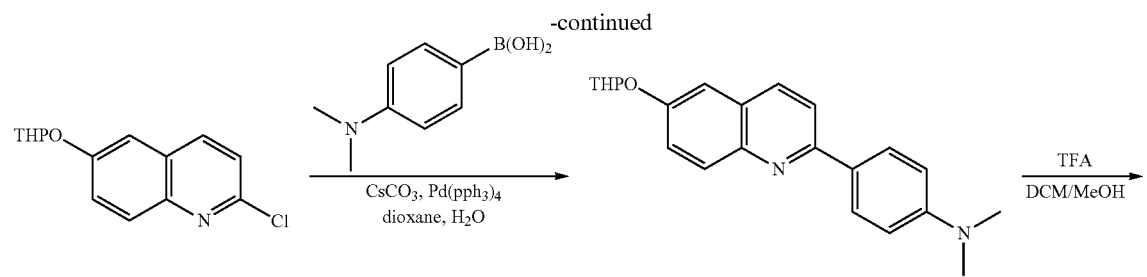
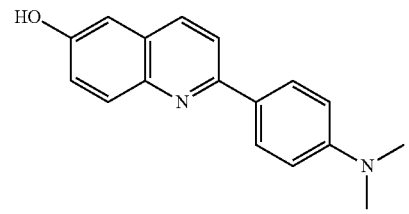
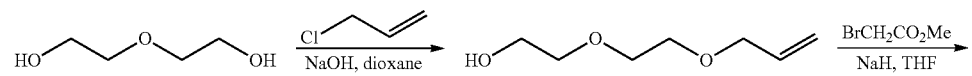
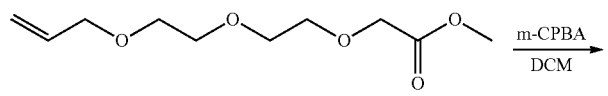
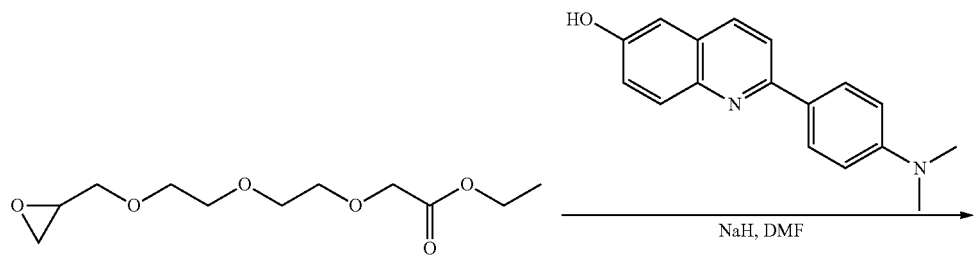
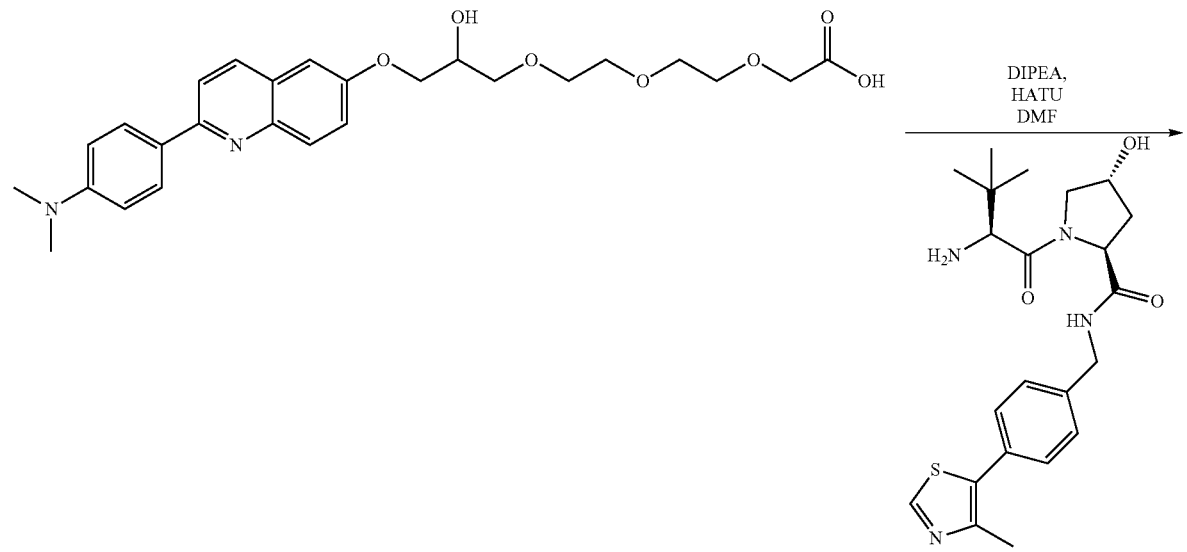

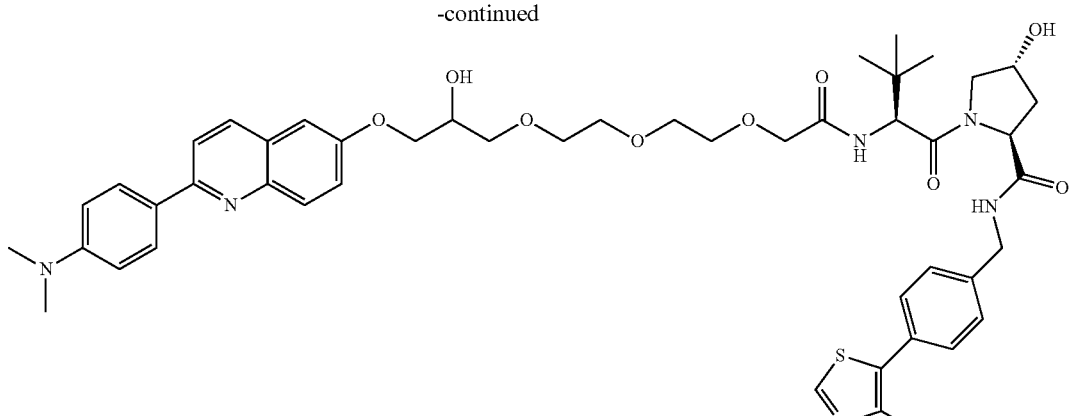

Compound 43

¹HNMR (400 MHz, CD₃OD): δ 1.04 (s, 9H), 2.05-2.13 (m, 1H), 2.21-2.23 (m, 1H), 2.46 (s, 3H), 3.05 (s, 6H), 3.65-3.74 (m, 10H), 3.79-3.90 (m, 2H), 3.98-4.07 (m, 2H), 4.13-4.22 (m, 3H), 4.33-4.37 (m, 1H), 4.50-4.62 (m, 3H), 4.70 (s, 1H), 6.89 (d, J=8.8 Hz, 2H), 7.25-7.26 (m, 1H), 7.38-7.44 (m, 5H), 7.83 (d, J=8.8 Hz, 1H), 7.94-7.97 (m, 3H), 8.17 (d, J=8.8 Hz, 1H), 8.85 (s, 1H).

Using procedures described for Compound 43 the following were prepared: Compound 45, Compound 46, Compound 47.

Synthetic Scheme for Exemplary Compound 8

(2S,4R)-1-((S)-2-(tert-butyl)-15-((2-(4-(dimethyl-amino)phenyl)quinolin-6-yl)oxy)-4-oxo-6,9,12-tri-oxa-3-azapentadecanoyl)-4-hydroxy-N-(4-(4-methylthiazol-5-yl)benzyl)pyrrolidine-2-carboxamide

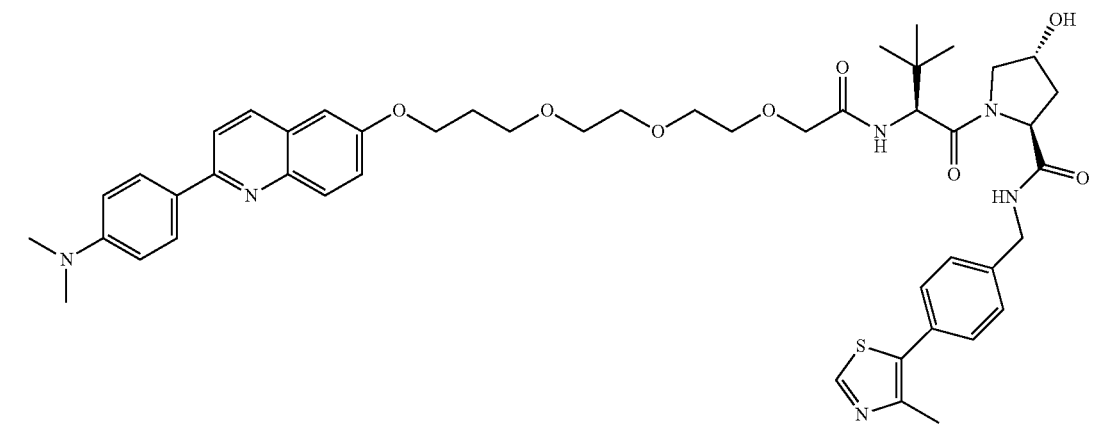 [SMILES: Cc1ncsc1-c1ccc(CNC(=O)[C@@H]2C[C@@H](O)CN2C(=O)[C@@H](NC(=O)COCCOCCOCCCOc2ccc3nc(-c4ccc(N(C)C)cc4)ccc3c2)C(C)(C)C)cc1]

Prepared according to the scheme below using procedures described above and common procedures known to those skilled in the art.

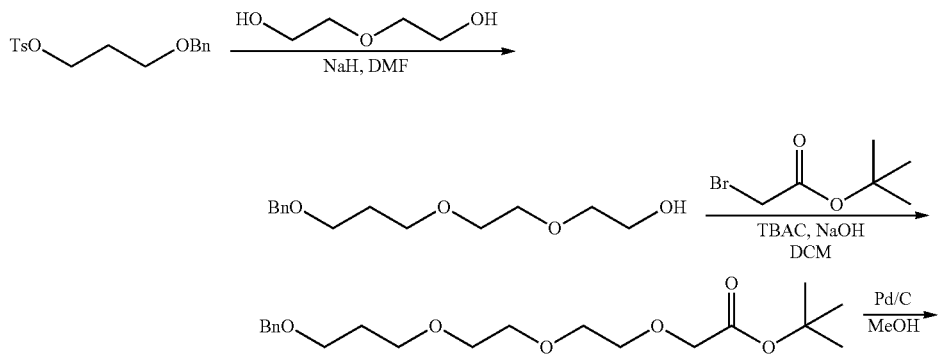

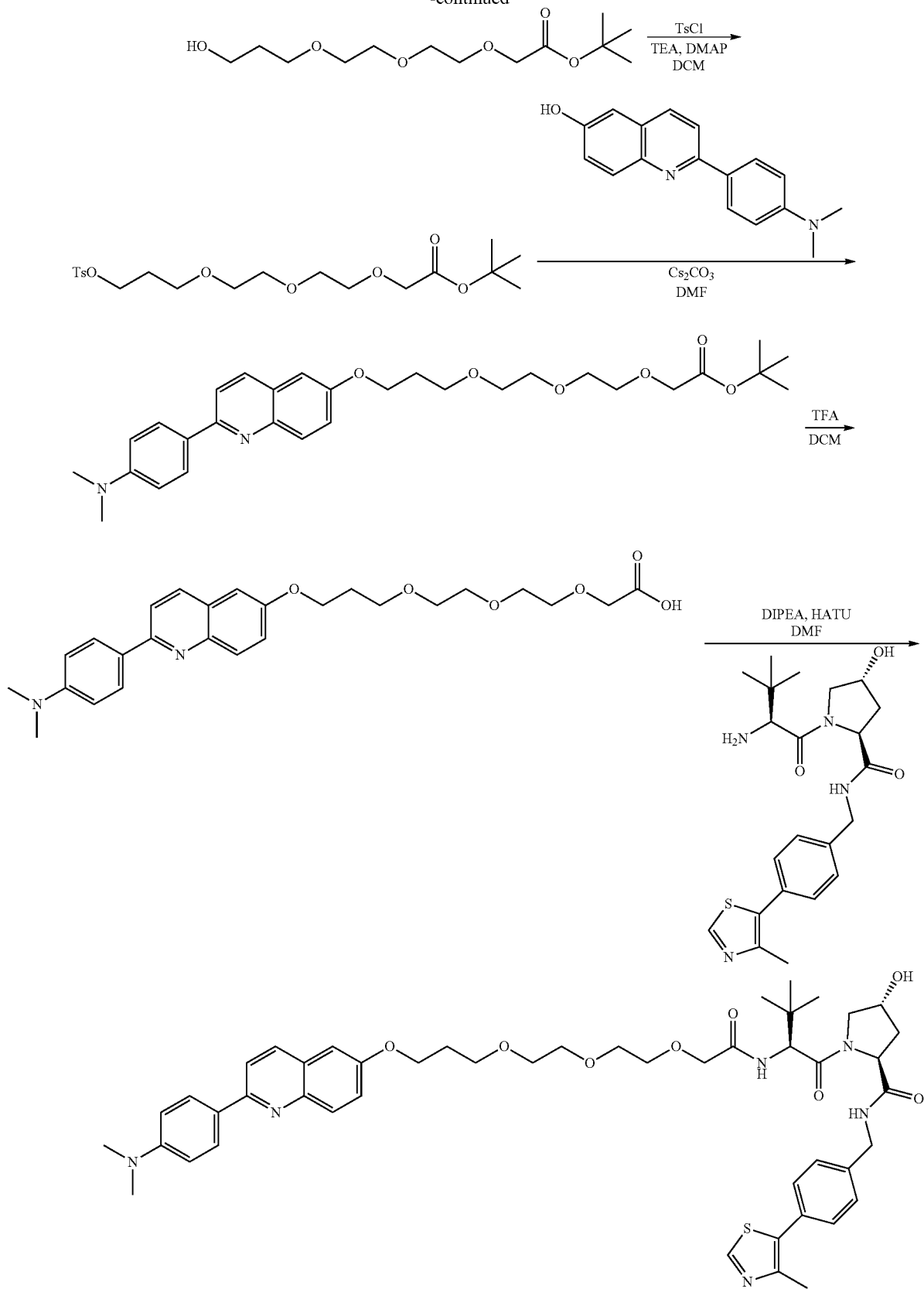
Compound 6

¹HNMR (400 MHz, CD₃OD): δ 1.01, 1.03 (two singles, 9H), 2.07-2.25 (m, 4H), 2.45, 2.47 (two singles, 3H), 3.04 (s, 6H), 3.65-3.71 (m, 10H), 3.78-3.86 (m, 2H), 4.01-4.06 (m, 2H), 4.18-4.21 (m, 2H), 4.32-4.36 (m, 1H), 4.50-4.60 (m, 3H), 4.68-4.70 (m, 1H), 6.88 (d, J=9.2 Hz, 2H), 7.23-7.26 (m, 1H), 7.34-7.44 (m, 5H), 7.82 (d, J=8.4 Hz, 1H), 7.92-7.96 (m, 3H), 8.16 (d, J=8.8 Hz, 1H), 8.85, 8.86 (two singles, 1H).

Using procedures described for Compound 8 the following were prepared: Compound 9, Compound 27, Compound 28, Compound 29, Compound 30, Compound 31, Compound 32, Compound 33, Compound 34, Compound 35, Compound 36, Compound 37, Compound 38, Compound 39, Compound 40, Compound 44.

Synthetic Scheme of Exemplary Compound 49

3-(4-((14-((5-(5H-pyrido[4,3-b]indol-7-yl)pyridin-2-yl)oxy)-3,6,9,12-tetraoxatetradecyl)amino)-1-oxoisoindolin-2-yl)piperidine-2,6-dione

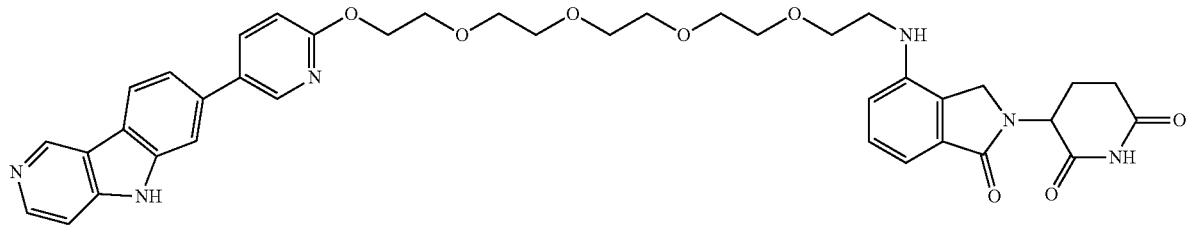 [SMILES: O=C1CCC(N2Cc3c(NCCOCCOCCOCCOCCOc4ccc(-c5ccc6c(c5)[nH]c5ccncc56)cn4)cccc3C2=O)C(=O)N1]

Prepared according to the scheme below using procedures described above and common procedures known to those skilled in the art.

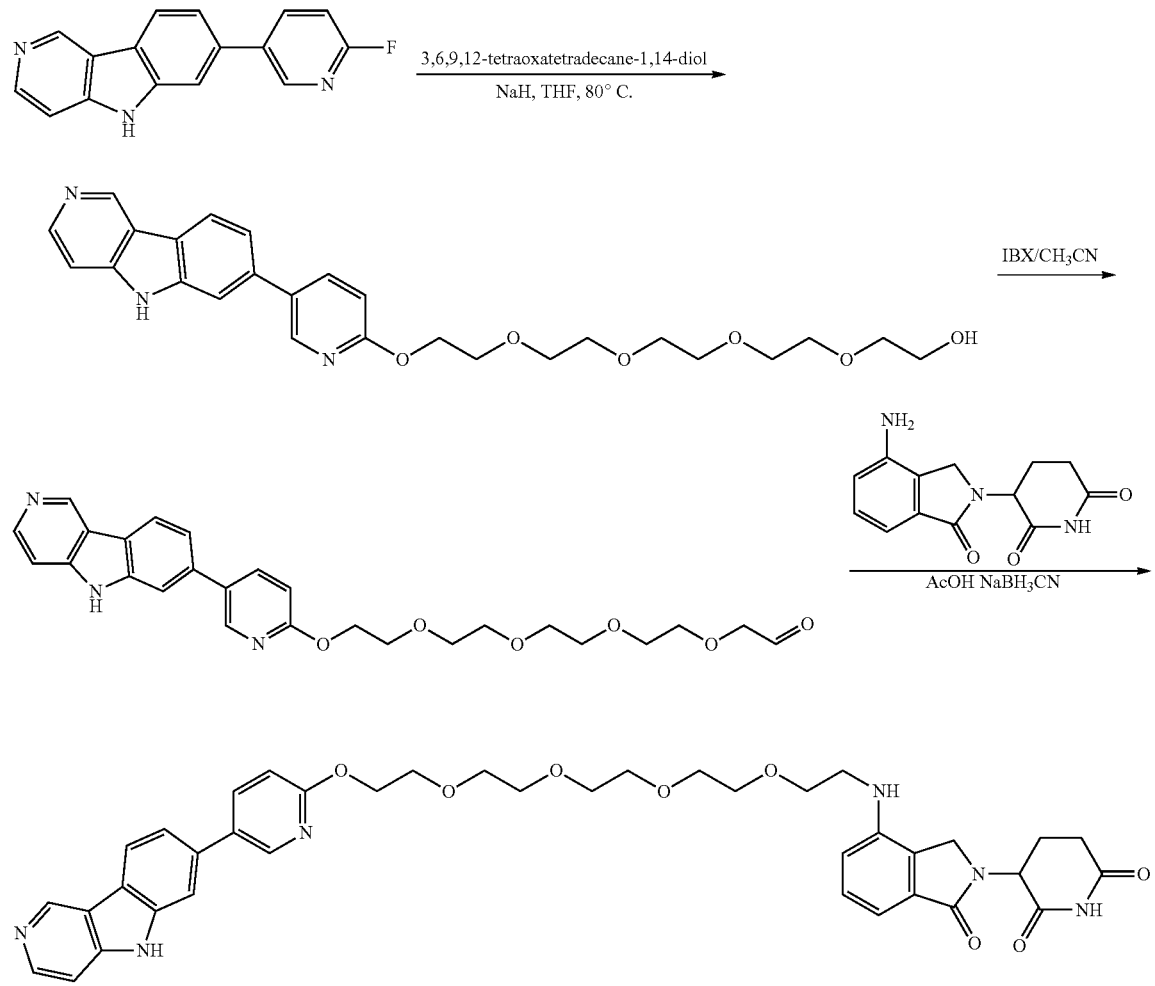

Compound 49

¹H NMR (400 MHz, CD₃OD): δ 9.36 (s, 1H), 8.39-8.45 (m, 3H), 8.30 (d, J=8.0 Hz, 1H), 8.01 (dd, J=2.4, 6.4 Hz, 1H), 7.78 (s, 1H), 7.70 (d, J=6.0 Hz, 1H), 7.59 (d, J=8.4 Hz, 1H), 7.26 (t, J=7.6 Hz, 1H), 7.03 (d, J=7.6 Hz, 1H), 6.90 (d, J=8.8 Hz, 1H), 6.80 (d, J=8.0 Hz, 1H), 5.12 (dd, J=5.2, 13.6 Hz, 1H), 4.47 (t, J=4.4 Hz, 2H), 4.27 (d, J=2.4 Hz, 2H), 3.85 (d, J=4.4 Hz, 2H), 3.62-3.68 (m, 14H), 3.36 (t, J=5.6 Hz, 2H), 2.75-2.95 (m, 2H), 2.35-2.47 (m, 1H), 2.10-2.21 (m, 1H).

Compound 218 can be prepared using procedures analogous to those of Compound 195.

Compound 219 can be prepared using procedures analogous to those of Compounds 73/180/112.

Compound 220 can be prepared using procedures analogous to those of Compounds 73/173.

Compound 221 can be prepared using procedures analogous to those of Compounds 111/127.

Compound 222 can be prepared using procedures analogous to those of Compounds 141/180.

Compound 223 can be prepared using procedures analogous to those of Compounds 102/180.

Compounds 224 and 225 can be prepared according to the schemes below.

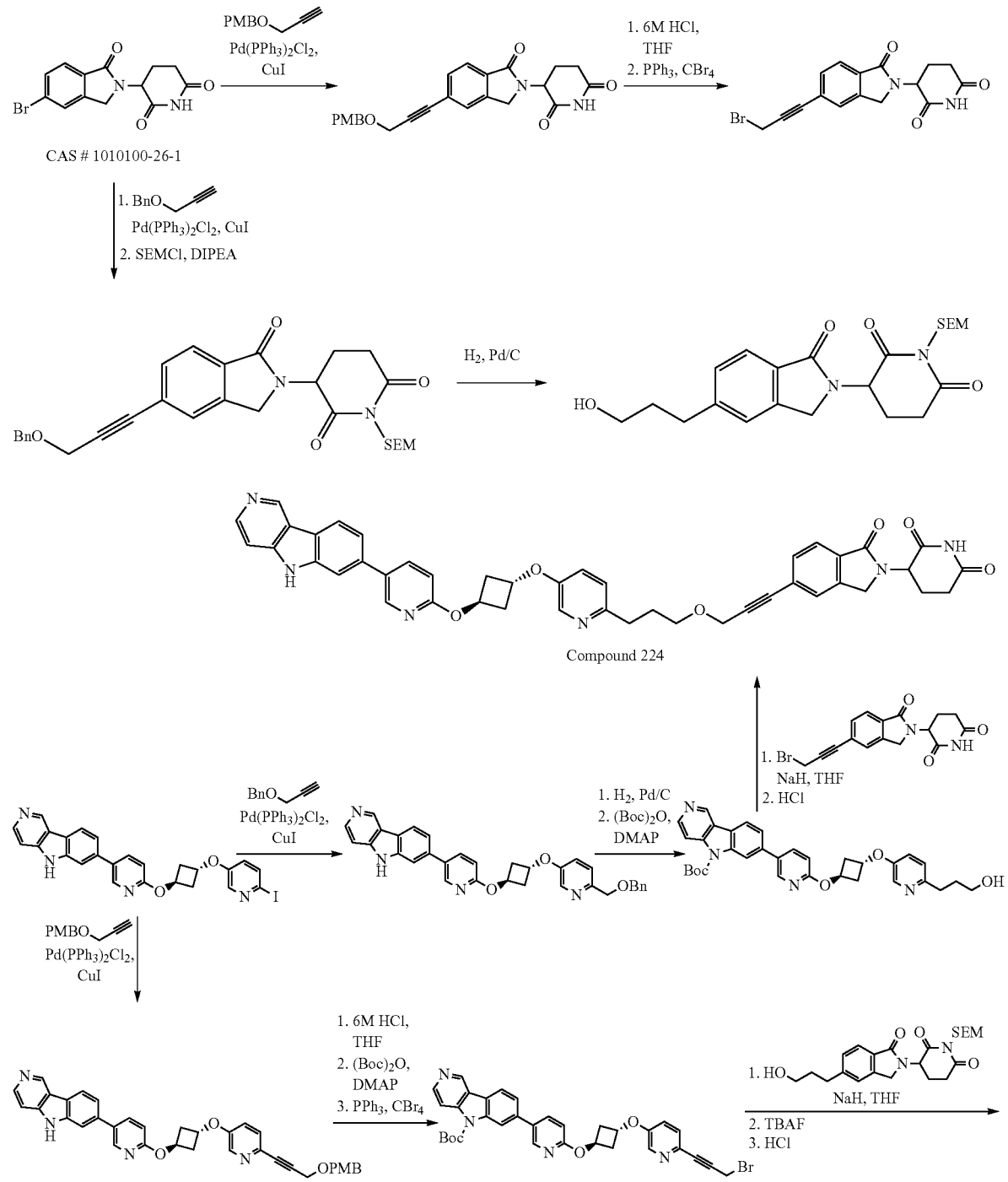

-continued

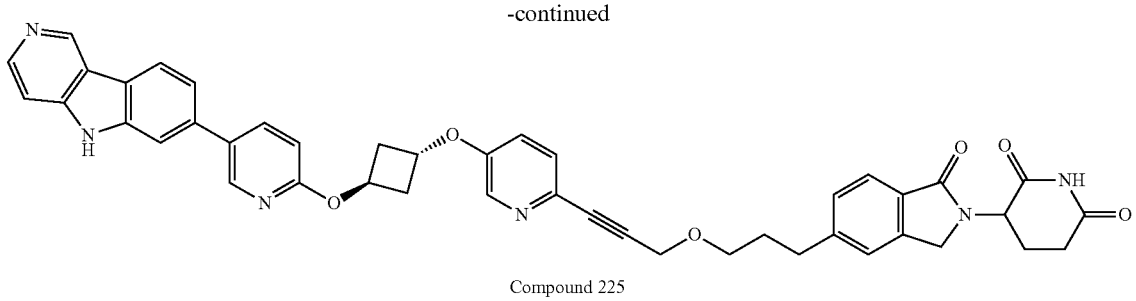

Compound 225

Using approaches described above (including general approaches for Compounds 73, 173 and 180), Compound 226 through 234 can be prepared in analogous ways by using common procedures known to those skilled in the art.

Additionally, combining these approaches with procedures described above for Compounds 138, 139, 140 and 203, Compound 235 through 240 can be prepared.

Compounds 241 through 247 can be prepared by using procedures analogous to those of Compounds 82/198 and 180.

Compounds 248 through 251 can be prepared based on the Compound 82 followed by additional linker elaboration in a manner analogous to approaches described above and known to those skilled in the art.

Compounds 252 through 256 can be prepared based on the approaches to Compounds 104, 99 and 198, and combination thereof.

Additional examples, Compounds 257 through 330, can be prepared based on the fundamental PTM, ULM and linker approaches described above and combined with applicable functional and protecting group elaborations known to those skilled in the art.

Exemplary PROTAC of the present disclosure can be prepared from the PTM embodiments of the present disclosure using the methods of linker and E3 ligase-binding moiety attachment previously described.

Exemplary PROTAC of the present disclosure are represented by the structures in Tables 1 and 2, while data associated with the exemplary PROTACs is shown in Tables 2 and 3.

TABLE 1

Exemplary PROTAC of the present disclosure.

| Ex. | Structure | (M + H)+ | NMR data | Activity* |
|-----|-----------|----------|----------|-----------|
| 1 | 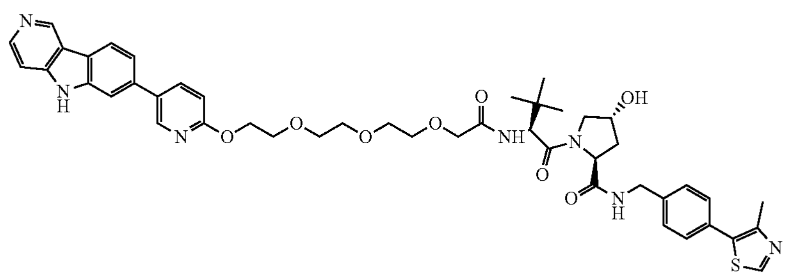 [SMILES: Cc1ncsc1-c1ccc(CNC(=O)[C@@H]2C[C@@H](O)CN2C(=O)[C@@H](NC(=O)COCCOCCOCCOc2ccc(-c3ccc4c(c3)[nH]c3ccncc34)cn2)C(C)(C)C)cc1] | 864.3 | ¹HNMR (400 MHz, MeOD): δ 9.39 (s, 1H), 8.82 (s, 1H), 8.47-8.45 (m, 2H), 8.33 (d, J = 8.0 Hz, 1H), 8.05 (d, J = 6.4 Hz, 1H), 7.81 (s, 1H), 7.73 (d, J = 6.0 Hz, 1H), 7.63 (d, J = 6.0 Hz, 1H), 7.43-7.36 (m, 4H), 6.92 (d, J = 8.4 Hz, 1H), 4.78 (s, 1H), 4.69-4.50 (m, 5H), 4.43-4.31 (m, 1H), 4.04-4.02 (m, 2H), 3.87-3.85 (m, 3H), 3.73-3.64 (m, 9H), 2.40 (s, 3H), 2.25-2.19 (m, 1H), 2.15-2.10 (m, 1H), 1.03 (s, 9H). | C |
| 2 | 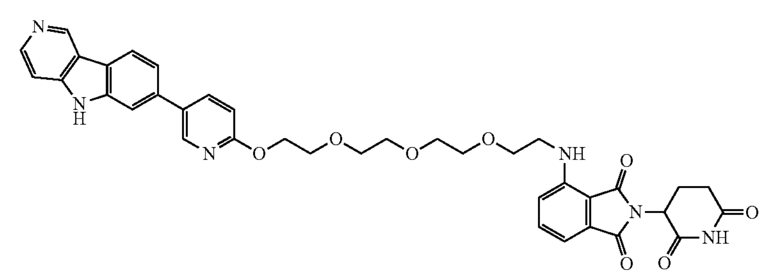 [SMILES: O=C1CCC(N2C(=O)c3cccc(NCCOCCOCCOCCOc4ccc(-c5ccc6c(c5)[nH]c5ccncc56)cn4)c3C2=O)C(=O)N1] | 693.3 | ¹H NMR (400 MHz, CDCl₃): δ 9.29 (s, 2H), 8.52-8.51 (m, 1H), 8.50 (s, 1H), 8.11 (d, J = 8.0 Hz, 1H), 7.54 (s, 1H), 7.50-7.35 (m, 3H), 6.96 (d, J = 7.2 Hz, 1H), 6.83-6.81 (m, 2H), 6.39 (s, 1H), 4.93-4.91 (m, 1H), 4.53 (s, 2H), 3.88 (s, 2H), 3.72-3.3.60 (m, 10H), 3.40-3.30 (m, 2H), 2.88-2.70 (m, 3H), 2.15-2.10 (m, 1H). | A |

TABLE 1-continued

Exemplary PROTAC of the present disclosure.

| Ex. | Structure | (M + H)+ | NMR data | Activity* |
|---|---|---|---|---|
| 3 | 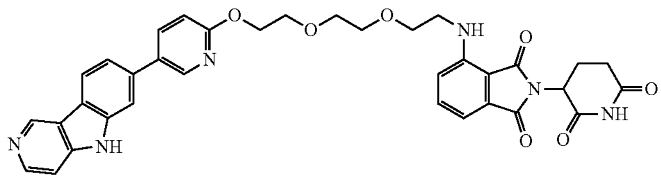 [SMILES: O=C1CCC(N2C(=O)c3cccc(NCCOCCOCCOc4ccc(-c5ccc6c(c5)[nH]c5ccncc56)cn4)c3C2=O)C(=O)N1] | 649.3 | ¹H NMR (400 MHz, CDCl₃): δ 9.32 (s, 1H), 8.67 (s, 1H), 8.46-8.54 (m, 2H), 8.15 (d, J = 8.0 Hz, 1H), 7.87 (d, J = 8.0 Hz, 1H), 7.58 (s, 1H), 7.35-7.47 (m, 2H), 7.26 (s, 1H), 6.85-6.99 (m, 3H), 6.48 (s, 1H), 4.92 (m, 1H), 4.56-4.58 (m, 2H), 3.93 (s, 2H), 3.41-3.77 (m, 9H), 2.71-2.85 (m, 3H), 2.02 (s, 1H). | A |
| 4 | 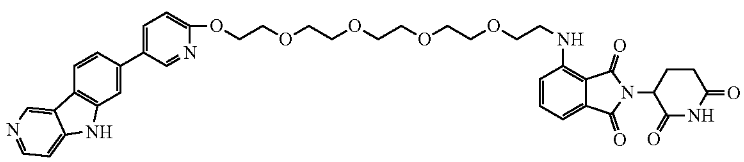 [SMILES: O=C1CCC(N2C(=O)c3cccc(NCCOCCOCCOCCOCCOc4ccc(-c5ccc6c(c5)[nH]c5ccncc56)cn4)c3C2=O)C(=O)N1] | 737.4 | ¹H NMR (400 MHz, CDCl₃): δ 9.30 (s, 1H), 8.90 (br, 1H), 8.52 (d, J = 5.6 Hz, 1H), 8.42 (d, J = 2.8 Hz, 1H), 8.14 (d, J = 8.0 Hz, 1H), 7.49 (dd, J = 2.4, 8.8 Hz, 1H), 7.57 (s, 1H), 7.26-7.46 (m, 3H), 6.97 (d, J = 7.2 Hz, 1H), 6.81-6.87 (m, 2H), 6.35-6.46 (m, 1H), 4.89-4.98 (m, 1H), 4.54 (t, J = 4.8 Hz, 2H), 3.90 (t, J = 4.8 Hz, 2H), 3.61-3-74 (m, 15H), 3.37-3.81 (m, 2H), 2.65-2.92 (m, 3H), 2.07-2.15 (m, 1H). | A |
| 5 | 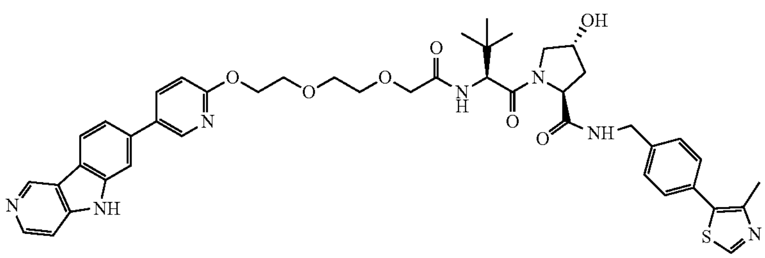 [SMILES: Cc1ncsc1-c1ccc(CNC(=O)[C@@H]2C[C@@H](O)CN2C(=O)[C@@H](NC(=O)COCCOCCOc2ccc(-c3ccc4c(c3)[nH]c3ccncc34)cn2)C(C)(C)C)cc1] | 820.4 | | C |
| 6 | 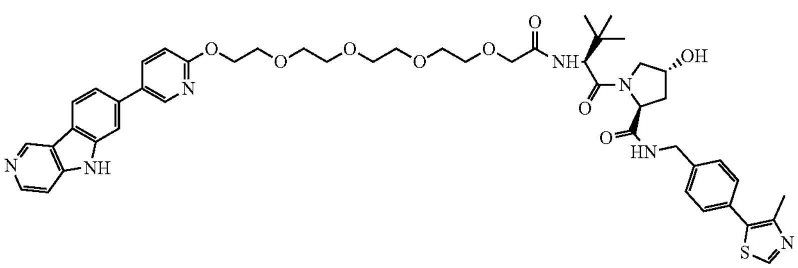 [SMILES: Cc1ncsc1-c1ccc(CNC(=O)[C@@H]2C[C@@H](O)CN2C(=O)[C@@H](NC(=O)COCCOCCOCCOCCOc2ccc(-c3ccc4c(c3)[nH]c3ccncc34)cn2)C(C)(C)C)cc1] | 908.4 | | C |
| 7 | 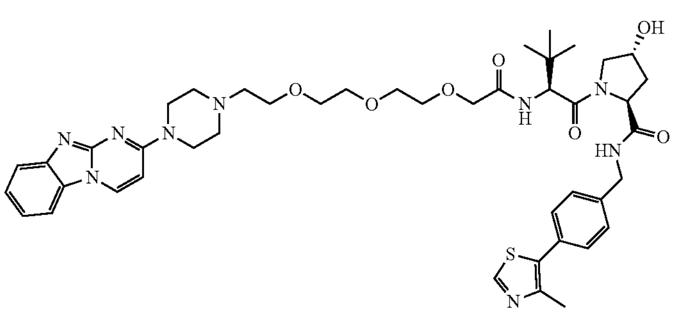 | 856.5 | ¹H NMR (400 MHz, MeOD): δ 8.85 (s, 1H), 8.71 (d, J = 7.6 Hz, 1H), 7.70 (d, J = 8.0 Hz, 1H), 7.55 (d, J = 8.0 Hz, 1H), 7.34-7.42 (m, 5H), 7.22-7.23 (m, 1H), 6.76 (d, J = 7.6 Hz, 1H), 4.68 (s, 1H), 4.47-4.57 (m, 4H), 4.30-4.39 (m, 1H), 4.05 (s, 3H), 3.56-4.87 (m, 23H), 2.64 (s, 4H), 2.45 (s, 3H), 2.19 (br, 1H), 2.04 (br, 1H), 1.03 (s, 9H). | C |

TABLE 1-continued

Exemplary PROTAC of the present disclosure.

| Ex. | Structure | (M + H)+ | NMR data | Activity* |
|---|---|---|---|---|
| 8 | 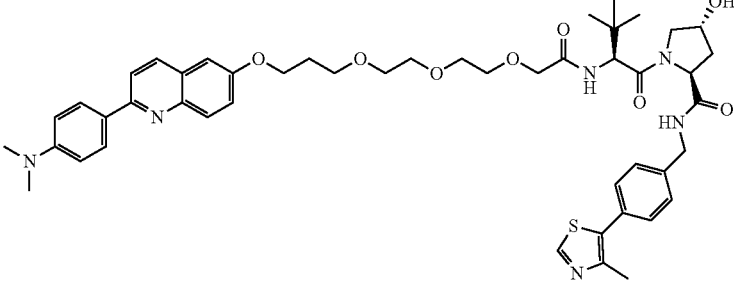 | 881.6 | $^1$HNMR (400 MHz, CD$_3$OD): δ 1.02 (s, 9H), 2.07-2.25 (m, 4H), 2.46 (s, 3H), 3.04 (s, 6H), 3.65-3.71 (m, 10H), 3.78-3.86 (m, 2H), 4.01-4.06 (m, 2H), 4.18-4.21 (m, 2H), 4.32-4.36 (m, 1H), 4.50-4.60 (m, 3H), 4.68-4.70 (m, 1H), 6.88 (d, J = 9.2 Hz, 2H), 7.23-7.26 (m, 1H), 7.34-7.44 (m, 5H), 7.82 (d, J = 8.4 Hz, 1H), 7.92-7.96 (m, 3H), 8.16 (d, J = 8.8 Hz, 1H), 8.86 (s, 1H). | C |
| 9 | 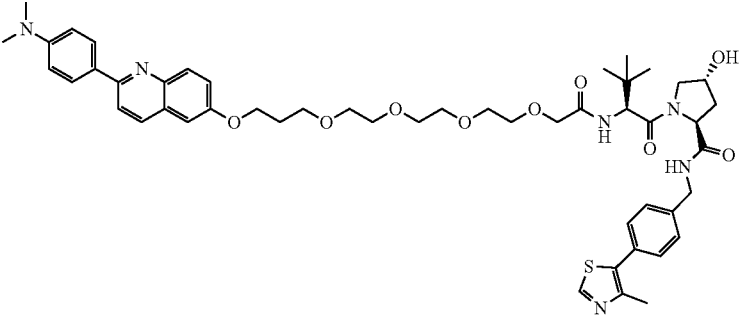 [SMILES: Cc1ncsc1-c1ccc(CNC(=O)[C@@H]2C[C@@H](O)CN2C(=O)[C@@H](NC(=O)COCCOCCOCCOCCCOc2ccc3nc(-c4ccc(N(C)C)cc4)ccc3c2)C(C)(C)C)cc1] | 925.6 | $^1$HNMR (400 MHz, CD$_3$OD): δ 1.04 (s, 9H), 2.08-2.12 (m, 3H), 2.20-2.23 (m, 1H), 2.46 (s, 3H), 3.04 (s, 6H), 3.62-3.71 (m, 14H), 3.78-3.89 (m, 2H), 4.01-4.19 (m, 2H), 4.14-4.23 (m, 2H), 4.33-4.37 (m, 1H), 4.51-4.58 (m, 3H), 4.68-4.70 (m, 1H), 6.68 (d, J = 8.4 Hz, 1H), 7.24 (br, 1H), 7.36-7.45 (m, 5H), 7.62-7.64 (m, 1H), 7.79-7.84 (m, 1H), 7.93-7.97 (m, 3H), 8.17 (d, J = 8.0 Hz, 1H), 8.68 (s, 1H). | C |
| 10 | 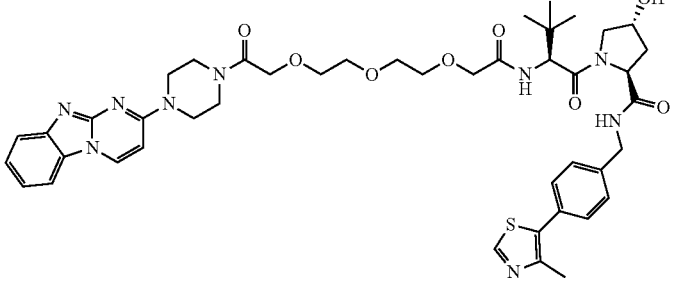 | 870.5 | 1H NMR (400 MHz, MeOD): δ 8.85 (s, 1H), 8.77 (d, J = 8.0 Hz, 1H), 7.83 (d, J = 8.0 Hz, 1H), 7.57 (d, J = 8.0 Hz, 1H), 7.37-7.45 (m, 5H), 7.25 (t, J = 8.0 Hz, 1H), 6.79 (d, J = 8.0 Hz, 1H), 4.68 (s, 1H), 4.49-4.60 (m, 3H), 4.24-4.36 (m, 3H), 4.01-4.06 (m, 2H), 3.91-3.98 (m, 2H), 3.86-3.89 (m, 2H), 3.65-3.80 (m, 14H), 2.45 (s, 3H), 2.20-2.26 (m, 1H), 2.04-2.11 (m, 1H), 1.03 (s, 9H). | C |
| 11 | 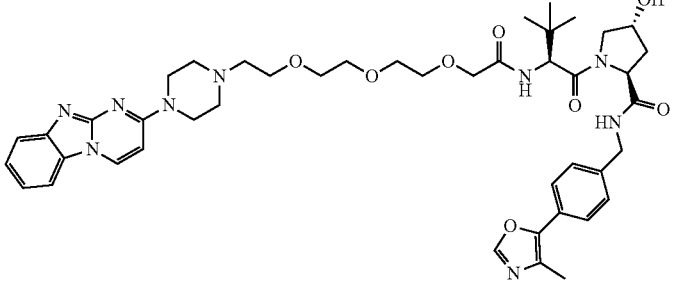 | 840.6 | $^1$H NMR (400 MHz, MeOD): δ 8.70 (d, J = 7.6 Hz, 1H), 8.11 (s, 1H), 7.80 (d, J = 8.4 Hz, 1H), 7.53-7.55 (m, 3H), 7.43 (d, J = 8.4 Hz, 2H), 7.37 (t, J = 8.0 Hz, 2H), 7.23 (d, J = 7.6 Hz, 1H), 6.76 (d, J = 7.6 Hz, 1H), 4.84 (s, 1H), 4.53-4.60 (m, 1H), 4.49 (s, 1H), 4.31-4.35 (m, 1H), 4.05 (s, 2H), 3.77-3.80 (m 5H), 3.65-3.70 (m, 10H), 2.64-2.66 (m, 6H), 2.36 (s, 3H), 2.11-2.20 (m, 1H), 2.04-2.10 (m, 1H), 1.04 (s, 9H). | C |

TABLE 1-continued

Exemplary PROTAC of the present disclosure.

| Ex. | Structure | (M + H)+ | NMR data | Activity* |
|---|---|---|---|---|
| 12 | 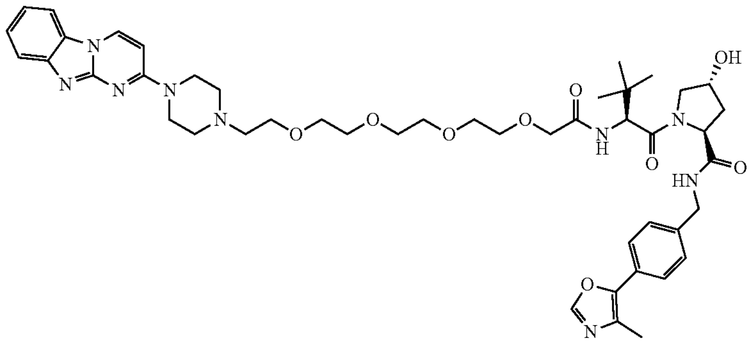 [SMILES: Cc1ncoc1-c1ccc(CNC(=O)[C@@H]2C[C@@H](O)CN2C(=O)[C@@H](NC(=O)COCCOCCOCCOCCN2CCN(c3ccn4c(n3)nc3ccccc34)CC2)C(C)(C)C)cc1] | 884.4 | ¹H NMR (400 MHz, MeOD): δ 8.71 (br, 1H), 8.12 (s, 1H), 7.80-7.82 (m, 1H), 7.43-7.56 (m, 3H), 7.35-7.39 (m, 3H), 7.24-7.25 (m, 1H), 6.76-6.78 (m, 1H), 4.49 (s, 1H), 4.54-4.58 (m, 3H), 4.32-4.36 (m, 1H), 4.04 (s, 1H), 3.81-3.92 (m, 5H), 3.61-3.69 (m, 12H), 3.35 (s 1H), 2.66-2.75 (m, 6H), 2.37 (s, 3H), 2.20-2.22 (m, 1H), 2.07-2.15 (m, 1H), 1.04 (s, 9H). | C |
| 13 | 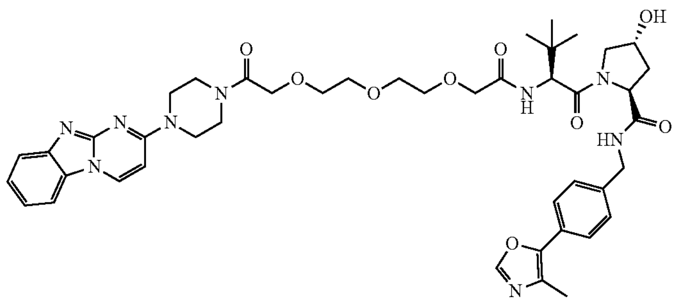 [SMILES: Cc1ncoc1-c1ccc(CNC(=O)[C@@H]2C[C@@H](O)CN2C(=O)[C@@H](NC(=O)COCCOCCOCC(=O)N2CCN(c3ccn4c(n3)nc3ccccc34)CC2)C(C)(C)C)cc1] | 854.5 | ¹H NMR (400 MHz, MeOD): δ 8.79 (d, J = 7.6 Hz, 1H), 8.12 (s, 1H), 7.85 (d, J = 8.0 Hz, 1H), 7.54-7.58 (m, 3H), 7.39-7.43 (m, 2H), 7.28 (t, J = 7.6 Hz, 1H), 6.83 (d, J = 8.0 Hz, 1H), 4.68 (s, 1H), 4.67 (s, 1H), 4.55-4.61 (m, 1H), 4.44 (br, 1H), 4.29-4.35 (m, 5H), 3.80-4.03 (m, 8H), 3.71-3.82 (m, 13H), 3.37 (s, 3H), 2.20-2.22 (s, 1H), 2.08-2.10 (m, 1H), 1.04 (s, 9H). | C |
| 14 | 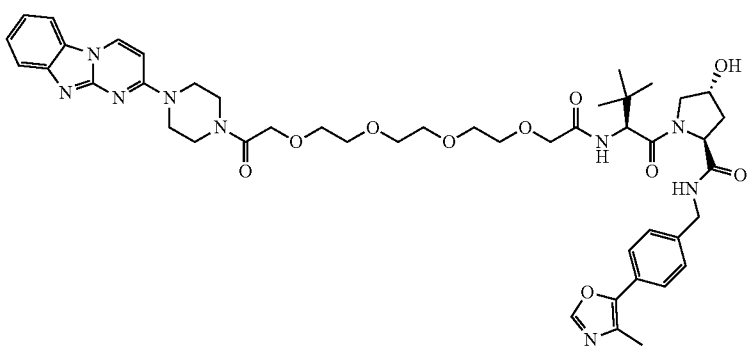 [SMILES: Cc1ncoc1-c1ccc(CNC(=O)[C@@H]2C[C@@H](O)CN2C(=O)[C@@H](NC(=O)COCCOCCOCCOCC(=O)N2CCN(c3ccn4c(n3)nc3ccccc34)CC2)C(C)(C)C)cc1] | 898.6 | ¹H NMR (400 MHz, MeOD): δ 8.76 (d, J = 7.2 Hz, 1H), 8.09 (s, 1H), 7.84 (d, J = 7.2 Hz, 1H), 7.35-7.63 (m, 6H), 7.28 (t, J = 7.6 Hz, 1H), 6.82 (d, J = 7.6 Hz, 1H), 4.68 (s, 1H), 4.50-4.61 (m, 3H), 4.28-4.39 (m, 3H), 4.06 (s, 2H), 3.86-3.97 (m, 3H), 3.78-3.81 (m, 1H), 3.55-3.76 (m, 16H), 3.18-3.23 (m, 2H), 2.35 (s, 3H), 2.21-2.26 (m, 1H), 2.04-2.10 (m, 1H), 1.04 (s, 9H). | C |
| 15 | 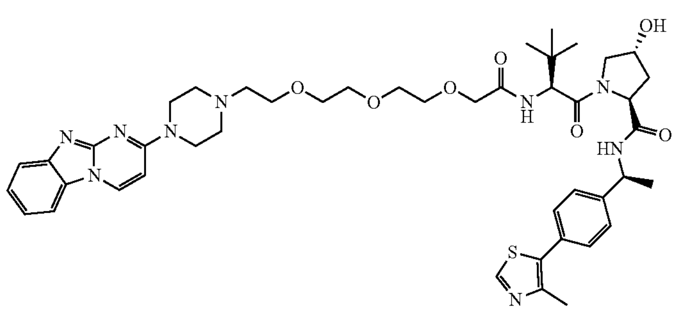 | 870.6 | ¹H NMR (400 MHz, MeOD): 8.85 (s, 1H), 8.76 (d, J = 8.0 Hz, 1H), 7.83 (d, J = 8.0 Hz, 1H), 7.56 (d, J = 7.6 Hz, 1H), 7.37-7.40 (m, 6H), 7.26 (t, J = 7.2 Hz, 1H), 6.84 (d, J = 8.0 Hz, 1H), 4.99-5.01 (m, 1H), 4.68 (s, 1H), 4.57 (t, J = 7.6 Hz, 1H), 4.44 (s, 1H), 4.05 (br, 2H), 3.83-3.91 (m, 5H), 3.68-3.76 (m, 12H), 2.70 (m, 6H), 2.45 (s, 3H), 2.17-2.20 (m, 1H), 1.96-2.05 (m, 1H), 1.56 (d, J = 7.2 Hz, 3H), 1.05 (s, 9H). | C |

TABLE 1-continued

Exemplary PROTAC of the present disclosure.

| Ex. | Structure | (M + H)+ | NMR data | Activity* |
|---|---|---|---|---|
| 16 | 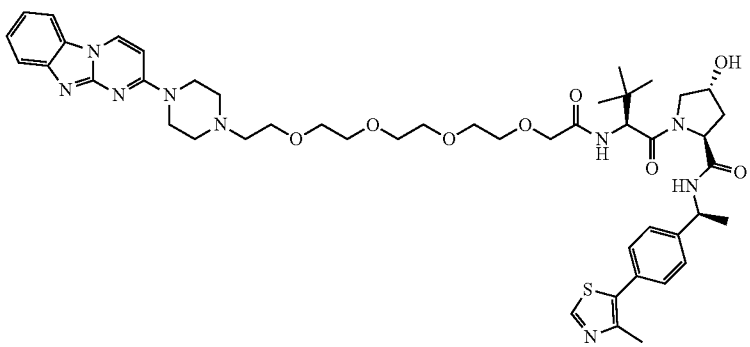 | 914.6 | ¹H NMR (400 MHz, MeOD): δ 8.80-8.85 (m, 2H), 7.88 (d, J = 8.0 Hz, 1H), 7.57 (d, J = 8.0 Hz, 1H), 7.32-7.46 (m, 7H), 6.93 (d, J = 8.0 Hz, 1H), 4.99-5.01 (m, 1H), 4.68 (s, 1H), 4.55-4.57 (m, 1H), 4.43 (s, 1H), 4.04 (s, 2H), 3.80-3.94 (m, 4H), 3.83-3.85 (m, 15H), 2.72-2.74 (m, 6H), 2.46 (s, 3H), 2.12-2.13 (m, 1H), 1.97-1.99 (m, 1H), 1.96-2.05 (m, 1H), 1.56 (d, J = 7.2 Hz, 3H), 1.05 (s, 9H). | C |
| 17 | 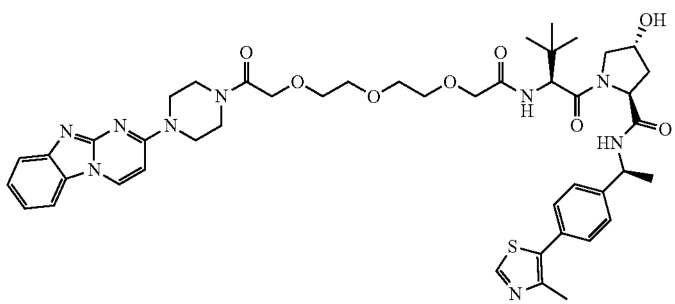 | 884.5 | ¹H NMR (400 MHz, MeOD): δ 8.85 (s, 1H), 8.78 (d, J = 7.6 Hz, 1H), 7.83 (d, J = 7.6 Hz, 1H), 7.57 (d, J = 7.6 Hz, 1H), 7.35-7.40 (m, 6H), 7.23 (t, J = 8.0 Hz, 1H), 4.98-5.00 (m, 1H), 4.67 (s, 1H), 4.55-4.57 (m, 1H), 4.34-4.43 (m, 3H), 3.83-4.03 (m, 7H), 3.72-3.74 (m, 16H), 2.46 (s, 3H), 2.17-2.21 (m, 1H), 1.95-2.10 (m, 1H), 1.31 (d, J = 8.8 Hz, 3H), 1.03 (s, 9H). | C |
| 18 | 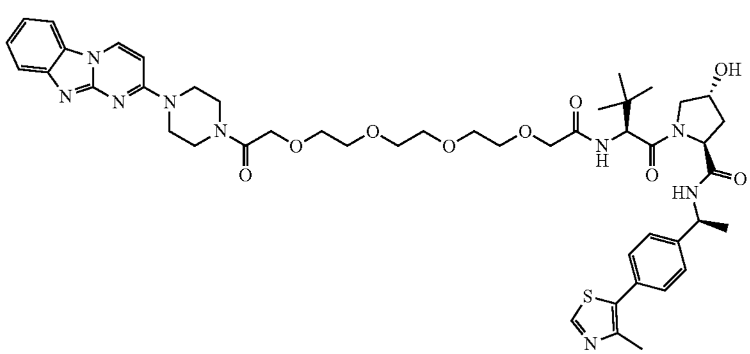 | 928.7 | ¹H NMR (400 MHz, MeOD): δ 8.75-8.86 (m, 2H), 7.85 (d, J = 8.0 Hz, 1H), 7.56 (d, J = 8.0 Hz, 1H), 7.34-7.42 (m, 5H), 7.27 (t, J = 7.6 Hz, 1H), 6.79-6.85 (m, 1H), 4.94-5.04 (m, 1H), 4.67 (s, 1H), 4.55-4.61 (m, 1H), 4.44 (br, 1H), 4.29-4.35 (m, 2H), 4.07 (s, 2H), 3.83-3.96 (m, 4H), 3.61-3.79 (m, 16H), 3.18-3.23 (m, 2H), 2.45 (s, 3H), 2.18-2.23 (m, 1H), 1.92-1.99 (m, 1H), 1.48-1.57 (m, 3H), 1.03 (s, 9H). | C |
| 19 | 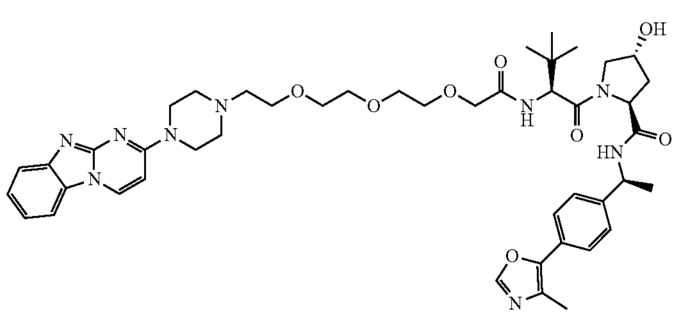 [SMILES: Cc1ncsc1-c1ccc([C@H](C)NC(=O)[C@@H]2C[C@@H](O)CN2C(=O)[C@@H](NC(=O)COCCOCCOCCN2CCN(c3ccn4c(n3)nc3ccccc34)CC2)C(C)(C)C)cc1] | 854.6 | ¹H NMR (400 MHz, MeOD): δ 8.76 (d, J = 7.6 Hz, 1H), 8.11 (s, 1H), 7.84 (d, J = 8.0 Hz, 1H), 7.56 (t, J = 8.4 Hz, 3H), 7.40 (d, J = 8.4 Hz, 3H), 7.27 (t, J = 8.0 Hz, 1H), 6.85 (m, J = 7.6 Hz, 1H), 4.98-4.50 (m, 1H), 4.75 (s, 1H), 4.57 (t, J = 7.6 Hz, 1H), 4.43 (s, 1H), 4.05 (s, 2H), 3.83-3.91 (m, 5H), 3.67-3.76 (m, 12H), 2.70-2.71 (m, 6H), 2.37 (s, 3H), 2.17-2.19 (m, 1H), 1.95-2.10 (m, 1H), 1.55 (d, J = 6.4 Hz, 3H), 1.05 (s, 9H). | C |

TABLE 1-continued

Exemplary PROTAC of the present disclosure.

| Ex. | Structure | (M + H)⁺ | NMR data | Activity* |
|---|---|---|---|---|
| 20 | 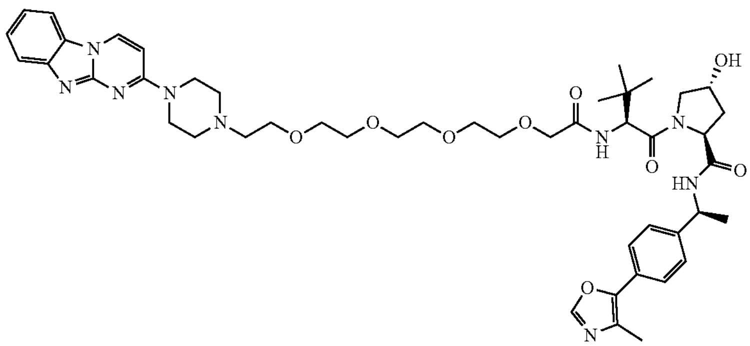 [SMILES: Cc1ncoc1-c1ccc([C@H](C)NC(=O)[C@@H]2C[C@@H](O)CN2C(=O)[C@@H](NC(=O)COCCOCCOCCOCCN2CCN(c3ccn4c(n3)nc3ccccc34)CC2)C(C)(C)C)cc1] | 898.6 | ¹H NMR (400 MHz, MeOD): δ 8.72 (d, J = 8.0 Hz, 1H), 8.11 (s, 1H), 7.81 (d, J = 8.0 Hz, 1H), 7.54-7.56 (m, 3H), 7.35-7.41 (m, 3H), 7.24 (t, J = 8.0 Hz, 1H), 6.79 (d, J = 8.0 Hz, 1H), 4.96-4.50 (m, 1H), 4.68 (s, 1H), 4.55-4.59 (m, 1H), 4.43 (s, 1H), 4.04 (s, 2H), 3.74-3.89 (m, 5H), 3.68-3.70 (m, 18H), 2.68-2.72 (m, 6H), 2.37 (s, 3H), 2.17-2.19 (m, 1H), 1.95-2.10 (m, 1H), 1.50 (d, J = 6.4 Hz, 3H), 1.04 (s, 9H). | C |
| 21 | 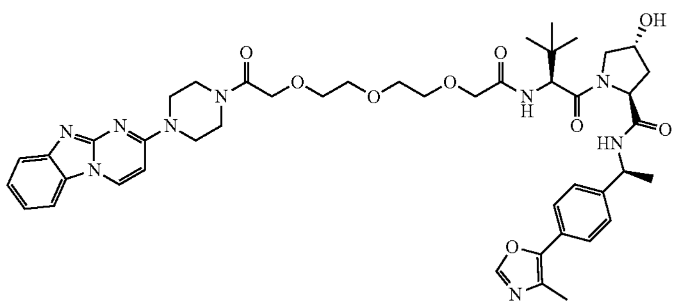 [SMILES: Cc1ncoc1-c1ccc([C@H](C)NC(=O)[C@@H]2C[C@@H](O)CN2C(=O)[C@@H](NC(=O)COCCOCCOCC(=O)N2CCN(c3ccn4c(n3)nc3ccccc34)CC2)C(C)(C)C)cc1] | 868.3 | ¹H NMR (400 MHz, MeOD): δ 8.77 (d, J = 8.0 Hz, 1H), 8.12 (s, 1H), 7.82 (d, J = 8.0 Hz, 1H), 7.56-7.58 (m, 3H), 7.35-7.41 (m, 3H), 7.23 (d, J = 8.0 Hz, 1H), 6.79 (d, J = 7.6 Hz, 1H), 4.98-4.99 (m, 1H), 4.67 (s, 1H), 4.55-4.59 (m, 1H), 4.43 (s, 1H), 4.33-4.35 (m, 2H), 3.86-4.01 (m, 7H), 3.72-3.74 (m, 14H), 2.38 (s, 3H), 2.17-2.19 (m, 1H), 1.95-2.05 (m, 1H), 1.48 (d, J = 6.8 Hz, 3H), 1.03 (s, 9H). | C |
| 22 | 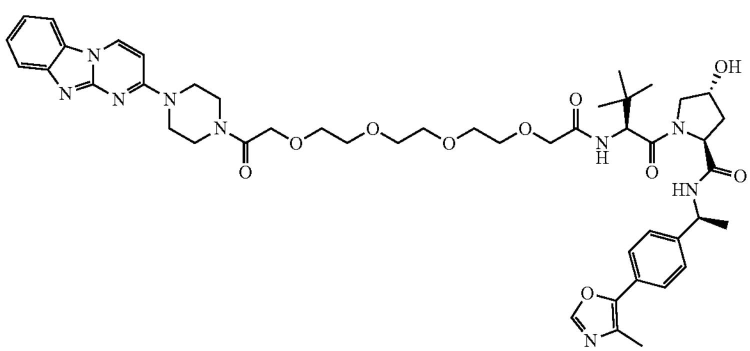 [SMILES: Cc1ncoc1-c1ccc([C@H](C)NC(=O)[C@@H]2C[C@@H](O)CN2C(=O)[C@@H](NC(=O)COCCOCCOCCOCC(=O)N2CCN(c3ccn4c(n3)nc3ccccc34)CC2)C(C)(C)C)cc1] | 912.6 | ¹H NMR (400 MHz, MeOD): δ 8.75-8.81 (m, 1H), 8.06-8.10 (m, 1H), 7.86 (d, J = 8.0 Hz, 1H), 7.55-7.61 (m, 3H), 7.35-7.43 (m, 3H), 7.25-7.31 (m, 1H), 6.81-6.88 (m, 1H), 4.94-5.04 (m, 1H), 4.67 (s, 1H), 4.55-4.60 (m, 1H), 4.43 (br, 1H), 4.35 (s, 2H), 4.07 (s, 2H), 3.91-3.97 (m, 3H), 3.82-3.85 (m, 1H), 3.61-3.79 (m, 16H), 3.18-3.23 (m, 2H), 2.37 (s, 3H), 2.18-2.23 (m, 1H), 1.92-1.99 (m, 1H), 1.48-1.56 (m, 3H), 1.04 (s, 9H). | C |
| 23 | 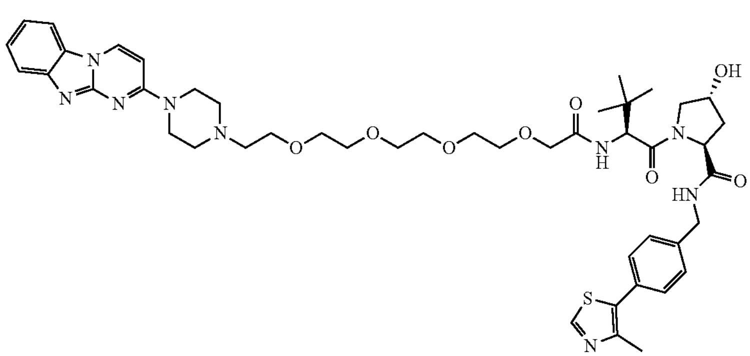 | 900.6 | ¹H NMR (400 MHz, MeOD): δ 8.85 (s, 1H), 8.70 (d, J = 8.0 Hz, 1H), 7.79 (d, J = 8.0 Hz, 1H), 7.54 (d, J = 8.0 Hz, 1H), 7.34-7.44 (m, 5H), 7.24 (t, J = 6.8 Hz, 4.8 Hz, 1H), 6.75 (d, J = 8.0 Hz, 1H), 4.69 (s, 1H), 4.57 (m, 3H), 4.50 (d, J = 4.8 Hz, 1H), 4.04 (s, 2H), 3.85 (s, 6H), 3.60-3.69 (m, 15H), 2.66 (s, 6H), 2.65 (s, 3H), 2.08-2.45 (m, 2H), 2.28 (s, 2H), 1.04 (s, 9H). | C |

TABLE 1-continued

Exemplary PROTAC of the present disclosure.

| Ex. | Structure | (M + H)+ | NMR data | Activity* |
|---|---|---|---|---|
| 24 | 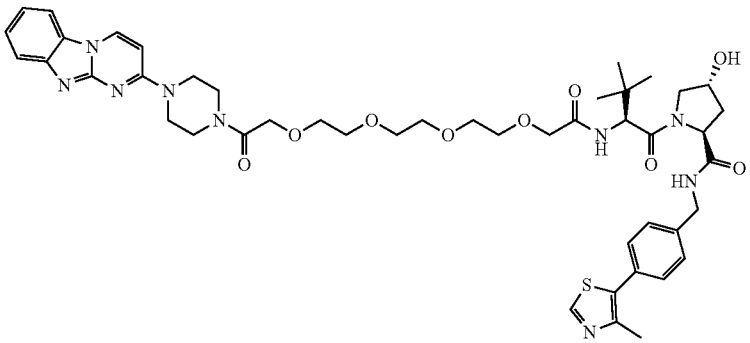 [SMILES: Cc1ncsc1-c1ccc(CNC(=O)[C@@H]2C[C@@H](O)CN2C(=O)[C@@H](NC(=O)COCCOCCOCCOCC(=O)N2CCN(c3ccn4c(n3)nc3ccccc34)CC2)C(C)(C)C)cc1] | 914.6 | 1H NMR (400 MHz, MeOD): δ 8.84 (s, 1H), 8.77 (d, J = 8.0 Hz, 1H), 8.83 (d, J = 8.0 Hz, 1H), 7.57 (d, J = 8.0 Hz, 1H), 7.37-7.45 (m, 5H), 7.24-7.28 (m, 1H), 6.81 (d, J = 8.0 Hz, 1H), 4.86 (s, 1H), 4.50-4.63 (m, 3H), 4.26-4.36 (m, 3H), 3.91-4.03 (m, 4H), 3.86-3.89 (m, 2H), 3.74-3.81 (m, 2H), 3.60-3.72 (m, 16H), 2.45 (s, 3H), 2.18-2.26 (m, 1H), 2.05-2.11 (m, 1H), 1.03 (s, 9H). | C |
| 25 | 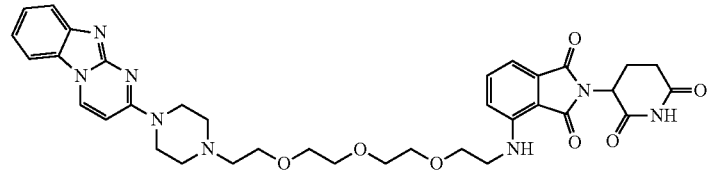 [SMILES: O=C1CCC(N2C(=O)c3cccc(NCCOCCOCCOCCN4CCN(c5ccn6c(n5)nc5ccccc56)CC4)c3C2=O)C(=O)N1] | 685.4 | 1H NMR (400 MHz, MeOD): δ 8.68 (d, J = 8.0 Hz, 1H), 7.80 (d, J = 7.2 Hz, 1H), 7.55 (d, J = 8.0 Hz, 1H), 7.39-7.43 (m, 2H), 7.24 (m, J = 7.6 Hz, 1H), 6.95 (t, J = 7.6 Hz, 2H), 6.76 (d, J = 7.6 Hz, 1H), 4.74 (m, 1H), 3.87 (br, 4H), 3.63-3.73 (m, 14H), 3.54 (s, 3H), 3.46-3.48 (m, 2H), 3.37 (s, 1H), 2.47 (t, J = 6.8 Hz, 2H), 2.33 (t, J = 6.8 Hz, 2H). | C |
| 26 | 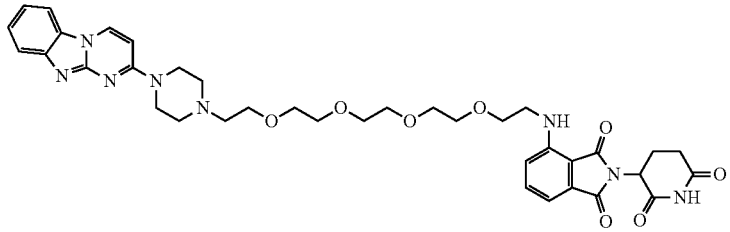 [SMILES: O=C1CCC(N2C(=O)c3cccc(NCCOCCOCCOCCOCCN4CCN(c5ccn6c(n5)nc5ccccc56)CC4)c3C2=O)C(=O)N1] | 729.4 | $^1$H NMR (400 MHz, CD$_3$OD): δ 8.65 (d, J = 8.0 Hz, 1H), 7.77 (d, J = 8.0 Hz, 1H), 7.54 (d, J = 8.0 Hz, 1H), 7.35-7.43 (m, 2H), 7.24 (t, J = 8.0 Hz, 1H), 6.95 (t, J = 8.8 Hz, 2H), 6.75 (d, J = 7.6 Hz, 1H), 5.03 (dd, J = 4.2, 12.4 Hz, 1H), 4.58 (br, 4H), 3.70 (br, 4H), 3.60-3.70 (m, 18H), 3.45-3.46 (m, 2H), 2.80-2.85 (m, 1H), 2.66-2.75 (m, 2H), 2.09-2.12 (m, 1H). | C |
| 27 | 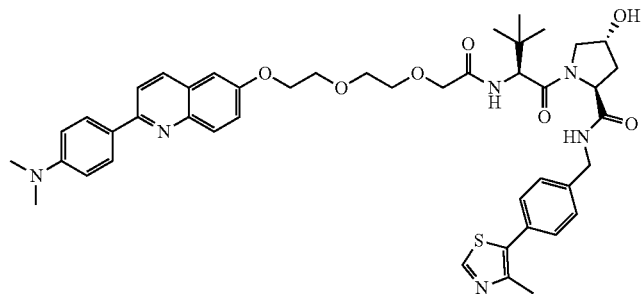 [SMILES: Cc1ncsc1-c1ccc(CNC(=O)[C@@H]2C[C@@H](O)CN2C(=O)[C@@H](NC(=O)COCCOCCOc2ccc3nc(-c4ccc(N(C)C)cc4)ccc3c2)C(C)(C)C)cc1] | 823.7 | $^1$HNMR (400 MHz, CD$_3$OD): δ 1.02-1.05 (m, 9H), 2.07-2.13 (m, 1H), 2.21-2.26 (m, 1H), 2.43-2.47 (m, 3H), 3.05 (s, 6H), 3.76-3.83 (m, 5H), 3.88-3.99 (m, 3H), 4.07-4.12 (m, 2H), 4.30-4.35 (m, 3H), 4.47-4.52 (m, 2H), 4.57-4.61 (m, 1H), 4.71-4.73 (m, 1H), 6.87-6.90 (m, 2H), 7.24-7.29 (m, 1H), 7.35-7.43 (m, 5H), 7.70-7.72 (m, 1H), 7.81-7.83 (m, 1H), 7.91-7.96 (m, 3H), 8.14-8.17 (m, 1H), 8.84 (s, 1H). | C |

TABLE 1-continued

Exemplary PROTAC of the present disclosure.

| Ex. | Structure | (M + H)+ | NMR data | Activity* |
|---|---|---|---|---|
| 28 | 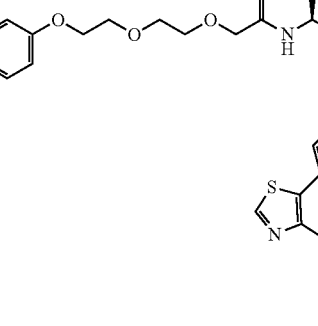 | 837.7 | ¹HNMR (400 MHz, CD₃OD): δ 1.04 (s, 9H), 1.42-1.58 (m, 3H), 1.94-2.01 (m, 1H), 2.17-2.23 (m, 1H), 2.46 (s, 3H), 3.04 (s, 6H), 3.75-3.85 (m, 6H), 3.97-3.98 (m, 2H), 4.08-4.09 (m, 2H), 4.33-4.35 (m, 2H), 4.45 (br, 1H), 4.56-4.60 (m, 1H), 4.70-4.72 (m, 1H), 4.94-4.97 (m, 1H), 6.87-6.90 (m, 2H), 7.30-7.43 (m, 6H), 7.68-7.71 (m, 1H), 7.84-7.86 (m, 1H), 7.95-7.98 (m, 3H), 8.19-8.21 (m, 1H), 8.45-8.47 (m, 1H), 8.86 (s, 1H). | C |
| 29 | 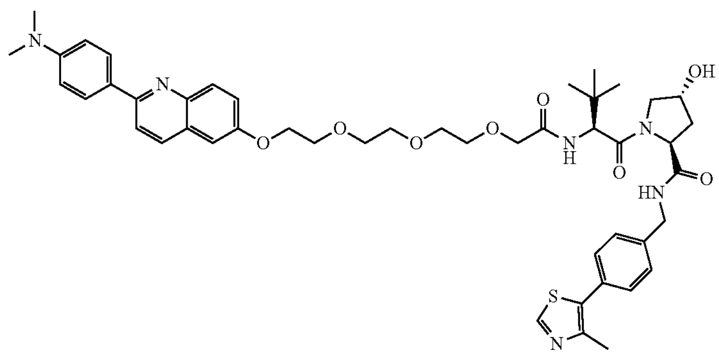 [SMILES: Cc1ncsc1-c1ccc(CNC(=O)[C@@H]2C[C@@H](O)CN2C(=O)[C@@H](NC(=O)COCCOCCOCCOc2ccc3nc(-c4ccc(N(C)C)cc4)ccc3c2)C(C)(C)C)cc1] | 867.7 | ¹HNMR (400 MHz, CD₃OD): δ 1.02 (s, 9H), 2.07-2.13 (m, 1H), 2.21-2.26 (m, 1H), 2.46 (s, 3H), 3.05 (s, 6H), 3.72-3.77 (m, 9H), 3.87-3.92 (m, 3H), 3.99-4.09 (m, 2H), 4.26-4.58 (m, 2H), 4.33-4.37 (m, 1H), 4.50-4.54 (m, 2H), 4.57-4.61 (m, 1H), 4.70-4.72 (m, 1H), 6.89 (d, J = 8.8 Hz, 2H), 7.26 (d, J = 2.8 Hz, 1H), 7.37-7.45 (m, 5H), 7.66 (d, J = 9.6 Hz, 1H), 7.85 (d, J = 8.4 Hz, 1H), 7.94-7.98 (m, 3H), 8.19 (d, J = 8.8 Hz, 1H), 8.86 (s, 1H). | C |
| 30 | 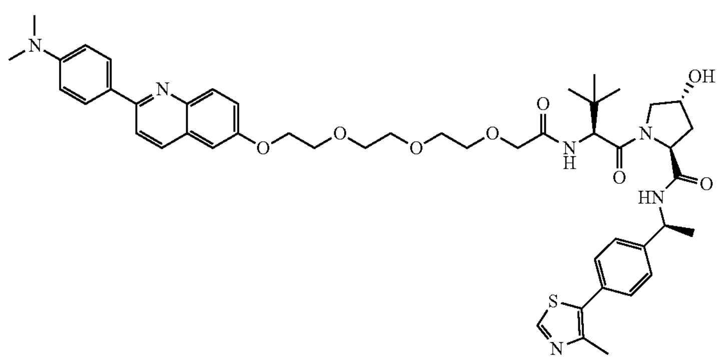 [SMILES: Cc1ncsc1-c1ccc([C@H](C)NC(=O)[C@@H]2C[C@@H](O)CN2C(=O)[C@@H](NC(=O)COCCOCCOCCOc2ccc3nc(-c4ccc(N(C)C)cc4)ccc3c2)C(C)(C)C)cc1] | 881.4 | ¹HNMR (400 MHz, CD₃OD): δ 1.04 (s, 9H), 1.46-1.53 (m, 3H), 1.96-2.04 (m, 1H), 2.19-2.21 (m, 1H), 2.49 (s, 3H), 3.05 (s, 6H), 3.73-3.81 (m, 9H), 3.84-3.87 (m, 1H), 3.95-3.97 (m, 2H), 4.04-4.06 (m, 2H), 4.30-4.33 (m, 2H), 4.44-4.46 (m, 1H), 4.54-4.61 (m, 2H), 4.70 (s, 1H), 4.96-5.00 (m, 1H), 6.89 (m, 2H), 7.29-7.30 (m, 1H), 7.36-7.43 (m, 5H), 7.86 (d, J = 8.8 Hz, 1H), 7.94-7.98 (m, 3H), 8.20 (d, J = 8.8 Hz, 1H), 8.86 (s, 1H). | C |
| 31 | 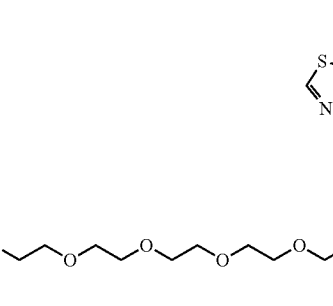 | 911.4 | ¹H NMR (400 MHz, CD₃OD): δ 1.04 (s, 9H), 2.07-2.15 (m, 1H), 2.22-2.26 (m, 1H), 2.47 (s, 3H), 3.06 (s, 6H), 3.61-3.75 (s, 12H), 3.82-3.83 (m, 1H), 3.89-3.93 (m, 2H), 4.01-4.07 (m, 2H), 4.28-4.40 (m, 3H), 4.49-4.69 (m, 5H), 6.87-6.97 (m, 2H), 7.27-7.42 (m, 6H), 7.62-7.67 (br, 1H), 7.83-7.98 (m, 4H), 8.17-8.23 (m, 1H), 8.88 (s, 1H). | C |

TABLE 1-continued

Exemplary PROTAC of the present disclosure.

| Ex. | Structure | (M + H)+ | NMR data | Activity* |
|---|---|---|---|---|
| 32 | 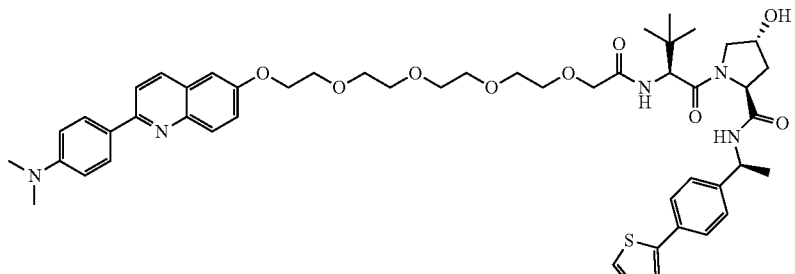 | 925.4 | 1H NMR (400 MHz, CD3OD): δ 1.06 (s, 9H), 1.50-1.58 (m, 3H), 1.94-2.03 (m, 1H), 2.17-2.25 (m, 1H), 2.48 (s, 3H), 3.06 (s, 6H), 3.70-3.77 (m, 12H), 3.85-3.89 (s, 1H), 3.90-4.05 (m, 4H), 4.29-4.35 (m, 2H), 4.43-4.49 (m, 1H), 4.56-4.61 (m, 1H), 4.67-4.71 (m, 1H), 4.99-5.02 (m, 2H), 6.88-6.91 (m, 2H), 7.30-7.41 (m, 5H), 7.63-7.66 (m, 1H), 7.87-7.99 (m, 4H), 8.19-8.23 (m, 1H), 8.50-8.52 (m, 1H), 8.87 (s, 1H). | C |
| 33 | 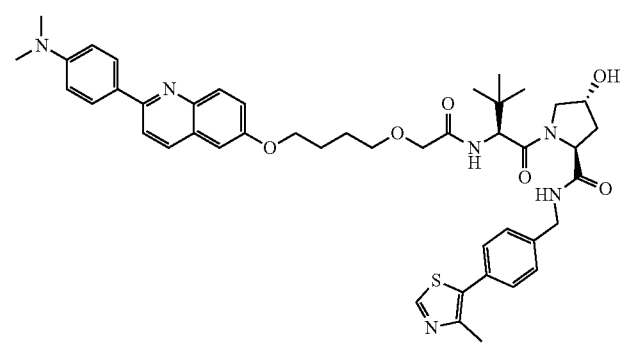 [SMILES: Cc1ncsc1-c1ccc(CNC(=O)[C@@H]2C[C@@H](O)CN2C(=O)[C@@H](NC(=O)COCCCCOc2ccc3nc(-c4ccc(N(C)C)cc4)ccc3c2)C(C)(C)C)cc1] | 807.4 | 1H NMR (400 MHz, CD3OD): δ 1.05 (s, 9H), 1.89-2.03 (m, 4H), 2.10-2.14 (m, 1H), 2.22-2.26 (m, 1H), 2.46 (s, 3H), 3.05 (s, 6H), 3.67-3.70 (m, 2H), 3.81-3.91 (m, 2H), 3.98-4.09 (m, 2H), 4.17-4.20 (m, 2H), 4.34-4.38 (m, 1H), 4.53-4.62 (m, 3H), 7.71-7.73 (m, 1H), 6.88-6.91 (m, 2H), 7.24-7.28 (m, 1H), 7.34-7.47 (m, 5H), 7.58-7.60 (m, 1H), 7.82-7.84 (m, 1H), 7.91-7.97 (m, 3H), 8.15-8.17 (m, 1H), 8.83 (s, 1H). | C |
| 34 | 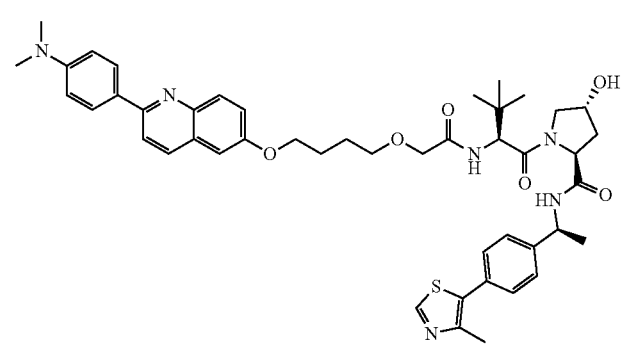 [SMILES: Cc1ncsc1-c1ccc([C@H](C)NC(=O)[C@@H]2C[C@@H](O)CN2C(=O)[C@@H](NC(=O)COCCCCOc2ccc3nc(-c4ccc(N(C)C)cc4)ccc3c2)C(C)(C)C)cc1] | 821.4 | 1H NMR (400 MHz, CD3OD): δ 1.04 (s, 9H), 1.49-1.60 (m, 3H), 1.89-1.95 (m, 2H), 1.97-2.03 (m, 3H), 2.19-2.24 (m, 1H), 2.48 (s, 3H), 3.05 (s, 6H), 3.69 (t, J = 6.0 Hz, 2H), 3.75-3.79 (m, 1H), 3.85-3.88 (m, 1H), 3.99-4.09 (m, 2H), 4.19-4.22 (m, 2H), 4.46 (br, 1H), 4.56-4.62 (m, 1H), 4.70-4.73 (m, 1H), 4.98-5.05 (m, 1H), 6.88-6.91 (m, 2H), 7.27-7.29 (m, 1H), 7.38-7.44 (m, 5H), 7.57 (d, J = 9.6 Hz, 1H), 7.80-7.87 (m, 1H), 7.94-7.98 (m, 3H), 8.76-8.22 (m, 1H), 8.52 (d, J = 7.6 Hz, 1H), 8.86 (s, 1H). | C |
| 35 | 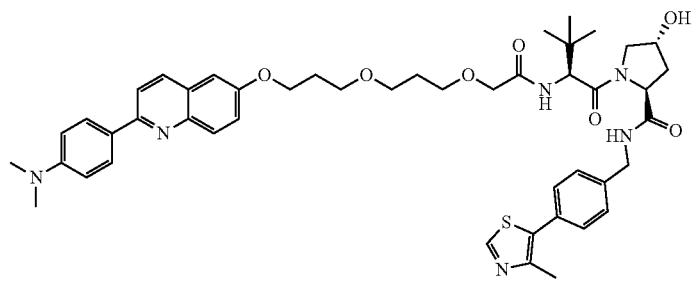 [SMILES: Cc1ncsc1-c1ccc(CNC(=O)[C@@H]2C[C@@H](O)CN2C(=O)[C@@H](NC(=O)COCCCOCCCOc2ccc3nc(-c4ccc(N(C)C)cc4)ccc3c2)C(C)(C)C)cc1] | 851.4 | 1H NMR (400 MHz, CD3OD): δ 1.03 (s, 9H), 1.91-1.92 (m, 2H), 2.05-2.26 (m, 4H), 2.45 (s, 3H), 3.04 (s, 6H), 3.62-3.68 (m, 6H), 3.79-4.00 (m, 4H), 4.15-4.25 (m, 2H), 4.33-4.36 (m, 1H), 4.50-4.61 (m, 3H), 4.69-4.71 (m, 1H), 6.88 (d, J = 8.0 Hz, 2H), 7.22-7.26 (m, 1H), 7.31-7.43 (m, 4H), 7.54 (d, J = 8.4 Hz, 1H), 7.81-7.96 (m, 4H), | C |

TABLE 1-continued

Exemplary PROTAC of the present disclosure.

| Ex. | Structure | (M + H)⁺ | NMR data | Activity* |
|---|---|---|---|---|
|  |  |  | 8.16 (d, J = 8.4 Hz, 1H), 8.84, 8.86 (s, 1H). |  |
| 36 | 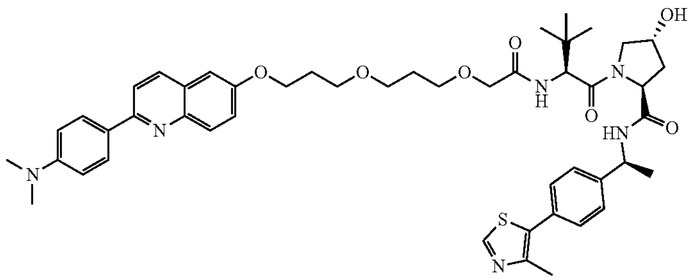 [SMILES: Cc1ncsc1-c1ccc([C@H](C)NC(=O)[C@@H]2C[C@@H](O)CN2C(=O)[C@@H](NC(=O)COCCCOCCCOc2ccc3nc(-c4ccc(N(C)C)cc4)ccc3c2)C(C)(C)C)cc1] | 865.6 | ¹H NMR (400 MHz, CD₃OD): δ 1.04 (s, 9H), 1.46-1.58 (m, 3H), 1.92-2.00 (m, 3H), 2.12-2.21 (m, 3H), 2.47 (s, 3H), 3.04 (s, 6H), 3.62-3.97 (m, 10H), 4.23 (t, J = 5.2 Hz, 2H), 4.35-4.45 (m, 1H), 4.57-4.70 (m, 2H), 4.98-5.01 (m, 1H), 6.88 (d, J = 8.4 Hz, 2H), 7.27-7.56 (m, 7H), 7.79-8.02 (m, 4H), 8.17-8.23 (m, 1H), 8.52 (d, J = 6.8 Hz, 1H), 8.87 (s, 1H). | C |
| 37 | 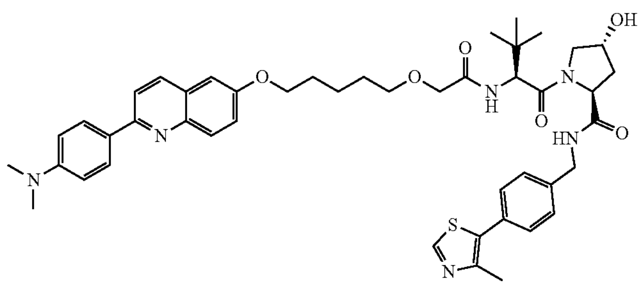 [SMILES: Cc1ncsc1-c1ccc(CNC(=O)[C@@H]2C[C@@H](O)CN2C(=O)[C@@H](NC(=O)COCCCCCOc2ccc3nc(-c4ccc(N(C)C)cc4)ccc3c2)C(C)(C)C)cc1] | 821.4 | ¹HNMR (400 MHz, CD₃OD): δ 1.03, 1.05 (two singles, 9H), 1.64-1.72 (m, 2H), 1.74-1.80 (m, 2H), 1.88-1.95 (m, 2H), 2.07-2.14 (m, 1H), 2.22-2.27 (m, 1H), 2.43, 2.46 (two singles, 3H), 3.04 (s, 6H), 3.63 (t, J = 6.0 Hz, 2H), 3.80-3.83 (m, 1H), 3.88-3.91 (m, 1H), 3.96-4.05 (m, 2H), 4.13 (t, J = 6.4 Hz, 2H), 4.32-4.34 (m, 1H), 4.48-4.55 (m, 2H), 4.58-4.63 (m, 1H), 4.69-4.74 (m, 1H), 6.88 (d, J = 8.8 Hz, 2H), 7.20 (s, 1H), 7.33-7.46 (m, 5H), 7.57 (d, J = 9.6 Hz, 1H), 7.81 (d, J = 6.0 Hz, 1H), 7.93 (t, J = 10.0 Hz, 3H), 8.14 (d, J = 8.8 Hz, 1H), 8.81 (s, 1H). | C |
| 38 | 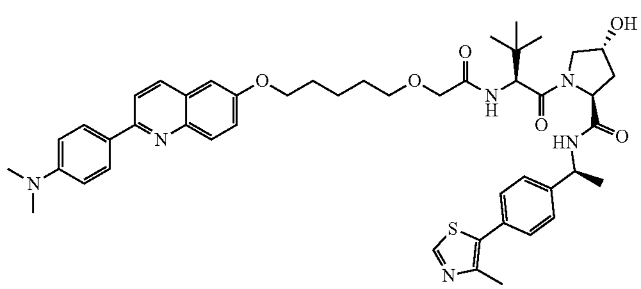 [SMILES: Cc1ncsc1-c1ccc([C@H](C)NC(=O)[C@@H]2C[C@@H](O)CN2C(=O)[C@@H](NC(=O)COCCCCCOc2ccc3nc(-c4ccc(N(C)C)cc4)ccc3c2)C(C)(C)C)cc1] | 835.4 | ¹HNMR (400 MHz, CD₃OD): δ 1.04 (s, 9H), 1.44-1.58 (m, 3H), 1.66-1.81 (m, 4H), 1.89-2.02 (m, 3H), 2.14-2.31 (m, 1H), 2.46 (s, 3H), 3.05 (s, 6H), 3.63 (t, J = 6.4 Hz, 2H), 3.74-3.78 (m, 1H), 3.85-3.88 (m, 1H), 3.96-4.06 (m, 2H), 4.14-4.19 (m, 2H), 4.37-4.46 (m, 1H), 4.56-4.62 (m, 1H), 4.67-4.77 (m, 1H), 4.94-5.04 (m, 1H), 6.89 (d, J = 9.2 Hz, 2H), 7.26 (t, J = 3.2 Hz, 1H), 7.35-7.43 (m, 5H), 7.56 (d, J = 9.6 Hz, 1H), 7.81-7.88 (m, 1H), 8.00-7.91 (m, 3H), 8.18 (d, J = 8.4 Hz, 1H), 8.49 (d, J = 7.2 Hz, 1H), 8.86 (s, 1H). | C |

TABLE 1-continued

Exemplary PROTAC of the present disclosure.

| Ex. | Structure | (M + H)⁺ | NMR data | Activity* |
|---|---|---|---|---|
| 39 | 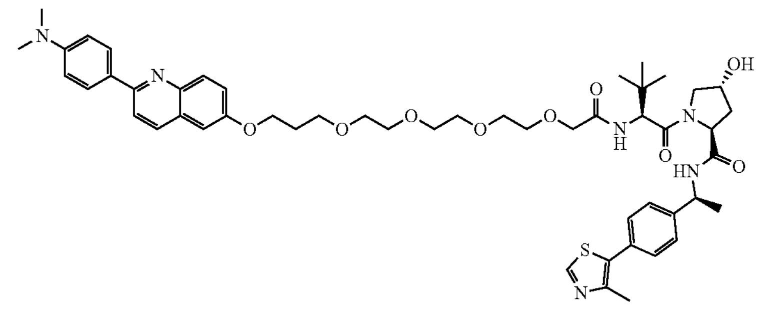 [SMILES: Cc1ncsc1-c1ccc([C@H](C)NC(=O)[C@@H]2C[C@@H](O)CN2C(=O)[C@@H](NC(=O)COCCOCCOCCOCCCOc2ccc3nc(-c4ccc(N(C)C)cc4)ccc3c2)C(C)(C)C)cc1] | 939.4 | ¹HNMR (400 MHz, CD₃OD): δ 1.04 (s, 9H), 1.48-1.57 (m, 3H), 1.95-2.22 (m, 5H), 2.47 (s, 3H), 3.06 (s, 6H), 3.60-3.66 (m, 12H), 3.70-3.86 (m, 4H), 3.97-4.06 (m, 2H), 4.24 (t, J = 6.0 Hz, 2H), 4.44 (br, 1H), 4.58 (t, J = 8.4 Hz, 1H), 4.68-4.70 (m, 1H), 4.99-5.02 (m, 1H), 6.89 (d, J = 8.4 Hz, 2H), 7.27 (s, 1H), 7.37-7.43 (m, 5H), 7.61-7.63 (m, 1H), 7.84 (d, J = 8.4 Hz, 1H), 7.95-7.97 (m, 3H), 7.81-7.82 (m, 1H), 8.86 (s, 1H). | C |
| 40 | 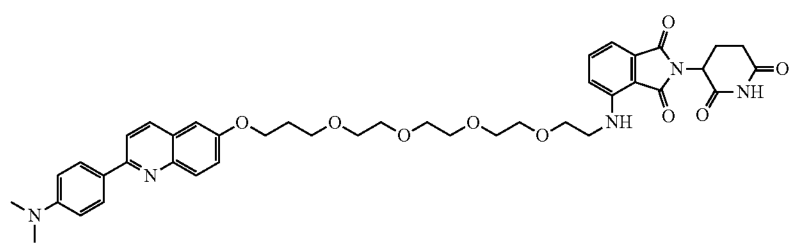 [SMILES: CN(C)c1ccc(-c2ccc3cc(OCCCOCCOCCOCCOCCNc4cccc5c4C(=O)N(C4CCC(=O)NC4=O)C5=O)ccc3n2)cc1] | 754.4 | ¹HNMR (400 MHz, CD₃OD): δ 1.92-2.00 (m, 2H), 2.55-2.74 (m, 4H), 2.93 (s, 6H), 3.28-3.37 (m, 4H), 3.46-3.53 (m, 12H), 3.60 (t, J = 6.2 Hz, 2H), 4.11 (t, J = 6.2 Hz, 2H), 4.89-4.93 (m, 1H), 6.41-6.44 (m, 1H), 6.76 (d, J = 8.8 Hz, 2H), 6.89 (t, J = 7.6 Hz, 2H), 7.13 (d, J = 2.4 Hz, 1H), 7.23-7.26 (m, 1H), 7.36-7.40 (m, 1H), 7.69 (d, J = 8.8 Hz, 1H), 7.80-7.84 (m, 3H), 8.05 (d, J = 8.8 Hz, 1H). | C |
| 41 | 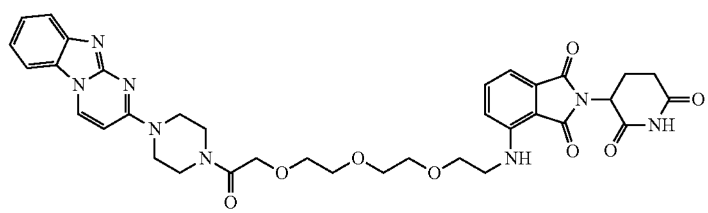 [SMILES: O=C1CCC(N2C(=O)c3cccc(NCCOCCOCCOCC(=O)N4CCN(c5ccn6c(n5)nc5ccccc56)CC4)c3C2=O)C(=O)N1] | 699.4 | ¹H NMR (400 MHz, MeOD): δ 8.46 (d, J = 8.0 Hz, 1H), 7.64 (d, J = 8.0 Hz, 1H), 7.45 (d, J = 8.0 Hz, 1H), 7.27 (t, J = 7.6 Hz, 1H), 7.06-7.14 (m, 2H), 6.57-6.71 (m, 3H), 4.89-4.96 (m, 1H), 4.18 (s, 2H), 3.84 (s, 2H), 3.46-3.70 (m, 16H), 3.30 (s, 2H), 2.58-2.76 (m, 3H), 1.99-2.07 (m, 3H). | C |
| 42 | 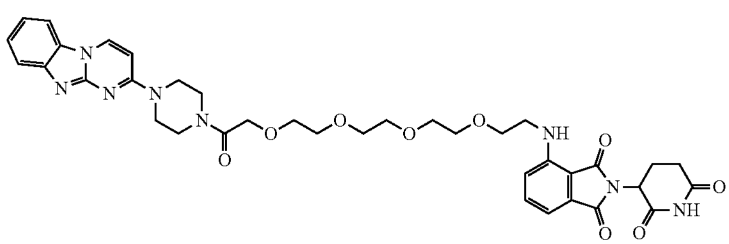 [SMILES: O=C1CCC(N2C(=O)c3cccc(NCCOCCOCCOCCOCC(=O)N4CCN(c5ccn6c(n5)nc5ccccc56)CC4)c3C2=O)C(=O)N1] | 743.7 | 1H NMR (400 MHz, MeOD): δ 8.65 (d, J = 8.0 Hz, 1H), 7.77 (d, J = 8.0 Hz, 1H), 7.55 (d, J = 8.0 Hz, 1H), 7.31-7.40 (m, 2H), 7.21-7.28 (m, 1H), 6.84-7.90 (m, 2H), 6.76 (d, J = 8.0 Hz, 1H), 5.00-5.04 (m, 1H), 4.30 (s, 2H), 3.85-3.95 (m, 4H), 3.63-3.70 (m, 18H), 3.38 (s, 2H), 2.61-2.90 (m, 3H), 2.02-2.21 (m, 1H). | C |

TABLE 1-continued

Exemplary PROTAC of the present disclosure.

| Ex. | Structure | (M + H)⁺ | NMR data | Activity* |
|---|---|---|---|---|
| 43 | 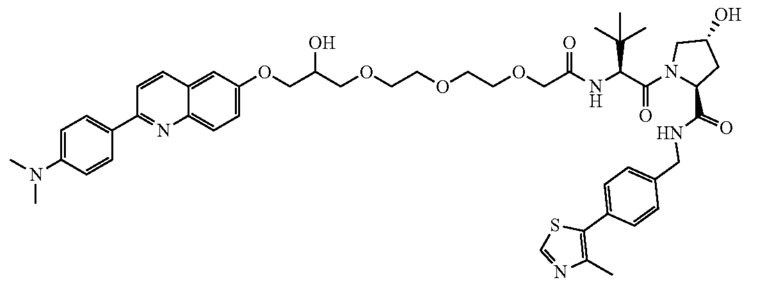 [SMILES: Cc1ncsc1-c1ccc(CNC(=O)[C@@H]2C[C@@H](O)CN2C(=O)[C@@H](NC(=O)COCCOCCOCC(O)COc2ccc3nc(-c4ccc(N(C)C)cc4)ccc3c2)C(C)(C)C)cc1] | 897.4 | ¹HNMR (400 MHz, CD₃OD): δ 1.04 (s, 9H), 2.05-2.13 (m, 1H), 2.21-2.23 (m, 1H), 2.46 (s, 3H), 3.05 (s, 6H), 3.65-3.74 (m, 10H), 3.79-3.90 (m, 2H), 3.98-4.07 (m, 2H), 4.13-4.22 (m, 3H), 4.33-4.37 (m, 1H), 4.50-4.62 (m, 3H), 4.70 (s, 1H), 6.89 (d, J = 8.8 Hz, 2H), 7.25-7.26 (m, 1H), 7.38-7.44 (m, 5H), 7.83 (d, J = 8.8 Hz, 1H), 7.94-7.97 (m, 3H), 8.17 (d, J = 8.8 Hz, 1H), 8.85 (s, 1H). | C |
| 44 | 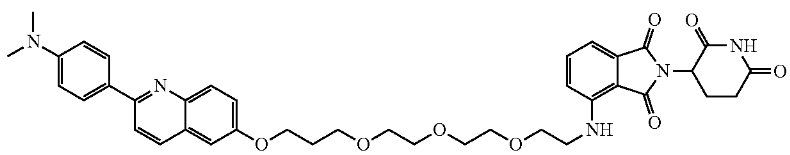 [SMILES: CN(C)c1ccc(-c2ccc3cc(OCCCOCCOCCOCCNc4cccc5c4C(=O)N(C4CCC(=O)NC4=O)C5=O)ccc3n2)cc1] | 710.3 | ¹HNMR (400 MHz, CDCl₃): δ 2.07-2.13 (m, 4H), 2.68-2.88 (m, 4H), 3.04 (s, 6H), 3.33-3.45 (m, 2H), 3.64-3.69 (m, 11H), 4.16-4.18 (m, 2H), 4.86-4.90 (m, 1H), 6.42-6.44 (m, 1H), 6.81-6.85 (m, 3H), 7.06-7.07 (m, 2H), 7.32 (d, J = 8.8 Hz, 1H), 7.41-7.45 (m, 1H), 7.74-7.77 (m, 1H), 7.98-8.07 (m, 5H). | C |
| 45 | 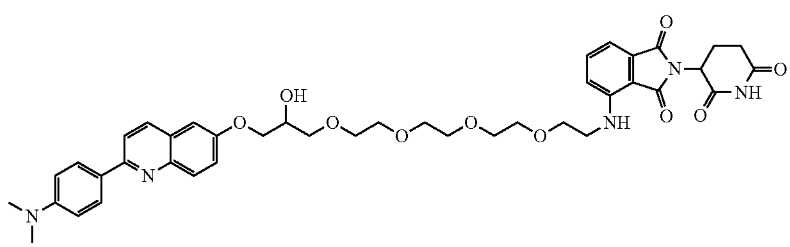 [SMILES: CN(C)c1ccc(-c2ccc3cc(OCC(O)COCCOCCOCCOCCNc4cccc5c4C(=O)N(C4CCC(=O)NC4=O)C5=O)ccc3n2)cc1] | 770.3 | ¹H NMR (400 MHz, CDCl₃): δ 2.07-2.11 (m, 1H), 2.62-2.87 (m, 4H), 3.04 (s, 6H), 3.40-3.43 (m, 2H), 3.65-3.78 (m, 16H), 4.13 (d, J = 5.2 Hz, 2H), 4.24 (t, J = 4.2 Hz, 1H), 4.87-4.91 (m, 1H), 6.45-6.47 (m, 1H), 6.81-6.87 (m, 3H), 7.06, 7.07 (two singles, 2H), 7.33-7.36 (m, 1H), 7.44 (t, J = 7.8 Hz, 1H), 7.76 (d, J = 8.8 Hz, 1H), 8.01-8.10 (m, 4H), 8.56 (br. s, 1H). | C |
| 46 | 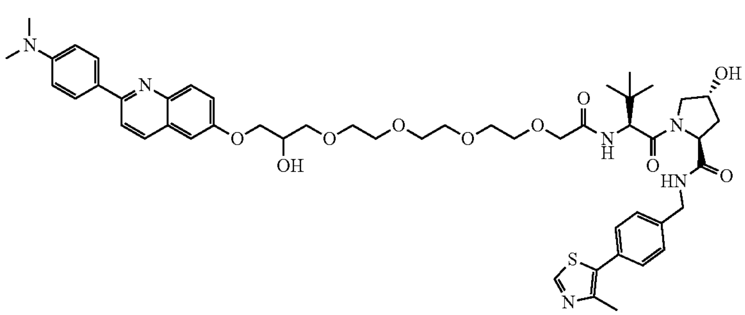 [SMILES: Cc1ncsc1-c1ccc(CNC(=O)[C@@H]2C[C@@H](O)CN2C(=O)[C@@H](NC(=O)COCCOCCOCCOCC(O)COc2ccc3nc(-c4ccc(N(C)C)cc4)ccc3c2)C(C)(C)C)cc1] | 941.4 | ¹HNMR (400 MHz, CD₃OD): δ 1.02, 1.04 (two singles, 9H), 2.05-2.12 (m, 1H), 2.21-2.27 (m, 1H), 2.46, 2.47 (two singlets, 3H), 3.07 (s, 6H), 3.63-3.70 (m, 14H), 3.79-3.90 (m, 2H), 3.98-4.07 (m, 2H), 4.13-4.24 (m, 3H), 4.33-4.37 (m, 1H), 4.50-4.61 (m, 3H), 4.69-4.71 (m, 1H), 6.89 (d, J = 8.8 Hz, 2H), 7.33-7.48 (m, 6H), 7.90 (d, J = 8.8 Hz, 1H), 7.97-7.99 (m, 3H), 8.17 (d, J = 8.8 Hz, 1H), 8.87, 8.88 (two singlets, 1H). | C |

TABLE 1-continued

Exemplary PROTAC of the present disclosure.

| Ex. | Structure | (M + H)+ | NMR data | Activity* |
|---|---|---|---|---|
| 47 | 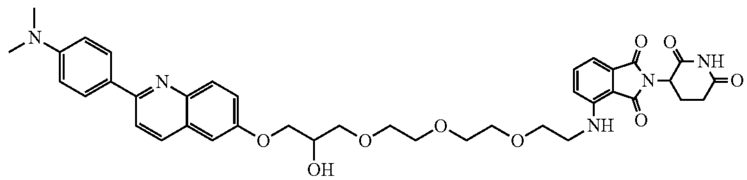 [SMILES: CN(C)c1ccc(-c2ccc3cc(OCC(O)COCCOCCOCCNc4cccc5c4C(=O)N(C4CCC(=O)NC4=O)C5=O)ccc3n2)cc1] | 726.3 | 1H NMR (400 Hz, CDCl₃): δ 2.01-2.24 (m, 2H), 2.68-2.88 (m, 3H), 3.04 (s, 6H), 3.24 (s, 1H), 3.43 (s, 2H), 3.69 (s, 10 H), 4.15-4.24 (m, 3H), 4.83-4.96 (m, 1H), 5.27-5.42 (m, 1H), 6.48 (s, 1H), 6.77-6.83 (m, 3H), 7.07 (s, 2H), 7.34-7.44 (m, 2H), 7.73-7.83 (m, 1H), 7.98-8.05 (m, 4H), 8.27 (s, 1H). | C |
| 48 | 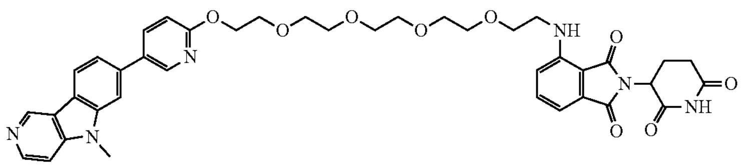 [SMILES: Cn1c2ccncc2c2ccc(-c3ccc(OCCOCCOCCOCCOCCNc4cccc5c4C(=O)N(C4CCC(=O)NC4=O)C5=O)nc3)cc21] | 751.2 | ¹H NMR (400 MHz, MeOD): δ 9.24 (s, 1H), 8.50 (d, J = 2.0 Hz 1H), 8.45 (d, J = 5.6 Hz, 2H), 8.26 (d, J = 8.4 Hz, 1H), 8.06-8.09 (m, 1H), 7.80 (s, 1H), 7.57 (t, J = 8.0 Hz, 2H), 7.44 (t, J = 8.4 Hz, 1H), 6.98 (d, J = 8.4 Hz, 1H), 6.92-6.94 (m, 2H), 4.95-5.09 (m, 1H), 4.49-4.53 (m, 2H), 3.96 (s, 3H), 3.88 (d, J = 4.8 Hz, 2H), 3.63-3.70 (m, 14H), 3.41 (t, J = 6.4 Hz, 2H), 2.64-2.82 (m, 3H). | A |
| 49 | 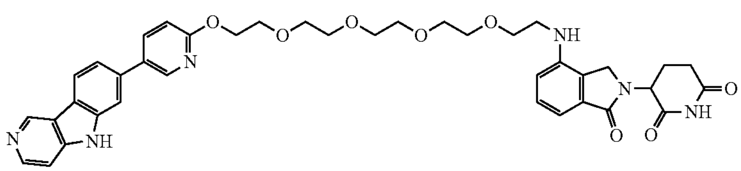 [SMILES: O=C1CCC(N2Cc3c(OCCOCCOCCOCCOCCOc4ccc(-c5ccc6c(c5)[nH]c5ccncc56)cn4)cccc3C2=O)C(=O)N1] | 723.3 | ¹H NMR (400 MHz, CD₃OD): δ 9.36 (s, 1H), 8.39-8.45 (m, 3H), 8.30 (d, J = 8.0 Hz, 1H), 8.01 (dd, J = 2.4, 6.4 Hz, 1H), 7.78 (s, 1H), 7.70 (d, J = 6.0 Hz, 1H), 7.59 (d, J = 8.4 Hz, 1H), 7.26 (t, J = 7.6 Hz, 1H), 7.03 (d, J = 7.6 Hz, 1H), 6.90 (d, J = 8.8 Hz, 1H), 6.80 (d, J = 8.0 Hz, 1H), 5.12 (dd, J = 5.2, 13.6 Hz, 1H), 4.47 (t, J = 4.4 Hz, 2H), 4.27 (d, J = 2.4 Hz, 2H), 3.85 (d, J = 4.4 Hz, 2H), 3.62-3.68 (m, 14H), 3.36 (t, J = 5.6 Hz, 2H), 2.75-2.95 (m, 2H), 2.35-2.47 (m, 1H), 2.10-2.21 (m, 1H). | A |

TABLE 1-continued

Exemplary PROTAC of the present disclosure.

| Ex. | Structure | (M + H)+ | NMR data | Activity* |
|---|---|---|---|---|
| 50 | 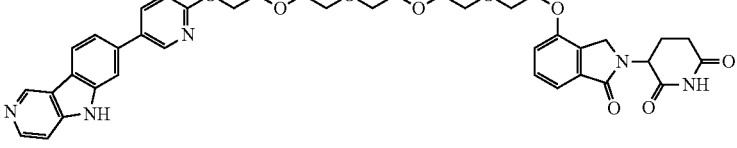 | 724.3 | $^1$H NMR (400 MHz, CDCl$_3$): δ 9.29 (s, 1H), 8.52 (s, 1H), 8.36 (s, 1H), 8.13 (d, J = 8.0 Hz, 1H), 7.81 (d, J = 8.0 Hz, 1H), 7.53 (s, 1H), 7.34-7.43 (m, 4H), 6.99 (d, J = 8.4 Hz, 1H), 6.82 (d, J = 8.8 Hz, 1H), 5.16-5.21 (m, 1H), 4.52 (s, 2H), 4.39-4.43 (m, 1H), 4.27-4.31 (m, 1H), 4.18 (d, J = 3.2 Hz, 2H), 3.82-3.89 (m, 4H), 3.64-3.72 (m, 14H), 2.85-2.89 (m, 1H), 2.72-2.81 (m, 1H), 2.27-2.38 (m, 1H), 2.13-2.24 (m, 1H). | A |

*Each compound was tested at 1000 nM, 300 nM and 100 nM as described below. The highest amount of degradation observed at any dosage for each compound is capture in Table 1 as follows:

A: ≤50% tau protein remaining after 72 hours of incubation with the test compound;
B: ≤80% and >50% tau protein remaining after 72 hours of incubation with the test compound;
C: >80% tau protein remaining after 72 hours of incubation with the test compound.

TABLE 2

Exemplary PROTAC of the present disclosure.

| Ex. | Structure | Degradation activity* | MH + (1) [MH + (2), if isotope] | NMR transcript |
|---|---|---|---|---|
| 51 | 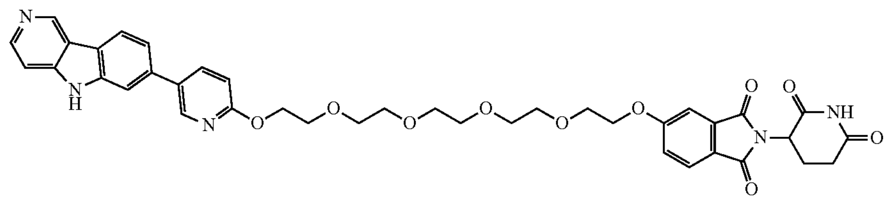 [SMILES: O=C1CCC(N2C(=O)c3ccc(OCCOCCOCCOCCOCCOc4ccc(-c5ccc6c(c5)[nH]c5ccncc56)cn4)cc3C2=O)C(=O)N1] | A | 738.3 | ¹H NMR (400 MHz, CDCl₃): δ 12.34-12.48 (m, 1H), 9.19-9.29 (m, 1H), 8.80 (s, 1H), 8.29-8.42 (m, 1H, 8.02-8.14 (m, 1H), 7.95 (s, 1H), 7.69-7.81 (m, 1H), 7.60 (s, 2H), 7.17 (s, 1H), 7.09 (s, 1H), 6.62 (s, 1H), 4.97 (s, 1H), 4.43 (s, 2H), 4.14 (s, 2H), 3.88 (d, J = 24.1 Hz, 3H), 3.78 (d, J = 8.2 Hz, 2H), 3.69 (d, J = 10.0 Hz, 6H), 2.80 (m, 4H), 1.99-2.29 (m, 4H). |
| 52 | 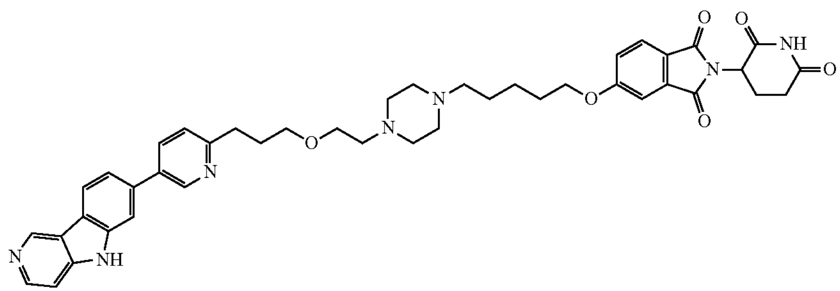 [SMILES: O=C1CCC(N2C(=O)c3ccc(OCCCCCN4CCN(CCOCCCc5ccc(-c6ccc7c(c6)[nH]c6ccncc67)cn5)CC4)cc3C2=O)C(=O)N1] | C | 758.3 | ¹HNMR (400 MHz, MeOD): δ 9.25 (s, 1H), 8.79 (s, 1H), 8.37-8.39 (d, J = 8 Hz, 1H), 8.28-8.30 (d, J = 8 Hz, 1H), 8.11-8.13 (d, J = 8 Hz, 1H), 7.80 (s, 1H), 7.75-7.77 (d, J = 8 Hz, 1H), 7.60 (s, 1H), 7.49-7.51 (d, J = 8 Hz, 1H), 7.43-7.45 (d, J = 8 Hz, 1H), 7.33 (s, 1H), 5.07-5.09 (m, 1H), 4.06-4.09 (m, 2H), 3.57-3.60 (m, 2H), 3.51-3.54 (m, 2H), 2.93-2.95 (m, 2H), 2.91-2.93 (m, 1H), 2.59-2.75 (m, 12H), 2.37-2.41 (m, 2H), 2.04-2.06 (m, 3H), 1.78-1.80 (m, 2H), 1.46-1.55 (m, 5H). |
| 53 | 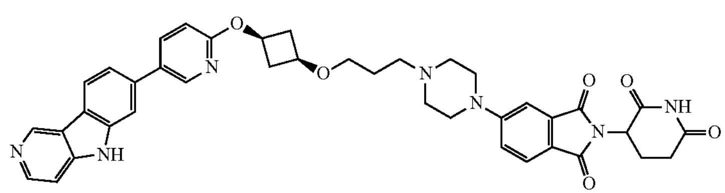 [SMILES: O=C1CCC(N2C(=O)c3ccc(N4CCN(CCCO[C@H]5C[C@@H](Oc6ccc(-c7ccc8c(c7)[nH]c7ccncc78)cn6)C5)CC4)cc3C2=O)C(=O)N1] | C | 714.3 | ¹H NMR (400 MHz, CDCl₃): δ 9.34 (s, 1H), 8.55 (d, J = 5.6 Hz, 1H), 8.44 (m, 2H), 8.20 (d, J = 8.4 Hz, 1H), 7.87-7.92 (m, 3H), 7.68 (d, J = 8.4 Hz, 1H), 7.60 (s, 1H), 7.48-7.50 (d, J = 5.6 Hz, 1H), 7.38 (d, J = 5.6 Hz, 1H), 7.06 (m, 1H), |

TABLE 2-continued

Exemplary PROTAC of the present disclosure.

| Ex. | Structure | Degradation activity* | MH + (1) [MH + (2), if isotope] | NMR transcript |
|---|---|---|---|---|
| | | | | 6.84 (d, J = 8.8 Hz, 2H), 4.93-4.94 (m, 2H), 3.75 (m, 2H), 3.42-3.49 (m, 6H), 2.72-2.98 (m, 5H), 2.61 (s, 4H), 2.53 (t, J = 7.2 Hz, 2H), 2.15-2.18 (m, 2H), 1.81 (t, J = 6.8 5 Hz, 2H). |
| 54 | 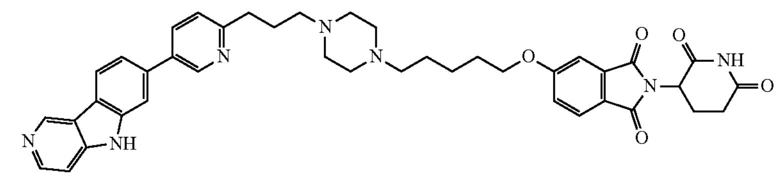 [SMILES: O=C1CCC(N2C(=O)c3ccc(OCCCCCN4CCN(CCCc5ccc(-c6ccc7c(c6)[nH]c6ccncc67)cn5)CC4)cc3C2=O)C(=O)N1] | C | 714.3 | ¹H NMR (400 MHz, CD₃OD): δ 9.31 (s, 1H), 8.83 (s, 1H), 8.42 (d, J = 6.1 Hz, 2H), 8.34 (d, J = 8.3 Hz, 1H), 8.14 (d, J = 8.0 Hz, 1H), 7.84 (s, 1H), 7.78 (d, J = 8.5 Hz, 1H), 7.61 (dd, J = 16.5, 6.4 Hz, 2H), 7.47 (d, J = 8.3 Hz, 1H), 7.36 (s, 1H), 7.28 (d, J = 8.2 Hz, 1H), 5.06-5.13 (m, 1H), 4.14 (s, 2H), 2.83 (m, 18H), 2.04 (s, 3H), 1.87 (s, 2H), 1.69 (s, 2H), 1.55 (s, 2H). |
| 55 | 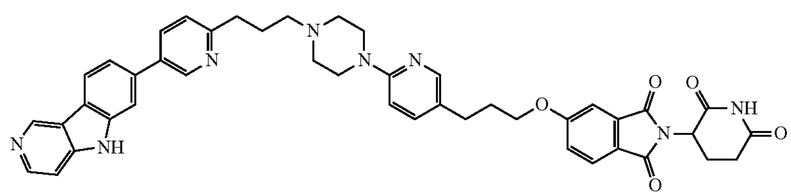 [SMILES: O=C1CCC(N2C(=O)c3ccc(OCCCc4ccc(N5CCN(CCCc6ccc(-c7ccc8c(c7)[nH]c7ccncc78)cn6)CC5)nc4)cc3C2=O)C(=O)N1] | C | 763.3 | ¹H NMR (400 MHz, MeOD): δ 9.62 (s, 1H), 9.03 (s, 1H), 8.58 (d, J = 6.8 Hz, 1H), 8.52 (d, J = 8.0 Hz, 1H), 8.31-8.40 (m, 1H), 8.08 (s, 1H), 7.87-7.99 (m, 2H), 7.78-7.87 (m, 3H), 7.68-7.72 (m, 1H), 7.26-7.30 (m, 2H), 7.10-7.14 (m, 1H), 5.08-5.12 (m, 1H), 4.17 (t, J = 6.0 Hz, 2H), 3.81-3.92 (m, 4H), 3.50-3.60 (m, 4H), 3.30-3.40 (m, 2H), 3.10-3.18 (m, 2H), 2.71-2.86 (m, 5H), 2.30-2.33 (m, 2H), 2.10-2.16 (m, 3H), |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 56 | 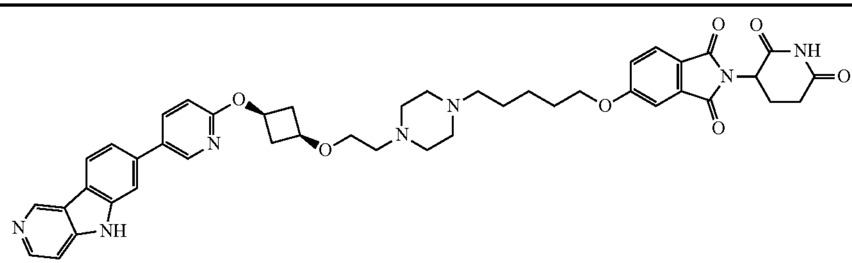 | C | 786.3 | ¹H NMR (400 MHz, CDCl₃) δ 9.33 (s, 1H), 8.89 (s, 1H), 8.53 (s, 1H), 8.42 (s, 1H), 8.18 (d, J = 8.2 Hz, 1H), 7.87 (d, J = 6.2 Hz, 1H), 7.77 (d, J = 8.2 Hz, 1H), 7.62 (s, 1H), 7.49 (d, J = 7.7 Hz, 1H), 7.42 (s, 1H), 7.29 (d, J = 11.5 Hz, 1H), 7.17 (d, J = 6.4 Hz, 1H), 6.82 (d, J = 8.2 Hz, 1H), 5.34 (s, 2H), 5.00-4.87 (m, 1H), 4.07 (s, 2H), 3.75 (s, 1H), 3.57 (s, 1H), 3.04-2.49 (m, 10H), 2.20 (m, 4H), 2.01 (s, 4H), 1.85 (s, 3H), 1.75-1.55 (m, 3H), 1.52 (s, 2H). |
| 57 | 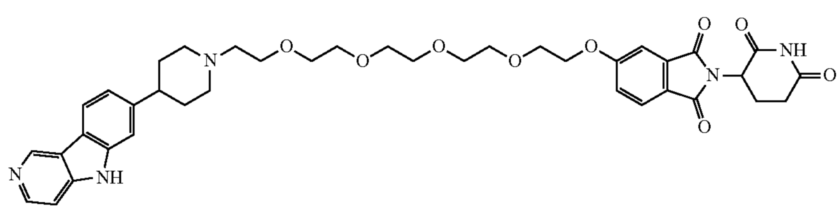 [SMILES: O=C1CCC(N2C(=O)c3ccc(OCCOCCOCCOCCOCCN4CCC(c5ccc6c(c5)[nH]c5ccncc56)CC4)cc3C2=O)C(=O)N1] | C | 728.3 | ¹H NMR (400 MHz, CD₃OD): δ 9.30 (s, 1H), 8.42-8.60 (m, 2H), 8.19 (d, J = 8.0 Hz, 1H), 7.60-7.65 (m, 2H), 7.52 (s, 1H), 7.31 (d, J = 8.0 Hz, 1H), 7.19 (s, 1H), 7.12-7.14 (m, 1H), 5.07-5.10 (m, 1H), 4.12 (t, J = 4.0 Hz, 2H), 3.66-3.86 (m, 18H), 3.37 (s, 2H), 3.15-3.20 (m, 3H), 2.71-2.76 (m, 3H), 2.09-2.22 (m, 5H). |
| 58 | 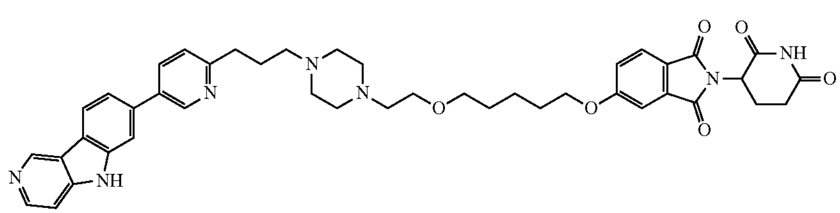 [SMILES: O=C1CCC(N2C(=O)c3ccc(OCCCCCOCCN4CCN(CCCc5ccc(-c6ccc7c(c6)[nH]c6ccncc67)cn5)CC4)cc3C2=O)C(=O)N1] | C | 758.3 | ¹H NMR (400 MHz, CD₃OD): δ 9.25 (s, 1H), 8.79 (s, 1H), 8.39 (d, J = 6.0 Hz, 1H), 8.30 (d, J = 8.0 Hz, 1H), 8.12 (d, J = 8.0 Hz, 1H), 7.79 (s, 1H), 7.76 (d, J = 8.4 Hz, 1H), 7.59 (d, J = 8.0 Hz, 1H), 7.52 (d, J = 5.2 Hz, 1H), 7.44 (d, J = 8.0 Hz, 1H), 7.35 (d, J = 6.0 Hz, 1H), 5.07-5.09 (m, 1H), 4.13 (t, J = 6.4 Hz, 2H), 3.59 (t, |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 59 | 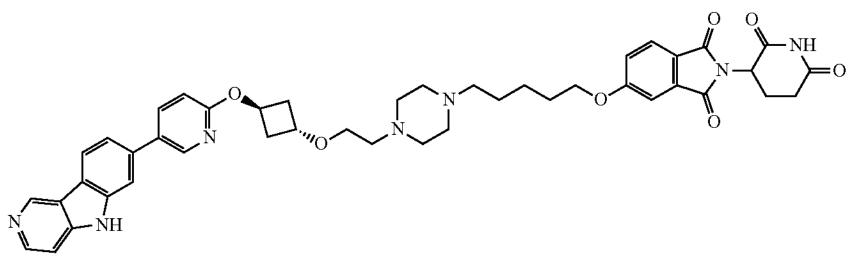 [SMILES: O=C1CCC(N2C(=O)c3ccc(OCCCCCN4CCN(CCO[C@H]5C[C@H](Oc6ccc(-c7ccc8c(c7)[nH]c7ccncc78)cn6)C5)CC4)cc3C2=O)C(=O)N1] | C | 786.3 | ¹H NMR (400 MHz, DMSO-d₆) δ 11.79 (s, 1H), 11.11 (s, 1H), 9.35 (s, 1H), 8.55 (s, 1H), 8.42 (d, J = 5.4 Hz, 1H), 8.29 (d, J = 8.2 Hz, 1H), 8.17 (s, 1H), 8.11 (d, J = 8.6 Hz, 1H), 7.82 (d, J = 8.6 Hz, 1H), 7.76 (s, 1H), 7.55 (d, J = 8.2 Hz, 1H), 7.48 (d, J = 5.6 Hz, 1H), 7.42 (s, 1H), 7.34 (d, J = 8.0 Hz, 1H), 6.93 (d, J = 8.6 Hz, 1H), 5.31 (s, 1H), 5.11 (dd, J = 12.9, 5.2 Hz, 1H), 4.17 (d, J = 6.7 Hz, 3H), 3.42 (d, J = 5.4 Hz, 2H), 2.96-2.78 (m, 2H), 2.60 (dd, J = 34.5, 18.5 Hz, 2H), 2.37 (dd, J = 44.1, 5.8 Hz, 13H), 2.01 (d, J = 14.9 Hz, 2H), 1.76 (s, 2H), 1.41 (dd, J = 43.8, 29.4 Hz, 4H), 1.23 (s, 2H). |
| | | | | J = 5.2 Hz, 2H), 3.47 (t, J = 6.0 Hz, 2H), 2.47-2.88 (m, 16H), 1.98-2.1 (m, 4H), 1.80-1.84 (m, 2H), 1.55-1.57 (m, 5H). |
| 60 | 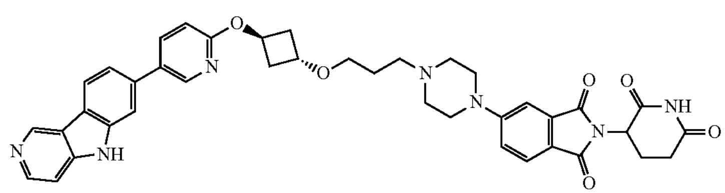 [SMILES: O=C1CCC(N2C(=O)c3ccc(N4CCN(CCCO[C@H]5C[C@H](Oc6ccc(-c7ccc8c(c7)[nH]c7ccncc78)cn6)C5)CC4)cc3C2=O)C(=O)N1] | C | 714.3 | ¹H NMR (400 MHz, DMSO-d₆): δ 11.07 (s, 1H), 9.76 (s, 1H), 8.67 (d, J = 6.0 Hz, 1H), 8.60 (s, 1H), 8.52 (d, J = 8.4 Hz, 1H), 8.16 (d, J = 8.4 Hz, 1H), 8.80-8.02 (m, 2H), 7.77 (t, J = 8.4 Hz, 2H), 7.50 (s, 1H), 7.37 (d, J = 8.0 Hz, 1H), 6.96 (d, J = 8.8 Hz, 1H), 5.36 (m, 1H), 5.07-5.11 (m, 1H), 4.24 (br, 3H), 3.62 (br, 9H), 3.55 (s, 3H), 3.17-3.25 (m, 6H), 2.86-2.93 (m, |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 61 | 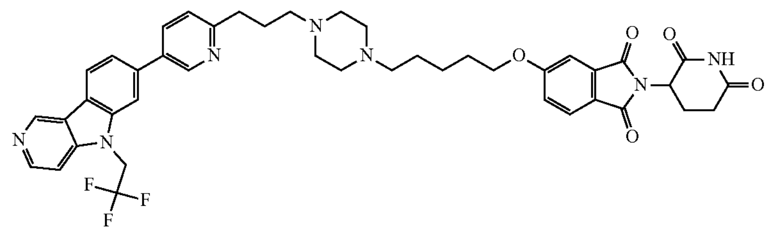 [SMILES: O=C1CCC(N2C(=O)c3ccc(OCCCCCN4CCN(CCCc5ccc(-c6ccc7c8cnccc8n(CC(F)(F)F)c7c6)cn5)CC4)cc3C2=O)C(=O)N1] | C | 796.3 | ¹H NMR (400 MHz, CD₃OD) δ 9.35 (s, 1H), 8.89 (s, 1H), 8.55 (d, J = 5.8 Hz, 1H), 8.40 (d, J = 8.0 Hz, 1H), 8.17-8.22 (m, 1H), 8.05 (s, 1H), 7.81 (d, J = 8.3 Hz, 1H), 7.74 (d, J = 5.6 Hz, 1H), 7.51 (d, J = 8.2 Hz, 1H), 7.40 (s, 1H), 7.33 (s, 1H), 5.40 (d, J = 9.1 Hz, 2H), 5.08-5.16 (m, 1H), 4.95 (s, 4H), 4.59 (s, 2H), 4.18 (t, J = 6.2 Hz, 1H), 2.91-3.00 (m, 2H), 2.58-2.91 (m, 9H), 2.12-2.18 (m, 1H), 2.06 (s, 2H), 1.89 (s, 2H), 1.69 (s, 2H), 1.57 (s, 2H). 1H), 2.38-2.62 (m, 4H), 1.07-2.04 (m, 1H). |
| 62 | 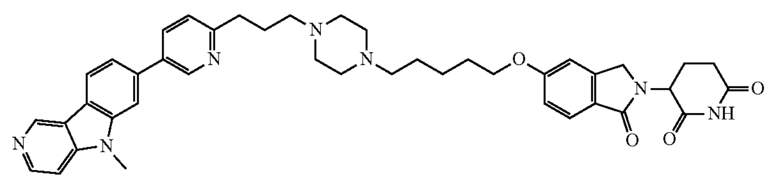 [SMILES: Cn1c2ccncc2c2ccc(-c3ccc(CCCN4CCN(CCCCCOc5ccc6c(c5)CN(C5CCC(=O)NC5=O)C6=O)CC4)nc3)cc21] | C | 714.3 | ¹HNMR (400 MHz, MeOD): δ 9.27 (s, 1H), 8.86 (d, J = 2.0 Hz, 1H), 8.46 (d, J = 6.0 Hz, 1H), 8.33 (d, J = 8.0 Hz, 1H), 8.16 (d, J = 2.4 Hz, 1H), 7.90 (s, 1H), 7.59-7.70 (m, 3H), 7.47 (d, J = 6.0 Hz, 1H), 7.03-7.09 (m, 2H), 5.06-5.12 (m, 1H), 4.42 (d, J = 5.6 Hz, 2H), 4.07 (t, J = 6.4 Hz, 2H), 3.99 (s, 3H), 2.89-2.96 (m, 3H), 2.51-2.75 (m, 13H), 2.12-2.24 (m, 1H), 2.01-2.03 (m, 3H), 1.82-1.84 (m, 2H), 1.52-1.63 (m, 6H). |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 63 | 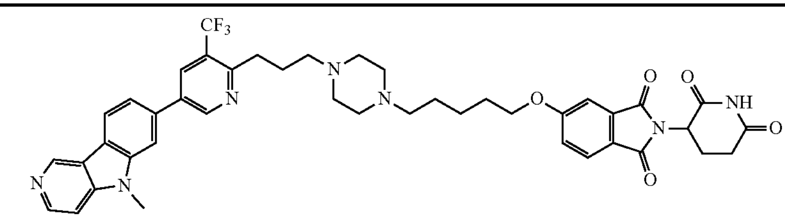 | C | 796.2 | ¹H NMR (400 MHz, CD₃OD): δ 9.25 (s, 1H), 8.45 (s, 1H), 8.23 (d, J = 7.6 Hz, 1H), 7.76 (d, J = 8.4 Hz, 1H), 7.66 (s, 1H), 7.59 (d, J = 8.0 Hz, 1H), 7.39 (d, J = 8.4 Hz, 1H), 7.35 (s, 2H), 7.26-7.28 (m, 1H), 6.06 (s, 1H), 5.72 (s, 1H), 5.06-5.08 (m, 1H), 4.30 (d, J = 6.4 Hz, 1H), 4.11-4.15 (m, 2H), 3.90-3.94 (m, 4H), 3.70-3.74 (m, 2H), 3.03-3.06 (m, 2H), 2.82-2.88 (m, 4H), 2.71-2.75 (m, 6H), 2.51-2.55 (m, 3H), 2.05-2.25 (m, 2H), 1.82-1.86 (m, 2H), 1.61-1.63 (m, 2H), 1.51-1.52 (m, 2H). |
| 64 | 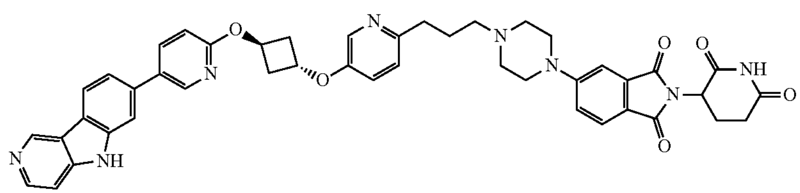 [SMILES: O=C1CCC(N2C(=O)c3ccc(N4CCN(CCCc5ccc(O[C@H]6C[C@H](Oc7ccc(-c8ccc9c(c8)[nH]c8ccncc89)cn7)C6)cn5)CC4)cc3C2=O)C(=O)N1] | C | 791.2 | ¹H NMR (400 MHz, CD₃OD) δ 9.42 (s, 1H), 8.53 (d, J = 2.3 Hz, 1H), 8.50 (d, J = 6.1 Hz, 1H), 8.38 (d, J = 8.1 Hz, 1H), 8.13 (d, J = 8.0 Hz, 2H), 7.87 (s, 1H), 7.71-7.78 (m, 2H), 7.68 (d, J = 8.3 Hz, 1H), 7.42 (s, 1H), 7.33 (s, 2H), 7.29 (d, J = 8.6 Hz, 1H), 6.99 (d, J = 8.6 Hz, 1H), 5.51 (s, 2H), 5.06-5.14 (m, 2H), 3.55 (s, 4H), 2.58-3.03 (m, 15H), 2.04 (m, 3H). |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 65 | 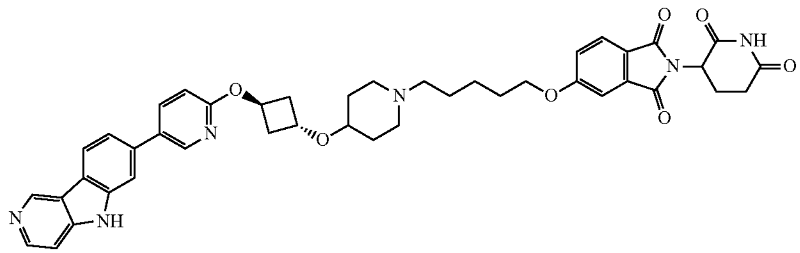 | C | 757.4 | ¹H NMR: (400 MHz, DMSO-d₆) δ: 11.80 (s, 1H), 11.11 (s, 1H), 9.35 (s, 1H), 8.55 (d, J = 2.4 Hz, 1H), 8.42 (d, J = 5.6 Hz, 1H), 8.29 (d, J = 8.4 Hz, 1H), 8.18 (s, 3H), 8.11 (dd, J = 2.4, 8.8 Hz, 1H), 7.83 (d, J = 8.4 Hz, 1H), 7.76 (s, 1H), 7.55 (d, J = 8.4 Hz, 1H), 7.48 (d, J = 5.6 Hz, 1H), 7.42 (d, J = 2.0 Hz, 1H), 7.35 (dd, J = 2.0, 8.4 Hz, 1H), 6.92 (d, J = 8.4 Hz, 1H), 5.30 (d, J = 3.6 Hz, 1H), 5.11 (dd, J = 5.6, 13.2 Hz, 1H), 4.35 (t, J = 6.4 Hz, 1H), 4.17 (t, J = 6.4 Hz, 2H), 2.93-2.84 (m, 2H), 2.77 (s, 2H), 2.63-2.54 (m, 3H), 2.37 (d, J = 6.0 Hz, 4H), 2.22-1.98 (m, 4H), 1.87-1.74 (m, 4H), 1.53-1.38 (m, 6H). |
| 66 | 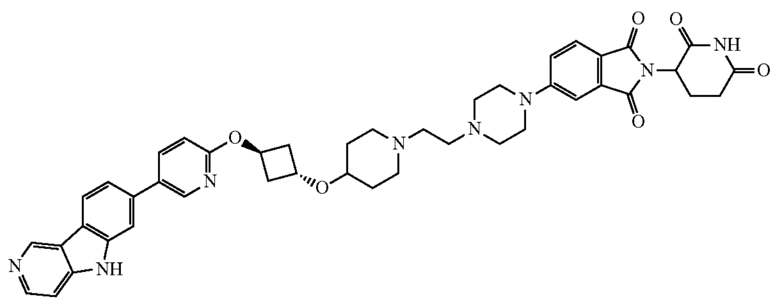 [SMILES: O=C1CCC(N2C(=O)c3ccc(N4CCN(CCN5CCC(O[C@H]6C[C@H](Oc7ccc(-c8ccc9c(c8)[nH]c8ccncc89)cn7)C6)CC5)CC4)cc3C2=O)C(=O)N1] | C | 783.6 | ¹H NMR (400 MHz, DMSO-d₆): δ 13.21 (s, 1H), 11.08 (s, 2H), 9.76 (s, 1H), 8.67 (d, J = 6.6 Hz, 1H), 8.61 (s, 1H), 8.52 (d, J = 8.3 Hz, 1H), 8.17 (d, J = 8.3 Hz, 1H), 8.02 (d, J = 7.1 Hz, 2H), 7.82-7.72 (m, 3H), 7.46 (s, 2H), 7.35 (s, 2H), 6.96 (d, J = 8.5 Hz, 1H), 5.34 (s, 1H), 5.08 (d, J = 7.7 Hz, 2H), 4.40 (s, 2H), 3.23 (s, 4H), 3.15 (s, 4H), 3.02 (s, 4H), 2.95-2.83 (m, 4H), 2.59 (d, J = 15.7 Hz, 4H), 2.44 (s, 2H), 2.01 (s, 5H), 1.77 (d, J = 14.7 Hz, 2H). |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 67 | 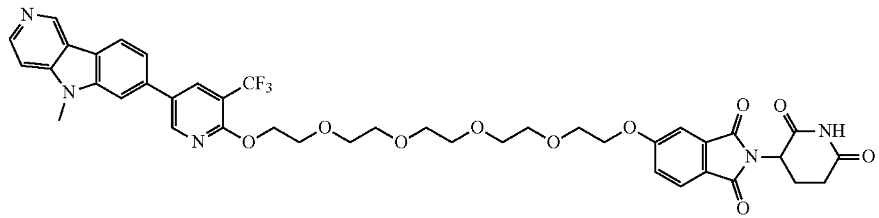 [SMILES: Cn1c2ccncc2c2ccc(-c3cnc(OCCOCCOCCOCCOCCOc4ccc5c(c4)C(=O)N(C4CCC(=O)NC4=O)C5=O)c(C(F)(F)F)c3)cc21] | A | 820.5 | $^1$H NMR (400 MHz, CD$_3$OD): δ 9.25 (s, 1H), 8.79 (s, 1H), 8.37-8.39 (d, J = 8.0 Hz, 1H), 8.28-8.39 (d, J = 8.0 Hz, 2H), 7.89 (s, 1H), 7.63-7.65 (d, J = 8.0 Hz, 1H), 7.54-7.56 (m, 2H), 7.26 (s, 1H), 7.18-7.20 (m, 1H), 5.02-5.05 (m, 1H), 4.62-4.64 (m, 2H), 4.17-4.19 (m, 2H), 3.95 (s, 3H), 3.88-3.90 (m, 2H), 3.82-3.84 (m, 2H), 3.61-3.71 (m, 13H), 2.55-2.81 (m, 3H), 2.95-2.99 (m, 2H). |
| 68 | 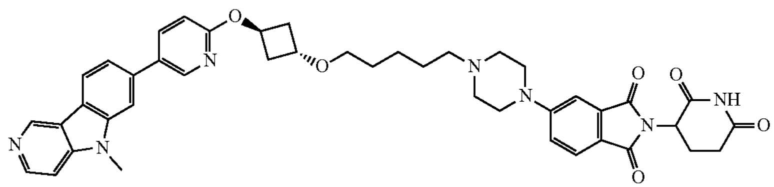 [SMILES: Cn1c2ccncc2c2ccc(-c3ccc(O[C@H]4C[C@H](OCCCCCN5CCN(c6ccc7c(c6)C(=O)N(C6CCC(=O)NC6=O)C7=O)CC5)C4)nc3)cc21] | C | 756.6 | $^1$H NMR (400 MHz, DMSO-d6): δ 11.12 (s, 1H), 9.37 (s, 1H), 8.64 (s, 1H), 8.50 (d, J = 4.0 Hz, 1H), 8.33 (d, J = 12.0 Hz, 1H), 8.00 (s, 1H), 7.68-7.60 (m, 3H), 7.34 (d, J = 4.0 Hz, 1H), 7.25 (dd, J = 8.0 Hz, 4.0 Hz, 1H), 6.94 (d, J = 8.0 Hz, 1H), 5.32 (t, J = 4.0 Hz, 1H), 5.07 (dd, J = 12.0 Hz, 8.0 Hz, 1H), 4.20-4.17 (m, 1H), 3.96 (s, 3H), 4.46 (s, 6H), 2.88-2.84 (m, 1H), 2.59-2.54 (m, 7H), 2.43-2.32 (m, 6H), 2.02-1.98 (m, 1H), 1.57-1.49 (m, 4H), 1.38-1.34 (m, 2H). |
| 69 | 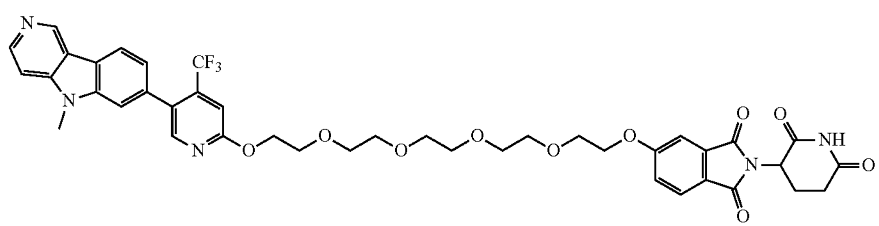 | A | 820.5 | $^1$H NMR (400 MHz, CD$_3$OD): δ 9.21 (s, 1H), 8.79 (s, 1H), 8.38 (d, J = 8.0 Hz, 2H), 7.62 (d, J = 8.0 Hz, 1H), 7.46-7.49 (m, 2H), 7.26 (s, 1H), 7.15-7.19 (m, 2H), 7.07 (s, 1H), 4.95-4.99 (m, 1H), 4.45-4.47 (m, 2H), 4.15-4.18 (m, 2H), 3.77-3.82 (m, 7H), 3.54-3.62 (m, 9H), |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 70 | 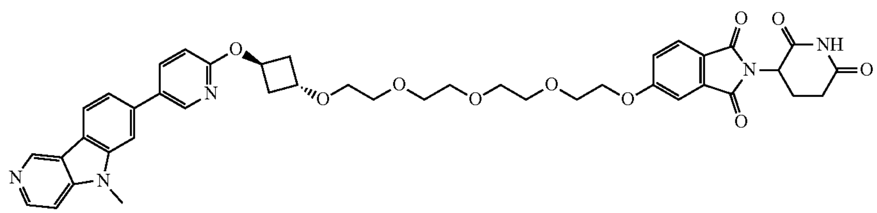 [SMILES: Cn1c2ccncc2c2ccc(-c3ccc(O[C@H]4C[C@H](OCCOCCOCCOCCOc5ccc6c(c5)C(=O)N(C5CCC(=O)NC5=O)C6=O)C4)nc3)cc21] | A | 778.5 | ¹H NMR (400 MHz, DMSO-d6): δ 11.10 (s, 1H), 9.36 (s, 1H), 8.62 (s, 1H), 8.50 (s, 1H), 8.31 (d, J = 8.2 Hz, 1H), 8.18 (d, J = 8.8 Hz, 1H), 7.97 (s, 1H), 7.81 (d, J = 8.3 Hz, 1H), 7.60 (d, J = 8.0 Hz, 2H), 7.43 (s, 1H), 7.35 (d, J = 7.8 Hz, 1H), 6.93 (d, J = 8.7 Hz, 1H), 5.31 (s, 1H), 5.11 (dd, J = 12.8, 5.1 Hz, 1H), 4.31 (s, 2H), 4.22 (s, 1H), 3.95 (s, 3H), 3.79 (s, 2H), 3.64-3.48 (m, 10H), 3.45 (d, J = 4.9 Hz, 3H), 2.86 (d, J = 13.2 Hz, 1H), 2.45-2.40 (m, 2H), 2.37-2.30 (m, 2H), 2.02 (d, J = 6.5 Hz, 1H), 2.45-2.77 (m, 3H), 1.91-1.95 (m, 1H), 1.12-1.16 (m, 1H). |
| 71 | 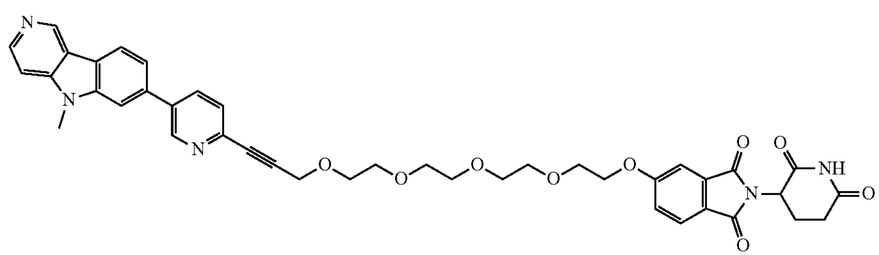 [SMILES: Cn1c2ccncc2c2ccc(-c3ccc(C#CCOCCOCCOCCOCCOc4ccc5c(c4)C(=O)N(C4CCC(=O)NC4=O)C5=O)nc3)cc21] | A | 746.5 | ¹H NMR (400 MHz, DMSO-d₆): δ 9.39 (s, 1H), 8.38 (d, J = 8.4 Hz, 1H), 8.30 (d, J = 2.0 Hz, 1H), 8.28 (d, J = 3.0 Hz, 1H), 8.11 (s, 1H), 7.80 (d, J = 8.4 Hz, 1H), 7.72 (d, J = 7.6 Hz, 1H), 7.63-7.68 (m, 2H), 7.44 (d, J = 2.0 Hz, 1H), 7.34-7.36 (m, 1H), 5.08-5.12 (m, 1H), 4.48 (s, 2H), 4.31 (t, J = 3.6 Hz, 2H), 3.98 (s, 3H), 3.80 (s, 3H), 3.53-3.79 (m, 12H), 1.95-2.08 (m, 2H). |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 72 | 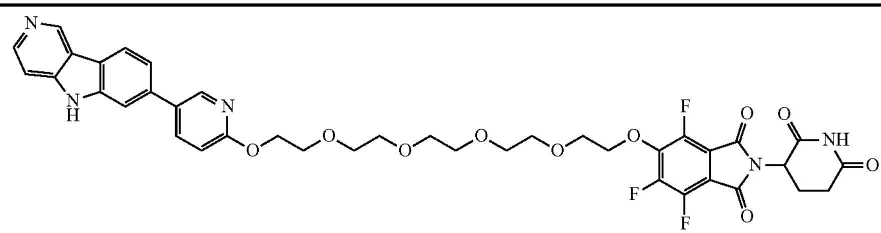 | C | 792.5 | ¹H NMR (400 MHz, CD₃OD): δ 13.19 (s, 1H), 9.77 (s, 1H), 8.62-8.68 (m, 2H), 8.52 (d, J = 8.0 Hz, 1H), 8.16 (s, 1H), 8.01-8.02 (m, 2H), 7.80-7.81 (m, 1H), 7.15-7.28 (m, 1H), 6.99 (d, J = 8.0 Hz, 1H), 5.15-5.23 (m, 1H), 4.43-4.45 (m, 2H), 3.77-3.89 (m, 4H), 3.49-3.60 (m, 12H), 2.86-3.05 (m, 3H), 1.99-2.01 (m, 1H). |
| 73 | 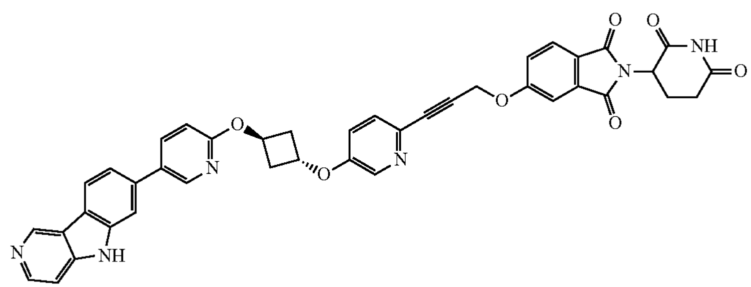 [SMILES: O=C1CCC(N2C(=O)c3ccc(OCC#Cc4ccc(O[C@H]5C[C@H](Oc6ccc(-c7ccc8c(c7)[nH]c7ccncc78)cn6)C5)cn4)cc3C2=O)C(=O)N1] | A | 719.4 | ¹H NMR (400 MHz, DMSOd-6): δ 2.04-2.07 (m, 1H), 2.57-2.77 (m, 6H), 2.86-2.93 (m, 1H), 5.10-5.14 (m, 2H), 5.32 (s, 2H), 5.38-5.48 (m, 1H), 6.97 (d, J = 8.0 Hz, 1H), 7.32-7.33 (m, 1H), 7.46-7.58 (m, 5H), 7.77 (s, 1H), 7.90 (d, J = 7.2 Hz, 1H), 8.14 (d, J = 7.2 Hz, 1H), 8.25 (s, 1H), 8.30 (d, J = 7.6 Hz, 1H), 8.43 (s, 1H), 8.56 (s, 1H), 9.36 (s, 1H), 11.12 (s, 1H), 11.82 (s, 1H). |
| 74 | 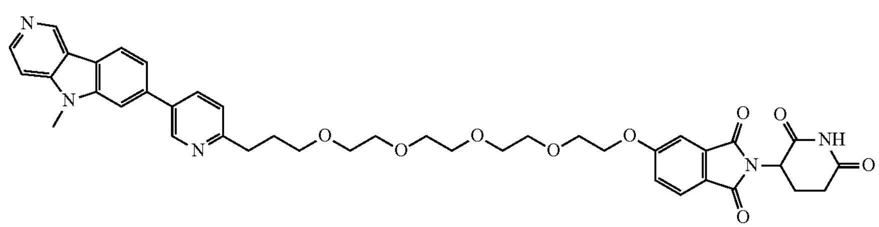 [SMILES: Cn1c2ccncc2c2ccc(-c3ccc(CCCOCCOCCOCCOCCOc4ccc5c(c4)C(=O)N(C4CCC(=O)NC4=O)C5=O)nc3)cc21] | A | 750.5 | ¹H NMR (400 MHz, CDCl₃): δ 9.65 (s, 1H), 9.22 (s, 1H), 8.67-8.73 (m, 2H), 8.47 (d, J = 7.6 Hz, 1H), 8.36 (d, J = 8.0 Hz, 1H), 7.97 (s, 1 H), 7.83 (s, 1H), 7.81 (s, 1H), 7.59-7.71 (m, 2H), 7.04 (d, J = 9.2 Hz, 2H), 4.93-4.96 (m, 1H), 4.10 (s, 5H), 3.87 (s, 1H), 3.55-3.76 (m, 18H), 3.26 (s, 2H), 2.12-2.16 (m, 2H). |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 75 | 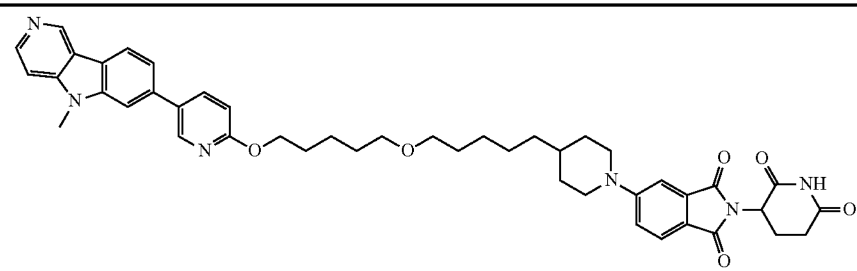 | C | 771.6 | ¹H NMR (400 MHz, DMSO-d₆) δ= 9.38-11.07 (s, 1H), 9.32 (m, 1H), 8.66-8.63 (d, J = 12 Hz 1H), 8.50-8.48 (m, J = 8 Hz 1H), 8.36 (s, 2H), 8.34-8.29 (m, 1H), 8.21-8.14 (m, 1H), 7.99-7.94 (m, 1H), 7.61 (s, 3H), 7.28-7.22 (m, 1H), 7.19-7.12 (m, 1H), 6.96-6.89 (m, 1H), 5.09-5.00 (m, 1H), 4.36-4.29 (m, 2H), 3.95 (s, 5H), 3.34 (s, 4H), 2.87 (s, 2H), 2.99-2.78 (m, 1H), 2.82-2.73 (m, 1H), 2.04-1.93 (m, 1H), 1.82-1.65 (m, 4H), 1.61-1.52 (m, 2H), 1.52-1.41 (m, 5H), 1.28 (s, 4H), 1.22-1.05 (m, 4H). |
| 76 | 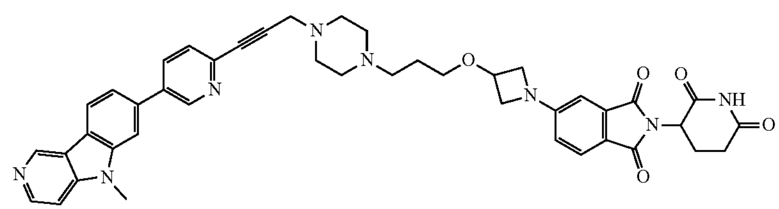 [SMILES: Cn1c2ccncc2c2ccc(-c3ccc(C#CCN4CCN(CCCOC5CN(c6ccc7c(c6)C(=O)N(C6CCC(=O)NC6=O)C7=O)C5)CC4)nc3)cc21] | C | 751.5 | ¹H NMR (400 MHz, CD₃OD): δ 9.32 (s, 1H), 8.96 (s, 1H), 8.45-8.52 (m, 2H), 8.37 (d, J = 8.0 Hz, 1H), 8.27-8.31 (m, 1H), 7.98 (s, 1H), 7.61-7.98 (m, 4H), 6.82 9s, 1H), 6.65-6.67 (m, 1H), 5.01-5.05 (m, 1H), 4.59 (m, 1H), 4.27 (t, J = 8.4 Hz, 1H), 4.02 (s, 3H), 3.88-3.91 (m, 2H), 3.70 (s, 2H), 3.57 (t, J = 6.0 Hz, 2H), 3.41 (m, 1H), 3.13-3.17 (m, 2H), 2.66-2.86 (m, 11H), 2.02-2.03 (m, 3H). |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 77 | 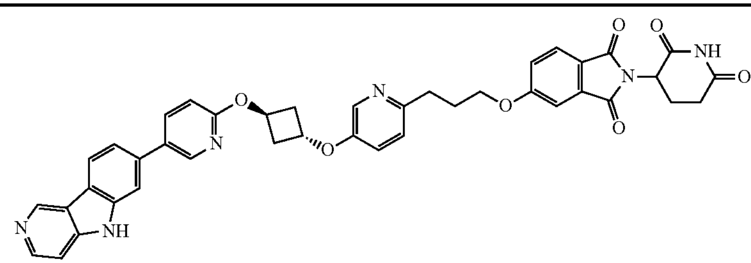 | C | 723.5 | $^1$H NMR (400 MHz, CD$_3$OD): δ 9.56 (s, 1H), 8.54-8.56 (m, 2H), 8.45 (d, J = 8.4 Hz, 1H), 8.37 (d, J = 2.4 Hz, 1H), 8.13 (d, J = 8.0 Hz, 1H), 7.97 (d, J = 8.0 Hz, 1H), 7.88 (d, J = 8.8 Hz, 2H), 7.81 (d, J = 8.4 Hz, 1H), 7.79 (s, 1H), 7.76-7.78 (d, J = 8 Hz, 1H), 7.29 (s, 1H), 7.21 (d, J = 8.0 Hz, 1H), 6.98 (d, J = 8.0 Hz, 1H), 5.48-5.52 (m, 1H), 5.32-5.34 (m, 1H), 5.18-5.22 (m, 1H), 5.06-5.10 (m, 1H), 4.25-4.28 (m, 2H), 3.21-3.23 (m, 3H), 2.78-2.81 (m, 5H), 2.67-2.70 (m, 2H), 2.30-2.33 (m, 2H), 2.17-2.19 (m, 1H), 1.97-2.07 (m, 3H). |
| 78 | 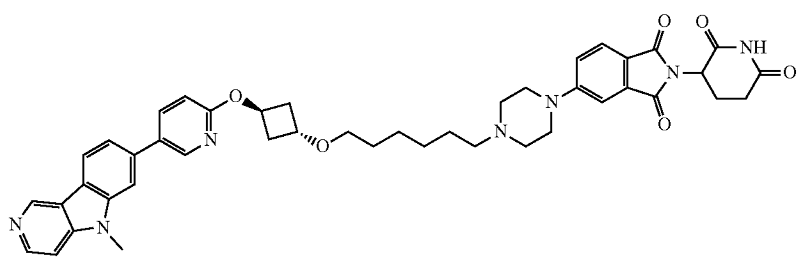 [SMILES: Cn1c2ccncc2c2ccc(-c3ccc(O[C@H]4C[C@H](OCCCCCCN5CCN(c6ccc7c(c6)C(=O)N(C6CCC(=O)NC6=O)C7=O)CC5)C4)nc3)cc21] | C | 770.6 | $^1$H NMR (400 MHz, DMSO-d6): δ 11.08 (s, 1H), 9.35 (s, 1H), 8.64 (t, J = 3.9 Hz, 1H), 8.49 (d, J = 4.7 Hz, 1H), 8.32 (d, J = 8.1 Hz, 1H), 8.19 (dd, J = 8.6, 2.5 Hz, 1H), 7.98 (s, 1H), 7.68-7.48 (m, 3H), 7.31 (d, J = 7.8 Hz, 1H), 7.20 (t, J = 9.5 Hz, 1H), 6.94 (d, J = 8.6 Hz, 1H), 5.07 (dd, J = 12.9, 5.3 Hz, 1H), 4.33 (t, J = 6.5 Hz, 2H), 3.95 (s, 3H), 3.65 (m, 1H), 3.51-3.41 (m, 3H), 3.36-3.23 (m, 5H), 2.95-2.83 (m, 6H), 2.43-2.28 (m, 1H), 2.05-1.96 (m, 1H), 1.79-1.73 (m, 1H), 1.67-1.61 (m, 1H), 1.42 (m, 7H). |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 79 | 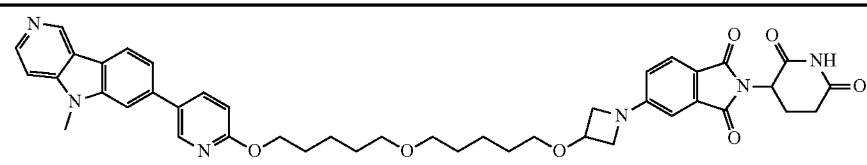 | A | 759.6 | $^1$H NMR (400 MHz, CDCl$_3$): δ 9.35 (s, 1H), 8.59 (d, J = 5.7 Hz, 1H), 8.49 (s, 1H), 8.28 (s, 1H), 8.21 (d, J = 10.6 Hz, 1H), 8.00 (s, 1H), 7.91 (d, J = 11.0 Hz, 1H), 7.63 (d, J = 8.2 Hz, 1H), 7.57 (s, 1H), 7.51 (d, J = 9.3 Hz, 1H), 7.37 (d, J = 5.9 Hz, 1H), 6.85 (d, J = 8.6 Hz, 1H), 6.77 (s, 1H), 4.92 (m, 1H), 4.45 (s, 1H), 4.36 (t, J = 6.6 Hz, 2H), 4.16-4.26 (m, 2H), 3.83-3.98 (m, 4H), 3.44 (m, 4H), 2.63-2.92 (m, 3H), 2.11 (d, J = 6.4 Hz, 2H), 1.79-1.89 (m, 3H), 1.44-1.70 (m, 10H). |
| 80 | 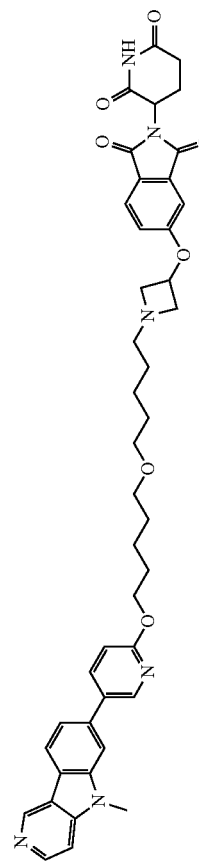 | A | 759.6 | $^1$H NMR (400 MHz, DMSO-d$_6$): δ 11.12 (s, 1H), 9.35 (s, 1H), 8.63 (d, J = 2.3 Hz, 1H), 8.50 (s, 1H), 8.31 (d, J = 8.1 Hz, 1H), 8.18 (dd, J = 8.6, 2.5 Hz, 1H), 7.96 (s, 1H), 7.80 (d, J = 8.8 Hz, 1H), 7.60 (d, J = 6.8 Hz, 2H), 7.23 (d, J = 7.2 Hz, 2H), 6.93 (d, J = 8.6 Hz, 1H), 5.10 (m, 1H), 5.02-4.95 (m, 1H), 4.32 (t, J = 6.6 Hz, 2H), 3.95 (s, 3H), 3.70 (t, J = 6.8 Hz, 2H), 2.99-2.95 (m, 2H), 2.86 (d, J = 12.1 Hz, 2H), 2.64 (br, 1H), 2.55 (br, 2H), 2.33 (s, 2H), 2.06-1.96 (m, 3H), 1.81-1.70 (m, 3H), 1.60-1.40 (m, 8H). |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 81 | 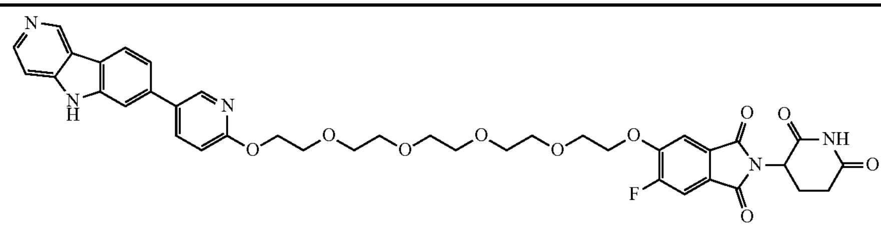 | A | 756.5 | ¹H NMR (400 MHz, CDCl₃): δ 9.31 (s, 1H), 8.51 (s, 1H), 8.40 (s, 1H), 8.11 (d, J = 8.0 Hz, 1H), 7.82-7.83 (m, 1H), 7.60 (s, 1H), 7.37-7.45 (m, 3H), 6.84 (d, J = 8.0 Hz, 1H), 4.92-4.95 (m, 1H), 4.53 (t, J = 4.8 Hz, 2H), 4.24 (t, J = 4.8 Hz, 2H), 3.89-3.91 (m, 4H), 3.67-3.75 (m, 12H), 2.74-2.92 (m, 3H), 2.12-2.16 (m, 1H). |
| 82 | 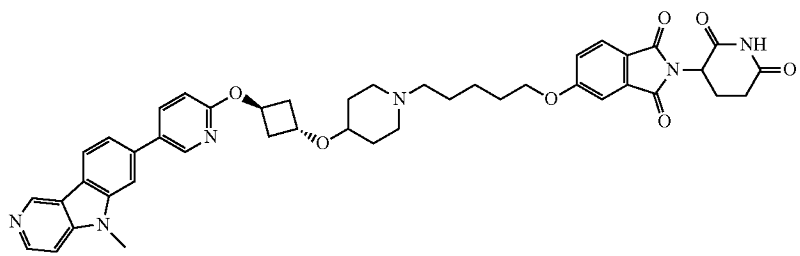 [SMILES: Cn1c2ccncc2c2ccc(-c3ccc(O[C@H]4C[C@H](OC5CCN(CCCCCOc6ccc7c(c6)C(=O)N(C6CCC(=O)NC6=O)C7=O)CC5)C4)nc3)cc21] | C | 771.6 | ¹H NMR (400 MHz, DMSO-d₆): δ 11.12 (s, 1H), 9.36 (s, 1H), 8.64 (d, J = 2.2 Hz, 1H), 8.50 (d, J = 5.7 Hz, 1H), 8.32 (d, J = 8.2 Hz, 1H), 8.19 (dd, J = 8.8, 2.6 Hz, 2H), 7.98 (s, 1H), 7.83 (d, J = 8.3 Hz, 1H), 7.62 (d, J = 8.4 Hz, 2H), 7.43 (d, J = 2.0 Hz, 1H), 7.35 (d, J = 8.4 Hz, 1H), 6.94 (d, J = 8.7 Hz, 1H), 5.31 (s, 1H), 5.12 (dd, J = 12.9, 5.3 Hz, 1H), 4.40-4.32 (m, 1H), 4.18 (t, J = 6.4 Hz, 2H), 3.96 (s, 3H), 2.88 (d, J = 13.2 Hz, 2H), 2.74 (s, 2H), 2.36 (m, 6H), 2.07 (s, 3H), 1.88-1.70 (m, 4H), 1.60-1.34 (m, 6H). |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 83 | 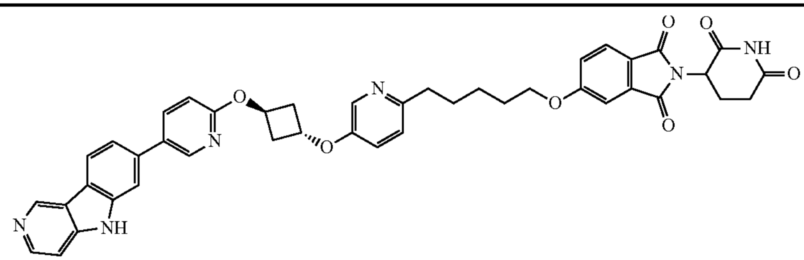 | C | 751.5 | 1H NMR (400 MHz, CD3OD): δ 9.58 (s, 1H), 8.58 (d, J = 6.4 Hz, 1H), 8.54-8.55 (d, J = 4 Hz, 1H), 8.47 (d, J = 8.4 Hz, 1H), 8.39 (d, J = 2.8 Hz, 1H), 8.12-8.17 (m, 2H), 7.97-8.01 (m, 2H), 7.91 (d, J = 9.2 Hz, 1H), 7.79-7.83 (m, 2H), 7.39 (s, 1H), 7.32 (d, J = 8.0 Hz, 1H), 7.01 (d, J = 8.4 Hz, 1H), 5.50-5.53 (m, 1H), 5.22-5.24 (m, 1H), 5.12-5.14 (m, 1H), 4.18-4.21 (m, 2H), 3.04-3.07 (m, 2H), 2.74-2.84 (m, 7H), 2.18-2.20 (m, 1H), 2.09-2.13 (m, 1H), 2.02-2.06 (m, 1H), 1.85-1.95 (m, 4H), 1.55-1.65 (m, 4H). |
| 84 | 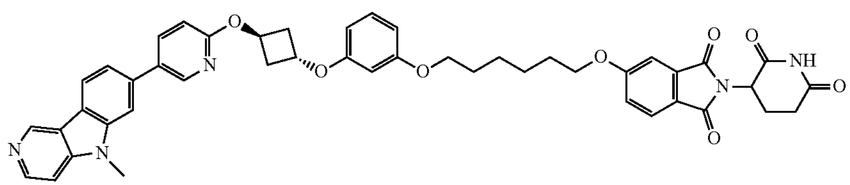 [SMILES: Cn1c2ccncc2c2ccc(-c3ccc(O[C@H]4C[C@H](Oc5cccc(OCCCCCCOc6ccc7c(c6)C(=O)N(C6CCC(=O)NC6=O)C7=O)c5)C4)nc3)cc21] | C | 794.5 | 1H NMR (400 MHz, CDCl3): δ 9.34 (s, 1H), 8.58 (d, J = 5.6 Hz, 1H), 8.21-8.48 (m, 2H), 8.20 (d, J = 8.4 Hz, 1H), 7.88-7.91 (m, 1H), 7.76 (d, J = 8.4 Hz, 1H), 7.56 (s, 1H), 7.51 (d, J = 8.0 Hz, 1H), 7.33-7.36 (m, 2H), 7.16-7.18 (m, 2H), 6.86 (d, J = 8.4 Hz, 1H), 6.39-6.51 (m, 3H), 5.52-5.54 (m, 1H), 4.94-4.96 (m, 2H), 4.07-4.10 (m, 2H), 3.91-3.97 (m, 5H), 3.22-3.24 (m, 1H), 2.69-2.76 (m, 7H), 2.14-2.16 (m, 1H), 1.82-1.86 (m, 4H), 1.54-1.57 (m, 4H). |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 85 | 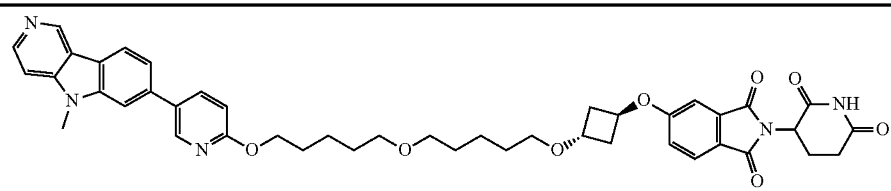 | A | 774.6 | ¹H NMR (400 MHz, CDCl₃): δ 9.32 (s, 1H), 8.58-8.59 (d, J = 4.0 Hz, 2H), 8.48 (s, 1H), 8.16-8.18 (d, J = 8.0 Hz, 1H), 7.89-7.91 (d, J = 8.0 Hz, 1H), 7.74-7.76 (d, J = 8.0 Hz, 1H), 7.56 (s, 1H), 7.47-7.49 (d, J = 8.0 Hz, 1H), 7.32-7.33 (d, J = 4.0 Hz, 1H), 7.19 (s, 1H), 7.06-7.08 (d, J = 8.0 Hz, 1H), 6.84-6.86 (d, J = 8.0 Hz, 1H), 4.93 (m, 2H), 4.35-4.38 (m, 2H), 4.21 (s, 1H), 3.90 (s, 3H), 3.35-3.49 (m, 7H), 2.68-2.95 (m, 3H), 2.44-2.51 (m, 4H), 2.15 (m, 1H), 1.88 (m, 2H), 1.56-1.68 (m, 9H), 1.44 (d, J = 8.0 Hz, 2H). |
| 86 | 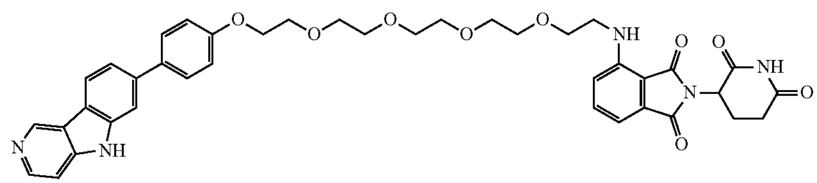 [SMILES: O=C1CCC(N2C(=O)c3cccc(NCCOCCOCCOCCOCCOc4ccc(-c5ccc6c(c5)[nH]c5ccncc56)cc4)c3C2=O)C(=O)N1] | C | 736.5 | ¹H NMR (400 MHz, CDCl₃): δ 9.28 (s, 2H), 8.50 (s, 1H), 8.08 (s, 1H), 7.35-7.57 (m, 6H), 6.94-6.96 (m, 3H), 6.77 (s, 1H), 6.38 (s, 1H), 4.88-4.90 (m, 1H), 4.14 (s, 2H), 3.60-3.86 (m, 17H), 3.31-3.34 (m, 2H), 2.66-2.86 (m, 3H), 2.03-2.05 (m, 1H). |
| 87 | 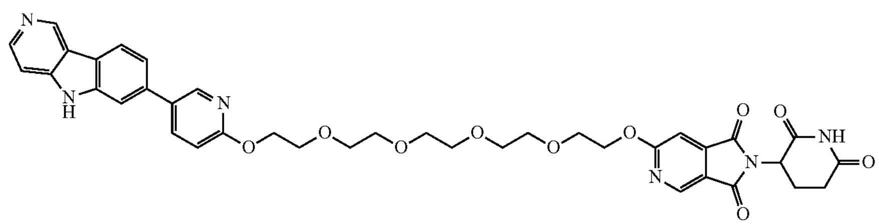 [SMILES: O=C1CCC(N2C(=O)c3cnc(OCCOCCOCCOCCOCCOc4ccc(-c5ccc6c(c5)[nH]c5ccncc56)cn4)cc3C2=O)C(=O)N1] | C | 739.5 | ¹H NMR (400 MHz, CDCl₃): δ 9.28 (s, 1H), 8.42 (s, 1H), 8.37-8.39 (m, 2H), 8.06 (d, J = 8.0 Hz, 1H), 7.80 (d, J = 8.0 Hz, 1H), 7.62 (s, 1H), 7.40-7.45 (m, 3H), 6.09 (s, 1H), 6.82 (d, J = 8.8 Hz, 1H), 4.94-4.99 (m, 1H), 4.54 (t, J = 4.8 Hz, 4H), 3.86-3.91 (m, 4H), 3.66-3.75 (m, 12H), 2.73-2.92 (m, 3H), 2.20-2.22 (m, 1H). |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 88 | 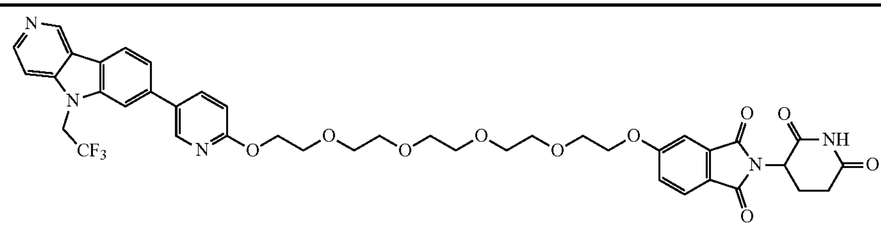 | A | 820.5 | ¹H NMR (400 MHz, CDCl₃): δ 9.35 (s, 1H), 8.63 (d, J = 7.6 Hz, 1H), 8.45 (s, 1H), 8.21 (d, J = 8.0 Hz, 1H), 8.16 (s, 1H), 7.87-7.90 (m, 1H), 7.75 (d, J = 8.4 Hz, 1H), 7.53-7.58 (m, 2H), 7.39 (s, 1H), 7.35 (s, 1H), 7.21 (d, J = 8.4 Hz, 1H), 6.91 (d, J = 8.8 Hz, 1H), 4.87-4.92 (m, 3H), 4.55 (t, J = 4.8 Hz, 2H), 4.24 (t, J = 4.8 Hz, 2H), 3.90 (t, J = 4.4 Hz, 3H), 3.66-3.73 (m, 12 H), 2.76-2.87 (m, 3H), 2.09-2.16 (m, 1H). |
| 89 | 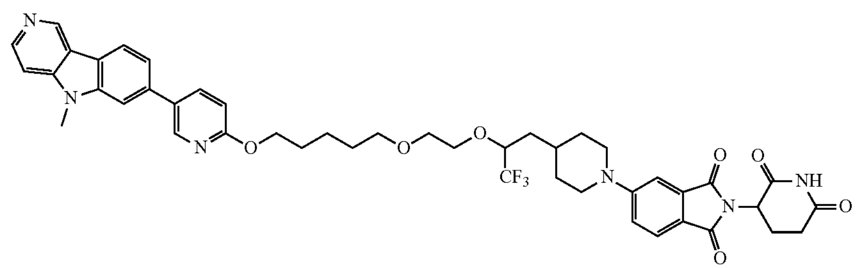 [SMILES: Cn1c2ccncc2c2ccc(-c3ccc(OCCCCCOCCOC(CC4CCN(c5ccc6c(c5)C(=O)N(C5CCC(=O)NC5=O)C6=O)CC4)C(F)(F)F)nc3)cc21] | C | 841.6 | ¹H NMR: (400 MHz, DMSO-d₆) δ: 11.09 (s, 1H), 9.36 (s, 1H), 8.61 (d, J = 2.4 Hz, 1H), 8.50 (d, J = 5.6 Hz, 1H), 8.31 (d, J = 8.0 Hz, 1H), 8.21 (s, 1H), 8.15 (dd, J = 2.8, 8.8 Hz, 1H), 7.95 (s, 1H), 7.65-7.57 (m, 3H), 7.29 (s, 1H), 7.23-7.18 (m, 1H), 6.90 (d, J = 8.8 Hz, 1H), 5.04 (dd, J = 5.6, 12.8 Hz, 1H), 4.31 (t, J = 6.4 Hz, 2H), 4.14 (br s, 1H), 4.10-3.99 (m, 3H), 3.96 (s, 3H), 3.87 (d, J = 11.6 Hz, 2H), 3.74 (dd, J = 5.6, 10.8 Hz, 2H), 3.02-2.81 (m, 4H), 1.98-1.86 (m, 2H), 1.85-1.72 (m, 4H), 1.63-1.15 (m, 9H). |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 90 | 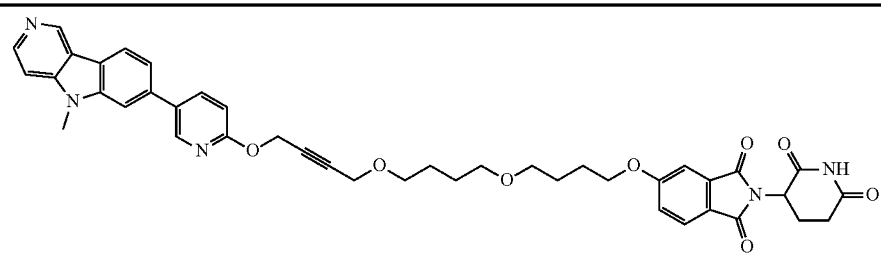 | A | 744.5 | ¹HNMR (400 MHz, CDCl₃): δ 9.35 (s, 1H), 8.60 (s, 1H), 8.50 (s, 1H), 8.20 (d, J = 8.0 Hz, 2H), 7.75 (d, J = 8.0 Hz, 1H), 7.55 (s, 1H), 7.49 (d, J = 8.0 Hz, 1H), 7.32 (d, J = 10.0 Hz, 2H), 7.16 (d, J = 8.0 Hz, 1H), 6.92 (d, J = 8.4 Hz, 1H), 5.10 (s, 2H), 4.98-5.00 (m, 1H), 4.21 (s, 2H), 4.07-4.10 (m, 2H), 3.90 (s, 3H), 3.44-3.54 (m, 7H), 2.76-2.87 (m, 3H), 2.18-2.23 (m, 2H), 1.88-1.92 (m, 3H), 1.72-1.75 (m, 4H). |
| 91 | 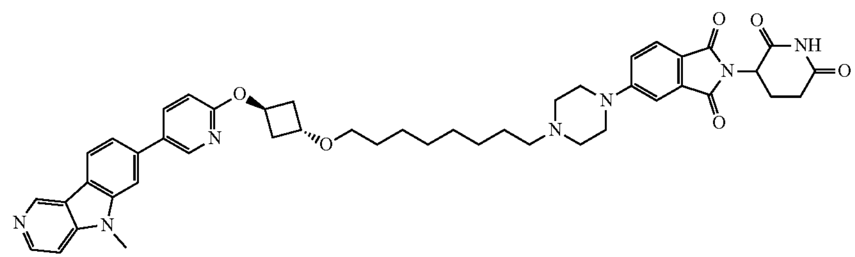 [SMILES: Cn1c2ccncc2c2ccc(-c3ccc(O[C@H]4C[C@H](OCCCCCCCCN5CCN(c6ccc7c(c6)C(=O)N(C6CCC(=O)NC6=O)C7=O)CC5)C4)nc3)cc21] | C | 798.6 | 1H NMR (400 MHz, CD₃OD): δ 9.33 (s, 1H), 8.51-8.53 (m, 2H), 8.33-8.34 (m, 1H), 8.09-8.11 (m, 1H), 7.84 (s, 1H), 7.59-7.62 (m, 3H), 7.30 (s, 1H), 7.17 (d, J = 8.4 Hz, 1H), 6.90 (d, J = 8.4 Hz, 1H), 5.32-5.35 (m, 1H), 3.99 (s, 3H), 3.40-3.47 (m, 13H), 2.69-2.71 (m, 6H), 2.50-2.52 (m, 4H), 2.03-2.18 (m, 5H), 1.59-1.60 (m, 6H). |
| 92 | 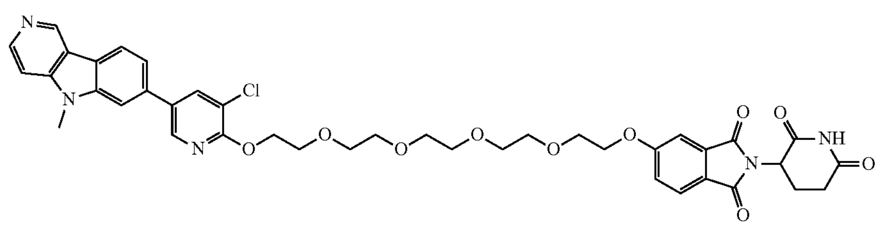 [SMILES: Cn1c2ccncc2c2ccc(-c3cnc(OCCOCCOCCOCCOCCOc4ccc5c(c4)C(=O)N(C4CCC(=O)NC4=O)C5=O)c(Cl)c3)cc21] | A | 786.5 | ¹H NMR (400 MHz, CDCl₃): δ 9.32 (s, 1H), 8.68 (s, 1H), 8.58 (s, 1H), 8.35 (s, 1H), 8.18 (d, J = 8.0 Hz, 1H), 7.97 (s, 1H), 7.74 (d, J = 8.4 Hz, 1H), 7.52 (s, 1H), 7.45 (d, J = 8.0 Hz, 1H), 7.27-7.34 (m, 2H), 7.20 (d, J = 7.6 Hz, 1H), 4.92-4.96 (m, 1H), 4.61 (s, 2H), 4.23 (s, 2H), 3.89-3.94 (m, 8H), 3.68-3.78 (m, 11H), 2.72-2.90 (m, 3H), 2.01-2.12 (m, 1H). |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 93 | 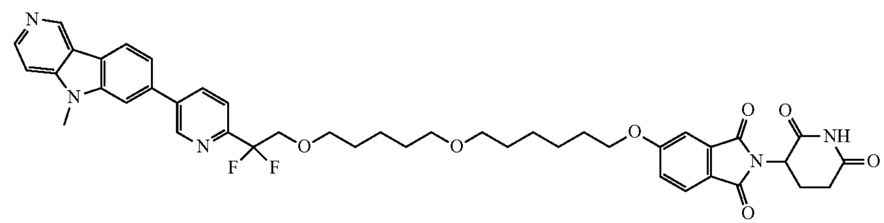 [SMILES: Cn1c2ccncc2c2ccc(-c3ccc(C(F)(F)COCCCCCOCCCCCCOc4ccc5c(c4)C(=O)N(C4CCC(=O)NC4=O)C5=O)nc3)cc21] | C | 782.5 | ¹H NMR (400 MHz, CDCl₃): δ 9.35 (br, 1H), 8.94 (s, 1H), 8.59 (s, 1H), 8.21 (d, J = 8.0 Hz, 1H), 8.01-8.09 (m, 2H), 7.73 (d, J = 8.4 Hz, 1H), 7.69 (d, J = 8.0 Hz, 1H), 7.58 (s, 1H), 7.51 (d, J = 8.4 Hz, 1H), 7.31 (d, J = 5.2 Hz, 1H), 7.24 (s, 1H), 7.09 (dd, J = 8.0, 2.0 Hz, 1H), 4.85-4.90 (m, 1H), 4.10 (t, J = 8.0 Hz, 1H), 3.98 (t, J = 6.4 Hz, 1H), 3.87 (s, 3H), 3.51 (t, J = 6.4 Hz, 1H), 3.27-3.32 (m, 4H), 2.65-2.85 (m, 3H), 2.04-2.08 (m, 1H), 1.71-1.76 (m, 4H), 1.45-1.52 (m, 8H), 0.75-0.85 (m, 4H). |
| 94 | 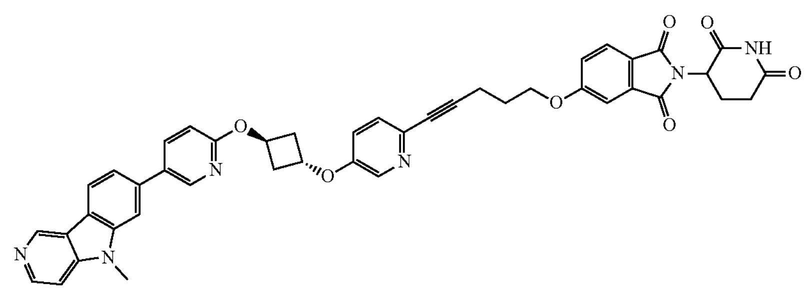 [SMILES: Cn1c2ccncc2c2ccc(-c3ccc(O[C@H]4C[C@H](Oc5ccc(C#CCCCOc6ccc7c(c6)C(=O)N(C6CCC(=O)NC6=O)C7=O)nc5)C4)nc3)cc21] | C | 761.5 | ¹HNMR (400 MHz, DMSO-d₆): δ: 11.04 (s, 1H), 9.29 (s, 1H), 8.58 (d, J = 2.0 Hz, 1H), 8.43 (d, J = 5.6 Hz, 1H), 8.25 (d, J = 8.0 Hz, 1H), 8.12-8.16 (m, 2H), 7.92 (s, 1H), 7.78 (d, J = 7.6 Hz, 1H), 7.56 (d, J = 6.0 Hz, 2H), 7.40 (s, 1H), 7.33 (d, J = 8.4 Hz, 2H), 7.20-7.22 (m, 1H), 6.92 (d, J = 4.4 Hz, 1H), 5.37 (s, 4H), 4.25 (t, J = 6.0 Hz, 2H), 3.89 (s, 3H), 2.43-2.65 (m, 9H), 1.98 (t, J = 6.4 Hz, 3H). |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 95 | 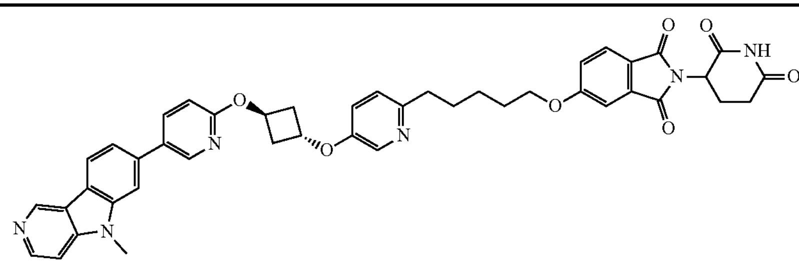 | C | 765.5 | ¹HNMR (400 MHz, CDCl₃): δ: 9.32 (s, 1H), 8.59 (d, J = 4.8 Hz, 1H), 8.49 (s, 1H), 8.20 (d, J = 8.8 Hz, 1H), 8.16 (s, 1H), 8.08 (s, 1H), 7.94 (d, J = 7.2 Hz, 1H), 7.77 (d, J = 8.0 Hz, 1H), 7.56 (s, 1H), 7.49 (d, J = 8.4 Hz, 1H), 7.32 (s, 2H), 7.17 (d, J = 8.0 Hz, 1H), 7.07 (s, 1H), 6.87 (d, J = 8.8 Hz, 1H), 5.52 (s, 1H), 4.94-4.97 (m, 2H), 4.08 (s, 2H), 3.91 (s, 3H), 2.73-2.92 (m, 8H), 2.13-2.15 (m, 2H), 1.86-1.88 (m, 2H), 1.78-1.80 (m, 2H), 1.46-1.54 (m, 2H). |
| 96 | 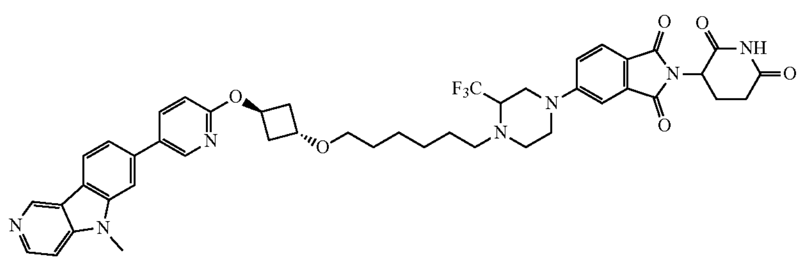 | B | 838.6 | ¹H NMR: 400 MHz, DMSO-d6 δ: 11.09 (s, 1H), 9.38 (s, 1H), 8.64 (d, J = 2.4 Hz, 1H), 8.51 (d, J = 5.6 Hz, 1H), 8.33 (d, J = 8.0 Hz, 1H), 8.19 (dd, J = 2.4, 8.8 Hz, 1H), 8.14 (s, 1H), 7.99 (s, 1H), 7.72-7.59 (m, 3H), 7.21 (d, J = 2.0 Hz, 1H), 7.12 (dd, J = 2.0, 8.8 Hz, 1H), 6.94 (d, J = 8.4 Hz, 1H), 5.38-5.26 (m, 1H), 5.06 (dd, J = 5.3, 12.9 Hz, 1H), 4.24-4.13 (m, 1H), 3.96 (s, 3H), 3.95-3.88 (m, 1H), 3.72 (d, J = 15.2 Hz, 1H), 3.68-3.63 (m, 1H), 3.53 (d, J = 7.2 Hz, 1H), 3.31 (s, 2H), 3.07-2.75 (m, 4H), 2.74-2.54 (m, 4H), 2.44-2.29 (m, 4H), 2.06-1.94 (m, 1H), 1.50 (td, J = 7.0, 13.8 Hz, 4H), 1.33 (s, 4H). |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 97 | 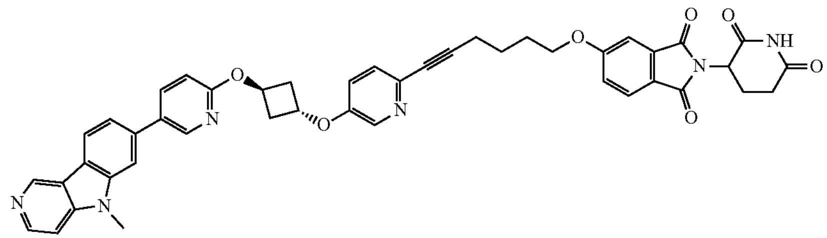 [SMILES: Cn1c2ccncc2c2ccc(-c3ccc(O[C@H]4C[C@H](Oc5ccc(C#CCCCCOc6ccc7c(c6)C(=O)N(C6CCC(=O)NC6=O)C7=O)nc5)C4)nc3)cc21] | B | 775.5 | 1H NMR (400 MHz, CDCl₃): δ 8.42-8.48 (m, 2H), 8.17-8.23 (m, 2H), 7.93 (d, J = 2 Hz, 1H), 7.75 (d, J = 8.4 Hz, 1H), 7.51-7.58 (m, 1H), 7.34 (s, 1H), 7.26-7.28 (m, 1H), 7.19 (d, J = 1.6 Hz, 1H), 7.05-7.17 (m, 1H), 6.87 (d, J = 8.4 Hz, 1H), 5.52-5.54 (m, 1H), 4.96-4.98 (m, 2H), 4.14-4.17 (m, 2H), 3.91 (s, 3H), 2.73-2.88 (m, 8H), 2.52-2.55 (m, 2H), 2.02-2.15 (m, 3H), 1.81-1.85 (m, 2H). |
| 98 | 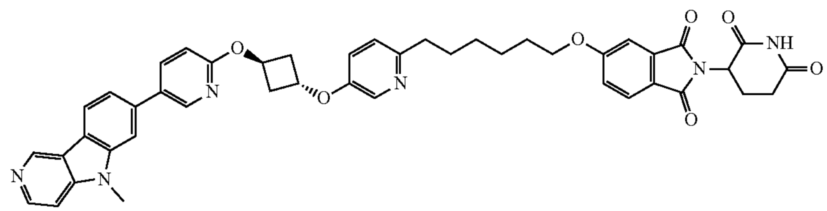 | B | 779.5 | 1H NMR (400 MHz, CDCl₃): δ 8.48 (s, 1H), 8.26 (d, J = 7.6 Hz, 1H), 8.17 (s, 1H), 7.94 (d, J = 8.4 Hz, 1H), 7.57-7.63 (m, 2H), 7.28-7.34 (m, 1H), 7.17-7.20 (m, 1H), 7.06 (s, 1H), 6.90 (d, J = 8.4 Hz, 1H), 5.53-5.55 (m, 1H), 4.97-5.01 (m, 2H), 4.06-4.16 (m, 2H), 3.98 (s, 3H), 2.71-2.88 (m, 8H), 2.51-2.53 (m, 1H), 2.02-2.21 (m, 4H), 1.62-1.85 (m, 4H), 1.51-1.56 (m, 4H), 0.82-0.92 (m, 2H). |
| 99 | 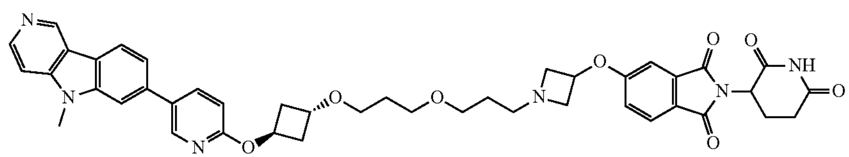 [SMILES: Cn1c2ccncc2c2ccc(-c3ccc(O[C@H]4C[C@H](OCCCOCCCN5CC(Oc6ccc7c(c6)C(=O)N(C6CCC(=O)NC6=O)C7=O)C5)C4)nc3)cc21] | A | 773.5 | 1H NMR (400 MHz, DMSO-d6): δ 1.40-1.56 (m, 2H), 1.62-1.75 (m, 2H), 1.83-2.09 (m, 2H), 2.34-2.50 (m, 3H), 2.58-2.73 (m, 1H), 2.83-2.93 (m, 1H), 3.01-3.13 (m, 2H), 3.37-3.52 (m, 8H), 3.77 (s, 2H), 3.95 (s, 3H), 4.18 (s, 1H), 5.02-5.13 (m, 2H), 5.29-5.37 (m, 1H), 6.94 (d, J = 8.0 Hz, 1H), 7.21-7.29 (m, 2H), 7.59-7.65 (m, 2H), 7.80 (d, J = |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 100 | 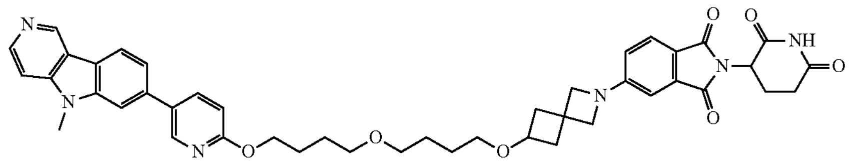 [SMILES: Cn1c2ccncc2c2ccc(-c3ccc(OCCCCOCCCCOC4CC5(C4)CN(c4ccc6c(c4)C(=O)N(C4CCC(=O)NC4=O)C6=O)C5)nc3)cc21] | C | 771.6 | ¹H NMR (400 MHz, CDCl₃): δ 1.65-1.67 (m, 6H), 1.74-1.81 (m, 2H), 1.87-1.94 (m, 2H), 2.00-2.06 (m, 1H), 2.09-2.14 (m, 1H), 2.18-2.24 (m, 2H), 2.54-2.59 (m, 2H), 2.68-2.90 (m, 3H), 3.37-3.53 (m, 5H), 3.91 (t, J = 7.6 Hz, 3H), 3.98 (d, J = 8.0 Hz, 3H), 4.39 (t, J = 6.4 Hz, 2H), 4.90-4.94 (m, 1H), 6.45 (d, J = 1.6 Hz, 1H), 6.72 (d, J = 1.6 Hz, 1H), 6.85 (d, J = 8.4 Hz, 1H), 7.35 (d, J = 6 Hz, 1H), 7.50 (d, J = 8.0 Hz, 1H), 7.56 (s, 1H), 7.61 (d, J = 8.0 Hz, 1H), 7.91 (d, J = 2.4 Hz, 1H), 8.05 (s, 1H), 8.21 (d, J = 8.0 Hz, 1H), 8.49 (d, J = 2.4 Hz, 1H), 8.60 (d, J = 5.6 Hz, 1H), 9.34 (s, 1H). 7.2 Hz, 1H), 7.97 (s, 1H), 8.18 (d, J = 7.6 Hz, 1H), 8.31 (d, J = 7.6 Hz, 1H), 8.50 (d, J = 5.2 Hz, 1H), 8.63 (s, 1H), 9.35 (s, 1H), 11.11 (s, 1H). |
| 101 | 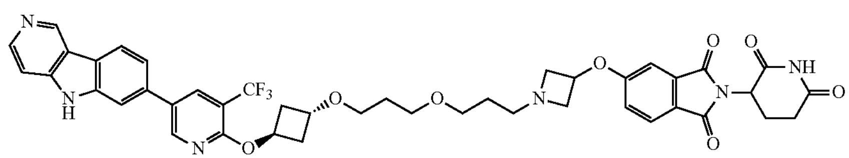 | A | 827.5 | 1H NMR (400 MHz D6-DMSO): δ 1.56-1.59 (m, 2H), 1.71-1.77 (m, 2H), 1.95-2.05 (m, 2H), 2.34-2.46 (m, 3H), 2.50-2.67 (m, 3H), 2.83-2.93 (m, 1H), 3.32-3.49 (m, 9H), 3.88-3.92 (m, 1H), 4.17-4.20 (m, 1H), 4.55 (t, J = 5.6 Hz, 1H), 5.05-5.13 (m, 2H), 5.46-5.49 (m, 1H), 7.25-7.28 (m, 2H), 7.52 (d, J = 5.6 Hz, 1H), 7.63 (d, J = 8.0 Hz, 1H), 7.82 (d, J = 8.0 Hz, 1H), 7.87 (s, 1H), |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 102 | 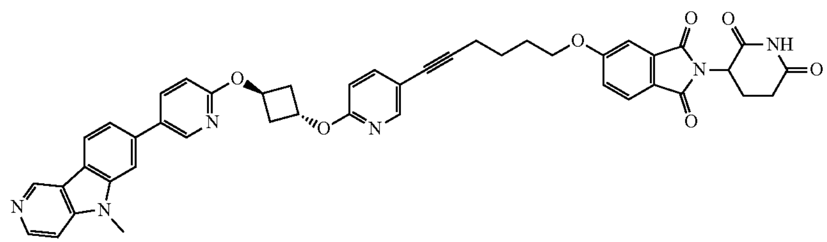 | C | 775.5 | ¹HNMR (400 MHz, DMSO-d₆): δ 1.73 (d, J = 7.2 Hz, 2H), 1.91 (d, J = 7.2 Hz, 2H), 2.01-2.08 (m, 1H), 2.51-2.67 (m, 8H), 2.83-2.94 (m, 1H), 3.96 (s, 3H), 4.24 (t, J = 6.0 Hz, 2H), 5.12 (dd, J = 12.8, 5.2 Hz, 1H), 5.31-5.52 (m, 2H), 6.99 (d, J = 8.4 Hz, 1H), 6.83 (d, J = 8.6 Hz, 1H), 7.36 (d, J = 8.2 Hz, 1H), 7.44 (s, 1H), 7.58-7.75 (m, 3H), 7.82 (d, J = 8.2 Hz, 1H), 7.99 (s, 1H), 8.10-8.28 (m, 2H), 8.33 (d, J = 8.2 Hz, 1H), 8.52 (s, 1H), 8.64 (d, J = 1.6 Hz, 1H), 9.40 (s, 1H), 11.11 (s, 1H), 11.86 (s, 1H). |
| 103 | 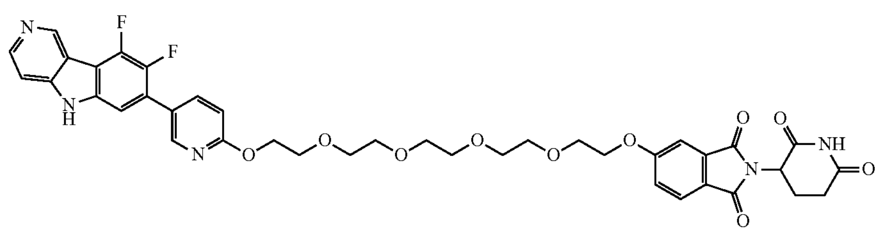 [SMILES: O=C1CCC(N2C(=O)c3ccc(OCCOCCOCCOCCOCCOc4ccc(-c5cc6[nH]c7ccncc7c6c(F)c5F)cn4)cc3C2=O)C(=O)N1] | ND | 774.5 | ¹H NMR (400 MHz, CD₃OD): δ 9.46 (s, 1H), 8.63 (d, J = 6.8 Hz, 1H), 8.38 (s, 1H), 8.00 (d, J = 6.8 Hz, 1H), 7.96 (d, J = 8.8 Hz, 1H), 7.67 (d, J = 8.4 Hz, 1H), 7.61 (d, J = 4.8 Hz, 1H), 7.29 (s, 1H), 7.23 (d, J = 8.4 Hz, 1H), 6.93 (d, J = 8.8 Hz, 1H), 5.05 (m, 1H), 4.54-4.45 (m, 2H), 4.26-4.19 (m, 2H), 3.86 (m, 4H), 3.70-3.65 (m, 12H), 2.86-2.62 (m, 3H), 2.10-2.04 (m, 1H). |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 104 | 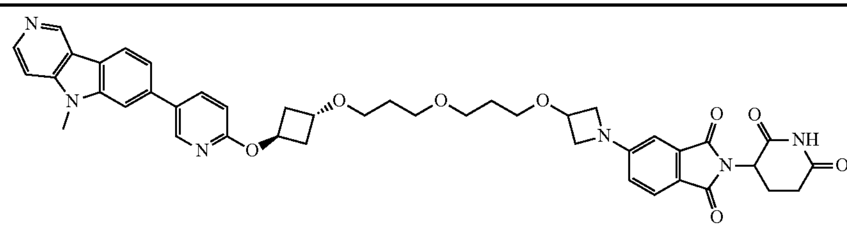 | A | 773.5 | ¹H NMR (400 MHz, DMSO-d6): δ 1.73-1.79 (m, 4H), 1.97-1.99 (m, 2H), 2.31-2.37 (m, 2H), 2.40-2.49 (m, 2H), 2.54-2.59 (m, 1H), 2.83-2.88 (m, 1H), 3.38 (t, J = 6.4 Hz, 2H), 3.43-3.49 (m, 6H), 3.82-3.85 (m, 2H), 3.75 (s, 3H), 4.16-4.18 (m, 1H), 4.20-4.26 (m, 2H), 4.43-4.47 (m, 1H), 5.02-5.07 (m, 1H), 5.31-5.34 (m, 1H), 6.62-6.64 (m, 1H), 6.78-6.79 (m, 1H), 6.93 (t, J = 8.4 Hz, 1H), 7.59-6.72 (m, 3H), 7.96 (s, 1H), 8.17-8.19 (m, 1H), 8.30 (d, J = 8.0 Hz, 1H), 8.49 (d, J = 6.4 Hz, 1H), 8.62-8.63 (m, 1H), 9.35 (s, 1H), 11.06 (s, 1H). |
| 105 | 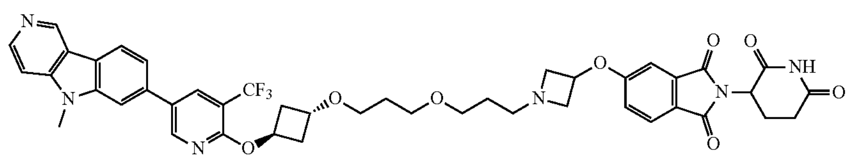 [SMILES: Cn1c2ccncc2c2ccc(-c3cnc(O[C@H]4C[C@H](OCCCOCCCN5CC(Oc6ccc7c(c6)C(=O)N(C6CCC(=O)NC6=O)C7=O)C5)C4)c(C(F)(F)F)c3)cc21] | A | 841.5 | ¹H NMR (400 MHz, DMSO-d6): δ 1.56-1.60 (m, 2H), 1.74 (t, J = 6.4 Hz, 2H), 1.99-2.04 (m, 2H), 2.33-2.39 (m, 3H), 2.55-2.66 (m, 3H), 2.83-2.91 (m, 1H), 3.11-3.13 (m, 2H), 3.36-3.44 (m, 6H), 3.55-3.64 (m, 2H), 3.88-3.93 (m, 1H), 3.97 (s, 3H), 4.17-4.20 (m, 1H), 5.06-5.12 (m, 2H), 5.47-5.49 (m, 1H), 7.27 (s, 2H), 7.65 (d, J = 6.0 Hz, 1H), 7.70 (d, J = 8.4 Hz, 1H), 7.80 (d, J = 8.0 Hz, 1H), 8.10 (s, 1H), 8.35 (s, 1H), 8.50-8.53 (m, 2H), 8.90 (s, 1H), 9.40 (s, 1H), 11.10 (s, 1H). |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 106 | 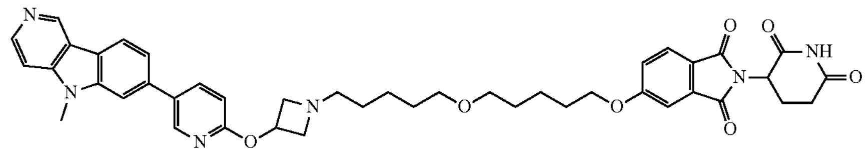 | B | 759.6 | ¹H NMR (400 MHz, DMSO-d6): δ 1.54-1.68 (m, 10H), 1.84-1.88 (m, 2H), 2.12-2.14 (m, 1H), 2.77-2.93 (m, 5H), 3.40-3.45 (m, 4H), 3.64-3.75 (m, 4H), 3.91 (s, 3H), 4.09 (t, J = 6.4 Hz, 2H), 4.39-4.46 (m, 1H), 4.89-4.99 (m, 1H), 5.41-5.50 (m, 1H), 6.90 (d, J = 8.4 Hz, 1H), 7.14-7.2 (m, 1H), 7.32-7.35 (m, 2H), 7.48 (d, J = 8.0 Hz, 1H), 7.55 (s, 1H), 7.76 (d, J = 8.0 Hz, 1H), 7.92-8.00 (m, 1H), 8.21 (d, J = 8.0 Hz, 1H), 8.43 (d, J = 2.0 Hz, 1H), 8.59 (d, J = 5.6 Hz, 1H), 9.33 (s, 1H). |
| 107 | 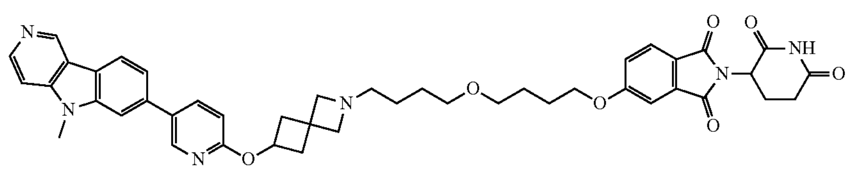 [SMILES: Cn1c2ccncc2c2ccc(-c3ccc(OC4CC5(C4)CN(CCCCOCCCCOc4ccc6c(c4)C(=O)N(C4CCC(=O)NC4=O)C6=O)C5)nc3)cc21] | C | 771.6 | 1HNMR (400 MHz, CDCl₃): δ 1.61-1.65 (m, 2H), 1.72-1.77 (m, 4H), 1.90-1.93 (m, 2H), 1.99-2.04 (m, 1H), 2.14-2.22 (m, 3H), 2.44-2.49 (m, 2H), 2.78-3.01 (m, 6H), 3.44-3.49 (m, 4H), 3.92 (s, 3H), 3.99-4.05 (m, 2H), 4.14 (t, J = 6.2 Hz, 2H), 4.94-4.98 (m, 1H), 5.17-5.20 (m, 1H), 6.81 (d, J = 8.4 Hz, 1H), 7.19-7.21 (m, 1H), 7.33-7.37 (m, 2H), 7.49 (d, J = 8.4 Hz, 1H), 7.56 (s, 1H), 7.78 (d, J = 8.4 Hz, 1H), 7.90-7.93 (m, 1H), 8.21 (d, J = 8.4 Hz, 1H), 8.35 (br, 1H), 8.45-8.46 (m, 1H), 8.59 (d, J = 5.6 Hz, 1H), 9.34 (s, 1H). |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 108 | 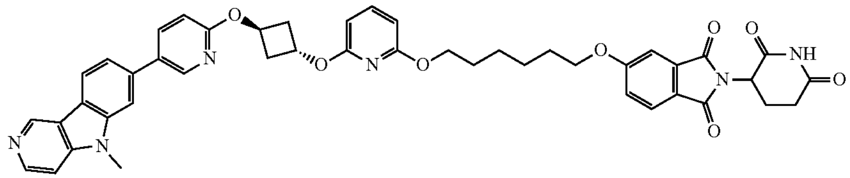 [SMILES: Cn1c2ccncc2c2ccc(-c3ccc(O[C@H]4C[C@H](Oc5cccc(OCCCCCCOc6ccc7c(c6)C(=O)N(C6CCC(=O)NC6=O)C7=O)n5)C4)nc3)cc21] | C | 795.5 | ¹H NMR (400 MHz, DMSOd-6): δ 1.43-1.44 (m, 4H), 1.70-1.74 (m, 4H), 1.98-2.04 (m, 1H), 2.44-2.47 (m, 1H), 2.56-2.60 (m, 1H), 2.65 (t, J = 6.0 Hz, 4H), 2.83-2.92 (m, 1H), 3.95 (s, 3H), 4.10 (t, J = 6.0 Hz, 2H), 4.22 (t, J = 6.4 Hz, 2H), 5.07-5.11 (m, 1H), 5.30-5.35 (m, 1H), 5.39-5.45 (m, 1H), 6.34-6.37 (m, 2H), 6.98 (d, J = 8.4 Hz, 1H), 7.24-7.26 (m, 1H), 7.33 (d, J = 2.0 Hz, 1H), 7.59-7.65 (m, 3H), 7.72 (d, J = 8.0 Hz, 1H), 7.97 (s, 1H), 8.17-8.21 (m, 1H), 8.31 (d, J = 8.0 Hz, 1H), 8.50 (d, J = 6.0 Hz, 1H), 8.65 (d, J = 2.0 Hz, 1H), 9.36 (s, 1H), 11.10 (s, 1H). |
| 109 | 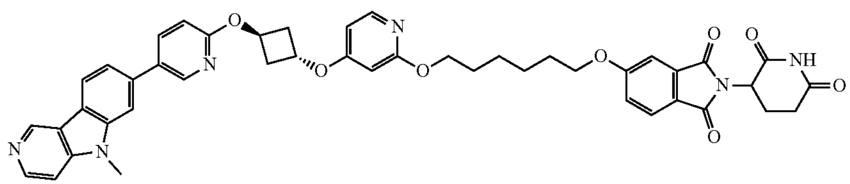 [SMILES: Cn1c2ccncc2c2ccc(-c3ccc(O[C@H]4C[C@H](Oc5ccnc(OCCCCCCOc6ccc7c(c6)C(=O)N(C6CCC(=O)NC6=O)C7=O)c5)C4)nc3)cc21] | C | 795.5 | ¹H NMR (400 MHz, DMSOd-6): δ 1.47 (s, 4H), 1.72-1.78 (m, 4H), 2.02-2.05 (m, 2H), 2.33 (s, 1H), 2.63-2.66 (m, 4H), 2.88-2.89 (m, 1H), 3.41-3.49 (m, 2H), 3.96 (s, 2H), 4.18-4.23 (m, 3H), 5.04-5.12 (m, 2H), 5.42 (br, 1H), 6.19 (s, 1H), 6.55-6.56 (m, 1H), 6.98 (d, J = 8.4 Hz, 1H), 7.34 (d, J = 7.2 Hz, 1H), 7.41 (s, 1H), 6.63 (s, 2H), 7.81-7.83 (m, 1H), 7.95-7.97 (m, 2H), 8.21 (d, J = 8.4 Hz, 1H), 8.32 (d, J = 7.2 Hz, 1H), 8.50 (d, J = 4.0 Hz, 1H), 8.64 (s, 1H), 9.36 (s, 1H), 11.11 (s, 1H). |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 110 | 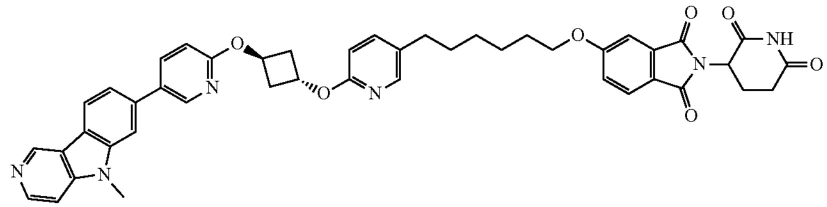 [SMILES: Cn1c2ccncc2c2ccc(-c3ccc(O[C@H]4C[C@H](Oc5ccc(CCCCCCOc6ccc7c(c6)C(=O)N(C6CCC(=O)NC6=O)C7=O)cn5)C4)nc3)cc21] | C | 779.5 | ¹H NMR (400 MHz, DMSO-d₆): δ 1.36 (d, J = 7.6 Hz, 2H), 1.45 (d, J = 6.8 Hz, 2H), 1.52-1.61 (m, 2H), 1.70-1.80 (m, 2H), 1.98-2.02 (m, 3H), 2.54-2.70 (m, 6H), 2.89 (t, J = 16.6 Hz, 1H), 3.96 (s, 3H), 4.16 (d, J = 5.0 Hz, 2H), 5.12 (dd, J = 12.8, 4.4 Hz, 1H), 5.36-5.43 (m, 2H), 6.77 (d, J = 8.4 Hz, 1H), 6.99 (d, J = 8.0 Hz, 1H), 7.34 (d, J = 8.8 Hz, 1H), 7.42 (s, 1H), 7.60-7.64 (m, 3H), 7.83 (d, J = 8.0 Hz, 1H), 7.97 (dd, J = 14.0, 6.4 Hz, 2H), 8.33 (d, J = 8.4 Hz, 1H), 8.21 (d, J = 8.0 Hz, 1H), 8.50 (d, J = 4.8 Hz, 1H), 8.65 (s, 1H), 9.37 (s, 1H), 11.11 (s, 1H). |
| 111 | 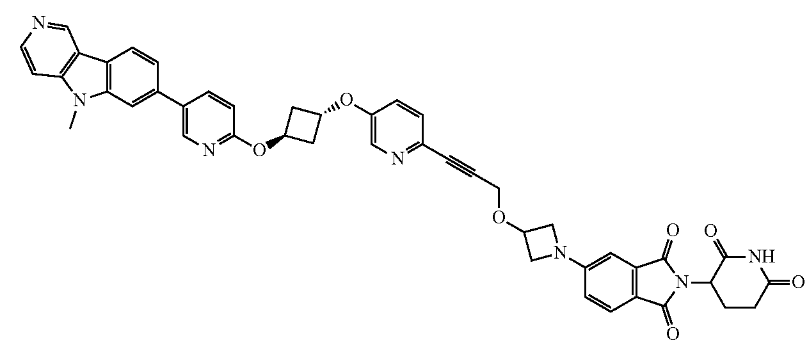 [SMILES: Cn1c2ccncc2c2ccc(-c3ccc(O[C@H]4C[C@H](Oc5ccc(C#CCOC6CN(c7ccc8c(c7)C(=O)N(C7CCC(=O)NC7=O)C8=O)C6)nc5)C4)nc3)cc21] | C | 788.5 | ¹HNMR (400 MHz, DMSO-d6): δ 1.98-2.02 (m, 1H), 2.54-2.73 (m, 6H), 2.83-2.92 (m, 1H), 3.95-3.97 (m, 5H), 4.31-4.34 (m, 2H), 4.50 (s, 2H), 4.67-4.72 (m, 1H), 5.04-5.13 (m, 2H), 5.42-5.48 (m, 1H), 6.67-6.69 (m, 1H), 6.82 (s, 1H), 6.69-7.01 (m, 1H), 7.33-7.36 (m, 1H), 7.53-7.55 (m, 1H), 7.63-7.67 (m, 3H), 8.01 (s, 1H), 8.21-8.26 (m, 2H), 8.33-8.37 (m, 1H), 8.51-8.55 (m, 1H), 8.65-8.66 (m, 1H), 9.39 (s, 1H), 11.07 (s, 1H). |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 112 | 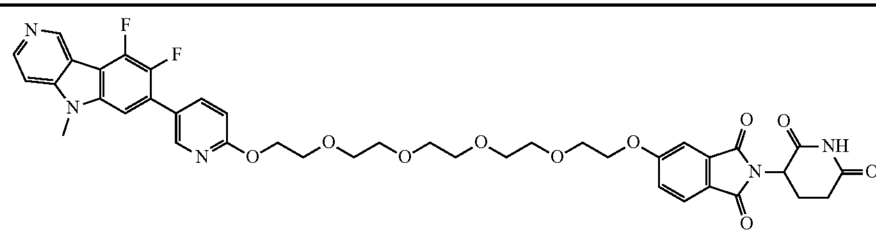 | A | 788.5 | ¹HNMR (400 MHz, CDCl₃): δ 11.09 (s, 1H), 9.25 (s, 1H), 8.50 (s, 1H), 8.59 (s, 1H), 8.07 (d, J = 8.4 Hz, 1H), 7.79 (d, J = 8.4 Hz, 1H), 7.69-7.73 (m, 2H), 7.75 (d, J = 8.4 Hz, 1H), 7.42 (s, 1H), 7.34 (d, J = 8.4 Hz, 1H), 7.02 (d, J = 8.4 Hz, 1H), 5.08-5.13 (m, 1H), 4.46 (d, J = 4.4 Hz, 2H), 4.30-4.34 (m, 2H), 3.95 (s, 3H), 3.79 (s, 4H), 3.60 (s, 4H), 3.56 (s, 4H), 3.53 (s, 4H), 2.85-2.88 (m, 1H), 2.61 (s, 2H). |
| 113 | 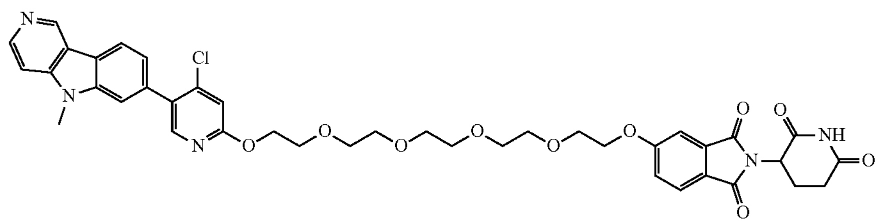 [SMILES: Cn1c2ccncc2c2ccc(-c3cnc(OCCOCCOCCOCCOCCOc4ccc5c(c4)C(=O)N(C4CCC(=O)NC4=O)C5=O)cc3Cl)cc21] | C | 786.5 | ¹HNMR (400 MHz, DMSO-d₆): δ 11.11 (s, 1H), 9.35 (s, 1H), 8.50 (s, 1H), 8.38 (s, 1H), 8.29 (d, J = 8.0 Hz, 1H), 7.87 (s, 1H), 7.75 (d, J = 8.0 Hz, 1H), 7.62 (d, J = 5.6 Hz, 1H), 7.52 (d, J = 8.0 Hz, 1H), 7.34 (d, J = 8.4 Hz, 2H), 7.27 (d, J = 10.4 Hz, 1H), 5.13-5.08 (m, 1H), 4.34-4.32 (m, 2H), 4.23-4.21 (m, 2H), 3.91 (s, 3H), 3.77-3.71 (m, 4H), 3.54-3.46 (m, 12 H), 2.91-2.87 (m, 1H), 2.61-2.57 (m, 3H). |
| 114 | 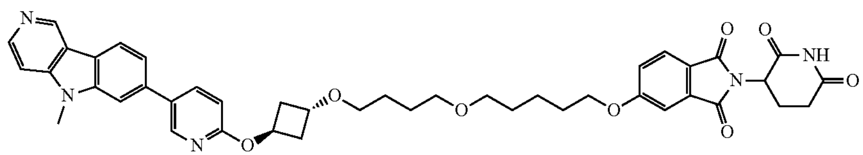 [SMILES: Cn1c2ccncc2c2ccc(-c3ccc(O[C@H]4C[C@H](OCCCCOCCCCCOc5ccc6c(c5)C(=O)N(C5CCC(=O)NC5=O)C6=O)C4)nc3)cc21] | C | 760.5 | ¹H NMR (400 MHz, CDCl₃): δ 1.52-1.59 (m, 2H), 1.63-1.67 (m, 5H), 1.83-1.90 (m, 1H), 2.11-2.16 (m, 2H), 2.43-2.54 (m, 4H), 2.71-7.92 (m, 4H), 3.39-3.49 (m, 6H), 3.95 (s, 3H), 4.08 (t, J = 6.4 Hz, 2H), 4.23-4.29 (m, 1H), 4.94 (dd, J = 5.2, 12.0 Hz, 1H), 6.83 (d, J = 8.4 Hz, 1H), 7.17 (dd, J = 2.0, 8.0 Hz, 1H), 7.32 (d, |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 115 | 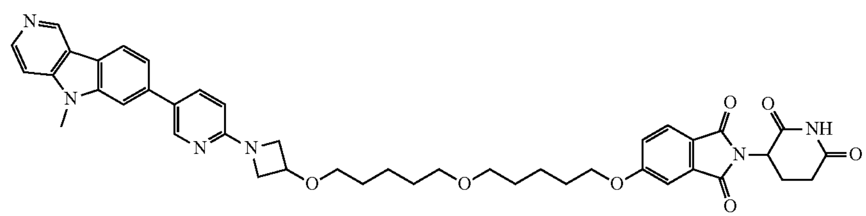 [SMILES: Cn1c2ccncc2c2ccc(-c3ccc(N4CC(OCCCCCOCCCCCOc5ccc6c(c5)C(=O)N(C5CCC(=O)NC5=O)C6=O)C4)nc3)cc21] | C | 759.6 | 1H NMR (400 MHz, DMSO-d6): δ 1.34-1.38 (m, 2H), 1.40-1.58 (m, 8H), 1.74-1.77 (m, 2H), 2.01-2.04 (m, 1H), 2.54-2.61 (m, 1H), 2.84-2.93 (m, 1H), 3.32-3.42 (m, 7H), 3.77-3.81 (m, 2H), 3.96 (s, 3H), 4.15 (t, J = 6.4 Hz, 2H), 4.21 (t, J = 8.8 Hz, 2H), 4.40-4.45 (m, 1H), 5.10 (dd, J = 12.8 Hz, 1H), 6.52 (d, J = 8.8 Hz, 1H), 7.32 (dd, J = 8.0 Hz, 1H), 7.39 (s, 1H), 7.58 (d, J = 8.0 Hz, 1H), 7.65 (d, J = 6.0 Hz, 1H), 7.80 (d, J = 8.4 Hz, 1H), 7.91 (s, 1H), 8.01 (dd, J = 8.4 Hz, 1H), 8.29 (d, J = 8.0 Hz, 1H), 8.50 (d, J = 5.6 Hz, 1H), 8.58 (s, 1H), 9.36 (s, 1H), 11.10 (s, 1H). |
| 116 | 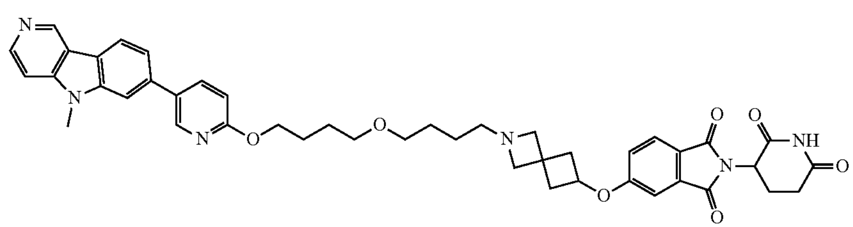 [SMILES: Cn1c2ccncc2c2ccc(-c3ccc(OCCCCOCCCCN4CC5(CC(Oc6ccc7c(c6)C(=O)N(C6CCC(=O)NC6=O)C7=O)C5)C4)nc3)cc21] | C | 771.6 | 1HNMR (400 MHz, CDCl3): δ 1.39-1.42 (m, 2H), 1.47-1.52 (m, 2H), 1.64-1.70 (m, 2H), 1.77-1.82 (m, 2H), 2.01-2.07 (m, 1H), 2.21-2.26 (m, 2H), 2.54-2.64 (m, 3H), 2.75-2.90 (m, 5H), 3.42-3.45 (m, 3H), 3.61-3.71 (m, 4H), 3.95 (s, 3H), 4.35 (t, J = 6.2 Hz, 2H), 4.78-4.82 (m, 1H), 5.09-5.13 (m, 1H), 6.94 (d, J = 8.4 |

(The first entry's NMR transcript continues above example 115's structure as: J = 1.6 Hz, 1H), 7.44 (d, J = 6.0 Hz, 1H), 7.54 (d, J = 8.0 Hz, 1H), 7.60 (s, 1H), 7.75 (d, J = 8.4 Hz, 1H), 7.91 (dd, J = 2.4, 8.8 Hz, 1H), 8.14 (m, 1H), 8.21 (d, J = 8.0 Hz, 1H), 8.48 (d, J = 2.4 Hz, 1H), 8.58 (d, J = 5.2 Hz, 1H), 9.34 (s, 1H).)

TABLE 2-continued

Exemplary PROTAC of the present disclosure.

| Ex. | Structure | Degradation activity* | MH + (1) [MH + (2), if isotope] | NMR transcript |
|---|---|---|---|---|
| | | | | Hz, 1H), 7.20-7.25 (m, 2H), 7.60-7.63 (m, 2H), 7.79 (d, J = 8.0 Hz, 1H), 7.97 (s, 1H), 8.18-8.20 (m, 1H), 8.31 (d, J = 8.0 Hz, 1H), 8.48 (d, J = 5.2 Hz, 1H), 8.65 (s, 1H), 9.34 (s, 1H), 11.11 (s, 1H). |
| 117 | 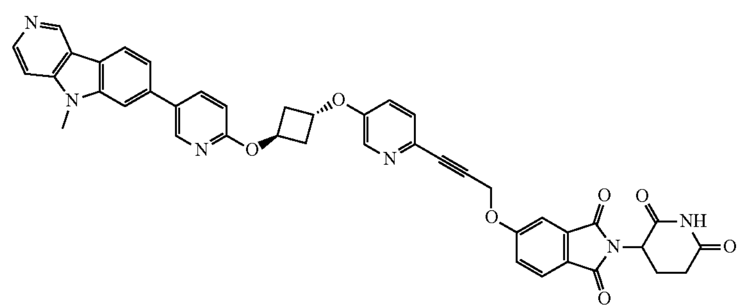 [SMILES: Cn1c2ccncc2c2ccc(-c3ccc(O[C@H]4C[C@H](Oc5ccc(C#CCOc6ccc7c(c6)C(=O)N(C6CCC(=O)NC6=O)C7=O)nc5)C4)nc3)cc21] | C | 733.4 | $^1$H NMR (400 MHz, CD$_3$OD): δ 1.92-1.94 (m, 1H), 2.02-2.10 (m, 2H), 2.62-2.65 (m, 5H), 3.90 (s, 3H), 4.97-5.02 (m, 2H), 5.10 (s, 2H), 5.37 (t, J = 6 Hz, 1H), 6.85 (d, J = 8.4 Hz, 1H), 7.20-7.22 (m, 1H), 7.34-7.41 (m, 2H), 7.45 (d, J = 2.0 Hz, 1H), 7.50-7.56 (m, 2H), 7.75-7.77 (m, 2H), 8.02-8.06 (m, 2H), 8.21 (d, J = 8.0 Hz, 1H), 8.37 (d, J = 6.0 Hz, 1H), 8.42 (d, J = 2.4 Hz, 1H), 9.18 (s, 1H). |
| 118 | 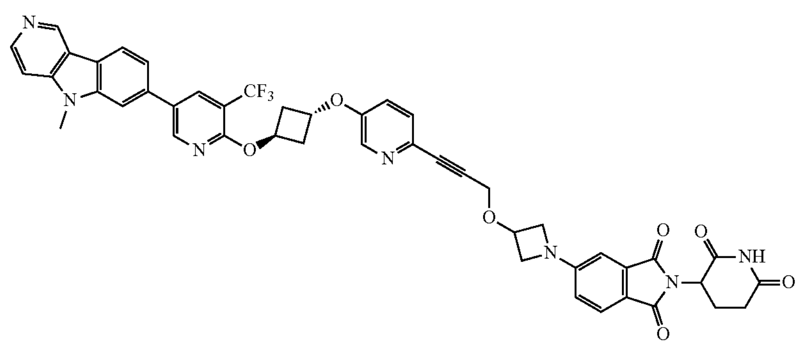 [SMILES: Cn1c2ccncc2c2ccc(-c3cnc(O[C@H]4C[C@H](Oc5ccc(C#CCOC6CN(c7ccc8c(c7)C(=O)N(C7CCC(=O)NC7=O)C8=O)C6)nc5)C4)c(C(F)(F)F)c3)cc21] | C | 856.5 | $^1$H NMR (400 MHz, DMSO-d6): δ 1.98-2.03 (m, 1H), 2.09-2.15 (m, 1H), 2.20-2.24 (m, 1H), 2.70-2.87 (m, 5H), 4.01-4.04 (m, 4H), 4.29-4.34 (m, 1H), 4.46 (s, 2H), 4.75-4.79 (m, 1H), 4.89-4.95 (m, 1H), 5.00-5.06 (m, 1H), 5.33-5.40 (m, 2H), 5.65-5.70 (m, 1H), 6.53-6.55 (m, 1H), 6.79 (s, 1H), 7.08-7.11 (m, 1H), 7.40 (d, J = 8.0 Hz, 1H), 7.56-7.65 (m, 4H), 7.95 (s, 1H), 8.19-8.30 (m, 3H), 8.60-8.64 (m, 2H), 9.38 (s, 1H). |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 119 | 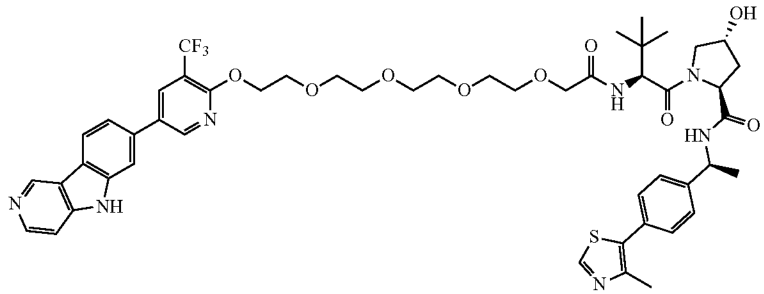 [SMILES: Cc1ncsc1-c1ccc([C@H](C)NC(=O)[C@@H]2C[C@@H](O)CN2C(=O)[C@@H](NC(=O)COCCOCCOCCOCCOc2ncc(-c3ccc4c(c3)[nH]c3ccncc34)cc2C(F)(F)F)C(C)(C)C)cc1] | C | 990.7 | ¹H NMR (400 MHz, DMSO-d₆): δ 0.93 (s, 9H), 1.35 (t, J = 6.8 Hz, 3H), 1.77-1.78 (s, 1H), 2.02-2.04 (m, 1H), 2.44 (s, 3H), 3.53-3.64 (m, 14H), 3.80-3.85 (m, 2H), 3.95 (s, 2H), 4.28 (s, 1H), 4.44 (d, J = 8.2 Hz, 1H), 4.54 (d, J = 9.6 Hz, 1H), 4.58-4.63 (m, 2H), 4.90 (s, 1H), 5.12 (s, 1H), 7.26-7.50 (m, 5H), 7.54 (d, J = 5.8 Hz, 1H), 7.66 (d, J = 8.2 Hz, 1H), 7.90 (s, 1H), 8.35 (d, J = 8.0 Hz, 1H), 8.42-8.45 (m, 3H), 8.85 (s, 1H), 8.97 (s, 1H), 9.41 (s, 1H), 11.92 (s, 1H). |
| 120 | 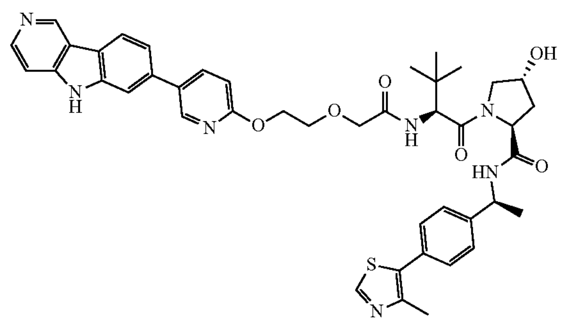 [SMILES: Cc1ncsc1-c1ccc([C@H](C)NC(=O)[C@@H]2C[C@@H](O)CN2C(=O)[C@@H](NC(=O)COCCOc2ccc(-c3ccc4c(c3)[nH]c3ccncc34)cn2)C(C)(C)C)cc1] | C | 790.5 | ¹H NMR (400 MHz, DMSO-d6): δ 0.95 (s, 9H), 1.37-1.47 (m, 3H), 1.75-1.81 (m, 1H), 2.03-2.08 (m, 1H), 2.44 (s, 3H), 3.16-3.17 (m, 4H), 3.29 (s, 2H), 3.54-3.63 (m, 2H), 3.89 (s, 2H), 4.06 (s, 3H), 4.26-4.31 (m, 1H), 4.44-4.51 (m, 3H), 4.56-4.61 (m, 1H), 4.90-4.96 (m, 1H), 5.10-5.17 (m, 1H), 7.06-7.10 (m, 1H), 7.36-7.38 (m, 2H), 7.42-7.48 (m, 3H), 7.53-7.56 (m, 1H), 7.57-7.61 (m, 1H), 7.80 (s, 1H), 8.10-8.14 (m, 1H), 8.32 (s, 1H), 8.44-8.46 (m, 2H), 8.58 (d, J = 2.0 Hz, 1H), 8.97 (s, 1H), 9.40 (s, 1H), 11.90-11.98 (m, 1H). |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 121 | 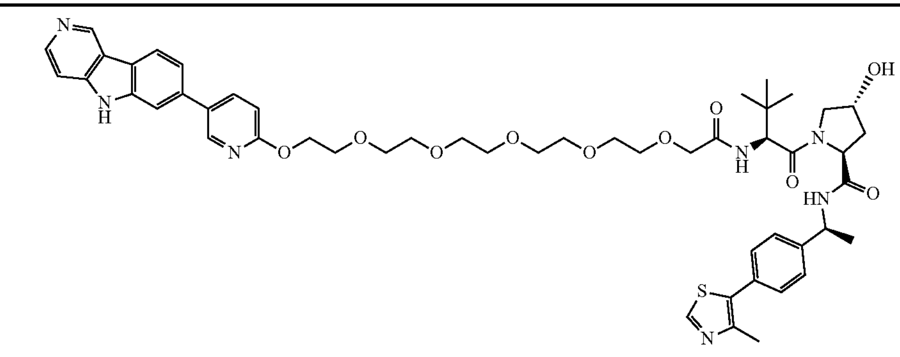 | B | 966.7 | ¹H NMR (400 MHz, DMSOd-6): δ 0.93 (s, 9H), 1.36-1.47 (m, 3H), 1.73-1.80 (m, 1H), 1.96-2.09 (m, 2H), 3.23-3.60 (m, 16H), 3.79 (t, J = 3.6 Hz, 2H), 3.96 (s, 2H), 4.28 (s, 1H), 4.42-4.46 (m, 3H), 4.54 (d, J = 9.6 Hz, 1H), 4.90 (t, J = 7.6 Hz, 1H), 5.12 (s, 1H), 6.97 (d, J = 8.4 Hz, 1H), 7.35-7.43 (m, 5H), 7.65-7.69 (m, 2H), 7.87 (s, 1H), 8.12-8.15 (m, 1H), 8.37-8.43 (m, 2H), 8.51 (d, J = 5.6 Hz, 1H), 8.59 (d, J = 1.6 Hz, 1H), 8.97 (s, 1H), 9.51 (s, 1H), 12.28 (s, 1H). |
| 122 | 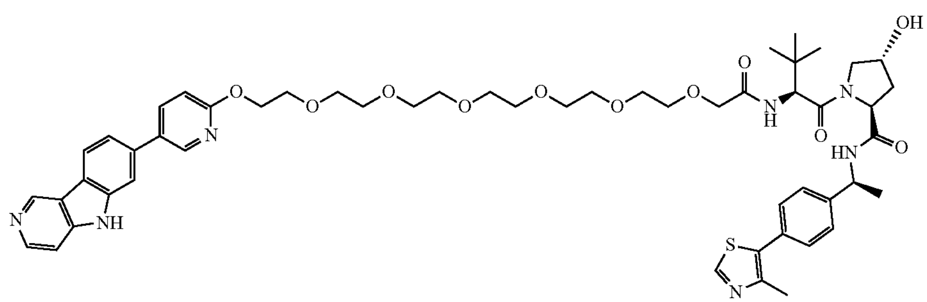 [SMILES: Cc1ncsc1-c1ccc([C@H](C)NC(=O)[C@@H]2C[C@@H](O)CN2C(=O)[C@@H](NC(=O)COCCOCCOCCOCCOCCOCCOc2ccc(-c3ccc4c(c3)[nH]c3ccncc34)cn2)C(C)(C)C)cc1] | C | 1010.7 | ¹H NMR (400 MHz, DMSOd-6): δ 0.93 (s, 9H), 1.36 (d, J = 7.2 Hz, 3H), 1.73-1.80 (m, 1H), 2.01-2.05 (m, 1H), 2.44 (s, 1H), 3.51-3.60 (m, 20H), 3.78 (t, J = 4.4 Hz, 2H), 3.95 (s, 2H), 4.06-4.10 (m, 1H), 4.27 (s, 1H), 4.42-4.46 (m, 3H), 4.54 (d, J = 9.6 Hz, 1H), 4.90 (t, J = 7.2 Hz, 1H), 5.12 (d, J = 3.6 Hz, 1H), 6.97 (d, J = 8.8 Hz, 1H), 7.35-7.38 (m, 3H), 7.41-7.43 (m, 2H), 7.48 (d, J = 5.6 Hz, 1H), 7.56 (d, J = 8.0 Hz, 1H), 7.77 (s, 1H), 8.10-8.13 (m, 1H), 8.30 (d, J = 8.0 Hz, 1H), 8.42 (d, J = 6.0 Hz, 2H), 8.56 (d, J = 2.4 Hz, 1H), 8.97 (s, 1H), 9.35 (s, 1H), 11.79 (s, 1H). |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 123 | 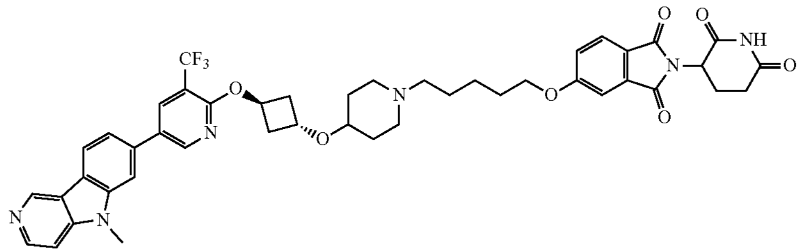 [SMILES: Cn1c2ccncc2c2ccc(-c3cnc(O[C@H]4C[C@H](OC5CCN(CCCCCOc6ccc7c(c6)C(=O)N(C6CCC(=O)NC6=O)C7=O)CC5)C4)c(C(F)(F)F)c3)cc21] | C | 839.6 | ¹HNMR (400 MHz, DMSO-d₆): δ 11.11 (s, 1H), 9.39 (s, 1H), 8.91 (s, 1H), 8.51 (s, 1H), 8.36 (d, J = 8.0 Hz, 1H), 8.19 (s, 1H), 8.10 (s, 1H), 7.83 (d, J = 8.4 Hz, 1H), 7.71 (d, J = 8.4 Hz, 1H), 7.64 (d, J = 5.2 Hz, 1H), 7.43 (s, 1H), 7.34 (d, J = 8.0 Hz, 1H), 5.42-5.47 (m, 1H), 5.09-5.14 (m, 1H), 4.36 (s, 1H), 4.18 (t, J = 6.4 Hz, 2H), 4.24 (t, J = 4.8 Hz, 2H), 3.98 (s, 3H), 2.80-2.91 (m, 1H), 2.74-2.76 (m, 2H), 2.40-2.46 (m, 4H), 2.32 (t, J = 6.4 Hz, 2H), 2.05-2.07 (m, 4H), 1.76-1.82 (m, 4H), 1.44-1.48 (m, 4H). |
| 124 | 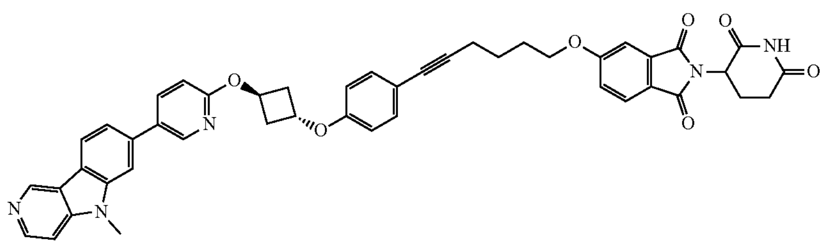 | C | 774.5 | 1H NMR (400 MHz, CDCl₃): δ 8.49 (s, 1H), 8.22 (m, J = 7.6 Hz, 1H), 8.17 (s, 1H), 7.94 (d, J = 2 Hz, 1H), 7.76 (d, J = 8.4 Hz, 1H), 7.59 (s, 1H), 7.52 (d, J = 7.6 Hz, 1H), 7.34 (d, J = 1.2 Hz, 1H), 7.30-7.27 (m, 4H), 7.20-7.18 (m, 1H), 6.87 (d, J = 8.8 Hz, 1H), 6.74 (d, J = 8.4 Hz, 2H), 5.52-5.54 (m, 1H), 4.97-4.94 (m, 2H), 4.16 (t, J = 6.0 Hz, 2H), 3.92 (s, 3H), 2.88-2.69 (m, 8H), 2.50 (t, J = 6.8 Hz, 2H), 2.16-2.13 (m, 2H), 1.82-1.78 (m, 2H). |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 125 | 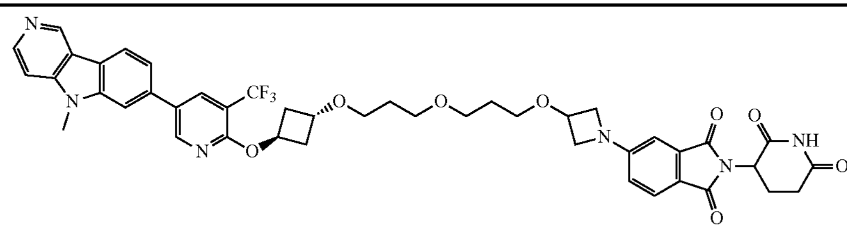 | C | 841.5 | ¹H NMR (400 MHz, DMSO-d6): δ 1.85-1.90 (m, 4H), 2.08-2.19 (m, 2H), 2.20-2.26 (m, 2H), 2.44-2.57 (m, 4H), 2.70-2.90 (m, 3H), 3.45-3.49 (m, 2H), 3.53-3.56 (m, 6H), 3.88-3.91 (m, 2H), 4.22-4.29 (m, 3H), 4.47-4.48 (m, 1H), 4.90-4.94 (m, 1H), 5.53-5.55 (m, 1H), 6.51 (d, J = 8.0 Hz, 1H), 6.77 (s, 1H), 7.47 (d, J = 17.2 Hz, 2H), 7.58 (s, 1H), 7.60 (d, J = 8.4 Hz, 1H), 8.16 (s, 1H), 8.23-8.28 (m, 2H), 8.60 (s, 2H), 9.41 (s, 1H). |
| 126 | 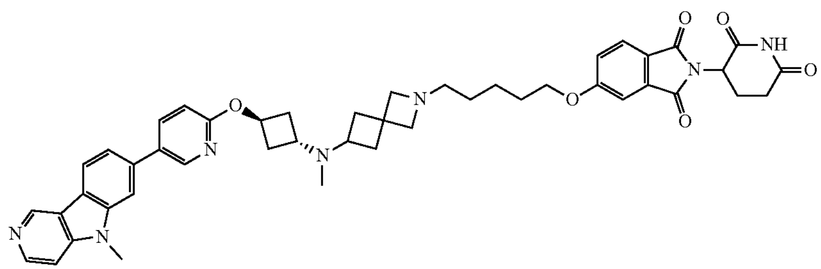 [SMILES: Cn1c2ccncc2c2ccc(-c3ccc(O[C@H]4C[C@H](N(C)C5CC6(C5)CN(CCCCCOc5ccc7c(c5)C(=O)N(C5CCC(=O)NC5=O)C7=O)C6)C4)nc3)cc21] | B | 796.6 | ¹H NMR (400 MHz, DMSO-d6): δ 1.42-1.51 (m, 4H), 1.75-1.79 (m, 2H), 2.03-2.06 (m, 1H), 2.54 (s, 3H), 2.58-2.68 (m, 5H), 2.81-2.94 (m, 2H), 3.11-3.17 (m, 2H), 3.61-3.71 (m, 3H), 3.98-4.11 (m, 6H), 4.15 (s, 3H), 4.17-4.23 (m, 3H), 5.10-5.14 (m, 1H), 5.25-5.31 (m, 1H), 7.03 (d, J = 8.4 Hz, 1), 7.33-7.42 (m, 2H), 7.84-7.89 (m, 1H), 8.22-8.32 (m, 3H), 8.55 (d, J = 8.0 Hz, 1H), 8.71 (s, 1H), 8.78 (d, J = 6.4 Hz, 1H), 9.78 (s, 1H), 10.05 (brs, 1H), 10.51 (brs, 1H), 11.11 (s, 1H). |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 127 | 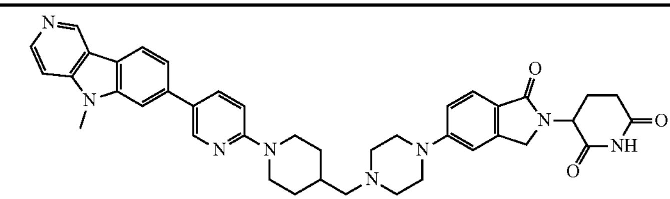 | C | 683.5 | ¹H NMR (400 MHz, DMSO-d6): δ 1.11-1.23 (m, 4H), 1.82-1.99 (m, 4H), 2.30-2.39 (m, 3H), 2.60 (br, 4H), 2.86-2.94 (m, 3H), 3.17 (s, 2H), 3.98 (s, 3H), 4.10 (br, 1H), 4.21 (d, J = 16.8 Hz, 1H), 4.32-4.41 (m, 3H), 5.05 (dd, J = 13.2 Hz, 1H), 6.96 (d, J = 9.2 Hz, 1H), 706-7.08 (m, 2H), 7.53 (d, J = 8.4 Hz, 1H), 7.62 (d, J = 8.0 Hz, 1H), 7.69 (d, J = 6.0 Hz, 1H), 7.95 (s, 1H), 8.02 (dd, J = 9.2 Hz, 1H), 8.30 (dd, J = 8.4 Hz, 1H), 8.51 (d, J = 5.6 Hz, 1H), 8.64 (s, 1H), 9.38 (s, 1H), 10.95 (s, 1H). |
| 128 | 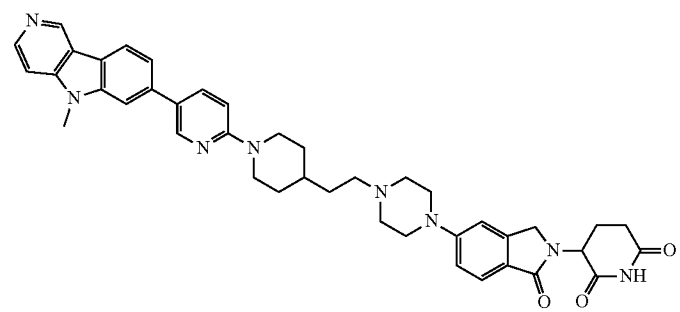 [SMILES: Cn1c2ccncc2c2ccc(-c3ccc(N4CCC(CCN5CCN(c6ccc7c(c6)CN(C6CCC(=O)NC6=O)C7=O)CC5)CC4)nc3)cc21] | C | 697.6 | ¹H NMR (400 MHz, DMSO-d6) δ 1.16-1.23 (m, 3H), 1.40-1.50 (m, 2H), 161 (br, 1H), 1.76-1.78 (m, 2H), 1.94-1.96 (m, 1H), 2.38-2.41 (s, 3H), 2.51-2.56 (m, 4H), 2.82-2.90 (m, 3H), 3.29-3.33 (m, 4H), 3.95 (s, 3H), 4.18-4.22 (m, 1H), 4.30-4.39 (m, 3H), 5.02-5.08 (m, 1H), 6.95 (d, J = 8.8 Hz, 1H), 7.05-7.06 (m, 2H), 7.50-7.69 (m, 3H), 7.91 (s, 1H), 8.00 (d, J = 8.8, 2.2 Hz, 1H), 8.28 (d, J = 8.0 Hz, 1H), 8.48 (d, J = 5.8 Hz, 1H), 8.62 (d, J = 2.0 Hz, 1H), 9.33 (s, 1H), 10.95 (s, 1H). |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 129 | 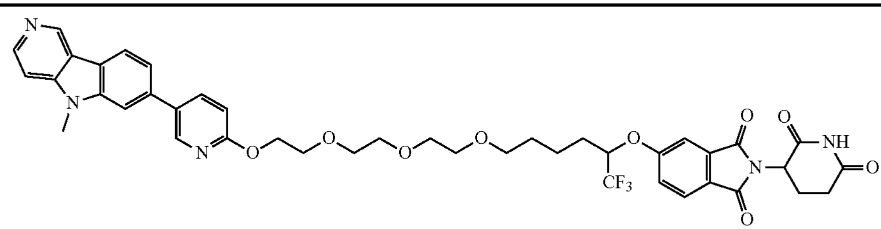 | C | 818.5 | ¹HNMR (400 MHz, CDCl₃): δ 9.25 (s, 1H), 8.48 (s, 1H), 8.39 (s, 1H), 8.09 (d, J = 8.0 Hz, 1H), 7.82 (d, J = 8.0 Hz, 1H), 7.72 (d, J = 8.4 Hz, 1H), 7.46 (s, 1H), 7.36-7.41 (m, 2H), 7.19-7.24 (m, 2H), 6.82 (d, J = 8.8 Hz, 1H), 4.86-4.91 (m, 1H), 4.58-4.63 (m, 1H), 4.45-4.48 (m, 2H), 3.78-3.82 (m, 5H), 3.55-3.80 (m, 9H), 3.39-3.50 (m, 3H), 2.69-2.82 (m, 6H), 1.96-2.05 (m, 2H), 1.81-1.89 (m, 2H). |
| 130 | 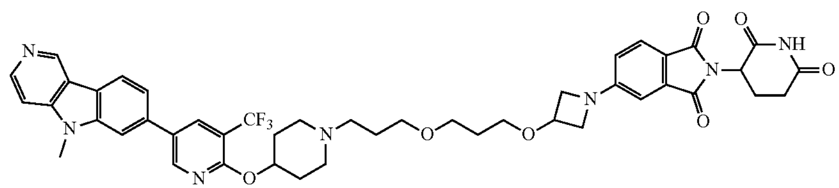 [SMILES: Cn1c2ccncc2c2ccc(-c3cnc(OC4CCN(CCCOCCCOC5CN(c6ccc7c(c6)C(=O)N(C6CCC(=O)NC6=O)C7=O)C5)CC4)c(C(F)(F)F)c3)cc21] | B | 854.6 | ¹H NMR (400 MHz, DMSO-d6): δ 1.74-1.80 (m, 4H), 1.85-1.92 (m, 2H), 1.97-2.02 (m, 2H), 2.02-2.15 (m, 2H), 2.54-2.58 (m, 2H), 2.67-2.91 (m, 4H), 3.41-3.50 (m, 8H), 3.81-3.88 (m, 2H), 3.98 (s, 3H), 4.25 (t, J = 7.8 Hz, 2H), 4.44-4.49 (m, 1H), 5.05 (dd, J = 5.2, 12.8 Hz, 1H), 5.33-5.40 (m, 1H), 6.66 (dd, J = 1.6, 8.4 Hz, 1H), 6.80 (d, J = 1.2 Hz, 1H), 7.63-7.72 (m, 3H), 8.10 (s, 1H), 8.36 (d, J = 8.4 Hz, 1H), 8.51 (d, J = 4.8 Hz, 2H), 8.92 (s, 1H), 9.39 (s, 1H), 11.06 (s, 1H). |
| 131 | 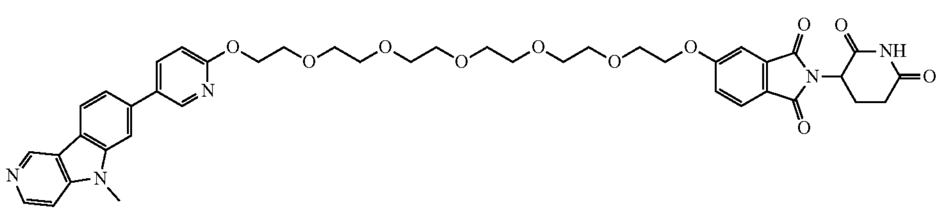 [SMILES: Cn1c2ccncc2c2ccc(-c3ccc(OCCOCCOCCOCCOCCOCCOc4ccc5c(c4)C(=O)N(C4CCC(=O)NC4=O)C5=O)nc3)cc21] | A | 796.5 | 1H NMR (400 MHz, DMSOd-6): δ 1.99-2.05 (m, 1H), 2.55-2.67 (m, 3H), 2.84-2.93 (m, 1H), 3.51-3.60 (m, 16H), 3.77 (d, J = 3.6 Hz, 4H), 4.02 (s, 3H), 4.28 (m, 2H), 4.45 (t, J = 3.6 Hz, 2H), 5.09-5.13 (m, 1H), 6.98 (d, J = 8.4 Hz, 1H), 7.32-7.35 (m, |

TABLE 2-continued

Exemplary PROTAC of the present disclosure.

| Ex. | Structure | Degradation activity* | MH + (1) [MH + (2), if isotope] | NMR transcript |
|---|---|---|---|---|
| | | | | 1H), 7.41 (d, J = 0.8 Hz, 1H), 7.70 (d, J = 8.0 Hz, 1H), 7.78-7.82 (m, 2H), 8.06 (s, 1H), 8.20-8.23 (m, 1H), 8.38 (d, J = 8.4 Hz, 1H), 8.58 (d, J = 6.4 Hz, 1H), 8.66 (d, J = 1.6 Hz, 1H), 8.66 (s, 1H), 9.48 (s, 1H), 11.12 (s, 1H). |
| 132 | 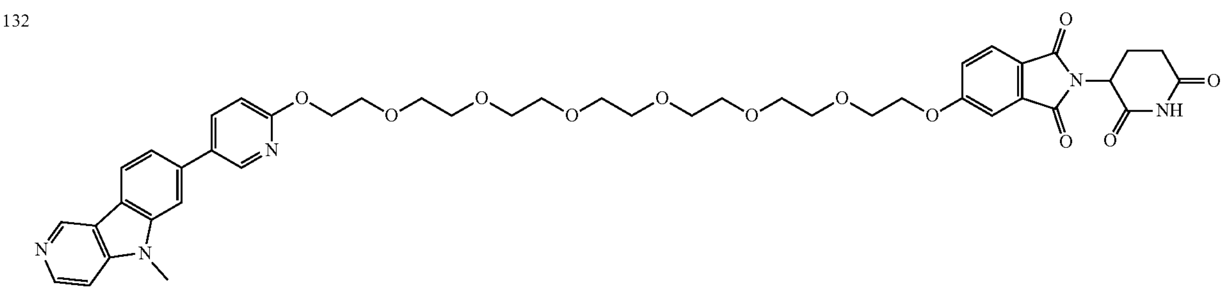 | A | 840.6 | 1HNMR (400 MHz, DMSO-d6): δ 2.01-2.05 (m, 1H), 2.56-2.67 (m, 2H), 2.84-2.89 (m, 1H), 3.49-3.59 (m, 20H), 3.75-3.79 (m, 4H), 3.96 (s, 3H), 4.27-4.29 (m, 2H), 4.43-4.45 (m, 2H), 5.09-5.13 (m, 1H), 6.96-6.99 (m, 1H), 7.32-7.35 (m, 1H), 7.41-7.42 (m, 1H), 7.62-7.65 (m, 2H), 7.79-7.81 (m, 1H), 7.99 (s, 1H), 8.19-8.21 (m, 1H), 8.31-8.34 (m, 1H), 8.50-8.51 (m, 1H), 8.64-8.65 (m, 1H), 9.37 (s, 1H), 11.11 (s, 1H). |
| 133 | 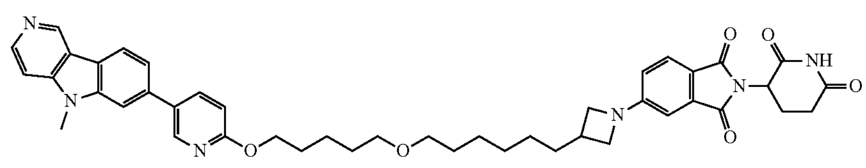 [SMILES: Cn1c2ccncc2c2ccc(-c3ccc(OCCCCCOCCCCCCC4CN(c5ccc6c(c5)C(=O)N(C5CCC(=O)NC5=O)C6=O)C4)nc3)cc21] | A | 757.6 | 1H NMR (400 Hz, D6-DMSO): δ 1.24-1.35 (m, 7H), 1.46-1.57 (m, 8H), 1.72-1.82 (m, 2H), 1.98-2.01 (m, 3H), 2.57-2.74 (m, 3H), 2.81-2.99 (m, 2H), 3.57-3.59 (m, 2H), 3.98 (s, 3H), 4.06-4.08 (m, 2H), 4.33 (s, 2H), 5.03-5.06 (m, 1H), 6.54-6.66 (m, 1H), 6.69 (s, 1H), 6.93-6.95 (m, 1H), 7.57-7.71 (m, 3H), 8.02 (s, 1H), 8.19-8.21 (m, 1H), 8.34-8.36 (m, 1H), 8.53-8.58 (m, 1H), 8.66 (s, 1H), 9.41 (s, 1H), 11.08 (s, 1H). |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 134 | 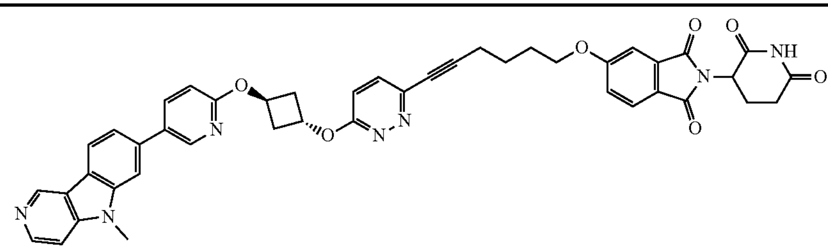 | B | 776.5 | ¹HNMR (400 MHz, DMSO-d₆): δ 1.74-1.78 (m, 2H), 1.92-1.95 (m, 2H), 2.03-2.07 (m, 1H), 2.54-2.62 (m, 4H), 2.68-2.71 (m, 4H), 2.85-2.93 (m, 1H), 3.96 (s, 3H), 4.23-4.27 (m, 2H), 5.09-5.14 (m, 1H), 5.45-5.48 (m, 1H), 5.55-5.58 (m, 1H), 7.01 (d, J = 8.8 Hz, 1H), 7.24-7.26 (m, 1H), 7.36-7.38 (m, 1H), 7.45 (m, 1H), 7.62-7.68 (m, 3H), 7.82 (d, J = 8.0 Hz, 1H), 7.99 (s, 1H), 8.21-8.24 (m, 1H), 8.33 (d, J = 8.0 Hz, 1H), 8.49-8.51 (m, 1H), 8.64-8.65 (m, 1H), 9.37 (s, 1H), 11.12 (s, 1H). |
| 135 | 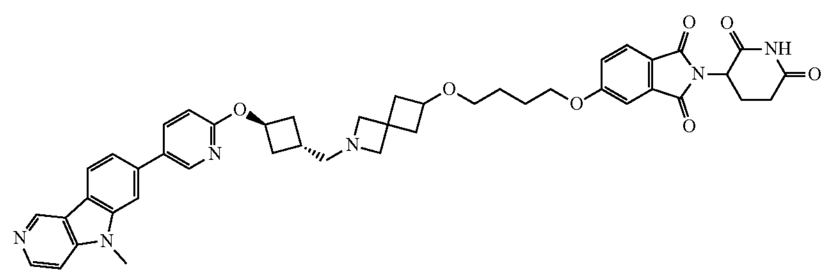 [SMILES: Cn1c2ccncc2c2ccc(-c3ccc(O[C@H]4C[C@H](CN5CC6(CC(OCCCCOc7ccc8c(c7)C(=O)N(C7CCC(=O)NC7=O)C8=O)C6)C5)C4)nc3)cc21] | B | 783.6 | ¹H NMR (400 MHz, DMSO-d₆): 1.60-1.80 (m, 6H), 1.92-2.07 (m, 5H), 2.16-2.26 (m, 3H), 2.34-2.40 (m, 2H), 2.55-2.67 (m, 4H), 2.84-2.93 (m, 1H), 3.26-3.31 (m, 4H), 3.78-3.82 (m, 1H), 3.96 (s, 3H), 4.18 (t, J = 6.0 Hz, 2H), 5.05-5.27 (m, 2H), 6.90-6.94 (m, 1H), 7.33-7.35 (m, 1H), 7.42 (s, 1H), 7.60-7.63 (m, 2H), 7.83 (d, J = 8.4 Hz, 1H), 7.98 (s, 1H), 8.17-8.20 (m, 1H), 8.32 (d, J = 8.0 Hz, 1H), 8.51 (d, J = 6.0 Hz, 1H), 8.62 (s, 1H), 9.36 (s, 1H), 11.12 (s, 1H). |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 136 | 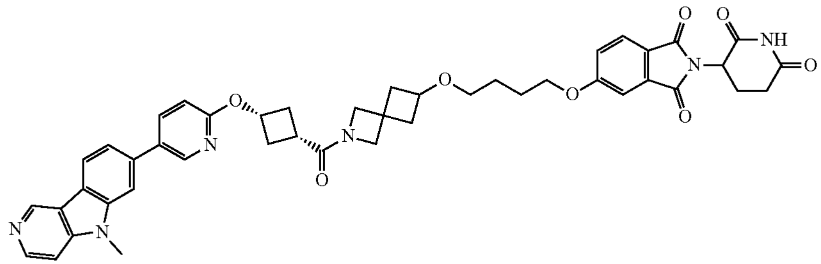 [SMILES: Cn1c2ccncc2c2ccc(-c3ccc(O[C@H]4C[C@@H](C(=O)N5CC6(CC(OCCCCOc7ccc8c(c7)C(=O)N(C7CCC(=O)NC7=O)C8=O)C6)C5)C4)nc3)cc21] | C | 797.5 | 1HNMR (400 MHz, DMSO-d₆): δ 1.61-1.65 (m, 2H), 1.77-1.80 (m, 2H), 1.99-2.08 (m, 4H), 2.14-2.20 (m, 2H), 2.44-2.46 (m, 3H), 2.55-2.61 (m, 4H), 2.72-2.76 (m, 1H), 2.85-2.93 (m, 1H), 3.79-3.84 (m, 3H), 3.96 (s, 3H), 4.04-4.09 (m, 2H), 4.17-4.20 (m, 2H), 5.10-5.14 (m, 2H), 6.93 (d, J = 8.4 Hz, 1H), 7.34-7.42 (m, 2H), 7.61-7.65 (m, 2H), 7.83 (d, J = 8.0 Hz, 1H), 7.99 (s, 1H), 8.18-8.20 (m, 1H), 8.32 (d, J = 8.4 Hz, 1H), 8.50 (d, J = 6.0 Hz, 1H), 8.62 (d, J = 0.8 Hz, 1H), 9.37 (s, 1H), 11.12 (s, 1H). |
| 137 | 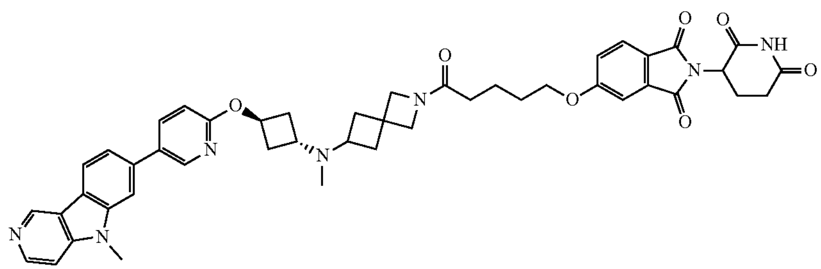 [SMILES: Cn1c2ccncc2c2ccc(-c3ccc(O[C@H]4C[C@H](N(C)C5CC6(C5)CN(C(=O)CCCCOc5ccc7c(c5)C(=O)N(C5CCC(=O)NC5=O)C7=O)C6)C4)nc3)cc21] | C | 810.6 | ¹H NMR (400 MHz, DMSO-d6): δ 1.58-1.63 (m, 2H), 1.72-1.77 (m, 2H), 2.03-2.11 (m, 3H), 2.33-2.47 (m, 8H), 2.54-2.62 (m, 2H), 2.78-2.90 (m, 3H), 3.41-3.48 (m, 3H), 3.75-3.79 (m, 1H), 3.80-3.87 (m, 1H), 4.02 (s, 3H), 4.06 (s, 1H), 4.13-4.18 (m, 3H), 5.10-5.14 (m, 1H), 5.25-5.28 (m, 1H), 6.96-7.00 (m, 1H), 7.33-7.42 (m, 2H), 7.70 (d, J = 8.4 Hz, 1H), 7.80-7.84 (m, 2H), 8.06 (s, 1H), 8.23-8.26 (m, 1H), 8.39 (d, J = 8.0 Hz, 1H), 8.57-8.67 (m, 2H), 9.49 (s, 1H), 11.12 (s, 1H). |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 138 | 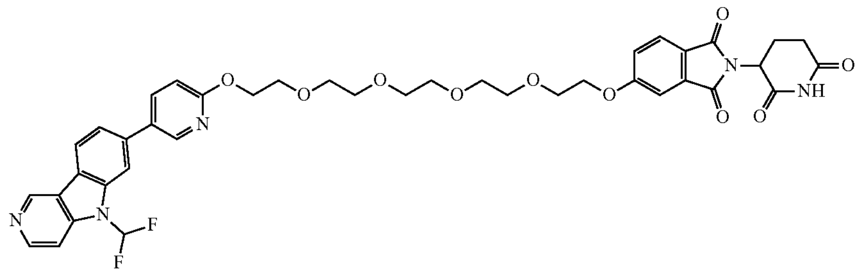 [SMILES: O=C1CCC(N2C(=O)c3ccc(OCCOCCOCCOCCOCCOc4ccc(-c5ccc6c7cnccc7n(C(F)F)c6c5)cn4)cc3C2=O)C(=O)N1] | B | 788.5 | $^1$H NMR (400 MHz, DMSO-d6): δ 2.01-2.04 (m, 1H), 2.56-2.67 (m, 2H), 2.83-2.93 (m, 1H), 3.52-3.59 (m, 12H), 3.78 (s, 4H), 4.29 (s, 2H), 4.45 (s, 2H), 5.11 (d, J = 12.8 Hz, 1H), 6.98 (d, J = 8.8 Hz, 1H), 7.34 (d, J = 8.4 Hz, 1H), 7.43 (s, 1H), 7.76-7.83 (m, 3H), 8.14-8.18 (m, 2H), 8.36-8.50 (m, 2H), 8.61-8.65 (m, 2H), 9.49 (s, 1H), 11.11 (s, 1H). |
| 139 | 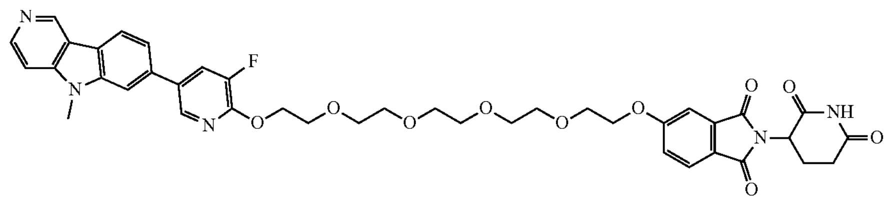 [SMILES: Cn1c2ccncc2c2ccc(-c3cnc(OCCOCCOCCOCCOCCOc4ccc5c(c4)C(=O)N(C4CCC(=O)NC4=O)C5=O)c(F)c3)cc21] | B | 770.5 | $^1$H NMR (400 MHz, DMSOd-6): δ 2.00-2.03 (m, 1H), 2.59-2.74 (m, 2H), 2.87 (t, J = 11.6 Hz, 1H), 3.52-3.60 (m, 12H), 3.80 (d, J = 19.2 Hz, 4H), 4.03 (s, 3H), 4.28 (s, 2H), 4.54 (s, 2H), 5.11 (d, J = 12.8 Hz, 1H), 7.33 (d, J = 7.6 Hz, 1H), 7.42 (s, 1H), 7.78 (m, 2H), 7.86 (d, J = 4.0 Hz, 1H), 8.13 (s, 1H), 8.27 (d, J = 11.2 Hz, 1H), 8.41 (d, J = 7.6 Hz, 1H), 8.52 (s, 1H), 8.61 (d, J = 4.8 Hz, 1H), 9.53 (s, 1H), 11.11 (s, 1H). |
| 140 | 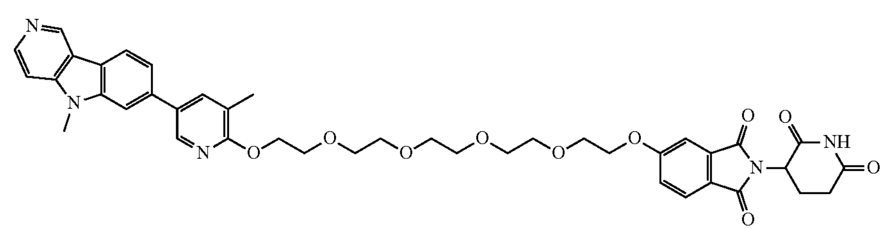 [SMILES: Cc1cc(-c2ccc3c4cnccc4n(C)c3c2)cnc1OCCOCCOCCOCCOCCOc1ccc2c(c1)C(=O)N(C1CCC(=O)NC1=O)C2=O] | A | 766.5 | $^1$H NMR (400 MHz, DMSO-d6): δ 1.99-2.05 (m, 1H), 2.26 (s, 3H), 2.52-2.60 (m, 2H), 2.89 (s, 1H), 3.48-3.65 (m, 12H), 3.74-3.83 (m, 4H), 4.04 (s, 3H), 4.24-4.31 (m, 2H), 4.44-4.50 (m, 2H), 5.08-5.13 (m, 1H), 7.32-7.34 (m, 1H), 7.41 (d, J = 2.0 Hz, 1H), 7.72 (d, J = 8.4 Hz, 1H), 7.79 (d, J = 8.4 Hz, 1H), 7.87 (d, J = 6.0 Hz, 1H), 8.04-8.10 (m, |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 141 | 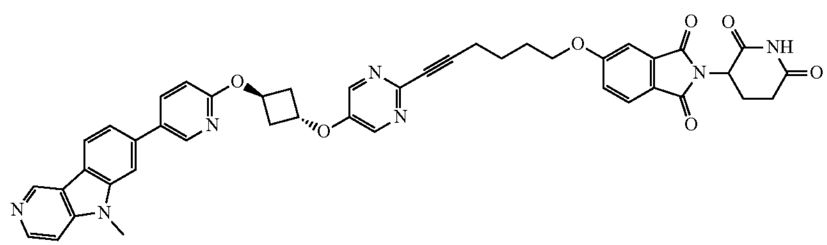 [SMILES: Cn1c2ccncc2c2ccc(-c3ccc(O[C@H]4C[C@H](Oc5cnc(C#CCCCCOc6ccc7c(c6)C(=O)N(C6CCC(=O)NC6=O)C7=O)nc5)C4)nc3)cc21] | C | 776.5 | 1H NMR (400 Hz, DMSO-d6): δ 1.72-1.78 (m, 2H), 1.91-2.10 (m, 4H), 2.54-2.57 (m, 2H), 2.67-2.72 (m, 3H), 3.30 (s, 3H), 3.97 (s, 3H), 4.25 (t, J = 6.4 Hz, 2H), 5.11-5.18 (m, 2H), 5.41-5.48 (m, 1H), 7.01 (d, J = 8.8 Hz, 1H), 7.36 (dd, J = 8.8, 2.0 Hz, 1H), 7.46 (d, J = 2.0 Hz, 2H), 7.63-7.67 (m, 2H), 7.82 (d, J = 8.0 Hz, 1H), 8.01 (s, 1H), 8.23 (dd, J = 8.8, 2.4 Hz, 1H), 8.35 (d, J = 8.0 Hz, 1H), 8.44 (s, 2H), 8.52 (d, J = 5.6 Hz, 1H), 8.65 (d, J = 2.4 Hz, 1H), 9.39 (s, 1H), 11.12 (s, 1H) |
| 142 | 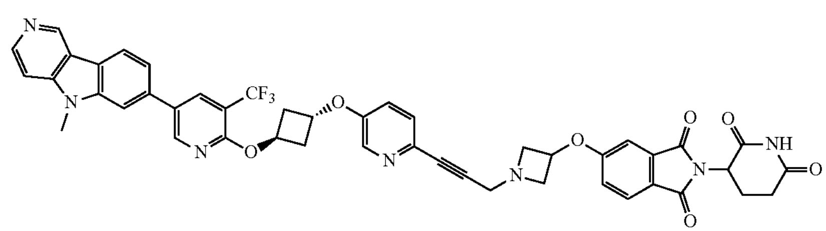 [SMILES: Cn1c2ccncc2c2ccc(-c3cnc(O[C@H]4C[C@H](Oc5ccc(C#CCN6CC(Oc7ccc8c(c7)C(=O)N(C7CCC(=O)NC7=O)C8=O)C6)nc5)C4)c(C(F)(F)F)c3)cc21] | C | 856.5 | 1H NMR (400 MHz, CD3OD): δ 1.90-1.94 (m, 2H), 1.99-2.04 (m, 1H), 2.34-2.40 (m, 1H), 2.65-2.70 (m, 4H), 3.46-3.50 (m, 1H), 3.55-3.61 (m, 2H), 3.86-3.90 (m, 1H), 3.96 (s, 3H), 4.89 (m, 2H), 4.95-5.01 (m, 2H), 5.24 (t, J = 4.6 Hz, 1H), 5.53-5.59 (m, 1H), 7.12-7.24 (m, 3H), 7.42 (d, J = 5.2 Hz, 1H), 7.60 (d, J = 8.0 Hz, 1H), 7.70-7.72 (m, 2H), 7.88 (s, 1H), 8.06 (d, J = 2.8 Hz, 1H), 8.28-8.30 (m, 2H), 8.42 (d, J = 6.4 Hz, 1H), 8.67 (d, J = 2.0 Hz, 1H), 9.29 (s, 1H). |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 143 | 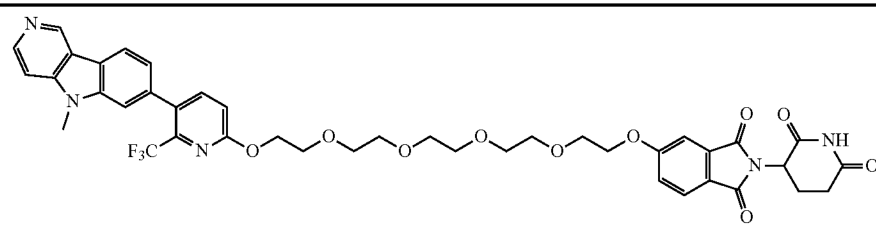 | B | 820.5 | ¹H NMR (400 MHz, DMSO-d6): δ 2.01-2.06 (m, 1H), 2.54-2.68 (m, 2H), 2.84-2.93 (m, 1H), 3.40-3.44 (m, 6H), 3.47-3.51 (m, 4H), 3.56-3.58 (m, 2H), 3.70 (br, 2H), 3.78-3.81 (m, 2H), 3.94 (s, 3H), 4.21 (br, 2H), 4.52 (t, J = 4.0 Hz, 2H), 5.11 (d, J = 12.8 Hz, 1H), 7.26 (d, J = 8.4 Hz, 1H), 7.34 (s, 1H), 7.64 (t, J = 6.8 Hz, 2H), 7.69 (d, J = 6.0 Hz, 1H), 7.74 (d, J = 8.4 Hz, 1H), 8.01 (s, 1H), 8.17 (d, J = 7.6 Hz, 1H), 8.34 (d, J = 8.4 Hz, 1H), 8.53 (d, J = 5.6 Hz, 1H), 9.40 (s, 1H), 11.12 (s, 1H). |
| 144 | 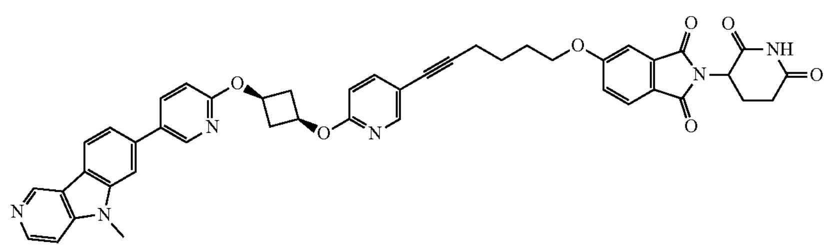 [SMILES: Cn1c2ccncc2c2ccc(-c3ccc(O[C@H]4C[C@@H](Oc5ccc(C#CCCCCOc6ccc7c(c6)C(=O)N(C6CCC(=O)NC6=O)C7=O)cn5)C4)nc3)cc21] | C | 775.5 | ¹H NMR (400 MHz, DMSO-d6): δ 1.68-1.75 (m, 2H), 1.88-1.95 (m, 2H), 2.03-2.08 (m, 1H), 2.16-2.23 (m, 2H), 2.52-2.65 (m, 3H), 2.85-2.93 (m, 1H), 3.08-3.14 (m, 2H), 3.31 (m, 1H), 3.96 (s, 3H), 4.24 (t, J = 6.4 Hz, 2H), 4.94-5.05 (m, 2H), 5.12 (dd, J = 5.2, 12.8 Hz, 1H), 6.81 (d, J = 8.8 Hz, 1H), 6.97 (d, J = 8.8 Hz, 1H), 7.36 (dd, J = 2.0, 8.4 Hz, 1H), 7.44 (d, J = 2.0 Hz, 1H), 7.61-7.70 (m, 3H), 7.82 (d, J = 8.0 Hz, 1H), 7.99 (s, 1H), 8.19-8.21 (m, 2H), 8.32 (d, J = 8.0 Hz, 1H), 8.51 (m, 1H), 8.65 (d, J = 2.0 Hz, 1H), 9.38 (m, 1H), 11.12 (s, 1H). |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 145 | 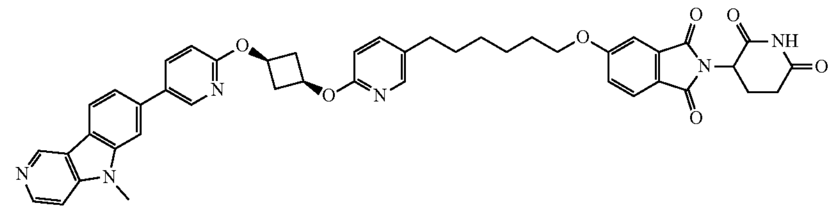 [SMILES: Cn1c2ccncc2c2ccc(-c3ccc(O[C@H]4C[C@@H](Oc5ccc(CCCCCCOc6ccc7c(c6)C(=O)N(C6CCC(=O)NC6=O)C7=O)cn5)C4)nc3)cc21] | C | 779.5 | ¹H NMR (400 MHz, DMSO-d6): δ 1.32-1.38 (m, 2H), 1.42-1.47 (m, 2H), 1.53-1.61 (m, 2H), 1.71-1.78 (m, 2H), 2.01-2.07 (m, 1H), 2.15-2.22 (m, 2H), 2.53-2.61 (m, 4H), 2.84-2.94 (m, 1H), 3.08-3.15 (m, 2H), 4.14-4.17 (m, 5H), 4.91-5.06 (m, 2H), 5.12 (dd, J = 5.6, 12.8 Hz, 1H), 6.78 (d, J = 8.4 Hz, 1H), 7.01 (d, J = 8.4 Hz, 1H), 7.33 (dd, J = 2.0, 8.4 Hz, 1H), 7.41 (d, J = 2.0 Hz, 1H), 7.61 (dd, J = 2.0, 8.4 Hz, 1H), 7.81-7.88 (m, 2H), 8.00 (d, J = 2.0 Hz, 1H), 8.20-8.28 (m, 3H), 8.56 (d, J = 8.4 Hz, 1H), 8.71-8.76 (m, 2H), 9.80 (s, 1H), 11.12 (s, 1H). |
| 146 | 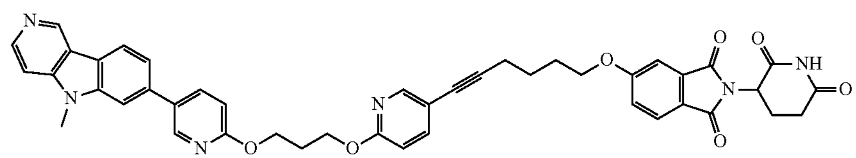 [SMILES: Cn1c2ccncc2c2ccc(-c3ccc(OCCCOc4ccc(C#CCCCCOc5ccc6c(c5)C(=O)N(C5CCC(=O)NC5=O)C6=O)cn4)nc3)cc21] | C | 763.5 | ¹H NMR (400 MHz, DMSO-d6): δ 1.67-1.75 (m, 2H), 1.87-197 (m, 2H), 2.03-2.07 (m, 1H), 2.20-2.23 (m, 2H), 2.53-2.67 (m, 4H), 2.85-2.94 (m, 1H), 3.98 (s, 3H), 4.23 (t, J = 6.0 Hz, 2H), 4.42-4.49 (m, 4H), 5.10-5.14 (m, 1H), 6.80 (d, J = 8.4 Hz, 1H), 6.96 (d, J = 5.2 Hz, 1H), 7.34-7.36 (m, 1H), 7.40 (d, J = 2.0 Hz, 1H), 7.63-7.69 (m, 3H), 7.82 (d, J = 8.4 Hz, 1H), 8.00 (s, 1H), 8.19-8.21 (m, 2H), 8.34 (d, J = 8.0 Hz, 1H), 8.51 (d, J = 6.0 Hz, 1H), 8.64 (d, J = 2.4 Hz, 1H), 9.40 (s, 1H), 11.12 (s, 1H). |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 147 | 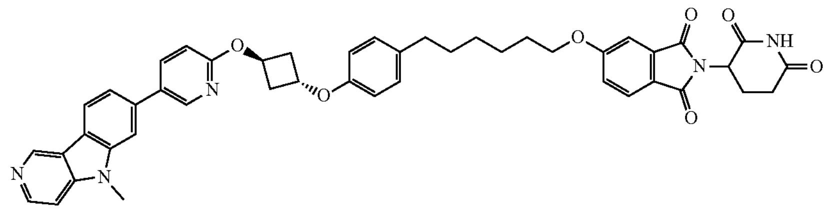 [SMILES: Cn1c2ccncc2c2ccc(-c3ccc(O[C@H]4C[C@H](Oc5ccc(CCCCCCOc6ccc7c(c6)C(=O)N(C6CCC(=O)NC6=O)C7=O)cc5)C4)nc3)cc21] | C | 778.5 | ¹HNMR (400 MHz, CDCl₃): δ: 9.32 (s, 1H), 8.58 (d, J = 5.6 Hz, 1H), 8.49 (s, 1H), 8.21 (d, J = 8.0 Hz, 1H), 8.01 (s, 1H), 7.92 (d, J = 7.6 Hz, 1H), 7.77 (d, J = 8.0 Hz, 1H), 7.56 (s, 1H), 7.50 (d, J = 8.0 Hz, 1H), 7.32 (s, 2H), 7.17 (d, J = 8.8 Hz, 1H), 7.08 (d, J = 8.4 Hz, 2H), 6.86 (d, J = 8.4 Hz, 1H), 6.75 (d, J = 7.6 Hz, 2H), 5.49 (s, 1H), 4.94 (s, 2H), 4.07 (t, J = 6.4 Hz, 2H), 3.91 (s, 3H), 2.68-2.88 (m, 8H), 2.57 (t, J = 6.8 Hz, 2H), 2.01 (s, 2H), 1.83 (t, J = 6.8 Hz, 3H), 1.62-1.65 (m, 2H). |
| 148 | 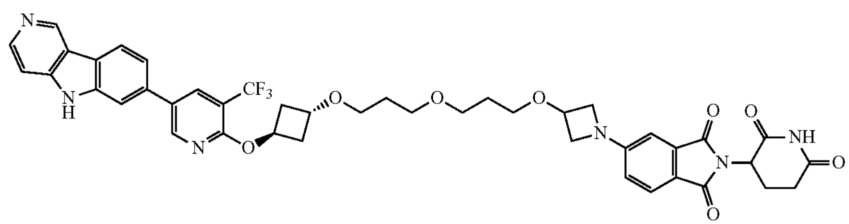 | B | 827.5 | ¹H NMR (400 MHz, DMSO-d6): δ 1.73-1.79 (m, 4H), 1.95-2.01 (m, 2H), 1.99-2.04 (m, 2H), 2.33-2.39 (m, 2H), 2.44-2.46 (m, 2H), 2.54-2.67 (m, 1H), 2.82-2.91 (m, 1H), 3.37-3.49 (m, 8H), 3.81-3.84 (m, 2H), 4.17-4.25 (m, 3H), 4.43-4.48 (m, 1H), 5.01-5.06 (m, 1H), 5.45-5.50 (m, 1H), 6.61-6.64 (m, 1H), 6.77 (d, J = 4.8 Hz, 1H), 7.60 (d, J = 8.4 Hz, 1H), 7.73 (d, J = 6.8 Hz, 1H), 7.97 (s, 1H), 8.471-8.43 (m, 2H), 8.54 (d, J = 6.4 Hz, 1H), 8.85 (d, J = 4.8 Hz, 1H), 9.55 (s, 1H), 11.06 (s, 1H), 12.44 (s, 1H). |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 149 | 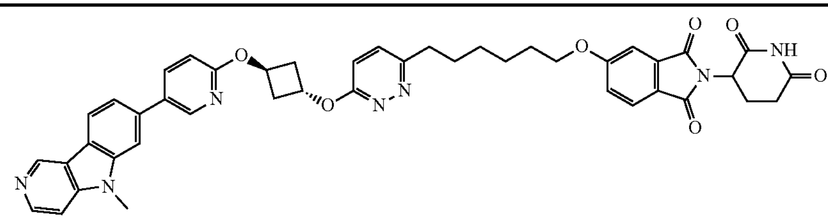 | B | 780.5 | ¹HNMR (400 MHz, DMSO-d₆): δ 1.36-1.49 (m, 4H), 1.66-1.77 (m, 4H), 2.02-2.06 (m, 1H), 2.54-2.68 (m, 6H), 2.81-2.94 (m, 3H), 3.16-3.17 (m, 1H), 3.99 (s, 3H), 4.15-4.18 (m, 2H), 5.09-5.14 (m, 1H), 5.44-5.53 (m, 1H), 7.02 (d, J = 8.8 Hz, 1H), 7.16-7.18 (m, 1H), 7.33-7.35 (m, 1H), 7.45 (m, 1H), 7.54-7.56 (m, 1H), 7.65-7.67 (m, 1H), 7.72-7.73 (m, 1H), 7.81-7.83 (d, J = 8.0 Hz, 1H), 8.03 (s, 1H), 8.22-8.24 (m, 1H), 8.35-8.37 (d, J = 8.0 Hz, 1H), 8.52-8.57 (m, 1H), 8.64-8.65 (m, 1H), 9.42 (s, 1H), 11.11 (s, 1H). |
| 150 | 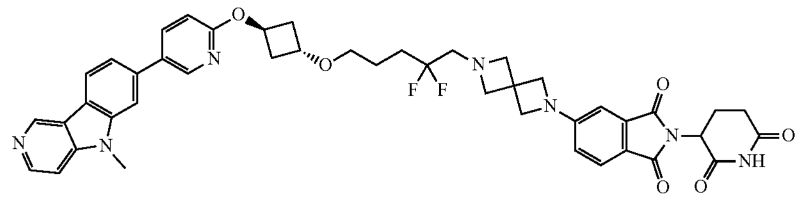 [SMILES: Cn1c2ccncc2c2ccc(-c3ccc(O[C@H]4C[C@H](OCCCC(F)(F)CN5CC6(C5)CN(c5ccc7c(c5)C(=O)N(C5CCC(=O)NC5=O)C7=O)C6)C4)nc3)cc21] | B | 804.5 | ¹H NMR: (400 MHz, DMSO-d₆) δ: 10.95 (s, 1H), 9.14 (br s, 1H), 8.15 (s, 1H), 7.52 (d, J = 9.0 Hz, 1H), 7.18-7.04 (m, 5H), 6.83 (d, J = 6.7 Hz, 2H), 6.65 (d, J = 8.5 Hz, 1H), 6.61 (s, 1H), 6.54-6.47 (m, 3H), 6.26 (d, J = 8.5 Hz, 2H), 5.05 (dd, J = 5.0, 13.3 Hz, 1H), 4.38-4.26 (m, 1H), 4.24-4.11 (m, 1H), 3.78 (br t, J = 6.5 Hz, 4H), 3.54-3.31 (m, 3H), 3.03-2.83 (m, 8H), 2.62-2.52 (m, 3H), 2.47-2.31 (m, 1H), 2.21-2.04 (m, 3H), 2.01-1.87 (m, 3H), 1.71 (br d, J = 10.7 Hz, 2H). |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 151 | 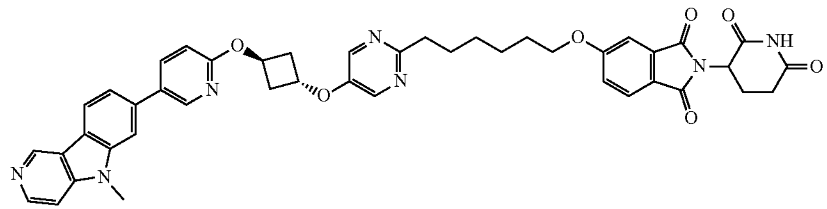 [SMILES: Cn1c2ccncc2c2ccc(-c3ccc(O[C@H]4C[C@H](Oc5cnc(CCCCCCOc6ccc7c(c6)C(=O)N(C6CCC(=O)NC6=O)C7=O)nc5)C4)nc3)cc21] | B | 780.5 | 1H NMR (400 Hz, DMSO-d6): δ 1.21-1.26 (m, 1H), 1.33-1.48 (m, 4H), 1.69-1.73 (m, 4H), 1.01-2.07 (m, 1H), 2.57-2.68 (m, 5H), 2.79-2.93 (m, 3H), 4.02 (s, 3H), 4.16 (t, J = 6.4 Hz, 2H), 5.09-5.13 (m, 2H), 5.41-5.48 (m, 1H), 7.01 (d, J = 8.8 Hz, 1H), 7.35 (dd, J = 8.4, 1.6 Hz, 1H), 7.46 (d, J = 0.8 Hz, 1H), 7.69 (d, J = 8.0 Hz, 1H), 7.79-7.83 (m, 2H), 8.07 (s, 1H), 8.23 (dd, J = 8.4, 1.2 Hz, 1H), 8.37-8.45 (m, 3H), 8.58 (d, J = 6.0 Hz, 1H), 8.67 (s, 1H), 9.49 (s, 1H), 11.11 (s, 1H). |
| 152 | 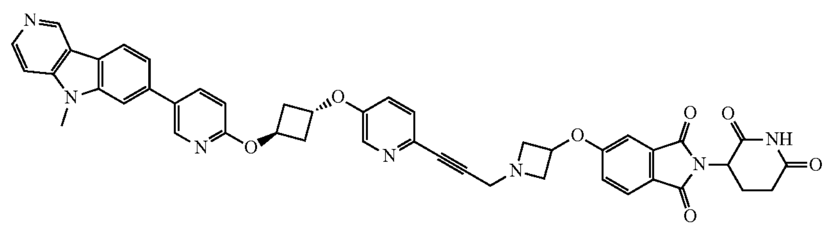 [SMILES: Cn1c2ccncc2c2ccc(-c3ccc(O[C@H]4C[C@H](Oc5ccc(C#CCN6CC(Oc7ccc8c(c7)C(=O)N(C7CCC(=O)NC7=O)C8=O)C6)nc5)C4)nc3)cc21] | A | 788.5 | 1H NMR (400 MHz, DMSO-d6): δ 2.01-2.06 (m, 1H), 2.53-2.73 (m, 6H), 2.84-2.92 (m, 1H), 3.59 (s, 2H), 3.81 (t, J = 6.8 Hz, 2H), 3.96 (s, 3H), 5.07-5.14 (m, 3H), 5.42-5.47 (m, 1H), 6.99 (d, J = 8.4 Hz, 1H), 7.28-7.33 (m, 3H), 7.48 (d, J = 8.4 Hz, 1H), 7.62-7.65 (m, 2H), 7.84 (d, J = 8.0 Hz, 1H), 7.99 (s, 1H), 8.20-8.24 (m, 2H), 8.33 (d, J = 8.0 Hz, 1H), 8.51 (m, 1H), 8.65 (d, J = 2.4 Hz, 1H), 9.38 (m, 1H), 11.11 (s, 1H). |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 153 | 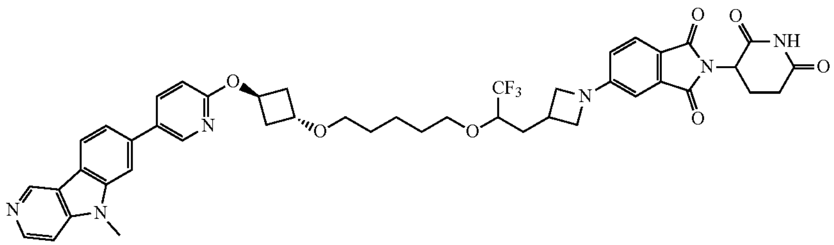 [SMILES: Cn1c2ccncc2c2ccc(-c3ccc(O[C@H]4C[C@H](OCCCCCOC(CC5CN(c6ccc7c(c6)C(=O)N(C6CCC(=O)NC6=O)C7=O)C5)C(F)(F)F)C4)nc3)cc21] | B | 839.6 | 1H NMR (400 MHz, DMSO-d6): δ 1.38-1.41 (m, 2H), 1.54-1.59 (m, 4H), 1.92-1.96 (m, 3H), 2.23-2.45 (m, 5H), 2.82-3.02 (m, 2H), 3.34 (t, J = 6.0 Hz, 2H), 3.56-3.62 (m, 1H), 3.67-3.79 (m, 3H), 4.04-4.05 (m, 1H), 4.14-4.21 (m, 6H), 5.01-5.06 (m, 1H), 5.29-5.35 (m, 1H), 6.61 (d, J = 8.0 Hz, 1H), 6.74 (s, 1H), 6.96 (d, J = 8.4 Hz, 1H), 7.61 (d, J = 8.0 Hz, 1H), 7.86 (d, J = 8.0 Hz, 1H), 8.21-8.25 (m, 3H), 8.53 (d, J = 8.4 Hz, 1H), 8.68 (d, J = 1.6 Hz, 1H), 8.77 (d, J = 6.8 Hz, 1H), 9.77 (s, 1H), 11.07 (s, 1H). |
| 154 | 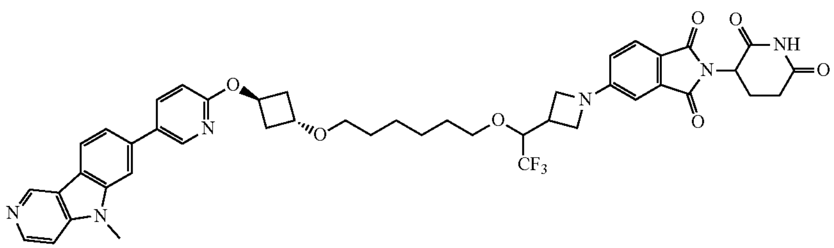 [SMILES: Cn1c2ccncc2c2ccc(-c3ccc(O[C@H]4C[C@H](OCCCCCCOC(C5CN(c6ccc7c(c6)C(=O)N(C6CCC(=O)NC6=O)C7=O)C5)C(F)(F)F)C4)nc3)cc21] | C | 839.6 | 1HNMR (400 MHz, DMSO-d6): δ 1.26 (s, 4H), 1.36-1.37 (m, 2H), 1.49-1.54 (m, 2H), 1.97-2.00 (m, 1H), 2.29-2.42 (m, 4H), 2.53-2.59 (m, 2H), 2.83-2.91 (m, 1H), 3.17-3.23 (m, 3H), 3.65-3.71 (m, 1H), 3.78-3.89 (m, 2H), 3.96 (s, 3H), 3.98-4.02 (m, 1H), 4.11-4.22 (m, 3H), 4.33-4.36 (m, 1H), 5.04-5.08 (m, 1H), 5.28-5.34 (m, 1H), 6.68-6.70 (m, 1H), 6.83-6.84 (m, 1H), 6.93-6.95 (m, 1H), 7.61-7.66 (m, 3H), 7.98 (s, 1H), 8.17-8.20 (m, 1H), 8.31-8.33 (m, 1H), 8.49-8.51 (m, 1H), 8.63-8.64 (m, 1H), 9.36 (s, 1H), 11.07 (s, 1H). |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 155 | 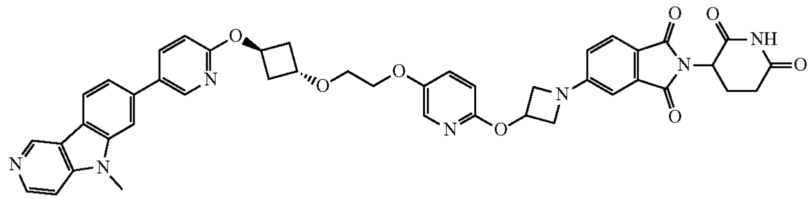 [SMILES: Cn1c2ccncc2c2ccc(-c3ccc(O[C@H]4C[C@H](OCCOc5ccc(OC6CN(c7ccc8c(c7)C(=O)N(C7CCC(=O)NC7=O)C8=O)C6)nc5)C4)nc3)cc21] | C | 794.5 | 1H NMR (400 MHz, DMSO-d6): δ 2.33-2.50 (m, 6H), 2.54-2.60 (m, 1H), 2.83-2.93 (m, 1H), 3.68 (t, J = 4.4 Hz, 2H), 3.96 (s, 3H), 4.01 (d, J = 3.6 Hz, 2H), 4.15 (t, J = 4.0 Hz, 2H), 4.28-4.33 (m, 1H), 4.45-4.49 (m, 2H), 4.04 (s, 1H), 5.06 (d, J = 5.2 Hz, 1H), 5.31-5.36 (m, 1H), 5.43-5.48 (m, 1H), 6.71 (dd, J = 2.0 Hz, 1H), 6.88 (t, J = 9.2 Hz, 2H), 6.95 (d, J = 8.8 Hz, 1H), 7.50 (d, J = 3.2 Hz, 1H), 7.61-7.65 (m, 1H), 7.91 (d, J = 2.8 Hz, 1H), 7.99 (s, 1H), 8.18-8.20 (m, 1H), 8.33 (d, J = 8.0 Hz, 1H), 8.50 (d, J = 6.0 Hz, 1H), 8.65 (d, J = 2.4 Hz, 1H), 9.37 (s, 1H), 11.08 (s, 1H). |
| 156 | 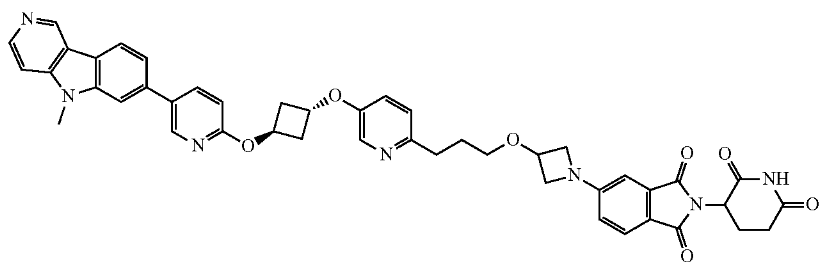 [SMILES: Cn1c2ccncc2c2ccc(-c3ccc(O[C@H]4C[C@H](Oc5ccc(CCCOC6CN(c7ccc8c(c7)C(=O)N(C7CCC(=O)NC7=O)C8=O)C6)nc5)C4)nc3)cc21] | C | 792.5 | 1H NMR (400 MHz, DMSO-d6): δ 1.93-2.01 (m, 3H), 2.54-2.70 (m, 6H), 2.85 (t, J = 7.2 Hz, 2H), 3.45 (t, J = 6 Hz, 2H), 3.79-3.81 (m, 2H), 4.15 (s, 3H), 4.22-4.26 (m, 2H), 4.43-4.45 (m, 1H), 5.03-5.10 (m, 3H), 5.43-5.46 (m, 1H), 6.67 (d, J = 8.4 Hz, 1H), 6.81 (s, 1H), 7.04 (d, J = 8.4 Hz, 1H), 7.46-7.56 (m, 2H), 7.65 (d, J = 8.4 Hz, 1H), 7.88 (d, J = 8.4 Hz, 1H), 8.21-8.30 (m, 4H), 8.55 (d, J = 8 Hz, 1H), 8.71-8.79 (m, 2H), 9.77 (s, 1H), 11.07 (s, 1H). |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 157 | 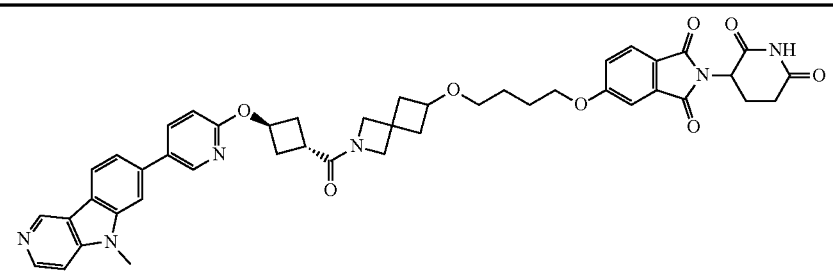 | C | 797.5 | 1HNMR (400 MHz, DMSO-d6): δ 1.61-1.66 (m, 2H), 1.75-1.82 (m, 2H), 1.99-2.06 (m, 4H), 2.29-2.33 (m, 2H), 2.43-2.45 (m, 3H), 2.55-2.61 (m, 3H), 2.56-2.93 (m, 1H), 3.06-3.09 (m, 1H), 3.31 (s, 1H), 3.80-3.88 (m, 3H), 3.96 (s, 3H), 4.00-4.06 (m, 2H), 4.18 (t, J = 7.4 Hz, 2H), 5.10-5.14 (m, 1H), 5.28-5.33 (m, 1H), 6.93 (d, J = 8.8 Hz, 1H), 7.33-7.36 (m, 1H), 7.42 (d, J = 1.6 Hz, 1H), 7.61-7.64 (m, 2H), 7.83 (d, J = 8.4 Hz, 1H), 7.98 (s, 1H), 8.18-8.20 (m, 1H), 8.32 (d, J = 8.0 Hz, 1H), 8.50 (d, J = 5.6 Hz, 1H), 8.63 (d, J = 2.0 Hz, 1H), 9.37 (s, 1H), 11.12 (s, 1H) |
| 158 | 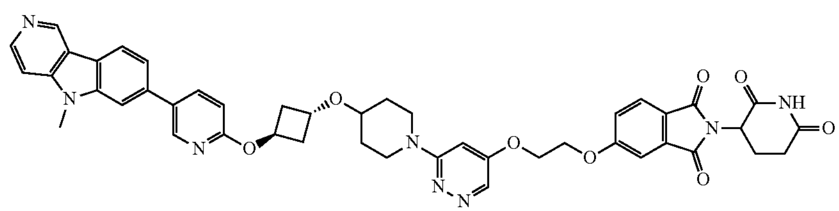 [SMILES: Cn1c2ccncc2c2ccc(-c3ccc(O[C@H]4C[C@H](OC5CCN(c6cc(OCCOc7ccc8c(c7)C(=O)N(C7CCC(=O)NC7=O)C8=O)cnn6)CC5)C4)nc3)cc21] | C | 823.5 | 1H NMR (400 MHz, DMSO-d6): δ 1.45-1.47 (m, 2H), 1.89-1.92 (m, 2H), 1.97-2.07 (m, 3H), 2.40-2.44 (m, 4H), 2.55-2.67 (m, 1H), 2.84-2.94 (m, 1H), 3.16-3.25 (m, 2H), 3.56-3.64 (m, 1H), 4.05 (s, 3H), 4.10-4.13 (m, 2H), 4.42-4.45 (m, 1H), 4.51-4.58 (m, 3H), 5.10-5.15 (m, 1H), 5.31-5.35 (m, 1H), 6.78 (s, 1H), 6.97 (d, J = 8.8 Hz, 1H), 7.40-7.42 (m, 1H), 7.51 (s, 1H), 7.85-7.89 (m, 2H), 8.10 (s, 1H), 8.21-8.24 (m, 1H), 8.35 (d, J = 1.6 Hz, 1H), 8.42 (d, J = 8.4 Hz, 1H), 8.62 (d, J = 6.0 Hz, 1H), 8.67 (d, J = 2.4 Hz, 1H), 9.54 (s, 1H), 11.12 (s, 1H). |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 159 | 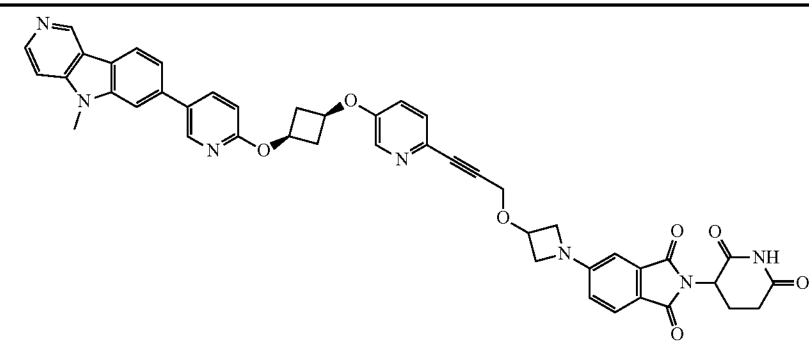 | C | 788.5 | 1H NMR (400 MHz, DMSO-d6): δ 1.99-2.03 (m, 2H), 2.21-2.24 (m, 2H), 2.54-2.67 (m, 2H), 2.83-2.92 (m, 1H), 3.16-3.27 (m, 2H), 3.95-3.98 (m, 4H), 3.30-3.34 (m, 2H), 4.49 (s, 2H), 4.66-4.72 (m, 2H), 5.01-5.08 (m, 2H), 6.68 (d, J = 8.4 Hz, 1H), 6.82 (s, 1H), 6.98 (d, J = 8.4 Hz, 1H), 7.37 (dd, J = 8.4 Hz, 1H), 7.54 (d, J = 8.8 Hz, 1H), 7.62-7.67 (m, 3H), 7.99 (s, 1H), 8.21 (d, J = 8.4 Hz, 1H), 8.26 (d, J = 2.8 Hz, 1H), 8.33 (d, J = 8.4 Hz, 1H), 8.50 (d, J = 5.6 Hz, 1H), 8.65 (d, J = 2.0 Hz, 1H), 9.37 (s, 1H), 11.07 (s, 1H). |
| 160 | 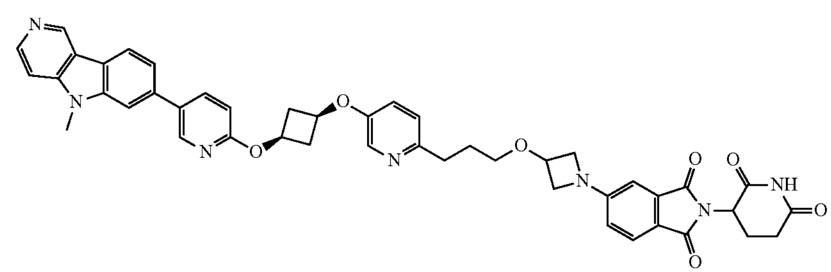 [SMILES: Cn1c2ccncc2c2ccc(-c3ccc(O[C@H]4C[C@@H](Oc5ccc(CCCOC6CN(c7ccc8c(c7)C(=O)N(C7CCC(=O)NC7=O)C8=O)C6)nc5)C4)nc3)cc21] | B | 792.5 | 1H NMR (400 MHz, DMSO-d6): δ 1.88-1.95 (m, 2H), 1.97-2.03 (m, 2H), 2.16-2.23 (m, 2H), 2.54-2.60 (m, 1H), 2.67-2.76 (m, 2H), 2.83-2.92 (m, 1H), 3.14-3.21 (m, 2H), 3.43 (t, J = 6.4 Hz, 2H), 3.84 (d, J = 8.8 Hz, 2H), 3.97 (s, 3H), 4.23-4.27 (m, 2H), 4.43-4.48 (m, 1H), 4.56-4.63 (m, 1H), 5.00-5.08 (m, 2H), 6.66 (d, J = 8.0 Hz, 1H), 6.81 (s, 1H), 6.98 (d, J = 8.8 Hz, 1H), 7.20 (d, J = 8.8 Hz, 1H), 7.24-7.27 (m, 1H), 7.62-7.66 (m, 3H), 8.00 (s, 1H), 8.16 (d, J = 2.8 Hz, 1H), 8.21 (d, J = 8.4 Hz, 1H), 8.33 (d, J = 8.0 Hz, 1H), 8.51 (d, J = 5.6 Hz, 1H), 8.65 (d, J = |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 161 | 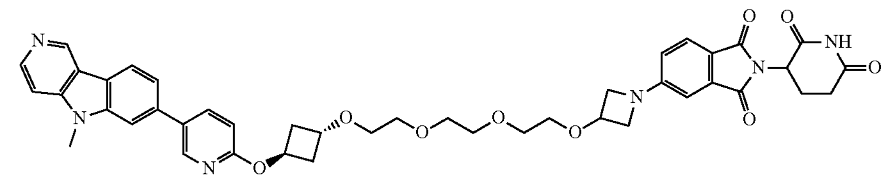 [SMILES: Cn1c2ccncc2c2ccc(-c3ccc(O[C@H]4C[C@H](OCCOCCOCCOC5CN(c6ccc7c(c6)C(=O)N(C6CCC(=O)NC6=O)C7=O)C5)C4)nc3)cc21] | C | 789.5 | 1H NMR (400 MHz, DMSO-d6): δ 2.30-2.36 (m, 2H), 2.40-2.46 (m, 3H), 2.54-2.58 (m, 2H), 2.82-2.91 (m, 1H), 3.44-3.47 (m, 2H), 3.54-3.57 (m, 10H), 3.85 (d, J = 9.2 Hz, 2H), 3.95 (s, 3H), 4.20-4.25 (m, 3H), 4.48-4.50 (m, 1H), 5.04 (t, J = 12.8 Hz, 1H), 5.28-5.33 (m, 1H), 6.62 (d, J = 8.4 Hz, 1H), 6.77 (d, J = 2.0 Hz, 1H), 6.93 (d, J = 8.8 Hz, 1H), 7.60-7.62 (m, 3H), 7.97 (s, 1H), 8.17-8.20 (m, 1H), 8.49 (d, J = 6.0 Hz, 1H), 8.63 (d, J = 2.4 Hz, 1H), 9.36 (s, 1H), 11.07 (s, 1H). |
| 162 | 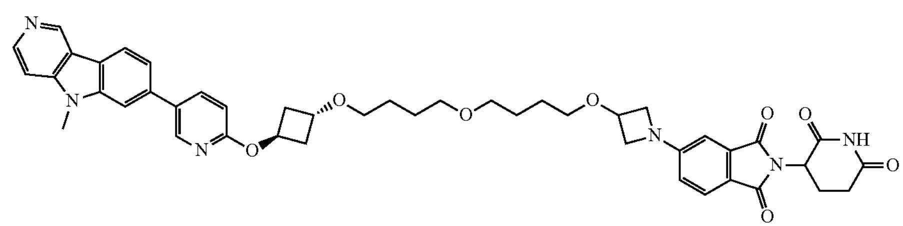 [SMILES: Cn1c2ccncc2c2ccc(-c3ccc(O[C@H]4C[C@H](OCCCCOCCCCOC5CN(c6ccc7c(c6)C(=O)N(C6CCC(=O)NC6=O)C7=O)C5)C4)nc3)cc21] | A | 801.6 | 1H NMR (400 MHz, DMSO-d6): δ 1.56 (s, 8H), 1.98-2.01 (m, 1H), 2.34-2.46 (m, 6H), 2.59-2.67 (m, 2H), 2.83-2.92 (m, 1H), 3.38-3.42 (m, 6H), 3.83 (d, J = 5.6 Hz, 2H), 3.96 (s, 3H), 4.18-4.25 (m, 3H), 4.44 (s, 1H), 5.03-5.07 (m, 1H), 5.29-5.33 (m, 1H), 6.63 (d, J = 7.6 Hz, 1H), 6.78 (s, 1H), 6.93 (d, J = 8.8 Hz, 1H), 7.61-7.63 (m, 3H), 7.98 (s, 1H), 8.18 (d, J = 8.4 Hz, 1H), 8.31 (d, J = 8.0 Hz, 1H), 8.49 (d, J = 5.6 Hz, 1H), 8.64 (s, 1H), 9.36 (s, 1H), 11.07 (s, 1H). |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 163 | 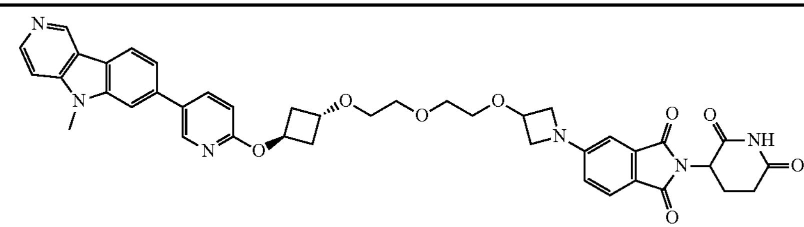 | C | 745.5 | 1H NMR (400 MHz, DMSO-d6): δ 1.94-2.00 (m, 1H), 2.31-2.48 (m, 4H), 3.97 (s, 3H), 2.57 (s, 2H), 2.81-2.89 (m, 1H), 3.47-3.49 (m, 2H), 3.54-3.64 (m, 6H), 3.84-3.89 (m, 2H), 4.21-4.29 (m, 3H), 4.52 (s, 1H), 5.02-5.06 (m, 1H), 5.29-5.35 (s, 1H), 6.63-6.66 (m, 1H), 6.79 (d, J = 2.0 Hz, 1H), 6.93 (d, J = 8.8 Hz, 1H), 7.59-7.66 (m, 2H), 7.69 (d, J = 6.0 Hz, 1H), 7.99 (s, 1H), 8.17-8.20 (m, 1H), 8.34 (d, J = 8.0 Hz, 1H), 8.53 (d, J = 6.0 Hz, 1H), 8.62 (d, J = 2.4 Hz, 1H), 9.40 (s, 1H), 11.07 (s, 1H). |
| 164 | 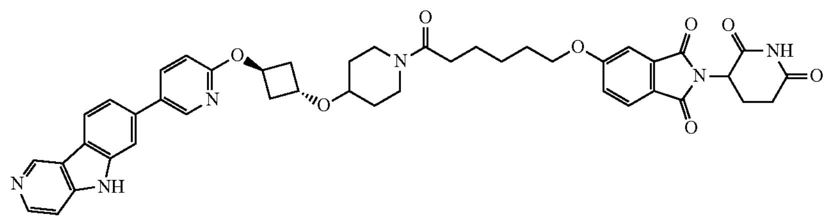 [SMILES: O=C1CCC(N2C(=O)c3ccc(OCCCCCC(=O)N4CCC(O[C@H]5C[C@H](Oc6ccc(-c7ccc8c(c7)[nH]c7ccncc78)cn6)C5)CC4)cc3C2=O)C(=O)N1] | C | 785.5 | 1H NMR (400 MHz, CDCl3): δ 1.52-1.57 (m, 3H), 1.61-1.65 (m, 2H), 1.70-1.74 (m, 2H), 1.98-2.01 (m, 2H), 2.13-2.17 (m, 1H), 2.34-2.41 (m, 2H), 2.47-2.50 (m, 2H), 2.78-2.88 (m, 2H), 3.20-3.28 (m, 2H), 3.54-3.72 (m, 3H), 4.00-4.10 (m, 3H), 4.39-4.44 (m, 1H), 4.95 (dd, J = 5.2, 12.0 Hz, 1H), 5.31-5.42 (m, 4H), 6.82 (d, J = 8.4 Hz, 1H), 7.17 (d, J = 8.8 Hz, 1H), 7.31-7.34 (m, 2H), 7.48-7.51 (m, 2H), 7.68 (s, 1H), 7.77 (d, J = 8.8 Hz, 1H), 7.87 (d, J = 7.2 Hz, 1H), 8.11 (d, J = 8.0 Hz, 1H), 8.32 (s, 1H), 8.41-8.45 (m, 2H), 9.23 (s, 1H). |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 165 | 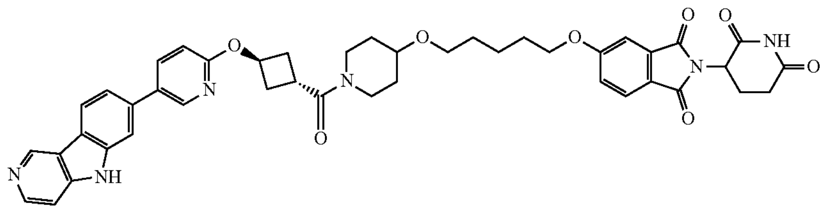 [SMILES: O=C1CCC(N2C(=O)c3ccc(OCCCCCOC4CCN(C(=O)[C@H]5C[C@H](Oc6ccc(-c7ccc8c(c7)[nH]c7ccncc78)cn6)C5)CC4)cc3C2=O)C(=O)N1] | C | 785.5 | 1HNMR (400 MHz, DMSO-d6): δ 1.35-1.38 (m, 2H), 1.47-1.57 (m, 4H), 1.74-1.81 (m, 4H), 1.99-2.07 (m, 2H), 2.32-2.39 (m, 2H), 2.57 (s, 1H), 2.62-2.67 (m, 2H), 2.82-2.91 (m, 1H), 3.12-3.18 (m, 3H), 3.41-3.51 (m, 4H), 3.85-3.89 (m, 1H), 4.17-4.20 (m, 2H), 5.09-5.14 (m, 1H), 5.18-5.22 (m, 1H), 6.92 (d, J = 8.4 Hz, 1H), 7.33-7.36 (m, 1H), 7.42 (d, J = 1.6 Hz, 1H), 7.47 (d, J = 5.6 Hz, 1H), 7.54 (d, J = 8.4 Hz, 1H), 7.76 (s, 1H), 7.82 (d, J = 8.4 Hz, 1H), 8.10-8.12 (m, 1H), 8.29 (d, J = 8.0 Hz, 1H), 8.42 (d, J = 6.0 Hz, 1H), 8.54 (d, J = 2.4 Hz, 1H), 9.35 (s, 1H), 11.11 (s, 1H), 11.81 (s, 1H). |
| 166 | 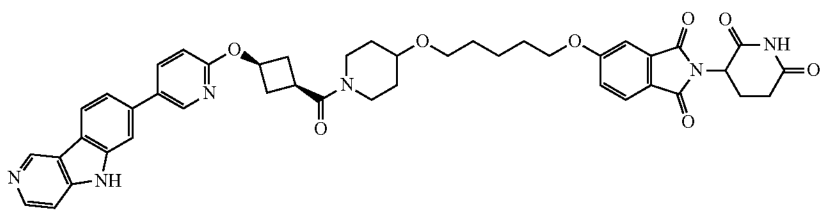 [SMILES: O=C1CCC(N2C(=O)c3ccc(OCCCCCOC4CCN(C(=O)[C@H]5C[C@@H](Oc6ccc(-c7ccc8c(c7)[nH]c7ccncc78)cn6)C5)CC4)cc3C2=O)C(=O)N1] | C | 785.5 | 1H NMR (400 MHz, DMSO-d6): δ 1.31-1.37 (m, 2H), 1.48-1.50 (m, 2H), 1.55-1.57 (m, 2H), 1.76-1.79 (m, 4H), 2.03-2.06 (m, 1H), 2.18-2.27 (m, 2H), 2.55-2.70 (m, 3H), 2.85-2.92 (m, 1H), 3.06-3.17 (m, 4H), 3.42-3.48 (m, 3H), 3.57-3.60 (m, 1H), 3.79-3.83 (m, 1H), 4.17 (t, J = 5.2 Hz, 2H), 5.11-5.15 (m, 2H), 6.91 (d, J = 8.8 Hz, 1H), 7.33-7.36 (m, 1H), 7.42 (s, 1H), 7.48 (d, J = 5.6 Hz, 1H), 7.55 (d, J = 8.4 Hz, 1H), 7.77 (s, 1H), 7.82 (d, J = 8.0 Hz, 1H), 8.09-8.12 (m, 1H), 8.29 (d, J = 8.0 Hz, 1H), 8.42 (d, J = 5.6 |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 167 | 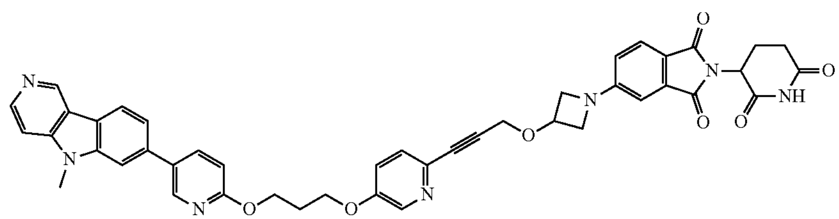 [SMILES: Cn1c2ccncc2c2ccc(-c3ccc(OCCCOc4ccc(C#CCOC5CN(c6ccc7c(c6)C(=O)N(C6CCC(=O)NC6=O)C7=O)C5)nc4)nc3)cc21] | C | 776.5 | 1HNMR (400 MHz, DMSO-d6): δ 1.99-2.03 m, 2H 2.23-2.27 (m, 2H), 2.56-2.60 (m, 2H), 2.81-2.94 (m, 1H), 3.92-3.94 (m, 1H), 3.96 (s, 3H), 4.24-4.32 (m, 4H), 4.48-4.52 (m, 4H), 4.65-4.72 (m, 1H), 5.03-5.08 (m, 1H), 6.65-6.67 (m, 1H), 6.80-6.81 (m, 1H), 6.97 (t, J = 8.0 Hz, 1H), 7.45-7.46 (m, 1H), 7.53-7.55 (m, 1H), 7.61-7.66 (m, 3H), 7.97 (s, 3H), 8.16-8.21 (m, 1H), 8.31-8.34 (m, 2H), 8.49-8.50 (m, 1H), 8.63-8.64 (m, 1H), 9.36 (s, 1H), 11.07 (s, 1H). |
| 168 | 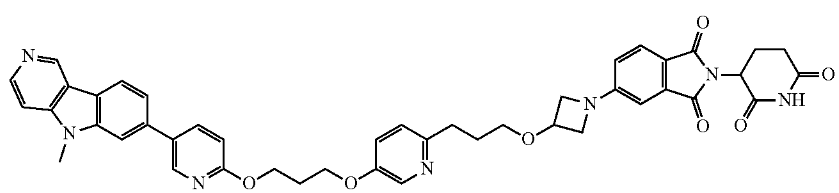 [SMILES: Cn1c2ccncc2c2ccc(-c3ccc(OCCCOc4ccc(CCCOC5CN(c6ccc7c(c6)C(=O)N(C6CCC(=O)NC6=O)C7=O)C5)nc4)nc3)cc21] | B | 780.5 | 1HNMR (400 MHz, DMSO-d6): δ 1.86-1.93 (m, 2H), 1.91-2.04 (m, 2H), 2.19-2.27 (m, 2H), 2.69-2.77 (m, 2H), 2.81-2.94 (m, 2H), 3.39-3.46 (m, 2H), 3.81-3.84 (m, 2H), 3.96 (s, 3H), 4.14-4.28 (m, 4H), 4.41-4.54 (m, 3H), 5.02-5.10 (m, 1H), 6.65-6.67 (m, 1H), 6.80-6.81 (m, 1H), 6.97 (t, J = 8.0 Hz, 1H), 7.18-7.20 (m, 1H), 7.32-7.34 (m, 1H), 7.59-7.66 (m, 3H), 7.98 (s, 1H), 8.16-8.21 (m, 2H), 8.31-8.34 (m, 1H), 8.49-8.50 (m, 1H), 8.63-8.64 (m, 1H), 9.36 (s, 1H), 11.07 (s, 1H). |

Row above 167 (continuation of previous entry NMR): Hz, 1H), 8.53 (d, J = 2.0 Hz, 1H), 9.35 (s, 1H), 11.10 (s, 1H), 11.86 (s, 1H).

TABLE 2-continued

Exemplary PROTAC of the present disclosure.

| Ex. | Structure | Degradation activity* | MH + (1) [MH + (2), if isotope] | NMR transcript |
|---|---|---|---|---|
| 169 | 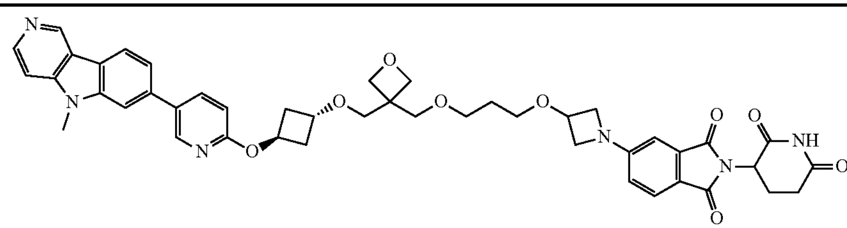 | A | 815.6 | 1H NMR (400 MHz, DMSO-d6): δ 1.79-1.84 (m, 2H), 1.94-2.01 (m, 1H), 2.37-2.40 (m 2H), 2.43-2.49 (m, 4H), 2.52-2.62 (m, 2H), 2.82-2.91 (m, 1H), 3.48-3.56 (m, 6H), 3.60 (s, 2H), 3.81-3.84 (m, 2H), 3.96 (s, 2H), 4.17-4.30 (m, 3H), 4.35 (s, 3H), 4.43-4.49 (m, 1H), 5.00-5.09 (m, 1H), 5.31-5.39 (m, 1H), 6.56-6.66 (m, 1H), 6.76 (s, 1H), 6.94 (d, J = 8.4 Hz, 1H), 7.52-7.67 (m, 2H), 7.67-7.85 (m, 1H), 7.99 (s, 1H), 8.13-8.52 (m, 3H), 8.64 (d, J = 1.6 Hz, 1H), 9.28-9.62 (m, 1H), 11.07 (s, 1H). |
| 170 | 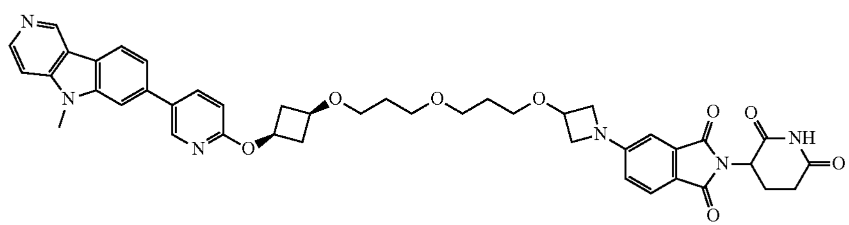 [SMILES: Cn1c2ccncc2c2ccc(-c3ccc(O[C@H]4C[C@@H](OCCCOCCCOC5CN(c6ccc7c(c6)C(=O)N(C6CCC(=O)NC6=O)C7=O)C5)C4)nc3)cc21] | A | 773.5 | 1H NMR (400 MHz, DMSO-d6): δ 1.71-1.77 (m, 4H), 1.94-1.97 (m, 3H), 2.54-2.58 (m, 1H), 2.86-2.88 (m, 3H), 3.16 (d, J = 3.6 Hz, 1H), 3.38-3.46 (m, 8H), 3.75 (d, J = 6.8 Hz, 1H), 3.80-3.84 (m, 2H), 4.03 (s, 3H), 4.19-4.23 (m, 2H), 4.41-4.42 (m, 1H), 4.83-4.90 (m, 1H), 5.01-5.06 (m, 1H), 6.61-6.63 (m, 1H), 6.76 (d, J = 0.8 Hz, 1H), 6.95 (d, J = 8.4 Hz, 1H), 7.60 (d, J = 8.4 Hz, 1H), 7.71 (d, J = 8.4 Hz, 1H), 7.88 (d, J = 6.0 Hz, 1H), 8.08 (s, 1H), 8.20-8.22 (m, 1H), 8.41 (d, J = 8.0 Hz, 1H), 8.61 (d, J = 6.4 Hz, 1H), 8.66 (d, J = 2.4 Hz, 1H), 9.55 (s, 1H), 11.06 (s, 1H). |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 171 | 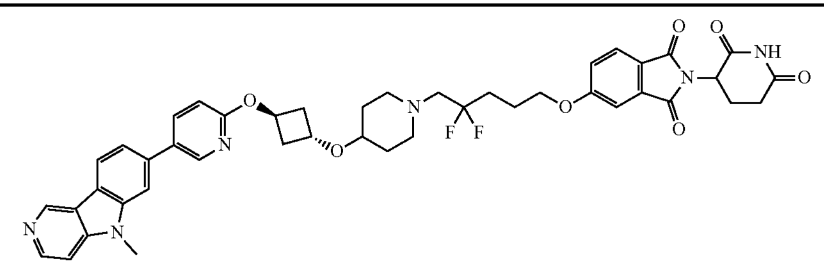 | C | 807.5 | ¹H NMR: (400 MHz, DMSO-d₆) δ = 11.11 (s, 1H), 9.35 (s, 1H) δ = 8.64 (s, 1H), 8.49-8.48 (d, J = 4 Hz 1H), 8.33-8.31 (d, J = 8 Hz 1H), δ = 8.17 (s, 1H), δ = 7.97 (s, 1H) 7.85-7.83 (d, J = 8 Hz 1H), 7.62-7.61 (d, J = 4 Hz 2H), 7.43 (s, 1H), 6.94-6.92 (d, J = 8 Hz 1H), 5.31-5.29 (m, 1H), 5.12-5.10 (m, 1H), 4.34 (s, 5H), 4.25-4.23 (d, J = 8 Hz 1H), 3.95 (s, 3H), 2.77 (m, 2H), 2.73 (m, 4H), 2.53-2.52 (m, 1H), 2.39-2.38 (m, 4H), 1.91-1.90 (m, 4H), 1.75 (m, 2H), 1.43 (m, 2H), 1.41 (m, 2H). |
| 172 | 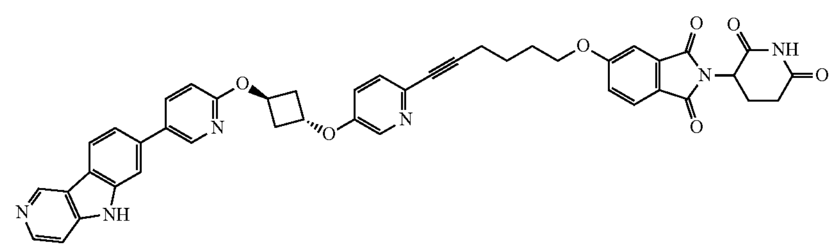 | C | 761.5 | ¹H NMR (400 MHz, DMSO-d6): δ 1.68-1.77 (m, 2H), 1.89-1.96 (m, 2H), 2.02-2.08 (m, 1H), 2.53-2.69 (m, 8H), 2.85-2.94 (m, 1H), 4.25 (t, J = 6.2 Hz, 2H), 5.05-5.14 (m, 2H), 5.41-5.47 (m, 1H), 7.01 (d, J = 8.4 Hz, 1H), 7.26-7.45 (m, 4H), 7.80-7.84 (m, 2H), 7.99-8.03 (m, 2H), 8.18-8.21 (m, 2H), 8.51-8.68 (m, 3H), 9.77 (s, 1H), 11.11 (s, 1H), 13.17 (s, 1H). |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 173 | 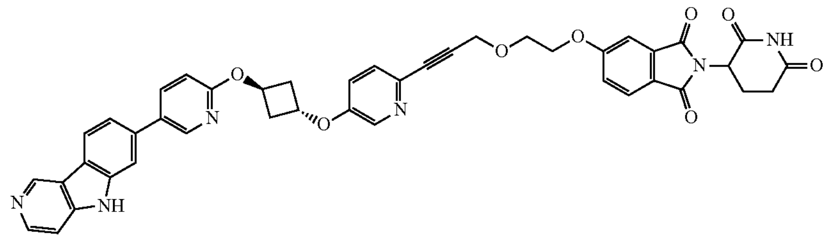 [SMILES: O=C1CCC(N2C(=O)c3ccc(OCCOCC#Cc4ccc(O[C@H]5C[C@H](Oc6ccc(-c7ccc8c(c7)[nH]c7ccncc78)cn6)C5)cn4)cc3C2=O)C(=O)N1] | A | 763.5 | 1H NMR (400 MHz, DMSO-d6): δ 2.02-2.08 (m, 1H), 2.52-2.76 (m, 6H), 2.85-2.93 (m, 1H), 3.89-3.95 (m, 2H), 4.37-4.42 (m, 2H), 4.49 (s, 2H), 5.06-5.14 (m, 2H), 5.40-5.47 (m, 1H), 6.99 (d, J = 8.4 Hz, 1H), 7.30-7.33 (m, 1H), 7.38-7.40 (m, 1H), 7.46-7.48 (m, 2H), 7.62-7.64 (m, 2H), 7.82-7.84 (m, 2H), 8.14-8.17 (m, 1H), 8.24 (d, J = 2.8 Hz, 1H), 8.36-8.38 (m, 1H), 8.49 (d, J = 6 Hz, 1H), 8.58 (d, J = 2.0 Hz, 1H), 9.47 (s, 1H), 11.11 (s, 1H), 12.14-12.28 (m, 1H). |
| 174 | 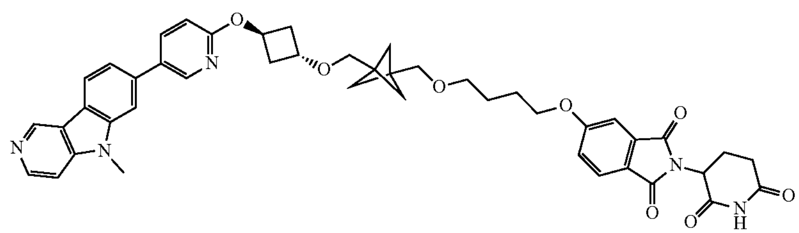 [SMILES: Cn1c2ccncc2c2ccc(-c3ccc(O[C@H]4C[C@H](OCC56CC(COCCCCOc7ccc8c(c7)C(=O)N(C7CCC(=O)NC7=O)C8=O)(C5)C6)C4)nc3)cc21] | ND | 784.5 | 1H NMR (400 MHz, DMSO-d6): δ 1.60 (s, 6H), 1.62-1.69 (m, 2H), 1.77-1.82 (m, 2H), 2.01-2.06 (m, 1H), 2.30-2.44 (m, 4H), 2.54-2.67 (m, 2H), 2.84-2.93 (m, 1H), 3.31 (br, 2H), 3.38 (s, 2H), 3.45 (t, J = 6.4 Hz, 2H), 3.96 (s, 3H), 4.20 (t, J = 6.4 Hz, 3H), 5.11 (dd, J = 12.8 Hz, 1H), 5.28-5.34 (m, 1H), 6.94 (d, J = 8.8 Hz, 1H), 7.35 (dd, J = 8.4 Hz, 1H), 7.42 (s, 1H), 7.61-7.64 (m, 2H), 7.83 (d, J = 8.4 Hz, 1H), 7.99 (s, 1H), 8.19 (dd, J = 8.4 Hz, 1H), 8.32 (d, J = 8.0 Hz, 1H), 8.50 (d, J = 5.6 Hz, 1H), 8.64 (d, J = 2.4 Hz, 1H), 9.37 (s, 1H), 11.11 (s, 1H). |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 175 | 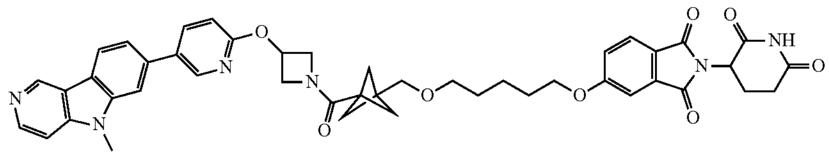 [SMILES: Cn1c2ccncc2c2ccc(-c3ccc(OC4CN(C(=O)C56CC(COCCCCCOc7ccc8c(c7)C(=O)N(C7CCC(=O)NC7=O)C8=O)(C5)C6)C4)nc3)cc21] | C | 797.5 | 1H NMR (400 Hz, D6-DMSO): δ 1.44-1.58 (m, 5H), 1.75-1.79 (m, 2H), 1.92 (s, 6H), 2.01-2.05 (m, 2H), 2.50-2.61 (m, 2H), 2.83-2.94 (m, 1H), 3.40 (t, J = 6.4 Hz, 2H), 3.86-3.89 (m, 1H), 3.96 (s, 3H), 4.17 (t, J = 6.4 Hz, 2H), 4.22-4.25 (m, 1H), 4.29-4.34 (m, 1H), 4.67-4.72 (m, 1H), 5.08-5.13 (m, 1H), 5.41-5.43 (m, 1H), 7.03 (d, J = 8.8 Hz, 1H), 7.34 (dd, J = 1.6, 8.4 Hz, 1H), 7.42 (s, 1H), 7.62 (d, J = 6.4 Hz, 2H), 7.82 (d, J = 8.4 Hz, 1H), 7.99 (s, 1H), 8.24 (dd, J = 2.4, 8.8 Hz, 1H), 8.33 (d, J = 8.4 Hz, 1H), 8.50 (d, J = 5.6 Hz, 1H), 8.65 (d, J = 2.0 Hz 1H), 9.36 (s, 1H), 11.10 (s, 1H). |
| 176 | 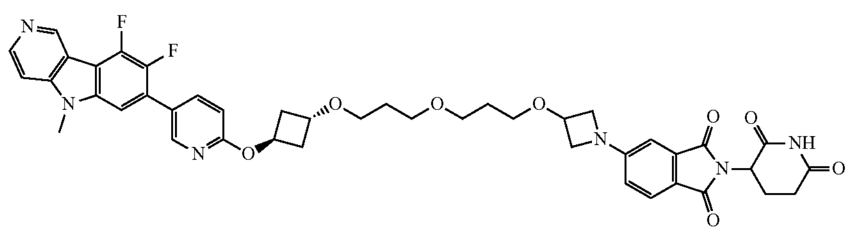 [SMILES: Cn1c2ccncc2c2c(F)c(F)c(-c3ccc(O[C@H]4C[C@H](OCCCOCCCOC5CN(c6ccc7c(c6)C(=O)N(C6CCC(=O)NC6=O)C7=O)C5)C4)nc3)cc21] | C | 809.5 | 1H NMR (400 MHz, DMSO-d6): δ 1.71-1.81 (m, 4H), 1.97-2.01 (m, 1H), 2.33-2.37 (m, 2H), 2.40-2.46 (m, 2H), 2.54-2.58 (m, 2H), 2.82-2.91 (m, 1H), 3.38 (t, J = 6.4 Hz, 2H), 3.43-3.49 (m, 6H), 3.81-3.84 (m, 2H), 3.94 (s, 3H), 4.16-4.25 (m, 3H), 4.43-4.48 (m, 1H), 5.01-5.06 (m, 1H), 5.30-5.36 (m, 1H), 6.61-6.64 (m, 1H), 6.77 (d, J = 1.6 Hz, 1H), 6.98 (d, J = 8.4 Hz, 1H), 7.60 (d, J = 8.4 Hz, 1H), 7.69-7.72 (m, 2H), 8.05 (d, J = 8.8 Hz, 1H), 8.49 (s, 1H), 8.58 (d, J = 6.0 Hz, 1H), 9.24 (s, 1H), 11.06 (s, 1H). |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 177 | 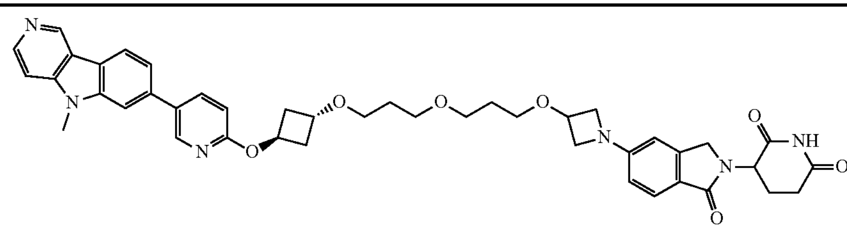 | A | 759.6 | 1H NMR (400 MHz, DMSO-d6): δ 1.71-1.80 (m, 4H), 1.90-1.93 (m, 1H), 2.28-2.37 (m, 3H), 2.40-2.44 (m, 2H), 2.56-2.57 (m, 1H), 2.83-2.92 (m, 1H), 3.37 (t, J = 6.0 Hz, 2H), 3.43-3.48 (m, 6H), 3.67-3.70 (m, 2H), 3.95 (s, 3H), 4.11-4.19 (m, 4H), 4.23-4.27 (m, 1H), 4.42-4.44 (m, 1H), 4.99-5.03 (m, 1H), 5.31-5.34 (m, 1H), 6.46-6.49 (m, 2H), 6.94 (d, J = 8.8 Hz, 1H), 7.47 (d, J = 8.4 Hz, 1H), 7.60-7.63 (m, 2H), 7.97 (s, 1H), 8.17-8.20 (m, 1H), 8.32 (d, J = 8.0 Hz, 1H), 8.50 (d, J = 6.0 Hz, 1H), 8.64 (d, J = 2.0 Hz, 1H), 9.37 (s, 1H), 10.92 (s, 1H). |
| 178 | 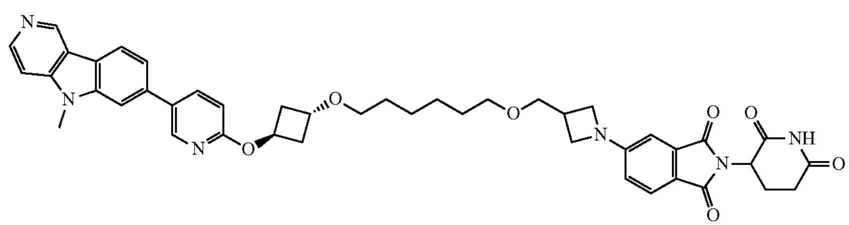 | A | 771.6 | 1HNMR (400 MHz, DMSO-d6): δ 1.32 (s, 4H), 1.50-1.52 (m, 4H), 2.00-2.04 (m, 1H), 2.31-2.44 (m, 5H), 2.55-2.60 (m, 1H), 2.83-2.90 (m, 1H), 2.95-3.02 (m, 1H), 3.28-3.31 (m, 2H), 3.42-3.45 (m, 2H), 3.57-3.59 (m, 2H), 3.73-3.77 (m, 2H), 4.06-4.10 (m, 2H), 4.14-4.20 (m, 4H), 5.02-5.07 (m, 1H), 5.32-5.34 (m, 1H), 6.61-6.63 (m, 1H), 6.76 (s, 1H), 6.96-6.99 (m, 1H), 7.59-7.61 (m, 1H), 7.85-7.87 (m, 1H), 8.20-8.26 (m, 3H), 8.52-8.55 (m, 1H), 8.70 (br, 1H), 8.76-8.78 (m, 1H), 9.77 (s, 1H), 11.06 (s, 1H). |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 179 | 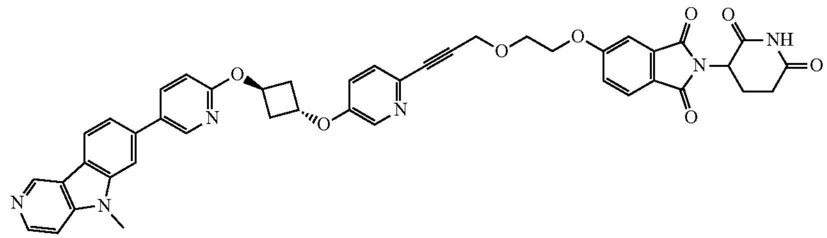 | A | 777.5 | ¹H NMR (400 MHz, DMSO-d6): δ 2.02-2.08 (m, 1H), 2.55-2.73 (m, 6H), 2.84-2.91 (m, 1H), 3.89-3.93 (m, 2H), 3.97 (s, 3H), 4.36-4.42 (m, 2H), 4.49 (s, 2H), 5.05-5.15 (m, 2H), 5.44 (s, 1H), 7.00 (d, J = 8.8 Hz, 1H), 7.30-7.33 (m, 1H), 7.37-7.40 (m, 1H), 7.45-7.49 (m, 2H), 7.63-7.67 (m, 2H), 7.83 (d, J = 8.4 Hz, 1H), 8.00 (s, 1H), 8.20-8.25 (m, 2H), 8.34 (d, J = 8.4 Hz, 1H), 8.52 (d, J = 6.0 Hz, 1H), 8.65 (d, J = 2.0 Hz, 1H), 9.39 (s, 1H), 11.11 (s, 1H). |
| 180 | 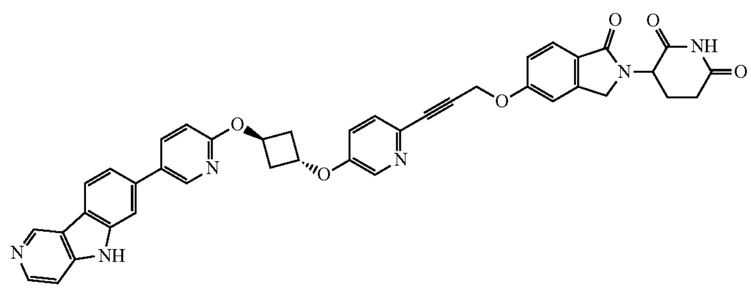 | A | 705.4 | ¹HNMR (400 MHz, DMSO-d6): δ 1.97-2.00 (m, 1H), 2.33-2.44 (m, 2H), 2.55-2.67 (m, 4H), 2.86-2.96 (m, 1H), 4.29 (d, J = 17.2 Hz, 1H), 4.42 (d, J = 16.8 Hz, 1H), 5.06-5.10 (m, 2H), 5.18 (s, 2H), 5.42-5.45 (m, 1H), 6.99 (d, J = 8.4 Hz, 1H), 7.17 (d, J = 8.0 Hz, 1H), 7.29-7.33 (m, 2H), 7.50 (d, J = 8.4 Hz, 1H), 7.68 (d, J = 8.0 Hz, 2H), 7.74 (d, J = 5.6 Hz, 1H), 7.89 (s, 1H), 8.16 (d, J = 7.6 Hz, 1H), 8.24 (s, 1H), 8.41 (d, J = 7.6 Hz, 1H), 8.53-8.59 (m, 2H), 9.56 (s, 1H), 10.97 (s, 1H), 12.54 (br, 1H). |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 181 | 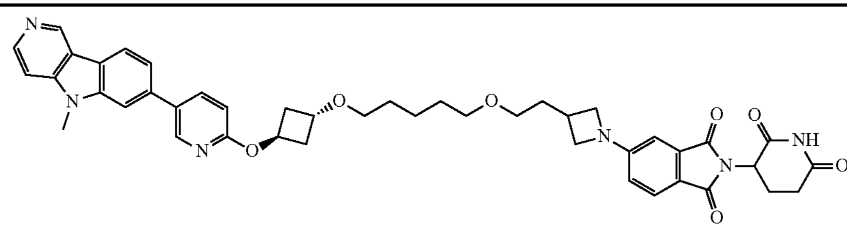 | B | 771.6 | 1HNMR (400 MHz, DMSO-d6): δ 1.34-1.41 (m, 2H), 1.48-1.57 (m, 4H), 1.84-1.89 (m, 2H), 1.95-1.99 (m, 1H), 2.31-2.46 (m, 5H), 2.54-2.58 (m, 2H), 2.79-2.92 (m, 2H), 3.35-3.42 (m, 4H), 3.68-3.71 (m, 2H), 3.95 (s, 3H), 4.11-4.19 (m, 3H), 5.01-5.05 (m, 1H), 5.29-5.35 (m, 1H), 6.59 (d, J = 8.0 Hz, 1H), 6.73 (s, 1H), 6.93 (d, J = 8.0 Hz, 1H), 7.59-7.62 (m, 3H), 7.96 (s, 1H), 8.16-8.19 (m, 1H), 8.30-8.32 (d, J = 8.0 Hz, 1H), 8.49 (d, J = 8.0 Hz, 1H), 8.61-8.62 (m, 1H), 9.35 (s, 1H), 11.06 (s, 1H). |
| 182 | 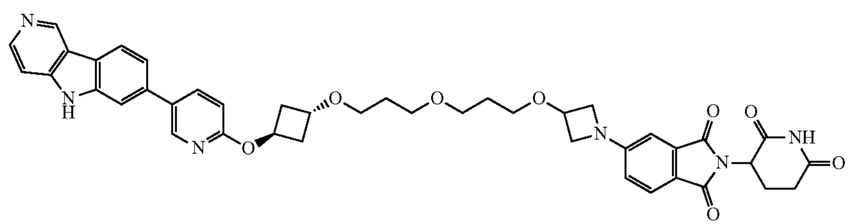 | A | 759.5 | 1H NMR (400 MHz, DMSO-d6): δ 1.73-1.79 (m, 4H), 1.97-2.00 (m, 1H), 2.33-2.45 (m, 5H), 2.54-2.58 (m, 1H), 2.82-2.90 (m, 1H), 3.37 (t, J = 6.4 Hz, 2H), 3.43-3.49 (m, 6H), 3.81-3.84 (m, 2H), 4.16-4.20 (m, 1H), 4.22-4.26 (m, 2H), 4.43-4.47 (m, 1H), 5.02-5.06 (m, 1H), 5.31-5.34 (m, 1H), 6.63 (d, J = 8.4 Hz, 1H), 6.78 (s, 1H), 6.93 (d, J = 8.4 Hz, 1H), 7.60-7.65 (m, 2H), 7.72 (d, J = 6.0 Hz, 1H), 7.86 (s, 1H), 8.11-8.14 (m, 1H), 8.39 (d, J = 8.4 Hz, 1H), 8.53 (d, J = 6.0 Hz, 1H), 8.57 (d, J = 2.0 Hz, 1H), 9.53 (s, 1H), 11.06 (s, 1H), 12.42 (s, 1H). |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 183 | 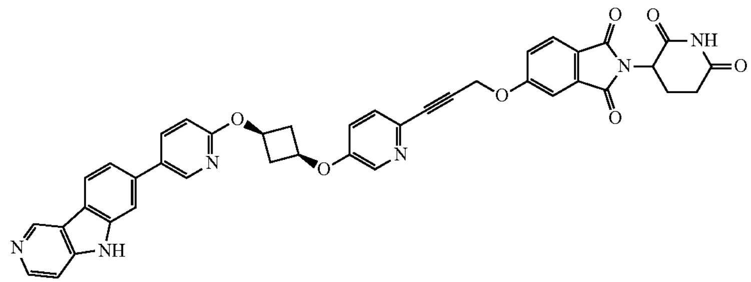 [SMILES: O=C1CCC(N2C(=O)c3ccc(OCC#Cc4ccc(O[C@H]5C[C@@H](Oc6ccc(-c7ccc8c(c7)[nH]c7ccncc78)cn6)C5)cn4)cc3C2=O)C(=O)N1] | A | 719.4 | ¹H NMR (400 MHz, DMSO-d6): δ 2.03-2.07 (m, 1H), 2.18-2.24 (m, 2H), 2.54-2.62 (m, 1H), 2.84-2.94 (m, 1H), 3.17-3.20 (m, 3H), 4.67 (t, J = 6.4 Hz, 1H), 5.01 (t, J = 6.8 Hz, 1H), 5.11-5.15 (m, 1H), 5.32 (s, 2H), 6.97 (d, J = 8.4 Hz, 1H), 7.33-7.36 (m, 1H), 7.45-7.52 (m, 2H), 7.58 (d, J = 1.6 Hz, 1H), 7.68 (d, J = 8.0 Hz, 1H), 7.74 (d, J = 5.6 Hz, 1H), 7.89 (s, 1H), 7.91 (s, 1H), 8.14-8.16 (m, 1H), 8.25 (d, J = 2.8 Hz, 1H), 8.41 (d, J = 8.4 Hz, 1H), 8.54-8.55 (d, 1H), 8.58 (d, J = 2.4 Hz, 1H), 9.56 (s, 1H), 11.12 (s, 1H), 12.49 (s, 1H). |
| 184 | 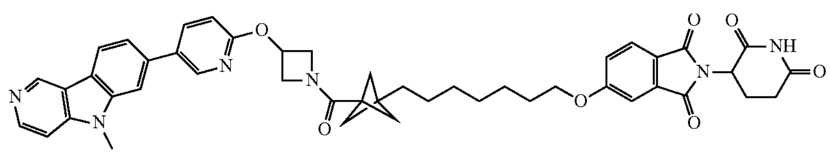 [SMILES: Cn1c2ccncc2c2ccc(-c3ccc(OC4CN(C(=O)C56CC(CCCCCCCOc7ccc8c(c7)C(=O)N(C7CCC(=O)NC7=O)C8=O)(C5)C6)C4)nc3)cc21] | A | 795.6 | 1H NMR (400 Hz, D6-DMSO): δ 1.30-1.50 (m, 8H), 1.72-1.79 (m, 2H), 1.84 (s, 6H), 1.97-2.06 (m, 2H), 2.56-2.67 (m, 2H), 2.84-2.93 (m, 1H), 3.85-3.88 (m, 1H), 3.99 (s, 3H), 4.13-4.18 (m, 3H), 4.21-4.24 (m, 1H), 4.29-4.33 (m, 1H), 4.67-4.71 (m, 1H), 5.09-5.13 (m, 1H), 5.41-5.45 (m, 1H), 7.06 (d, J = 8.8 Hz, 1H), 7.34 (d, J = 8.0 Hz, 1H), 7.41 (s, 1H), 7.66 (d, J = 8.4 Hz, 1H), 7.62 (d, J = 5.6 Hz, 1H), 7.82 (d, J = 8.4 Hz, 1H), 8.04 (s, 1H), 8.23-8.29 (m, 1H), 8.37 (d, J = 8.0 Hz, 1H), 8.55 (d, J = 5.6 Hz, 1H), 8.66 (s, 1H), 9.44 (s, 1H), 11.11 (s, 1H). |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 185 | 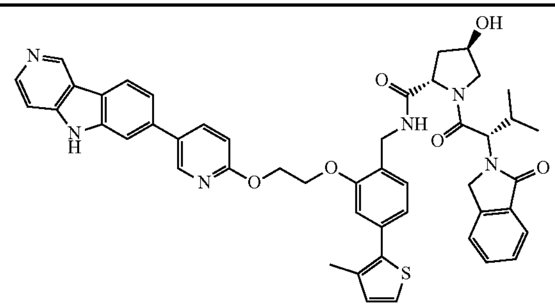 | C | 836.5 | 1H NMR (400 MHz, DMSO-d6): δ 0.67 (d, J = 6.8 Hz, 3H), 0.83-0.88 (m, 3H), 1.97-2.02 (m, 2H), 2.31-2.33 (m, 1H), 2.46 (s, 3H), 3.51 (s, 1H), 3.66-3.72 (m, 2H), 4.22-4.26 (m, 2H), 4.34-4.42 (m, 4H), 4.49-4.51 (m, 2H), 4.68 (d, J = 10.0 Hz, 1H), 5.05 (d, J = 4.4 Hz, 1H), 5.32 (t, J = 4.8 Hz, 1H), 6.58 (d, J = 9.6 Hz, 1H), 6.99 (d, J = 7.2 Hz, 1H), 7.06 (s, 1H), 7.31 (d, J = 8.0 Hz, 1H), 7.47-7.53 (m, 2H), 7.58-7.63 (m, 4H), 7.69 (d, J = 6.8 Hz, 1H), 7.77 (s, 1H), 7.96-7.99 (m, 1H), 8.31-8.33 (m, 2H), 8.40 (m, 1H), 8.48 (d, J = 6.0 Hz, 1H), 8.98 (s, 1H), 9.45 (s, 1H). |
| 186 | 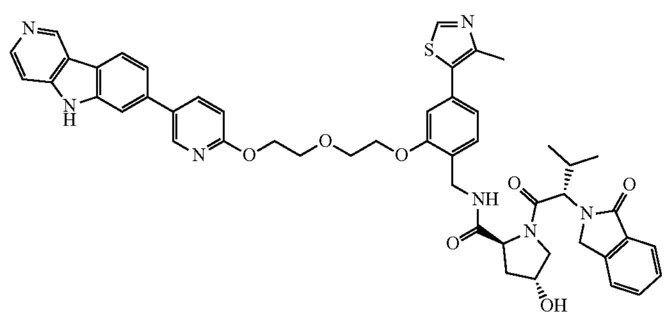 [SMILES: Cc1ncsc1-c1ccc(CNC(=O)[C@@H]2C[C@@H](O)CN2C(=O)[C@H](C(C)C)N2Cc3ccccc3C2=O)c(OCCOCCOc2ccc(-c3ccc4c(c3)[nH]c3ccncc34)cn2)c1] | B | 880.6 | 1H NMR (400 MHz, DMSO-d6): δ 0.72 (d, J = 6.8 Hz, 3H), 0.96 (d, J = 6.4 Hz, 3H), 1.89-1.96 (m, 1H), 2.02-2.08 (m, 1H), 2.28-2.34 (m, 1H), 2.47 (s, 3H), 3.68-3.70 (m, 1H), 3.75-3.80 (m, 1H), 3.88-3.92 (m, 4H), 4.20-4.39 (m, 5H), 4.40-4.58 (m, 5H), 4.71 (d, J = 10.8 Hz, 1H), 5.10 (d, J = 3.6 Hz, 1H), 6.95 (d, J = 8.8 Hz, 1H), 7.02 (d, J = 7.6 Hz, 1H), 7.07 (s, 1H), 7.34 (d, J = 8.0 Hz, 1H), 7.46-7.53 (m, 1H), 7.56-7.67 (m, 4H), 7.70 (d, J = 7.6 Hz, 1H), 7.84 (s, 1H), 8.11-8.14 (m, 1H), 8.36-8.40 (m, 2H), 8.50 (d, J = 6.0 Hz, 1H), 8.58 (d, J = 2.4 |

TABLE 2-continued

Exemplary PROTAC of the present disclosure.

| Ex. | Structure | Degradation activity* | MH + (1) [MH + (2), if isotope] | NMR transcript |
|---|---|---|---|---|
| | | | | Hz, 1H), 8.98 (s, 1H), 9.48 (s, 1H), 12.16-12.29 (m, 1H). |
| 187 | 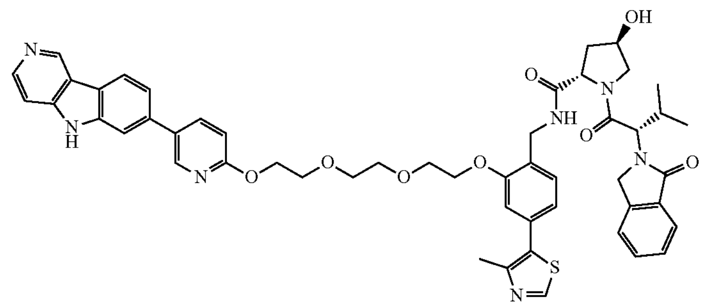 [SMILES: Cc1ncsc1-c1ccc(CNC(=O)[C@@H]2C[C@@H](O)CN2C(=O)[C@H](C(C)C)N2Cc3ccccc3C2=O)c(OCCOCCOCCOc2ccc(-c3ccc4c(c3)[nH]c3ccncc34)cn2)c1] | C | 924.6 | 1H NMR (400 MHz, DMSO-d6): δ 0.71 (d, J = 6.8 Hz, 3H), 0.95 (d, J = 6.8 Hz, 3H), 1.89-2.07 (m, 3H), 2.26-2.39 (m, 2H), 2.46 (s, 3H), 3.64-3.70 (m, 5H), 3.75-3.83 (m, 5H), 4.18-4.23 (m, 2H), 4.27-4.36 (m, 3H), 4.39-4.46 (m, 4H), 4.52-4.57 (m, 1H), 4.69-4.72 (m, 1H), 5.08 (d, J = 4.0 Hz, 1H), 6.95 (d, J = 8.0 Hz, 1H), 7.01 (d, J = 8.0 Hz, 1H), 7.05 (s, 1H), 7.34 (d, J = 8.0 Hz, 1H), 7.47-7.51 (m, 1H), 7.55-7.60 (m, 4H), 7.70 (d, J = 8.0 Hz, 1H), 7.80 (s, 1H), 8.09-8.11 (m, 1H), 8.31-8.34 (m, 1H), 8.36-8.39 (m, 1H), 8.45 (d, J = 4.8 Hz, 1H), 8.55 (m, 1H), 8.98 (s, 1H), 9.41 (s, 1H). |
| 188 | 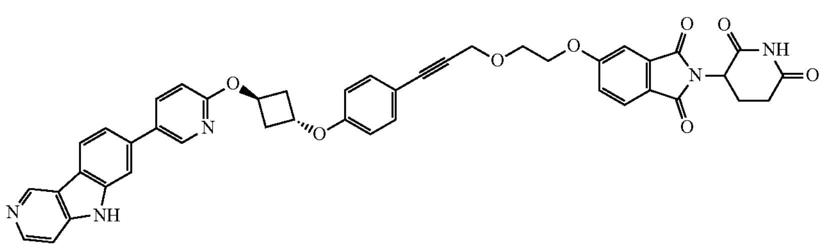 | B | 762.5 | 1H NMR (400 MHz, DMSO-d6): δ 2.02-2.08 (m, 1H), 2.51-2.78 (m, 6H), 2.85-2.94 (m, 1H), 3.86-3.92 (m, 2H), 4.38-4.40 (m, 2H), 4.45 (s, 2H), 4.98-5.03 (m, 1H), 5.09-5.15 (m, 1H), 5.40-5.45 (m, 1H), 6.88 (d, J = 8.8 Hz, 2H), 6.99 (d, J = 8.4 Hz, 1H), 7.36-7.40 (m, 3H), 7.47 (d, J = 2.0 Hz, 1H), 7.61-7.67 (m, 2H), 7.82-7.85 (m, 2H), 8.14-8.17 (m, 1H), 8.37 (d, J = 8.0 Hz, 1H), 8.50 (d, J = 6.0 Hz, 1H), 8.58 (d, J = |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 189 | 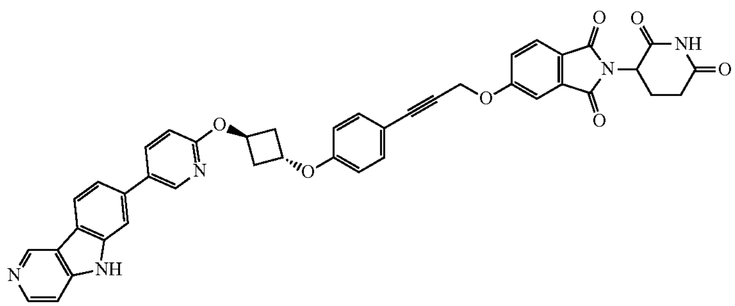 [SMILES: O=C1CCC(N2C(=O)c3ccc(OCC#Cc4ccc(O[C@H]5C[C@H](Oc6ccc(-c7ccc8c(c7)[nH]c7ccncc78)cn6)C5)cc4)cc3C2=O)C(=O)N1] | B | 718.4 | 1H NMR (400 MHz, DMSO-d6): δ 2.03-2.08 (m, 1H), 2.54-2.70 (m, 6H), 2.84-2.92 (m, 1H), 4.98-5.03 (m, 1H), 5.10-5.16 (m, 1H), 5.27 (s, 2H), 5.39-5.45 (m, 1H), 6.89 (d, J = 8.8 Hz, 1H), 6.99 (d, J = 8.8 Hz, 2H), 7.40 (d, J = 2.4 Hz, 1H), 9.48 (s, 1H), 11.12 (s, 1H), 12.22 (br, 1H). 8.8 Hz, 2H), 7.45-7.47 (m, 1H), 7.57 (d, J = 2.0 Hz, 1H), 7.65-7.70 (m, 2H), 7.86-7.91 (m, 2H), 8.14-8.17 (m, 1H), 8.39 (d, J = 8.0 Hz, 1H), 8.52 (d, J = 6.4 Hz, 1H), 8.58 (d, J = 2.4 Hz, 1H), 9.52 (s, 1H), 11.12 (s, 1H), 12.37 (s, 1H). |
| 190 | 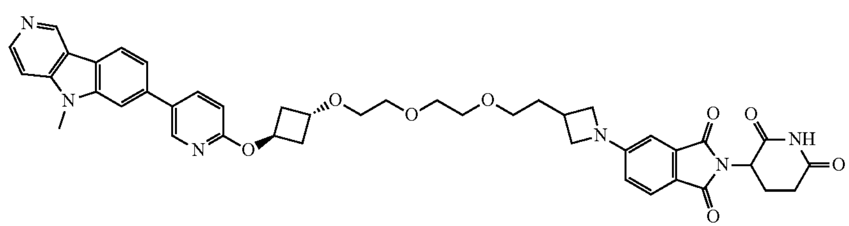 | C | 773.5 | 1H NMR (400 MHz, DMSO-d6): δ 1.84-1.89 (m, 2H), 1.95-2.03 (m, 3H), 2.31-2.39 (m, 4H), 2.81-2.88 (m, 2H), 3.45-3.55 (m, 12H), 3.68 (m, 2H), 4.10 (s, 3H), 4.24 (m, 1H), 5.00-5.04 (m, 1H), 5.03 (s, 1H), 6.55-6.58 (m, 1H), 6.70 (s, 1H), 6.94-6.97 (m, 1H), 7.56-7.57 (m, 1H), 7.80-7.82 (m, 1H), 8.11-8.23 (m, 3H), 8.48-8.51 (m, 1H), 8.67-8.73 (m, 2H), 9.69 (s, 1H), 11.06 (s, 1H). |

TABLE 2-continued
Exemplary PROTAC of the present disclosure.
| Ex. | Structure | Degradation activity* | MH + (1) [MH + (2), if isotope] | NMR transcript |
|---|---|---|---|---|
| 191 | 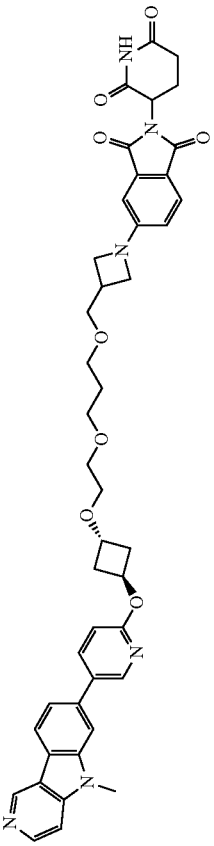 | A | 773.5 | 1HNMR (400 MHz, DMSO-d6): δ 1.72-1.78 (m, 2H), 1.95-2.01 (m, 1H), 2.31-2.46 (m, 4H), 2.54-2.67 (m, 2H), 2.82-2.91 (m, 1H), 2.95-3.02 (m, 1H), 3.44-3.52 (m, 8H), 3.58-3.60 (m, 2H), 3.73-3.76 (m, 2H), 3.97 (s, 3H), 4.07 (t, J = 8.0 Hz, 2H), 4.20-4.25 (m, 1H), 5.02-5.06 (m, 1H), 5.29-5.35 (m, 1H), 6.59-6.61 (m, 1H), 6.74-6.75 (m, 1H), 6.93-6.95 (d, J = 8.0 Hz, 1H), 7.58-7.68 (m, 3H), 7.99 (s, 1H), 8.17-8.20 (m, 1H), 8.33 (d, J = 8.0 Hz, 1H), 8.52 (d, J = 8.0 Hz, 1H), 8.63-8.64 (m, 1H), 9.39 (s, 1H), 11.07 (s, 1H). |
| 192 | 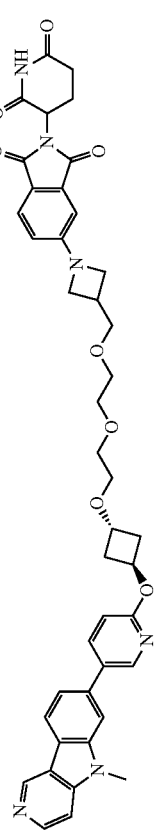 | C | 759.5 | 1HNMR (400 MHz, DMSO-d6): δ 1.95-1.99 (m, 1H), 2.08 (s, 1H), 2.31-2.37 (m, 2H), 2.41-2.46 (m, 3H), 2.54-2.58 (m, 1H), 2.83-2.89 (m, 1H), 2.96-3.01 (m, 1H), 3.44-3.46 (m, 1H), 3.53-3.57 (m, 6H), 3.64-3.66 (m, 2H), 3.74-3.78 (m, 2H), 3.95 (s, 3H), 4.08 (t, J = 8.4 Hz, 2H), 4.21-4.23 (m, 1H), 5.01-5.06 (m, 1H), 5.30-5.33 (m, 1H), 6.60 (d, J = 9.6 Hz, 1H), 6.75 (s, 1H), 6.93 (d, J = 8.4 Hz, 1H), 7.58-7.64 (m, 3H), 7.97 (s, 2H), 8.17-8.20 (m, 1H), 8.31 (d, J = 8.0 Hz, 1H), 8.49 (d, J = 5.6 Hz, 1H), 8.62-8.63 (m, 1H), 9.36 (s, 1H), 11.06 (s, 1H); |

TABLE 2-continued
Exemplary PROTAC of the present disclosure.
| Ex. | Structure | Degradation activity* | MH + (1) [MH + (2), if isotope] | NMR transcript |
|---|---|---|---|---|
| 193 | 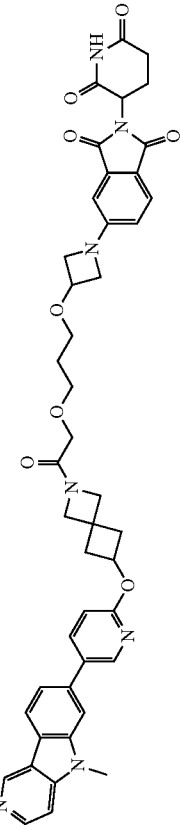 | B | 798.5 | 1H NMR: (400 MHz, DMSO-d6) δ 11.07 (br s, 1H), 9.36 (s, 1H), 8.66-8.58 (m, 1H), 8.49 (d, J = 5.8 Hz, 1H), 8.32 (d, J = 8.2 Hz, 1H), 8.23 (s, 2H), 8.18 (dd, J = 2.5, 8.7 Hz, 1H), 7.97 (s, 1H), 7.66-7.58 (m, 3H), 6.92 (d, J = 8.7 Hz, 1H), 6.81 (br d, J = 2.3 Hz, 1H), 6.69-6.63 (m, 1H), 5.16-5.08 (m, 1H), 5.08-5.02 (m, 1H), 4.47 (br s, 1H), 4.30-4.22 (m, 3H), 4.19 (s, 1H), 3.99 (s, 1H), 3.95 (s, 3H), 3.95-3.89 (m, 4H), 3.86 (br s, 3H), 3.49-3.48 (m, 2H), 2.92-2.81 (m, 1H), 2.74 (br d, J = 6.5 Hz, 2H), 2.58 (br s, 1H), 2.54 (s, 2H), 2.30-2.26 (m, 1H), 1.98 (br d, J = 4.9 Hz, 1H), 1.85-1.74 (m, 2H). |
| 194 | 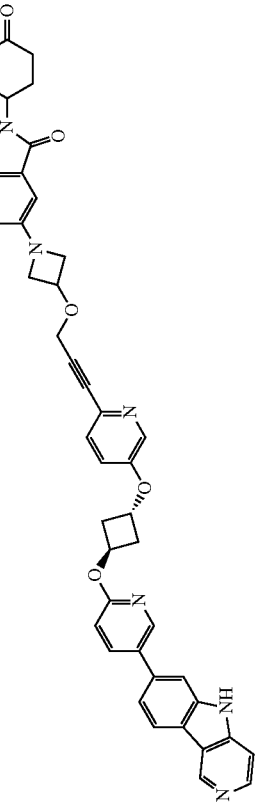 | C | 774.5 | 1HNMR (400 MHz, DMSO-d6): δ 1.93-2.11 (m, 2H), 2.54-2.74 (m, 5H), 2.54-2.93 (m, 1H), 3.95-3.98 (m, 2H), 4.31-4.34 (m, 2H), 4.49 (s, 3H), 4.67-4.73 (m, 1H), 5.04-5.14 (m, 2H), 5.41-5.47 (m, 1H), 6.67-6.69 (m, 1H), 6.82-6.83 (m, 1H), 6.99 (d, J = 8.0 Hz, 1H), 7.33-7.36 (m, 1H), 7.53-7.55 (m, 1H), 7.65-7.72 (m, 3H), 7.88 (s, 3H), 8.15-8.18 (m, 1H), 8.25-8.26 (m, 1H), 8.40 (d, J = 8.0 Hz, 1H), 8.52-8.54 (m, 3H), 8.58-8.59 (m, 1H), 9.54 (s, 1H), 11.07 (s, 1H). |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 195 | 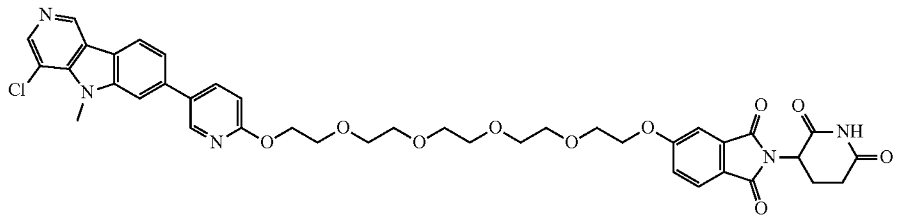 [SMILES: Cn1c2cc(-c3ccc(OCCOCCOCCOCCOCCOc4ccc5c(c4)C(=O)N(C4CCC(=O)NC4=O)C5=O)nc3)ccc2c2cncc(Cl)c21] | A | 786.5 | 1H NMR (400 MHz, DMSO-d6): δ 2.01-2.04 (m, 1H), 2.50-2.60 (m, 2H), 2.83-2.92 (m, 1H), 3.52-3.59 (m, 12H), 3.77-3.79 (m, 4H), 4.27-4.28 (m, 5H), 4.43-4.46 (m, 2H), 5.08-5.13 (m, 1H), 6.96 (d, J = 8.4 Hz, 1H), 7.32-7.34 (m, 1H), 7.41 (s, 1H), 7.67 (d, J = 8.0 Hz, 1H), 7.79 (d, J = 8.4 Hz, 1H), 8.03 (s, 1H), 8.19-8.22 (m, 1H), 8.35 (d, J = 8.0 Hz, 1H), 8.44 (s, 1H), 8.64-8.65 (m, 1H), 9.22 (s, 1H), 11.10 (s, 1H). |
| 196 | 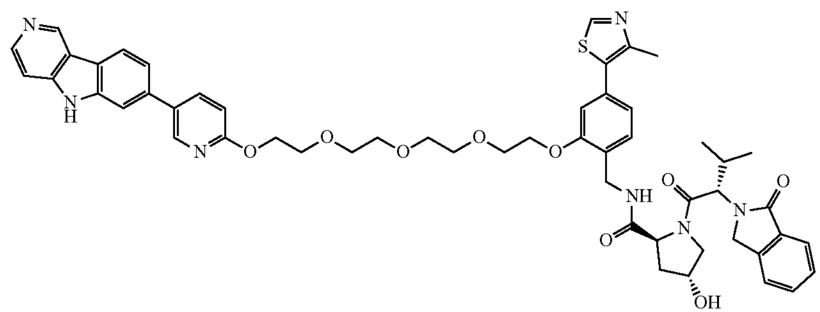 [SMILES: Cc1ncsc1-c1ccc(CNC(=O)[C@@H]2C[C@@H](O)CN2C(=O)[C@H](C(C)C)N2Cc3ccccc3C2=O)c(OCCOCCOCCOCCOc2ccc(-c3ccc4c(c3)[nH]c3ccncc34)cn2)c1] | C | 968.6 | 1H NMR (400 MHz, DMSO-d6): δ 0.71 (d, J = 6.8 Hz, 3H), 0.95 (d, J = 6.8 Hz, 3H), 1.89-2.07 (m, 3H), 2.27-2.35 (m, 2H), 2.46 (s, 3H), 3.57-3.58 (m, 5H), 3.63-3.68 (m, 4H), 3.76-3.81 (m, 5H), 4.17-4.19 (m, 2H), 4.27-4.34 (m, 3H), 4.39-4.46 (m, 4H), 4.52-4.57 (m, 1H), 4.69-4.72 (m, 1H), 5.09 (m, 1H), 6.95 (d, J = 8.8 Hz, 1H), 7.01 (d, J = 8.8 Hz, 1H), 7.04 (s, 1H), 7.34 (d, J = 8.0 Hz, 1H), 7.47-7.51 (m, 1H), 7.60-7.64 (m, 4H), 7.70 (d, J = 8.0 Hz, 1H), 7.83 (s, 1H), 8.09-8.14 (m, 1H), 8.34-8.38 (m, 2H), 8.49 (d, J = 4.8 Hz, 1H), 8.55-8.56 (m, 1H), 8.97 (s, 1H), 9.47 (s, 1H). |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 197 | 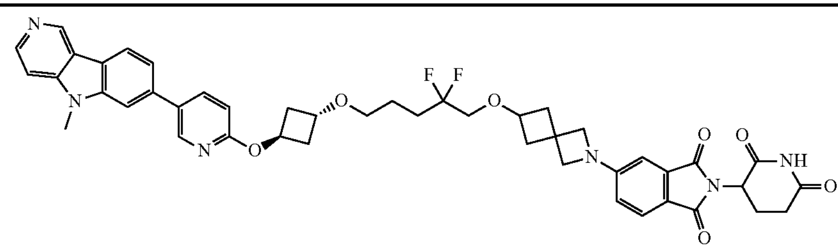 | C | 819.5 | 1H NMR: (400 MHz, CDCl3) δ 9.37 (s, 1H), 8.61 (d, J = 6.0 Hz, 1H), 8.51 (d, J = 2.4 Hz, 1H), 8.24 (d, J = 8.0 Hz, 1H), 7.95-7.93 (m, 1H), 7.64 (d, J = 8.0 Hz, 1H), 7.59 (s, 1H), 7.54 (d, J = 8.0 Hz, 1H), 7.4 (d, J = 6.0 Hz, 1H), 6.87 (d, J = 8.0 Hz, 1H), 6.76 (d, J = 2.4 Hz, 1H), 6.50-6.48 (m, 1H), 5.44-5.41 (m, 1H), 4.96 (dd, J = 5.2, 12.4 Hz, 1H), 4.31-4.27 (m, 1H), 4.07-4.02 (m, 5H), 3.94 (s, 3H), 3.59 (t, J = 12.4 Hz, 2H), 3.47 (t, J = 6.4 Hz, 2H), 2.92-2.78 (m, 3H), 2.65-2.48 (m, 6H), 2.32-2.27 (m, 2H), 2.19-1.99 (m, 4H), 1.86-1.79 (m, 1H). |
| 198 | 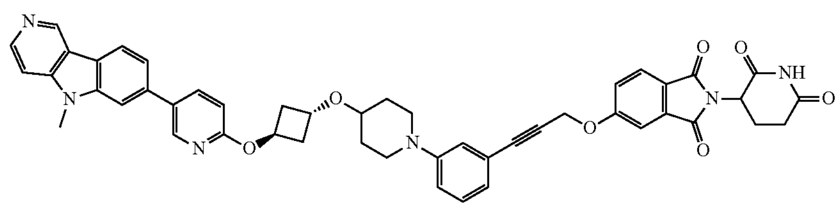 [SMILES: Cn1c2ccncc2c2ccc(-c3ccc(O[C@H]4C[C@H](OC5CCN(c6cccc(C#CCOc7ccc8c(c7)C(=O)N(C7CCC(=O)NC7=O)C8=O)c6)CC5)C4)nc3)cc21] | A | 815.5 | 1HNMR (400 MHz, CD3OD): δ 1.46-1.55 (m, 2H), 1.84-1.94 (m, 2H), 2.03-2.07 (m, 1H), 2.35-2.46 (m, 4H), 2.58-2.62 (m, 1H), 2.85-2.94 (m, 3H), 3.50-3.56 (m, 3H), 3.99 (m, 3H), 4.38-4.44 (m, 1H), 5.11-5.16 (m, 1H), 5.28 (s, 2H), 5.31-5.34 (m, 1H), 6.80-6.82 (m, 1H), 6.95-7.01 (m, 3H), 7.18-7.22 (m, 1H), 7.45-7.48 (m, 1H), 7.57-7.58 (m, 1H), 7.66-7.68 (m, 1H), 7.75-7.81 (m, 1H), 7.89-7.91 (m, 1H), 8.03 (s, 1H), 8.19-8.22 (m, 1H), 8.36-8.66 (m, 3H), 9.42 (br, 1H), 11.12 (s, 1H). |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 199 | 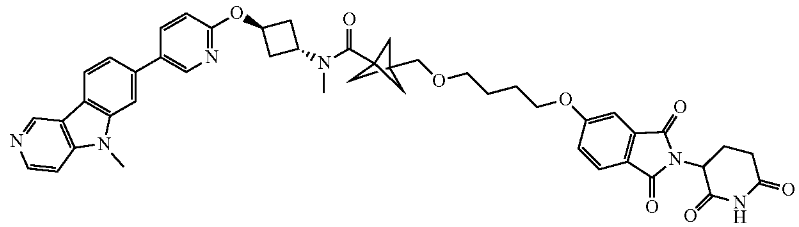 [SMILES: Cn1c2ccncc2c2ccc(-c3ccc(O[C@H]4C[C@H](N(C)C(=O)C56CC(COCCCCOc7ccc8c(c7)C(=O)N(C7CCC(=O)NC7=O)C8=O)(C5)C6)C4)nc3)cc21] | C | 811.6 | 1H NMR (400 MHz, CDCl3): δ 1.71-1.98 (m, 6H), 2.06-2.15 (m, 8H), 2.46-2.57 (m, 2H), 2.57-2.88 (m, 4H), 2.96-3.10 (m, 2H), 3.43-3.56 (m, 3H), 3.94 (s, 3H), 4.05-4.20 (m, 2H), 4.91-5.01 (m, 1H), 5.05-5.26 (m, 1H), 5.31-5.42 (m, 1H), 6.82-6.94 (m, 1H), 7.14-7.23 (m, 1H), 7.31-7.45 (m, 2H), 7.48-7.65 (m, 2H), 7.73-7.81 (m, 1H), 7.89-7.99 (m, 1H), 8.19-8.28 (m, 1H), 8.38-8.67 (m, 3H), 9.32-9.42 (m, 1H). |
| 200 | 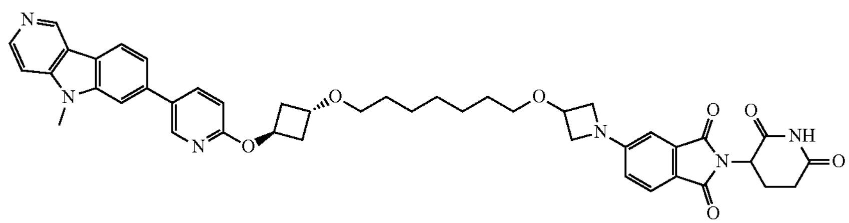 [SMILES: Cn1c2ccncc2c2ccc(-c3ccc(O[C@H]4C[C@H](OCCCCCCCOC5CN(c6ccc7c(c6)C(=O)N(C6CCC(=O)NC6=O)C7=O)C5)C4)nc3)cc21] | A | 711.6 | 1H NMR (400 MHz, DMSO-d6): δ 1.23 (s, 4H), 1.50-1.54 (m, 4H), 1.97-2.03 (m, 2H), 2.33-2.37 (m, 2H), 2.40-2.46 (m, 2H), 2.54-2.67 (m, 2H), 2.83-2.92 (m, 2H), 3.31 (t, J = 6.4 Hz, 2H), 3.41 (t, J = 6.4 Hz, 2H), 3.82-3.85 (m, 2H), 4.14 (s, 3H), 4.16-4.26 (m, 3H), 4.43-4.48 (m, 1H), 5.03-5.07 (m, 1H), 5.32-5.35 (m, 1H), 6.63-6.66 (m, 1H), 6.78 (s, 1H), 6.98 (d, J = 8.8 Hz, 1H), 7.62 (d, J = 8.4 Hz, 1H), 7.87 (d, J = 8.4 Hz, 1H), 8.20-8.26 (m, 3H), 8.53 (d, J = 8.4 Hz, 1H), 8.70 (d, J = 2.0 Hz, 1H), 8.76 (d, J = 6.8 Hz, 1H), 9.76 (s, 1H), 11.07 (s, 1H). |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 201 | 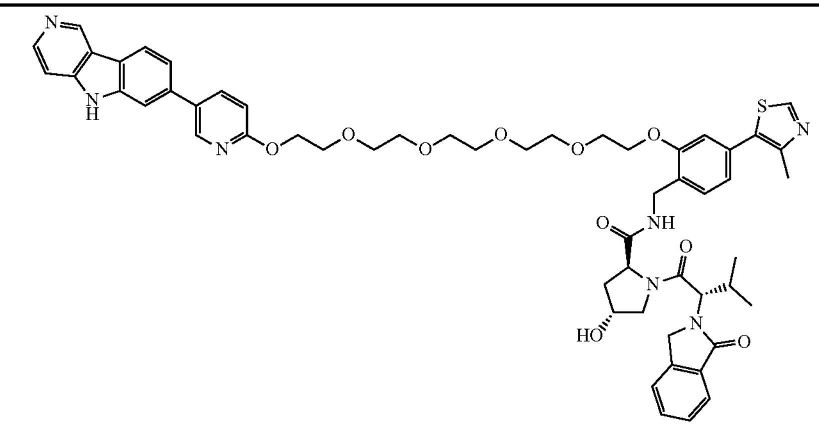 | C | 1012.7 | 1H NMR (400 MHz, DMSO-d6): δ 0.72 (d, J = 6.4 Hz, 3H), 0.95 (d, J = 6.4 Hz, 3H), 1.89-1.95 (m, 1H), 2.03-2.08 (m, 1H), 2.16-2.35 (m, 2H), 2.46 (s, 3H), 3.52-3.58 (m, 10H), 3.62-3.70 (m, 4H), 3.77-3.78 (m, 5H), 4.14-4.21 (m, 2H), 4.27-4.34 (m, 3H), 4.39-4.47 (m, 4H), 4.52-4.57 (m, 1H), 4.70-4.72 (m, 1H), 5.09-5.10 (m, 1H), 6.95-7.04 (m, 3H), 7.34 (d, J = 8.0 Hz, 1H), 7.47-7.51 (m, 1H), 7.58-7.62 (m, 2H), 7.65-7.73 (m, 3H), 7.87 (s, 1H), 8.11-8.14 (m, 1H), 8.36-8.40 (m, 2H), 8.53 (d, J = 6.4 Hz, 1H), 8.56-8.58 (m, 1H), 8.97 (s, 1H), 9.54 (s, 1H). |
| 202 | 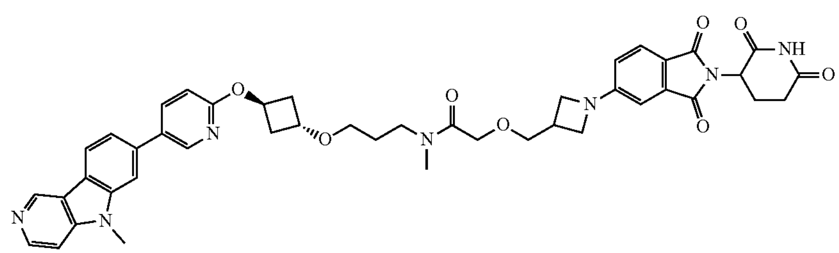 [SMILES: CN(CCCO[C@H]1C[C@H](Oc2ccc(-c3ccc4c5cnccc5n(C)c4c3)cn2)C1)C(=O)COCC1CN(c2ccc3c(c2)C(=O)N(C2CCC(=O)NC2=O)C3=O)C1] | B | 800.6 | 1H NMR (400 MHz, DMSO-d6): δ 1.66-1.82 (m, 3H), 1.95-2.00 (m, 1H), 2.28-2.47 (m, 6H), 2.54-2.60 (m, 1H), 2.81-2.91 (m, 4H), 2.97-3.11 (m, 2H), 3.34-3.38 (m, 1H), 3.66-3.69 (m, 2H), 3.78-3.86 (m, 2H), 3.96 (s, 3H), 4.07-4.11 (m, 2H), 4.19-4.23 (m, 3H), 5.00-5.07 (m, 1H), 5.29-5.35 (m, 1H), 6.58-6.64 (m, 1H), 6.73-6.78 (m, 1H), 6.91-6.96 (m, 1H), 7.57-7.67 (m, 3H), 7.95-8.00 (m, 1H), 8.15-8.21 (m, 1H), 8.29-8.35 (m, 1H), 8.48-8.54 (m, 1H), 8.60-8.66 (m, 1H), 9.38 (s, 1H), 11.05 (s, 1H). |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 203 | 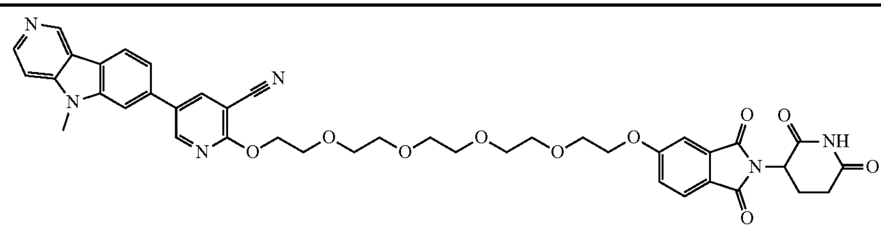 | A | 777.5 | 1H NMR: (400 MHz, DMSO-d6): 11.13 (s, 1H), 9.37 (s, 1H), 8.96 (d, J = 2.5 Hz, 1H), 8.81 (d, J = 2.5 Hz, 1H), 8.51 (d, J = 5.8 Hz, 1H), 8.35 (d, J = 8.2 Hz, 1H), 8.25 (s, 1H), 8.10 (d, J = 0.9 Hz, 1H), 7.79 (d, J = 8.3 Hz, 1H), 7.74-7.67 (m, 1H), 7.63 (d, J = 5.6 Hz, 1H), 7.41 (d, J = 2.1 Hz, 1H), 7.33 (dd, J = 2.3, 8.3 Hz, 1H), 5.19-5.04 (m, 1H), 4.60 (dd, J = 3.9, 5.4 Hz, 2H), 4.32-4.22 (m, 2H), 3.96 (s, 3H), 3.86-3.81 (m, 2H), 3.79-3.74 (m, 2H), 3.65-3.52 (m, 12H), 2.92-2.82 (m, 1H), 2.63-2.54 (m, 2H), 2.07-1.97 (m, 1H) |
| 204 | 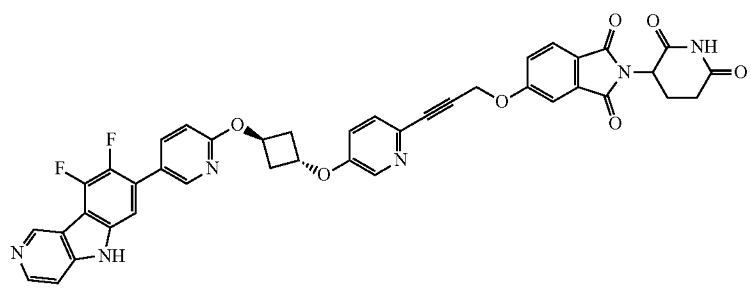 [SMILES: O=C1CCC(N2C(=O)c3ccc(OCC#Cc4ccc(O[C@H]5C[C@H](Oc6ccc(-c7cc8[nH]c9ccncc9c8c(F)c7F)cn6)C5)cn4)cc3C2=O)C(=O)N1] | C | 755.4 | 1H NMR (400 MHz, CDCl3): δ 1.98-2.03 (m, 2H), 2.18-2.22 (m, 2H), 2.69-2.77 (m, 4H), 5.33-5.36 (m, 1H), 5.48-5.52 (m, 1H), 6.86 (d, J = 8.4 Hz, 1H), 7.05 (dd, J = 2.4, 8.4 Hz, 1H), 7.22 (d, J = 4.8 Hz, 1H), 7.32 (dd, J = 2.0, 8.4 Hz, 1H), 7.37 (d, J = 7.2 Hz, 2H), 7.49 (d, J = 1.6 Hz, 1H), 7.80 (d, J = 8.4 Hz, 1H), 7.87 (d, J = 8.8 Hz, 1H), 8.20 (d, J = 2.8 Hz, 1H), 8.35 (s, 1H), 8.57 (d, J = 6.0 Hz, 1H), 9.38 (s, 1H). |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 205 | 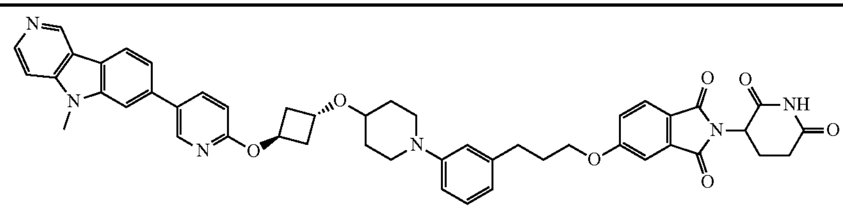 | A | 819.6 | 1HNMR (400 MHz, CD3OD): δ 1.44-1.58 (m, 2H), 1.84-1.91 (m, 2H), 2.04-2.07 (m, 3H), 2.34-2.44 (m, 4H), 2.62-2.93 (m, 7H), 3.46-3.49 (m, 2H), 3.99 (m, 3H), 4.14-4.17 (m, 2H), 4.39-4.42 (m, 1H), 5.11-5.15 (m, 1H), 5.32-5.34 (m, 1H), 6.63-6.64 (m, 1H), 6.75-6.78 (m, 2H), 6.95-6.97 (m, 1H), 7.09-7.13 (m, 1H), 7.36-7.38 (m, 1H), 7.43 (s, 1H), 7.66-7.73 (m, 2H), 7.83-7.85 (m, 1H), 8.02 (s, 1H), 8.20-8.22 (m, 1H), 8.36-8.38 (m, 1H), 8.53-8.55 (m, 1H), 8.66 (s, 1H), 9.43 (s, 1H), 11.12 (s, 1H). |
| 206 | 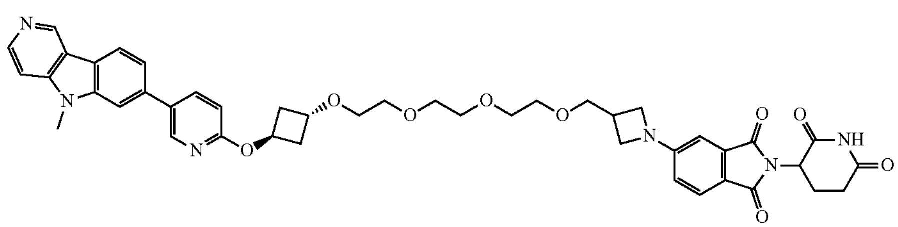 [SMILES: Cn1c2ccncc2c2ccc(-c3ccc(O[C@H]4C[C@H](OCCOCCOCCOCC5CN(c6ccc7c(c6)C(=O)N(C6CCC(=O)NC6=O)C7=O)C5)C4)nc3)cc21] | B | 803.6 | 1HNMR (400 MHz, DMSO-d6): δ 1.97-2.00 (m, 1H), 2.32-2.37 (m, 2H), 2.42-2.46 (m, 2H), 2.54-2.58 (m, 2H), 2.82-2.91 (m, 1H), 2.95-3.01 (m, 1H), 3.44-3.46 (m, 2H), 3.53-3.64 (m, 10H), 3.62-3.64 (m, 2H), 3.72-3.75 (m, 2H), 4.02 (s, 3H), 4.06 (t, J = 8.0 Hz, 2H), 4.20-4.24 (m, 1H), 5.02-5.06 (m, 1H), 5.29-5.34 (m, 1H), 6.58-6.60 (m, 1H), 6.73-6.75 (m, 1H), 6.95 (d, J = 8.0 Hz, 1H), 7.58 (d, J = 8.0 Hz, 1H), 7.69 (d, J = 8.0 Hz, 1H), 7.82-7.84 (m, 1H), 8.06 (s, 1H), 8.19-8.22 (m, 1H), 8.39 (d, J = 8.0 Hz, 1H), 8.58-8.59 (m, 1H), 8.65-8.66 (m, 1H), 9.49 (s, 1H), 11.07 (s, 1H). |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 207 | 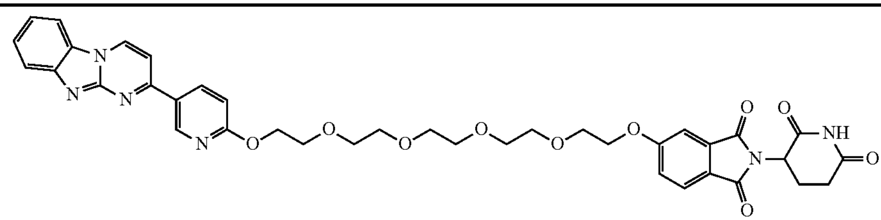 | B | 739.5 | 1H NMR (400 MHz, DMSO-d6): δ: 11.13 (s, 1H), 9.57 (d, J = 7.2 Hz, 1H), 9.13 (d, J = 2.4 Hz, 1H), 8.63 (dd, J = 2.5, 8.8 Hz, 1H), 8.31 (d, J = 8.2 Hz, 1H), 7.87-7.77 (m, 3H), 7.59-7.48 (m, 1H), 7.45-7.39 (m, 2H), 7.35 (dd, J = 2.3, 8.3 Hz, 1H), 7.05 (d, J = 8.8 Hz, 1H), 5.11 (dd, J = 5.3, 12.8 Hz, 1H), 4.53-4.48 (m, 2H), 4.32-4.27 (m, 2H), 3.81-3.76 (m, 4H), 3.62-3.58 (m, 4H), 3.55 (dd, J = 2.8, 5.5 Hz, 4H), 3.52 (s, 4H), 2.94-2.84 (m, 1H), 2.65-2.54 (m, 2H), 2.09-2.00 (m, 1H). |
| 208 | 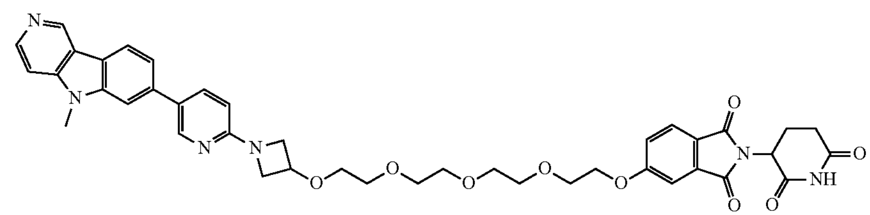 [SMILES: Cn1c2ccncc2c2ccc(-c3ccc(N4CC(OCCOCCOCCOCCOc5ccc6c(c5)C(=O)N(C5CCC(=O)NC5=O)C6=O)C4)nc3)cc21] | A | 763.5 | 1H NMR (400 MHz, DMSO-d6): δ 1.99-2.06 (m, 1H), 2.52-2.61 (m, 2H), 2.83-2.92 (m, 1H), 3.52-3.63 (m, 12H), 3.76-3.84 (m, 4H), 3.97 (s, 3H), 4.19-4.23 (m, 2H), 4.26-4.32 (m, 2H), 4.45-4.50 (m, 1H), 5.08-5.13 (m, 1H), 6.52 (d, J = 8.8 Hz, 1H), 7.33-7.35 (m, 1H), 7.43 (d, J = 2.0 Hz, 1H), 7.60 (d, J = 8.0 Hz, 1H), 7.71 (d, J = 6.0 Hz, 1H), 7.80 (d, J = 8.4 Hz, 1H), 7.92 (s, 1H), 8.00-8.03 (m, 1H), 8.31 (d, J = 8.4 Hz, 1H), 8.52 (d, J = 6.0 Hz, 1H), 8.58 (d, J = 2.0 Hz, 1H), 9.40 (s, 1H), 11.11 (s, 1H). |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 209 | 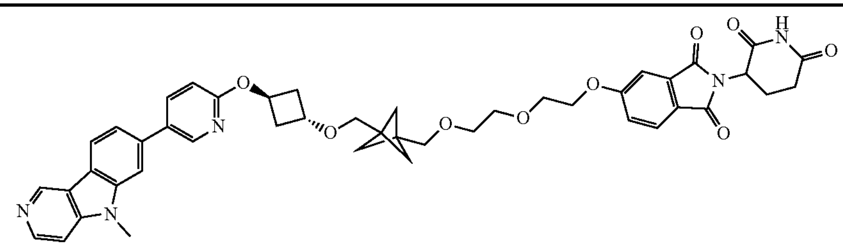 | A | 800.5 | 1H NMR (400 MHz, CDCl3): δ 1.70 (s, 6H), 2.12-2.18 (m, 1H), 2.48-2.59 (m, 4H), 2.76-2.84 (m, 2H), 2.86-2.93 (m, 1H), 3.39 (s, 2H), 3.52 (s, 2H), 3.67-3.69 (m, 2H), 3.72-3.75 (m, 2H), 3.91-3.94 (m, 2H), 4.12 (s, 3H), 4.28-4.36 (m, 4H), 4.93-4.99 (m, 1H), 6.99 (d, J = 8.8 Hz, 1H), 7.19-7.24 (m, 1H), 7.37 (d, J = 2.0 Hz, 1H), 7.70-7.82 (m, 4H), 8.16-8.19 (m, 2H), 8.40 (d, J = 8. Hz, 1H), 8.70-8.72 (m, 2H), 9.61 (s, 1H). |
| 210 | 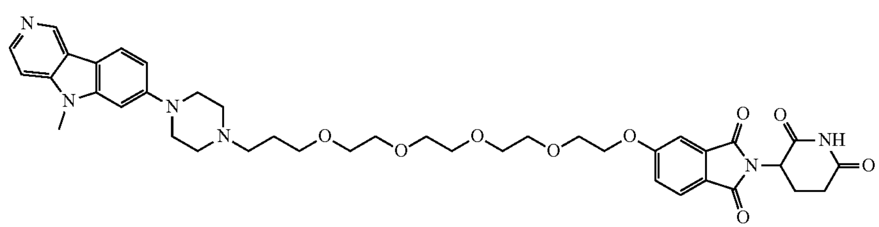 [SMILES: Cn1c2ccncc2c2ccc(N3CCN(CCCOCCOCCOCCOCCOc4ccc5c(c4)C(=O)N(C4CCC(=O)NC4=O)C5=O)CC3)cc21] | C | 757.6 | 1H NMR (400 MHz, DMSO-d6): δ: 15.03 (br s, 1H), 11.18-10.95 (m, 2H), 9.55 (s, 1H), 8.64 (br d, J = 6.5 Hz, 1H), 8.30 (br d, J = 8.3 Hz, 1H), 8.09 (br d, J = 6.9 Hz, 1H), 7.81 (br d, J = 8.5 Hz, 1H), 7.48-7.23 (m, 4H), 5.11 (br dd, J = 5.0, 12.7 Hz, 1H), 4.30 (br s, 2H), 4.11 (br d, J = 13.1 Hz, 2H), 4.02 (s, 3H), 3.78 (br s, 2H), 3.70-3.48 (m, 18H), 3.19 (br s, 3H), 2.96-2.82 (m, 1H), 2.62-2.55 (m, 3H), 2.04 (br s, 3H), |
| 211 | 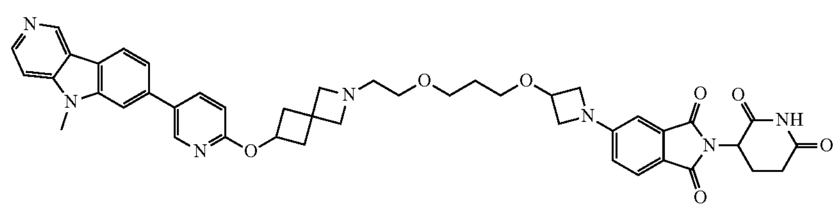 [SMILES: Cn1c2ccncc2c2ccc(-c3ccc(OC4CC5(C4)CN(CCOCCCOC4CN(c6ccc7c(c6)C(=O)N(C6CCC(=O)NC6=O)C7=O)C4)C5)nc3)cc21] | C | 784.6 | 1H NMR (400 MHz, CDCl3): δ: 9.33 (s, 1H), 8.59 (d, J = 5.6 Hz, 1H), 8.47 (d, J = 2.1 Hz, 1H), 8.21 (d, J = 8.2 Hz, 1H), 7.92 (dd, J = 2.3, 8.3 Hz, 1H), 7.65 (d, J = 8.2 Hz, 1H), 7.55 (s, 1H), 7.49 (d, J = 8.0 Hz, 1H), 7.34 (d, J = 6.0 Hz, 1H), 6.86-6.77 (m, 2H), 6.55 (br d, J = 6.8 Hz, 1H), 5.17 (quin, J = |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 212 | 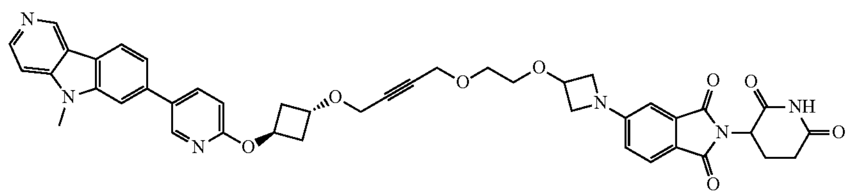 [SMILES: Cn1c2ccncc2c2ccc(-c3ccc(O[C@H]4C[C@H](OCC#CCOCCOC5CN(c6ccc7c(c6)C(=O)N(C6CCC(=O)NC6=O)C7=O)C5)C4)nc3)cc21] | A | 769.5 | 1H NMR (400 MHz, CDCl3): δ: 9.39 (s, 1H), 8.61 (d, J = 6.0 Hz, 1H), 8.52-8.43 (m, 2H), 8.32-8.04 (m, 2H), 7.93 (dd, J = 2.6, 8.6 Hz, 1H), 7.63 (d, J = 8.3 Hz, 1H), 7.59 (s, 1H), 7.53 (dd, J = 1.4, 8.1 Hz, 1H), 7.42 (d, J = 6.0 Hz, 1H), 6.85 (d, J = 8.5 Hz, 1H), 6.78 (d, J = 2.0 Hz, 1H), 6.52 (dd, J = 2.1, 8.3 Hz, 1H), 5.46-5.35 (m, 1H), 4.93 (dd, J = 5.2, 12.4 Hz, 1H), 4.61-4.43 (m, 2H), 4.29-4.27 (m, 2H), 4.27-4.21 (m, 2H), 4.20-4.16 (m, 5H), 3.78-3.63 (m, 4H), 2.92-2.67 (m, 3H), 2.64-2.55 (m, 2H), 2.51 (td, J = 3.5, 7.0 Hz, 2H), 2.16-2.08 (m, 1H). |
| 213 | 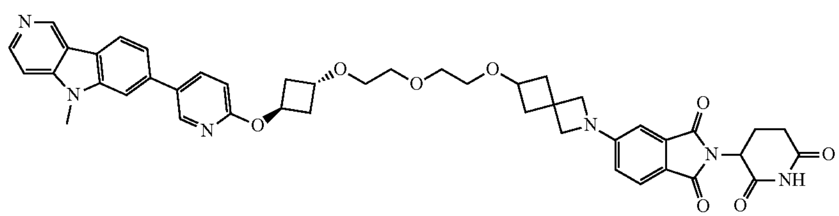 [SMILES: Cn1c2ccncc2c2ccc(-c3ccc(O[C@H]4C[C@H](OCCOCCOC5CC6(C5)CN(c5ccc7c(c5)C(=O)N(C5CCC(=O)NC5=O)C7=O)C6)C4)nc3)cc21] | C | 785.5 | 1H NMR (400 MHz, CDCl3): δ: 9.38 (s, 1H), 8.59 (d, J = 5.9 Hz, 1H), 8.48 (d, J = 2.3 Hz, 2H), 8.22 (d, J = 8.0 Hz, 1H), 7.92 (dd, J = 2.6, 8.5 Hz, 1H), 7.61-7.55 (m, 2H), 7.49 (dd, J = 1.3, 8.1 Hz, 1H), 7.40 (d, J = 6.0 Hz, 1H), 6.85 (d, J = 8.5 Hz, 1H), 6.72 (d, J = 2.0 Hz, 1H), 6.45 (dd, J = 2.1, 8.3 Hz, 1H), 5.47-5.35 (m, |

(First row, partial NMR at top): 6.9 Hz, 1H), 4.93 (dd, J = 5.1, 12.0 Hz, 1H), 4.49 (br s, 1H), 4.25 (br t, J = 7.5 Hz, 2H), 3.96-3.84 (m, 5H), 3.57-3.35 (m, 10H), 2.93-2.66 (m, 7H), 2.39-2.27 (m, 2H), 2.16-2.08 (m, 1H), 1.93-1.82 (m, 2H).

TABLE 2-continued

Exemplary PROTAC of the present disclosure.

| Ex. | Structure | Degradation activity* | MH + (1) [MH + (2), if isotope] | NMR transcript |
|---|---|---|---|---|
| 214 | 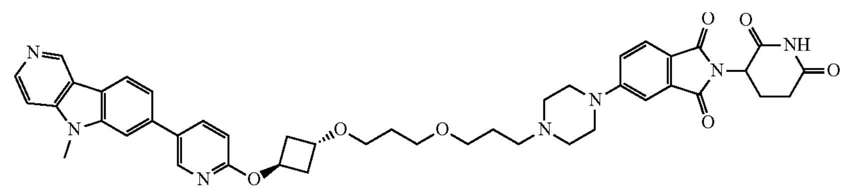 [SMILES: Cn1c2ccncc2c2ccc(-c3ccc(O[C@H]4C[C@H](OCCCOCCCN5CCN(c6ccc7c(c6)C(=O)N(C6CCC(=O)NC6=O)C7=O)CC5)C4)nc3)cc21] | | | 1H), 4.92 (dd, J = 5.3, 12.2 Hz, 1H), 4.39-4.27 (m, 1H), 4.07-3.95 (m, 5H), 3.93 (s, 3H), 3.72-3.64 (m, 4H), 3.57 (ddd, J = 3.7, 5.8, 11.9 Hz, 4H), 2.91-2.76 (m, 3H), 2.59 (ddd, J = 4.0, 6.9, 13.4 Hz, 4H), 2.52-2.43 (m, 2H), 2.32-2.23 (m, 2H), 2.16-2.07 (m, 1H), |
| 215 | 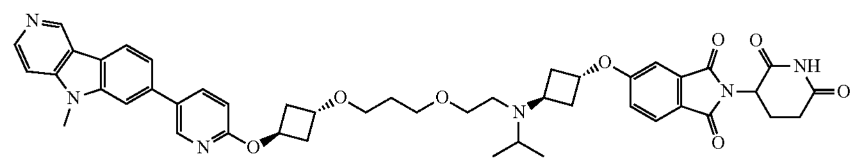 [SMILES: CC(C)N(CCOCCCO[C@H]1C[C@H](Oc2ccc(-c3ccc4c5cnccc5n(C)c4c3)cn2)C1)[C@H]1C[C@H](Oc2ccc3c(c2)C(=O)N(C2CCC(=O)NC2=O)C3=O)C1] | | 786.6 | |
| 216 | 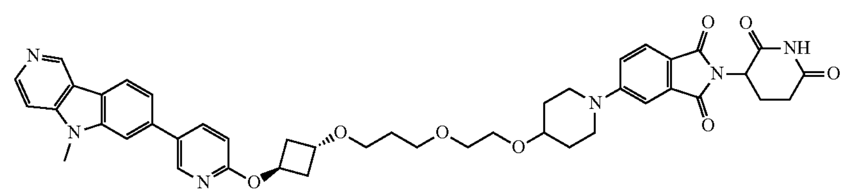 [SMILES: Cn1c2ccncc2c2ccc(-c3ccc(O[C@H]4C[C@H](OCCCOCCOC5CCN(c6ccc7c(c6)C(=O)N(C6CCC(=O)NC6=O)C7=O)CC5)C4)nc3)cc21] | | | |
| 217 | 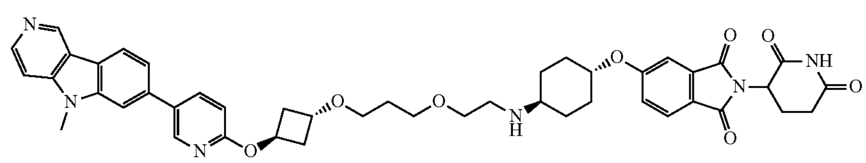 [SMILES: Cn1c2ccncc2c2ccc(-c3ccc(O[C@H]4C[C@H](OCCCOCCN[C@H]5CC[C@H](Oc6ccc7c(c6)C(=O)N(C6CCC(=O)NC6=O)C7=O)CC5)C4)nc3)cc21] | | | |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 218 | 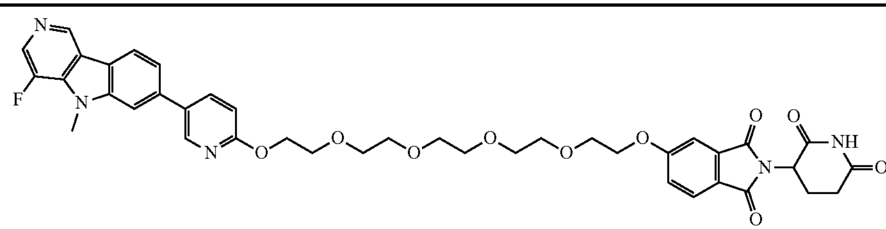 | | | |
| 219 | 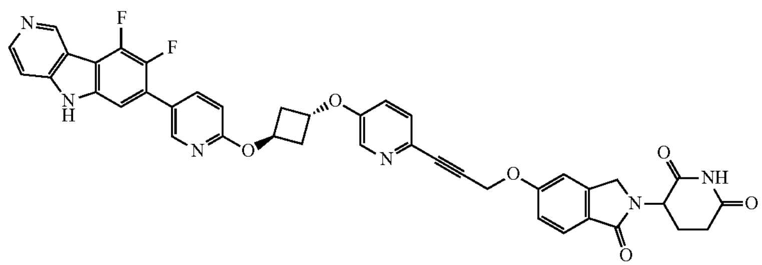 [SMILES: O=C1CCC(N2Cc3cc(OCC#Cc4ccc(O[C@H]5C[C@H](Oc6ccc(-c7cc8[nH]c9ccncc9c8c(F)c7F)cn6)C5)cn4)ccc3C2=O)C(=O)N1] | | | |
| 220 | 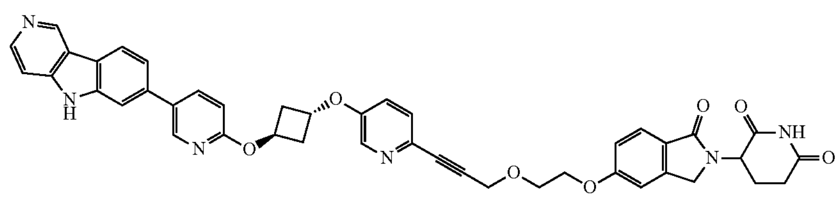 [SMILES: O=C1CCC(N2Cc3cc(OCCOCC#Cc4ccc(O[C@H]5C[C@H](Oc6ccc(-c7ccc8c(c7)[nH]c7ccncc78)cn6)C5)cn4)ccc3C2=O)C(=O)N1] | | | |
| 221 | 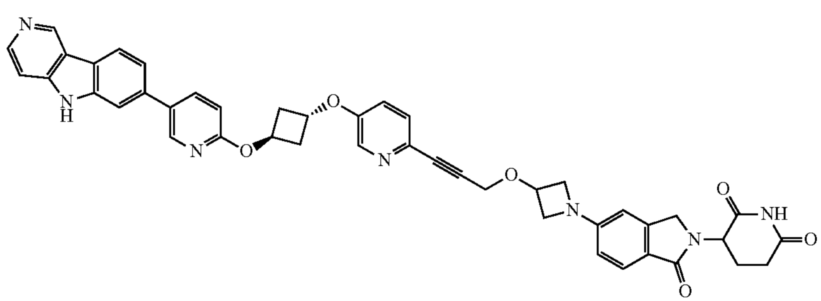 [SMILES: O=C1CCC(N2Cc3cc(N4CC(OCC#Cc5ccc(O[C@H]6C[C@H](Oc7ccc(-c8ccc9c(c8)[nH]c8ccncc89)cn7)C6)cn5)C4)ccc3C2=O)C(=O)N1] | | | |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 222 | 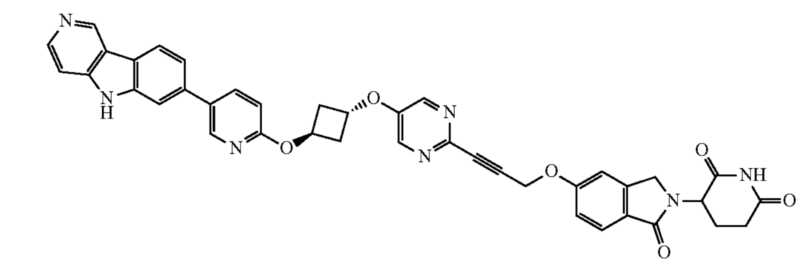 [SMILES: O=C1CCC(N2Cc3cc(OCC#Cc4ncc(O[C@H]5C[C@H](Oc6ccc(-c7ccc8c(c7)[nH]c7ccncc78)cn6)C5)cn4)ccc3C2=O)C(=O)N1] | | | |
| 223 | 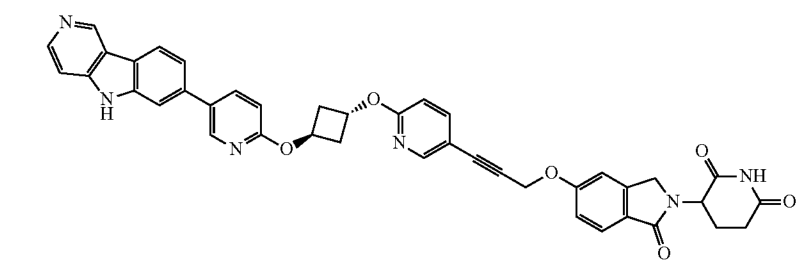 [SMILES: O=C1CCC(N2Cc3cc(OCC#Cc4ccc(O[C@H]5C[C@H](Oc6ccc(-c7ccc8c(c7)[nH]c7ccncc78)cn6)C5)nc4)ccc3C2=O)C(=O)N1] | | | |
| 224 | 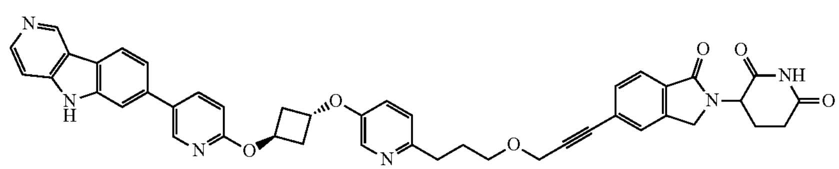 [SMILES: O=C1CCC(N2Cc3cc(C#CCOCCCc4ccc(O[C@H]5C[C@H](Oc6ccc(-c7ccc8c(c7)[nH]c7ccncc78)cn6)C5)cn4)ccc3C2=O)C(=O)N1] | | | |
| 225 | 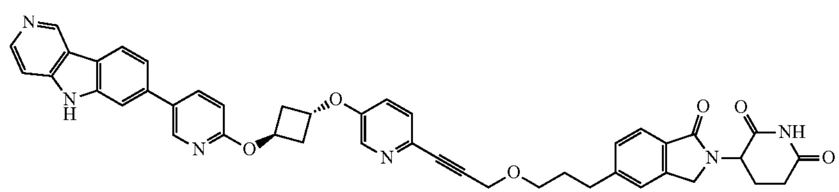 [SMILES: O=C1CCC(N2Cc3cc(CCCOCC#Cc4ccc(O[C@H]5C[C@H](Oc6ccc(-c7ccc8c(c7)[nH]c7ccncc78)cn6)C5)cn4)ccc3C2=O)C(=O)N1] | | | |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 226 | 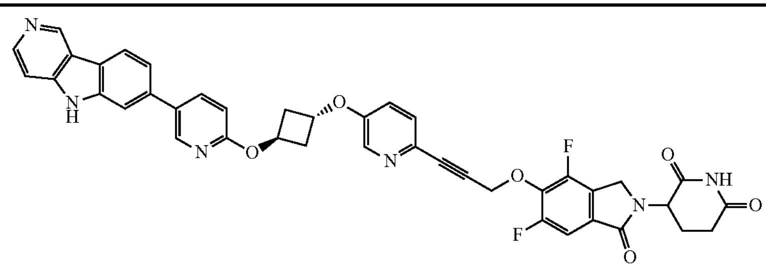 | | | |
| 227 | 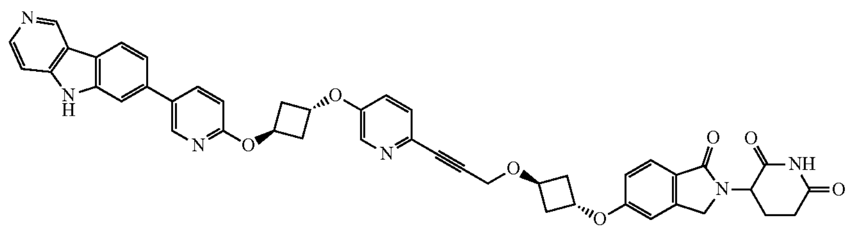 [SMILES: O=C1CCC(N2Cc3cc(O[C@H]4C[C@H](OCC#Cc5ccc(O[C@H]6C[C@H](Oc7ccc(-c8ccc9c(c8)[nH]c8ccncc89)cn7)C6)cn5)C4)ccc3C2=O)C(=O)N1] | | | |
| 228 | 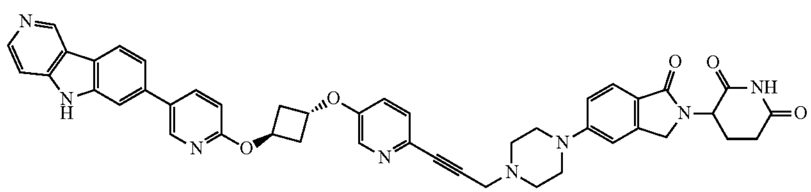 [SMILES: O=C1CCC(N2Cc3cc(N4CCN(CC#Cc5ccc(O[C@H]6C[C@H](Oc7ccc(-c8ccc9c(c8)[nH]c8ccncc89)cn7)C6)cn5)CC4)ccc3C2=O)C(=O)N1] | | | |
| 229 | 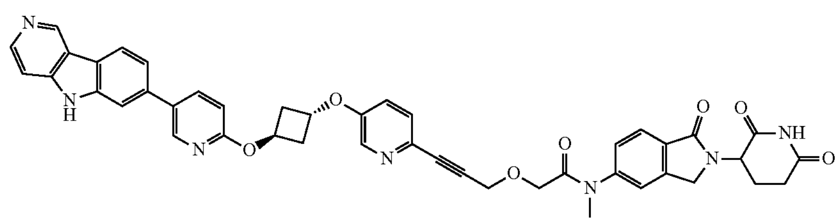 [SMILES: CN(C(=O)COCC#Cc1ccc(O[C@H]2C[C@H](Oc3ccc(-c4ccc5c(c4)[nH]c4ccncc45)cn3)C2)cn1)c1ccc2c(c1)CN(C1CCC(=O)NC1=O)C2=O] | | | |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 230 | 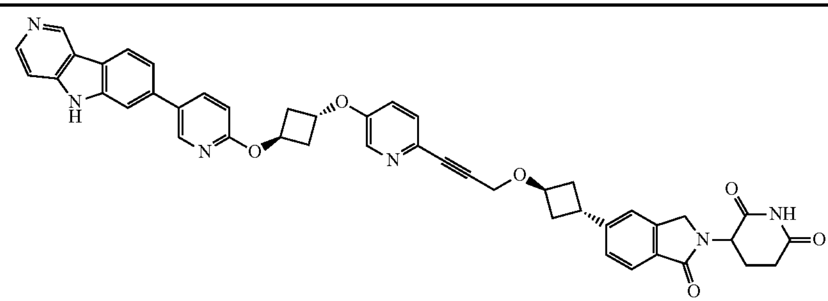 | | | |
| 231 | 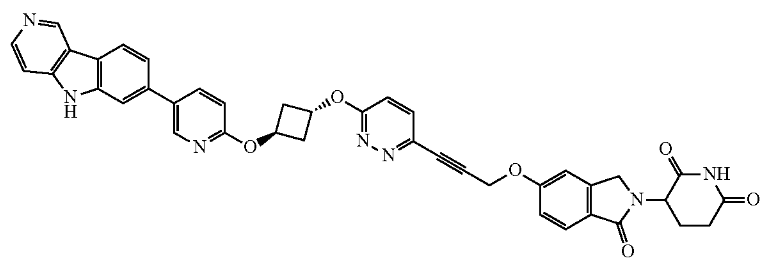 | | | |
| 232 | 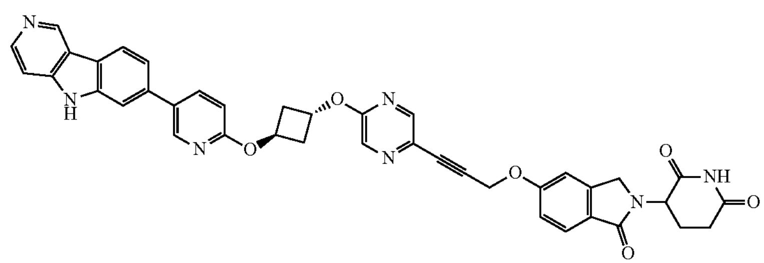 [SMILES: O=C1CCC(N2Cc3cc(OCC#Cc4cnc(O[C@H]5C[C@H](Oc6ccc(-c7ccc8c(c7)[nH]c7ccncc78)cn6)C5)cn4)ccc3C2=O)C(=O)N1] | | | |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 233 | 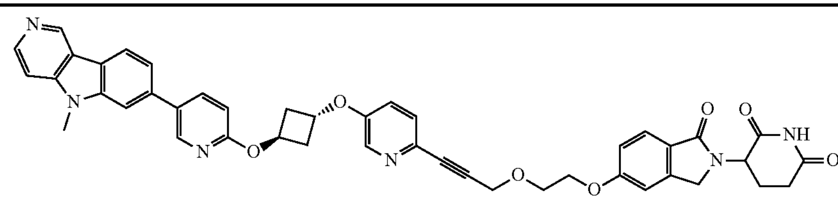 | | | |
| 234 | 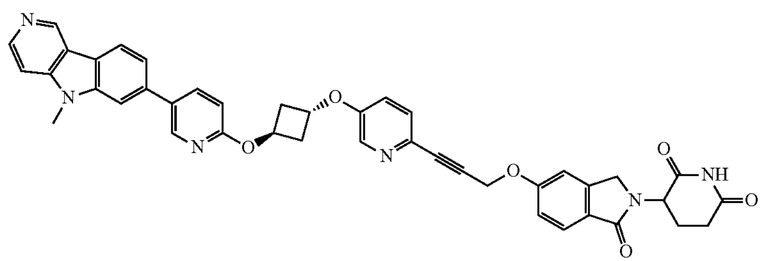 [SMILES: Cn1c2ccncc2c2ccc(-c3ccc(O[C@H]4C[C@H](Oc5ccc(C#CCOc6ccc7c(c6)CN(C6CCC(=O)NC6=O)C7=O)nc5)C4)nc3)cc21] | | | |
| 235 | 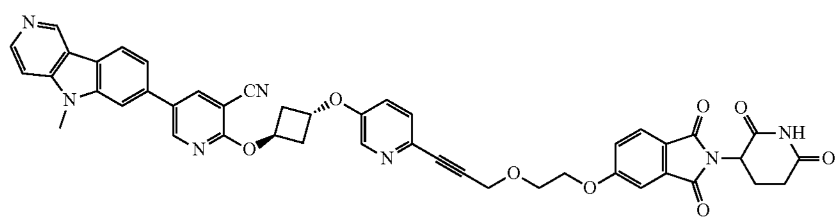 [SMILES: Cn1c2ccncc2c2ccc(-c3cnc(O[C@H]4C[C@H](Oc5ccc(C#CCOCCOc6ccc7c(c6)C(=O)N(C6CCC(=O)NC6=O)C7=O)nc5)C4)c(C#N)c3)cc21] | | | |
| 236 | 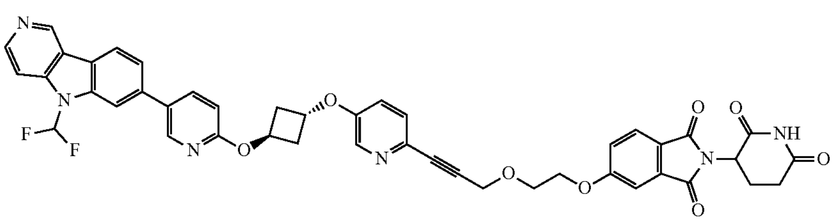 [SMILES: O=C1CCC(N2C(=O)c3ccc(OCCOCC#Cc4ccc(O[C@H]5C[C@H](Oc6ccc(-c7ccc8c9cnccc9n(C(F)F)c8c7)cn6)C5)cn4)cc3C2=O)C(=O)N1] | | | |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 237 | 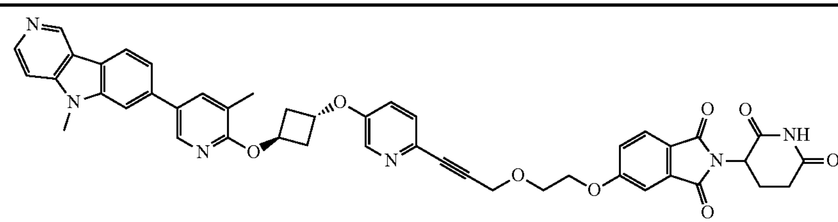 | | | |
| 238 | 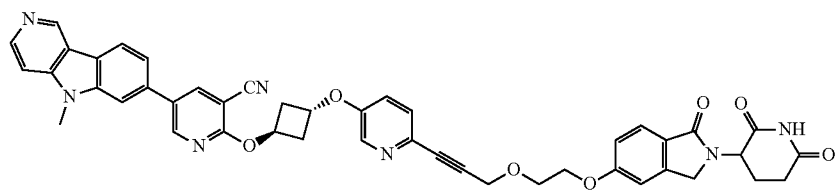 [SMILES: Cn1c2ccncc2c2ccc(-c3cnc(O[C@H]4C[C@H](Oc5ccc(C#CCOCCOc6ccc7c(c6)CN(C6CCC(=O)NC6=O)C7=O)nc5)C4)c(C#N)c3)cc21] | | | |
| 239 | 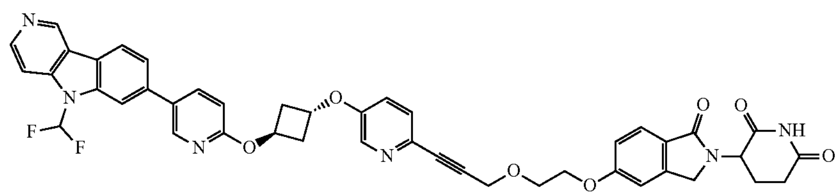 [SMILES: O=C1CCC(N2Cc3cc(OCCOCC#Cc4ccc(O[C@H]5C[C@H](Oc6ccc(-c7ccc8c9cnccc9n(C(F)F)c8c7)cn6)C5)cn4)ccc3C2=O)C(=O)N1] | | | |
| 240 | 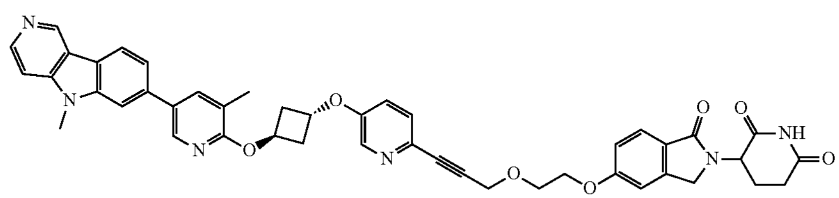 | | | |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 241 | 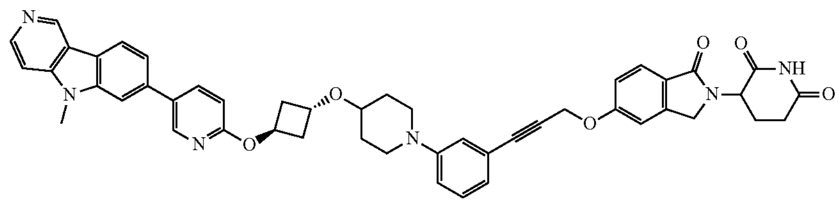 | | | |
| 242 | 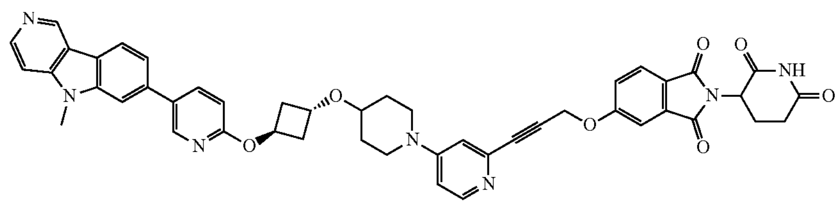 [SMILES: Cn1c2ccncc2c2ccc(-c3ccc(O[C@H]4C[C@H](OC5CCN(c6ccnc(C#CCOc7ccc8c(c7)C(=O)N(C7CCC(=O)NC7=O)C8=O)c6)CC5)C4)nc3)cc21] | | | |
| 243 | 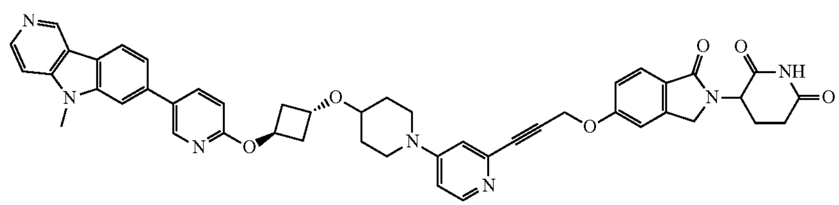 [SMILES: Cn1c2ccncc2c2ccc(-c3ccc(O[C@H]4C[C@H](OC5CCN(c6ccnc(C#CCOc7ccc8c(c7)CN(C7CCC(=O)NC7=O)C8=O)c6)CC5)C4)nc3)cc21] | | | |
| 244 | 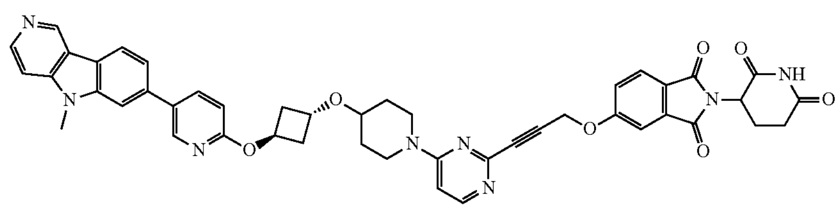 | | | |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 245 | 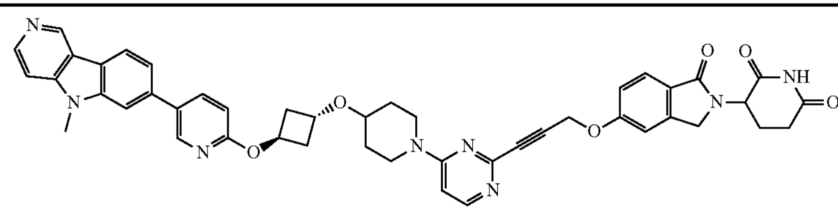 | | | |
| 246 | 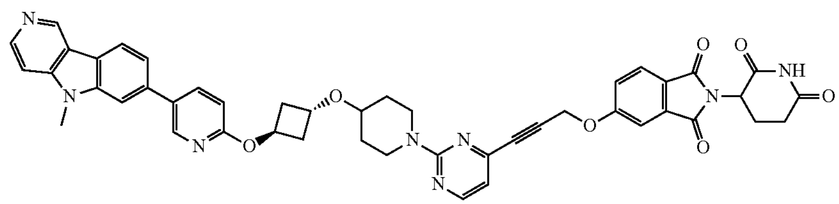 | | | |
| 247 | 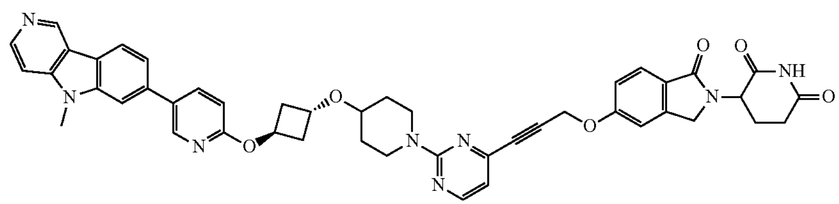 [SMILES: Cn1c2ccncc2c2ccc(-c3ccc(O[C@H]4C[C@H](OC5CCN(c6ccnc(C#CCOc7ccc8c(c7)CN(C7CCC(=O)NC7=O)C8=O)n6)CC5)C4)nc3)cc21] | | | |
| 248 | 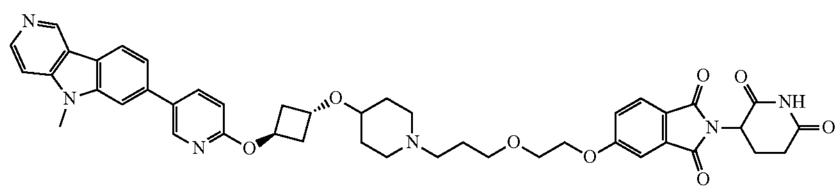 [SMILES: Cn1c2ccncc2c2ccc(-c3ccc(O[C@H]4C[C@H](OC5CCN(CCCOCCOc6ccc7c(c6)C(=O)N(C6CCC(=O)NC6=O)C7=O)CC5)C4)nc3)cc21] | | | |
| 249 | 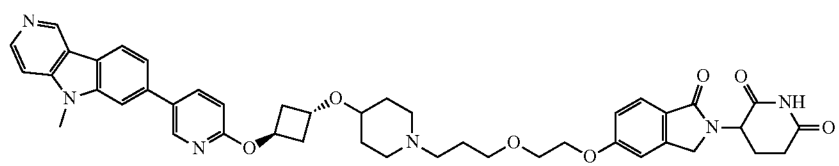 [SMILES: Cn1c2ccncc2c2ccc(-c3ccc(O[C@H]4C[C@H](OC5CCN(CCCOCCOc6ccc7c(c6)CN(C6CCC(=O)NC6=O)C7=O)CC5)C4)nc3)cc21] | | | |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 250 | 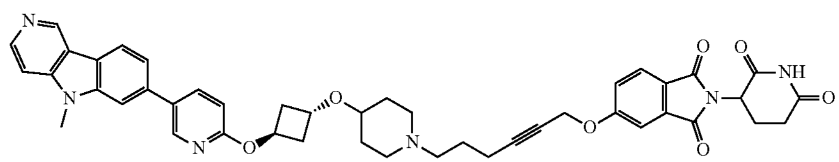 [SMILES: Cn1c2ccncc2c2ccc(-c3ccc(O[C@H]4C[C@H](OC5CCN(CCCC#CCOc6ccc7c(c6)C(=O)N(C6CCC(=O)NC6=O)C7=O)CC5)C4)nc3)cc21] | | | |
| 251 | 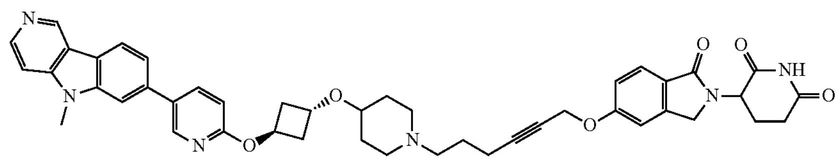 [SMILES: Cn1c2ccncc2c2ccc(-c3ccc(O[C@H]4C[C@H](OC5CCN(CCCC#CCOc6ccc7c(c6)CN(C6CCC(=O)NC6=O)C7=O)CC5)C4)nc3)cc21] | | | |
| 252 | 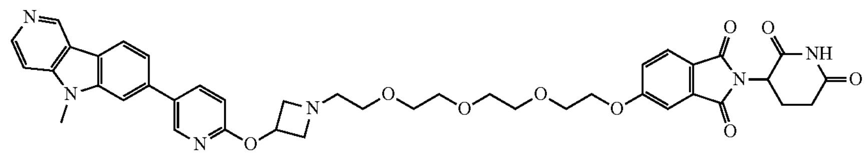 [SMILES: Cn1c2ccncc2c2ccc(-c3ccc(OC4CN(CCOCCOCCOCCOc5ccc6c(c5)C(=O)N(C5CCC(=O)NC5=O)C6=O)C4)nc3)cc21] | | | |
| 253 | 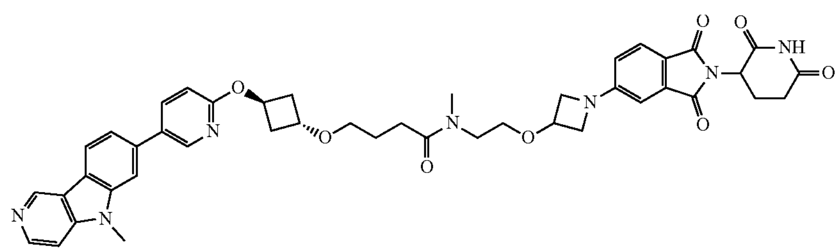 [SMILES: CN(CCOC1CN(c2ccc3c(c2)C(=O)N(C2CCC(=O)NC2=O)C3=O)C1)C(=O)CCCO[C@H]1C[C@H](Oc2ccc(-c3ccc4c5cnccc5n(C)c4c3)cn2)C1] | | | |
| 254 | 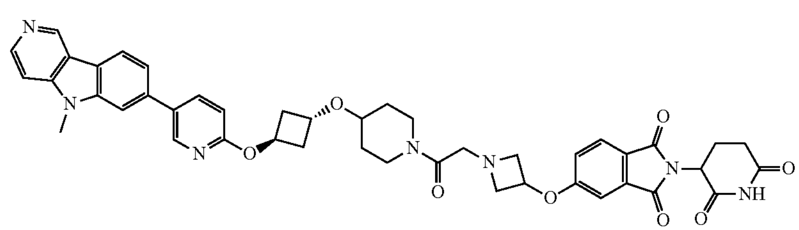 [SMILES: Cn1c2ccncc2c2ccc(-c3ccc(O[C@H]4C[C@H](OC5CCN(C(=O)CN6CC(Oc7ccc8c(c7)C(=O)N(C7CCC(=O)NC7=O)C8=O)C6)CC5)C4)nc3)cc21] | | | |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 255 | 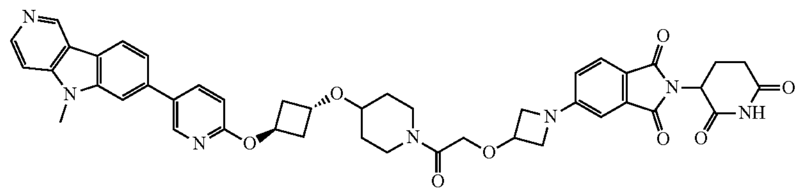 [SMILES: Cn1c2ccncc2c2ccc(-c3ccc(O[C@H]4C[C@H](OC5CCN(C(=O)COC6CN(c7ccc8c(c7)C(=O)N(C7CCC(=O)NC7=O)C8=O)C6)CC5)C4)nc3)cc21] | | | |
| 256 | 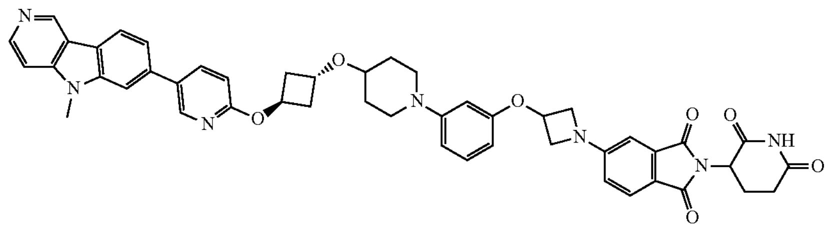 [SMILES: Cn1c2ccncc2c2ccc(-c3ccc(O[C@H]4C[C@H](OC5CCN(c6cccc(OC7CN(c8ccc9c(c8)C(=O)N(C8CCC(=O)NC8=O)C9=O)C7)c6)CC5)C4)nc3)cc21] | | | |
| 257 | 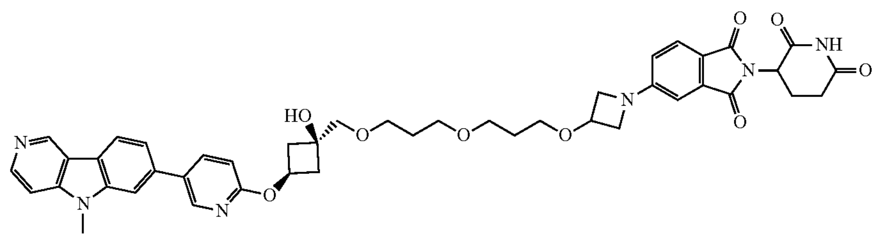 [SMILES: Cn1c2ccncc2c2ccc(-c3ccc(O[C@H]4C[C@](O)(COCCCOCCCOC5CN(c6ccc7c(c6)C(=O)N(C6CCC(=O)NC6=O)C7=O)C5)C4)nc3)cc21] | | | |
| 258 | 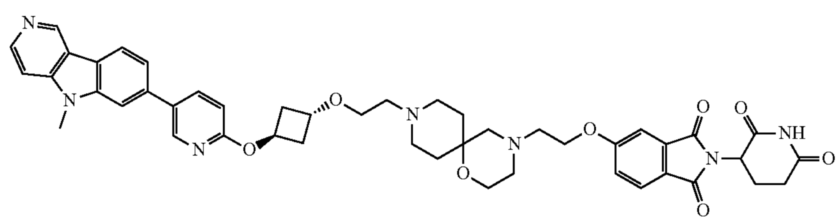 [SMILES: Cn1c2ccncc2c2ccc(-c3ccc(O[C@H]4C[C@H](OCCN5CCC6(CC5)CN(CCOc5ccc7c(c5)C(=O)N(C5CCC(=O)NC5=O)C7=O)CCO6)C4)nc3)cc21] | | | |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 259 | 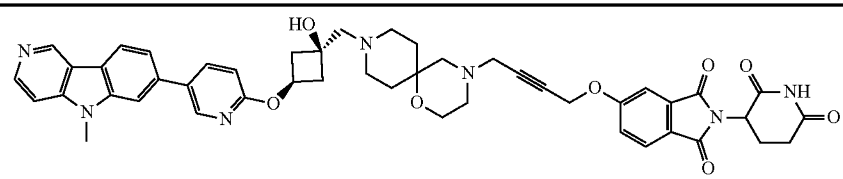 | | | |
| 260 | 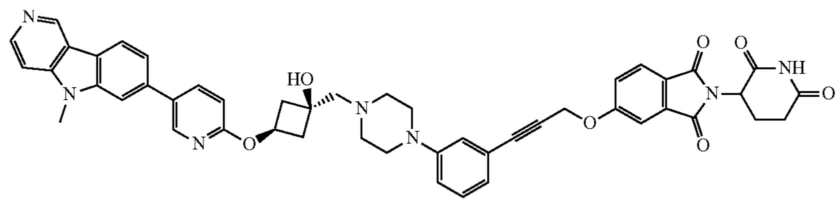 [SMILES: Cn1c2ccncc2c2ccc(-c3ccc(O[C@H]4C[C@](O)(CN5CCN(c6cccc(C#CCOc7ccc8c(c7)C(=O)N(C7CCC(=O)NC7=O)C8=O)c6)CC5)C4)nc3)cc21] | | | |
| 261 | 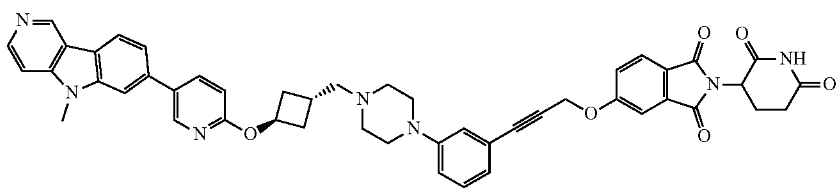 [SMILES: Cn1c2ccncc2c2ccc(-c3ccc(O[C@H]4C[C@H](CN5CCN(c6cccc(C#CCOc7ccc8c(c7)C(=O)N(C7CCC(=O)NC7=O)C8=O)c6)CC5)C4)nc3)cc21] | | | |
| 262 | 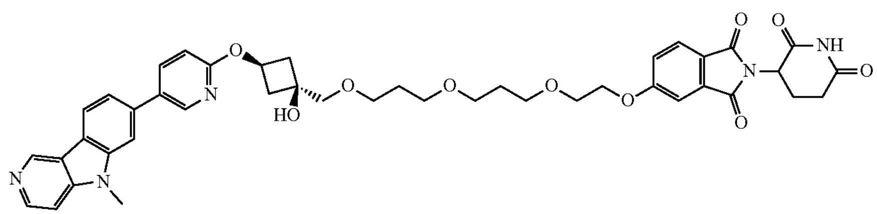 [SMILES: Cn1c2ccncc2c2ccc(-c3ccc(O[C@H]4C[C@](O)(COCCCOCCCOCCOc5ccc6c(c5)C(=O)N(C5CCC(=O)NC5=O)C6=O)C4)nc3)cc21] | | | |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 263 | 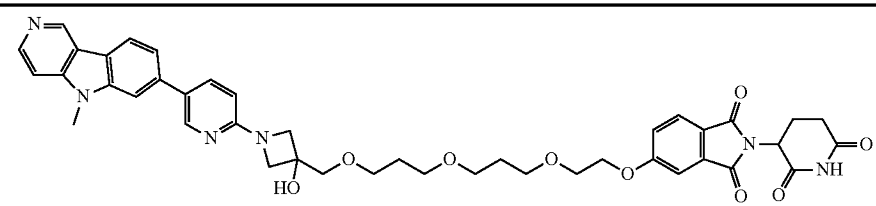 | | | |
| 264 | 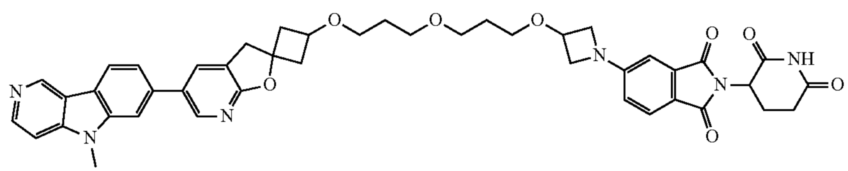 [SMILES: Cn1c2ccncc2c2ccc(-c3cnc4c(c3)CC3(CC(OCCCOCCCOC5CN(c6ccc7c(c6)C(=O)N(C6CCC(=O)NC6=O)C7=O)C5)C3)O4)cc21] | | | |
| 265 | 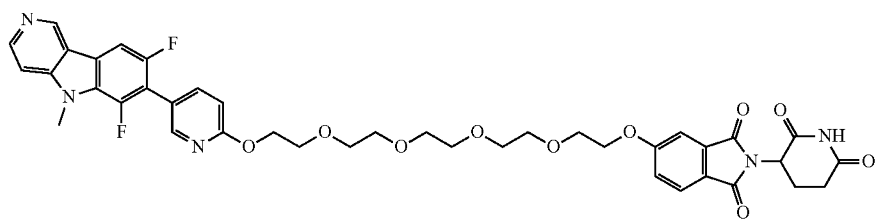 [SMILES: Cn1c2ccncc2c2cc(F)c(-c3ccc(OCCOCCOCCOCCOCCOc4ccc5c(c4)C(=O)N(C4CCC(=O)NC4=O)C5=O)nc3)c(F)c21] | | | |
| 266 | 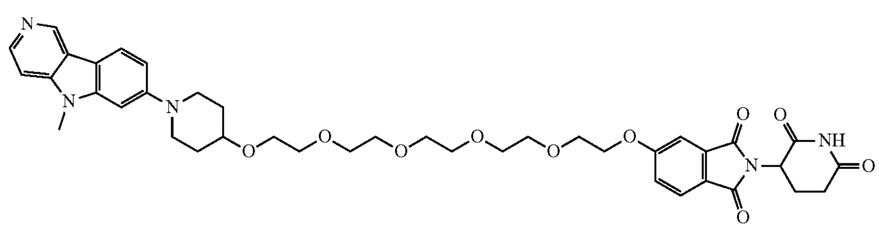 [SMILES: Cn1c2ccncc2c2ccc(N3CCC(OCCOCCOCCOCCOCCOc4ccc5c(c4)C(=O)N(C4CCC(=O)NC4=O)C5=O)CC3)cc21] | | | |
| 267 | 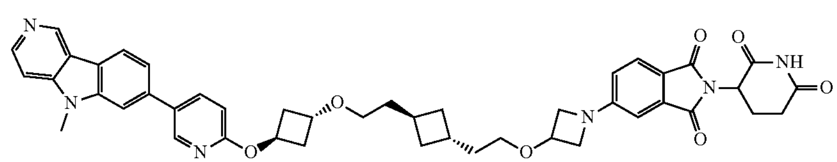 [SMILES: Cn1c2ccncc2c2ccc(-c3ccc(O[C@H]4C[C@H](OCC[C@H]5C[C@H](CCOC6CN(c7ccc8c(c7)C(=O)N(C7CCC(=O)NC7=O)C8=O)C6)C5)C4)nc3)cc21] | | | |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 268 | 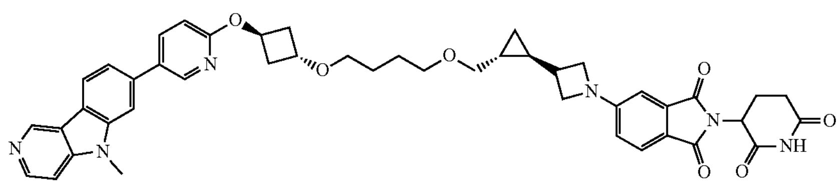 [SMILES: Cn1c2ccncc2c2ccc(-c3ccc(O[C@H]4C[C@H](OCCCCOC[C@@H]5C[C@H]5C5CN(c6ccc7c(c6)C(=O)N(C6CCC(=O)NC6=O)C7=O)C5)C4)nc3)cc21] | | | |
| 269 | 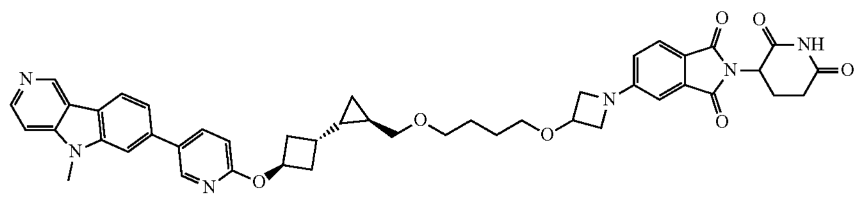 [SMILES: Cn1c2ccncc2c2ccc(-c3ccc(O[C@H]4C[C@H](C5C[C@H]5COCCCCOC5CN(c6ccc7c(c6)C(=O)N(C6CCC(=O)NC6=O)C7=O)C5)C4)nc3)cc21] | | | |
| 270 | 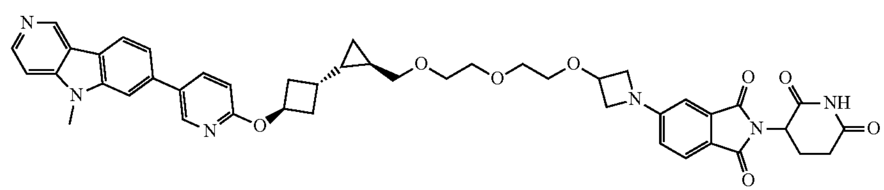 [SMILES: Cn1c2ccncc2c2ccc(-c3ccc(O[C@H]4C[C@H](C5C[C@H]5COCCOCCOC5CN(c6ccc7c(c6)C(=O)N(C6CCC(=O)NC6=O)C7=O)C5)C4)nc3)cc21] | | | |
| 271 | 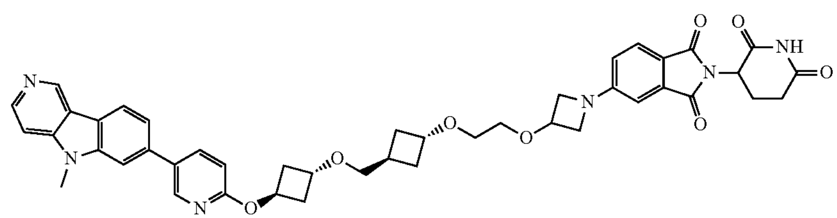 [SMILES: Cn1c2ccncc2c2ccc(-c3ccc(O[C@H]4C[C@H](OC[C@H]5C[C@H](OCCOC6CN(c7ccc8c(c7)C(=O)N(C7CCC(=O)NC7=O)C8=O)C6)C5)C4)nc3)cc21] | | | |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 272 | 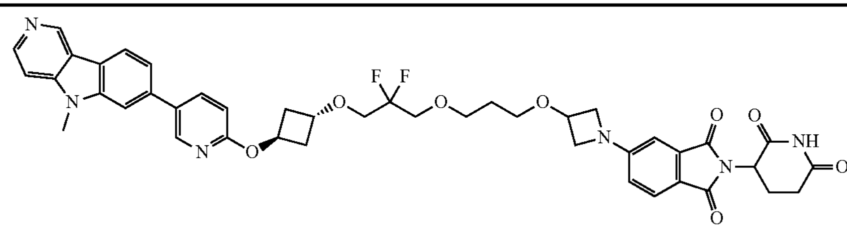 | | | |
| 273 | 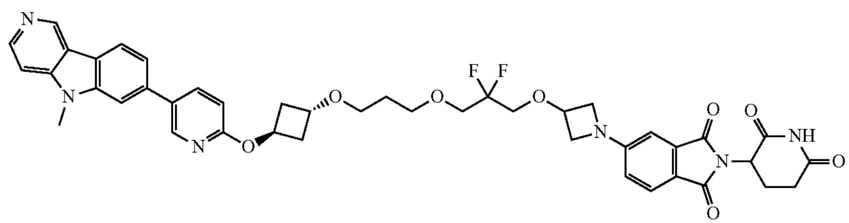 [SMILES: Cn1c2ccncc2c2ccc(-c3ccc(O[C@H]4C[C@H](OCCCOCC(F)(F)COC5CN(c6ccc7c(c6)C(=O)N(C6CCC(=O)NC6=O)C7=O)C5)C4)nc3)cc21] | | | |
| 274 | 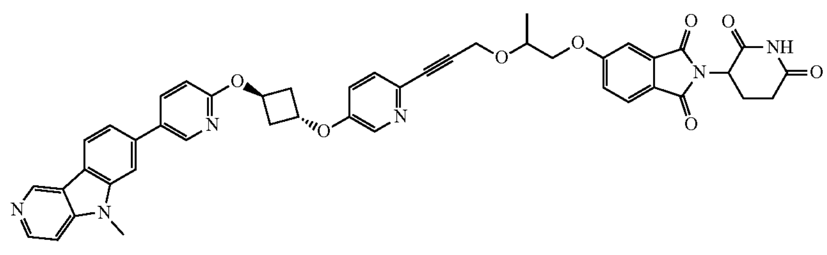 [SMILES: CC(COc1ccc2c(c1)C(=O)N(C1CCC(=O)NC1=O)C2=O)OCC#Cc1ccc(O[C@H]2C[C@H](Oc3ccc(-c4ccc5c6cnccc6n(C)c5c4)cn3)C2)cn1] | | | |
| 275 | 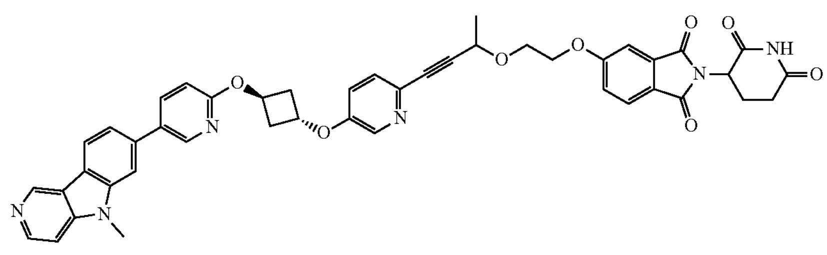 [SMILES: CC(C#Cc1ccc(O[C@H]2C[C@H](Oc3ccc(-c4ccc5c6cnccc6n(C)c5c4)cn3)C2)cn1)OCCOc1ccc2c(c1)C(=O)N(C1CCC(=O)NC1=O)C2=O] | | | |

TABLE 2-continued
Exemplary PROTAC of the present disclosure.
| Ex. | Structure | Degradation activity* | MH + (1) [MH + (2), if isotope] | NMR transcript |
|---|---|---|---|---|
| 276 | 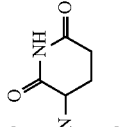 | | | |
| 277 | 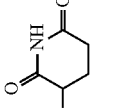 | | | |
| 278 | 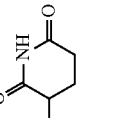 | | | |
| 279 | 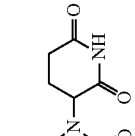 | | | |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 280 | 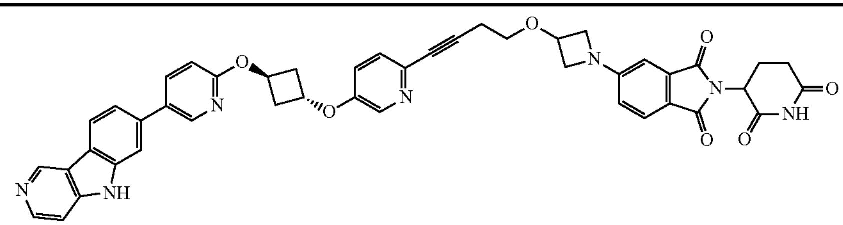 | | | |
| 281 | 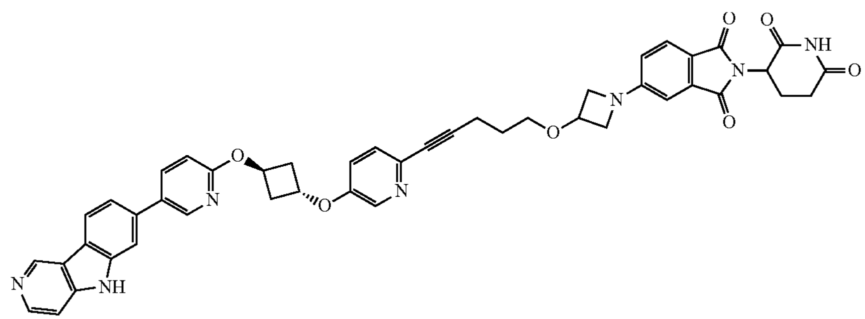 [SMILES: O=C1CCC(N2C(=O)c3ccc(N4CC(OCCCC#Cc5ccc(O[C@H]6C[C@H](Oc7ccc(-c8ccc9c(c8)[nH]c8ccncc89)cn7)C6)cn5)C4)cc3C2=O)C(=O)N1] | | | |
| 282 | 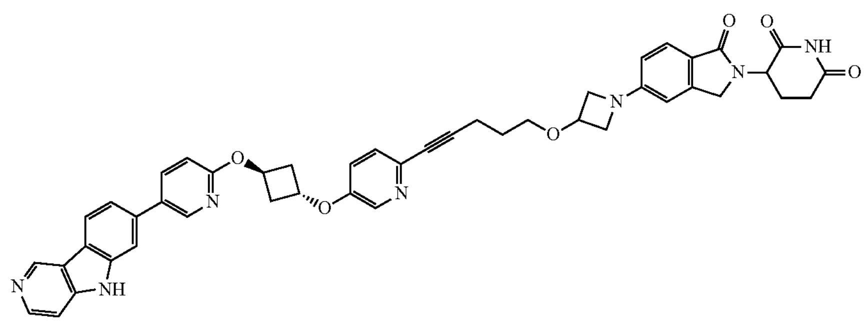 [SMILES: O=C1CCC(N2Cc3cc(N4CC(OCCCC#Cc5ccc(O[C@H]6C[C@H](Oc7ccc(-c8ccc9c(c8)[nH]c8ccncc89)cn7)C6)cn5)C4)ccc3C2=O)C(=O)N1] | | | |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 283 | 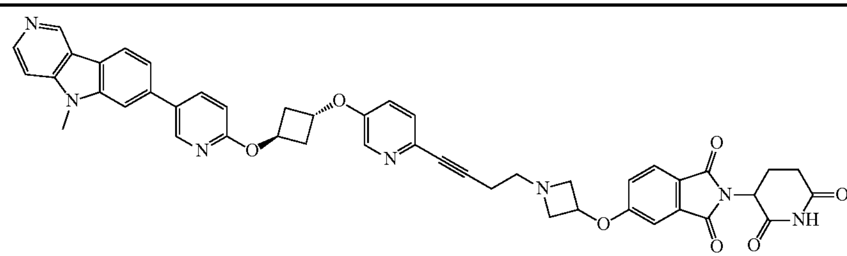 | | | |
| 284 | 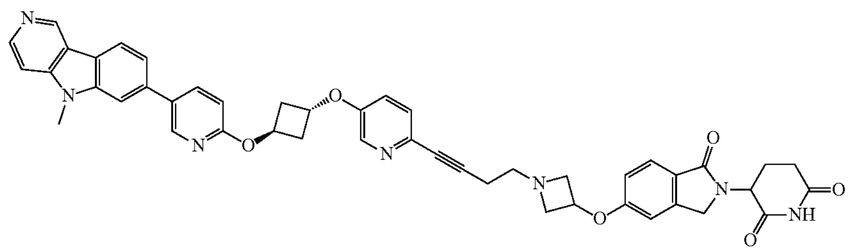 [SMILES: Cn1c2ccncc2c2ccc(-c3ccc(O[C@H]4C[C@H](Oc5ccc(C#CCCN6CC(Oc7ccc8c(c7)CN(C7CCC(=O)NC7=O)C8=O)C6)nc5)C4)nc3)cc21] | | | |
| 285 | 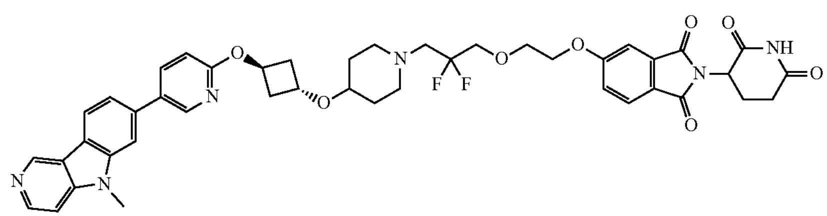 [SMILES: Cn1c2ccncc2c2ccc(-c3ccc(O[C@H]4C[C@H](OC5CCN(CC(F)(F)COCCOc6ccc7c(c6)C(=O)N(C6CCC(=O)NC6=O)C7=O)CC5)C4)nc3)cc21] | | | |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 286 | 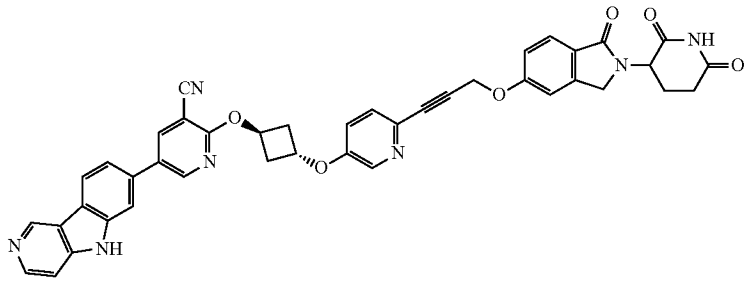 | | | |
| 287 | 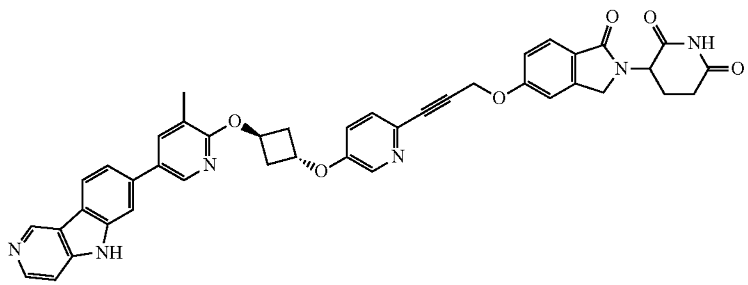 [SMILES: Cc1cc(-c2ccc3c(c2)[nH]c2ccncc23)cnc1O[C@H]1C[C@H](Oc2ccc(C#CCOc3ccc4c(c3)CN(C3CCC(=O)NC3=O)C4=O)nc2)C1] | | | |
| 288 | 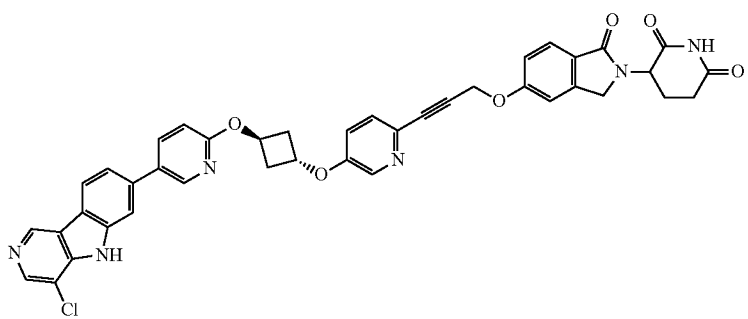 [SMILES: O=C1CCC(N2Cc3cc(OCC#Cc4ccc(O[C@H]5C[C@H](Oc6ccc(-c7ccc8c(c7)[nH]c7c(F)cncc78)cn6)C5)cn4)ccc3C2=O)C(=O)N1] | | | |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 289 | 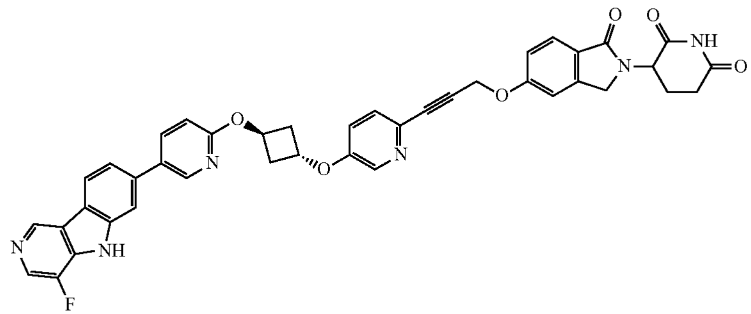 | | | |
| 290 | 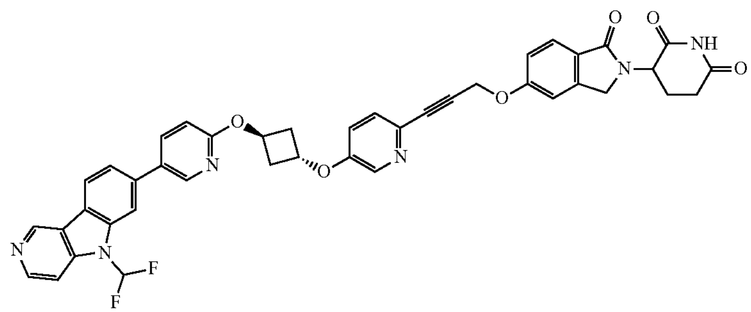 [SMILES: O=C1CCC(N2Cc3cc(OCC#Cc4ccc(O[C@H]5C[C@H](Oc6ccc(-c7ccc8c9cnccc9n(C(F)F)c8c7)cn6)C5)cn4)ccc3C2=O)C(=O)N1] | | | |
| 291 | 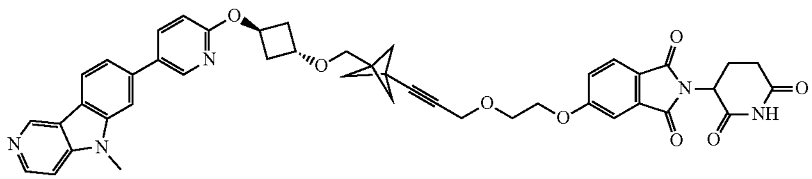 [SMILES: Cn1c2ccncc2c2ccc(-c3ccc(O[C@H]4C[C@H](OCC56CC(C#CCOCCOc7ccc8c(c7)C(=O)N(C7CCC(=O)NC7=O)C8=O)(C5)C6)C4)nc3)cc21] | | | |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 292 | 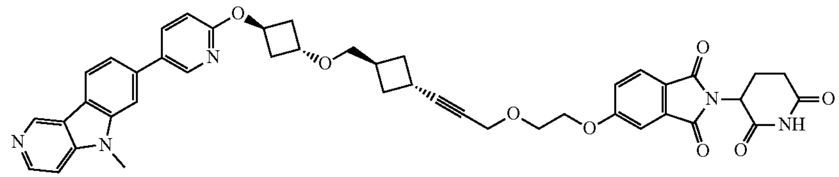 [SMILES: Cn1c2ccncc2c2ccc(-c3ccc(O[C@H]4C[C@H](OC[C@H]5C[C@H](C#CCOCCOc6ccc7c(c6)C(=O)N(C6CCC(=O)NC6=O)C7=O)C5)C4)nc3)cc21] | | | |
| 293 | 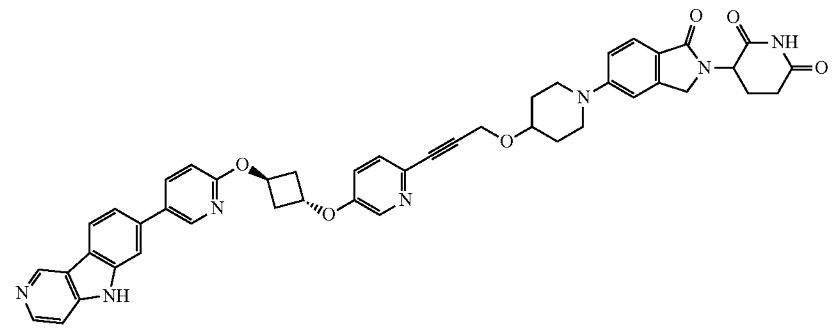 [SMILES: O=C1CCC(N2Cc3cc(N4CCC(OCC#Cc5ccc(O[C@H]6C[C@H](Oc7ccc(-c8ccc9c(c8)[nH]c8ccncc89)cn7)C6)cn5)CC4)ccc3C2=O)C(=O)N1] | | | |
| 294 | 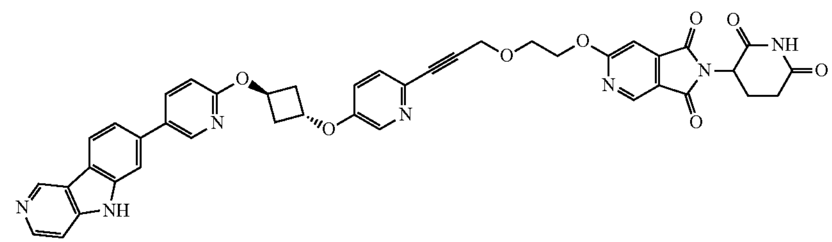 | | | |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 295 | 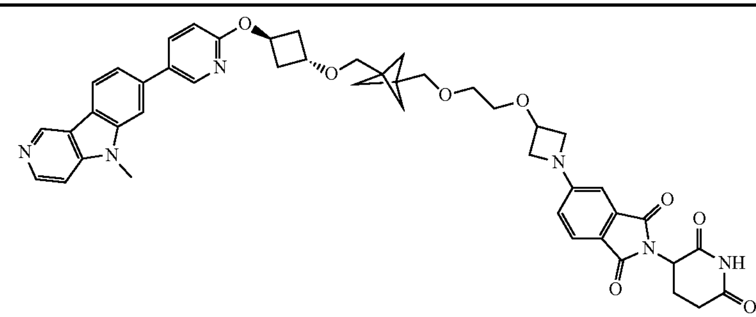 | | | |
| 296 | 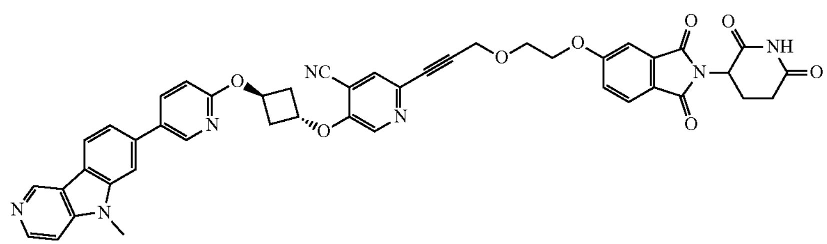 [SMILES: Cn1c2ccncc2c2ccc(-c3ccc(O[C@H]4C[C@H](Oc5cnc(C#CCOCCOc6ccc7c(c6)C(=O)N(C6CCC(=O)NC6=O)C7=O)cc5C#N)C4)nc3)cc21] | | | |
| 297 | 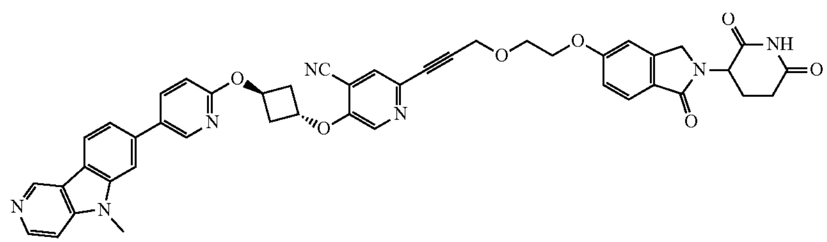 [SMILES: Cn1c2ccncc2c2ccc(-c3ccc(O[C@H]4C[C@H](Oc5cnc(C#CCOCCOc6ccc7c(c6)CN(C6CCC(=O)NC6=O)C7=O)cc5C#N)C4)nc3)cc21] | | | |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 298 | 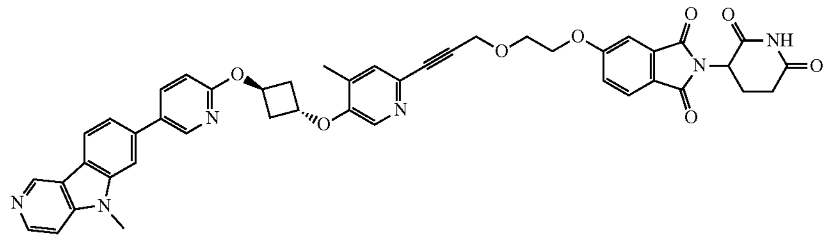 [SMILES: Cc1cc(C#CCOCCOc2ccc3c(c2)C(=O)N(C2CCC(=O)NC2=O)C3=O)ncc1O[C@H]1C[C@H](Oc2ccc(-c3ccc4c5cnccc5n(C)c4c3)cn2)C1] | | | |
| 299 | 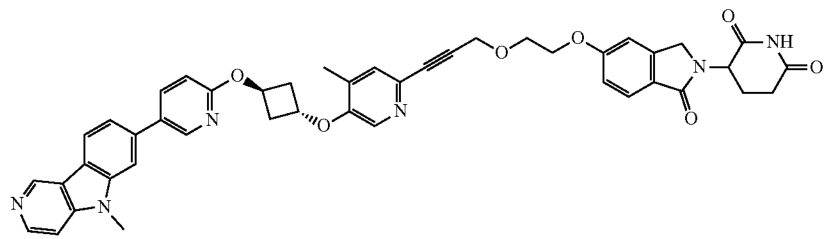 [SMILES: Cc1cc(C#CCOCCOc2ccc3c(c2)CN(C2CCC(=O)NC2=O)C3=O)ncc1O[C@H]1C[C@H](Oc2ccc(-c3ccc4c5cnccc5n(C)c4c3)cn2)C1] | | | |
| 300 | 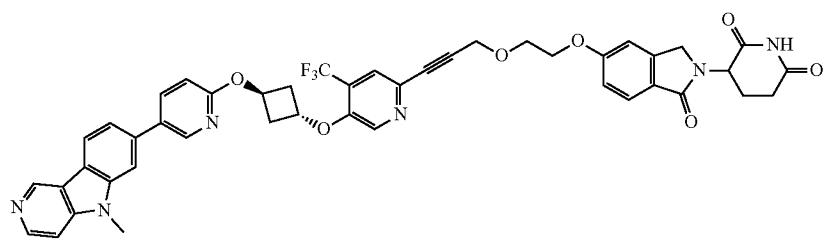 [SMILES: Cn1c2ccncc2c2ccc(-c3ccc(O[C@H]4C[C@H](Oc5cnc(C#CCOCCOc6ccc7c(c6)CN(C6CCC(=O)NC6=O)C7=O)cc5C(F)(F)F)C4)nc3)cc21] | | | |
| 301 | 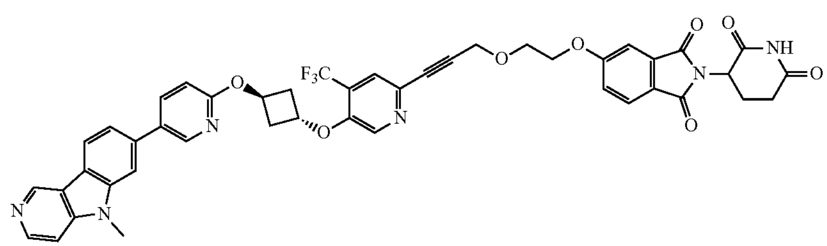 [SMILES: Cn1c2ccncc2c2ccc(-c3ccc(O[C@H]4C[C@H](Oc5cnc(C#CCOCCOc6ccc7c(c6)C(=O)N(C6CCC(=O)NC6=O)C7=O)cc5C(F)(F)F)C4)nc3)cc21] | | | |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 302 | 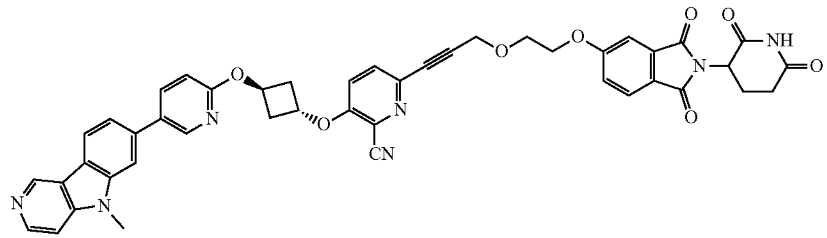 [SMILES: Cn1c2ccncc2c2ccc(-c3ccc(O[C@H]4C[C@H](Oc5ccc(C#CCOCCOc6ccc7c(c6)C(=O)N(C6CCC(=O)NC6=O)C7=O)nc5C#N)C4)nc3)cc21] | | | |
| 303 | 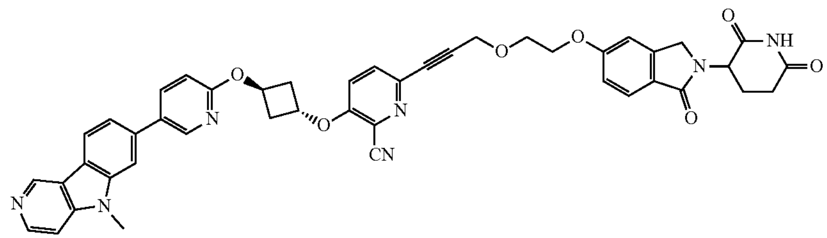 [SMILES: Cn1c2ccncc2c2ccc(-c3ccc(O[C@H]4C[C@H](Oc5ccc(C#CCOCCOc6ccc7c(c6)CN(C6CCC(=O)NC6=O)C7=O)nc5C#N)C4)nc3)cc21] | | | |
| 304 | 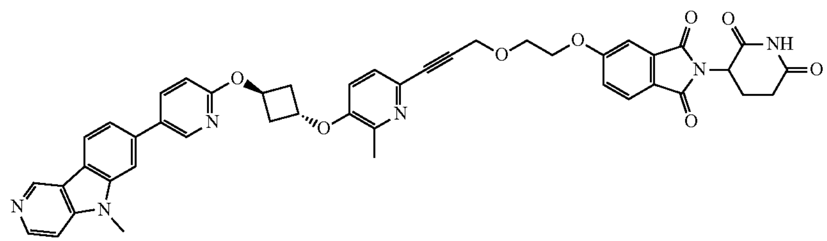 [SMILES: Cc1nc(C#CCOCCOc2ccc3c(c2)C(=O)N(C2CCC(=O)NC2=O)C3=O)ccc1O[C@H]1C[C@H](Oc2ccc(-c3ccc4c5cnccc5n(C)c4c3)cn2)C1] | | | |
| 305 | 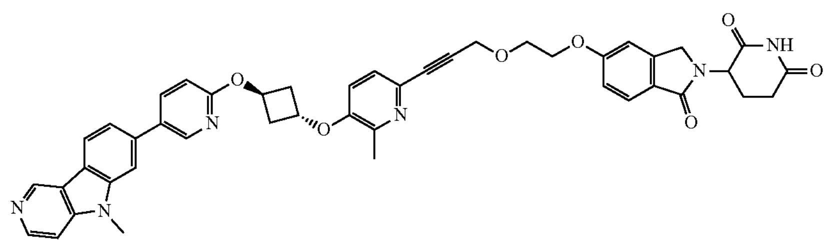 [SMILES: Cc1nc(C#CCOCCOc2ccc3c(c2)CN(C2CCC(=O)NC2=O)C3=O)ccc1O[C@H]1C[C@H](Oc2ccc(-c3ccc4c5cnccc5n(C)c4c3)cn2)C1] | | | |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 306 | 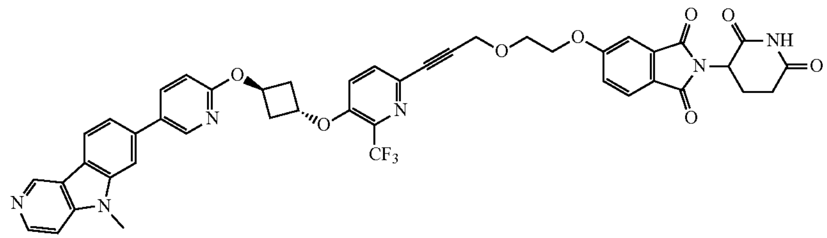 | | | |
| 307 | 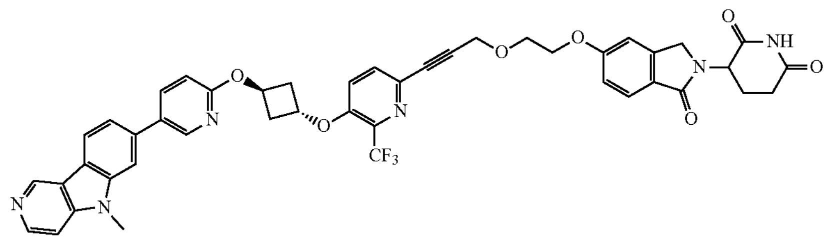 | | | |
| 308 | 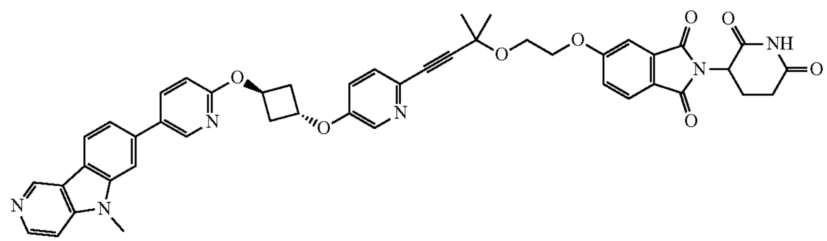 [SMILES: Cn1c2ccncc2c2ccc(-c3ccc(O[C@H]4C[C@H](Oc5ccc(C#CC(C)(C)OCCOc6ccc7c(c6)C(=O)N(C6CCC(=O)NC6=O)C7=O)nc5)C4)nc3)cc21] | | | |
| 309 | 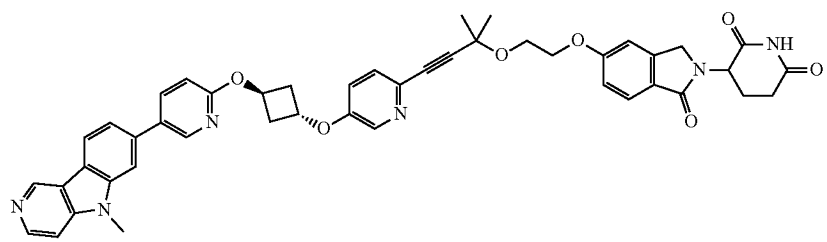 [SMILES: Cn1c2ccncc2c2ccc(-c3ccc(O[C@H]4C[C@H](Oc5ccc(C#CC(C)(C)OCCOc6ccc7c(c6)CN(C6CCC(=O)NC6=O)C7=O)nc5)C4)nc3)cc21] | | | |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 310 | 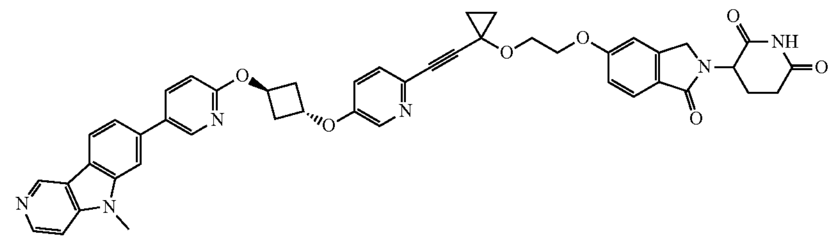 | | | |
| 311 | 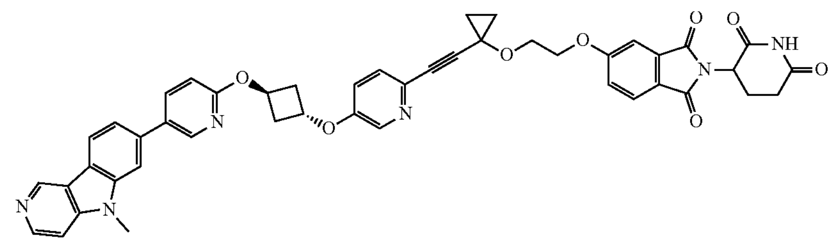 [SMILES: Cn1c2ccncc2c2ccc(-c3ccc(O[C@H]4C[C@H](Oc5ccc(C#CC6(OCCOc7ccc8c(c7)C(=O)N(C7CCC(=O)NC7=O)C8=O)CC6)nc5)C4)nc3)cc21] | | | |
| 312 | 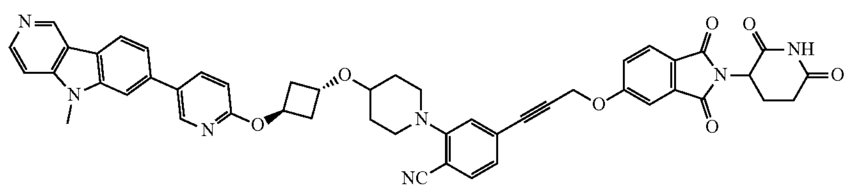 [SMILES: Cn1c2ccncc2c2ccc(-c3ccc(O[C@H]4C[C@H](OC5CCN(c6cc(C#CCOc7ccc8c(c7)C(=O)N(C7CCC(=O)NC7=O)C8=O)ccc6C#N)CC5)C4)nc3)cc21] | | | |
| 313 | 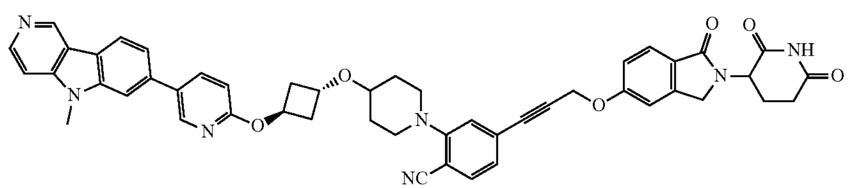 | | | |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 314 | 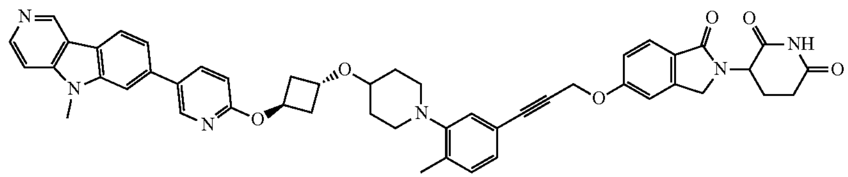 | | | |
| 315 | 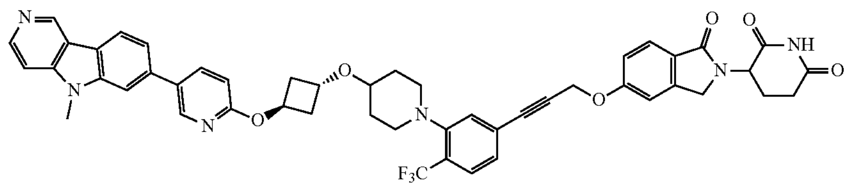 | | | |
| 316 | 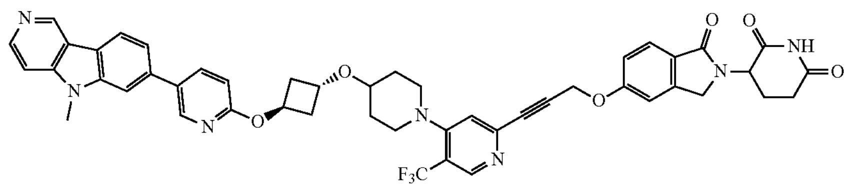 [SMILES: Cn1c2ccncc2c2ccc(-c3ccc(O[C@H]4C[C@H](OC5CCN(c6cc(C#CCOc7ccc8c(c7)CN(C7CCC(=O)NC7=O)C8=O)ccc6C#N)CC5)C4)nc3)cc21] | | | |
| 317 | 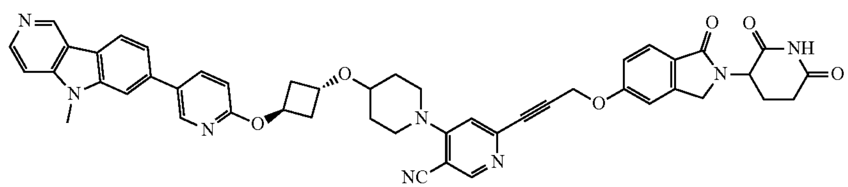 [SMILES: Cn1c2ccncc2c2ccc(-c3ccc(O[C@H]4C[C@H](OC5CCN(c6cc(C#CCOc7ccc8c(c7)CN(C7CCC(=O)NC7=O)C8=O)ncc6C#N)CC5)C4)nc3)cc21] | | | |
| 318 | 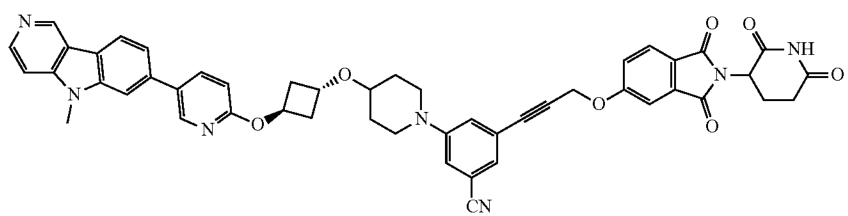 | | | |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 319 | 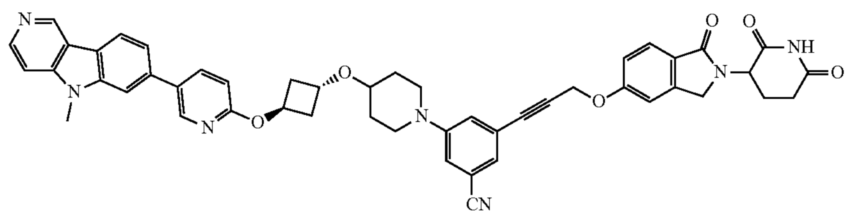 [SMILES: Cn1c2ccncc2c2ccc(-c3ccc(O[C@H]4C[C@H](OC5CCN(c6cc(C#N)cc(C#CCOc7ccc8c(c7)CN(C7CCC(=O)NC7=O)C8=O)c6)CC5)C4)nc3)cc21] | | | |
| 320 | 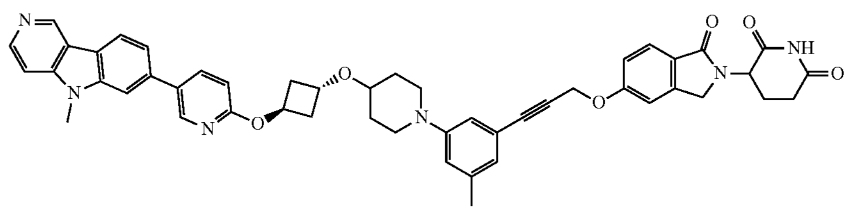 [SMILES: Cc1cc(C#CCOc2ccc3c(c2)CN(C2CCC(=O)NC2=O)C3=O)cc(N2CCC(O[C@H]3C[C@H](Oc4ccc(-c5ccc6c7cnccc7n(C)c6c5)cn4)C3)CC2)c1] | | | |
| 321 | 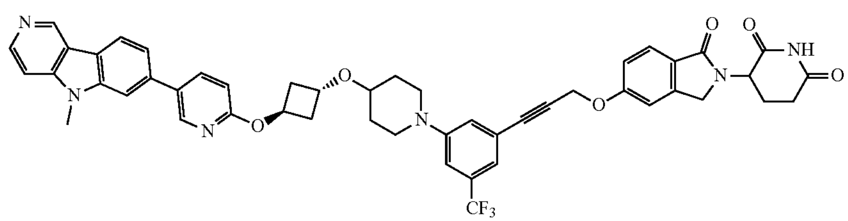 [SMILES: Cn1c2ccncc2c2ccc(-c3ccc(O[C@H]4C[C@H](OC5CCN(c6cc(C#CCOc7ccc8c(c7)CN(C7CCC(=O)NC7=O)C8=O)nc(C(F)(F)F)c6)CC5)C4)nc3)cc21] | | | |
| 322 | 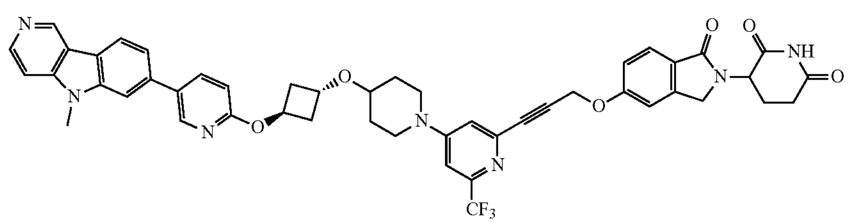 | | | |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 323 | 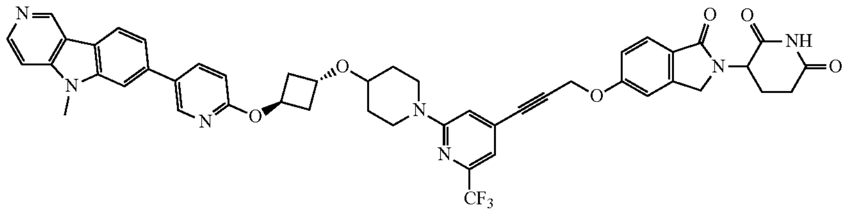 [SMILES: Cn1c2ccncc2c2ccc(-c3ccc(O[C@H]4C[C@H](OC5CCN(c6cc(C#CCOc7ccc8c(c7)CN(C7CCC(=O)NC7=O)C8=O)cc(C(F)(F)F)n6)CC5)C4)nc3)cc21] | | | |
| 324 | 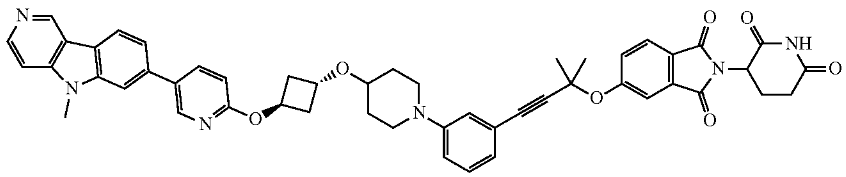 [SMILES: Cn1c2ccncc2c2ccc(-c3ccc(O[C@H]4C[C@H](OC5CCN(c6cccc(C#CC(C)(C)Oc7ccc8c(c7)C(=O)N(C7CCC(=O)NC7=O)C8=O)c6)CC5)C4)nc3)cc21] | | | |
| 325 | 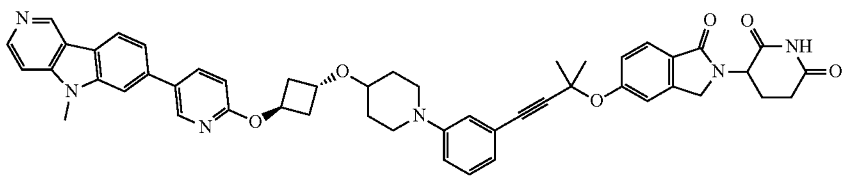 [SMILES: Cn1c2ccncc2c2ccc(-c3ccc(O[C@H]4C[C@H](OC5CCN(c6ccnc(C#CC(C)(C)Oc7ccc8c(c7)CN(C7CCC(=O)NC7=O)C8=O)c6)CC5)C4)nc3)cc21] | | | |
| 326 | 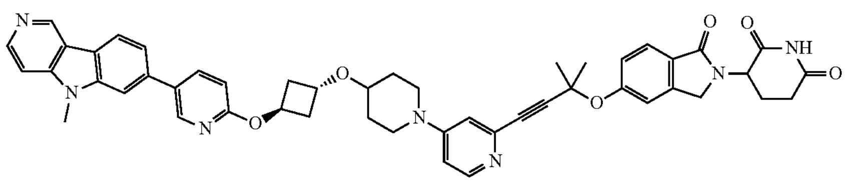 | | | |
| 327 | 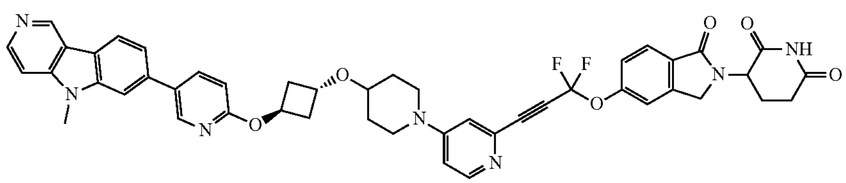 [SMILES: Cn1c2ccncc2c2ccc(-c3ccc(O[C@H]4C[C@H](OC5CCN(c6ccnc(C#CC(F)(F)Oc7ccc8c(c7)CN(C7CCC(=O)NC7=O)C8=O)c6)CC5)C4)nc3)cc21] | | | |

TABLE 2-continued

Exemplary PROTAC of the present disclosure.

| Ex. | Structure | Degradation activity* | MH + (1) [MH + (2), if isotope] | NMR transcript |
|---|---|---|---|---|
| 328 | 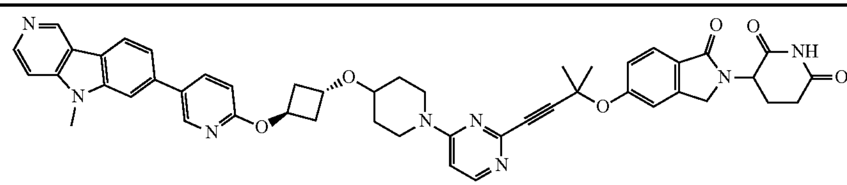 | | | |
| 329 | 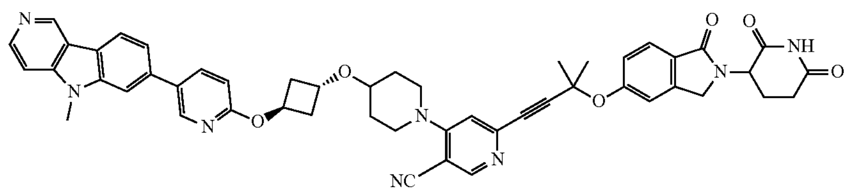 [SMILES: Cn1c2ccncc2c2ccc(-c3ccc(O[C@H]4C[C@H](OC5CCN(c6cc(C#CC(C)(C)Oc7ccc8c(c7)CN(C7CCC(=O)NC7=O)C8=O)ncc6C#N)CC5)C4)nc3)cc21] | | | |
| 330 | 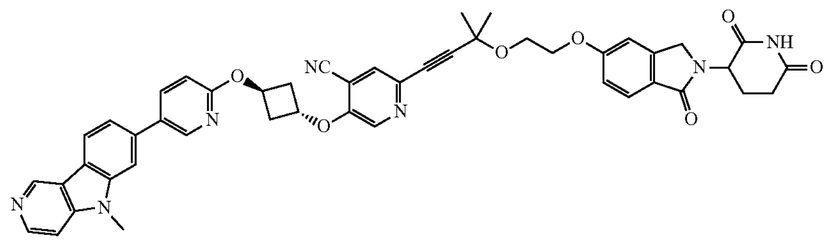 [SMILES: Cn1c2ccncc2c2ccc(-c3ccc(O[C@H]4C[C@H](Oc5cnc(C#CC(C)(C)OCCOc6ccc7c(c6)CN(C6CCC(=O)NC6=O)C7=O)cc5C#N)C4)nc3)cc21] | | | |

*Each compound was tested at 300 nM, 100 nM, 33 nM, and 11 nM as described below. The highest amount of degradation observed at any dosage for each compound is capture in Table 2 as follows:
A: ≤50% tau protein remaining after 72 hours of incubation with the test compound;
B: ≤80% and >50% tau protein remaining after 72 hours of incubation with the test compound;
C: >80% tau protein remaining after 72 hours of incubation with the test compound.

Tau Protein In Vitro Degradation Assay

To determine effect of PROTACs on tau protein degradation SK-N-SH cells were seeded in a 24-well tissue culture-treated plate for at least 18-hours prior to compound addition. Tau PROTACs were evaluated for tau degradation by lysing the cells in lysis buffer with protease inhibitors following a 72-hour incubation with tau PROTACs at 1000 nM, 300 nM and 100 nM for Table 1 and 300 nM, 100 nM, 33 nM and 11 nM for Table 2. Cell lysates were run on standard SDS-PAGE gels, and tau levels were detected by Western blotting using Tau-13 antibody from Abcam (Cambridge, UK) that binds to all forms of human tau. The highest amount of degradation observed at any dosage for each compound is shown in Tables 1 and 2 above.

Tau Protein In Vivo Degradation

In the study 21 male BI6 wildtype mice, divided into seven groups of three mice, were treated single time via a bilateral intrahippocampal injection with vehicle ECP-1 ([5% EtOH and 5% Cremophore RH40 in pH 7.4 phosphate buffer]; group A; see the FIGURE) or Compound 4 tau PROTAC ([3 μL of 1 mg/mL solution in ECP-1]; groups B to G; see the FIGURE). All animals were sacrificed at certain time points after the test item or vehicle injection as shown in the FIGURE, and brain samples were collected. The hippocampus was resected, and levels of total tau were measured with Meso Scale Discovery assay kit. Results are presented in the FIGURE.

Specific Embodiments

An aspect of the present disclosure provides a bifunctional compound having the chemical structure:

ULM-L-PTM, or a pharmaceutically acceptable salt, enantiomer, stereoisomer, solvate, polymorph or prodrug thereof,
wherein:
the ULM is a small molecule E3 ubiquitin ligase binding moiety that binds an E3 ubiquitin ligase;
the PTM is a Tau protein targeting moiety; and
the L is a bond or a chemical linking moiety connecting ULM and PTM.

In any aspect or embodiment described herein, the E3 ubiquitin ligase binding moiety that targets a E3 ubiquitin ligase selected from the group consisting of Von Hippel-Lindau (VLM) and cereblon (CLM).

In any aspect or embodiment described herein, the PTM is represented by Formula I, II, III, IV, V, VI, VII, VIII, IX, X, or XI:

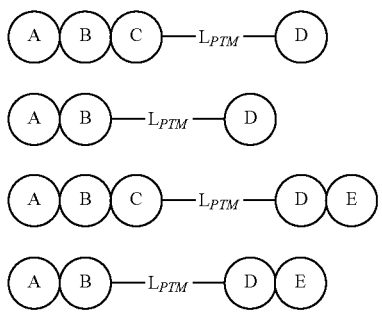

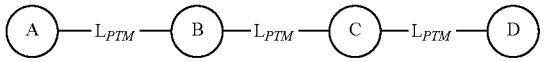

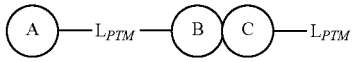

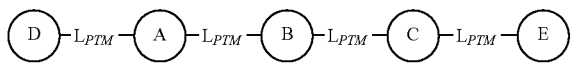

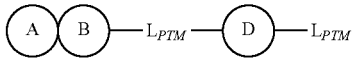

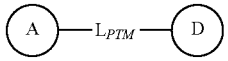

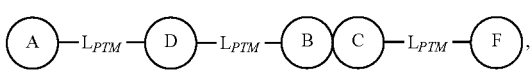

wherein:
A, B, C, D, E, and F are independently selected from an optionally substituted 5- or 6-membered aryl or heteroaryl ring, an optionally substituted 4- to 7-membered cycloalkyl or a heterocycloalkyl, where contact between circles indicates ring fusion; and $L_{PTM}$ is selected from a bond, an alkyl, an alkenyl or an alkynyl, optionally interrupted by one or more rings (i.e., cycloalkyl, heterocycloalkyl, aryl or heteroaryl), or one or more functional groups selected from the groups —O—, —S—, —NR$^1_{PTM}$— (where R$^1_{PTM}$ is selected from H or alkyl), —N═N—, —S(O)—, —SO$_2$—, —C(O)—, —NHC(O)—, —C(O)NH—, —NHSO$_2$—, —NHC(O)NH—, —NHC(O)O—, or —OC(O)NH—, wherein the said functional group is optionally located at either end of the linker.

In any aspect or embodiment described herein, at least one of A, B, C, F, or a combination thereof is selected from optionally substituted 5- or 6-membered aryl or heteroaryl rings.

In any aspect or embodiment described herein, the rings (e.g., aryl and heteroaryl rings) of A, B, C, D and E of PTM are optionally substituted with 1-8 substituents each independently selected from alkyl, alkenyl, haloalkyl, halogen, hydroxyl, alkoxy, fluoroalkoxy, amino, alkylamino, dialkylamino, acylamino, trifluoromethyl and cyano, wherein the said alkyl and alkenyl groups are further optionally substituted.

In any aspect or embodiment described herein, the PTM is Formula I and:
A, B and C rings are independently 5- or 6-membered fused aryl or heteroaryl rings;
$L_{PTM}$ is selected from a bond or an alkyl; and
D is selected from a 6-membered aryl, heteroaryl or heterocycloalkyl,
wherein A, B, C and D are optionally substituted with alkyl, haloalkyl, halogen, hydroxyl, alkoxy, amino, alkylamino, dialkylamino, trifluoromethyl or cyano.

In any aspect or embodiment described herein, the PTM is Formula I and:

A and C are a phenyl or a 6-membered heteroaryl ring;
B is a 5-membered heteroaryl ring;
L$_{PTM}$ is a bond; and
D is a 6-membered heteroaryl or a 6-membered heterocycloalkyl ring,
wherein each A, B, C and D is optionally independently substituted with alkyl, haloalkyl, halogen, hydroxyl, alkoxy, amino, dialkylamino, trifluoromethyl, or cyano, and wherein a nitrogen atom of any of the A, B, C and D rings is not directly connected to a heteroatom or to a carbon atom, to which another heteroatom is directly attached.

In any aspect or embodiment described herein, the PTM is Formula III or IV and:
A, B and C are 5- or 6-membered fused aryl or heteroaryl rings;
L$_{PTM}$ is selected from a bond or an alkyl; and
D and E are 5- or 6-membered fused aryl or heteroaryl rings;
wherein A, B, C, D and E are optionally substituted with alkyl, haloalkyl, halogen, hydroxyl, alkoxy, amino, alkylamino, dialkylamino, trifluoromethyl, or cyano.

In any aspect or embodiment described herein, the PTM is represented by a chemical structure selected from the group consisting of:

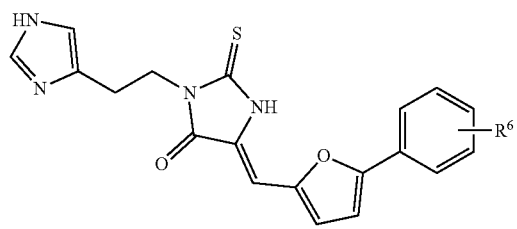

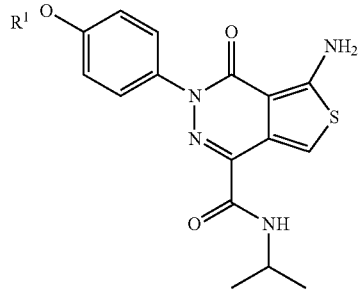

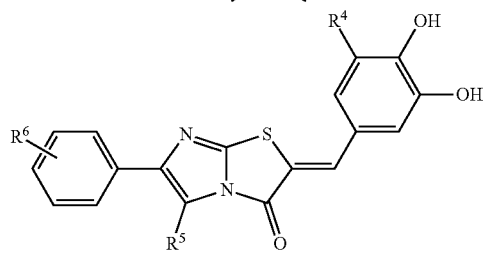

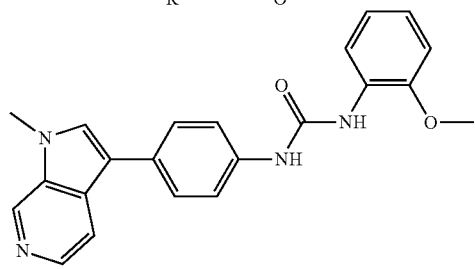

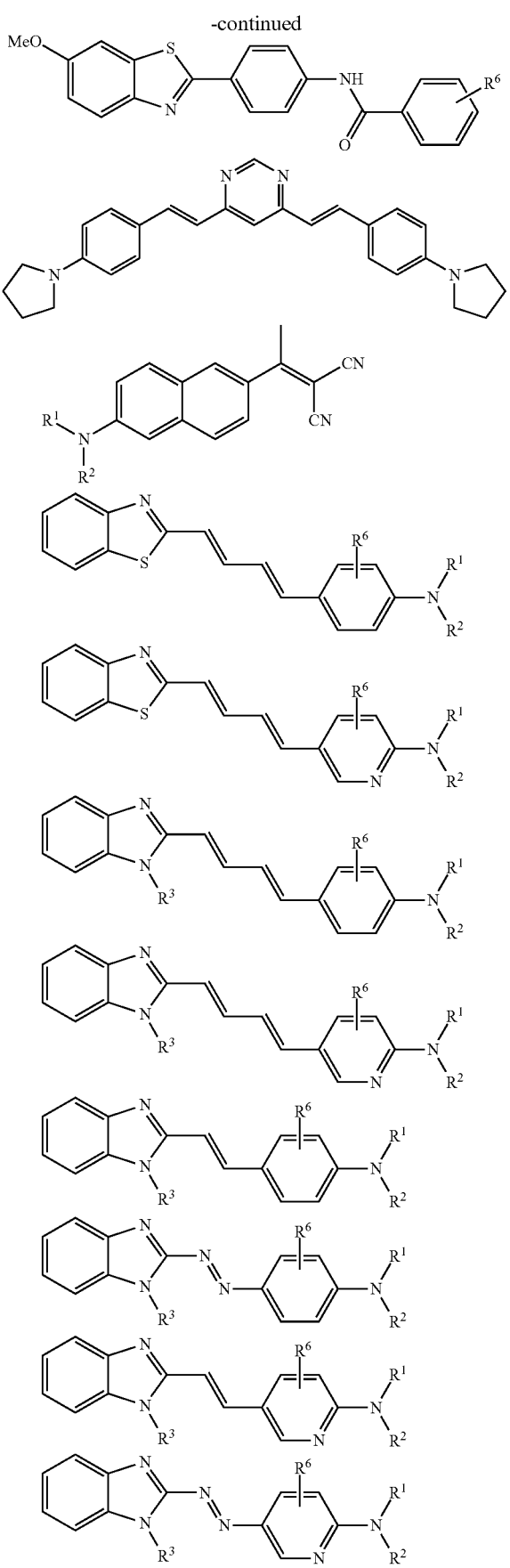

903

-continued

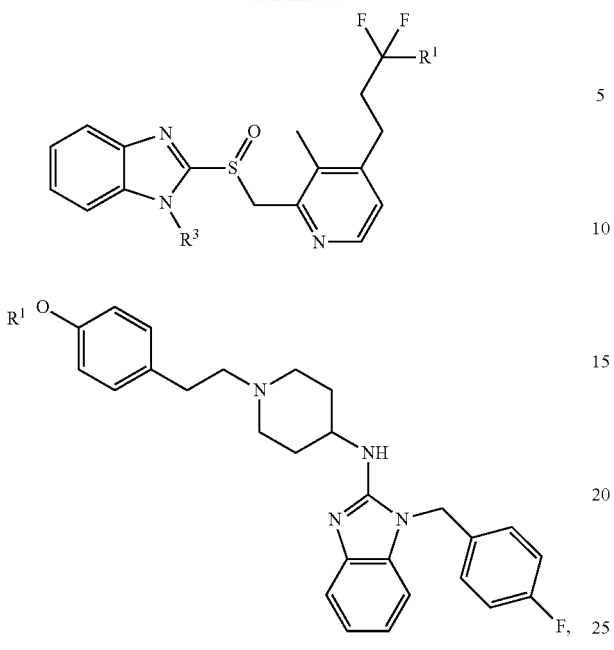

wherein:
R¹, R² and R³ are independently selected from H, methyl, ethyl, 2-fluoroethyl and 2,2,2-trifluoroethyl;
R⁴ and R⁵ are independently selected from H, methyl, ethyl and halogen; and
R⁶ is 1 to 2 substituents independently selected from H, methyl, ethyl and halogen.

In any aspect or embodiment described herein, the PTM is represented by a chemical structure selected from the group consisting of:

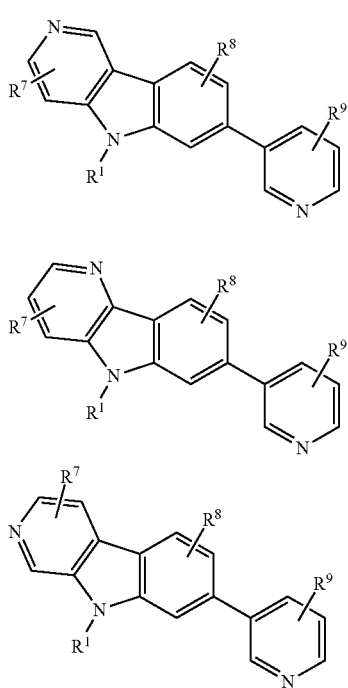

904

-continued

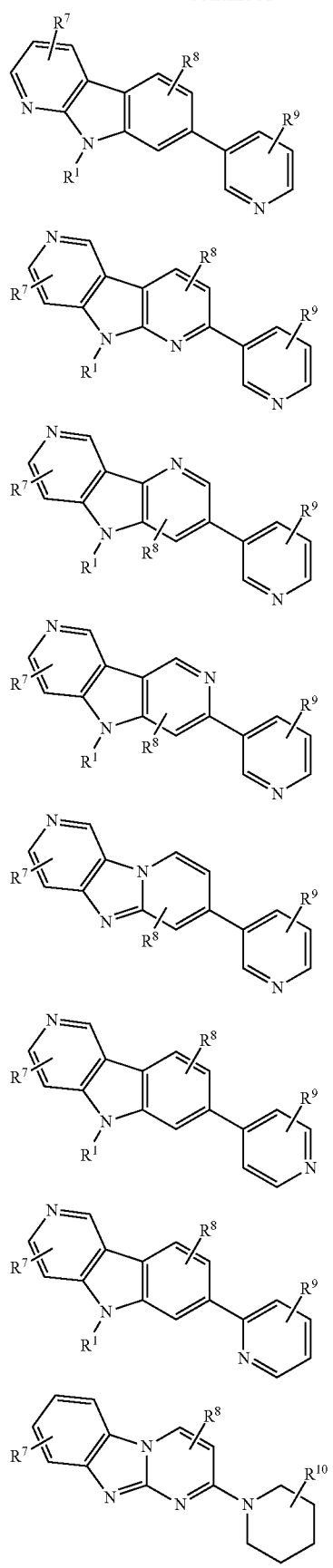

905
-continued
906
-continued
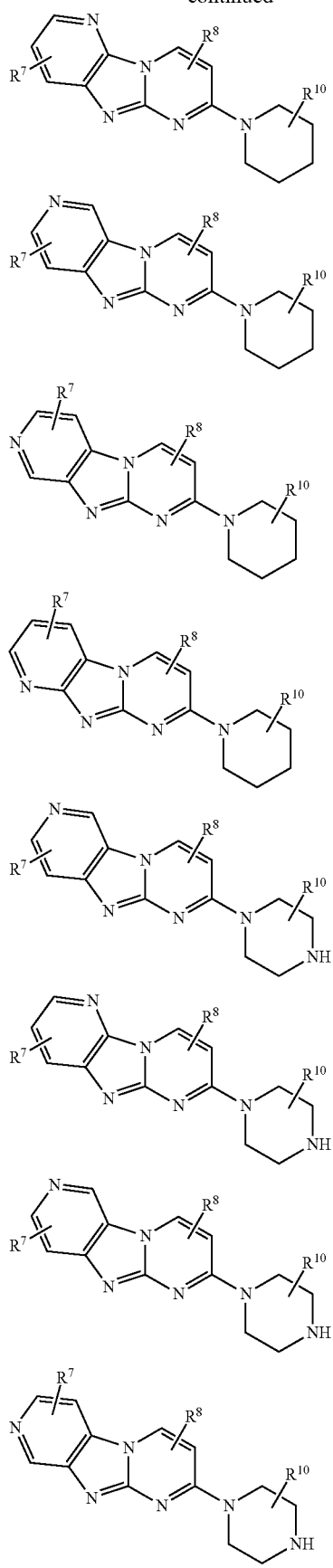
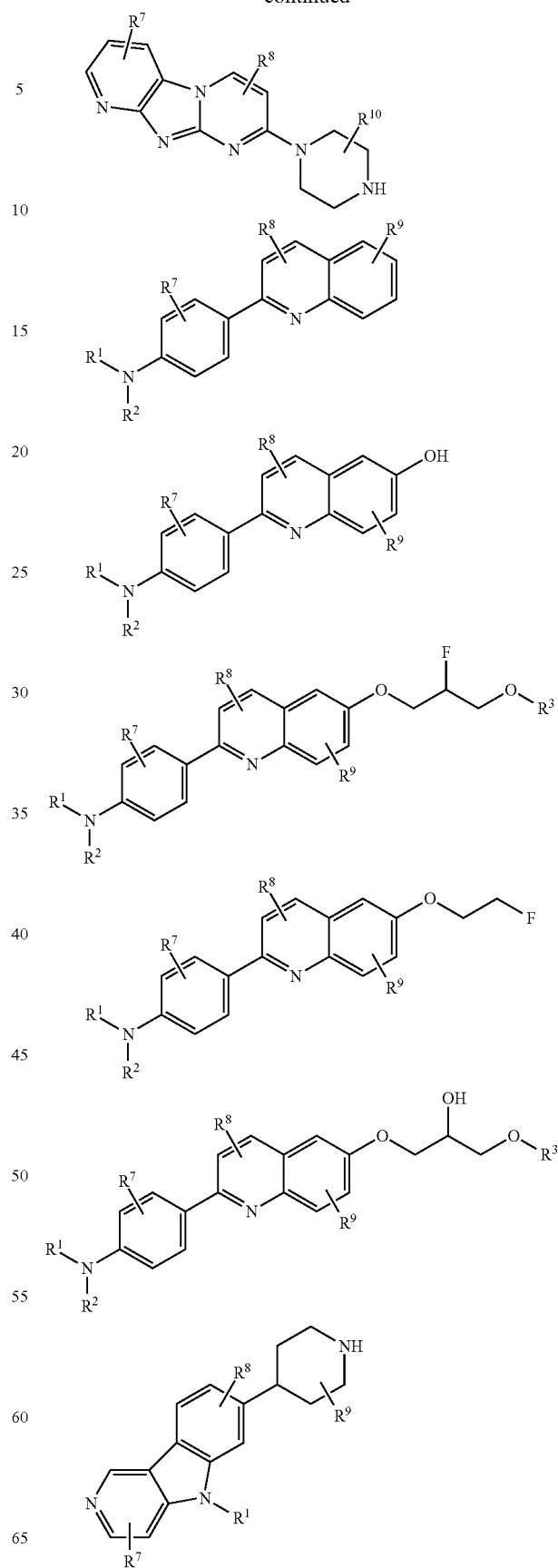

907
-continued

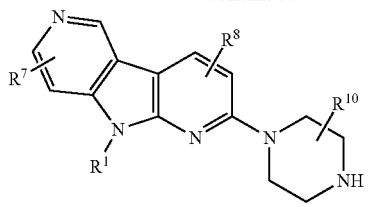

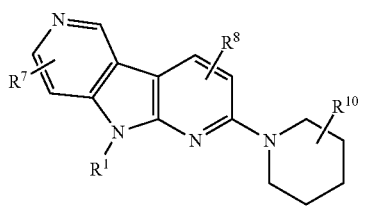

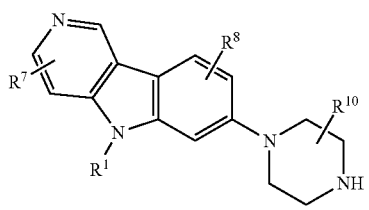

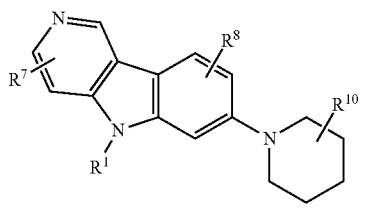

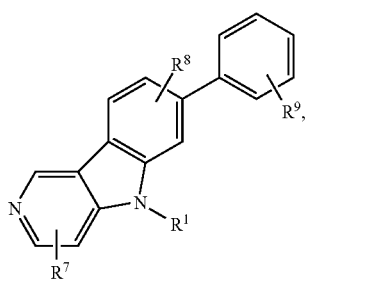

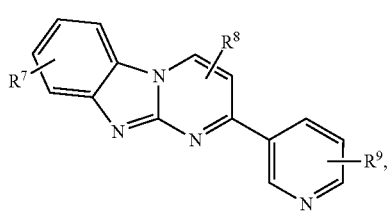

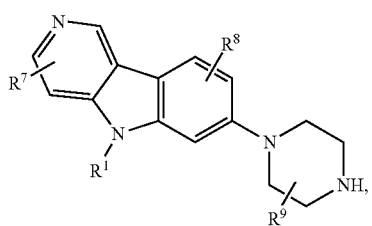

908
-continued

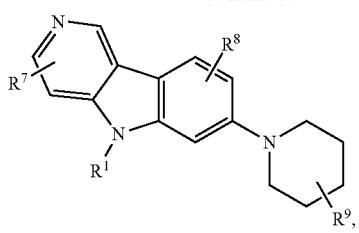

wherein:
$R^1$, $R^2$ and $R^3$ are independently selected from H, optionally substituted alkyl, methyl, ethyl, 2-fluoroethyl and 2,2,2-trifluoroethyl; and
$R^7$, $R^8$, $R^9$ and $R^{10}$ are 1 to 8 substituents independently selected from H, optionally substituted alkyl, haloalkyl, halogen, hydroxyl, alkoxy, amino, dialkylamino, acetylamino, trifluoromethyl, or cyano.

In any aspect or embodiment described herein, the PTM is represented by a chemical structure selected from the group consisting of:

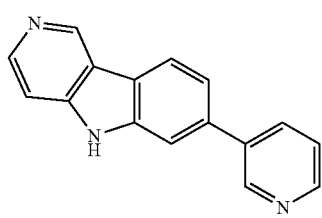

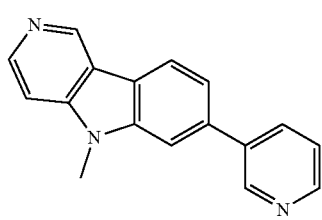

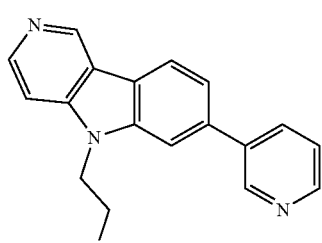

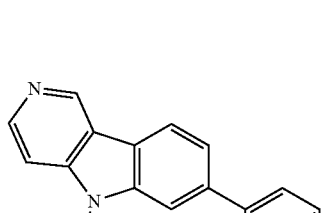
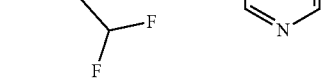

909
-continued
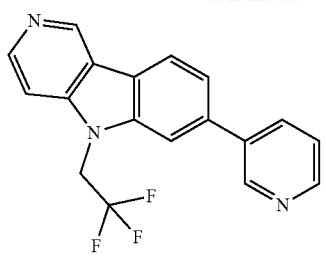
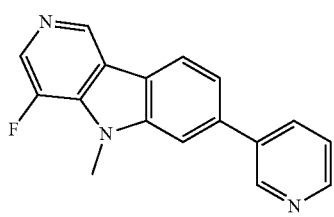
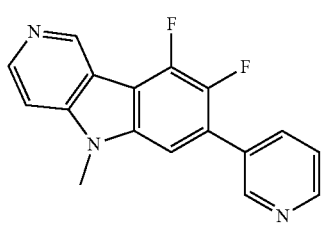
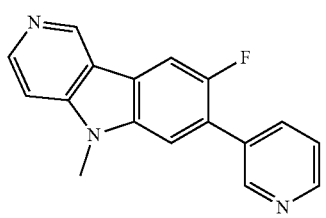
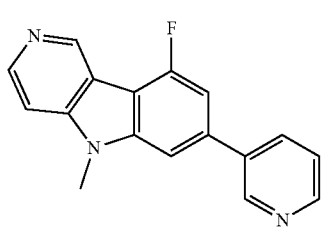
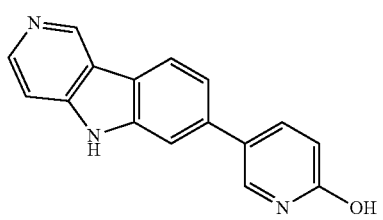
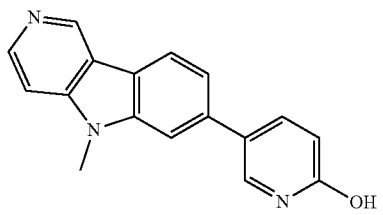
910
-continued
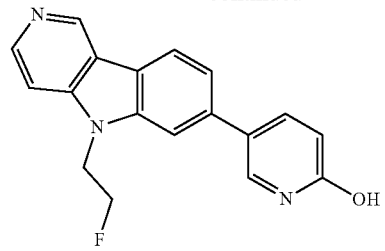
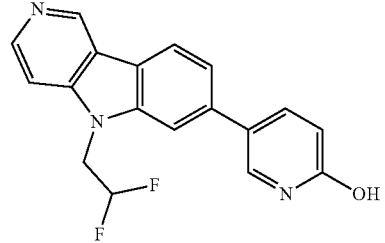
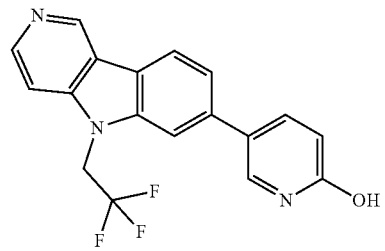
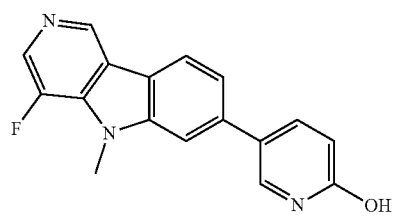
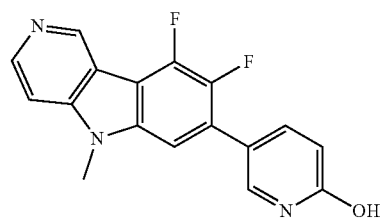
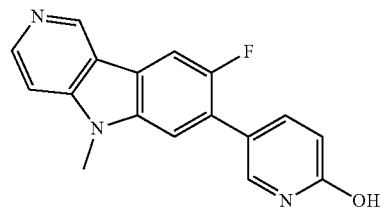
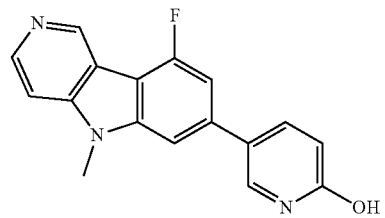

911
-continued
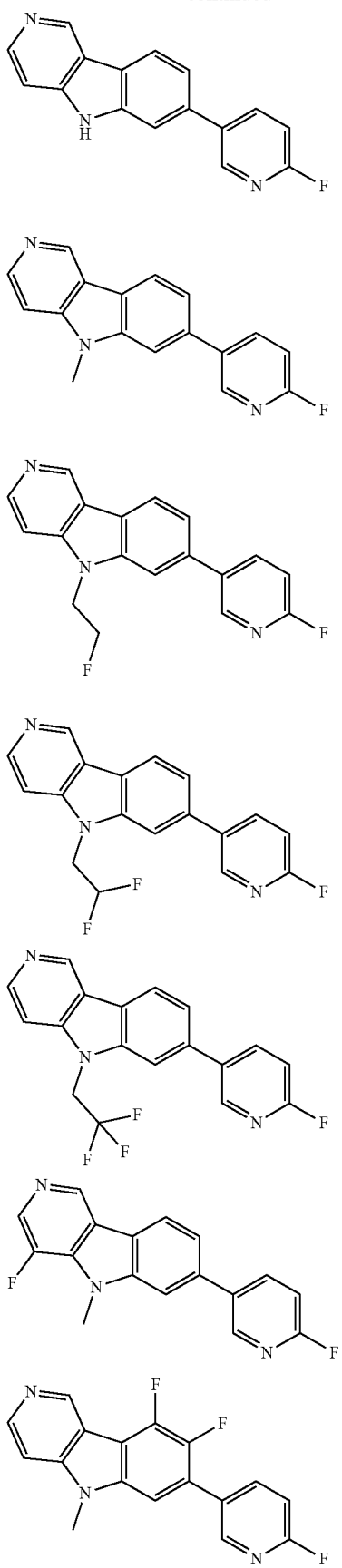
912
-continued
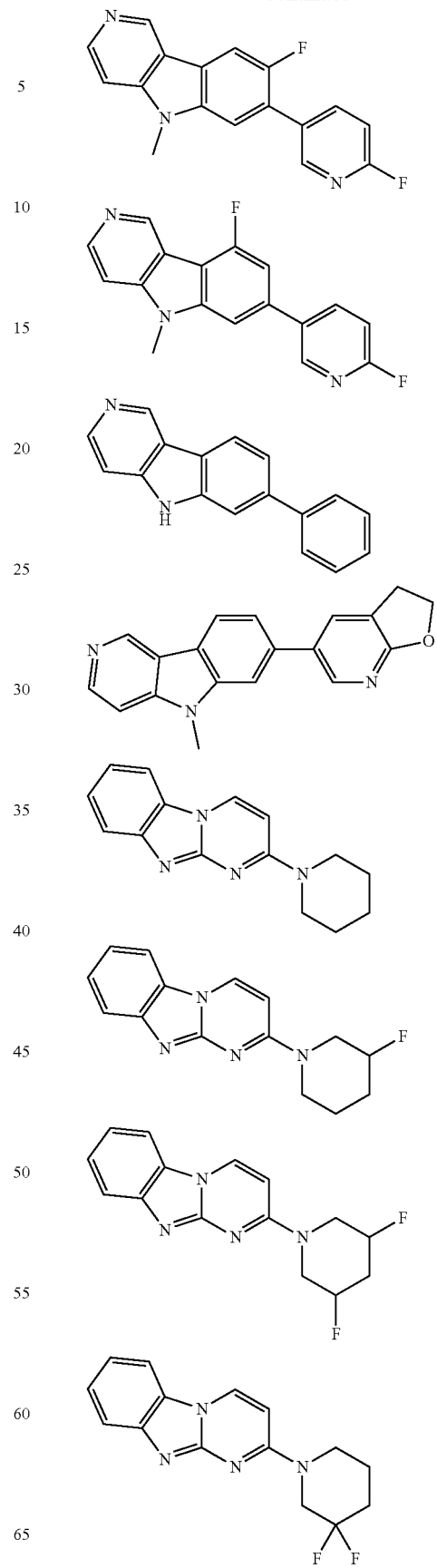

913
-continued

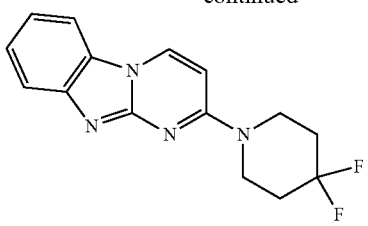
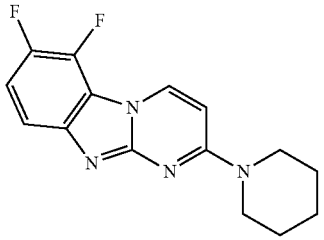
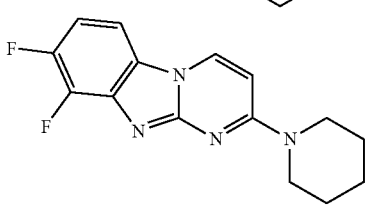
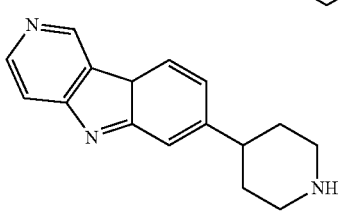
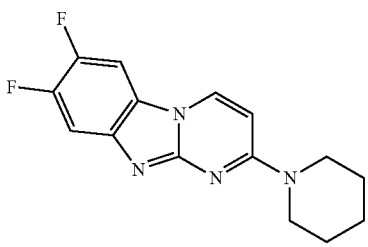
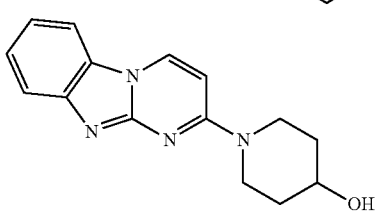
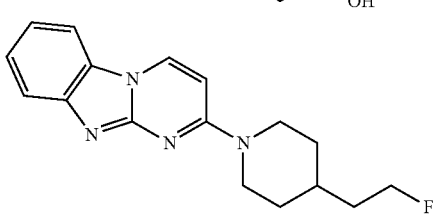
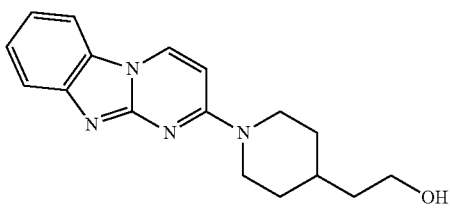

914
-continued

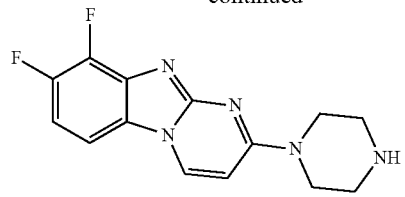
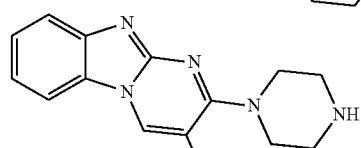
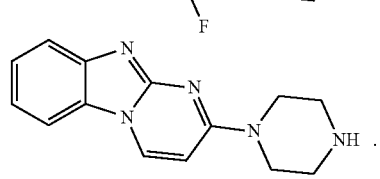

In any aspect or embodiment described herein, the ULM is a Von Hippel-Lindau (VHL) ligase-binding moiety (VLM) represented by the structure:

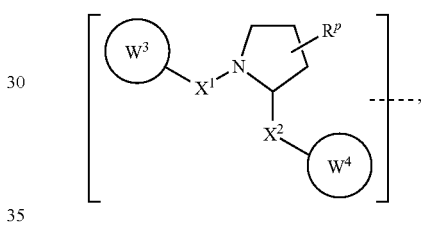

wherein:
$X^1$, $X^2$ are each independently selected from the group of a bond, O, $NR^{Y3}$, $CR^{Y3}R^{Y4}$, C=O, C=S, SO, and $SO_2$;
$R^{Y3}$, $R^{Y4}$ are each independently selected from the group of H, linear or branched $C_{1-6}$ alkyl, optionally substituted by 1 or more halo, $C_{1-6}$ alkoxyl);
$R^P$ is 1, 2, or 3 groups, each independently selected from the group H, halo, —OH, $C_{1-3}$ alkyl;
$W^3$ is selected from the group of an optionally substituted -T-N($R^{1a}R^{1b}$), an optionally substituted -T-N($R^{1a}R^{1b}$) $X^3$, -T-Aryl, an optionally substituted -T-Heteroaryl, an optionally substituted -T-Heterocycle, an optionally substituted —$NR^1$-T-Aryl, an optionally substituted —$NR^1$-T-Heteroaryl or an optionally substituted —$NR^1$-T-Heterocycle;
$X^3$ is C=O, $R^1$, $R^{1a}$, $R^{1b}$;
$R^1$, $R^{1a}$, $R^{1b}$ are each independently selected from the group consisting of H, linear or branched $C_1$-$C_6$ alkyl group optionally substituted by 1 or more halo or —OH groups, $R^{Y3}$C=O, $R^{Y3}$C=S, $R^{Y3}$SO, $R^{Y3}SO_2$, N($R^{Y3}R^{Y4}$)C=O, N($R^{Y3}R^{Y4}$)C=S, N($R^{Y3}R^{Y4}$)SO, and N($R^{Y3}R^{Y4}$)$SO_2$;
T is selected from the group of an optionally substituted alkyl, —$(CH_2)_n$— group, wherein each one of the methylene groups is optionally substituted with one or two substituents selected from the group of halogen, methyl, a linear or branched $C_1$-$C_6$ alkyl group optionally substituted by 1 or more halogen or —OH groups or an amino acid side chain optionally substituted;

n is 0 to 6;
W$^4$ is

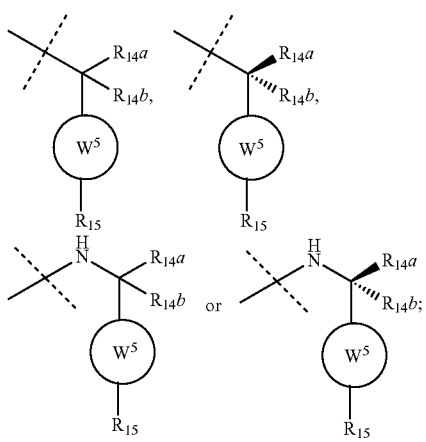

$R_{14a}$, $R_{14b}$, are each independently selected from the group of H, haloalkyl, or optionally substituted alkyl;
W$^5$ is selected from the group of a phenyl or a 5-10 membered heteroaryl; and
$R_{15}$ is selected from the group of H, halogen, CN, OH, NO$_2$, NR$_{14a}$R$_{14b}$, OR$_{14a}$, CONR$_{14a}$R$_{14b}$, NR$_{14a}$COR$_{14b}$, SO$_2$NR$_{14a}$R$_{14b}$, NR$_{14}$a SO$_2$R$_{14b}$, optionally substituted alkyl, optionally substituted haloalkyl, optionally substituted haloalkoxy; aryl, heteroaryl, cycloalkyl, or cycloheteroalkyl,
wherein the dashed line indicates the site of attachment of at least one PTM, another ULM (ULM') or a chemical linker moiety coupling at least one PTM or a ULM' or both to ULM.

In any aspect or embodiment described herein, the ULM is a Von Hippel-Lindau (VHL) ligase-binding moiety (VLM) represented by the structure:

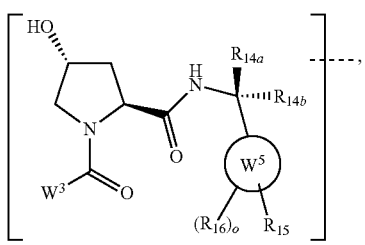

wherein:
W$^3$ is selected from the group of an optionally substituted aryl, optionally substituted heteroaryl, or

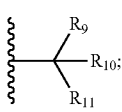

$R_9$ and $R_{10}$ are independently hydrogen, optionally substituted alkyl, optionally substituted cycloalkyl, optionally substituted hydroxyalkyl, optionally substituted heteroaryl, or haloalkyl, or $R_9$, $R_{10}$, and the carbon atom to which they are attached form an optionally substituted cycloalkyl;

$R_{11}$ is selected from the group of an optionally substituted heterocyclic, optionally substituted alkoxy, optionally substituted heteroaryl, optionally substituted aryl,

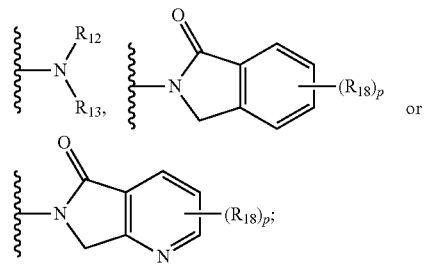

$R_{12}$ is selected from the group of H or optionally substituted alkyl;
$R_{13}$ is selected from the group of H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl;
$R_{14a}$, $R_{14b}$, are each independently selected from the group of H, haloalkyl, or optionally substituted alkyl;
W$^5$ is selected from the group of a phenyl or a 5-10 membered heteroaryl;
$R_{15}$ is selected from the group of H, halogen, CN, OH, NO$_2$, NR$_{14a}$R$_{14b}$, OR$_{14a}$, CONR$_{14a}$R$_{14b}$, NR$_{14a}$COR$_{14b}$, SO$_2$NR$_{14a}$R$_{14b}$, NR$_{14}$a SO$_2$R$_{14b}$, optionally substituted alkyl, optionally substituted haloalkyl, optionally substituted haloalkoxy; aryl, heteroaryl, cycloalkyl, or cycloheteroalkyl (each independently optionally substituted);
$R_{16}$ is independently selected from the group of H, halo, optionally substituted alkyl, optionally substituted haloalkyl, hydroxy, or optionally substituted haloalkoxy;
o is 0, 1, 2, 3, or 4;
$R_{18}$ is independently selected from the group of halo, optionally substituted alkoxy, cyano, optionally substituted alkyl, haloalkyl, haloalkoxy or a linker; and
p is 0, 1, 2, 3, or 4, and wherein the dashed line indicates the site of attachment of at least one PTM, another ULM (ULM') or a chemical linker moiety coupling at least one PTM or a ULM' or both to ULM.

In any aspect or embodiment described herein, the ULM has a chemical structure selected from the group of:

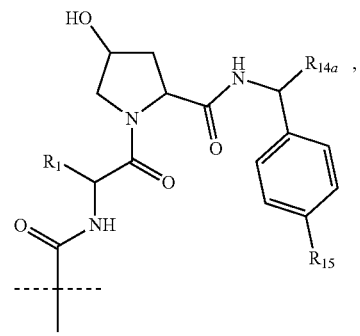

-continued

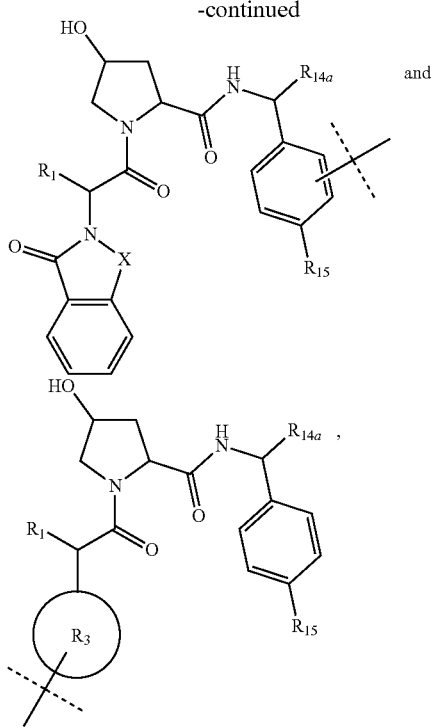

and wherein:
R₁ is H, ethyl, isopropyl, tert-butyl, sec-butyl, cyclopropyl, cyclobutyl, cyclopentyl, or cyclohexyl; optionally substituted alkyl, optionally substituted hydroxyalkyl, optionally substituted heteroaryl, or haloalkyl;
$R_{14a}$ is H, haloalkyl, optionally substituted alkyl, methyl, fluoromethyl, hydroxymethyl, ethyl, isopropyl, or cyclopropyl;
$R_{15}$ is selected from the group consisting of H, halogen, CN, OH, NO₂, optionally substituted heteroaryl, optionally substituted aryl; optionally substituted alkyl, optionally substituted haloalkyl, optionally substituted haloalkoxy, cycloalkyl, or cycloheteroalkyl;
X is C, CH₂, or C=O; and
R₃ is a bond or an optionally substituted 5 or 6 membered heteroaryl, wherein the dashed line indicates the site of attachment of at least one PTM, another ULM (ULM') or a chemical linker moiety coupling at least one PTM or a ULM' or both to ULM.

In any aspect or embodiment described herein, the ULM comprises a group according to the chemical structure:

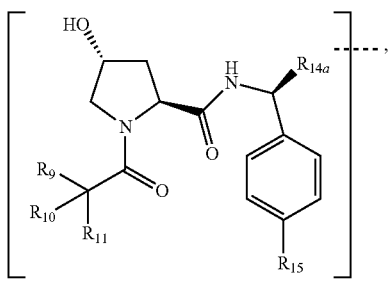

wherein:
$R_{14a}$ is H, haloalkyl, optionally substituted alkyl, methyl, fluoromethyl, hydroxymethyl, ethyl, isopropyl, or cyclopropyl;

R₉ is H;
R₁₀ is H, ethyl, isopropyl, tert-butyl, sec-butyl, cyclopropyl, cyclobutyl, cyclopentyl, or cyclohexyl;
R₁₁ is

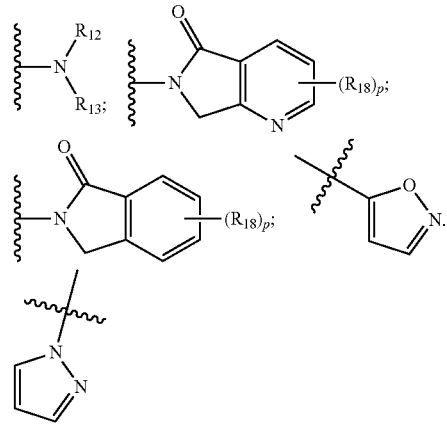

or optionally substituted heteroaryl;
p is 0, 1, 2, 3, or 4;
each $R_{18}$ is independently halo, optionally substituted alkoxy, cyano, optionally substituted alkyl, haloalkyl, haloalkoxy or a linker;
$R_{12}$ is H, C=O;
$R_{13}$ is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl; and
$R_{15}$ is selected from the group consisting of H, halogen, Cl, CN, OH, NO₂, optionally substituted heteroaryl, optionally substituted aryl;

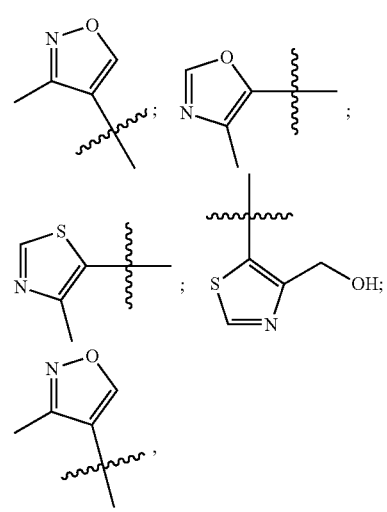

wherein the dashed line indicates the site of attachment of at least one PTM, another ULM (ULM') or a chemical linker moiety coupling at least one PTM or a ULM' or both to ULM.

In any aspect or embodiment described herein, the ULM comprises a group selected from the structure consisting of:

919
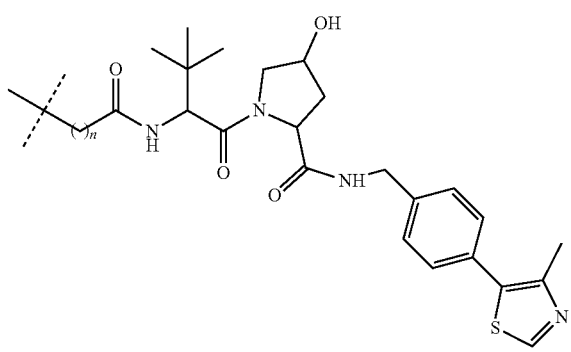
ULM-a2
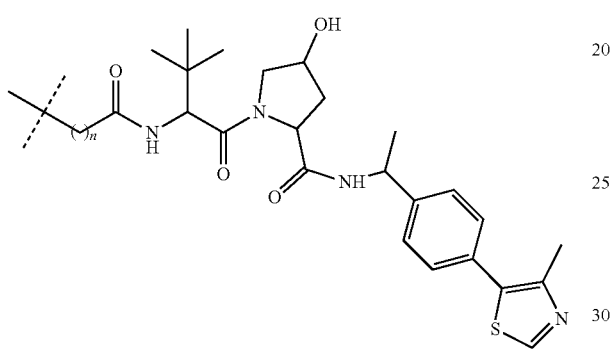
ULM-a3
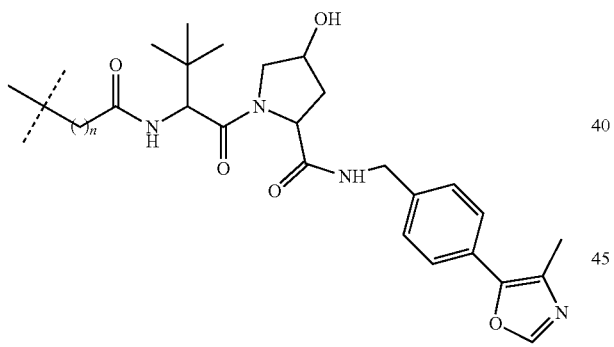
ULM-a4
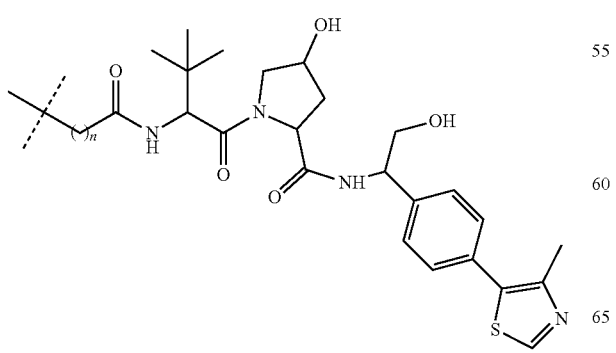
920
-continued
ULM-a5
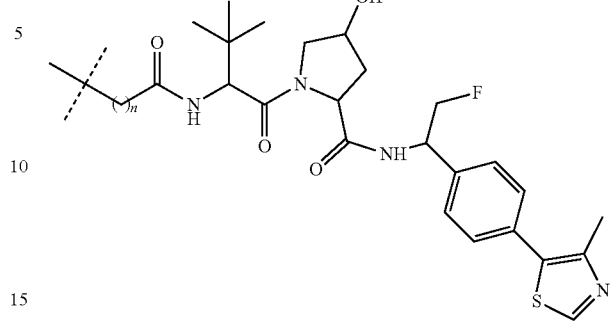
ULM-a6
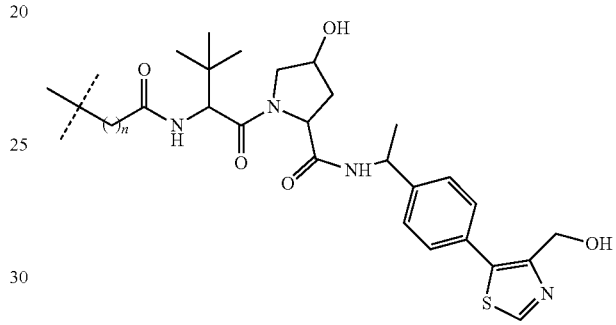
ULM-a7
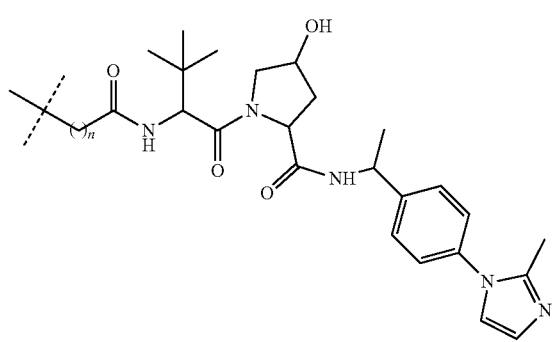
ULM-a8
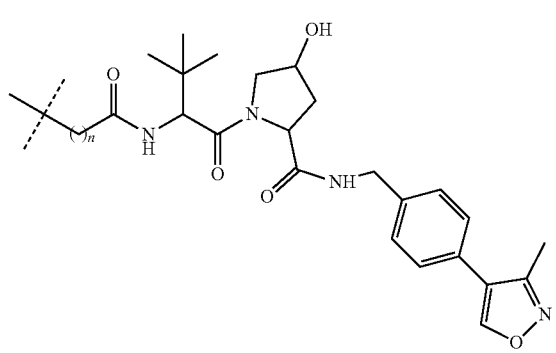

-continued
ULM-a9
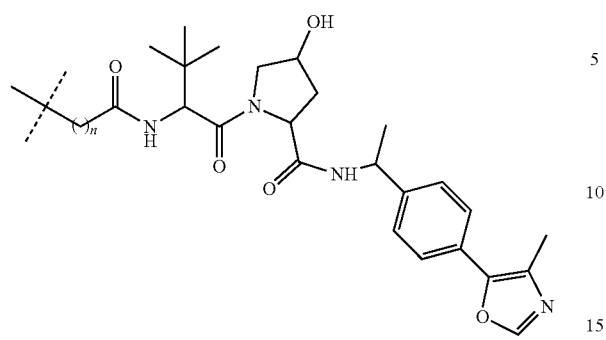
ULM-a13
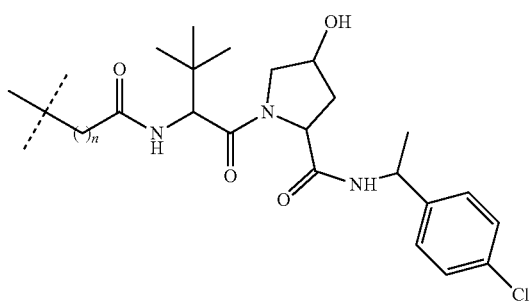
ULM-a10, ULM-a14
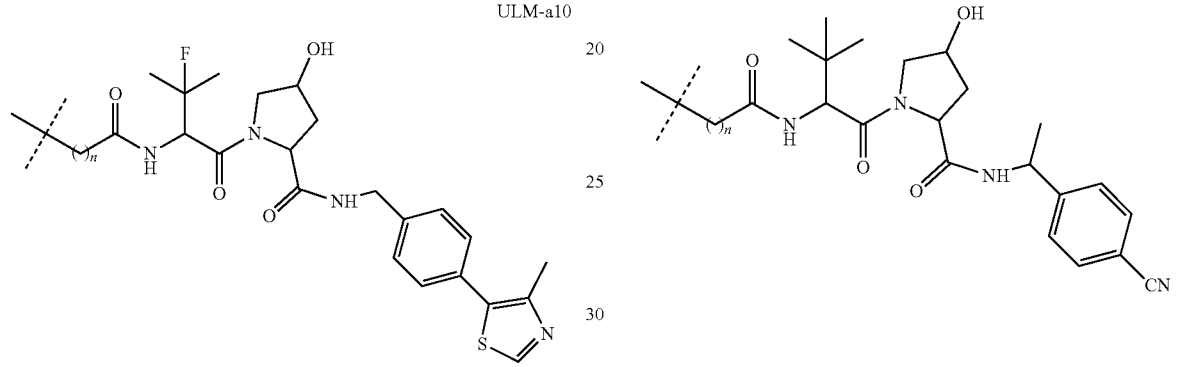
ULM-a11, ULM-a15
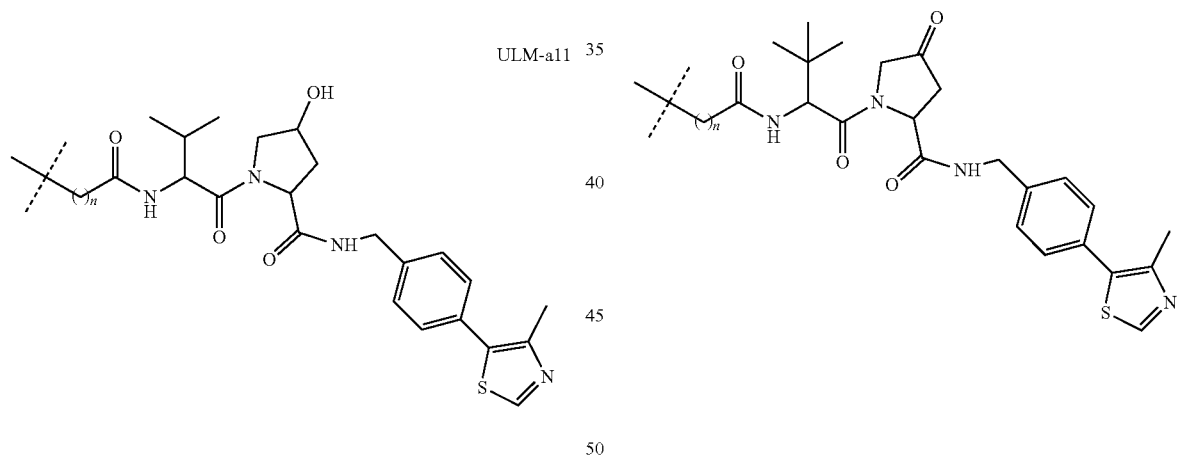
ULM-a12
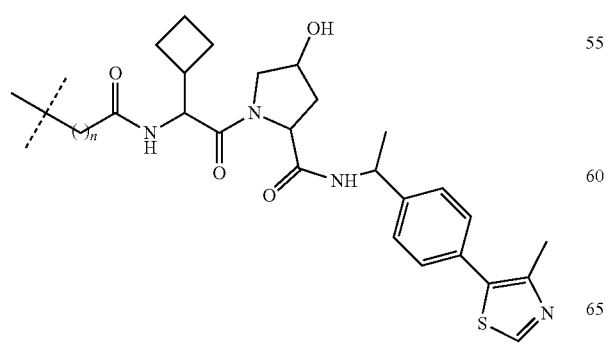
ULM-b1
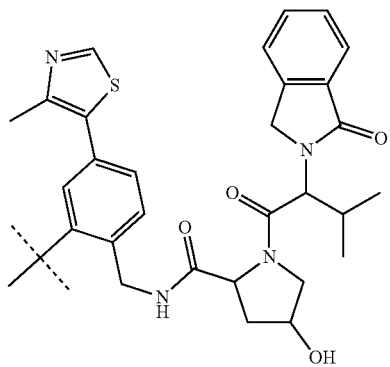

ULM-b2
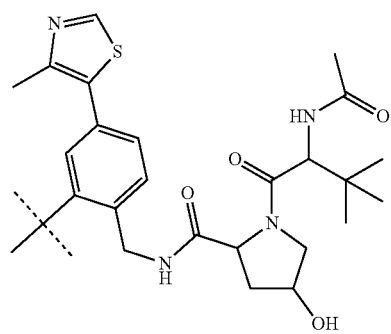
ULM-b3
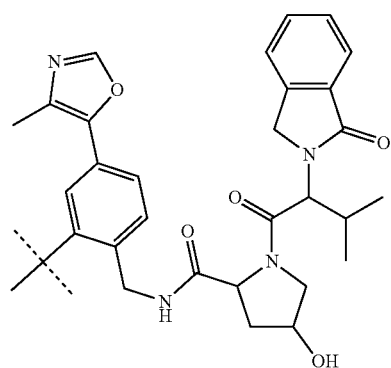
ULM-b4
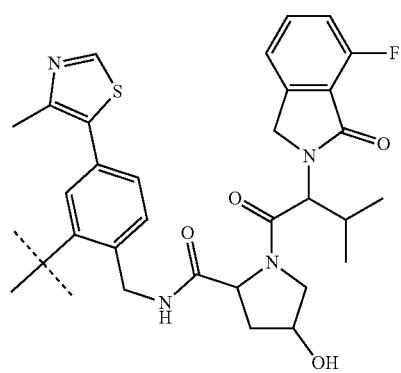
ULM-b5
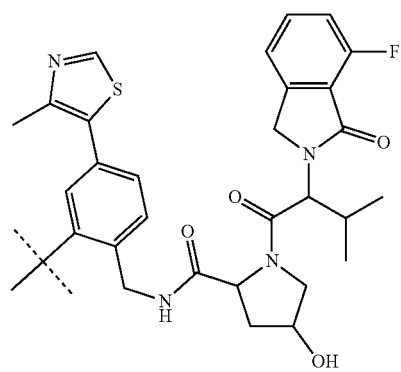
ULM-b6
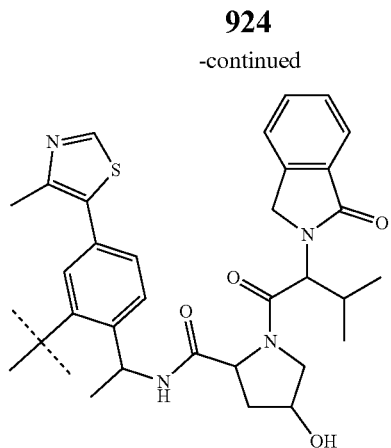
ULM-b7
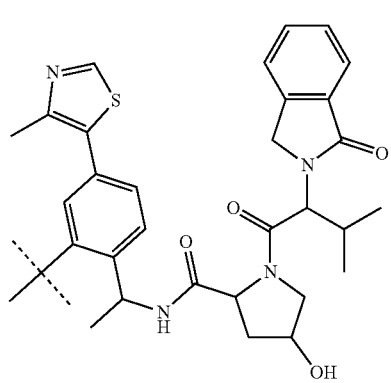
ULM-b8
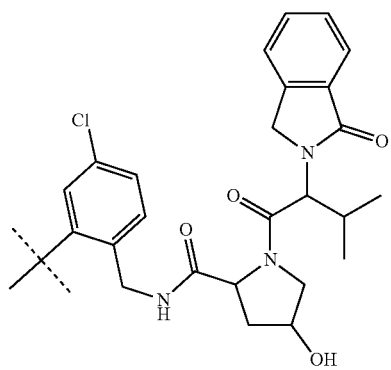
ULM-b9
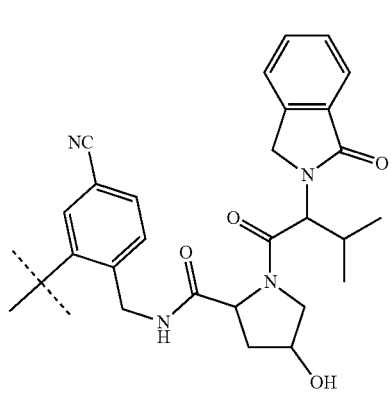

ULM-b10
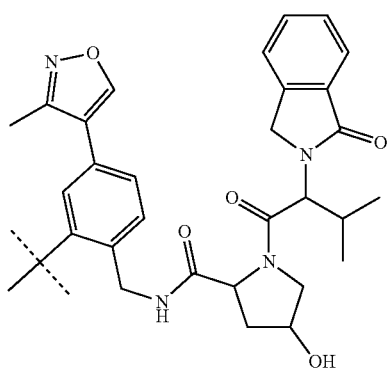
ULM-c2
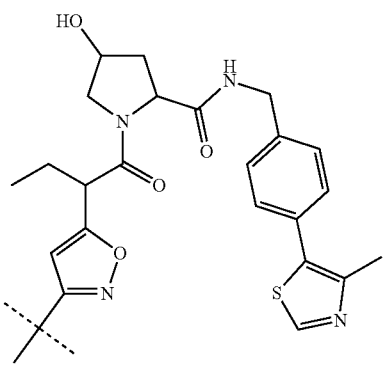
ULM-b11
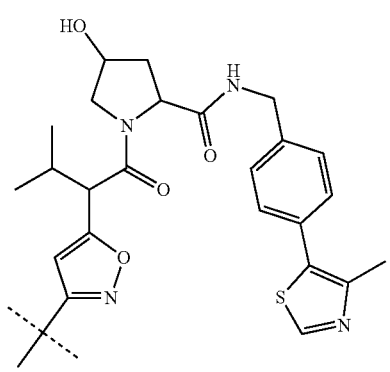
ULM-c3
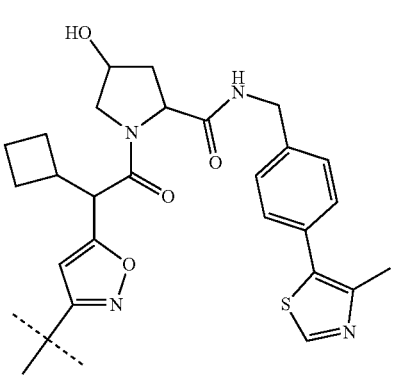
ULM-b12
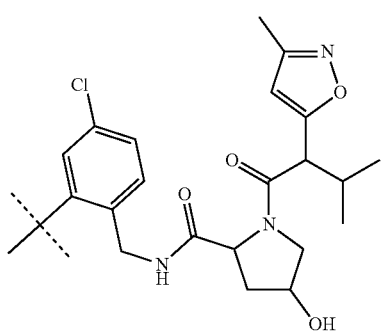
ULM-c4
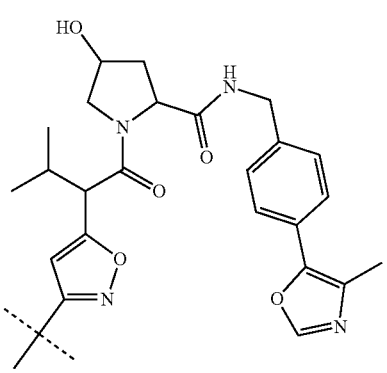
ULM-c1
ULM-c5

ULM-c6 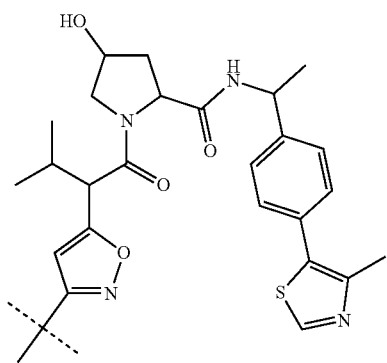
ULM-c10 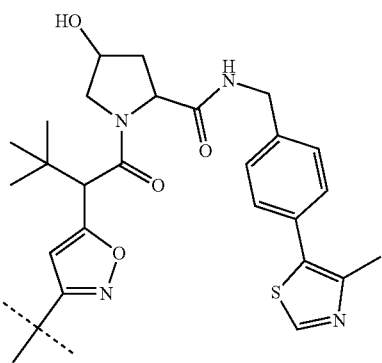
ULM-c7 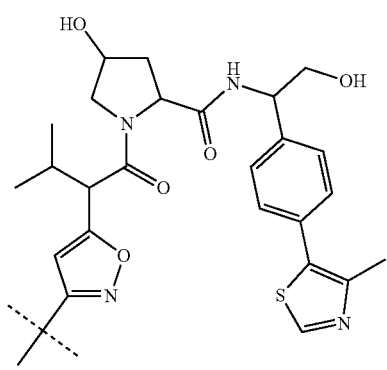
ULM-c11 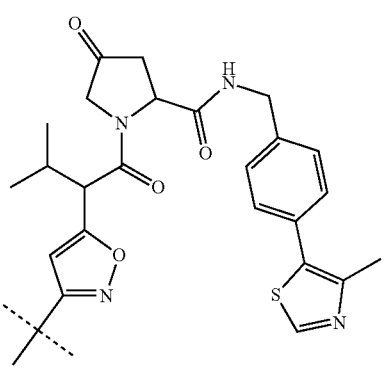
ULM-c8 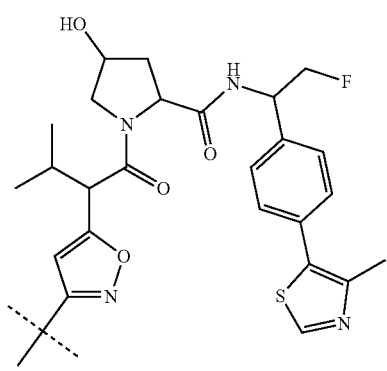
ULM-c12 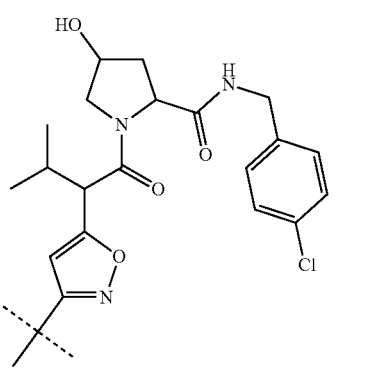
ULM-c9 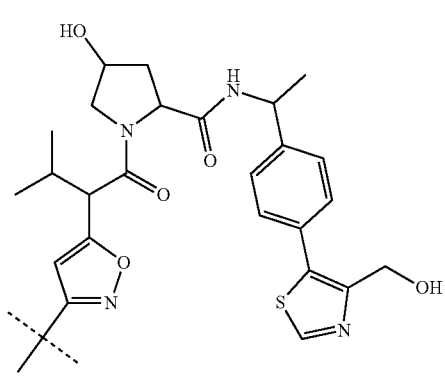
ULM-c13 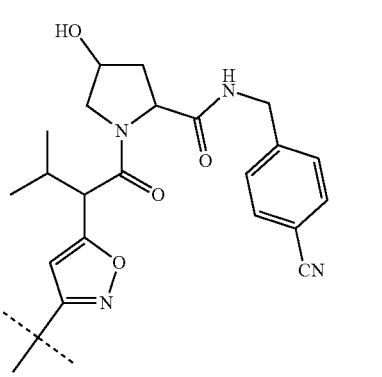

ULM-c14 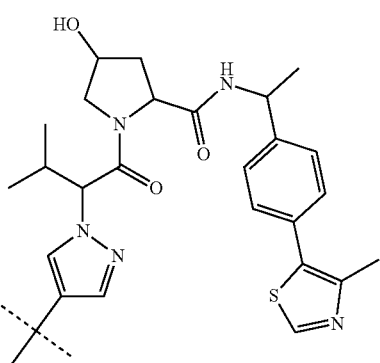
ULM-c15 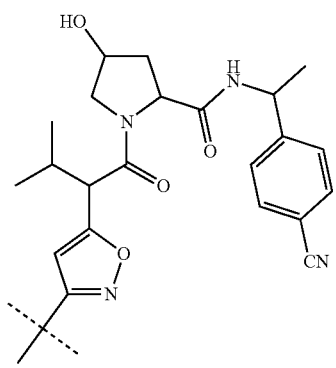
ULM-d1 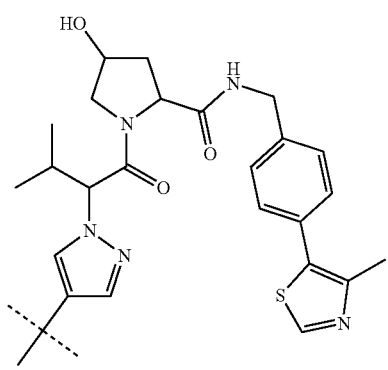
ULM-d2 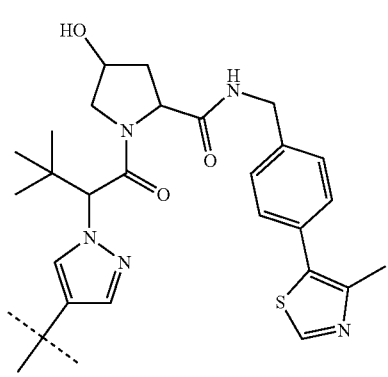
ULM-d3 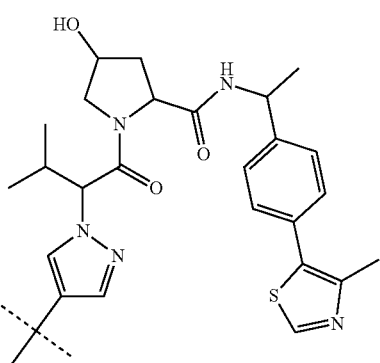
ULM-d4 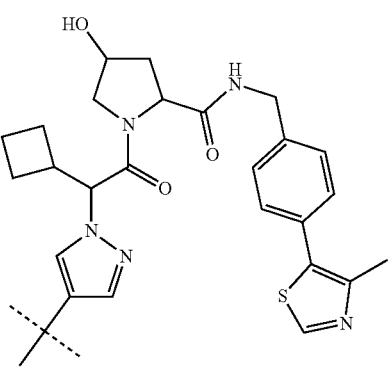
ULM-d5 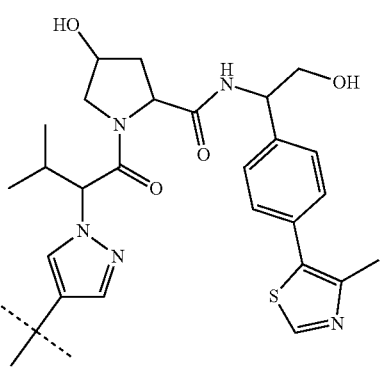
ULM-d6 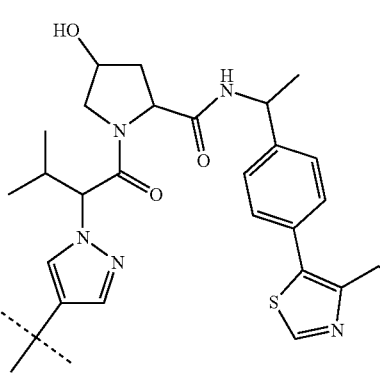

931
-continued
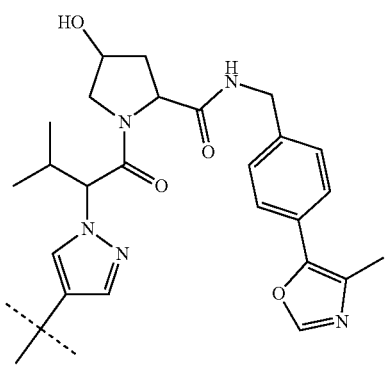
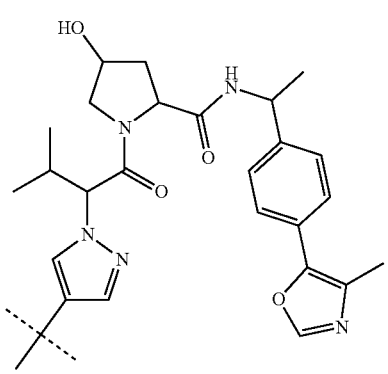
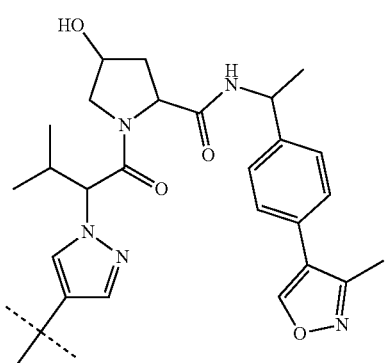
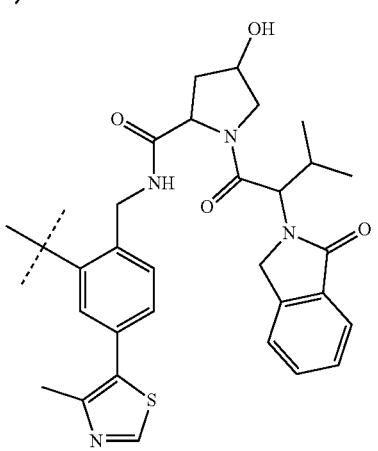
932
-continued
ULM-d7
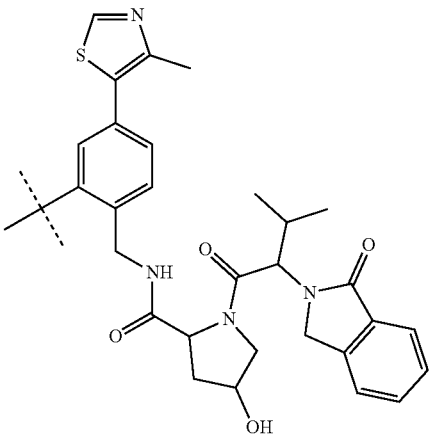
ULM-d8
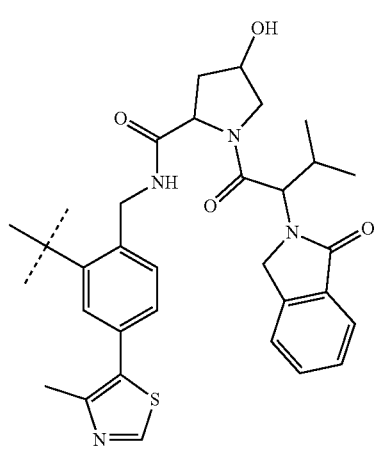
ULM-d9
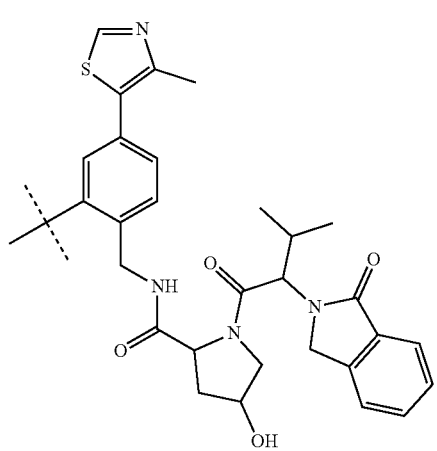

933
-continued

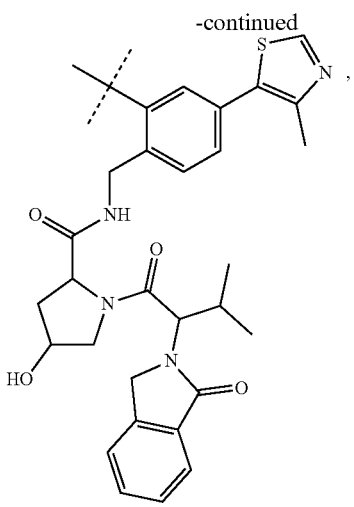

wherein the phenyl ring in ULM-a1 through ULM-a15, ULM-b1 through ULM-b12, ULM-c1 through ULM-c15 and ULM-d1 through ULM-d9 is optionally substituted with fluorine, lower alkyl and alkoxy groups, and wherein the dashed line indicates the site of attachment of at least one PTM, another ULM (ULM') or a chemical linker moiety coupling at least one PTM or a ULM' or both to ULM-a.

In any aspect or embodiment described herein, the ULM is a cereblon ligase-binding moiety (CLM) that is a thalidomide, lenalidomide, pomalidomide, analogs thereof, isosteres thereof, or derivatives thereof.

In any aspect or embodiment described herein, the CLM has a chemical structure represented by:

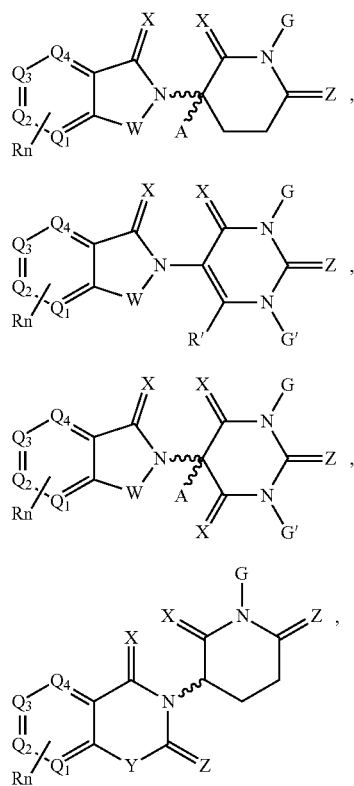

934
-continued

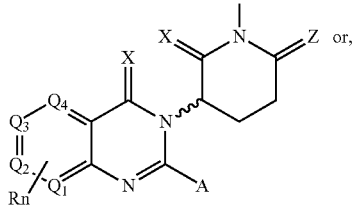 (e)

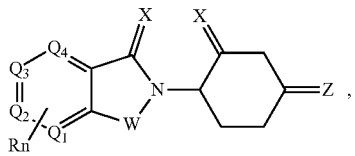 (f), wherein:
W is selected from the group consisting of $CH_2$, CHR, C=O, $SO_2$, NH, and N-alkyl;
each X is independently selected from the group consisting of O, S, and $H_2$;
Y is selected from the group consisting of $CH_2$, —C=CR', NH, N-alkyl, N-aryl, N-hetaryl, N-cycloalkyl, N-heterocyclyl, O, and S;
Z is selected from the group consisting of O, S, and $H_2$;
G and G' are independently selected from the group consisting of H, alkyl (linear, branched, optionally substituted with R'), OH, R'OCOOR, R'OCONRR", $CH_2$-heterocyclyl optionally substituted with R', and benzyl optionally substituted with R';
$Q_1$, $Q_2$, $Q_3$, and $Q_4$ represent a carbon C substituted with a group independently selected from R', N or N-oxide;
A is independently selected from the group H, alkyl, cycloalkyl, Cl and F;
R comprises —CONR'R", —OR', —NR'R", —SR', —$SO_2$R', —$SO_2$NR'R", —CR'R"—, —CR'NR'R"—, -aryl, -hetaryl, -alkyl (linear, branched, optionally substituted), -cycloalkyl, -heterocyclyl, —P(O)(OR')R", —P(O)R'R", —OP(O)(OR')R", —OP(O)R'R", —Cl, —F, —Br, —I, —$CF_3$, —CN, —NR'$SO_2$NR'R", —NR'CONR'R", —CONR'COR", —NR'C(=N—CN)NR'R", —C(=N—CN)NR'R", —NR'C(=N—CN)R", —NR'C(=C—$NO_2$)NR'R", —$SO_2$NR'COR", —$NO_2$, —$CO_2$R', —C(C=N—OR')R", —CR'=CR'R", —CCR', —S(C=O)(C=N—R')R", —$SF_5$ or —$OCF_3$;
R' and R" are independently selected from the group consisting of a bond, H, N, N-oxide, alkyl (linear, branched), cycloalkyl, aryl, heteroaryl, heterocyclic, —C(=O)R, or heterocyclyl, each of which is optionally substituted;
∿ represents a bond that may be stereospecific ((R) or (S)) or non-stereospecific; and
$R_n$ comprises a functional group or an atom,
wherein n is an integer from 1-4, and wherein
when n is 1, $R_n$ is modified to be covalently joined to the linker group (L), and
when n is 2, 3, or 4, then one $R_n$ is modified to be covalently joined to the linker group (L), and any other $R_n$ is optionally modified to be covalently joined to a PTM, a CLM, a second CLM having the same chemical structure as the CLM, a CLM', a second linker, or any multiple or combination thereof.

In any aspect or embodiment described herein, the CLM has a chemical structure represented by:

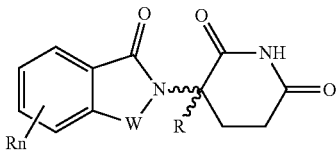

wherein:
W is independently selected from the group CH$_2$, C=O, NH, and N-alkyl;
R is independently selected from a H, methyl, alkyl;
⌇⌇⌇ represents a bond that may be stereospecific ((R) or (S)) or non-stereospecific; and
Rn comprises 1-4 independently selected functional groups or atoms, and optionally, one of which is modified to be covalently joined to a PTM, a chemical linker group (L), a CLM (or CLM') or combination thereof.

In any aspect or embodiment described herein, the CLM has a chemical structure represented by:

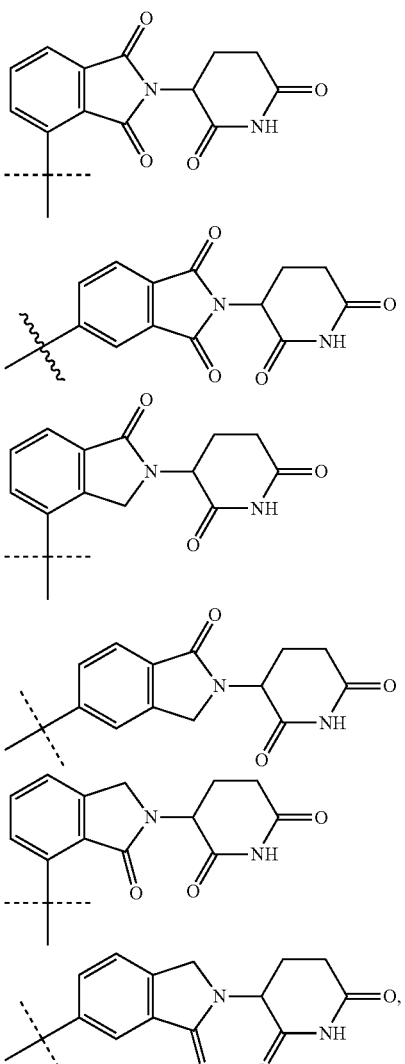

wherein the dashed lines indicate linker attachment points.

In any aspect or embodiment described herein, the linker (L) comprises a chemical structural unit represented by the formula:

-(A)$_q$-, wherein:
A is a group which is connected to the ULM or the PTM moiety; and
q is an integer greater than or equal to 1,
wherein A is selected from the group consisting of, a bond, CR$^{L1}$R$^{L2}$, O, S, SO, SO$_2$, NR$^{L3}$SO$_2$NR$^{L3}$, SONR$^{L3}$, CONR$^{L3}$, NR$^{L3}$CONR$^{L4}$, NR$^{L3}$SO$_2$NR$^{L4}$, CO, CR$^{L1}$=CR$^{L2}$, C≡C, SiR$^{L1}$R$^{L2}$P(O)R$^{L1}$, P(O)OR$^{L1}$, NR$^{L3}$C(=NCN)NR$^{L4}$, NR$^{L3}$C(=NCN), NR$^{L3}$C(=CNO$_2$)NR$^{L4}$, C$_{3-11}$cycloalkyl optionally substituted with 0-6 R$^{L1}$ and/or R$^{L2}$ groups, C$_{3-11}$heterocyclyl optionally substituted with 0-6 R$^{L1}$ and/or R$^{L2}$ groups, aryl optionally substituted with 0-6 R$^{L1}$ and/or R$^{L2}$ groups, heteroaryl optionally substituted with 0-6 R$^{L1}$ and/or R$^{L2}$ groups, where R$^{L1}$ or R$^{L2}$, each independently are optionally linked to other groups to form cycloalkyl and/or heterocyclyl moiety, optionally substituted with 0-4 R$^{L5}$ groups;
R$^{L1}$, R$^{L2}$, R$^{L3}$, R$^{L4}$ and R$^{L5}$ are, each independently, H, halo, C$_{1-8}$alkyl, OC$_{1-8}$alkyl, SC$_{1-8}$alkyl, NHC$_{1-8}$alkyl, N(C$_{1-8}$alkyl)$_2$, C$_{3-11}$cycloalkyl, aryl, heteroaryl, C$_{3-11}$heterocyclyl, OC$_{1-8}$cycloalkyl, SC$_{1-8}$cycloalkyl, NHC$_{1-8}$cycloalkyl, N(C$_{1-8}$cycloalkyl)$_2$, N(C$_{1-8}$cycloalkyl)(C$_{1-8}$alkyl), OH, NH$_2$, SH, SO$_2$C$_{1-8}$alkyl, P(O)(OC$_{1-8}$alkyl)(C$_{1-8}$alkyl), P(O)(OC$_{1-8}$alkyl)$_2$, CC—C$_{1-8}$alkyl, CCH, CH=CH(C$_{1-8}$alkyl), C(C$_{1-8}$alkyl)=CH(C$_{1-8}$alkyl), C(C$_{1-8}$alkyl)=C(C$_{1-8}$alkyl)$_2$, Si(OH)$_3$, Si(C$_{1-8}$alkyl)$_3$, Si(OH)(C$_{1-8}$alkyl)$_2$, COC$_{1-8}$alkyl, CO$_2$H, halogen, CN, CF$_3$, CHF$_2$, CH$_2$F, NO$_2$, SFs, SO$_2$NHC$_{1-8}$alkyl, SO$_2$N(C$_{1-8}$alkyl)$_2$, SONHC$_{1-8}$alkyl, SON(C$_{1-8}$alkyl)$_2$, CONHC$_{1-8}$alkyl, CON(C$_{1-8}$alkyl)$_2$, N(C$_{1-8}$alkyl)CONH(C$_{1-8}$alkyl), N(C$_{1-8}$alkyl)CON(C$_{1-8}$alkyl)$_2$, NHCONH(C$_{1-8}$alkyl), NHCON(C$_{1-8}$alkyl)$_2$, NHCONH$_2$, N(C$_{1-8}$alkyl)SO$_2$NH(C$_{1-8}$alkyl), N(C$_{1-8}$alkyl) SO$_2$N(C$_{1-8}$alkyl)$_2$, NH SO$_2$NH(C$_{1-8}$alkyl), NH SO$_2$N(C$_{1-8}$alkyl)$_2$, NH SO$_2$NH$_2$.

In any aspect or embodiment described herein, the linker (L) comprises a group represented by a general structure selected from the group consisting of:
—N(R)—(CH2)$_m$-O(CH2)$_n$-O(CH2)$_o$-O(CH2)$_p$-O(CH2)$_q$-O(CH2)$_r$-OCH2-,
O—(CH2)$_m$-O(CH2)$_n$-O(CH2)$_o$-O(CH2)$_p$-O(CH2)$_q$-O(CH2)$_r$-OCH2-,
O—(CH2)$_m$-O(CH2)$_n$-O(CH2)$_o$-O(CH2)$_p$-O(CH2)$_q$-O(CH2)$_r$-O—;
—N(R)—(CH2)$_m$-O(CH2)$_n$-O(CH2)$_o$-O(CH2)$_p$-O(CH2)$_q$-O(CH2)$_r$-O—;
(CH2)$_m$-O(CH2)$_n$-O(CH2)$_o$-O(CH2)$_p$-O(CH2)$_q$-O(CH2)$_r$-O—;
(CH2)$_m$-O(CH2)$_n$-O(CH2)$_o$-O(CH2)$_p$-O(CH2)$_q$-O(CH2)$_r$-OCH2-;

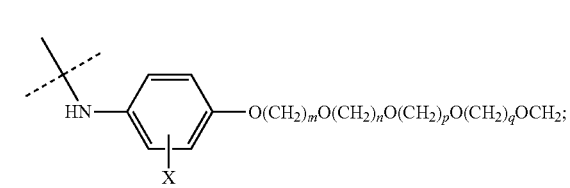

937
-continued
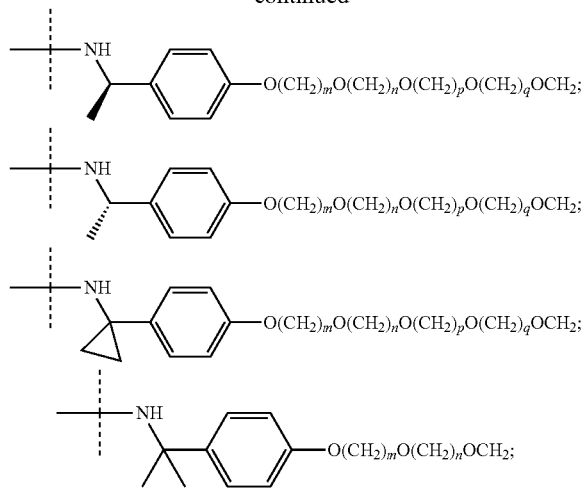
938
-continued
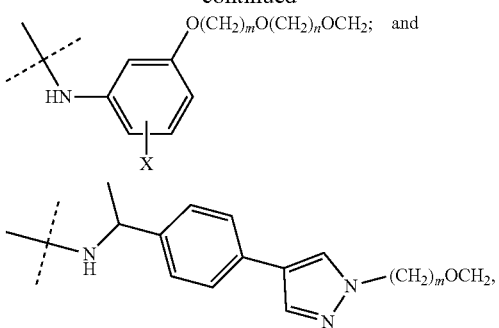
wherein each m, n, o, p, q, and r, is independently 0, 1, 2, 3, 4, 5, 6, with the proviso that when the number is zero, there is no N—O or O—O bond; R is selected from the group H, methyl or ethyl, and X is selected from the group H or F;
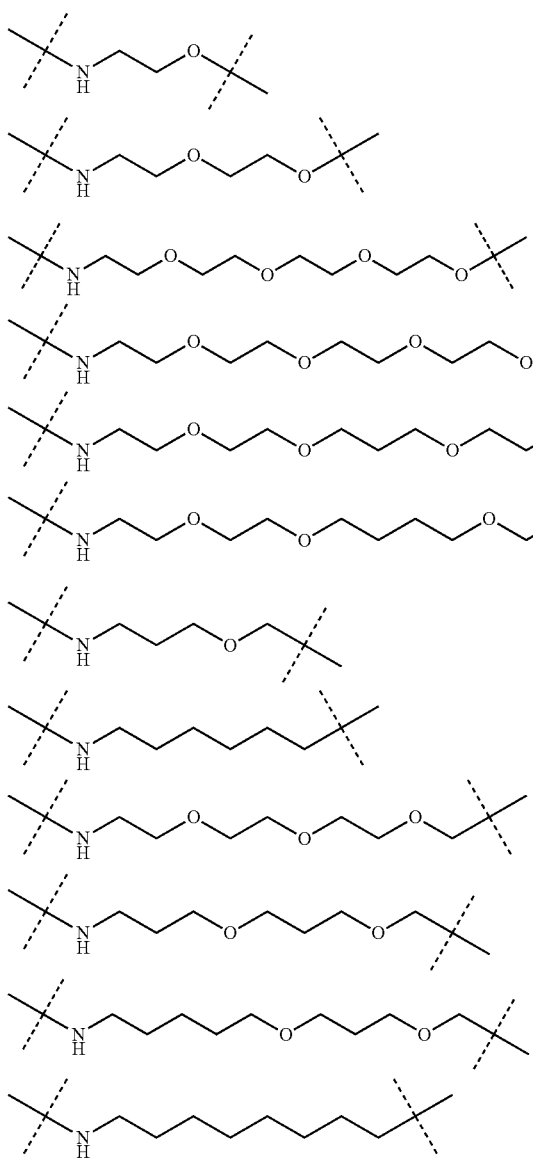
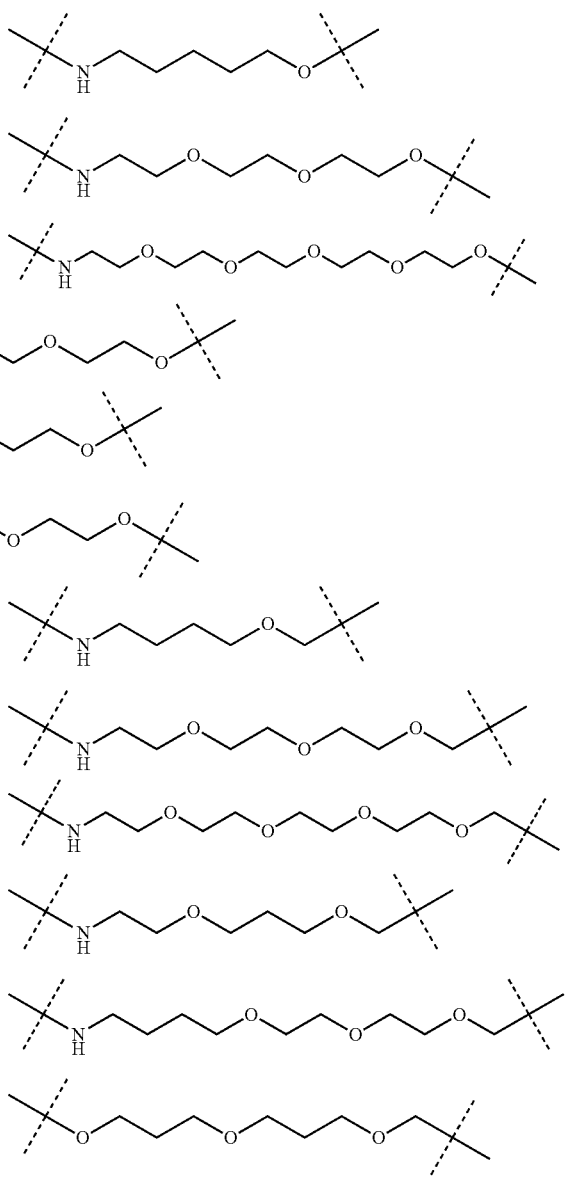

939
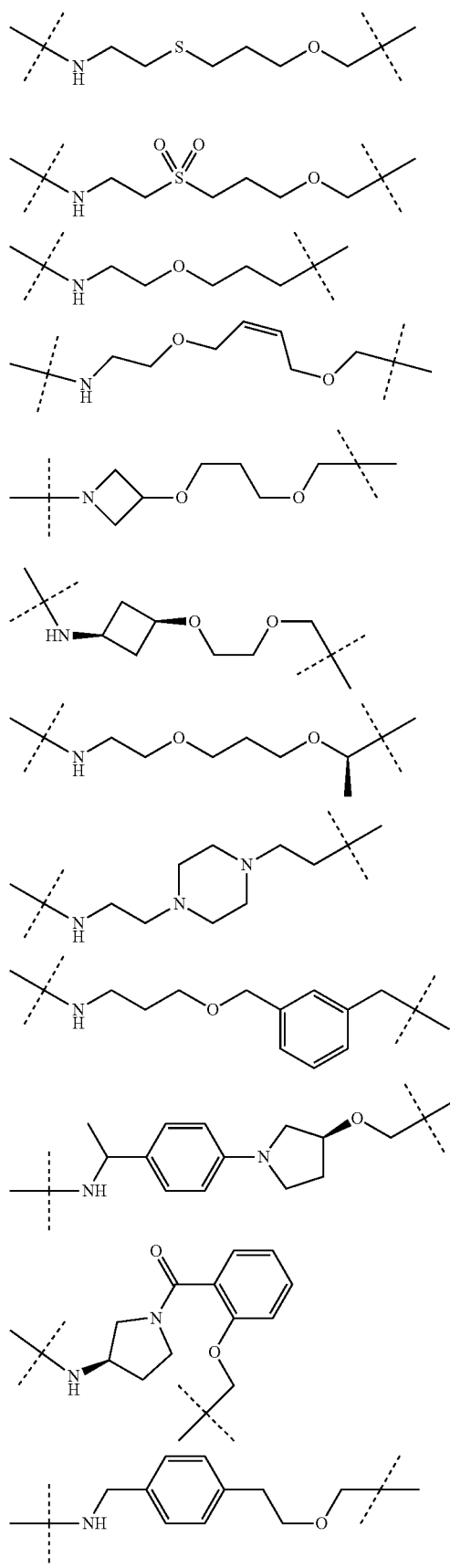
940
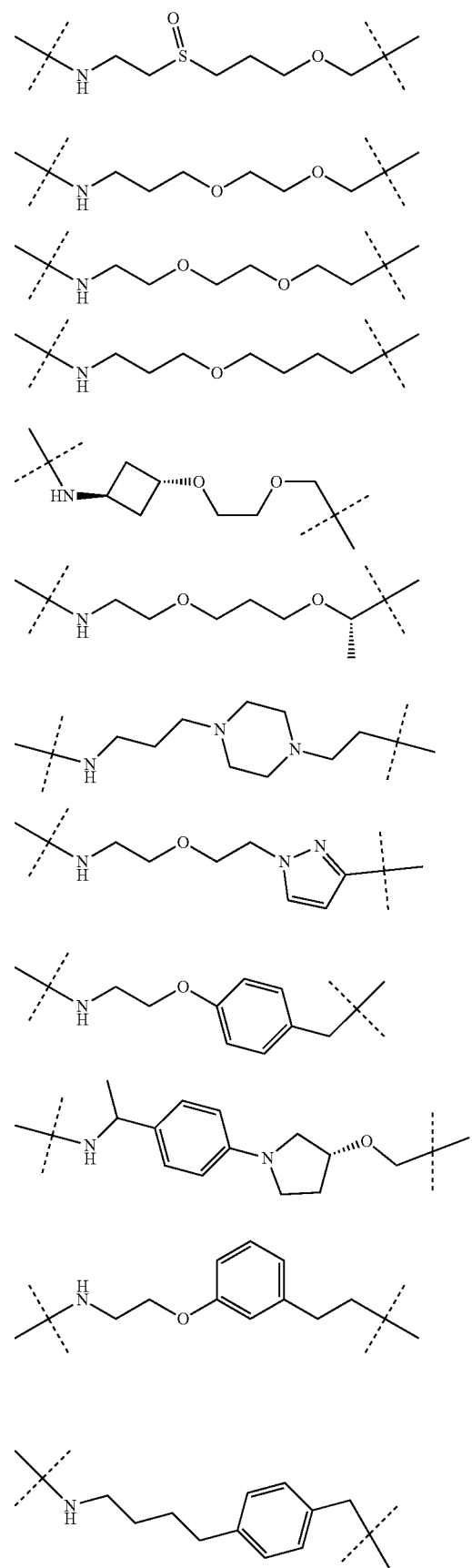

941
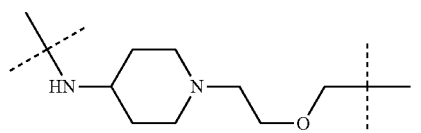
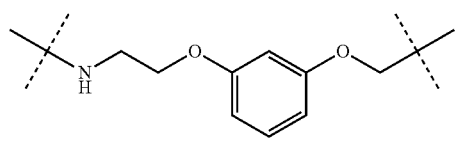
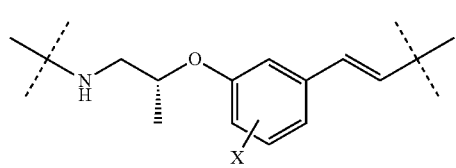
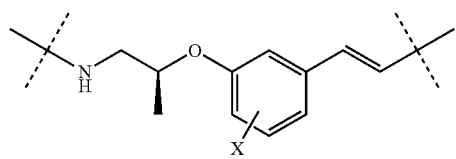
X = H, F
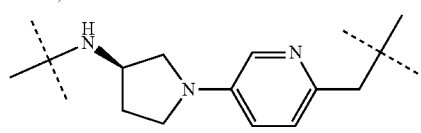
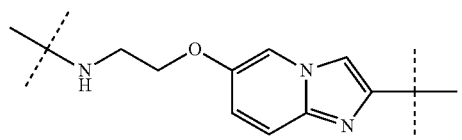
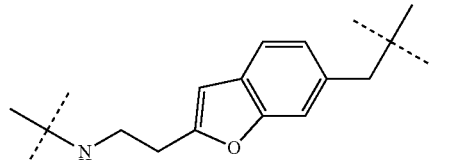
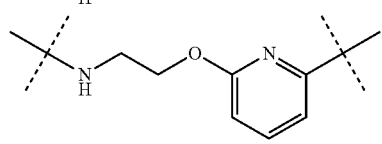
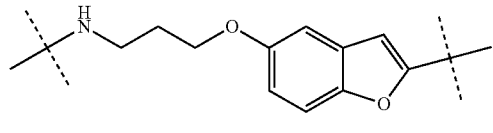
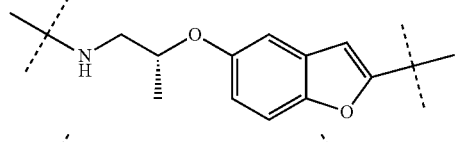
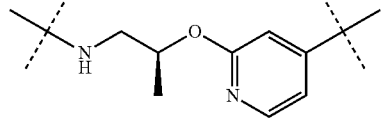
942
-continued
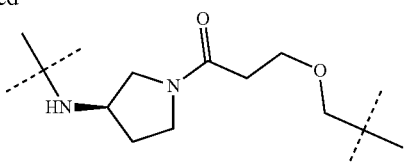
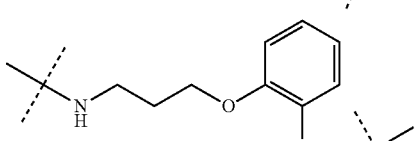
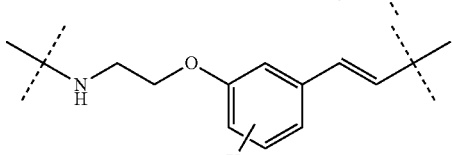
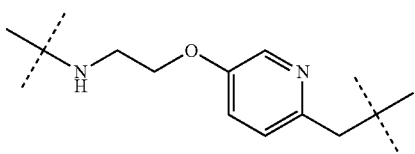
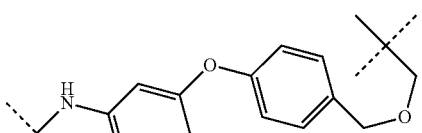
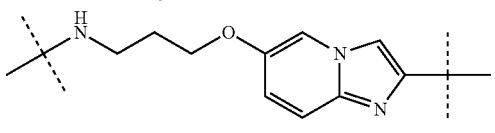
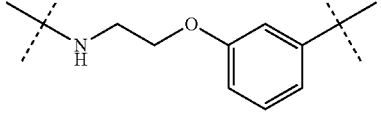
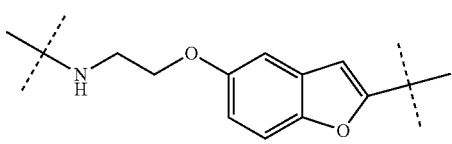
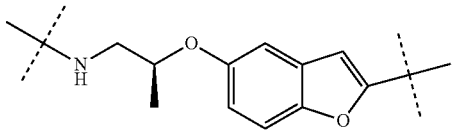
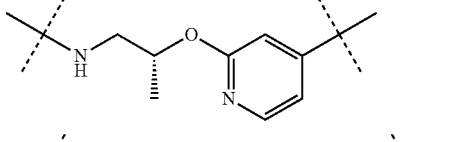
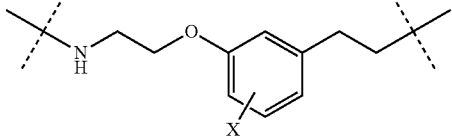

943
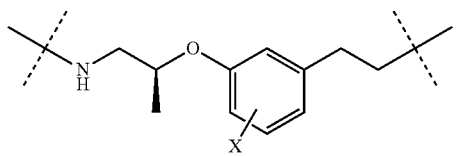
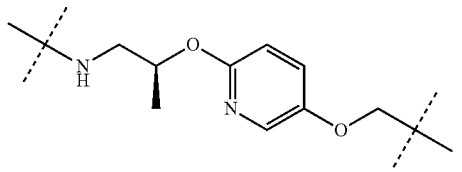
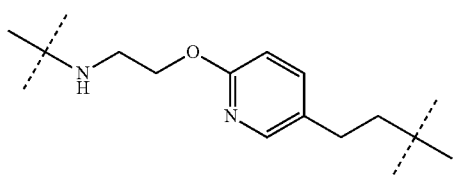
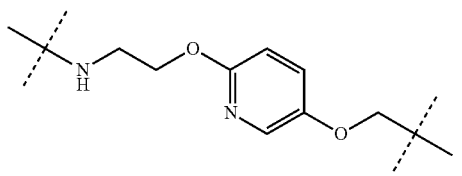
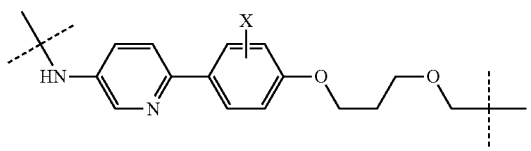
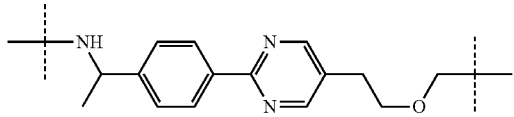
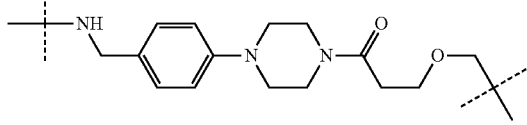
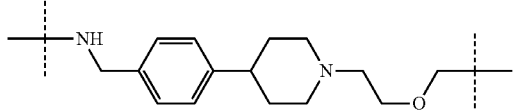
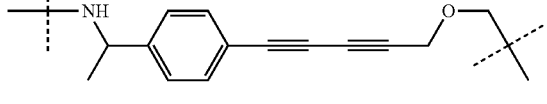
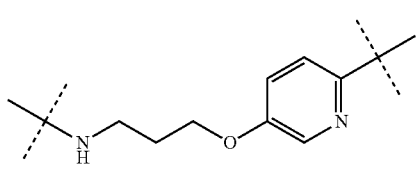
944
-continued
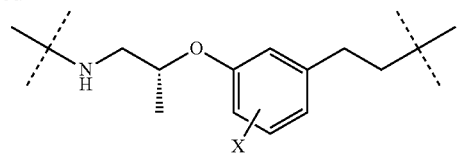
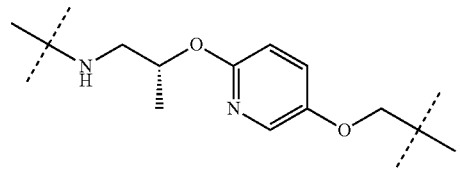
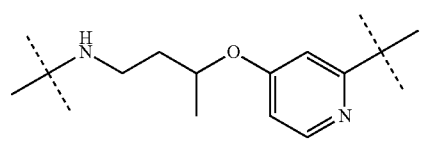
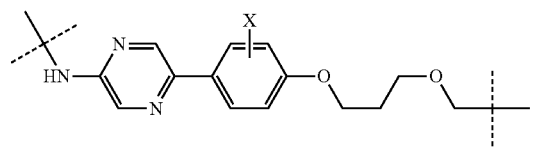
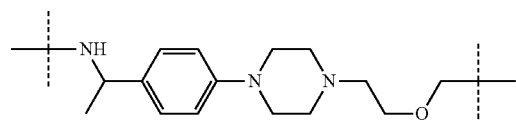
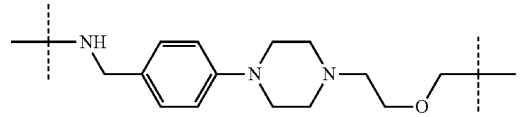
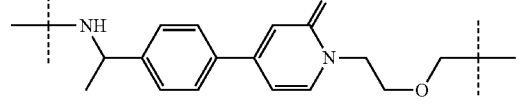
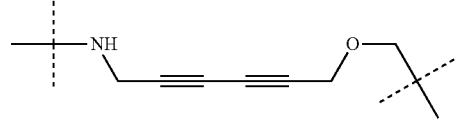
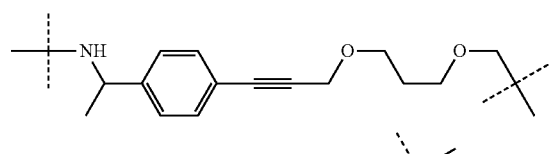
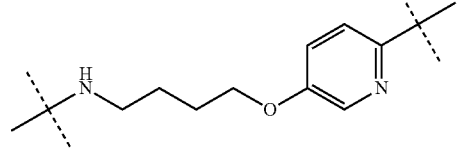
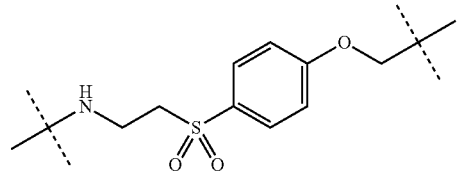

-continued
| 945 | 946 |
|---|---|
| 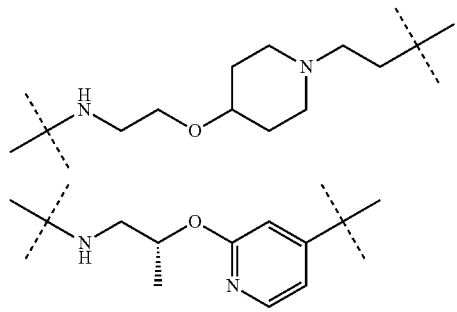 | 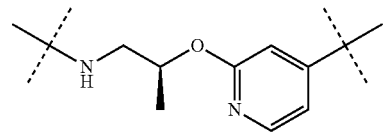 |
| 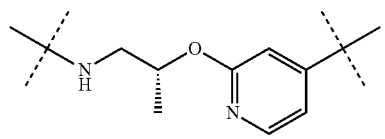 | 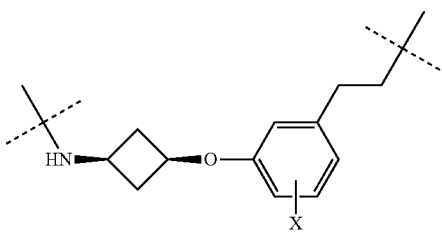 |
|  | X = H, F |
| 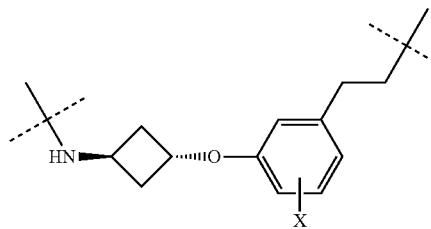 | 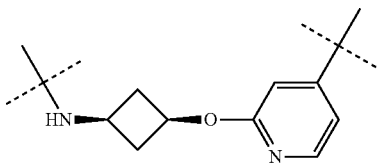 |
| 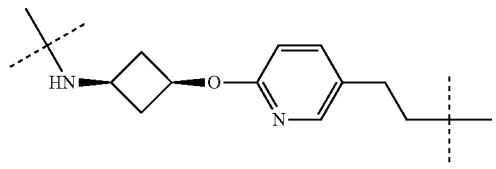 | 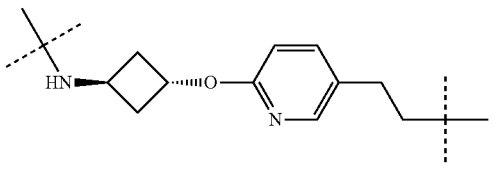 |
| 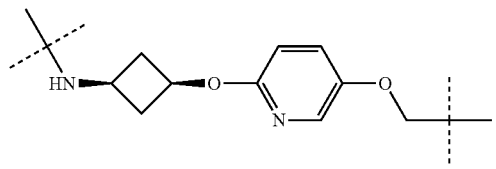 | 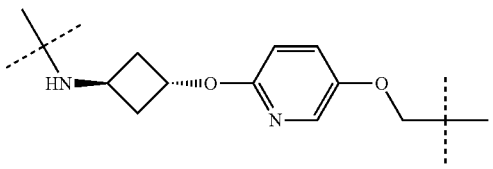 |
| 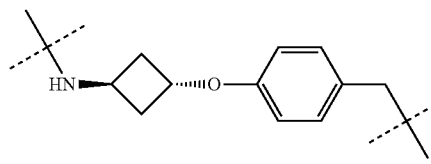 | 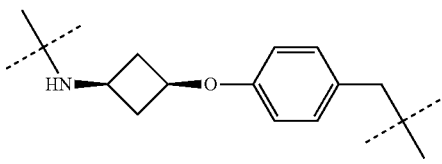 |
| 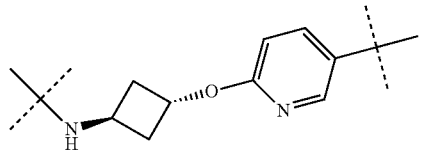 | 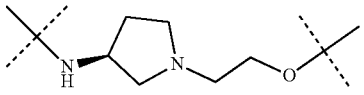 |
| 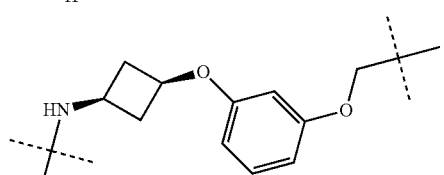 | 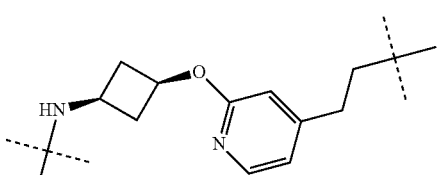 |
| 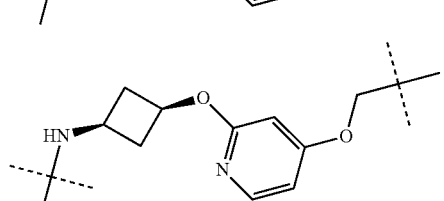 | 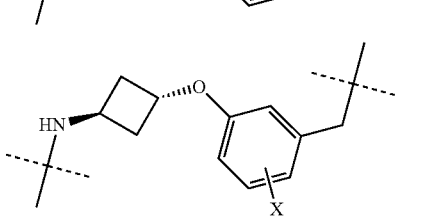 |

-continued
| 947 | 948 |
|---|---|
| 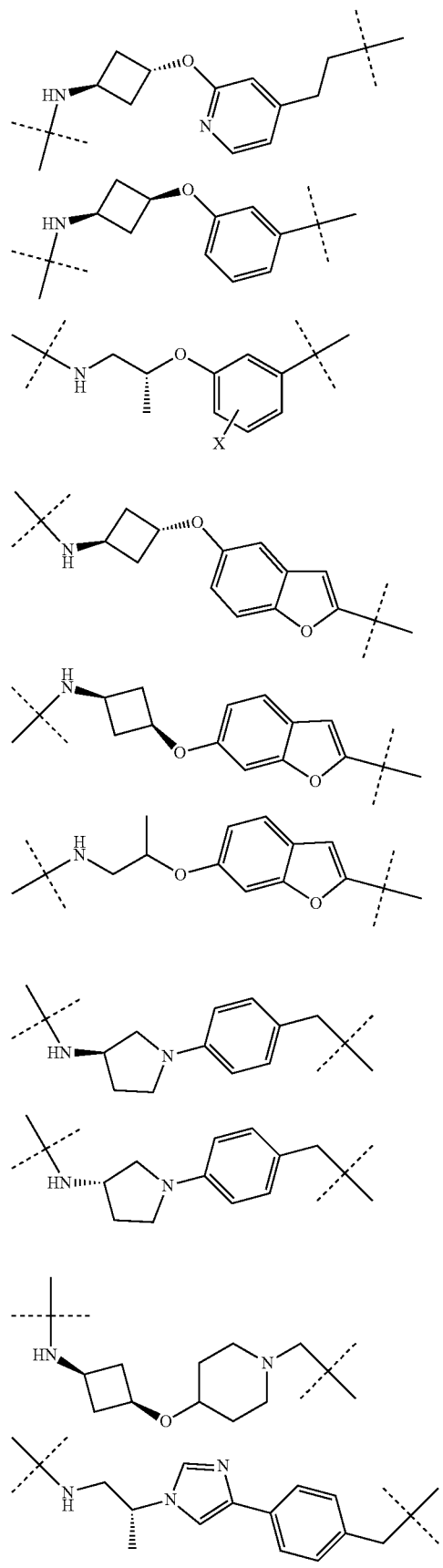 | 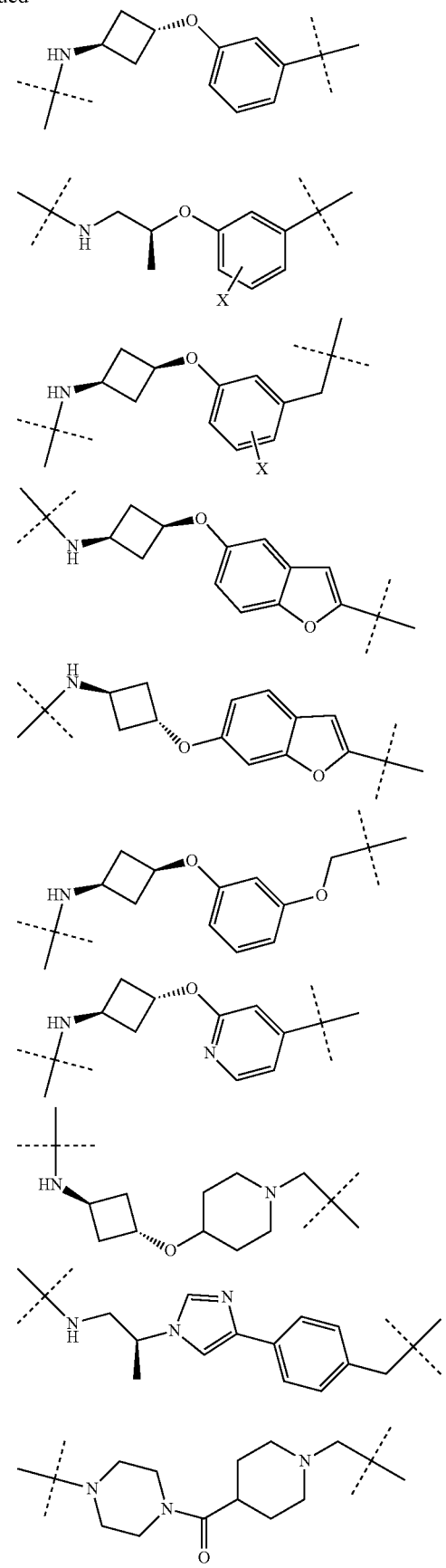 |

949 950
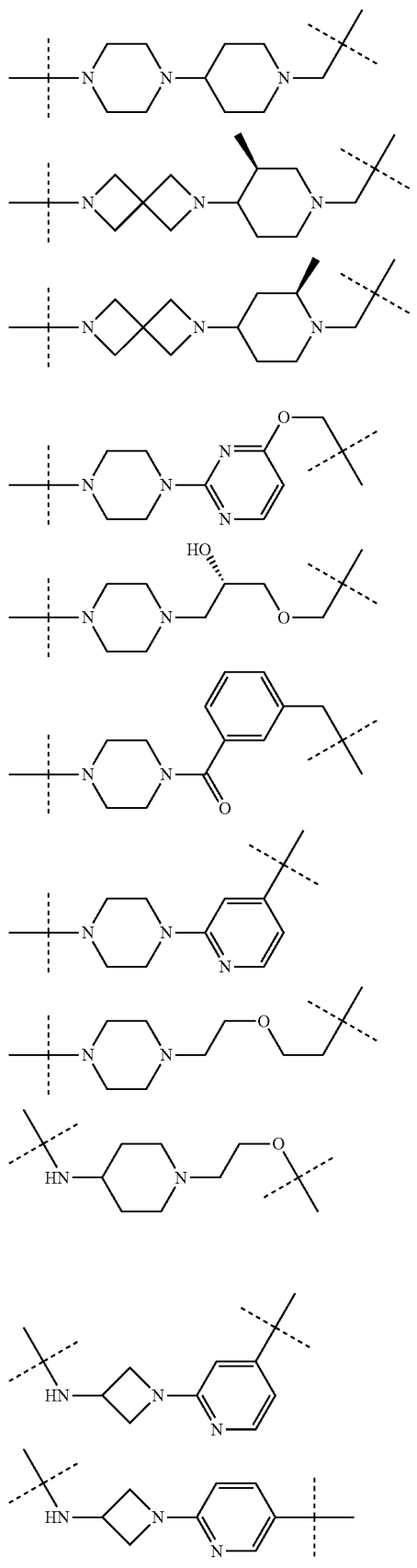 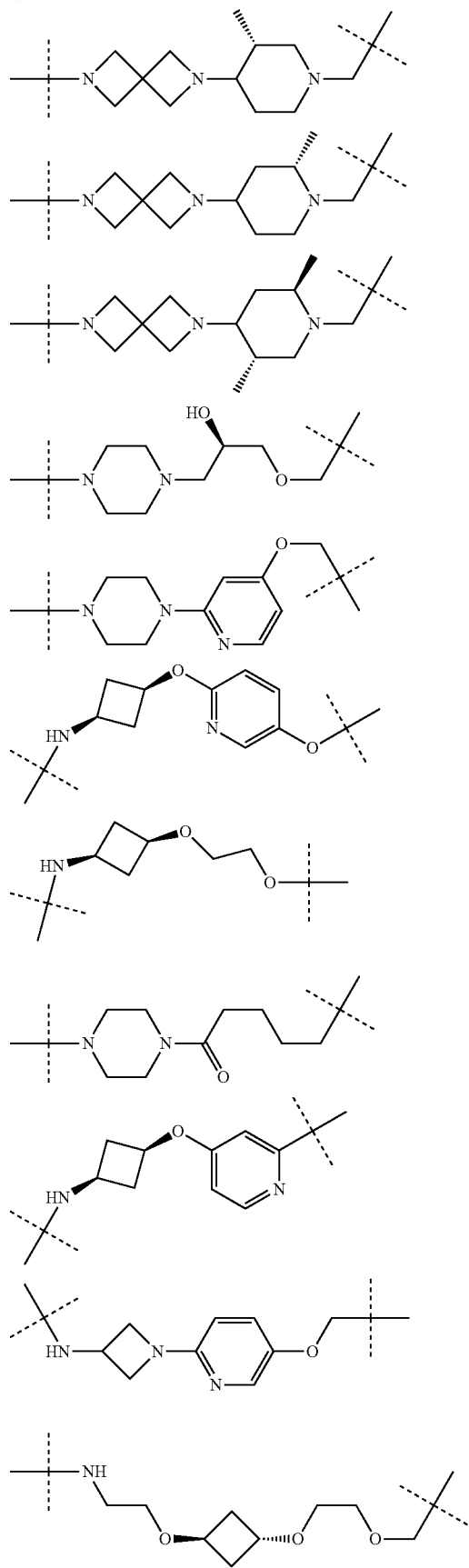

951
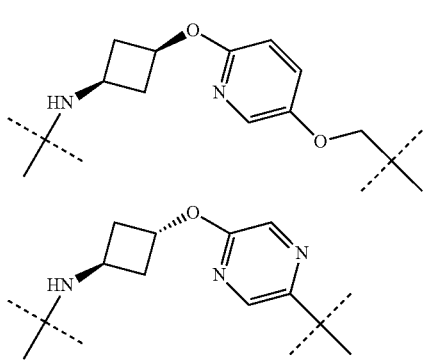
952
-continued
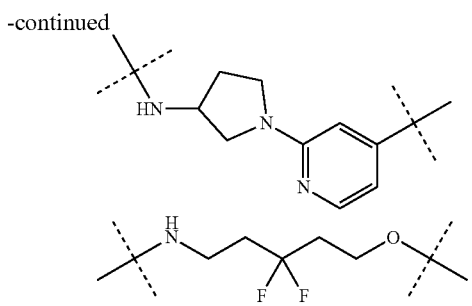
In any aspect or embodiment described herein, the linker (L) is selected from the group consisting of:
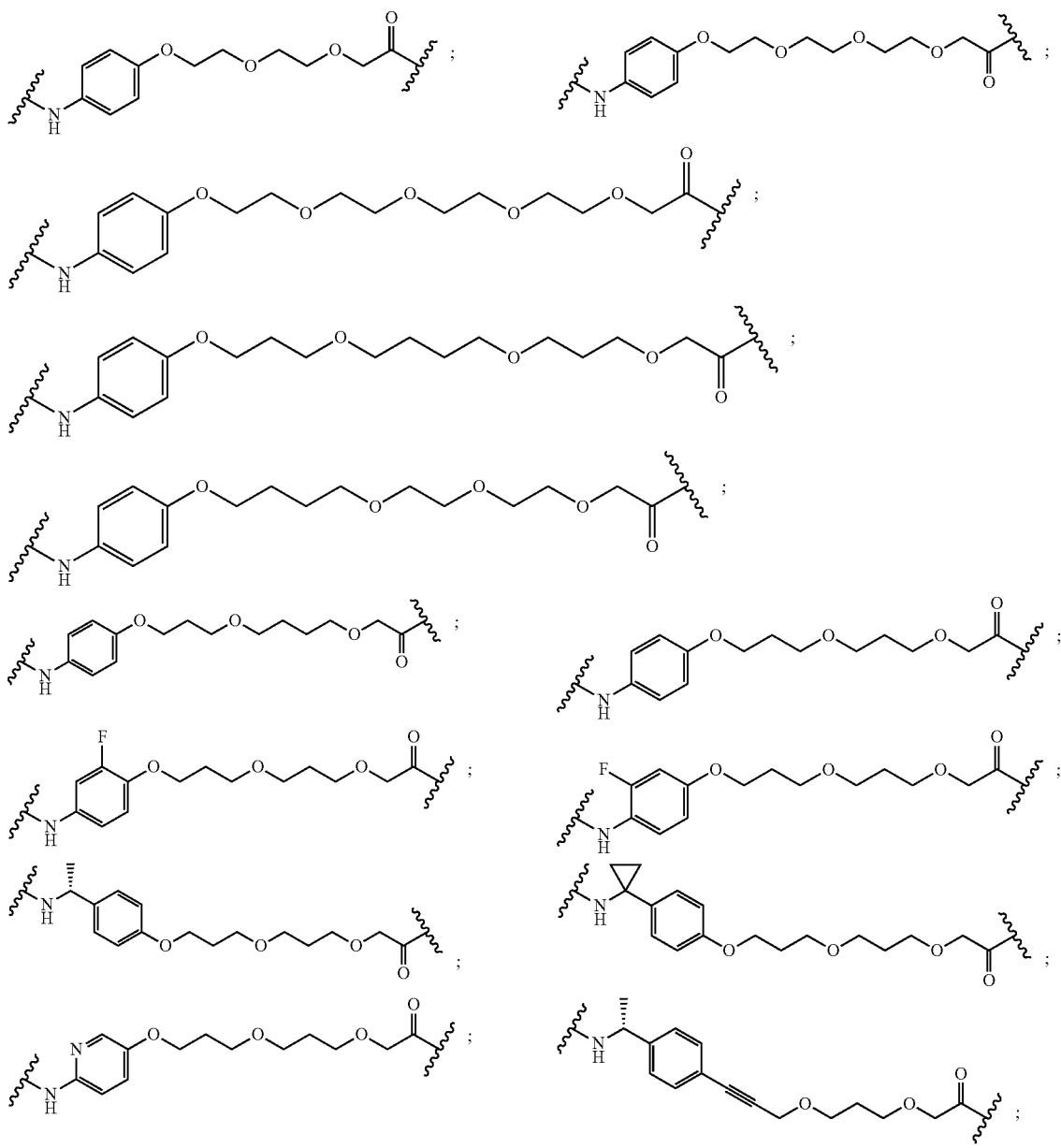

-continued
| 953 | 954 |
|---|---|
| 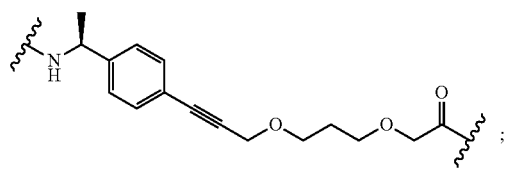 | 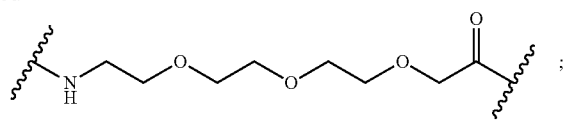 |
| 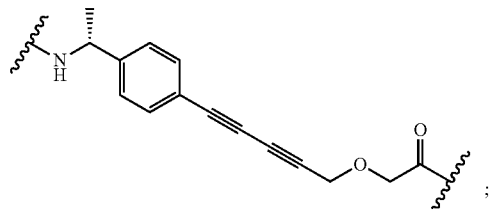 | 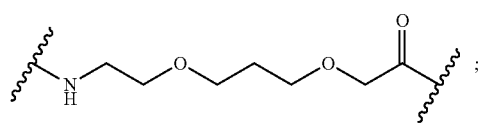 |
| 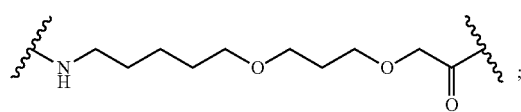 | 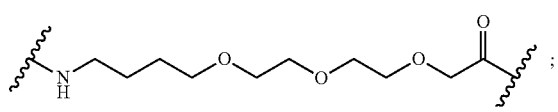 |
| 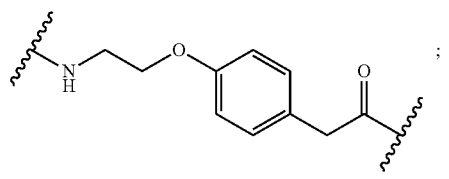 | 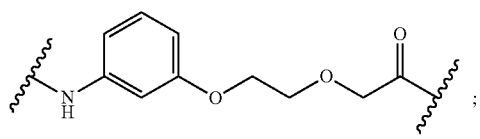 |
| 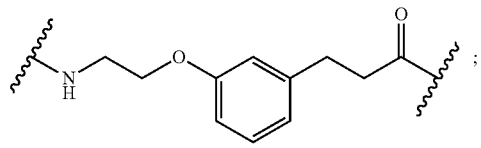 | 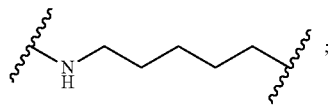 |
| 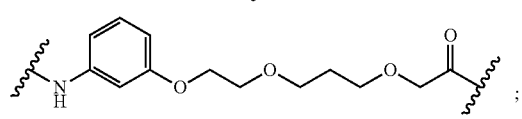 | 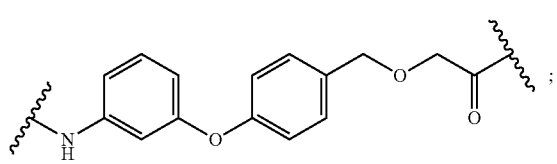 |
| 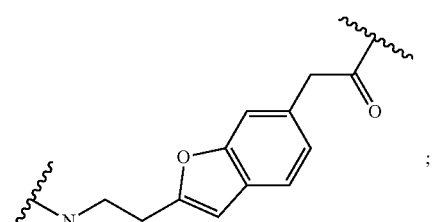 | 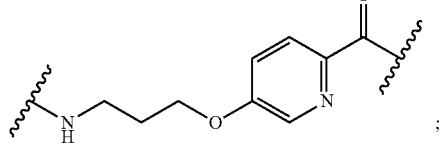 |
| 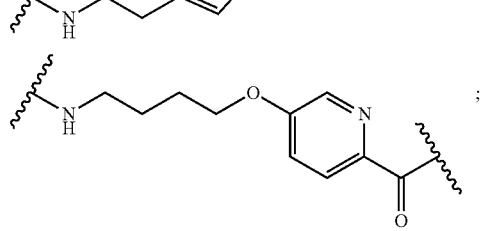 | 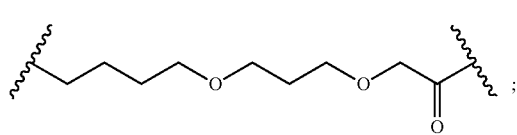 |
| 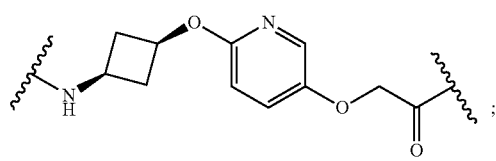 | 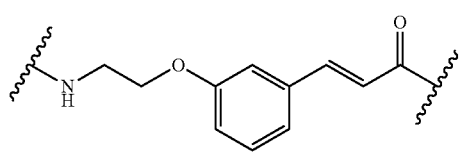 |
| 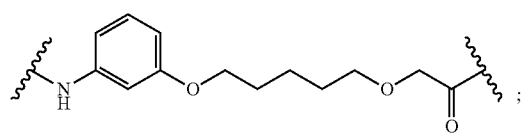 | 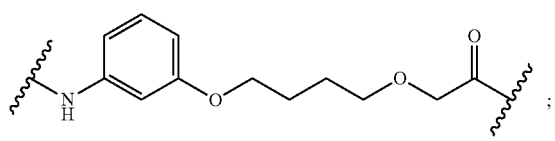 |

955 956
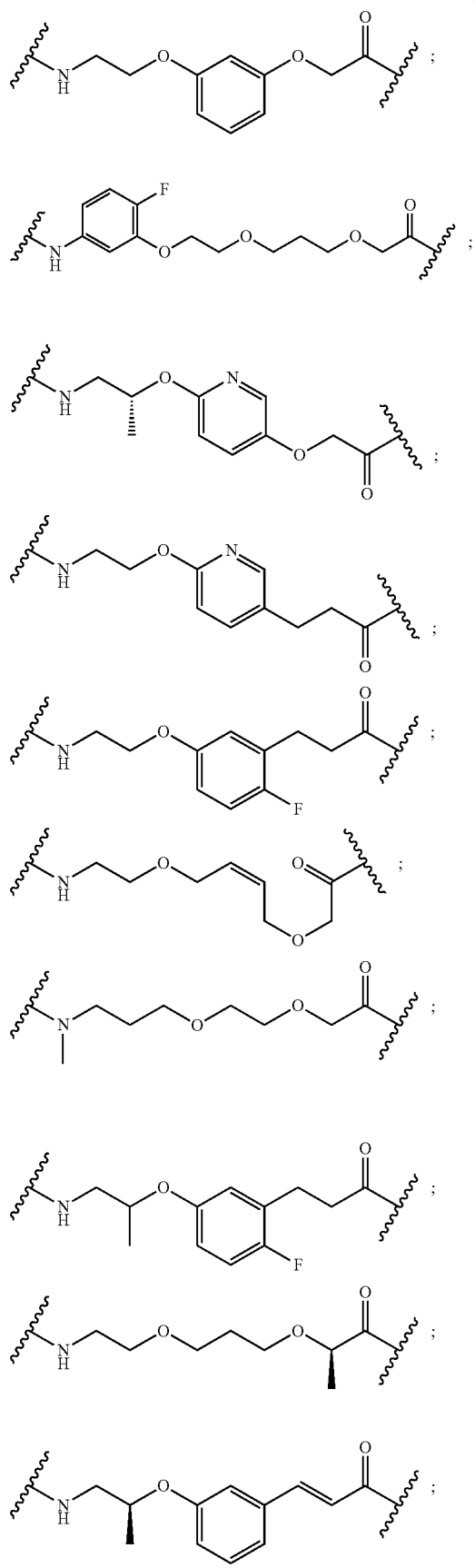
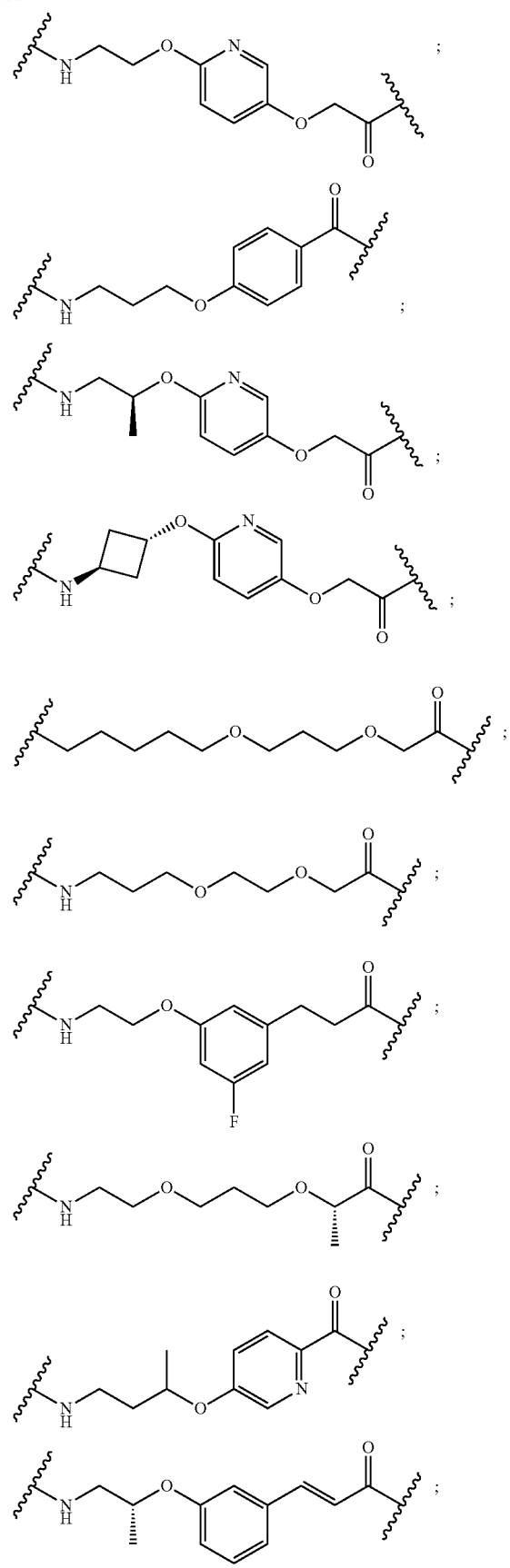

957
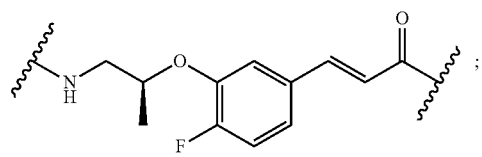
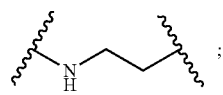
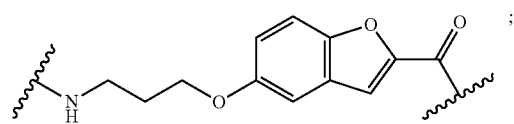
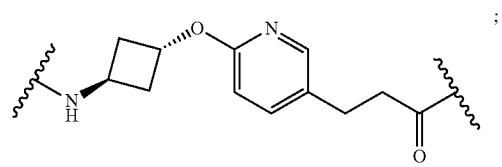
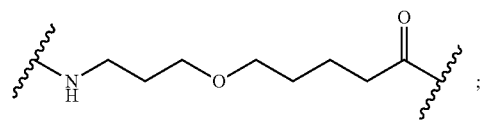
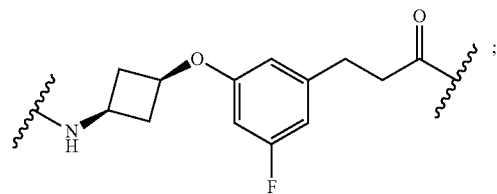
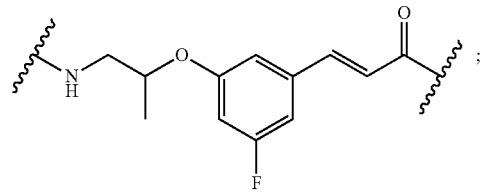
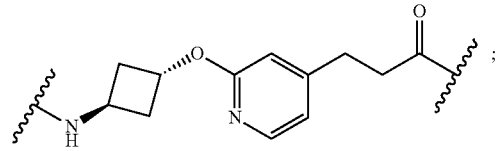
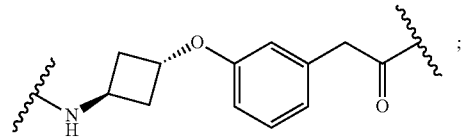
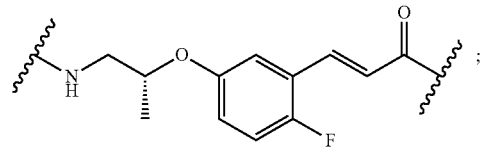
-continued
958
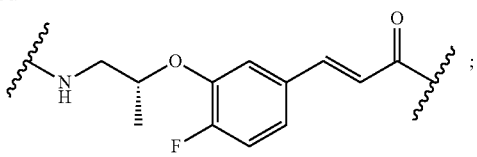
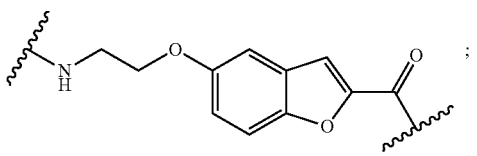
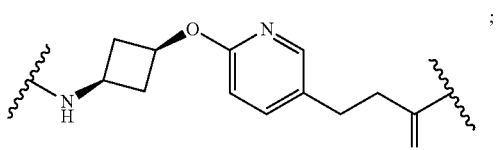
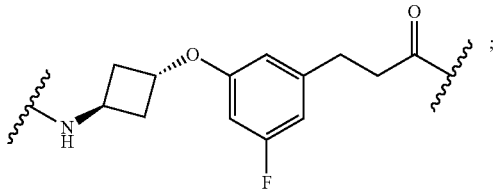
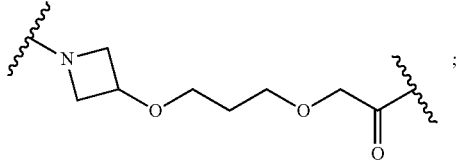
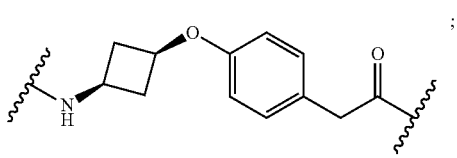
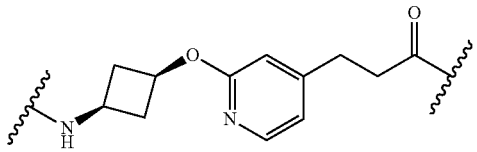
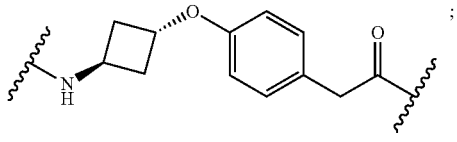
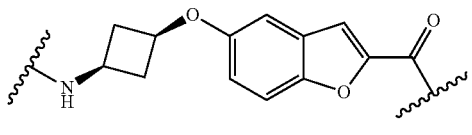
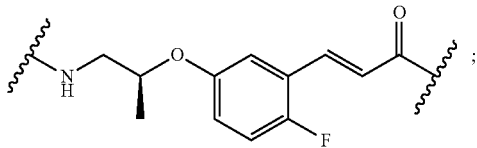

959 960
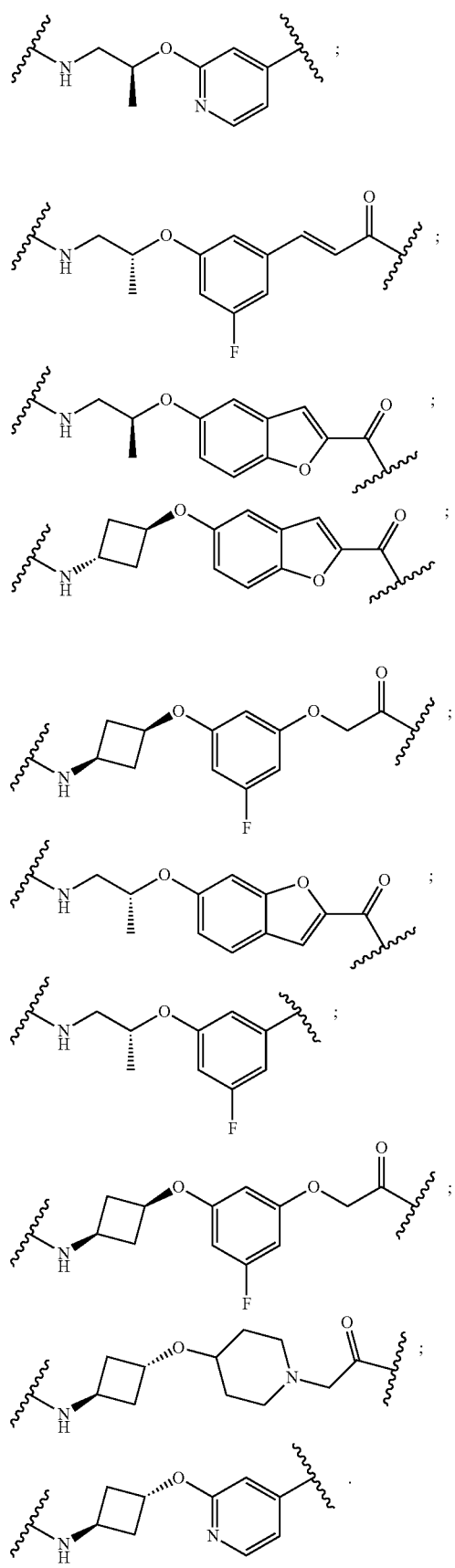
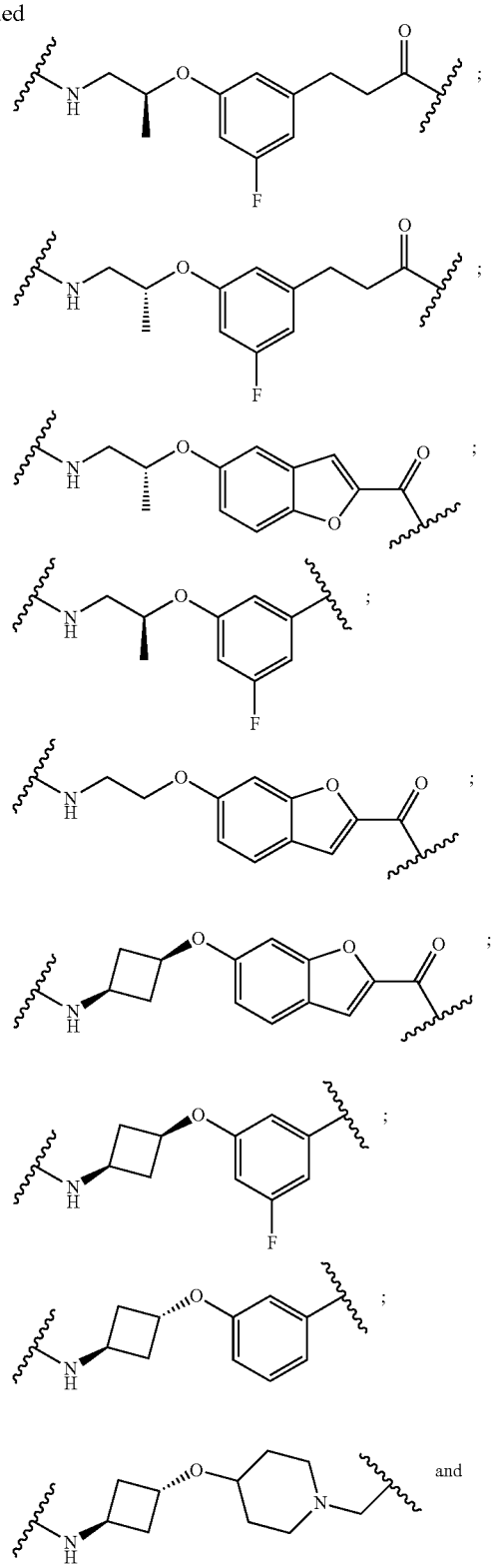

In any aspect or embodiment described herein, the linker (L) is selected from the group consisting of:
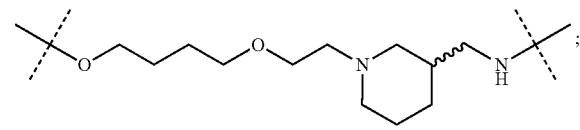
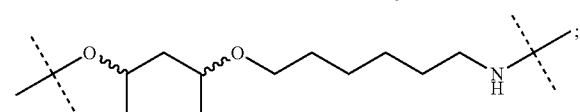
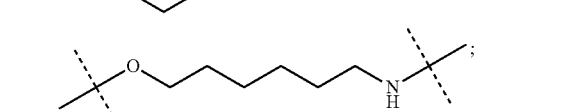
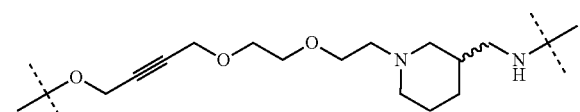
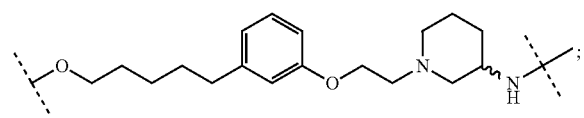
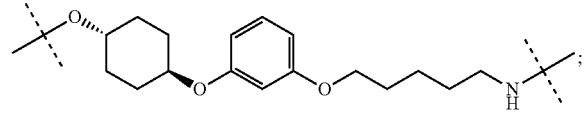
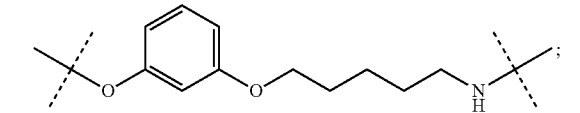
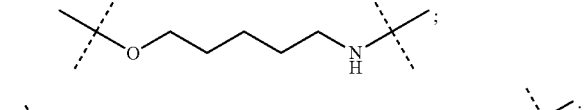
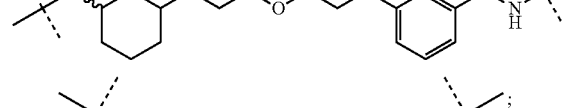
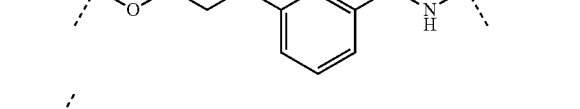
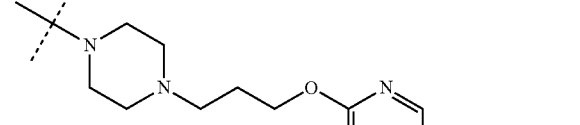
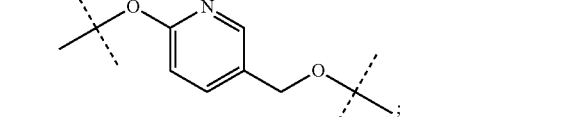
-continued
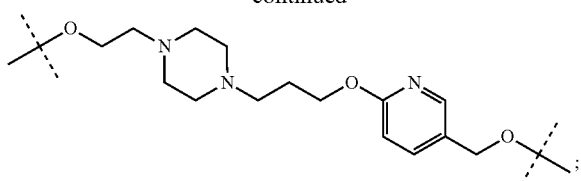
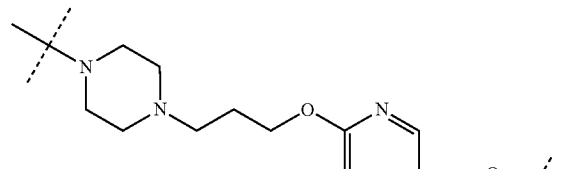
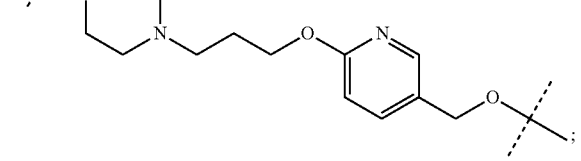
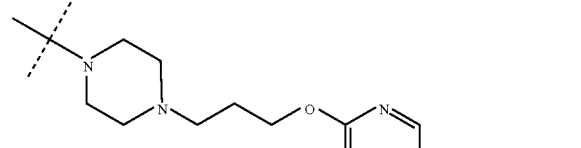
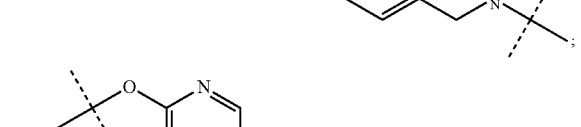
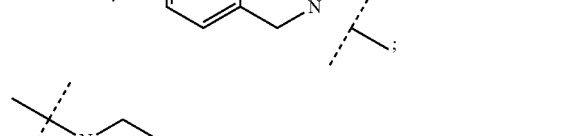
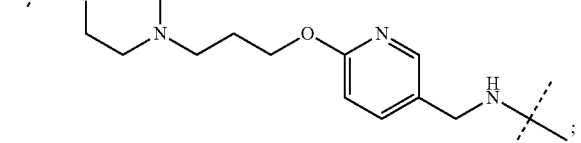
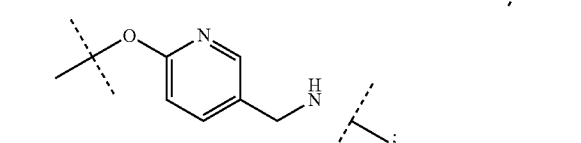
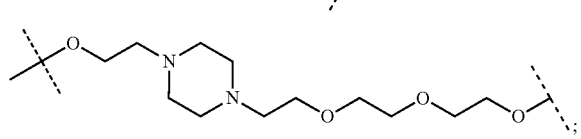
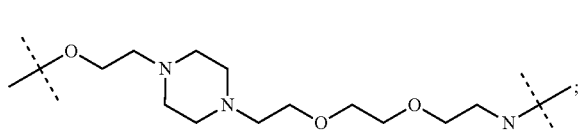

963
-continued
964
-continued
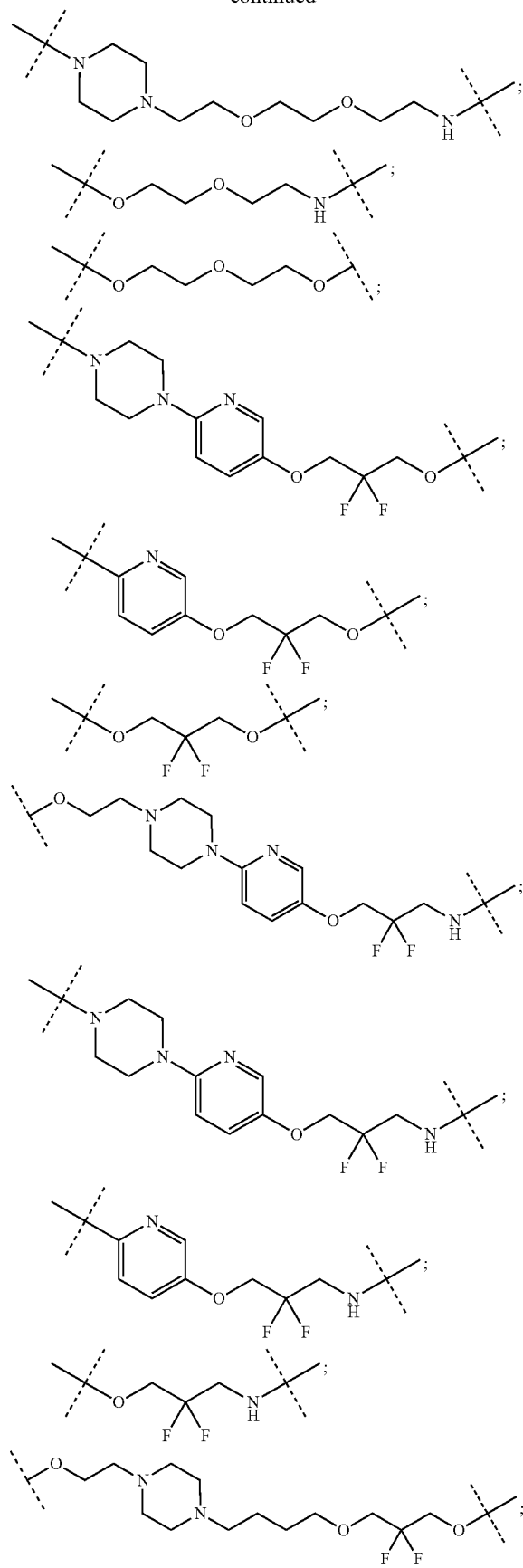
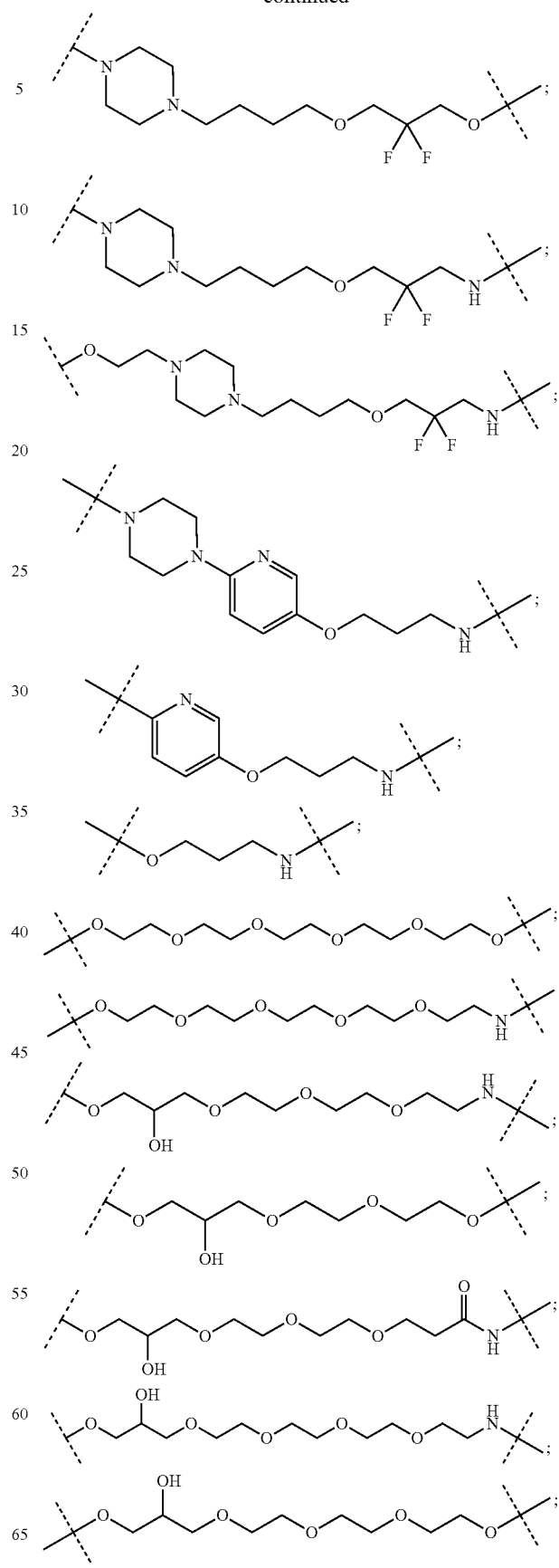

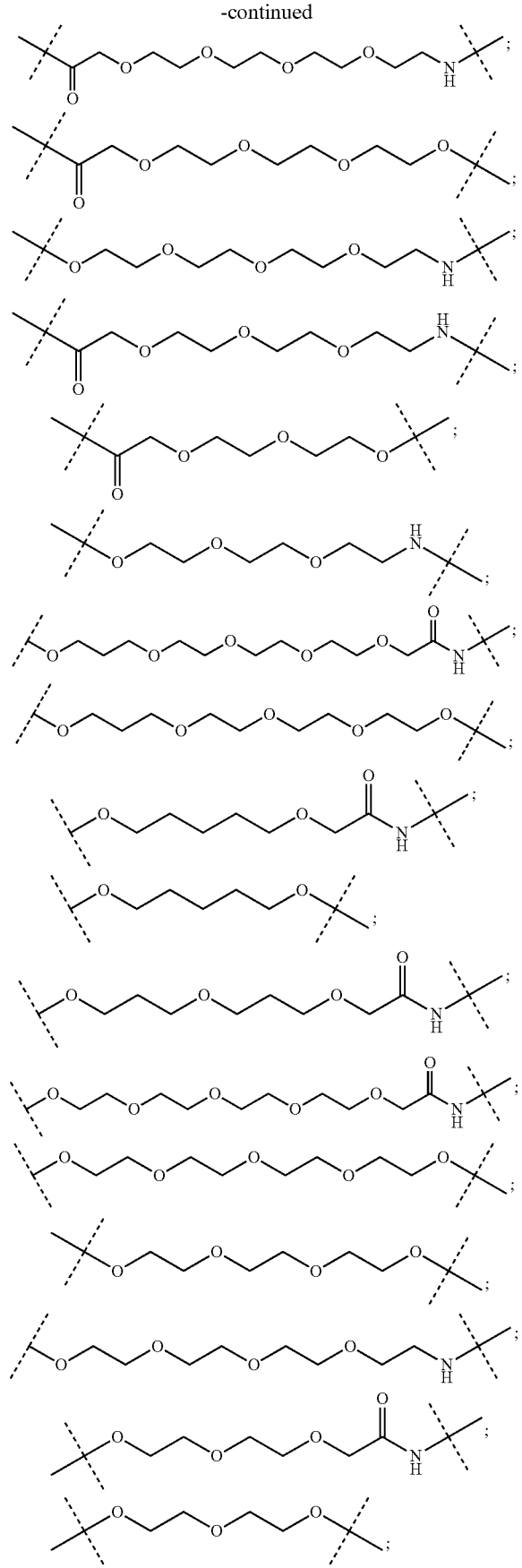
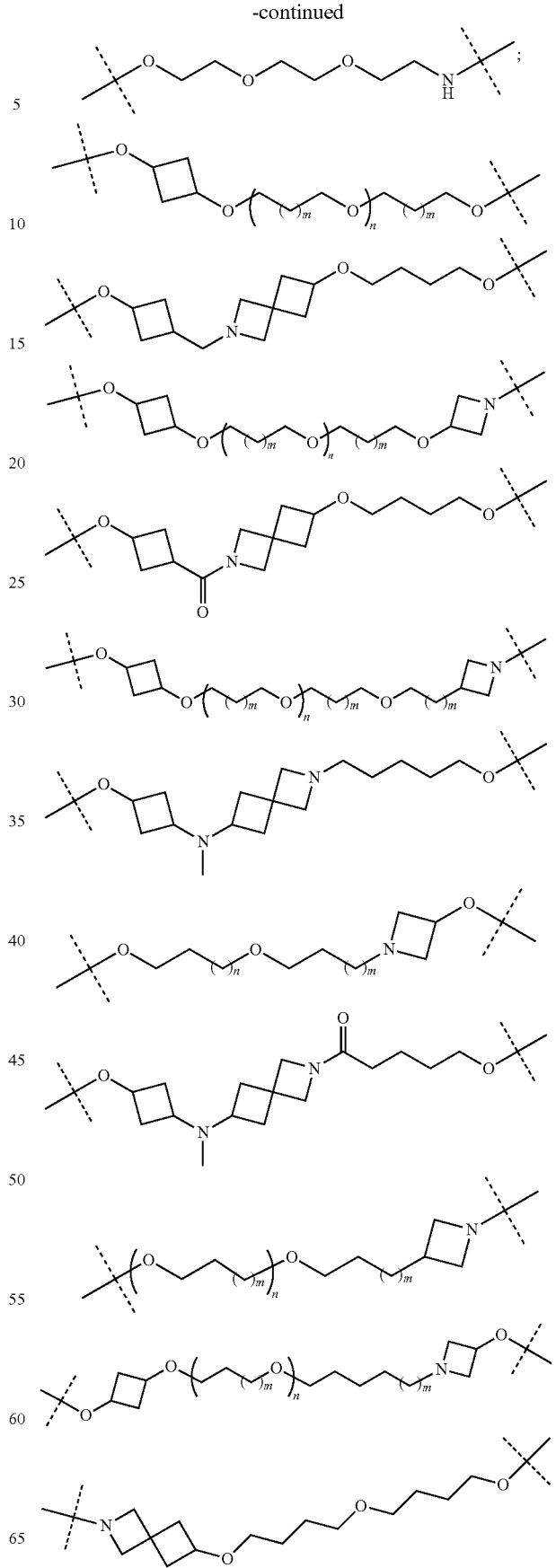

967
-continued
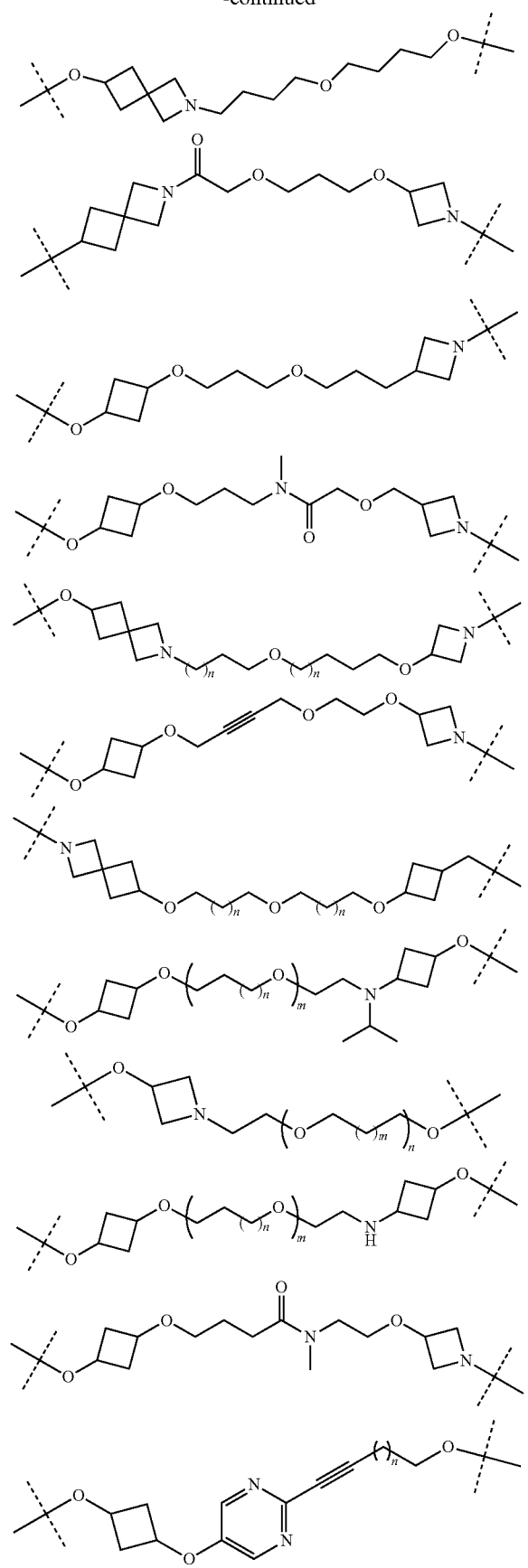
968
-continued
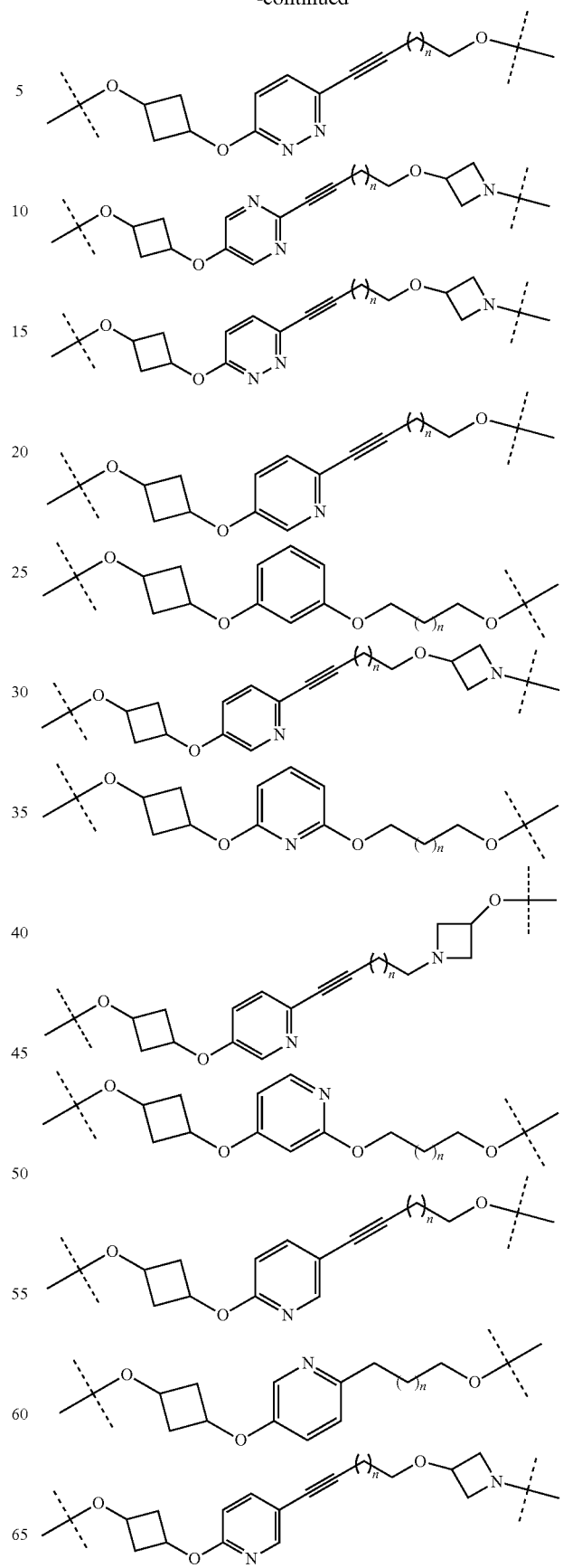

969
-continued
970
-continued
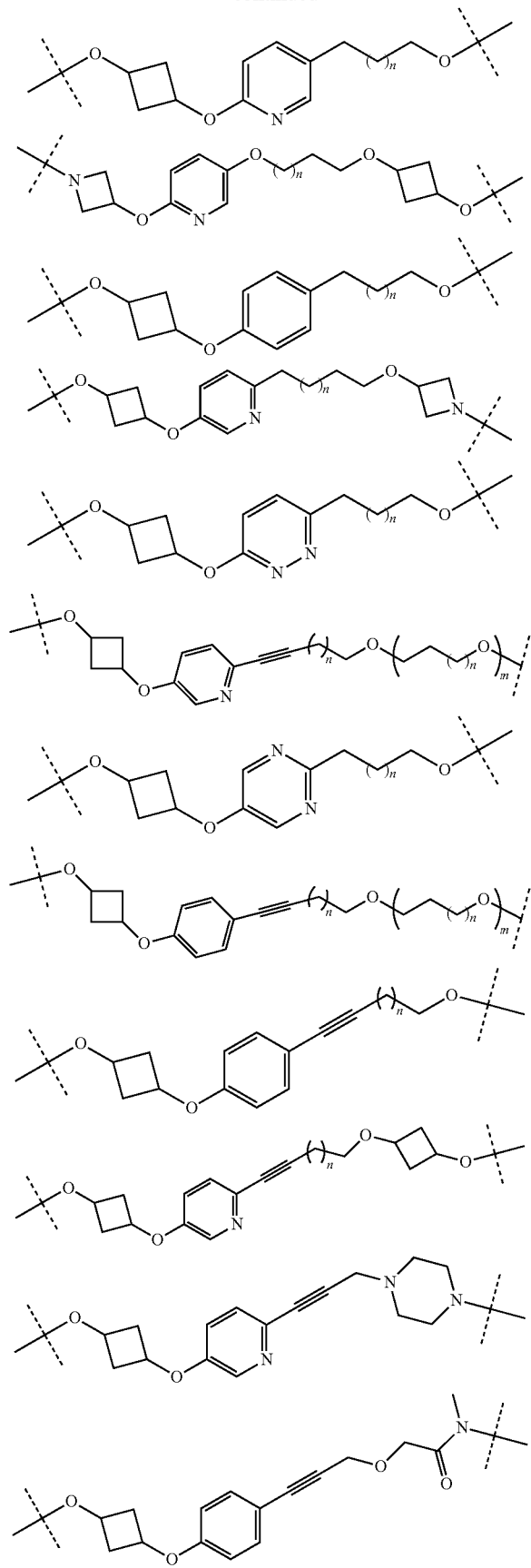
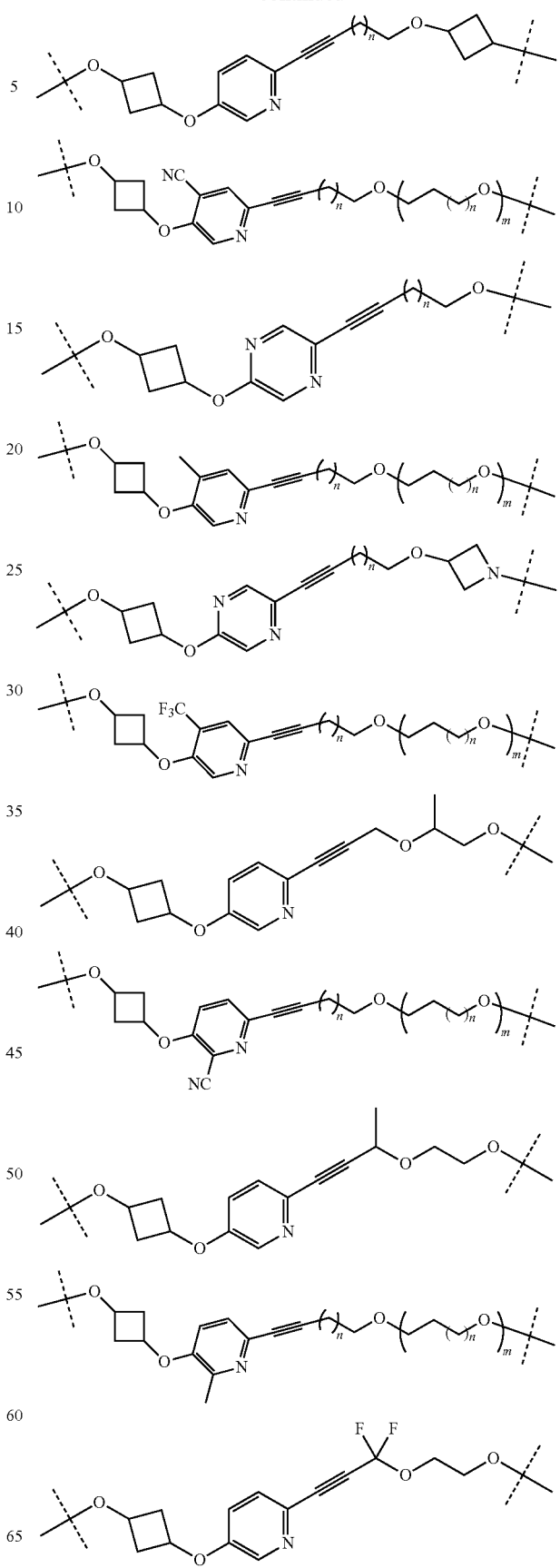

971
-continued
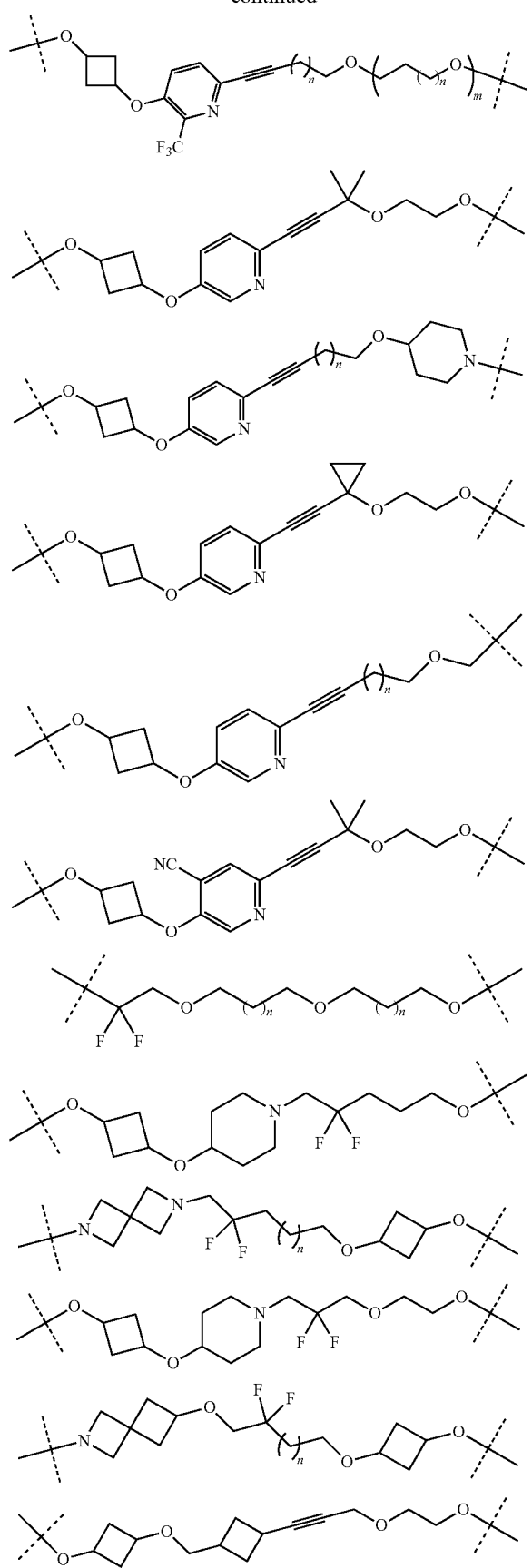
972
-continued
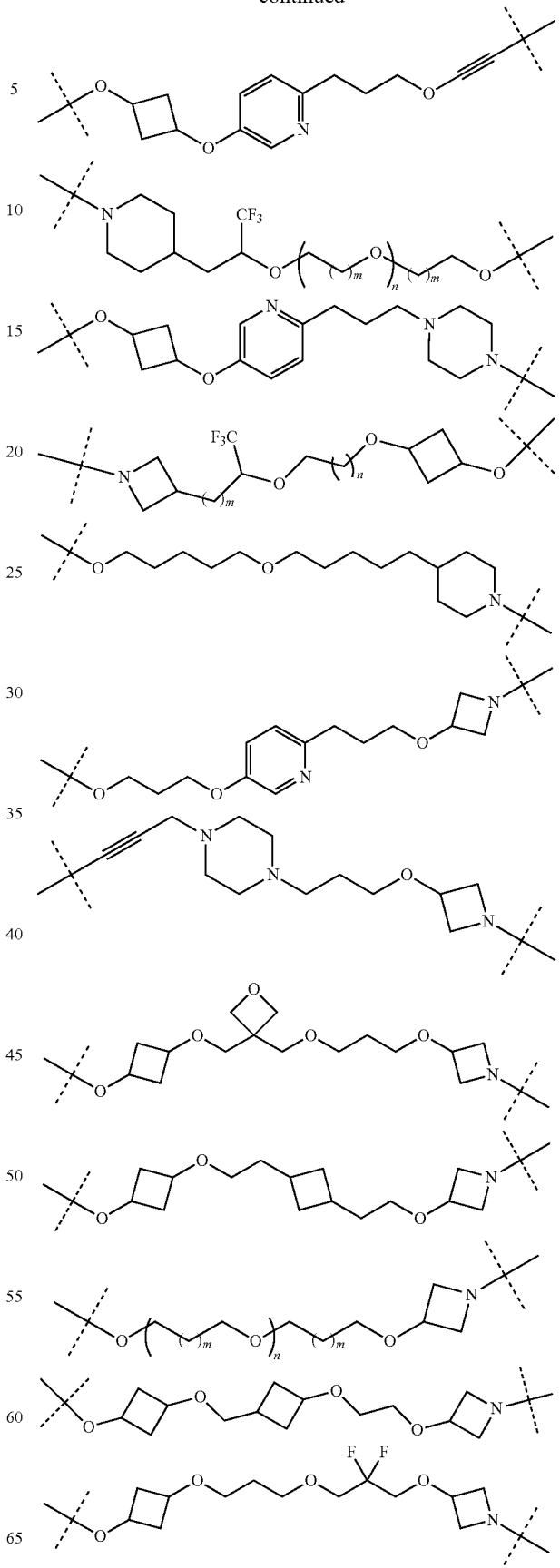

973
-continued
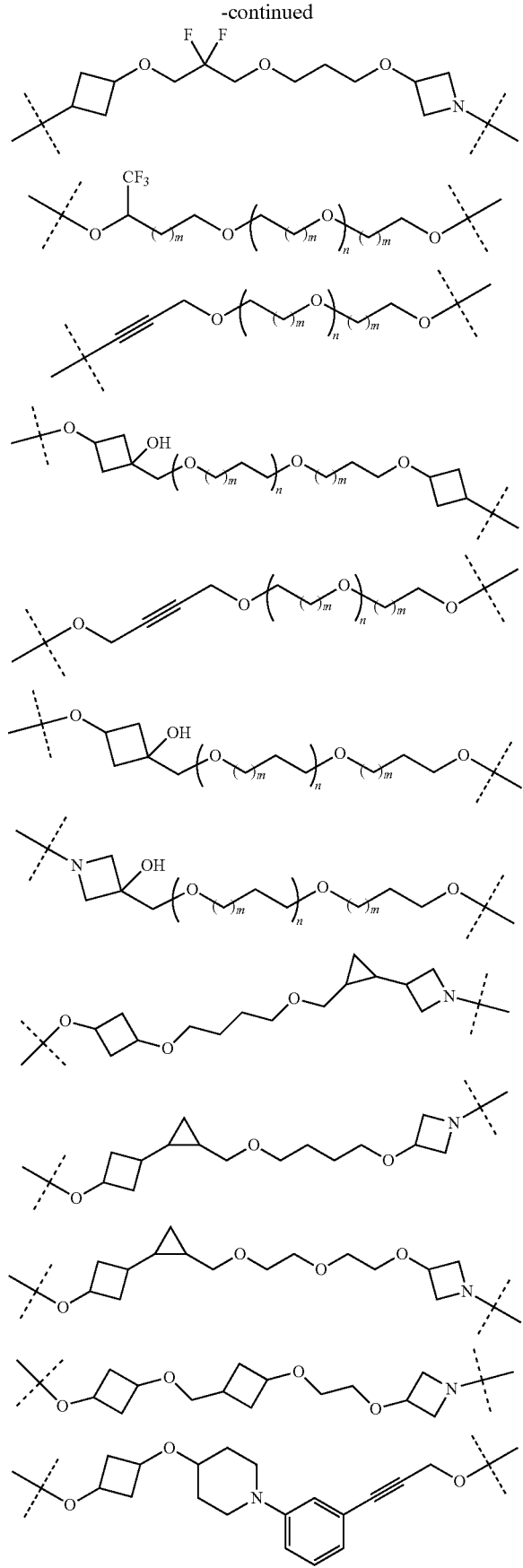
974
-continued
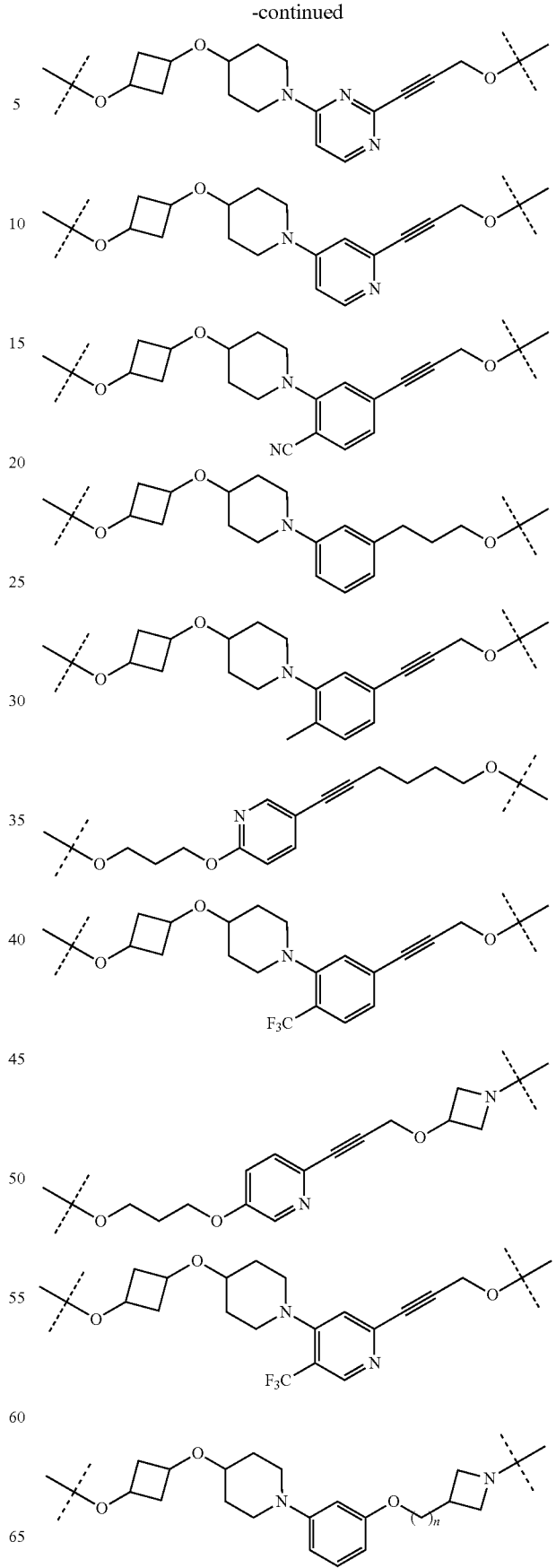

975
-continued
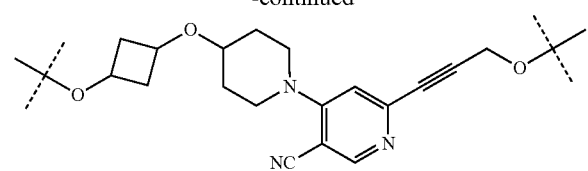
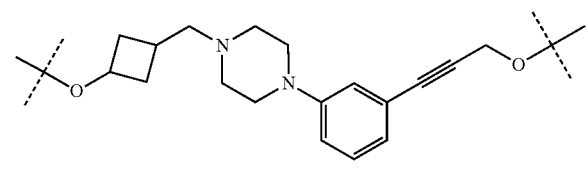
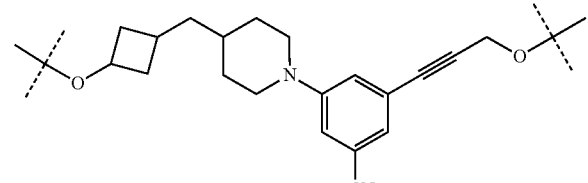
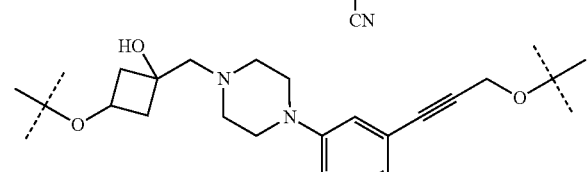
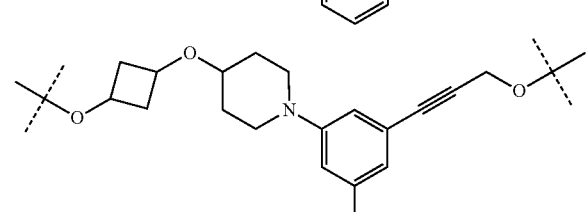
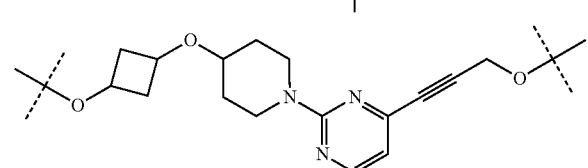
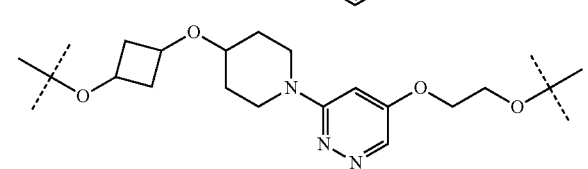
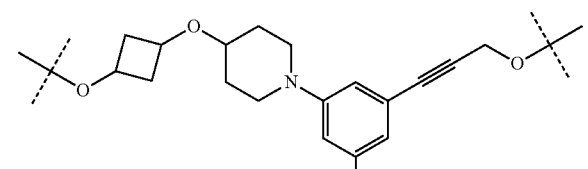
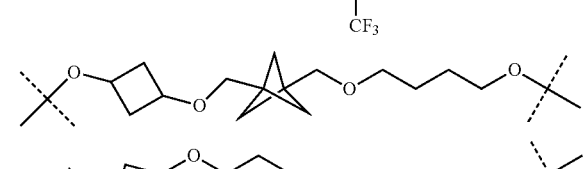
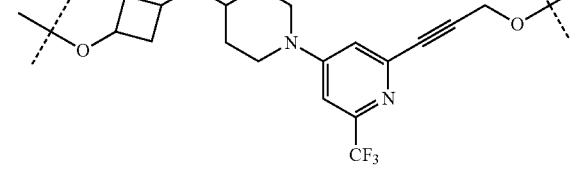
976
-continued
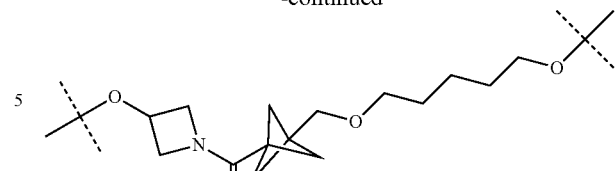
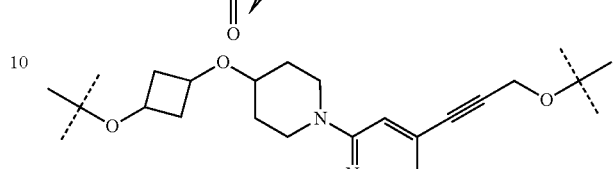
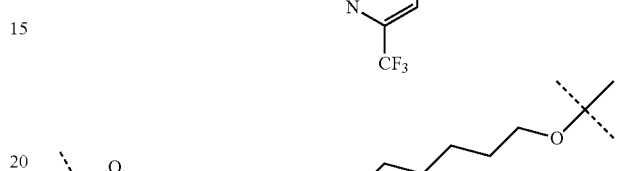
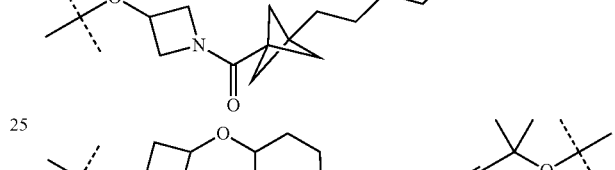
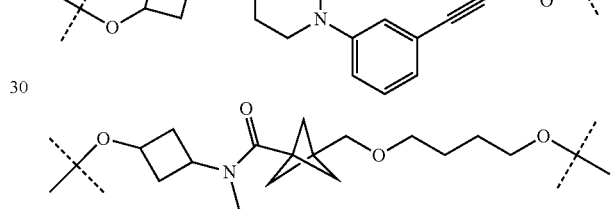
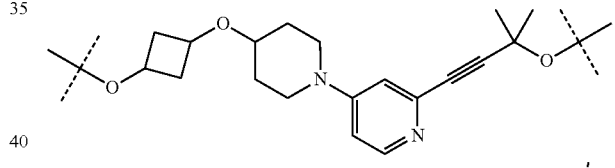
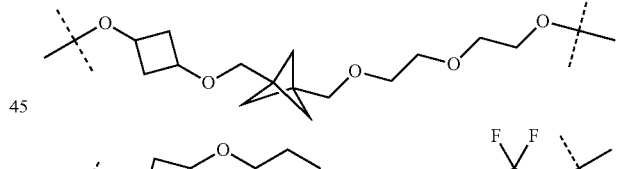
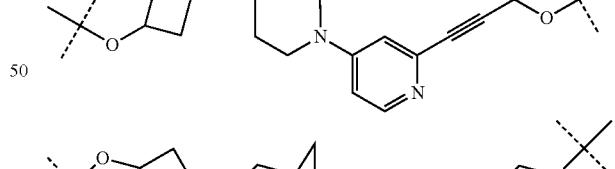
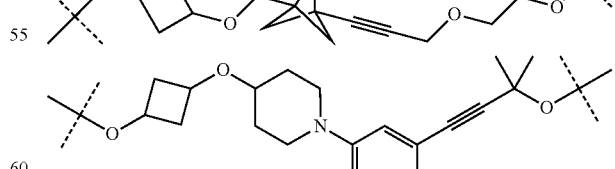
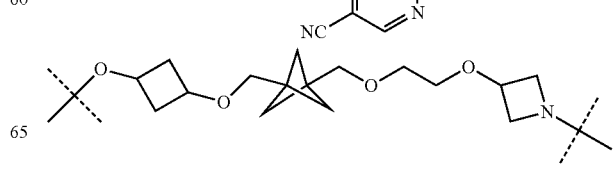

977
-continued
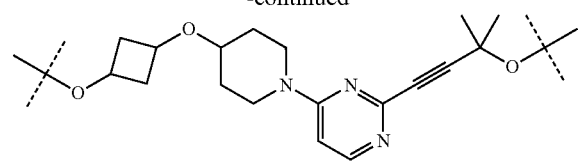
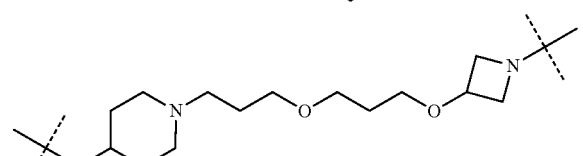
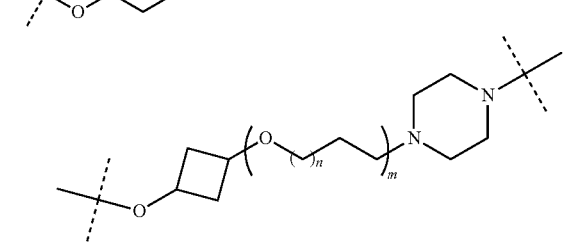
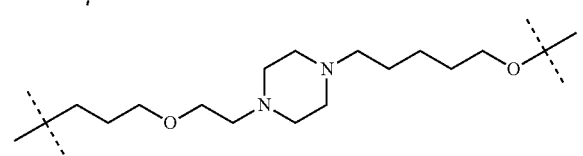
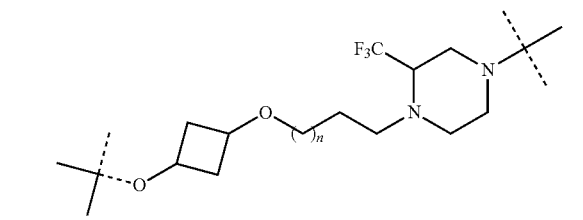
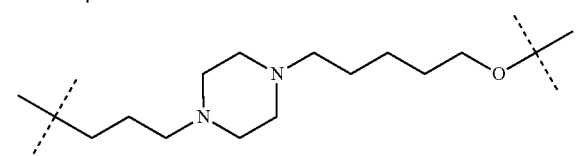
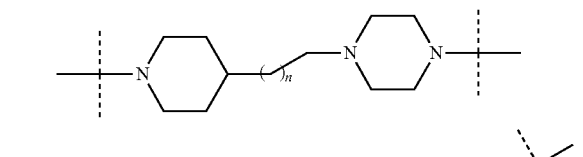
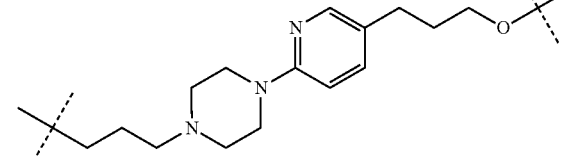
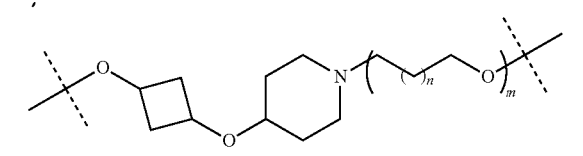
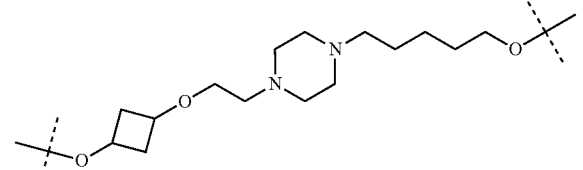
978
-continued
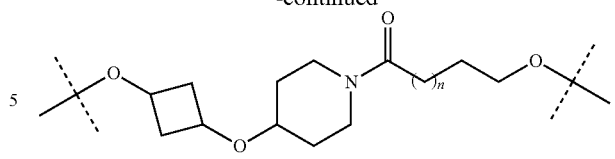
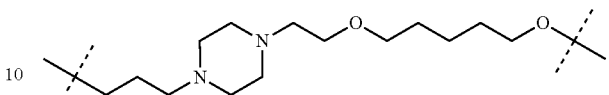
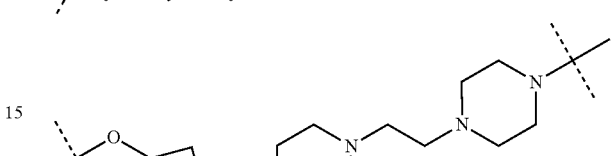
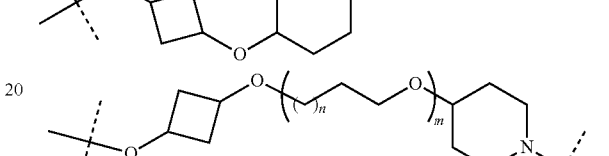
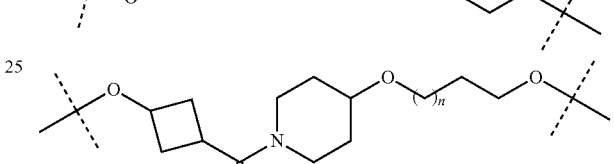
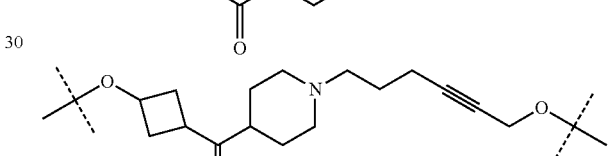
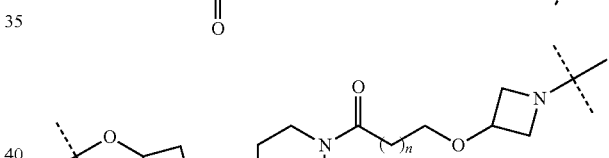
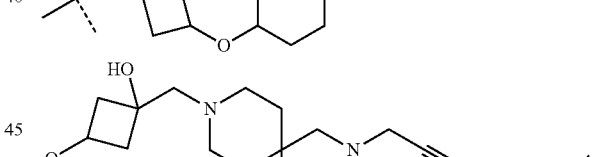
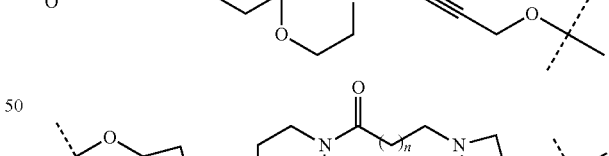
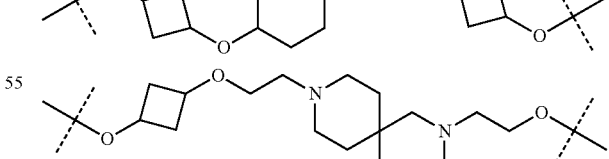
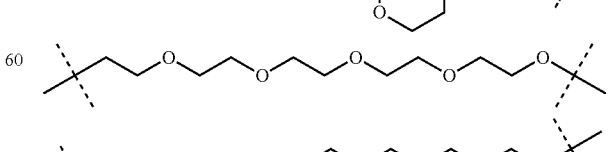
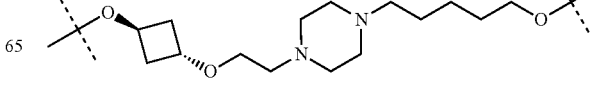

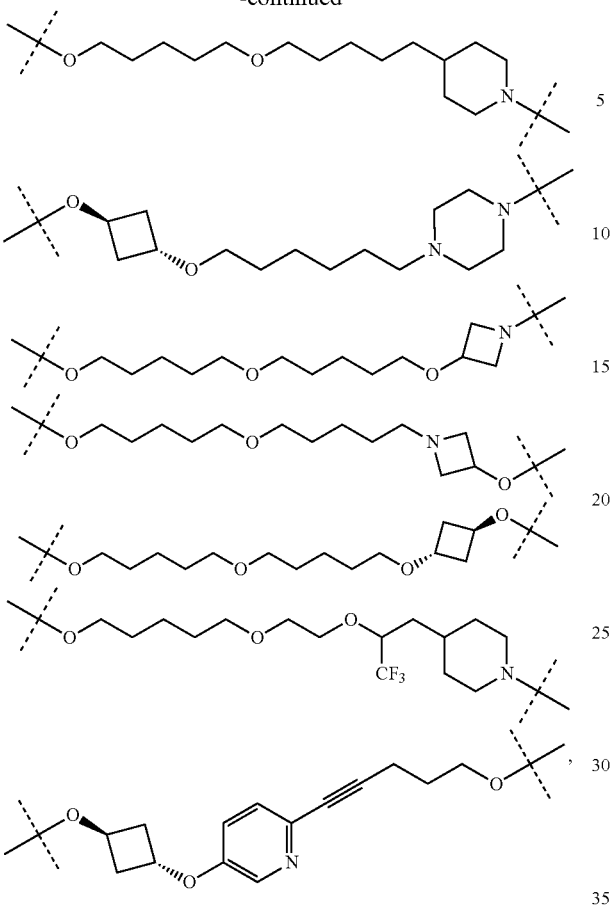

wherein each n and m is independently 0, 1, 2, 3, 4, 5, or 6.

In any aspect or embodiment described herein, the L comprises the following chemical structure:

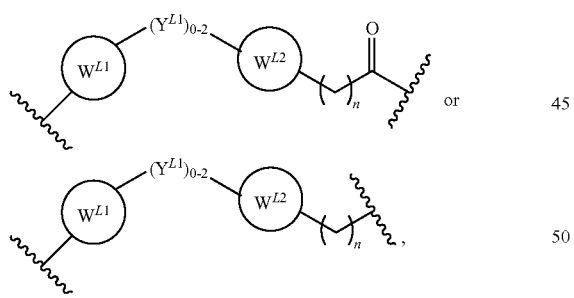

wherein:
W$^{L1}$ and W$^{L2}$ are each independently a 4-8 membered ring with 0-4 heteroatoms, optionally substituted with RQ, each RQ is independently a H, halo, OH, CN, CF$_3$, C1-C6 alkyl (linear, branched, optionally substituted), C1-C6 alkoxy (linear, branched, optionally substituted), or 2 RQ groups taken together with the atom they are attached to, form a 4-8 membered ring system containing 0-4 heteroatoms;
Y$^{L1}$ is each independently a bond, C1-C6 alkyl (linear, branched, optionally substituted) and optionally one or more C atoms are replaced with O; or C1-C6 alkoxy (linear, branched, optionally substituted); and a dashed line indicates the attachment point to the PTM or ULM moieties.

In any aspect or embodiment described herein, L comprises the following chemical structure:

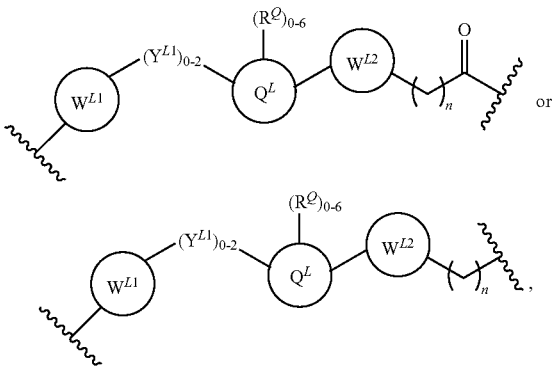

wherein:
W$^{L1}$ and W$^{L2}$ are each independently aryl, heteroaryl, cyclic, heterocyclic, C$_{1-6}$ alkyl, bicyclic, biaryl, biheteroaryl, or biheterocyclic, each optionally substituted with R$^Q$, each R$^Q$ is independently a H, halo, OH, CN, CF$_3$, hydroxyl, nitro, C≡CH, C$_{2-6}$ alkenyl, C$_{2-6}$ alkynyl, C$_1$-C$_6$ alkyl (linear, branched, optionally substituted), C$_1$-C$_6$ alkoxy (linear, branched, optionally substituted), OC$_{1-3}$alkyl (optionally substituted by 1 or more —F), OH, NH$_2$, NR$^{Y1}$R$^{Y2}$, CN, or 2 R$^Q$ groups taken together with the atom they are attached to, form a 4-8 membered ring system containing 0-4 heteroatoms;
Y$^{L1}$ is each independently a bond, NR$^{YL1}$, O, S, NR$^{YL2}$, CR$^{YL1}$R$^{YL2}$, C=O, C=S, SO, SO$_2$, C$_1$-C$_6$ alkyl (linear, branched, optionally substituted) and optionally one or more C atoms are replaced with O; C$_1$-C$_6$ alkoxy (linear, branched, optionally substituted);
Q$^L$ is a 3-6 membered alicyclic or aromatic ring with 0-4 heteroatoms, optionally bridged, optionally substituted with 0-6 R$^Q$, each R$^Q$ is independently H, C$_{1-6}$ alkyl (linear, branched, optionally substituted by 1 or more halo, C1-6 alkoxyl), or 2 R$^Q$ groups taken together with the atom they are attached to, form a 3-8 membered ring system containing 0-2 heteroatoms);
R$^{YL1}$, R$^{YL2}$ are each independently H, OH, C$_{1-6}$ alkyl (linear, branched, optionally substituted by 1 or more halo, C$_{1-6}$ alkoxyl), or R$^1$, R$^2$ together with the atom they are attached to, form a 3-8 membered ring system containing 0-2 heteroatoms);
n is 0-10; and
a dashed line indicates the attachment point to the PTM or ULM moieties.

In any aspect or embodiment described herein, the L is a polyethylenoxy group optionally substituted with aryl or phenyl comprising from 1 to 10 ethylene glycol units.

In any aspect or embodiment described herein, the compound comprises multiple ULMs, multiple PTMs, multiple linkers or any combinations thereof.

In any aspect or embodiment described herein, the compound is selected from the group consisting of Compounds 1-330 (Table 1 or Table 2).

In any aspect or embodiment described herein, the compound is selected from Table 1 or Table 2 (i.e., from compounds 1-330).

In any aspect or embodiment described herein, the compound has a chemical structure selected from Formulas CI through CV:
Formula CI
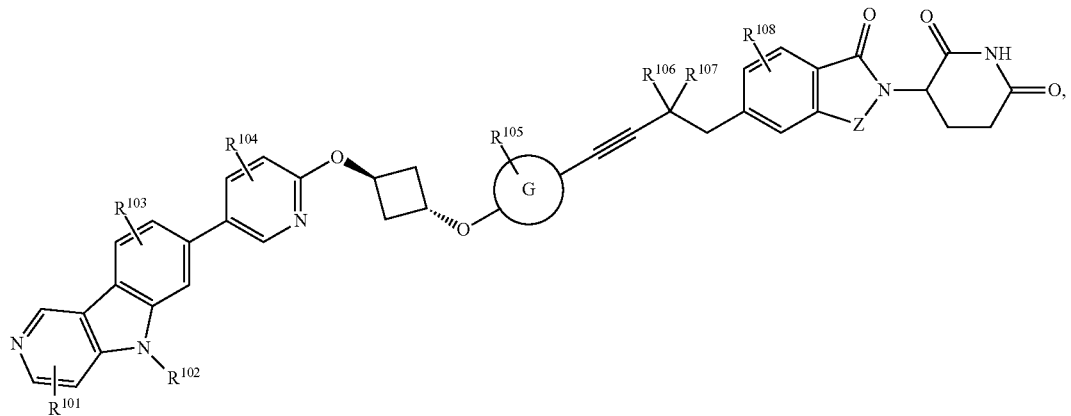
Formula CII
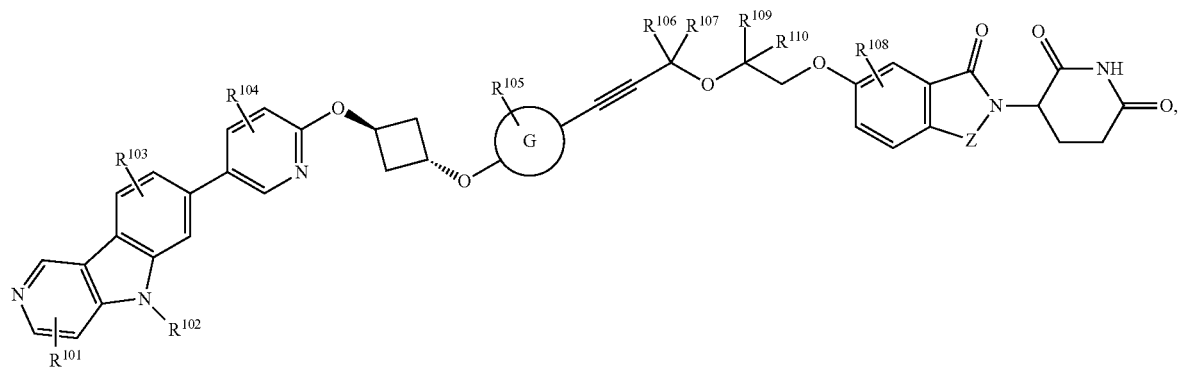
Formula CIII
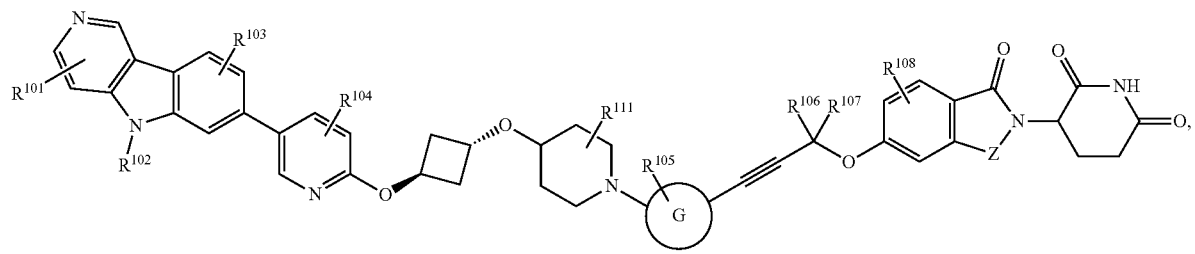
Formula CIV
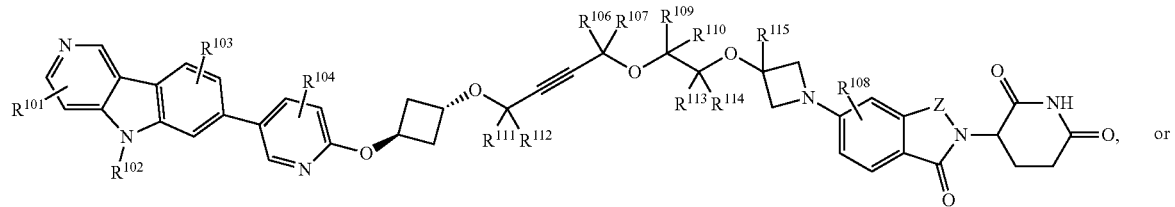
or Formula CV

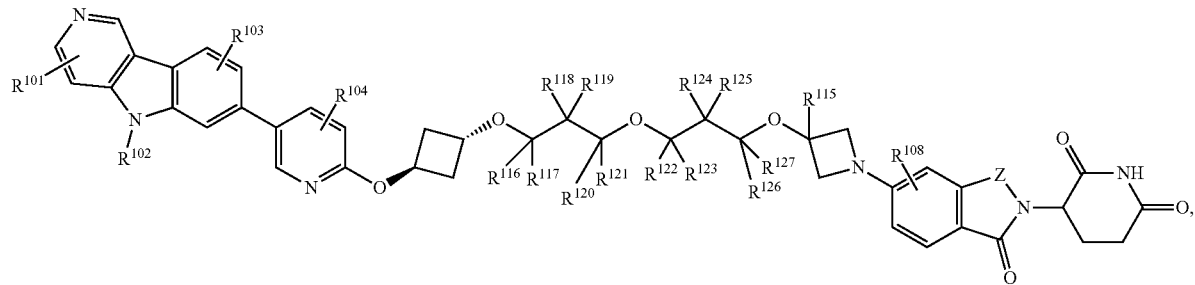

wherein:
R[101] is 1-2 substituents independently selected from H, alkyl, halogen, haloalkyl or cyano;
R[102] is selected from H, alkyl, haloalkyl, cycloalkyl or heterocycloalkyl;
R[103] is 1-2 substituents independently selected from H, alkyl, halogen, haloalkyl or cyano;
R[104] is 1-2 substituents independently selected from H, alkyl, halogen, haloalkyl or cyano;
R[105] is 1-2 substituents independently selected from H, alkyl, halogen, haloalkyl or cyano;
R[106], R[107], R[109], R[110], R[111], R[112], R[113], R[114], R[116], R[117], R[120], R[121], R[126], R[127], R[122] and R[123] are each independently selected from H, alkyl, halogen or haloalkyl;
R[108] is 1-2 substituents independently selected from H, alkyl, halogen, haloalkyl, cyano or methoxy;
R[115] is selected from H, alkyl and haloalkyl;
R[118] and R[119] are independently selected from H, alkyl, halogen or haloalkyl, or R[118] and R[119] taken together with the carbon atom to which they are attached represent a 3-6-membered cycloalkyl or heterocycloalkyl ring, such as cyclopropane or an oxetane;
R[124] and R[125] are independently selected from H, alkyl, halogen or haloalkyl, or R[124] and R[125] taken together with the carbon atom to which they are attached represent a 3-6-membered cycloalkyl or heterocycloalkyl ring, such as cyclopropane or an oxetane;
G is a phenyl or a 5- or 6-membered heteroaryl ring; and
Z is CH₂ or C=O.

A further aspect of the disclosure provides a composition comprising an effective amount of a bifunctional compound of the present disclosure, and a pharmaceutically acceptable carrier.

In any aspect or embodiment described herein, the composition further comprises at least one of additional bioactive agent, another bifunctional compound of any of claims 1-29, or a combination thereof.

In any aspect or embodiment described herein, the additional bioactive agent is an anti-neurodegenerative agent.

In any aspect or embodiment described herein, the additional bioactive agent is a P-gp inhibitor.

In any aspect or embodiment described herein, the P-gp inhibitor is Amiodarone, Azithromycin, Captopril, Clarithromycin, Cyclosporine, Piperine, Quercetin, Quinidine, Quinine, Reserpine, Ritonavir, Tariquidar, Elacridar or Verapamil.

Another aspect of the disclosure provides a composition comprising a pharmaceutically acceptable carrier and an effective amount of at least one compound of the present disclosure for treating a disease or disorder in a subject, the method comprising administering the composition to a subject in need thereof, wherein the compound is effective in treating or ameliorating at least one symptom of the disease or disorder.

In any aspect or embodiment described herein, the disease or disorder is associated with Tau accumulation and aggregation.

In any aspect or embodiment described herein, the disease or disorder is a neurodegenerative disease associated with Tau accumulation and aggregation.

In any aspect or embodiment described herein, the disease or disorder is Acquired Epileptiform Aphasia, Acute Disseminated Encephalomyelitis, ADHD, Adie's Pupil, Adie's Syndrome, Adrenoleukodystrophy, Agenesis of the Corpus Callosum, Agnosia, Aicardi Syndrome, AIDS-Neurological Complications, Alexander Disease, Alpers' Disease, Alternating Hemiplegia, Alzheimer's Disease, Amyotrophic Lateral Sclerosis, Anencephaly, Aneurysm, Angelman Syndrome, Angiomatosis, Anoxia, Aphasia, Apraxia, Arachnoid Cysts, Arachnoiditis, Arnold-Chiari Malformation, Arteriovenous Malformation, Asperger Syndrome, Ataxia, Ataxia, Telangiectasia, Ataxias and Cerebellar/Spinocerebellar Degeneration, Attention Deficit-Hyperactivity Disorder, Autism, Autonomic Dysfunction, Back Pain, Barth Syndrome Batten Disease, Becker's Myotonia, Behcet's Disease, Bell's Palsy, Benign Essential Blepharospasm, Benign Focal Amyotrophy, Benign Intracranial Hypertension, Bernhardt-Roth Syndrome, Binswanger's Disease, Blepharospasm, Bloch-Sulzberger Syndrome, Brachial Plexus Birth Injuries, Brachial Plexus Injuries, Bradbury-Eggleston Syndrome, Brain and Spinal Tumors, Brain Aneurysm, Brain Injury, Brown-Sequard Syndrome, Bulbospinal Muscular Atrophy, Canavan Disease, Carpal Tunnel Syndrome Causalgia, Cavernomas, Cavernous Angioma, Cavernous Malformation, Central Cervical Cord Syndrome, Central Cord Syndrome, Central Pain Syndrome, Cephalic Disorders, Cerebellar Degeneration, Cerebellar Hypoplasia, Cerebral Aneurysm, Cerebral Arteriosclerosis, Cerebral Atrophy, Cerebral Beriberi, Cerebral Gigantism, Cerebral Hypoxia, Cerebral Patsy, Cerebro-Oculo-Facio-Skeletal Syndrome, Charcot-Marie-Tooth Disease, Chiari Malformation, Chorea, Choreoacanthocytosis, Chronic Inflammatory Demyelinating Polyneuropathy (CIDP), Chronic Orthostatic Intolerance, Chronic Pain Cockayne Syndrome Type II, Coffin Lowry Syndrome, COFS, Colpocephaly, Coma and Persistent Vegetative State, Complex Regional Pain Syndrome, Congenital Facial Diplegia, Congenital Myasthenia, Congenital Myopathy, Congenital Vascular Cavernous, Malformations, Corticobasal Degeneration, Cranial Arteritis, Craniosynostosis, Creutzfeldt-Jakob Disease, Cumulative Trauma Disorders, Cushing's Syndrome, Cytomegalic Inclusion Body Disease, Cytomegalovirus Infection, Dancing Eyes-Dancing Feet Syndrome, Dandy-Walker Syndrome, Dawson Disease, De Morsier's Syndrome, Deep Brain Stimulation for Parkinson's Disease, Dejerine-Klumpke Palsy, Dementia, Dementia-Multi-Infarct, Dementia-Semantic, Dementia-Subcortical, Dementia With Lewy Bodies, Dentate Cerebellar Ataxia, Dentatorubral Atrophy, Dermatomyositis, Developmental Dyspraxia, Devic's Syndrome, Diabetic Neuropathy, Diffuse Sclerosis, Dysautonomia, Dysgraphia, Dyslexia, Dysphagia, Dyspraxia, Dyssynergia Cerebellaris, Myoclonica, Dyssynergia Cerebellaris Progressiva, Dystonias, Early Infantile Epileptic, Encephalopathy, Empty Sella Syndrome, Encephalitis Lethargica, Encephaloceles, Encephalopathy, Encephalotrigeminal Angiomatosis, Epilepsy, Erb-Duchenne and Dejerine-Klumpke Palsies, Erb's Palsy, Fabry's Disease, Fahr's Syndrome, Fainting, Familial Dysautonomia, Familial Hemangioma, Familial Idiopathic Basal Ganglia, Calcification, Familial Periodic Paralyses, Familial Spastic Paralysis, Febrile Seizures, Fisher Syndrome, Floppy Infant Syndrome, Friedreich's Ataxia, Frontotemporal, Dementia, Gaucher's Disease, Gerstmann's Syndrome, Gerstmann-Straussler-Scheinker, Disease, Giant Cell Arteritis, Giant Cell Inclusion Disease, Globoid Cell Leukodystrophy, Glossopharyngeal Neuralgia, Guillain-Barre Syndrome, Hallervorden-Spatz Disease, Head Injury, Headache, Hemicrania Continua, Hemifacial Spasm, Hemiplegia Alterans, Hereditary Neuropathies, Hereditary Spastic Paraplegia, Heredopathia Atactica Polyneuritiformis, Herpes Zoster, Herpes Zoster Oticus, Hirayama Syndrome, Holmes-Adie syndrome, Holoprosencephaly, HTLV-1 Associated, Myelopathy, Huntington's Disease, Hydranencephaly, Hydrocephalus, Hydrocephalus-Normal Pressure, Hydromyelia, Hyperactivity, Hypercortisolism, Hypersomnia, Hypertonia, Hypotonia,—Infantile, Hypoxia, Immune-Mediated Encephalomyelitis, Inclusion Body Myositis, Incontinentia Pigmenti, Infantile Hypotonia, Infantile Neuroaxonal Dystrophy, Infantile Phytanic Acid Storage Disease, Infantile Refsum Disease, Infantile Spasms, Inflammatory Myopathy, Iniencephaly, Intestinal Lipodystrophy, Intracranial Cysts, Intracranial Hypertension, Isaac's Syndrome, Joubert Syndrome, Kearns-Sayre Syndrome, Kennedy's Disease, Kinsbourne syndrome, Kleine-Levin Syndrome, Klippel-Feil Syndrome, Klippel-Trenaunay Syndrome (KTS), Kliver-Bucy Syndrome, Korsakoffs Amnesic Syndrome, Krabbe Disease, Kugelberg-Welander Disease, Kuru, Lambert-Eaton Myasthenic Syndrome, Landau-Kleffner Syndrome, Lateral Femoral, Cutaneous Nerve Entrapment, Lateral Medullary Syndrome, Learning Disabilities, Leigh's Disease, Lennox-Gastaut Syndrome, Lesch-Nyhan Syndrome, Leukodystrophy, Levine-Critchley Syndrome, Lewy Body Dementia, Lipid Storage Diseases, Lissencephaly, Locked-In Syndrome, Lou Gehrig's Disease, Lupus-Neurological, Sequelae, Lyme Disease-Neurological Complications, Machado-Joseph Disease, Macrencephaly, Mania, Megalencephaly, Melkersson-Rosenthal Syndrome, Meningitis, Meningitis and Encephalitis, Menkes Disease, Meralgia Paresthetica, Metachromatic, Leukodystrophy, Microcephaly, Migraine, Miller Fisher Syndrome, Mini-Strokes, Mitochondrial Myopathies, Mobius Syndrome, Monomelic Amyotrophy, Motor Neuron Diseases, Moyamoya Disease, Mucolipidoses, Mucopolysaccharidoses, Multifocal Motor Neuropathy, Multi-Infarct Dementia, Multiple Sclerosis, Multiple System Atrophy, Multiple System Atrophy with Orthostatic Hypotension, Muscular Dystrophy, Myasthenia-Congenital, Myasthenia Gravis, Myelinoclastic Diffuse Sclerosis, Myoclonic Encephalopathy of Infants, Myoclonus, Myopathy, Myopathy-Congenital, Myopathy-Thyrotoxic, Myotonia, Myotonia Congenita, Narcolepsy, Neuroacanthocytosis, Neurodegeneration with Brain Iron Accumulation, Neurofibromatosis, Neuroleptic Malignant Syndrome, Neurological Complications of AIDS, Neurological Complications Of Lyme Disease, Neurological Consequences of Cytomegalovirus Infection, Neurological Manifestations of Pompe Disease, Neurological Sequelae Of Lupus, Neuromyelitis Optica, Neuromyotonia, Neuronal Ceroid, Lipofuscinosis, Neuronal Migration Disorders, Neuropathy-Hereditary, Neurosarcoidosis, Neurotoxicity, Nevus Cavernosus, Niemann-Pick Disease, Normal Pressure Hydrocephalus, Occipital Neuralgia, Obesity, Occult Spinal Dysraphism Sequence, Ohtahara Syndrome, Olivopontocerebellar Atrophy, Opsoclonus Myoclonus, Orthostatic Hypotension, O'Sullivan-McLeod Syndrome, Overuse Syndrome, Pain-Chronic, Paine, Pantothenate Kinase-Associated Neurodegeneration, Paraneoplastic Syndromes, Paresthesia, Parkinson's Disease, Paroxysmal Choreoathetosis, Paroxysmal Hemicrania, Parry-Romberg, Pelizaeus-Merzbacher Disease, Pena Shokeir II Syndrome, Perineural Cysts, Periodic Paralyses, Peripheral Neuropathy, Periventricular Leukomalacia, Persistent Vegetative State, Pervasive Developmental Disorders, Phytanic Acid Storage Disease, Pick's Disease, Pinched Nerve, Piriformis Syndrome, Pituitary Tumors, Polymyositis, Pompe Disease, Porencephaly, Postherpetic Neuralgia, Postinfectious Encephalomyelitis, Post-Polio Syndrome, Postural Hypotension, Postural Orthostatic, Tachycardia Syndrome, Postural Tachycardia Syndrome, Primary Dentatum Atrophy, Primary Lateral Sclerosis, Primary Progressive Aphasia, Prion Diseases, Progressive Hemifacial Atrophy, Progressive Locomotor Ataxia, Progressive Multifocal, Leukoencephalopathy, Progressive Sclerosing Poliodystrophy, Progressive Supranuclear, Palsy, Prosopagnosia, Pseudotumor Cerebri, Ramsay Hunt Syndrome I (formerly known as), Ramsay Hunt Syndrome II (formerly known as), Rasmussen's Encephalitis, Reflex Sympathetic Dystrophy Syndrome, Refsum Disease, Refsum Disease-Infantile, Repetitive Motion Disorders, Repetitive Stress Injuries, Restless Legs Syndrome, Retrovirus-Associated Myelopathy, Rett Syndrome, Reye's Syndrome, Riley-Day Syndrome, Sacral Nerve Root Cysts, Saint Vitus Dance, Salivary Gland Disease, Sandhoff Disease, Schilder's Disease, Schizencephaly, Seitelberger Disease, Seizure Disorder, Semantic Dementia, Septo-Optic Dysplasia, Shaken Baby Syndrome, Shingles Shy-Drager Syndrome, Sjogren's Syndrome, Sleep Apnea, Sleeping Sickness, Sotos Syndrome, Spasticity, Spina Bifida, Spinal Cord Infarction, Spinal Cord Injury, Spinal Cord Tumors, Spinal Muscular Atrophy, Spinocerebellar Atrophy, Spinocerebellar, Degeneration, Steele-Richardson-Olszewski Syndrome, Stiff-Person Syndrome, Striatonigral Degeneration, Stroke, Sturge-Weber Syndrome, Subacute Sclerosing Panencephalitis, Subcortical Arteriosclerotic Encephalopathy, SUNCT Headache Swallowing Disorders, Sydenham Chorea, Syncope, Syphilitic Spinal Sclerosis, Syringohydromyelia, Syringomyelia, Systemic Lupus Erythematosus, Tabes Dorsalis Tardive Dyskinesia, Tarlov Cysts, Tay-Sachs Disease, Temporal Arteritis, Tethered Spinal Cord Syndrome, Thomsen's Myotonia, Thoracic Outlet Syndrome, Thyrotoxic Myopathy, Tic Douloureux, Todd's Paralysis, Tourette Syndrome, Transient Ischemic Attack, Transmissible Spongiform Encephalopathies, Transverse Myelitis, Traumatic Brain Injury, Tremor, Trigeminal Neuralgia, Tropical Spastic Paraparesis, Tuberous Sclerosis, Vascular Erectile Tumor, Vasculitis including Temporal Arteritis, Von Economo's Disease, Von Hippel-Lindau Disease (VHL), Von Recklinghausen's Disease, Wallenberg's Syndrome, Werdnig-Hoffman Disease, Wernicke-Korsakoff Syndrome, West Syndrome, Whiplash, Whipple's Disease, Williams Syndrome, Wilson's Disease, X-Linked Spinal and Bulbar Muscular Atrophy, or Zellweger Syndrome.

In any aspect or embodiment described herein, the disease or disorder is a neurological disorder with at least one of Huntington's disease, muscular dystrophy, Parkinson's disease, Alzheimer's disease, Batten disease, Injuries to the spinal cord and brain, Seizure disorders, epilepsy, brain tumors, meningitis, autoimmune diseases such as multiple sclerosis, neurofibromatosis, Depression, Amyotrophic Lateral Sclerosis, Arteriovenous Malformation, Brain Aneurysm, Dural Arteriovenous Fistulae, Headache, Memory Disorders, Peripheral Neuropathy, Post-Herpetic Neuralgia, Spinal Cord Tumor and Stroke.

In any aspect or embodiment described herein, the disease or disorder is Alzheimer's disease.

1027                                -continued                                1028
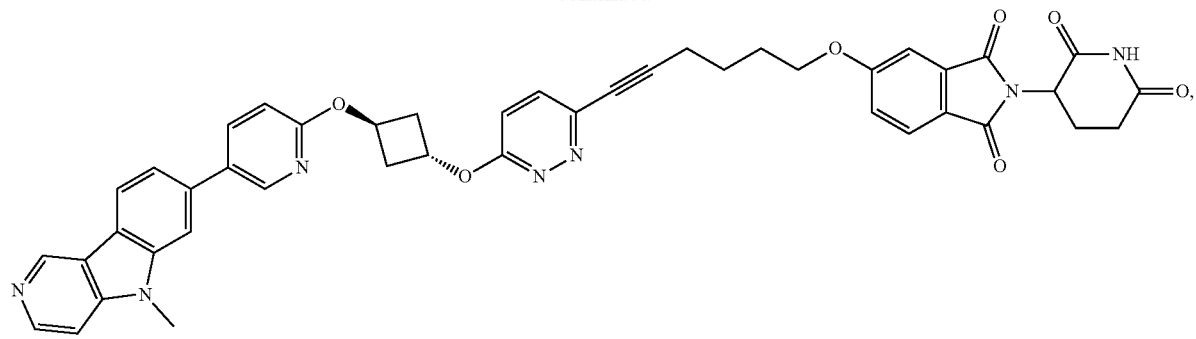
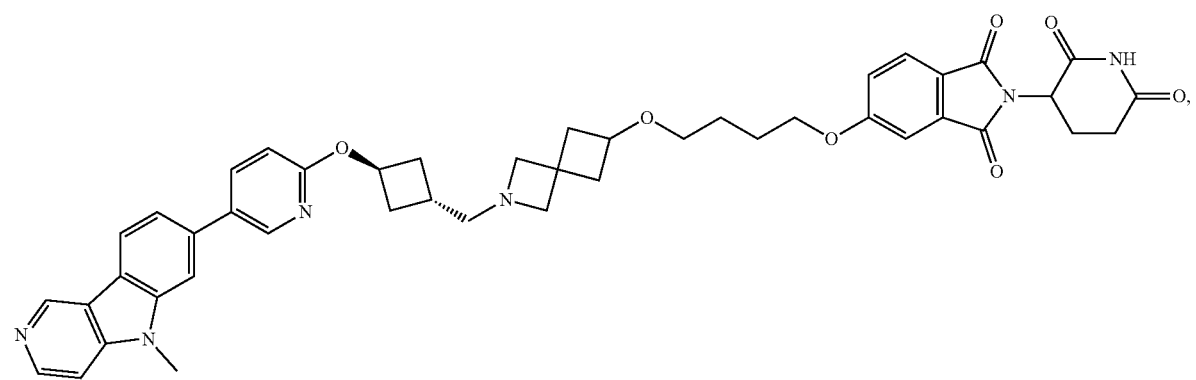
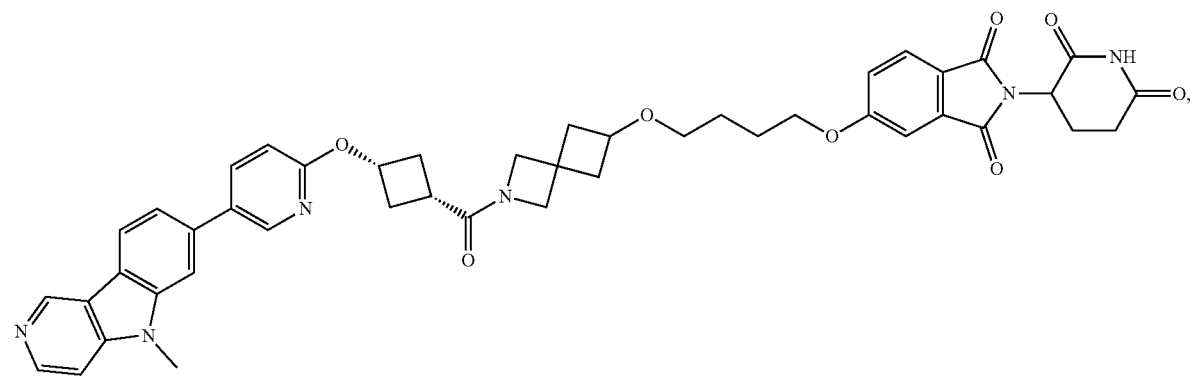
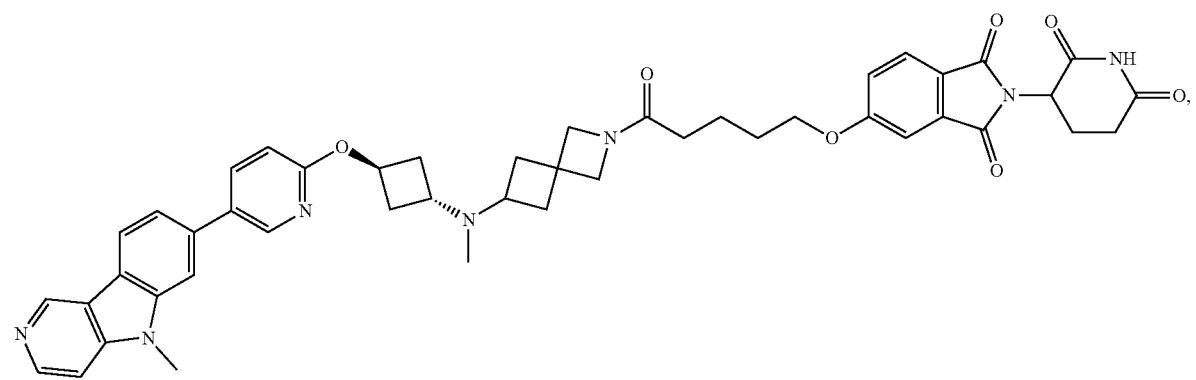

1029 1030
-continued
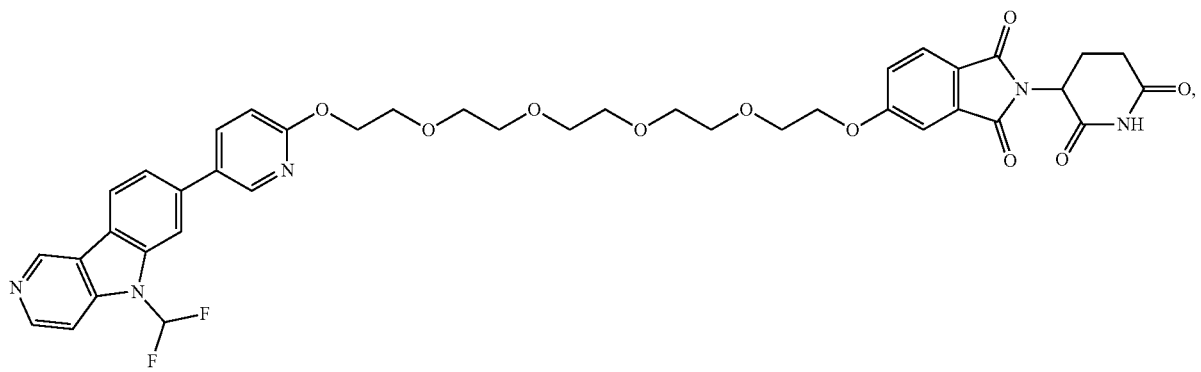
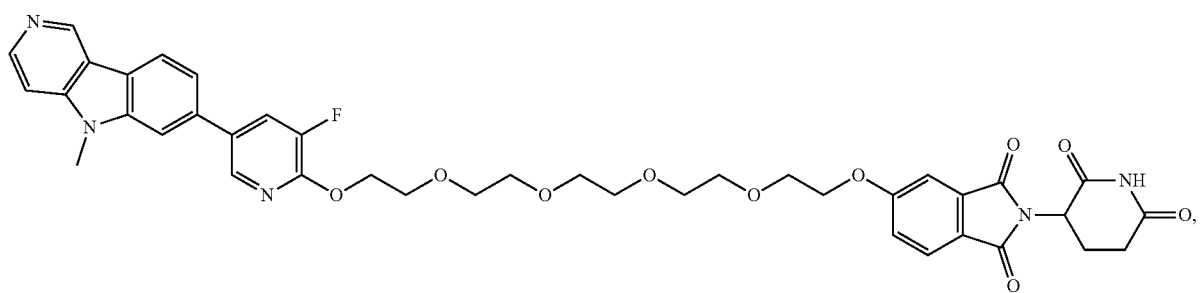
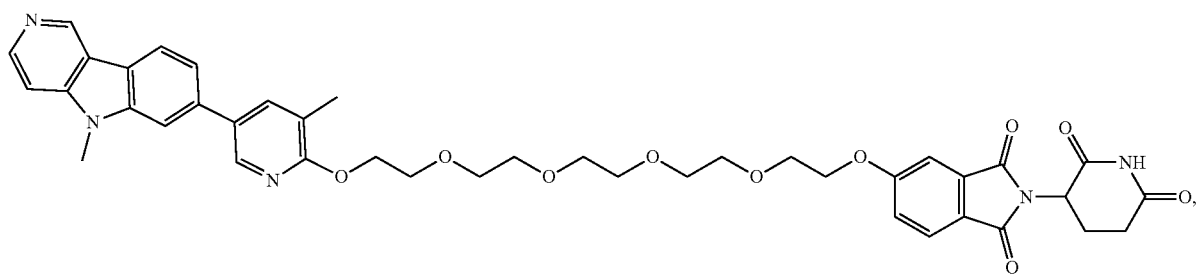
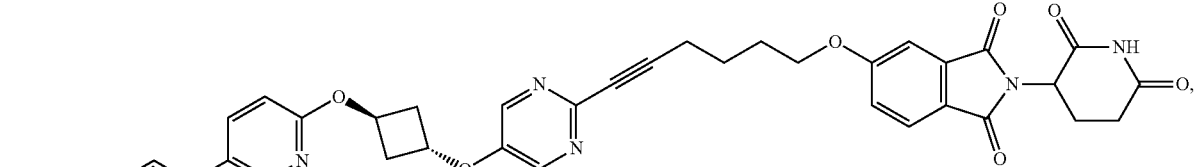
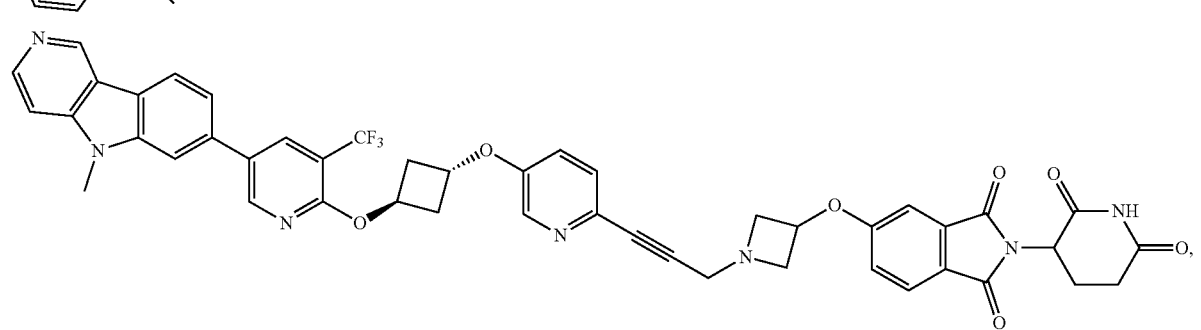

1031 1032
-continued
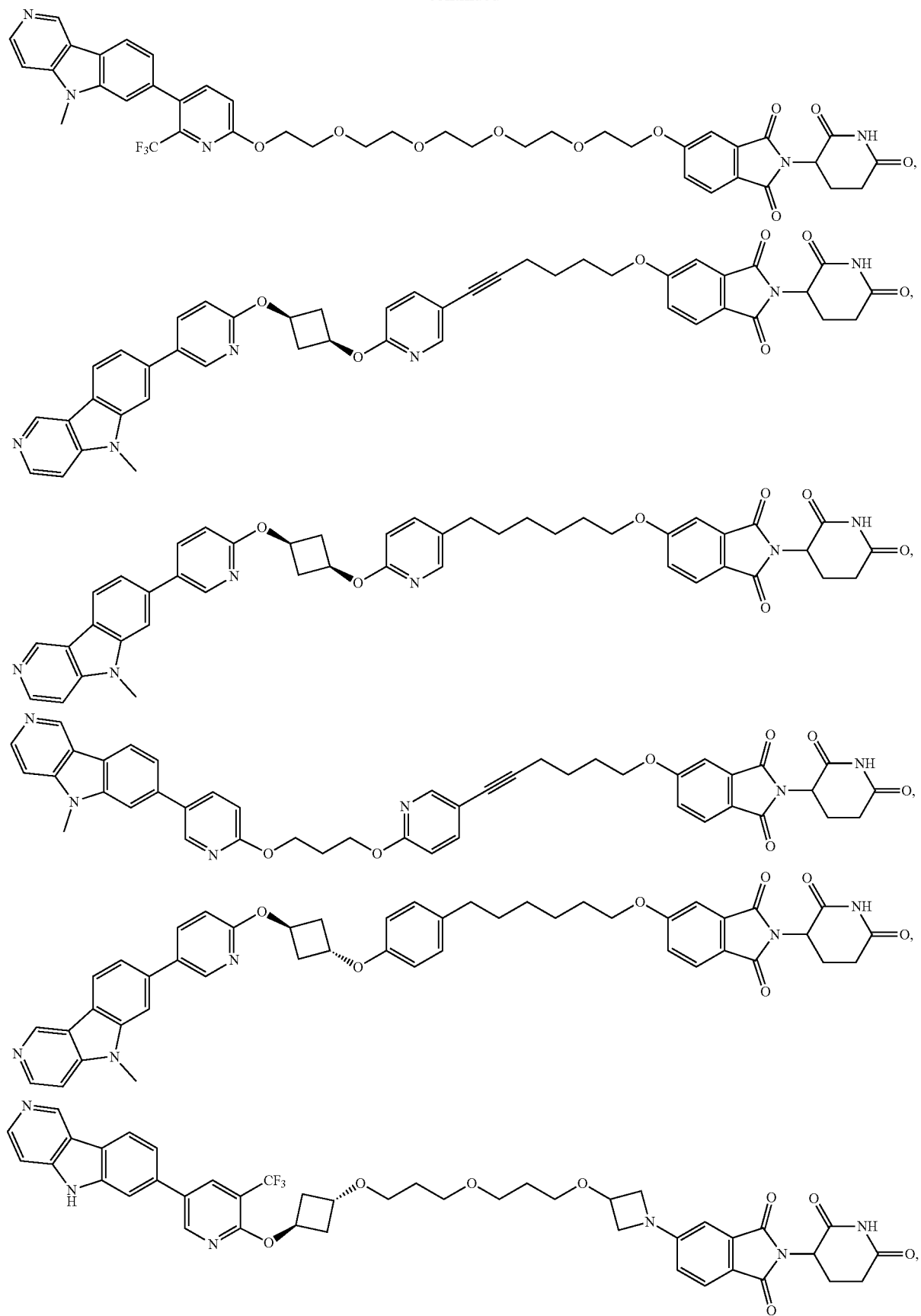

1033                                      1034
-continued
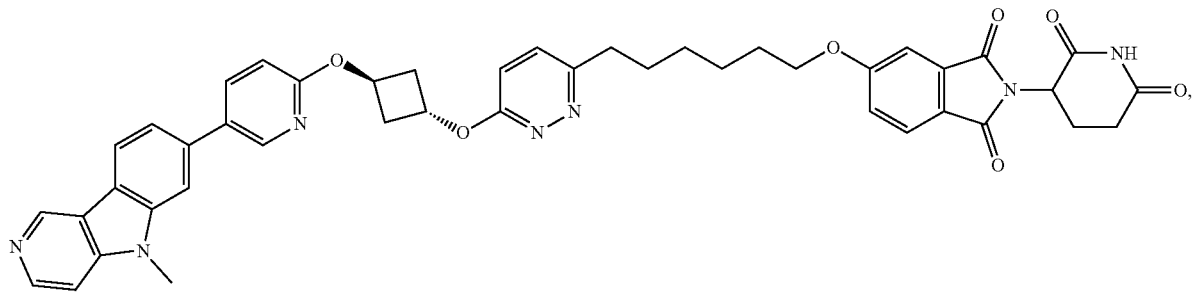
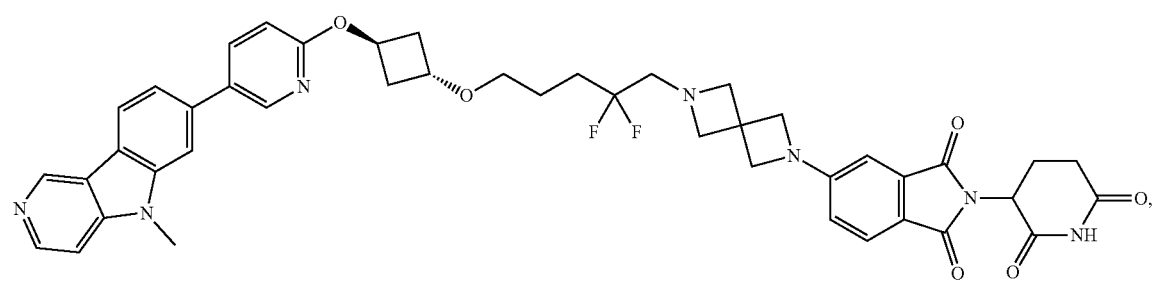
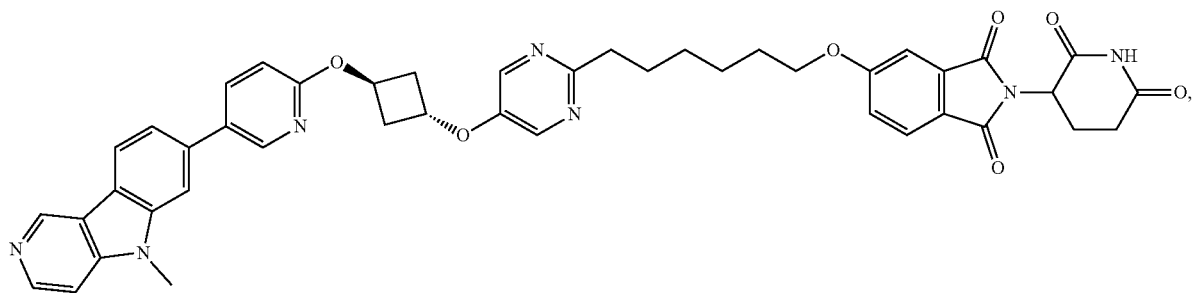
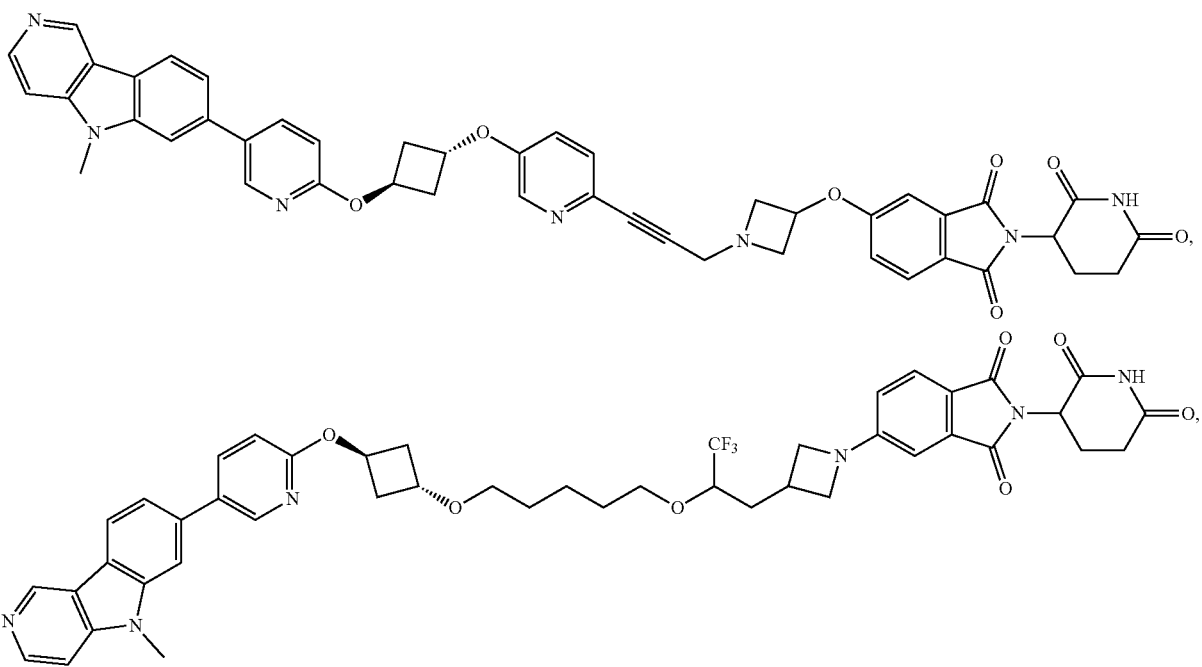

1035 1036
-continued
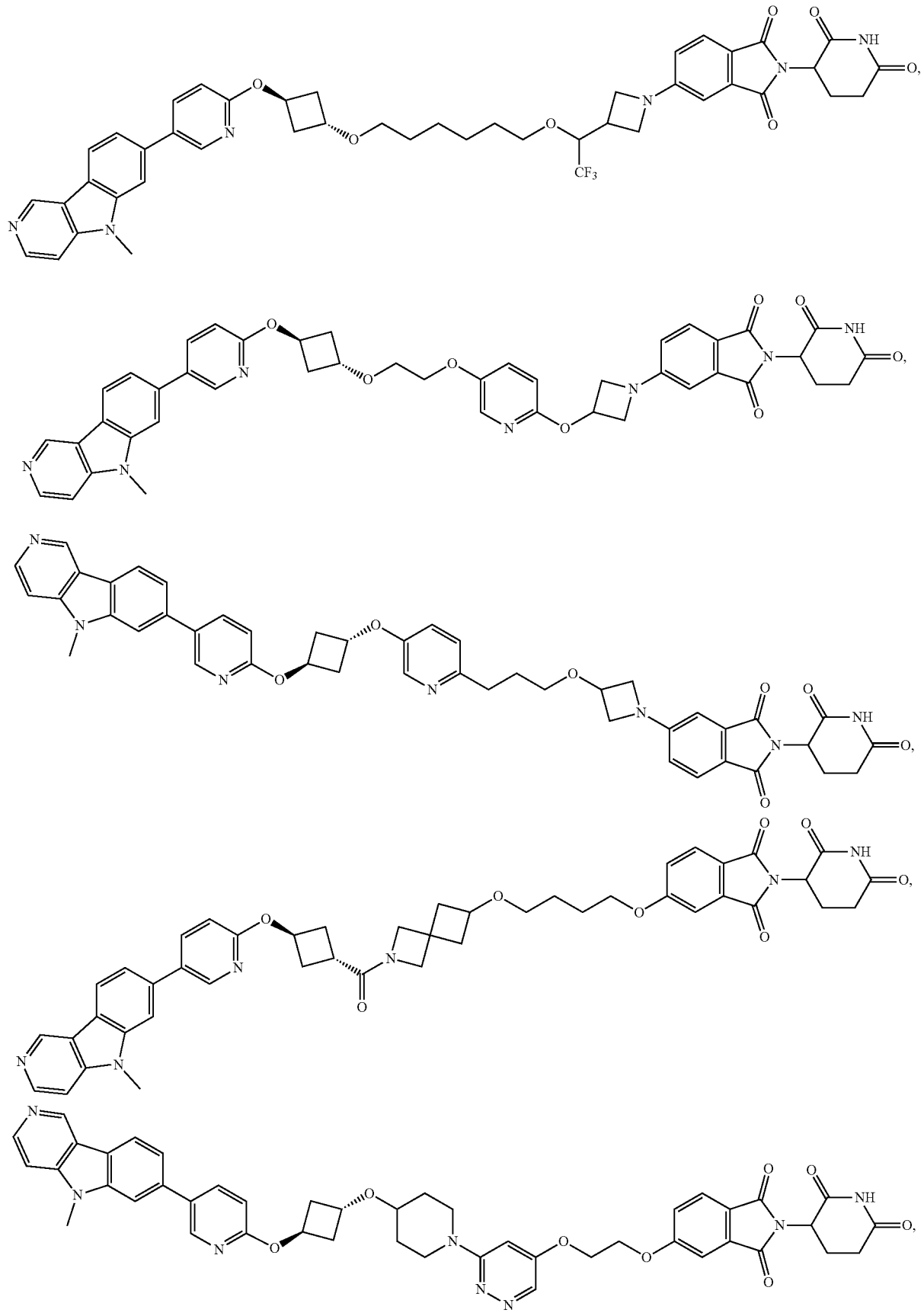

1037 1038
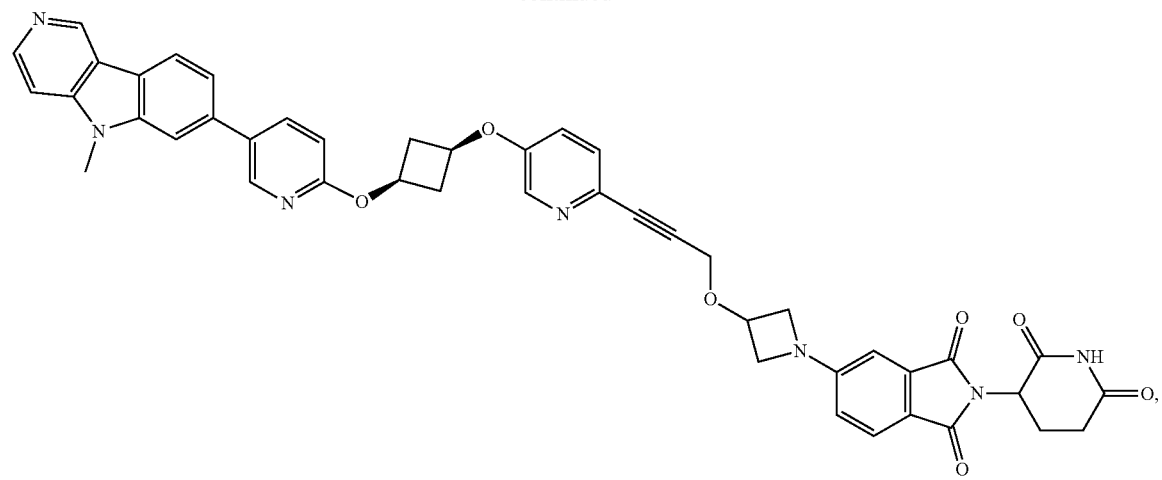
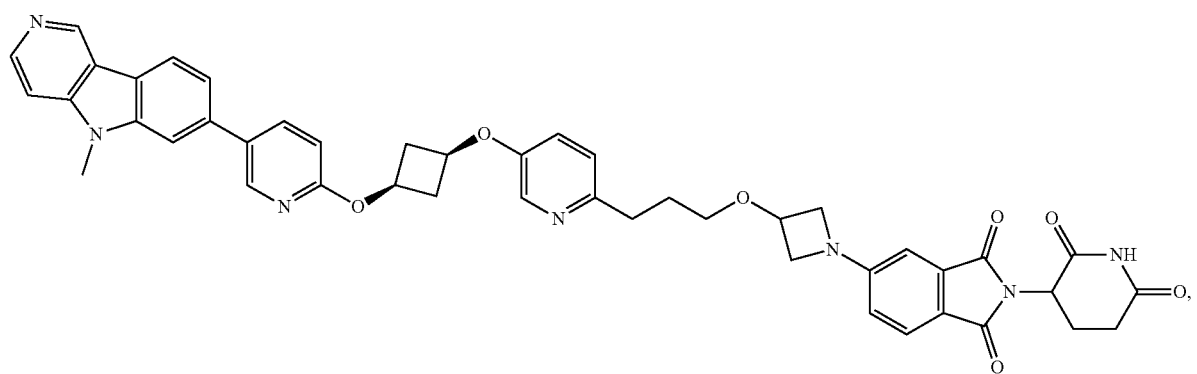
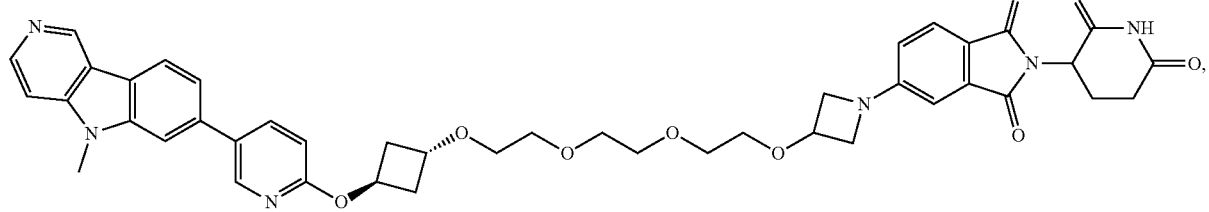
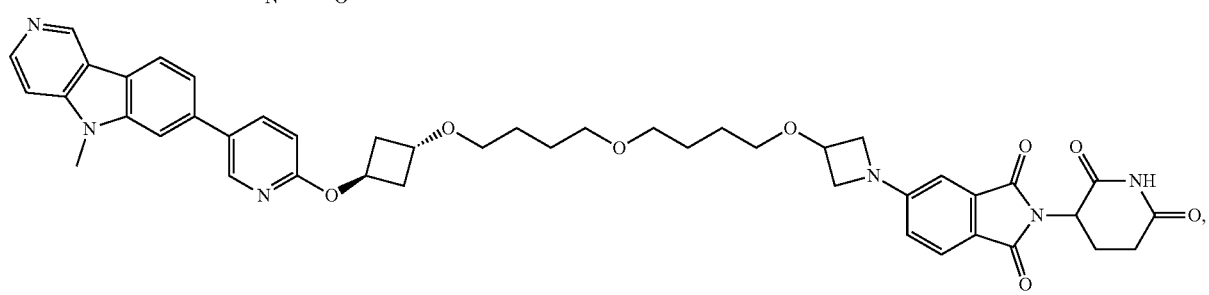
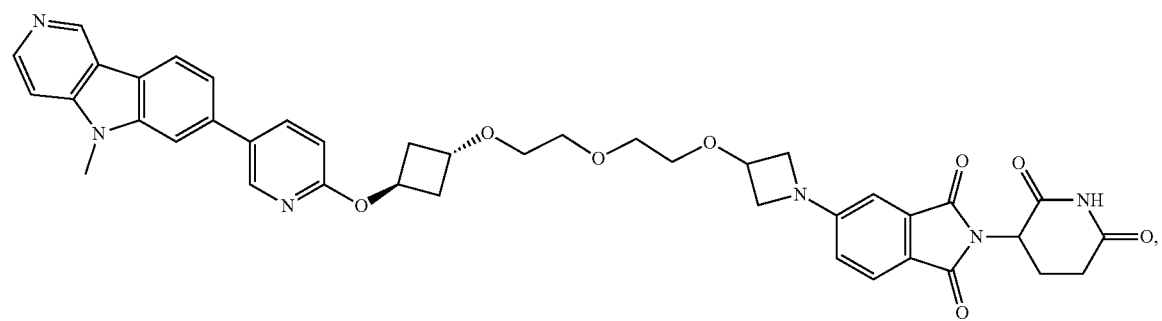

1039 -continued 1040
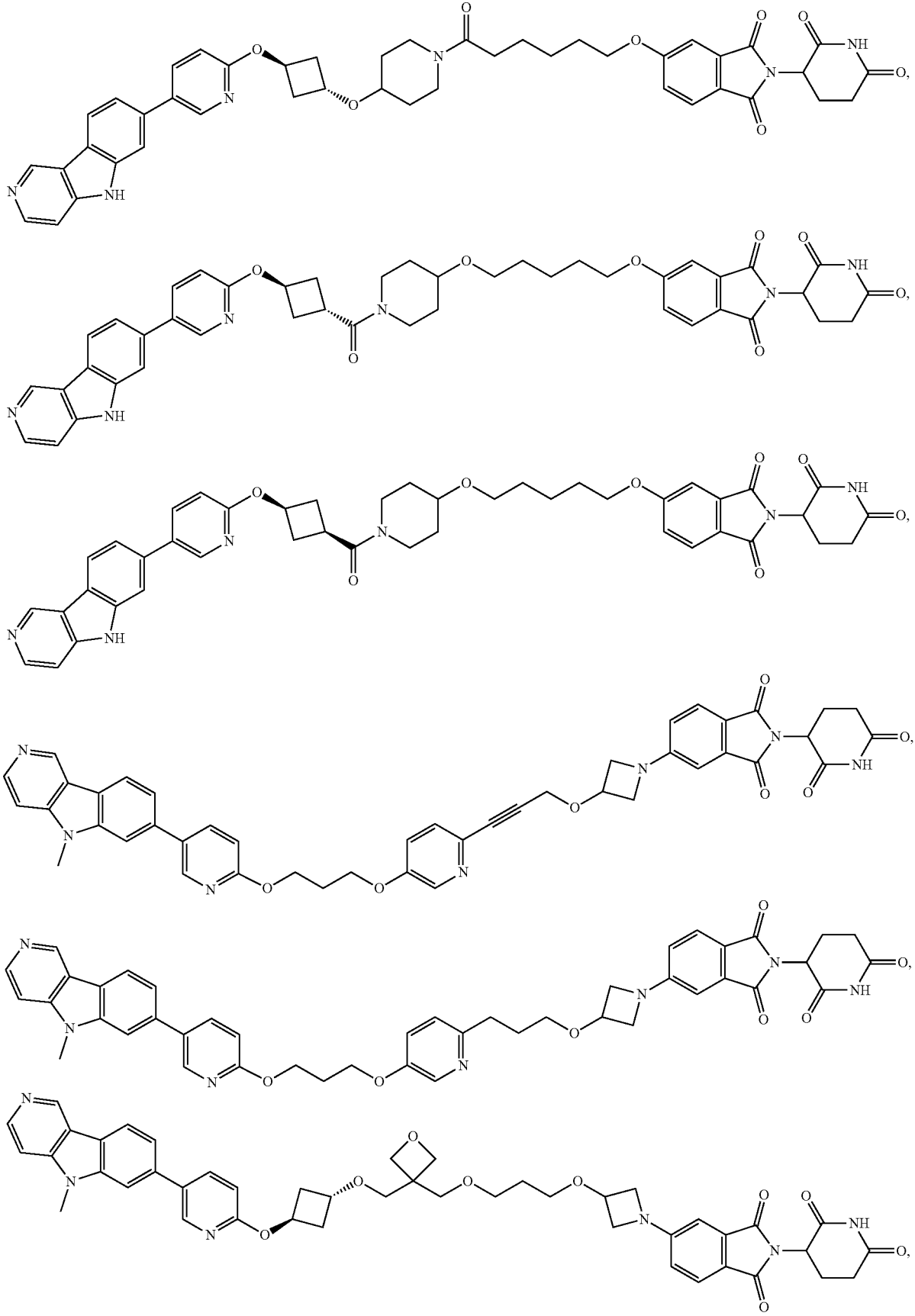

1041 1042
-continued
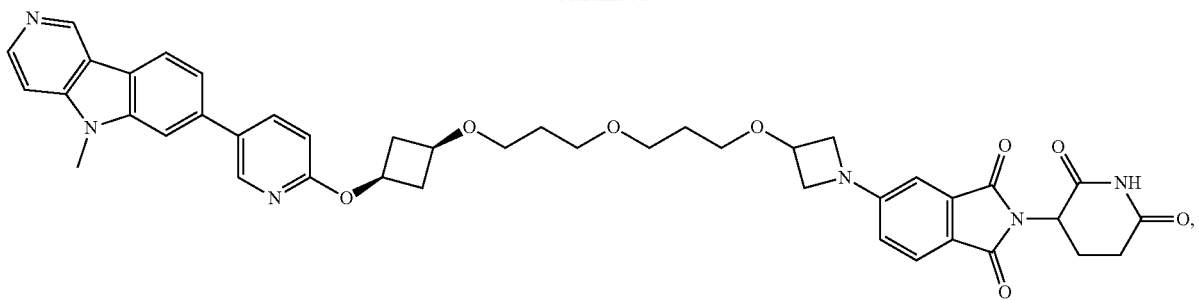
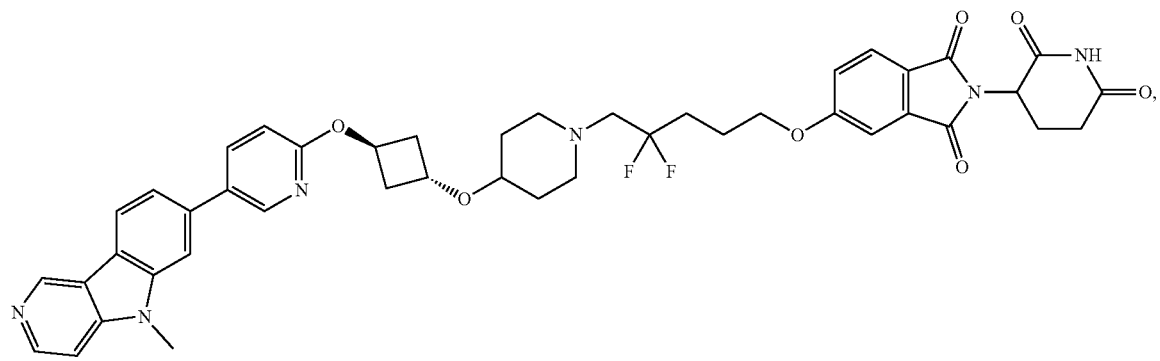
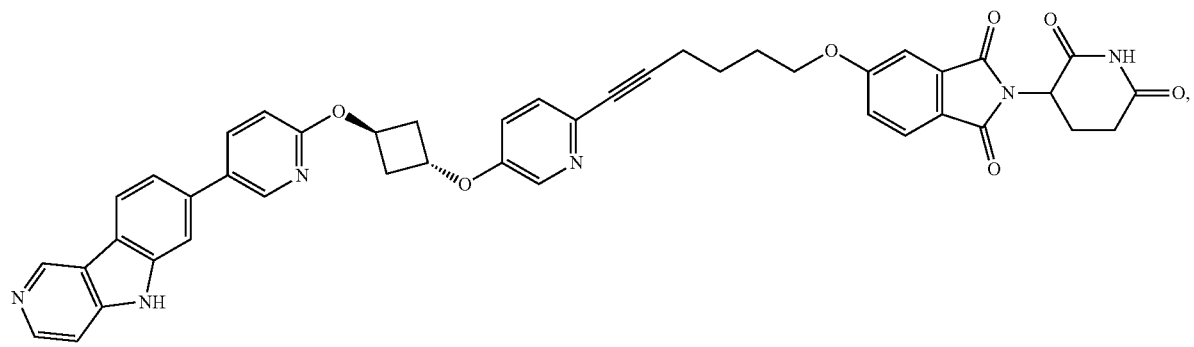
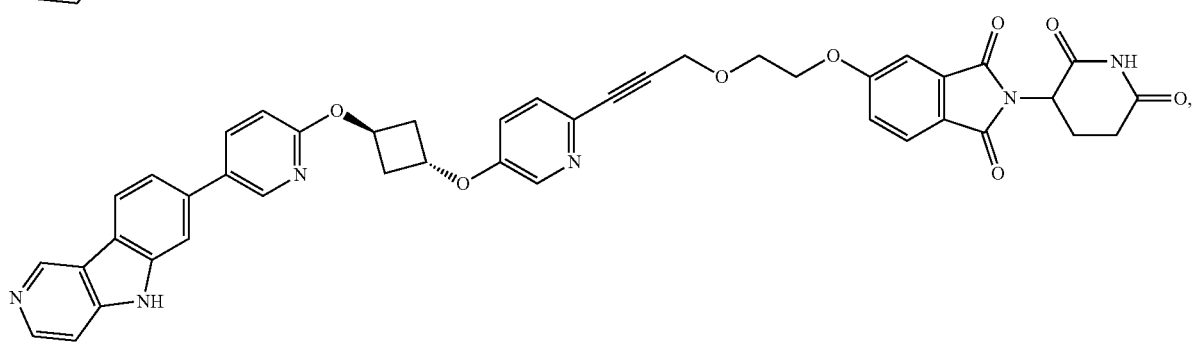
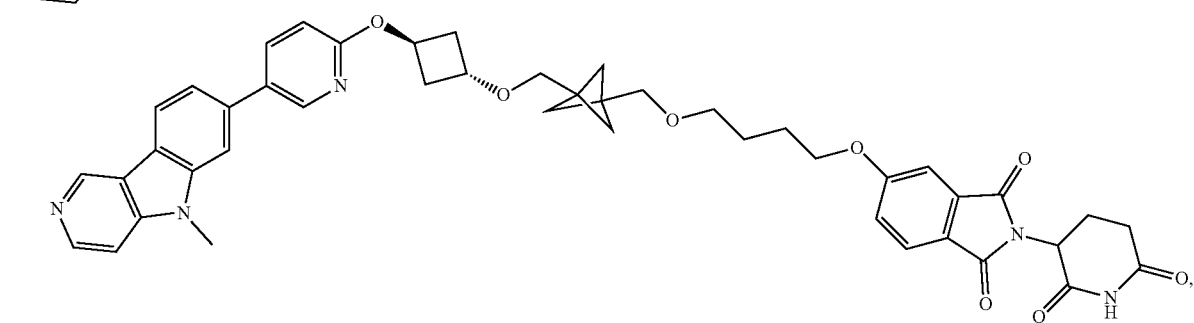

1043
-continued
1044
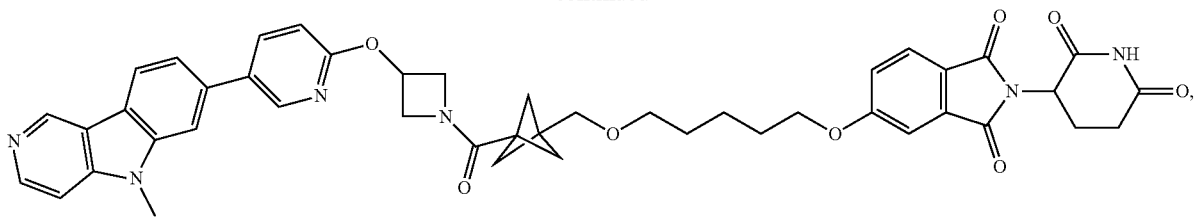
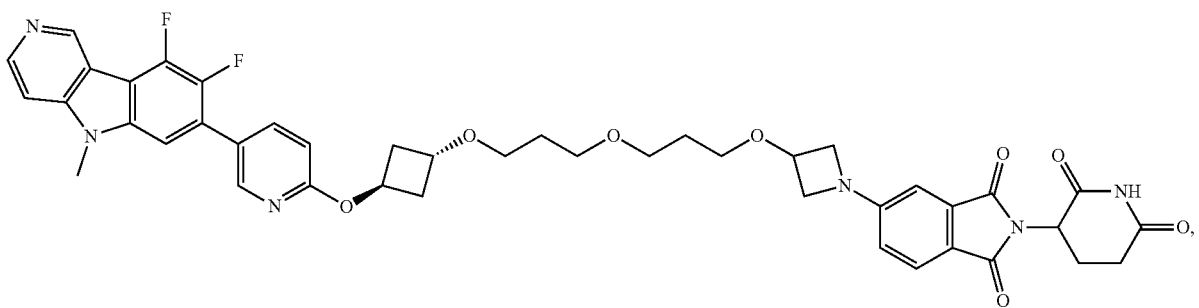
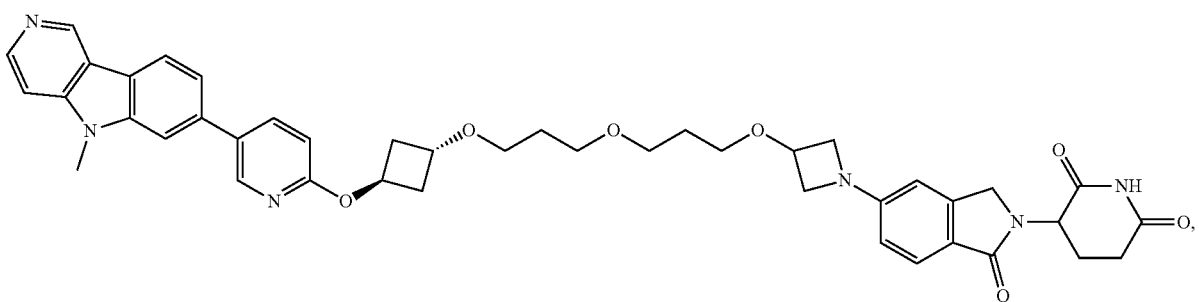
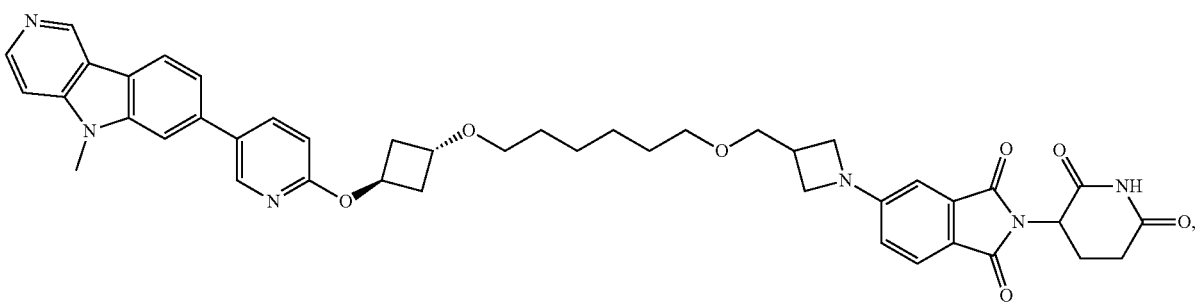
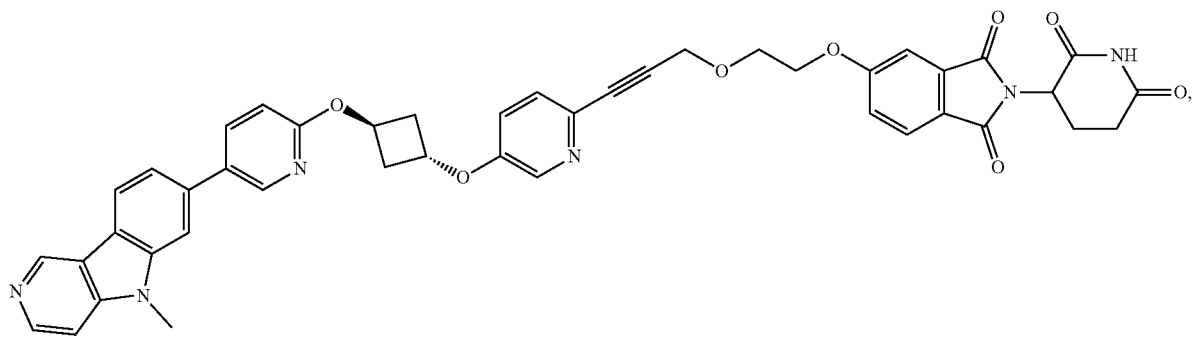

1045 1046
-continued
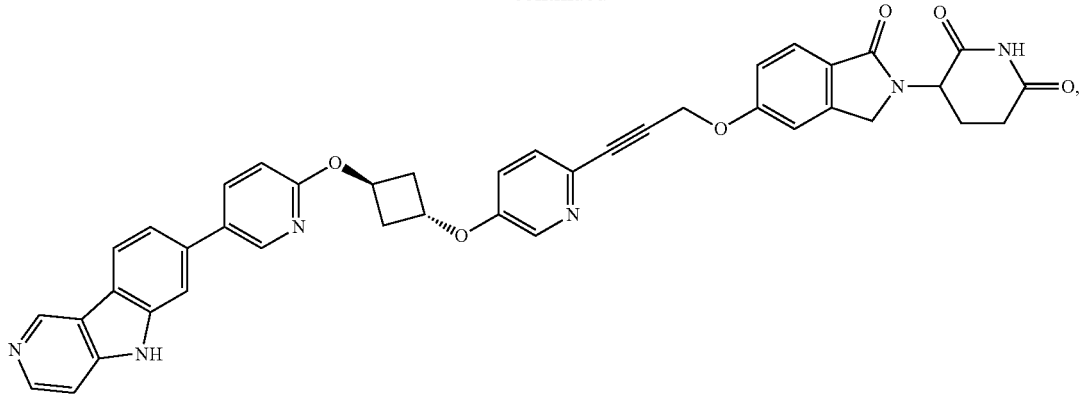
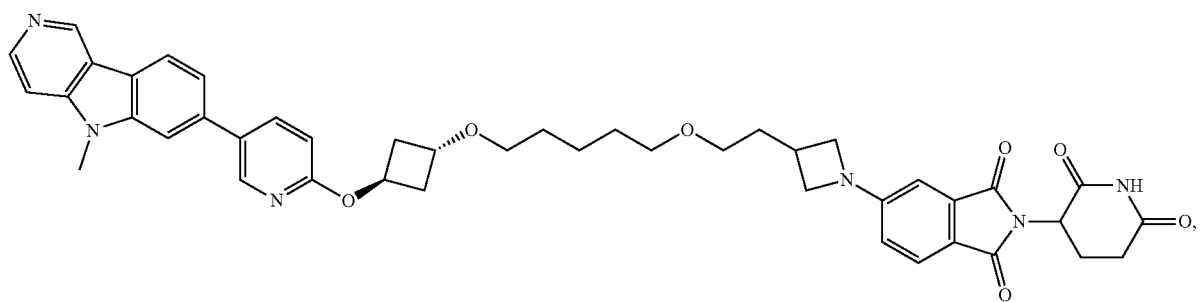 [SMILES: Cn1c2ccncc2c2ccc(-c3ccc(O[C@H]4C[C@H](OCCCCCOCCC5CN(c6ccc7c(c6)C(=O)N(C6CCC(=O)NC6=O)C7=O)C5)C4)nc3)cc21]
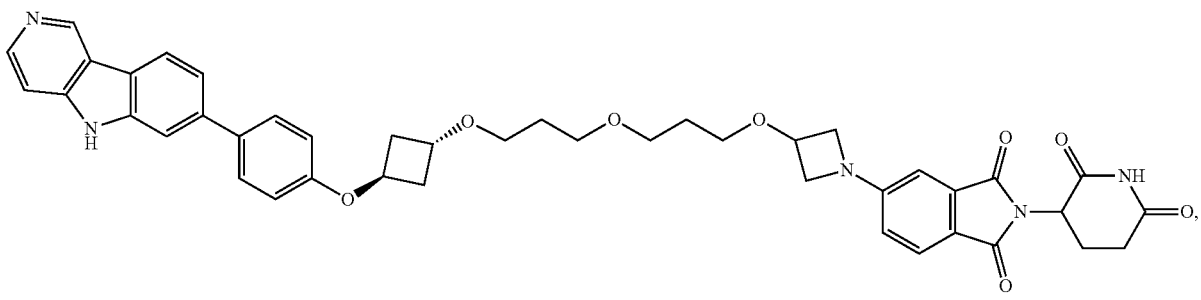
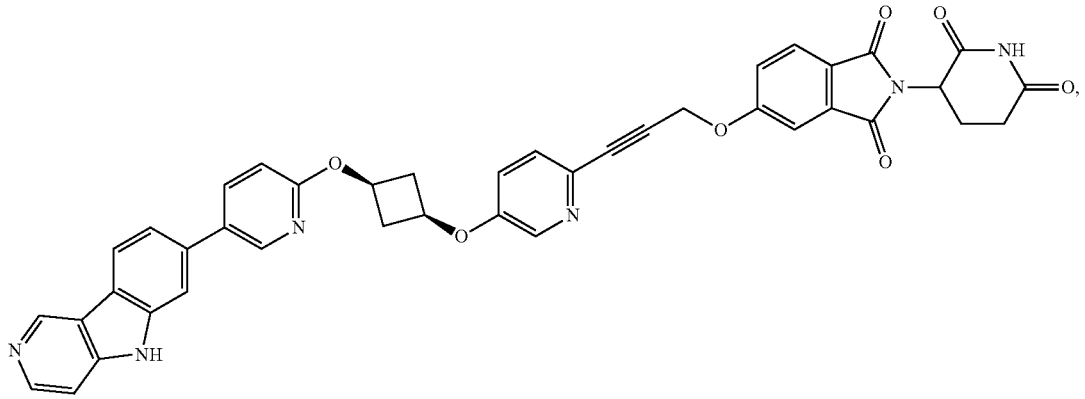
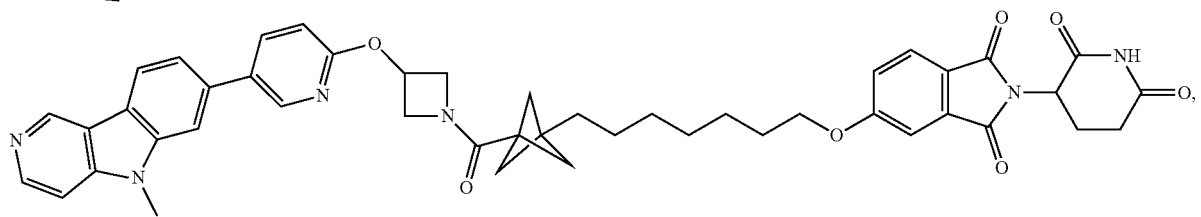

1047
1048
-continued
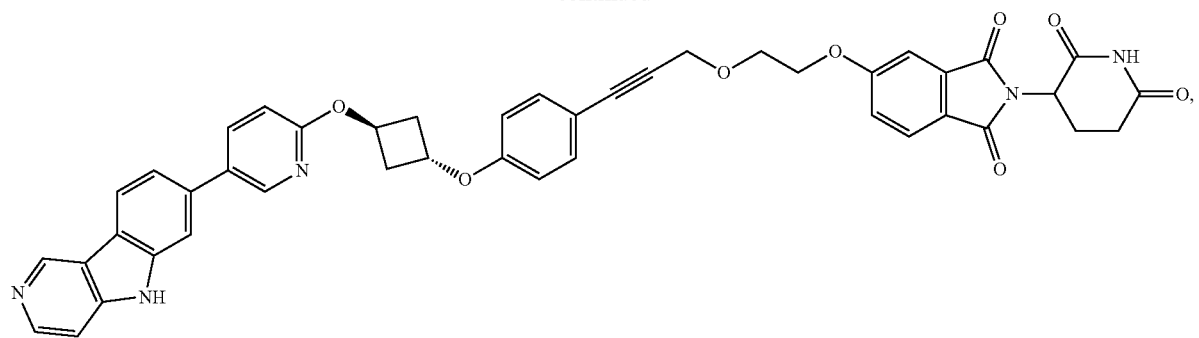
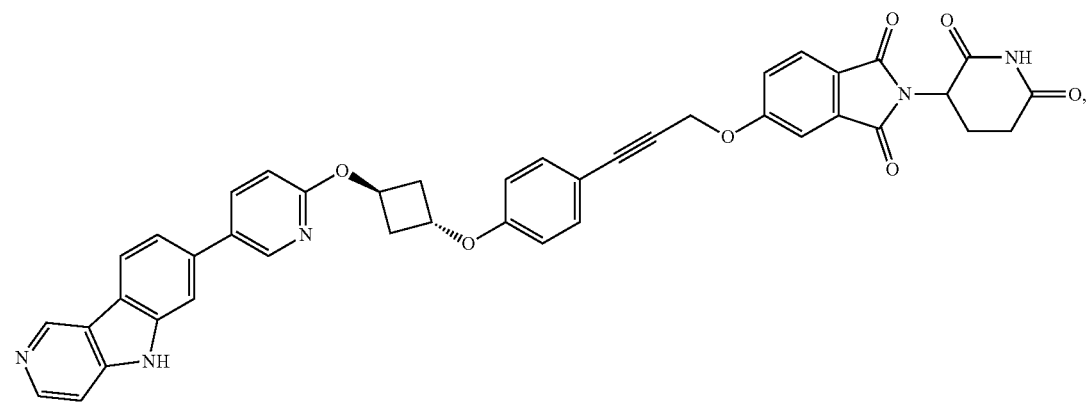
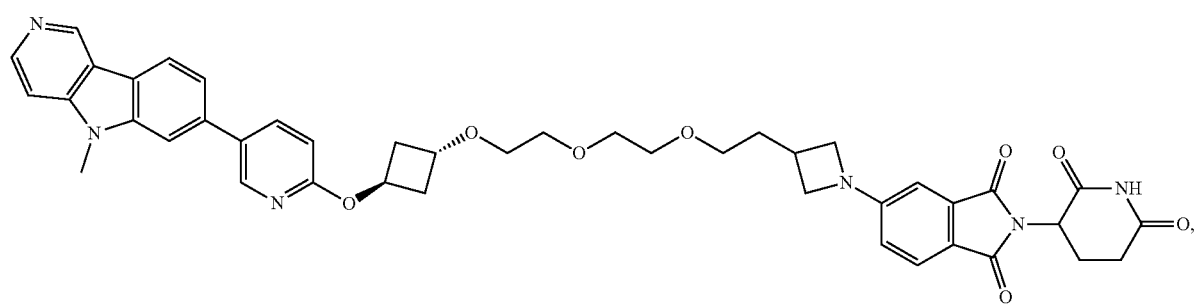
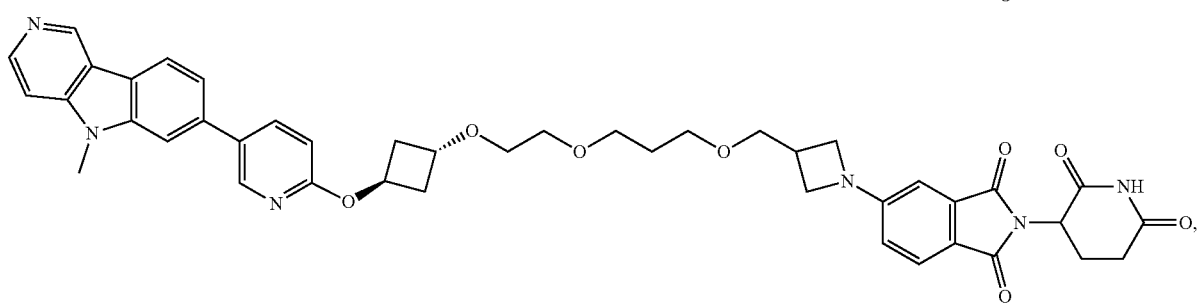
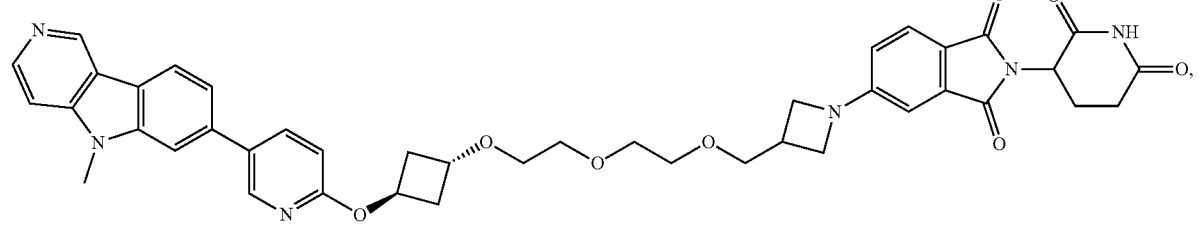

1049 1050
-continued
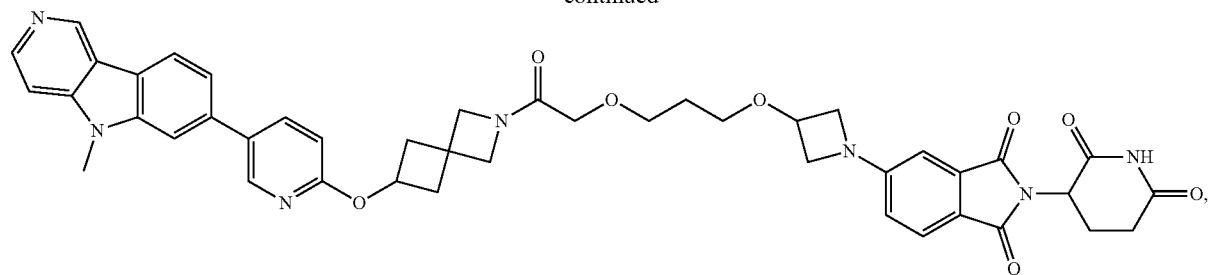
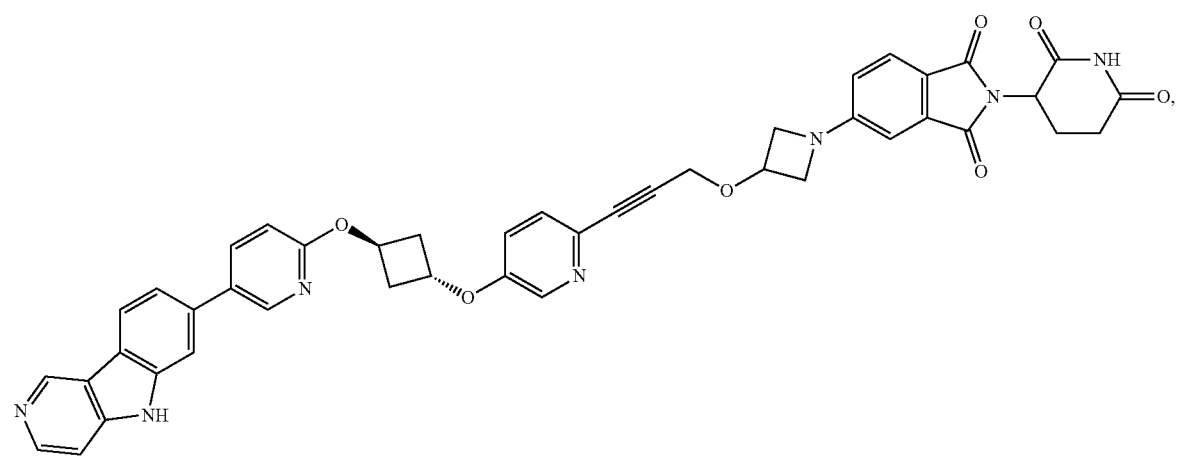
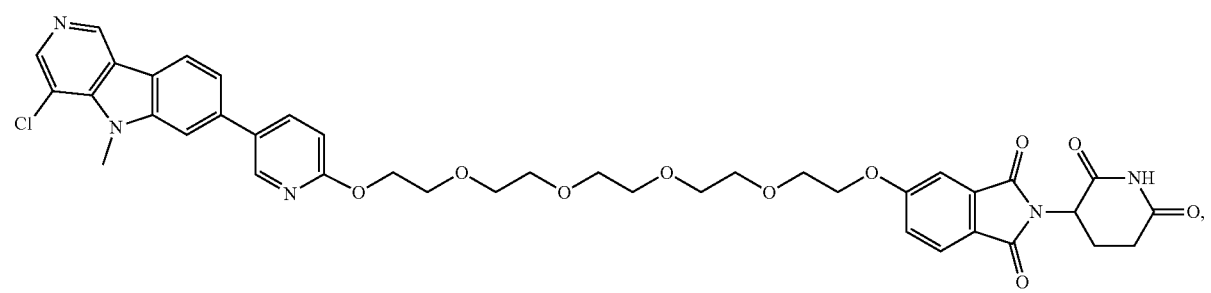
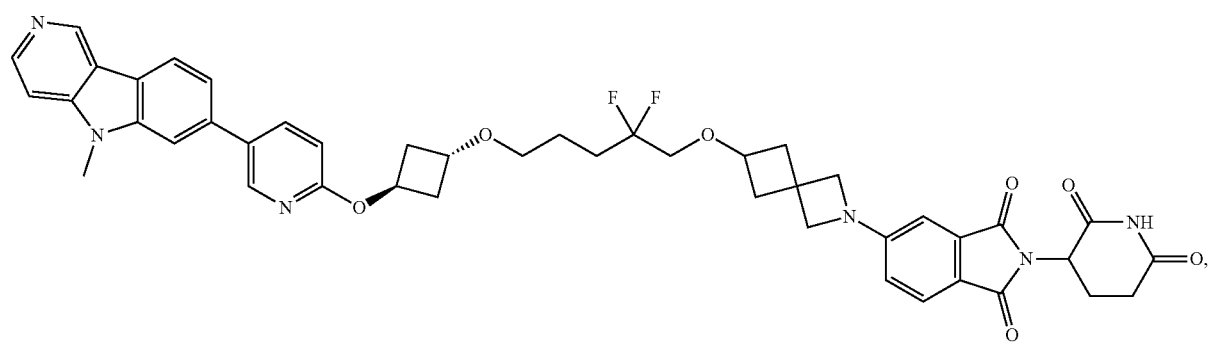
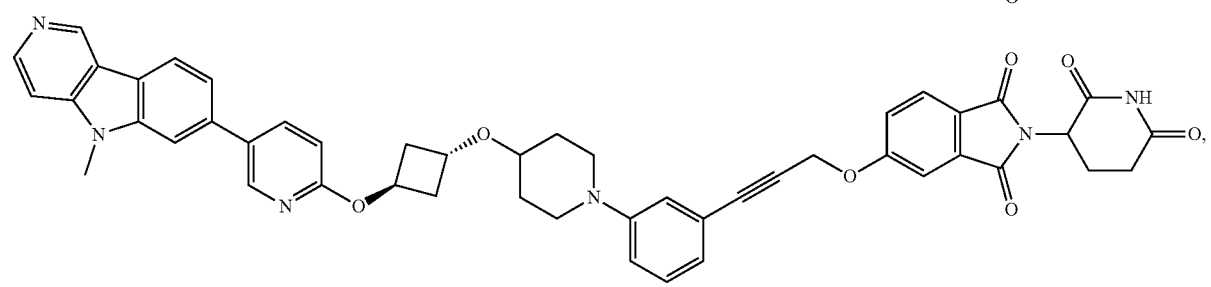

-continued
1051
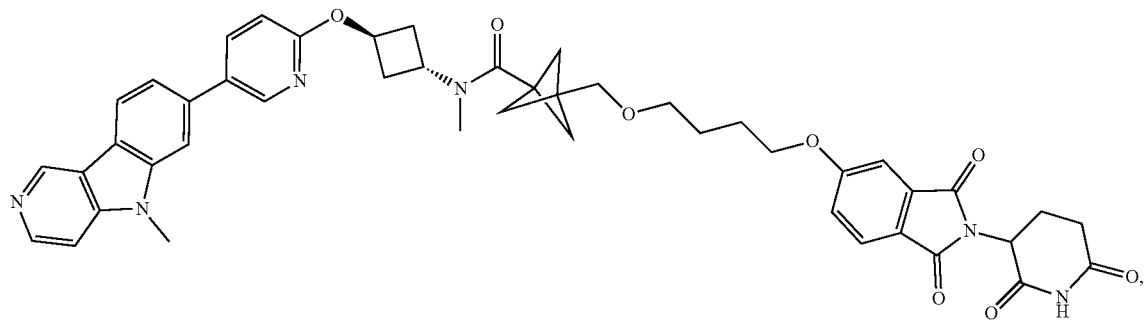
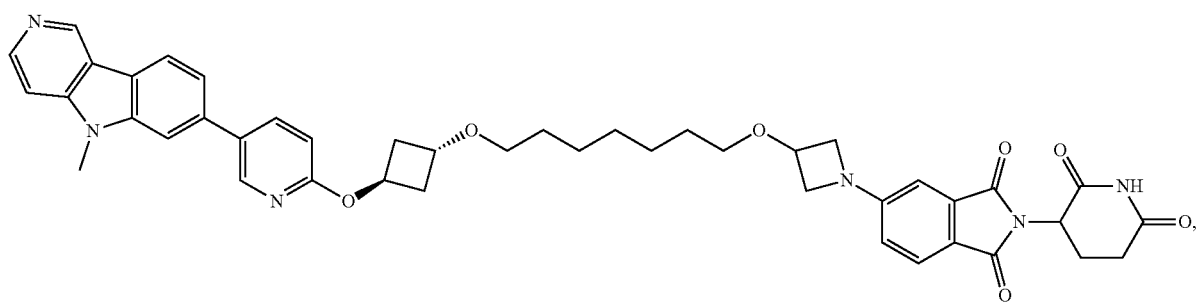
1052
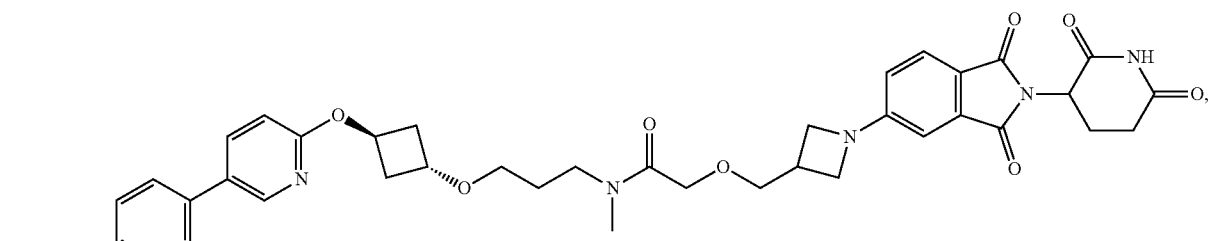
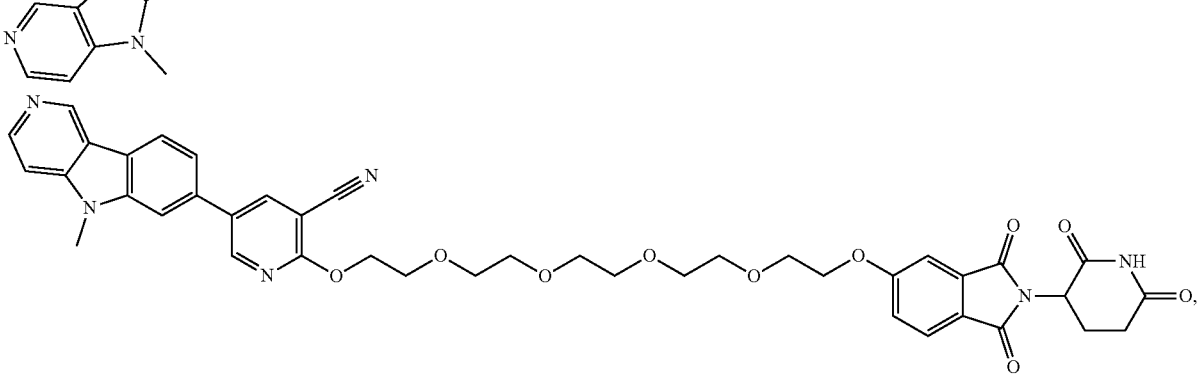
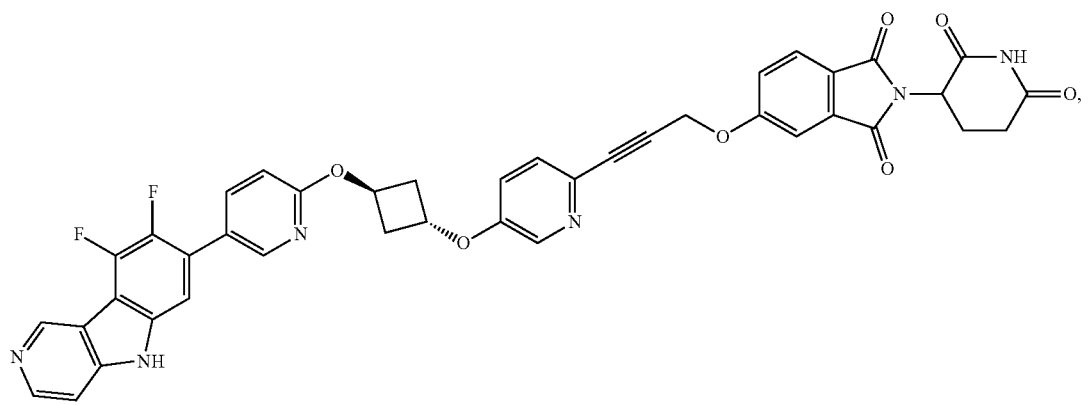

1053                                          1054
-continued
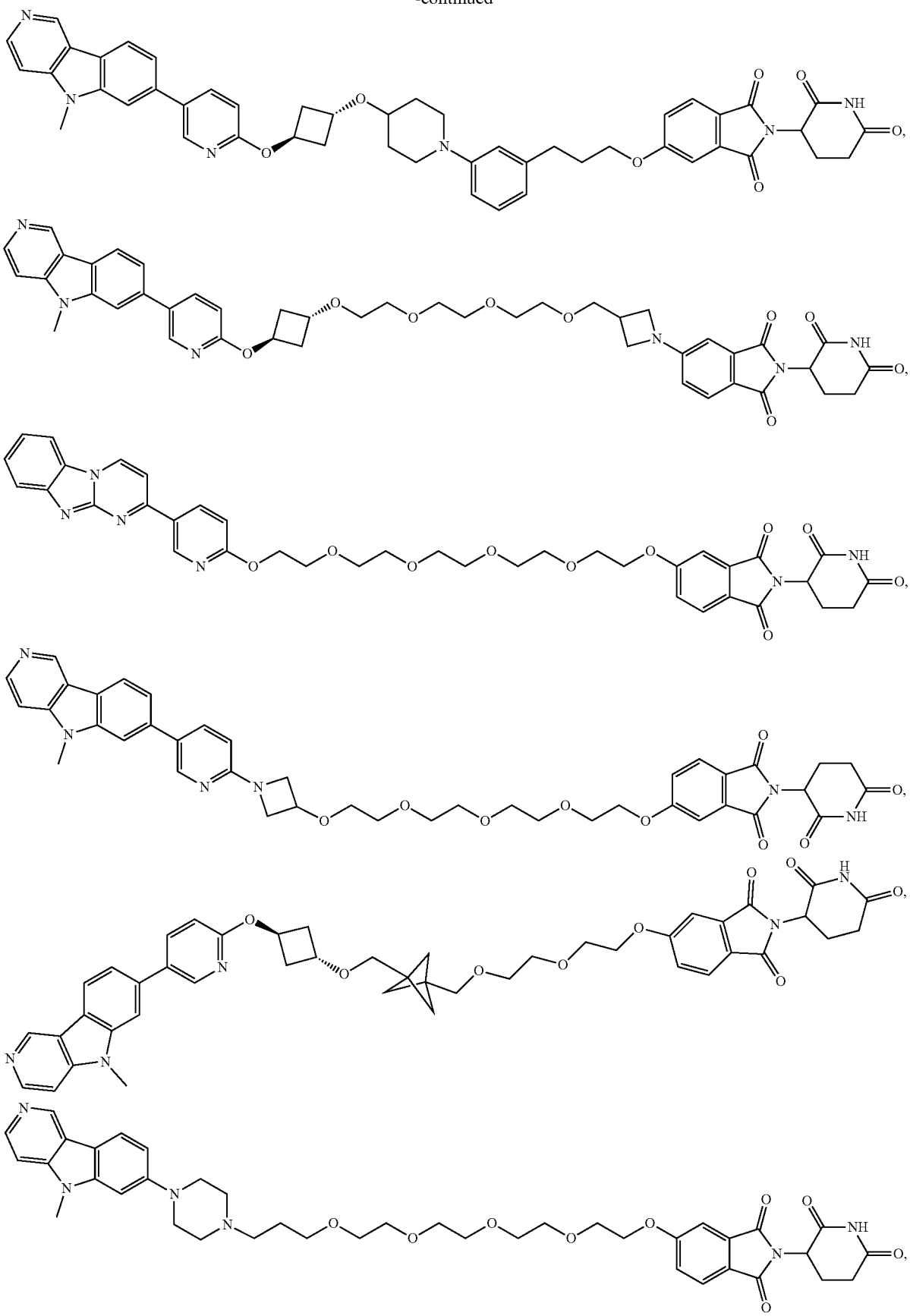

1055 1056
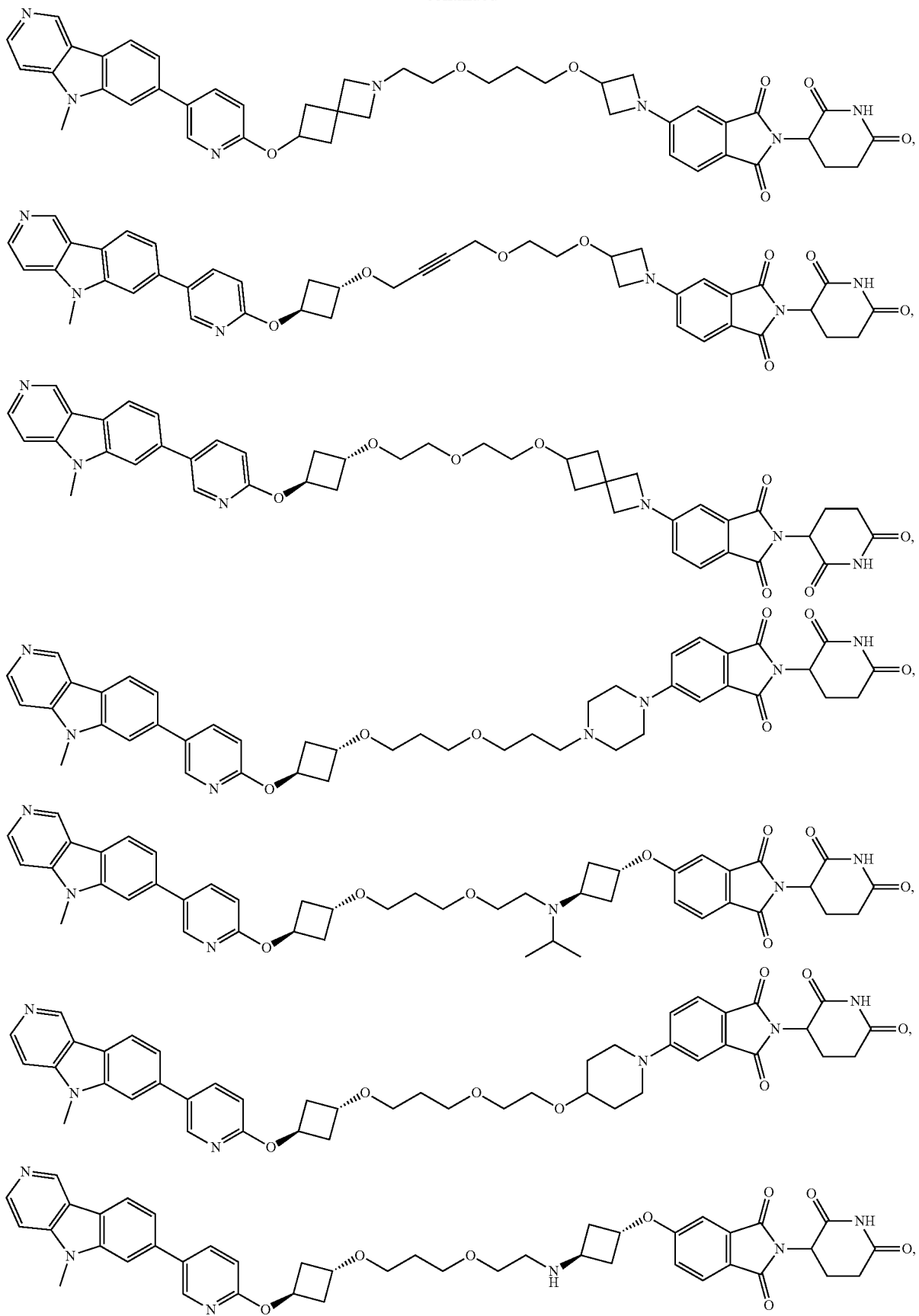

1057 1058
-continued
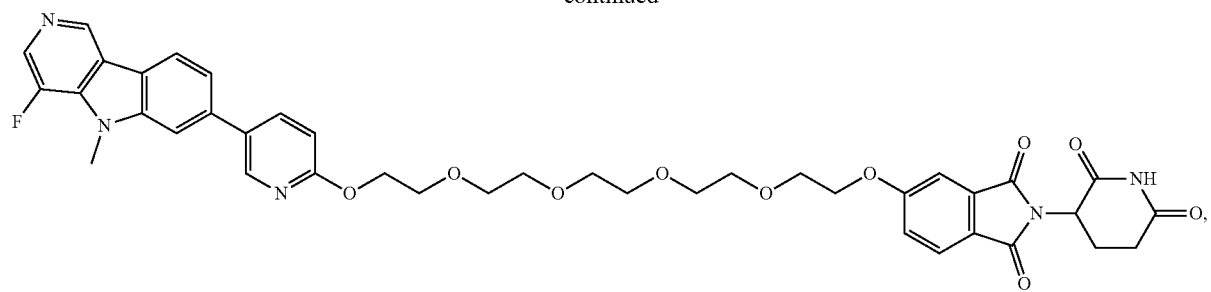
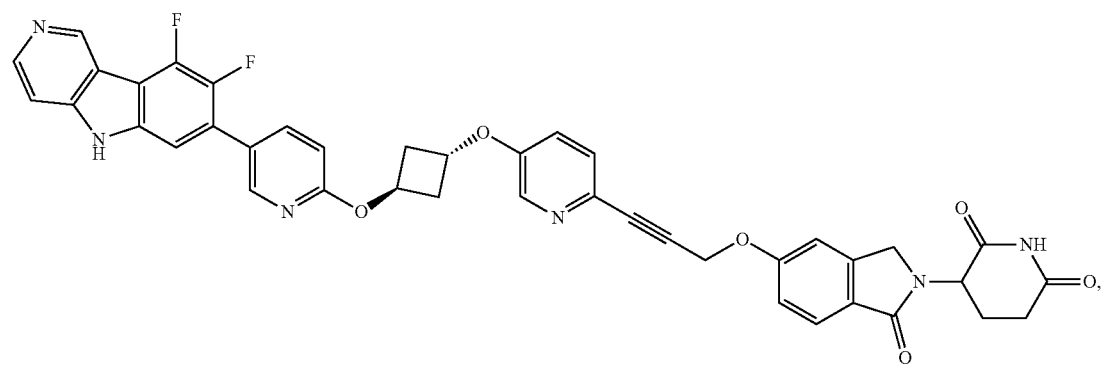
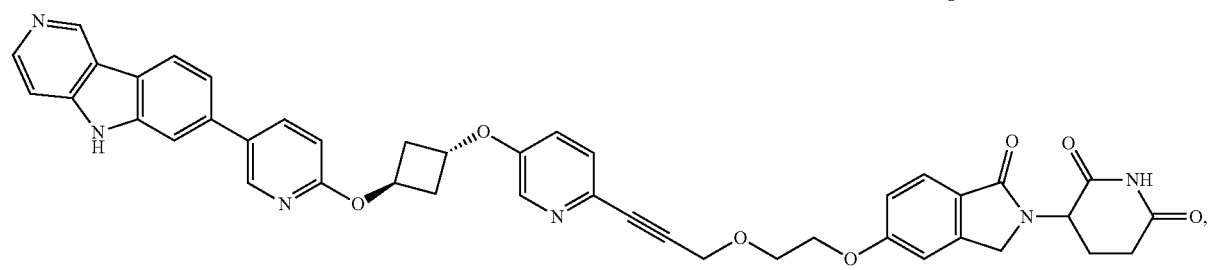
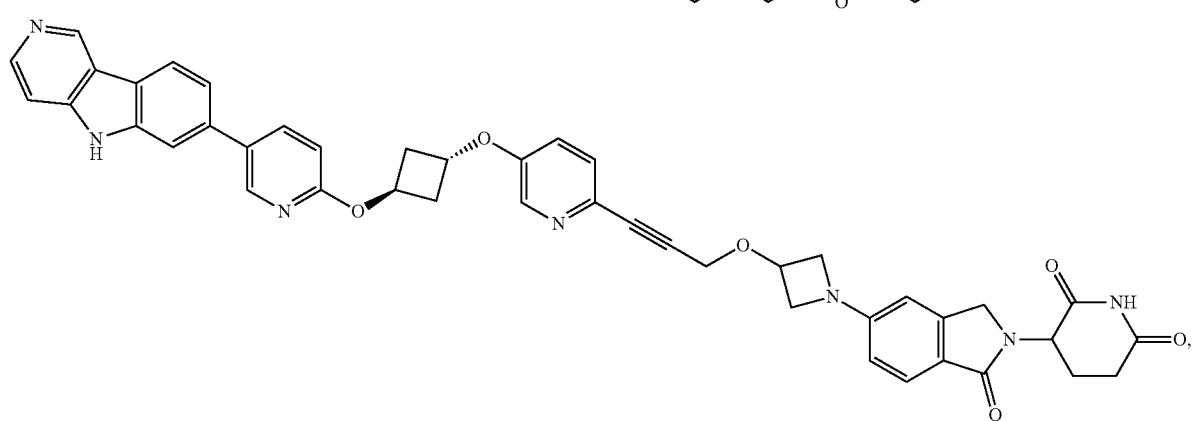
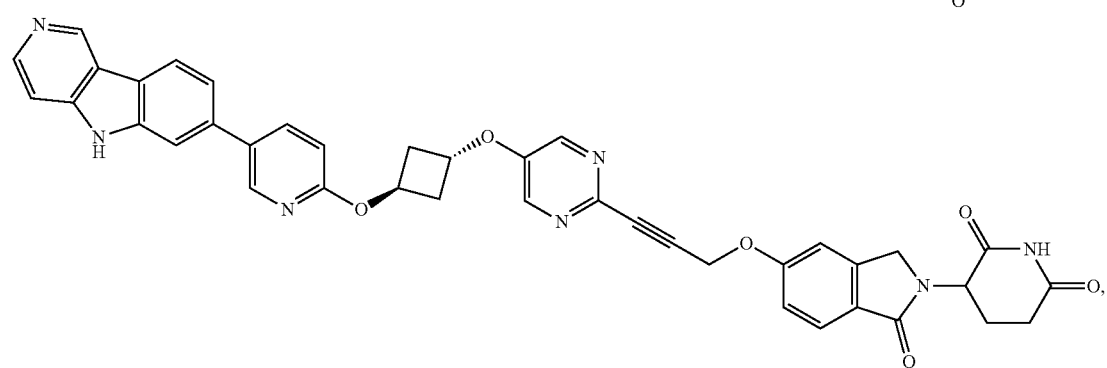

1059                                                                                 1060
-continued
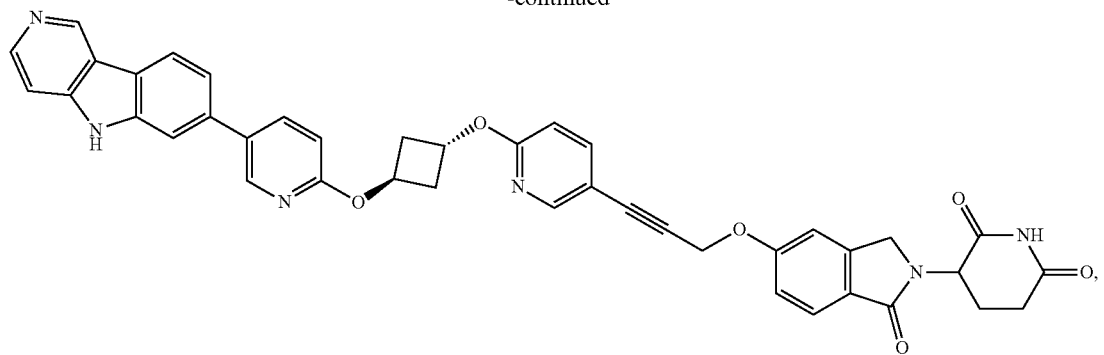
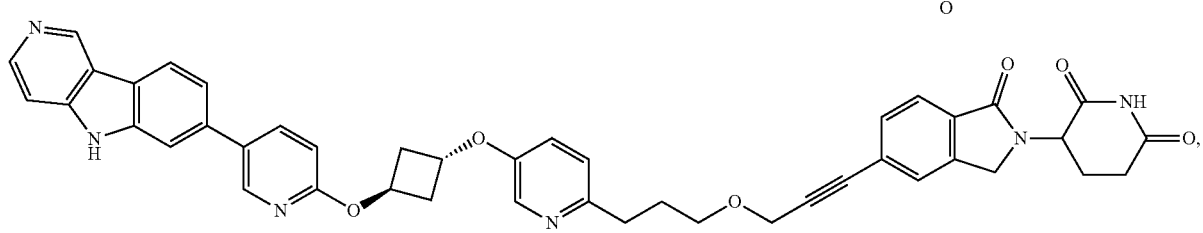
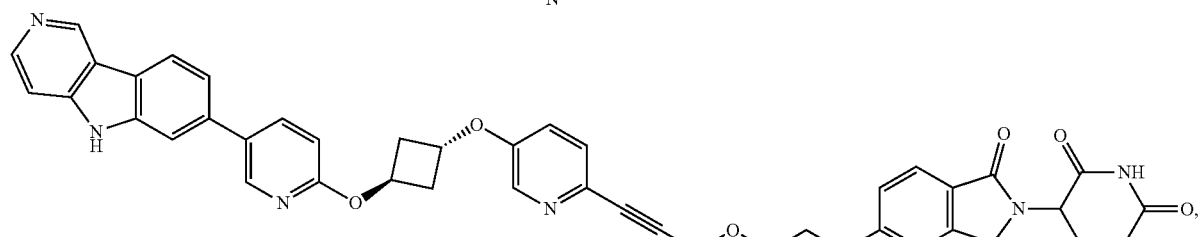
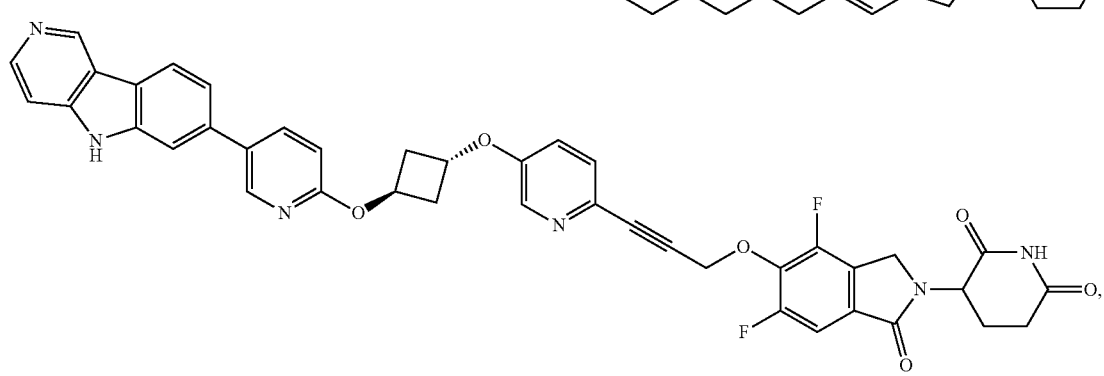
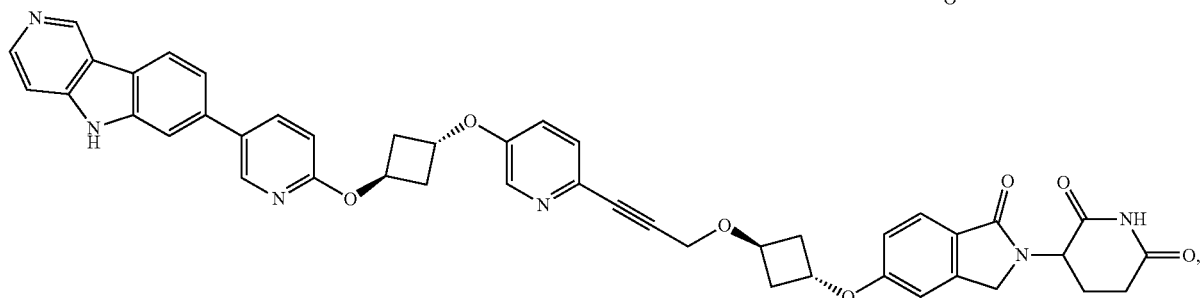
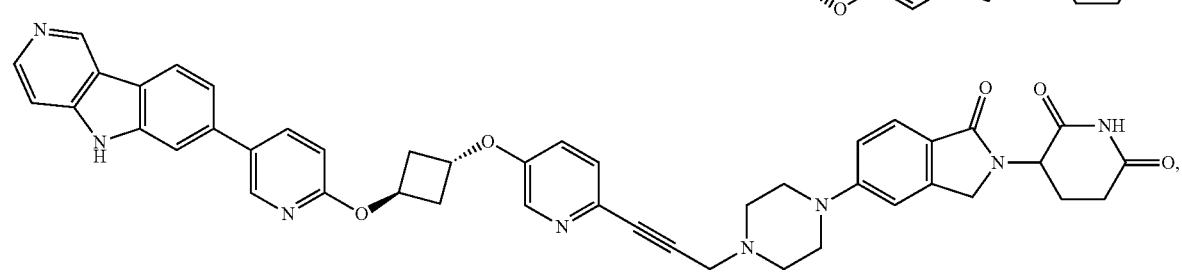

1061 1062
-continued
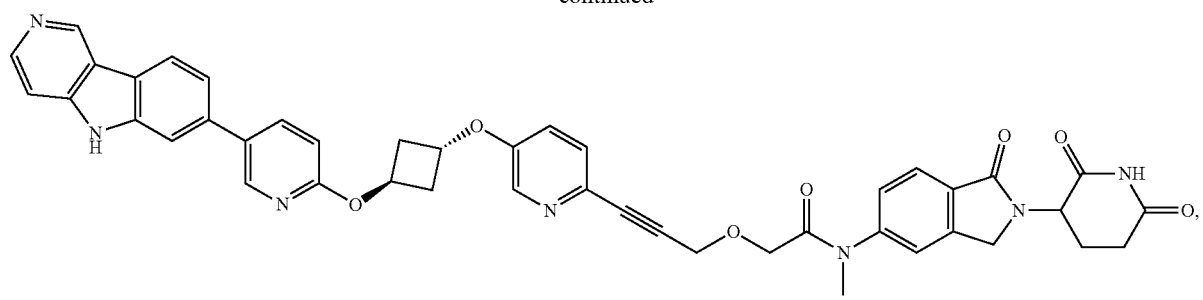
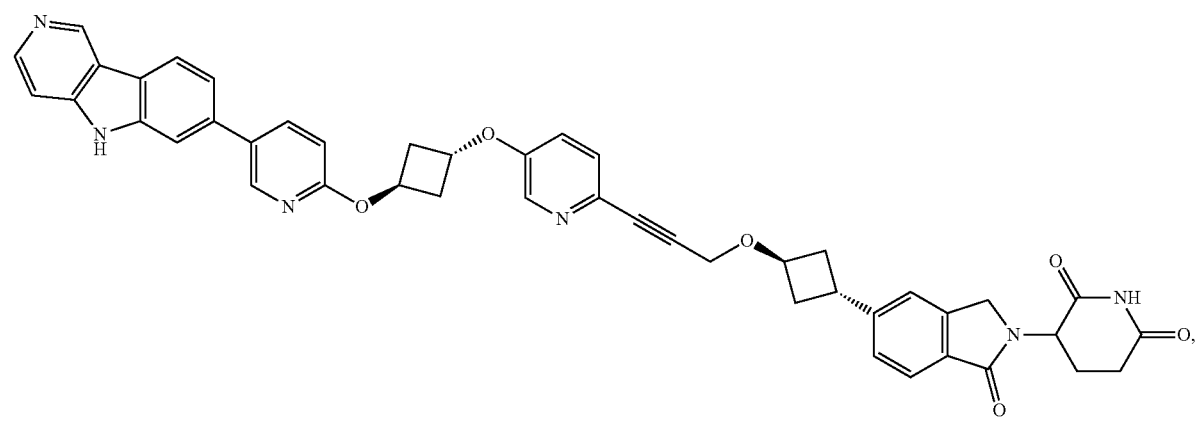
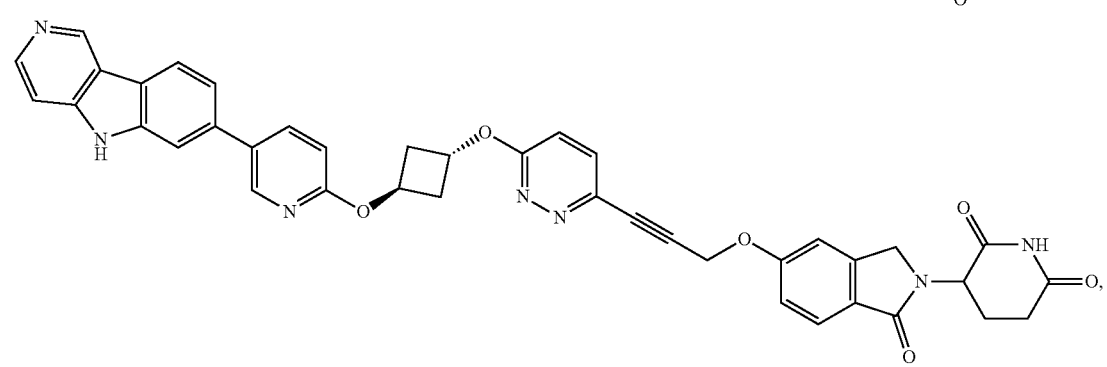
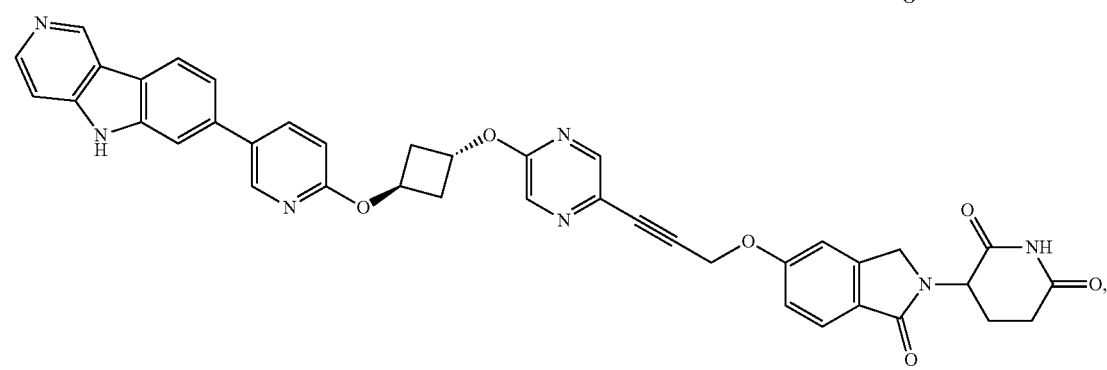
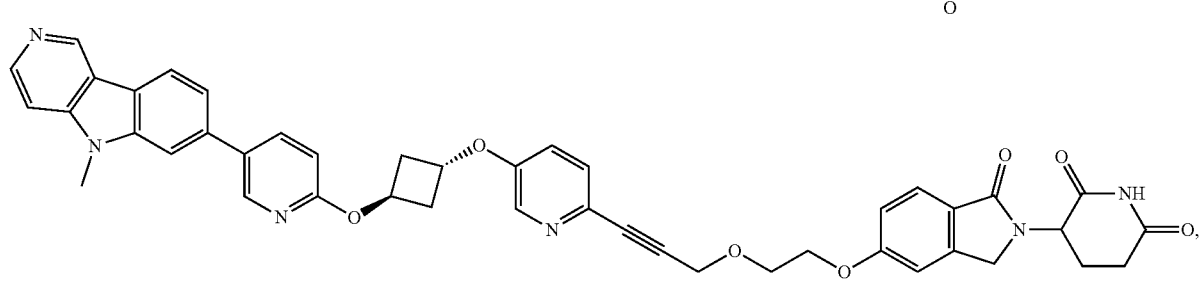

1063
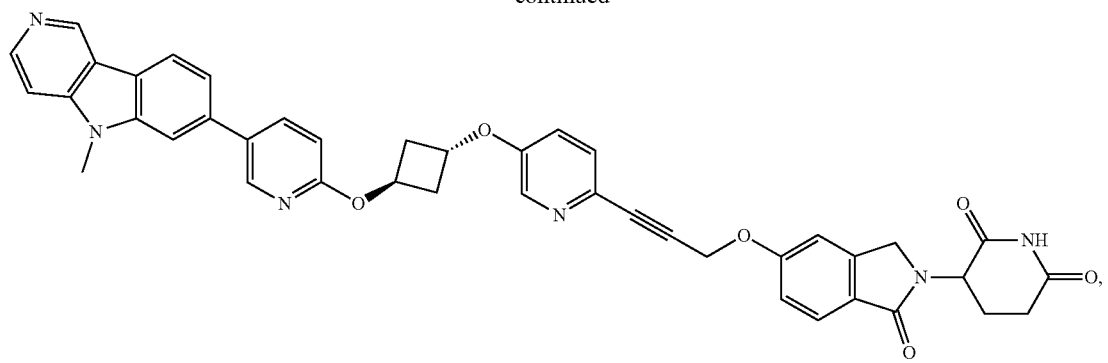
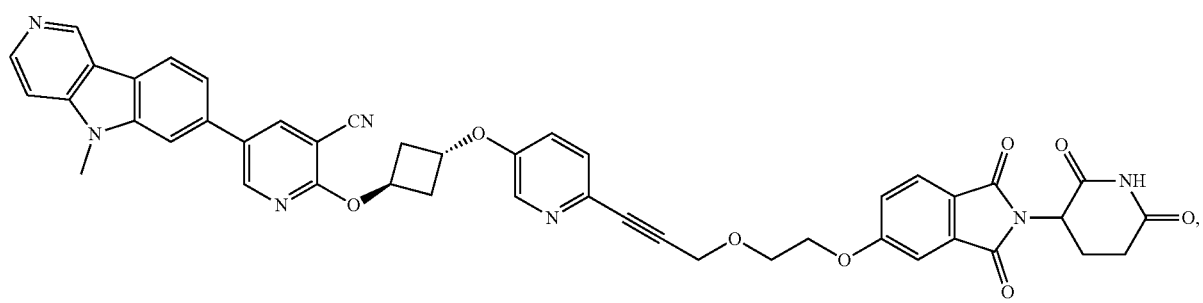
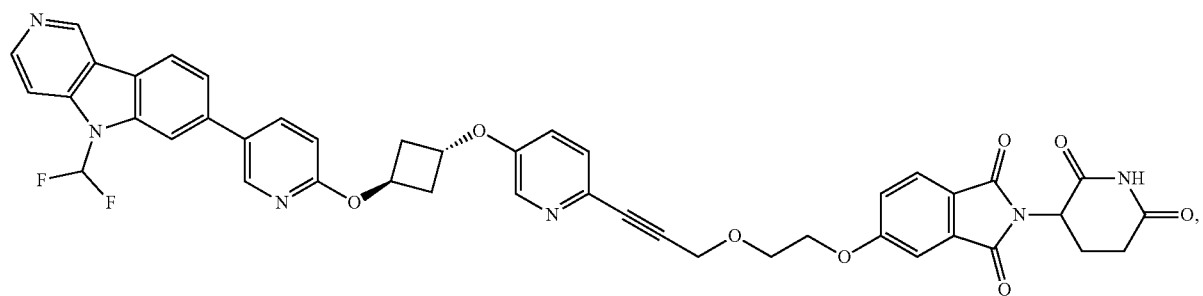
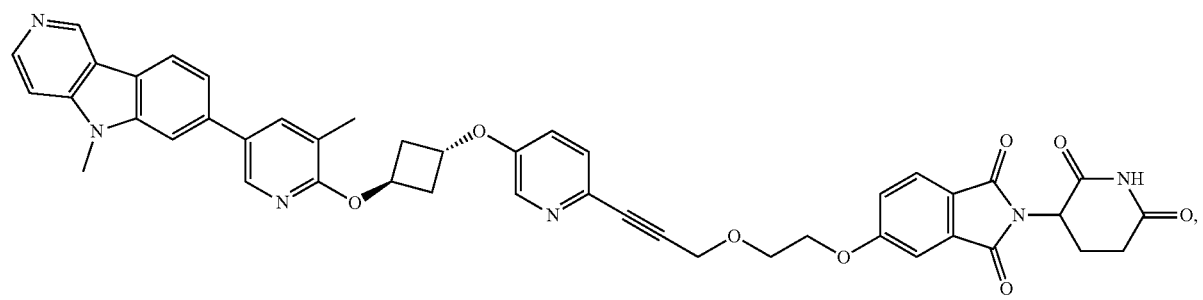
1064
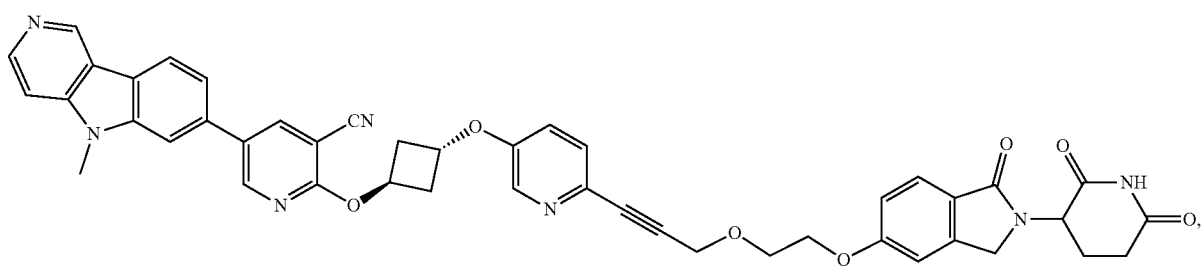

1065 1066
-continued
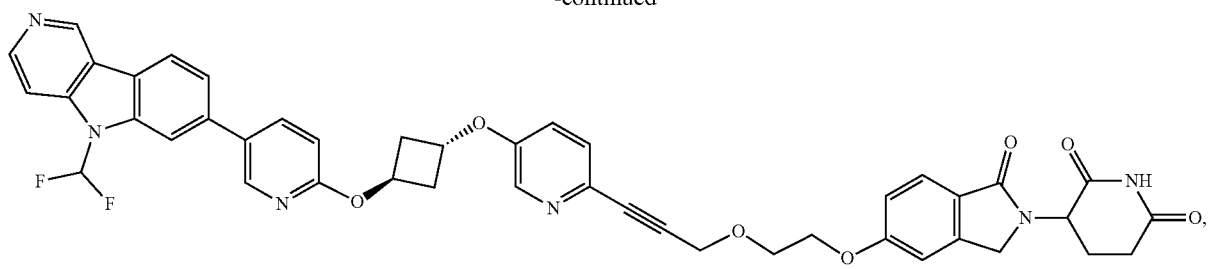
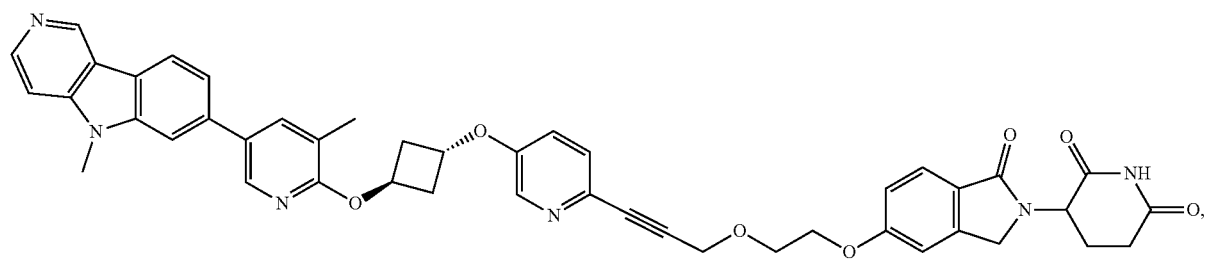
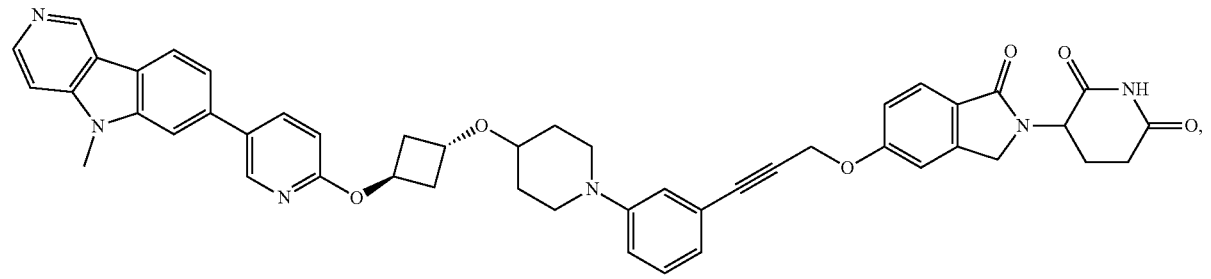
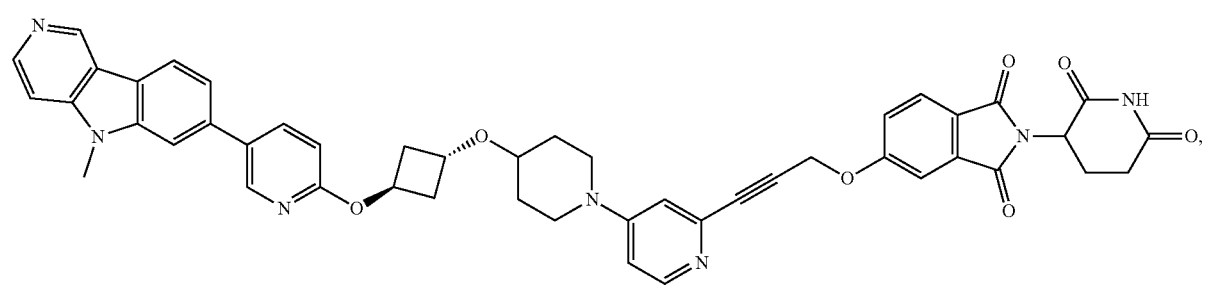
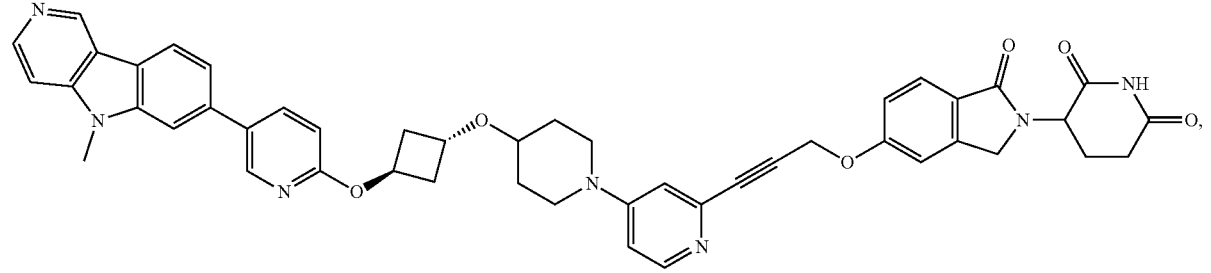
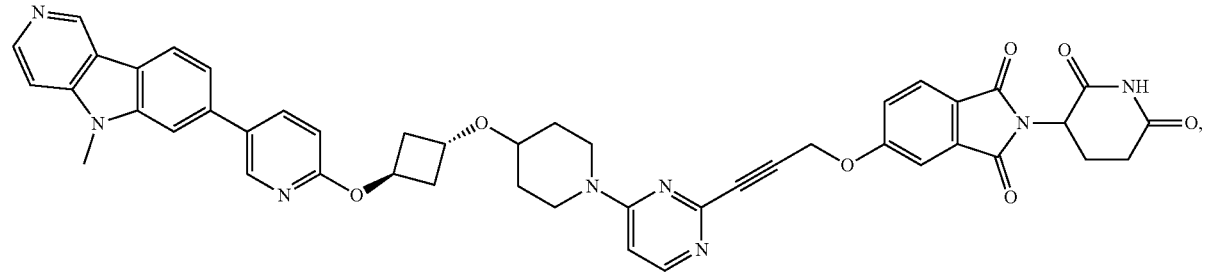

1067 1068
-continued
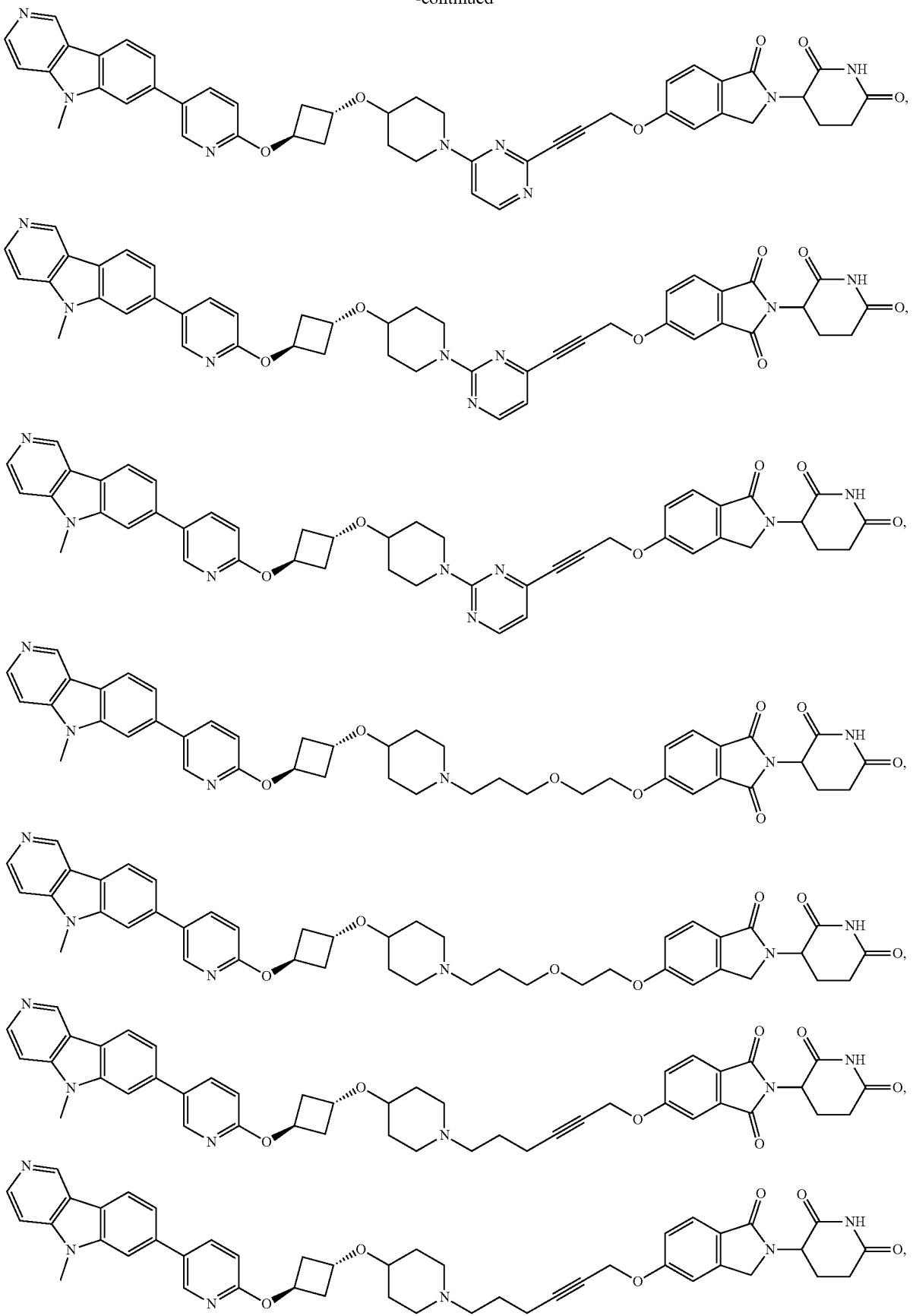

1069 1070
-continued
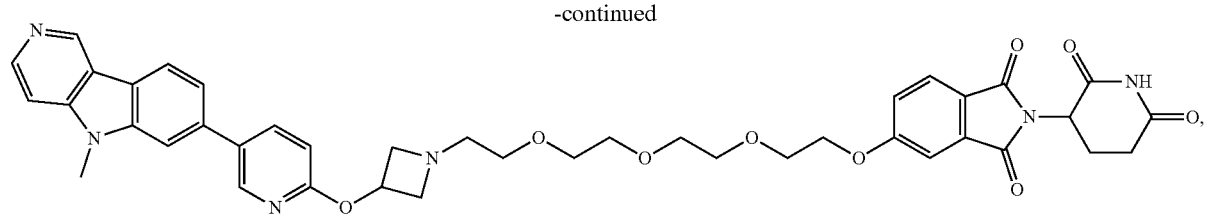
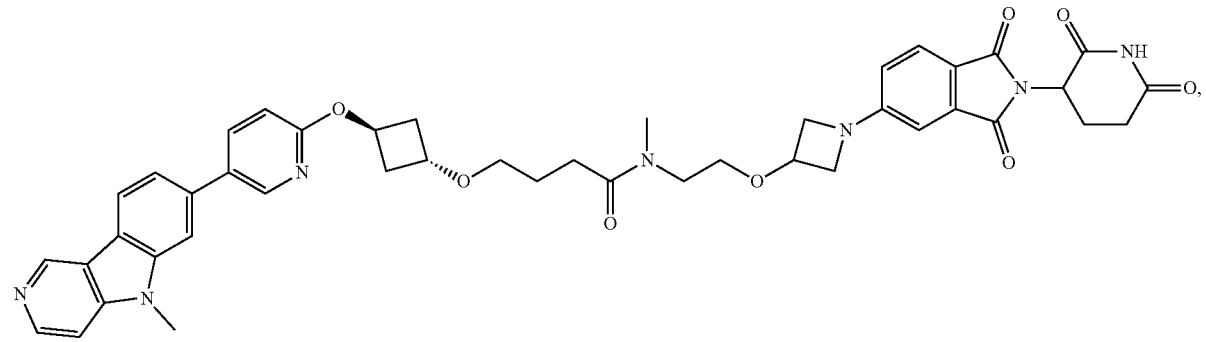
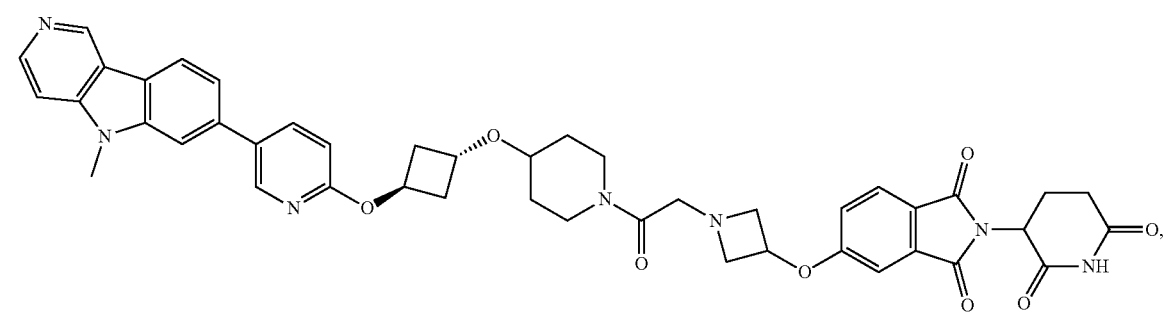
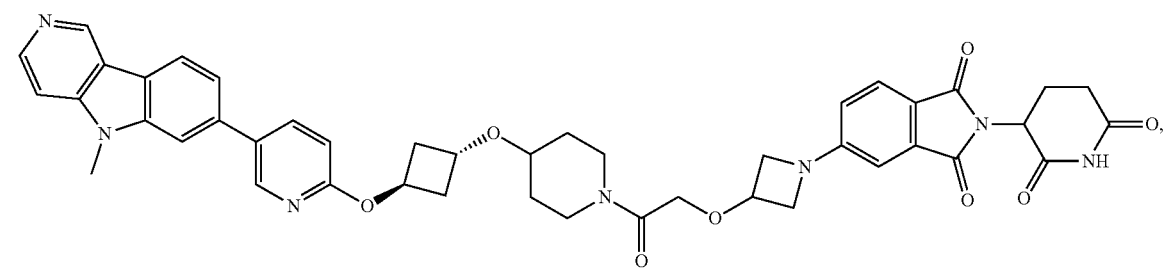
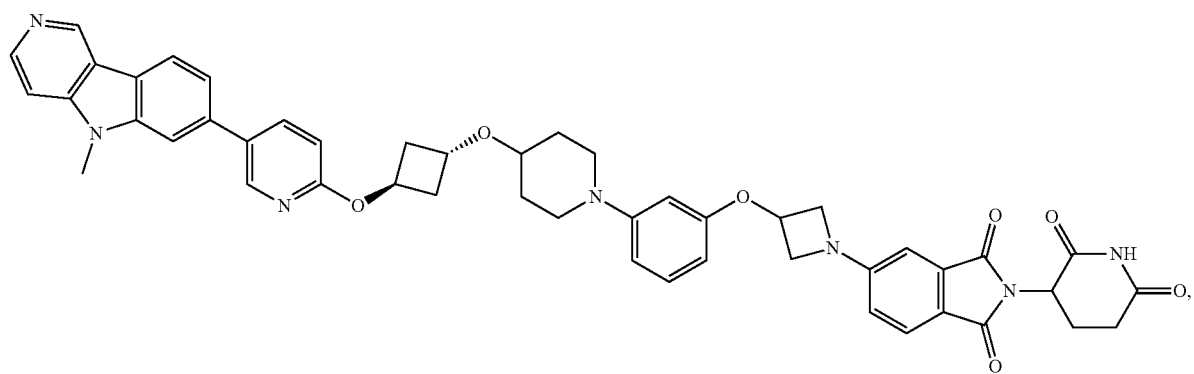

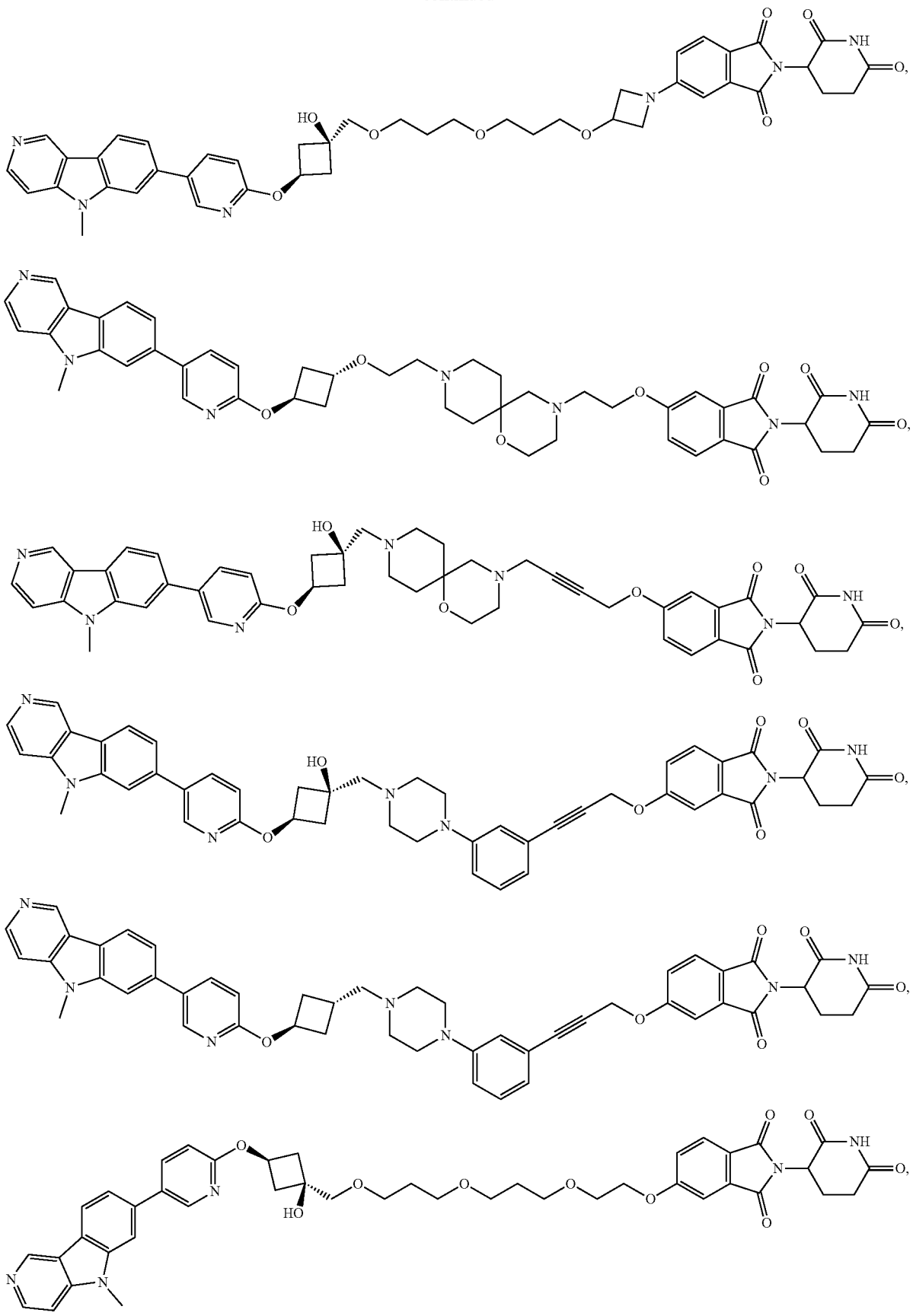

1073                                                1074
-continued
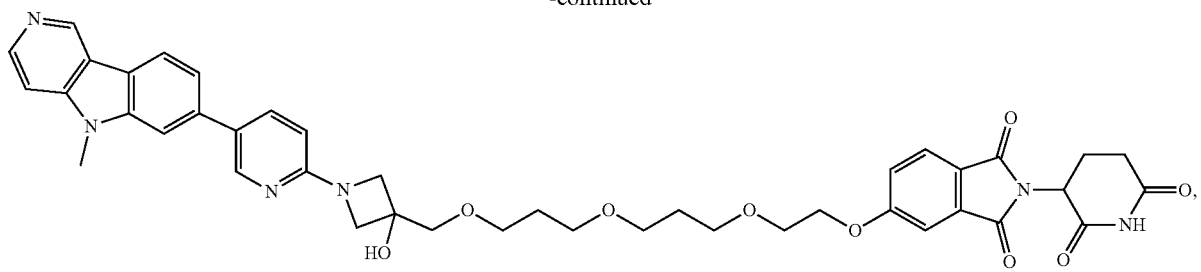
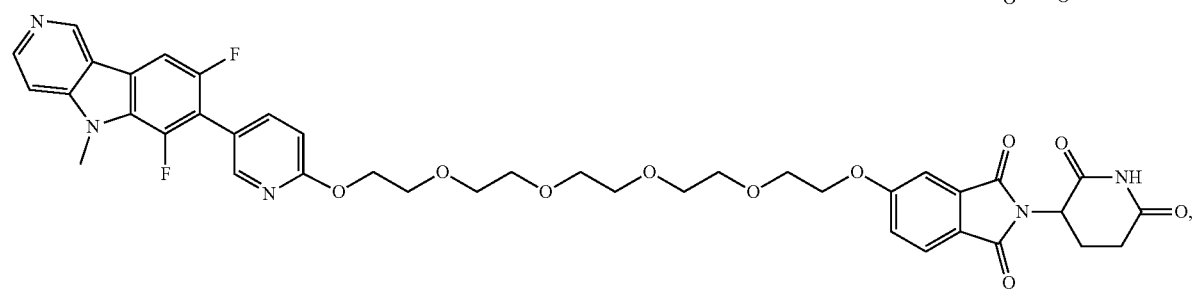
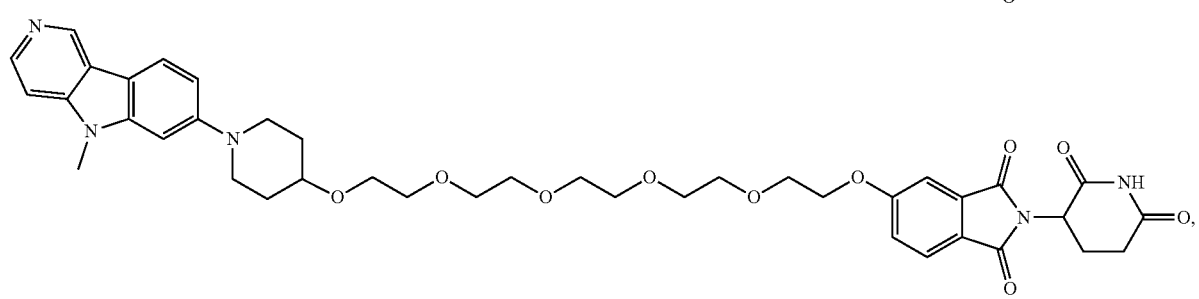
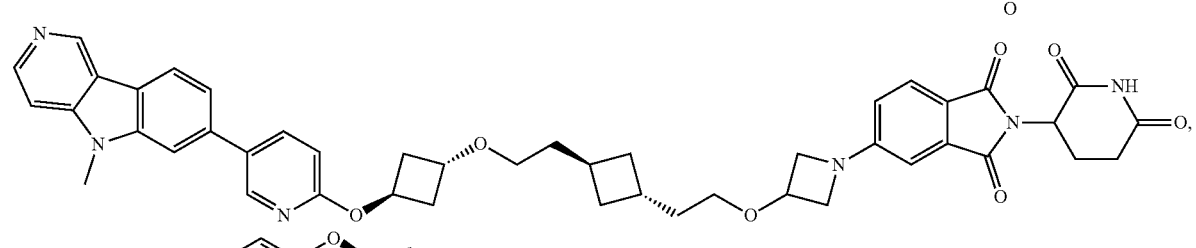
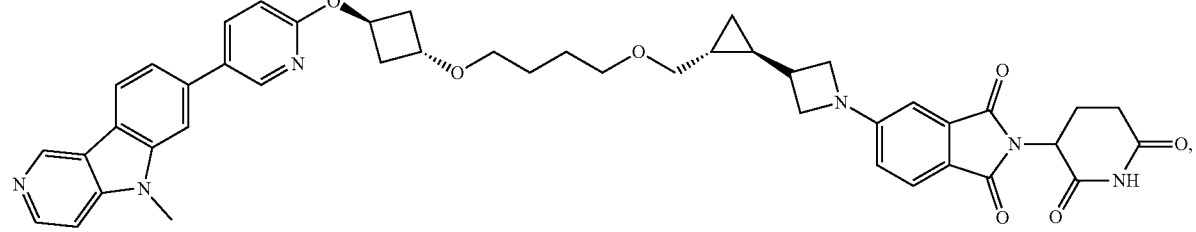
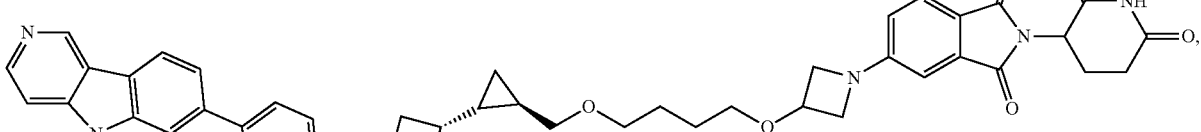
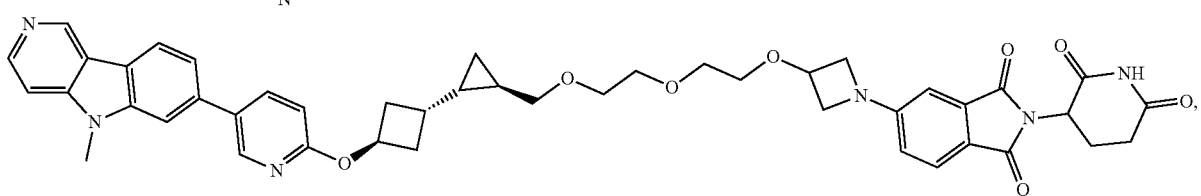

1075                                    1076
-continued
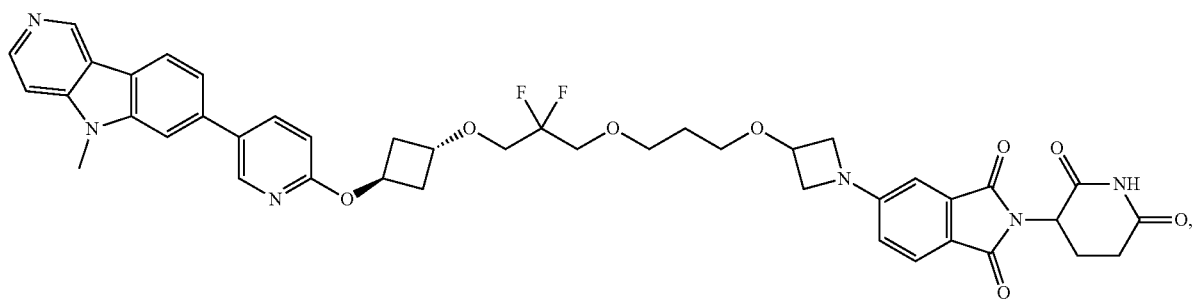
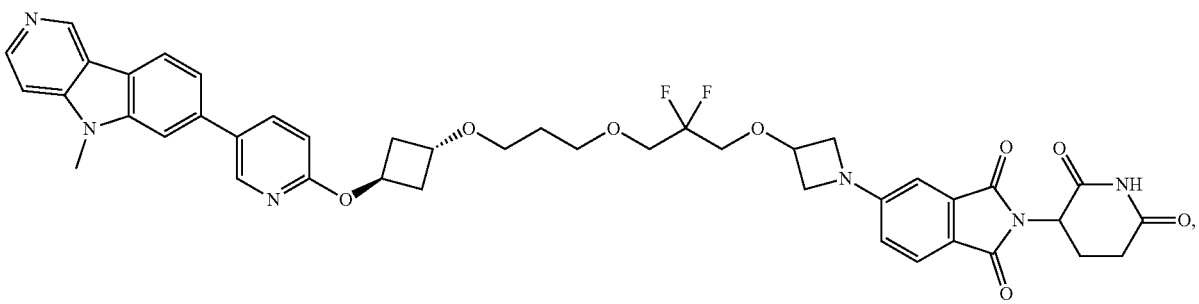
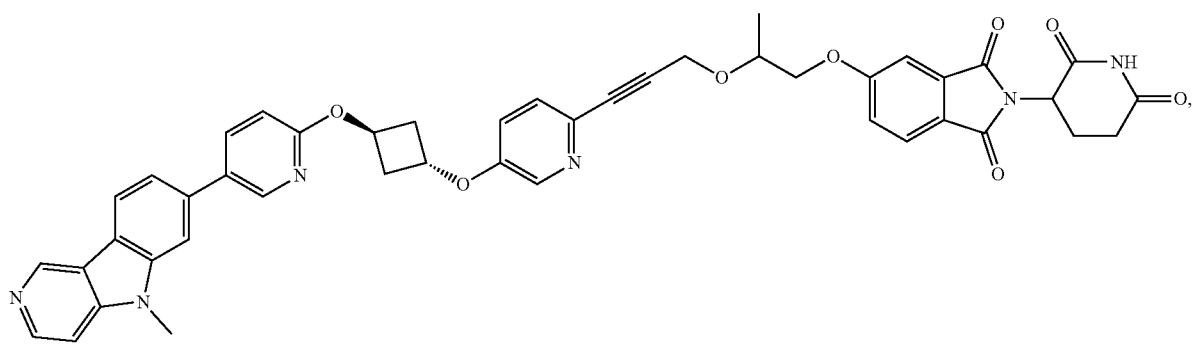
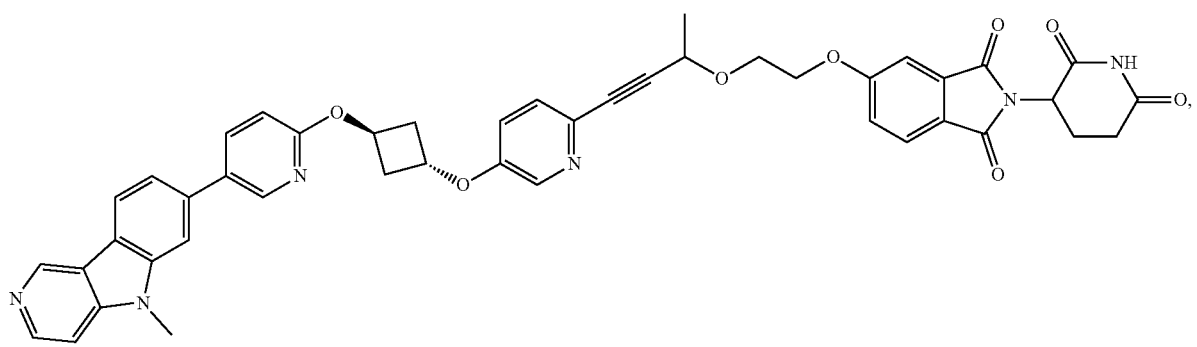

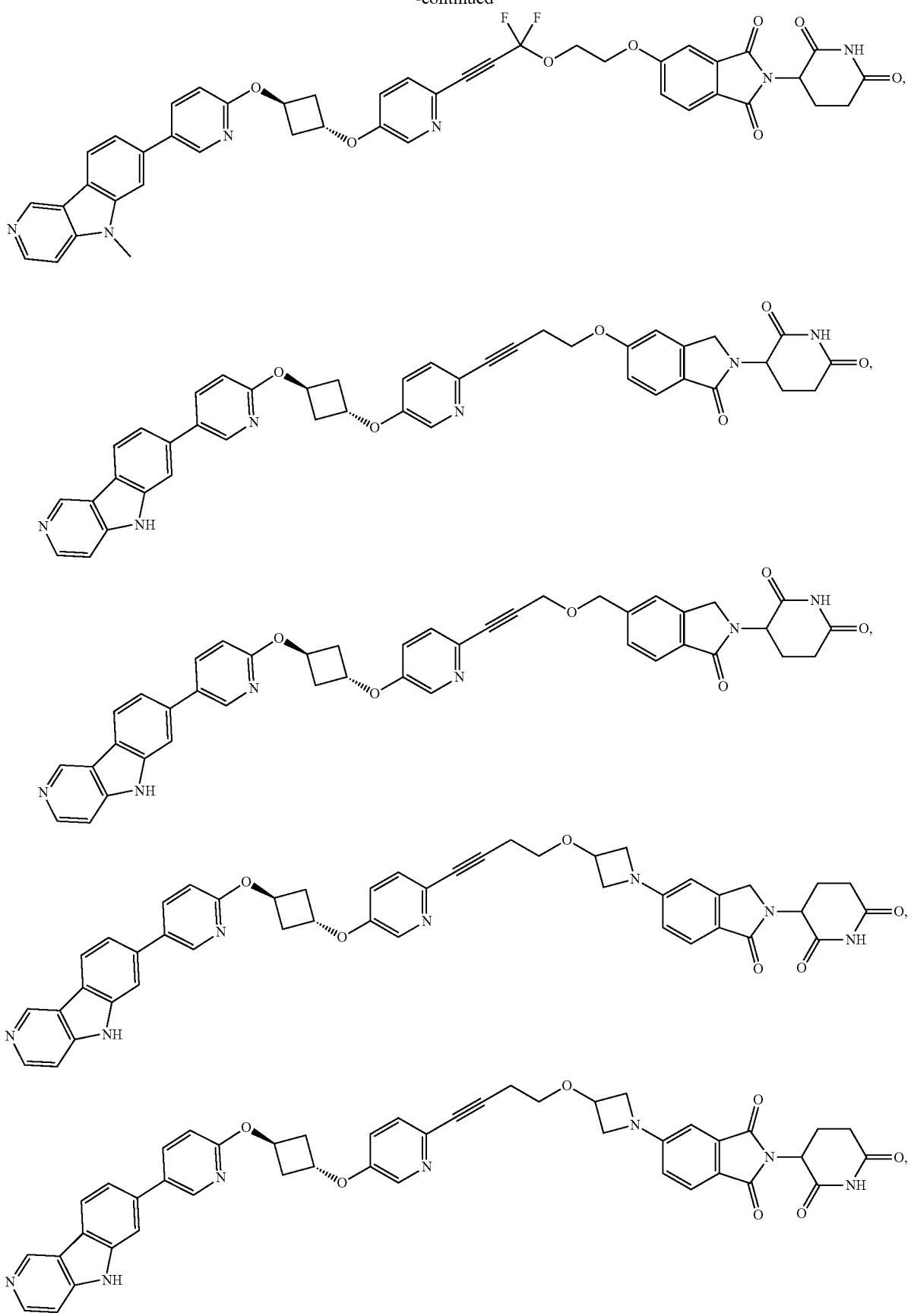

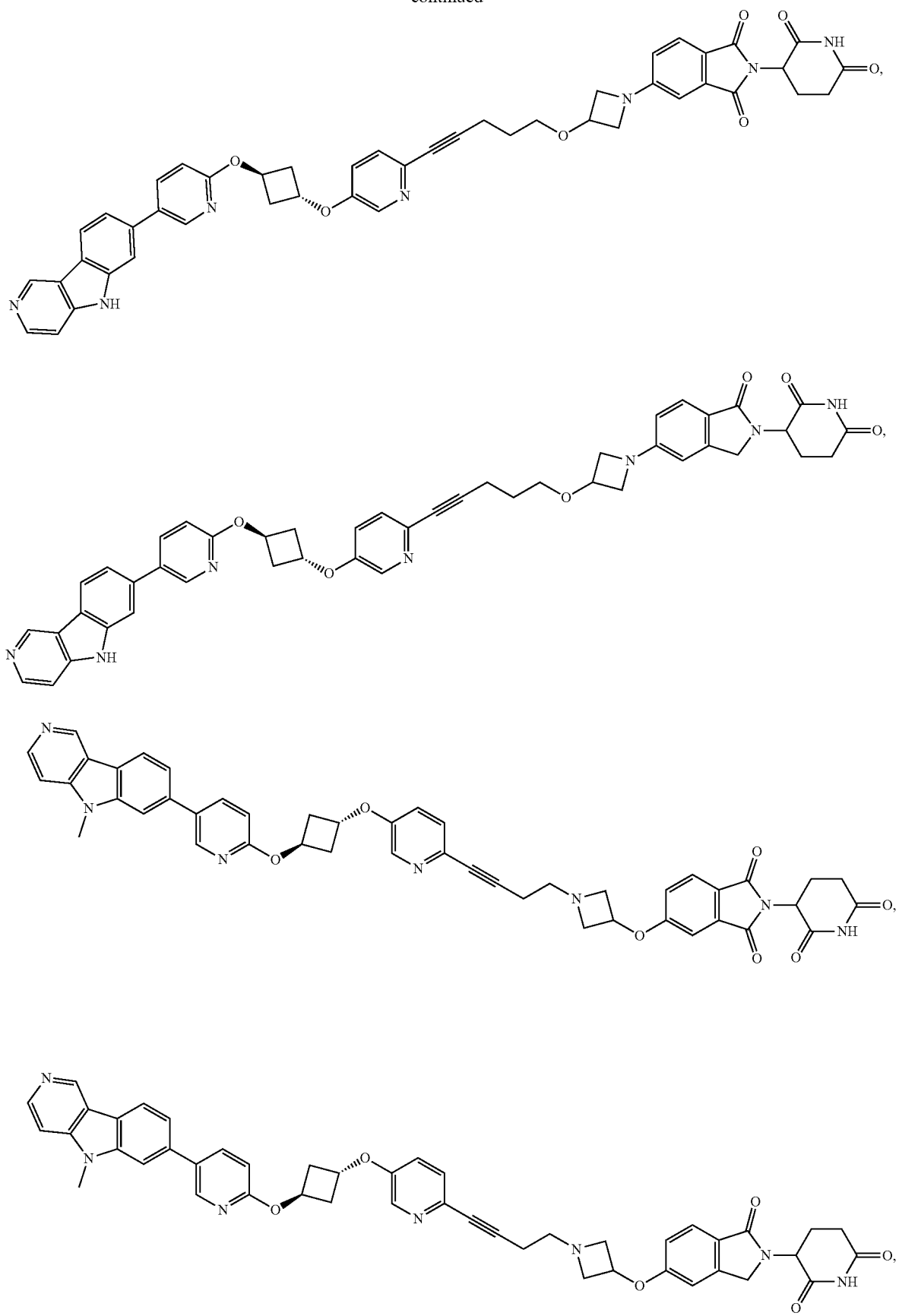

1081                                        1082
-continued
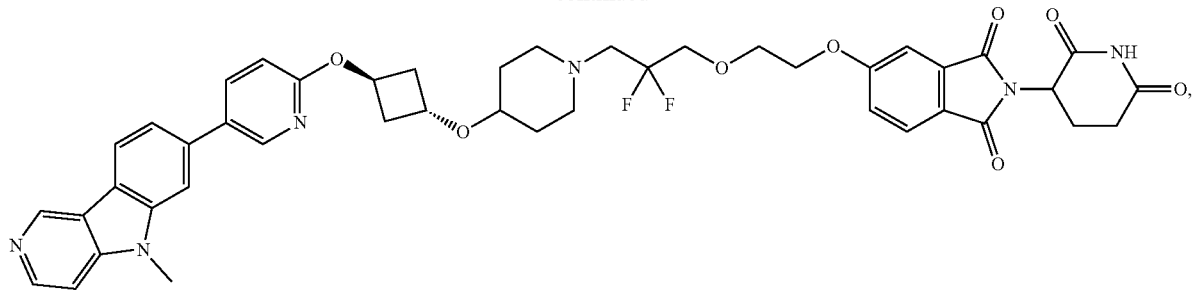
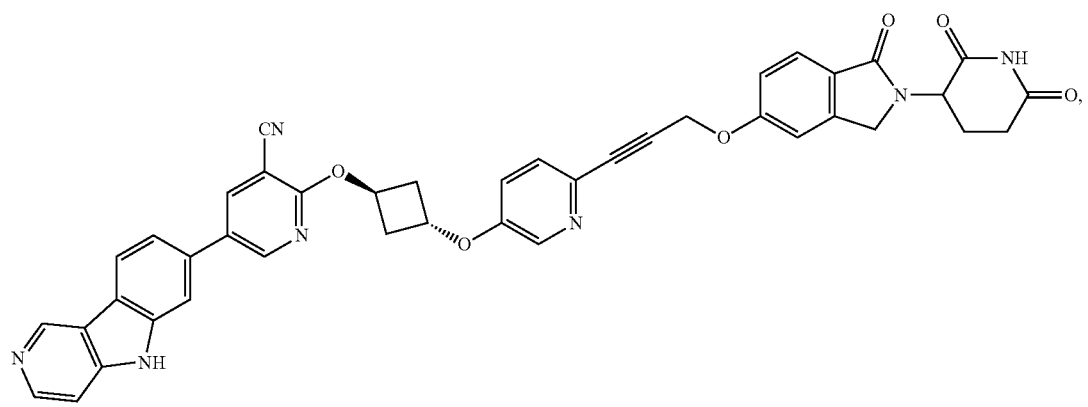
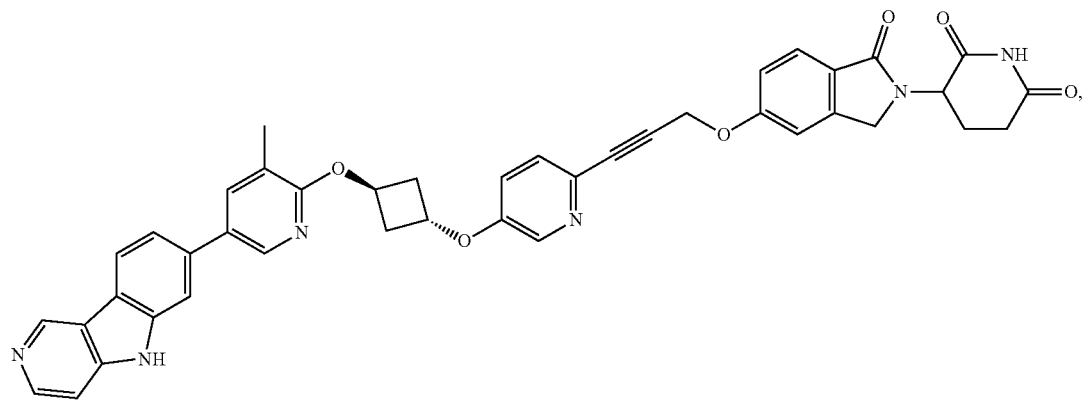
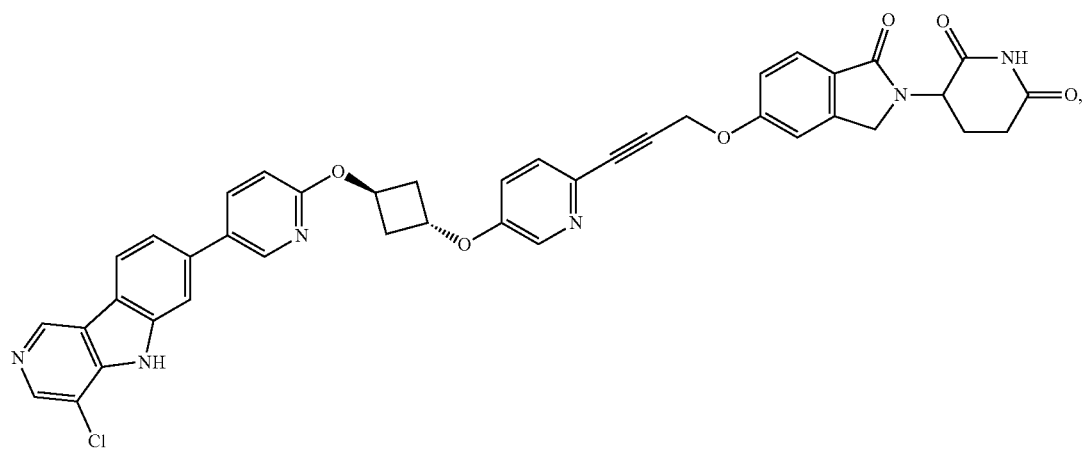

1083 1084
-continued
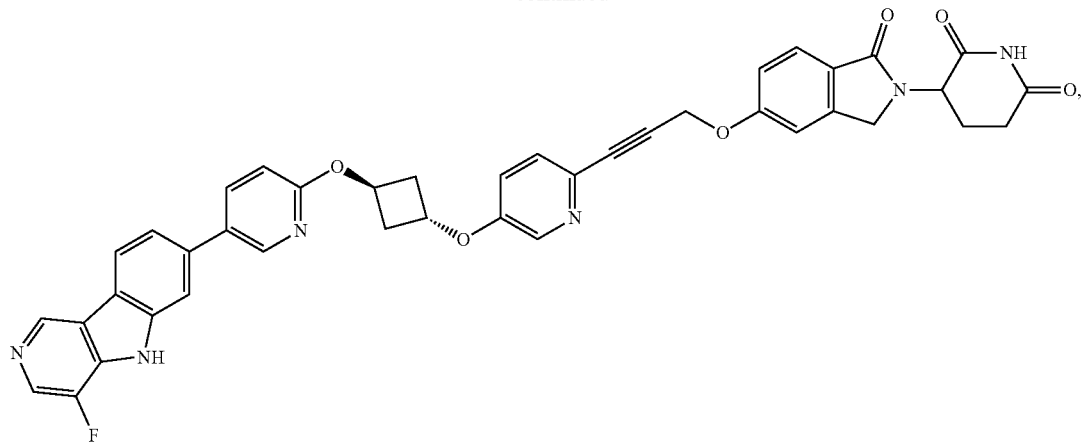
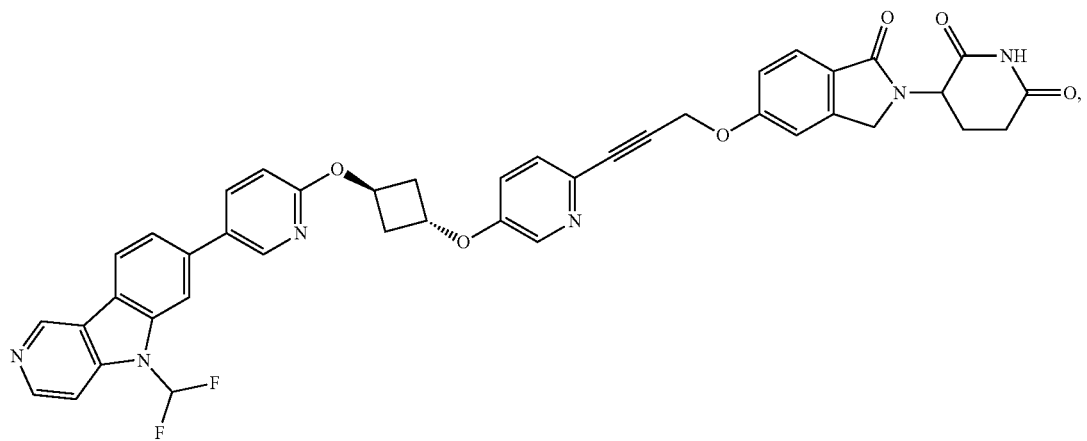
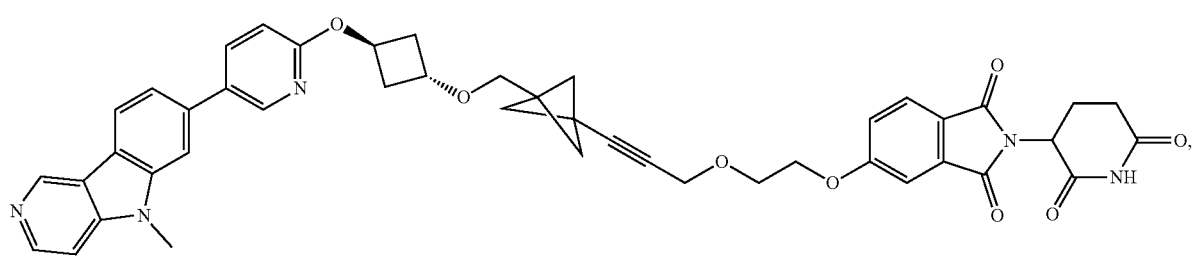
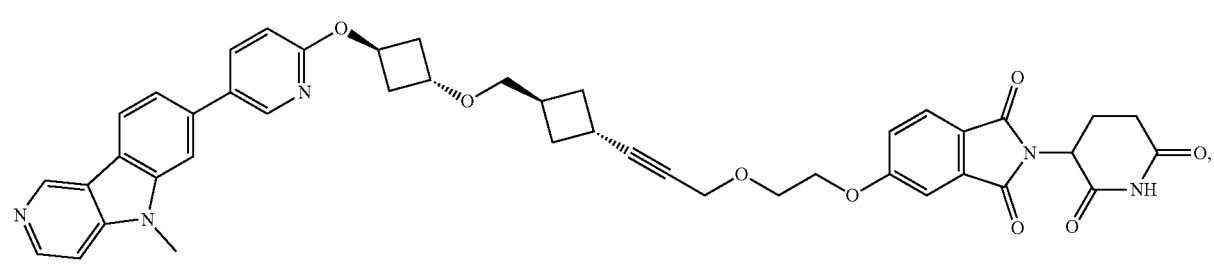

1085 1086
-continued
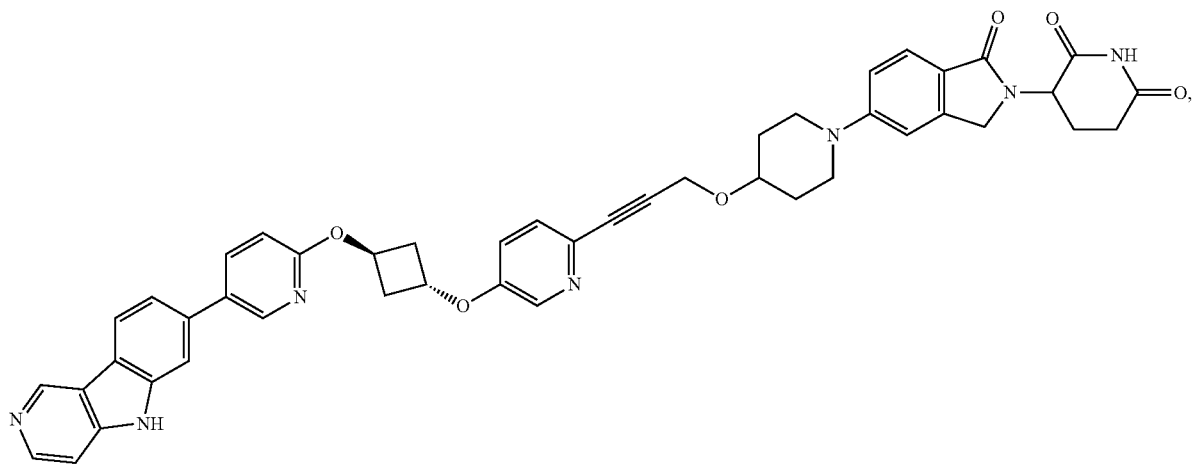
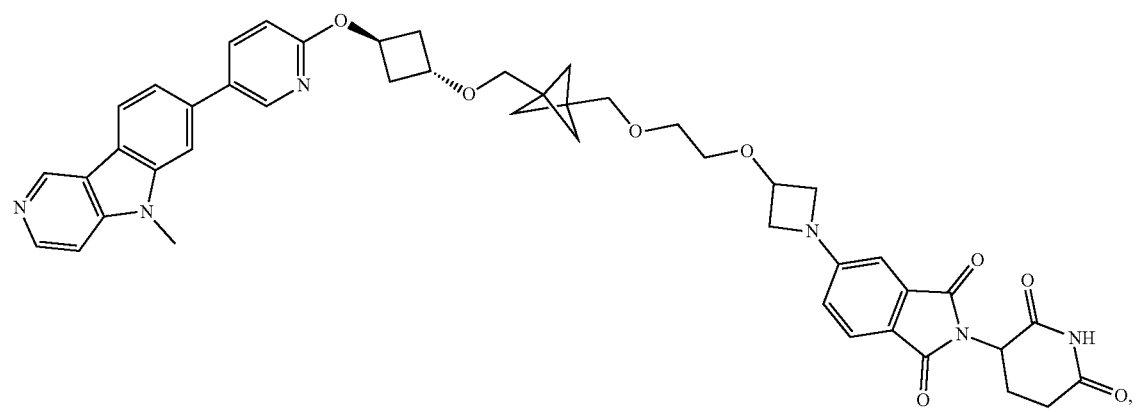
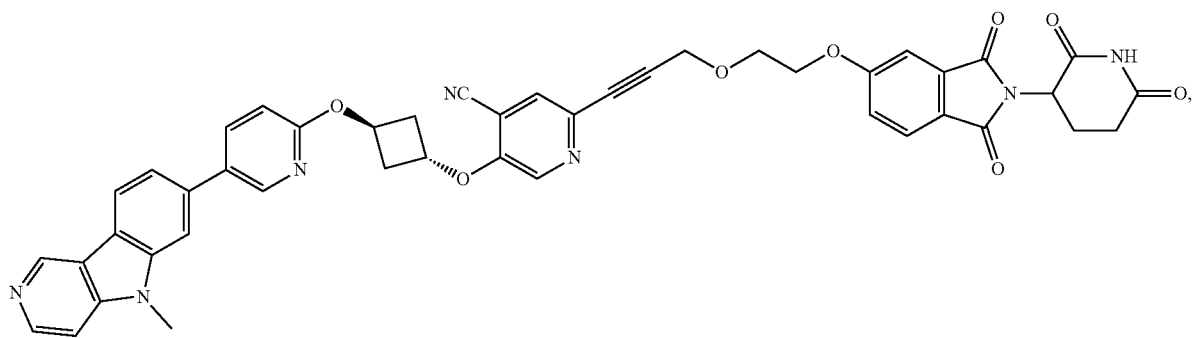
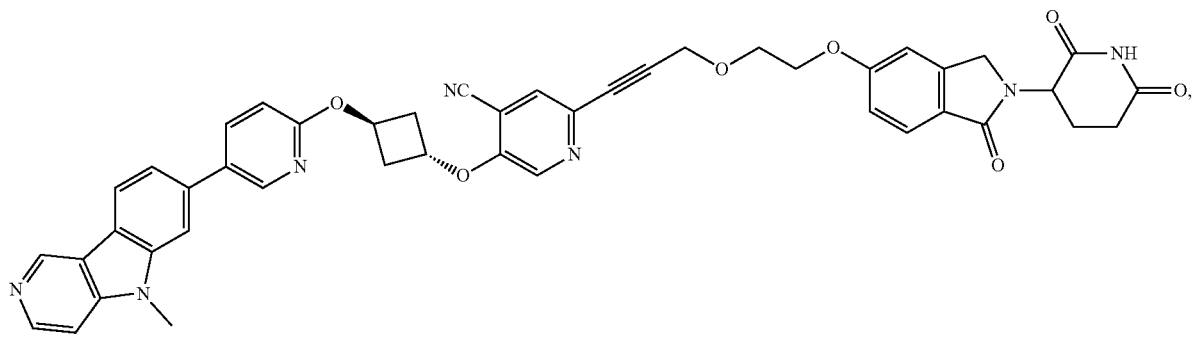

1087
-continued
1088
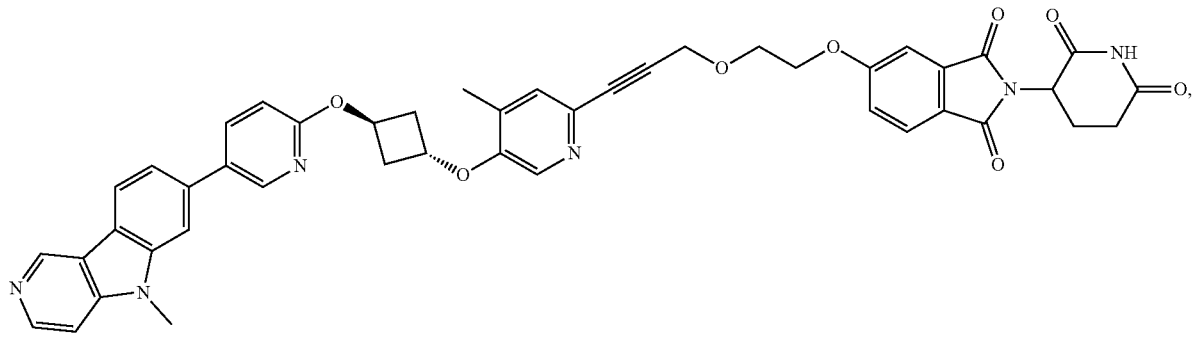
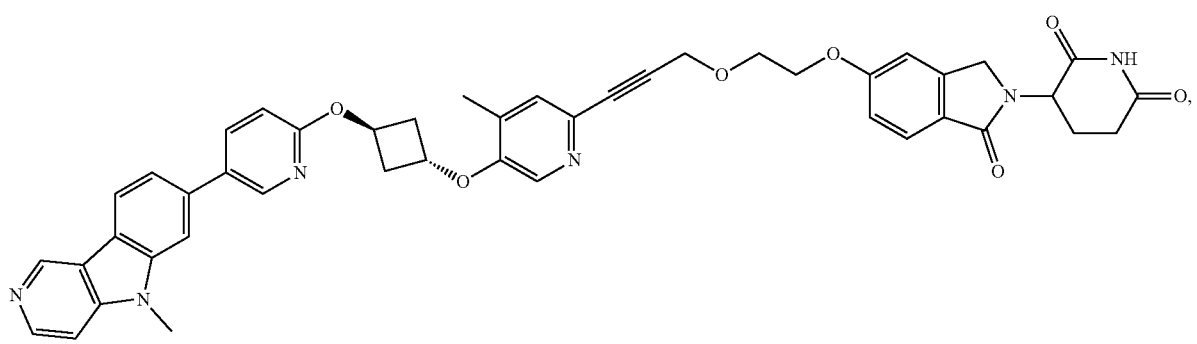
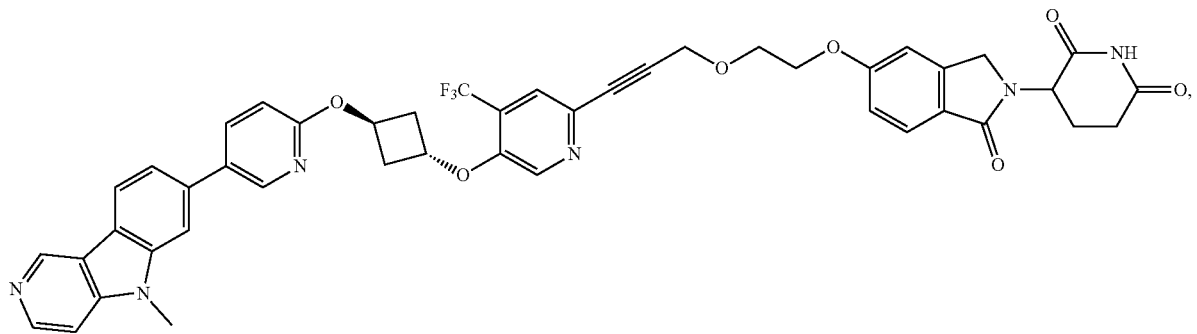
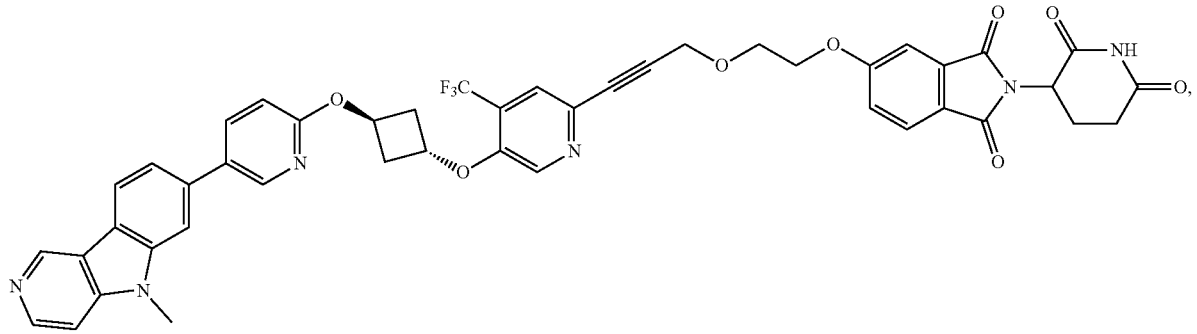
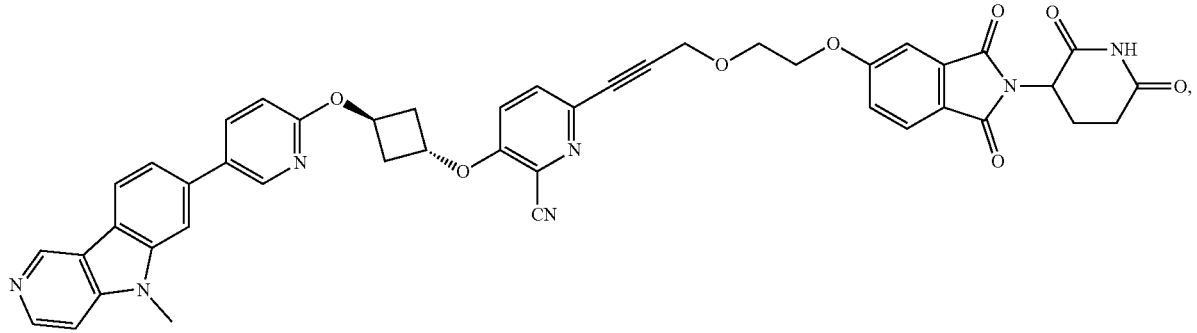

1089
-continued
1090
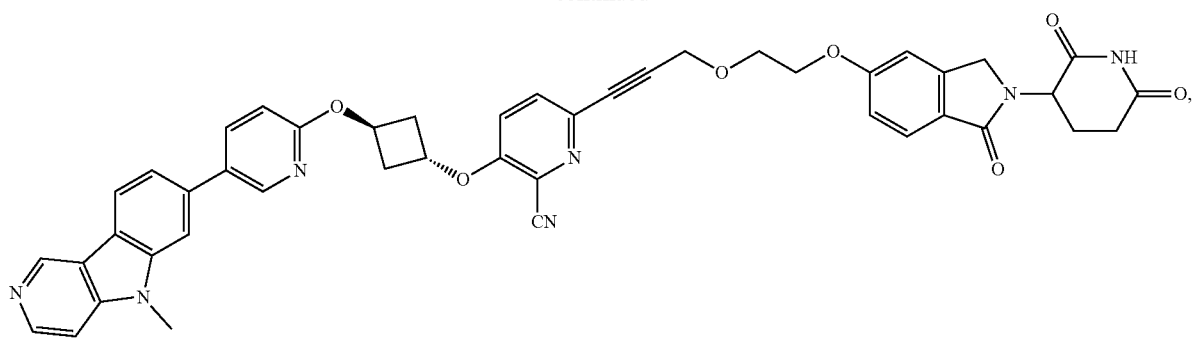
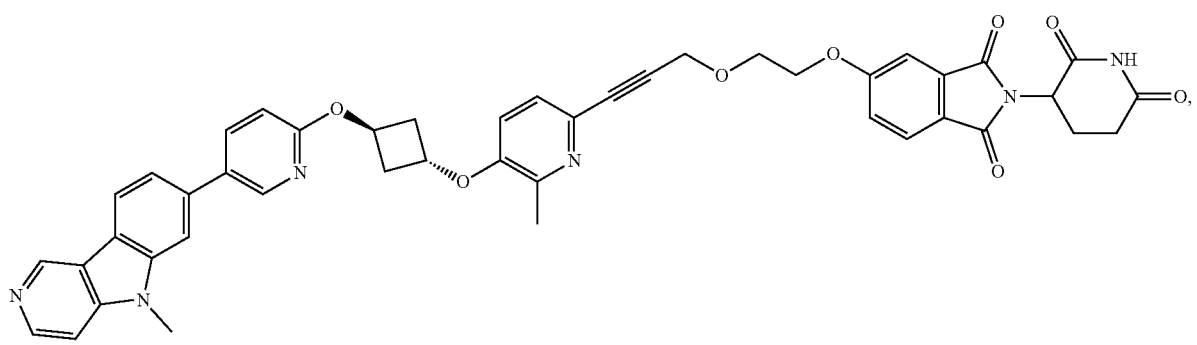
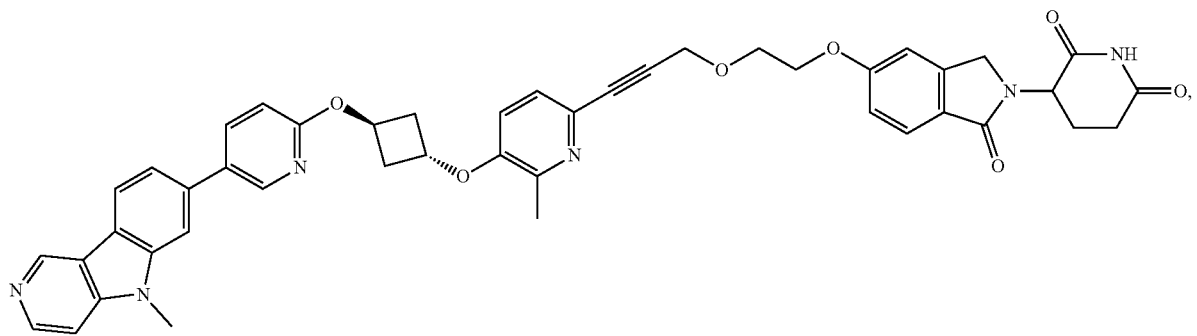
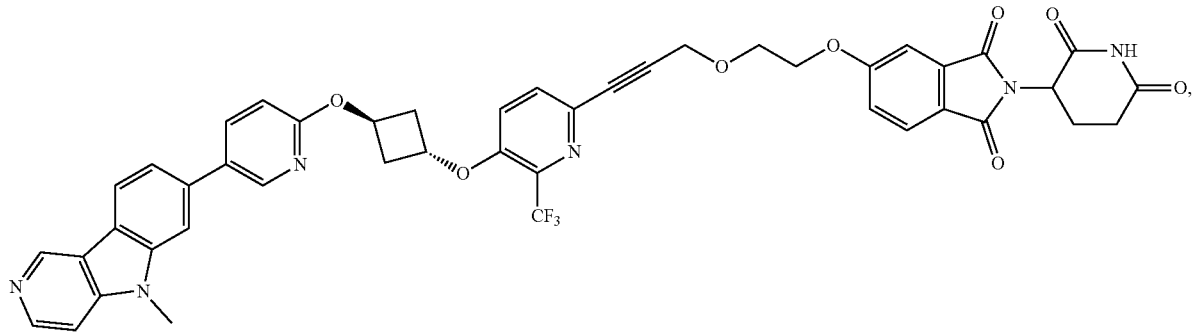
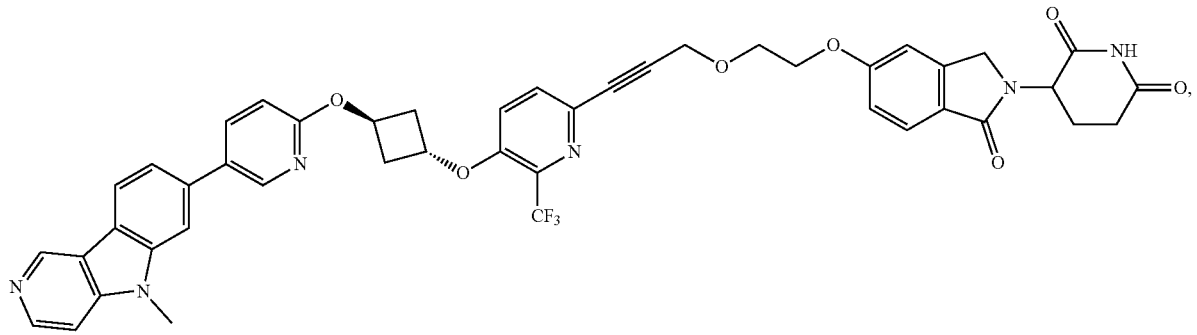

-continued
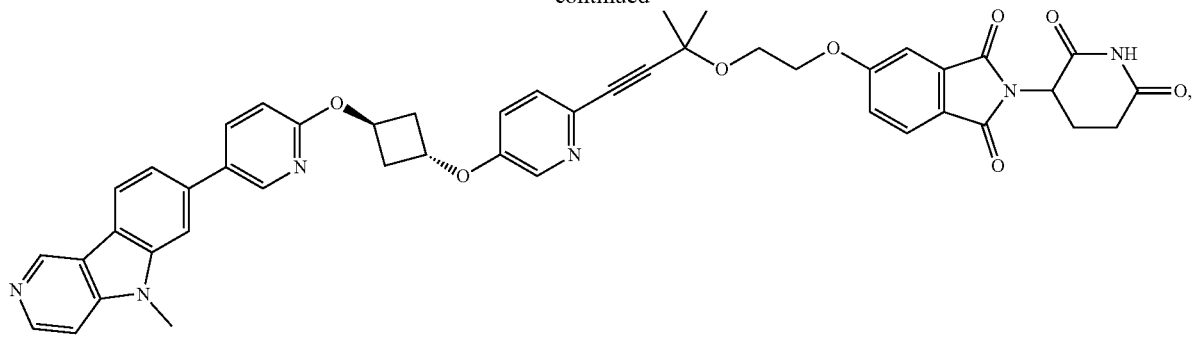
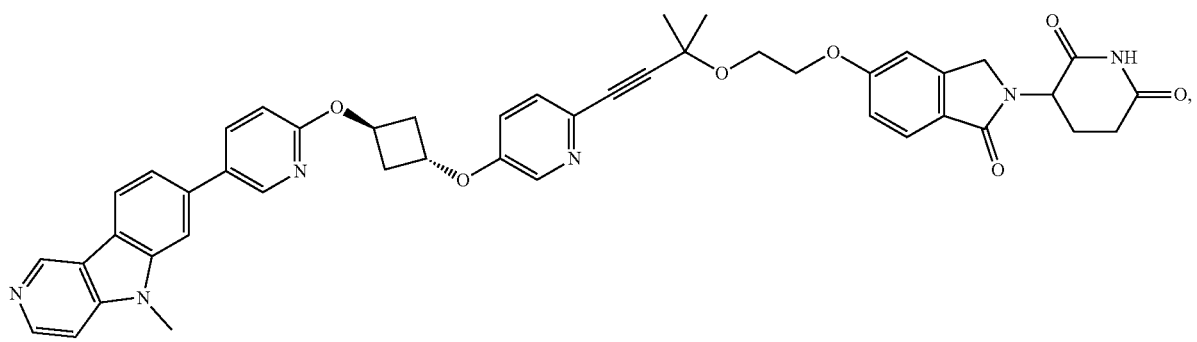
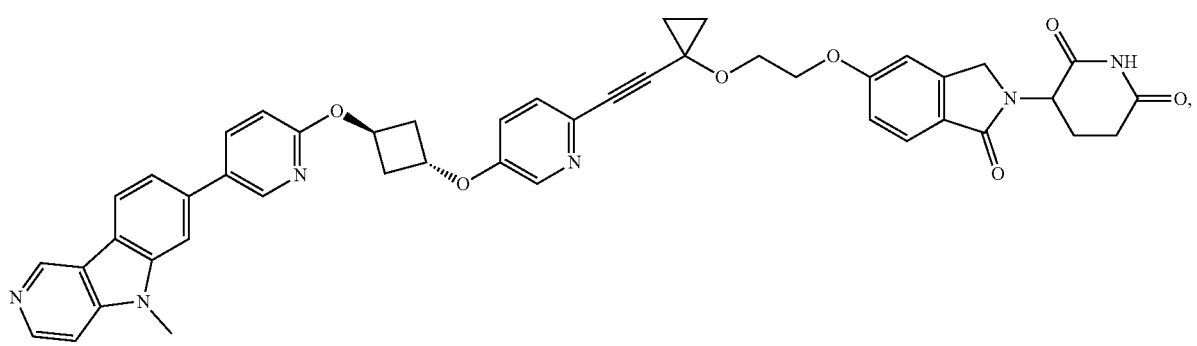
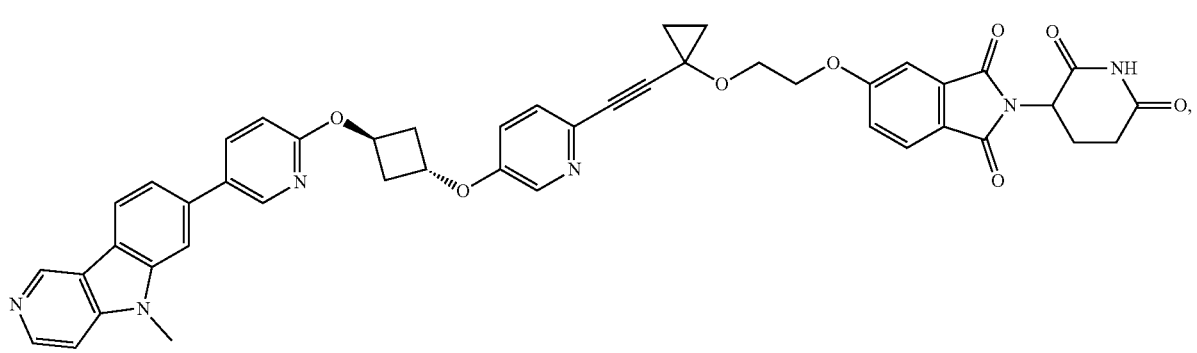
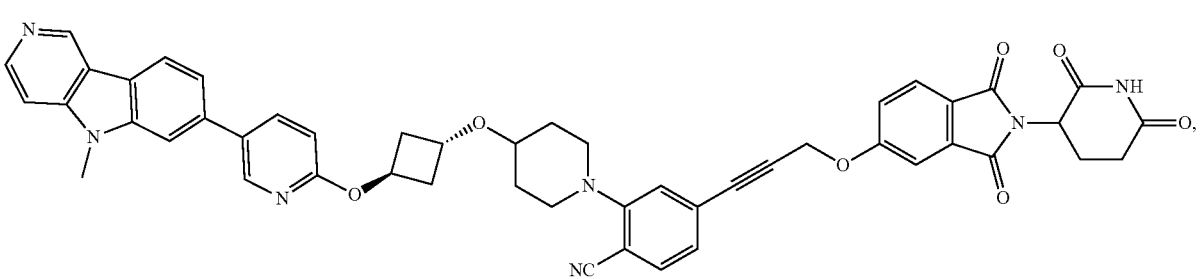

1093                                                    1094
-continued
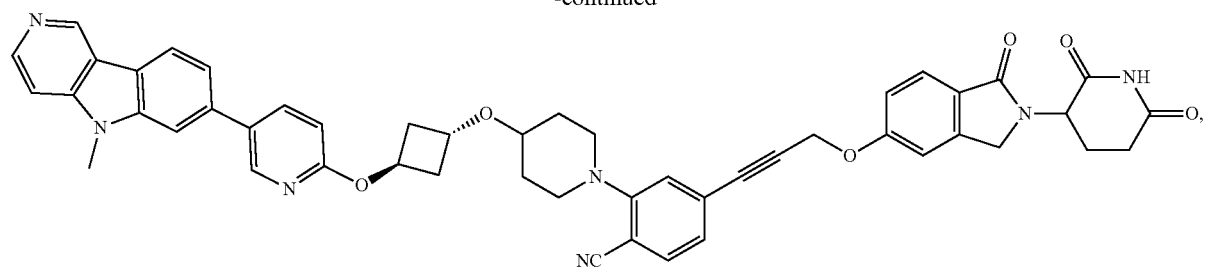
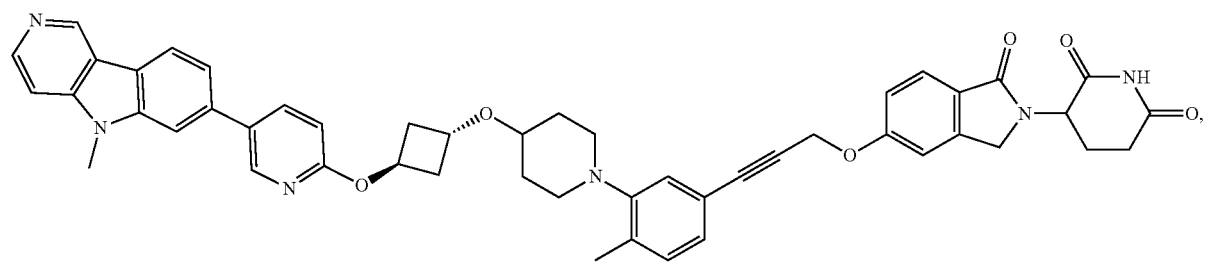
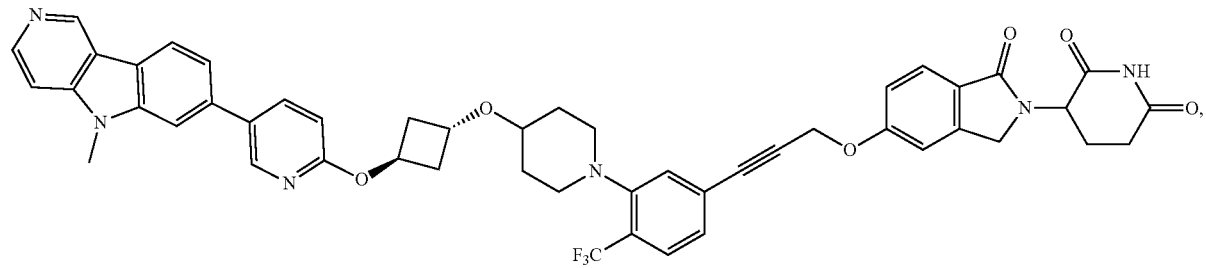
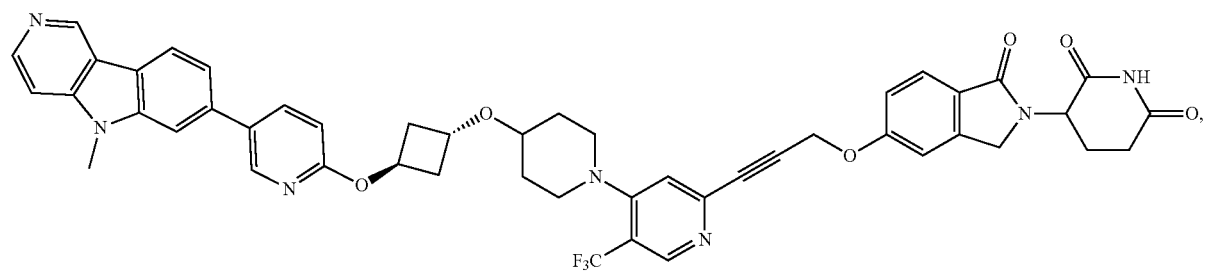
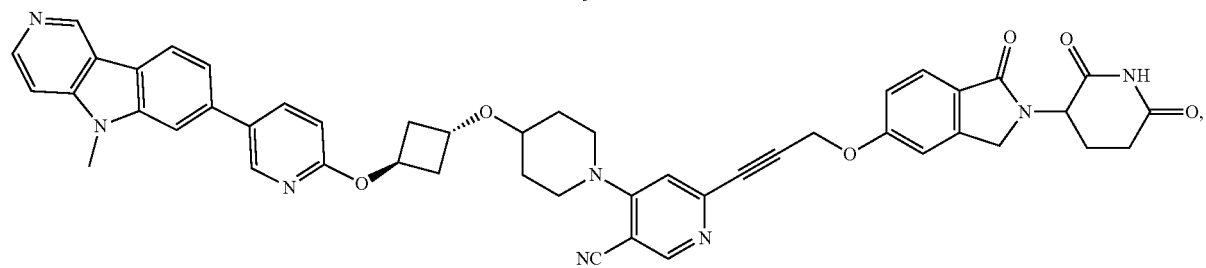
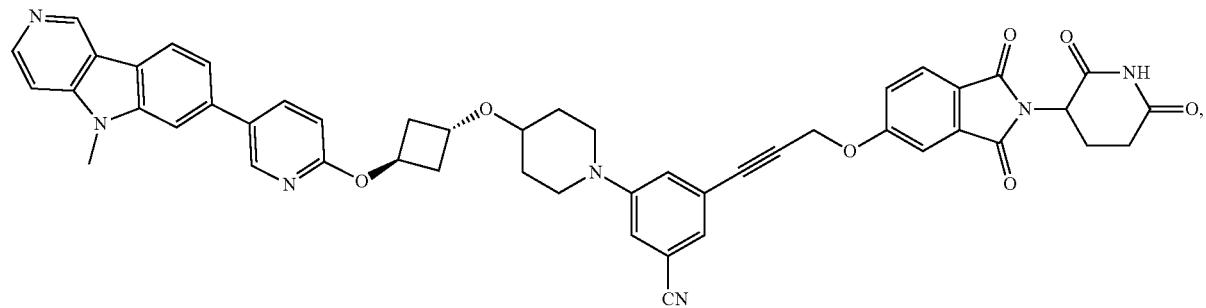

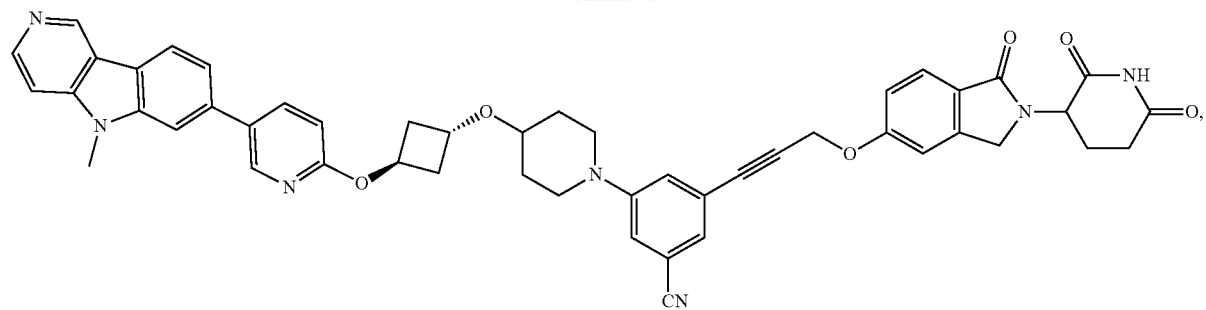
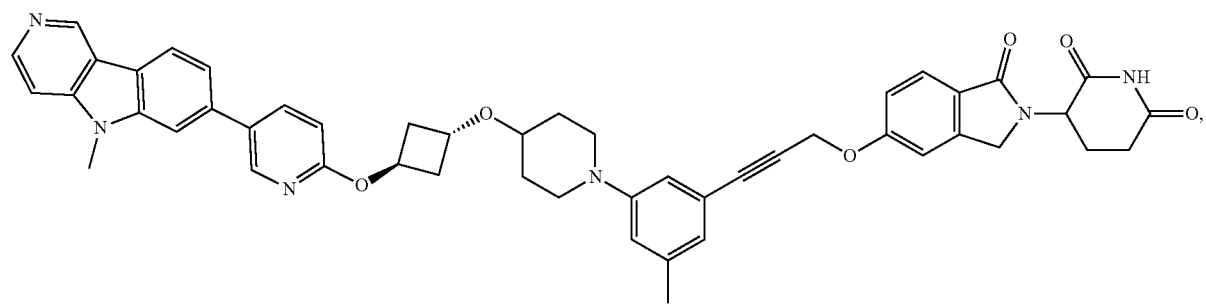
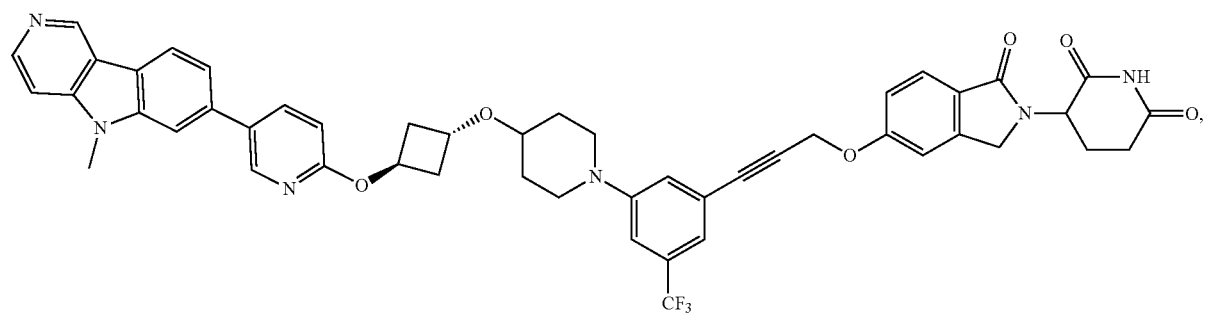
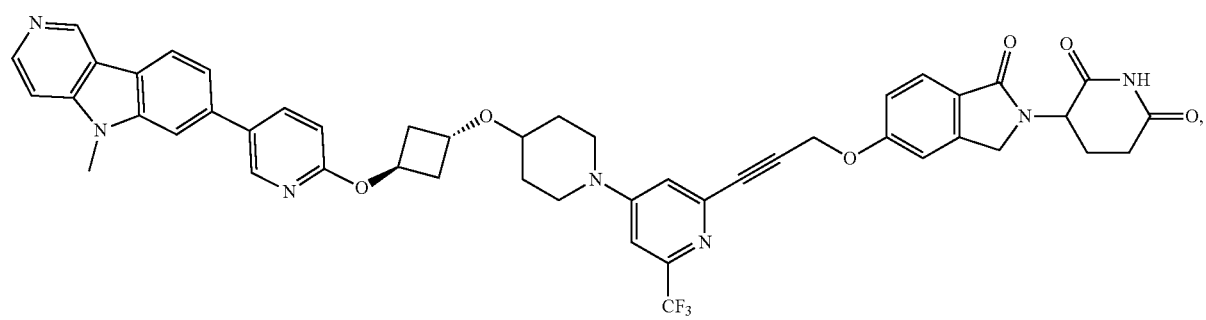
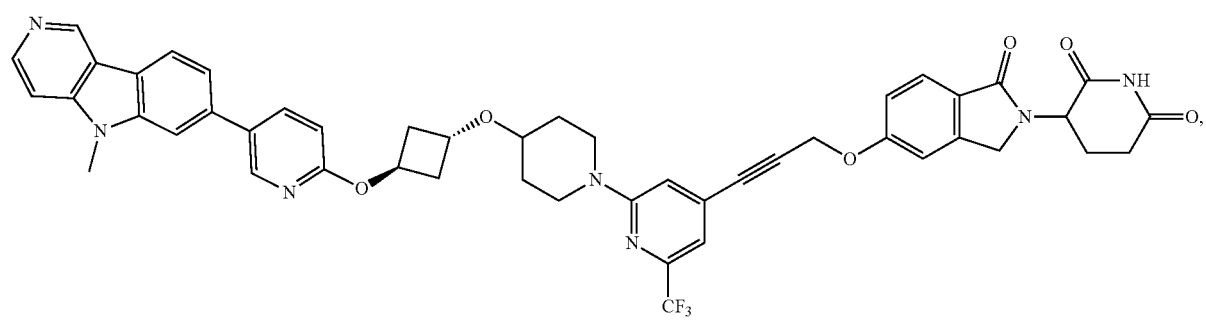

1097 1098
-continued
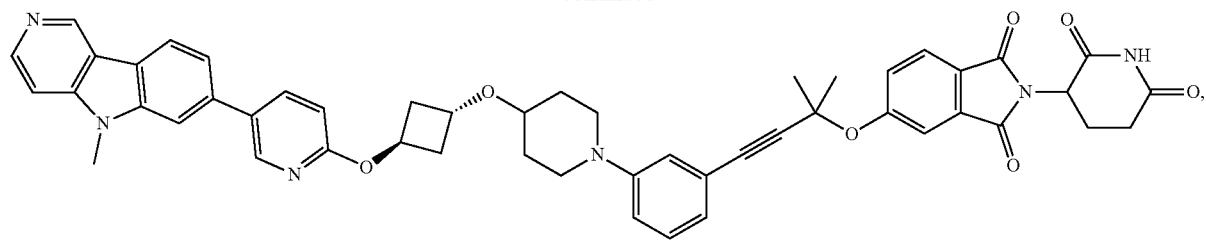
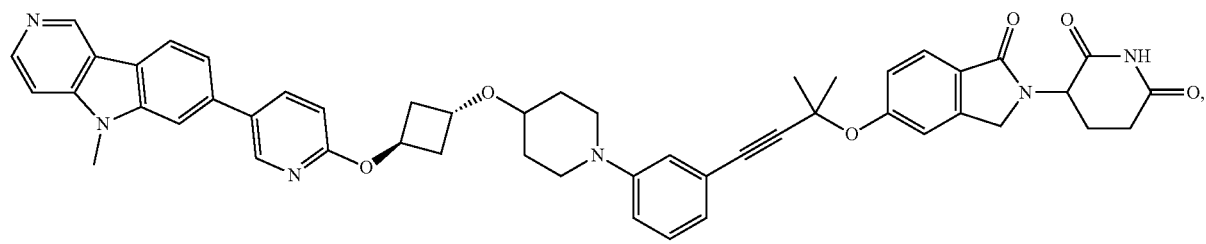
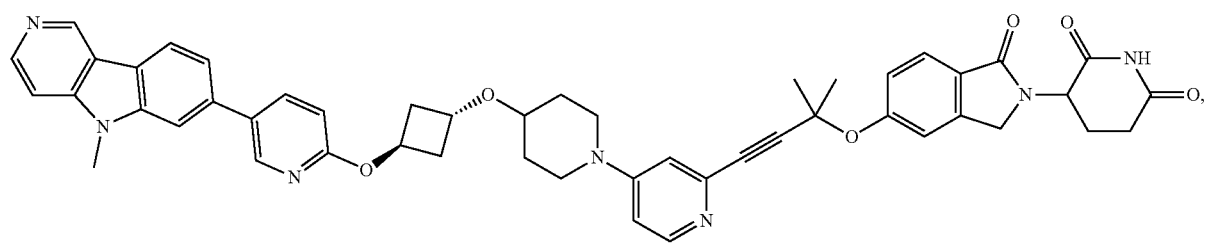
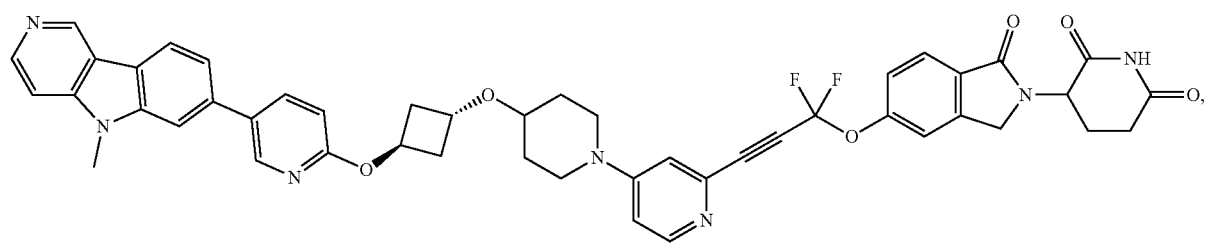
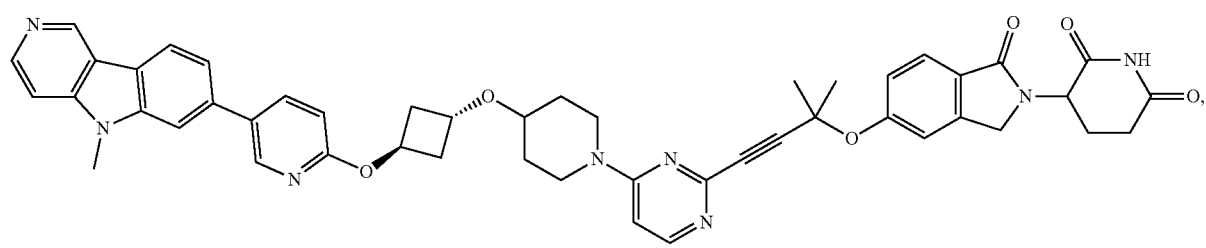
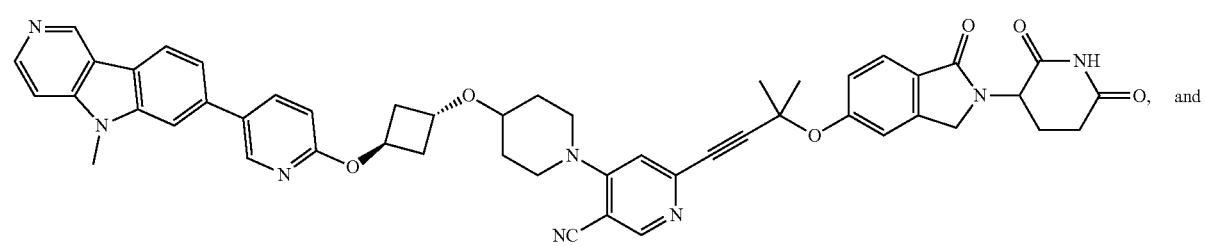
and -continued
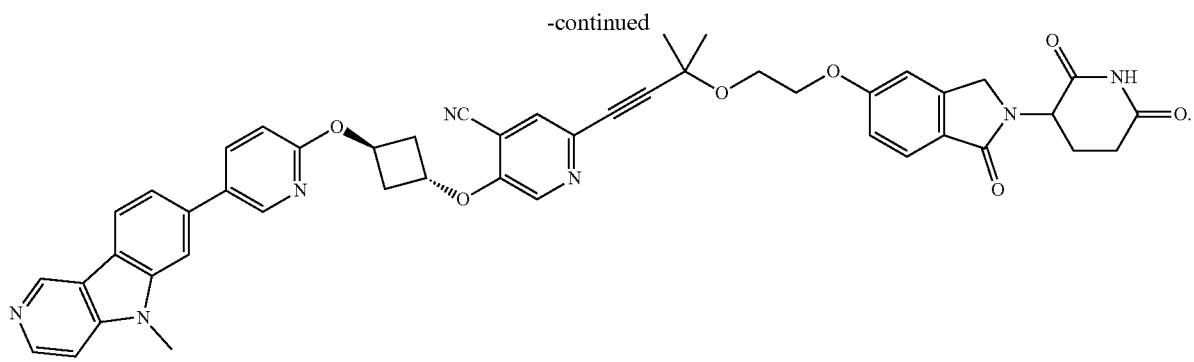
16. A compound selected from the group consisting of:
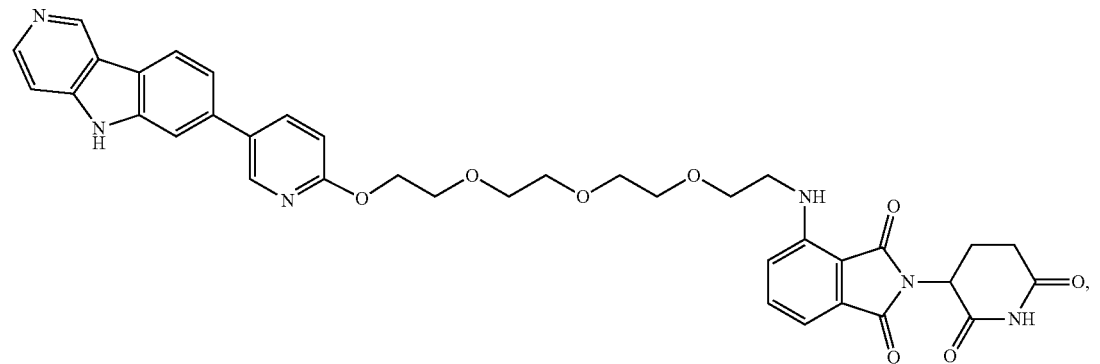
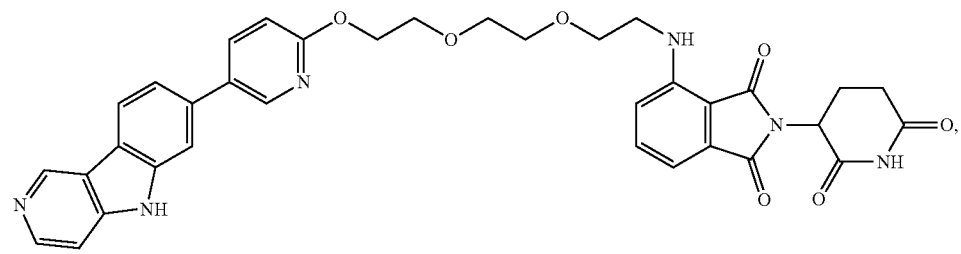
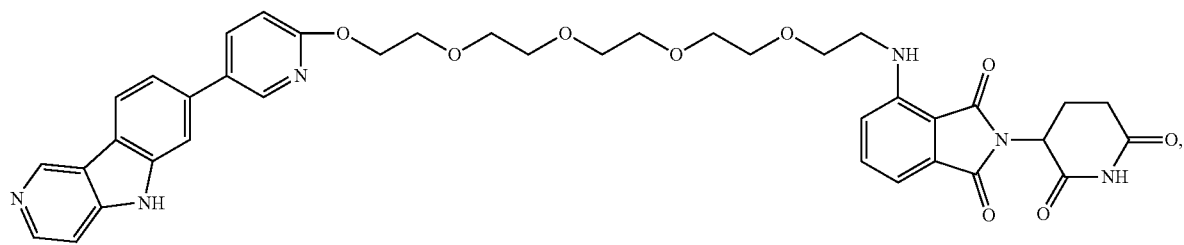
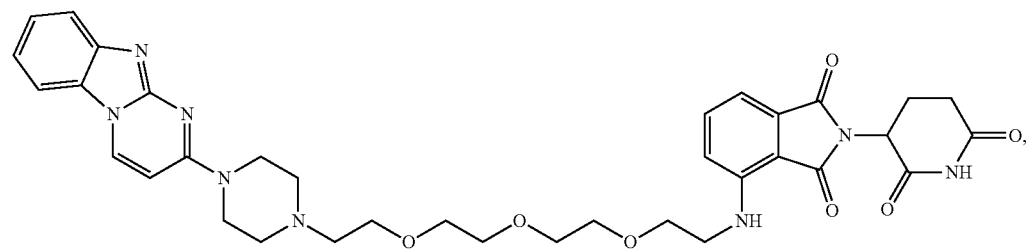

-continued
1101
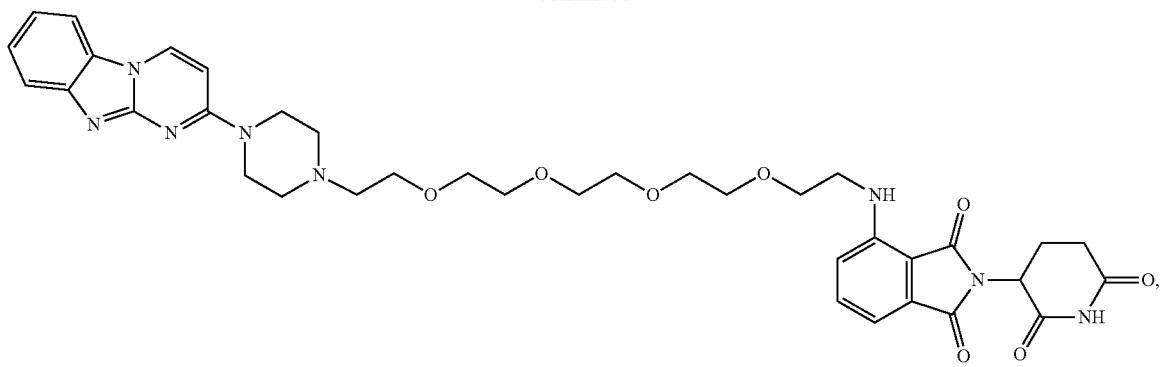
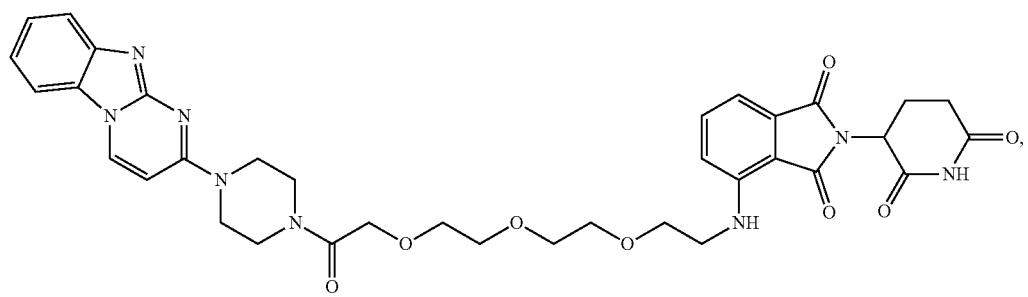
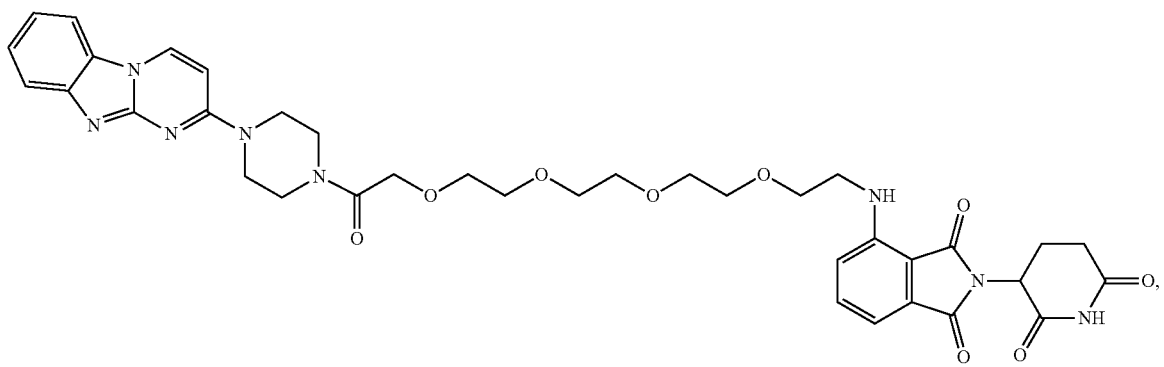
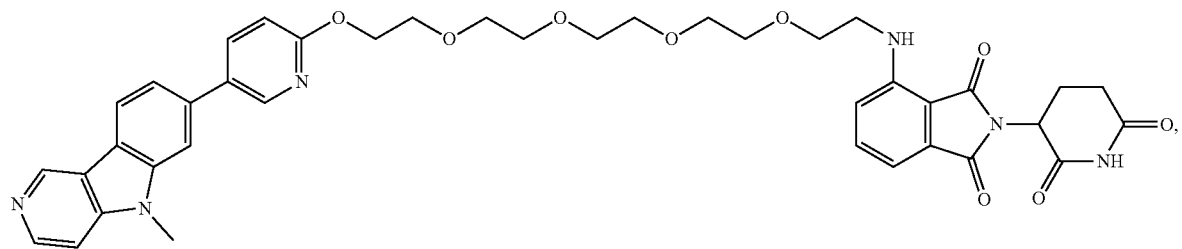
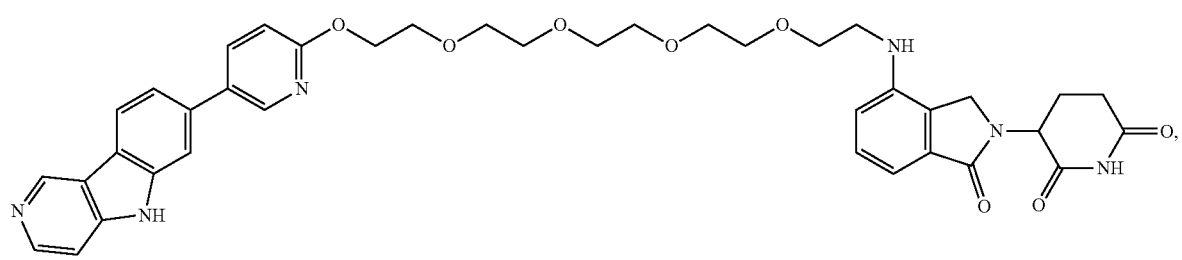

1103                                                           1104
-continued
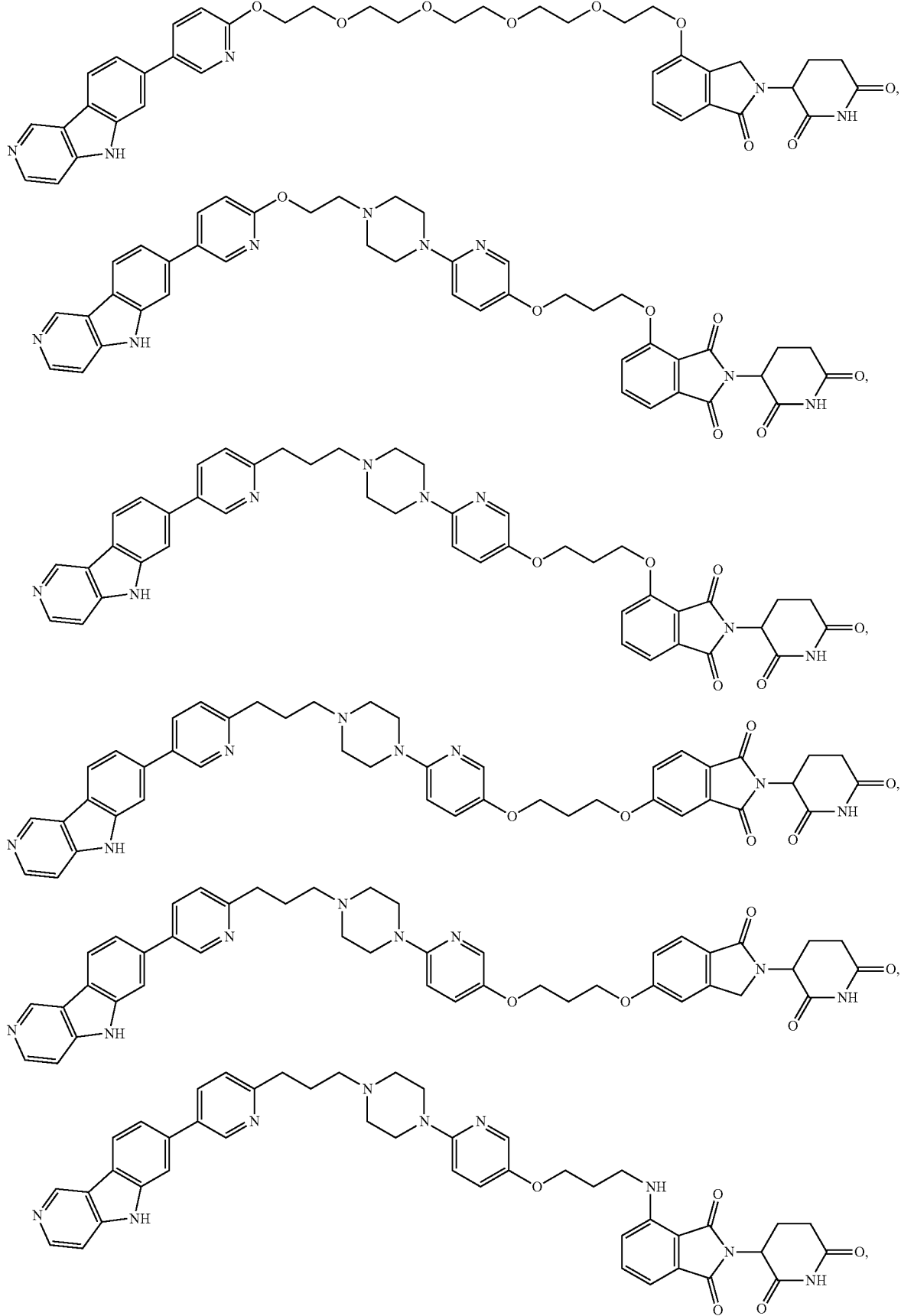

-continued
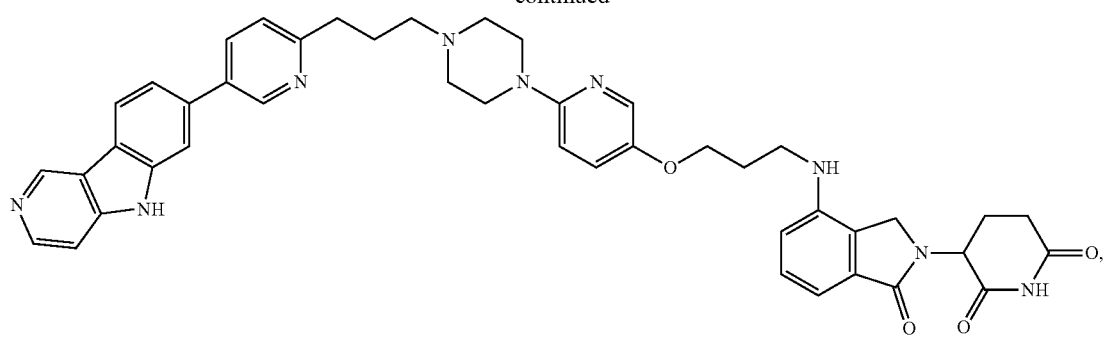
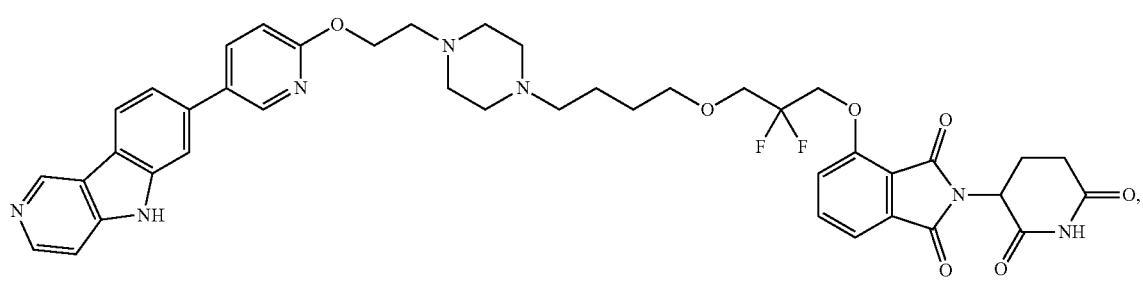
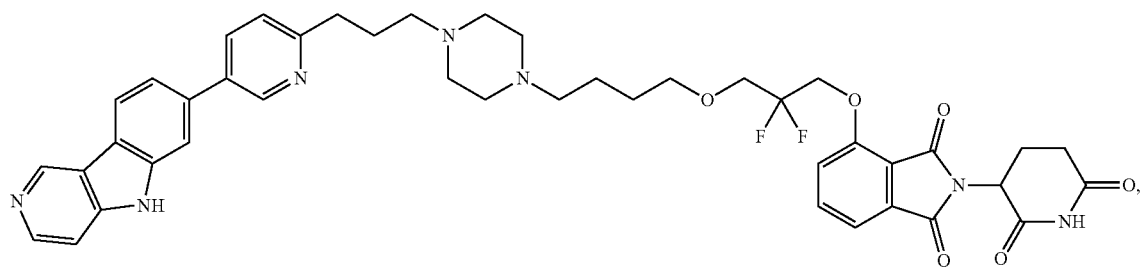
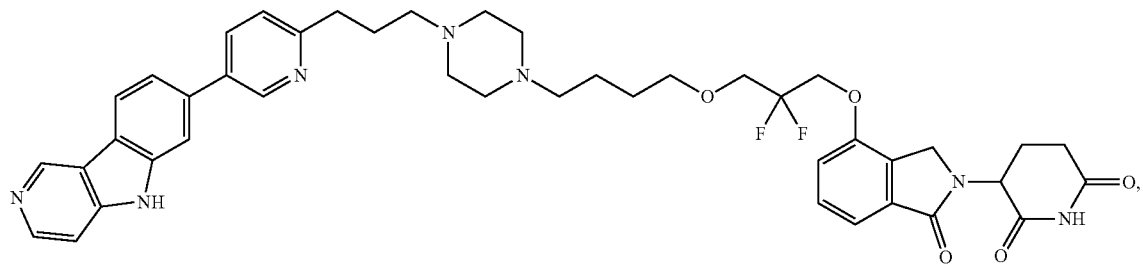
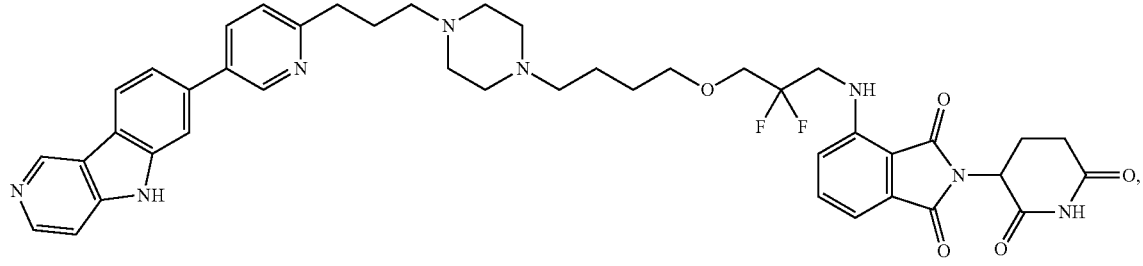
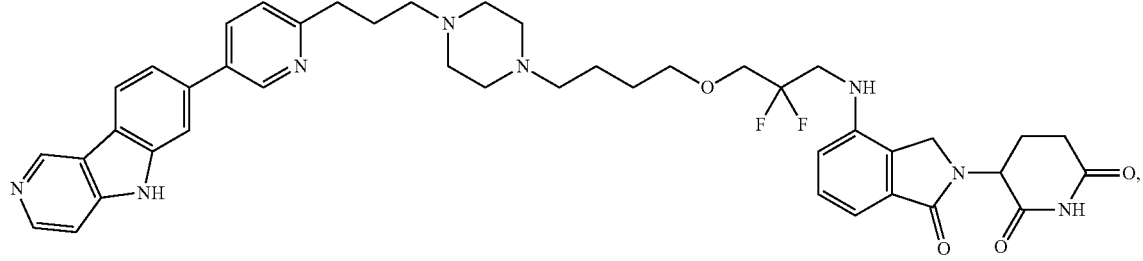

1107 1108
-continued
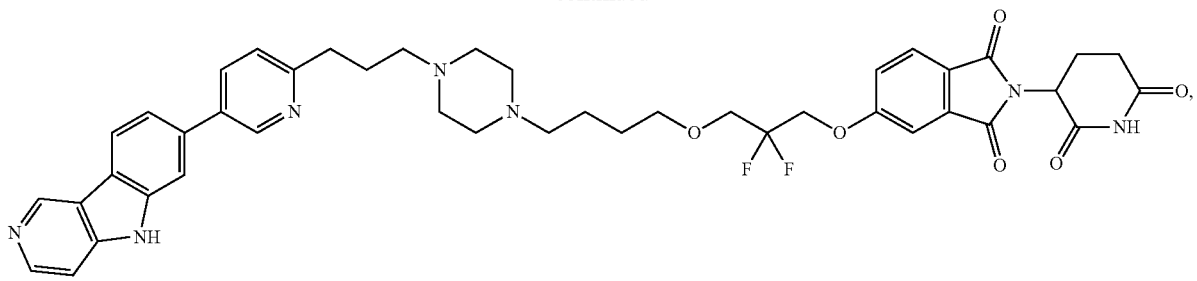
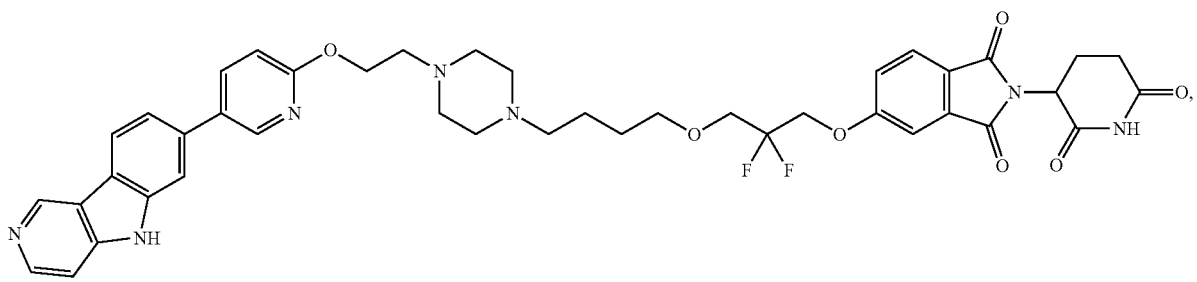
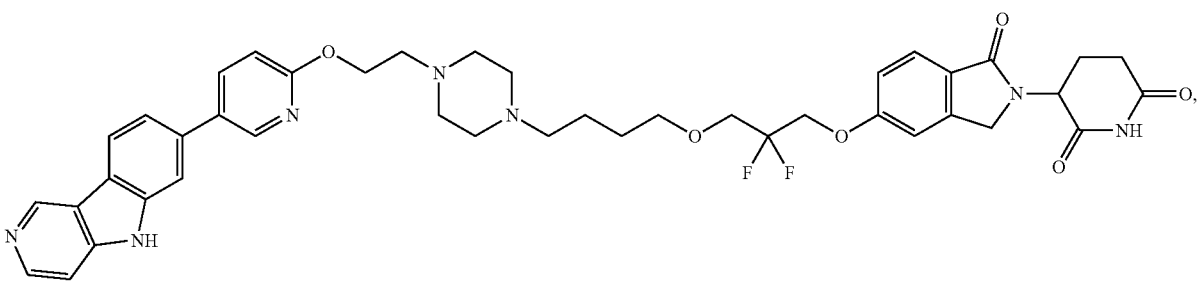
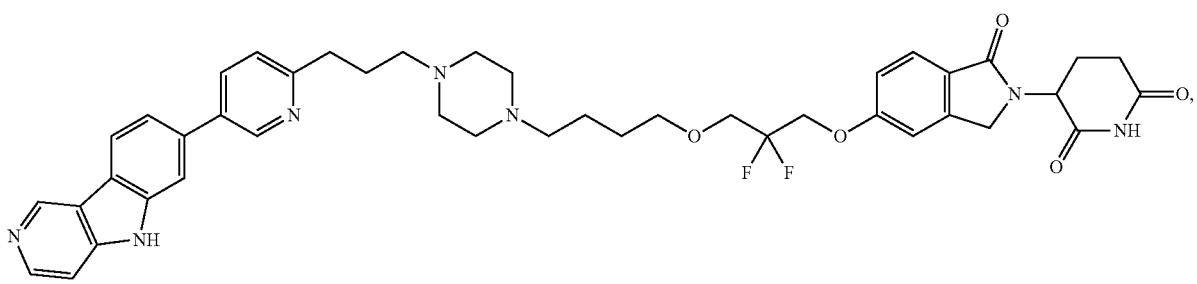
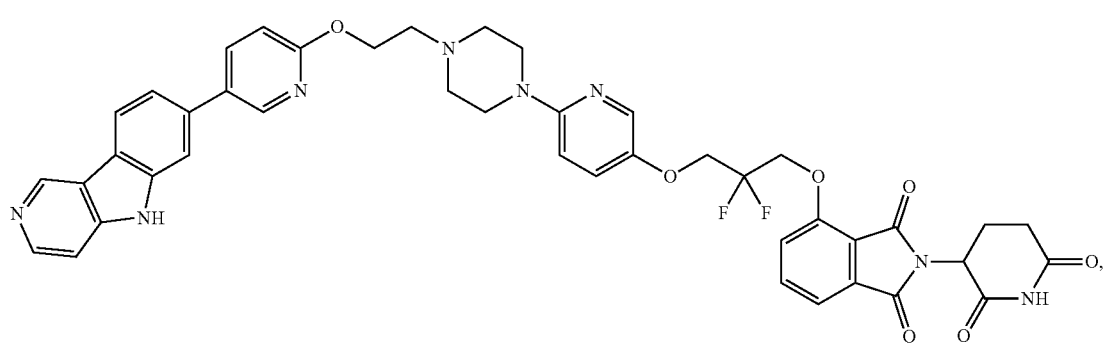

-continued
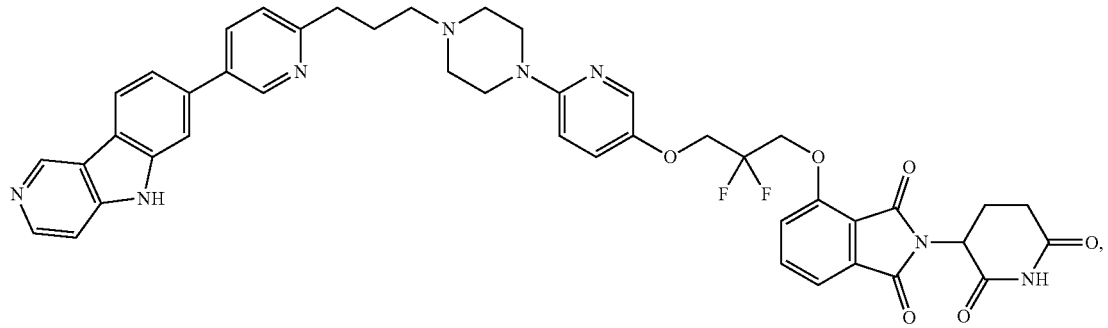
1109
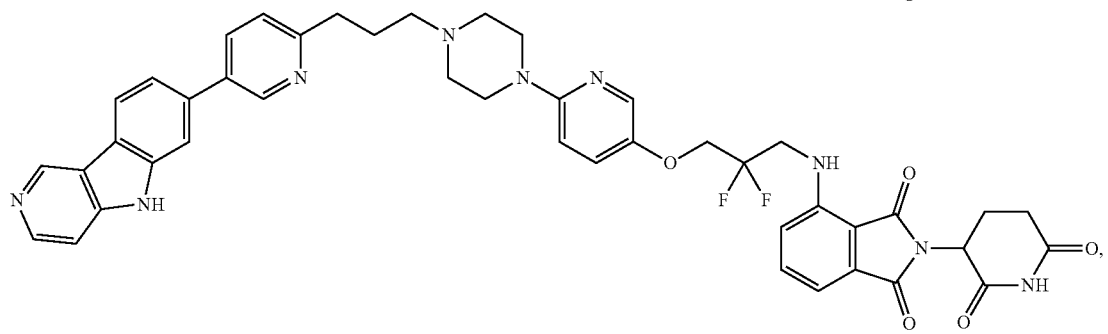
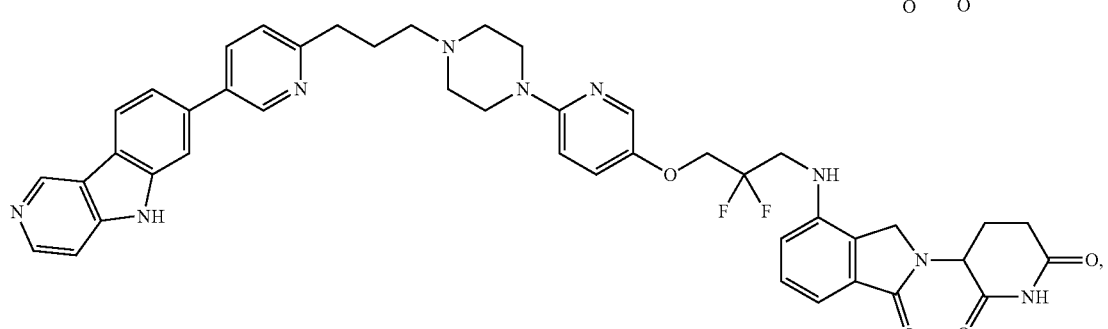
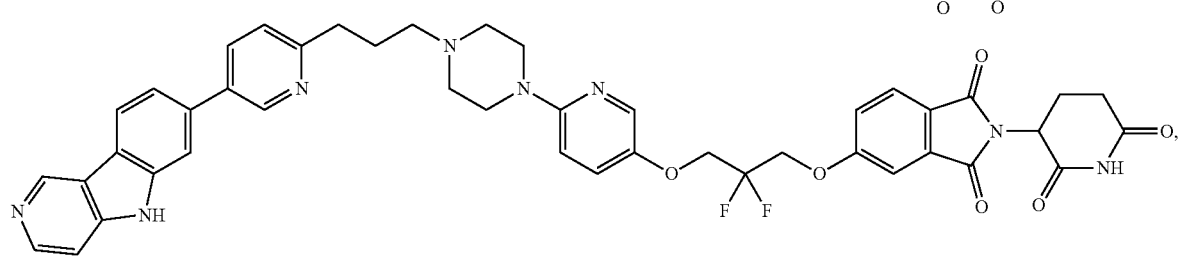
1110
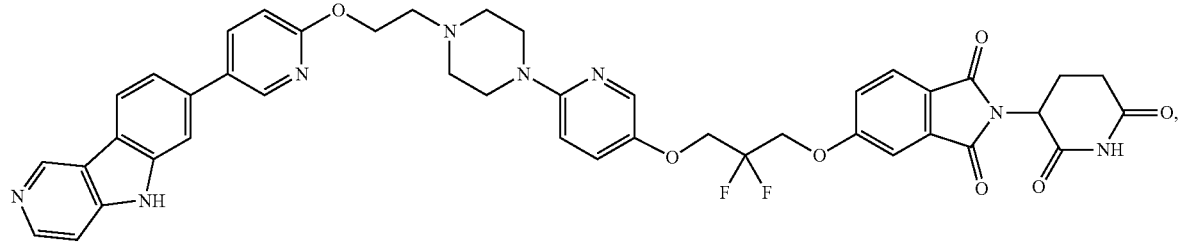
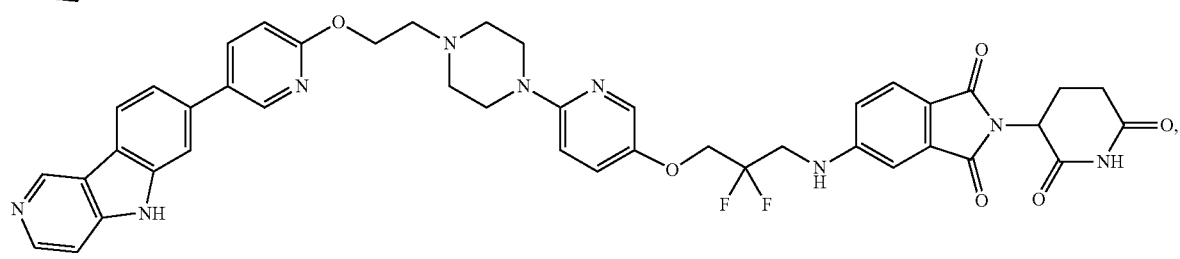

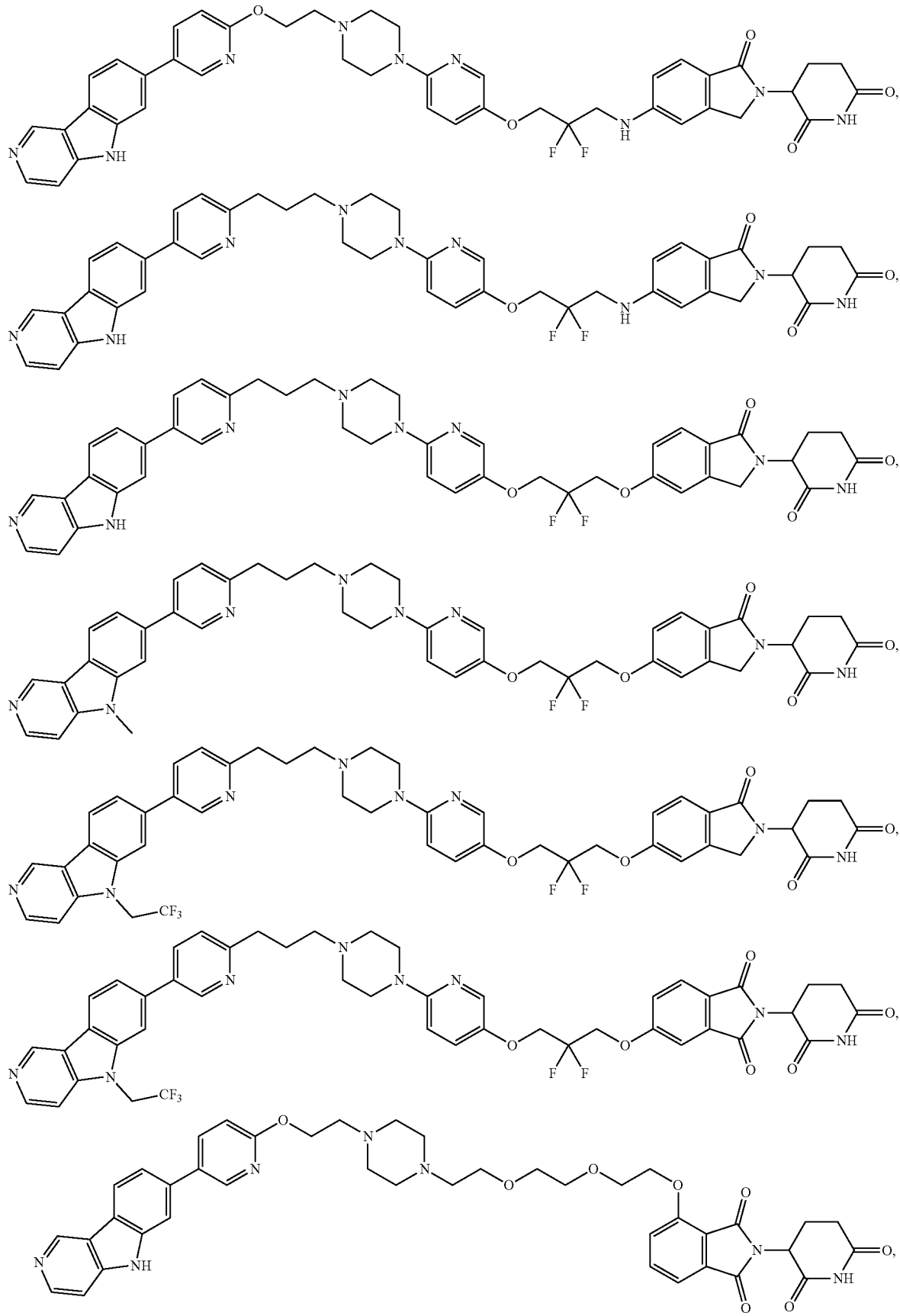

-continued
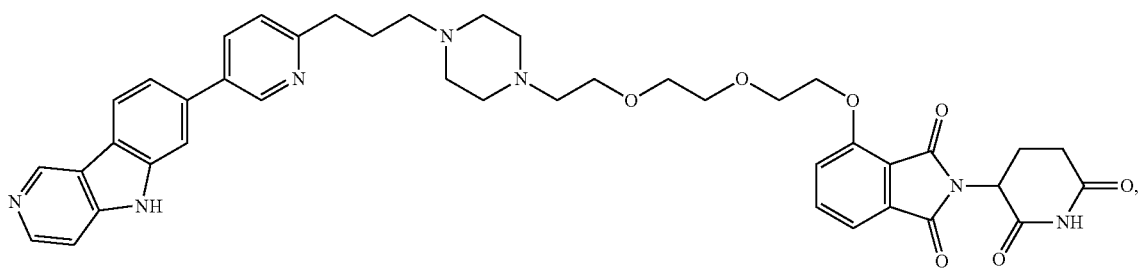
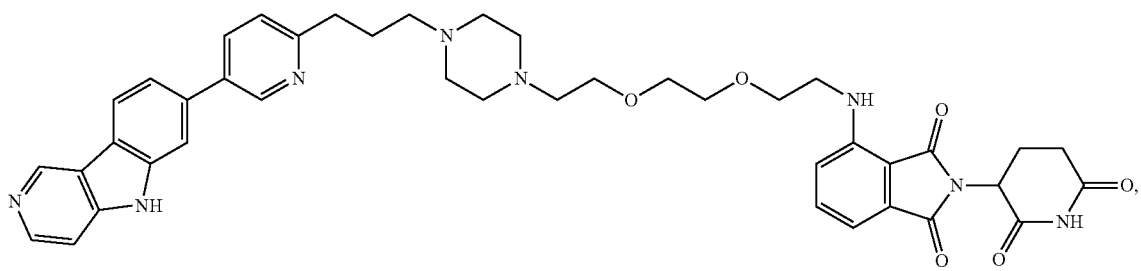
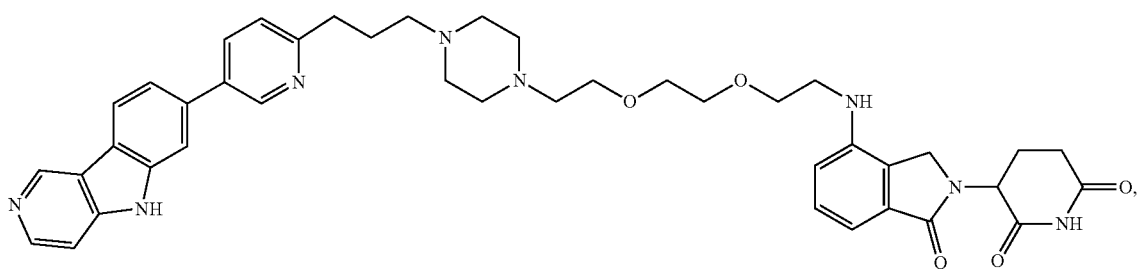
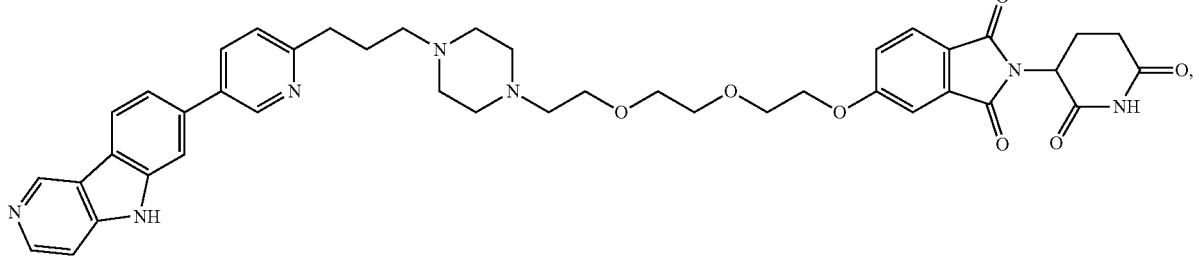
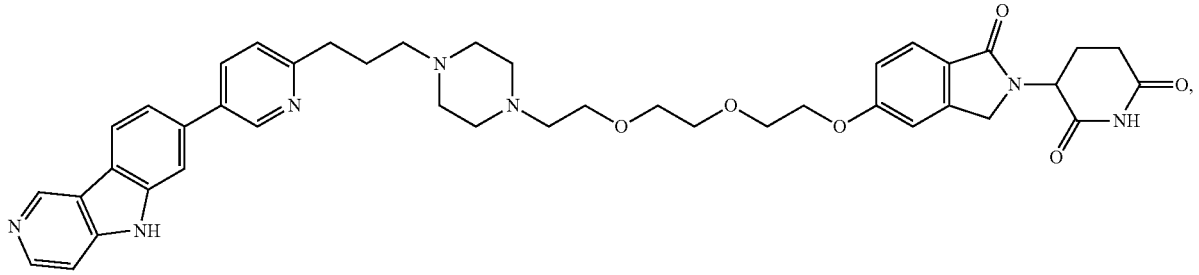
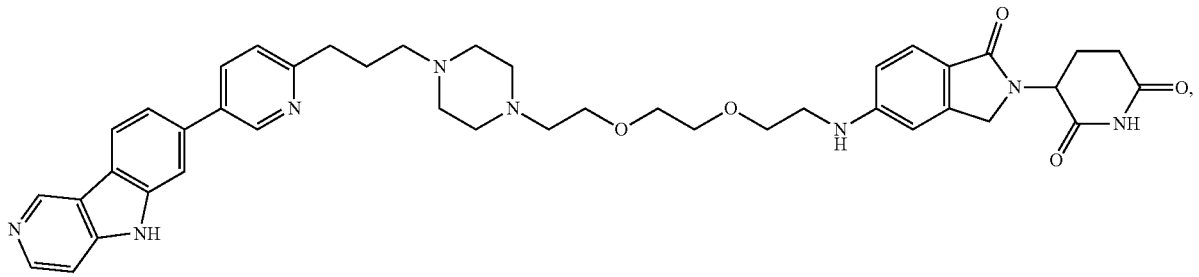

-continued
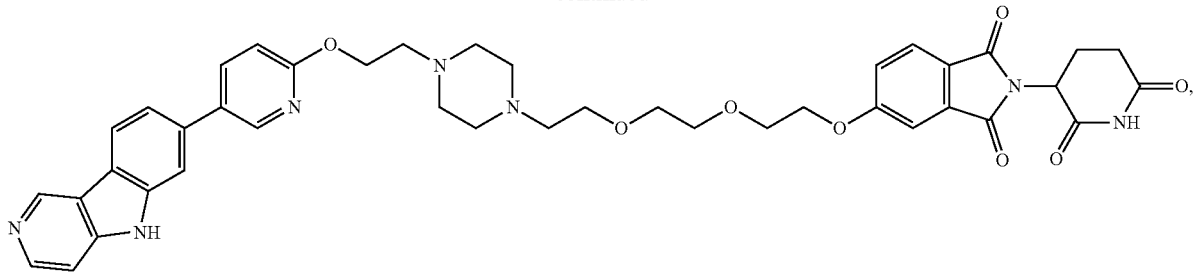
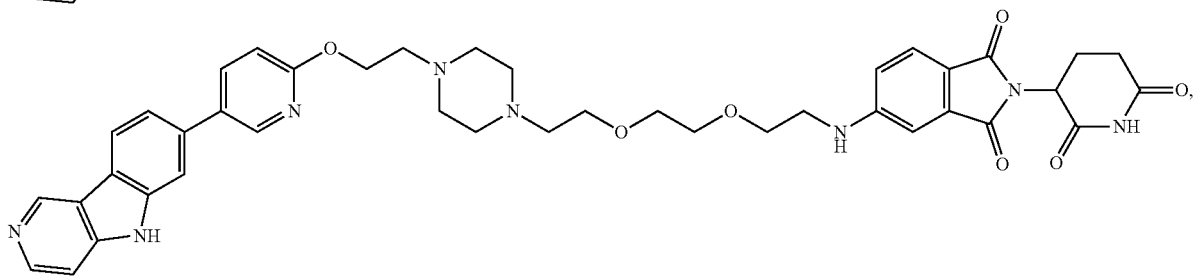
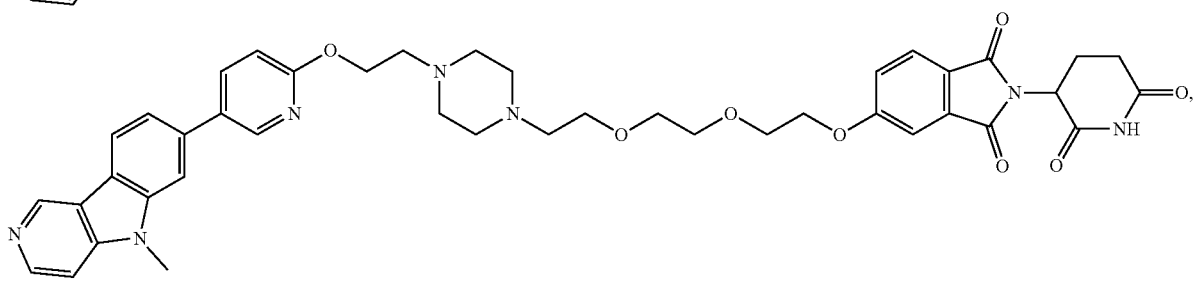
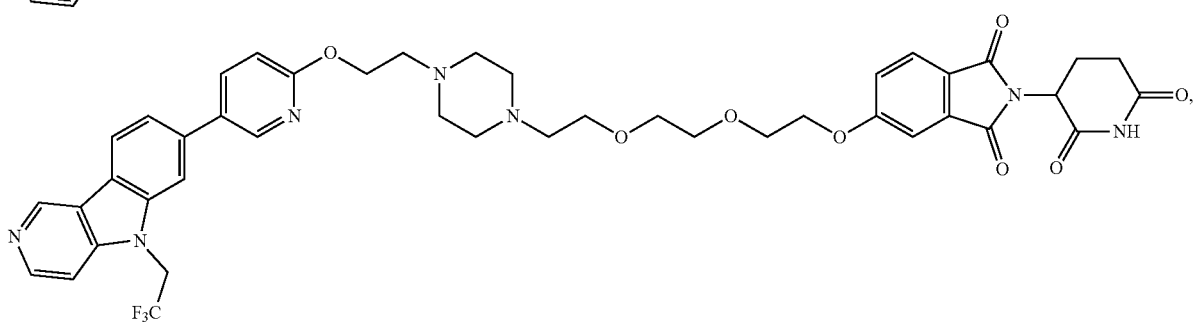
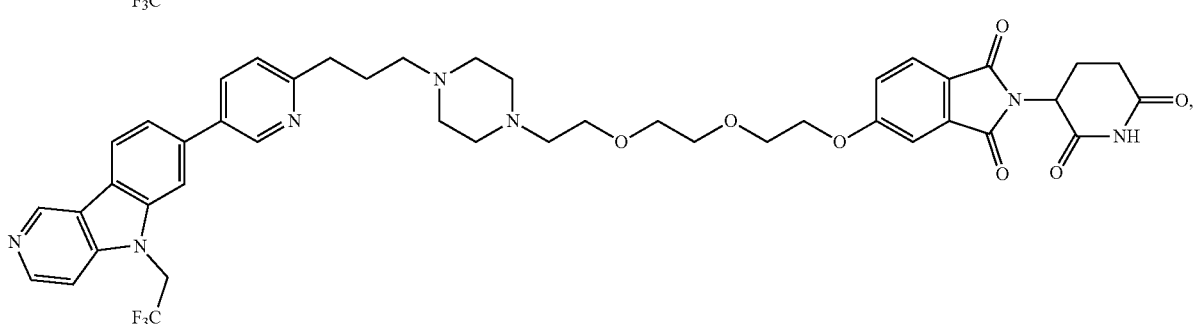
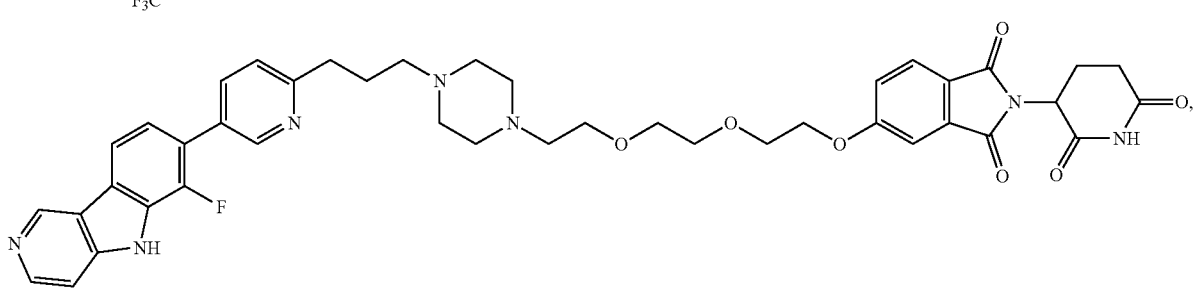

1117                                              1118
-continued
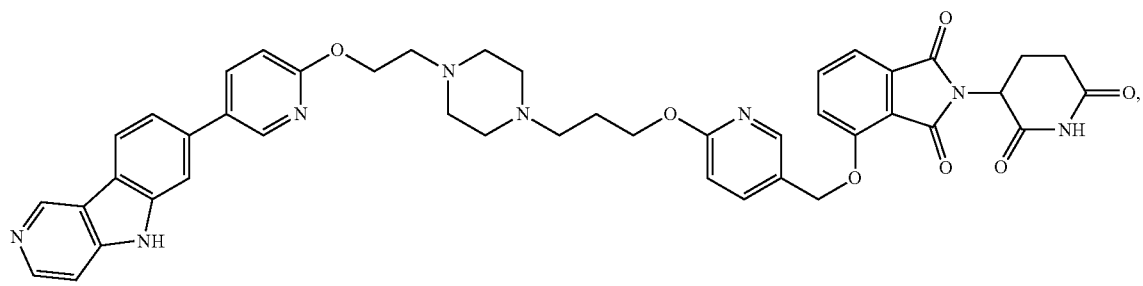
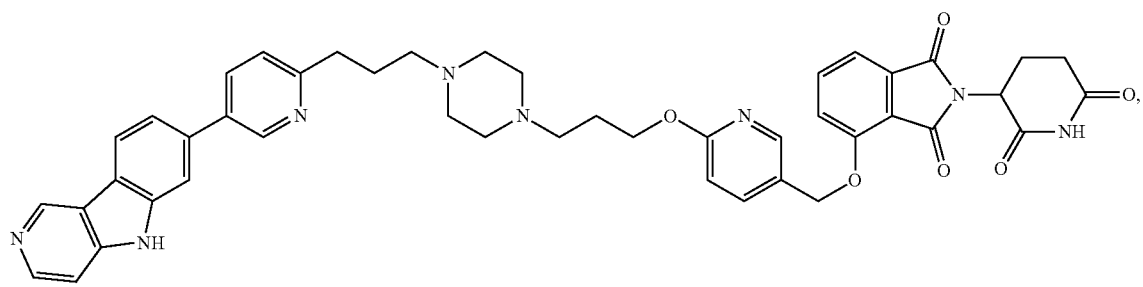
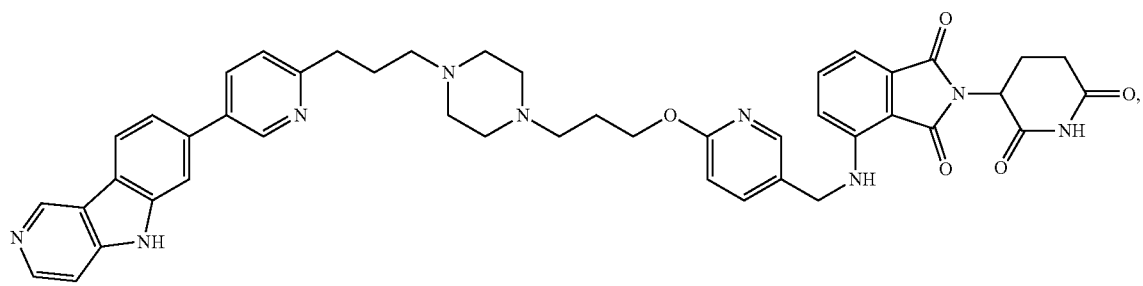
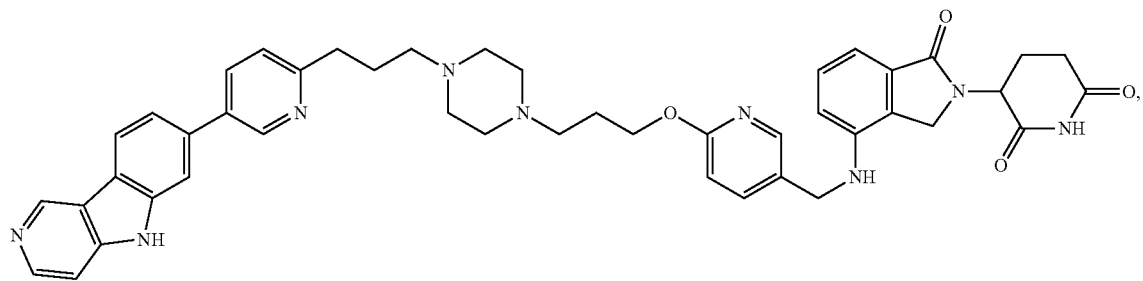
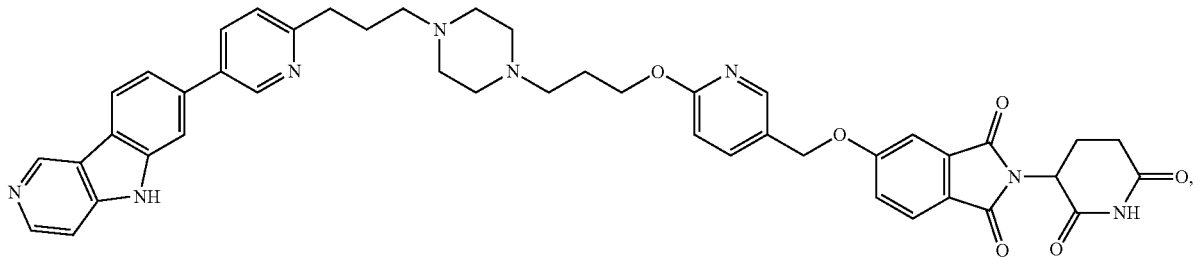
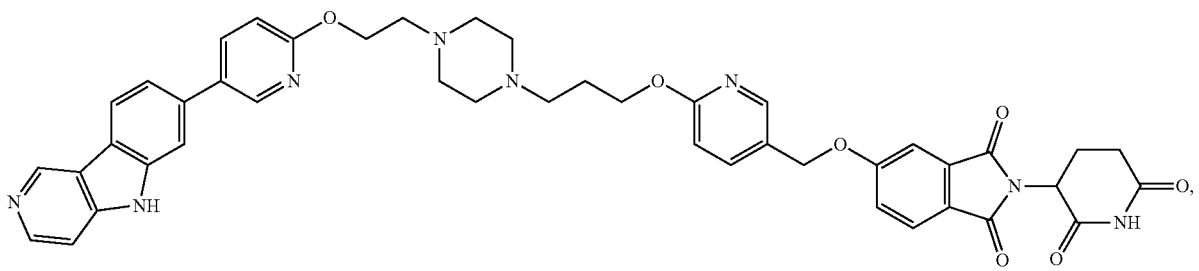

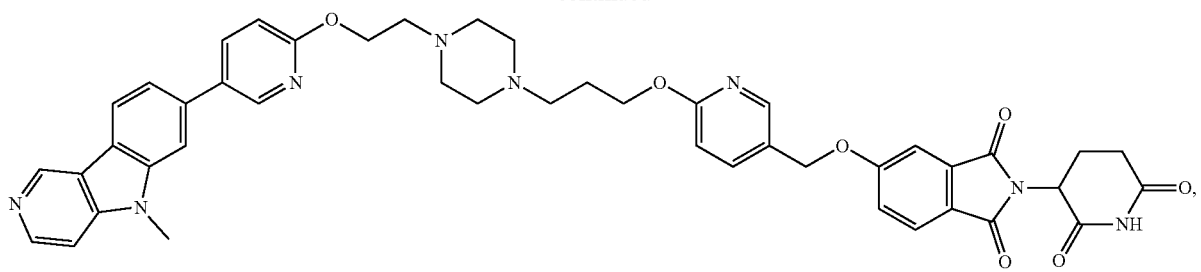
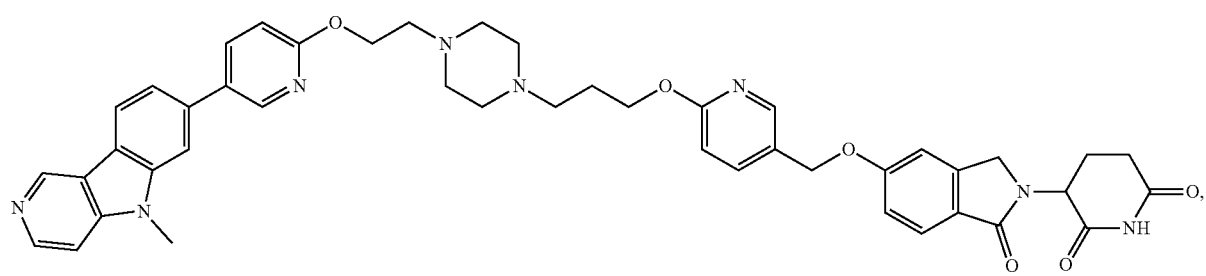
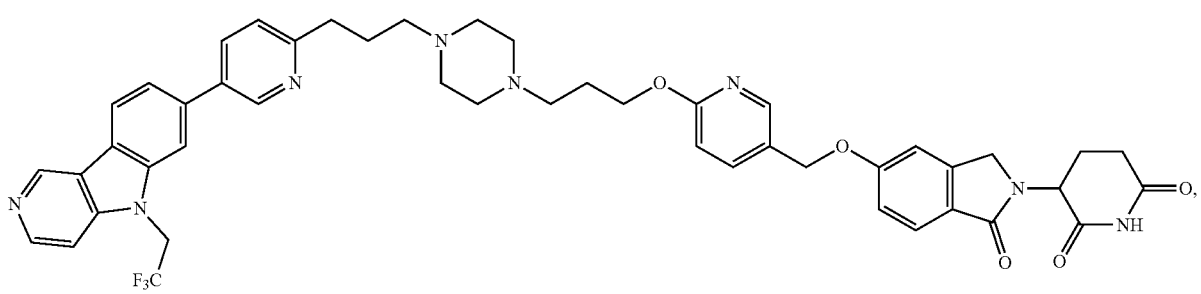
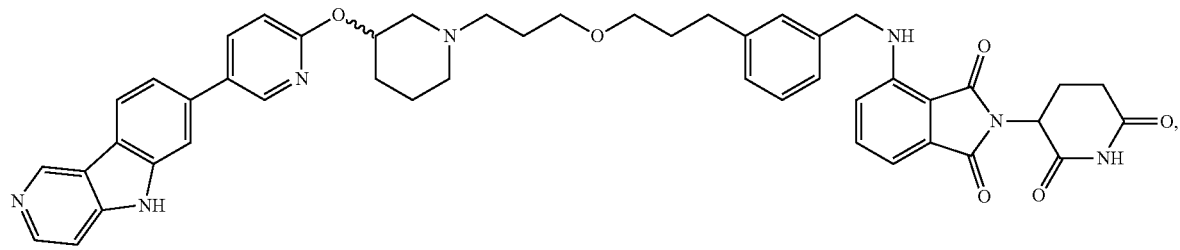
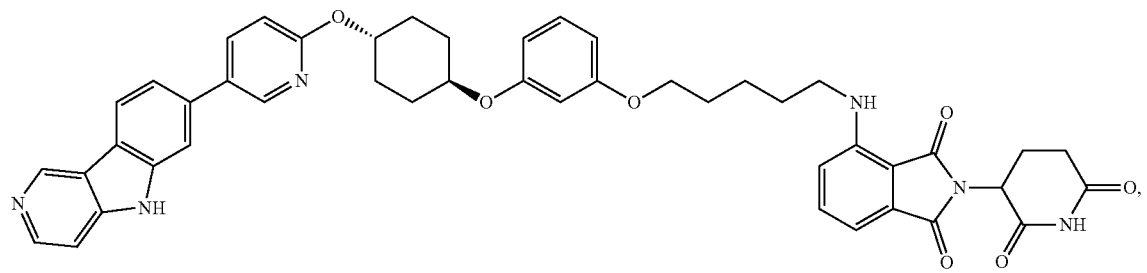
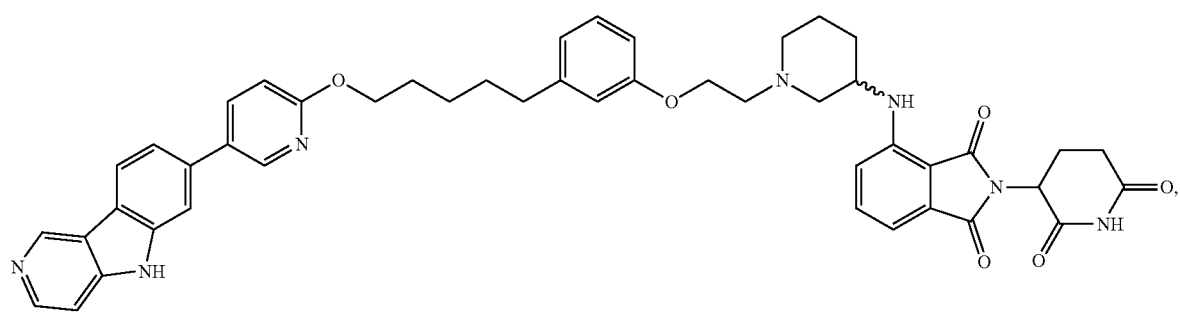

1121       -continued       1122
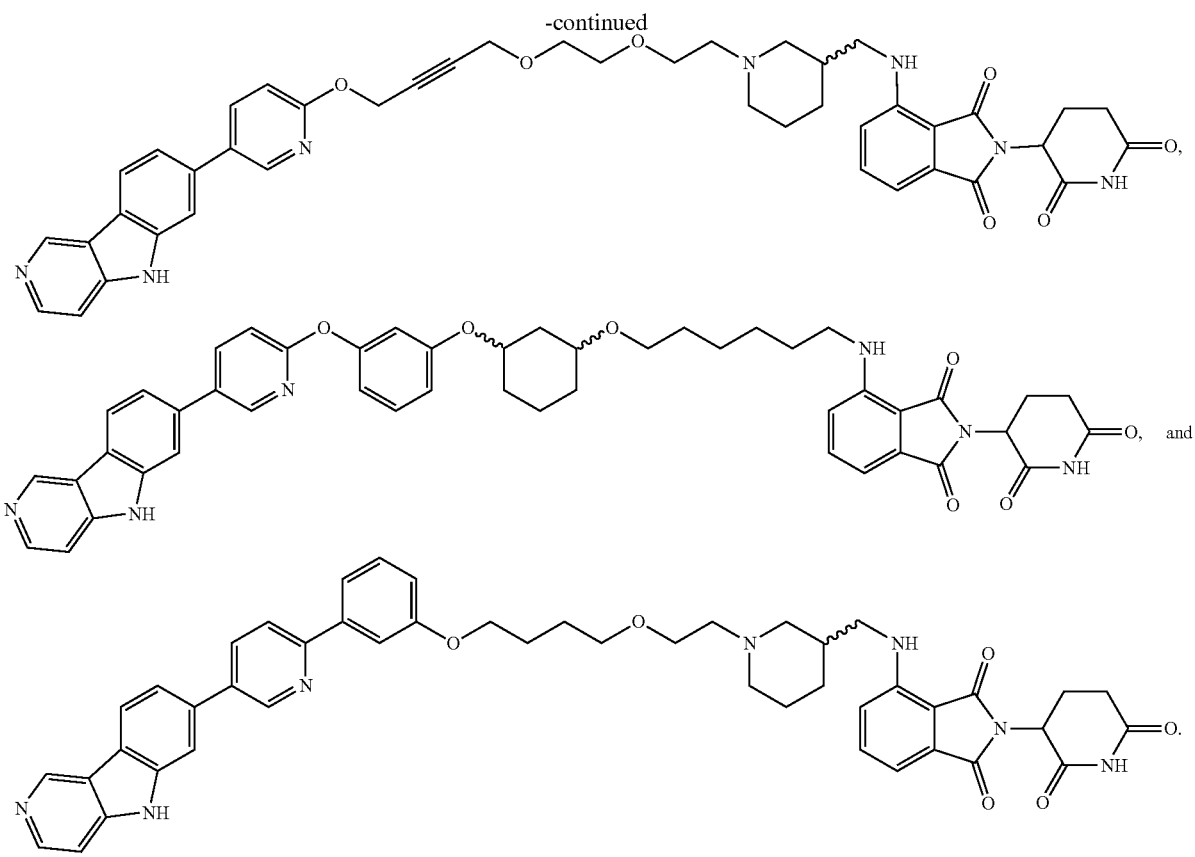

What is claimed is:

1. A bifunctional compound having the chemical structure:

CLM-L-PTM, or a pharmaceutically acceptable salt thereof,
wherein:
(a) the L is a chemical linking moiety connecting the CLM and the PTM;
(b) the CLM is an E3 ubiquitin ligase binding moiety that binds cereblon E3 ubiquitin ligase and that has a chemical structure selected from:

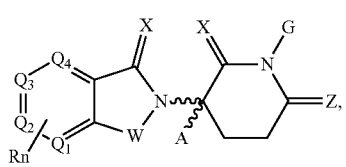
(a)

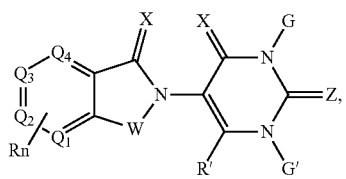
(b)

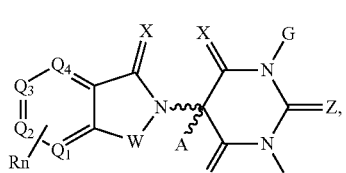
(c)

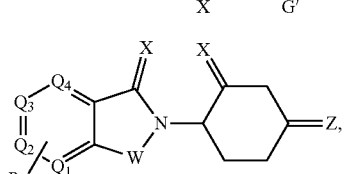
(f)

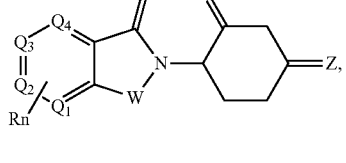

wherein:
W is selected from the group consisting of $CH_2$, CHR, and C=O;
each X is independently selected from the group consisting of O, S, and absent;
Z is selected from the group consisting of O, S, and absent;

G and G' are independently selected from the group consisting of H, OH, $CH_2$-heterocyclyl optionally substituted with R', and benzyl optionally substituted with R';
$Q_1$, $Q_2$, $Q_3$, and $Q_4$ represent a carbon substituted with a group independently selected from H and R;
A is independently selected from the group consisting of H, alkyl, cycloalkyl, Cl, and F;
n is an integer from 1 to 4;
R is —CONR'R", —OR', —NR'R", —SR', —$SO_2$R', —$SO_2$NR'R", —CR'R"—, —CR'NR'R"—, -aryl, -heteroaryl, -alkyl, -cycloalkyl, -heterocyclyl, —P(O)(OR')R", —P(O)R'R", —OP(O)(OR')R", —OP(O)R'R", —Cl, —F, —Br, —I, —$CF_3$, —CN, —NR'$SO_2$NR'R", —NR'CONR'R", —CONR'COR", —NR'C(=N—CN)NR'R", —C(=N—CN)NR'R", —NR'C(=N—CN)R", —NR'C(=C—$NO_2$)NR'R", —$SO_2$NR'COR", —$NO_2$, —$CO_2$R', —C(C=N—OR')R", —CR'=CR'R", —CCR', —S(C=O)(C=N—R') R", —$SF_5$ or —$OCF_3$, wherein one R is modified to be covalently joined to the chemical linking moiety;
R' and R" are independently selected from the group consisting of a bond, H, optionally substituted alkyl, optionally substituted cycloalkyl, optionally substituted aryl, optionally substituted heteroaryl, and optionally substituted heterocyclyl; and
∿∿∿ represents a bond that may be stereospecific ((R) or (S)) or non-stereospecific; and
(c) the PTM is a Tau protein targeting moiety of Formula I:

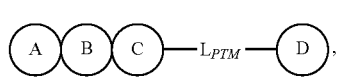

I wherein:
rings A and C are independently selected from a 5- or 6-membered aryl and 5- or 6-membered heteroaryl; and
ring B is a 5-membered aryl or 5-membered heteroaryl, wherein:
contact between circles indicates ring fusion; and
rings A, B, and C are each independently optionally substituted with 1-3 substituents independently selected from alkyl, alkenyl, haloalkyl, halogen, hydroxyl, alkoxy, fluoroalkoxy, amino, alkylamino, dialkylamino, acylamino, and cyano;
ring D is an optionally substituted 6-membered aryl or an optionally substituted 6-membered heteroaryl, wherein ring D is optionally substituted with 1-3 substituents independently selected from alkyl, alkenyl, haloalkyl, halogen, hydroxyl, alkoxy, fluoroalkoxy, amino, alkylamino, dialkylamino, acylamino, and cyano; and
$L_{PTM}$ is a bond or alkyl.

2. The compound according to claim 1, wherein:
A and C rings are independently a 5- or 6-membered aryl or a 5- or 6-membered heteroaryl;
ring B is a 5-membered aryl or a 5-membered heteroaryl;
$L_{PTM}$ is selected from a bond and an alkyl; and
ring D is selected from a 6-membered aryl and a 6-membered heteroaryl,
wherein A, B, C and D rings are optionally substituted with 1-3 substituents independently selected from alkyl, haloalkyl, halogen, hydroxyl, alkoxy, amino, alkylamino, dialkylamino, and cyano.

3. The compound according to claim 1, wherein rings A, B, C, and D are each optionally substituted with 1-3 substituents independently selected from alkyl, haloalkyl, and halogen.

4. The compound according to claim 1, wherein ring D is a substituted 6-membered aryl or a substituted 6-membered heteroaryl, wherein ring D is substituted with 1-3 substituents independently selected from alkyl, alkenyl, haloalkyl, halogen, hydroxyl, alkoxy, fluoroalkoxy, amino, alkylamino, dialkylamino, acylamino, and cyano.

5. The compound according to claim 1, wherein ring D is an unsubstituted 6-membered aryl or an unsubstituted 6-membered heteroaryl.

6. The compound of claim 1, wherein ring D is a selected from a 6-membered heteroaryl, wherein ring D is optionally substituted with 1-3 substituents, each substituent independently selected from alkyl, alkenyl, haloalkyl, halogen, hydroxyl, alkoxy, fluoroalkoxy, amino, alkylamino, dialkylamino, acylamino, and cyano.

7. The compound according to claim 1, wherein the CLM has a chemical structure represented by:

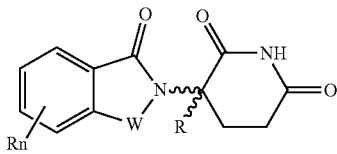

wherein:
W is independently selected from the group consisting of $CH_2$ and C=O;
A is independently selected from the group consisting of H, methyl, and alkyl;
n is an integer from 1 to 4;
one R is modified to be covalently joined to the chemical linking moiety; and
∿ represents a bond that may be stereospecific ((R) or (S)) or non-stereospecific.

8. The compound according to claim 1, wherein the CLM has a chemical structure represented by:

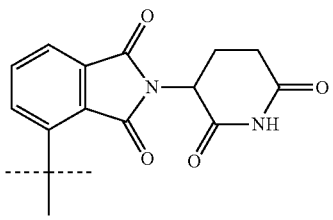

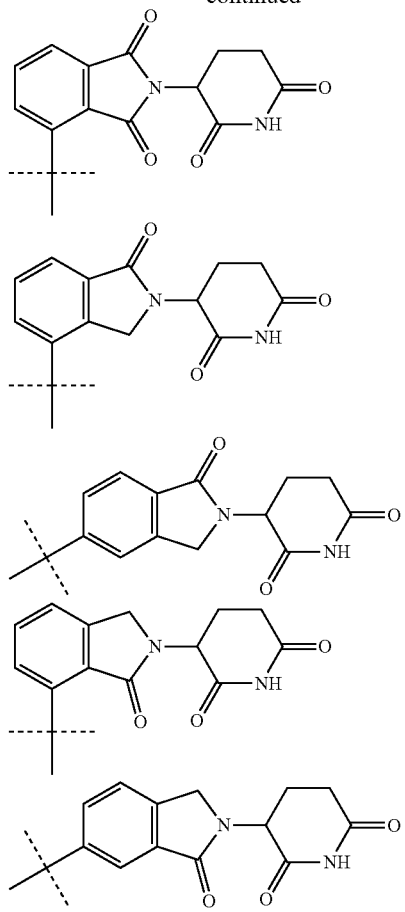

wherein the

indicate the chemical linking moiety attachment points.

9. The compound according to claim 1, wherein the chemical linking moiety comprises a chemical structural unit represented by the formula:

$-(A^L)_q-$, wherein:
$A^L$ is a group which is connected to the CLM or the PTM;
q is an integer greater than or equal to 1,
each $A^L$ is independently selected from the group consisting of $CR^{L1}R^{L2}$, O, S, SO, $SO_2$, $NR^{L3}$, $SO_2NR^{L3}$, $SONR^{L3}$, $CONR^{L3}$, $NR^{L3}CONR^{L4}$, $NR^{L3}SO_2NR^{L4}$, CO, $CR^{L1}=CR^{L2}$, C≡C, $SiR^{L1}R^{L2}$, $P(O)R^{L1}$, $P(O)OR^{L1}$, $NR^{L3}C(=NCN)NR^{L4}$, $NR^{L3}C(=NCN)$, $C_{3-11}$ heterocycloalkyl optionally substituted with 1-6 $R^{L1}$ and/or $R^{L2}$ groups, $C_{3-11}$ heterocyclyl optionally substituted with 1-6 $R^{L1}$ and/or $R^{L2}$ groups, aryl optionally substituted with 1-6 $R^{L1}$ and/or $R^{L2}$ groups, and heteroaryl optionally substituted with 1-6 $R^{L1}$ and/or $R^{L2}$ groups, where $R^{L1}$ or $R^{L2}$, each independently, are optionally linked to other groups to form a cycloalkyl or heterocyclyl moiety that is optionally substituted with 1-4 $R^{L5}$ groups; and $R^{L1}$, $R^{L2}$, $R^{L3}$, $R^{L4}$ and $R^{L5}$ are, each independently, H, halogen, $C_{1-8}$alkyl, $OC_{1-8}$alkyl, $SC_{1-8}$alkyl, $NHC_{1-8}$alkyl, $N(C_{1-8}alkyl)_2$, $C_{3-11}$cycloalkyl, aryl, heteroaryl, $C_{3-11}$heterocyclyl, $OC_{3-8}$cycloalkyl, $SC_{3-8}$cycloalkyl, $NHC_{3-8}$cycloalkyl, $N(C_{3-8}cycloalkyl)_2$, $N(C_{3-8}cycloalkyl)(C_{1-8}alkyl)$, OH, $NH_2$, SH, $SO_2C_{1-8}$alkyl, $P(O)(OC_{1-8}alkyl)(C_{1-8}alkyl)$, $P(O)(OC_{1-8}alkyl)_2$, $C\equiv C-C_{1-8}$ alkyl, $C\equiv CH$, $CH=CH(C_{1-8}alkyl)$, $C(C_{1-8}alkyl)=CH(C_{1-8}alkyl)$, $C(C_{1-8}alkyl)=C(C_{1-8}alkyl)_2$, $Si(OH)_3$, $Si(C_{1-8}alkyl)_3$, $Si(OH)(C_{1-8}alkyl)_2$, $COC_{1-8}$ alkyl, $CO_2H$, CN, $CF_3$, $CHF_2$, $CH_2F$, $NO_2$, $SF_5$, $SO_2NHC_{1-8}$alkyl, $SO_2N(C_{1-8}alkyl)_2$, $SONHC_{1-8}$alkyl, $SON(C_{1-8}alkyl)_2$, $CONHC_{1-8}$alkyl, $CON(C_{1-8}alkyl)_2$, $N(C_{1-8}alkyl)CONH(C_{1-8}alkyl)$, $N(C_{1-8}alkyl)CON(C_{1-8}alkyl)_2$, $NHCONH(C_{1-8}alkyl)$, $NHCON(C_{1-8}alkyl)_2$, $NHCONH_2$, $N(C_{1-8}alkyl)SO_2NH(C_{1-8}alkyl)$, $N(C_{1-8}alkyl)SO_2N(C_{1-8}alkyl)_2$, $NHSO_2NH(C_{1-8}alkyl)$, $NHSO_2N(C_{1-8}alkyl)_2$, or $NHSO_2NH_2$.

10. The compound according to claim 1, wherein the PTM is represented by a chemical structure selected from the group consisting of:

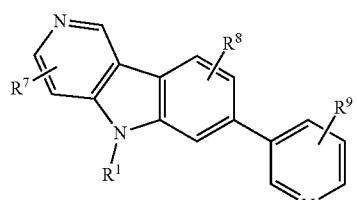

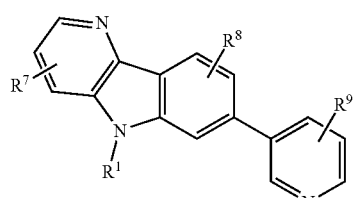

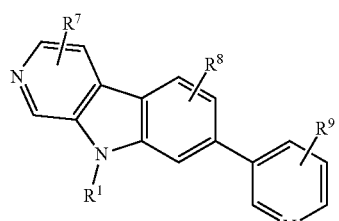

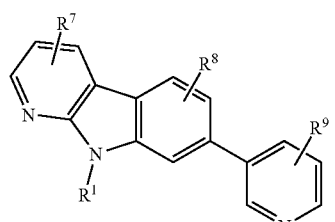

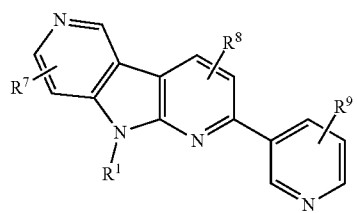

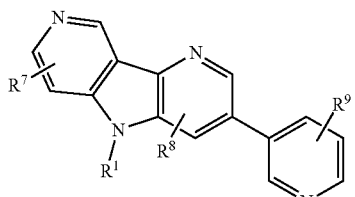

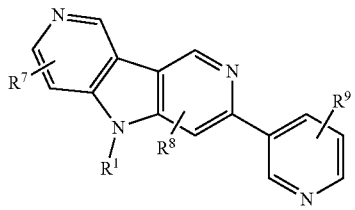

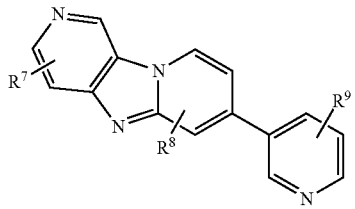

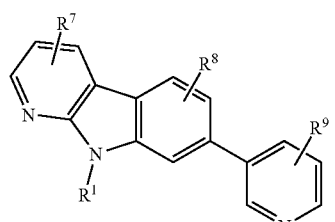

wherein:
$R^1$ is selected from H, optionally substituted alkyl, methyl, ethyl, 2-fluoroethyl, and 2,2,2-trifluoroethyl; and $R^7$, $R^8$, and $R^9$ are 1 to 2 substituents independently selected from H, optionally substituted alkyl, haloalkyl, halogen, hydroxyl, alkoxy, amino, dialkylamino, and cyano.

11. The compound according to claim 1, wherein the PTM is represented by a chemical selected from the group consisting of:

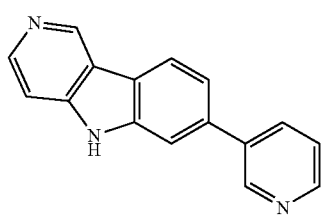

993 | 994
-continued | -continued
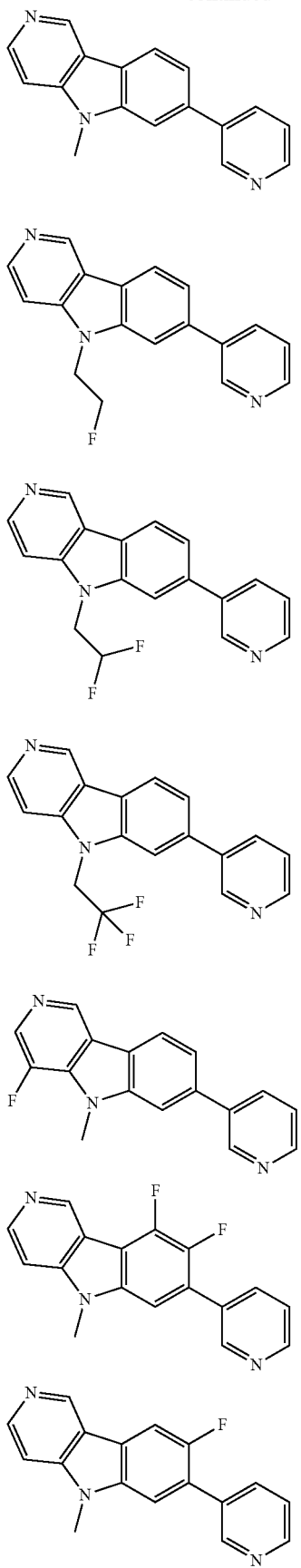
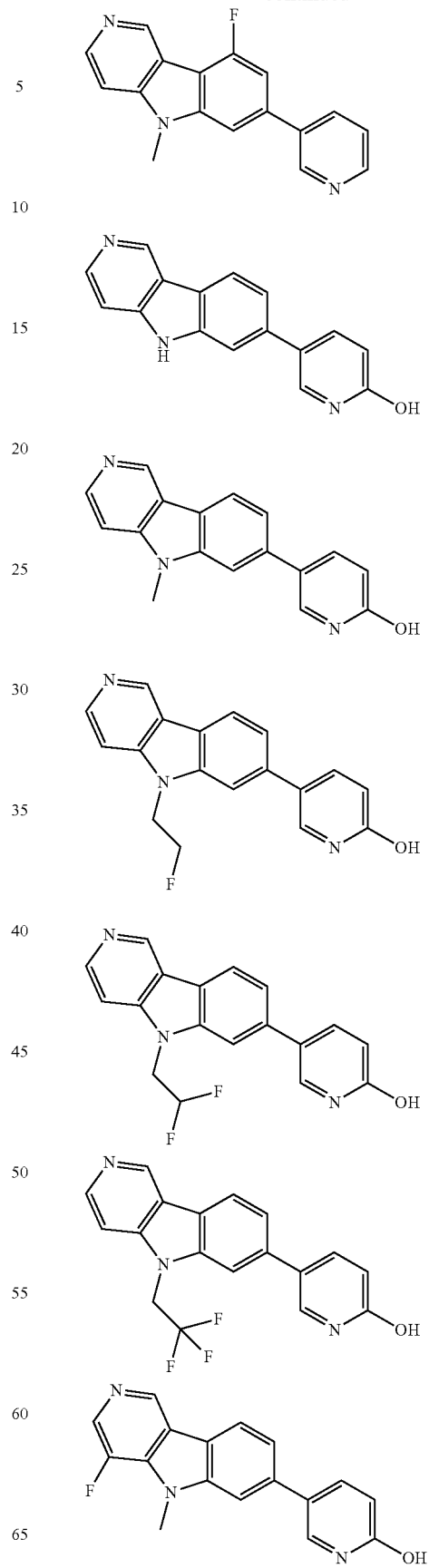

995
-continued

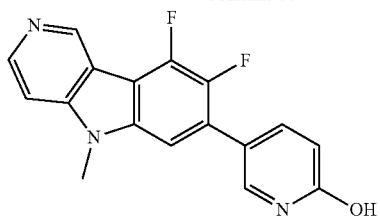
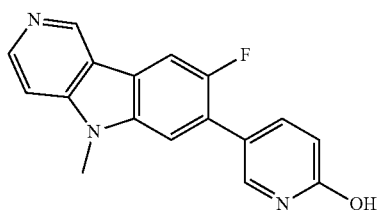
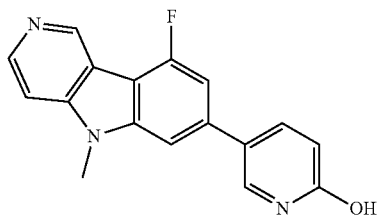
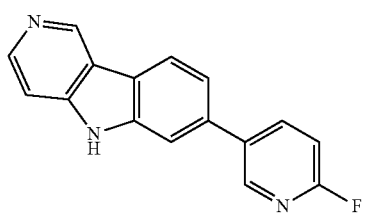
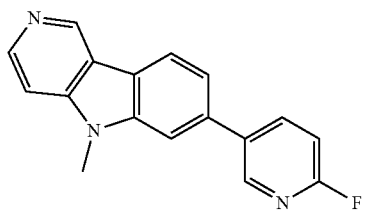
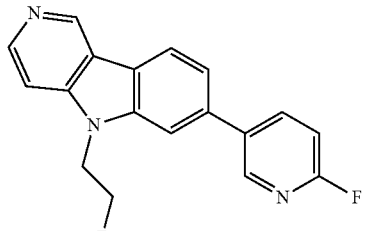
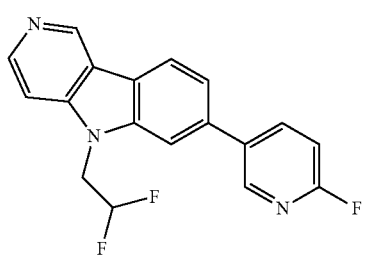

996
-continued

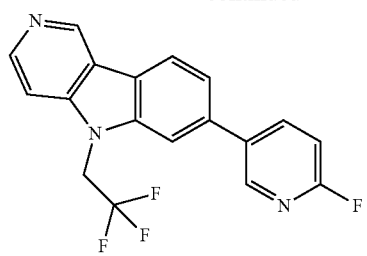
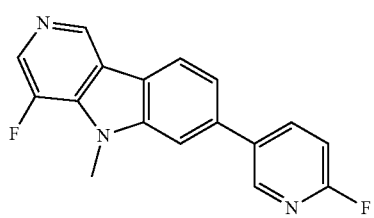
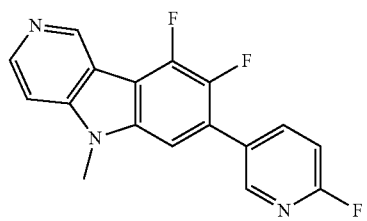
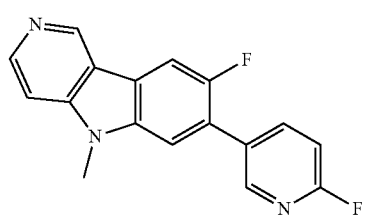
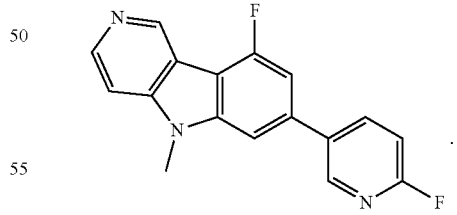

and

12. A composition comprising a bifunctional compound or a pharmaceutically acceptable salt thereof of claim 1, and a pharmaceutically acceptable carrier.

13. The composition of claim 12, wherein the composition further comprises at least one additional bioactive agent.

14. The composition of claim 13, wherein the additional bioactive agent is an anti-neurodegenerative agent.

15. A compound selected from the group consisting of:
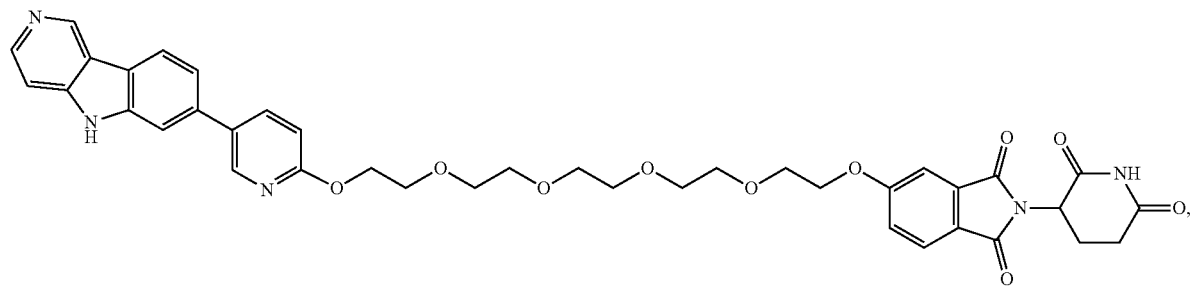
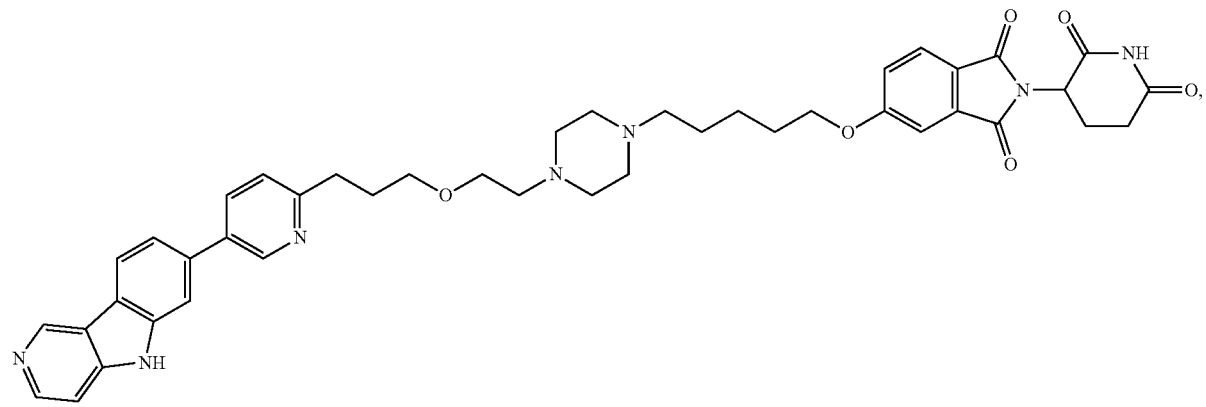
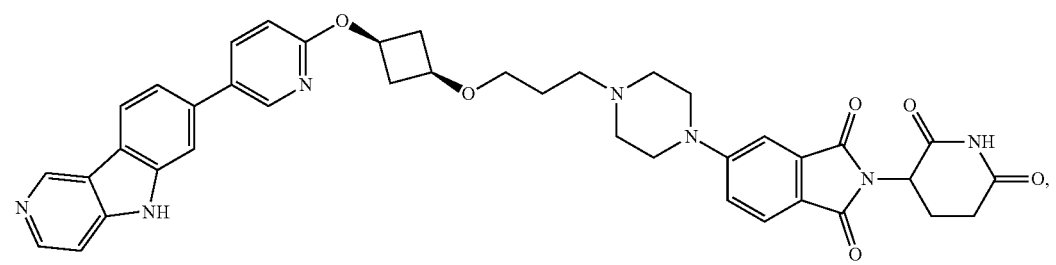
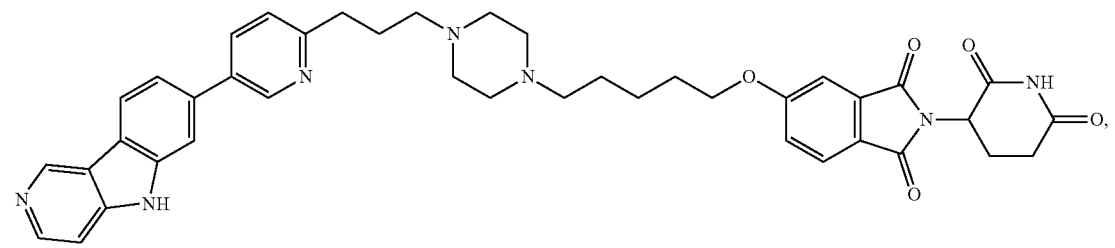
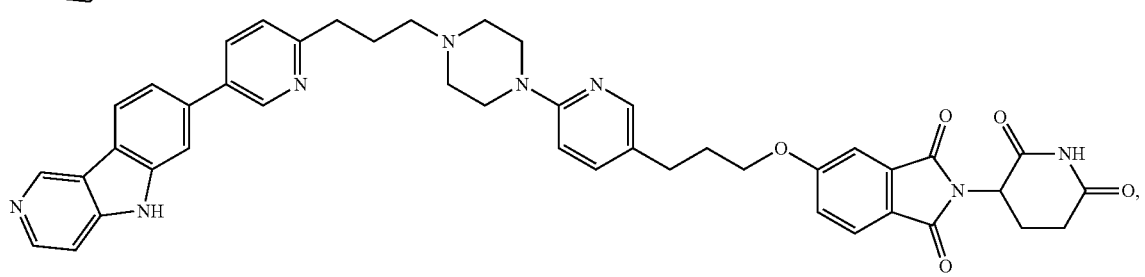

999 1000
-continued
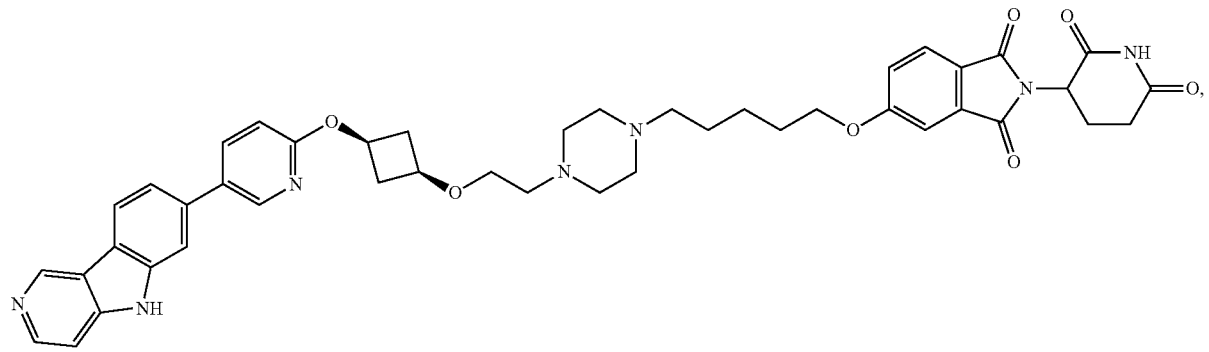
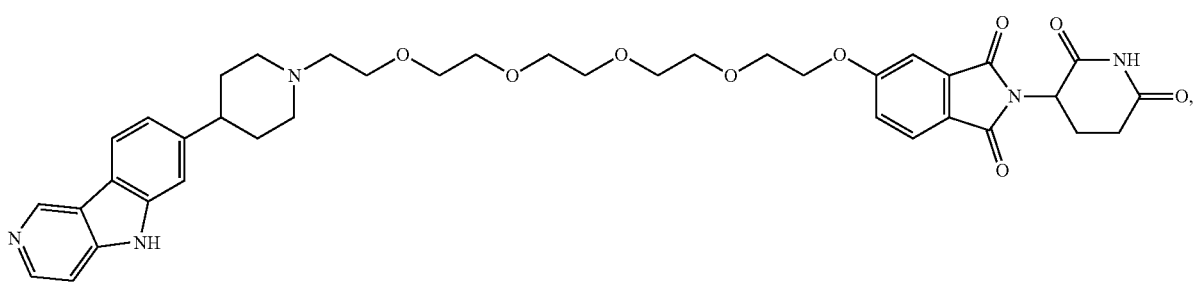
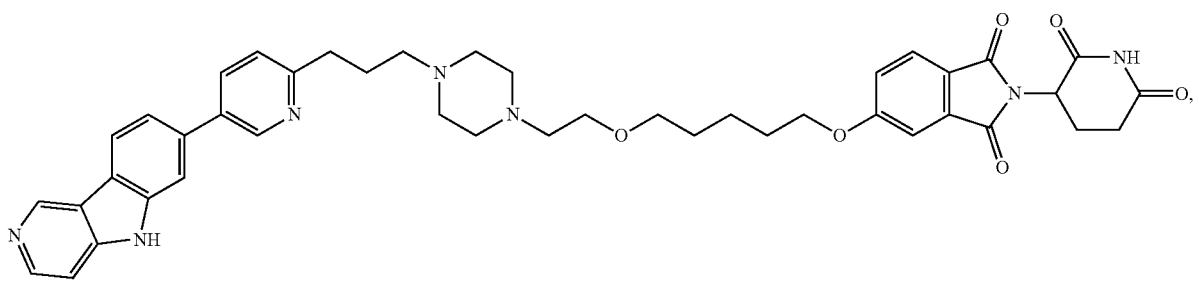
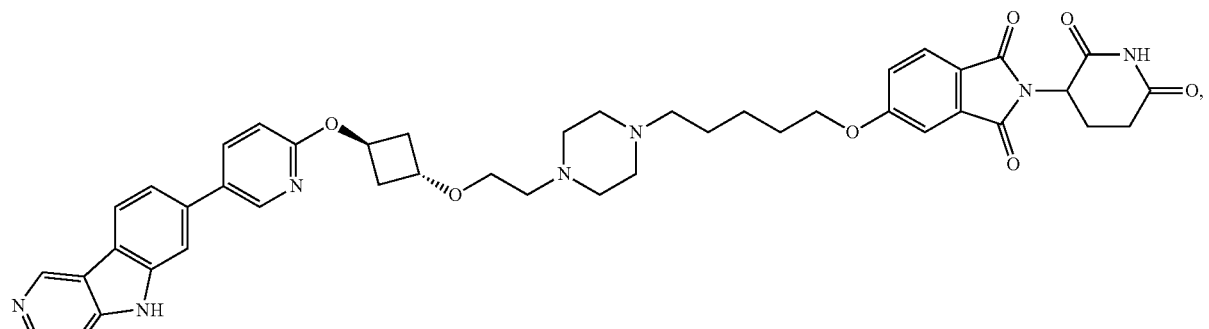
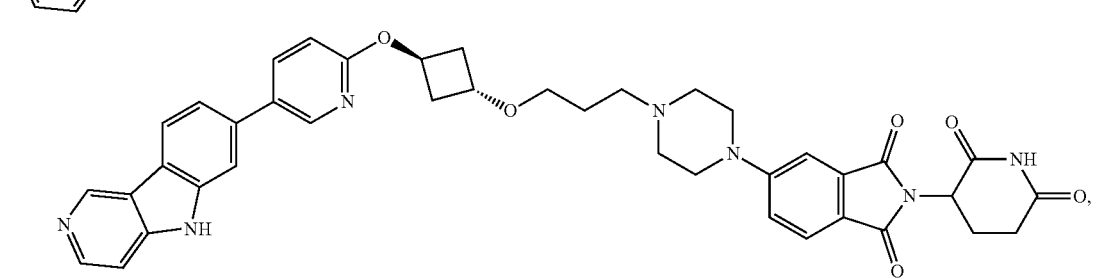

-continued
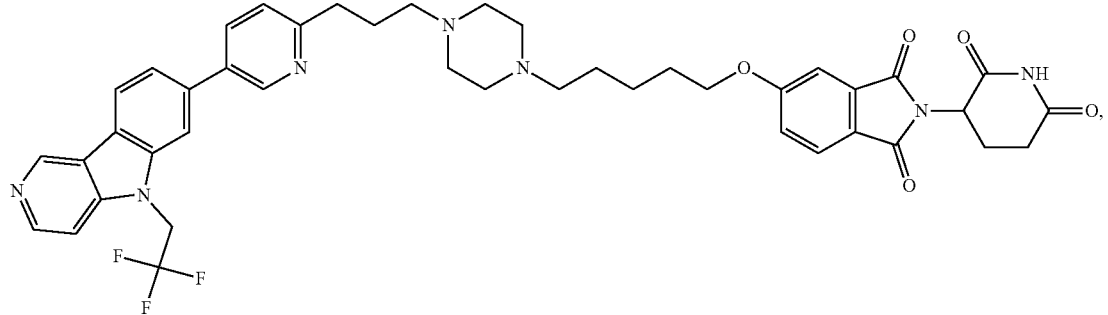
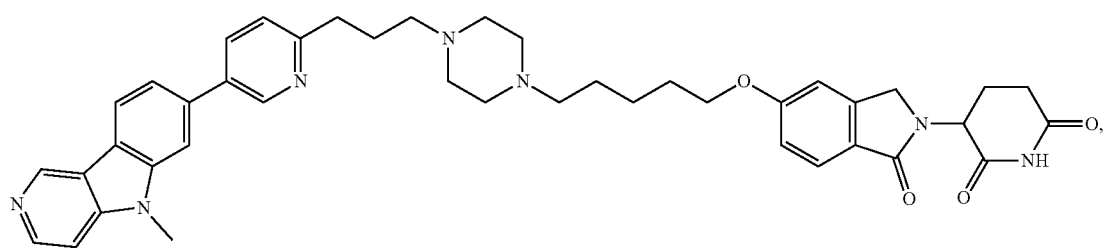
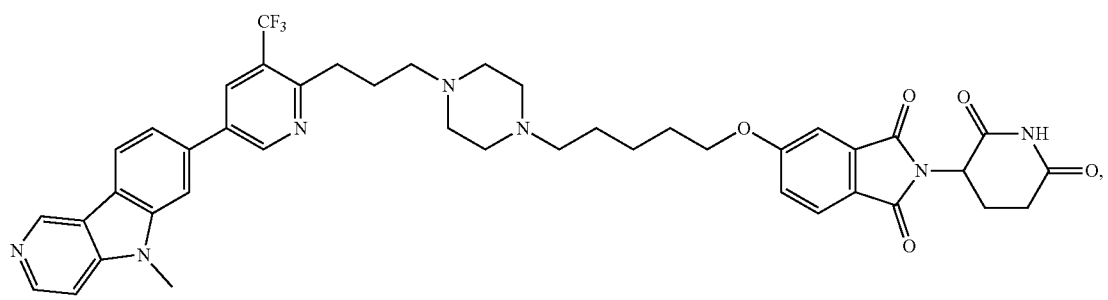
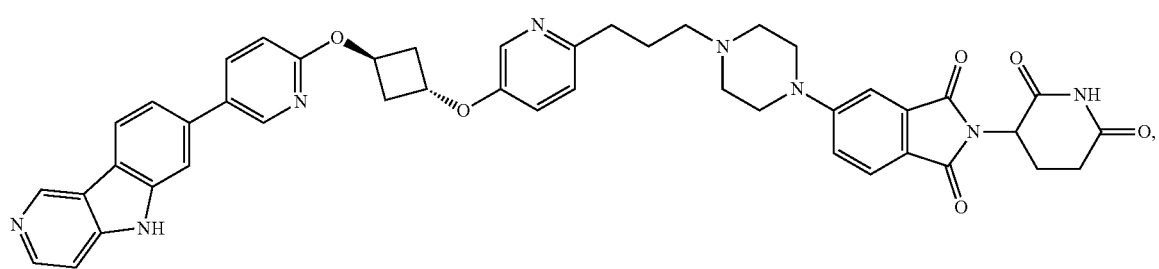
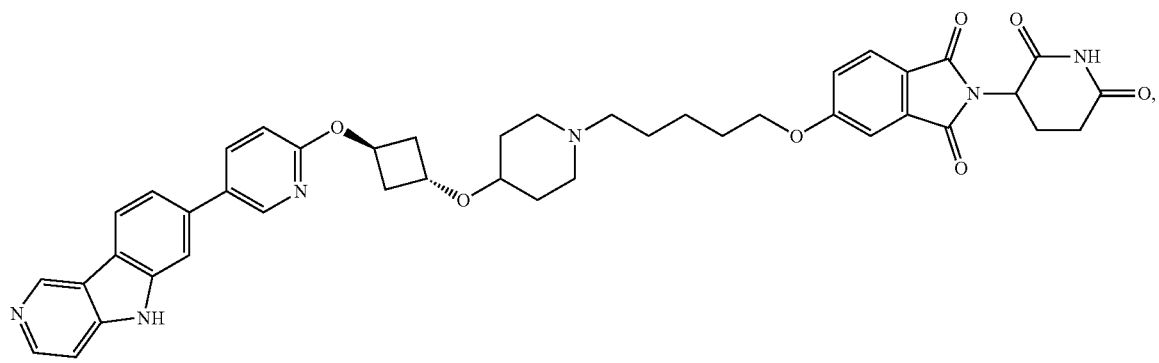

-continued
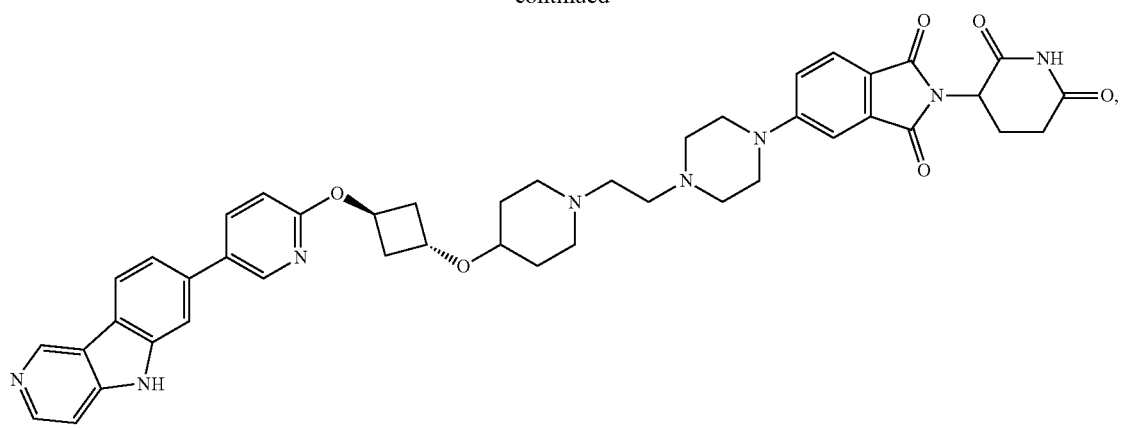
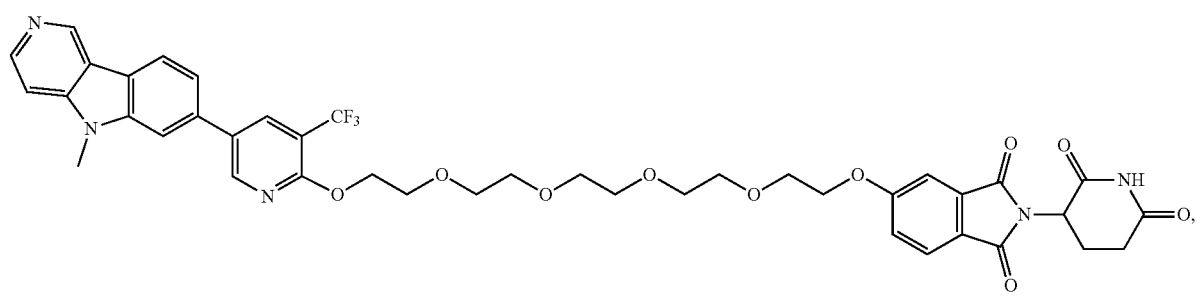
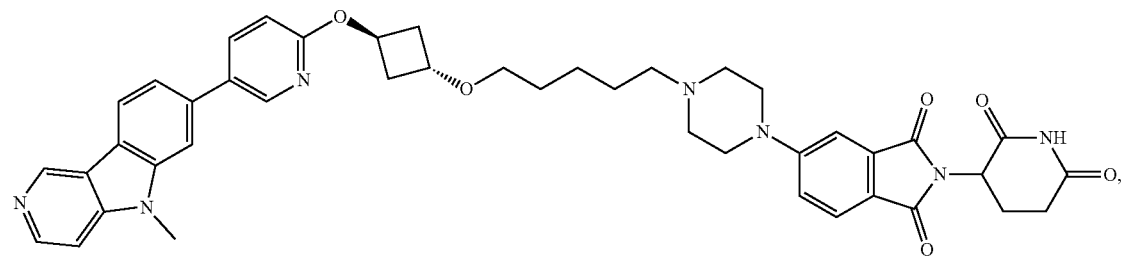
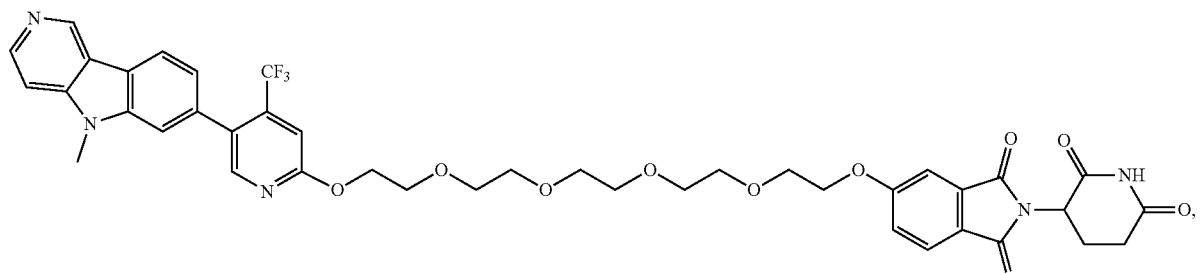
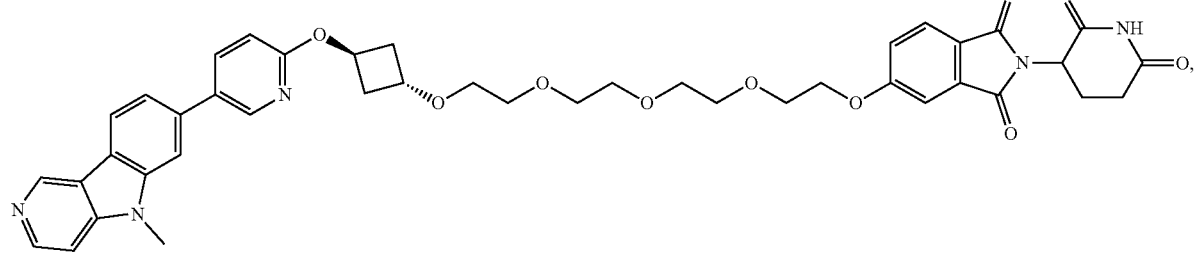

1005 1006
-continued
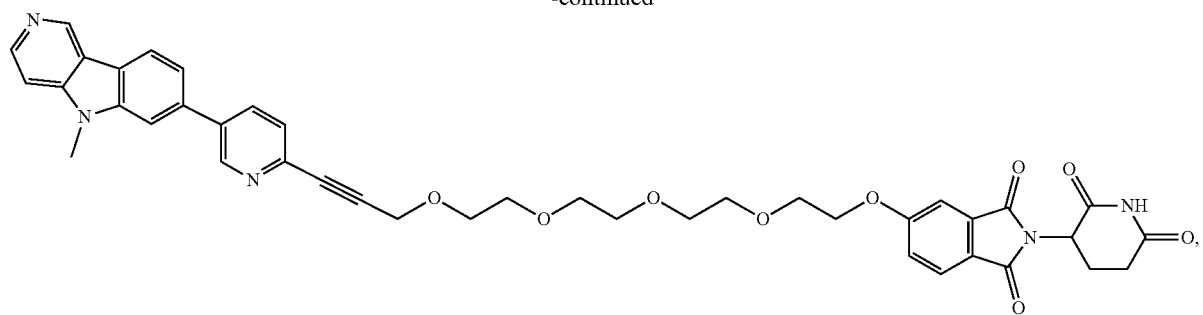
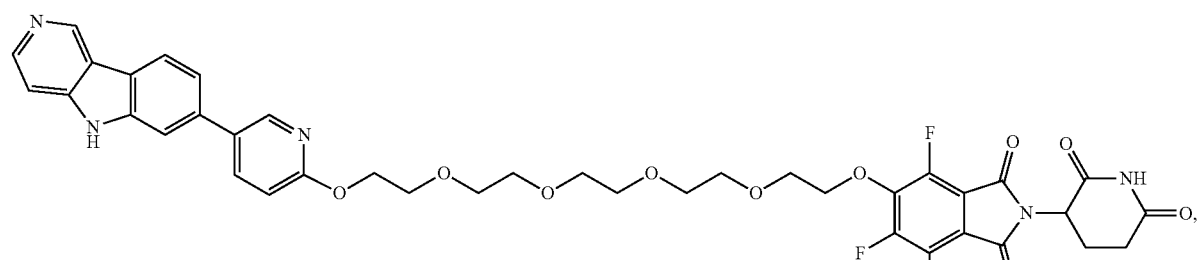
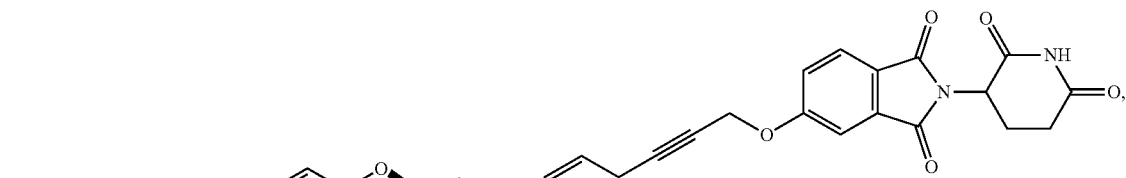
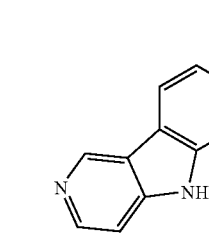
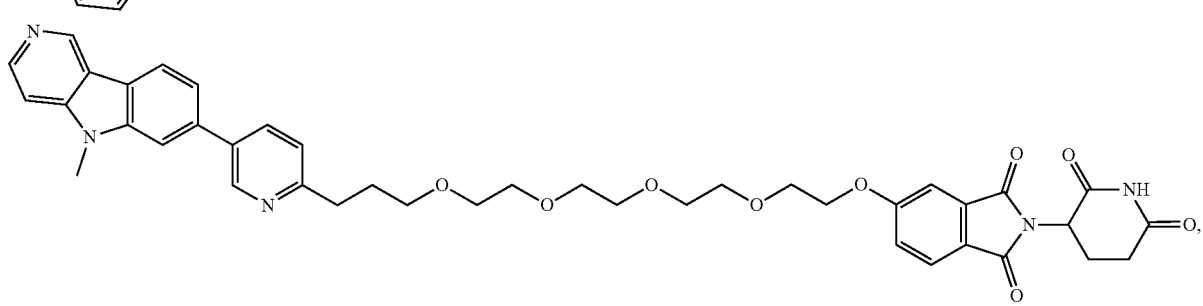
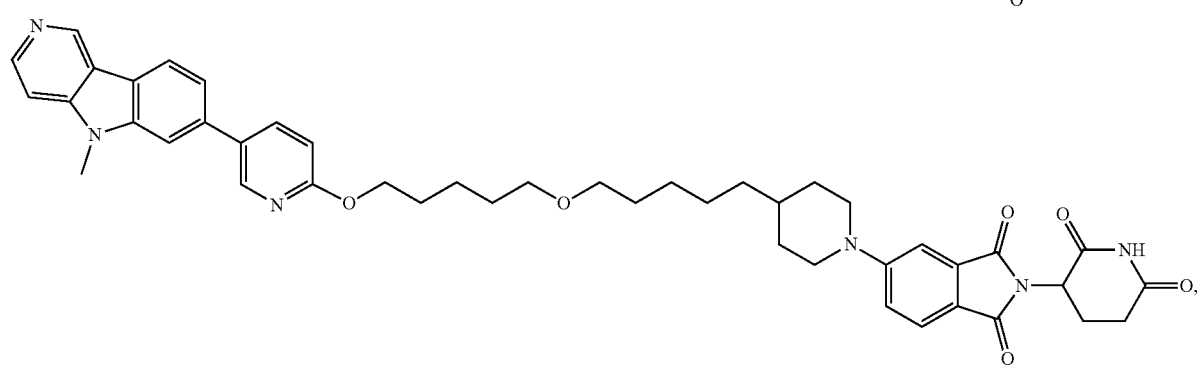

1007                                         1008
-continued
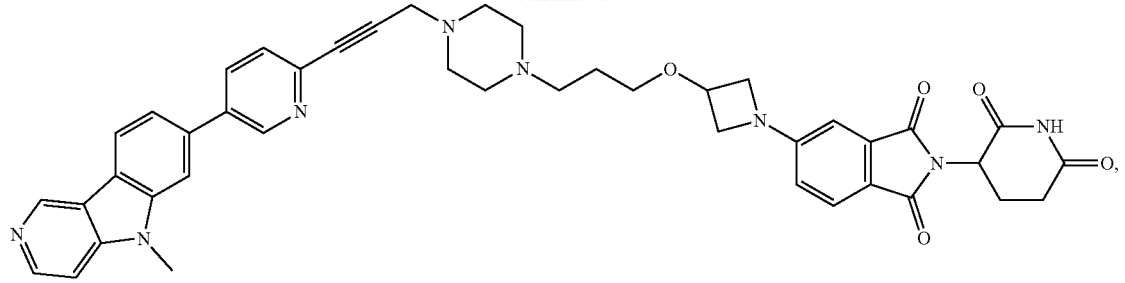
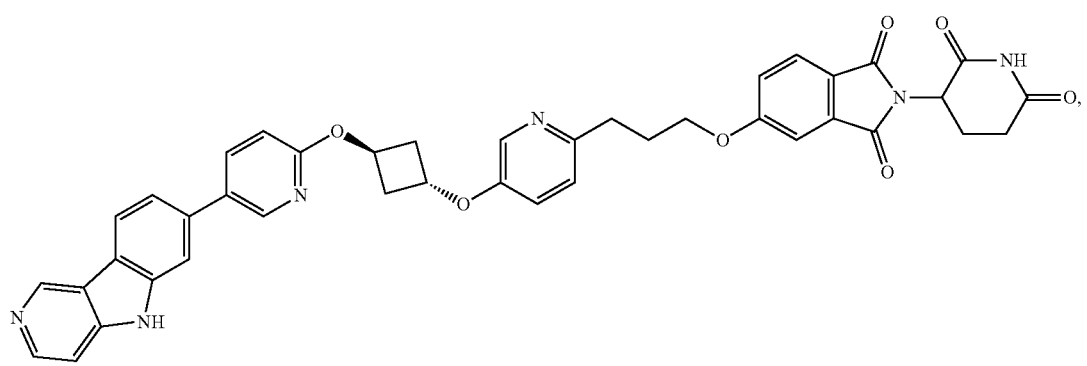
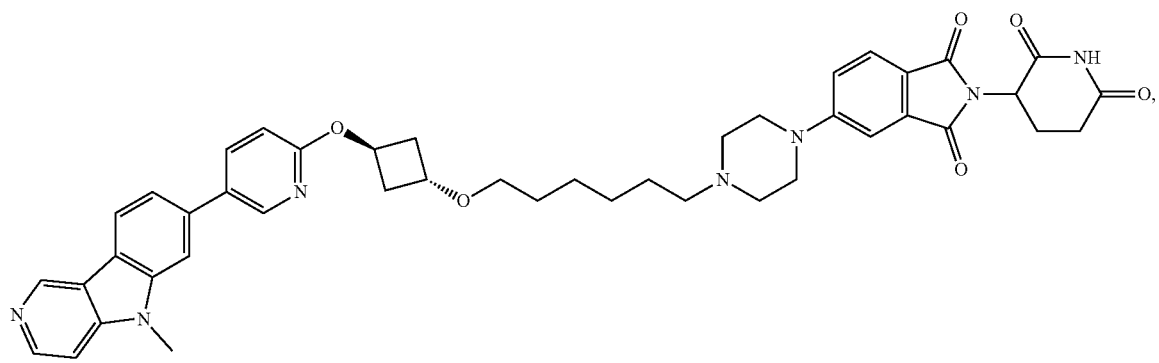
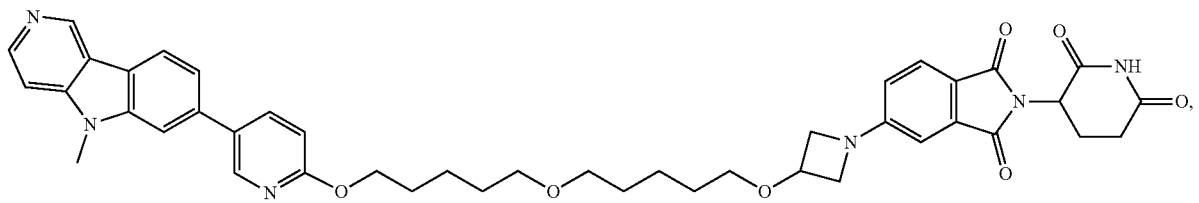
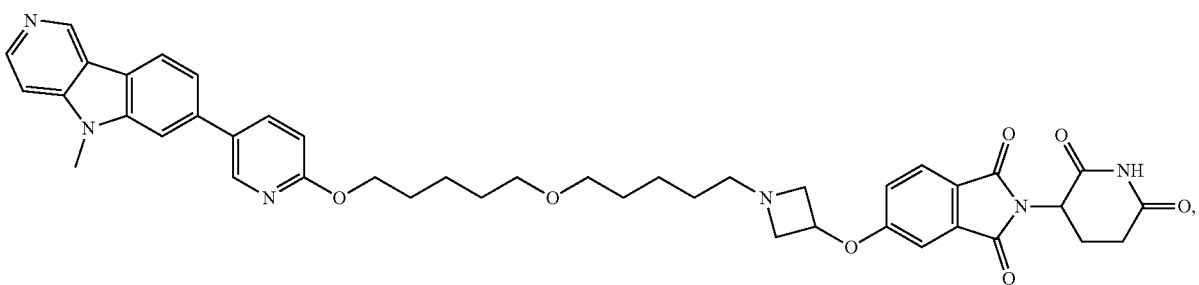

-continued
| 1009 | 1010 |
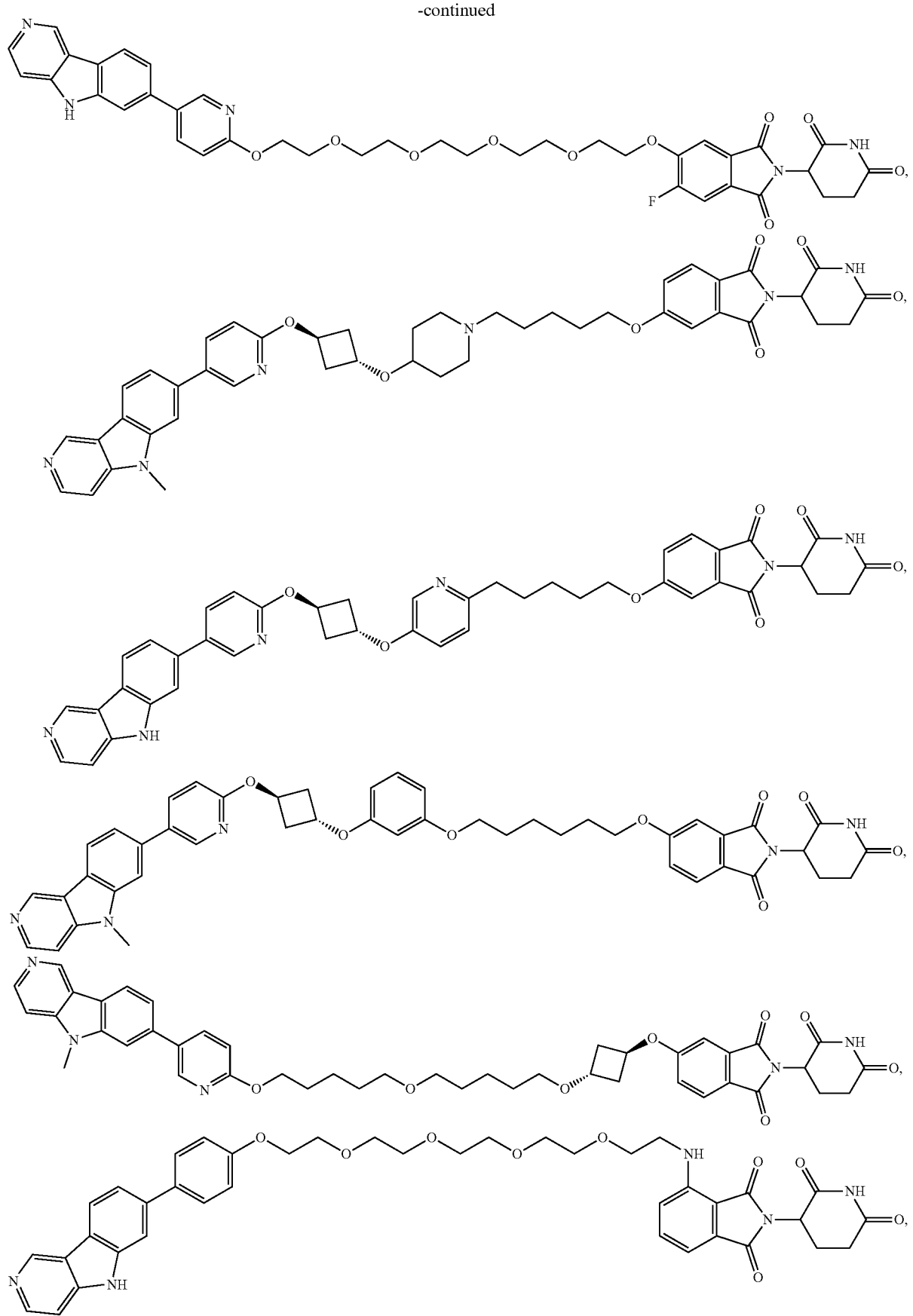

1011                                                                1012
-continued
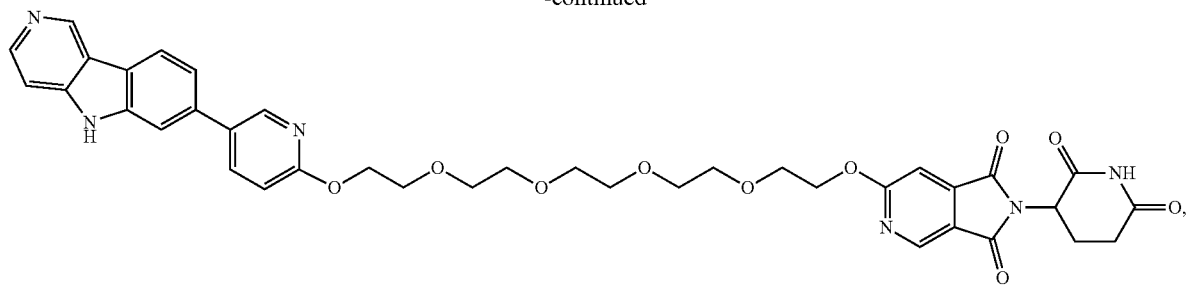
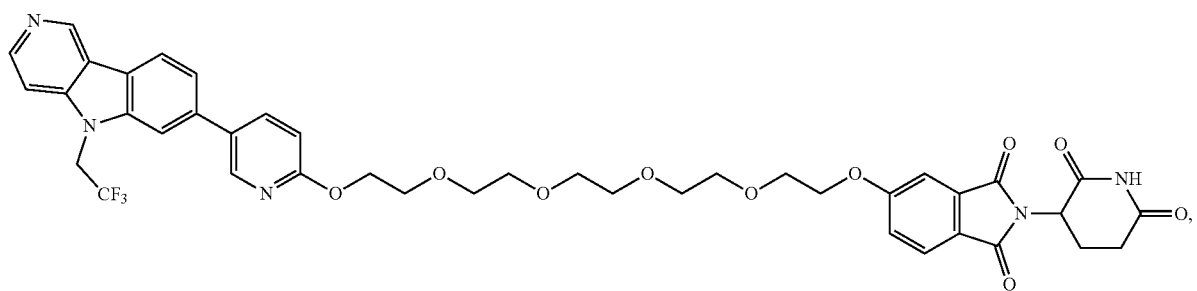
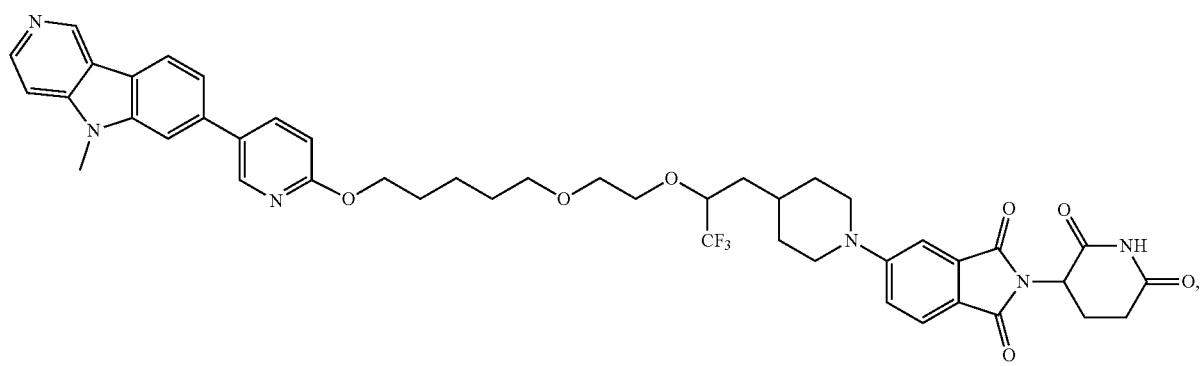
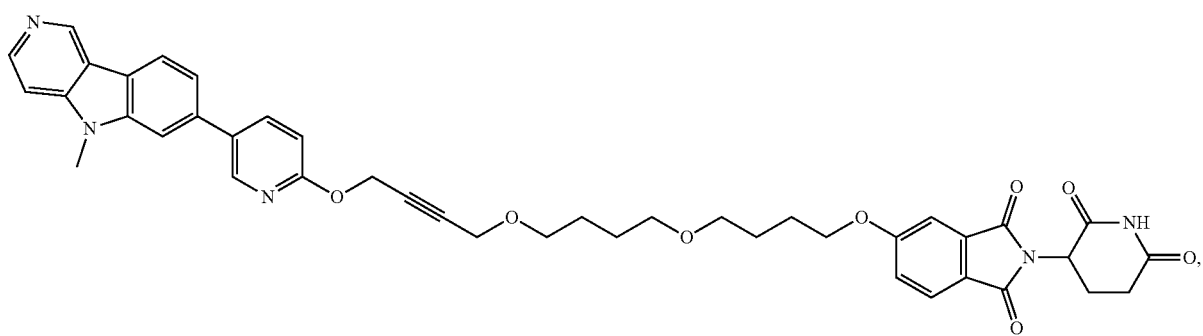
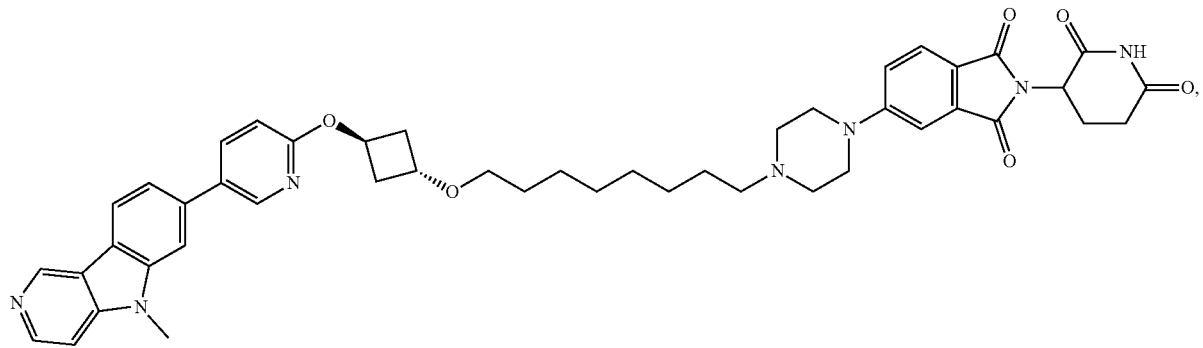

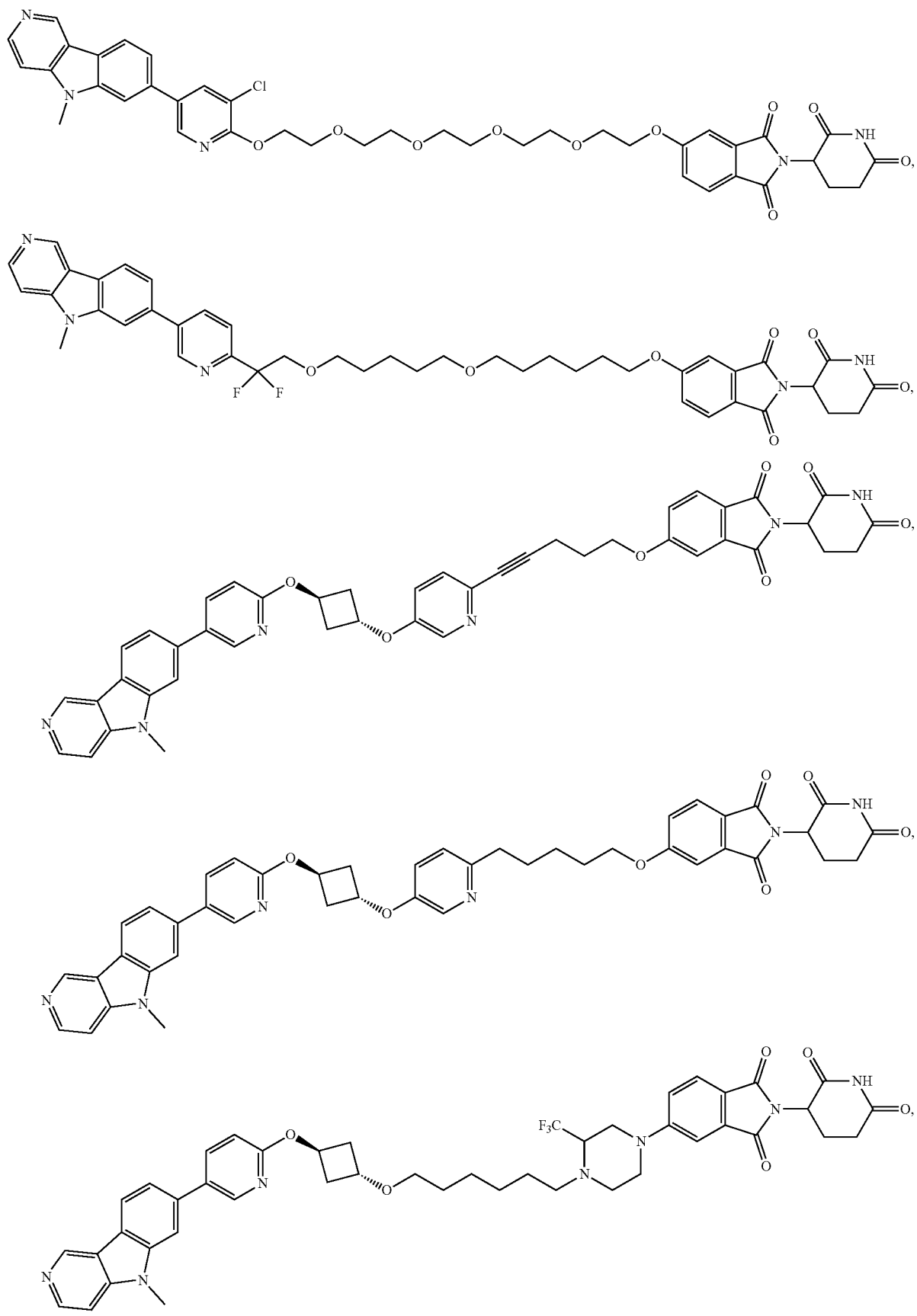

1015 1016
-continued
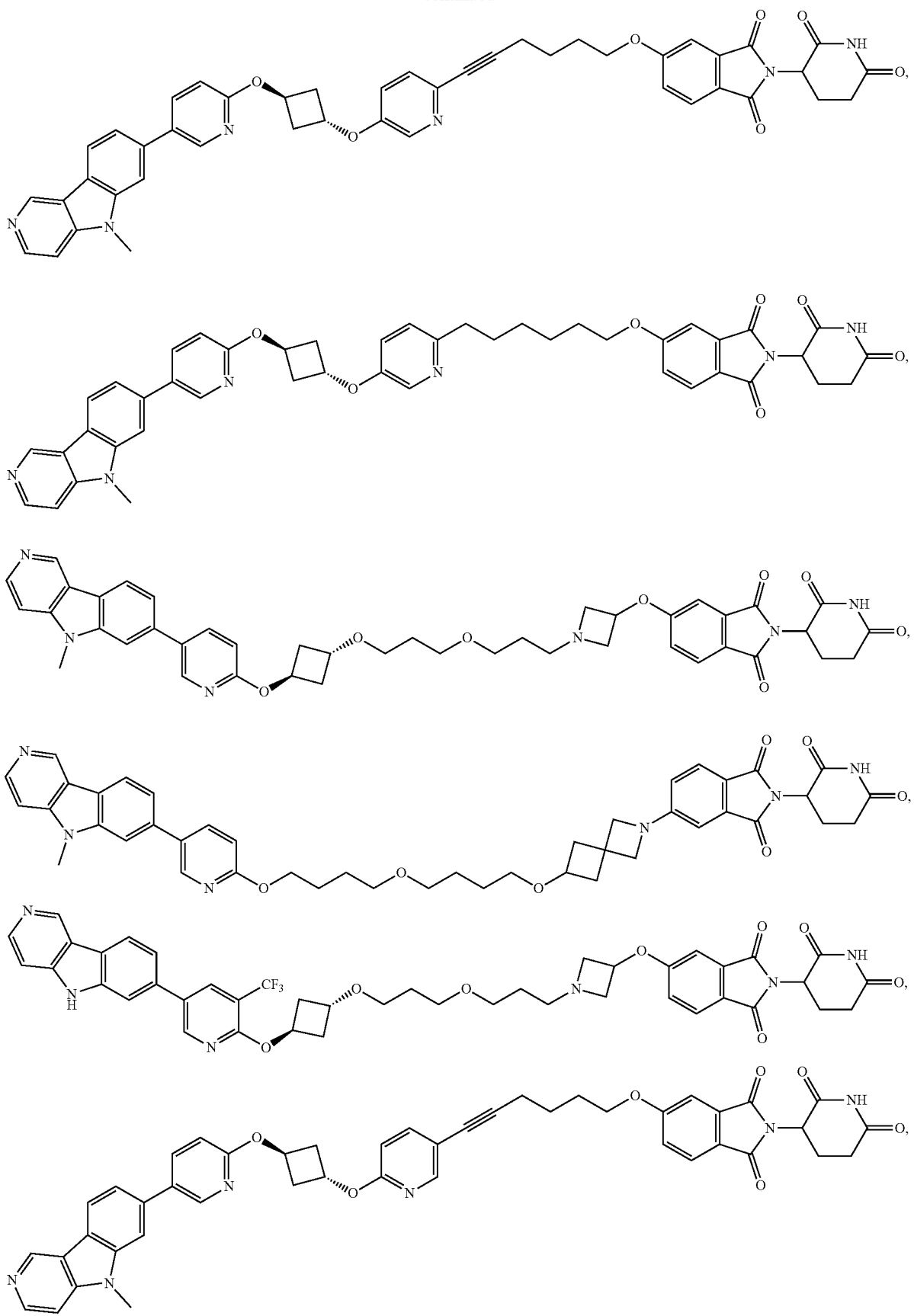

US 11,458,123 B2
1017                                    1018
-continued
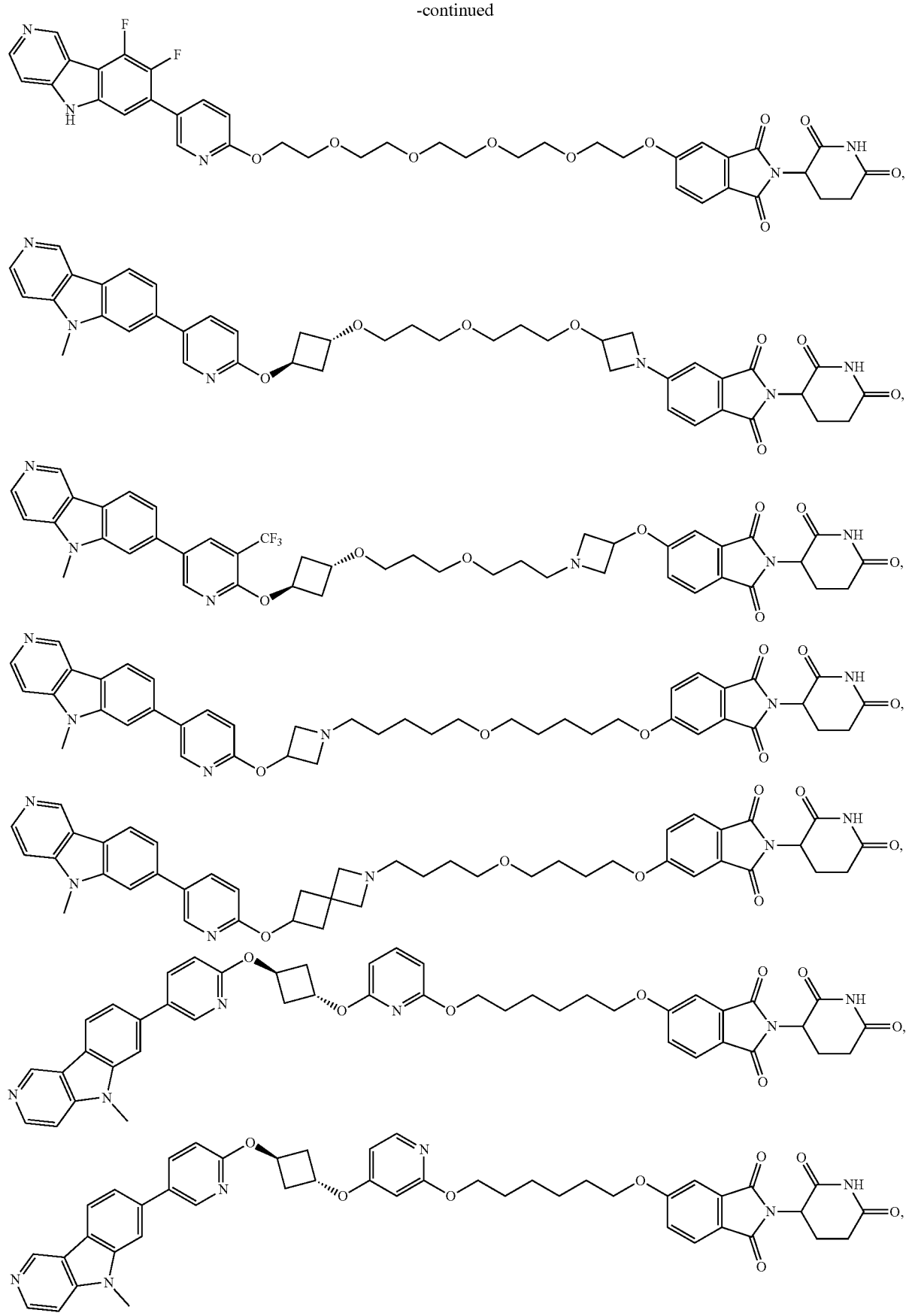

1019                                                  1020
-continued
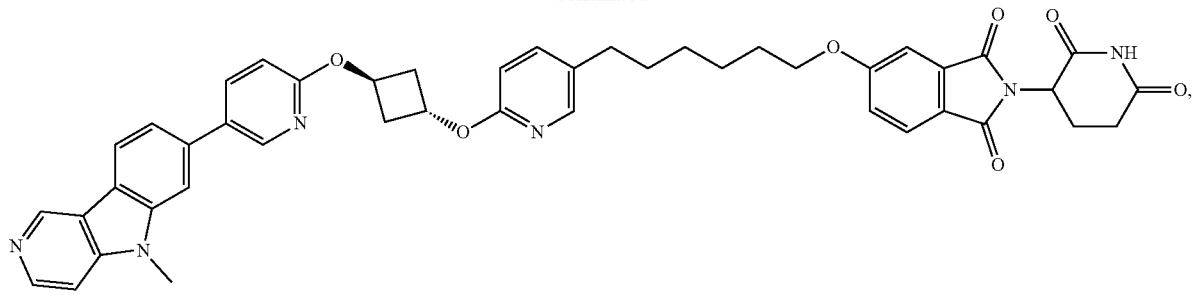
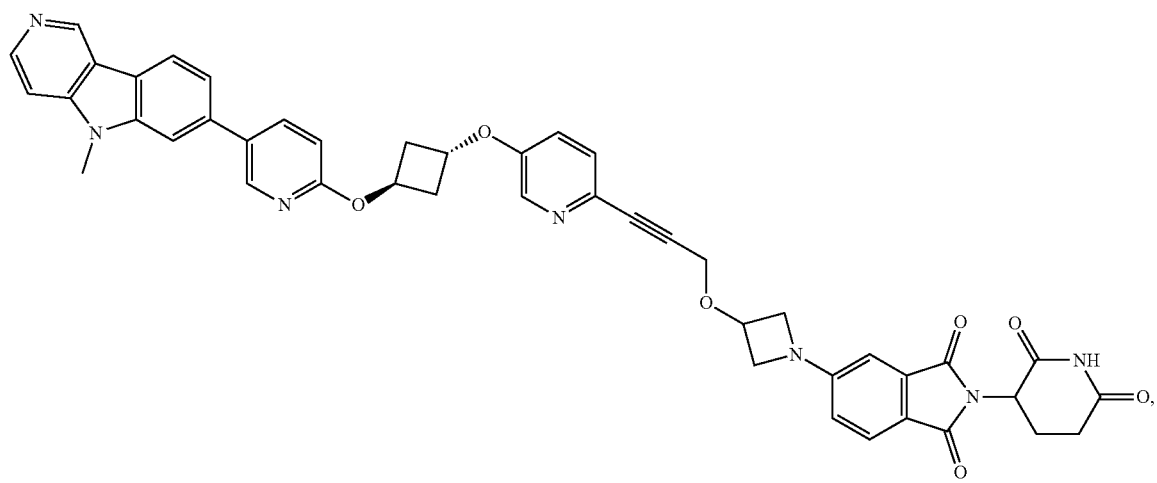
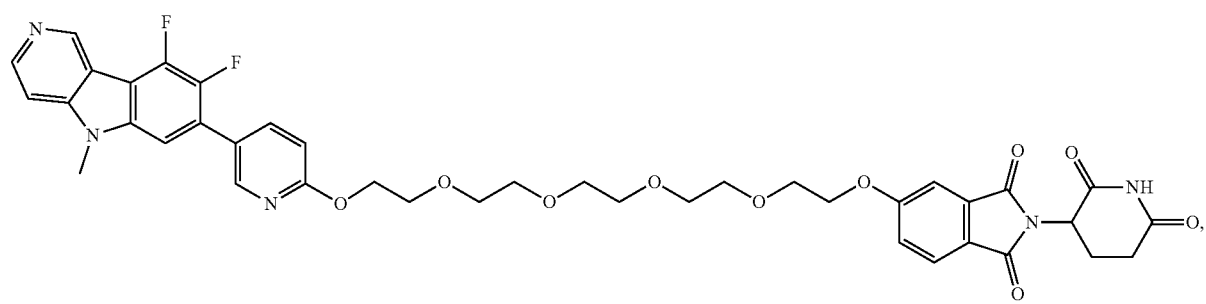
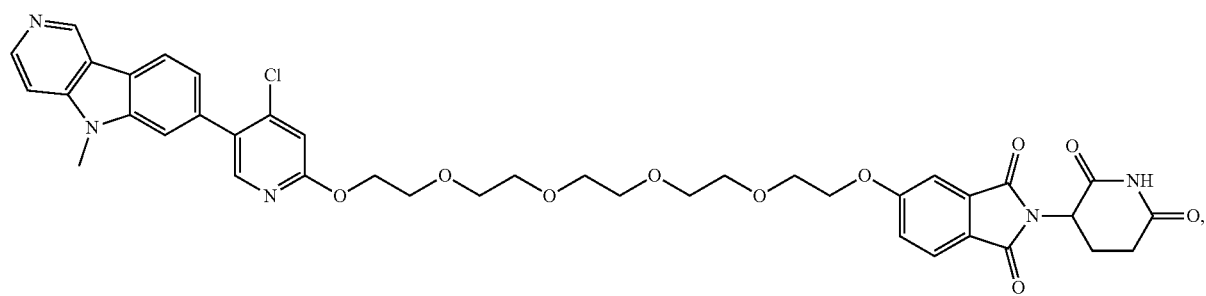
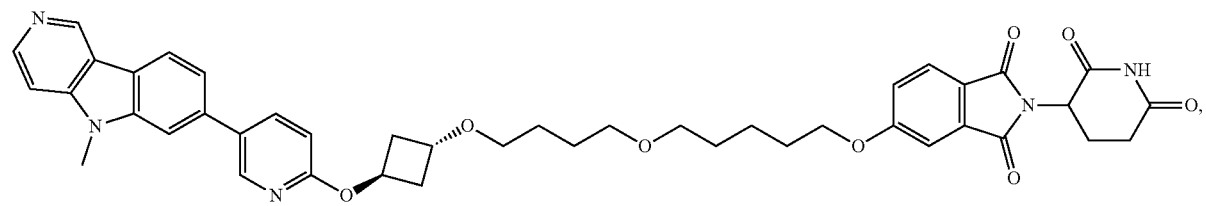

1021
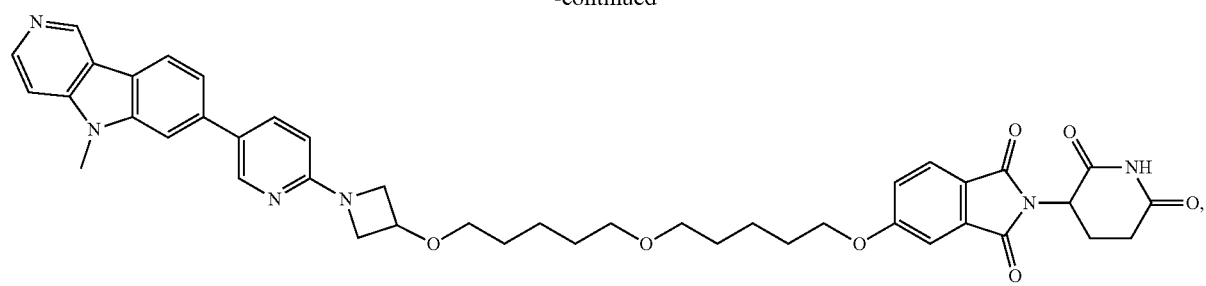
1022
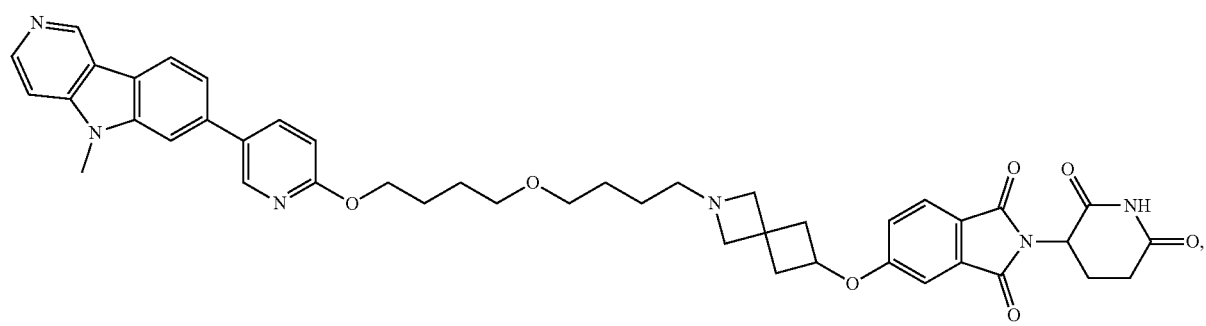
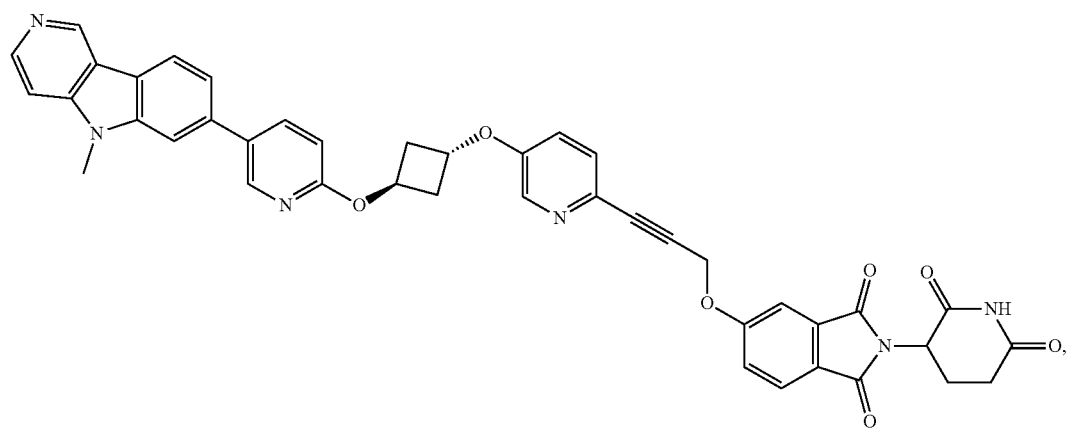
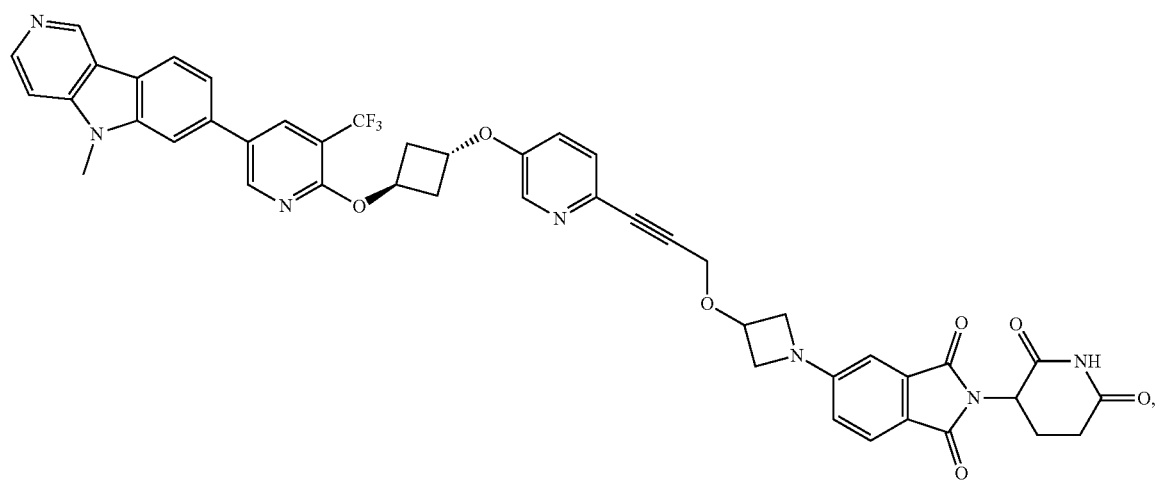

1023    1024
-continued
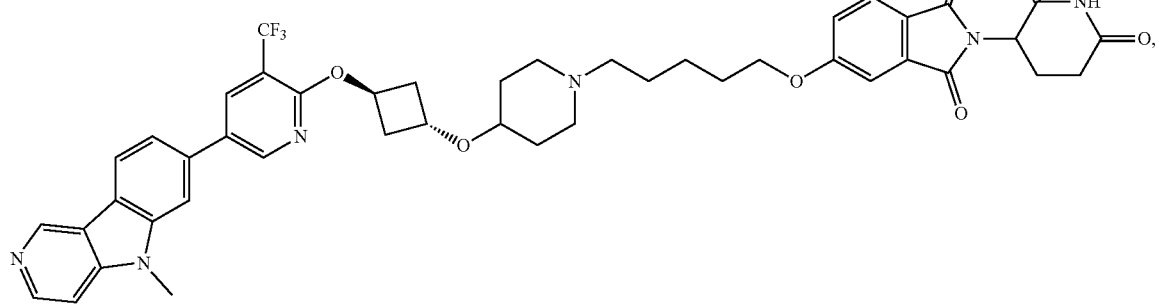
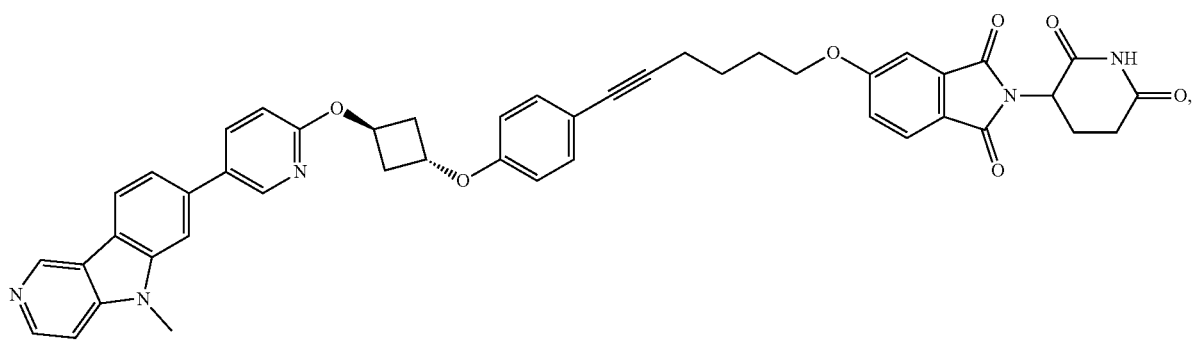
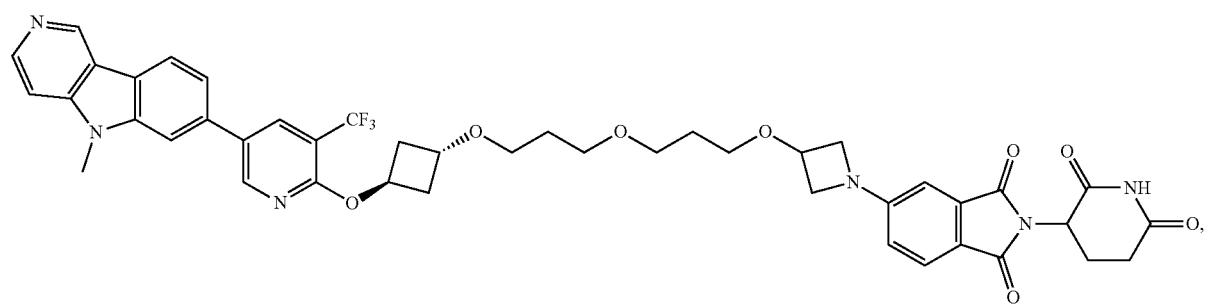
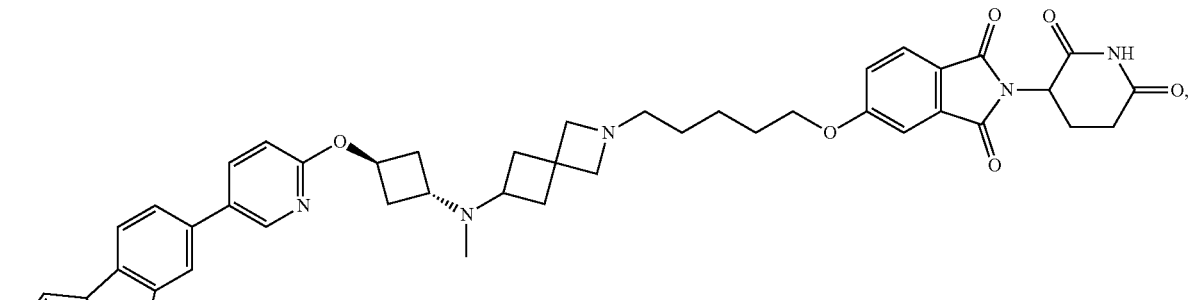
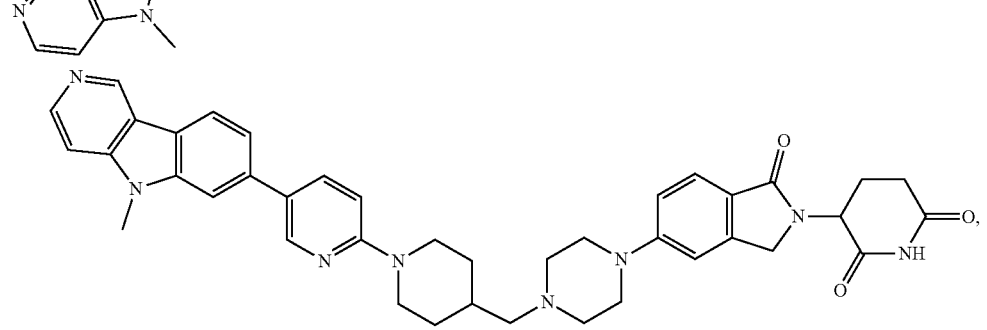

1025
-continued
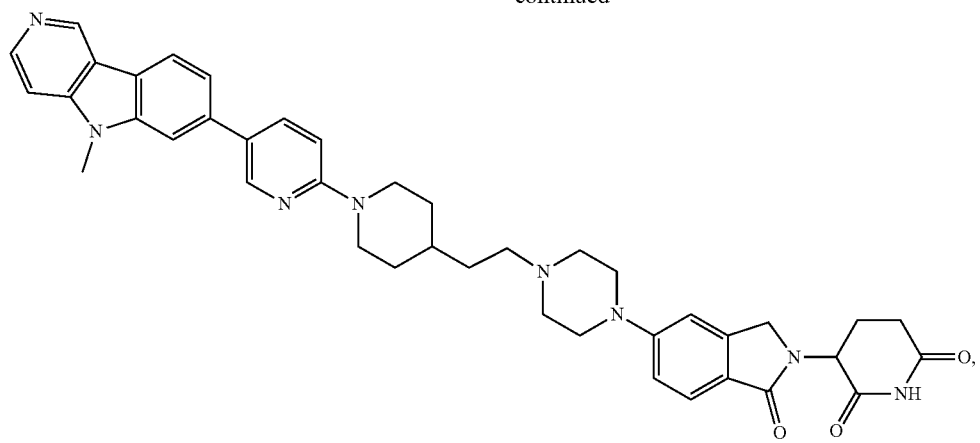
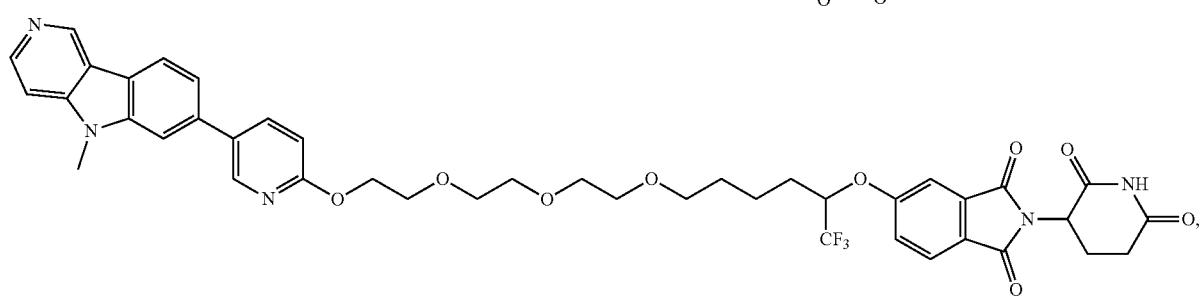
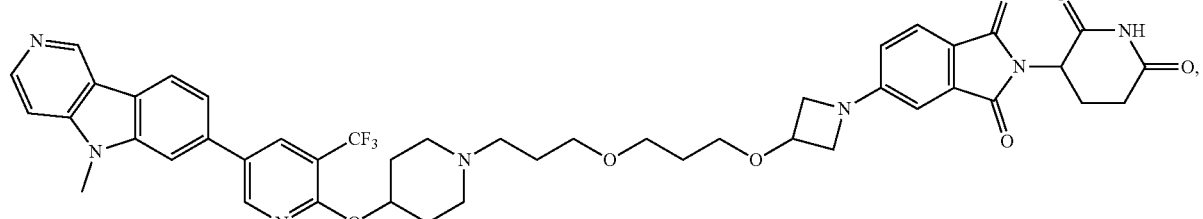
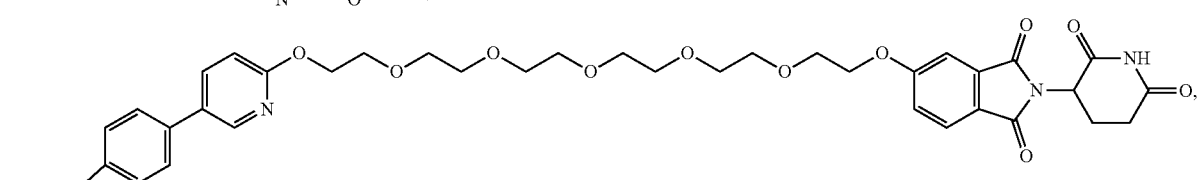
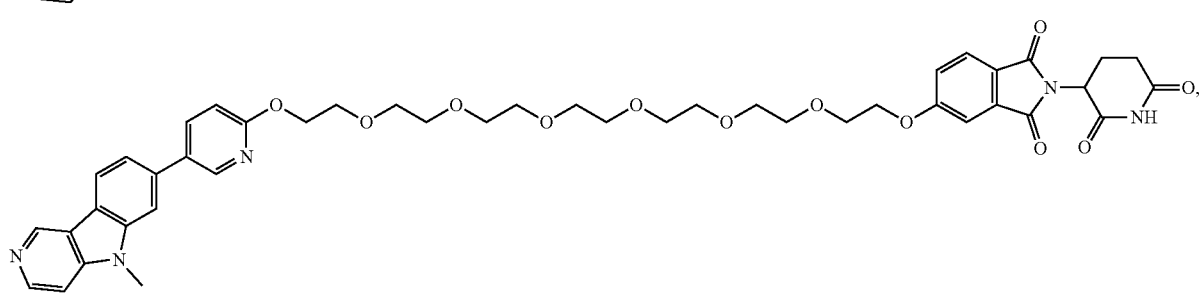
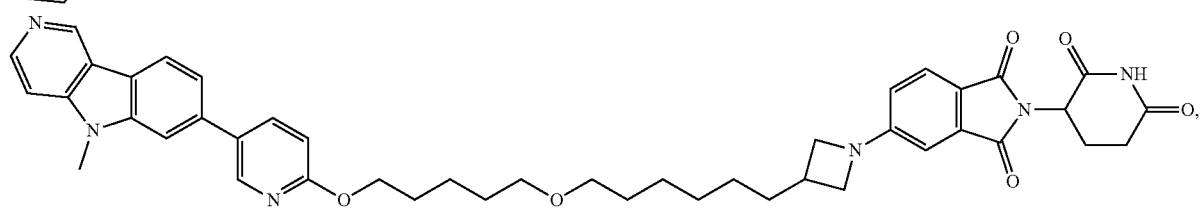
1026